US009282746B2

(12) United States Patent
Amin et al.

(10) Patent No.: US 9,282,746 B2
(45) Date of Patent: Mar. 15, 2016

(54) PERHYDROLASE

(71) Applicant: Danisco US Inc., Palo Alto, CA (US)

(72) Inventors: Neelam S. Amin, Palo Alto, CA (US); Matthew G. Boston, Dixon, CA (US); Richard R. Bott, Burlingame, CA (US); Maguerite A. Cervin, San Mateo, CA (US); Edward M. Concar, San Francisco, CA (US); Marc E. Gustwiller, Cincinnati, OH (US); Brian E. Jones, Leidschendam (NL); Klaus Liebeton, Zwingenberg (DE); Gregory S. Miracle, Hamilton, OH (US); Hiroshi Oh, Cincinnati, OH (US); Ayrookaran J. Poulose, Belmont, CA (US); Sandra W. Ramer, Sunnyvale, CA (US); Jeffrey J. Scheibel, Loveland, OH (US); Walter Weyler, San Francisco, CA (US); Gregory M. Whited, Belmont, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 14/273,384

(22) Filed: May 8, 2014

(65) Prior Publication Data

US 2014/0302003 A1 Oct. 9, 2014

Related U.S. Application Data

(63) Continuation of application No. 10/581,014, filed as application No. PCT/US2004/040438 on Dec. 3, 2004, now Pat. No. 8,772,007.

(60) Provisional application No. 60/526,764, filed on Dec. 3, 2003.

(51) Int. Cl.

| | |
|---|---|
| *C12N 9/14* | (2006.01) |
| *C12N 9/18* | (2006.01) |
| *C12P 21/06* | (2006.01) |
| *C12N 1/20* | (2006.01) |
| *C11D 3/386* | (2006.01) |
| *C11D 3/00* | (2006.01) |
| *C07H 21/04* | (2006.01) |
| *A01N 63/00* | (2006.01) |
| *C12N 9/16* | (2006.01) |
| *C12N 9/50* | (2006.01) |
| *C12N 9/52* | (2006.01) |

(52) U.S. Cl.

CPC ............ *A01N 63/00* (2013.01); *C11D 3/38636* (2013.01); *C12N 9/16* (2013.01); *C12N 9/50* (2013.01); *C12N 9/52* (2013.01)

(58) Field of Classification Search

None

See application file for complete search history.

(56) References Cited

U.S. PATENT DOCUMENTS

| | | | |
|---|---|---|---|
| 3,823,070 | A | 7/1974 | Minato et al. |
| 3,974,082 | A | 8/1976 | Weyn |
| 4,008,125 | A | 2/1977 | Kurozumi et al. |
| 4,261,868 | A | 4/1981 | Hora et al. |
| 4,400,237 | A | 8/1983 | Kruger et al. |
| 4,404,128 | A | 9/1983 | Anderson |
| 4,415,657 | A | 11/1983 | Umezawa et al. |
| 4,430,243 | A | 2/1984 | Bragg |
| 4,594,324 | A | 6/1986 | Dalton et al. |
| 4,683,195 | A | 7/1987 | Mullis et al. |
| 4,683,202 | A | 7/1987 | Mullis |
| 4,965,188 | A | 10/1990 | Mullis et al. |
| 4,977,252 | A | 12/1990 | Chiu |
| 5,030,240 | A | 7/1991 | Wiersema et al. |
| 5,108,457 | A | 4/1992 | Poulouse et al. |
| 5,204,015 | A | 4/1993 | Caldwell et al. |
| 5,240,835 | A | 8/1993 | Pettrone et al. |
| 5,254,283 | A | 10/1993 | Arnold et al. |
| 5,296,161 | A | 3/1994 | Wiersema et al. |
| 5,296,616 | A | 3/1994 | Namekawa et al. |
| 5,338,474 | A | 8/1994 | Kaiserman et al. |
| 5,352,594 | A | 10/1994 | Poulose et al. |
| 5,354,559 | A | 10/1994 | Morehouse |
| 5,370,770 | A | 12/1994 | Johnson et al. |
| 5,486,303 | A | 1/1996 | Capeci et al. |
| 5,489,392 | A | 2/1996 | Capeci et al. |
| 5,516,448 | A | 5/1996 | Capeci et al. |
| 5,565,422 | A | 10/1996 | Del Greco et al. |
| 5,569,645 | A | 10/1996 | Dinniwell et al. |
| 5,574,005 | A | 11/1996 | Welch et al. |
| 5,576,282 | A | 11/1996 | Miracle et al. |
| 5,595,967 | A | 1/1997 | Miracle et al. |

(Continued)

FOREIGN PATENT DOCUMENTS

| | | |
|---|---|---|
| EP | 0268456 | 5/1988 |
| EP | 0280232 | 8/1988 |

(Continued)

OTHER PUBLICATIONS

Akoh, C.C., et al., "GDSL family of serine esterases/lipases." *Progress in Lipid Research* 43(6): 534-552, 2011.

(Continued)

*Primary Examiner* — Iqbal H Chowdhury

(74) *Attorney, Agent, or Firm* — Danisco US Inc.

(57) ABSTRACT

The present invention provides methods and compositions comprising at least one perhydrolase enzyme for cleaning and other applications. In some particularly preferred embodiments, the present invention provides methods and compositions for generation of peracids. The present invention finds particular use in applications involving cleaning, bleaching and disinfecting.

13 Claims, 19 Drawing Sheets

(56) References Cited

U.S. PATENT DOCUMENTS

| | | | |
|---|---|---|---|
| 5,597,936 | A | 1/1997 | Perkins et al. |
| 5,601,750 | A | 2/1997 | Domke et al. |
| 5,691,297 | A | 11/1997 | Nassano et al. |
| 5,785,812 | A | 7/1998 | Linsten et al. |
| 5,879,584 | A | 3/1999 | Bianchetti et al. |
| 5,935,826 | A | 8/1999 | Blue et al. |
| 5,989,526 | A | 11/1999 | Aaslyng et al. |
| 6,165,318 | A | 12/2000 | Paren et al. |
| 6,225,464 | B1 | 5/2001 | Hiler, II et al. |
| 6,306,812 | B1 | 10/2001 | Perkins et al. |
| 6,326,348 | B1 | 12/2001 | Vinson et al. |
| 6,379,653 | B1 | 4/2002 | Asyng et al. |
| 6,569,286 | B1 | 5/2003 | Withenshaw et al. |
| 7,754,460 | B2 | 7/2010 | Amin et al. |
| 8,772,007 | B2 | 7/2014 | Amin et al. |
| 2002/0007516 | A1 | 1/2002 | Wang |
| 2003/0191033 | A1 | 10/2003 | Ryu et al. |
| 2007/0105740 | A1 | 5/2007 | Dicosimo et al. |

FOREIGN PATENT DOCUMENTS

| | | |
|---|---|---|
| EP | 0359087 | 3/1990 |
| EP | 0375102 | 6/1990 |
| EP | 1255888 | 9/2001 |
| GB | 2094826 | 9/1982 |
| WO | WO91/17235 | 11/1991 |
| WO | WO97/11151 | 3/1997 |
| WO | WO00/32601 | 6/2000 |
| WO | WO01/16172 | 3/2001 |
| WO | WO01/64993 | 9/2001 |
| WO | WO03/002810 | 1/2003 |
| WO | WO03/083125 | 10/2013 |

OTHER PUBLICATIONS

Bennett, M., et al., "Nucleotide sequence and predicted functions of the entire Sinorhizobium meliloti pSymA megaplasmid." *Proceedings of the Nat. Acad. Sci* 98(17): 9883-9888, 2011.

Bernhardt, P., et al., "Molecular Basis of Perhydrolase Activity in Serine Hydrolases." *Angewandte Chemi* 44(18): 2742-2746, 2005.

Goffin, C., et al., "Biochemistry and comparitive genomics of SxxK superfamily acyltransferases offer a club to the mycobacterial paradox: presence of penicillin-susceptible target proteins versus lack of efficiency of penicillin as therapeutic agent." *Microbiology and Molecular Biology Reviews* 66(4): 702-728, 2002.

Mathews, I., et al., "Structure of a novel enzyme that catalyzes acyl transfer to alcohols in aqueous conditions." *Biochemistry* 46(31): 8969-8979, 2007.

Molgaard, A., et al., "Rhamnogalacturonan acetylesterase elucidates the structure and function of a new family of hydrolases." *Structure 2000* 8(4): 373-383, 2000.

Sakai, Y., et al., "A novel arylesterase active toward 7-Aminocephalosporanic Acid from Agrobacterium radiobacter IFO 12607: Nucleotide sequence, gene expression in *Escherichia coli*, and site-directed mutagenesis." *J. of Fermentation and Bioengineering*.

Upton, C., et al., "A new family of lipolytic enzymes." *TIBS* 20: 178-179, 1995.

GenBank Accession No. AAO7232, Arylesterase precursor [Vibrio vulnificus CMCP6], Kim, Y.R., et al., Jan. 25, 2011.

GenBank Accession No. AAC38796, outer membrane esterase [*Salmonella enteric* subsp. *enterica serovar* Typhimurium], Carinato, M.E., et al., Jul. 20, 1998.

GenBank Accession No. AAD02335, arylesterase [Agrobactgerium tumefaciens], Sakai, Y., et al., Jan. 5, 1999.

GenBank Accession No. AAK53448, lipase/phospholipase B [Moraxella bovis], Farn, J.L., et al., Oct. 30, 2001.

GenBank Accession No. AAK65750, hydrolase [Sinorhizobium meliloti 1021], Barnett, M.J., et al., Nov. 16, 2010.

GenBank Accession No. AAK65755, hydrolase [Sinorhizobium meliloti 1021], Barnett, M.J., et al, Nov. 16, 2010.

GenBank Accession No. AAK87224, arylesterase [Agrobacterium fabrum str. C58], Wood, D.W., et al, Dec. 3, 2012.

GenBank Accession No. AAK89941, arylesterase [Agrobacterium fabrum str. C58], Wood,D.W., et al, Jun. 5, 2013.

GenBank Accession No. BAB47978 arylesterase [Mesorhizobium loti MAFF303099], Kaneko,T., et al., May 16, 2009.

GenBank Accession No. CAC46027 Probable arylesterase protein [Sinorhizobium meliloti], Capela, D., et al., Aug. 1, 2011.

ATCC Accession No. 10143, *M. smegmatis, Mycobacterium smegmatis* (Trevisan) Lehmann and Neumann, 1953.

ATCC Accession No. 19686, *Mycobacterium parafortuitum*, Tsukamura et al., 1966.

NCBI Accession No. NP_066654, hypothetical protein [Agrobacterium rhizogenes], Moriguchu, K., et al., Jun. 10, 2013.

NCBI Reference Sequence: NP_865748, hypothetical protein RB3832 [Rhodopirellula baltica SH 1], Wecker,P., et al., Jul. 22, 2013.

UniProt Accession No. Q46ZX5, Cupriavidus pinatubonensis (strain JMP 134 / LMG 1197) (Ralstonia eutropha (strain JMP 134)), Hammon, N., et al., Sep. 13, 2005.

UniProt Accession No. Q7NRP5, Acyl-CoA thioesterase, Vasconcelos, A.T.R.,et al., Oct. 31, 2006.

UniProt Accession No. Q88KH2, Pseudomonas putida (strain KT2440), Nelson, K.E., et al., Jun. 1, 2003.

UniProtKB/Swiss-Prot: Accession No. Q8UAC0, Arylesterase (AGR_L_2749p), Wood, D.W., et al., Oct. 31, 2006.

UniProtKB/Swiss-Prot Accession No. Q8UFG4, Arylesterase (AGR_C_2642p), Wood, D.W., et al., Oct. 31, 2006.

UniProtKB/Swiss-Prot: Q8X0I0, Putative arylesterase protein, Salanoubat,M., et al., Oct. 31, 2006.

UniProt. Accession No. Q92XZ1, Rhizobium meliloti (strain 1021) (Ensifer meliloti) (Sinorhizobium meliloti), Barnett, M.J., et al., Dec. 1, 2001.

UniProt Accession No. Q98MY5, Aryl esterase. II, Kaneko, T., et al. Oct. 1, 2001.

UniProt Accession No. Q9EV56, Rhizobium meliloti (Ensifer meliloti) (Sinorhizobium meliloti), Soto, M.J., et al., Mar. 1, 2001.

UniProt Accession No. Q9KWA6, Agrobacterium rhizogenes, Moriguchi, K., et al., Oct. 1, 2000.

UniProt Accession No. Q9KWB1, Agrobacterium rhizogenes, Moriguchi, K., et al., Oct. 1, 2000.

International Search Report and the Written Opinion of the International Searching Authority for International Application No. PCT/US2004/040438 dated Nov. 29, 2005.

International Preliminary Report on Patentability dated Jun. 7, 2006.

Partial European Search Report of European Application No. EP10 01 1491 dated Feb. 4, 2011.

Extended European Search Report of European Patent Application No. 10 01 1491 dated May 20, 2011.

Partial European Search Report of European Application No. EP10011487.5 dated Feb. 10, 2011.

Extended European Search Report of European Patent Application No. 1001487.5 dated Jun. 8, 2011.

Extended European Search Report of European Patent Application No. 13176407 dated Oct. 21, 2013.

UniProt Accession No. Q9KWA6, Moriguchi, K., et al., Hypothetical protein riorf78, Agrobacterium rhizogenes, Oct. 31, 2006.

UniProt Accession No. Q9KWB1, Moriguchi, K., et al., Hypothetical protein rior73, Agrobacterium rhizogenes, Oct. 31, 2006.

UniProtKB/Swiss-Prot Accession No. Q46ZX5, Putative arylesterase protein, Copeland, A., et al., Oct. 31, 2006.

UnitProt Accession No. Q92XZ6_RHIME, Rhizobium meliloti (strain 1021) (Ensifer meliloti) (Sinorhizobium meliloti), Barnett, M.J., et al. Dec. 1, 2011.

NCBI Accession No. NP_102192, arylesterase [Mesorhizobium loti MAFF303099], Kaneko, T., et al., Jun. 10, 2013.

NCBI Reference Sequence WP_010968046.1, hydrolase [Sinorhizobium meliloti], May 15, 2013.

(56) References Cited

OTHER PUBLICATIONS

NCBI Reference Sequence WP_00353461.1, arylesterase [Sinorhizobium meliloti], Jul. 18, 2013.
NCBI Reference Sequence YP_007574712.1, Esterase [Sinorhizobium meliloti 2011], Carrere, S., et al., Jun. 11, 2013.
NCBI Reference Sequence NP_436338.2, hydrolase [Sinorhizobium meliloti 1021], Barnett, M.J., et al., Jun. 27, 2013.
NCBI Reference Sequence NP_066654.1, Maeda, Y. et al., "hypothetical protein [Agrobacterium rhizogenes]" Jun. 10, 2013.
Zock, J., et al., "The *Bacillus subtilis pnbA* gene encoding p-nitrobenzyl esterase: cloning, sequence and high-level expression in *Escherichia coli*." *Gene* 151: 37-43, 1994.

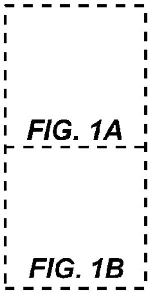
FIG. 1
FIG. 1A
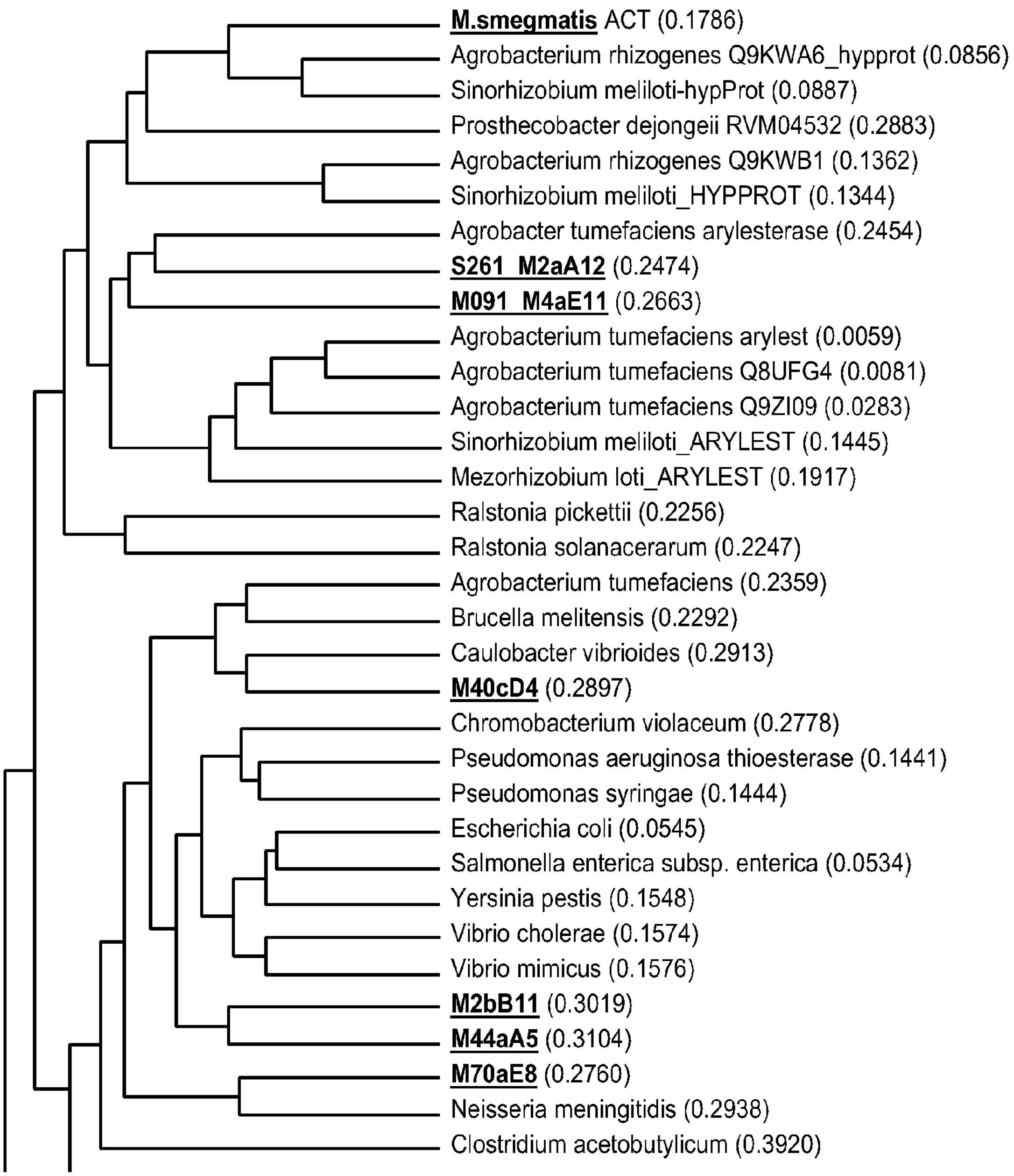

Chymotrypsin --His57—Asp102—Ser195

Subtilisin --Asp32—His64—Ser215

α/β Hydrolase --Ser126—Asp176—His206--

Perhydrolase -Ser11—Asp192—His195---

FIGURE 6

| | Volume (ml) | Protein (mg/ml) | Total Protein (mg) | pNB Activity d410/min/ml | SpAc d410/min/mg | Total activity d410 | Recovery (%) | Purification (fold) |
|---|---|---|---|---|---|---|---|---|
| Crude extract | 128 | 7.5 | 960 | 3840 | 512 | 491520 | 100 | 1.0 |
| 55C 10min | 118 | 5.4 | 637 | 3760 | 696 | 443680 | 90 | 1.4 |
| Phenyl seph | 241 | 0.37 | 89 | 1700 | 4595 | 409700 | 83 | 9.0 |
| HQ Anion | 0.74 | 22.7 | 17 | 250000 | 11013 | 185000 | 38 | 21.5 |

PERHYDROLASE

The present application is a continuation application of U.S. application Ser. No. 10/581,014, filed Sep. 11, 2007, now U.S. Pat. No. 8,772,007, which is a U.S. National Stage application of International Application No. PCT/US04/40438, filed Dec. 3, 2004, which claims priority under 35 U.S.C. §119 to U.S. Provisional Patent Application Ser. No. 60/526,764, filed Dec. 3, 2003, which are hereby incorporated herein in their entireties.

FIELD OF THE INVENTION

The present invention provides methods and compositions comprising at least one perhydrolase enzyme for cleaning and other applications. In some particularly preferred embodiments, the present invention provides methods and compositions for generation of peracids. The present invention finds particular use in applications involving cleaning, bleaching and disinfecting.

BACKGROUND OF THE INVENTION

Detergent and other cleaning compositions typically include a complex combination of active ingredients. For example, most cleaning products include a surfactant system, enzymes for cleaning, bleaching agents, builders, suds suppressors, soil-suspending agents, soil-release agents, optical brighteners, softening agents, dispersants, dye transfer inhibition compounds, abrasives, bactericides, and perfumes. Despite the complexity of current detergents, there are many stains that are difficult to completely remove. Furthermore, there is often residue build-up, which results in discoloration (e.g., yellowing) and diminished aesthetics due to incomplete cleaning. These problems are compounded by the increased use of low (e.g., cold water) wash temperatures and shorter washing cycles. Moreover, many stains are composed of complex mixtures of fibrous material, mainly incorporating carbohydrates and carbohydrate derivatives, fiber, and cell wall components (e.g., plant material, wood, mud/clay based soil, and fruit). These stains present difficult challenges to the formulation and use of cleaning compositions.

In addition, colored garments tend to wear and show appearance losses. A portion of this color loss is due to abrasion in the laundering process, particularly in automated washing and drying machines. Moreover, tensile strength loss of fabric appears to be an unavoidable result of mechanical and chemical action due to use, wearing, and/or washing and drying. Thus, a means to efficiently and effectively wash colored garments so that these appearance losses are minimized is needed.

Cleaning compositions that comprise esterases, lipases and cutinases are well-known in the art. However, these enzymes have a very low ratio of perhydrolysis to hydrolysis. This results in the conversion of most of the ester substrate into acid, instead of the more desirable peracid. This is a serious drawback, since formula space and cost considerations render it feasible to include only a limited amount of substrate.

In sum, despite improvements in the capabilities of cleaning compositions, there remains a need in the art for detergents that remove stains, maintain fabric color and appearance, and prevent dye transfer. In addition, there remains a need for detergent and/or fabric care compositions that provide and/or restore tensile strength, as well as provide anti-wrinkle, anti-bobbling, and/or anti-shrinkage properties to fabrics, as well as provide static control, fabric softness, maintain the desired color appearance, and fabric anti-wear properties and benefits. In particular, there remains a need for the inclusion of compositions that are capable of removing the colored components of stains, which often remain attached to the fabric being laundered. In addition, there remains a need for improved methods and compositions suitable for textile bleaching.

In addition to the fabric and garment cleaning area, bleaching is commonly used in the pulp and paper industry. Prior to production of paper, pulp is typically treated to remove undesirable colored contaminants. This provides pulp that is suitable for production of paper of higher quality than pulp that is not treated to remove colored contaminants and other undesirable components present in pulp. For example, in the paper recycling industry, removal of ink is necessary. Although standard methods are suitable for deinking paper with oil or water-based inks, the increased use of electrostatic inks has made deinking problematic, as these inks are much more difficult to remove. There are various methods available for deinking paper, including the use of enzymes (See e.g., U.S. Pat. No. 5,370,770). However, there remains a need in the art for efficient, cost-effective methods for treatment of pulp for paper (recycled and new) product production.

Bleaching is also commonly used in the personal care market (e.g., dental whiteners, hair bleachers, etc.). Although personal care bleaching products have improved over the years, there remains a need for mild, easy to use, cost-effective bleaching methods for this setting.

SUMMARY OF THE INVENTION

The present invention provides methods and compositions comprising at least one perhydrolase enzyme for cleaning and other applications. In some particularly preferred embodiments, the present invention provides methods and compositions for generation of peracids. The present invention finds particular use in applications involving cleaning, bleaching and disinfecting.

In some embodiments, the present invention provides compositions comprising at least one perhydrolase, wherein the perhydrolase exhibits a perhydrolysis to hydrolysis ratio that is greater than 1.

The present invention also provides isolated perhydrolases, wherein the perhydrolases exhibit a perhydrolysis to hydrolysis ratio that is greater than 1. In some preferred embodiments, the perhydrolase is *M. smegmatis* perhydrolase. In alternative preferred embodiments, the perhydrolase is at least approximately about 35% homologous to *M. smegmatis* perhydrolase. In further embodiments, the perhydrolase is at least approximately about 40%, 45%, 50%, 55%, 60%, 65%, 70%, 75%, 80%, 85%, 90%, 95%, or 99% homologous to *M. smegmatis* perhydrolase. In additional preferred embodiments, the perhydrolase comprises the amino acid sequence set forth in SEQ ID NO:2. In some preferred embodiments, the perhydrolases have immunological cross-reactivity with *M. smegmatis* perhydrolase. In still further embodiments, the perhydrolase is at least a portion of *M. smegmatis* perhydrolase, wherein the perhydrolase has a perhydrolysis to hydrolysis ration that is greater than 1. In alternative embodiments, the perhydrolase is a structural homologue of *M. smegmatis* perhydrolase, in which the active site is homologous to at least one amino acid selected from the group consisting of S11, D192, and H195 of the *M. smegmatis* perhydrolase.

The present invention also provides isolated perhydrolase variants having amino acid sequences comprising at least one modification of an amino acid made at a position equivalent to a position in *M. smegmatis* perhydrolase comprising the amino acid sequence set forth in SEQ ID NO:2. In some embodiments, at least one modification is made at an amino acid position equivalent to a position in *M. smegmatis* perhydrolase comprising the amino acid sequence set forth in SEQ ID NO:2, wherein the modified amino acid is selected from the group consisting of Cys7, Asp10, Ser11, Leu12, Thr13, Trp14, Trp16, Pro24, Thr25, Leu53, Ser54, Ala55, Thr64, Asp65, Arg67, Cys77, Thr91, Asn94, Asp95, Tyr99, Val125, Pro138, Leu140, Pro146, Pro148, Trp149, Phe150, Ile153, Phe154, Thr159, Thr186, Ile192, Ile194, and Phe196. In further embodiments, the modification comprises at least one substitution at an amino acid position equivalent to a position in *M. smegmatis* perhydrolase comprising the amino acid sequence set forth in SEQ ID NO:2, wherein at least one substitution is selected from the group consisting of M1, K3, R4, I5, L6, C7, D10, S11, L12, T13, W14, W16, G15, V17, P18, V19, D21, G22, A23, P24, T25, E26, R27, F28, A29, P30, D31, V32, R33, W34, T35, G36, L38, Q40, Q41, D45, L42, G43, A44, F46, E47, V48, I49, E50, E51, G52, L53, S54, A55, R56, T57, T58, N59, I60, D61, D62, P63, T64, D65, P66, R67, L68, N69, G70, A71, S72, Y73, S76, C77, L78, A79, T80, L82, P83, L84, D85, L86, V87, N94, D95, T96, K97, Y99F100, R101, R102, P104, L105, D106, I107, A108, L109, G110, M111, S112, V113, L114, V115, T116, Q117, V118, L119, T120, S121, A122, G124, V125, G126, T127, T128, Y129, P146, P148, W149, F150, I153, F154, I194, and F196.

In some preferred embodiments, the variant perhydrolase exhibits a change in peracid hydrolysis compared to the wild-type perhydrolase. In some embodiments, the change in peracid hydrolysis is a decrease, while in other embodiments, the change in peracid hydrolysis is an increase.

In some alternative preferred embodiments, the variant perhydrolase exhibits a ratio of peracid hydrolysis of about 0.1 or less, in comparison with wild-type perhydrolase. In alternative preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of R4, L12, G15, P18, R27, W34L38, A44, E51, G52, L53, S54, T58, R67, L68, S72, A79, T80, D85, L86, V87, N94, K97, R101, V118, L119, G124, G126, and I194.

In further alternative embodiments, the variant perhydrolase exhibits a ratio of peracid hydrolysis of about 0.2 or less, in comparison with wild-type perhydrolase. In yet additional embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of R4, I5, D10, L12, W14, G15, P18, V19, T25, R27, W34, L38, A44, I49, E50, E51, G52, L53, S54, A55, R56, T58, N59, D62, T64, D65, R67, L68, N69, S72, S76, C77, A79, T80, L82, P83, D85, L86, V87, N94, T96, K97, R101, L82, P83, L86, V87, N94, T96, K97, F100, R101, L109, M111, L114, V118, L119, A122, G124, G126, T127, Y129, W149, and I194.

In additional embodiments, the variant perhydrolase exhibits a ratio of peracid hydrolysis of about 0.3 or less, in comparison with wild-type perhydrolase. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of R4, I5, D10, L12, W14, G15, L12, P18, V19, G22, A23, T25, E26, R27, W34, G36, L38, Q41, L42, G43, A44, I49, E50, E51, G52, L53, S54, A55, R56, T57, N59, T58, D62, T64, D65, R67, L68, N69, G70, S72, Y73, S76, C77, A79, T80, L82, P83, D85, L86, V87, N94, T96, K97, Y99, F100, R101, R102, P104, L109, G110, M111, L114, V118, L119, A122, G124, V125, G126, T127, Y129, W149, F154, and I194.

In yet further embodiments, the variant perhydrolase exhibits a ratio of peracid hydrolysis of about 0.4 or less, in comparison with wild-type perhydrolase. In some preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of R4, I5, L6, D10, S11, L12, W14, G15, W16, P18, V19, G22, A23, T25, E26, R27, F28, W34, T35, G36, L38, Q41, L42, G43, A44, D45, E47, I49, E50, E51, G52, L53, S54, A55, R56, T57, T58, N59, T58, I60, D62, T64, D65, R67, L68, N69, G70, S72, Y73, S76, C77, A79, T80, L82, P83, D85, L86, V87, N94, P66, T96, K97, Y99, F100, R101, R102, P104, I107, L109, G110, M111, S112, L114, V118, L119, S121, A122, G124, V125, G126, T127, Y129, W149, F150, F154, I194, and F196.

In some embodiments, the variant perhydrolase exhibits a ratio of peracid hydrolysis of about 0.5 or less, in comparison with wild-type perhydrolase. In some preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y129, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, Y99, G190, V191, G193, T197, N201, D203, L208, A209, V212, L215, and L216.

In additional embodiments, the variant perhydrolase exhibits a ratio of peracid hydrolysis of about 0.6 or less, in comparison with wild-type perhydrolase. In some preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y129, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, V125, V19, W16, Y129, Y73, Y99, G190, V191, G193, T197, N201, D203, L208, A209, V212, L215, and L216.

In yet additional embodiments, the variant perhydrolase exhibits a ratio of peracid hydrolysis of about 0.7 or less, in comparison with wild-type perhydrolase. In some preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y129, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, A122, A29, A71, A79, C7, D106, D21, D61, D65, D85, E47, E50, F150, F196, F28, F46, G124, G126, G15, G36, G70, I49, I5, I60, L105, L109, L12, L38, L42, L53, L84, L86, M111, N59, P146, P24, P66, Q41, R102, R27, R56, S112, S121, S54, S72, T116, T120, T127, T128, T13, T57, T64, V125, V17, V19, W14, W149, W16, Y129, Y73, Y99, G190, V191, G193, T197, N201, D203, L208, A209, V212, L215, and L216.

In still further embodiments, the variant perhydrolase exhibits a ratio of peracid hydrolysis of about 0.8 or less, in comparison with wild-type perhydrolase. In some preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y1d29, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, A122, A29, A71, A79, C7, D106, D21, D61, D65, D85, E47, E50, F150, F196, F28, F46, G124, G126, G15, G36, G70, I49, I5, I60, L105, L109, L12, L38, L42, L53, L84, L86, M111, N59, P146, P24, P66, Q41, R102, R27, R56, S112, S121, S54, S72, T116, T120, T127, T128, T13, T57, T64, V125, V17, V19, W14, W149, W16, Y129, Y99, A108, A122, A23, A29, A44, A55, A71, A79, C77, D45, D61, D65, D85, D95, E47, E51, F150, F196, F46, G110, G126, G36, G43, G52, I107, I194, I49, I5, I60, I89, L114, L42, L53, L68, L78, L84, M111, N59, N94, P146, P24, P30, P63, P66, P83, Q117, R101, R4, S112, S121, S72, T116, T120, T127, T13, T57, T96, V113, V125, V17, V19, V32, V87, W149, Y129, Y73, G190, V191, G193, T197, N201, D203, L208, A209, V212, L215, and L216.

In additional embodiments, the variant perhydrolase exhibits a ratio of peracid hydrolysis of about 1.5 or greater, in comparison with wild-type perhydrolase. In some preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y129, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, A122, A29, A71, A79, C7, D106, D21, D61, D65, D85, E47, E50, F150, F196, F28, F46, G124, G126, G15, G36, G70, I49, I5, I60, L105, L109, L12, L38, L42, L53, L84, L86, M111, N59, P146, P24, P66, Q41, R102, R27, R56, S112, S121, S54, S72, T116, T120, T127, T128, T13, T57, T64, V125, V17, V19, W14, W149, W16, Y129, Y99, A108, A122, A23, A29, A44, A55, A71, A79, C77, D45, D61, D65, D85, D95, E47, E51, F150, F196, F46, G110, G126, G36, G43, G52, I107, I194, I49, I5, I60, I89, L114, L42, L53, L68, L78, L84, M111, N59, N94, P146, P24, P30, P63, P66, P83, Q117, R101, R4, S112, S121, S72, T116, T120, T127, T13, T57, T96, V113, V125, V17, V19, V32, V87, W149, Y129, and Y73, Y99, A108, A44, C7, D10, D106, D31, D61, D85, E26, E51, F100, F28, F46, G110, G22, G36, G43, G52, G70, I107, I153, I49, I5, I89, K3, L105, L53, L6, L78, L86, M1, N69, P104, P146, P18, P24, P30, P83, Q117, Q40, Q41, R102, R27, R33, R4, S121, S72, S76, T120, T128, T13, T35, T80, T96, V115, V118, V32V48, V87, W34, G190, V191, G193, T197, E198, A199, R202, D203, G205, V206, A209, E210, Q211, S214, and L215.

In additional embodiments, the variant perhydrolase exhibits a ratio of peracid hydrolysis between about 1.2 and about 1.5, in comparison with wild-type perhydrolase. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, C7, D106, D31, D61, D85, E26, E50, E51, F100, F150, F28, F46, G110, G126, G22, G70, I107, K3, L105, L42, L6, L78, M111, N59, N69, P104, P146, P148, P18, P30, P63, Q117, Q40, Q41, R102, R27, R33, R4, S54, S76, T116, T120, T128, T64, T80, T96, V113, V115, V118, W34, and Y73.

In yet further embodiments, the present invention provides variant perhydrolases in which the variant perhydrolases exhibit a change in perhydrolysis, such that the ratio of variant perhydrolase perhydrolysis to wild-type perhydrolase perhydrolysis is at least about 1.2. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of C7, D10, L12, G15, P18, V19, G22, T25, E26, R27, F28, A29, P30, D31, G36, Q40, Q41, L42, G43, A44, D45, F46, E47, I49, E51, L53, S54, A55, T57, D61, P63, T64, D65, P66, R67, L68, N69, A71, S72, Y73, S76, L78, A79, T80, L82, P83, D85, L86, D95, K97, R101, T103, P104, L105, D106, I107, L109, M111, V113, Q117, V118, S121, G124, V125, G126, T127, P148, F150, I153, F154, and F196.

In further embodiments, the variant perhydrolase exhibits a change in perhydrolysis, such that the ratio of variant perhydrolase perhydrolysis to wild-type perhydrolase perhydrolysis is about 0.8 or less. In some embodiments, the variant perhydrolase comprising at least one modification comprises at least one substitution at an amino acid position equivalent to a position in *M. smegmatis* perhydrolase comprising the amino acid sequence set forth in SEQ ID NO:2, wherein at least one substitution is selected from the group consisting of A108, A122, A23, A29, A44, A55, A71, A79, C7, C77, D10, D106, D21, D45, D61, D62, D65, D85, E26, E47, E50, E51, F100, F150, F154, F196, F28, F46, G110, G124, G126, G15, G22, G36, G52, G70, I107, I153, I194, I49, I5, I60, I89, K3, K97, L105, L109, L114, L119, L12, L38, L42, L53, L6, L68, L78, L82, L84, K86, M1, M111, N59N94, P146, P18, P24, P30, P66, P83, Q40, Q41, R101, R102, R27, R33, R4, R56, R67, S11, S112, S54, S72, S76, T103, T116, T120, T127, T128, T13, T25, T35, T57, T64, T80, T96, V113, V115, V118, V125, V17, V19, V32, V48, V87, W13, W149, W16, W34, Y129, Y73, and Y99.

In alternative embodiments, the present invention provides variant perhydrolases comprising at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A108, A122, A23, A29, A44, A55, A71, A79, C7, C77, D10, D106, D21, D31, D45, D61, D62, D65, D85, E26, E47, E50, E51, F100, F150, F154F196, F28, F46, G110, G124, G126, G15, G22, G36, G43, G52, G70, I107, I153, I194, I49, I5, I60, I89, K3, K97, L105, L109, L114, L119, L12, L38, L42, L53, L6, L68, L78, L82, L84, L86, M1, M111, N59, N69, N94, P104, P146, P148, P18, P24, P30, P63, P66, P83, Q117, Q40, Q41, R101, R102, R27, R33, R4, R56, R67, S11, S112, S121, S54, S72, S76, T103, T116, T120, T127, T128, T13, T25, T35, T57, T58, T64, T80, T96, V113, V115, V118, V125, V17, V19, V32, V48, V87, W14, W149, W16, W34, Y129, Y73, and Y99.

In yet additional embodiments, the variant perhydrolase exhibits a change in perhydrolysis, such that the ratio of variant perhydrolase perhydrolysis to wild-type perhydrolase perhydrolysis is between about 1.2 and about 2. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of C7, D10, L12, G15, P18, V19, G22, T25, E26, R27, F28, A29, P30, D31, G36, Q40, Q41, L42, G43, A44, D45, F46, E47, I49, E51, L53, S54, A55, T57, D61, P63, T64, D65, P66, R67, L68, N69, A71, S72, Y73, S76, L78, A79, T80, L82, P83, D85, L86, D95, K97, R101, T103, P104, L105, D106, I107, L109, M111, V113, Q117, V118, S121, G124, V125, G126, T127, P148, F150, I153, F154, F196, G190, E198, A199, R202, D203, V206, A209, E210, Q211, and V212.

In still further embodiments, the variant perhydrolase exhibits a change in perhydrolysis, such that the ratio of variant perhydrolase perhydrolysis to wild-type perhydrolase perhydrolysis is between about 2 and about 2.5. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A44, C7, D10, D85, D95, E26, E47, I107, L12, L42, P104, P148, S54, Q40, Q117, D203, V206, E210. In still further embodiments, the variant perhydrolase exhibits a change in perhydrolysis, such that the ratio of variant perhydrolase perhydrolysis to wild-type perhydrolase perhydrolysis is between about 2.5 and about 3. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A44, C7, I107, K97, L12, L78, P104, Q40, and V125.

In further embodiments, the variant perhydrolase exhibits a change in perhydrolysis, such that the ratio of variant perhydrolase perhydrolysis to wild-type perhydrolase perhydrolysis is between about 3.0 and about 5. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of D10, D85, L53, L78, and S54.

In still further embodiments, the variant perhydrolase exhibits a change in perhydrolysis, such that the ratio of variant perhydrolase perhydrolysis to wild-type perhydrolase perhydrolysis is about 0.1 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, and W34.

In further embodiments, the variant perhydrolase exhibits a change in perhydrolysis, such that the ratio of variant perhydrolase perhydrolysis to wild-type perhydrolase perhydrolysis is about 0.2 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, and Y73.

In additional embodiments, the variant perhydrolase exhibits a change in perhydrolysis, such that the ratio of variant perhydrolase perhydrolysis to wild-type perhydrolase perhydrolysis is about 0.3 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, and Y129.

In yet additional embodiments, the variant perhydrolase exhibits a change in perhydrolysis, such that the ratio of variant perhydrolase perhydrolysis to wild-type perhydrolase perhydrolysis is about 0.4 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, and V87.

In additional embodiments, the variant perhydrolase exhibits a change in perhydrolysis, such that the ratio of variant perhydrolase perhydrolysis to wild-type perhydrolase perhydrolysis is about 0.5 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, V87, A23, A55, D10, D23, E26, E50, E51, F150, G110, G126, G15, G36, I107, I49, I5, K97, L109, L119, L12 L38, L6, L68, L84, L86, M111, N59, P146, P24, Q40, R101, R102, R27, R33, R4, R56, S112, S72, S76, T127, T25, T35, T80, T96, V115, V32, V87, W34, and Y129.

In further embodiments, the variant perhydrolase exhibits a change in perhydrolysis, such that the ratio of variant perhydrolase perhydrolysis to wild-type perhydrolase perhydrolysis is about 0.6 or less. In some embodiments, the variant perhydrolase comprises at least one modification comprising t least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, V87, A23, A55, D10, D23, E26, E50, E51, F150, G110, G126, G15, G36, I107, I49, I5, K97, L109, L119, L12 L38, L6, L68, L84, L86, M111, N59, P146, P24, Q40, R101, R102, R27, R33, R4, R56, S112, S72, S76, T127, T25, T35, T80, T96, V115, V32, V87, W34, Y129, A108, A44, A55, D21, D62, F150, g126, G36, G52, I107, I5, I89, L109, L114, L119, L12, L42, L53, L6, L68, L78, L84, P146, P24, P66, P83, R27, S112, S72, S76, T120, T127, T13, T35, T57, T58, T80, T96, V115, V118, V32, V48, V87, W149, and Y73.

In yet further embodiments, the variant perhydrolase exhibits a change in perhydrolysis, such that the ratio of variant perhydrolase perhydrolysis to wild-type perhydrolase perhydrolysis is about 0.7 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, V87, A23, A55, D10, D23, E26, E50, E51, F150, G110, G126, G15, G36, I107, I49, I5, K97, L109, L119, L12 L38, L6, L68, L84, L86, M111, N59, P146, P24, Q40, R101, R102, R27, R33, R4, R56, S112, S72, S76, T127, T25, T35, T80, T96, V115, V32, V87, W34, Y129, A108, A44, A55, D21, D62, F150, g126, G36, G52, I107, I5, I89, L109, L114, L119, L12, L42, L53, L6, L68, L78, L84, P146, P24, P66, P83, R27, S112, S72, S76, T120, T127, T13, T35, T57, T58, T80, T96, V115, V118, V32, V48, V87, W149, Y73, A122, A23, A29, A71, A79, C7, D61, D62, D85, E26, E51, F100, F28, F46, G110, G126, G52, G70, I107, I49, I5, I60, I89, L109, L114, L12, L38, L68, L82, L86, M111, N59, N94, P83, R102, R33, R4, S112, S72, S76, T103, T116, T128, T25, T35, T57, T58, T64, V19, V32, V48, V87, Y129, Y73, and Y99.

In additional embodiments, the variant perhydrolase exhibits a change in perhydrolysis, such that the ratio of variant perhydrolase perhydrolysis to wild-type perhydrolase perhydrolysis is about 0.8 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, V87, A23, A55, D10, D23, E26, E50, E51, F150, G110, G126, G15, G36, I107, I49, I5, K97, L109, L119, L12, L38, L6, L68, L84, L86, M111, N59, P146, P24, Q40, R101, R102, R27, R33, R4, R56, S112, S72, S76, T127, T25, T35, T80, T96, V115, V32, V87, W34, Y129, A108, A44, A55, D21, D62, F150, g126, G36, G52, I107, I5, I89, L109, L114, L119, L12, L42, L53, L6, L68, L78, L84, P146, P24, P66, P83, R27, S112, S72, S76, T120, T127, T13, T35, T57, T58, T80, T96, V115, V118, V32, V48, V87, W149, Y73, A122, A23, A29, A71, A79, C7, D61, D62, D85, E26, E51, F100, F28, F46, G110, G126, G52, G70, I107, I49, I5, I60, I89, L109, L114, L12, L38, L68, L82, L86, M111, N59, N94, P83, R102, R33, R4, S112, S72, S76, T103, T116, T128, T25, T35, T57, T58, T64, V19, V32, V48, V87, Y129, Y73, Y99, A108, A122, A29, A55, C77, D10, D106, D45, D61, D62, D65, D85, E47, E50, F100, F150, F28, F46, G110, G124, G126, G15, G36, I153, I194, I5, I60, I89, K3, K97, L105, L109, L114, L119, L38, L42, L68, L84, L86, M1, N59, P24, P30, P83, R101, R27, R4, R56, S112, S54, S76, T103, T116, T120, T127, T128, T13, T35, T64, V113, V17, V19, V32, V48, V87, Y129, Y73, and Y99.

The present invention also provides perhydrolase variants, wherein the perhydrolase variants exhibit greater perhydrolysis activity and decreased peracid hydrolysis activity as compared to wild-type perhydrolase. In some embodiments, the variant perhydrolases exhibit perhydrolysis activity ratio of at least about 1.2, and peracid hydrolysis activity ratio of about 0.8 or less, as compared to wild-type perhydrolase. In alternative embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A29, A44, A55, A71, A79, C7, D10, D106, D31, D85, E26, E47, F150, F154, F196, F28, G124, G126, G36, G43, I153, L109, L42, L53, L109, L42, L53, L109, L42, L53, L68, L82, L86, M111, N69, P104, P148, P18, P63, P66, P83, Q117, Q40, R101, R67, S54, S121, S72, S76, T25, T64, V115, and V19.

In additional embodiments, the perhydrolase exhibits perhydrolysis activity ratio of at least about 1.2, a peracid hydrolysis activity ratio of about 0.8 or less, and a protein concentration ratio of at least 0.5, as compared to wild-type perhydrolase. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A29, A44, A71, A79, C7, D85, E26, E47, E51, F150, F154, F196, F28, G124, G126, G36, I153, L109, L12, L53, L68, L82, M111, N69, P104, P148, P18, P63, P66, P83, Q117, Q40, R101, R67, S121, S54, S72, S76, T25, T64, V125, and V19.

The present invention provides variant perhydrolases that exhibit an increase in expression of the perhydrolase variants, as compared to the expression of wild-type perhydrolase. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A2, I5, C7, F8, S11, L12, T13, W14, W16, V17, P18, V19, E20, G22, A23, P24, T25, A29, P30, V32, T35, G36, V37, A39, F46, E47, S54, A55, R56, T58, I60, D61, D62, P63, T64, P66, R67, L68, N69, G70, S72, Y73, L74, P75, S76, C77, L78, A79, T80, L82, P83, L84, L86, I89, T93, T96, K97, A98, Y99, F100, R101, R102, T103, P104, L105, D106, I107, A108, L109, G110, S112, V113, L114, V115, T116, Q117, V118, L119, T120, S121, A122, G124, V125, G126, T127, T128, Y129, P130, P132, K133, L135, V136, S138, P141, L142, A143, M145, H147, W149, F150, Q151, I153, G157, Q159, T161, T162, L164, A165, R166, V167, Y168, A170, L171, A172, M175, K176, P178, A182, G183, S184, V185, I186, T188, I194, F196, V191, N201, L208, A209, Q211, Q213, S214, L215, and L216.

The present invention also provides isolated proteins comprising homologs of *M. smegmatis* perhydrolase, wherein the homologs are proteins within the SGNH-hydrolase family of proteins. In alternative preferred embodiments, the isolated proteins have at least about 35% identity with the amino acid sequence of *M. smegmatis* perhydrolase, in which the protein comprises at least three residues selected from the group consisting of L6, W14, W34, L38, R56, D62, L74, L78, H81, P83, M90, K97, G110, L114, L135, F180, G205, S11, D192, and H195. In further embodiments, the perhydrolase is at least approximately about 40%, 45%, 50%, 55%, 60%, 65%, 70%, 75%, 80%, 85%, 90%, 95%, or 99% homologous to *M. smegmatis* perhydrolase. In additional preferred embodiments, the perhydrolase comprises the amino acid sequence set forth in SEQ ID NO:2.

The present invention also provides isolated proteins having at least about 38% identity with the amino acid sequence of *M. smegmatis* perhydrolase, wherein the protein exhibits perhydrolysis activity. In further embodiments, the perhydrolase is at least approximately about 40%, 45%, 50%, 55%, 60%, 65%, 70%, 75%, 80%, 85%, 90%, 95%, or 99% homologous to *M. smegmatis* perhydrolase. In additional preferred embodiments, the perhydrolase comprises the amino acid sequence set forth in SEQ ID NO:2.

The present invention also provides homologs of *M. smegmatis* perhydrolase, wherein the homologs are perhydrolases comprising at least one motif selected from the group consisting of GDSL-GRTT, GDSL-ARTT, GDSN-GRTT, GDSN-ARTT, and SDSL-GRTT. In preferred embodiments, the homologs exhibit perhydrolysis. In some particularly preferred embodiments, the homologs exhibit a perhydrolysis to hydrolysis ratio that is great than about 1. In still further embodiments, the homologs are immunologically cross-reactive with antibodies raised against *M. smegmatis* perhydrolase. In yet additional embodiments, antibodies raised against the homolog cross-react with *M. smegmatis* perhydrolase.

The present invention also provides isolated proteins having at least about 35% identity with the amino acid sequence of at least one *M. smegmatis* perhydrolase homolog, wherein the proteins exhibit perhydrolysis activity.

In some particularly preferred embodiments, the present invention provides proteins having perhydrolase activity, wherein the proteins are in the form of a multimer in solution. In some more preferred embodiments, the protein is a perhydrolase that comprises a dimer. In alternative particularly preferred embodiments, the protein is a perhydrolase that comprises an octamer. In still further embodiments, the protein is in the form of a multimer in solution and the protein is selected from the group consisting of *M. smegmatis perhydrolase, M. smegmatis* perhydrolase homologs, and *M. smegmatis* perhydrolase variants. In yet further embodiments, the protein is selected from the group consisting of modified serine hydrolases and modified cysteine hydrolases, wherein the modified serine hydrolases or modified cysteine hydrolases comprise increased perhydrolase activity as compared to unmodified serine hydrolases or unmodified cysteine hydrolases The present invention also provides proteins having perhydrolase activity, wherein the protein comprises at least one motif selected from the group consisting of GDSL-GRTT, GDSL-ARTT, GDSN-GRTT, GDSN-ARTT, and SDSL-GRTT. In some embodiments, the protein is obtained from a member of the *Rhizobiales*. In some preferred embodiments, the protein is obtained from a member of the genus *Mycobacterium.*

The present invention also provides isolated genes identified using at least one primer selected from the group consisting of SEQ ID NOS:21-69.

The present invention also provides methods for identifying a perhydrolase, comprising the steps of: identifying source of the perhydrolase; analyzing the source to identify sequences comprising at least one motif selected from the group consisting of GDSL-GRTT, GDSL-ARTT, GDSN-GRTT, GDSN-ARTT, and SDSL-GRTT; expressing the sequences identified in step b) to produce the perhydrolase; and testing the perhydrolase for perhydrolysis activity.

In some embodiments, the analyzing step is an amplification step wherein the primer sequences set forth in SEQ ID NOS: 21-69 are used to amplifying the sequences comprising at least one motif selected from the group consisting of GDSL-GRTT, GDSL-ARTT, GDSN-GRTT, GDSN-ARTT, and SDSL-GRTT. In still further embodiments, the source is selected from the group consisting of environmental sources and metagenomic sources. The present invention also provides proteins identified using the methods set forth herein. The present invention further provides isolated nucleic acid sequences encoding the proteins identified using the methods set forth herein. In some particularly preferred embodiments, the proteins exhibit a perhydrolysis to hydrolysis ratio that is greater than about 1. In still further embodiments, the proteins exhibit a perhydrolysis activity that is at least about 0.2, compared to the perhydrolysis activity exhibited by *M. smegmatis* perhydrolase. In yet additional embodiments, the proteins comprise at least three residues selected from the group consisting of L6, W14, W34, L38, R56, D62, L74, L78, H81, P83, M90, K97, G110, L114, L135, F180, G205, S11, D192, and H195.

In further embodiments, the analyzing step comprises searching at least one amino acid database. In yet further embodiments, the analyzing step comprises searching at least one nucleic acid database to identify nucleic acid sequences encoding the amino acid sequences of the perhydrolase. In still further embodiments, the source is selected from the group consisting of environmental sources and metagenomic sources. The present invention further provides isolated nucleic acid sequences encoding the proteins identified using the methods set forth herein. In some particularly preferred embodiments, the proteins exhibit a perhydrolysis to hydrolysis ratio that is greater than about 1. In still further embodiments, the proteins exhibit a perhydrolysis activity that is at least about 0.2, compared to the perhydrolysis activity exhibited by *M. smegmatis* perhydrolase. In yet additional embodiments, the proteins comprise at least three residues selected from the group consisting of L6, W14, W34, L38, R56, D62, L74, L78, H81, P83, M90, K97, G110, L114, L135, F180, G205, S11, D192, and H195, as set forth in SEQ ID NO:2.

The present invention also provides variant perhydrolases having altered substrate specificities as compared to wild-type *M. smegmatis* perhydrolase. In some embodiments, the variant perhydrolases have altered para nitrophenyl caproate (PNC) activity, as compared to wild-type *M. smegmatis* perhydrolase.

The present invention also provides variant perhydrolases having altered pI values as compared to wild-type *M. smegmatis* perhydrolase. In some embodiments, the variant perhydrolases comprise at least one positively charged mutation, while in alternative embodiments, the variant perhydrolases comprise at least one negatively charged mutation.

The present invention also provides variant perhydrolases that have increased stability, as compared to wild-type *M. smegmatis* perhydrolase. In some preferred embodiments, the stability of the variant perhydrolase is selected from the group consisting of thermostability, enzymatic stability, and chemical stability.

The present invention also provides variant perhydrolases, wherein the variant perhydrolase exhibits at least one altered surface property. In some preferred embodiments, the variants comprise at least one mutation comprising at least one substitution at sites selected from the group consisting of the residues set forth in Table 15-1.

The present invention also provides perhydrolase variants having at least one improved property as compared to wild-type perhydrolase.

The present invention also provides expression vectors comprising a polynucleotide sequence encoding at least one perhydrolase variant. The present invention further provides host cells comprising at least one such expression vector. In some preferred embodiments, a host cell is selected from the group consisting of *Bacillus* sp., *Streptomyces* sp., *Escherichia*, and *Pantoea* sp. The present invention also provides perhydrolases produced by the host cells.

The present invention also provides compositions comprising at least a portion of at least one perhydrolase. In some preferred embodiments, the perhydrolase comprises the amino acid sequence set forth in SEQ ID NO:2. In further embodiments, the perhydrolase is encoded by a polynucleotide sequence comprises SEQ ID NO:1. In additional embodiments, the sequence comprises at least a portion of SEQ ID NO:1. In further embodiments, the present invention provides expression vectors comprising the polynucleotide sequence encoding at least a portion of at least one perhydrolase. The present invention also provides host comprising at least one expression vectors. In some embodiments, the host cells are selected from the group consisting of *Bacillus* sp., *Streptomyces* sp., *Escherichia*, and *Pantoea* sp. The present invention also provides perhydrolases produced by these host cells.

The present invention also provides variant perhydrolases, wherein the perhydrolases comprise at least one substitution corresponding to the amino acid positions in SEQ ID NO:2, and wherein the variant perhydrolase has better performance in at least one property, compared to wild-type *M. smegmatis* perhydrolase.

The present invention further provides isolated polynucleotides comprising a nucleotide sequence (i) having at least about 70% identity to SEQ ID NO:1, or (ii) being capable of hybridizing to a probe derived from the nucleotide sequence set forth in SEQ ID NO:1, under conditions of intermediate to high stringency, or (iii) being complementary to the nucleotide sequence set forth in SEQ ID NO:1. In some embodiments, the present invention also provides vectors comprising these polynucleotide sequences. In additional embodiments, the present invention also provides host comprising at least one expression vectors. In some embodiments, the host cells are selected from the group consisting of *Bacillus* sp., *Streptomyces* sp., *Escherichia*, and *Pantoea* sp. The present invention also provides perhydrolases produced by these host cells.

The present invention also provides polynucleotides comprising a sequence complementary to at least a portion of the sequence set forth in SEQ ID NO:1.

The present invention also provides methods of producing enzymes having perhydrolase activity, comprising: transforming a host cell with an expression vector comprising a polynucleotide having at least 70% sequence identity to SEQ ID NO:1; cultivating the transformed host cell under conditions suitable for the host cell to produce the perhydrolase; and recovering the perhydrolase. In some preferred embodiments, the host cell is selected from the group consisting of *Streptomyces, Pantoea, Escherichia*, and *Bacillus* species.

The present invention also provides probes comprising a 4 to 150 polynucleotide sequence substantially identical to a corresponding fragment of SEQ ID NO:1, wherein the probe is used to detect a nucleic acid sequence coding for an enzyme having perhydrolase activity.

The present invention also provides cleaning compositions comprising: a) at least 0.0001 weight percent of a perhydrolase that exhibits a perhydrolysis to hydrolysis ratio that is greater than 1; b) a molecule comprising an ester moiety; and c) optionally, an adjunct ingredient.

The present invention further provides cleaning compositions comprising: a) at least 0.0001 weight percent of a perhydrolase that exhibits a perhydrolysis to hydrolysis ratio that is greater than 1; b) a material selected from the group consisting of a peroxygen source, hydrogen peroxide and mixtures thereof, the peroxygen source being selected from the group consisting of: a per-salt; an organic peroxyacid; urea hydrogen peroxide; a carbohydrate and carbohydrate oxidase mixture, and mixtures thereof; c) from about 0.01 to about 50 weight percent of a molecule comprising an ester moiety; and d) optionally, an adjunct ingredient.

The present invention also provides cleaning compositions comprising: a) from about 0.0001 to about 1 weight percent of a variant perhydrolase having an amino acid sequence comprising at least one modification of an amino acid made at a position equivalent to a position in *M. smegmatis* perhydrolase comprising the amino acid sequence set forth in SEQ ID NO:2; b) a material selected from the group consisting of a peroxygen source, hydrogen peroxide and mixtures thereof, the peroxygen source being selected from the group consisting of: a per-salt; an organic peroxyacid; urea hydrogen peroxide; a carbohydrate and carbohydrate oxidase mixture; and mixtures thereof; c) from about 0.01 to about 50 weight percent of a molecule comprising an ester moiety; and d) optionally, an adjunct ingredient. In some preferred embodiments, the cleaning compositions further comprise at least one adjunct ingredient. In some particularly preferred embodiments, the adjunct ingredient is selected from the group consisting of surfactants, builders, chelating agents, dye transfer inhibiting agents, deposition aids, dispersants, enzymes, and enzyme stabilizers, catalytic materials, bleach activators, bleach boosters, preformed peracids, polymeric dispersing agents, clay soil removalanti-redeposition agents, brighteners, suds suppressors, dyes, perfumes, structure elasticizing agents, fabric softeners, carriers, hydrotropes, processing aids, pigments and mixtures thereof.

In additional embodiments, the present invention provides cleaning compositions wherein: the perhydrolase exhibits a perhydrolysis to hydrolysis molar ratio that is greater than about 0.1; the per-salt is selected from the group consisting of alkalimetal perborate, alkalimetal percarbonate, alkalimetal perphosphates, alkalimetal persulphates and mixtures thereof; the carbohydrate is selected from the group consisting of mono-carbohydrates, di-carbohydrates, tri-carbohydrates, oligo-carbohydrates and mixtures thereof; the carbohydrate oxidase is selected from the group consisting of aldose oxidase (IUPAC classification EC1.1.3.9), galactose oxidase (IUPAC classification EC1.1.3.9), cellobiose oxidase (IUPAC classification EC1.1.3.25), pyranose oxidase (IUPAC classification EC1.1.3.10), sorbose oxidase (IUPAC classification EC1.1.3.11) hexose oxidase (IUPAC classification EC1.1.3.5). glucose oxidase (IUPAC classification EC1.1.3.4) and mixtures thereof; and the molecule comprising an ester moiety has the formula:

$$R^1O_x[(R^2)_m(R^3)_n]_p$$

(i) wherein $R^1$ is a moiety selected from the group consisting of H, substituted or unsubstituted alkyl, heteroalkyl, alkenyl, alkynyl, aryl, alkylaryl, alkylheteroaryl, and heteroaryl;

(ii) each $R^2$ is an alkoxylate moiety;

(iii) $R^3$ is an ester-forming moiety having the formula:

$R^4CO$— wherein $R^4$ is H, alkyl, alkenyl, alkynyl, aryl, alkylaryl, alkylheteroaryl, and heteroaryl;

(iv) x is 1 when $R^1$ is H; when $R^1$ is not H, x is an integer that is equal to or less than the number of carbons in $R^1$;

(v) p is an integer that is equal to or less than x;

(vi) m is an integer from 0 to 50; and (vii) n is at least 1

In alternative embodiments, the present invention provides cleaning compositions wherein: a) $R^1$ is an $C_2$-$C_{32}$ substituted or unsubstituted alkyl or heteroalkyl moiety; b) each $R^2$ is independently an ethoxylate or propoxylate moiety; and c) m is an integer from 1 to 12. In some embodiments, $R^3$ is an ester-forming moiety having the formula: $R^4CO$— wherein $R^4$ is: a) a substituted or unsubstituted alkyl, alkenyl or alkynyl moiety comprising from 1 to 22 carbon atoms; or b) a substituted or unsubstituted aryl, alkylaryl, alkylheteroaryl or heteroaryl moiety comprising from 4 to 22 carbon atoms.

In still further embodiments of the cleaning compositions, the molecule comprising the ester moiety has the formula:

$$R^1O_x[(R^2)_m(R^3)_n]_p$$

wherein: a) $R^1$ is H or a moiety that comprises a primary, secondary, tertiary or quaternary amine moiety, the $R^1$ moiety that comprises an amine moiety being selected from the group consisting of substituted or unsubstituted alkyl, heteroalkyl, alkenyl, alkynyl, aryl, alkylaryl, alkylheteroaryl, and heteroaryl; b) each $R^2$ is an alkoxylate moiety; c) $R^3$ is an ester-forming moiety having the formula: $R^4CO$— wherein $R^4$ may be H, substituted or unsubstituted alkyl, alkenyl, alkynyl, aryl, alkylaryl, alkylheteroaryl, and heteroaryl; d) x is 1 when $R^1$ is H; when $R^1$ is not H, x is an integer that is equal to or less than the number of carbons in $R^1$; e) p is an integer that is equal to or less than x; f) m is an integer from 0 to 12; and g) n is at least 1.

In still further embodiments of the present cleaning compositions, the molecule comprising an ester moiety has a weight average molecular weight of less than 600,000 Daltons. In yet additional embodiments, an adjunct ingredient is selected from the group consisting of surfactants, builders, chelating agents, dye transfer inhibiting agents, deposition aids, dispersants, enzymes, and enzyme stabilizers, catalytic materials, bleach activators, bleach boosters, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, pigments and mixtures thereof.

The present invention further provides methods of cleaning comprising the steps of: a) contacting a surface and/or an article comprising a fabric with any of the cleaning compositions provided above and/or a composition comprising any of the cleaning compositions provided above; and b) optionally washing and/or rinsing the surface or material.

In alternative embodiments, the present invention provides methods of cleaning, the method comprising the steps of: a) contacting a surface and/or an article comprising a fabric with any suitable cleaning composition provided above and/or a composition comprising any suitable cleaning provided above; and b) optionally washing and/or rinsing the surface or material.

The present invention also provides bleaching compositions comprising at least one perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides bleaching compositions comprising at least one perhydrolase variant having an amino acid sequence comprising at least one modification of an amino acid made at a position equivalent to a position in *M. smegmatis* perhydrolase comprising the amino acid sequence set forth in SEQ ID NO:2. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides bleaching compositions comprising at least one perhydrolase variant having at least one improved property as compared to wild-type perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides bleaching compositions comprising at least one perhydrolase variant comprising at least one substitution corresponding to the amino acid positions in SEQ ID NO:2, and wherein the variant perhydrolase has better performance in at least one property compared to wild-type *M. smegmatis* perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides bleaching compositions comprising at least one perhydrolase that is at least approximately about 35% homologous to *M. smegmatis* perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides disinfecting compositions comprising at least one perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides disinfecting compositions comprising at least one perhydrolase variant having an amino acid sequence comprising at least one modification of an amino acid made at a position equivalent to a position in *M. smegmatis* perhydrolase comprising the amino acid sequence set forth in SEQ ID NO:2. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides disinfecting compositions comprising at least one perhydrolase variant having at least one improved property as compared to wild-type perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides disinfecting compositions comprising at least one perhydrolase variant comprising at least one substitution corresponding to the amino acid positions in SEQ ID NO:2, and wherein the variant perhydrolase has better performance in at least one property compared to wild-type *M. smegmatis* perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides disinfecting compositions comprising at least one perhydrolase that is at least approximately about 35% homologous to *M. smegmatis* perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

In some preferred embodiments, the perhydrolase is at least approximately 70% homologous to *M. smegmatis* perhydrolase comprising the amino acid sequence set forth in SEQ ID NO:2. In some embodiments, the present invention provides perhydrolases that cross react with antibody generated against *M. smegmatis* perhydrolase, particularly that comprising the amino acid sequence set forth in SEQ ID NO:2. In further embodiments, the present invention provides perhydrolases that are structural homologs of the *M. smegmatis* perhydrolase, in which active site comprises sites homologous to S11, D192, and H195 of the *M. smegmatis* perhydrolase. In yet additional embodiments, the present invention provides perhydrolases comprising one or more modifications at the following residues: Cys7, Asp10, Ser11, Leu12, Thr13, Trp14, Trp16, Pro24, Thr25, Leu53, Ser54, Ala55, Thr64, Asp65, Arg67, Cys77, Thr91, Asn94, Asp95, Tyr99, Val125, Pro138, Leu140, Pro146, Pro148, Trp149, Phe150, Ile153, Phe154, Thr159, Thr186, Ile192, Ile194, and Phe196. However, it is not intended that the present invention be limited to perhydrolases with these modifications only at these residues, as perhydrolases with other modifications also find use with the present invention.

In some embodiments, at least one perhydrolase of the present invention is used in a cleaning process wherein an article to be cleaned is exposed to a sufficient amount of the at least one perhydrolase under conditions such that the perhydrolase cleans and/or bleaches, and/or decolorizes any/all stains present on the article (e.g., laundry and dish detergents). In some embodiments, the cleaning further comprises disinfecting. In some embodiments, the article cleaned, bleached and/or disinfected using at least one perhydrolase of the present invention comprises textiles and/or hard surfaces, while in other embodiments, the article is paper or pulp, and in still further embodiments, at least one perhydrolase is used as a personal care product to whiten or bleach hair, teeth, skin, etc. Thus, in some embodiments, the present invention provides compositions for use in various cleaning, bleaching, and/or disinfecting applications. Indeed, it is not intended that the present invention be limited to any particular application.

In some preferred embodiments, the perhydrolase comprises SEQ ID NO:2. In some preferred alternative embodiments, the perhydrolase is encoded by the nucleic acid sequence set forth in SEQ ID NO:1.

In some embodiments, the present invention provides enzymes with activities that result in high peracid/acid ratios. In alternative embodiments, the present invention provides the perhydrolase of *Mycobacterium smegmatis*, as well as sequence and/or structural homologs of this protein. In additional embodiments, the present invention provides enzymes that have been modified so as to express perhydrolase activity with a high perhydrolysis to hydrolase ratio either in addition to or instead of the enzyme's original activity. In additional embodiments, the present invention provides modified enzymes with altered substrate specificity, Km, kcat, perhydrolase activity, and/or peracid degradation activity.

In additional embodiments, the present invention provides means to identify, produce, and characterize enzymes that comprise the perhydrolysis activity of the present invention. The present invention further provides methods and compositions comprising at least one perhydrolase for cleaning, disinfecting, bleaching, and other applications, including but not limited to paper and pulp bleaching, fabric and garment cleaning, hard surface cleaning, and personal care applications (e.g., oral care, hair care, and skin care). In some preferred embodiments, the present invention provides methods and compositions for bleaching cotton and other fabrics. Indeed, the present invention finds use in the bleaching and cleaning of various textiles. It is not intended that the present invention be limited to any particular setting, application or use, as it is contemplated that it will find use in numerous areas where an enzymatic generation of peracids is desired over the use of preformed peracids or hydrogen peroxide or other bleaching chemicals, under conditions including but not limited to a wide range of pHs and temperatures. The present invention also finds use in applications where peracid hydrolysis is useful, such as in the clean up of peracids.

Furthermore, the present invention provides means to produce perhydrolase enzymes suitable for cleaning, disinfecting, bleaching, and other applications, including personal care.

DESCRIPTION OF THE FIGURES

FIGS. 1A and 1B provide a phylogenetic tree of *M. smegmatis* perhydrolase and other related sequences.

FIG. 6 provides a purification table showing the enzyme activity of the enzyme of the present invention through various steps in the purification process.

DESCRIPTION OF THE INVENTION

Figure 1B:
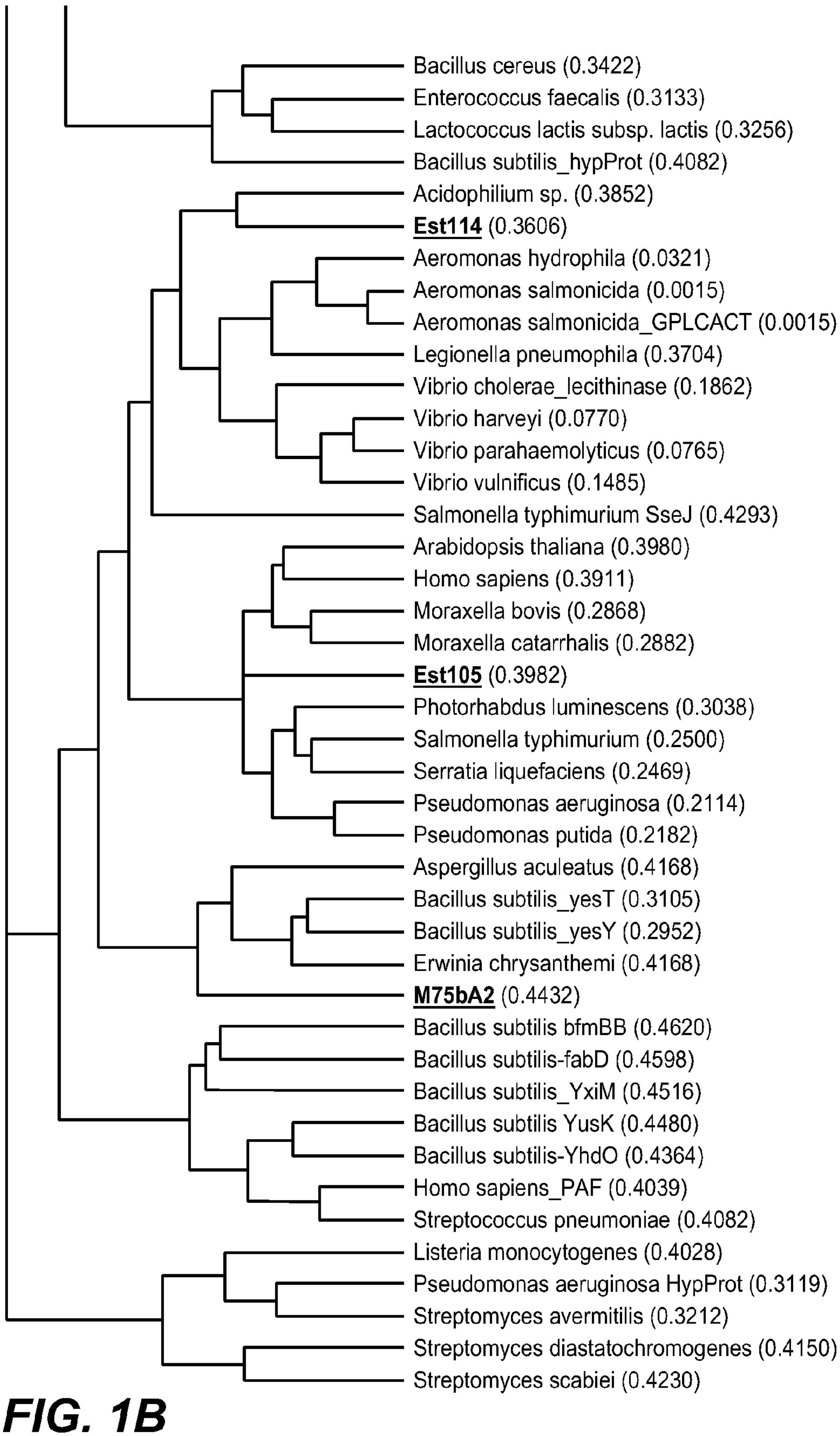

The present invention provides methods and compositions comprising at least one perhydrolase enzyme for cleaning and other applications. In some particularly preferred embodiments, the present invention provides methods and compositions for generation of peracids. In particular, the present invention provides improved methods and compositions comprising perhydrolysis enzymes with high peracid/acid ratios for cleaning, bleaching, disinfecting and other applications. In some preferred embodiments, the present invention provides improved methods and compositions for generation of peracids. The present invention finds particular use in applications involving cleaning, bleaching and disinfecting.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

DEFINITIONS

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology,* 2d Ed., John Wiley and Sons, NY (1994); and Hale and Marham, *The Harper Collins Dictionary of Biology*, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a", "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the term "bleaching" refers to the treatment of a material (e.g., fabric, laundry, pulp, etc.) or surface for a sufficient length of time and under appropriate pH and temperature conditions to effect a brightening (i.e., whitening) and/or cleaning of the material. Examples of chemicals suitable for bleaching include but are not limited to $ClO_2$, $H_2O_2$, peracids, $NO_2$, etc.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

As used herein, the term "perhydrolase" refers to an enzyme that is capable of catalyzing a reaction that results in the formation of sufficiently high amounts of peracid suitable for applications such as cleaning, bleaching, and disinfecting. In particularly preferred embodiments, the perhydrolase enzymes of the present invention produce very high perhydrolysis to hydrolysis ratios. The high perhydrolysis to hydrolysis ratios of these distinct enzymes makes these enzymes suitable for use in a very wide variety of applications. In additional preferred embodiments, the perhydrolases of the present invention are characterized by having distinct tertiary structure and primary sequence. In particularly preferred embodiments, the perhydrolases of the present invention comprises distinct primary and tertiary structures. In some particularly preferred embodiments, the perhydrolases of the present invention comprise distinct quaternary structure. In some preferred embodiments, the perhydrolase of the present invention is the *M. smegmatis* perhydrolase, while in alternative embodiments, the perhydrolase is a variant of this perhydrolase, while in still further embodiments, the perhydrolase is a homolog of this perhydrolase. In further preferred embodiments, a monomeric hydrolase is engineered to produce a multimeric enzyme that has better perhydrolase activity than the monomer. However, it is not intended that the present invention be limited to this specific *M. smegmatis* perhydrolase, specific variants of this perhydrolase, nor specific homologs of this perhydrolase.

As used herein, the term "multimer" refers to two or more proteins or peptides that are covalently or non-covalently associated and exist as a complex in solution. A "dimer" is a multimer that contains two proteins or peptides; a "trimer" contains three proteins or peptides, etc. As used herein, "octamer" refers to a multimer of eight proteins or peptides.

As used herein, the phrase "perhydrolysis to hydrolysis ratio" is the ratio of the amount of enzymatically produced peracid to that of enzymatically produced acid by the perhydrolase, under defined conditions and within a defined time. In some preferred embodiments, the assays provided herein are used to determine the amounts of peracid and acid produced by the enzyme.

As used herein, "personal care products" means products used in the cleaning, bleaching and/or disinfecting of hair, skin, scalp, and teeth, including, but not limited to shampoos, body lotions, shower gels, topical moisturizers, toothpaste, and/or other topical cleansers. In some particularly preferred embodiments, these products are utilized on humans, while in other embodiments, these products find use with non-human animals (e.g., in veterinary applications).

As used herein, "pharmaceutically-acceptable" means that drugs, medicaments and/or inert ingredients which the term describes are suitable for use in contact with the tissues of humans and other animals without undue toxicity, incompatibility, instability, irritation, allergic response, and the like, commensurate with a reasonable benefit/risk ratio.

As used herein, "cleaning compositions" and "cleaning formulations" refer to compositions that find use in the removal of undesired compounds from items to be cleaned, such as fabric, dishes, contact lenses, other solid substrates, hair (shampoos), skin (soaps and creams), teeth (mouthwashes, toothpastes) etc. The term encompasses any materials/compounds selected for the particular type of cleaning composition desired and the form of the product (e.g., liquid, gel, granule, or spray composition), as long as the composition is compatible with the perhydrolase and other enzyme(s) used in the composition. The specific selection of cleaning composition materials are readily made by considering the surface, item or fabric to be cleaned, and the desired form of the composition for the cleaning conditions during use.

The terms further refer to any composition that is suited for cleaning, bleaching, disinfecting, and/or sterilizing any object and/or surface. It is intended that the terms include, but are not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

Indeed, the term "cleaning composition" as used herein, includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pretreat types.

As used herein, the terms "detergent composition" and "detergent formulation" are used in reference to mixtures which are intended for use in a wash medium for the cleaning of soiled objects. In some preferred embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. Indeed, it is intended that in addition to perhydrolase, the term encompasses detergents that contain surfactants, transferase(s), hydrolytic enzymes, oxido reductases, builders, bleaching agents, bleach activators, bluing agents and fluorescent dyes, caking inhibitors, masking agents, enzyme activators, antioxidants, and solubilizers.

As used herein, "enhanced performance" in a detergent is defined as increasing cleaning of bleach-sensitive stains (e.g., grass, tea, wine, blood, dingy, etc.), as determined by usual evaluation after a standard wash cycle. In particular embodiments, the perhydrolase of the present invention provides enhanced performance in the oxidation and removal of colored stains and soils. In further embodiments, the perhydrolase of the present invention provides enhanced performance in the removal and/or decolorization of stains. In yet additional embodiments, the perhydrolase of the present invention provides enhanced performance in the removal of lipid-based stains and soils. In still further embodiments, the perhydrolase of the present invention provides enhanced performance in removing soils and stains from dishes and other items.

As used herein the term "hard surface cleaning composition," refers to detergent compositions for cleaning hard surfaces such as floors, walls, tile, bath and kitchen fixtures, and the like. Such compositions are provided in any form, including but not limited to solids, liquids, emulsions, etc.

As used herein, "dishwashing composition" refers to all forms for compositions for cleaning dishes, including but not limited to granular and liquid forms.

As used herein, "fabric cleaning composition" refers to all forms of detergent compositions for cleaning fabrics, including but not limited to, granular, liquid and bar forms.

As used herein, "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers.

As used herein, "textile materials" is a general term for fibers, yarn intermediates, yarn, fabrics, and products made from fabrics (e.g., garments and other articles).

As used herein, "fabric" encompasses any textile material. Thus, it is intended that the term encompass garments, as well as fabrics, yarns, fibers, non-woven materials, natural materials, synthetic materials, and any other textile material.

As used herein, the term "compatible," means that the cleaning composition materials do not reduce the enzymatic activity of the perhydrolase to such an extent that the perhydrolase is not effective as desired during normal use situations. Specific cleaning composition materials are exemplified in detail hereinafter.

As used herein, "effective amount of perhydrolase enzyme" refers to the quantity of perhydrolase enzyme necessary to achieve the enzymatic activity required in the specific application (e.g., personal care product, cleaning composition, etc.). Such effective amounts are readily ascertained by one of ordinary skill in the art and are based on many factors, such as the particular enzyme variant used, the cleaning application, the specific composition of the cleaning composition, and whether a liquid or dry (e.g., granular, bar) composition is required, and the like.

As used herein, "non-fabric cleaning compositions" encompass hard surface cleaning compositions, dishwashing compositions, personal care cleaning compositions (e.g., oral cleaning compositions, denture cleaning compositions, personal cleansing compositions, etc.), and compositions suitable for use in the pulp and paper industry.

As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Oral care compositions that find use in conjunction with the perhydrolases of the present invention are well known in the art (See e.g., U.S. Pat. Nos. 5,601,750, 6,379,653, and 5,989,526, all of which are incorporated herein by reference).

As used herein, "pulp treatment compositions" refers to the use of the present perhydrolase enzymes in compositions suitable for use in papermaking. It is intended that the term encompass compositions suitable for the treatment of any pulp material, including wood, as well as non-wood materials, such as "agricultural residues" and "fiber crops," including but not limited to wheat straw, rice straw, corn stalks, bagasse (sugar cane), rye grass straw, seed flax straw, flax straw, kenaf, industrial hemp, sisal, textile flat straw, hesperaloe, etc. Thus, the present invention also encompasses the use of the perhydrolases of the present invention in pulp treatment methods.

As used herein, "oxidizing chemical" refers to a chemical that has the capability of bleaching pulp or any other material. The oxidizing chemical is present at an amount, pH and temperature suitable for bleaching. The term includes, but is not limited to hydrogen peroxide and peracids.

As used herein, "acyl" is the general name for organic acid groups, which are the residues of carboxylic acids after removal of the —OH group (e.g., ethanoyl chloride, $CH_3CO—Cl$, is the acyl chloride formed from ethanoic acid, $CH_3COO—H$). The names of the individual acyl groups are formed by replacing the "-ic" of the acid by "-yl."

As used herein, the term "acylation" refers to the chemical transformation which substitutes the acyl (RCO—) group into a molecule, generally for an active hydrogen of an —OH group.

As used herein, the term "transferase" refers to an enzyme that catalyzes the transfer of functional compounds to a range of substrates.

As used herein, "leaving group" refers to the nucleophile which is cleaved from the acyl donor upon substitution by another nucleophile.

As used herein, the term "enzymatic conversion" refers to the modification of a substrate to an intermediate or the modification of an intermediate to an end-product by contacting the substrate or intermediate with an enzyme. In some embodiments, contact is made by directly exposing the substrate or intermediate to the appropriate enzyme. In other embodiments, contacting comprises exposing the substrate or intermediate to an organism that expresses and/or excretes the enzyme, and/or metabolizes the desired substrate and/or intermediate to the desired intermediate and/or end-product, respectively.

As used herein, the phrase "detergent stability" refers to the stability of a detergent composition. In some embodiments, the stability is assessed during the use of the detergent, while in other embodiments, the term refers to the stability of a detergent composition during storage.

As used herein, the phrase, "stability to proteolysis" refers to the ability of a protein (e.g., an enzyme) to withstand proteolysis. It is not intended that the term be limited to the use of any particular protease to assess the stability of a protein.

As used herein, "oxidative stability" refers to the ability of a protein to function under oxidative conditions. In particular, the term refers to the ability of a protein to function in the presence of various concentrations of $H_2O_2$ and/or peracid. Stability under various oxidative conditions can be measured either by standard procedures known to those in the art and/or by the methods described herein. A substantial change in oxidative stability is evidenced by at least about a 5% or greater increase or decrease (in most embodiments, it is preferably an increase) in the half-life of the enzymatic activity, as compared to the enzymatic activity present in the absence of oxidative compounds.

As used herein, "pH stability" refers to the ability of a protein to function at a particular pH. In general, most enzymes have a finite pH range at which they will function. In addition to enzymes that function in mid-range pHs (i.e., around pH 7), there are enzymes that are capable of working under conditions with very high or very low pHs. Stability at various pHs can be measured either by standard procedures known to those in the art and/or by the methods described herein. A substantial change in pH stability is evidenced by at least about 5% or greater increase or decrease (in most embodiments, it is preferably an increase) in the half-life of the enzymatic activity, as compared to the enzymatic activity at the enzyme's optimum pH. However, it is not intended that the present invention be limited to any pH stability level nor pH range.

As used herein, "thermal stability" refers to the ability of a protein to function at a particular temperature. In general, most enzymes have a finite range of temperatures at which they will function. In addition to enzymes that work in mid-range temperatures (e.g., room temperature), there are enzymes that are capable of working in very high or very low temperatures. Thermal stability can be measured either by known procedures or by the methods described herein. A substantial change in thermal stability is evidenced by at least about 5% or greater increase or decrease (in most embodiments, it is preferably an increase) in the half-life of the catalytic activity of a mutant when exposed to a different temperature (i.e., higher or lower) than optimum temperature for enzymatic activity. However, it is not intended that the present invention be limited to any temperature stability level nor temperature range.

As used herein, the term "chemical stability" refers to the stability of a protein (e.g., an enzyme) towards chemicals that adversely affect its activity. In some embodiments, such chemicals include, but are not limited to hydrogen peroxide, peracids, anionic detergents, cationic detergents, non-ionic detergents, chelants, etc. However, it is not intended that the present invention be limited to any particular chemical stability level nor range of chemical stability.

As used herein, the phrase "perhydrolase activity improvement" refers to the relative improvement of perhydrolase activity, in comparison with a standard enzyme. In some embodiments, the term refers to an improved rate of perhydrolysis product, while in other embodiments, the term encompasses perhydrolase compositions that produce less hydrolysis product. In additional embodiments, the term refers to perhydrolase compositions with altered substrate specificity.

As used herein, the phrase "alteration in substrate specificity" refers to changes in the substrate specificity of an enzyme. In some embodiments, a change in substrate specificity is defined as a difference between the $K_{cat}/K_m$ ratio observed with an enzyme compared to enzyme variants or other enzyme compositions. Enzyme substrate specificities vary, depending upon the substrate tested. The substrate specificity of an enzyme is determined by comparing the catalytic efficiencies it exhibits with different substrates. These determinations find particular use in assessing the efficiency of mutant enzymes, as it is generally desired to produce variant enzymes that exhibit greater ratios for particular substrates of interest. For example, the perhydrolase enzymes of the present invention are more efficient in producing peracid from an ester substrate than enzymes currently being used in cleaning, bleaching and disinfecting applications. Another example of the present invention is a perhydrolase with a lower activity on peracid degradation compared to the wild type. Another example of the present invention is a perhydrolase with higher activity on more hydrophobic acyl groups than acetic acid. However, it is not intended that the present invention be limited to any particular substrate composition nor any specific substrate specificity.

As used herein, "surface property" is used in reference to an electrostatic charge, as well as properties such as the hydrophobicity and/or hydrophilicity exhibited by the surface of a protein.

As used herein, the phrase "is independently selected from the group consisting of . . . " means that moieties or elements that are selected from the referenced Markush group can be the same, can be different or any mixture of elements as indicated in the following example:

A molecule having 3 R groups wherein each R group is independently selected from the group consisting of A, B and C. Here the three R groups may be: AAA, BBB, CCC, AAB, AAC, BBA, BBC, CCA, CCB, or ABC.

In reference to chemical compositions, the term "substituted" as used herein, means that the organic composition or radical to which the term is applied is:

(a) made unsaturated by the elimination of at least one element or radical; or (b) at least one hydrogen in the compound or radical is replaced with a moiety containing one or more (i) carbon, (ii) oxygen, (iii) sulfur, (iv) nitrogen or (v) halogen atoms; or (c) both (a) and (b).

Moieties which may replace hydrogen as described in (b) immediately above, that contain only carbon and hydrogen atoms, are hydrocarbon moieties including, but not limited to, alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Moieties containing oxygen atoms that may replace hydrogen as described in (b) immediately above include, but are not limited to, hydroxy, acyl or keto, ether, epoxy, carboxy, and ester containing groups. Moieties containing sulfur atoms that may replace hydrogen as described in (b) immediately above include, but are not limited to, the sulfur-containing acids and acid ester groups, thioether groups, mercapto groups and thioketo groups. Moieties containing nitrogen atoms that may replace hydrogen as described in (b) immediately above include, but are not limited to, amino groups, the nitro group, azo groups, ammonium groups, amide groups, azido groups, isocyanate groups, cyano groups and nitrile groups. Moieties containing halogen atoms that may replace hydrogen as described in (b) immediately above include chloro, bromo, fluoro, iodo groups and any of the moieties previously described where a hydrogen or a pendant alkyl group is substituted by a halo group to form a stable substituted moiety.

It is understood that any of the above moieties (b)(i) through (b)(v) can be substituted into each other in either a monovalent substitution or by loss of hydrogen in a polyvalent substitution to form another monovalent moiety that can replace hydrogen in the organic compound or radical.

As used herein, the terms "purified" and "isolated" refer to the removal of contaminants from a sample. For example, perhydrolases are purified by removal of contaminating proteins and other compounds within a solution or preparation that are not perhydrolases. In some embodiments, recombinant perhydrolases are expressed in bacterial or fungal host cells and these recombinant perhydrolases are purified by the removal of other host cell constituents; the percent of recombinant perhydrolase polypeptides is thereby increased in the sample.

As used herein, "protein of interest," refers to a protein (e.g., an enzyme or "enzyme of interest") which is being analyzed, identified and/or modified. Naturally-occurring, as well as recombinant proteins find use in the present invention.

As used herein, "protein" refers to any composition comprised of amino acids and recognized as a protein by those of skill in the art. The terms "protein," "peptide" and polypeptide are used interchangeably herein. Wherein a peptide is a portion of a protein, those skilled in the art understand the use of the term in context.

As used herein, functionally and/or structurally similar proteins are considered to be "related proteins." In some embodiments, these proteins are derived from a different genus and/or species, including differences between classes of organisms (e.g., a bacterial protein and a fungal protein). In some embodiments, these proteins are derived from a different genus and/or species, including differences between classes of organisms (e.g., a bacterial enzyme and a fungal enzyme). In additional embodiments, related proteins are provided from the same species. Indeed, it is not intended that the present invention be limited to related proteins from any particular source(s). In addition, the term "related proteins" encompasses tertiary structural homologs and primary sequence homologs (e.g., the perhydrolase of the present invention). In further embodiments, the term encompasses proteins that are immunologically cross-reactive. In most particularly preferred embodiments, the related proteins of the present invention very high ratios of perhydrolysis to hydrolysis.

As used herein, the term "derivative" refers to a protein which is derived from a protein by addition of one or more amino acids to either or both the C- and N-terminal end(s), substitution of one or more amino acids at one or a number of different sites in the amino acid sequence, and/or deletion of one or more amino acids at either or both ends of the protein or at one or more sites in the amino acid sequence, and/or insertion of one or more amino acids at one or more sites in the amino acid sequence. The preparation of a protein derivative is preferably achieved by modifying a DNA sequence which encodes for the native protein, transformation of that DNA sequence into a suitable host, and expression of the modified DNA sequence to form the derivative protein.

Related (and derivative) proteins comprise "variant proteins." In some preferred embodiments, variant proteins differ from a parent protein and one another by a small number of amino acid residues. The number of differing amino acid residues may be one or more, preferably 1, 2, 3, 4, 5, 10, 15, 20, 30, 40, 50, or more amino acid residues. In some preferred embodiments, the number of different amino acids between variants is between 1 and 10. In some particularly preferred embodiments, related proteins and particularly variant proteins comprise at least 35%, 40%, 45%, 50%, 55%, 60%, 65%, 70%, 75%, 80%, 85%, 90%, 95%, 97%, 98%, or 99% amino acid sequence identity. Additionally, a related protein or a variant protein as used herein, refers to a protein that differs from another related protein or a parent protein in the number of prominent regions. For example, in some embodiments, variant proteins have 1, 2, 3, 4, 5, or 10 corresponding prominent regions that differ from the parent protein.

Several methods are known in the art that are suitable for generating variants of the perhydrolase enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

In particularly preferred embodiments, homologous proteins are engineered to produce enzymes with the desired activity(ies). In some particularly preferred embodiments, the engineered proteins are included within the SGNH-hydrolase family of proteins. In some most preferred embodiments, the engineered proteins comprise at least one or a combination of the following conserved residues: L6, W14, W34, L38, R56, D62, L74, L78, H81, P83, M90, K97, G110, L114, L135, F180, G205. In alternative embodiments, these engineered proteins comprise the GDSL-GRTT and/or ARTT motifs. In further embodiments, the enzymes are multimers, including but not limited to dimers, octamers, and tetramers. In yet additional preferred embodiments, the engineered proteins exhibit a perhydrolysis to hydrolysis ratio that is greater than 1.

An amino acid residue of a perhydrolase is equivalent to a residue of *M. smegmatis* perhydrolase if it is either homologous (i.e., having a corresponding position in either the primary and/or tertiary structure) or analogous to a specific residue or portion of that residue in *M. smegmatis* perhydrolase (i.e., having the same or similar functional capacity to combine, react, and/or chemically interact).

In some embodiments, in order to establish homology to primary structure, the amino acid sequence of a perhydrolase is directly compared to the *M. smegmatis* perhydrolase primary sequence and particularly to a set of residues known to be invariant in all perhydrolases for which sequence is known. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *M. smegmatis* perhydrolase are defined. In preferred embodiments, alignment of conserved residues conserves 100% of such residues. However, alignment of greater than 75% or as little as 50% of conserved residues are also adequate to define equivalent residues. In preferred embodiments, conservation of the catalytic serine and histidine residues are maintained. Conserved residues are used to define the corresponding equivalent amino acid residues of *M. smegmatis* perhydrolase in other perhydrolases (e.g., perhydrolases from other *Mycobacterium* species, as well as any other organisms).

In some embodiments of the present invention, the DNA sequence encoding *M. smegmatis* perhydrolase is modified. In some embodiments, the following residues are modified: Cys7, Asp10, Ser11, Leu12, Thr13, Trp14, Trp16, Pro24, Thr25, Leu53, Ser54, Ala55, Thr64, Asp65, Arg67, Cys77, Thr91, Asn94, Asp95, Tyr99, Val125, Pro138, Leu140, Pro146, Pro148, Trp149, Phe150, Ile153, Phe154, Thr159, Thr186, Ile192, Ile194, and Phe196. However, it is not intended that the present invention be limited to sequence that are modified at these positions. Indeed, it is intended that the present invention encompass various modifications and combinations of modifications.

In additional embodiments, equivalent residues are defined by determining homology at the level of tertiary structure for a perhydrolase whose tertiary structure has been determined by x-ray crystallography. In this context, "equivalent residues" are defined as those for which the atomic coordinates of two or more of the main chain atoms of a particular amino acid residue of the carbonyl hydrolase and *M. smegmatis* perhydrolase (N on N, CA on CA, C on C, and O on O) are within 0.13 nm and preferably 0.1 nm after alignment. Alignment is achieved after the best model has been oriented and positioned to give the maximum overlap of atomic coordinates of non-hydrogen protein atoms of the perhydrolase in question to the *M. smegmatis* perhydrolase. As known in the art, the best model is the crystallographic model giving the lowest R factor for experimental diffraction data at the highest resolution available. Equivalent residues which are functionally and/or structurally analogous to a specific residue of *M. smegmatis* perhydrolase are defined as those amino acids of the perhydrolases that preferentially adopt a conformation such that they either alter, modify or modulate the protein structure, to effect changes in substrate binding and/or catalysis in a manner defined and attributed to a specific residue of the *M. smegmatis* perhydrolase. Further, they are those residues of the perhydrolase (in cases where a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *M. smegmatis* perhydrolase. The coordinates of the three dimensional structure of *M. smegmatis* perhydrolase were determined and are set forth herein (See e.g., Example 14) and find use as outlined above to determine equivalent residues on the level of tertiary structure.

In some embodiments, some of the residues identified for substitution, insertion or deletion are conserved residues whereas others are not. The perhydrolase mutants of the present invention include various mutants, including those encoded by nucleic acid that comprises a signal sequence. In some embodiments of perhydrolase mutants that are encoded by such a sequence are secreted by an expression host. In some further embodiments, the nucleic acid sequence comprises a homolog having a secretion signal.

Characterization of wild-type and mutant proteins is accomplished via any means suitable and is preferably based on the assessment of properties of interest. For example, pH and/or temperature, as well as detergent and/or oxidative stability is/are determined in some embodiments of the present invention. Indeed, it is contemplated that enzymes having various degrees of stability in one or more of these characteristics (pH, temperature, proteolytic stability, detergent stability, and/or oxidative stability) will find use. In still other embodiments, perhydrolases with low peracid degradation activity are selected.

As used herein, "expression vector" refers to a DNA construct containing a DNA sequence that is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid," "expression plasmid," and "vector" are often used interchangeably as the plasmid is the most commonly used form of vector at present. However, the invention is intended to include such other forms of expression vectors that serve equivalent functions and which are, or become, known in the art.

In some preferred embodiments, the perhydrolase gene is ligated into an appropriate expression plasmid. The cloned perhydrolase gene is then used to transform or transfect a host cell in order to express the perhydrolase gene. This plasmid may replicate in hosts in the sense that it contains the well-known elements necessary for plasmid replication or the plasmid may be designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed, by the host), a transcription terminator (a polyadenylation region for eukaryotic host cells) which is exogenous or is supplied by the endogenous terminator region of the perhydrolase gene. In some embodiments, a selection gene such as an antibiotic resistance gene that enables continuous cultural maintenance of plasmid-infected host cells by growth in antimicrobial-containing media is also included.

The following cassette mutagenesis method may be used to facilitate the construction of the perhydrolase variants of the present invention, although other methods may be used.

First, as described herein, a naturally-occurring gene encoding the perhydrolase is obtained and sequenced in whole or in part. Then, the sequence is scanned for a point at which it is desired to make a mutation (deletion, insertion or substitution) of one or more amino acids in the encoded perhydrolase. The sequences flanking this point are evaluated for the presence of restriction sites for replacing a short segment of the gene with an oligonucleotide pool which when expressed will encode various mutants. Such restriction sites are preferably unique sites within the protein gene so as to facilitate the replacement of the gene segment. However, any convenient restriction site which is not overly redundant in the perhydrolase gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA and/or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, "corresponding to," refers to a residue at the enumerated position in a protein or peptide, or a residue that is analogous, homologous, or equivalent to an enumerated residue in a protein or peptide.

As used herein, "corresponding region," generally refers to an analogous position along related proteins or a parent protein.

The terms "nucleic acid molecule encoding," "nucleic acid sequence encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "analogous sequence" refers to a sequence within a protein that provides similar function, tertiary structure, and/or conserved residues as the protein of interest (i.e., typically the original protein of interest). For example, in epitope regions that contain an alpha helix or a beta sheet structure, the replacement amino acids in the analogous sequence preferably maintain the same specific structure. The term also refers to nucleotide sequences, as well as amino acid sequences. In some embodiments, analogous sequences are developed such that the replacement amino acids result in a variant enzyme showing a similar or improved function. In some preferred embodiments, the tertiary structure and/or conserved residues of the amino acids in the protein of interest are located at or near the segment or fragment of interest. Thus, where the segment or fragment of interest contains, for example, an alpha-helix or a beta-sheet structure, the replacement amino acids preferably maintain that specific structure.

As used herein, "homologous protein" refers to a protein (e.g., perhydrolase) that has similar action and/or structure, as a protein of interest (e.g., an perhydrolase from another source). It is not intended that homologs be necessarily related evolutionarily. Thus, it is intended that the term encompass the same or similar enzyme(s) (i.e., in terms of structure and function) obtained from different species. In some preferred embodiments, it is desirable to identify a homolog that has a quaternary, tertiary and/or primary structure similar to the protein of interest, as replacement for the segment or fragment in the protein of interest with an analogous segment from the homolog will reduce the disruptiveness of the change. In some embodiments, homologous proteins have induce similar immunological response(s) as a protein of interest.

As used herein, "homologous genes" refers to at least a pair of genes from different species, which genes correspond to each other and which are identical or very similar to each other. The term encompasses genes that are separated by speciation (i.e., the development of new species) (e.g., orthologous genes), as well as genes that have been separated by genetic duplication (e.g., paralogous genes). These genes encode "homologous proteins."

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "wild-type" and "native" proteins are those found in nature. The terms "wild-type sequence," and "wild-type gene" are used interchangeably herein, to refer to a sequence that is native or naturally occurring in a host cell. In some embodiments, the wild-type sequence refers to a sequence of interest that is the starting point of a protein engineering project. The genes encoding the naturally-occurring protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

The term "recombinant DNA molecule" as used herein refers to a DNA molecule that is comprised of segments of DNA joined together by means of molecular biological techniques.

The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

The degree of homology between sequences may be determined using any suitable method known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FAS TA, and TFASTA in the Wisconsin Genetics Software Package (Genetics Computer Group, Madison, Wis.); and Devereux et al., Nucl. Acid Res., 12:387-395 [1984]).

For example, PILEUP is a useful program to determine sequence homology levels. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). One particularly useful BLAST program is the WU-BLAST-2 program (See, Altschul et al., Meth. Enzymol., 266:460-480 [1996]). parameters "W," "T," and "X" determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1989]) alignments (B) of 50, expectation (E) of 10, M'5, N'-4, and a comparison of both strands.

As used herein, "percent (%) nucleic acid sequence identity" is defined as the percentage of nucleotide residues in a candidate sequence that are identical with the nucleotide residues of the sequence.

As used herein, the term "hybridization" refers to the process by which a strand of nucleic acid joins with a complementary strand through base pairing, as known in the art.

As used herein, the phrase "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Alternatively, or in addition, hybridization conditions can be based upon the salt or ionic strength conditions of hybridization and/or one or more stringency washes. For example, 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe.

For applications requiring high selectivity, it is typically desirable to use relatively stringent conditions to form the hybrids (e.g., relatively low salt and/or high temperature conditions are used).

The phrases "substantially similar and "substantially identical" in the context of at least two nucleic acids or polypeptides typically means that a polynucleotide or polypeptide comprises a sequence that has at least about 40% identity, more preferable at least about 50% identity, yet more preferably at least about 60% identity, preferably at least about 75% identity, more preferably at least about 80% identity, yet more preferably at least about 90%, still more preferably about 95%, most preferably about 97% identity, sometimes as much as about 98% and about 99% sequence identity, compared to the reference (i.e., wild-type) sequence. Sequence identity may be determined using known programs such as BLAST, ALIGN, and CLUSTAL using standard parameters. (See e.g., Altschul, et al., J. Mol. Biol. 215:403-410 [1990]; Henikoff et al., Proc. Natl. Acad. Sci. USA 89:10915 [1989]; Karin et al., Proc. Natl. Acad. Sci. USA 90:5873 [1993]; and Higgins et al., Gene 73:237-244 [1988]). Software for performing BLAST analyses is publicly available through the National Center for Biotechnology Information. Also, databases may be searched using FASTA (Pearson et al., Proc. Natl. Acad. Sci. USA 85:2444-2448 [1988]). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, "equivalent residues" refers to proteins that share particular amino acid residues. For example, equivalent resides may be identified by determining homology at the level of tertiary structure for a protein (e.g., perhydrolase) whose tertiary structure has been determined by x-ray crystallography. Equivalent residues are defined as those for which the atomic coordinates of two or more of the main chain atoms of a particular amino acid residue of the protein having putative equivalent residues and the protein of interest (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins analyzed. The preferred model is the crystallographic model giving the lowest R factor for experimental diffraction data at the highest resolution available, determined using methods known to those skilled in the art of crystallography and protein characterizationanalysis.

As used herein, the terms "hybrid perhydrolases" and "fusion perhydrolases" refer to proteins that are engineered from at least two different or "parental" proteins. In preferred embodiments, these parental proteins are homologs of one another. For example, in some embodiments, a preferred hybrid perhydrolase or fusion protein contains the N-terminus of a protein and the C-terminus of a homolog of the protein. In some preferred embodiment, the two terminal ends are combined to correspond to the full-length active protein.

The term "regulatory element" as used herein refers to a genetic element that controls some aspect of the expression of nucleic acid sequences. For example, a promoter is a regulatory element which facilitates the initiation of transcription of an operably linked coding region. Additional regulatory elements include splicing signals, polyadenylation signals and termination signals.

As used herein, "host cells" are generally prokaryotic or eukaryotic hosts which are transformed or transfected with vectors constructed using recombinant DNA techniques known in the art. Transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

The term "introduced" in the context of inserting a nucleic acid sequence into a cell, means transformation, transduction or transfection. Means of transformation include protoplast transformation, calcium chloride precipitation, electroporation, naked DNA and the like as known in the art. (See, Chang and Cohen, Mol. Gen. Genet., 168:111-115 [1979]; Smith et al., Appl. Env. Microbiol., 51:634 [1986]; and the review article by Ferrari et al., in Harwood, *Bacillus*, Plenum Publishing Corporation, pp. 57-72 [1989]).

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

The term "stable transfection" or "stably transfected" refers to the introduction and integration of foreign DNA into the genome of the transfected cell. The term "stable transfectant" refers to a cell which has stably integrated foreign or exogenous DNA into the genomic DNA of the transfected cell.

The terms "selectable marker" or "selectable gene product" as used herein refer to the use of a gene which encodes an enzymatic activity that confers resistance to an antibiotic or drug upon the cell in which the selectable marker is expressed.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both. Selection of cells by growth in the presence of a drug (e.g., an inhibitor of an inhibitable enzyme) may result in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "co-amplification" refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the terms "amplifiable marker," "amplifiable gene," and "amplification vector" refer to a marker, gene or a vector encoding a gene which permits the amplification of that gene under appropriate growth conditions.

As used herein, the term "amplifiable nucleic acid" refers to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc. Natl. Acad. Sci. USA 69:3038 [1972]). Other nucleic acids are not replicated by this amplification enzyme. Similarly, in the case of T7 RNA polymerase, this amplification enzyme has a stringent specificity for its own promoters (See, Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to amplification methods (e.g., the polymerase chain reaction), refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195, 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}P$-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the terms "restriction endonucleases" and "restriction enzymes" refer to bacterial enzymes, each of which cut double-stranded DNA at or near a specific nucleotide sequence.

The Present Invention

In some most particularly preferred embodiments, the present invention finds use in the enzymatic generation of peracids from ester substrates and hydrogen peroxide. In some preferred embodiments, the substrates are selected from one or more of the following: formic acid, acetic acid, propionic acid, butyric acid, valeric acid, caproic acid, caprylic acid, nonanoic acid, decanoic acid, dodecanoic acid, myristic acid, palmitic acid, stearic acid, and oleic acid. Importantly, the present invention provides means for effective cleaning, bleaching, and disinfecting over broad pH and temperature ranges. In some embodiments, the pH range utilized in this generation is 4-12. In alternative embodiments, the temperature range utilized is between 5° and 90° C. The present invention provides advantages over the presently used systems (See e.g., EP Appln. 87-304933.9) in that bleaching is possible at the optimum pH of peracid oxidation, as well as providing bleaching at neutral pH, acidic pHs, and at low temperatures. While the present invention is described herein most fully in regard to laundry and fabric care, it is not intended that the present invention be limited to these applications. Indeed, the present invention finds use in various settings, particularly those in which bleaching by peracids and/or hydrogen peroxide are desired, including but not limited to laundry, fabric treatment, pulp and paper processing, personal care applications, disinfection and cleaning of hard surfaces. For example, it is contemplated that the compositions of the present invention will find use in bleaching of pulp, including use in methods such as those set forth in U.S. Pat. Nos. 6,569,286, 5,785,812, 6,165,318, and 4,400,237, all of which are herein incorporated by reference.

Historically, sodium perborate, and more recently, sodium percarbonate, have been used as bleaching compounds, particularly in European laundry detergents. This compound decomposes rapidly in aqueous solution to yield hydrogen peroxide ($H_2O_2$), which is the active bleaching species. As sodium perborate is more active at temperatures above 80° C., and less active in the temperature range of 40-60° C. (i.e., wash temperatures that have become most commonly preferred as of the 1950s), bleaching activators have been incorporated into laundry detergents that contain sodium perborate. Indeed, most laundry detergents contain bleaching activators. These activators are compounds with O- or N-bounded acetyl groups that are able to react with the strongly nucleophilic hydroperoxy anion to yield peroxyacetic acid. Since the reacting species is hydroperoxy anion, alkaline pHs are essential for the efficient conversion of these activators to peracids. The peroxyacetic acid is decomposed in weakly basic media to form singlet oxygen (See, Hofmann et al., J. Prakt. Chem., 334:293-297 [1992]).

Hydrogen peroxide is a particularly effective bleach at high temperatures (e.g., >40° C.) and pH (>10), conditions that are typically used in washing fabrics in some settings. However, as indicated above, cold water washing is becoming more commonly used and results in less effective bleaching by $H_2O_2$ than use of hot water. To overcome this low temperature disadvantage, detergent formulations typically include bleach boosters, such as TAED (N,N,N'N'-tetraacetylethylenediamine), NOBS (nonanoyloxybenzene sulfonate), etc. These boosters combine with $H_2O_2$ to form peracetic acid, a peracid species that is more effective than $H_2O_2$ alone. Although it helps the bleaching capability of detergent, the TAED reaction is only approximately 50% efficient, as only two out of the four acetyl groups in TAED are converted to peracids. Additionally, conversion of TAED into peracetic acid by hydrogen peroxide is efficient only at alkaline pHs and high temperatures. Thus, the TAED reaction is not optimized for use in all bleaching applications (e.g., those involving neutral or acidic pHs, and cold water). The present invention provides means to overcome the disadvantages of TAED use. For example, the present invention finds use in cold water applications, as well as those involving neutral or acidic pH levels. Furthermore, the present invention provides means for peracid generation from hydrogen peroxide, with a high perhydrolysis to hydrolysis ratio. The present invention further provides advantages over compositions that contain enzymes such as esterases and lipases) which have very low perhydrolysis to hydrolysis ratios.

In addition to its applications in detergents, the present invention provides methods and compositions for the use of peracids in textile bleaching and in various other applications. In some embodiments, the present invention provides one-step methods for textile processing applications, including but not limited to one-step desizing, scouring and bleaching processes (See e.g., EP WO 03002810, EP 1255888, WO 0164993, and US 20020007516, all of which are hereby incorporated by reference). As described in greater detail herein, in some embodiments, bleaching involves processing textile material before it is dyed and/or after it is incorporated into textile goods. However, it is not intended that the present invention be limited to any particular regimen of use nor any particular textile material.

Furthermore, the peracetic technology of the present invention finds use as an effective bactericide (See, Baldry, J. Appl. Bacteriol., 54:417-423 [1983]). Thus, the present invention provides compositions and methods for the sterilization/disinfection of various objects, including but not limited to medical devices, medical equipment, industrial equipment, and fermenters, as well as any additional object that needs to be sterilized or disinfected. As discussed in greater detail below, during the development of the present invention, the enzyme of the present invention was used in a standard cell kill experiment to demonstrate this suitability. In additional embodiments, the present invention provides compositions and methods suitable for use in biofilm control, such as in cooling towers.

Also as described in more detail in the Examples below, the present invention provides many advantages for cleaning and/or sterilization of a wide range of objects, including but not limited to clothing, fabrics, medical devices, etc. In addition, the present invention provides compositions that are effective in cleaning, bleaching, and disinfecting, over a range of wash temperatures and pHs. In additional embodiments, the present invention finds use in degradation of peracids through the perhydrolase peracid degradation activity. In some preferred embodiments, this activity is used in peracid waste clean up applications.

Furthermore, the perhydrolase enzymes of the present invention are active on various acyl donor substrates, as well as being active at low substrate concentrations, and provide means for efficient perhydrolysis due to the high peracid:acid ratio. Indeed, it has been recognized that higher perhydrolysis to hydrolysis ratios are preferred for bleaching applications (See e.g., U.S. Pat. Nos. 5,352,594, 5,108,457, 5,030,240, 3,974,082, and 5,296,616, all of which are herein incorporated by reference). In preferred embodiments, the perhydrolase enzymes of the present invention provide perhydrolysis to hydrolysis ratios that are greater than 1. In particularly preferred embodiments, the perhydrolase enzymes provide a perhydrolysis to hydrolysis ratio greater than 1 and are find use in bleaching.

In addition, it has been shown to be active in commonly used detergent formulations (e.g., Aria Futur, WOB, etc.). Thus, the present invention provides many advantages in various cleaning settings.

As indicated above, key components to peracid production by enzymatic perhydrolysis are enzyme, ester substrate, and hydrogen peroxide. Hydrogen peroxide can be either added directly in batch, or generated continuously "in situ." Current washing powders use batch additions of $H_2O_2$, in the form of percarbonate or perborate salts that spontaneously decompose to $H_2O_2$. The perhydrolase enzymes of the present invention find use in the same washing powder batch method as the $H_2O_2$ source. However, these enzymes also find use with any other suitable source of $H_2O_2$, including that generated by chemical, electro-chemical, and/or enzymatic means. Examples of chemical sources are the percarbonates and perborates mentioned above, while an example of an electrochemical source is a fuel cell fed oxygen and hydrogen gas, and an enzymatic example includes production of $H_2O_2$ from the reaction of glucose with glucose oxidase. The following equation provides an example of a coupled system that finds use with the present invention.

$$\text{Glucose} + H_2O \xrightarrow{\text{Glucose oxidase}} \text{gluconic acid} + H_2O_2$$

$$+$$

$$H_2O_2 + \text{ester substrate} \xrightarrow{\text{Perhydrolase}} \text{alcohol} + \text{peracid}$$

It is not intended that the present invention be limited to any specific enzyme, as any enzyme that generates $H_2O_2$ with a suitable substrate finds use in the methods of the present invention. For example, lactate oxidases from *Lactobacillus* species which are known to create $H_2O_2$ from lactic acid and oxygen find use with the present invention. Indeed, one advantage of the methods of the present invention is that the generation of acid (e.g., gluconic acid in the above example) reduces the pH of a basic solution to the pH range in which the peracid is most effective in bleaching (i.e., at or below the pKa). Other enzymes (e.g., alcohol oxidase, ethylene glycol oxidase, glycerol oxidase, amino acid oxidase, etc.) that can generate hydrogen peroxide also find use with ester substrates in combination with the perhydrolase enzymes of the present invention to generate peracids. In some preferred embodiments, the ester substrates are selected from one or more of the following acids: formic acid, acetic acid, propionic acid, butyric acid, valeric acid, caproic acid, caprylic acid, nonanoic acid, decanoic acid, dodecanoic acid, myristic acid, palmitic acid, stearic acid, and oleic acid. Thus, as described herein, the present invention provides definite advantages over the currently used methods and compositions for detergent formulation and use, as well as various other applications.

DETAILED DESCRIPTION OF THE PRESENT INVENTION

The present invention provides methods and compositions comprising at least one perhydrolase enzyme for cleaning and other applications. In some particularly preferred embodiments, the present invention provides methods and compositions for generation of peracids. The present invention finds particular use in applications involving cleaning, bleaching and disinfecting.

Cloning and Characterization of *M. smegmatis* Perhydrolase

The cloning of the *M. smegmatis* perhydrolase (i.e., referred to herein as the "phd" gene, which encodes the "Phd" protein; this perhydrolase gene is sometimes herein referred to as the "act" gene and the protein is sometimes referred to as the "Act" protein) of the present invention was based on peptide sequence data from the acyltransferase purified from *Mycobacterium parafortuitum* (previously known as *Corynebacterium oxydans*) and published information regarding the 7-aminocephalosporanic acid (7-ACA) arylesterase gene of *Agrobacterium radiobacter* (Sakai et al., J. Ferment. Bioengineer., 85: 138-143 [1998]). Two peptide sequences from purified *M. parafortuitum* acyltransferase were found to be similar to internal N- and C-terminal regions of the *A. radiobacter* 7-ACA-arylesterase (47% and 42% identity respectively).

A set of PCR primers was designed based on the amino acid sequence of these internal peptides (designated "AtintF" and "AtintR"). Another set of primers was developed based on the 5' and 3' ends ("ATNcoI" and "ATBamH1") of the *A. radiobacter* 7-ACA DNA sequence. A single product of the expected size was amplified from *M. parafortuitum* chromosomal DNA using both sets of primers. The full length product, amplified by the ATNcoI/ATBamH1 primer pair, was cloned into pET16b and transformed into BL21 cells (Novagen, Madison, Wis.). This clone had a sequence identical to that of the *A. radiobacter* 7-ACA gene. As it was determined that purified *M. parafortuitum* perhydrolase was not the 7-ACA acyl esterase, it was concluded that this was not the gene encoding the perhydrolase of the present invention.

Thus, efforts were further focused on *M. smegmatis* for cloning and expression of the perhydrolase of the present invention. To identify the *M. parafortuitum* gene based on enzyme activity screening, a plasmid library of *M. parafortuitum* DNA in *M. smegmatis* was constructed using a plasmid with a promoter to drive expression of cloned genes.

Surprisingly, *M. smegmatis* itself was found to be positive for perhydrolase and acyltransferase activity. Thus, in some instances herein, the perhydrolase is referred to as "ACT" (or "Act"). A protein BLAST search of the *M. smegmatis* unfinished genome using the sequence of the *A. radiobacter* 7-ACA identified a 2 kb contig containing an ORF (open reading frame) that encoded a hypothetical protein that was similar but not identical to the 7-ACA protein. Based on this sequence, primers were designed and used to amplify the gene from *M. smegmatis* (ATCC 10143). By adding an *E. coli* ribosome binding site upstream of the start codon, a clone that expressed active enzyme was obtained. The vector used was either pCR2.1TOPO or pBluntIITOPO (Invitrogen, Carlsbad, Calif.), in *E. coli* Top10 cells. The gene was expressed constitutively from the plasmid-encoded lac promoter. This enzyme carried out the same reactions as the originally described *M. parafortuitum* acyltransferase.

During the characterization of the perhydrolase of the present invention, standard protein BLAST searches identified a few proteins (<20) with sequence similarity of 30-80%. This group included the 7-ACA arylesterases from *A. radiobacter* and other organisms, which have 43% identity with *M. smegmatis* perhydrolase. All of the identified homologs with at least 40% similarity have a GDS motif very near the N-terminal end. All of the proteins also contain most of the conserved residues which could place them within the suggested GDSL family of lipolytic enzymes (See e.g., Upton and Buckley, Trends Biochem. Sci., 20:178 [1995]). However, enzymes mentioned in this paper do not appear on homology searches with the perhydrolase protein. Indeed these proteins have less than 20% similarity with the perhydrolase and its homologs, suggesting that the acyltransferase-related (and perhydrolase of the present invention) enzymes form a subfamily.

The natural function of the enzyme of the present invention and the closely related proteins, apart from the 7-ACA arylesterase, have not been biochemically determined *M. smegmatis* appears to be the only organism with the acyltransferase/perhydrolase in an operon with a putative penicillin binding protein (PBP). While it is not intended that the present invention be limited to any particular mechanism, this suggests that the enzyme may be involved in cell wall synthesis/structure or modification of molecules taken up from the environment. There are no homologues of the perhydrolase of the present invention that have been identified in *M. tuberculosis* or *M. leprae* to date. However, some organisms were determined to have multiple homologues (e.g., *S. meliloti*).

During the development of the present invention, various mutations were made in the *M. smegmatis* perhydrolase in order to assess its activity. This enzyme contains two cysteine residues, which were hypothesized as potentially forming disulfide bonds, both of which were changed to alanine, in order to determine whether or not the C residues had any effect on the activity of the enzyme. Activity assay results obtained using the transesterification (in aqueous solution) assay described herein indicated that C7A, as well as C77A, and a double mutant (C7A and C77A) were of the same size and specific activity.

Many enzymes have the amino acid serine as part of their active site and are therefore referred to, among other designations, as "serine hydrolases." The active site may consist of a catalytic triad of S (serine), D (aspartic acid) and H (histidine). Examples of such enzymes include, but are not limited to subtilisin (D32-H64-S215), chymotrypsin (H57-D102-5195) and lipases in the alpha/beta hydrolase family (e.g., S126-D176-H206). A typical motif for lipases is the GDSL motif (Upton and Buckley, supra [1995]) in which the S is the active site serine. Since the perhydrolase of the present invention was determined to have a GDSL (amino acids 9-12) motif, the S11 was mutated to an A, in order to confirm the involvement of this S in the active site. As indicated in the Examples, the activity assay results indicated that S11A had only 1% of the activity of the wild-type enzyme. Deletion of the C-terminal 25 amino acids also resulted in abrogation of the activity, suggesting that these amino acids either contained a residue involved directly in the active site, and/or that the structure of the protein was affected such that the active site was no longer able to catalyze the reactions. In addition, the predicted active site residues, D192 and H195 were mutated to A. Neither mutant had activity, confirming that the active site residues of the perhydrolase of the present invention consist of S11, D192 and H195. However, it is not intended that the present invention be limited to any particular mechanism, nor is the present invention limited to mutation(s) at any particular active site residues.

Cloning of *M. parafortuitum* Perhydrolase

There were some differences between the N-terminal peptide sequence obtained from the *M. parafortuitum* enzyme and the N-terminal sequence of *M. smegmatis* perhydrolase. However, there was a sequence in the C-terminal region of the *M. smegmatis* perhydrolase identical to the C-terminal peptide sequence of the *M. parafortuitum* enzyme. Two primers were designed to amplify a partial sequence of the *M. parafortuitum* perhydrolase gene; the sequence of the reverse primer was identical to the sequence of the corresponding region in *M. smegmatis* perhydrolase gene, and the sequence of the forward primer was based on *M. smegmatis* codon usage. The forward primer, MP5: 5'-ATGGGTACCCGACGAATTCTGTCCTTCGGTGATTCCCTGACCT-3' (SEQ ID NO:11) and the reverse primer MPC-intR 5'-GATTCCGTCGACGCCGTCGGTGCTGATCACCGAACCCGCGTCGAAGAACGG-3' (SEQ ID NO:12). The partial gene was amplified from the chromosome of *M. parafortuitum* and cloned into pCR2.1TOPO (Invitrogen, Carlsbad, Calif.). Sequence analysis showed that the enzyme is very similar, but not identical to the *M. smegmatis* perhydrolase (77% identity). Based on the molecular weights of the monomers of the perhydrolases determined by SDS-PAGE (MP AT: 26 kDa, MSAT: 24 kDa, MP cloned AT: ~18 kDa), the clone from primers made to the internal fragment was determined to be missing approximately 70 amino acids (~8 kDa). The remaining sequence at the 5'-end of the *M. parafortuitum* gene can be obtained by any of several methods suitable and familiar to those skilled in the art of molecular biology, including, but not limited to, inverse PCR, probing of plasmid/cosmid libraries of *M. parafortuitum* chromosomal DNA, sequencing of the gene directly from chromosomal DNA (e.g., as performed by Fidelity Systems, Bethesda Md.).

Expression of the *M. smegmatis* Perhydrolase

The perhydrolase is an intracellular protein in its native host. Production of the perhydrolase in non-native hosts may also be done intracellularly. However, in some embodiments, a signal sequence is added to the perhydrolase, which facilitates expression of the perhydrolase by secretion into the periplasm (i.e., in Gram-negative organisms, such as *E. coli*), or into the extracellular space (i.e., in Gram-positive organisms, such as *Bacillus* and *Actinomycetes*), or eukaryotic hosts (e.g., *Trichoderma, Aspergillus, Saccharomyces*, and *Pichia*). Of course, these are just a few examples of possible prokaryotic and eukaryotic hosts. It is not intended that the present invention be limited to these specific hosts, as various other organisms find use as expression hosts in the present invention.

A variety of commercially available expression systems, including but not limited to pBAD, plac, T7, find use in the expression of the perhydrolase in Gram-negative hosts (e.g., *E. coli*). In some embodiments, the same types of promoters find use in another Gram-negative host, *Pantoea citrea*.

To test expression in *E. coli* two strategies were used: 1) adding an RBS (ribosome binding site) to the 5' end of the phd gene and cloning the gene into pCRBLUNTIITOPO (Invitrogen), thus allowing expression directly from the pLac promoter available in that vector; and 2) cloning the phd gene under control of the T7 promoter in the plasmid pET16b (Novagen). In the latter system, expression of the gene is inducible by addition of IPTG to the growing culture and use of a specific host cell (e.g., BL21(λDE3)pLysS (Novagen)) that contains the 2DE3 lysogen encoding the T7 RNA polymerase. The first strategy produces a plasmid capable of allowing expression of the perhydrolase protein in other Gram-negative hosts (e.g., *P. citrea*).

To express protein in *E. coli* or *P. citrea* using the first strategy, cultures were grown from single, purified colonies at 37° C. overnight in L broth plus the appropriate antibiotic (example, kanamycin 50 µg/ml). Expression of the protein was determined by the pNB assay (See, Example 1) after lysis of the cells.

Expression of the perhydrolase using the T7 expression system requires induction of the culture with the addition of IPTG (e.g., 100 mmole IPTG added at an $OD_{550}$ of 0.4). Overnight cultures, inoculated from a single colony, are used to inoculate the expression culture of the desired volume (25 mls to several liters) at an $OD_{550}$ of 0.1. The expression culture was then grown at the desired temperature (e.g., 25° C., 30° C., 37° C.) until an $OD_{550}$ of 0.4 was reached, after which IPTG was added. Expression was allowed to continue for 3 hours to overnight. Protein expression was monitored by pNB activity assay as described in Example 1. Usually, expression from the T7 system gives a high titer of protein, sufficient for further analysis such as crystallography.

*Bacillus* species are well-known as suitable hosts for expression of extracellular proteins (e.g., proteases). Intracellular expression of proteins is less well known. Expression of the perhydrolase protein intracellularly in *Bacillus subtilis* can be done using a variety of promoters, including, but not limited to pVeg, pSPAC, pAprE, or pAmyE in the absence of a signal sequence on the 5' end of the gene. In some embodiments, expression is achieved from a replicating plasmid (high or low copy number), while in alternative embodiments, expression is achieved by integrating the desired construct into the chromosome. Integration can be done at any locus, including but not limited to the aprE, amyE, or pps locus. In some embodiments, the perhydrolase is expressed from one or more copies of the integrated construct. In alternative embodiments, multiple integrated copies are obtained by the integration of a construct capable of amplification (e.g., linked to an antibiotic cassette and flanked by direct repeat sequences), or by ligation of multiple copies and subsequent integration into the chromosome. In some embodiments, expression of the perhydrolase with either the replicating plasmid or the integrated construct is monitored using the pNB activity assay (described herein) in an appropriate culture.

As with *Bacillus*, in some embodiments, expression of the perhydrolase in the Gram-positive host *Streptomyces* is done using a replicating plasmid, while in other embodiments, expression of the perhydrolase is accomplished via integration of the vector into the *Streptomyces* chromosome. Any promoter capable of being recognized in *Streptomyces* finds use in driving transcription of the perhydrolase gene (e.g., glucose isomerase promoter, A4 promoter). Replicating plasmids, either shuttle vectors or *Streptomyces* only, also find use in the present invention for expression (e.g., pSECGT).

Structure of *M. smegmatis* Perhydrolase

Figure 3:
FIG. 3 provides a schematic of four structural families of serine hydrolases, including perhydrolase (SGNH-hydrolase family), chymotrypsin, subtilisin, and α/β hydrolase.
Figure 4:
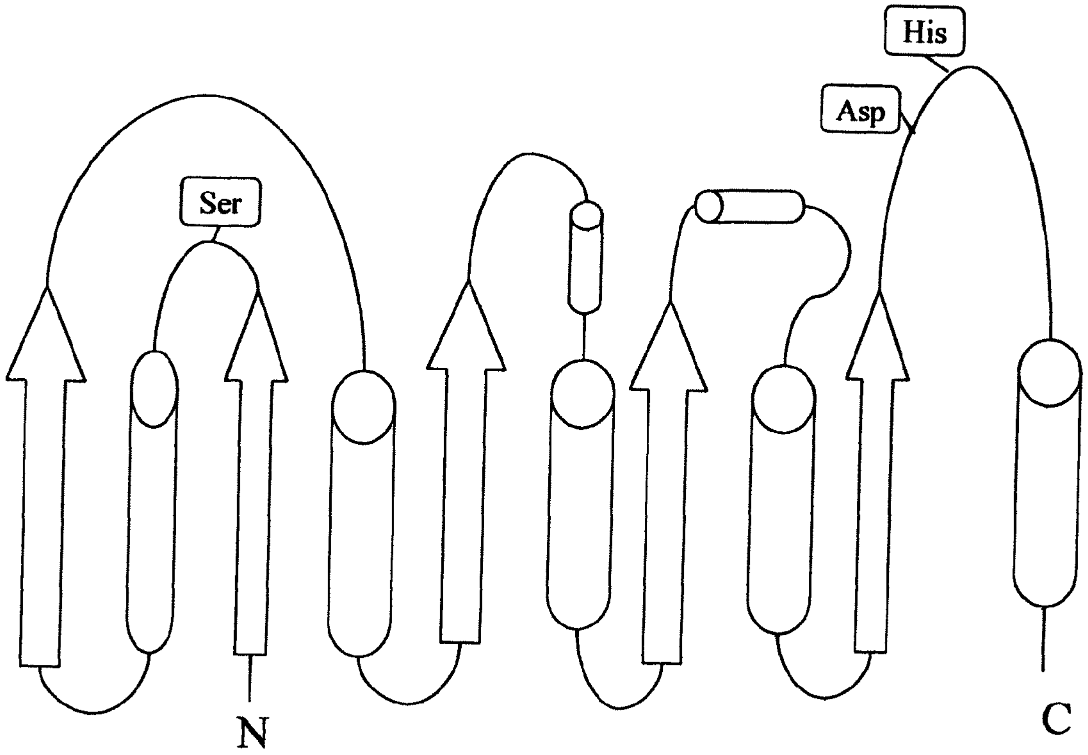
FIG. 4 provides a diagram of the structure of the perhydrolase fold.

The crystal structure of the *M. smegmatis* perhydrolase was determined to 2.2 Angstroms. The structure confirmed findings with gel filtration sizing columns, that indicated this enzyme is an octamer. The structure of the monomer places the enzyme in the class known as SGNH-hydrolases (See e.g., Molgaard et al., Structure 8: 373-383 [2000]). The active site residues were identified as S11-D192-H195, based on homology, confirming the identification of the catalytic triad based on loss of activity in the S11A, D192A, and H195A mutations described above. FIG. 3 provides schematics showing the structure of the *M. smegmatis* perhydrolase, as well as other serine hydrolases. As indicated, this enzyme has a different structure than the enzymes shown here (chymotrypsin, subtilisin, and α/β hydrolase). Indeed, the structural analysis of the perhydrolases of the present invention indicates that this group of enzymes has a different form and active site than do these other enzymes. A schematic diagram of the structure of the monomer is illustrated in FIG. 4. The structures of four other enzymes in the SGNH-hydrolase family have been solved, namely *Aspergillus aculeates* rhamnogalucturonan acetylesterase (RGAE), *Bos taurus* platelet activating factor (PAF-AH(1b)a), *Streptomyces scabies* esterase (SsEst) and the thioesterase/Protease I/Phospholipase $L_1$ (TAP or Tes) from *E. coli*. Very little sequence or functional homology is present in these enzymes. Basically, the sequence identity is reserved for the residues involved in the active site and those defining the family. While the overall folding of the enzymes is similar (See e.g., Molgaard et al., supra [2000], for overlaying of structures), there are structural differences. For example, there is a loop covering the active site in SsEst, compared to RGAE and TAP which have active sites that are surface-exposed. The *M. smegmatis* perhydrolase has an active site that is somewhat buried. The binding residues of the *M. smegmatis* perhydrolase were identified as Cys7, Asp10, Ser11, Leu12, Thr13, Trp14, Trp16, Pro24, Thr25, Leu53, Ser54, Ala55, Thr64, Asp65, Arg67, Cys77, Thr91, Asn94, Asp95, Tyr99, Val125, Pro138, Leu140, Pro146, Pro148, Trp149, Phe150, Ile153, Phe154, Thr159, Thr186, Ile192, Ile194, and Phe196. These sites were derived from direct observation and by modeling studies to model substrate binding to the enzyme, using methods known in the art.

As indicated above, the *M. smegmatis* perhydrolase was found to be an octamer in the crystalline state. However, it is contemplated to be either a hexamer or octamer in solution. The octamer is seen to be a tetramer of dimers, two molecules are much more closely and extensively interacting and these are termed the "act transferase" dimers. Several of the conserved sites are found along this dimer interface. For example, residues Trp 14, Arg 27, Arg 56, His 81 and Pro 83, were found to be conserved in natural isolates that have perhydrolase activity and are contemplated to be critical in forming the interface. In addition one other residue, Glu 51, which is conserved in all but one of the natural isolates (and in that case it is a homologous enzyme) was identified.

One additional feature of interest in that in the natural isolates showing perhydrolase activity, all share an insertion of residues 69-81. This region forms a loop that is at the dimer interface. Without this loop, it is believed that much of the dimer interface would be lost and it is likely that dimers and subsequent aggregation would not occur. Thus, there is a correlation of the insertion with the structural aggregation particularly dimer formations and the appearance of perhydrolase activity. However, it is not intended that the present invention be limited to any particular mechanisms.

Key residues were found to be associated with desired activity in selected homologs. Indeed, there are several conserved residues that are contemplated to have importance for acyltransferase activity. These include Leu 6, Trp 14, Arg 27, Trp 34, Asp 62, Leu74, Leu 78 His 81, Pro83, Met 90, Lys 97, and Leu 114.

In additional analyses, the association of the perhydrolase with carbamate was investigated. The native octamer was determined in space group P4 with unit cell dimensions: a=98.184 b=98.184 and c=230.119 $\alpha$=90.00 $\beta$=90.00 $\gamma$=90.00, this crystal diffracted to about 2.0 Å. The carbamate-inhibited crystal grew in the space group P1 with unit cell dimensions a=67.754, b=80.096, and c=85.974 $\alpha$=104.10°, $\beta$=112.10°, and $\gamma$=97.40° and these crystals diffract to a resolution exceeding 1.0 Å.

The carbamate was bound in a manner to exploit the interactions between the keto oxygen of the carbamate and residues forming the oxyanion hole, the amide N atoms of Ser 11 and Ala 55 and Asn 94 ND2. The hydrophobic side chain extends along the hydrophobic surface of the binding site out into the surface opening between pairs of dimers in the octamer structure. The carbamate moiety direction highlights the pivotal role of the S54V mutation. The hydrophobic moiety passes adjacent to the side chain of ser 54. Mutating the serine side to valine increased the hydrophobicity, and also served as a gatekeeper to prevent hydrophilic nucleophiles (e.g., water) for competing with desired deacylating nucleophiles. The residues surrounding the carbamate moiety on the same and neighboring molecules forming the extended entry are expected to influence the selection of the optimal deacylating nucleophile. The structure showed that each monomer was inhibited with carbamate covalently attached. Thus, all octamer active sites were found to be active and functional. The side chain of carbamate resembles the leaving groups of the substrates tested. Thus, the carbamate moiety indicates the access direction for substrate.

*M. smegmatis* Perhydrolase is an SGNH-Hydrolase

The perhydrolase of the present invention has certain components that indicate it is in the SGNH-hydrolase family of enzymes. This family is defined by having the four conserved amino acids SGN and H in four blocks, similar to the blocks that describe the lipolytic family of enzymes (See, Upton and Buckley, supra). In the case of the *M. smegmatis* perhydrolase, these correspond to S11, G52, N94 and H195 which correspond to Blocks I II, III and V according to Upton and Buckley (Upton and Buckley, supra) and Molgaard et al. (Molgaard et al., supra). These amino acids are also conserved within the closest sequence homologs of the perhydrolase.

As indicated herein, the sequences were aligned using the Alignment program in Vector NTi (Informax, Invitrogen) In the following alignment providing a comparison of homolog sequences, the double underline indicates the residues involved in the active site. AR: *Agrobacterium rhizogenes* Q9KWA6; RR: *Rhizobium rhizogenes* NF006; SM: *Sinorhizobium meliloti* RSM02162; MS: *Mycobacterium smegmatis* Act; MP: *Mycobacterium parafortuitum* Phd partial sequence; PD: *Prosthecobacter dejongeii* RVM04532. The amino acids within the blocks defining the SGNH-hydrolase family are indicated in bold letters.

```
                             Block I                                      Block II
                               GDS                                            G
AR(1)     ----------MAESRSILCFGDSLTWGWIPVPESSP TLRYPFEQRWTGAMAAALGDGYSIIEEGLSARTTSVED--PN

RR(1)     ----------MAESRSILCFGDSLTWGWIPVPESSP TLRYPFEQRWTGAMAAALGDGYSIIEEGLSARTTSVED-PN

RM(1)     MTINSHSWRTLMVEKRSVLCFGDSLTWGWIPVKESSP TLRYPYEQRWTGAMAARLGDGYHIIEEGLSARTTSLDD-PN

SM(1)     -----------MVEKRSVLCFGDSRTWGWIPVKESSP TLRYPYEQRWTGAMAARLGDGYHIIEEGLSARTTSLDD-PN

MS(1)     -------------MAKRILCFGDSLTWGWVPVEDGAP TERFAPDVRWTGVLAQQLGADFEVIEEGLSARTTNIDD-PT

MP        -------------GIRRILSFGDSLTWGWIPVEEGVP TERFPRDVRWTGVLADLLGDRYEVIEEGLSARTTTAED-PA

PD(1)     --------------MKTILCFGDSNTWGYDPASMTAPFPRRHGPEVRWTGVLAKALGAGFRVIEEGQNGRTTVHED--PL

                                        Block III
                                       GxND
AR(67)    DPRLNGSAYLPMALASHLPLDLVIILLGTNDTKSYFRRTPYEIANGMGKLAGQVLTSAGGIGTPYPAPKLLIVSPPPLAP

RR(67)    DPRLNGSAYLPMALASHLPLDLVIILLGTNDTKSYFRRTPYEIANGMGLKAGQVLTSAGGIGTPYPAPKLLIVSPPPLAP

RM(78)    DARLNGSTYLPMALASHLPLDLVIIMLGTNDTKSYFHRTPYEIANGMGKLVGQVLTCAGGVGTPYPAPKVLVVAPPPLAP

SM(67)    DARLNGSTYLPMALASHLPLDLVIIMLGTNDTKSYFHRTPYEIANGMGKLVGQVLTCAGGVGTPYPAPKVLVVAPPPLAP

MS(65)    DPRLNGASYLPSCLATHLPLDLVIIMLGTNDTKAYFRRTPLDIALGMSVLVTQVLTSAGGVGTTYPAPKVLVVSPPPLAP

MP(65)    DPRLNGSQYLPSCLASHLPLDLVILMLATNDTKANFGRTPFDIATGMGVLATQVLTSAGGVGTSYPAPQVLIVAPPPLGE

PD(65)    NICRKGKDYLPACLESHKPLDLVILMLGTNDLKSTFNVPPGEIAAGAGVLGRMILAGDAGP-ENRPPQLLLMCPPKVRDL

                                                          Block V
                                                           DGIHF
                                                                       (SEQ ID NO: 14)
AR(147)   MPDPWFEGMFGGGYEKSLELAKQYKALANFLKVDFLDAGEFVKTDGCDGIHFSAETNITLGHAIAAKVEAIFSQEAKNAA

                                                                       (SEQ ID NO: 15)
RR(147)   MPDPWFEGMFGGGYEKSLELAKQYKALANFLKVDFLDAGEFVKTDGCDGIHFSAETNITLGHAIAAKVEAIFSQEAKNAA
```

-continued (SEQ ID NO: 16)
RM(158) MPDPWFEGMFGGGYEKSKELSGLYKALADFMKVEFFAAGDCISTDGIDGIHLSAETNIRLGHAIADKVAALF--------

(SEQ ID NO: 17)
SM(147) MPDPWFEGMFGGGYEKSKELSGLYKALADFMKVEFFAAGDCISTDGIDGIHLSAETNIRLGHAIADKVAALF--------

(SEQ ID NO: 18)
MS(145) MPHPWFQLIFEGGEQKTTELARVYSALASFMKVPFFDAGSVISTDGVDGIHFTEANNRDLGVALAEQVRSLL--------

(SEQ ID NO: 19)
MP 145) LPHPWFDLVFSGGREKTAELARVYSALASFMKVPFFDAGSVISTDMVDGI-----------------------------

(SEQ ID NO: 20)
PD(144) SAMPDLDAKIPHGAARSAEFPRHYKAQAVALKCEYFNSQEIVETSPVDGIHLEASEHLKLGEALAEKVKVLLG-------

The primers used to identify homologs for each of the Blocks indicated above are provided below:

Block I (forward 5'-3)
1e: acggtcctgtgctttggngaytcnyt (SEQ ID NO: 21)

1f: acggtcctgtgctttggngayagyyt (SEQ ID NO: 22)

1g: gcggtcctgttctwnggngaytcnyt (SEQ ID NO: 23)

1h: gcggtcctgttctwnggngayagyyt (SEQ ID NO: 24)

1i: gctcgaaccgtcctctgttttggngaytcnyt (SEQ ID NO: 25)

1j: gctcgaaccgtcctctgttttggngayagyyt (SEQ ID NO: 26)

1k: gctcgaaccgtcctctgtttnggngaytc (SEQ ID NO: 27)

1l: gctcgaaccgtcctctgttttggngaytcnytn (SEQ ID NO: 28)

1m: gctcgaaccgtcctctgttttggngaytcnytg (SEQ ID NO: 29)

1A: gccaagcgaattctgtgtttcggngaytcnyt (SEQ ID NO: 30)

1B: gccaagcgaattctgtgtttcggngayagyyt (SEQ ID NO: 31)

Block III (reverse 5'-3)
3c: attccgcgcttcagrtcrttnvtncc (SEQ ID NO: 32)

3d: attccgcgcttcagrtcrttnwgncc (SEQ ID NO: 33)

3e: attccgcgcttcagrtcrttnscncc (SEQ ID NO: 34)

3f: attccgcgcttcagrtcrttnrancc (SEQ ID NO: 35)

3k: attccgcgcttcagrtcrttnrtncc (SEQ ID NO: 36)

3l: attccgcgcttcagrtcrttnytncc (SEQ ID NO: 37)

3m: attccgcgcttcagrtcrttnsgncc (SEQ ID NO: 38)

3n: attccgcgcttcagrtcrttnwcncc (SEQ ID NO: 39)

3o: attccgcgcttcagrtcrttnyancc (SEQ ID NO: 40)

3p: attccgcgcttgrsrtcrttnrtncc (SEQ ID NO: 41)

3q: attccgcgcttgrsrtcrttnytncc (SEQ ID NO: 42)

3r: attccgcgcttgrsrtcrttnsgncc (SEQ ID NO: 43)

3s: attccgcgcttgrsrtcrttnwcnnn (SEQ ID NO: 44)

3t: attccgcgcttgrsrtcrttnyancc (SEQ ID NO: 45)

-continued

3A: gcgccggaagtaggccttggtrtcrttnvtncc (SEQ ID NO: 46)

3B: gcgccggaagtaggccttggtrtcrttnwgncc (SEQ ID NO: 47)

3C: gcgccggaagtaggccttggtrtcrttnscncc (SEQ ID NO: 48)

3D: gcgccggaagtaggccttggtrtcrttnrancc (SEQ ID NO: 49)

Block III (forward 5'-3)
3g: cggaattatcatgctgggnabnaayga (SEQ ID NO: 50)

3h: cggaattatcatgctgggncwnaayga (SEQ ID NO: 51)

3i: cggaattatcatgctgggngsnaayga (SEQ ID NO: 52)

3j: cggaattatcatgctgggntynaayga (SEQ ID NO: 53)

3u: ccggaattatcatgctnggnabnaayga (SEQ ID NO: 54)

3v: ccggaattatcatgctnggncwnaayga (SEQ ID NO: 55)

3w: ccggaattatcatgctnggngsnaayga (SEQ ID NO: 56)

3x: ccggaattatcatgctnggntynaayga (SEQ ID NO: 57)

Block V (reverse 5'-3)
5c: acccttagcgtttggrtgnrtnccrtc (SEQ ID NO: 58)

5d: atccttagcgtttggrtgnavnccrtc (SEQ ID NO: 59)

5e: aatcttagccgtgrrrtgnrtnccrtc (SEQ ID NO: 60)

5f: aatcttagccgtgrrrtgnrcnccrtc (SEQ ID NO: 61)

5g: aatcttagccgtgrrrtgntrnccrtc (SEQ ID NO: 62)

5h: ccgctggtcctcatctggrtgnrtnccrtc (SEQ ID NO: 63)

5i: ccgctggtcctcatctggrtgnrcnccrtc (SEQ ID NO: 64)

5j: ccgctggtcctcatctggrtgntrnccrtc (SEQ ID NO: 65)

5k: ccgctggtcctcatcraartgnrtncc (SEQ ID NO: 66)

5A: cgattgttcgcctcgtgtgaartgnrtnccrtc (SEQ ID NO: 67)

5B: cgattgttcgcctcgtgtgaartgnrcnccrtc (SEQ ID NO: 68)

5C: cgattgttcgcctcgtgtgaartgntrnccrtc (SEQ ID NO: 69)

As described in greater detail herein, the sequence and structure results are supported by the activity data that indicate the perhydrolase enzymes of the present invention differ from lipolytic enzymes known in the art.

Identification of Homologs

As well known in the art, proteins with a desired activity may be identified in several ways, including but not limited to: 1) searching available databases for proteins with sequence homology (30-100%); 2) screening environmental isolates for the desired activity; and 3) examining type strains from ATCC of the genus identified to have activities (e.g., *Mycobacterium* and *Corynebacterium*, as described herein in particular embodiments).

By doing a standard protein-protein BLAST search, several homologs were identified from fully or partially sequenced genomes. From the known gene sequence, several homologs were amplified by PCR from the chromosome of the parent organism and cloned into a pET expression vector, essentially as described for the cloning of phd from *M. smegmatis* into pET16b. Homologues identified by this BLAST search included: *Agrobacterium rhizogenes* Q9KWA6, *A. rhizogenes* Q9KWB1 *A. tumefaciens* Q8UFG4, *A. tumefaciens* Q8UAC0 (now AgrL, identical to 7-ACA arylesterase), *A. tumefaciens* Q9ZI09, *A. tumefaciens* (radiobacter) ACA, *Prosthecobacter. dejongeii* RVM04532, *Rhizobium. loti* Q98MY5, *R. meliloti* Q92XZ1, *R. meliloti* Q9EV56, *R. rhizogenes* NF006, *R. rhizogenes* NF00602875, *R. solanacerarum* Q8XQI0, *Sinorhizobium meliloti* RSM02162, *S. meliloti* RSM05666, *Mesorhizobium loti* RML000301, *A. rhizogenes* Q9KWA6, and *A. rhizogenes* Q9KWB1.

Figure 2:
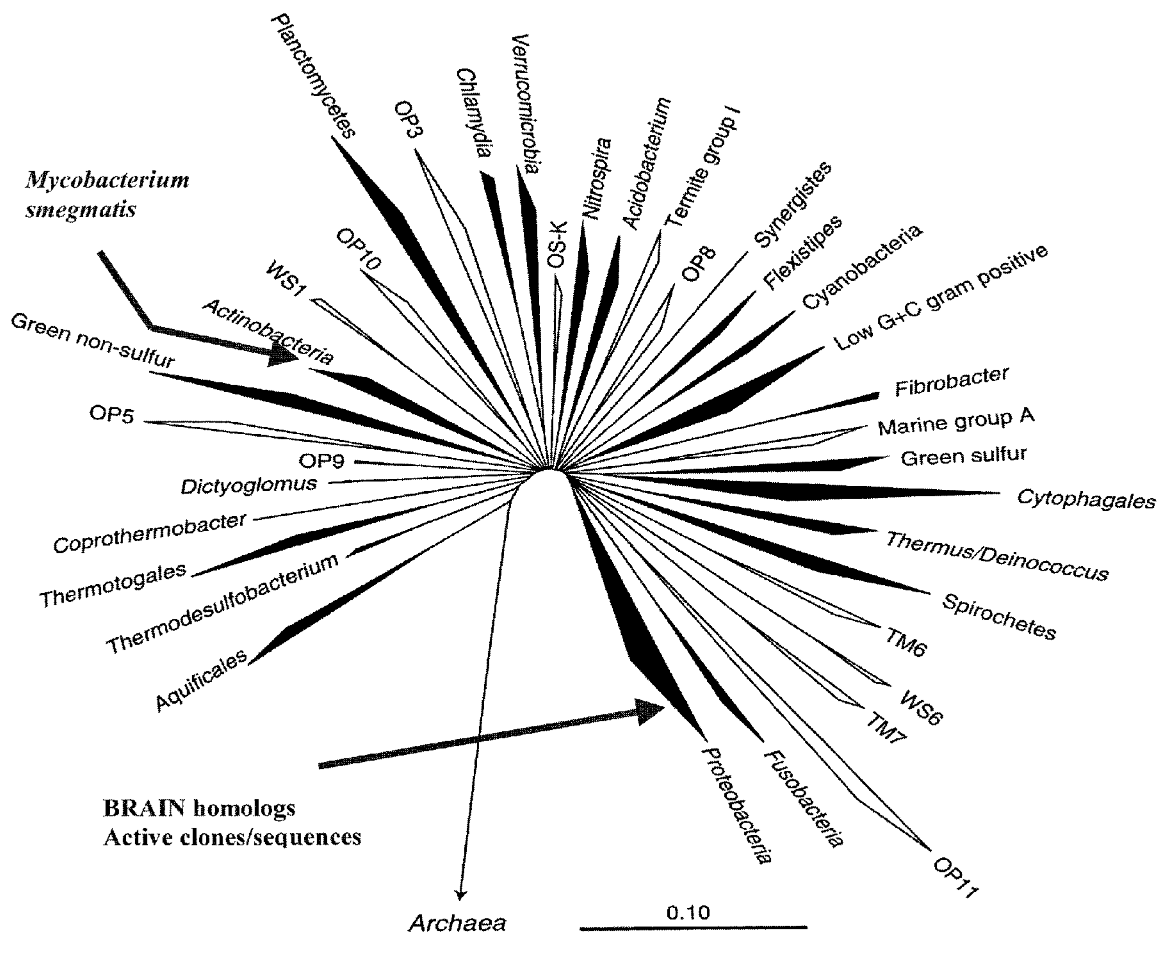
FIG. 2 provides an overview phylogenetic tree, showing the major branches of the bacteria and the origin of the active clones/sequences compared to *M. smegmatis.*

Based on these results, a homology tree of proteins with sequence homology (20-80%) to *M. smegmatis* perhydrolase was generated. As shown in FIG. 2, an enzyme in the family of lipolytic enzymes described by Upton and Buckley (supra) is that of *V. mimicus*. This phylogenetic tree was generated using the alignment program in Vector NTi (Informax, Invitrogen). The green arrow indicates *M. smegmatis* perhydrolase, the red arrow indicates *A. radiobacter* 7-ACA arylesterase, the blue arrow indicates *E. coli* TAP, and the black arrow indicates *A. aculeates* RGAE.

As further indicated in FIG. 2, the perhydrolase is not closely related to this enzyme. The perhydrolase and its closest relatives, *Prosthecobacter dejongeii* RVM04532, *R. rhizogenes* NF006, *A. rhizogenes* Q9KWA6, *R. meliloti* Q92XZ1, *S. meliloti* RSM02162, *A. rhizogenes* Q9KWB1 and *R. rhizogenes* NF00602875 come off their own branch (i.e., a branch that is different from the 7-ACA arylesterase-like proteins and the RGAE/TAP-like proteins). However, it is contemplated that some additional, more distantly related homologs will find use in the present invention due to perhydrolase activity or will serve as a suitable backbone for modification to the desired perhydrolase activity.

In addition to the sequence and homology analysis, environmental isolates were grown on a rich medium (N-MISO: g/l: glucose 10 g, yeast extract 10 g, $KNO_3$ 1.5, $KH_2PO_4$ 3.4 g, $NaH_2PO_4.H_20$ 3.4 g, Salt Solution C 10 ml [Salt Solution C: g/l: $MgSO_4.7H_2O$ 25, $FeSO_47H_2O$ 2.8, $MnSO_4H_2O$ 1.7, NaCl 0.6, $NaMoSO_4.2H_2O$, $ZnSO_4.7H_2O$ 0.06, in 0.1N HCl]), assayed and those positive for the transesterification reaction were purified as described in the Examples. This is one of the screening methods that can be used to identify perhydrolase. These data show that the present invention finds use in identification of additional enzymes with the desired perhydrolase activity.

Additional Investigations of Homologues

In addition to the above analyses, an enzyme library of novel "GDSL-type" esterases which are homologous to the prototype *M. smegmatis* perhydrolase was created. In order to identify new "GDSL"-type esterases, a sequence homology based screening procedure was established and used to screen libraries set up from complex metagenomic DNA (at BRAIN).

An enzyme library comprising 19 "GDSL"-type esterases (See, below) was developed. The sequences in this library were:

```
S248_M2bB11 (DNA)
                                          (SEQ ID NO: 70)
ATGTTCGCGCTTTGCACGGCCGCGTCAGCGGCCCCCGATCGCACCGTCGT

CTTTTTTGGGGACAGCCTGACCGCGGGGTACGGCCTCGATGACCCGCAGA

CCCAGTCCTACCCGGCCAGGATCCAGGAGAAGGTCGACGCCGCGGGCCTG

CGCTGGAAGGTCGTGAATGCCGGCCTCTCGGGCGAGACGAGCGCCGGCGG

CCTGCGGCGGGTCGACTGGGTGCTCGGCCAGCACATCGACGCCTTTGTCC

TGGCGCTTGGCGCCAACGATGGCCTGCGGGGGATCGACCCCCAGGTCACG

AGGGCCAATCTCCAGGAGATCATCAACCGGGTCCGCTCCCGGTGGCCCCG

CGCGGCGATCGTCATCGCCGGGATGAAAATGCCCCAGAGCATGGGACAGG

ACTACGCCGCGAATTTTGACCGGATCTTCCCCGGTCTCGCCGCGAGGAAT

TCGGCCACGCTCATCCCCTTTCTATTAGAAGGGGTCGCCGCCCATCCTAG

CCTCAACCAAGGCGACGGCATCCACCCGACGGCCGCCGGGGACGCACTCG

TTGCAGGGACCGTGTGGACGTACCTGCTTCCGATCCTGCGGTCAGCACAC

TAA

S248_M2bB11 (Amino Acid)
                                          (SEQ ID NO: 71)
MFALCTAASAAPDRTVVFFGDSLTAGYGLDDPQTQSYPARIQEKVDAAGL

RWKVVNAGLSGETSAGGLRRVDWVLGQHIDAFVLALGANDGLRGIDPQVT

RANLQEIINRVRSRWPRAAIVIAGMKMPQSMGQDYAANFDRIFPGLAARN

SATLIPFLLEGVAAHPSLNQGDGIHPTAAGDALVAGTVWTYLLPILRSAH

S248_M40cD4 (DNA)
                                          (SEQ ID NO: 72)
ATGCGCTTTGCTAAGCTCACTGCCGTCATCTTTGCCCTGATAGTCTTGCA

CAGCCCCCTTGCCGCCGCCGCGCCGCCCACCGTGATGGTGTTTGGCGACA

GTCTGACCGCCGGGTTGGGATTGCCGGCCGATGCTGCATTTCCGGCGCAG

CTCCAGGCAAAGCTGCACGATATGGGTATCCTGCAGAAATCGCCGCGCGC

GCCACCTCGGGGCAAACGACGGCCGGCGGGTTGGCGAGCCTTGCGGATGC

GCTGGCCGCAAAGCCGGATTTGGTGATCCTCGAACTCGGCGCCAATGACA

TGCTGCGCGCGGTCGATCCGGCCAGCGTGCGCGCCAATCTCGATGCAATG

ATGACGAAAATCCAGGCGAGCGGCGCTAAACTGCTGCTGACCGGAATGCA

GGCGGCGCCCAATTGGGGCGAGGACTATAAGCACGATTTCGACCGCCTTT

ATCCCGAGCTTGCGAAGGCGCACGGGGTGACGCTTTATCCATTCTTTCTT

GATGGGGTGGCGCTGGACCCGGCGCTGAACCAGGCGGATGGAATGCACCC

GAACGCCAAGGGGGTCGCCGTGATCGTCGACCGTATCGCGCCCGTCGTCG

CCAAGATGCTGAGAGGCCAGTCATAA

S248_M40cD4 (Amino Acid)
                                          (SEQ ID NO: 73)
MRFAKLTAVIFALIVLHSPLAAAAPPTVMVFGDSLTAGLGLPADAAFPAQ

LQAKLHDMGIPAEIAARATSGQTTAGGLASLADALAAKPDLVILELGAND

MLRAVDPASVRANLDAMMTKIQASGAKLLLTGMQAAPNWGEDYKHDFDRL

YPELAKAHGVTLYPFFLDGVALDPALNQADGMHPNAKGVAVIVDRIAPVV

AKMLRGQS
```

-continued

S248_M44aA5 (DNA)

(SEQ ID NO: 74)

ATGATCGCATGGCTTACCGGATGCGGCAGCGCAAAGACGCAACCGCAGCC
CGCAAGTTCCATCCCGCCATCCAGTATTCCAGCAACCGCAAAACCTGCGA
CAACGGATATCAGACCGATCATCGTTGCTTTCGGCGACAGCCTGACTGCA
GGATACGGCGTCAGTAGTGAACAAAGCTATCCGGCCAATCTTCAACGCGA
TCTGGATGCGCGTGGATATCATGCCCACGTCATCAACGAAGGCATCAGCG
GCAACACATCGAAAGACGGCGTTCTCAGGGCCCAGGCGATTGCGGCACTC
CATCCGGCTGTCGTCATCGTTGCCTTCGGCGGCAACGACGGTCTGCGTGG
CCTCCCCATCGGAGACACGGAAATGAATCTGGCAACGATCATCTCAACCA
TGCAGCATGCCCATGCCAAGGTAATTTTAGGCGGAATTACTTTGCCTCCC
AACTATGGCAGCGAATACATCGCCAAATTCAATGCGATCTATAAAAAGCA
GGCAGCCGCGTATCATGTGCCCCTGCTGCCCTTCATGCTGAAGGGGGTGT
ATGGCGTGCCCGGTTCCATGCAGAGCGACGGCATCCATCCGACCGCCAAG
GGCTGCCAGCAAGTGGCCAGAAACTTCCTGCCCTTGTTATTGCCGCTCCT
GCACAAATCAGGGAAGAAATCCATGGAGTCGAAAGCATTGTCTCGACGTC
ATTAA

S248_M44aA5 (Amino Acid)

(SEQ ID NO: 75)

MIAWLTGCGSAKTQPQPASSIPPSSIPATAKPATTDIRPIIVAFGDSLTA
GYGVSSEQSYPANLQRDLDARGYHAHVINEGISGNTSKDGVLRAQAIAAL
HPAVVIVAFGGNDGLRGLPIGDTEMNLATIISTMQHAHAKVILGGITLPP
NYGSEYIAKFNAIYKKQAAAYHVPLLPFMLKGVYGVPGSMQSDGIHPTAK
GCQQVARNFLPLLLPLLHKSGKKSMESKALSRRH

S261_M2aA12 (DNA)

(SEQ ID NO: 76)

ATGAAAAACATCCTTGCATTTGGCGACAGTCTGACCTGGGGTTTTGTGGC
CGGACAGGATGCGCGCCATCCGTTTGAAACCCGCTGGCCAAACGCATTGG
CGGCCGGCCTTGGGGGCAAAGCCCGCGTAATTGAAGAGGGTCAGAACGGC
CGCACTACGGTGTTCGACGATGCCGCCACCTTCGAATCTCGAAATGGCTC
GGTGGCATTGCCGCTGCTACTGATCAGCCACCAGCCGTTGGACCTGGTAA
TCATCATGCTCGGCACCAATGACATCAAGTTTGCCGCCCGCTGCCGCGCC
TTTGATGCTTCAATGGGCATGGAACGGCTGATCCAGATCGTCAGAAGTGC
CAACTACATGAAGGGCTACAAGATACCTGAAATCCTCATCATATCGCCGC
CCAGCCTCGTGCCGACGCAGGATGAATGGTTCAACGACCTCTGGGGCCAT
GCCATCGCCGAGTCAAAACTCTTCGCCAAGCACTACAAGCGCGTGGCCGA
AGAACTGAAAGTGCATTTCTTTGATGCAGGCACGGTGGCCGTCGCCGACA
AGACCGACGGCGGACATCTCGATGCTGTGAATACTAAAGCCATTGGCGTC
GCATTGGTGCCGGTGGTGAAATCAATACTCGCTCTCTAA

S261_M2aA12 (Amino Acid)

(SEQ ID NO: 77)

MKNILAFGDSLTWGFVAGQDARHPFETRWPNALAAGLGGKARVIEEGQNG
RTTVFDDAATFESRNGSVALPLLLISHQPLDLVIIMLGTNDIKFAARCRA
FDASMGMERLIQIVRSANYMKGYKIPEILIISPPSLVPTQDEWFNDLWGH
AIAESKLFAKHYKRVAEELKVHFFDAGTVAVADKTDGGHLDAVNTKAIGV
ALVPVVKSILAL

S279_M70aE8 (DNA)

(SEQ ID NO: 78)

ATGCCGAAAATAGCCAAACTCGCGCCGTCGGATGTGATCGTAGCTTTCGG
CGACAGTCTGACGTTCGGCACCGGCGCAACGGAAGCGGAGAGTTATCCCA
TCGTGCTCGCACAATTGATCGGTCGCACCGTGGTGCGCGCGGGTGTGCCG
GGTGAGGTAACCGAAGGCGGGCTTGCGCGCCTGACCGACGTTATCGAAGA
ACACAAGCCGAAGCTGATTATTGTTTGCCTGGGCGGCAACGACATGCTGC
GCAAGGTCCAGGAAGACCAGACCCGCGCCAATTTGCGCGCCATTATTAAA
ACCATCAAGGCGCAAGGCATCGCCGTGGTACTGGTCGGTGTGCCGAAGCC
CGCGCTGGTGACCAGTGCGCCGCCGTTCTACGAGGAGATCGCCAAAGAGT
TCGGTATCCCTTACGAAGGCAAGATTGTTACCGACGTGTTGTACCAACGC
GATCAGAAATCCGATTCCATACATCCCAATGCCAAAGGCTATCGGCGCAT
GGCCGAAGCGATAGCCACGCTGCTGAAAAAATCCGGAGCCATTTAA

S279:M70aE8 (Amino Acid)

(SEQ ID NO: 79)

MPKIAKLAPSDVIVAFGDSLTFGTGATEAESYPIVLAQLIGRTVVRAGVP
GEVTEGGLARLTDVIEEHKPKLIIVCLGGNDMLRKVQEDQTRANLRAIIK
TIKAQGIAVVLVGVPKPALVTSAPPEYEEIAKEFGIPYEGKIVTDVLYQR
DQKSDSIHPNAKGYRRMAEAIATLLKKSGAI

S279_M75bA2 (DNA)

(SEQ ID NO: 80)

ATGGAACGGACCGGCCGCGCTGGCGATCGGTGTCGGCGTGGGGCTGGCGA
GCCTGAGCCCGGTCGCGCTGGCGACGCCGCCGCGGGGCACCGTGCCGGTG
TTCACCCGATCGGGGACAGCCTGACGGACGAGTATTTTGAGCCGTTCTTC
CAGTGGGGGTTCTGCGGGAAGTCGTGGGCCGAGATTTTGGTGGAGACGGG
GCGGGCGAGCATGGGCCCGACGGCGCAGCAGGCGGGGATCAGCGAGCCGG
AGGGATGGTCGGATCCGCGGAACACGGGGTATCAGCACAACTGGGCGCGG
TACTCGTGGAGCTCCTCAGACGCGCTGACCGAGGAGTCGCCGGGGGCGAC
GCTGAGCGTGCTGCTTGGGGCGGAGTACGCGGTGGTGTTCATTGGGACCA
ACGACTTCAATCCGTCGTGGCCGGCGTATCAGAGCGTGTATCTGAGCCAG
TGGAGCGACGAGCAGATCGACACGTACGTGAACGGGGTGGTGCAGAACAT
CGCGCAGATGGTGGACTCGCTGAAGTCGGTCGGGGCGAAGGTGGTGCTTG
CGCCGCCGGTGGATTTTCAGTTCGCGGGGTTCCTGCGGAACTCATGCCCG
GATCCGATGCTGCGCGAGCAGGCGGGTATTCTGACACGGAAGTGCCACGA
CCGGGTGCGGTCGATGGCGCGGCAGAAGCACGTGGTGTTCGTGGACATGT
GGCGGCTGAACCGCGATTTGTTCGGCAACGGGTTCGCGATCAGCTACGGC
CTTCGGAACACGGTGCGCGTGGGGGACTCGGAGATCGGGCTGCAACTGGC
CGGGCTGACGGGATCGGCGGGGCTGGTTCCGGACGGGATCCATCCGCAGC
GGGTGGTGCAGGGGATCTGGGCGAATGCGTTCATCGTGGGTCTGAACGCG
CATGGGGCGAACATCGCGCCCATCGGCGAGGCGGAGATGTGCGCGATGGG
GGGGGTCGTGTACGGGGGAACGGACACGCTGGCGAACTTCCTGCCGCCGG

-continued

TCGCGGGCTACGTGGAGGACTTCCGCAACGCGGGGGACTTCGTGTGCACG

GCGGACTTCAACCATGACCTTGGCGTGACGCCGACGGACATCTTCGCGTT

CATCAACGCGTGGTTCATGAATGATCCCTCGGCGCGGATGAGCAACCCGG

AGCACACGCAGATCGAGGACATCTTCGTGTTTCTGAATCTGTGGCTGGTG

GGGTGCTAA

S279_M75bA2 (Amino Acid)

(SEQ ID NO: 81)

MERTGRAGDRCRRGAGEPEPGRAGDAAAGHRAGVHPIGDSLTDEYFEPFF

QWGFCGKSWAEILVETGRASMGPTAQQAGISEPEGWSDPRNTGYQHNWAR

YSWSSSDALTEESPGATLSVLLGAEYAVVFIGTNDFNPSWPAYQSVYLSQ

WSDEQIDTYVNGVVQNIAQMVDSLKSVGAKVVLAPPVDFQFAGFLRNSCP

DPMLREQAGILTRKCHDRVRSMARQKHVVFVDMWRLNRDLFGNGFAISYG

LRNTVRVGDSEIGLQLAGLTGSAGLVPDGIHPQRVVQGIWANAFIVGLNA

HGANIAPIGEAEMCAMGGVVYGGTDTLANFLPPVAGYVEDFRNAGDFVCT

ADFNHDLGVTPTDIFAFINAWFMNDPSARMSNPEHTQIEDIFVFLNLWLV

GC

M091_M4aE11 (DNA)

(SEQ ID NO: 82)

ATGAAGACCATTCTCGCCTATGGCGACAGCCTGACCTATGGGGCCAACCC

GATCCCGGGCGGGCCGCGGCATGCCTATGAGGATCGCTGGCCCACGGCGC

TGGAGCAGGGGCTGGGCGGCAAGGCGCGGGTGATTGCCGAGGGGCTGGGT

GGTCGCACCACGGTGCATGACGACTGGTTTGCGAATGCGGACAGGAACGG

TGCGCGGGTGCTGCCGACGCTGCTCGAGAGCCATTCGCCGCTCGACCTGA

TCGTCATCATGCTCGGCACCAACGACATCAAGCCGCATCACGGGCGGACG

GCCGGCGAGGCCGGGCGGGGCATGGCGCGGCTGGTGCAGATCATCCGCGG

GCACTATGCCGGCCGCATGCAGGACGAGCCGCAGATCATCCTCGTGTCGC

CGCCGCCGATCATCCTCGGCGACTGGGCGGACATGATGGACCATTTCGGC

CCGCACGAAGCGATCGCCACCTCGGTGGATTTCGCTCGCGAGTACAAGAA

GCGGGCCGACGAGCAGAAGGTGCATTTCTTCGACGCCGGCACGGTGGCGA

CGACCAGCAAGGCCGATGGCATCCACCTCGACCCGGCCAATACGCGCGCC

ATCGGGGCAGGGCTGGTGCCGCTGGTGAAGCAGGTGCTCGGCCTGTAA

M091_M4aE11 (Amino Acid)

(SEQ ID NO: 83)

MKTILAYGDSLTYGANPIPGGPRHAYEDRWPTALEQGLGGKARVIAEGLG

GRTTVHDDWFANADRNGARVLPTLLESHSPLDLIVIMLGTNDIKPHHGRT

AGEAGRGMARLVQIIRGHYAGRMQDEPQIILVSPPPIILGDWADMMDHFG

PHEAIATSVDFAREYKKRADEQKVHFFDAGTVATTSKADGIHLDPANTRA

IGAGLVPLVKQVLGL

Est105 (DNA)

(SEQ ID NO: 84)

ATGCGCACGCTTCACCGAAGCCTGCTCGCAAGCGCGGCCGCGCTTTTTCT

AGCGGCATCCGGCAACGCAACGGCGCAGTTCTCGAACGTCTATTTCTTCG

GCGACAGCCTGACCGACGCGGGTTCCTTCAAGCCTGTGCTGCCTCCTGGT

ACAGGATTATTCACGACGAATCCCGGCCCGGTATGGCCGCAGGTATTCGG

GGCGAACTACGGCGTCGCGGTGACGCCCGCAAACCAGGGTGGGACCGATT

-continued

ATGCGCAGGGTGGCGCGCGCGTGACGAGCCTGCCTGGCGTTCCGACGTCG

CAGCCGACCGGCAGCGCGGTACCGATCGCTACGCAGATTTCGCAGTTCCT

CGGCTCGGGTCCGGCGGATCCGAACGCATTCTATTCGGTGTGGGGCGGCG

CGAACGACATCTTTTTCCAGCTGGGGTTGGCGCAGGCGGGCATGGCGACG

CCGGCGCAGGTCCAGTCGGCCGTCGGCTTGGCCGCGGTCCAGCTGGCGCA

GGCAACTGCGGCGCTCAACGCCAGCGGCGCGCGATTCATCACGGTTATCA

ACGTGCCGGACATCGGTAAAACGCCGTTCGGCGTCGGCTCCGGTCAAGGA

GCGCAGATCACCGCTCTGTCGTCTTTCTTCAACAGCACGCTGTTCGGCGC

GCTCGACGCCACGGGCATCCAGACGATGCGCGTGAACGGGTTCGCGGTGC

TGAACGAGGTGGTCGCGGACCCGGCGGCTTATGGCTTCGCGAATGCATCA

ACGCCAGCGTGCGGGGCCACGCCATCGCTCGTCTGCACGTCGGCGAACTT

CGTCACGCCCTTGGCCGCGCAGACCTTCCTCTTCGCAGACGGCGTTCACC

CCACCACGGCCGGGCACGCCCTCATCGCCCAAGCGGTCCAGGCGATGATC

ACCGGTCCCCAACAGATGGCGGCGTTGGGCGACGCCCCGCTCGCCGTCGA

GCAGGCCAACTTCCGCGCGCTCGACAACCGCATGTGGTCGAGCCTCAATG

CGCCGCGCAGCCCGGGCAAGCTCCAGGGTTGGGCGGCCTACGACTACAGC

CACACGGACCTGCAGGCGGGACCGACCAATGGCAGCGGACACATGAACAC

CGTTGCGGTCGGGGTCGACATGAAAGTCTCCGATCATATGCTCGCCGGCG

CGATGTTCGGCTATACCAACACCAAGGGCGACTTCGGCGGCCCCGGCGGC

GGATACACACTGAAGCAGCCTGTGGGCACTGCCTATGCGGGTTACGGCGT

GGGCCCTTGGTATGTCGGCGCGACGCTCGGCACAGGTGGCCTCGACTACT

CGGACGTCACGCGCGCCATCCCGCTTGGCTTGGCGGTTCGCACCGAGAGC

GCCGAGGCCCGAGGCTACGAGTTCACGGGCCGGATCCTCGGCGGCTACTG

GTTCACGATGCGCGACCTGATGCACGGGCCGTACGCGCGTCTCGCGTGGA

CGAAGGCCGTCGTCAAGCGGTTTTCCGAGGAGAGCACCGACAGCACGGCG

TTGAACTACGACAGGCAGGAGCGCAAGCAACTGCTGTGGAGCCTCGGATG

GCAACTCGCCGGCAACGTCGGCAGCATCCGTCCCTACGCGCGGGCGACCT

GGGAGATCGACTCCAAGGATCAGGACCGCAGCGTTGGCGCATCGTCGGTC

ACGCTGGGCGGCTTTTACAGTGTTCCGGTCGCGAAGCCGGACAATAGCTA

TGCGCTCTTCAGCCTCGGCGCGAGTACCGAGCTCGGGAGCGTCACCGGGT

TTGTCGCGGGCTCGGCCACCGCAGGCCGGGCGGATGCCAACTATTGGGCG

GTCACGGTCGGCCTGCGGATGCCGTTGTAG

Est105 (Amino Acid)

(SEQ ID NO: 85)

MRTLHRSLLASAAALFLAASGNATAQFSNVYFFGDSLTDAGSFKPVLPPG

TGLFTTNPGPVWPQVFGANYGVAVTPANQGGTDYAQGGARVTSLPGVPTS

QPTGSAVPIATQISQFLGSGPADPNAFYSVWGGANDIFFQLGLAQAGMAT

PAQVQSAVGLAAVQLAQATAALNASGARFITVINVPDIGKTPFGVGSGQG

AQITALSSFFNSTLFGALDATGIQTMRVNGFAVLNEVVADPAAYGFANAS

TPACGATPSLVCTSANFVTPLAAQTFLFADGVHPTTAGHALIAQAVQAMI

TGPQQMAALGDAPLAVEQANFRALDNRMWSSLNAPRSPGKLQGWAAYDYS

-continued

HTDLQAGPTNGSGHMNTVAVGVDMKVSDHMLAGAMFGYTNTKGDFGGPGG

GYTLKQPVGTAYAGYGVGPWYVGATLGTGGLDYSDVTRAIPLGLAVRTES

AEARGYEFTGRILGGYWFTMRDLMHGPYARLAWTKAVVKRFSEESTDSTA

LNYDRQERKQLLWSLGWQLAGNVGSIRPYARATWEIDSKDQDRSVGASSV

TLGGFYSVPVAKPDNSYALFSLGASTELGSVTGFVAGSATAGRADANYWA

VTVGLRMPL

Est114 (DNA)

(SEQ ID NO: 86)

ATGGGGCGATCGAGAGTTCTGAAGGCTGTTTTCCTGGTGGCGTGCCTTGT

GGGTCGGCTCGCGGCGCATGCCGAGGCGTCGCCCATCGTGGTCTACGGCG

ATAGCCTCTCTGACAACGGCAATCTGTTTGCGCTCACCGGCGGTGTCGCG

CCGCCCTCGCCGCCGTACTTCAACGGACGGTTTTCTAATGGCCCGGTGGC

CGTGGAGTATCTCGCGGCCGCGCTGGGATCTCCGCTGATCGATTTCGCGG

TCGGCGGGGCGACGACCGGCCTCGGCGTCAACGGCGATCCCGGTGGTTCG

CCGACGAGTCTCGGCGCGGCGGGATTGCCGGGGCTTCAGACGACATTCGC

CGCCACGCAAGGCACGCTGGGTCCGTACGTTGGTGGTCTCTTCGTGGTGT

GGGCGGGTCCGAACGACTTCTTGTCGCCCTCGCCGCTTGACACGAACGCT

TTTCAGATTGCGAACCGGGCCGTGTCCAACATCCTCGGCGTGGTGGCATC

ACTTCAGGCACTCGGCGTCGAGCGCATCCTCGTCCCCGGCATGCCCGATC

TCGGTCTGACGCCCGCTCTTCAGCCCATCGCAGGCGCAGCCACCGCGTTC

ACCGATTTGTTCAACTCGATGCTGCGCGCGGGCTTGCCGAACGACGTGCT

GTACCTGGACACGGCGACAATCTTCCGATCGATCGTGGCAGACCCTGGGG

CCTACGGCTTGACCAACGTGACCACGCCGTGCCTGATTGGTGCGACCGTC

TGCGCGAATCCGGATCAGTACCTGTTCTGGGATGGTATTCATCCTACGAC

GGCGGGGCACGCGATCTTGGGCAATGCCCTCGTCGCCCAGGCAGTCCCCG

AGCCCGCGACCATGGTGCTCGTGCTGACGGGTCTGTCCATGCACGTGATT

GCGCGCCGGCGGCGGGCGTAA

Est114 (Amino Acid)

(SEQ ID NO: 87)

MGRSRVLKAVFLVACLVGRLAAHAEASPIVVYGDSLSDNGNLFALTGGVA

PPSPPYFNGRFSNGPVAVEYLAAALGSPLIDFAVGGATTGLGVNGDPGGS

PTSLGAAGLPGLQTTFAATQGTLGPYVGGLFVVWAGPNDFLSPSPLDTNA

FQIANRAVSNILGVVASLQALGVERILVPGMPDLGLTPALQPIAGAATAF

TDLFNSMLRAGLPNDVLYLDTATIFRSIVADPGAYGLTNVTTPCLIGATV

CANPDQYLFWDGIHPTTAGHAILGNALVAQAVPEPATMVLVLTGLSMHVI

ARRRRA

*Sinorhizobium meliloti* SmeI (SMa1993) (DNA)

(SEQ ID NO: 88)

ATGACAATCAACAGCCATTCATGGAGGACGTTAATGGTGGAAAAGCGCTC

AGTACTGTGCTTTGGGGATTCGCTGACATGGGGCTGGATTCCGGTGAAGG

GATCCTCACCGACCTTGCGCTATCCCTATGAACAACGGTGGACCGGCGCA

ATGGCCGCGAGGCTTGGCGACGGTTACCACATCATCGAAGAGGGGCTGAG

CGCCCGCACCACCAGCCTCGACGACCCCAACGACGCGCGGCTCAACGGCA

GCACCTACCTGCCCATGGCACTCGCCAGCCACCTCCCACTCGACCTCGTC

ATCATCATGCTGGGCACGAACGACACGAAATCCTATTTCCACCGCACGCC

TTACGAGATCGCCAACGGCATGGGCAAGCTAGTCGGCCAGGTGCTGACCT

GCGCCGGTGGCGTCGGCACGCCATATCCCGCGCCGAAGGTGCTTGTCGTC

GCTCCGCCGCCGCTCGCGCCGATGCCCGACCCGTGGTTCGAAGGCATGTT

CGGCGGCGGCTACGAGAAGTCGAAGGAACTCTCCGGCCTCTACAAGGCGC

TTGCCGATTTCATGAAGGTCGAGTTTTTCGCCGCCGGTGATTGCATTTCC

ACCGATGGGATCGACGGCATTCACCTCTCGGCGGAAACCAACATCAGACT

CGGGCACGCGATCGCGGACAAAGTTGCGGCGTTGTTC

*Sinorhizobium meliloti* SmeI (SMa1993)
(Amino Acid)

(SEQ ID NO: 89)

MTINSHSWRTLMVEKRSVLCFGDSLTWGWIPVKGSSPTLRYPYEQRWTGA

MAARLGDGYHIIEEGLSARTTSLDDPNDARLNGSTYLPMALASHLPLDLV

IIMLGTNDTKSYFHRTPYEIANGMGKLVGQVLTCAGGVGTPYPAPKVLVV

APPPLAPMPDPWFEGMFGGGYEKSKELSGLYKALADFMKVEFFAAGDCIS

TDGIDGIHLSAETNIRLGHAIADKVAALF

*Sinorhizobium meliloti* SmeII (Q92XZ1) (DNA)

(SEQ ID NO: 90)

ATGGAGGAGACAGTGGCACGGACCGTTCTATGCTTCGGAGATTCCAACAC

TCACGGCCAGGTACCTGGCCGCGGACCGCTTGATCGCTACCGACGCGAAC

AGCGCTGGGGCGGTGTTCTGCAAGGCCTGCTCGGCCCGAACTGGCAGGTT

ATCGAAGAAGGCCTGAGCGGACGCACGACCGTGCATGACGATCCGATCGA

AGGTTCGCTCAAGAACGGCCGGACCTATCTGCGCCCCTGTCTGCAGAGCC

ATGCACCACTCGACCTTATCATCATTATGCTCGGCACCAATGACCTGAAG

CGGCGCTTCAACATGCCACCGTCCGAGGTCGCAATGGGCATCGGCTGTCT

CGTGCACGATATCCGAGAACTCTCGCCCGGCCGGACCGGCAACGATCCCG

AAATCATGATCGTCGCCCCGCCGCCGATGCTGGAAGATCTCAAGGAATGG

GAGTCGATTTTCTCAGGCGCACAGGAAAAATCTCGCAAGCTGGCGCTGGA

GTTCGAGATAATGGCGGATTCTCTGGAGGCGCATTTCTTCGACGCCGGTA

CGGTCTGCCAGTGTTCGCCGGCCGATGGCTTCCACATCGACGAGGATGCC

CACCGCCTGCTCGGCGAGGCTCTCGCCCAGGAAGTGCTGGCGATCGGGTG

GCCCGATGCGTAA

*Sinorhizobium meliloti* SmeII (Q92XZ1)
(Amino Acid)

(SEQ ID NO: 91)

MEETVARTVLCFGDSNTHGQVPGRGPLDRYRREQRWGGVLQGLLGPNWQV

IEEGLSGRTTVHDDPIEGSLKNGRTYLRPCLQSHAPLDLIIIMLGTNDLK

RRFNMPPSEVAMGIGCLVHDIRELSPGRTGNDPEIMIVAPPPMLEDLKEW

ESIFSGAQEKSRKLALEFEIMADSLEAHFFDAGTVCQCSPADGFHIDEDA

HRLLGEALAQEVLAIGWPDA

*Sinorhizobium meliloti* SmeIII (Q9EV56) (DNA)

(SEQ ID NO: 92)

ATGAAGACAGTCCTTTGCTACGGTGACAGTCTGACCTGGGGATACGATGC

AACCGGTTCCGGCCGGCATGCGCTGGAGGACCGTTGGCCGAGCGTGCTGC

AGAAGGCGCTCGGTTCGGACGCGCATGTCATCGCCGAAGGGCTGAACGGG

-continued

CGGACGACCGCCTATGACGACCATCTCGCCGATTGCGACCGGAACGGCGC

GCGTGTCCTCCCGACGGTCCTGCACACCCACGCGCCACTCGATCTCATCG

TGTTCATGCTCGGCTCGAACGACATGAAGCCGATCATTCACGGCACCGCT

TTCGGCGCGGTGAAGGGCATCGAGCGCCTCGTCAATCTGGTGCGCAGGCA

CGACTGGCCGACGGAAACGGAGGAGGGGCCCGAGATTCTCATCGTCTCGC

CGCCGCCGCTCTGCGAGACGGCCAACAGCGCCTTTGCCGCCATGTTCGCG

GGCGGGGTCGAGCAATCCGCAATGCTGGCGCCGCTTTATCGCGATCTCGC

CGACGAGCTCGACTGCGGCTTCTTCGACGGCGGATCGGTGGCCAGGACGA

CGCCGATCGACGGTGTCCACCTCGACGCGGAGAACACCCGGGCGGTCGGC

AGAGGGTTGGAGCCTGTCGTGCGGATGATGCTCGGGCTTTAA

*Sinorhizobium meliloti* SmeIII (Q9EV56)
(Amino Acid)

(SEQ ID NO: 93)

MKTVLCYGDSLTWGYDATGSGRHALEDRWPSVLQKALGSDAHVIAEGLNG

RTTAYDDHLADCDRNGARVLPTVLHTHAPLDLIVFMLGSNDMKPIIHGTA

FGAVKGIERLVNLVRRHDWPTETEEGPEILIVSPPPLCETANSAFAAMFA

GGVEQSAMLAPLYRDLADELDCGFFDGGSVARTTPIDGVHLDAENTRAVG

RGLEPVVRMMLGL

*Agrobacterium tumefaciens* Atu III
(AAD02335) (DNA)

(SEQ ID NO: 94)

ATGGTGAAGTCGGTCCTCTGCTTTGGCGATTCCCTCACCTGGGGATCAAA

TGCGGAAACGGGTGGCCGGCACAGCCATGACGATCTTTGGCCGAGCGTCT

TGCAGAAGGCGCTCGGTCCTGACGTGCATGTGATTCACGAAGGTCTGGGT

GGTCGCACCACCGCCTATGACGACAACACCGCCGATTGCGACCGCAACGG

CGCGCGGGTTCTTCCGACGTTGTTGCACAGCCATGCGCCGCTGGATCTGG

TGATTGTCATGCTCGGGACCAACGACCTGAAGCCGTCAATCCATGGATCG

GCGATCGTTGCCATGAAGGGTGTCGAAAGGCTGGTGAAGCTCACGCGCAA

CCACATCTGGCAGGTGCCGGACTGGGAGGCGCCTGACGTGCTGATCGTCG

CACCGCCGCAGCTGTGTGAAACGGCCAATCCGTTCATGGGCGCGATCTTT

CGTGATGCGATCGATGAATCGGCGATGCTGGCGTCCGTTTACCGGGACCT

TGCCGACGAGCTTGATTGCGGCTTTTTCGATGCGGGTTCCGTCGCCCGAA

CGACGCCGGTGGATGGCGTTCATCTCGATGCTGAAAATACGCGGGCCATC

GGGCGGGGGCTGGAGCCCGTCGTTCGCATGATGCTCGGACTTTAA

*Agrobacterium tumefaciens* Atu III
(AAD02335) (Amino Acid)

(SEQ ID NO: 95)

MVKSVLCFGDSLTWGSNAETGGRHSHDDLWPSVLQKALGPDVHVIHEGLG

GRTTAYDDNTADCDRNGARVLPTLLHSHAPLDLVIVMLGTNDLKPSIHGS

AIVAMKGVERLVKLTRNHIWQVPDWEAPDVLIVAPPQLCETANPFMGAIF

RDAIDESAMLASVYRDLADELDCGFFDAGSVARTTPVDGVHLDAENTRAI

GRGLEPVVRMMLGL

*Mesorhizobium loti* Mlo I (Q98MY5) (DNA)

(SEQ ID NO: 96)

ATGAAGACGGTGCTTTGCTACGGCGACTCGCTGACCTGGGGCTACAATGC

CGAAGGCGGCCGCCATGCGCTGGAAGACCGCTGGCCGAGCGTGCTGCAAG

CAGCGTTAGGCGCCGGCGTGCAAGTGATTGCCGATGGCCTCAACGGCCGC

ACCACGGCCTTCGACGATCATCTGGCCGGTGCTGATCGCAACGGCGCCAG

GCTGCTGCCGACGGTCCTGACGACGCACGCGCCGATCGACCTGATCATCT

TCATGCTCGGCGCCAACGACATGAAGCCTTGGATCCACGGCAATCCGGTC

GCAGCCAAGCAAGGCATCCAGCGGTTGATCGACATCGTGCGTGGTCACGA

CTACCCGTTCGACTGGCCGGCGCCGCAGATCCTGATCGTCGCGCCGCCTG

TAGTCAGCCGCACCGAAAATGCCGACTTCAAGGAAATGTTCGCCGGTGGC

GATGACGCCTCGAAGTTTTTGGCACCGCAATATGCCGCGCTCGCCGACGA

AGCCGGCTGTGGCTTCTTCGACGCCGGCAGCGTGGCCCAAACCACACCGC

TCGATGGCGTTCACCTCGATGCCGAAAACACGCGAGAAATCGGCAAGGCG

CTGACGCCGATCGTGCGCGTCATGCTGGAATTGTAA

*Mesorhizobium loti* Mlo I (Q98MY5)
(Amino Acid)

(SEQ ID NO: 97)

MKTVLCYGDSLTWGYNAEGGRHALEDRWPSVLQAALGAGVQVIADGLNGR

TTAFDDHLAGADRNGARLLPTVLTTHAPIDLIIFMLGANDMKPWIHGNPV

AAKQGIQRLIDIVRGHDYPFDWPAPQILIVAPPVVSRTENADFKEMFAGG

DDASKFLAPQYAALADEAGCGFFDAGSVAQTTPLDGVHLDAENTREIGKA

LTPIVRVMLEL

*Moraxella bovis* Mbo (AAK53448) (DNA)

(SEQ ID NO: 98)

ATGAAAAAATCCGCCTTTGCCAAATACTCAGCACTTGCCCTAATGGTTGG

GATGTGCCTGCACACCGCTTACGCCAAGGAGTTTAGCCAAGTCATCATTT

TTGGGGACAGCTTGTCCGATACAGGTCGCCTAAAAGATATGGTCGCCCGA

AAAGATGGCACCCTTGGCAACACCTTACAGCCATCTTTTACCACCAACCC

CGACCCTGTATGGTCAAGCTTATTTGCCCAAAGTTATGGCAAAACCGCCA

GTCCCAACACGCCTGACAATCCCACTGGCACTAACTATGCCGTGGGCGGA

GCTCGCTCTGGCTCGGAGGTCAATTGGAATGGTTTTGTGAATGTACCCTC

CACCAAAACGCAAATCACCGACCATTTGACCGCCACAGGTGGCAAAGCCG

ACCCTAATACCCTGTATGCCATTTGGATTGGCTCTAATGACTTAATTTCA

GCTTCTCAAGCCACCACAACAGCCGAAGCCCAAAACGCCATTAAAGGTGC

GGTAACTCGCACCGTGATAGACATCGAAACACTCAATCAAGCAGGGGCGA

CAACCATTTTGGTGCCAAATGTGCCTGATTTGAGCCTCACGCCCCGAGCC

ATCTATGGCGAAAGCCTCATGGCAGGCGTGCAAGACAAAGCCAAACTCGC

CTCAAGTCTGTATAATAGCGGTCTGTTTGAAGCATTAAATCAATCCACCG

CCAACATCATCCCTGCCAACACCTTTGCCCTACTCCAAGAAGCGACCACA

AATAAAGAAGCCTTTGGTTTTAAAAACACGCAAGGCGTGGCGTGTCAAAT

GCCCGCTCGTACCACAGGGGCGGATGATGTGGCTTCTACTTCCTTGGCAT

GTACCAAAGCCAATCTTATAGAAAACGGGGCAAATGACACCTACGCCTTT

GCCGATGACATTCACCCATCGGGACGCACGCACCGCATTTTGGCACAGTA

TTACCGTTCTATCATGGACGCCCCTACTCACATGGGTAAACTCTCAGGCG

AGCTTGTCAAAACAGGTTCAGCCCACGACCGTCATGTTTACCGTCAGCTT

GACAGGCTTAGTGGCTCACAGCACAGCATTTGGGCAAACGTCTATGCCAG

-continued

CGACCGTACCGACCCCACCACCCAAATCGGCTTGGACGTGGCAGGTTCAT

CAAGCCATACAGGGGCGTATCTGAGCCACCAAAACCAAGATTATGTGCTG

GATGACACCCTATCATCAGATGTCAAAACCATTGGCATGGGGCTGTATCA

TCGCCATGACATCGGCAATGTCCGTCTAAAAGGCGTGGCAGGTATCGACC

GACTTAGCGTGGATACGCACCGCCATATCGACTGGGAGGGGACAAGCCGT

TCGCACACCGCAGATACCACCGCCAGACGTTTTCATGCAGGGCTACAAGC

CAGCTATGGCATAGACATGGGCAAAGCCACCGTGCGTCCGCTTATCGGCG

TACATGCCCAAAAAGTCAAAGTAAATGACATGACCGAGAGCGAATCAACT

TTATCCACCGCCATGCGTTTTGGCGAGCAAGAACAAAAGTCCCTACAAGG

CGAGATTGGCGTCGATGTGGCTTATCCGATTAGCCCTGCTTTGACTCTGA

CGGGCGGTATCGCTCACGCTCATGAGTTTAACGATGATGAACGCACCATT

AATGCCACTTTAACCTCCATTCGTGAATACACGAAGGGCTTTAATACAAG

CGTTAGCACCGACAAATCTCACGCCACCACCGCTCATCTGGGCGTACAAG

GGCAACTTGGCAAGGCAAATATTCATGCAGGCGTTCACGCCACCCACCAA

GACAGCGATACAGACGTGGGTGGTTCGCTTGGGGTTCGCTTGATGTTTTA

A

*Moraxella bovis* Mbo (AAK53448) (Amino Acid)

(SEQ ID NO: 99)

MKKSAFAKYSALALMVGMCLHTAYAKEFSQVIIFGDSLSDTGRLKDMVAR

KDGTLGNTLQPSFTTNPDPVWSSLFAQSYGKTASPNTPDNPTGTNYAVGG

ARSGSEVNWNGFVNVPSTKTQITDHLTATGGKADPNTLYAIWIGSNDLIS

ASQATTTAEAQNAIKGAVTRTVIDIETLNQAGATTILVPNVPDLSLTPRA

IYGESLMAGVQDKAKLASSLYNSGLFEALNQSTANIIPANTFALLQEATT

NKEAFGFKNTQGVACQMPARTTGADDVASTSLACTKANLIENGANDTYAF

ADDIHPSGRTHRILAQYYRSIMDAPTHMGKLSGELVKTGSAHDRHVYRQL

DRLSGSQHSIWANVYASDRTDPTTQIGLDVAGSSSHTGAYLSHQNQDYVL

DDTLSSDVKTIGMGLYHRHDIGNVRLKGVAGIDRLSVDTHRHIDWEGTSR

SHTADTTARRFHAGLQASYGIDMGKATVRPLIGVHAQKVKVNDMTESEST

LSTAMRFGEQEQKSLQGEIGVDVAYPISPALTLTGGIAHAHEFNDDERTI

NATLTSIREYTKGFNTSVSTDKSHATTAHLGVQGQLGKANIHAGVHATHQ

DSDTDVGGSLGVRLMF

*Chromobacterium violaceum* Cvi (Q7NRP5) (DNA)

(SEQ ID NO: 100)

ATGCGCTCTATCGTCTGCAAAATGCTGTTCCCTTTGTTGCTGCTGTGGCA

GCTGCCCGCCCTGGCCGCCACCGTGCTGGTGTTCGGCGACAGCCTGTCCG

CCGGCTACGGCCTGGCCCCGGGCCAGGGATGGGCGGCGCTGCTGGCGCGC

GACCTCTCGCCCCGGCACAAGGTGGTCAACGCCAGCGTGTCCGGCGAAAC

CAGCGCCGGCGGCCTGTCCAGGCTGCCCGACGCGCTCGCCCGCCACCAGC

CCGACGTGCTGGTGCTGGAACTCGGCGCCAACGATGGCCTGCGCGGCCTG

CCGATGGCTGACATGAGGCGCAACCTGCAGCGGATGATAGACCTGGCCCA

GGCGCGCAAGGCCAAGGTGCTGCTGGTGGGCATGGCGCTGCCACCCAACT

ATGGCCCCCGCTACGGCGCCGAGTTCCGCGCCGTTTATGACGATTTGGCC

-continued

CGCCGCAACCGCCTGGCCTACGTGCCGCTGCTGGTCGAGGGCTTCGCCGG

CGACCTCGGCGCCTTCCAGCCCGACGGCCTGCATCCCCGCGCGGAGAAGC

AGGCCACCATGATGCGCACGGTCAAGGCAAAACTGCCAGTGAAATAA

*Chromobacterium violaceum* Cvi (Q7NRP5) (Amino Acid)

(SEQ ID NO: 101)

MRSIVCKMLFPLLLLWQLPALAATVLVFGDSLSAGYGLAPGQGWAALLAR

DLSPRHKVVNASVSGETSAGGLSRLPDALARHQPDVLVLELGANDGLRGL

PMADMRRNLQRMIDLAQARKAKVLLVGMALPPNYGPRYGAEFRAVYDDLA

RRNRLAYVPLLVEGFAGDLGAFQPDGLHPRAEKQATMMRTVKAKLPVK

*Vibrio vulnificus* Vvu (AA007232) (DNA)

(SEQ ID NO: 102)

ATGTTTTTCCTTTCTAGCGTCGCACACGCAACCGAGAAAGTGTTAATTCT

TGGCGACAGCCTAAGTGCAGGATACAACATGTCTGCAGAGCAGGCTTGGC

CTAATTTGTTACCAGAAGCATTGAATACATACGGAAAAAACGTAGAAGTG

ATCAACGCCAGTATCTCTGGAGACACAACCGGCAATGGACTATCTCGTCT

GCCTGAGTTGTTAAAAACGCACTCACCAGACTGGGTGCTTATTGAGTTGG

GTGCCAATGATGGCTTGCGAGGTTTCCCGCATAAAGTGATCTCTTCAAAC

CTTTCGCGAATGATTCAACTCAGTAAAGCCTCAGACGCTAAAGTCGCATT

GATGCAAATTCGTGTACCGCCTAACTATGGCAAGCGCTACACCGATGCAT

TTGTCGAACTCTACCCTACGCTTGCTGAACATCACCAAGTCCCGTTGCTC

CCCTTTTTCTTAGAGGAAGTGATCGTGAAACCGGAATGGATGATGCCTGA

TGGCTTACACCCAATGCCCGAAGCTCAGCCTTGGATCGCTCAATTTGTTG

CAAAAACGTTTTACAAACATCTCTAA

*Vibrio vulnificus* Vvu (AA007232) (Amino Acid)

(SEQ ID NO: 103)

MFFLSSVAHATEKVLILGDSLSAGYNMSAEQAWPNLLPEALNTYGKNVEV

INASISGDTTGNGLSRLPELLKTHSPDWVLIELGANDGLRGFPHKVISSN

LSRMIQLSKASDAKVALMQIRVPPNYGKRYTDAFVELYPTLAEHHQVPLL

PFFLEEVIVKPEWMMPDGLHPMPEAQPWIAQFVAKTFYKHL

*Ralstonia eutropha* Reu (ZP00166901) (DNA)

(SEQ ID NO: 104)

ATGCCATTGACCGCGCCGTCTGAAGTCGATCCGCTGCAAATCCTGGTCTA

TGCCGATTCGCTTTCGTGGGGCATCGTGCCCGGCACCCGCCGGCGGCTTC

CCTTCCCGGTTCGCTGGCCAGGCCGGCTCGAACTCGGCCTGAACGCCGAC

GGCGGCGCCCCGGTCCGCATCATCGAGGACTGCCTGAACGGCCGGCGCAC

CGTCTGGGACGACCCATTCAAACCGGGCCGCAACGGCTTGCAAGGGCTGG

CGCAGCGCATCGAGATCCATTCCCCGGTGGCGCTCGTGGTTTTGATGCTG

GGCAACAACGATTTCCAGTCCATGCATCCGCACAACGCCTGGCATGCGGC

ACAGGGCGTCGGCGCGCTGGTCCACGCCATCCGGACGGCGCCGATCGAAC

CGGGAATGCCGGTGCCGCCGATCCTGGTGGTGGTGCCGCCGCCGATCCGC

ACGCCCTGCGGGCCGCTCGCGCCCAAGTTCGCCGGCGGCGAACACAAGTG

GGCAGGCCTGCCCGAGGCGCTGCGCGAACTGTGCGCCACTGTCGACTGCT

CGCTGTTCGATGCGGGTACCGTGATCCAGAGCAGTGCCGTCGACGGCGTA

-continued

CACCTTGACGCCGATGCCCATGTCGCCCTGGGCGATGCCCTGCAACCGGT

CGTTCGTGCGCTGCTCGCCGAATCCTCGGGACATCCCTCCTAA

*Ralstonia eutropha* Reu (ZP00166901)
(Amino Acid)
(SEQ ID NO: 105)

MPLTAPSEVDPLQILVYADSLSWGIVPGTRRRLPFPVRWPGRLELGLNAD

GGAPVRIIEDCLNGRRTVWDDPFKPGRNGLQGLAQRIEIHSPVALVVLML

GNNDFQSMHPHNAWHAAQGVGALVHAIRTAPIEPGMPVPPILVVVPPPIR

TPCGPLAPKFAGGEHKWAGLPEALRELCATVDCSLFDAGTVIQSSAVDGV

HLDADAHVALGDALQPVVRALLAESSGHPS

*Salmonella typhimurium* Stm (AAC38796) (DNA)
(SEQ ID NO: 106)

ATGACCCAAAAGCGTACCCTGCTAAAATACGGCATACTCTCGCTGGCGCT

GGCCGCGCCATTATCTGCCTGTGCGTTTGACTCTCTTACGGTGATTGGCG

ATAGCCTTAGCGATACCGGTAATAACGGTCGCTGGACCTGGGATAGTGGT

CAAAATAAGCTCTACGACGAACAGTTGGCCGAACGATATGGGCTGGAATT

AAGCCCTTCCAGCAATGGCGGCTCTAATTATGCCGCCGGCGGCGCGACGG

CGACCCCGGAATTAAACCCGCAGGATAATACCGCGGATCAGGTACGGCAG

TGGCTTGCCAAAACGGGGGGAAAAGCCGACCACAACGGTTTGTATATTCA

CTGGGTCGGCGGAAACGATCTGGCGGCGGCCATCGCGCAACCAACCATGG

CACAGCAAATAGCCGGTAATAGCGCCACTAGCGCGGCGGCGCAGGTAGGG

CTGTTACTGGATGCCGGCGCCGGGCTGGTCGTGGTGCCAAACGTACCGGA

TATTAGTGCGACGCCAATGCTTCTGGAGGCGGTAATCACCGCTGGGCTGG

GCGCAGCGGCGCCCCCGGCGCTAAAAGCGGCGTTAGATGCGCTGGCGGAG

GGCGCTACGCCCGATTTCGCCAGTCGGCAACAGGCGATCCGCAAGGCGCT

GCTGGCGGCGGCTGCAACGGTAAGCAGCAATCCATTTATTCAGCAACTGC

TCGTTGAACAACTGCTGGCGGGCTATGAAGCGGCGGCAGGGCAGGCGTCA

GCTCTGACCGATTATTATAATCAGATGGAAGAGAAGGGGCTGGAGCAACA

CGGCGGCAATATAGCCCGTGCCGATATCAACGGCCTCTTTAAGGAAATTC

TTGCCAACCCGCAGGCGTTTGGTCTGACAAATACCGTAGGTATGGCCTGC

CCGCCTGGCGTATCCGCTTCGGCGTGCTCCTCGGCAATGCCTGGATTTAA

TGCGTCGCAGGACTATGTGTTTGCCGATCATTTACATCCCGGTCCGCAGG

TCCATACCATTATTGCGCAATATATTCAGTCGATCATTGCCGCGCCGGTA

CAGGCGACATACCTGAACCAAAGCGTTCAGTCGATGGCGCAAGGCAGTCG

TACCACGCTTGACAGCCGTTATCAGCAGCTTCGCCAGGGGGAAAATCCTG

TTGGTTCGCTGGGCATGTTCGGCGGATACAGCGGGGGATATCAACGTTAT

GATAATAATGAGGCCGACGGGAACGGTAATCATAATAATCTGACGGTTGG

CGTCGATTATCAGCTTAACGAGCAGGTTCTGCTGGGAGGGCTGATAGCCG

GTTCTCTGGATAAGCAACATCCTGACGATAATTATCGTTATGATGCCCGC

GGTTTTCAGGCCGCCGTATTCAGCCATTTACGCGCCGGTCAGGCGTGGCT

GGATAGCGATTTACACTTTCTGTCCGCTAAATTCAGTAACATTCAGCGCA

GTATAACGCTCGGTGCGCTAAGACGGGTGGAAGAGGGCGAAACCAACGGT

CGGCTGTCGGGCGCGAGCTTAACCAGCGGTTATGATTTTGTCATGGTGCC

-continued

GTGGTTAACGACCGGACCGATGCTGCAATATGCATGGGATTACAGCCACG

TTAATGGTTATAGCGAGAAGCTCAATACCAGTACATCAATGCGTTTTGGT

GACCAAAACGCCCATTCGCAGGTGGGTAGCGCGGGTTGGCGTCTGGATCT

TCGCCACAGCATCATTCACTCCTGGGCGCAGATTAATTATCGCCGTCAGT

TTGGCGATGATACGTATGTGGCGAACGGCGGCCTTAAATCGACCGCGCTG

ACGTTTAGCCGCGACGGAAAAACGCAGGATAAAAACTGGGTTGATATCGC

GATTGGCGCAGATTTTCCGCTGTCGGCAACGGTGTCCGCTTTCGCCGGGC

TGTCGCAAACGGCAGGGTTAAGCGATGGCAATCAAACCCGTTATAACGTT

GGGTTTAGCGCCCGATTTTAA

*Salmonella typhimurium* Stm (AAC38796)
(Amino Acid)
(SEQ ID NO: 107)

MTQKRTLLKYGILSLALAAPLSACAFDSLTVIGDSLSDTGNNGRWTWDSG

QNKLYDEQLAERYGLELSPSSNGGSNYAAGGATATPELNPQDNTADQVRQ

WLAKTGGKADHNGLYIHWVGGNDLAAAIAQPTMAQQIAGNSATSAAAQVG

LLLDAGAGLVVVPNVPDISATPMLLEAVITAGLGAAAPPALKAALDALAE

GATPDFASRQQAIRKALLAAAATVSSNPFIQQLLVEQLLAGYEAAAGQAS

ALTDYYNQMEEKGLEQHGGNIARADINGLFKEILANPQAFGLTNTVGMAC

PPGVSASACSSAMPGFNASQDYVFADHLHPGPQVHTIIAQYIQSIIAAPV

QATYLNQSVQSMAQGSRTTLDSRYQQLRQGENPVGSLGMFGGYSGGYQRY

DNNEADGNGNHNNLTVGVDYQLNEQVLLGGLIAGSLDKQHPDDNYRYDAR

GFQAAVFSHLRAGQAWLDSDLHFLSAKFSNIQRSITLGALRRVEEGETNG

RLSGASLTSGYDFVMVPWLTTGPMLQYAWDYSHVNGYSEKLNTSTSMRFG

DQNAHSQVGSAGWRLDLRHSIIHSWAQINYRRQFGDDTYVANGGLKSTAL

TFSRDGKTQDKNWVDIAIGADFPLSATVSAFAGLSQTAGLSDGNQTRYNV

GFSARF

In total, nine of the new "GDSL"-type esterases were identified in 6 metagenomic libraries and BRAIN's esterase/lipase library. Eight of these genes were heterologously expressed in *E. coli* and the resulting enzymes analyzed for activity in the assays described herein. The characterization of these enzymes for perhydrolase activity revealed that one displayed the desired activity. A second one was predicted to show this activity due to the presence of amino acids conserved among this group of enzymes.

Comparison of the sequences of enzymes for which the presence or absence of the desired perhydrolase activity was determined led to the identification of 19 amino acid positions which were conserved among the enzymes which displayed the desired perhydrolase activity. Thus, it is contemplated that these conserved amino acids are essential for the perhydrolase reaction and/or is a structural feature of perhydrolase enzymes.

One of the identified structural motifs ("G/ARTT") conserved among esterases with the desired perhydrolase activity was used to design degenerate primers which provided the means to focus the screening on true perhydrolases among "GDSL"-type esterases. Indeed, the use of these "G/ARTT" primers led to the identification of enzymes with the desired perhydrolase activity from the metagenome. However, it is not intended that the use of the metagenome be limited to any particular assay method. Indeed, it is contemplated that the metagenome be searched by assaying for a particular enzyme activity or activities desired (e.g., perhydrolysis and/or acyltransferase (cofactor dependent or independent) activity). In addition, screening using poly and/or monoclonal anti-sera directed against a protein of interest finds use in the present invention. In additional embodiments, the metagenome is searched using degenerate primer sets based on the sequence of the protein of interest.

In addition, the knowledge of the structure/function relationship of perhydrolases allowed searching for these enzymes in genome sequences of cultivable microorganisms. Of 16 "GDSL"-type esterases identified in different bacterial isolates, the corresponding genes of 10 enzymes were amplified and heterologously expressed in *E. coli*. The resulting enzyme samples of seven clones were analyzed using the assays described herein. Of five samples characterized to date, 4 enzymes indeed showed the desired activity and all results confirmed the proposed relationship between primary structural determinants and the function of perhydrolases. Thus, an enzyme library of 19, "GDSL"-type esterases comprising at least 6 perhydrolases with the desired perhydrolase activity was set up. The identified correlation between the structure and function of perhydrolases provides a definition of the sequence space used by enzymes with the desired perhydrolase activity.

Comparisons were made of protein sequences of enzymes for which the absence or presence of the desired perhydrolase activity. This revealed a correlation between the presence of certain amino acids and the capability to perform perhydrolase reactions. This knowledge was used to identify enzymes containing these conserved amino acids in sequenced genomes from cultivable microorganisms. The following enzymes were identified and experiments to amplify the genes from the genomic DNA of the corresponding strains using specific primers were performed.

TABLE 1

"GDSL"-type Esterases with a "GRTT"-Motif From Bacterial Isolates

| Isolate | Protein Identifier | Acronym | Amplicon | Expression Vector |
|---|---|---|---|---|
| *Sinorhizobium meliloti* | Sma1993 | Sme I | yes | pLO_SmeI |
| *Sinorhizobium meliloti* | Q92XZ1 | Sme II | yes | pET26_SmeII |
| *Sinorhizobium meliloti* | Q9EV56 | Sme III | yes | pET26_SmeIII |
| *Agrobacterium rhizogenes* | Q9KWB1 | Arh I | no | — |
| *Agrobacterium rhizogenes* | Q9KWA6 | Arh II | no | — |
| *Agrobacterium tumefaciens* | AAD02335 | Atu III | yes | pET26_AtuIII |
| *Mesorhizobium loti* | Q98MY5 | Mlo I | yes | pET26_Mlo |
| *Mesorhizobium loti* | ZP_00197751 | Mlo II | no | — |
| *Ralstonia solanacearum* | Q8XQI0 | Rso | no | — |
| *Ralstonia eutropha* | ZP_00166901 | Reu | yes | n.d. |
| *Moraxella bovis* | AAK53448 | Mbo | yes | pET26_Mbo |
| *Burkholderia cepacia* | ZP_00216984 | Bce | no | — |
| *Chromobacterium violaceum* | Q7NRP5 | Cvi | yes | pET26_Cvi |
| *Pirellula* sp. | NP_865746 | Psp | n.d. | n.d. |
| *Vibrio vulnificus* | AA007232 | Vvu | yes | pET26_Vvu |
| *Salmonella typhimurium* | AAC38796 | Sty | yes | pET26_Sty |

In the cases of *A. rhizogenes, M. loti* (enzyme II), *R. solanacearum* and *B. cepacia* no amplicon could be generated. It was thought that this was probably due to genetic differences between the strains used in this investigation and those used for the sequencing of the genes deposited in the public domain databases. One reason might be that the corresponding genes are located on plasmids which are not present in the strains used in this investigation. However, it is not intended that the present invention be limited to any particular mechanism or theory.

The amplicons from all other strains were sequenced. In many cases there were differences between the sequence from the databases and the sequence determined during the development of the present invention. By sequencing two clones from independent amplifications, mutations introduced by the polymerase could be nearly excluded. The sequences of the genes and the deduced amino acid sequences of "GDSL"-type esterases with a "GRTT"-motif or variations from bacterial isolates are provided below:

SMa1993_*Sinorhizobium meliloti* (Sme I) (SEQ ID NOS:88 and 89)

Q92XZ1_*Sinorhizobium meliloti* (Sme II) (SEQ ID NOS:90 and 91)

Q9EV56_*Sinorhizobium meliloti* (Sme III) (SEQ ID NOS: 92 and 93)

AAD02335_*Agrobacterium tumefaciens* (Atu III) (SEQ ID NOS: 94 and 95)

Q98MY5_*Mesorhizobium loti* (Mlo I) (SEQ ID NOS:96 and 97)

ZP_00166901_*Ralstonia eutropha* (Reu) (SEQ ID NOS: 104 and 105)

AAK53448_*Moraxella bovis* (Mbo) (SEQ ID NOS: 98 and 99)

Q7NRP5_*Chromobacterium violaceum* (Cvi) (SEQ ID NOS:100 and 101)

AA007232_*Vibrio vulnificus* (Vvu) (SEQ ID NOS:102 and 103)

AAC38796_*Salmonella typhimurium* (Stm) (SEQ ID NOS: 106 and 107)

Q9KWB1_*Agrobacterium rhizogenes* (Arh I)

(SEQ ID NO: 108)

```
MICHKGGEEMRSVLCYGDSNTHGQIPGGSPLDRYGPNERWPGVLRRELGS

QWYVIEEGLSGRTTVRDDPIEGTMKNGRTYLRPCLMSHAILDLVIIMLGT

NDLKARFGQPPSEVAMGIGCLVYDIRELAPGPGGKPPEIMVVAPPPMLDD

IKEWEPIFSGAQEKSRRLALEFEIIADSLEVHFFDAATVASCDPCDGFHI

NREAHEALGTALAREVEAIGWR
```

(SEQ ID NO: 109)

```
ATGATTTGCCATAAAGGTGGGGAGGAAATGCGGTCAGTCTTATGCTACGG

CGACTCGAATACGCACGGCCAGATTCCGGGGGGCTCACCGCTCGACCGAT

ACGGGCCGAACGAGCGCTGGCCTGGCGTTTTGAGACGGGAGCTTGGAAGC

CAGTGGTATGTGATCGAGGAGGGCCTGAGTGGCCGCACGACGGTTCGCGA

CGATCCGATCGAGGGCACGATGAAAAACGGCCGGACCTACCTGCGTCCGT

GCCTCATGAGCCACGCGATCCTCGATCTCGTGATTATCATGCTCGGGACG

AACGACCTGAAAGCGCGCTTCGGTCAACCGCCATCGGAAGTGGCGATGGG

GATCGGCTGCCTCGTCTACGATATCAGGGAGCTGGCGCCCGGACCGGGCG

GCAAGCCCCCCGAAATCATGGTGGTTGCTCCGCCGCCGATGCTGGACGAT
```

-continued

ATCAAGGAATGGGAACCCATATTTTCCGGCGCCCAGGAGAAATCCCGGCG

TCTCGCGCTTGAGTTTGAAATTATTGCTGATTCGCTTGAAGTACACTTCT

TTGACGCCGCGACCGTCGCATCGTGTGATCCTTGCGATGGTTTTCACATC

AACCGGGAAGCGCATGAAGCCTTGGGAACAGCGCTTGCCAGGGAAGTGGA

GGCGATCGGTTGGAGATGATGA

Q9KWA6_*Agrobacterium rhizogenes* (Arh II)

(SEQ ID NO: 110)

MAESRSILCFGDSLTWGWIPVPESSPTLRYPFEQRWTGAMAAALGDGYSI

IEEGLSARTTSVEDPNDPRLNGSAYLPMALASHLPLDLVIILLGTNDTKS

YFRRTPYEIANGMGKLAGQVLTSAGGIGTPYPAPKLLIVSPPPLAPMPDP

WFEGMFGGGYEKSLELAKQYKALANFLKVDFLDAGEFVKTDGCDGIHFSA

ETNITLGHAIAAKVEAIFSQEAKNAAA (SEQ ID NO: 111)

ATGGCAGAGAGCCGCTCAATATTATGTTTTGGGGATTCACTCACATGGGG

TTGGATTCCGGTACCGGAGTCGTCGCCGACGCTCAGATATCCCTTTGAGC

AGCGCTGGACCGGTGCAATGGCTGCGGCACTCGGTGACGGCTATTCAATC

ATCGAGGAAGGCCTTTCCGCCCGCACGACCAGCGTCGAGGATCCGAACGA

TCCCAGGCTGAACGGCAGCGCCTACCTGCCGATGGCGCTCGCCAGCCATC

TGCCGCTCGATCTCGTCATCATCCTTCTCGGCACCAACGACACCAAGTCC

TATTTCCGCCGCACGCCCTATGAGATCGCCAACGGCATGGGCAAGCTTGC

CGGACAGGTTCTGACCTCGGCCGGCGGGATCGGCACGCCCTACCCTGCCC

CGAAGCTTCTGATCGTTTCGCCGCCGCCGCTCGCTCCCATGCCTGACCCG

TGGTTCGAAGGCATGTTCGGTGGCGGTTACGAAAAGTCGCTCGAACTCGC

AAAGCAGTACAAGGCGCTCGCCAACTTCCTGAAGGTCGACTTCCTCGACG

CCGGCGAGTTTGTAAAGACCGACGGCTGCGATGGAATCCATTTCTCCGCC

GAGACGAACATCACGCTCGGCCATGCGATCGCGGCGAAGGTCGAAGCGAT

TTTCTCACAAGAGGCGAAGAACGCTGCGGCTTAG

ZP_00197751_*Mesorhizobium loti* (Mlo II)

(SEQ ID NO: 112)

MKTILCYGDSLTWGYDAVGPSRHAYEDRWPSVLQGRLGSSARVIAEGLCG

RTTAFDDWVAGADRNGARILPTLLATHSPLDLVIVMLGTNDMKSFVCGRA

IGAKQGMERIVQIIRGQPYSFNYKVPSILLVAPPPLCATENSDFAEIFEG

GMAESQKLAPLYAALAQQTGCAFFDAGTVARTTPLDGIHLDAENTRAIGA

GLEPVVRQALGL (SEQ ID NO: 113)

ATGAAGACCATCCTTTGTTACGGTGACTCCCTCACTTGGGGCTATGATGC

CGTCGGACCCATGAAGACCATCCTTTGTTACGGTGACTCCCTCACTTGGG

GCTATGATGCCGTCGGACCCTCACGGCATGCTTATGAGGATCGATGGCCC

TCCGTACTGCAAGGCCGCCTCGGTAGCAGTGCGCGGGTGATCGCCGAGGG

GCTTTGCGGCCGCACAACTGCGTTTGACGACTGGGTCGCTGGTGCGGACC

GGAACGGTGCGCGCATCCTGCCGACGCTTCTTGCGACCCATTCACCGCTT

GACCTCGTTATCGTCATGCTCGGGACGAACGACATGAAATCGTTCGTTTG

CGGGCGCGCTATCGGCGCCAAGCAGGGGATGGAGCGGATCGTCCAGATCA

TCCGCGGGCAGCCTTATTCCTTCAATTATAAGGTACCGTCGATTCTTCTC

-continued

GTGGCGCCGCCGCCGCTGTGCGCTACCGAAAACAGCGATTTCGCGGAAAT

TTTTGAAGGTGGCATGGCTGAATCGCAAAAGCTCGCGCCGCTTTATGCCG

CGCTGGCCCAGCAAACCGGATGCGCCTTCTTCGATGCAGGCACTGTGGCC

CGCACGACACCGCTCGACGGTATTCACCTCGATGCTGAAAACACGCGCGC

CATTGGTGCCGGCCTGGAGCCGGTGGTCCGCCAAGCGCTTGGATTGTGA

Q8XQI0_*Ralstonia solanacearum* (Rso)

(SEQ ID NO: 114)

MQQILLYSDSLSWGIIPGTRRRLPFAARWAGVMEHALQAQGHAVRIVEDC

LNGRTTVLDDPARPGRNGLQGLAQRIEAHAPLALVILMLGTNDFQAIFRH

TAQDAAQGVAQLVRAIRQAPIEPGMPVPPVLIVVPPAITAPAGAMADKFA

DAQPKCAGLAQAYRATAQTLGCHVFDANSVTPASRVDGIHLDADQHAQLG

RAMAQVVGTLLAQ (SEQ ID NO: 115)

ATGCAACAGATCCTGCTCTATTCCGACTCGCTCTCCTGGGGCATCATCCC

CGGCACCCGCCGGCGCCTGCCGTTCGCCGCCCGCTGGGCCGGGGTCATGG

AACACGCGCTGCAGGCGCAAGGGCACGCCGTGCGCATCGTCGAAGACTGC

CTCAATGGACGCACCACGGTGCTCGACGATCCCGCGCGGCCGGGGCGCAA

CGGACTGCAGGGGCTCGCGCAGCGGATCGAAGCGCACGCCCCGCTTGCCC

TGGTCATCCTGATGCTCGGCACCAACGACTTCCAGGCGATCTTCCGGCAC

ACCGCCCAGGACGCGGCGCAAGGCGTGGCGCAGCTGGTGCGGGCCATCCG

CCAGGCGCCGATCGAACCCGGCATGCCGGTGCCGCCCGTGCTGATCGTGG

TGCCGCCGGCCATCACCGCGCCGGCCGGGGCGATGGCCGACAAGTTTGCC

GACGCGCAGCCCAAGTGCGCCGGCCTTGCGCAGGCCTATCGGGCAACGGC

GCAAACGCTAGGCTGCCACGTCTTCGATGCGAACAGCGTCACGCCGGCCA

GCCGCGTGGACGGCATCCACCTCGATGCCGACCAGCATGCGCAGCTGGGC

CGGGCGATGGCGCAGGTCGTCGGGACGCTGCTTGCGCAATAA

ZP_00216984 *Burkholderia cepacia* (Bce)

(SEQ ID NO: 116)

ATGACGATGACGCAGAAAACCGTGCTCTGCTACGGCGATTCGAACACGCA

TGGCACACGCCCGATGACGCATGCTGGCGGACTGGGGCGGTTTGCACGCG

AAGAACGCTGGACCGGCGTGCTGGCGCAAACGCTCGGTGCGAGCTGGCGG

GTCATTGAAGAAGGGTTGCCCGCGCGTACGACCGTGCATGACGATCCGAT

CGAAGGCCGGCACAAGAATGGTTTGTCGTATCTGCGCGCGTGCGTCGAAA

GCCACTTGCCCGTCGATGTCGTCGTGCTGATGCTCGGGACCAACGATCTG

AAGACACGCTTCTCGGTCACGCCCGCCGACATCGCGACATCGGTCGGCGT

ATTGCTTGCCAAGATCGCTGCGTGCGGCGCCGGTCCGTCCGGTGCGTCAC

CGAAGCTCGTGCTGATGGCGCCTGCGCCGATCGTCGAGGTCGGATTCCTC

GGCGAGATCTTTGCGGGCGGCGCAGCGAAGTCGCGGCAGCTCGCGAAGCG

GTACGAACAGGTGGCAAGCGATGCCGGTGCGCACTTTCTCGATGCCGGCG

CGATCGTCGAGGTGAGCCCGGTGGATGGCGTTCACTTCGCGGCCGATCAG

CATCGTGTGCTCGGGCAGCGGGTCGCTGCCCTTCTGCAGCAGATTGCGTA

A

-continued (SEQ ID NO: 117)
MTMTQKTVLCYGDSNTHGTRPMTHAGGLGRFAREERWTGVLAQTLGASWR

VIEEGLPARTTVHDDPIEGRHKNGLSYLRACVESHLPVDVVVLMLGTNDL

KTRFSVTPADIATSVGVLLAKIAACGAGPSGASPKLVLMAPAPIVEVGFL

GEIFAGGAAKSRQLAKRYEQVASDAGAHFLDAGAIVEVSPVDGVHFAADQ

HRVLGQRVAALLQQIA

NP_865746 *Pirellula sp* (Psp)
(SEQ ID NO: 118)
MHSILIYGDSLSWGIIPGTRRRFAFHQRWPGVMEIELRQTGIDARVIEDC

LNGRRTVLEDPIKPGRNGLDGLQQRIEINSPLSLVVLFLGTNDFQSVHEF

HAEQSAQGLALLVDAIRRSPFEPGMPTPKILLVAPPTVHHPKLDMAAKFQ

NAETKSTGLADAIRKVSTEHSCEFFDAATVTTTSVVDGVHLDQEQHQALG

TALASTIAEILADC (SEQ ID NO: 119)
ATGCATTCAATCCTCATCTATGGCGATTCTCTCAGTTGGGGAATCATTCC

CGGCACGCGTCGTCGCTTCGCGTTCCATCAGCGTTGGCCGGGCGTCATGG

AGATTGAACTGCGACAAACTGGAATCGATGCCCGCGTCATCGAAGACTGC

CTCAATGGCCGACGAACCGTCTTGGAAGATCCAATCAAACCCGGACGCAA

TGGCCTGGATGGTTTGCAGCAACGGATCGAAATCAATTCACCTCTGTCAC

TGGTCGTGCTCTTTCTGGGGACCAACGATTTCCAGTCCGTCCACGAATTC

CATGCCGAGCAATCGGCACAAGGACTCGCACTGCTTGTCGACGCCATTCG

TCGCTCCCCTTTCGAACCAGGAATGCCGACACCGAAAATCCTGCTTGTCG

CACCACCGACGGTTCACCACCCGAAACTTGATATGGCGGCGAAGTTCCAA

AACGCGGAAACGAAATCGACGGGACTCGCAGATGCGATTCGCAAGGTCTC

AACAGAACACTCCTGCGAATTCTTCGATGCGGCCACGGTCACCACAACAA

GTGTCGTCGACGGAGTCCATCTCGATCAAGAACAACATCAAGCACTCGGT

ACCGCACTGGCATCGACAATCGCTGAAATACTAGCAGACTGTTGA

As indicated above, the above sequences are the protein sequences and the coding sequences of "GDSL-type" esterases with a "GRTT"-motif or similar motifs from different bacterial isolates. The DNA sequences represent the target-DNA from which specific primers were deduced. All amplicons were ligated as NdeI/XhoI-fragments to pET26 thereby eliminating the pelB-leader sequence of this vector.

All of the "GDSL-type" esterases from these isolates were expressed in *E. coli* Rosetta (DE3) at 28° C. The expression was induced by addition of 100 μM IPTG at an $O.D._{580}=1$ and the cells were harvested 20 h after induction. Only the cells expressing the enzymes from *M. bovis* and *S. typhimurium* were collected 4 h after induction, since previous experiments had shown that the highest activity could be obtained at this point of time. Table 2 summarizes the expression experiments.

TABLE 2

Expression and Characterization of "GDSL"-type Esterases From Bacterial Isolates for Perhydrolase Activity

| Strain | Enzyme | Expression Level[2] | Solubility[3] | Activity[4] | Perhydrolase Activity | GRTT-Motif |
|---|---|---|---|---|---|---|
| S. meliloti | Sme I | +++ | ++ | 5770.0 | yes | ARTT |
| S. meliloti | Sme II | +++ | +++ | 85.0 | yes | GRTT |
| S. meliloti | Sme III | +++ | ++ | 746.5 | n.d. | GRTT |
| A. tumefaciens | Atu III | n.d.[5] | n.d. | n.d. | n.d. | GRTT |
| M. loti | Mlo I | +++ | ++ | 1187.3 | yes | GRTT |
| M. bovis[1] | Mbo | + | n.d. | 25.2 | yes | ARTT |
| C. violaceum | Cvi | + | + | 2422.7 | n.d. | GETS |
| V. vulnificus | Vvu | n.d. | n.d. | n.d. | n.d. | GDTT |
| R. eutropha | Reu | n.d. | n.d. | n.d. | n.d. | GRRT |
| S. typhimurium[1] | Sty | + | n.d. | 17.2 | no | SRTT |

[1] outer membrane localized autotransporter protein
[2] expression level: + moderate overexpression; ++ strong overexpression; +++ very strong overexpression as judged from SDS-PAGE-analysis
[3] as judged by SDS-PAGE-analysis
[4] towards p-nitrophenyl butyrate
[6] not determined With the exception of the enzyme from *S. typhimurium*, all other enzymes tested showed the desired perhydrolase activity, confirming the correlation between the presence of certain conserved amino acids an the capability to perform perhydrolase reactions. Although the enzyme from *S. typhimurium* contains the GRTT-motif, it is different from the other enzymes by the location of this motif downstream from block V. In all other enzymes, this motif is located between block I and III, indicating that it might have a different function in the enzyme from *S. typhimurium*. Thus, the absence of perhydrolase activity in the enzyme from *S. typhimurium* also supports the identified structure/function-relationship of the perhydrolases provided by the present invention.

Screening of New "GDSL-Type" Esterases in Metagenome Libraries
  i) Library S279
    The full-length sequence of the gene from clone M75bA2 was completed, as provided below.

```
  1 tgggcggttt cgcggagtcg agcagggaga gatgctcctg ggtcgtacga gttggtacgg
      g   r   f   r   g   v   e   q   g   e   m   l   l   g   r   t   s   w   y

 61 aggcatcgtt gaagatctca cgcctgcttg aatgcgcgcg gatatggaac ggaccggccg
      g   g   i   v   e   d   l   t   p   a   -   m   r   a   d   m   e   r   t   g

121 cgctggcgat cggtgtcggc gtggggctgg cgagcctgag cccggtcgcg ctggcgacgc
      r   a   g   d   r   c   r   r   g   a   g   e   p   e   p   g   r   a   g   d

181 cgccgcgggg caccgtgccg gtgttcaccc gatcggggac agcctgacgg acgagtattt
      a   a   a   g   h   r   r   g   v   h   p   i   **g   d   s   l**   t   d   e   y

241 tgagccgttc ttccagtggg ggttctgcgg gaagtcgtgg gccgagattt tggtggagac
      f   e   p   f   f   q   w   g   f   c   g   k   s   w   a   e   i   l   v   e

301 ggggcgggcg agcatgggcc cgacggcgca gcaggcgggg atcagcgagc cggagggatg
      t   g   r   a   s   m   g   p   t   a   q   q   a   g   i   s   e   p   e   g
```

-continued

```
 361 gtcggatccg cggaacacgg ggtatcagca caactgggcg cggtactcgt ggagctcctc
     w  s  d  p   r  n  t   g  y  q   h  n  w  a   r  y  s   w  s  s

 421 agacgcgctg accgaggagt cgccgggggc gacgctgagc gtgctgcttg gggcggagta
     s  d  a  l   t  e  e   s  p  g   a  t  l  s   v  l  l   g  a  e

 481 cgcggtggtg ttcattggga ccaacgactt caatccgtcg tggccggcgt atcagagcgt
     y  a  v  v   f  i  g   t  n  d   f  n  p  s   w  p  a   y  q  s

 541 gtatctgagc cagtggagcg acgagcagat cgacacgtac gtgaacgggg tggtgcagaa
     v  y  l  s   q  w  s   d  e  q   i  d  t  y   v  n  g   v  v  q

 601 catcgcgcag atggtggact cgctgaagtc ggtcggggcg aaggtggtgc ttgcgccgcc
     n  i  a  q   m  v  d   s  l  k   s  v  g  a   k  v  v   l  a  p

 661 ggtggatttt cagttcgcgg ggttcctgcg gaactcatgc ccggatccga tgctgcgcga
     p  v  d  f   q  f  a   g  f  l   r  n  s  c   p  d  p   m  l  r

 721 gcaggcgggt attctgacac ggaagtgcca cgaccgggtg cggtcgatgg cgcggcagaa
     e  q  a  g   i  l  t   r  k  c   h  d  r  v   r  s  m   a  r  q

 781 gcacgtggtg ttcgtggaca tgtggcggct gaaccgcgat ttgttcggca acgggttcgc
     k  h  v  v   f  v  d   m  w  r   l  n  r  d   l  f  g   n  g  f

 841 gatcagctac ggccttcgga acacggtgcg cgtgggggac tcggagatcg ggctgcaact
     a  i  s  y   g  l  r   n  t  v   r  v  g  d   s  e  i   g  l  q

 901 ggccgggctg acgggatcgg cggggctggt tccggacggg atccatccgc agcgggtggt
     l  a  g  l   t  g  s   a  g  l   v  p  d  g   i  h  p   q  r  v

 961 gcaggggatc tgggcgaatg cgttcatcgt gggtctgaac gcgcatgggg cgaacatcgc
     v  q  g  i   w  a  n   a  f  i   v  g  l  n   a  h  g   a  n  i

1021 gcccatcggc gaggcggaga tgtgcgcgat ggggggggtc gtgtacgggg gaacggacac
     a  p  i  g   e  a  e   m  c  a   m  g  g  v   v  y  g   g  t  d

1081 gctggcgaac ttcctgccgc cggtcgcggg ctacgtggag gacttccgca acgcggggga
     t  l  a  n   f  l  p   p  v  a   g  y  v  e   d  f  r   n  a  g

1141 cttcgtgtgc acggcggact tcaaccatga ccttggcgtg acgccgacgg acatcttcgc
     d  f  v  c   t  a  d   f  n  h   d  l  g  v   t  p  t   d  i  f

1201 gttcatcaac gcgtggttca tgaatgatcc ctcggcgcgg atgagcaacc cggagcacac
     a  f  i  n   a  w  f   m  n  d   p  s  a  r   m  s  n   p  e  h

1261 gcagatcgag gacatcttcg tgtttctgaa tctgtggctg gtggggtgct gaggcagagt
     t  q  i  e   d  i  f   v  f  l   n  l  w  i   v  g  c   -  g  r

1321 gggaaggggg tcagcccact tcgcgcgtct ggaagaggat gacggcgacg gagaggaaga
     v  g  r  g   s  a  h   f  a  r   l  e  e  d   d  g  d   g  e  e
```

In the sequence of S279_M75bA2 provided above (DNA, SEQ ID NO:80; and amino acid sequence, SEQ ID NO:81), the coding sequence running from position 104 through 1312 is shown on a grey background. Conserved structural motifs are shown underlined and in bold.

The derived amino acid sequence showed the highest homology to a hypothetical protein (Y17D7A.2) from *Caenorhabditis elegans* (BlastP2; swisspir), although with a very high E-value of 2.5 (i.e., indicating a non-reliable hit). The fact that no esterase is among the homologous proteins identified by the BlastP2-analysis indicates that this enzyme is a rather unusual "GDSL-type" esterase. Furthermore, the enzyme is characterized by unusually long peptides between the N-terminus and the "GDSL"-motif and the "DXXH"-motif of block V (containing the active site aspartic acid and histidine) and the C-terminus. The very C-terminal sequence shows similarity to a membrane lipoprotein lipid attachment site. A corresponding signal sequence of lipoproteins was not identified. The gene encoding M75bA5 was amplified but no further efforts were taken for this enzyme since it did not have the conserved amino acids typical of the perhydrolase of the present invention.

ii) Library S248

The clone carrying the sequence-tag SP7_3j5h which could have been part of a gene encoding a "GDSL"-type esterase was identified (M31bA11), and the sequence was elongated. This facilitated the determination that this sequence did not encode a "GDSL-type" esterase, because block V could not be identified. The generation of this amplicon can be explained by an "unspecific" hybridization of primer 5h with the first mismatches at nucleotides 10, 14 and 15 from the 3-terminus of the primer. The sequence showed the highest homology to a hypothetical protein (KO3E5.5) from *Caenorhabditis elegans* with an E-value of 1.6, indicating a non-reliable hit. The sequence-tag from clone S248_M31bA11 is provided below.

```
  1 cggaattatc atgctgggtt ttaatgacca gcgcgagagg atcaacgaca acctcgatta
       r  n  y  h  a  g  f  -  -  p  a  r  e  d  q  r  q  p  r  l
      g  i  i  m  l  q  f  n  d  q  r  e  r  i  n  d  n  l  d
       e  l  s  c  w  v  l  m  t  s  a  r  g  s  t  t  t  s  i

 61 ctgggacgcc taccactccg tcctgggcga gagacagttt tattccggca attccaagat
       l  g  r  l  p  l  r  p  g  r  e  t  v  l  f  r  q  f  q  d
     y  w  d  a  y  h  s  v  l  g  e r  q  f  y  s  g  n  s  k
      t  g  t  p  t  t  p  s  w  a  r d  s  f  l  p  a  i  p  r

121 gttcgtcccc atcaccaaga tcgcggtgaa ggcgcgcaag acccggttca ccaatcagat
       v  r  p  h  h  q  d  r  g  e  g  a  q  d  p  v  h  q  s  d
     m  f  v  p  i  t  k  i  a  v  k  a  r  k  t  r  f  t  n  q
      c  s  s  p  s  p  r  s  r  -  r  r  a  r  p  g  s  p  i  r

181 ttttcctcag tccggccgca acgtcgatgt caccaccacg gacggcacac tcccccacgc
       f  s  s  v  r  p  q  r  r  c  h  h  h  g  r  h  t  p  p  r
     i  f  p  q  s  g  r  n  v  d  v  t  t  t  d  g  t  l  p  h
      f  f  l  s  p  a  a  t  s  m  s  p  p  r  t  a  h  s  p  t

241 caccatgtcc ctggtcgagc actacatccg ggcctgccgc ctgcgcaccc agatcgttcc
       h  h  v  p  g  r  a  l  h  p  g  l  p  p  a  h  p  d  r  s
     a  t  m  s  l  v  e  h  y  i  r  a  c  r  l  r  t  q  i  v
      p  p  c  p  w  s  s  t  t  s  g  p  a  a  c  a  p  r  s  f

301 ggccctgatc gttaacggcg attgcgaagg catgtacagc atctatgtcg gctggtcgaa
       g  p  d  r  -  r  r  l  r  r  h  v  q  h  l  c  r  l  v  e
     p  a  l  i  v  n  g  d  c  e  g  m  y  s  i  y  v  g  w  s
      r  p  -  s  l  t  a  i  a  k  a  c  t  a  s  m  s  a  g  r

361 aaccaccaag catgttgttt cacgtgaaac aaagccggtc gaaagcgacg gcatggaatt
       n  h  q  a  c  c  f  t  -  n  k  a  g  r  k  r  r  h  g  i
     k  t  t  k  h  v  v  s  r  e  t  k  p  v  e  s  d  g  m  e
      k  p  p  s  m  i  f  h  v  k  q  s  r  s  k  a  t  a  w  n

421 tcccgaactg ggcgaagccg acgacatcac cgaagaaacg cttgagtgtg gccttcccga
       s  r  t  g  r  s  r  r  h  h  r  r  n  a  -  v  w  p  s  r
     f  p  e  l  g  e  a  d  d  i  t  e  e  t  l  e  c  g  l  p
      f  p  n  w  a  k  p  t  t  s  p  k  k  r  l  s  v  a  f  p

481 catcgaattg atctcggacg ccgatcttct cgtccttcca ccagcgccga caacattcca
       h  r  i  d  i  g  r  r  s  s  r  p  s  t  s  a  d  n  i  p
     d  i  e  l  i  s  d  a  d  l  l  v  l  p  p  a  p  t  t  f
      t  s  n  -  s  r  t  p  i  f  s  s  f  h  q  r  r  q  h  s

541 aggcgcttga gatgggcggg ttcggtcacg atcttgcgcc gtggacaagg gcaaggtccg
       r  r  l  r  w  a  g  s  v  t  i  l  r  r  g  q  g  q  g  p
     q  g  a  -  d  g  r  v  r  s  r  s  c  a  v  d  k  g  k  v
      k  a  l  e  m  g  g  f  g  h  d  l  a  p  w  t  r  a  r  s

601 cagatgatcg acgaggcgcg atcaccgaga tgccgcgacg atctgtcgac gctatgtcac
       q  m  i  d  e  a  r  s  p  r  c  r  d  d  l  s  t  l  c  h
     r  r  -  s  t  r  r  d  h  r  d  a  a  t  i  c  r  r  y  v
      a  d  d  r  r  g  a  i  t  e  m  p  r  r  s  v  d  a  m  s

661 cagcgcatgt ccgacggtgg aatgcaagac aggtnggntn gatcgggg (SEQ ID NO: 120)
       q  r  m  s  d  g  g  m  q  d  r  ?  ?  ?  s  g  (SEQ ID NO: 121)
     t  s  a  c  p  t  v  e  c  k  t  g  ?  ?  d  r    (SEQ ID NO: 122)
      p  a  h  v  r  r  w  n  a  r  q  ?  ?  ?  i  g  (SEQ ID NO: 123)
```

In the above sequence-tag of the clone S248_M31bA11, the primers 3j and 5h are indicated. Hybridization between primer and template is indicated by arrows, mismatches by open circles. Putative conserved structural motifs are indicated in bold and underlined.

Several further sequence-tags were generated using different primer pairs of the primers 2 and 5 but none turned out to encode a "GDSL"-type esterases. The screening of this library was completed.

iii) Library M091

The elongation of the amplicon SP3__1j5h, which was identified in the insert-DNA of clone M24dG12 proved that the corresponding sequence does not encode a "GDSL"-type esterase. Whereas the sequence encoding a putative block V (DGTHP; SEQ ID NO:124) was found, the corresponding sequence encoding block I was missing. The amplicon was generated due to an "unspecific" hybridization of primer 1j with the first mismatches at positions 5, 10, 11 and 12 from the 3'-terminus of the primer. The sequence-tag of clone M091_M24dG12 s shown below:

```
  1 gcctgatggc ttcgagttcg tcgaattcac ctcgccccag cccggcgtgc tggaggcggt
       a  -  w   l  r  v   r  r  i  h   l  a  p   a  r  r   a  g  g  g
         p  d  g   f  e  f   v  e  f   t  s  p  q   p  g  v   l  e  a
         l  m   a  s  s  s   s  n  s   p  r  p   s  p  a  c   w  r  r

 61 gtttgaaaag ctgggtttca ccctggtcgc caagcaccgg tccaaggatg tggtgctgta
       v  -  k   a  g  f   h  p  g  r   q  a  p   v  q  g   c  g  a  v
     v  f  e  k   l  g  f   t  l  v   a  k  h  r   s  k  d   v  v  l
      c  l  k   s  w  v  s   p  w  s   p  s  t   g  p  r  m   w  c  c

121 ccgccagaac ggcatcaact tcatcctgaa ccgcgagccc cacagccagg ccgcctactt
       p  p  e   r  h  q   l  h  p  e   p  r  a   p  q  p   g  r  l  l
     y  r  q  n   g  i  n   f  i  l   n  r  e  p   h  s  q   a  a  y
      t  a  r   t  a  s  t   s  s  -   t  a  s   p  t  a  r   p  p  t

181 tggtgccgag catggcccct ccgcctgtgg cctggccttc cgtgtgaagg atgcgcataa
       w  c  r   a  w  p   l  r  l  w   p  g  l   p  c  e   g  c  a  -
     f  g  a  e   h  g  p   s  a  c   g  l  a  f   r  v  k   d  a  h
      l  v  p   s  m  a  p   p  p  v   a  w  p   s  v  -  r   m  r  i

241 ggcttataac cgcgcgctgg aactgggcgc ccagcccatc gagatcccca ccggccccat
       g  l  -   p  r  a   g  t  g  r   p  a  h   r  d  p   h  r  p  h
     k  a  y  n   r  a  l   e  l  g   a  q  p  i   e  i  p   t  g  p
      r  l  i   t  a  r  w   n  w  a   p  s  p   s  r  s  p   p  a  p

301 ggaactgcgc ctgcccgcca tcaagggcat tggcggcgcc gcctctgtat ttgatcgacc
       g  t  a   p  a  r   h  q  g  h   w  r  r   r  l  c   i  -  s  t
     m  e  l  r   l  p  a   i  k  g   i  g  g  a   a  s  v   f  d  r
      w  n  c   a  c  p  p   s  r  a   l  a  a   p  l  y  l   i  d

361 gctttgaaga cggcaagtcc atctacgaca tcgacttcga gttcatcgaa ggcgtggacc
       a  l  k   t  a  s   p  s  t  t   s  t  s   s  s  s   k  a  w  t
     p  l  -  r   r  q  v   h  l  r   h  r  l  r   v  h  r   r  r  g
      r  f  e   d  g  k  s   i  y  d   i  d  f   e  f  i  e   g  v  d

421 gccgccccgc ggggcatggc ctgaacgaga tcgatcacct cacgcacaac gtgtaccggg
       a  a  p   r  g  m   a  -  t  r   s  i  t   s  r  t   t  c  t  g
     p  p  p  r   g  a  w   p  e  r   d  r  s  p   h  a  q   r  v  p
      r  r  p   a  g  h  g   l  n  e   i  d  h   l  t  h  n   v  y  r

481 gccgcatggg cttctgggcc aacttctacg aaaagctgtt caacttccgc gaaatccgct
       a  a  w   a  s  g   p  t  s  t   k  s  c   s  t  s   a  k  s  a
     g  p  h  g   l  l  g   q  l  l   r  k  a  v   q  l  p   r  n  p
      g  r  m   g  f  w  a   n  f  y   e  k  l   f  n  f  r   e  i  r

541 acttcgacat ccagggcgaa tacacgggcc tgacctccaa ggccatgacc gcgcccgacg
       t  s  t   s  r  a   n  t  r  a   -  p  p   r  p  -   p  r  p  t
     l  l  r  h   p  g  r   i  h  g   p  d  l  q   g  h  d   r  a  r
      y  f  d   i  q  g  e   y  t  g   l  t  s   k  a  m  t   a  p  d

601 gcaagattcg catcccgctg aacgaagagt ccaagcaggg cggcggccag atcgaagaat
       a  r  f   a  s  r   -  t  k  s   p  s  r   a  a  a   r  s  k  n
     r  q  d  s   h  p  a   e  r  r   v  q  a  g   r  r  p   d  r  r
      g  k  i   r  i  p  l   n  e  e   s  k  q   g  g  g  q   i  e  e

661 ttttgatgca attcaacggc gagggcattc agcacatcgc gctgatctgc gacaacctgc
       f  -  c   n  s  t   a  r  a  f   s  t  s   r  -  s   a  t  t  c
     i  f  d  a   i  q  r   r  g  h   s  a  h  r   a  d  l   r  q  p
      f  l  m   q  f  n  g   e  g  i   q  h  i   a  l  i  c   d  n  l

721 tggacgtggt ggacaagctg ggcatggccg gcgtgcagct ggccaccgcg cccaacgagg
       w  t  w   w  t  s   w  a  w  p   a  c  s   w  p  p   r  p  t  r
     a  g  r  g   g  q  a   g  h  g   r  r  a  a   g  h  r   a  q  r
      l  d  v   v  d  k  l   g  m  a   g  v  q   l  a  t  a   p  n  e

781 tctattacga aatgctggac acccgcctgc ccggccacgg ccagccggtg cccgagctgc
       s  i  t   k  c  w   t  p  a  c   p  a  t   a  s  r   c  p  s  c
```

-continued

```
     g   l   l   r   n   a   g   h   p   p   a   r   p   r   p   a   g   a   r   a
       v   y   y   e   m   l   d   t   r   l   p   g   h   g   q   p   v   p   e   l
```

```
 841 agtcgcgcgg catcttgctg gacggcacca cggccgacgg cacgcacccg cctgctagct
       s   r   a   a   s   c   w   t   a   p   r   p   t   a   r   t   r   l   l   a
     a   v   a   r   h   l   a   g   r   h   h   g   r   r   h   a   p   a   c   -
       q   s   r   g   i   l   l   d   g   t   t   a   d   q   t   h   p   p   a   s
```

```
 901 tcagatcttc tccacgccca tgctgggccc ggtgttcttc gaattcatcc agcgcgaggg
       s   d   l   l   h   a   h   a   g   p   g   v   l   r   i   h   p   a   r   g
     l   q   i   f   s   t   p   m   l   g   p   v   f   f   e   f   i   q   r   e
       f   r   s   s   p   r   p   c   w   a   r   c   s   s   n   s   s   s   a   r

 961 cgactaccgc gacggctttg gcgaaggcaa cttcaaggcg ctgttcgagt cgctggaacg
       r   l   p   r   r   l   w   r   r   q   l   q   g   a   v   r   v   a   g   t
     g   d   y   r   d   g   f   g   e   g   n   f   k   a   l   f   e   s   l   e
       a   t   t   a   t   a   l   a   k   a   t   s   r   r   c   s   s   r   w   n

1021 cgaccagatc cgccgtggtg tgctgaacac ataagacatc agacatccag ggttaaccct
       r   p   d   p   p   w   c   a   e   h   i   r   h   q   t   s   r   v   n   p
     r   d   q   i   r   r   g   v   l   n   t   -   d   i   r   h   p   g   l   t
       a   t   r   s   a   v   v   c   -   t   h   k   t   s   d   i   q   g   -   p

1081 gcacaggtgc ctatactgcg cgctccccgg aactcaaaag gatcccgatg tcgctccgta
       a   q   v   p   i   l   r   a   p   r   n   s   k   g   s   r   c   r   s   v
     l   h   r   c   l   y   c   a   l   p   g   t   q   k   d   p   d   v   a   p
       c   t   g   a   y   t   a   r   s   p   e   l   k   r   i   p   m   s   l   r

1141 gcaccctgtt cagcaccctt ttggccggcg cagccactgt cgcgctggcg cagaacccgt
       a   p   c   s   a   p   f   w   p   a   q   p   l   s   r   w   r   r   t   r
     -   h   p   v   q   h   p   f   g   r   r   s   h   c   r   a   g   a   e   p
       s   t   l   f   s   t   l   l   a   g   a   a   t   v   a   l   a   q   n   p

1201 ctgcccgctc acatcg (SEQ ID NO: 125)
       l   p   a   h   i  (SEQ ID NO: 126)
     v   c   p   l   t   s (SEQ ID NO: 127)
       s   a   r   s   h    (SEQ ID NO: 128)
```

Sequence-tag of the clone M091_M24dG12. The primers 1j and 5h are indicated in the above sequence-tag of the clone M091_M24dG12. Hybridization between primer and template is indicated by arrows, mismatches by open circles. Putative conserved structural motifs are depicted in bold and underlined.

A further sequence-tag (SP1__2b5h) was generated using the primer pair 2b/5h. A BlastX-analysis of the sequence from this tag yielded the highest homology to an arylesterase from *Agrobacterium tumefaciens*, with 70% identity. The single clone carrying the corresponding gene was identified (M4aE11) and the full length sequence determined to be as shown below:

```
  1 atgaagacca ttctcgccta tggcgacagc ctgacctatg ggccaaccc gatcccgggc
      m   k   t   i   l   a   y   g   d   s   l   t   y   g   a   n   p   i   p   g

 61 gggccgcggc atgcctatga ggatcgctgg cccacggcgc tggagcaggg gctgggcggc
      g   p   r   h   a   y   e   d   r   w   p   t   a   l   e   q   g   l   g   g

121 aaggcgcggg tgattgccga ggggctgggt ggtcgcacca cggtgcatga cgactggttt
      k   a   r   v   i   a   e   g   l   g   g   r   t   t   v   h   d   d   w   f

181 gcgaatgcgg acaggaacgg tgcgcgggtg ctgccgacgc tgctcgagag ccattcgccg
      a   n   a   d   r   n   g   a   r   v   l   p   t   l   l   e   s   h   s   p

241 ctcgacctga tcgtcatcat gctcggcacc aacgacatca agccgcatca cgggcggacg
      l   d   l   i   v   i   m   l   g   t   n   d   i   k   p   h   h   g   r   t

301 gccggcgagg ccgggcgggg catggcgcgg ctggtgcaga tcatccgcgg gcactatgcc
      a   g   e   a   g   r   g   m   a   r   l   v   q   i   i   r   g   h   y   a

361 ggccgcatgc aggacgagcc gcagatcatc ctcgtgtcgc cgccgccgat catcctcggc
      g   r   m   q   d   e   p   q   i   i   l   v   s   p   p   p   i   i   l   g

421 gactgggcgg acatgatgga ccatttcggc ccgcacgaag cgatcgccac ctcggtggat
      d   w   a   d   m   m   d   h   f   g   p   h   e   a   i   a   t   s   v   d

481 ttcgctcgcg agtacaagaa gcgggccgac gagcagaagg tgcatttctt cgacgccggc
      f   a   r   e   y   k   k   r   a   d   e   q   k   v   h   f   f   d   a   g
```

-continued

```
541 acggtggcga cgaccagcaa ggccgatggc atccacctcg acccggccaa tacgcgcgcc
      t  v  a   t  t  s   k  a  d  g   i  h  l   d  p  a   n  t  r  a

601 atcggggcag ggctggtgcc gctggtgaag caggtgctcg gcctgtaa (SEQ ID NO: 129)
      i  g  a   g  l  v   p  l  v  k   q  v  l   g  l  — (SEQ ID NO: 130)
```

Figure 5:
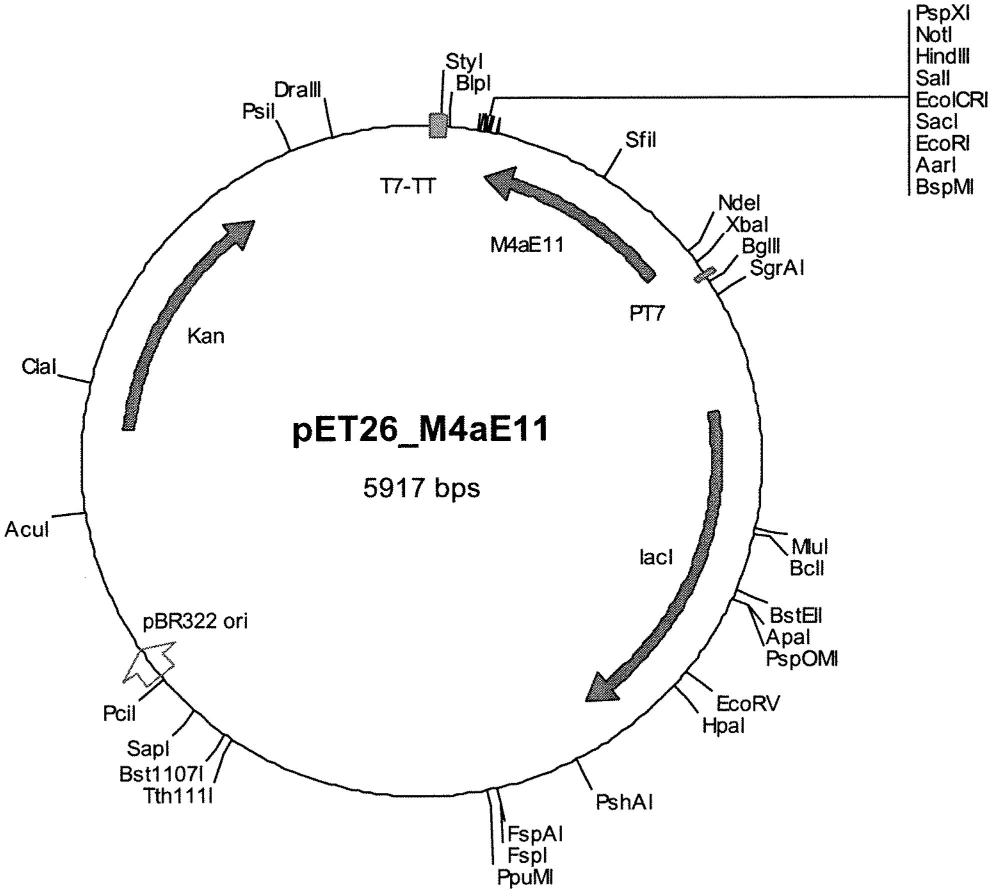
FIG. 5 provides a map of plasmid pET26-M4aE11.

In the above sequence, the conserved structural motifs are shown in bold and underlined. The BlastP-analysis with the deduced full length amino acid sequence identified the same hit with a identity of 48%. The primary structure of this enzyme showed the "GRTT"-motif proving the usefulness of the primers directed towards block 2 for the identification of "GRTT"-esterases. The gene was amplified to introduce unique restriction enzyme recognition sites and the absence of second site mutations was confirmed by sequencing. The gene was ligated to pET26 and was expressed in *E. coli* Rosetta (DE3). The vector map is provided in FIG. 5. Expression and control strains were cultivated in LB in the presence of kanamycin (25 µg/ml), chloramphenicol (12.5 µg/ml), and 1% glucose. At an $OD_{580}$ of 1, expression was induced by addition of 100 µM IPTG. Samples were taken at 2, 4, and 20 hours after induction. Cells were separated from the culture supernatant by centrifugation and after resuspending in sample buffer, they wee incubated for 10 minutes at 90° C. An amount of cells representing an $OD_{580}$ of 0.1 was applied to a 4-12% acryl amide gradient gel, which was stained with Coomassie Brilliant Blue R250.

Strong overexpression of the gene was detected already 2 h after induction with 100 µM IPTG, as determined by SDS-PAGE analysis of crude cell extracts from *E. coli* Rosetta (DE3) pET26_M4aE11. The amount of protein representing M4aE11 (calculated size 23.2 kDa) increased further over time.

Esterase activity of crude cell extracts from strains expressing the "GDSL"-type esterase M4aE11 was determined. An amount of cells corresponding to an $O.D._{580}=2$ were resuspended in 200 µl of 5 mM Tris/HCl pH 8.0, and lysed by ultrasonication. Then, 20 µl of each sample were used to determine the esterase activity towards p-nitrophenyl butyrate in a total volume of 200 µl. The activity was corrected for the background activity of the control strain. The activity towards p-nitrophenylbutyrate reached about 125 nmol/ml×min 20 h after induction.

In addition, SDS-PAGE analysis of the soluble and insoluble fraction of crude cell extracts from *E. coli* Rosetta (DE3) pET26_M4aE11 was conducted. Cells from a culture induced with 100 µM IPTG and harvested 4 h and 20 h after induction were lysed by ultrasonication and separated into soluble and insoluble fraction by centrifugation. Sample buffer was added and directly comparable amounts of soluble and insoluble fractions were applied to a 4-12% acryl amide gradient gel, which was stained with Coomassie Brilliant Blue R250. The results of this analysis of the solubility revealed that M4aE11 is partially (estimated 80%) soluble. The screening of the library M091 was completed.

Thus, in total nine different "GDSL"-type esterases were identified in 6 different large insert metagenomic libraries and the esterases/lipases BRAIN's library comprising more than 4.3 Gbp. Eight of these genes were heterologously expressed in *E. coli*. The resulting enzyme samples of seven clones were characterized for the desired perhydrolase activity. Two of the enzymes displayed this activity. Table 3 summarizes the screening, expression and characterization of the metagenomic "GDSL"-type esterases.

TABLE 3

Expression and Characterization of Metagenomic "GDSL"-Type Esterases

| GDSL-type Esterase | Homology[1] | Expression[2] Level | Solubility[3] | Activity[4] | Perhydrolase Activity |
|---|---|---|---|---|---|
| S248_M2bB11 | 12.9% | ++ | + | 136 | – |
| S248_M40cD4 | 14.8% | +++ | ++ | 50 | –/+[6] |
| S248_M44aA5 | 12.4% | +++ | ++ | 75 | –/+ |
| S261_M2aA12 | 36.9% | ++ | ++ | 72 | +[7] |
| S279_M70aE8 | 11.9% | +++ | + | 167 | – |
| S279_M75bA2 | 5.7% | n.d[5]. | n.d. | n.d. | n.d.[5] |
| M091_M4aE11 | 33.9% | +++ | ++ | 125 | n.d. |
| Est105 | 4.3% | +++ | – | – | n.d. |
| Est114 | 7.8% | n.d. | n.d. | 13 | – |

[1]identity to the prototype enzyme from *M. smegmatis* calculated with the dialign algorithm (Morgenstern et al., 1996)
[2]expression level: + moderate overexpression; ++ strong overexpression; +++ very
[3]strong overexpression as judged from SDS-PAGE-analysis as judged by SDS-PAGE-analysis
[4]towards p-nitrophenyl butyrate; given as nmol/(ml × min)
[5]not determined
[6]perhydrolysis activity 2x background
[7]perhydrolase activity more than 2x background Engineering of the Perhydrolase Based on the structure of the perhydrolase, residues which may alter substrate specificity (e.g., Km, kcat, Vmax, chain length, etc.) and/or the multimeric nature of the protein were identified. However, it is not intended that the present invention be limited to any particular residues. Nonetheless, site saturation libraries of residues D10, L12, T13, W14, W16, S54, A55, N94, K97, Y99, P146, W149, F150, I194, F196, are constructed, as well as combinatorial libraries of residues: E51A, Y73A, H81D, T127Q and single mutations of the active site residues D192A, H195A and a site saturation library of the conserved D95. Methods for production of such libraries are known to those skilled in the art and include commercially available kits as the Stratagene Quikchange™ Site-directed mutagenesis kit and/or Quikchange™ Multi-Site-directed mutagenesis kit.

Perhydrolase Activity

The use of enzymes obtained from microorganisms is long-standing. Indeed there are numerous biocatalysts known in the art. For example, U.S. Pat. No. 5,240,835 (herein incorporated by reference) provides a description of the transacylase activity of obtained from *C. oxydans* and its production. In addition, U.S. Pat. No. 3,823,070 (herein incorporated by reference) provides a description of a *Corynebacterium* that produces certain fatty acids from an n-paraffin. U.S. Pat. No. 4,594,324 (herein incorporated by reference) provides a description of a *Methylcoccus capsulatus* that oxidizes alkenes. Additional biocatalysts are known in the art (See e.g., U.S. Pat. Nos. 4,008,125 and 4,415,657; both of which are herein incorporated by reference). EP 0 280 232 describes the use of a *C. oxydans* enzyme in a reaction between a diol and an ester of acetic acid to produce monoacetate. Additional references describe the use of a *C. oxydans* enzyme to make chiral hydroxycarboxylic acid from a prochiral diol. Additional details regarding the activity of the *C. oxydans* transacylase as well as the culture of *C. oxydans*, preparation and purification of the enzyme are provided by U.S. Pat. No.

5,240,835 (incorporated by reference, as indicated above). Thus, the transesterification capabilities of this enzyme, using mostly acetic acid esters were known. However, the determination that this enzyme could carry out perhydrolysis reaction was quite unexpected. It was even more surprising that these enzymes exhibit very high efficiencies in perhydrolysis reactions. For example, in the presence of tributyrin and water, the enzyme acts to produce butyric acid, while in the presence of tributyrin, water and hydrogen peroxide, the enzyme acts to produce mostly peracetic acid and very little butyric acid. This high perhydrolysis to hydrolysis ratio is a unique property exhibited by the perhydrolase class of enzymes of the present invention and is a unique characteristic that is not exhibited by previously described lipases, cutinases, nor esterases.

The perhydrolase of the present invention is active over a wide pH and temperature range and accepts a wide range of substrates for acyl transfer. Acceptors include water (hydrolysis), hydrogen peroxide (perhydrolysis) and alcohols (classical acyl transfer). For perhydrolysis measurements, enzyme is incubated in a buffer of choice at a specified temperature with a substrate ester in the presence of hydrogen peroxide. Typical substrates used to measure perhydrolysis include esters such as ethyl acetate, triacetin, tributyrin, ethoxylated neodol acetate esters, and others. In addition, the wild type enzyme hydrolyzes nitrophenylesters of short chain acids. The latter are convenient substrates to measure enzyme concentration. Peracid and acetic acid can be measured by the assays described herein. Nitrophenylester hydrolysis is also described.

Although the primary example used during the development of the present invention is the *M. smegmatis* perhydrolase, any perhydrolase obtained from any source which converts the ester into mostly peracids in the presence of hydrogen peroxide finds use in the present invention.

Substrates

In some preferred embodiments of the present invention, esters comprising aliphatic and/or aromatic carboxylic acids and alcohols are utilized with the perhydrolase enzymes of the present invention. In some preferred embodiments, the substrates are selected from one or more of the following: formic acid, acetic acid, propionic acid, butyric acid, valeric acid, caproic acid, caprylic acid, nonanoic acid, decanoic acid, dodecanoic acid, myristic acid, palmitic acid, stearic acid, and oleic acid. In additional embodiments, triacetin, tributyrin, neodol esters, and/or ethoxylated neodol esters serve as acyl donors for peracid formation.

Cleaning and Detergent Formulations

The detergent compositions of the present invention are provided in any suitable form, including for example, as a liquid diluent, in granules, in emulsions, in gels, and pastes. When a solid detergent composition is employed, the detergent is preferably formulated as granules. Preferably, the granules are formulated to additionally contain a protecting agent (See e.g., U.S. application Ser. No. 07/642,669 filed Jan. 17, 1991, incorporated herein by reference). Likewise, in some embodiments, the granules are formulated so as to contain materials to reduce the rate of dissolution of the granule into the wash medium (See e.g., U.S. Pat. No. 5,254, 283, incorporated herein by reference in its entirety). In addition, the perhydrolase enzymes of the present invention find use in formulations in which substrate and enzyme are present in the same granule. Thus, in some embodiments, the efficacy of the enzyme is increased by the provision of high local concentrations of enzyme and substrate (See e.g., U.S. Patent Application Publication US2003/0191033, herein incorporated by reference).

Many of the protein variants of the present invention are useful in formulating various detergent compositions. A number of known compounds are suitable surfactants useful in compositions comprising the protein mutants of the invention. These include nonionic, anionic, cationic, anionic or zwitterionic detergents (See e.g., U.S. Pat. Nos. 4,404,128 and 4,261,868). A suitable detergent formulation is that described in U.S. Pat. No. 5,204,015 (previously incorporated by reference). Those in the art are familiar with the different formulations which find use as cleaning compositions. As indicated above, in some preferred embodiments, the detergent compositions of the present invention employ a surface active agent (i.e., surfactant) including anionic, nonionic and ampholytic surfactants well known for their use in detergent compositions. Some surfactants suitable for use in the present invention are described in British Patent Application No. 2 094 826 A, incorporated herein by reference. In some embodiments, mixtures surfactants are used in the present invention.

Suitable anionic surfactants for use in the detergent composition of the present invention include linear or branched alkylbenzene sulfonates; alkyl or alkenyl ether sulfates having linear or branched alkyl groups or alkenyl groups; alkyl or alkenyl sulfates; olefin sulfonates; alkane sulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3.

Ampholytic surfactants that find use in the present invention include quaternary ammonium salt sulfonates, betaine-type ampholytic surfactants, and the like. Such ampholytic surfactants have both the positive and negative charged groups in the same molecule.

Nonionic surfactants that find use in the present invention generally comprise polyoxyalkylene ethers, as well as higher fatty acid alkanolamides or alkylene oxide adduct thereof, fatty acid glycerine monoesters, and the like.

In some preferred embodiments, the surfactant or surfactant mixture included in the detergent compositions of the present invention is provided in an amount from about 1 weight percent to about 95 weight percent of the total detergent composition and preferably from about 5 weight percent to about 45 weight percent of the total detergent composition. In various embodiments, numerous other components are included in the compositions of the present invention. Many of these are described below. It is not intended that the present invention be limited to these specific examples. Indeed, it is contemplated that additional compounds will find use in the present invention. The descriptions below merely illustrate some optional components.

Proteins, particularly the perhydrolase of the present invention can be formulated into known powdered and liquid detergents having pH between 3 and 12.0, at levels of about 0.001 to about 5% (preferably 0.1% to 0.5%) by weight. In some embodiments, these detergent cleaning compositions further include other enzymes such as proteases, amylases, mannanases, peroxidases, oxido reductases, cellulases, lipases, cutinases, pectinases, pectin lyases, xylanases, and/or endoglycosidases, as well as builders and stabilizers.

In addition to typical cleaning compositions, it is readily understood that perhydrolase variants of the present invention find use in any purpose that the native or wild-type enzyme is used. Thus, such variants can be used, for example, in bar and liquid soap applications, dishcare formulations, surface cleaning applications, contact lens cleaning solutions or products, waste treatment, textile applications, pulp-bleaching, disinfectants, skin care, oral care, hair care, etc. Indeed, it is not intended that any variants of the perhydrolase of the present invention be limited to any particular use. For example, the variant perhydrolases of the present invention may comprise, in addition to decreased allergenicity, enhanced performance in a detergent composition (as compared to the wild-type or unmodified perhydrolase).

The addition of proteins to conventional cleaning compositions does not create any special use limitations. In other words, any temperature and pH suitable for the detergent are also suitable for the present compositions, as long as the pH is within the range in which the enzyme(s) is/are active, and the temperature is below the described protein's denaturing temperature. In addition, proteins of the invention find use in cleaning, bleaching, and disinfecting compositions without detergents, again either alone or in combination with a source of hydrogen peroxide, an ester substrate (e.g., either added or inherent in the system utilized, such as with stains that contain esters, pulp that contains esters etc), other enzymes, surfactants, builders, stabilizers, etc. Indeed it is not intended that the present invention be limited to any particular formulation or application.

Substrates

In some preferred embodiments of the present invention, esters comprising aliphatic and/or aromatic carboxylic acids and alcohols are utilized with the perhydrolase enzymes in the detergent formulations of the present invention. In some preferred embodiments, the substrates are selected from one or more of the following: formic acid, acetic acid, propionic acid, butyric acid, valeric acid, caproic acid, caprylic acid, nonanoic acid, decanoic acid, dodecanoic acid, myristic acid, palmitic acid, stearic acid, and oleic acid. Thus, in some preferred embodiments, detergents comprising at least one perhydrolase, at least one hydrogen peroxide source, and at least one ester acid are provided.

Hydrolases

In addition to the perhydrolase described herein, various hydrolases find use in the present invention, including but not limited to carboxylate ester hydrolase, thioester hydrolase, phosphate monoester hydrolase, and phosphate diester hydrolase which act on ester bonds; a thioether hydrolase which acts on ether bonds; and α-amino-acyl-peptide hydrolase, peptidyl-amino acid hydrolase, acyl-amino acid hydrolase, dipeptide hydrolase, and peptidyl-peptide hydrolase which act on peptide bonds, all these enzymes having high perhydrolysis to hydrolysis ratios (e.g., >1). Preferable among them are carboxylate ester hydrolase, and peptidyl-peptide hydrolase. Suitable hydrolases include: (1) proteases belonging to the peptidyl-peptide hydrolase class (e.g., pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D, bromelin, keratinase, chymotrypsin C, pepsin C, aspergillopeptidase B, urokinase, carboxypeptidase A and B, and aminopeptidase); (2) carboxylate ester hydrolase including carboxyl esterase, lipase, pectin esterase, and chlorophyllase; and (3) enzymes having high perhydrolysis to hydrolysis ratios. Especially effective among them are lipases, as well as esterases that exhibit high perhydrolysis to hydrolysis ratios, as well as protein engineered esterases, cutinases, and lipases, using the primary, secondary, tertiary, and/or quaternary structural features of the perhydrolases of the present invention.

The hydrolase is incorporated into the detergent composition as much as required according to the purpose. It should preferably be incorporated in an amount of 0.0001 to 5 weight percent, and more preferably 0.02 to 3 weight percent. This enzyme should be used in the form of granules made of crude enzyme alone or in combination with other enzymes and/or components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. In some embodiments, the granules are formulated so as to contain an enzyme protecting agent and a dissolution retardant material (i.e., material that regulates the dissolution of granules during use).

Cationic Surfactants and Long-Chain Fatty Acid Salts

Such cationic surfactants and long-chain fatty acid salts include saturated or fatty acid salts, alkyl or alkenyl ether carboxylic acid salts, a-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts include those disclosed in British Patent Application No. 2 094 826 A, the disclosure of which is incorporated herein by reference. The composition may contain from about 1 to about 20 weight percent of such cationic surfactants and long-chain fatty acid salts.

Builders

In some embodiments of the present invention, the composition contains from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Examples of suitable divalent sequestering agents are disclosed in British Patent Application No. 2 094 826 A, the disclosure of which is incorporated herein by reference.

In additional embodiments, compositions of the present invention contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Anti-Redeposition Agents

In yet additional embodiments of the present invention, the compositions contain from about 0.1 to about 5 weight percent of one or more of the following compounds as antiredeposition agents: polyethylene glycol, polyvinyl alcohol, polyvinylpyrrolidone and carboxymethylcellulose. In some preferred embodiments, a combination of carboxymethylcellulose and/or polyethylene glycol are utilized with the composition of the present invention as useful dirt removing compositions.

Bleaching Agents

The use of the perhydrolases of the present invention in combination with additional bleaching agent(s) such as sodium percarbonate, sodium perborate, sodium sulfate/hydrogen peroxide adduct and sodium chloride/hydrogen peroxide adduct and/or a photo-sensitive bleaching dye such as zinc or aluminum salt of sulfonated phthalocyanine further improves the detergent effects. In additional embodiments, the perhydrolases of the present invention are used in combination with bleach boosters (e.g., TAED and/or NOBS).

Bluing Agents and Fluorescent Dyes

In some embodiments of the present invention, bluing agents and fluorescent dyes are incorporated in the composition. Examples of suitable bluing agents and fluorescent dyes are disclosed in British Patent Application No. 2 094 826 A, the disclosure of which is incorporated herein by reference.

Caking Inhibitors

In some embodiments of the present invention in which the composition is powdered or solid, caking inhibitors are incorporated in the composition. Examples of suitable caking inhibitors include p-toluenesulfonic acid salts, xylenesulfonic acid salts, acetic acid salts, sulfosuccinic acid salts, talc, finely pulverized silica, clay, calcium silicate (e.g., Micro-Cell by Johns Manville Co.), calcium carbonate and magnesium oxide.

Antioxidants

The antioxidants include, for example, tert-butyl-hydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxy-phenyl)cyclohexane.

Solubilizers

In some embodiments, the compositions of the present invention also include solubilizers, including but not limited to lower alcohols (e.g., ethanol, benzenesulfonate salts, and lower alkylbenzenesulfonate salts such as p-toluenesulfonate salts), glycols such as propylene glycol, acetylbenzene-sulfonate salts, acetamides, pyridinedicarboxylic acid amides, benzoate salts and urea.

In some embodiments, the detergent composition of the present invention are used in a broad pH range of from acidic to alkaline pH. In a preferred embodiment, the detergent composition of the present invention is used in mildly acidic, neutral or alkaline detergent wash media having a pH of from above 4 to no more than about 12.

In addition to the ingredients described above, perfumes, buffers, preservatives, dyes and the like also find use with the present invention. These components are provided in concentrations and forms known to those in the art.

In some embodiments, the powdered detergent bases of the present invention are prepared by any known preparation methods including a spray-drying method and a granulation method. The detergent base obtained particularly by the spray-drying method and/or spray-drying granulation method are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. After the spray-drying, perfumes, enzymes, bleaching agents, inorganic alkaline builders may be added. With a highly dense, granular detergent base obtained such as by the spray-drying-granulation method, various ingredients may also be added after the preparation of the base.

When the detergent base is a liquid, it may be either a homogeneous solution or an inhomogeneous dispersion.

The detergent compositions of this invention may be incubated with fabric, for example soiled fabrics, in industrial and household uses at temperatures, reaction times and liquor ratios conventionally employed in these environments. The incubation conditions (i.e., the conditions effective for treating materials with detergent compositions according to the present invention), are readily ascertainable by those of skill in the art. Accordingly, the appropriate conditions effective for treatment with the present detergents correspond to those using similar detergent compositions which include wild-type perhydrolase.

As indicated above, detergents according to the present invention may additionally be formulated as a pre-wash in the appropriate solution at an intermediate pH where sufficient activity exists to provide desired improvements softening, depilling, pilling prevention, surface fiber removal or cleaning. When the detergent composition is a pre-soak (e.g., pre-wash or pre-treatment) composition, either as a liquid, spray, gel or paste composition, the perhydrolase enzyme is generally employed from about 0.00001% to about 5% weight percent based on the total weight of the pre-soak or pre-treatment composition. In such compositions, a surfactant may optionally be employed and when employed, is generally present at a concentration of from about 0.0005 to about 1 weight percent based on the total weight of the pre-soak. The remainder of the composition comprises conventional components used in the pre-soak (e.g., diluent, buffers, other enzymes (proteases), etc.) at their conventional concentrations.

Cleaning Compositions Comprising Perhydrolase

The cleaning compositions of the present invention may be advantageously employed for example, in laundry applications, hard surface cleaning, automatic dishwashing applications, as well as cosmetic applications such as dentures, teeth, hair and skin. However, due to the unique advantages of increased effectiveness in lower temperature solutions and the superior color-safety profile, the enzymes of the present invention are ideally suited for laundry applications such as the bleaching of fabrics. Furthermore, the enzymes of the present invention find use in both granular and liquid compositions.

The enzymes of the present invention also find use in cleaning additive products. Cleaning additive products including the enzymes of the present invention are ideally suited for inclusion in wash processes where additional bleaching effectiveness is desired. Such instances include, but are not limited to low temperature solution cleaning applications. The additive product may be, in its simplest form, one or more of the enzymes of the present invention. Such additive may be packaged in dosage form for addition to a cleaning process where a source of peroxygen is employed and increased bleaching effectiveness is desired. Such single dosage form may comprise a pill, tablet, gelcap or other single dosage unit such as pre-measured powders or liquids. A filler or carrier material may be included to increase the volume of such composition. Suitable filler or carrier materials include, but are not limited to, various salts of sulfate, carbonate and silicate as well as talc, clay and the like. Filler or carrier materials for liquid compositions may be water or low molecular weight primary and secondary alcohols including polyols and diols. Examples of such alcohols include, but are not limited to, methanol, ethanol, propanol and isopropanol. The compositions may contain from about 5% to about 90% of such materials. Acidic fillers can be used to reduce pH. Alternatively, the cleaning additive may include activated peroxygen source defined below or the adjunct ingredients as defined below.

The cleaning compositions and cleaning additives of the present invention require an effective amount of the enzymes provided by the present invention. The required level of enzyme may be achieved by the addition of one or more species of the *M. smegmatis* perhydrolase, variants, homologues, and/or other enzymes or enzyme fragments having the activity of the enzymes of the present invention. Typically, the cleaning compositions of the present invention comprise at least 0.0001 weight percent, from about 0.0001 to about 1, from about 0.001 to about 0.5, or even from about 0.01 to about 0.1 weight percent of at least one enzyme of the present invention.

In some embodiments, the cleaning compositions of the present invention comprise a material selected from the group consisting of a peroxygen source, hydrogen peroxide and mixtures thereof, said peroxygen source being selected from the group consisting of:

(i) from about 0.01 to about 50, from about 0.1 to about 20, or even from about 1 to 10 weight percent of a per-salt, an organic peroxyacid, urea hydrogen peroxide and mixtures thereof;

(ii) from about 0.01 to about 50, from about 0.1 to about 20, or even from about 1 to 10 weight percent of a carbohydrate and from about 0.0001 to about 1, from about 0.001 to about 0.5, from about 0.01 to about 0.1 weight percent carbohydrate oxidase; and (iii) mixtures thereof.

Suitable per-salts include those selected from the group consisting of alkalimetal perborate, alkalimetal percarbonate, alkalimetal perphosphates, alkalimetal persulphates and mixtures thereof.

The carbohydrate may be selected from the group consisting of mono-carbohydrates, di-carbohydrates, tri-carbohydrates, oligo-carbohydrates and mixtures thereof. Suitable carbohydrates include carbohydrates selected from the group consisting of D-arabinose, L-arabinose, D-Cellobiose, 2-Deoxy-D-galactose, 2-Deoxy-D-ribose, D-Fructose, L-Fucose, D-Galactose, D-glucose, D-glycero-D-gulo-heptose, D-lactose, D-Lyxose, L-Lyxose, D-Maltose, D-Mannose, Melezitose, L-Melibiose, Palatinose, D-Raffinose, L-Rhamnose, D-Ribose, L-Sorbose, Stachyose, Sucrose, D-Trehalose, D-Xylose, L-Xylose and mixtures thereof.

Suitable carbohydrate oxidases include carbohydrate oxidases selected from the group consisting of aldose oxidase (IUPAC classification EC1.1.3.9), galactose oxidase (IUPAC classification EC1.1.3.9), cellobiose oxidase (IUPAC classification EC1.1.3.25), pyranose oxidase (IUPAC classification EC1.1.3.10), sorbose oxidase (IUPAC classification EC1.1.3.11) and/or hexose oxidase (IUPAC classification EC1.1.3.5), Glucose oxidase (IUPAC classification EC1.1.3.4) and mixtures thereof.

In some preferred embodiments, the cleaning compositions of the present invention also include from about 0.01 to about 99.9, from about 0.01 to about 50, from about 0.1 to 20, or even from about 1 to about 15 weight percent a molecule comprising an ester moiety. Suitable molecules comprising an ester moiety may have the formula:

$$R^1O_x[(R^2)_m(R^3)_n]_p$$

wherein $R^1$ is a moiety selected from the group consisting of H or a substituted or unsubstituted alkyl, heteroalkyl, alkenyl, alkynyl, aryl, alkylaryl, alkylheteroaryl, and heteroaryl; in one aspect of the present invention, $R^1$ may comprise from 1 to 50,000 carbon atoms, from 1 to 10,000 carbon atoms, or even from 2 to 100 carbon atoms;

each $R^2$ is an alkoxylate moiety, in one aspect of the present invention, each $R^2$ is independently an ethoxylate, propoxylate or butoxylate moiety;

$R^3$ is an ester-forming moiety having the formula:

$R^4CO$— wherein $R^4$ may be H, substituted or unsubstituted alkyl, alkenyl, alkynyl, aryl, alkylaryl, alkylheteroaryl, and heteroaryl, in one aspect of the present invention, $R^4$ may be substituted or unsubstituted alkyl, alkenyl, alkynyl, moiety comprising from 1 to 22 carbon atoms, an aryl, alkylaryl, alkylheteroaryl, or heteroaryl moiety comprising from 4 to 22 carbon atoms or $R^4$ may be a substituted or unsubstituted $C_1$-$C_{22}$ alkyl moiety or $R^4$ may be a substituted or unsubstituted $C_1$-$C_{12}$ alkyl moiety;

x is 1 when $R^1$ is H; when $R^1$ is not H, x is an integer that is equal to or less than the number of carbons in $R^1$ p is an integer that is equal to or less than x m is an integer from 0 to 50, an integer from 0 to 18, or an integer from 0 to 12, and n is at least 1.

In one aspect of the present invention, the molecule comprising an ester moiety is an alkyl ethoxylate or propoxylate having the formula $R^1O_x[(R^2)_m(R^3)_n]_p$ wherein:

$R^1$ is an $C_2$-$C_{32}$ substituted or unsubstituted alkyl or heteroalkyl moiety;

each $R^2$ is independently an ethoxylate or propoxylate moiety;

$R^3$ is an ester-forming moiety having the formula:

$R^4CO$— wherein $R^4$ may be H, substituted or unsubstituted alkyl, alkenyl, alkynyl, aryl, alkylaryl, alkylheteroaryl, and heteroaryl, in one aspect of the present invention, $R^4$ may be a substituted or unsubstituted alkyl, alkenyl, or alkynyl moiety comprising from 1 to 22 carbon atoms, a substituted or unsubstituted aryl, alkylaryl, alkylheteroaryl, or heteroaryl moiety comprising from 4 to 22 carbon atoms or $R^4$ may be a substituted or unsubstituted $C_1$-$C_{22}$ alkyl moiety or $R^4$ may be a substituted or unsubstituted $C_1$-$C_{12}$ alkyl moiety;

x is an integer that is equal to or less than the number of carbons in $R^1$ p is an integer that is equal to or less than x m is an integer from 1 to 12, and n is at least 1.

In one aspect of the present invention, the molecule comprising the ester moiety has the formula:

$$R^1O_x[(R^2)_m(R^3)_n]_p$$

wherein $R^1$ is H or a moiety that comprises a primary, secondary, tertiary or quaternary amine moiety, said $R^1$ moiety that comprises an amine moiety being selected from the group consisting of a substituted or unsubstituted alkyl, heteroalkyl, alkenyl, alkynyl, aryl, alkylaryl, alkylheteroaryl, and heteroaryl; in one aspect of Applicants' invention $R^1$ may comprise from 1 to 50,000 carbon atoms, from 1 to 10,000 carbon atoms, or even from 2 to 100 carbon atoms;

each $R^2$ is an alkoxylate moiety, in one aspect of the present invention each $R^2$ is independently an ethoxylate, propoxylate or butoxylate moiety;

$R^3$ is an ester-forming moiety having the formula:

$R^4CO$— wherein $R^4$ may be H, substituted or unsubstituted alkyl, alkenyl, alkynyl, aryl, alkylaryl, alkylheteroaryl, and heteroaryl, in one aspect of the present invention, $R^4$ may be a substituted or unsubstituted alkyl, alkenyl, or alkynyl moiety comprising from 1 to 22 carbon atoms, a substituted or unsubstituted aryl, alkylaryl, alkylheteroaryl, or heteroaryl moiety comprising from 4 to 22 carbon atoms or $R^4$ may be a substituted or unsubstituted $C_1$-$C_{22}$ alkyl moiety or $R^4$ may be a substituted or unsubstituted $C_1$-$C_{12}$ alkyl moiety;

x is 1 when $R^1$ is H; when $R^1$ is not H, x is an integer that is equal to or less than the number of carbons in $R^1$ p is an integer that is equal to or less than x m is an integer from 0 to 12 or even 1 to 12, and n is at least 1.

In any of the aforementioned aspects of the present invention, the molecule comprising an ester moiety may have a weight average molecular weight of less than 600,000 Daltons, less than 300,000 Daltons, less than 100,000 Daltons or even less than 60,000 Daltons.

Suitable molecules that comprise an ester moiety include polycarbohydrates that comprise an ester moiety.

The cleaning compositions provided herein will typically be formulated such that, during use in aqueous cleaning operations, the wash water will have a pH of from about 5.0 to about 11.5, or even from about 7.5 to about 10.5. Liquid product formulations are typically formulated to have a pH from about 3.0 and about 9.0. Granular laundry products are typically formulated to have a pH from about 9 to about 11. Techniques for controlling pH at recommended usage levels include the use of buffers, alkalis, acids, etc., and are well known to those skilled in the art.

When the enzyme(s) of the present invention is/are employed in a granular composition or liquid, it may be desirable for the enzyme(s) to be in the form of an encapsulated particle to protect such enzyme from other components of the granular composition during storage. In addition, encapsulation is also a means of controlling the availability of the enzyme(s) during the cleaning process and may enhance performance of the enzyme(s). In this regard, the enzyme(s) may be encapsulated with any encapsulating material known in the art.

The encapsulating material typically encapsulates at least part of the enzyme(s). Typically, the encapsulating material is water-soluble and/or water-dispersible. The encapsulating material may have a glass transition temperature (Tg) of 0° C. or higher. Glass transition temperature is described in more detail in WO 97/1151, especially from page 6, line 25 to page 7, line 2.

The encapsulating material may be selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof. When the encapsulating material is a carbohydrate, it may be typically selected from the group consisting of monosaccharides, oligosaccharides, polysaccharides, and combinations thereof. Typically, the encapsulating material is a starch. Suitable starches are described in EP 0 922 499; U.S. Pat. No. 4,977,252; U.S. Pat. No. 5,354,559 and U.S. Pat. No. 5,935,826.

The encapsulating material may be a microsphere made from plastic such as thermoplastics, acrylonitrile, methacrylonitrile, polyacrylonitrile, polymethacrylonitrile and mixtures thereof; commercially available microspheres that can be used are those supplied by Expancel of Stockviksverken, Sweden under the trademark EXPANCEL®, and those supplied by PQ Corp. of Valley Forge, Pa. U.S.A. under the tradename PM 6545, PM 6550, PM 7220, PM 7228, EXTENDOSPHERES®, LUXSIL®, Q-CEL® and SPHERICEL®.

Processes of Making and Using the Cleaning Compositions of the Present Invention The cleaning compositions of the present invention can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422 Del Greco et al.; U.S. Pat. No. 5,516,448; U.S. Pat. No. 5,489,392; and U.S. Pat. No. 5,486,303; all of which are incorporated herein by reference.

Adjunct Materials in Addition to the Enzymes of the Present Invention, Hydrogen Peroxide, and/or Hydrogen Peroxide Source and Material Comprising an Ester Moiety While not essential for the purposes of the present invention, the non-limiting list of adjuncts illustrated hereinafter are suitable for use in the instant cleaning compositions and may be desirably incorporated in certain embodiments of the invention, for example to assist or enhance cleaning performance, for treatment of the substrate to be cleaned, or to modify the aesthetics of the cleaning composition as is the case with perfumes, colorants, dyes or the like. It is understood that such adjuncts are in addition to the enzymes of the present invention, hydrogen peroxide and/or hydrogen peroxide source and material comprising an ester moiety. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, and 6,326,348, herein incorporated by reference. The aforementioned adjunct ingredients may constitute the balance of the cleaning compositions of the present invention.

Surfactants—The cleaning compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof.

The surfactant is typically present at a level of from about 0.1% to about 60%, from about 1% to about 50% or even from about 5% to about 40% by weight of the subject cleaning composition.

Builders—The cleaning compositions of the present invention may comprise one or more detergent builders or builder systems. When a builder is used, the subject cleaning composition will typically comprise at least about 1%, from about 3% to about 60% or even from about 5% to about 40% builder by weight of the subject cleaning composition.

Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

Chelating Agents—The cleaning compositions herein may contain a chelating agent, Suitable chelating agents include copper, iron and/or manganese chelating agents and mixtures thereof.

When a chelating agent is used, the cleaning composition may comprise from about 0.1% to about 15% or even from about 3.0% to about 10% chelating agent by weight of the subject cleaning composition.

Deposition Aid—The cleaning compositions herein may contain a deposition aid. Suitable deposition aids include, polyethylene glycol, polypropylene glycol, polycarboxylate, soil release polymers such as polytelephthalic acid, clays such as Kaolinite, montmorillonite, atapulgite, illite, bentonite, halloysite, and mixtures thereof.

Dye Transfer Inhibiting Agents—The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof.

When present in a subject cleaning composition, the dye transfer inhibiting agents may be present at levels from about 0.0001% to about 10%, from about 0.01% to about 5% or even from about 0.1% to about 3% by weight of the cleaning composition.

Dispersants—The cleaning compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Enzymes—The cleaning compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is cocktail of conventional applicable enzymes like protease, lipase, cutinase and/or cellulase in conjunction with amylase.

Enzyme Stabilizers—Enzymes for use in detergents can be stabilized by various techniques. The enzymes employed herein can be stabilized by the presence of water-soluble sources of calcium and/or magnesium ions in the finished compositions that provide such ions to the enzymes.

Catalytic Metal Complexes—The cleaning compositions of the present invention may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. No. 5,597,936; and U.S. Pat. No. 5,595,967. Such cobalt catalysts are readily prepared by known procedures, such as taught for example in U.S. Pat. No. 5,597,936, and U.S. Pat. No. 5,595,967.

Compositions herein may also suitably include a transition metal complex of a macropolycyclic rigid ligand—abreviated as “MRL”. As a practical matter, and not by way of limitation, the compositions and cleaning processes herein can be adjusted to provide on the order of at least one part per hundred million of the active MRL species in the aqueous washing medium, and will preferably provide from about 0.005 ppm to about 25 ppm, more preferably from about 0.05 ppm to about 10 ppm, and most preferably from about 0.1 ppm to about 5 ppm, of the MRL in the wash liquor.

Preferred transition-metals in the instant transition-metal bleach catalyst include manganese, iron and chromium. Preferred MRL’s herein are a special type of ultra-rigid ligand that is cross-bridged such as 5,12-diethyl-1,5,8,12-tetraazabicyclo[6.6.2]hexadecane.

Suitable transition metal MRLs are readily prepared by known procedures, such as taught for example in WO 00/332601, and U.S. Pat. No. 6,225,464.

Method of Use

The cleaning compositions disclosed herein of can be used to clean a situs inter alia a surface or fabric. Typically at least a portion of the situs is contacted with an embodiment of Applicants’ cleaning composition, in neat form or diluted in a wash liquor, and then the situs is optionally washed and/or rinsed. For purposes of the present invention, washing includes but is not limited to, scrubbing, and mechanical agitation. The fabric may comprise most any fabric capable of being laundered in normal consumer use conditions. The disclosed cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); HCl (hydrochloric acid); aa (amino acid); by (base pair); kb (kilobase pair); kD (kilodaltons); gm (grams); µg and ug (micrograms); mg (milligrams); ng (nanograms); µl and ul (microliters); ml (milliliters); mm (millimeters); nm (nanometers); µm and um (micrometer); M (molar); mM (millimolar); µM and uM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); EtOH (ethanol); PBS (phosphate buffered saline [150 mM NaCl, 10 mM sodium phosphate buffer, pH 7.2]); SDS (sodium dodecyl sulfate); Tris(tris(hydroxymethyl)aminomethane); TAED (N,N,N'N'-tetraacetylethylenediamine); w/v (weight to volume); v/v (volume to volume); Per (perhydrolase); per (perhydrolase gene); Ms (*M. smegmatis*); MS (mass spectroscopy); BRAIN (BRAIN Biotechnology Research and Information Network, AG, Zwingenberg, Germany); TIGR (The Institute for Genomic Research, Rockville, Md.); AATCC (American Association of Textile and Coloring Chemists); WFK (wfk Testgewebe GmbH, Bruggen-Bracht, Germany); Amersham (Amersham Life Science, Inc. Arlington Heights, Ill.); ICN (ICN Pharmaceuticals, Inc., Costa Mesa, Calif.); Pierce (Pierce Biotechnology, Rockford, Ill.); Amicon (Amicon, Inc., Beverly, Mass.); ATCC (American Type Culture Collection, Manassas, Va.); Amersham (Amersham Biosciences, Inc., Piscataway, N.J.); Becton Dickinson (Becton Dickinson Labware, Lincoln Park, N.J.); BioRad (BioRad, Richmond, Calif.); Clontech (CLONTECH Laboratories, Palo Alto, Calif.); Difco (Difco Laboratories, Detroit, Mich.); GIBCO BRL or Gibco BRL (Life Technologies, Inc., Gaithersburg, Md.); Novagen (Novagen, Inc., Madison, Wis.); Qiagen (Qiagen, Inc., Valencia, Calif.); Invitrogen (Invitrogen Corp., Carlsbad, Calif.); Genaissance (Genaissance Pharmaceuticals, Inc., New Haven, Conn.); DNA 2.0 (DNA 2.0, Menlo Park, Calif.); MIDI (MIDI Labs, Newark, Del.) InvivoGen (InvivoGen, San Diego, Calif.); Sigma (Sigma Chemical Co., St. Louis, Mo.); Sorvall (Sorvall Instruments, a subsidiary of DuPont Co., Biotechnology Systems, Wilmington, Del.); Stratagene (Stratagene Cloning Systems, La Jolla, Calif.); Roche (Hoffmann La Roche, Inc., Nutley, N.J.); Agilent (Agilent Technologies, Palo Alto, Calif.); Minolta (Konica Minolta, Ramsey, N.J.); and Zeiss (Carl Zeiss, Inc., Thornwood, N.Y.).

In the following Examples, various media were used. "TS" medium (per liter) was prepared using Tryptone (16 g) (Difco), Soytone (4 g) (Difco), Casein hydrolysate (20 g) (Sigma), $K_2HPO_4$ (10 g), and d $H_2O$ (to 1 L). The medium was sterilized by autoclaving. Then, sterile glucose was added to 1.5% final concentration. *Streptomyces* Production Medium (per liter) was prepared using citric acid ($H_2O$) (2.4 g), Biospringer yeast extract (6 g), $(NH_4)2SO_4$ (2.4 g), $MgSO_4.7H_2O$ (2.4 g), Mazu DF204 (5 ml), trace elements (5 ml). The pH was adjusted to 6.9 with NaOH. The medium was then autoclaved to sterilize. After sterilization, $CaCl_2.2H_2O$ (2 mls of 100 mg/ml solution), $KH_2PO_4$ (200 ml of a 13% (w/v) solution at pH6.9), and 20 mls of a 50% glucose solution were added to the medium.

In these experiments, a spectrophotometer was used to measure the absorbance of the products formed after the completion of the reactions. A reflectometer was used to measure the reflectance of the swatches. Unless otherwise indicated, protein concentrations were estimated by Coomassie Plus (Pierce), using BSA as the standard.

Example 1

Enzyme Analysis

In this Example, methods to assess enzyme purity and activity used in the subsequent Examples and throughout the present Specification are described.

Enzyme Activity Assay (pNB Assay)

This activity was measured by hydrolysis of p-nitrophenylbutyrate. The reaction mixture was prepared by adding 10 ul of 100 mM p-nitrophenylbutyrate in dimethylsulfoxide to 990 ml of 100 mM Tris-HCl buffer, pH 8.0 containing 0.1% triton X-100. The background rate of hydrolysis was measured before the addition of enzyme at 410 nm. The reaction was initiated by the addition of 10 ul of enzyme to 990 ml of the reaction and the change of absorbance at 410 nm was measured at room temperate (~23° C.). The background corrected results are reported as $\delta A_{410}$/min/ml or $\delta A_{410}$/min/mg protein.

Transesterification

Transesterification was measured by GC separation of products in buffered aqueous reactions. Reactions to measure ethyl acetate transesterification with propanol contained in 1 ml of 50 mM KPO4, pH 7.0; 200 mM ethyl acetate, 200 mM 1-propanol, and enzyme. Reactions to measure ethyl acetate transesterification with neopentyl glycol (NPG) contained in 1 ml of 50 mM KPO4, pH 7.0; 303 mM ethyl acetate, 100 mM NPG, and enzyme. The reactions were incubated at the indicated temperatures and for the indicated times. Separations were preformed using a 30M FFAP column (Phenomenex). The inlet split ratio was approximately 1:25, the injector was 250° C., head pressure of 10 psi He, and detection was by FID at 250° C. The chromatography program was 40° C. initial for 4 min, followed by a gradient of 15° C./min to 180° C. Components eluted in the following order and were not quantified; ethyl acetate, ethyl alcohol, propyl acetate, propyl alcohol, acetic acid, NPG diacetate, NPG monoacetate, and NPG.

Perhydrolase Used in Crystallography Studies

This perhydrolase preparation was used for crystallography studies. In addition, unlabelled protein was grown and purified in similar manner. A 500 ml preculture of *E. coli* BL21(DE3)/pLysS/pMSATNco1-1 was grown in a baffled 2.8 L Fernbach flask on LB containing 100 ug/ml carbenicillin. After overnight culture at 37° C. and 200 rpm on a rotary shaker, the cells were harvested by centrifugation and resuspended in M9 medium containing: glucose, 2 g/L; $Na_2HPO_4$, 6 g/L; $KH_2PO_4$, 3 g/L; $NH_4Cl$, 1 g/L; NaCl, 0.5 g/L; thiamine, 5 mg/L; $MgSO_4$, 2 mM; $CaCl_2$, 100 uM; Citric acid.$H_2O$, 40 mg/L; $MnSO_4.H_2O$, 30 mg/L; NaCl, 10 mg/L; $FeSO_4.7H_2O$, 1 mg/L; $CoCl_2.6H_2O$, 1 mg/L; $ZnSO_4.7H_2O$, 1 mg/L; $CuSO_4.5H_2O$, 100 ug/L; $H_3BO_3.5H_2O$, 100 ug/L; and $NaMoO_4.2H_2O$, 100 ug/L; and supplemented with carbenicillin, 100 mg/L. The resuspended cells were used to inoculate six Fernbach flasks containing 500 ml each of M9 medium supplemented with carbenicillin (100 mg/L). The cultures were incubated at 20° C. and 200 rpm on a rotary shaker until the $OD_{600}$ reached about 0.7 at which time 100 mg/L of lysine, threonine, and phenylalanine and 50 mg/L of leucine, isoleucine, valine, and selenomethionine were added. After further incubation for 30 min, IPTG was added to a final concentration of 50 uM. The cultures were then incubated overnight (~15 hr) and harvested by centrifugation. The cell pellet was washed 2 times with 50 mM $KPO_4$ buffer, pH 6.8. The yield was 28.5 μm wet weight of cells to which was added 114 ml of 100 mM $KPO_4$ buffer, pH 8.2 and 5 mg of DNase. This mixture was frozen at −80° C. and thawed 2 times.

The thawed cell suspension was lysed by disruption in a French pressure cell at 20K psi. The unbroken cells and cell membrane material were sedimented by centrifugation at 100K times g for 1 hour. The supernatant crude extract, 128 ml (CE) was then placed in a 600 ml beaker and stirred for 10 minutes in a 55° C. water bath to precipitate unstable proteins. After 10 min the beaker was stirred in ice water for 1 min followed by centrifugation at 15K times g for 15 mM The supernatant from this procedure, HT, contained 118 ml. The HT extract was then made 20% saturating in $(NH_4)_2SO_4$ by the slow addition of 12.7 g of $(NH_4)_2SO_4$. This was loaded on to a 10 cm×11.6 cm Fast Flow Phenyl Sepharose (Pharmacia) column equilibrated in 100 mM $KPO_4$ buffer, pH 6.8, containing 20% saturation (109 g/L) $(NH_4)_2SO_4$. After loading the extract the column was washed with 1700 ml of starting buffer and eluted with a two step gradient. The first step was a linear 1900 ml gradient from start buffer to the same buffer without $(NH_4)_2SO_4$, the second was a 500 ml elution with 100 mM $KPO_4$, pH 6.8 containing 5% EtOH. Active fractions, 241 ml, were pooled, diluted 100% with water and loaded onto a 1.6 mm×16 mm Poros HQ strong anion exchange column equilibrated in 100 mM Tris-HCl, pH 7.6. After loading the extract, the column was washed with 5 column volumes of starting buffer. The protein was eluted with a 15 column volume gradient from start buffer to start buffer containing 175 mM KCl. The active fractions were pooled and concentrated using a Centriprep 30 (Millipore) to 740 μl. FIG. 6 provides a purification table showing the enzyme activity of the enzyme of the present invention through various steps in the purification process.

The present application must be used to determine the respective values of the parameters of the present invention.

Unless otherwise noted, all component or composition levels are in reference to the active level of that component or composition, and are exclusive of impurities, for example, residual solvents or by-products, which may be present in commercially available sources.

Enzyme components weights provided herein are based on total active protein. All percentages and ratios were calculated by weight unless otherwise indicated. All percentages and ratios were calculated based on the total composition unless otherwise indicated.

Example 2

Determination of Ratio Between Peracid and Acid Formation

In this Example, methods for determining the ratio of perhydrolysis to hydrolysis are described. In particular, this Example provides methods for determining the ratio between peracid formation (i.e., perhydrolysis) and acid formation (i.e., hydrolysis) resulting from enzyme activity on an ester substrate in the presence of peroxide in an aqueous system.

A. Determination of Perhydrolysis to Hydrolysis Ratio

Preparation of Substrate

The substrates were prepared as described herein. Ethyl acetate (EtOAc) and other water soluble esters were diluted in a desired buffer to a concentration of 10 mM of ester. Tributyrin and other water insoluble substrates were prepared by making substrate swatches. Polyester swatches were cut from non-dyed polyester fabric (Polycotton, PCW 22) using a 5/8 inch punch and placed in a 24-well microtiter plate (Costar, Cell Culture Plate). The insoluble ester was diluted to 1.03 M in hexane. Then, 10 μL of the insoluble ester solution were then adsorbed onto the polyester swatch.

Determination of Hydrolysis (GC Assay)

The hydrolytic assay described below was used to determine the amount of substrate hydrolysis. In this assay, the assay solution was comprised of 50 mM potassium phosphate pH 7.5, 10 mM ester substrate, 29 mM hydrogen peroxide, and 20 mM potassium chloride in a total volume of 0.99 ml and an amount of enzyme that would generate 20 nmoles of acetic acid per minute at 25° C.

For measuring water insoluble ester hydrolysis, the reaction mixture was added to the insoluble ester fabric swatch. The swatch was prepared as described above ("Preparation of Substrate"). All the other conditions for the assay were the same except for exclusion of other ester substrates.

Hydrolytic activity was measured by monitoring the increase of acids generated by the enzyme from acyl donor substrates using gas chromatography coupled with flame ionization detection. The assay was conducted by first pipetting 50 μL of assay solution containing all the components except the enzyme into 200 mL of methanol (HPLC grade) to determine the amount of acid in the assay solution at time 0. Then, 10 μL of enzyme were added to the assay solution to a desired final concentration which produced approximately 20 nanomoles of acid per minute. A timer was started and 50 μL aliquots were taken from the assay solution and added to 200 μL of methanol at various times, typically 2, 5, 10, 15, 25, 40, and 60 minutes, after addition of the enzyme.

These methanol-quenched samples were then injected into a gas chromatograph coupled with a flame ionization detector (Agilent 6890N) and analyzed for hydrolytic components, acetic, and butyric acids. Gas chromatography was conducted using a nitroterephthalic acid modified polyethylene glycol column (Zebron FFAP; with dimensions: 30 m long, 250 um diameter, 250 nm film thickness). A 3 μL aliquot of sample was applied to the column by a splitless injection under constant a helium flow of 1.0 mL/minute. The inlet was maintained at a temperature of 250° C. and was purged of any remaining sample components after 2 minutes. When analyzing acetic acid, the temperature of the column was maintained at 75° C. for 1 minute after injection, increased 25° C./minute to 100° C., then increased 15° C./minute to 200° C.

When analyzing butyric acid, the temperature of the column was controlled as described above, except the temperature was additionally increased 25° C./minute to 225° C. and held at 225° C. for 1 minute. The flame ionization detector was maintained throughout the chromatography at 250° C. and under constant hydrogen flow of 25 mL/minute, air flow of 200 mL/minute, and a combined column and makeup helium flow of 30 mL/minute. The amount of hydrolyzed acid in the sample was then determined by integrating the acid peak in the chromatogram for total ion counts and calculating the acid from the ion count using a standard curve generated under the above conditions for acetic and butyric acids at varying concentrations in the assay solution (without enzyme).

Determination of Perhydrolysis (OPD Assay)

The perhydrolytic activity assay described below was used to determine the amount of peracid formed in the reaction. In these assays, the solution comprised 50 mM potassium phosphate pH 7.5, 10 mM ester substrate, 29 mM hydrogen peroxide, 20 mM potassium chloride, and 10 mM O-phenylenediamine.

When using water insoluble ester as the acyl donor, an ester adsorbed fabric swatch was used as the substrate, prepared as described above ("Preparation of Substrate").

Perhydrolytic activity was measured by monitoring the absorbance increase at 458 nm of oxidized O-phenylenediamine (OPD) by peracid generated with the enzyme. The perhydrolytic activity assay solution was prepared in the same manner as the hydrolytic activity assay solution, except that OPD was added to the assay solution to a final concentration of 10 mM. The OPD solution was prepared immediately before conducting the assay by dissolving 72 mg OPD (Sigma-Aldrich, dihydrochloride) in 19.94 mL of the same buffer and the pH was adjusted by slowly adding 60 μL of 13.5 M potassium hydroxide. The pH was measured and if needed, small quantities of potassium hydroxide were added to return the pH to the original pH of the buffer. Then, 495 μL of this OPD solution were added with the other assay components to a final assay volume of 0.990 mL. An assay quenching solution was also prepared by dissolving 36 mg OPD in 20 mL 100 mM citric acid and 70% ethanol.

The assay was typically conducted at 25° C. The assay was started by pipetting 100 μL of assay solution before the addition of the enzyme into 200 μL of quenching solution to determine the amount of perhydrolytic components and background absorbance in the assay solution at time 0. Then, 10 μL of enzyme were added to the assay solution to a desired final concentration which produced approximately 10 nanomoles of peracid per minute. A timer was started and 100 μL aliquots were taken from the assay solution and added to 200 μL of quenching solution at various times, typically 2, 5, 10, 15, 25, 40, and 60 minutes, after adding the enzyme. The quenched assay solutions were incubated for 30 minutes to allow any remaining peracid to oxidize the OPD. Then, 100 μL of each quenched assay solution was transferred to a 96-well microtiter plate (Costar) and the absorbance of the solution was measured at 458 nm by a spectrophotometric plate reader (Molecular Devices, SpectraMAX 250). The amount of peracid in each quenched sample was calculated using a standard curve generated under the above conditions with peracetic acid at varying concentrations in the assay solution (without enzyme).

Perhydrolysis/Hydrolysis Ratio:

Perhydrolysis/Hydrolysis ratio=Perhydrolysis measured in the Perhydrolysis assay/(Total acid detected in the hydrolysis assay−Perhydrolysis measured in the perhydrolysis assay)

Figure 7:
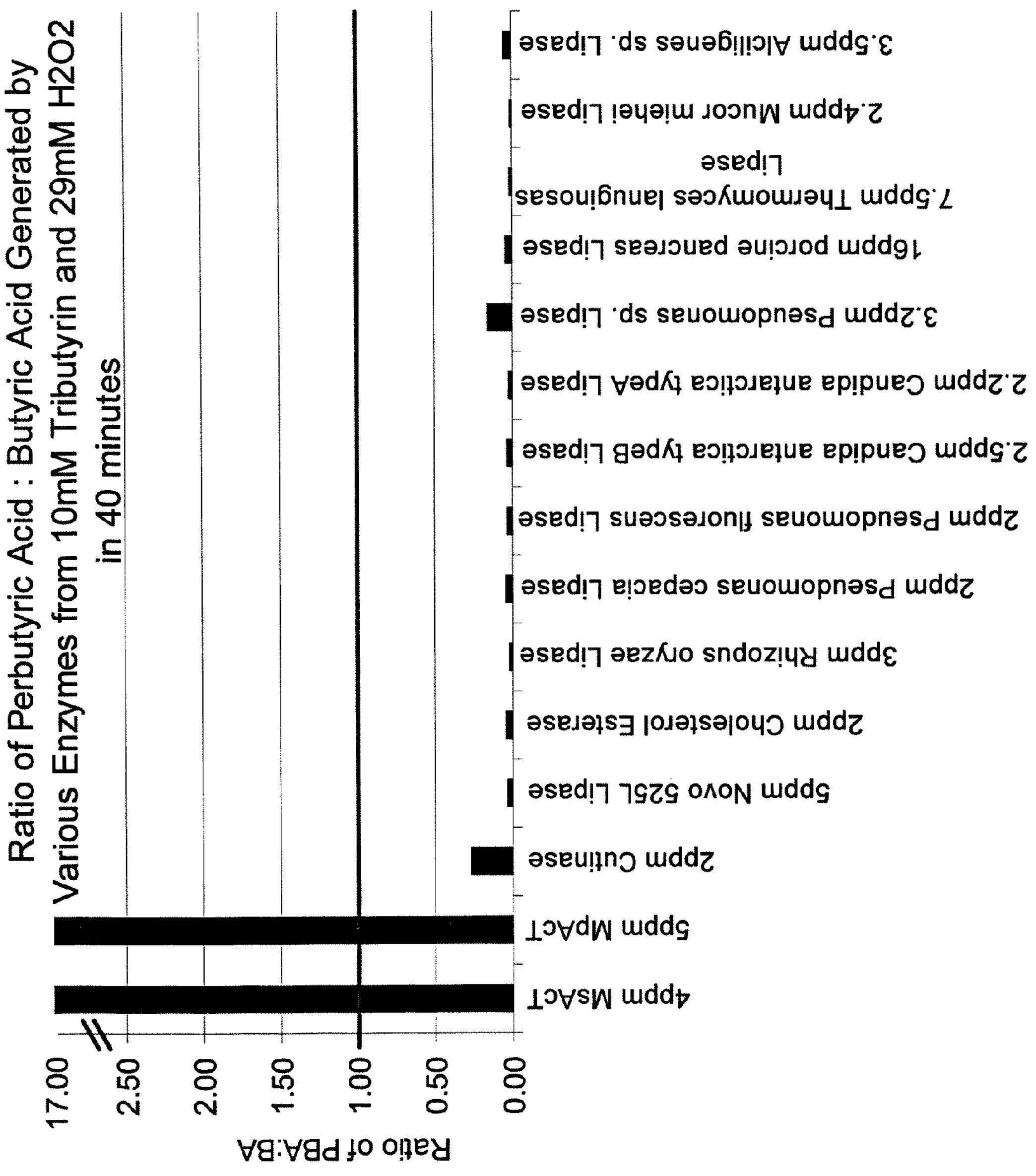
FIG. 7 provides a graph which shows the ratio of perbutyric acid to butyric acid generated by various enzymes from 10 mM tributyrin and 29 mM hydrogen peroxide in 40 minutes.
Figure 10:
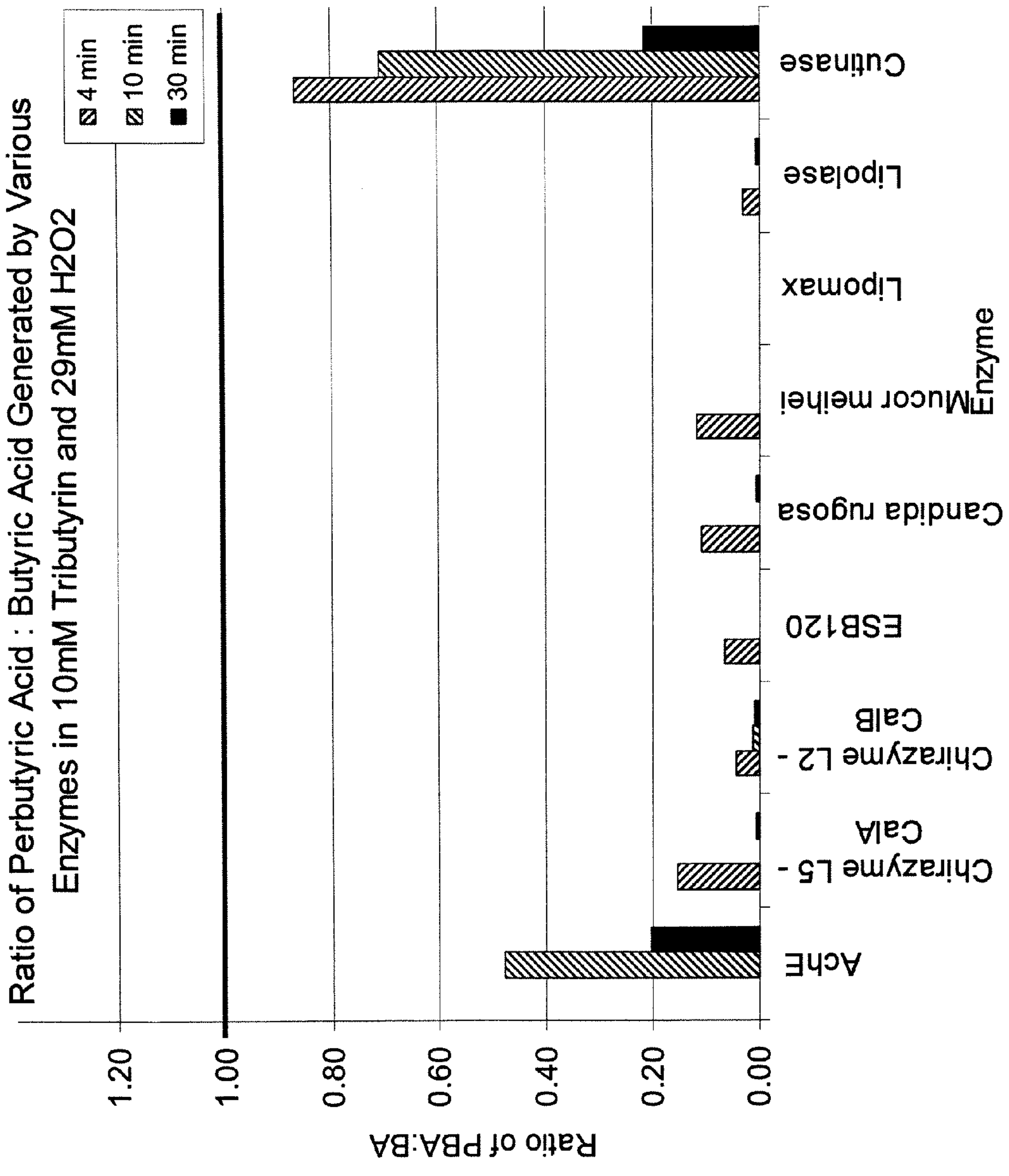
FIG. 10 provides a graph showing the ratio of perbutyric acid to butyric acid generated by various enzymes from 10 mM tributyrin and 29 mM hydrogen peroxide in 4, 10, and 30 minutes.
Figure 11:
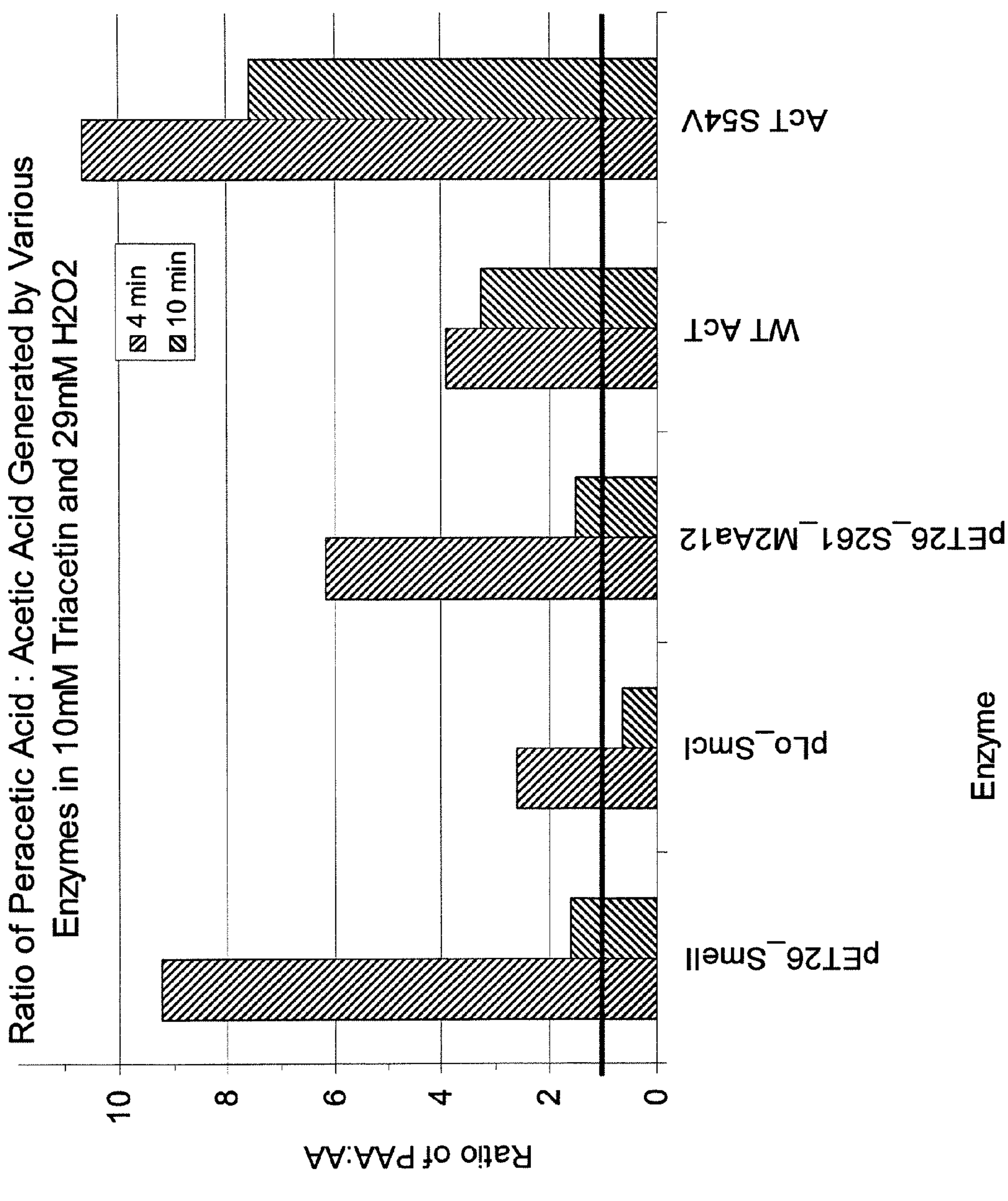
FIG. 11 provides a graph showing the ratio of peracetic acid to acetic acid generated by various enzymes from 10 mM triacetin and 29 mM hydrogen peroxide in 4 and 10 minutes.

The results of these experiments are provided in FIGS. 7, 10 and FIG. 11. FIG. 7 provides a graph which shows the ratio of perbutyric acid to butyric acid generated by various enzymes from 10 mM tributyrin and 29 mM hydrogen peroxide in 40 minutes. FIG. 10 shows the ratio of perbutyric acid to butyric acid generated by various enzymes from 10 mM tributyrin and 29 mM hydrogen peroxide in 4, 10, and 30 minutes. FIG. 11 shows the ratio of peracetic acid to acetic acid generated by various enzymes from 10 mM triacetin and 29 mM hydrogen peroxide in 4 and 10 minutes. The results obtained in these experiments indicated that *M. smegmatis* perhydrolase homologues exhibited a ratio above 1 in the OPD/GC assays described above, while other classes of enzymes exhibited ratios significantly below 1.

Figure 8:
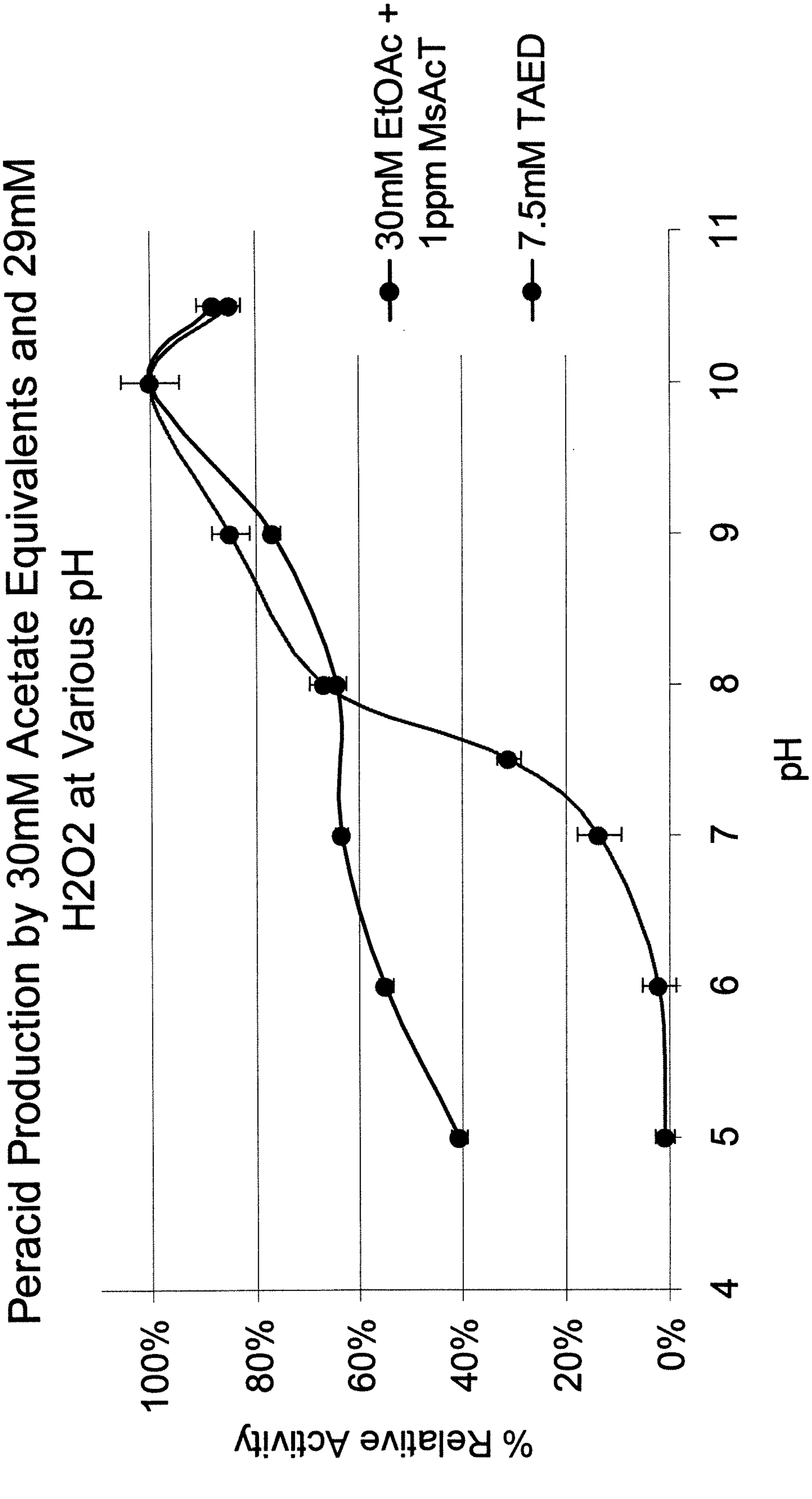
FIG. 8 provides a graph showing the peracid production by 30 mM acetate equivalents and 29 mM hydrogen peroxide, tested at various pHs. These results show that using the perhydrolase composition of the present invention, there is peracid generation over a wide pH range. In contrast, with TAED and hydrogen peroxide, peracid generation is limited to alkaline conditions.
Figure 9:
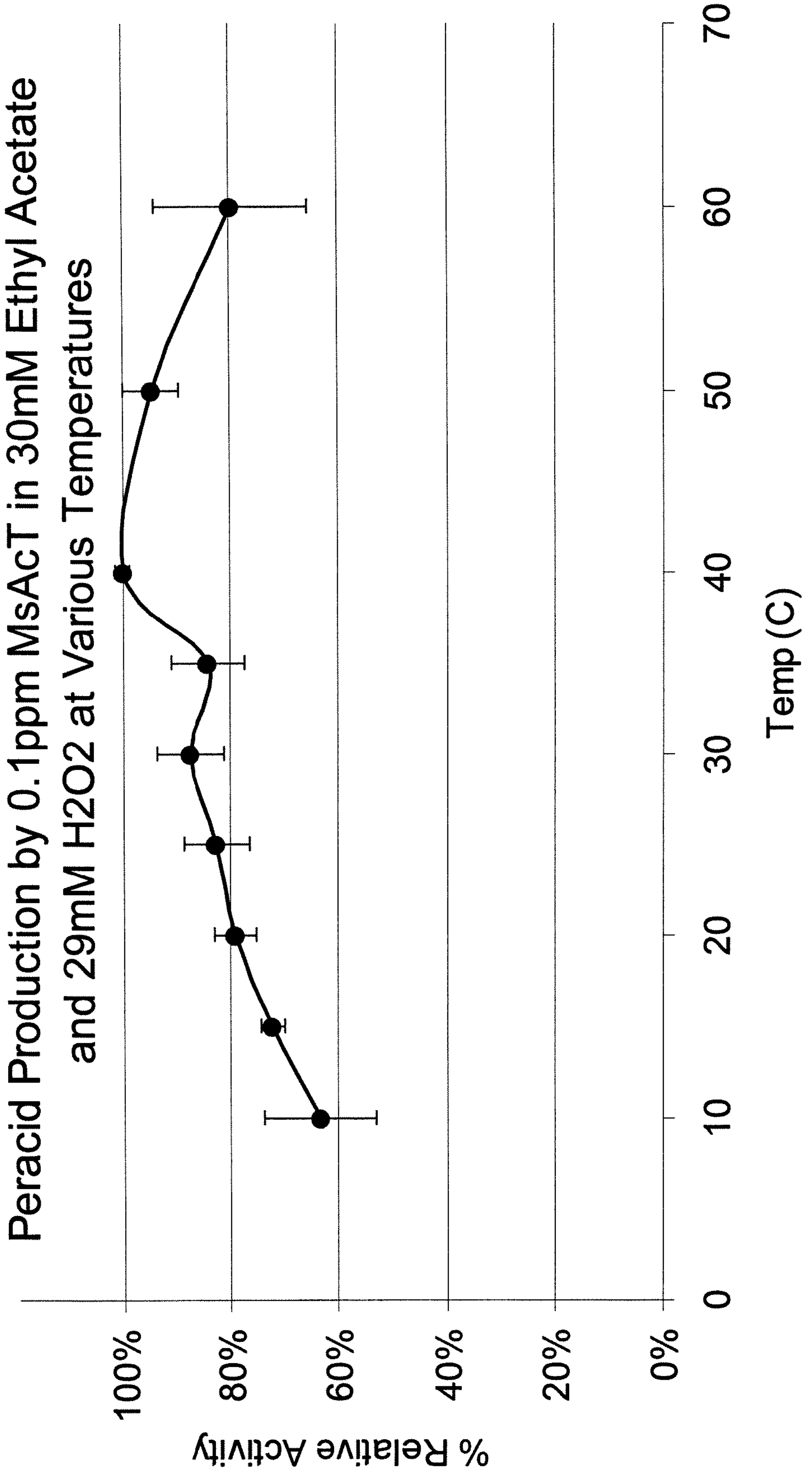
FIG. 9 provides a graph showing the peracid production by 0.1 ppm perhydrolase enzyme in 30 mM ethyl acetate and 20 mM hydrogen peroxide at various temperatures. These results show that the perhydrolase of the present invention works at a wide range of temperatures, including low temperatures.

Table 2-1 provides data showing the perhydrolysis activity of various homologues described herein on triacetin, as compared to the wild-type *M. smegmatis* perhydrolase. The results provided in Table 2-2 indicate that the perhydrolase has activity over a broad range of substrates. In addition to the results provided in these Tables, FIGS. 8 and 9 provide data showing that the perhydrolase of the present invention has broad pH and temperature range activities.

TABLE 2-1

Perhydrolysis Activity of Perhydrolase Homologues on Triacetin as Compared to *M. smegmatis* perhydrolase

| Experiment | Protein | Perhydrolysis Ratio (homolog to perhydrolase) |
|---|---|---|
| A. | pET26_Mlo | 0.6 |
| | pET26b_Mbo | 0.87 |
| | pET26_SmeII | 2.1 |
| | pET26b_Stm | 0.17 |
| | pLO_SmeI | 0.7 |
| | Perhydrolase | 1.0000 |
| | Blank | 0.0660 |
| B. | pET26_S261_M2aA12 | 1.5 |
| | Perhydrolase | 1 |
| | Blank | 0.3 |
| C. | pet26 M40cD4 | 0.14 |
| | pet26 M44aA5 | 0.16 |
| | Perhydrolase | 1 |
| | Blank | 0.01 |

TABLE 2-2

Peracid Production by 1 ppm Wild-Type Perhydrolase with 29 mM H2O2 and Various Esters

| Ester | nmol Peracetic Acid/min: 10 mM of Ester with 0.5% Neodol | 10 mM of Ester | 10 mM of Ester on Polycotton Swatch |
|---|---|---|---|
| Ethyl Acetate | | 5.00 | |
| Butyl Acetate | 8.06 | 8.72 | |
| Hexyl Acetate | 7.96 | 5.86 | |
| Octyl Acetate | 8.03 | 0.48 | |
| Ethyl Propionate | 0.90 | 1.43 | |
| Butyl Propionate | 2.47 | 3.39 | |
| Hexyl Propionate | 4.00 | 2.66 | |
| Isoamyl Acetate | 7.83 | | 17.69 |
| Citronellyl Acetate | 7.25 | | 4.27 |
| Citronellyl Propionate | 2.85 | | 3.21 |
| Dodecyl Acetate | 3.95 | | 0.19 |
| Neodol 23-3 Acetate | 2.25 | | 8.77 |
| Neodol 23-6.5 Acetate | 2.73 | | 10.12 |
| Neodol 23-9 Acetate | 2.97 | | 10.20 |
| Ethylene Glycol Diacetate | 13.30 | | |
| Propylene Glycol Diacetate | 13.17 | | |
| Triacetin | 11.91 | | |
| Tributyrin | 0.66 | | 2.70 |
| Ethyl Methoxyacetate | 0.49 | | |
| Linalyl Acetate | 0.30 | | |
| Ethyl Butyrate | 0.31 | | |
| Ethyl Isobutyrate | 0.10 | | |
| Ethyl 2-methylbutyrate | 0.11 | | |
| Ethyl Isovalerate | 0.37 | | |
| Diethyl Maleate | 0.75 | | |
| Ethyl Glycolate | 1.91 | | |

B. Typical Perhydrolase Peracid Generation Assay:

Perhydrolase is active over a wide pH and temperature range and accepts a wide range of substrates for acyl transfer. Acceptors include water (hydrolysis), hydrogen peroxide (perhydrolysis) and alcohols (classical acyl transfer). For perhydrolysis measurements enzyme was incubated in the buffer of choice at a specified temperature with a substrate ester in the presence of hydrogen peroxide. Typical substrates used to measure perhydrolysis include ethylacetate, triacetin, tributyrin, ethoxylated neodol acetate esters, and others. In addition, the wild type enzyme was found able to hydrolyze nitrophenylesters of short chain acids. The latter are convenient substrates to measure enzyme concentration. In some embodiments, peracid acid and acetic acid were measured by the ABTS or HPLC assays as described below. Nitrophenylester hydrolysis is also described below.

C. ABTS Assay (One Milliliter):

This assay provides a determination of peracetic acid produced by perhydrolase. This protocol was adapted from Karst et al., Analyst, 122:567-571 [1997]). Briefly, a 100 μL aliquot of solution to be analyzed was added to 1 mL 125 mM $K^+$ citrate pH 5, 1 mM ABTS, 50 μM KI. Absorbance was measured at 420 nm for highest sensitivity. However, multiple additional wavelengths were sometimes used over the broad absorption spectrum of ABTS. Calibration curves were constructed based on known peracid concentration series.

D. HPLC (Model—Agilent 1100) Determination of Perhydrolase Reaction Products:

For determination of the ratio of perhydrolysis to hydrolysis of the perhydrolase reaction, perhydrolase reaction samples were quenched by acidification to a final concentration of 0.24% methanesulfonic acid, and the products were separated by reverse phase HPLC on a Dionex OA column (cat #062903; Dionex Corporation, Sunnyvale, Calif.). The mobile phase was 100 mM $NaPO_4$, pH 3.9 (buffer was prepared by titrating 100 mM $Na_2PO_4$ with methanesulfonic acid to pH 3.9) run under isocratic conditions at 30° C. Detection was at 210 nm Concentrations of products were calculated by comparison of the integrated peak areas against calibration standards.

E. Nitrophenylester Hydrolysis Kinetic Assay

Enzyme and substrate were incubated in 100 mM Tris/HCl pH 8.0 (or 50 mM $B(OH)_3$ pH 9.5 or another buffer). Absorbance at 402 nm was monitored. In some experiments, the assay was carried out in standard 1 mL cuvettes, while in other experiments, microtiter plate wells were used. The latter method was used for the screening of mutant libraries. Enzyme concentration was determined by comparison to standard curves obtained under the same reaction conditions.

F. Para-Nitrophenylcaproate Hydrolysis Assay

The pNC6 substrate solution was prepared by mixing 1 mM pNC6 (100 mM stock solution), 1 ml DMSO, 19 mls 100 mM Phosphate (pH8), and glycerol to a final concentration of 10%. To assay samples, 10 μl of the cell lysate were added to 190 μl of the substrate solution, and assayed at 405 nm for 15 minutes in a spectrophotometer. The results are presented as the average of two experiments.

G. Para-Nitrophenyl Acetate (pNA) Hydrolysis Assay

Aliquots of the lysed cell supernatant were diluted 1-100 in 100 mM phosphate buffer (pH 8). To assay the samples, 5 μl of the 1-100 diluted cell supernatant were placed into each well of a microtiter plate. Then, 195 μl of reaction buffer/substrate mix (1 mM pNA, 100 mM phosphate, pH 8, 10% glycerol) were added, and the absorbance rate at 405 nm was measured over 3 minutes (kinetics program, microtiter plate reader). The results are presented as the average of two experiments.

Example 3

Assays Including Detergent Compositions

In this Example, assay systems used to screen for superior perhydrolase activity in detergents with particular substrates are provided. These assays include those that measure peracid degradation of perhydrolase, as well as the peracid synthesis activity of the enzyme.

Materials and Methods for Peracetic Acid Formation (PAF) and Peracetic Acid Degradation (PAD) Assays This section provides the materials and methods used to screen for a superior perhydrolases in Aria with C9E2OAC ester substrate Materials:

Aria Futur without bleach, perfume, or enzymes (P&G, Aria "C")

C9E2OAc (P&G)

30% Hydrogen Peroxide (Sigma)

32% Peroxyacetic acid ("peracid", PAA) (Sigma cat#) MW=76.05; 4.208M

Citric Acid, anhydrous MW=192.12

Potassium Hydroxide MW=56.11

ABTS (Sigma cat# A1888) MW=548.68

Potassium Iodide MW=166.0

Potassium Phosphate, mono and di-basic

Stock Solutions:

Ariel detergent stock: Aria Futur without bleach, perfume, or enzymes ("Aria C") was dissolved in water to 6.72 g/L. It was stirred at room temp for 30 minutes, then allowed to settle. Then, it was divided into convenient aliquots and stored at 4° C., until used. When made and used fresh, the solution was filtered, instead of settled 100 mM C9E2OAc in Ariel detergent stock: First, 30 μl C9E2OAc was added to 970 μl Aria detergent stock, using a positive displacement pipet. It was sonicated in a bath sonicator until a milky dispersion was formed (15-60 seconds). The dispersion was stable for about two hours. When used, 10 μl of dispersion per ml of reaction mix were used.

42 mM Peroxyacetic acid stock: Right before use, the Sigma 32% PAA solution was diluted 1:100 in water. Then 5.7 μl of the 42 mM stock per ml of reaction mix was added.

2 M hydrogen peroxide: One ml of 30% Sigma hydrogen peroxide was added to 3.41 ml water. This solution was prepared fresh, right before use. It was used at 10 μl per ml of reaction mix.

125 mM Citrate buffer pH 5.0: This was prepared to 24.0 grams per liter. It was made up in 800 ml, and titrated to pH 5.0 with 50% KOH. The volume was adjusted to 1 liter and stored at room temperature.

100 mM ABTS stock: This was prepared using 549 mg of ABTS in 10 ml of water. It was frozen at −80° C., in convenient aliquots in opaque Eppendorf tubes. The stock was stable indefinitely when kept frozen in the dark. ABTS will precipitate when thawed from −80° C. but goes back into solution upon mixing. In use, 10 μl of ABTS stock was used per ml of ABTS reagent.

250 mM KI: This was prepared as 415 mg in 10 ml water. It was kept at 4° C. It was diluted to 25 mM working stock, and 2 ul of working stock was used per ml of ABTS reagent.

25 mM Potassium Phosphate buffer, pH 8.0:

Method:

The night prior to performance of the assays, the plates containing lysed cells that contain perhydrolase were checked to be sure that they were frozen twice. On the day of the assay, 30 to 45 minutes were allowed for the plates to thaw. The ABTS reagent was prepared and the Multidrop (Multidrop 384 instrument, ThermoElectron) to fill the detection plates with 200 μl per well. Store the filled plates covered at room temperature in the dark until needed. Dilutions of the standards were prepared so that when 20 μl of the diluted standard were added to the 180 μl of the reaction mix, the concentration in the well was 1 ppm. Four 4 two-fold serial dilutions were prepared to a set of six standards: 1, 0.5, 0.25, 0.125, and 0.0625 ppm final concentration in the wells.

To test, 20 μl of the standards were added to the thawed 1:10 dilution plate. The reaction mixtures were prepared and the Multidrop used to fill one reaction plate for each plate to be assayed (180 μl/well). Note that the reaction mixtures are different for the PAF and PAD assays.

Peracid Hydrolysis (Peracid Degradation, PAD) Assay:

This assay measures the amount of peracetic acid remaining after a 100 minute incubation with enzyme in an Aria detergent background. The amount of peracid remaining is detected by reacting an aliquot of the reaction mixture with the ABTS detection reagent.

In this assay, 20 μl enzyme samples from the thawed 1:10 dilution plate were transferred, one column at a time with an 8 channel pipetter, into the corresponding column of the pre-filled PAD reaction plate. A timer was started as soon as transfer occurred from the first column; subsequent columns were transferred at 15 second intervals (i.e., the last column was finished 2 min 45 sec. after starting the first one). The plate was mixed for 30 seconds on the thermomixer (750 rpm, to avoid splashing). The plate was then transferred to a humidified chamber at 25° C. The plate was incubated for a total of 100 minutes from the time the first column of enzyme was added. At 100 minutes incubation, the reaction plate was removed from the incubator. Then, 20 ul aliquots of the reaction mixture were transferred to an ABTS reagent plate, in the same order and with the same 15 second time interval that the enzyme samples were originally added to the reaction plate. The ABTS plate was allowed to sit at room temperature for three minutes after the last column of reaction mixture was added. The plate was then read on the spectrophotometric plate reader at 420 and 740 nm.

Perhydrolysis (Peracid Formation, PAF) Assay

Multidrop Optimized Protocol: Screening for a Superior Perhydrolysis in Ariel with C9E2OAC Ester Substrate The same materials and stock solutions described above for PAD were used in these experiments, as indicated below.

Method:

The methods were designed to assay 20 μl aliquots from a 1:100 dilution plate. The 20 μl 1:100 dilution assay plates were produced during the process of obtaining the protein concentrations and were stored at −80° C. The plates were thawed for about 30 to 45 minutes before use. Dilutions of the S54V standards were prepared, so that when 2 μl of the diluted standard are added to the 20 μl of the 1:100 diluted cell lysate, the concentration in the well was 0.1 ppm. Four two-fold serial dilutions were prepared to produced a set of six standards: 0.1, 0.05, 0.025, 0.0125, and 0.00625 ppm final concentration in the wells. Then, 2 ul of the standards were added to the thawed 20 ul 1:100 dilution assay plates in the wells indicated.

Perhydrolysis (Peracid Formation, PAF) Assay:

This assay measures the amount of peroxyacetic acid that is produced in 10 minutes from the C9E2OAc substrate in an Aria detergent background. The amount of peracid formed is detected after 10 minutes by reacting an aliquot of the reaction mixture with the ABTS detection reagent.

The Multidrop was used to deliver 180 μl/well of the PAF reaction mix to the prepared 1:100 dilution plate. The timer was started and the reaction plate was placed on the thermomixer, with the temperature set at 25° C. The plate was covered and the solutions mixed for 30 seconds at 750 rpm. The plate was then allowed to rest on the thermomixer without mixing, for a total of 10 minutes from the time the reaction mix was added. At 10 minutes, the Multidrop was used to add 20 μl/well of the 10×ABTS reagent. The 10× reagent was a milky suspension. The thermomixer was used to briefly shake the plate. The ABTS reagent quickly went into solution. The plate was allowed to sit at room temperature for three minutes after the ABTS reagent was added. The plate was then read on the spectrophotometric plate reader at 420 nm.

Example 4

Cloning of *Mycobacterium smegmatis* Perhydrolase

In this Example, the cloning of *M. smegmatis* perhydrolase is described. An enzyme with acyltransferase activity was purified from *Corynebacterium oxydans* (now *Mycobacterium parafortuitum* ATCC19686). Two peptide sequences were obtained from the purified protein. One peptide was determined by Edman degradation from cyanogen bromide cleavage of the purified enzyme using methods known in the art. The sequence of this peptide was determined to be KVPFFDAGSVISTDGVDGI (SEQ ID NO:3). The second peptide was analyzed using N-terminal sequencing and was found to have the GTRRILSFGDSLTWGWIPV (SEQ ID NO:4). A BLAST search against the TIGR unfinished genome database identified a sequence of potential interest in *Mycobacterium smegmatis*, which is shown below:

```
                                                (SEQ ID NO: 2)
MAKRILCFGDSLTWGWVPVEDGAPTERFAPDVRWTGVLAQQLGADFEVI

EEGLSARTTNIDDPTDPRLNGASYLPSCLATHLPLDLVIIMLGTNDTKA

YFRRTPLDIALGMSVLVTQVLTSAGGVGTTYPAPKVLVVSPPPLAPMPH

PWFQLIFEGGEQKTTELARVYSALASFMKVPFFDAGSVISTDGVDGIHF

TEANNRDLGVALAEQVRSLL.
```

The corresponding DNA sequence of the gene is:

```
                                                (SEQ ID NO: 1)
5'-ATGGCCAAGCGAATTCTGTGTTTCGGTGATTCCCTGACCTGGGGCT

GGGTCCCCGTCGAAGACGGGGCACCCACCGAGCGGTTCGCCCCCGACGT

GCGCTGGACCGGTGTGCTGGCCCAGCAGCTCGGAGCGGACTTCGAGGTG

ATCGAGGAGGGACTGAGCGCGCGCACCACCAACATCGACGACCCCACCG

ATCCGCGGCTCAACGGCGCGAGCTACCTGCCGTCGTGCCTCGCGACGCA

CCTGCCGCTCGACCTGGTGATCATCATGCTGGGCACCAACGACACCAAG

GCCTACTTCCGGCGCACCCCGCTCGACATCGCGCTGGGCATGTCGGTGC

TCGTCACGCAGGTGCTCACCAGCGCGGGCGGCGTCGGCACCACGTACCC

GGCACCCAAGGTGCTGGTGGTCTCGCCGCCACCGCTGGCGCCCATGCCG

CACCCCTGGTTCCAGTTGATCTTCGAGGGCGGCGAGCAGAAGACCACTG

AGCTCGCCCGCGTGTACAGCGCGCTCGCGTCGTTCATGAAGGTGCCGTT

CTTCGACGCGGGTTCGGTGATCAGCACCGACGGCGTCGACGGAATCCAC

TTCACCGAGGCCAACAATCGCGATCTCGGGGTGGCCCTCGCGGAACAGG

TGCGGAGCCTGCTGTAA-3'
```

Primers were designed based on the gene sequence to amplify and clone the gene. The primers used for amplification were:

```
MsRBSF:
                                                (SEQ ID NO: 5)
5'-CTAACAGGAGGAATTAACCATGGCCAAGCGAATTCTGTGTTTCGGT

GATTCCCTGACCT-3'

MspetBamR:
                                                (SEQ ID NO: 6)
5'-GCGCGCGGATCCGCGCGCTTACAGCAGGCTCCGCACCTGTTCCGCG

AGGGCCACCCCGA-3'
```

The amplification of the gene was done by PCR using Taq DNA polymerase (Roche) per the manufacturer's instructions, with approximately 500 ng of chromosomal DNA from *Mycobacterium smegmatis* as the template DNA and the addition of 1% DMSO to the PCR reaction mix. Thirty picomoles of each of the primers MsRBSF and MspetBamR were added to the mix. The amplification cycle was: 30 cycles of (95° C. for 1 min, 55° C. for 1 min, 72° C. for 1 min).

Figure 12:
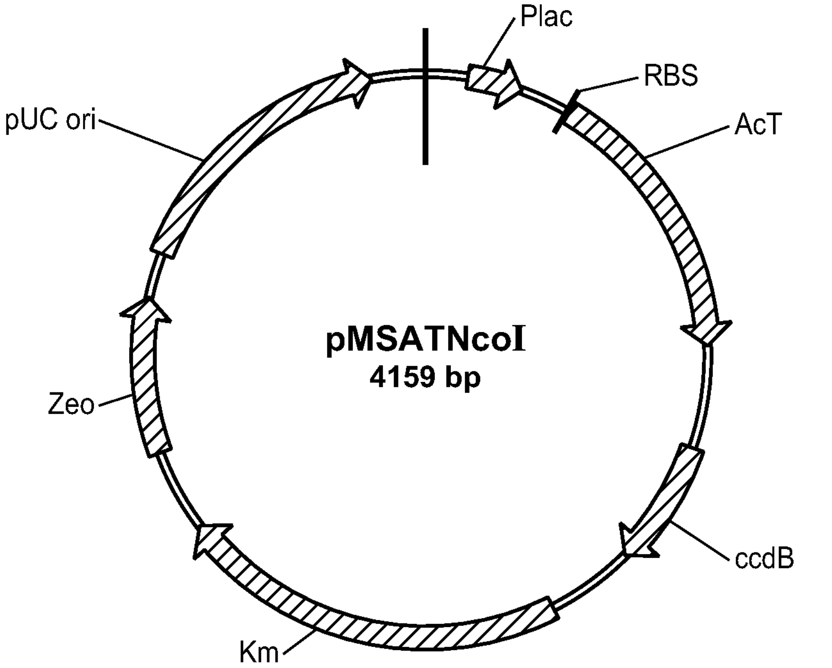
FIG. 12 provides a map of plasmid pMSATNcoI.

The fragments obtained from the PCR reaction were separated on a 1.2% agarose gel and a single band of the expected size of 651 bp (coding sequence and stop codon) was identified. This band was cloned directly into the pCR2.1 TOPO cloning vector (Invitrogen) and transformed into *E. coli* Top 10 cells (Invitrogen) with selection on L agar (10 g/l tryptone, 5 g/l yeast extract, 5 g/l NaCl, 20 g/l agar) containing 100 micrograms/ml carbenicillin and X-gal (20 micrograms/ml, Sigma-Aldrich) for blue/white selection and incubated overnight at 37° C. Five white colonies were analyzed for the presence of the PCR fragment. Each colony was used to inoculate 5 mls of L broth (L agar without the addition of agar) containing 100 micrograms/ml carbenicillin and the cultures were grown overnight at 37° C. with shaking at 200 rpm. Plasmid DNA was purified from the cultures using the Quikspin kit (Qiagen). The presence of the correct fragment was determined by restriction enzyme digest with EcoR1 to release the fragment, and sequencing using primers supplied by the pCR2.1 manufacturer (Invitrogen). The correct plasmid was designated pMSATNcoI (See, FIG. 12, for the map of this plasmid)). The sequence of this plasmid is provided below (SEQ ID NO: 13)

```
agcgcccaatacgcaaaccgcctctccccgcgcgttggccgattcatt
aatgcagctggcacgacaggtttcccgactggaaagcgggcagtgagc
gcaacgcaattaatgtgagttagctcactcattaggcaccccaggctt
tacactttatgcttccggctcgtatgttgtgtggaattgtgagcggat
aacaatttcacacaggaaacagctatgaccatgattacgccaagctat
ttaggtgacactatagaatactcaagctatgcatcaagcttggtaccg
agctcggatccactagtaacggccgccagtgtgctggaattcgccctt
ctaacaggaggaattaaccatggccaagcgaattctgtgtttcggtga
ttccctgacctggggctgggtccccgtcgaagacggggcacccaccga
gcggttcgcccccgacgtgcgctggaccggtgtgctggcccagcagct
cggagcggacttcgaggtgatcgaggagggactgagcgcgcgcaccac
caacatcgacgaccccaccgatccgcggctcaacggcgcgagctacct
gccgtcgtgcctcgcgacgcacctgccgctcgacctggtgatcatcat
gctgggcaccaacgacaccaaggcctacttccggcgcaccccgctcga
catcgcgctgggcatgtcggtgctcgtcacgcaggtgctcaccagcgc
gggcggcgtcggcaccacgtacccggcacccaaggtgctggtggtctc
gccgccaccgctggcgcccatgccgcacccctggttccagttgatctt
cgagggcggcgagcagaagaccactgagctcgcccgcgtgtacagcgc
gctcgcgtcgttcatgaaggtgccgttcttcgacgcgggttcggtgat
cagcaccgacggcgtcgacggaatccacttcaccgaggccaacaatcg
cgatctcggggtggccctcgcggaacaggtgcagagcctgctgtaaaa
gggcgaattctgcagatatccatcacactggcggccgctcgagcatgc
atctagagggcccaattcgccctatagtgagtcgtattacaattcact
ggccgtcgttttacaacgtcgtgactgggaaaaccctggcgttaccca
acttaatcgccttgcagcacatccccctttcgccagctggcgtaatag
cgaagaggcccgcaccgatcgcccttcccaacagttgcgcagcctata
cgtacggcagtttaaggtttacacctataaaagagagagccgttatcg
tctgtttgtggatgtacagagtgatattattgacacgccggggcgacg
gatggtgatccccctggccagtgcacgtctgctgtcagataaagtctc
ccgtgaactttacccggtggtgcatatcggggatgaaagctggcgcat
```

-continued

```
gatgaccaccgatatggccagtgtgccggtctccgttatcggggaaga
agtggctgatctcagccaccgcgaaaatgacatcaaaaacgccattaa
cctgatgttctggggaatataaatgtcaggcatgagattatcaaaaag
gatcttcacctagatccttttcacgtagaaagccagtccgcagaaacg
gtgctgaccccggatgaatgtcagctactgggctatctggacaaggga
aaacgcaagcgcaaagagaaagcaggtagcttgcagtgggcttacatg
gcgatagctagactgggcggttttatggacagcaagcgaaccggaatt
gccagctggggcgccctctggtaaggttgggaagccctgcaaagtaaa
gctggatggctttctcgccgccaaggatctgatggcgcaggggatcaa
gctctgatcaagagacaggatgaggatcgtttcgcatgattgaacaag
atggattgcacgcaggttctccggccgcttgggtggagaggctattcg
gctatgactgggcacaacagacaatcggctgctctgatgccgccgtgt
tccggctgtcagcgcaggggcgcccggttctttttgtcaagaccgacc
tgtccggtgccctgaatgaactgcaagacgaggcagcgcggctatcgt
ggctggccacgacgggcgttccttgcgcagctgtgctcgacgttgtca
ctgaagcgggaagggactggctgctattgggcgaagtgccggggcagg
atctcctgtcatctcaccttgctcctgccgagaaagtatccatcatgg
ctgatgcaatgcggcggctgcatacgcttgatccggctacctgcccat
tcgaccaccaagcgaaacatcgcatcgagcgagcacgtactcggatgg
aagccggtcttgtcgatcaggatgatctggacgaagagcatcaggggc
tcgcgccagccgaactgttcgccaggctcaaggcgagcatgcccgacg
gcgaggatctcgtcgtgacccatggcgatgcctgcttgccgaatatca
tggtggaaaatggccgcttttctggattcatcgactgtggccggctgg
gtgtggcggaccgctatcaggacatagcgttggctacccgtgatattg
ctgaagagcttggcggcgaatgggctgaccgcttcctcgtgctttacg
gtatcgccgctcccgattcgcagcgcatcgccttctatcgccttcttg
acgagttcttctgaattattaacgcttacaatttcctgatgcggtatt
ttctccttacgcatctgtgcggtatttcacaccgcatacaggtggcac
ttttcggggaaatgtgcgcggaacccctatttgtttatttttctaaat
acattcaaatatgtatccgctcatgagacaataaccctgataaatgct
tcaataatagcacgtgaggagggccaccatggccaagttgaccagtgc
cgttccggtgctcaccgcgcgcgacgtcgccggagcggtcgagttctg
gaccgaccggctcgggttctcccgggacttcgtggaggacgacttcgc
cggtgtggtccgggacgacgtgaccctgttcatcagcgcggtccagga
ccaggtggtgccggacaacaccctggcctgggtgtgggtgcgcggcct
ggacgagctgtacgccgagtggtcggaggtcgtgtccacgaacttccg
ggacgcctccgggccggccatgaccgagatcggcgagcagccgtgggg
gcgggagttcgccctcgcgacccggccggcaactgcgtgcacttcgtg
gccgaggagcaggactgacacgtgctaaaacttcatttttaatttaaa
aggatctaggtgaagatcctttttgataatctcatgaccaaaatccct
```

-continued taacgtgagttttcgttccactgagcgtcagaccccgtagaaaagatc aaaggatcttcttgagatcctttttttctgcgcgtaatctgctgcttg caaacaaaaaaaccaccgctaccagcggtggtttgtttgccggatcaa gagctaccaactctttttccgaaggtaactggcttcagcagagcgcag ataccaaatactgtccttctagtgtagccgtagttaggccaccacttc aagaactctgtagcaccgcctacatacctcgctctgctaatcctgtta ccagtggctgctgccagtggcgataagtcgtgtcttaccgggttggac tcaagacgatagttaccggataaggcgcagcggtcgggctgaacgggg ggttcgtgcacacagcccagcttggagcgaacgacctacaccgaactg agatacctacagcgtgagctatgagaaagcgccacgcttcccgaaggg agaaaggcggacaggtatccggtaagcggcagggtcggaacaggagag cgcacgagggagcttccagggggaaacgcctggtatctttatagtcct gtcgggtttcgccacctctgacttgagcgtcgatttttgtgatgctcg tcaggggggcggagcctatggaaaaacgccagcaacgcggcctttta cggttcctgggcttttgctggccttttgctcacatgttctttcctgcg ttatcccctgattctgtggataaccgtattaccgcctttgagtgagct gataccgctcgccgcagccgaacgaccgagcgcagcgagtcagtgagc gaggaagcggaag

Construction of Perhydrolase T7 Expression Plasmid

Figure 13:
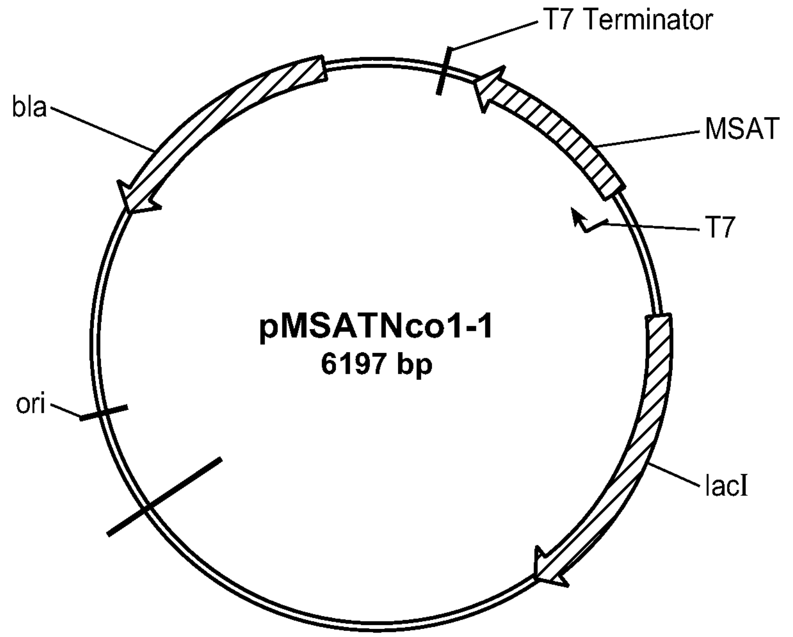
FIG. 13 provides a map of plasmid pMSATNco1-1.

The primer pair used to create pMSATNco1 was also used to create an NcoI site (CCATGG) in which the ATG is the start codon of the acyltransferase gene and a BamH1 (GGATCC) just after the TAA stop codon. The plasmid pMSATNco1 was digested with NcoI/BamH1 as recommended by the manufacturer (Roche) and the 658 bp fragment containing the perhydrolase gene was purified using standard procedures known in the art (e.g., Sambrook et al.). The fragment was ligated using standard procedures known in the art (e.g., Sambrook et al.) into the T7 promoter expression plasmid, pET16b (Novagen), also digested with NcoI/BamH1. The ligation reaction was transformed by standard procedures into *E. coli* Top 10 cells (Invitrogen) and selected on L agar containing 100 micrograms/ml carbenicillin overnight at 37° C. Ten colonies were picked from the several transformants and used to inoculate 5 ml of LB containing 100 micrograms/ml carbenicillin. Cultures were grown overnight at 37° C. with shaking at 200 rpm. Plasmid DNA was purified from the cultures using the Qiagen Quikspin kit (Qiagen). The presence of the correct fragment was determined by restriction enzyme digest with NcoI/BamH1 as directed by the manufacturer. The correct plasmid was designated pMSATNcoI-1 (See, FIG. 13, for the map of this plasmid). In this Figure, the following elements are indicated—LacI: gene encoding the Lad repressor protein, located at bp1455-2534, ori: plasmid origin of replication at bp 4471, bla: The β-lactamase gene located at bp 6089-5232; T7 promoter: located at bp1068-1052; T7 terminator: located at bp 259-213, per: the *M. smegmatis* perhydrolase gene located at 981-334. The sequence of this plasmid is provided below:

(SEQ ID NO: 131)

ttctcatgtttgacagcttatcatcgataagctttaatgcggtagttt atcacagttaaattgctaacgcagtcaggcaccgtgtatgaaatctaa -continued caatgcgctcatcgtcatcctcggcaccgtcaccctggatgctgtagg cataggcttggttatgccggtactgccgggcctcttgcgggatatccg gatatagttcctcctttcagcaaaaaacccctcaagacccgtttagag gccccaaggggttatgctagttattgctcagcggtggcagcagccaac tcagcttcctttcgggctttgttagcagccggatccgcgcgcttacag caggctccgcacctgttccgcgagggccaccccgagatcgcgattgtt ggcctcggtgaagtggattccgtcgacgccgtcggtgctgatcaccga acccgcgtcgaagaacggcaccttcatgaacgacgcgagcgcgctgta cacgcgggcgagctcagtggtcttctgctcgccgccctcgaagatcaa ctggaaccaggggtgcggcatgggcgccagcggtggcggcgagaccac cagcaccttgggtgccgggtacgtggtgccgacgccgcccgcgctggt gagcacctgcgtgacgagcaccgacatgcccagcgcgatgtcgagcgg ggtgcgccggaagtaggccttggtgtcgttggtgcccagcatgatgat caccaggtcgagcggcaggtgcgtcgcgaggcacgacggcaggtagct cgcgccgttgagccgcggatcggtggggtcgtcgatgttggtggtgcg cgcgctcagtccctcctcgatcacctcgaagtccgctccgagctgctg ggccagcacaccggtccagcgcacgtcgggggcgaaccgctcggtggg tgccccgtcttcgacggggacccagccccaggtcagggaatcaccgaa acacagaattcgcttggccatggtatatctccttcttaaagttaaaca aaattatttctagaggggaattgttatccgctcacaattcccctatag tgagtcgtattaatttcgcgggatcgagatctcgatcctctacgccgg acgcatcgtggccggcatcaccggcgccacaggtgcggttgctggcgc ctatatcgccgacatcaccgatggggaagatcgggctcgccacttcgg gctcatgagcgcttgtttcggcgtgggtatggtggcaggccccgtggc cgggggactgttgggcgccatctccttgcatgcaccattccttgcggc ggcggtgctcaacggcctcaacctactactgggctgcttcctaatgca ggagtcgcataagggagagcgtcgagatcccggacaccatcgaatggc gcaaaacctttcgcggtatggcatgatagcgcccggaagagagtcaat tcagggtggtgaatgtgaaaccagtaacgttatacgatgtcgcagagt atgccggtgtctcttatcagaccgtttcccgcgtggtgaaccaggcca gccacgtttctgcgaaaacgcgggaaaaagtggaagcggcgatggcgg agctgaattacattcccaaccgcgtggcacaacaactggcgggcaaac agtcgttgctgattggcgttgccacctccagtctggccctgcacgcgc cgtcgcaaattgtcgcggcgattaaatctcgcgccgatcaactgggtg ccagcgtggtggtgtcgatggtagaacgaagcggcgtcgaagcctgta aagcggcggtgcacaatcttctcgcgcaacgcgtcagtgggctgatca ttaactatccgctggatgaccaggatgccattgctgtggaagctgcct gcactaatgttccggcgttatttcttgatgtctctgaccagacaccca tcaacagtattattttctcccatgaagacggtacgcgactgggcgtgg agcatctggtcgcattgggtcaccagcaaatcgcgctgttagcgggcc -continued cattaagttctgtctcggcgcgtctgcgtctggctggctggcataaat atctcactcgcaatcaaattcagccgatagcggaacgggaaggcgact ggagtgccatgtccggttttcaacaaaccatgcaaatgctgaatgagg gcatcgttcccactgcgatgctggttgccaacgatcagatggcgctgg gcgcaatgcgcgccattaccgagtccgggctgcgcgttggtgcggata tctcggtagtgggatacgacgataccgaagacagctcatgttatatcc cgccgttaaccaccatcaaacaggattttcgcctgctggggcaaacca gcgtggaccgcttgctgcaactctctcagggccaggcggtgaagggca atcagctgttgcccgtctcactggtgaaaagaaaaaccaccctggcgc ccaatacgcaaaccgcctctccccgcgcgttggccgattcattaatgc agctggcacgacaggtttcccgactggaaagcgggcagtgagcgcaac gcaattaatgtaagttagctcactcattaggcaccgggatctcgaccg atgcccttgagagccttcaacccagtcagctccttccggtgggcgcgg ggcatgactatcgtcgccgcacttatgactgtcttctttatcatgcaa ctcgtaggacaggtgccggcagcgctctgggtcattttcggcgaggac cgctttcgctggagcgcgacgatgatcggcctgtcgcttgcggtattc ggaatcttgcacgccctcgctcaagccttcgtcactggtcccgccacc aaacgtttcggcgagaagcaggccattatcgccggcatggcggccgac gcgctgggctacgtcttgctggcgttcgcgacgcgaggctggatggcc ttccccattatgattcttctcgcttccggcggcatcgggatgcccgcg ttgcaggccatgctgtccaggcaggtagatgacgaccatcagggacag cttcaaggatcgctcgcggctcttaccagcctaacttcgatcactgga ccgctgatcgtcacggcgatttatgccgcctcggcgagcacatggaac gggttggcatggattgtaggcgccgccctataccttgtctgcctcccc gcgttgcgtcgcggtgcatggagccgggccacctcgacctgaatggaa gccggcggcacctcgctaacggattcaccactccaagaattggagcca atcaattcttgcggagaactgtgaatgcgcaaaccaacccttggcaga acatatccatcgcgtccgccatctccagcagccgcacgcggcgcatct cgggcagcgttgggtcctggccacgggtgcgcatgatcgtgctcctgt cgttgaggacccggctaggctggcggggttgccttactggttagcaga atgaatcaccgatacgcgagcgaacgtgaagcgactgctgctgcaaaa cgtctgcgacctgagcaacaacatgaatggtcttcggtttccgtgttt cgtaaagtctggaaacgcggaagtcagcgccctgcaccattatgttcc ggatctgcatcgcaggatgctgctggctaccctgtggaacacctacat ctgtattaacgaagcgctggcattgaccctgagtgattttctctggt cccgccgcatccataccgccagttgtttaccctcacaacgttccagta accgggcatgttcatcatcagtaacccgtatcgtgagcatcctctctc gtttcatcggtatcattacccccatgaacagaaatcccccttacacgg aggcatcagtgaccaaacaggaaaaaaccgcccttaacatggcccgct ttatcagaagccagacattaacgcttctggagaaactcaacgagctgg acgcggatgaacaggcagacatctgtgaatcgcttcacgaccacgctg -continued atgagctttaccgcagctgcctcgcgcgtttcggtgatgacggtgaaa acctctgacacatgcagctcccggagacggtcacagcttgtctgtaag cggatgccgggagcagacaagcccgtcagggcgcgtcagcgggtgttg gcgggtgtcggggcgcagccatgacccagtcacgtagcgatagcggag tgtatactggcttaactatgcggcatcagagcagattgtactgagagt gcaccatatatgcggtgtgaaataccgcacagatgcgtaaggagaaaa taccgcatcaggcgctcttccgcttcctcgctcactgactcgctgcgc tcggtcgttcggctgcggcgagcggtatcagctcactcaaaggcggta atacggttatccacagaatcaggggataacgcaggaaagaacatgtga gcaaaaggccagcaaaaggccaggaaccgtaaaaaggccgcgttgctg gcgtttttccataggctccgcccccctgacgagcatcacaaaaatcga cgctcaagtcagaggtggcgaaacccgacaggactataaagataccag gcgtttccccctggaagctccctcgtgcgctctcctgttccgaccctg ccgcttaccggatacctgtccgcctttctcccttcgggaagcgtggcg ctttctcatagctcacgctgtaggtatctcagttcggtgtaggtcgtt cgctccaagctgggctgtgtgcacgaaccccccgttcagcccgaccgc tgcgccttatccggtaactatcgtcttgagtccaacccggtaagacac gacttatcgccactggcagcagccactggtaacaggattagcagagcg aggtatgtaggcggtgctacagagttcttgaagtggtggcctaactac ggctacactagaaggacagtatttggtatctgcgctctgctgaagcca gttaccttcggaaaaagagttggtagctcttgatccggcaaacaaacc accgctggtagcggtggtttttttgtttgcaagcagcagattacgcgc agaaaaaaaggatctcaagaagatcctttgatcttttctacggggtct gacgctcagtggaacgaaaactcacgttaagggattttggtcatgaga ttatcaaaaaggatcttcacctagatccttttaaattaaaaatgaagt tttaaatcaatctaaagtatatatgagtaaacttggtctgacagttac caatgcttaatcagtgaggcacctatctcagcgatctgtctatttcgt tcatccatagttgcctgactccccgtcgtgtagataactacgatacgg gagggcttaccatctggccccagtgctgcaatgataccgcgagaccca cgctcaccggctccagatttatcagcaataaaccagccagccggaagg gccgagcgcagaagtggtcctgcaactttatccgcctccatccagtct attaattgttgccgggaagctagagtaagtagttcgccagttaatagt ttgcgcaacgttgttgccattgctgcaggcatcgtggtgtcacgctcg tcgtttggtatggcttcattcagctccggttcccaacgatcaaggcga gttacatgatcccccatgttgtgcaaaaaagcggttagctccttcggt cctccgatcgttgtcagaagtaagttggccgcagtgttatcactcatg gttatggcagcactgcataattctcttactgtcatgccatccgtaaga tgcttttctgtgactggtgagtactcaaccaagtcattctgagaatag tgtatgcggcgaccgagttgctcttgcccggcgtcaacacgggataat accgcgccacatagcagaactttaaaagtgctcatcattggaaaacgt -continued

```
tcttcggggcgaaaactctcaaggatcttaccgctgttgagatccagt

tcgatgtaacccactcgtgcacccaactgatcttcagcatcttttact

ttcaccagcgtttctgggtgagcaaaaacaggaaggcaaaatgccgca

aaaaagggaataagggcgacacggaaatgttgaatactcatactcttc

ctttttcaatattattgaagcatttatcagggttattgtctcatgagc

ggatacatatttgaatgtatttagaaaaataaacaaataggggttccg

cgcacatttccccgaaaagtgccacctgacgtctaagaaaccattatt

atcatgacattaacctataaaaataggcgtatcacgaggccctttcgt

cttcaagaa
```

This plasmid was transformed into the *E. coli* strain BL21 (λDE3)pLysS (Novagen), which contains the gene encoding the T7 RNA polymerase, with selection on LA containing 100 micrograms/ml carbenicillin. Cells were grown overnight at 37° C. One transformant was selected and the strain was designated MSATNco1.

Production of Perhydrolase in MSATNco1-1

Production of perhydrolase was done in cell culture. For example, 5 ml of LB with carbenicillin at a concentration of 100 micrograms/ml was inoculated with a single colony of MSATNco1 and grown overnight at 37° C. with shaking at 200 rpm. This culture was used to inoculate 100 ml of LB with carbenicillin at a concentration of 100 micrograms/ml (in a 250 ml baffled flask) to an $OD_{600}$ of 0.1. The cultures were grown at 30° C. with shaking at 200 rpm until they reached an $OD_{600}$ of 0.4. The expression of the perhydrolase gene was then induced by the addition of 100 micromolar IPTG and the incubation continued overnight. Cultures were harvested by centrifugation (10 min at 7000 rpm, Sorvall SS34 rotor), the supernatant was removed and the pellets washed in 50 mM $KPO_4$, pH 6.8. The cells were centrifuged again, the supernatants removed and the wet weight of the cells was determined. The cells were resuspended in 100 mM $KPO_4$ in a volume that was 4× the wet weight. The resuspended cells were frozen at −70° C. The cells were thawed and lysed in a French Pressure cell using standard procedures known in the art. The purification steps and assessment methods are provided in Example 1. FIG. 6 provides a purification table showing the enzyme activity of the perhydrolase of the present invention through various steps in the purification process.

*M. smegmatis* Perhydrolase is in an Operon

In additional experiments, it was determined that the *M. smegmatis* perhydrolase is part of an operon. The gene (phd) is the first gene in an operon that contains at least 2 genes, including phd, that are separated by 10 bp (GGCTGGGGGC [SEQ ID NO:7]) not including the TAA stop codon of phd. It is also possible that there are three genes in the operon, with the third being either 48 bp or 61 bp to the next ORF (open reading frame). The latter two candidate genes have no significant homology to proteins in the database.

A putative promoter was identified for *M. smegmatis* phd operon, TTGGGC (−35) SP (18) CCAGAT by sequence analysis and comparison with known *M. smegmatis* promoters (See e.g., Salazar et al., Microbiol., 149:773-784 [2003]). It is not intended that the present invention be limited to any particular promoter and/or construct design, as it is contemplated that other promoters and construct designs will find use in the present invention.

The second gene in the phd operon encodes a protein (putative PBP-3) with the sequence:

```
                                          (SEQ ID NO: 9)
mhlrpaltwllvvglfisvvgcssspdpadrfsafaealgrkdaaaaaaq

tsdpaaaeaaitamlagmgdaanysvaaepeegddagatlkytwtwgegr

dfgydttataaksgddwlitwsptylhrdltpdlrfqysedselqtpvld

rtgqplmtwqtygvitverahpesaaplaallapfdpattesvtaqlnsa

ddrvtvmklreddlgqvrdqlaqipgvtvreqgelltadrqlsspaisgl

delwhdritanagwsvylvdadgapaqqltstppkdtgpvrttldlrmql

laqqavaketrpavvvaisgstggilaaaqnpaadpqgaiafsglyppgs

tfktittaaaldaglatpdtpvacpgeltienrtipnddnfdlgtvplss

afshscntsmaalsdelppnaltdmakdfgigvdfmvpglttvtgrvpna

dnaaqrvengigqgtvtvspfglavaeaslahgstilptlvdgekttadt

psvplppnitdalrammrgtvtegtatalsdipdlggktgtaefgdnths

hgwfagiagdiafatlvvggdssapavaisgdflrpalag
```

The corresponding DNA sequence of the gene encoding the putative PBP-3:

```
                                                                        (SEQ ID NO: 8)
atgcacttacgtcccgctctgacgtggctcctggttgtcggtctgttcatatcggtcgtcggatgttcgtcgtccccggatccggccg

accggttctcggcgttcgccgaggcgctgggccgcaaggatgcggccgcggcggccgcccagaccagcgatccggcggcc

gcggaggcggccatcaccgcgatgctggccgggatgggcgacgccgcgaacgtctcggtggccgccgaacccgaggaagg

cgacgacgcgggcgcgacgctgaagtacacgtggacctggggtgagggccgcgacttcggctacgacaccaccgcgacggc

ggccaaatccggtgacgactggctgatcacctggtcccccaccgtgttgcaccgcgacctcaccccggatctgcgcttccagtac

agcgaggacagcgaattgcagaccccggtgctcgaccgcaccggccagccgttgatgacatggcagaccgtcggtgtcatcac

tgtcgaacgcgcacatccggagtcggccgcaccgctcgccgccctgctggcgcccttcgatccgaccaccaccaccgaatcgg

tcaccgcacaactcaattcgacgaccgatgaccgcgtgacggtgatgaagctgcgcgaggacgatctgggtcaggtgcgcgat

cagctcgcgcagatccccggcgtgaccgtgcgtgagcagggtgagctgctcaccgccgaccggcagctgtcctcgcccgccat

cagcggcctggacgagctgtggcacgaccggatcaccgccaacgcgggctggtcggtgtacctggtcgacgccgacggtgca
```

-continued cccgcacaacagctcacgtccacgccgcccaaggacaccgggcccgtgcgcaccacgctggacctgcgcatgcaactgctcg cgcagcaggccgtggccaaggagacccgcccggccgtggtggtcgcgatctccggatcgaccgggggcatcctggccgccg cacagaacccggccgccgatccgcaaggtgcgatcgcgttttcgggcctgtacccgccggggtcgacgttcaagaccatcacc acggcggcagccctcgacgcgggcctggccaccccggacacaccggtggcctgcccgggtgagctcaccatcgagaaccgc acgatccccaacgacgacaacttcgacctgggcaccgtgccgttgtcgtcggcgttctcgcactcctgcaacaccagcatggcc gccctgtccgacgagctgccgcccaacgcactgaccgacatggcaaaggacttcgggatcggcgtcgacttcatggtgcccgg cctgaccaccgtgaccggccgtgtccccaacgccgacaacgccgcccagcgtgtcgagaacggcatcggccagggcaccgt gaccgtcagcccgttcggcctcgccgtcgccgaggccagcctggcgcacggttcgacgatcctgccgacgctggtcgacggc gagaagaccacggccgacaccccgtcggtgccgttgccgcccaacatcaccgacgcgctgcgcgcgatgatgcgcggaacg gtcaccgagggcacggccaccgcgttgagcgacatccccgacctgggcggcaagaccggcacggcggaattcggcgacaac acgcactcgcacggctggttcgcgggcatcgcgggcgacatcgcgttcgcgacgctggtggtcggcggcgactcgtcggcac cggccgtcgcgatctcaggagacttcctgcgccccgcgctcgccggctag.

A standard BLAST search against the protein database identified homology with several penicillin binding proteins, class 3 (PBP-3). By sequence alignment and comparison to literature (e.g., Goffin and Ghysen, Microbiol. Mol. Biol. Rev., 66:702-38 [2002]) the PBP was found to contain the required bar codes (conserved protein sequences that define a class of proteins) to place it in the SxxK superfamily of acyl transferases, with a C-terminal domain acyl transferase and an N-terminal domain of unknown function, but with homology to the Pen$^r$ (i.e., penicillin resistant) protein fusions of class B-like II and III. This penicillin binding protein acyl transferase domain does not share significant homology with the perhydrolase of the present invention, although it does share homology with Co-A dependent acyl transferases known in the art. The amino acid sequence is provided below.

(SEQ ID NO: 10)

MHLRPALTWLLVVGLFISVVGCSSSPDPADRFSAFAEALGRKDAAAAAAQ

TSDPAAAEAAITAMLAGMGDAANVSVAAEPEEGDDAGATLKYTWTWGEGR

DFGYDTTATAAKSGDDWLITWSPTVLHRDLTPDLRFQYSEDSELQTPVLD

RTGQPLMTWQTVGVITVERAHPESAAPLAALLAPFDPTTTTESVTAQLNS

TTDDRVTVMKLREDDLGQVRDQLAQIPGVTVREQGELLTADRQLSSPAIS

GLDELWHDRITANAGWSVYLVDADGAPAQQLTSTPPKDTGPVRTTLDLRM

QLLAQQAVAKETRPAVVVAISGSTGGILAAAQNPAADPQGAIAFSGLYPP

GSTFKTITTAAALDAGLATPDTPVACPGELTIENRTIPNDDNFDLGTVPL

SSAFSHSCNTSMAALSDELPPNALTDMAKDFGIGVDFMVPGLTTVTGRVP

NADNAAQRVENGIGQGTVTVSPFGLAVAEASLAHGSTILPTLVDGEKTTA

DTPSVPLPPNITDALRAMMRGTVTEGTATALSDIPDLGGKTGTAEFGDNT

HSHGWFAGIAGDIAFATLVVGGDSSAPAVAISGDFLRPALAG

The family-identifying bar codes provided in the above review were: (19) V (20) G/A (140) PVxDRTG (142) TxDx3Q (22) TGGxLAx4 PaxDP (13) SxxK (51) SCN (131) KTG (50) marked in bold letters in the above sequence. The letters represent the amino acid sequence defining the bar code; the numbers in brackets are the intervening number of amino acids between the particular bar codes; "x" represents any amino acid, (i.e., the amino acids are not conserved within the bar code but the number of amino acids (e.g., x3 corresponding to 3 intervening amino acids) is conserved). Based on these results and other data, as described herein, it is clear that the perhydrolase of the present invention represents a unique enzyme class.

Example 5

Expression of the Perhydrolase in *P. citrea*

In this Example, methods used to express the perhydrolase in *P. citrea* are described. The plasmid pMSATNcoI was transformed into *P. citrea* by electroporation using the method essentially as known in the art (See e.g., Sambrook et al., supra) except that all cultures and recovery were done at 30° C. The transformants were plated on L agar+carbenicillin (200 μg/ml) and incubated overnight at 30° C. Three transformants were picked for analysis. Each colony was used to inoculate a 30 ml culture of LB+carbenicillin (200 μg/ml) and grown overnight at 30° C. with shaking at 200 rpm. The cells were pelleted by centrifugation, washed one time in 50 mM phosphate buffer pH 7.2, and finally resuspended in 4× the wet cell weight of 100 mM phosphate buffer pH 8.0. The cells were lysed by treatment with lysozyme (2 μl of a 10 mg/ml solution per one ml of *P. citrea* culture) at 37° C. for one hour. The cell debris was pelleted at 13,000 rpm in a microfuge for 5 min. The resulting supernatant was used for further analysis in SDS-PAGE and Western blots, as well as assays for enzyme activity.

SDS-PAGE analysis was carried out as known in the art (See e.g., Sambrook et al., supra) on the supernatants. Detection of the perhydrolase protein by Western blot was done using an anti-perhydrolase polyclonal anti-sera (prepared from purified perhydrolase protein by Covance). The blot was developed as per manufacturer's suggestions using the ECL plus kit (Amersham).

The enzymatic activity of the expressed perhydrolase was detected by the pNB (para-nitrophenylbutyrate) assay as described in Example 1, herein. The results are provided in the

TABLE 5-1

| Enzymatic Activity of Perhydrolase Expressed by *P. citrea* | | | |
|---|---|---|---|
| Clone | OD405 | Rate | Concentration (mg/liter) |
| *P. citreal* pMSATNcoI | 3.1129 | 0.47948 | 7.1922 |
| Control (*P. citrea*) | 2.6187 | −9.8312 | 0 |

The SDS-PAGE and Western blot results, as well as the assay results indicated that the perhydrolase is expressed by *P. citrea* and is active.

Example 6

Expression of the Perhydrolase in *Bacillus subtilis*

The perhydrolase was expressed intracellularly in *B. subtilis*. A variety of promoters find use in this embodiment, including but not limited to pSPAC, pAprE, pAmyE, pVeg, pHpaII. In some embodiments, the construct is present on a replicating plasmid (e.g., pBH1), while in other embodiments, it is integrated into the chromosome in one or more copies. Examples of sites for integration include, but are not limited to the aprE, the amyE, the veg or the pps regions. Indeed, it is contemplated that other sites known to those skilled in the art will find use in the present invention.

A. Intracellular Expression of the Perhydrolase in *Bacillus subtilis* from a Replicating Plasmid

*B. subtilis* expresses a lipase/esterase encoded by the gene pnbA that hydrolyzes the pNB substrate used to detect activity of the perhydrolase. To identify *B. subtilis* strains expressing the perhydrolase after transformation with replicating or integrating plasmids the pnbA gene (the entire coding sequence) was first deleted from the desired host using the loxP cassette deletion method described in WO 03/083125, herein incorporated by reference. It is also noted that other strains of *Bacillus* may contain one or more lipases/esterases capable of hydrolyzing the pNB or other substrate used as an indicator for perhydrolase activity. In some embodiments, for optimal expression and/or activity detection it is necessary to delete one or more of the lipases/esterases from the hosts. The *Bacillus subtilis* strain used in this Example has the genotype *Bacillus subtilis* comK pnbA (pnbA loxP-spec, aprE, nprE, degUHy32, oppA, spoIIE3501 and will be referred to as "*B. subtilis* pnbA" (See e.g., WO 03/083125, supra).

In these experiments, a consensus *Bacillus* ribosome binding site (RBS) was used. It is not intended that the consensus RBS be the only sequence used for expression, as a non-consensus RBS also finds use in the present invention. The RBS of pMSATNcoI (See, Example 4) was changed to a *Bacillus* consensus RBS from the 16S rRNA (5'-ATAAGGAGGTGATC-3' [SEQ ID NO:132]) of *B. subtilis* and a HindIII site was added to the 5' end of the RBS by PCR using a primer (502rbsforward primer) containing the desired changes. The reaction was carried out using an MJ Research PCR machine with 30 cycles of (1 min at 95° C., 1 min at 55° C., and 1 min at 72° C.). Template DNA (pMSATrbs) was added to a 50 μl reaction (10 ng) and 10 picomoles of each primer were used.

The PCR-generated phd cassette was cloned into the PCR cloning vector, pCR-Script CM (Stratagene) and transformed into *E. coli* Top10 cells (Invitrogen) to make pAH502R. The complete sequence of this plasmid is provided below.

(SEQ ID NO: 133)

```
ctaaattgtaagcgttaatattttgttaaaattcgcgttaaatttttgttaaatcagctcattttttaaccaataggccg

aaatcggcaaaatcccttataaatcaaaagaatagaccgagatagggttgagtgttgttccagtttggaacaagagtcca

ctattaaagaacgtggactccaacgtcaaagggcgaaaaaccgtctatcagggcgatggcccactacgtgaaccatcacc

ctaatcaagttttttggggtcgaggtgccgtaaagcactaaatcggaaccctaaagggagcccccgatttagagcttgac

ggggaaagccggcgaacgtggcgagaaaggaagggaagaaagcgaaaggagcgggcgctagggcgctggcaagtgtagc

ggtcacgctgcgcgtaaccaccacacccgccgcgcttaatgcgccgctacagggcgcgtcccattcgccattcaggctgcg

caactgttgggaagggcgatcggtgcgggcctcttcgctattacgccagctggcgaaagggggatgtgctgcaaggcgat

taagttgggtaacgccagggttttcccagtcacgacgttgtaaaacgacggccagtgagcgcgcgtaatacgactcacta

tagggcgaattgggtaccgggccccccctcgaggtcgacggtatcgataagcttgatatcgaattcctgcagcccggggg

atccgcccaagcttaaggaggtgatctagaattccatggccaagcgaattctgtgtttcggtgattccctgacctggggc

tgggtccccgtcgaagacggggcacccaccgagcggttcgcccccgacgtgcgctggaccggtgtgctggcccagcagct

cggagcggacttcgaggtgatcgaggagggactgagcgcgcgcaccaccaacatcgacgaccccaccgatccgcggctca

acggcgcgagctacctgccgtcgtgcctcgcgacgcacctgccgctcgacctggtgatcatcatgctgggcaccaacgac

accaaggcctacttccggcgcaccccgctcgacatcgcgctgggcatgtcggtgctcgtcacgcaggtgctcaccagcgc

gggcggcgtcggcaccacgtacccggcacccaaggtgctggtggtctcgccgccaccgctggcgcccatgccgcacccct

ggttccagttgatcttcgagggcggcgagcagaagaccactgagctcgcccgcgtgtacagcgcgctcgcgtcgttcatg

aaggtgccgttcttcgacgcgggttcggtgatcagcaccgacggcgtcgacggaatccacttcaccgaggccaacaatcg

cgatctcggggtggccctcgcggaacaggtgcggagcctgctgtaaaaggatccccgggaagcttgcatgggctagagcg
```

-continued gccgccaccgcggtggagctccagcttttgttccctttagtgagggttaattgcgcgcttggcgtaatcatggtcatagc tgtttcctgtgtgaaattgttatccgctcacaattccacacaacatacgagccggaagcataaagtgtaaagcctggggt gcctaatgagtgagctaactcacattaattgcgttgcgctcactgcccgctttccagtcgggaaacctgtcgtgccagct gcattaatgaatcggccaacgcgcggggagaggcggtttgcgtattgggcgctcttccgcttcctcgctcactgactcgc tgcgctcggtcgttcggctgcggcgagcggtatcagctcactcaaaggcggtaatacggttatccacagaatcaggggat aacgcaggaaagaacatgtgagcaaaaggccagcaaaaggccaggaaccgtaaaaaggccgcgttgctggcgtttttcca taggctccgcccccctgacgagcatcacaaaaatcgacgctcaagtcagaggtggcgaaacccgacaggactataaagat accaggcgtttccccctggaagctccctcgtgcgctctcctgttccgaccctgccgcttaccggatacctgtccgccttt ctcccttcgggaagcgtggcgctttctcatagctcacgctgtaggtatctcagttcggtgtaggtcgttcgctccaagct gggctgtgtgcacgaaccccccgttcagcccgaccgctgcgccttatccggtaactatcgtcttgagtccaacccggtaa gacacgacttatcgccactggcagcagccactggtaacaggattagcagagcgaggtatgtaggcggtgctacagagttc ttgaagtggtggcctaactacggctacactagaaggacagtatttggtatctgcgctctgctgaagccagttaccttcgg aaaaagagttggtagctcttgatccggcaaacaaaccaccgctggtagcggtggtttttttgtttgcaagcagcagatta cgcgcagaaaaaaaggatctcaagaagatcctttgatcttttctacggggtctgacgctcagtggaacgaaaactcacgt taagggattttggtcatgagattatcaaaaaggatcttcacctagatccttttcgaccgaataaatacctgtgacggaag atcacttcgcagaataaataaatcctggtgtccctgttgataccgggaagccctgggccaacttttggcgaaaatgagac gttgatcggcacgtaagaggttccaactttcaccataatgaaataagatcactaccgggcgtattttttgagttgtcgag attttcaggagctaaggaagctaaaatggagaaaaaaatcactggatataccaccgttgatatatcccaatggcatcgta aagaacattttgaggcatttcagtcagttgctcaatgtacctataaccagaccgttcagctggatattacggcctttta aagaccgtaaagaaaaataagcacaagttttatccggcctttattcacattcttgcccgcctgatgaatgctcatccgga attacgtatggcaatgaaagacggtgagctggtgatatgggatagtgttcacccttgttacaccgttttccatgagcaaa ctgaaacgttttcatcgctctggagtgaataccacgacgatttccggcagtttctacacatatattcgcaagatgtggcg tgttacggtgaaaacctggcctatttccctaaagggtttattgagaatatgtttttcgtctcagccaatccctgggtgag tttcaccagttttgatttaaacgtggccaatatggacaacttcttcgcccccgttttcaccatgggcaaatattatacgca aggcgacaaggtgctgatgccgctggcgattcaggttcatcatgccgtttgtgatggcttccatgtcggcagaatgctta atgaattacaacagtactgcgatgagtggcagggcggggcgtaatttttttaaggcagttattggtgcccttaaacgcct ggttgctacgcctgaataagtgataataagcggatgaatggcagaaattcgaaagcaaattcgacccggtcgtcggttca gggcagggtcgttaaatagccgcttatgtctattgctggtttaccggtttattgactaccggaagcagtgtgaccgtgtg cttctcaaatgcctgaggccagtttgctcaggctctccccgtggaggtaataattgacgatatgatcctttttttctgat caaaagtgctcatcattggaaaacgttcttcggggcgaaaactctcaaggatcttaccgctgttgagatccagttcgatg taacccactcgtgcacccaactgatcttcagcatcttttactttcaccagcgtttctgggtgagcaaaaacaggaaggca aaatgccgcaaaaaagggaataagggcgacacggaaatgttgaatactcatactcttcctttttcaatattattgaagca tttatcagggttattgtctcatgagcggatacatatttgaatgtatttagaaaaataaacaaataggggttccgcgcac atttccccgaaaagtgccac Transformants were selected on L agar containing 100 μg/ml carbenicillin. The construct was confirmed by sequencing and biochemical assays (e.g., pNB activity assay)

Primer set for pAH502R construction:

502rbsForward primer:

(SEQ ID NO: 134)

5'-ccaagcttaaggaggtgatctagaattccatggccaagcgaattctg tgtttcg-3'

-continued

502Reverse Primer:

(SEQ ID NO: 135)

5'-ggggatccttttacagcaggctccgcacct-3'

Figure 14:
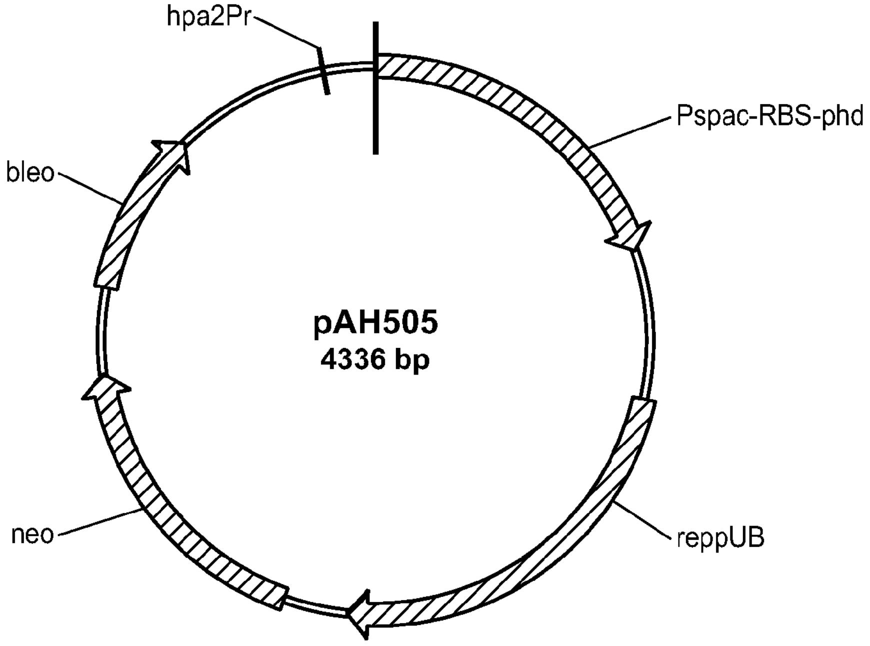
FIG. 14 provides a map of plasmid pAH505.

The HindIII-RBS-phd-BamH I DNA fragment from pAH502R was cloned into the pSPAC containing vector, pMUTIN4 (See, Vagner et al., Microbiol., 144, 3097-3104 [1998]) creating the construct pAH503. The complete sequence of pAH503 is provided below:

(SEQ ID NO: 136)
ataattctacacagcccagtccagactattcggcactgaaattatgggtgaagtggtcaagacctcactaggcaccttaa
aaatagcgcaccctgaagaagatttatttgaggtagcccttgcctacctagcttccaagaaagatatcctaacagcacaa
gagcggaaagatgttttgttctacatccagaacaacctctgctaaaattcctgaaaaattttgcaaaaagttgttgactt
tatctacaaggtgtggcataatgtgtggaattgtgagcgctcacaattaagcttaaggaggtgatctagaattccatggc
caagcgaattctgtgtttcggtgattccctgacctggggctgggtccccgtcgaagacggggcacccaccgagcggttcg
cccccgacgtgcgctggaccggtgtgctggcccagcagctcggagcggacttcgaggtgatcgaggagggactgagcgcg
cgcaccaccaacatcgacgaccccaccgatccgcggctcaacggcgcgagctacctgccgtcgtgcctcgcgacgcacct
gccgctcgacctggtgatcatcatgctgggcaccaacgacaccaaggcctacttccggcgcaccccgctcgacatcgcgc
tgggcatgtcggtgctcgtcacgcaggtgctcaccagcgcgggcggcgtcggcaccacgtacccggctcccaaggtgctg
gtggtctcgccgccaccgctggcgcccatgccgcacccctggttccagttgatcttcgagggcggcgagcagaagaccac
tgagctcgcccgcgtgtacagcgcgctcgcgtcgttcatgaaggtgccgttcttcgacgcgggttcggtgatcagcaccg
acggcgtcgacggaatccacttcaccgaggccaacaatcgcgatctcggggtggccctcgcggaacaggtgcggagcctg
ctgtaaaaggatccccagcttgttgatacactaatgcttttatatagggaaaaggtggtgaactactgtggaagttactg
acgtaagattacgggtcgaccgggaaaaccctggcgttacccaacttaatcgccttgcagcacatcccccttcgccagc
tggcgtaatagcgaagaggcccgcaccgatcgcccttcccaacagttgcgcagcctgaatggcgaatggcgctttgcctg
gtttccggcaccagaagcggtgccggaaagctggctggagtgcgatcttcctgaggccgatactgtcgtcgtcccctcaa
actggcagatgcacggttacgatgcgcccatctacaccaacgtaacctatcccattacggtcaatccgccgtttgttccc
acggagaatccgacgggttgttactcgctcacatttaatgttgatgaaagctggctacaggaaggccagacgcgaattat
ttttgatggcgttaactcggcgtttcatctgtggtgcaacgggcgctgggtcggttacggccaggacagtcgtttgccgt
ctgaatttgacctgagcgcatttttacgcgccggagaaaaccgcctcgcggtgatggtgctgcgttggagtgacggcagt
tatctggaagatcaggatatgtggcggatgagcggcattttccgtgacgtctcgttgctgcataaaccgactacacaaat
cagcgatttccatgttgccactcgctttaatgatgatttcagccgcgctgtactggaggctgaagttcagatgtgcggcg
agttgcgtgactacctacgggtaacagtttctttatggcagggtgaaacgcaggtcgccagcggcaccgcgcctttcggc
ggtgaaattatcgatgagcgtggtggttatgccgatcgcgtcacactacgtctgaacgtcgaaaacccgaaactgtggag
cgccgaaatcccgaatctctatcgtgcggtggttgaactgcacaccgccgacggcacgctgattgaagcagaagcctgcg
atgtcggtttccgcgaggtgcggattgaaaatggtctgctgctgctgaacggcaagccgttgctgattcgaggcgttaac
cgtcacgagcatcatcctctgcatggtcaggtcatggatgagcagacgatggtgcaggatatcctgctgatgaagcagaa
caactttaacgccgtgcgctgttcgcattatccgaaccatccgctgtggtacacgctgtgcgaccgctacggcctgtatg
tggtggatgaagccaatattgaaacccacggcatggtgccaatgaatcgtctgaccgatgatccgcgctggctaccggcg
atgagcgaacgcgtaacgcgaatggtgcagcgcgatcgtaatcacccgagtgtgatcatctggtcgctggggaatgaatc
aggccacggcgctaatcacgacgcgctgtatcgctggatcaaatctgtcgatccttcccgcccggtgcagtatgaaggcg
gcggagccgacaccacggccaccgatattatttgcccgatgtacgcgcgcgtggatgaagaccagcccttcccggctgtg
ccgaaatggtccatcaaaaaatggctttcgctacctggagagacgcgcccgctgatcctttgcgaatacgcccacgcgat
gggtaacagtcttggcggtttcgctaaatactggcaggcgtttcgtcagtatccccgtttacagggcggcttcgtctggg
actgggtggatcagtcgctgattaaatatgatgaaaacggcaacccgtggtcggcttacggcggtgattttggcgatacg
ccgaacgatcgccagttctgtatgaacggtctggtctttgccgaccgcacgccgcatccagcgctgacggaagcaaaaca
ccagcagcagtttttccagttccgtttatccgggcaaaccatcgaagtgaccagcgaatacctgttccgtcatagcgata
acgagctcctgcactggatggtggcgctggatggtaagccgctggcaagcggtgaagtgcctctggatgtcgctccacaa
ggtaaacagttgattgaactgcctgaactaccgcagccggagagcgccgggcaactctggctcacagtacgcgtagtgca
accgaacgcgaccgcatggtcagaagccgggcacatcagcgcctggcagcagtggcgtctggcggaaaacctcagtgtga -continued cgctccccgccgcgtcccacgccatcccgcatctgaccaccagcgaaatggatttttgcatcgagctgggtaataagcgt tggcaatttaaccgccagtcaggctttctttcacagatgtggattggcgataaaaaacaactgctgacgccgctgcgcga tcagttcacccgtgcaccgctggataacgacattggcgtaagtgaagcgacccgcattgaccctaacgcctgggtcgaac gctggaaggcggcgggccattaccaggccgaagcagcgttgttgcagtgcacggcagatacacttgctgatgcggtgctg attacgaccgctcacgcgtggcagcatcaggggaaaaccttatttatcagccggaaaacctaccggattgatggtagtgg tcaaatggcgattaccgttgatgttgaagtggcgagcgatacaccgcatccggcgcggattggcctgaactgccagctgg cgcaggtagcagagcgggtaaactggctcggattagggccgcaagaaaactatcccgaccgccttactgccgcctgtttt gaccgctgggatctgccattgtcagacatgtataccccgtacgtcttcccgagcgaaaacggtctgcgctgcgggacgcg cgaattgaattatggcccacaccagtggcgcggcgacttccagttcaacatcagccgctacagtcaacagcaactgatgg aaaccagccatcgccatctgctgcacgcggaagaaggcacatggctgaatatcgacggtttccatatggggattggtggc gacgactcctggagcccgtcagtatcggcggaattacagctgagcgccggtcgctaccattaccagttggtctggtgtca aaaataataataaccgggcaggccatgtctgcccgtatttcgcgtaaggaaatccattatgtactatttcaagctaattc cggtggaaacgaggtcatcatttccttccgaaaaaacggttgcatttaaatcttacatatgtaatactttcaaagactac atttgtaagatttgatgtttgagtcggctgaaagatcgtacgtaccaattattgtttcgtgattgttcaagccataacac tgtagggatagtggaaagagtgcttcatctggttacgatcaatcaaatattcaaacggagggagacgattttgatgaaac cagtaacgttatacgatgtcgcagagtatgccggtgtctcttatcagaccgtttcccgcgtggtgaaccaggccagccac gtttctgcgaaaacgcgggaaaaagtggaagcggcgatggcggagctgaattacattcccaaccgcgtggcacaacaact ggcgggcaaacagtcgttgctgattggcgttgccacctccagtctggccctgcacgcgccgtcgcaaattgtcgcggcga ttaaatctcgcgccgatcaactgggtgccagcgtggtggtgtcgatggtagaacgaagcggcgtcgaagcctgtaaagcg gcggtgcacaatcttctcgcgcaacgcgtcagtgggctgatcattaactatccgctggatgaccaggatgccattgctgt ggaagctgcctgcactaatgttccggcgttatttcttgatgtctctgaccagacacccatcaacagtattattttctccc atgaagacggtacgcgactgggcgtggagcatctggtcgcattgggtcaccagcaaatcgcgctgttagcgggcccatta agttctgtctcggcgcgtctgcgtctggctggctggcataaatatctcactcgcaatcaaattcagccgatagcggaacg ggaaggcgactggagtgccatgtccggttttcaacaaaccatgcaaatgctgaatgagggcatcgttcccactgcgatgc tggttgccaacgatcagatggcgctgggcgcaatgcgcgccattaccgagtccgggctgcgcgttggtgcggatatctcg gtagtgggatacgacgataccgaagacagctcatgttatatcccgccgtcaaccaccatcaaacaggattttcgcctgct ggggcaaaccagcgtggaccgcttgctgcaactctctcagggccaggcggtgaagggcaatcagctgttgcccgtctcac tggtgaaaagaaaaaccaccctggcgcccaatacgcaaaccgcctctccccgcgcgttggccgattcattaatgcagctg gcacgacaggtttcccgactggaaagcgggcagtgagcgcaacgcaattaatgtgagttaggcatcgcatcctgtctcgc gtcgtcggtgatgacggtgaaaacctctgacacatgcagctcccggagacggtcacagcttgtctgtaagcggatgccgg gagcagacaagcccgtcagggcgcgtcagcgggtgttggcgggtgtcggggcgcagccatgacccagtcacgtagcgata gcggagtgtatactggcttaactatgcggcatcagagcagattgtactgagagtgcaccatatgcggtgtgaaataccgc acagatgcgtaaggagaaaataccgcatcaggcgctcttccgcttcctcgctcactgactcgctgcgctcggtcgttcgg ctgcggcgagcggtatcagctcactcaaaggcggtaatacggttatccacagaatcaggggataacgcaggaaagaacat gtgagcaaaaggccagcaaaaggccaggaaccgtaaaaaggccgcgttgctggcgtttttccataggctccgcccccctg acgagcatcacaaaaatcgacgctcaagtcagaggtggcgaaacccgacaggactataaagataccaggcgtttccccct ggaagctccctcgtgcgctctcctgttccgaccctgccgcttaccggatacctgtccgcctttctcccttcgggaagcgt ggcgctttctcaatgctcacgctgtaggtatctcagttcggtgtaggtcgttcgctccaagctgggctgtgtgcacgaac cccccgttcagcccgaccgctgcgccttatccggtaactatcgtcttgagtccaacccggtaagacacgacttatcgcca ctggcagcagccactggtaacaggattagcagagcgaggtatgtaggcggtgctacagagttcttgaagtggtggcctaa -continued ctacggctacactagaaggacagtatttggtatctgcgctctgctgaagccagttaccttcggaaaaagagttggtagct
cttgatccggcaaacaaaccaccgctggtagcggtggtttttttgtttgcaagcagcagattacgcgcagaaaaaaagga
tctcaagaagatcctttgatcttttctacggggtctgacgctcagtggaacgaaaactcacgttaagggattttggtcat
gagattatcaaaaaggatcttcacctagatccttttaaattaaaaatgaagttttaaatcaatctaaagtatatatgagt
aaacttggtctgacagttaccaatgcttaatcagtgaggcacctatctcagcgatctgtctatttcgttcatccatagtt
gcctgactccccgtcgtgtagataactacgatacgggagggcttaccatctggccccagtgctgcaatgataccgcgaga
cccacgctcaccggctccagatttatcagcaataaaccagccagccggaagggccgagcgcagaagtggtcctgcaactt
tatccgcctccatccagtctattaattgttgccgggaagctagagtaagtagttcgccagttaatagtttgcgcaacgtt
gttgccattgctgcaggcatcgtggtgtcacgctcgtcgtttggtatggcttcattcagctccggttcccaacgatcaag
gcgagttacatgatcccccatgttgtgcaaaaaagcggttagctccttcggtcctccgatcgttgtcagaagtaagttgg
ccgcagtgttatcactcatggttatggcagcactgcataattctcttactgtcatgccatccgtaagatgcttttctgtg
actggtgagtactcaaccaagtcattctgagaatagtgtatgcggcgaccgagttgctcttgcccggcgtcaacacggga
taataccgcgccacatagcagaactttaaaagtgctcatcattggaaaacgttcttcggggcgaaaactctcaaggatct
taccgctgttgagatccagttcgatgtaacccactcgtgcacccaactgatcttcagcatcttttactttcaccagcgtt
tctgggtgagcaaaaacaggaaggcaaaatgccgcaaaaaagggaataagggcgacacggaaatgttgaatactcatact
cttcctttttcaatattattgaagcatttatcagggttattgtctcatgagcggatacatatttgaatgtatttagaaaa
ataaacaaataggggttccgcgcacatttccccgaaaagtgccacctgacgtctaagaaaccattattatcatgacatta
acctataaaaataggcgtatcacgaggccctttcgtcttcaagaattgatcctctagcacaaaagaaaaacgaaatgata
caccaatcagtgcaaaaaaagatataatgggagataagacggttcgtgttcgtgctgacttgcaccatatcataaaaatc
gaaacagcaaagaatggcggaaacgtaaaagaagttatggaaataagacttagaagcaaacttaagagtgtgttgatagt
gcagtatcttaaaattttgtataataggaattgaagttaaattagatgctaaaaatttgtaattaagaaggagtgattac
atgaacaaaaatataaaatattctcaaaactttttaacgagtgaaaaagtactcaaccaaataataaaacaattgaattt
aaaagaaaccgataccgtttacgaaattggaacaggtaaagggcatttaacgacgaaactggctaaaataagtaaacagg
taacgtctattgaattagacagtcatctattcaacttatcgtcagaaaaattaaaactgaatactcgtgtcactttaatt
caccaagatattctacagtttcaattccctaacaaacagaggtataaaattgttgggagtattccttaccatttaagcac
acaaattattaaaaaagtggtttttgaaagccatgcgtctgacatctatctgattgttgaagaaggattctacaagcgta
ccttggatattcaccgaacactagggttgctcttgcacactcaagtctcgattcagcaattgcttaagctgccagcggaa
tgctttcatcctaaaccaaaagtaaacagtgtcttaataaaacttacccgccataccacagatgttccagataaatattg
gaagctatatacgtactttgtttcaaaatgggtcaatcgagaatatcgtcaactgtttactaaaaatcagtttcatcaag
caatgaaacacgccaaagtaaacaatttaagtaccgttacttatgagcaagtattgtctatttttaatagttatctatta
tttaacgggaggaaataattctatgagtcgcttttgtaaatttggaaagttacacgttactaaagggaatgtagataaat
tattaggtatactactgacagcttccaaggagctaaagaggtccctagactctagacccggggatctctgcagtcggatc
tggtaatgactctctagcttgaggcatcaaataaaacgaaaggctcagtcgaaagactgggcctttcgttttatctgttg
tttgtcggtgaacgctctcctgagtaggacaaatccgccgctctagctaagcagaaggccatcctgacggatggcctttt
tgcgtttctacaaactcttgttaactctagagctgcctgccgcgtttcggtgatgaagatcttcccgatgattaattaat
tcagaacgctcggttgccgccgggcgtttttttatgcagcaatggcaagaacgttgctctaga The construction of pAH503 was confirmed by RFLP and pNB activity assays. The pSPAC-RBS-phd DNA cassette was isolated as a BglII/SmaI digest and then subcloned into the replicating plasmid pBH1, digested with BamH1/EcoRV (See e.g., EP 0275509) to create pAH505 (See, FIG. 14). The complete sequence of the plasmid is provided below.

(SEQ ID NO: 137)

gatcttccaagatatcctaacagcacaagagcggaaagatgttttgttctacatccagaacaacctctgctaaaattcctgaaaaattt tgcaaaaagttgttgactttatctacaaggtgtggcataatgtgtggaattgtgagcgctcacaattaagcttaaggaggtgatctag aattccatggccaagcgaattctgtgtttcggtgattccctgacctggggctgggtccccgtcgaagacggggcacccaccgagc ggttcgcccccgacgtgcgctggaccggtgtgctggcccagcagctcggagcggacttcgaggtgatcgaggagggactgag cgcgcgcaccaccaacatcgacgaccccaccgatccgcggctcaacggcgcgagctacctgccgtcgtgcctcgcgacgcac ctgccgctcgacctggtgatcatcatgctgggcaccaacgacaccaaggcctacttccggcgcaccccgctcgacatcgcgctg ggcatgtcggtgctcgtcacgcaggtgctcaccagcgcgggcggcgtcggcaccacgtacccggctcccaaggtgctggtggt ctcgccgccaccgctggcgcccatgccgcacccctggttccagttgatcttcgagggcggcgagcagaagaccactgagctcg cccgcgtgtacagcgcgctcgcgtcgttcatgaaggtgccgttcttcgacgcgggttcggtgatcagcaccgacggcgtcgacg gaatccacttcaccgaggccaacaatcgcgatctcggggtggccctcgcggaacaggtgcggagcctgctgtaaaaggatccc atcgcatgcggtacctctagaagaagcttggagacaaggtaaaggataaaacagcacaattccaagaaaaacacgatttagaac ctaaaaagaacgaatttgaactaactcataaccgagaggtaaaaaaagaacgaagtcgagatcagggaatgagtttataaaataa aaaaagcacctgaaaaggtgtctttttttgatggttttgaacttgttctttcttatcttgatacatatagaaataacgtcatttttattttagtt gctgaaaggtgcgttgaagtgttggtatgtatgtgttttaaagtattgaaaacccttaaaattggttgcacagaaaaaccccatctgtt aaagttataagtgactaaacaaataactaaatagatgggggtttcttttaatattatgtgtcctaatagtagcatttattcagatgaaaaa tcaagggttttagtggacaagacaaaaagtggaaaagtgagaccatggagagaaaagaaaatcgctaatgttgattactttgaact tctgcatattcttgaatttaaaaaggctgaaagagtaaaagattgtgctgaaatattagagtataaacaaaatcgtgaaacaggcgaa agaaagttgtatcgagtgtggttttgtaaatccaggctttgtccaatgtgcaactggaggagagcaatgaaacatggcattcagtca caaaaggttgttgctgaagttattaaacaaaagccaacagttcgttggttgtttctcacattaacagttaaaaatgtttatgatggcgaa gaattaaataagagtttgtcagatatggctcaaggatttcgccgaatgatgcaatataaaaaaattaataaaaatcttgttggttttatg cgtgcaacggaagtgacaataaataataaagataattcttataatcagcacatgcatgtattggtatgtgtggaaccaacttattttaa gaatacagaaaactacgtgaatcaaaaacaatggattcaattttggaaaaaggcaatgaaattagactatgatccaaatgtaaaagt tcaaatgattcgaccgaaaaataaatataaatcggatatacaatcggcaattgacgaaactgcaaaatatcctgtaaaggatacgga ttttatgaccgatgatgaagaaaagaatttgaaacgtttgtctgatttggaggaaggtttacaccgtaaaaggttaatctcctatggtg gtttgttaaaagaaatacataaaaaattaaaccttgatgacacagaagaaggcgatttgattcatacagatgatgacgaaaaagccg atgaagatggattttctattattgcaatgtggaattgggaacggaaaaattattttattaaagagtagttcaacaaacgggccagtttgt tgaagattagatgctataattgttattaaaaggattgaaggatgcttaggaagacgagttattaatagctgaataagaacggtgctctc caaatattcttatttagaaaagcaaatctaaaattatctgaaaagggaatgagaatagtgaatggaccaataataatgactagagaag aaagaatgaagattgttcatgaaattaaggaacgaatattggataaatatggggatgatgttaaggctattggtgtttatggctctcttg gtcgtcagactgatgggccctattcggatattgagatgatgtgtgtcatgtcaacagaggaagcagagttcagccatgaatggaca accggtgagtggaaggtggaagtgaattttgatagcgaagagattctactagattatgcatctcaggtggaatcagattggccgctt acacatggtcaatttttctctattttgccgatttatgattcaggtggatacttagagaaagtgtatcaaactgctaaatcggtagaagcc caaacgttccacgatgcgatttgtgcccttatcgtagaagagctgtttgaatatgcaggcaaatggcgtaatattcgtgtgcaagga ccgacaacatttctaccatccttgactgtacaggtagcaatggcaggtgccatgttgattggtctgcatcatcgcatctgttatacgac gagcgcttcggtcttaactgaagcagttaagcaatcagatcttccttcaggttatgaccatctgtgccagttcgtaatgtctggtcaac tttccgactctgagaaacttctggaatcgctagagaatttctggaatgggattcaggagtggacagaacgacacggatatatagtg gatgtgtcaaaacgcataccattttgaacgatgacctctaataattgttaatcatgttggttacgtatttattaacttctcctagtattagta attatcatggctgtcatggcgcattaacggaataaagggtgtgcttaaatcgggccattttgcgtaataagaaaaaggattaattatg agcgaattgaattaataataaggtaatagatttacattagaaaatgaaaggggattttatgcgtgagaatgttacagtctatcccggca ttgccagtcggggatattaaaaagagtataggtttttattgcgataaactaggtttcactttggttcaccatgaagatggattcgcagtt -continued ctaatgtgtaatgaggttcggattcatctatgggaggcaagtgatgaaggctggcgctctcgtagtaatgattcaccggtttgtacag gtgcggagtcgtttattgctggtactgctagttgccgcattgaagtagagggaattgatgaattatatcaacatattaagcctttgggc attttgcaccccaatacatcattaaaagatcagtggtgggatgaacgagactttgcagtaattgatcccgacaacaatttgattagctt ttttcaacaaataaaaagctaaaatctattattaatctgttcagcaatcgggcgcgattgctgaataaaagatacgagagacctctctt gtatctttttttatttgagtggttttgtccgttacactagaaaaccgaaagacaataaaaatttttattcttgctgagtctggctttcggtaag ctagacaaaacggacaaaataaaaattggcaagggtttaaaggtggagatttttttgagtgatcttctcaaaaaatactacctgtccct tgctgatttttaaacgagcacgagagcaaaacccccctttgctgaggtggcagagggcaggtttttttgtttcttttttctcgtaaaaaa aagaaaggtcttaaaggttttatggttttggtcggcactgccgacagcctcgcaggacacacactttatgaatataaagtatagtgtg ttatactttacttggaagtggttgccggaaagagcgaaaatgcctcacatttgtgccacctaaaaaggagcgatttacatatgagttat gcagtttgtagaatgcaaaaagtgaaatcagggg The ligation mixture for pAH505 was transformed into *Bacillus subtilis* pnbA. Correct transformants were verified by RFLP and sequencing of isolated plasmid DNA. One transformant was selected for analysis (*B. subtilis* pnbA/pAH505).

Expression of the perhydrolase in *Bacillus* was assayed using the pNB Activity Assay described herein, after growth of the desired strain in shake flask. The data showed that the perhydrolase was expressed in *B. subtilis* pnbA.

B. Intracellular Expression of the Perhydrolase in *B. subtilis* pnbA by Integration into the Chromosome An additional construct useful to determine expression of the perhydrolase (act) gene integrated into the chromosome of *B. subtilis* pnbA involved use of the spoVG promoter, which was found to drive expression of the perhydrolase gene in a non-replicating (i.e., integrating plasmid). In some embodiments, one site of integration is the aprE region of *B. subtilis*, although it is intended that integration occur at any suitable site. Indeed, it is not intended that the present invention be limited to this specific site nor this specific promoter, as various other suitable sites and promoters find use in the present invention.

The configuration of the promoter/gene at the aprE locus in the chromosome of *Bacillus subtilis* was as follows:

pAprE-aprE first 7 codons-translation stop-pSpoVG-ATG-perhydrolase gene from second codon The clone was constructed as described below. The primers used were:

Up5'F
(SEQ ID NO: 138)
caggctgcgcaactgttgggaag

FuaprEAct34R
(SEQ ID NO: 139)
agtagttcaccaccttttccctatataaaagcattagtgtatcaatttca
gatccacaatttttttgcttctcactctttac -continued FuaprEAct4F
(SEQ ID NO: 140)
Aattgatacactaatgcttttatatagggaaaaggtggtgaactact
atggccaagcgaattctgtgtttcggtg BsmI-DnAct504R
(SEQ ID NO: 141)
gtgagaggcattcggatccttttacagcaggctccg PCR fusion is a technique well known in the art, in which two or more fragments of DNA are generated either by restriction digest or by PCR amplification. The fragments have overlapping segments, usually at least 18 bases long. In the instance that two fragments are used, the 3' end of fragment #1 has an overlapping sequence with the 5' end of fragment #2. The two fragments are used as template in a PCR reaction in which the primer set used hybridizes to the 5' end of fragment #1 (forward primer) and the 3' end of fragment #2 (reverse primer). During the amplification, the two regions of overlap hybridize forming a single template from which the two primers can amplify a full length fragment, a "fusion" of fragments #1 and #2. Multiple fragments of any length can be used in such a reaction, limited only by the ability of the chosen polymerase to amplify long DNA pieces.

Figure 15:
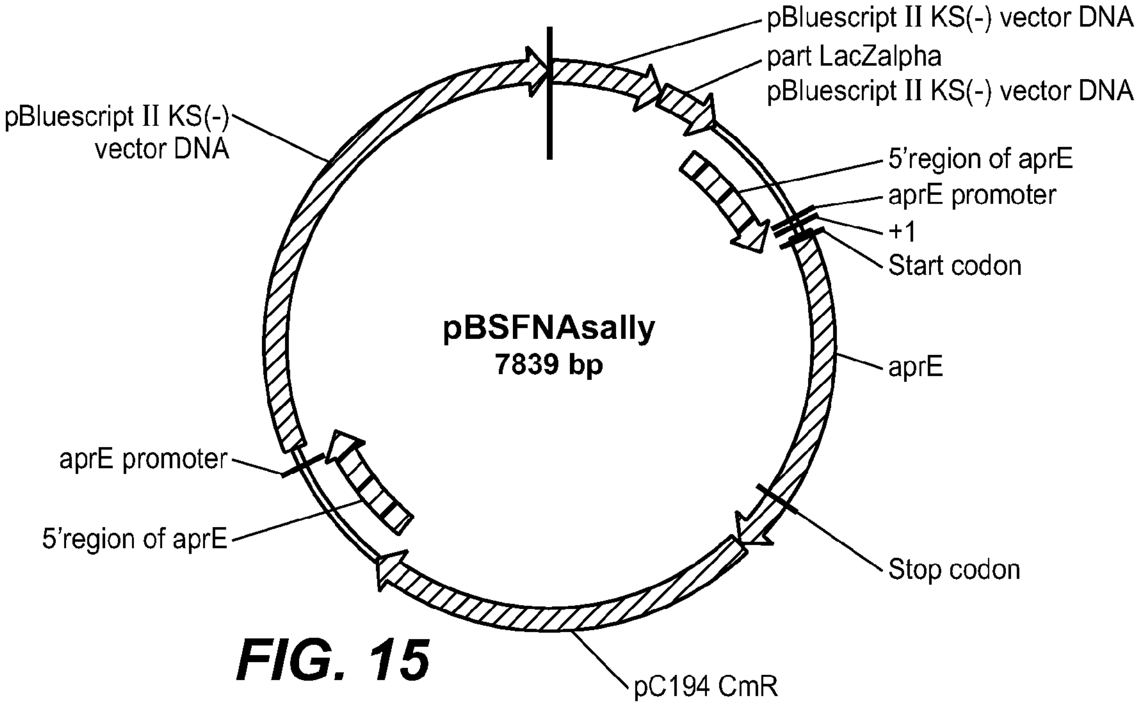
FIG. 15 provides a map of plasmid pSFNASally.

In the current example, the above construct was made by PCR fusion of two PCR products the above construct was made by PCR fusion of two PCR products. The first was a construct with the spoVG promoter added upstream of the phd gene. The second was the aprE promoter and first 7 codons of aprE, followed by a stop codon. Regions of 20 bp overlap were added on the 5' and 3' ends of the products respectively, to allow the PCR fusion reaction. The primer set FuaprEAct4F/BsmI-DnAct504R was used to amplify the perhydrolase gene from pAH505 as described above, which added the spoVG promoter sequence (contained within the primer) to the 5' end of the gene and changed the start codon from ATG to GTG. To create the second product (pAprE plus the first 7 codons of aprE) for the fusion, the primer set Up5'F/FuaprEAct34R was used to amplify a fragment from pBSFNASally. FIG. 15 provides a map of this plasmid. The complete sequence of pBSFNASally is provided below.

Figure 16:
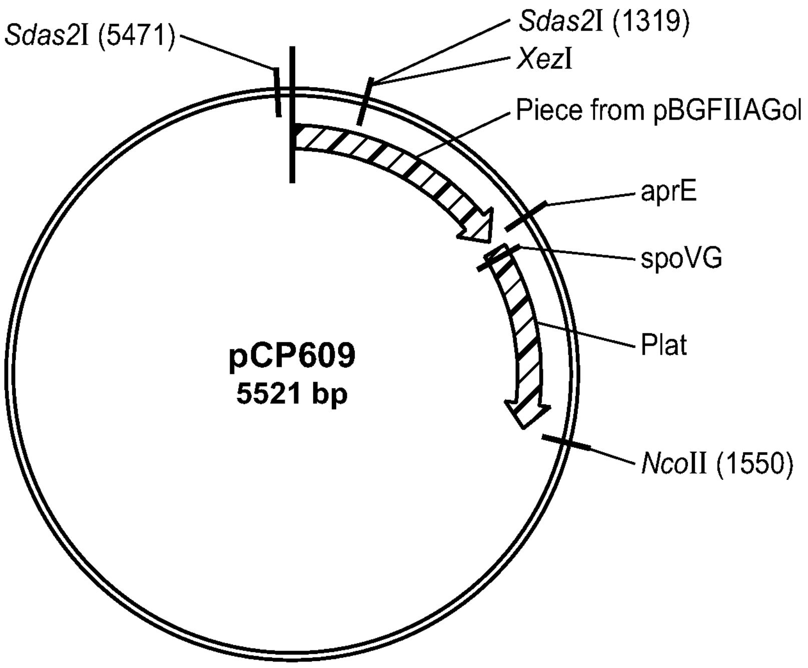
FIG. 16 provides a map of plasmid pCP606.

(SEQ ID NO: 142)

ctaaattgtaagcgttaatattttgttaaaattcgcgttaaatttttgttaaatcagctcattttttaaccaataggccgaaatcggcaaaat cccttataaatcaaaagaatagaccgagatagggttgagtgttgttccagtttggaacaagagtccactattaaagaacgtggactc caacgtcaaagggcgaaaaaccgtctatcagggcgatggcccactacgtgaaccatcaccctaatcaagttttttggggtcgagg tgccgtaaagcactaaatcggaaccctaaagggagcccccgatttagagcttgacggggaaagccggcgaacgtggcgagaa -continued aggaagggaagaaagcgaaaggagcgggcgctagggcgctggcaagtgtagcggtcacgctgcgcgtaaccaccacaccc gccgcgcttaatgcgccgctacagggcgcgtcccattcgccattcaggctgcgcaactgttgggaagggcgatcggtgcgggc ctcttcgctattacgccagctggcgaaagggggatgtgctgcaaggcgattaagttgggtaacgccagggttttcccagtcacgac gttgtaaaacgacggccagtgagcgcgcgtaatacgactcactatagggcgaattggagctccaccgcggtggcggccgctcta gaactagtggatcccccgggctgcaggaattctccattttcttctgctatcaaaataacagactcgtgattttccaaacgagctttcaa aaaagcctctgccccttgcaaatcggatgcctgtctataaaattcccgatattggttaaacagcggcgcaatggcggccgcatctgatgt ctttgcttggcgaatgttcatcttatttcttcctccctctcaataatttttcattctatccctttctgtaaagtttatttttcagaatactt ttatcatcatgctttgaaaaaatatcacgataatatccattgttctcacggaagcacacgcaggtcatttgaacgaatttttcgacagg aatttgccgggactcaggagcatttaacctaaaaaagcatgacatttcagcataatgaacatttactcatgtctattttcgttcttttctgt atgaaaatagttatttcgagtctctacggaaatagcgagagatgatatacctaaatagagataaaatcatctcaaaaaaatgggtcta ctaaaatattattccatctattacaataaattcacagaatagtcttttaagtaagtctactctgaattttttaaaaggagagggtaaaga gtgagaagcaaaaaattgtggatcagtttgctgtttgctttagcgttaatctttacgatggcgttcggcagcacatcctctgcccaggc ggcagggaaatcaaacggggaaaagaaatatattgtcgggtttaaacagacaatgagcacgatgagcgccgctaagaagaaag atgtcatttctgaaaaaggcgggaaagtgcaaaagcaattcaaatatgtagacgcagcttcagctacattaaacgaaaaagctgta aaagaattgaaaaaagacccgagcgtcgcttacgttgaagaagatcacgtagcacatgcgtacgcgcagtccgtgccttacggc gtatcacaaattaaagcccctgctctgcactctcaaggctacactggatcaaatgttaaagtagcggttatcgacagcggtatcgatt cttctcatcctgatttaaaggtagcaggcggagccagcatggttccttctgaaacaaatcctttccaagacaacaactctcacggaa ctcacgttgccggcacagttgcggctcttaataactcaatcggtgtattaggcgttgcgccaagcgcatcactttacgctgtaaaagt tctcggtgctgacggttccggccaatacagctggatcattaacggaatcgagtgggcgatcgcaaacaatatggacgttattaaca tgagcctcggcggaccttctggttctgctgctttaaaagcggcagttgataaagccgttgcatccggcgtcgtagtcgttgcggcag ccggtaacgaaggcacttccggcagctcaagcacagtgggctaccctggtaaatacccttctgtcattgcagtaggcgctgttgac agcagcaaccaaagagcatctttctcaagcgtaggacctgagcttgatgtcatggcacctggcgtatctatccaaagcacgcttcc tggaaacaaatacggcgcgttgaacggtacatcaatggcatctccgcacgttgccggagcggctgctttgattctttctaagcacc cgaactggacaaacactcaagtccgcagcagtttagaaaacaccactacaaaacttggtgattctttctactatggaaaagggctg atcaacgtacaggcggcagctcagtaaaacataaaaaaccggccttggccccgccggttttttattatttttcttcctccgcatgttca atccgctccataatcgacggatggctccctctgaaaattttaacgagaaacggcgggttgacccggctcagtcccgtaacggcca agtcctgaaacgtctcaatcgccgcttcccggtttccggtcagctcaatgccgtaacggtcggcggcgttttcctgataccgggag acggcattcgtaatcggatcctctagagtcgatttttacaagaattagctttatataatttctgtttttctaaagttttatcagctacaaaaga cagaaatgtattgcaatcttcaactaaatccatttgattctctccaatatgacgtttaataaatttctgaaatacttgatttctttgtttttct cagtatacttttccatgttataacacataaaaacaacttagttttcacaaactatgacaataaaaaaagttgctttttcccctttctatgtat gtttttactagtcatttaaaacgatacattaataggtacgaaaaagcaactttttttgcgcttaaaaccagtcataccaataacttaagg gtaactagcctcgccggcaatagttacccttattatcaagataagaaagaaaaggatttttcgctacgctcaaatcctttaaaaaaac acaaaagaccacatttttaatgtggtctttattcttcaactaaagcacccattagttcaacaaacgaaaattggataaagtgggatatt tttaaaatatatatttatgttacagtaatattgacttttaaaaaaggattgattctaatgaagaaagcagacaagtaagcctcctaaattc actttagataaaaatttaggaggcatatcaaatgaactttaataaaattgatttagacaattggaagagaaaagagatatttaatcatta tttgaaccaacaaacgacttttagtataaccacagaaattgatattagtgttttataccgaaacataaaacaagaaggatataaattta ccctgcatttattttcttagtgacaagggtgataaactcaaatacagcttttagaactggttacaatagcgacggagagttaggttattg ggataagttagagccactttatacaattttgatggtgtatctaaaacattctctggtatttggactcctgtaaagaatgacttcaaagag ttttatgatttatacctttctgatgtagagaaatataatggttcggggaaattgtttcccaaaacacctatacctgaaaatgctttttctcttt ctattattccatggacttcatttactgggtttaacttaaatatcaataataatagtaattaccttctacccattattacagcaggaaaattca -continued ttaataaaggtaattcaatatatttaccgctatctttacaggtacatcattctgtttgtgatggttatcatgcaggattgtttatgaactctat tcaggaattgtcagataggcctaatgactggcttttataatatgagataatgccgactgtactttttacagtcggttttctaatgtcacta acctgccccgttagttgaagaaggtttttatattacagctccagatccatatccttctttttctgaaccgacttctcctttttcgcttctttatt ccaattgctttattgacgttgagcctcggaacccttaacaatcccaaaacttgtcgaatggtcggcttaatagctcacgctatgccga cattcgtctgcaagtttagttaagggttcttctcaacgcacaataaattttctcggcataaatgcgtggtctaattttatttttaataacctt gatagcaaaaaatgccattccaatacaaaaccacatacctataatcgaccggaattaattctccattttcttctgctatcaaaataaca gactcgtgattttccaaacgagctttcaaaaaagcctctgccccttgcaaatcggatgcctgtctataaaattcccgatattggttaaa cagcggcgcaatggcggccgcatctgatgtctttgcttggcgaatgttcatcttatttcttcctccctctcaataatttttttcattctatcc cttttctgtaaagtttatttttcagaatacttttatcatcatgctttgaaaaaatatcacgataatatccattgttctcacggaagcacacgc aggtcatttgaacgaatttttttcgacaggaatttgccgggactcaggagcatttaacctaaaaaagcatgacatttcagcataatgaa catttactcatgtctattttcgttcttttctgtatgaaaatagttatttcgagtctctacggaaatagcgagagatgatatacctaaatag a gataaaatcatctcaaaaaaatgggtctactaaaatattattccatctattacaataaattcacagaatagtcttttaagtaagtctactct gaatttttttatcaagcttatcgataccgtcgacctcgagggggggcccggtacccagcttttgttccctttagtgagggttaattgcg cgcttggcgtaatcatggtcatagctgtttcctgtgtgaaattgttatccgctcacaattccacacaacatacgagccggaagcataa agtgtaaagcctggggtgcctaatgagtgagctaactcacattaattgcgttgcgctcactgcccgctttccagtcgggaaacctgt cgtgccagctgcattaatgaatcggccaacgcgcggggagaggcggtttgcgtattgggcgctcttccgcttcctcgctcactgac tcgctgcgctcggtcgttcggctgcggcgagcggtatcagctcactcaaaggcggtaatacggttatccacagaatcaggggata acgcaggaaagaacatgtgagcaaaaggccagcaaaaggccaggaaccgtaaaaaggccgcgttgctggcgtttttccatagg ctccgcccccctgacgagcatcacaaaaatcgacgctcaagtcagaggtggcgaaacccgacaggactataaagataccaggc gtttccccctggaagctccctcgtgcgctctcctgttccgaccctgccgcttaccggatacctgtccgcctttctcccttcgggaagc gtggcgctttctcatagctcacgctgtaggtatctcagttcggtgtaggtcgttcgctccaagctgggctgtgtgcacgaaccccc c gttcagcccgaccgctgcgccttatccggtaactatcgtcttgagtccaacccggtaagacacgacttatcgccactggcagcagc cactggtaacaggattagcagagcgaggtatgtaggcggtgctacagagttcttgaagtggtggcctaactacggctacactaga aggacagtatttggtatctgcgctctgctgaagccagttaccttcggaaaaagagttggtagctcttgatccggcaaacaaaccacc gctggtagcggtggtttttttgtttgcaagcagcagattacgcgcagaaaaaaaggatctcaagaagatcctttgatcttttctacgg ggtctgacgctcagtggaacgaaaactcacgttaagggattttggtcatgagattatcaaaaaggatcttcacctagatccttttaaat taaaaatgaagttttaaatcaatctaaagtatatatgagtaaacttggtctgacagttaccaatgcttaatcagtgaggcacctatctca gcgatctgtctatttcgttcatccatagttgcctgactccccgtcgtgtagataactacgatacgggagggcttaccatctggcccca gtgctgcaatgataccgcgagacccacgctcaccggctccagatttatcagcaataaaccagccagccggaagggccgagcgc agaagtggtcctgcaactttatccgcctccatccagtctattaattgttgccgggaagctagagtaagtagttcgccagttaatagttt gcgcaacgttgttgccattgctacaggcatcgtggtgtcacgctcgtcgtttggtatggcttcattcagctccggttcccaacgatca aggcgagttacatgatcccccatgttgtgcaaaaaagcggttagctccttcggtcctccgatcgttgtcagaagtaagttggccgca gtgttatcactcatggttatggcagcactgcataattctcttactgtcatgccatccgtaagatgcttttctgtgactggtgagtactcaa ccaagtcattctgagaatagtgtatgcggcgaccgagttgctcttgcccggcgtcaatacgggataataccgcgccacatagcag aactttaaaagtgctcatcattggaaaacgttcttcggggcgaaaactctcaaggatcttaccgctgttgagatccagttcgatgtaa cccactcgtgcacccaactgatcttcagcatcttttactttcaccagcgtttctgggtgagcaaaaacaggaaggcaaaatgccgca aaaaagggaataagggcgacacggaaatgttgaatactcatactcttcctttttcaatattattgaagcatttatcagggttattgtctc atgagcggatacatatttgaatgtatttagaaaaataaacaaataggggttccgcgcacatttccccgaaaagtgccac The two PCR products were subjected to fusion PCR as known in the art to create the 1.5 kb fusion. The resulting fusion product was then cloned into PCR2.1TOPO to produce pCP609 (See, FIG. 16) and sequence below).

Figure 17:
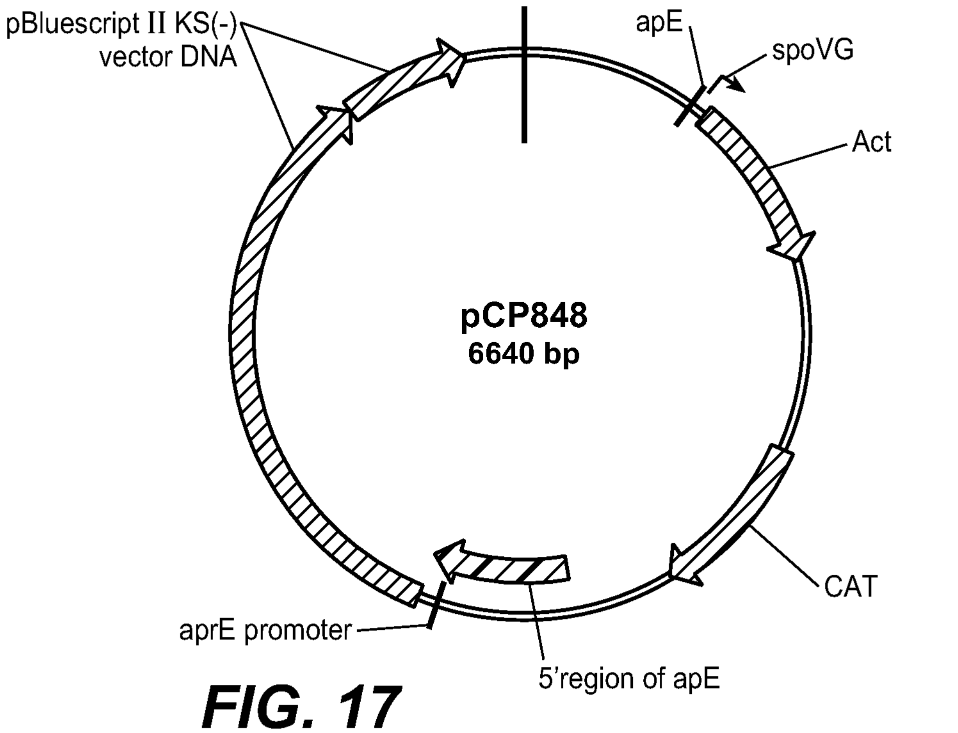
FIG. 17 provides a map of plasmid pCP649.

(SEQ ID NO: 143)

caggctgcgcaactgttgggaagggcgatcggtgcgggcctcttcgctattacgccagctggcgaaagggggatgtgctgcaa ggcgattaagttgggtaacgccagggttttcccagtcacgacgttgtaaaacgacggccagtgagcgcgcgtaatacgactcact atagggcgaattggagctccaccgcggtggcggccgctctagaactagtggatcccccgggctgcaggaattctccattttcttct gctatcaaaataacagactcgtgattttccaaacgagctttcaaaaaagcctctgccccttgcaaatcggatgcctgtctataaaattc ccgatattggttaaacagcggcgcaatggcggccgcatctgatgtctttgcttggcgaatgttcatcttatttcttcctccctctcaataatt ttttcattctatccctttttctgtaaagtttatttttcagaatacttttatcatcatgctttgaaaaaatatcacgataatatccattgttctca cggaagcacacgcaggtcatttgaacgaatttttcgacaggaatttgccgggactcaggagcatttaacctaaaaaagcatgaca tttcagcataatgaacatttactcatgtctattttcgttcttttctgtatgaaaatagttatttcgagtctctacggaaatagcgagagatga tatacctaaatagagataaaatcatctcaaaaaaatgggtctactaaaatattattccatctattacaataaattcacagaatagtctttt aagtaagtctactctgaatttttttaaaaggagagggtaaagagtgagaagcaaaaaattgtggatctgaaattgatacactaatgctt ttatatagggaaaaggtggtgaactactatggccaagcgaattctgtgtttcggtgattccctgacctggggctgggtccccgtcga agacggggcacccaccgagcggttcgcccccgacgtgcgctggaccggtgtgctggcccagcagctcggagcggacttcga ggtgatcgaggagggactgagcgcgcgcaccaccaacatcgacgaccccaccgatccgcggctcaacggcgcgagctacct gccgtcgtgcctcgcgacgcacctgccgctcgacctggtgatcatcatgctgggcaccaacgacaccaaggcctacttccggcg caccccgctcgacatcgcgctgggcatgtcggtgctcgtcacgcaggtgctcaccagcgcgggcggcgtcggcaccacgtacc cggctcccaaggtgctggtggtctcgccgccaccgctggcgcccatgccgcacccctggttccagttgatcttcgagggcggcg agcagaagaccactgagctcgcccgcgtgtacagcgcgctcgcgtcgttcatgaaggtgccgttcttcgacgcgggttcggtgat cagcaccgacggcgtcgacggaatccacttcaccgaggccaacaatcgcgatctcggggtggccctcgcggaacaggtgcgg agcctgctgtaaaaggatccgaatgcctctcacaagggcgaattctgcagatatccatcacactggcggccgctcgagcatgcat ctagagggcccaattcgccctatagtgagtcgtattacaattcactggccgtcgttttacaacgtcgtgactgggaaaaccctggcg ttacccaacttaatcgccttgcagcacatccccctttcgccagctggcgtaatagcgaagaggcccgcaccgatcgcccttcccaa cagttgcgcagcctgaatggcgaatggacgcgccctgtagcggcgcattaagcgcggcgggtgtggtggttacgcgcagcgtg accgctacacttgccagcgccctagcgcccgctcctttcgctttcttcccttcctttctcgccacgttcgccggctttccccgtcaagc tctaaatcgggggctccctttagggttccgatttagtgctttacggcacctcgaccccaaaaaacttgattagggtgatggttcacgt agtgggccatcgccctgatagacggtttttcgccctttgacgttggagtccacgttctttaatagtggactcttgttccaaactggaac aacactcaaccctatctcggtctattcttttgatttataagggattttgccgatttcggcctattggttaaaaaatgagctgatttaacaaa aatttaacgcgaattttaacaaaattcagggcgcaagggctgctaaaggaagcggaacacgtagaaagccagtccgcagaaacg gtgctgaccccggatgaatgtcagctactgggctatctggacaagggaaaacgcaagcgcaaagagaaagcaggtagcttgca gtgggcttacatggcgatagctagactgggcggttttatggacagcaagcgaaccggaattgccagctggggcgccctctggta aggttgggaagccctgcaaagtaaactggatggctttcttgccgccaaggatctgatggcgcaggggatcaagatctgatcaaga gacaggatgaggatcgtttcgcatgattgaacaagatggattgcacgcaggttctccggccgcttgggtggagaggctattcggct atgactgggcacaacagacaatcggctgctctgatgccgccgtgttccggctgtcagcgcaggggcgcccggttctttttgtcaag accgacctgtccggtgccctgaatgaactgcaggacgaggcagcgcggctatcgtggctggccacgacgggcgttccttgcgc agctgtgctcgacgttgtcactgaagcgggaagggactggctgctattgggcgaagtgccggggcaggatctcctgtcatccca ccttgctcctgccgagaaagtatccatcatggctgatgcaatgcggcggctgcatacgcttgatccggctacctgcccattcgacc accaagcgaaacatcgcatcgagcgagcacgtactcggatggaagccggtcttgtcgatcaggatgatctggacgaagagcatc aggggctcgcgccagccgaactgttcgccaggctcaaggcgcgcatgcccgacggcgaggatctcgtcgtgacccatggcga tgcctgcttgccgaatatcatggtggaaaatggccgcttttctggattcatcgactgtggccggctgggtgtggcggaccgctatca ggacatagcgttggctacccgtgatattgctgaagagcttggcggcgaatgggctgaccgcttcctcgtgctttacggtatcgccg ctcccgattcgcagcgcatcgccttctatcgccttcttgacgagttcttctgaattgaaaaaggaagagtatgagtattcaacatttcc -continued gtgtcgcccttattcccttttttgcggcattttgccttcctgtttttgctcacccagaaacgctggtgaaagtaaaagatgctgaagatc agttgggtgcacgagtgggttacatcgaactggatctcaacagcggtaagatccttgagagttttcgccccgaagaacgttttccaa tgatgagcacttttaaagttctgctatgtggcgcggtattatcccgtattgacgccgggcaagagcaactcggtcgccgcatacact attctcagaatgacttggttgagtactcaccagtcacagaaaagcatcttacggatggcatgacagtaagagaattatgcagtgctg ccataaccatgagtgataacactgcggccaacttacttctgacaacgatcggaggaccgaaggagctaaccgcttttttgcacaac atgggggatcatgtaactcgccttgatcgttgggaaccggagctgaatgaagccataccaaacgacgagcgtgacaccacgatg cctgtagcaatggcaacaacgttgcgcaaactattaactggcgaactacttactctagcttcccggcaacaattaatagactggatg gaggcggataaagttgcaggaccacttctgcgctcggcccttccggctggctggtttattgctgataaatctggagccggtgagcg tgggtctcgcggtatcattgcagcactggggccagatggtaagccctcccgtatcgtagttatctacacgacggggagtcaggca actatggatgaacgaaatagacagatcgctgagataggtgcctcactgattaagcattggtaactgtcagaccaagtttactcatata tactttagattgatttaaaacttcatttttaatttaaaaggatctaggtgaagatcctttttgataatctcatgaccaaaatcccttaacgtg agttttcgttccactgagcgtcagaccccgtagaaaagatcaaaggatcttcttgagatcctttttttctgcgcgtaatctgctgcttgc aaacaaaaaaaccaccgctaccagcggtggtttgtttgccggatcaagagctaccaactctttttccgaaggtaactggcttcagca gagcgcagataccaaatactgttcttctagtgtagccgtagttaggccaccacttcaagaactctgtagcaccgcctacatacctcg ctctgctaatcctgttaccagtggctgctgccagtggcgataagtcgtgtcttaccgggttggactcaagacgatagttaccggata aggcgcagcggtcgggctgaacggggggttcgtgcacacagcccagcttggagcgaacgacctacaccgaactgagatacct acagcgtgagctatgagaaagcgccacgcttcccgaagggagaaaggcggacaggtatccggtaagcggcagggtcggaac aggagagcgcacgagggagcttccagggggaaacgcctggtatctttatagtcctgtcgggtttcgccacctctgacttgagcgt cgatttttgtgatgctcgtcaggggggcggagcctatggaaaaacgccagcaacgcggcctttttacggttcctggccttttgctgg ccttttgctcacatgttctttcctgcgttatcccctgattctgtggataaccgtattaccgcctttgagtgagctgataccgctcgccgca gccgaacgaccgagcgcagcgagtcagtgagcgaggaagcggaagagcgcccaatacgcaaaccgcctctccccgcgcgtt ggccgattcattaatgcagctggcacgacaggtttcccgactggaaagcgggcagtgagcgcaacgcaattaatgtgagttagct cactcattaggcaccccaggctttacactttatgcttccggctcgtatgttgtgtggaattgtgagcggataacaatttcacacaggaa acagctatgaccatgattacgccaagcttggtaccgagctcggatccactagtaacggccgccagtgtgctggaattcgccctt The plasmid PCP609 was digested with BamH1/XmaI to release the fragment containing the pAprE-aprE-stop-pSpoVG-phd construct and ligated into pBSFNASally digested with XmaI/Bcl1 to give the plasmid pCP649. FIG. 17 provides a map of pCP649. The complete sequence of pCP649 is provided below.

(SEQ ID NO: 144)

tagaactagtggatcccccgggctgcaggaattctccattttcttctgctatcaaaataacagactcgtgattttccaaacgagctttc aaaaaagcctctgccccttgcaaatcggatgcctgtctataaaattcccgatattggttaaacagcggcgcaatggcggccgcatctga tgtctttgcttggcgaatgttcatcttatttcttcctccctctcaataatttttttcattctatcccttttctgtaaagtttatttttcagaatac ttttatcatcatgctttgaaaaaatatcacgataatatccattgttctcacggaagcacacgcaggtcatttgaacgaatttttttcgacag gaatttgccgggactcaggagcatttaacctaaaaaagcatgacatttcagcataatgaacatttactcatgtctattttcgttcttttct gtatgaaaatagttatttcgagtctctacggaaatagcgagagatgatatacctaaatagagataaaatcatctcaaaaaaatgggtc tactaaaatattattccatctattacaataaattcacagaatagtcttttaagtaagtctactctgaattttttttaaaaggagagggtaaag agtgagaagcaaaaaattgtggatctgaaattgatacactaatgcttttatatagggaaaaggtggtgaactactatggccaagcga attctgtgtttcggtgattccctgacctggggctgggtccccgtcgaagacggggcacccaccgagcggttcgcccccgacgtgc gctggaccggtgtgctggcccagcagctcggagcggacttcgaggtgatcgaggagggactgagcgcgcgcaccaccaacat cgacgaccccaccgatccgcggctcaacggcgcgagctacctgccgtcgtgcctcgcgacgcacctgccgctcgacctggtga tcatcatgctgggcaccaacgacaccaaggcctacttccggcgcaccccgctcgacatcgcgctgggcatgtcggtgctcgtca cgcaggtgctcaccagcgcgggcggcgtcggcaccacgtacccggctcccaaggtgctggtggtctcgccgccaccgctggc -continued gcccatgccgcacccctggttccagttgatcttcgagggcggcgagcagaagaccactgagctcgcccgcgtgtacagcgcgc tcgcgtcgttcatgaaggtgccgttcttcgacgcgggttcggtgatcagcaccgacggcgtcgacggaatccacttcaccgaggc caacaatcgcgatctcggggtggccctcgcggaacaggtgcggagcctgctgtaacggaatgcctctcacaaggatccaagcc gaattctgcagatatccatcacactggcggccgctcgagcatgcatctagagtcgatttttacaagaattagctttatataatttctgttt ttctaaagttttatcagctacaaaagacagaaatgtattgcaatcttcaactaaatccatttgattctctccaatatgacgtttaataaattt ctgaaatacttgatttctttgtttttctcagtatacttttccatgttataacacataaaaacaacttagttttcacaaactatgacaataaaa aaagttgcttttttcccctttctatgtatgtttttactagtcatttaaaacgatacattaataggtacgaaaaagcaactttttttgcgcttaa aaccagtcataccaataacttaagggtaactagcctcgccggcaatagttacccttattatcaagataagaaagaaaaggatttttcg ctacgctcaaatcctttaaaaaaacacaaaagaccacatttttttaatgtggtctttattcttcaactaaagcacccattagttcaacaaa cgaaaattggataaagtgggatatttttaaaatatatatttatgttacagtaatattgacttttaaaaaaggattgattctaatgaagaaag cagacaagtaagcctcctaaattcactttagataaaaatttaggaggcatatcaaatgaactttaataaaattgatttagacaattgga agagaaaagagatatttaatcattatttgaaccaacaaacgacttttagtataaccacagaaattgatattagtgttttataccgaaaca taaaacaagaaggatataaattttaccctgcatttattttcttagtgacaagggtgataaactcaaatacagcttttagaactggttaca atagcgacggagagttaggttattgggataagttagagccactttatacaattttgatggtgtatctaaaacattctctggtatttgga ctcctgtaaagaatgacttcaaagagttttatgatttatacctttctgatgtagagaaatataatggttcggggaaattgtttcccaaaac acctatacctgaaaatgctttttctctttctattattccatggacttcatttactgggtttaacttaaatatcaataataatagtaattaccttc tacccattattacagcaggaaaattcattaataaaggtaattcaatatatttaccgctatctttacaggtacatcattctgtttgtgatggtt atcatgcaggattgtttatgaactctattcaggaattgtcagataggcctaatgactggcttttataatatgagataatgccgactgtac tttttacagtcggttttctaatgtcactaacctgccccgttagttgaagaaggtttttatattacagctccagatccatatccttctttttctg aaccgacttctcctttttcgcttctttattccaattgctttattgacgttgagcctcggaacccttaacaatcccaaaacttgtcgaatggt cggcttaatagctcacgctatgccgacattcgtctgcaagtttagttaagggttcttctcaacgcacaataaattttctcggcataaatg cgtggtctaattttatttttaataaccttgatagcaaaaaatgccattccaatacaaaaccacatacctataatcgacctgcaggaatt aattcctccatttcttctgctatcaaaataacagactcgtgattttccaaacgagctttcaaaaaagcctctgccccttgcaaatcgga tgcctgtctataaaattcccgatattggcttaaacagcggcgcaatggcggccgcatctgatgtctttgcttggcgaatgttcatcttattt cttcctccctctcaataatttttttcattctatcccttttctgtaaagtttatttttcagaatacttttatcatcatgctttgaaaaaatatcac gataatatccattgttctcacggaagcacacgcaggtcatttgaacgaatttttttcgacaggaatttgccgggactcaggagcattta acctaaaaaagcatgacatttcagcataatgaacatttactcatgtctattttcgttcttttctgtatgaaaatagttatttcgagtctctac ggaaatagcgagagatgatatacctaaatagagataaaatcatctcaaaaaaatgggtctactaaaatattattccatctattacaata aattcacagaatagtcttttaagtaagtctactctgaatttttttatcaagcttatcgataccgtcgacctcgagggggggcccggtac ccagcttttgttccctttagtgagggttaattgcgcgcttggcgtaatcatggtcatagctgtttcctgtgtgaaattgttatccgctcac aattccacacaacatacgagccggaagcataaagtgtaaagcctggggtgcctaatgagtgagctaactcacattaattgcgttgc gctcactgcccgctttccagtcgggaaacctgtcgtgccagctgcattaatgaatcggccaacgcgcggggagaggcggtttgc gtattgggcgctcttccgcttcctcgctcactgactcgctgcgctcggtcgttcggctgcggcgagcggtatcagctcactcaaag gcggtaatacggttatccacagaatcaggggataacgcaggaaagaacatgtgagcaaaaggccagcaaaaggccaggaacc gtaaaaaggccgcgttgctggcgtttttccataggctccgcccccctgacgagcatcacaaaaatcgacgctcaagtcagaggtg gcgaaacccgacaggactataaagataccaggcgtttccccctggaagctccctcgtgcgctctcctgttccgaccctgccgctta ccggatacctgtccgcctttctcccttcgggaagcgtggcgctttctcatagctcacgctgtaggtatctcagttcggtgtaggtcgtt cgctccaagctgggctgtgtgcacgaaccccccgttcagcccgaccgctgcgccttatccggtaactatcgtcttgagtccaaccc ggtaagacacgacttatcgccactggcagcagccactggtaacaggattagcagagcgaggtatgtaggcggtgctacagagtt cttgaagtggtggcctaactacggctacactagaaggacagtatttggtatctgcgctctgctgaagccagttaccttcggaaaaag -continued agttggtagctcttgatccggcaaacaaaccaccgctggtagcggtggtttttttgtttgcaagcagcagattacgcgcagaaaaaa aggatctcaagaagatcctttgatcttttctacggggtctgacgctcagtggaacgaaaactcacgttaagggattttggtcatgaga ttatcaaaaaggatcttcacctagatccttttaaattaaaaatgaagttttaaatcaatctaaagtatatatgagtaaacttggtctgaca gttaccaatgcttaatcagtgaggcacctatctcagcgatctgtctatttcgttcatccatagttgcctgactccccgtcgtgtagataa ctacgatacgggagggcttaccatctggccccagtgctgcaatgataccgcgagacccacgctcaccggctccagatttatcagc aataaaccagccagccggaagggccgagcgcagaagtggtcctgcaactttatccgcctccatccagtctattaattgttgccgg gaagctagagtaagtagttcgccagttaatagtttgcgcaacgttgttgccattgctacaggcatcgtggtgtcacgctcgtcgtttg gtatggcttcattcagctccggttcccaacgatcaaggcgagttacatgatcccccatgttgtgcaaaaaagcggttagctccttcg gtcctccgatcgttgtcagaagtaagttggccgcagtgttatcactcatggttatggcagcactgcataattctcttactgtcatgccat ccgtaagatgcttttctgtgactggtgagtactcaaccaagtcattctgagaatagtgtatgcggcgaccgagttgctcttgcccggc gtcaatacgggataataccgcgccacatagcagaactttaaaagtgctcatcattggaaaacgttcttcggggcgaaaactctcaa ggatcttaccgctgttgagatccagttcgatgtaacccactcgtgcacccaactgatcttcagcatcttttactttcaccagcgtttctg ggtgagcaaaaacaggaaggcaaaatgccgcaaaaaagggaataagggcgacacggaaatgttgaatactcatactcttcctttt tcaatattattgaagcatttatcagggttattgtctcatgagcggatacatatttgaatgtatttagaaaaataaacaaataggggttccg cgcacatttccccgaaaagtgccacctaaattgtaagcgttaatattttgttaaaattcgcgttaaatttttgttaaatcagctcatttttta accaataggccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtgaaccatca ccctaatcaagttttttggggtcgaggtgccgtaaagcactaaatcggaaccctaaagggagcccccgatttagagcttgacggg gaaagccggcgaacgtggcgagaaaggaagggaagaaagcgaaaggagcgggcgctagggcgctggcaagtgtagcggt cacgctgcgcgtaaccaccacacccgccgcgcttaatgcgccgctacagggcgcgtcccattcgccattcaggctgcgcaactg ttgggaagggcgatcggtgcgggcctcttcgctattacgccagctggcgaaagggggatgtgctgcaaggcgattaagttgggt aacgccagggttttcccagtcacgacgttgtaaaacgacggccagtgagcgcgcgtaatacgactcactatagggcgaattgga gctccaccgcggtggcggccgctc All constructs were confirmed by sequence analysis. PCR reactions were done using Hercules polymerase (Roche) as per the manufacturer's directions.

pCP649 was transformed into *B. subtilis* comK pnbA and integrants selected on L agar containing chloramphenicol (5 μg/ml). The activity of the expressed perhydrolase was determined by the pNB activity assay as described herein. The results indicated that the perhydrolase was expressed and active

Example 7

Expression of the Perhydrolase in *Streptomyces*

In this Example, experiments conducted to assess the expression of the perhydrolase in *Streptomyces* are described. To test expression of the perhydrolase in *Streptomyces*, a replicating plasmid was constructed with the phd gene being expressed from either the glucose isomerase (GIT) or the A4 promoter. However, it is not intended that the present invention be limited to these specific promoters, as any suitable promoter will find use with the present invention. Also, although the strain used for perhydrolase expression in this Example was *Streptomyces lividans* TK-23, it is contemplated that any *Streptomyces* will find use in the present invention.

The *Streptomyces* strains were transformed and manipulated using methods known in the art (See e.g., Kieser et al., *Practical Streptomyces Genetics*, John Innes [2000]).

Construction of pSECGT-MSAT and pSECA4-MSAT

Figure 18:
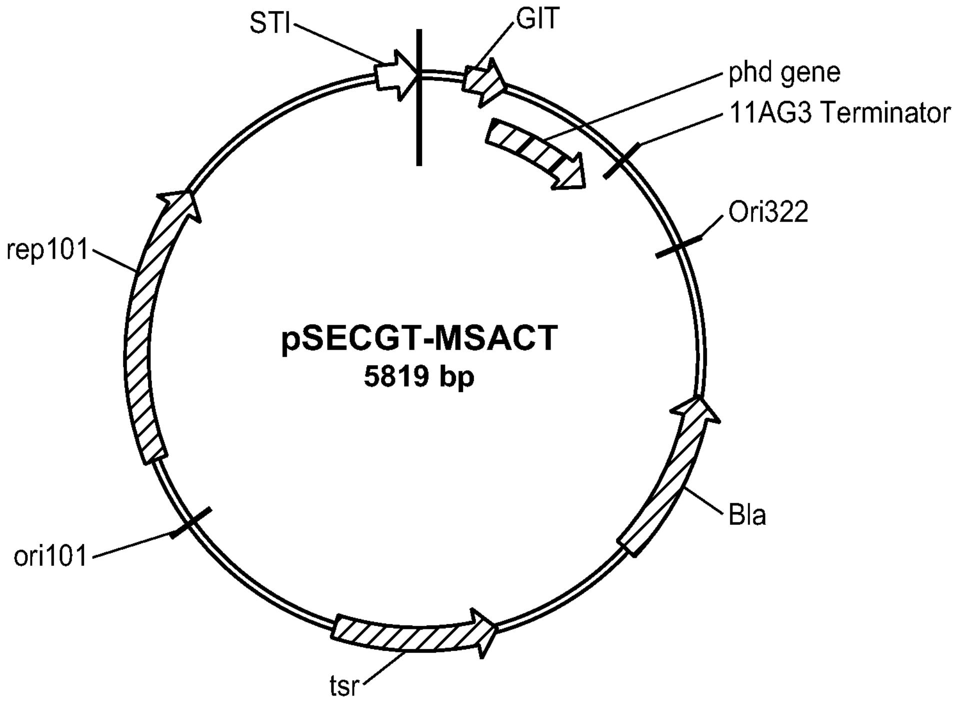
FIG. 18 provides a map of plasmid pSECGT-MSAT.

Using standard methods known in the art, the phd coding sequence (See, Example 4) was cloned into pSECGT to place the gene under control of the GI promoter. Similarly, the gene was cloned in the same plasmid with the A4 promoter using methods known in the art. Transformants were first selected in *E. coli*, verified by sequence analysis, and then transformed into *S. lividans* TK-23 using methods known in the art (See e.g., Kieser et al., [2000], supra). The correct clones expressed from the GI promoter and the A4 promoter were designated "pSECGT-MSAT" and "pSECA4-phd." The sequence of pSECGT-MSAT is provided below, while FIG. 18 provides a map of the plasmid.

Figure 19:
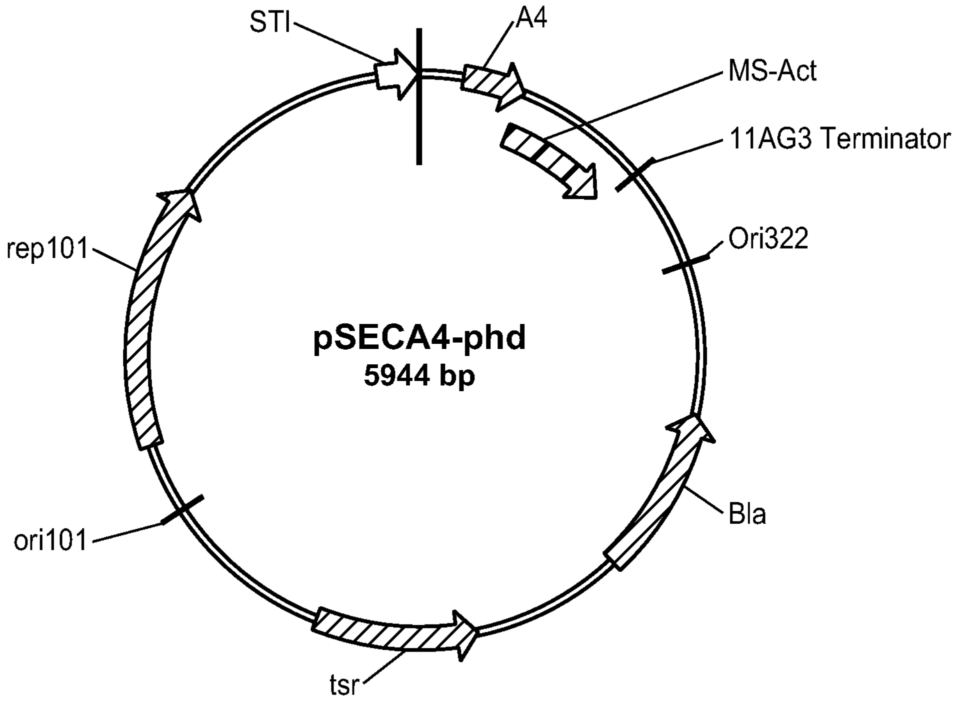
FIG. 19 provides a map of plasmid pSEGT-phdA4.

(SEQ ID NO: 145)

ctagagtcgaccacgcaggccgccaggtagtcgacgttgatctcgcagccgagcccggccggaccggcggcgctgagcgcg aggccgacggcgggacggccggcaccggtacgcggtggcgggtcgagttcggtgagcagcccaccggcgatcaggtcgtcg acgagcgcggagacggtggcccgggtgagcccggtgacggcggcaactcccgcgcgggagagccgatctgtgctgtttgcc -continued acggtatgcagcaccagcgcgagattatgggctcgcacgctcgactgtcggacgggggcactggaacgagaagtcaggcgag ccgtcacgcccttgacaatgccacatcctgagcaaataattcaaccactaaacaaatcaaccgcgtttcccggaggtaaccatggc caagcgaattctgtgtttcggtgattccctgacctggggctgggtccccgtcgaagacggggcacccaccgagcggttcgcccc cgacgtgcgctggaccggtgtgctggcccagcagctcggagcggacttcgaggtgatcgaggagggactgagcgcgcgcac caccaacatcgacgaccccaccgatccgcggctcaacggcgcgagctacctgccgtcgtgcctcgcgacgcacctgccgctcg acctggtgatcatcatgctgggcaccaacgacaccaaggcctacttccggcgcaccccgctcgacatcgcgctgggcatgtcgg tgctcgtcacgcaggtgctcaccagcgcgggcggcgtcggcaccacgtacccggcacccaaggtgctggtggtctcgccgcca ccgctggcgcccatgccgcacccctggttccagttgatcttcgagggcggcgagcagaagaccactgagctcgcccgcgtgta cagcgcgctcgcgtcgttcatgaaggtgccgttcttcgacgcgggttcggtgatcagcaccgacggcgtcgacggaatccacttc accgaggccaacaatcgcgatctcggggtggccctcgcggaacaggtgcggagcctgctgtaacgggatccgcgagcggatc ggctgaccggagcggggaggaggacgggcggccggcggaaaagtccgccggtccgctgaatcgctccccgggcacggac gtggcagtatcagcgccatgtccggcatatcccagccctccgcatgccccgaattcggcgtaatcatggtcatagctgtttcctgtg tgaaattgttatccgctcacaattccacacaacatacgagccggaagcataaagtgtaaagcctggggtgcctaatgagtgagcta actcacattaattgcgttgcgctcactgcccgctttccagtcgggaaacctgtcgtgccagctgcattaatgaatcggccaacgcgc ggggagaggcggtttgcgtattgggcgctcttccgcttcctcgctcactgactcgctgcgctcggtcgttcggctgcggcgagcg gtatcagctcactcaaaggcggtaatacggttatccacagaatcaggggataacgcaggaaagaacatgtgagcaaaaggcca gcaaaaggccaggaaccgtaaaaaggccgcgttgctggcgtttttccataggctccgcccccctgacgagcatcacaaaaatcg acgctcaagtcagaggtggcgaaacccgacaggactataaagataccaggcgtttccccctggaagctccctcgtgcgctctcct gttccgaccctgccgcttaccggatacctgtccgcctttctcccttcgggaagcgtggcgctttctcatagctcacgctgtaggtatc tcagttcggtgtaggtcgttcgctccaagctgggctgtgtgcacgaaccccccgttcagcccgaccgctgcgccttatccggtaac tatcgtcttgagtccaacccggtaagacacgacttatcgccactggcagcagccactggtaacaggattagcagagcgaggtatg taggcggtgctacagagttcttgaagtggtggcctaactacggctacactagaaggacagtatttggtatctgcgctctgctgaagc cagttaccttcggaaaaagagttggtagctcttgatccggcaaacaaaccaccgctggtagcggtggtttttttgtttgcaagcagc agattacgcgcagaaaaaaaggatctcaagaagatcctttgatcttttctacggggtctgacgctcagtggaacgaaaactcacgtt aagggattttggtcatgagattatcaaaaaggatcttcacctagatccttttaaattaaaaatgaagttttaaatcaatctaaagtatata tgagtaaacttggtctgacagttaccaatgcttaatcagtgaggcacctatctcagcgatctgtctatttcgttcatccatagttgcctg actccccgtcgtgtagataactacgatacgggagggcttaccatctggccccagtgctgcaatgataccgcgagacccacgctca ccggctccagatttatcagcaataaaccagccagccggaagggccgagcgcagaagtggtcctgcaactttatccgcctccatcc agtctattaattgttgccgggaagctagagtaagtagttcgccagttaatagtttgcgcaacgttgttgccattgctacaggcatcgtg gtgtcacgctcgtcgtttggtatggcttcattcagctccggttcccaacgatcaaggcgagttacatgatcccccatgttgtgcaaaa aagcggttagctccttcggtcctccgatcgttgtcagaagtaagttggccgcagtgttatcactcatggttatggcagcactgcataa ttctcttactgtcatgccatccgtaagatgcttttctgtgactggtgagtactcaaccaagtcattctgagaatagtgtatgcggcgacc gagttgctcttgcccggcgtcaatacgggataataccgcgccacatagcagaactttaaaagtgctcatcattggaaaacgttcttc ggggcgaaaactctcaaggatcttaccgctgttgagatccagttcgatgtaacccactcgtgcacccaactgatcttcagcatctttt actttcaccagcgtttctgggtgagcaaaaacaggaaggcaaaatgccgcaaaaaagggaataagggcgacacggaaatgttg aatactcatactcttcctttttcaatattattgaagcatttatcagggttattgtctcatgagcggatacatatttgaatgtatttagaaaaat aaacaaataggggttccgcgcacatttccccgaaaagtgccacctgacgtctaagaaaccattattatcatgacattaacctataaa aataggcgtatcacgaggccctttcgtctcgcgcgtttcggtgatgacggtgaaaacctcttgacacatgcagctcccggagacg gtcacagcttgtctgtaagcggatgccgggagcagacaagcccgtcagggcgcgtcagcgggtgttggcgggtgtcggggctg gcttaactatgcggcatcagagcagattgtactgagagtgcaccatatgcggtgtgaaataccgcacagatgcgtaaggagaaaa -continued taccgcatcaggcgccattcgccattcaggctgcgcaactgttgggaagggcgatcggtgcgggcctcttcgctattacgccagc tggcgaaagggggatgtgctgcaaggcgattaagttgggtaacgccagggttttcccagtcacgacgttgtaaaacgacggcca gtaagcttgcatgcctgcaggagtggggaggcacgatggccgctttggtcgacctcaacgagacgatgaagccgtggaacgac accaccccggcggccctgctggaccacacccggcactacaccttcgacgtctgatcatcactgacgaatcgaggtcgaggaac cgagcgtccgaggaacacaggcgcttatcggttggccgcgagattcctgtcgatcctctcgtgcagcgcgattccgagggaaac ggaaacgttgagagactcggtctggctcatcatggggatggaaaccgaggcggaagacgcctcctcgaacaggtcggaaggc ccacccttttcgctgccgaacagcaaggccagccgatccggattgtccccgagttccttcacggaaatgtcgccatccgccttgag cgtcatcagctgcataccgctgtcccgaatgaaggcgatggcctcctcgcgaccggagagaacgacgggaagggagaagacg taacctcggctggccctttggagacgccggtccgcgatgctggtgatgtcactgtcgaccaggatgatccccgacgctccgagc gcgagcgacgtgcgtactatcgcgccgatgttcccgacgatcttcaccccgtcgagaacgacgacgtccccacgccggctcgc gatatcgccgaacctggccgggcgagggacgcgggcgatgccgaatgtcttggccttccgctccccttgaacaactggttgac gatcgaggagtcgatgaggcggaccggtatgttctgccgcccgcacagatccagcaactcagatggaaaaggactgctgtcgct gccgtagacctcgatgaactccaccccggccgcgatgctgtgcatgaggggctcgacgtcctcgatcaacgttgtctttatgttgg atcgcgacggcttggtgacatcgatgatccgctgcaccgcgggatcggacggatttgcgatggtgtccaactcagtcatggtcgt cctaccggctgctgtgttcagtgacgcgattcctggggtgtgacaccctacgcgacgatggcggatggctgccctgaccggcaat caccaacgcaaggggaagtcgtcgctctctggcaaagctccccgctcttccccgtccgggacccgcgcggtcgatccccgcata tgaagtattcgccttgatcagtcccggtggacgcgccagcggcccgccggagcgacggactccccgacctcgatcgtgtcgcc ctgagcgtccacgtagacgttgcgtgagagcaggactgggccgccgccgaccgcaccgccctcaccaccgaccgcgaccgc gccatggccgccgccgacggcctggtcgccgccgccgcccgccggttcggcgcctgacccgaccaacccccgcggggcgc cggcacttcgtgctggcgccccgcccccacccaccaggagaccgaccatgaccgacttcgacggacgcctgaccgaggggac cgtgaacctggtccaggaccccaacggcggtggctggtccgcccactgcgctgagcccggttgcgactgggccgacttcgccg gaccgctcggcttccagggcctcgtggccatcgctcgccgacacacgcactgaccgcacgtcaaagccccgccggatacccg gcggggctctcttcggccctccaagtcacaccagccccaaggggcgtcgggagtggcggagggaacctctggcccgattggtg ccaggattcccaccagaccaaagagcaacgggccggacttcgcacctccgacccgtccgctcccagactcgcgccccttagcc gggcgagacaggaacgttgctcgtgcccagagtacggagcgatgccgaggcattgccagatcggcccgccgggccccgctg ccactgcgggaccgcaattgcccacacaccgggcaaacggccgcgtatctactgctcagaccgctgccggatggcagcgaag cgggcgatcgcgcgtgtgacgcgagatgccgcccgaggcaaaagcgaacaccttgggaaagaaacaacagagtttcccgcac ccctccgacctgcggtttctccggacggggtggatggggagagcccgagaggcgacagcctctgggaagtaggaagcacgtc gcggaccgaggctgcccgactgcggaaagccgcccggtacagccgccgccggacgctgtggcggatcagcggggacgccg cgtgcaagggctgcggccgcgccctgatggaccctgcctccggcgtgatcgtcgcccagacggcggccggaacgtccgtggt cctgggcctgatgcggtgcgggcggatctggctctgcccggtctgcgccgccacgatccggcacaagcgggccgaggagatc accgccgccgtggtcgagtggatcaagcgcgggggggaccgcctacctggtcaccttcacggcccgccatgggcacacggacc ggctcgcggacctcatggacgccctccagggcacccggaagacgccggacagcccccggcggccgggcgcctaccagcga ctgatcacgggcggcacgtgggccggacgccgggccaaggacgggcaccgggccgccgaccgcgagggcatccgagacc ggatcgggtacgtcggcatgatccgcgcgaccgaagtcaccgtggggcagatcaacggctggcacccgcacatccacgcgat cgtcctggtcggcggccggaccgagggggagcggtccgcgaagcagatcgtcgccaccttcgagccgaccggcgccgcgct cgacgagtggcaggggcactggcggtccgtgtggaccgccgccctgcgcaaggtcaaccccgccttcacgcccgacgaccg gcacggcgtcgacttcaagcggctggagaccgagcgcgacgccaacgacctcgccgagtacatcgccaagacccaggacgg gaaggcgcccgccctcgaactcgcccgcgccgacctcaagacggcgaccggcgggaacgtcgccccgttcgaactcctcgg acggatcggggacctgaccggcggcatgaccgaggacgacgccgccggggtcggctcgctggagtggaacctctcgcgctg gcacgagtacgagcgggcaacccggggacgccgggccatcgaatggacccgctacctgcggcagatgctcgggctcgacgg -continued cggcgacaccgaggccgacgacctcgatctgctcctggcggccgacgccgacggcggggagctgcgggccggggtcgccg tgaccgaggacggatggcacgcggtcacccgccgcgccctcgacctcgaggcgacccgggccgccgaaggcaaggacggc aacgaggattcggcggccgtgggcgaacgggtgcgggaggtcctggcgctggccgacgcggccgacacagtggtggtgctc acggcgggggaggtggccgaggcgtacgccgacatgctcgccgccctcgcccagcgccgcgaggaagcaactgcacgccg acggcgagagcaggacgacgaccaggacgacgacgccgacgaccgccaggagcgggccgcccggcacatcgcccggctc gcaagtgggcccacttcgcactaactcgctcccccccgccgtacgtcatcccggtgacgtacggcgggggtcggtgacgtacg cggcgacggcggccggggtcgaagccgcgggagtaatcctgggattactcgcccggggtcggccccgccggcacttcgtgca ggcggtacctcgcgcccgactcgcctcgctacgagacgtgccgcgtacggtcgtcggccatgagcaccaccacccccaggga cgccgacggcgcgaagctctgcgcctggtgcggctcggagatcaagcaatccggcgtcggccggagccgggactactgccg ccgctcctgccgccagcgggcgtacgaggcccggcgccagcgcgaggcgatcgtgtccgccgtggcgtcggcagtcgctcg ccgagatacgtcacgtgacgaaatgcagcagccttccattccgtcacgtgacgaaactcgggccgcaggtcagagcacggttcc gcccgctccggccctgccggacccccggctgcagctcgcccggccgccggtccccctgccgtccggcccgtcccagaggca gcgtcggcggctcctgcctcccccgcccggcgccgaccgggacccgcaaaccccttgatccgctgtcgggggtgatcactacg gtgggtgccgaagtgatcacggggaggactgatgcaccaccaggaccgggaccaggaccaggcgttagcggcagtgctggc cgcactgctcctggtcggcgggacgctgatcgtgcgggagctcctgggcctgtggcccgccgtggcggtcggcatggcgccc gccctcgccctctacggaggcccgcccgcggcccgccggatagccgtcgcggtcgaggtccgccggttccgccggcatcttgc ccaccacgatcgggcagccggatgaccggccacgacggagccgcacggctgaccagctcgacggccgccacctcatcgcgg cagcaggtgctccccagcaacccacgacggggctcagggtcgcctcacgcggctcagcaccgcgacggcgggggtacggc gctccgggaggctgacaggcgctcagacggccgcgtagggccgcgagtcccccacccctccccgctgccctgtcggcgagc acaacggcgatgcccgcagtcggcggagcaggcgccacgtaaaccgcccaccgatgccgcccccgtcgtgtgcgcgggccg gtcggcggccgggccggagcggggcgaagacaggagcgtcggccgggccgtgggccgggccgcgcggcccgctcgcgg gccgccttgatgacgtagggaaagttgtaccgcaaaaaacgcagcctgaactagttgcgatcct FIG. 19 provides a map of pSEGT-phdA4, while the sequence is provided below:

(SEQ ID NO: 146)

ctagagatcgaacttcatgttcgagttcttgttcacgtagaagccggagatgtgagaggtgatctggaactgctcaccctcgttggt ggtgacctggaggtaaagcaagtgacccttctggcggaggtggtaaggaacggggttccacggggagagagagatggccttg acggtcttgggaaggggagcttcngcgcgggggaggatggtcttgagagagggggagctagtaatgtcgtacttggacaggga gtgctccttctccgacgcatcagccacctcagcggagatggcatcgtgcagagacagacccccggaggtaaccatggccaagc gaattctgtgtttcggtgattccctgacctggggctgggtccccgtcgaagacggggcacccaccgagcggttcgcccccgacgt gcgctggaccggtgtgctggcccagcagctcggagcggacttcgaggtgatcgaggagggactgagcgcgcgcaccaccaa catcgacgaccccaccgatccgcggctcaacggcgcgagctacctgccgtcgtgcctcgcgacgcacctgccgctcgacctgg tgatcatcatgctgggcaccaacgacaccaaggcctacttccggcgcaccccgctcgacatcgcgctgggcatgtcggtgctcgt cacgcaggtgctcaccagcgcgggcggcgtcggcaccacgtacccggcacccaaggtgctggtggtctcgccgccaccgctg gcgcccatgccgcacccctggttccagttgatcttcgagggcggcgagcagaagaccactgagctcgcccgcgtgtacagcgc gctcgcgtcgttcatgaaggtgccgttcttcgacgcgggttcggtgatcagcaccgacggcgtcgacggaatccacttcaccgag gccaacaatcgcgatctcggggtggccctcgcggaacaggtgcggagcctgctgtaacaatggggatccgcgagcggatcgg ctgaccggagcggggaggaggacgggcggccggcggaaaagtccgccggtccgctgaatcgctccccgggcacggacgtg gcagtatcagcgccatgtccggcatatcccagccctccgcatgccccgaattcggcgtaatcatggtcatagctgtttcctgtgtga aattgttatccgctcacaattccacacaacatacgagccggaagcataaagtgtaaagcctggggtgcctaatgagtgagctaact -continued cacattaattgcgttgcgctcactgcccgctttccagtcgggaaacctgtcgtgccagctgcattaatgaatcggccaacgcgcgg ggagaggcggtttgcgtattgggcgctcttccgcttcctcgctcactgactcgctgcgctcggtcgttcggctgcggcgagcggta tcagctcactcaaaggcggtaatacggttatccacagaatcaggggataacgcaggaaagaacatgtgagcaaaaggccagca aaaggccaggaaccgtaaaaaggccgcgttgctggcgtttttccataggctccgcccccctgacgagcatcacaaaaatcgacg ctcaagtcagaggtggcgaaacccgacaggactataaagataccaggcgtttccccctggaagctccctcgtgcgctctcctgtt ccgaccctgccgcttaccggatacctgtccgcctttctcccttcgggaagcgtggcgctttctcatagctcacgctgtaggtatctca gttcggtgtaggtcgttcgctccaagctgggctgtgtgcacgaaccccccgttcagcccgaccgctgcgccttatccggtaactat cgtcttgagtccaacccggtaagacacgacttatcgccactggcagcagccactggtaacaggattagcagagcgaggtatgta ggcggtgctacagagttcttgaagtggtggcctaactacggctacactagaaggacagtatttggtatctgcgctctgctgaagcc agttaccttcggaaaaagagttggtagctcttgatccggcaaacaaaccaccgctggtagcggtggtttttttgtttgcaagcagca gattacgcgcagaaaaaaaggatctcaagaagatcctttgatcttttctacggggtctgacgctcagtggaacgaaaactcacgtta agggattttggtcatgagattatcaaaaaggatcttcacctagatccttttaaattaaaaatgaagttttaaatcaatctaaagtatatat gagtaaacttggtctgacagttaccaatgcttaatcagtgaggcacctatctcagcgatctgtctatttcgttcatccatagttgcctga ctccccgtcgtgtagataactacgatacgggagggcttaccatctggccccagtgctgcaatgataccgcgagacccacgctcac cggctccagatttatcagcaataaaccagccagccggaagggccgagcgcagaagtggtcctgcaactttatccgcctccatcca gtctattaattgttgccgggaagctagagtaagtagttcgccagttaatagtttgcgcaacgttgttgccattgctacaggcatcgtgg tgtcacgctcgtcgtttggtatggcttcattcagctccggttcccaacgatcaaggcgagttacatgatcccccatgttgtgcaaaaa agcggttagctccttcggtcctccgatcgttgtcagaagtaagttggccgcagtgttatcactcatggttatggcagcactgcataatt ctcttactgtcatgccatccgtaagatgcttttctgtgactggtgagtactcaaccaagtcattctgagaatagtgtatgcggcgaccg agttgctcttgcccggcgtcaatacgggataataccgcgccacatagcagaactttaaaagtgctcatcattggaaaacgttcttcg gggcgaaaactctcaaggatcttaccgctgttgagatccagttcgatgtaacccactcgtgcacccaactgatcttcagcatcttta ctttcaccagcgtttctgggtgagcaaaaacaggaaggcaaaatgccgcaaaaaagggaataagggcgacacggaaatgttga atactcatactcttcctttttcaatattattgaagcatttatcagggttattgtctcatgagcggatacatatttgaatgtatttagaaaaata aacaaataggggttccgcgcacatttccccgaaaagtgccacctgacgtctaagaaaccattattatcatgacattaacctataaaa ataggcgtatcacgaggccctttcgtctcgcgcgtttcggtgatgacggtgaaaacctcttgacacatgcagctcccggagacggt cacagcttgtctgtaagcggatgccgggagcagacaagcccgtcagggcgcgtcagcgggtgttggcgggtgtcggggctgg cttaactatgcggcatcagagcagattgtactgagagtgcaccatatgcggtgtgaaataccgcacagatgcgtaaggagaaaat accgcatcaggcgccattcgccattcaggctgcgcaactgttgggaagggcgatcggtgcgggcctcttcgctattacgccagct ggcgaaaggggggatgtgctgcaaggcgattaagttgggtaacgccagggttttcccagtcacgacgttgtaaaacgacggccag taagcttgcatgcctgcaggagtggggaggcacgatggccgctttggtcgacctcaacgagacgatgaagccgtggaacgaca ccaccccggcggccctgctggaccacacccggcactacaccttcgacgtctgatcatcactgacgaatcgaggtcgaggaacc gagcgtccgaggaacacaggcgcttatcggttggccgcgagattcctgtcgatcctctcgtgcagcgcgattccgagggaaacg gaaacgttgagagactcggtctggctcatcatggggatggaaaccgaggcggaagacgcctcctcgaacaggtcggaaggcc caccccttttcgctgccgaacagcaaggccagccgatccggattgtccccgagttccttcacggaaatgtcgccatccgccttgagc gtcatcagctgcataccgctgtcccgaatgaaggcgatggcctcctcgcgaccggagagaacgacgggaagggagaagacgt aacctcggctggccctttggagacgccggtccgcgatgctggtgatgtcactgtcgaccaggatgatccccgacgctccgagcg cgagcgacgtgcgtactatcgcgccgatgttcccgacgatcttcaccccgtcgagaacgacgacgtccccacgccggctcgcg atatcgccgaacctggccgggcgagggacgcgggcgatgccgaatgtcttggccttccgctccccccttgaacaactggttgacg atcgaggagtcgatgaggcggaccggtatgttctgccgcccgcacagatccagcaactcagatggaaaaggactgctgtcgctg ccgtagacctcgatgaactccaccccggccgcgatgctgtgcatgaggggctcgacgtcctcgatcaacgttgtctttatgttggat -continued cgcgacggcttggtgacatcgatgatccgctgcaccgcgggatcggacggatttgcgatggtgtccaactcagtcatggtcgtcc taccggctgctgtgttcagtgacgcgattcctggggtgtgacaccctacgcgacgatggcggatggctgccctgaccggcaatca ccaacgcaaggggaagtcgtcgctctctggcaaagctccccgctcttccccgtccgggacccgcgcggtcgatccccgcatatg aagtattcgccttgatcagtcccggtggacgcgccagcggcccgccggagcgacggactccccgacctcgatcgtgtcgccct gagcgtccacgtagacgttgcgtgagagcaggactgggccgccgccgaccgcaccgccctcaccaccgaccgcgaccgcgc catggccgccgccgacggcctggtcgccgccgccgcccgccggttcggcgcctgacccgaccaaccccgcggggcgccg gcacttcgtgctggcgccccgcccccacccaccaggagaccgaccatgaccgacttcgacggacgcctgaccgaggggaccg tgaacctggtccaggaccccaacggcggtggctggtccgcccactgcgctgagcccggttgcgactgggccgacttcgccgga ccgctcggcttccagggcctcgtggccatcgctcgccgacacacgcactgaccgcacgtcaaagccccgccggatacccggc ggggctctcttcggccctccaagtcacaccagccccaaggggcgtcgggagtggcggagggaacctctggcccgattggtgcc aggattcccaccagaccaaagagcaacgggccggacttcgcacctccgacccgtccgctcccagactcgcgccccttagccgg gcgagacaggaacgttgctcgtgcccagagtacggagcgatgccgaggcattgccagatcggcccgccgggccccgctgcca ctgcgggaccgcaattgcccacacaccgggcaaacggccgcgtatctactgctcagaccgctgccggatggcagcgaagcgg gcgatcgcgcgtgtgacgcgagatgccgcccgaggcaaaagcgaacaccttgggaaagaaacaacagagtttcccgcacccc tccgacctgcggtttctccggacggggtggatggggagagcccgagaggcgacagcctctgggaagtaggaagcacgtcgcg gaccgaggctgcccgactgcggaaagccgcccggtacagccgccgccggacgctgtggcggatcagcggggacgccgcgt gcaagggctgcggccgcgccctgatggaccctgcctccggcgtgatcgtcgcccagacggcggccggaacgtccgtggtcct gggcctgatgcggtgcgggcggatctggctctgcccggtctgcgccgccacgatccggcacaagcgggccgaggagatcacc gccgccgtggtcgagtggatcaagcgcgggggaccgcctacctggtcaccttcacggcccgccatgggcacacggaccggc tcgcggacctcatggacgccctccagggcacccggaagacgccggacagcccccggcggccgggcgcctaccagcgactg atcacgggcggcacgtgggccggacgccgggccaaggacgggcaccgggccgccgaccgcgagggcatccgagaccgga tcgggtacgtcggcatgatccgcgcgaccgaagtcaccgtggggcagatcaacggctggcacccgcacatccacgcgatcgtc ctggtcggcggccggaccgagggggagcggtccgcgaagcagatcgtcgccaccttcgagccgaccggcgccgcgctcgac gagtggcaggggcactggcggtccgtgtggaccgccgccctgcgcaaggtcaaccccgccttcacgcccgacgaccggcac ggcgtcgacttcaagcggctggagaccgagcgcgacgccaacgacctcgccgagtacatcgccaagacccaggacgggaag gcgcccgccctcgaactcgcccgcgccgacctcaagacggcgaccggcgggaacgtcgccccgttcgaactcctcggacgg atcggggacctgaccggcggcatgaccgaggacgacgccgccggggtcggctcgctggagtggaacctctcgcgctggcac gagtacgagcgggcaacccggggacgccgggccatcgaatggacccgctacctgcggcagatgctcgggctcgacggcggc gacaccgaggccgacgacctcgatctgctcctggcggccgacgccgacggcggggagctgcgggccggggtcgccgtgac cgaggacggatggcacgcggtcacccgccgcgccctcgacctcgaggcgacccgggccgccgaaggcaaggacggcaac gaggattcggcggccgtgggcgaacgggtgcgggaggtcctggcgctggccgacgcggccgacacagtggtggtgctcacg gcgggggaggtggccgaggcgtacgccgacatgctcgccgccctcgcccagcgccgcgaggaagcaactgcacgccgacg gcgagagcaggacgacgaccaggacgacgacgccgacgaccgccaggagcgggccgcccggcacatcgcccggctcgca agtgggcccacttcgcactaactcgctcccccccgccgtacgtcatcccggtgacgtacggcgggggtcggtgacgtacgcgg cgacggcggccggggtcgaagccgcgggagtaatcctgggattactcgcccggggtcggccccgccggcacttcgtgcaggc ggtacctcgcgcccgactcgcctcgctacgagacgtgccgcgtacggtcgtcggccatgagcaccaccaccccccagggacgc cgacggcgcgaagctctgcgcctggtgcggctcggagatcaagcaatccggcgtcggccggagccgggactactgccgccg ctcctgccgccagcgggcgtacgaggcccggcgccagcgcgaggcgatcgtgtccgccgtggcgtcggcagtcgctcgccg agatacgtcacgtgacgaaatgcagcagccttccattccgtcacgtgacgaaactcgggccgcaggtcagagcacggttccgcc cgctccggccctgccggaccccccggctgcagctcgcccggccgccggtccccctgccgtccggcccgtcccagaggcagcgt cggcggctcctgcctcccccgcccggcgccgaccgggacccgcaaacccccttgatccgctgtcgggggtgatcactacggtgg -continued gtgccgaagtgatcacggggaggactgatgcaccaccaggaccgggaccaggaccaggcgttagcggcagtgctggccgca ctgctcctggtcggcgggacgctgatcgtgcgggagctcctgggcctgtggcccgccgtggcggtcggcatggcgcccgccct cgccctctacggaggcccgcccgcggcccgccggatagccgtcgcggtcgaggtccgccggttccgccggcatcttgcccac cacgatcgggcagccggatgaccggccacgacggagccgcacggctgaccagctcgacggccgccacctcatcgcggcag caggtgctccccagcaacccacgacggggctcagggtcgcctcacgcggctcagcaccgcgacggcgggggtacggcgctc cgggaggctgacaggcgctcagacggccgcgtagggccgcgagtcccccacccctccccgctgccctgtcggcgagcacaa cggcgatgcccgcagtcggcggagcaggcgccacgtaaaccgcccaccgatgccgcccccgtcgtgtgcgcgggccggtcg gcggccgggccggagcggggcgaagacaggagcgtcggccgggccgtgggccgggccgcgcggcccgctcgcgggccg ccttgatgacgtagggaaagttgtaccgcaaaaaacgcagcctgaactagttgcgatcct Two colonies of *S. lividans* TK-23 pSECA4-phd were inoculated in 10 ml of TS medium+50 ppm thiostrepton and incubated at 37° C. with shaking at 200 rpm for 2 days. Three mls of broth were used to inoculate 50 ml of *Streptomyces* Production medium 1 and the culture was incubated for 4 days at 37° C. with shaking at 200 rpm.

A sample was taken to assay perhydrolase activity measurement as follows: 10 μls of 20 mg/ml lysozyme were added to 200 μl of sample. After 1 hour of incubation at 37° C., samples were centrifuged and activity was measured using the pNB activity assay described herein. SDS-PAGE and Western blots were also prepared using both clones (pSECA4-phd and pSECGT-MSAT), as known in the art. Briefly, after SDS-PAGE, the proteins were transferred to PVDF membrane and Western blot analysis was conducted. The perhydrolase was detected using an anti-perhydrolase polyclonal anti-sera (1:500 dilution) prepared against purified perhydrolase protein by Covance. The blot was developed using the ECL kit from Amersham. The results indicated that *Streptomyces lividans* strains were capable of expressing active perhydrolase.

Example 8

Site-Scanning Mutagenesis of the *M. smegmatis* Perhydrolase Gene

In this Example, experiments involving site-scanning mutagenesis of the *M. smegmatis* perhydrolase gene are described. In these experiments, the QuikChange® site-directed mutagenesis (QC; Stratagene) kit or the QuikChange® Multi Site-Directed mutagenesis (QCMS; Stratagene) kit was used to create site-saturation libraries at each codon in the entire *M. smegmatis* perhydrolase gene contained in the pMSAT-NcoI plasmid. Each perhydrolase codon was mutagenized by replacement with the NNGC (NNS; 32 combinations) degenerate codon, which encodes for all 20 amino acids and one stop codon. In the case of the QC method, complementary overlapping primers were designed for each codon of interest with 18 bases flanking the NNS codon (See, Tables 8-1 and 8-2). A comparison of cartridge purified versus unpurified primers (desalted only) revealed a better representation of amino acids in the libraries made with purified primers (15-19 amino acids versus 11-16 with unpurified primers). Thus, a majority of the libraries were created with the QC method and purified primers. A small number of the libraries were made using the QCMS method and a single 5' phosphorylated forward primer containing 18 bases flanking both sides of the NNS codon (See, Table 8-1), however this method resulted in a greater wild type background and fewer amino acid substitutions per site compared to the QC methods. Libraries "nsa301" and "nsa302" were made using the QCMS method, but a trinucleotide mix made up of a single codon for each of the 20 amino acids (i.e., rather than 32 possibilities encoded by NNS for the 20 amino acids) was incorporated within the primers at the sites of interest.

TABLE 8-1

Site-Saturation Forward Primers

| Residue | Primer | Primer Sequence |
|---|---|---|
| M1 | nsa202F | taacaggaggaattaaccnnsgccaagcgaattctgtgt (SEQ ID NO: 147) |
| A2 | nsa203F | caggaggaattaaccatgnnsaagcgaattctgtgtttc (SEQ ID NO: 148) |
| K3 | nsa204F | gaggaattaaccatggccnnscgaattctgtgtttcggt (SEQ ID NO: 149) |
| R4 | nsa205F | gaattaaccatggccaagnnsattctgtgtttcggtgat (SEQ ID NO: 150) |
| I5 | nsa206F | ttaaccatggccaagcgannsctgtgtttcggtgattcc (SEQ ID NO: 151) |
| L6 | nsa207F | accatggccaagcgaattnnstgtttcggtgattccctg (SEQ ID NO: 152) |
| C7 | nsa208F | atggccaagcgaattctgnnsttcggtgattccctgacc (SEQ ID NO: 153) |
| F8 | nsa209F | gccaagcgaattctgtgtnnsggtgattccctgacctgg (SEQ ID NO: 154) |
| G9 | nsa210F | aagcgaattctgtgtttcnnsgattccctgacctggggc (SEQ ID NO: 155) |
| D10 | nsa168F | cgaattctgtgtttcggtnnstccctgacctggggctgg (SEQ ID NO: 156) |

TABLE 8-1-continued

| Site-Saturation Forward Primers | | |
|---|---|---|
| Residue | Primer | Primer Sequence |
| S11 | nsa212F | attctgtgtttcggtgatnnsctgacctggggctgggtc (SEQ ID NO: 157) |
| L12 | nsa169F | ctgtgtttcggtgattccnnsacctggggctgggtcccc (SEQ ID NO: 158) |
| T13 | nsa170F | tgtttcggtgattccctgnnstggggctgggtccccgtc (SEQ ID NO: 159) |
| W14 | nsa171F | ttcggtgattccctgaccnnsggctgggtccccgtcgaa (SEQ ID NO: 160) |
| G15 | nsa216F | ggtgattccctgacctggnnstgggtccccgtcgaagac (SEQ ID NO: 161) |
| W16 | nsa172F | gattccctgacctggggcnnsgtccccgtcgaagacggg (SEQ ID NO: 162) |
| V17 | nsa218F | tccctgacctggggctggnnscccgtcgaagacggggca (SEQ ID NO: 163) |
| P18 | nsa219F | ctgacctggggctgggtcnnsgtcgaagacggggcaccc (SEQ ID NO: 164) |
| V19 | nsa220F | acctggggctgggtccccnnsgaagacggggcacccacc (SEQ ID NO: 165) |
| E20 | nsa221F | tggggctgggtccccgtcnnsgacggggcacccaccgag (SEQ ID NO: 166) |
| D21 | nsa222F | ggctgggtccccgtcgaannsggggcacccaccgagcgg (SEQ ID NO: 167) |
| G22 | nsa223F | tgggtccccgtcgaagacnnsgcacccaccgagcggttc (SEQ ID NO: 168) |
| A23 | nsa224F | gtccccgtcgaagacgggnnscccaccgagcggttcgcc (SEQ ID NO: 169) |
| P24 | nsa191F | cccgtcgaagacggggcannsaccgagcggttcgccccc (SEQ ID NO: 170) |
| T25 | nsa192F | gtcgaagacggggcacccnnsgagcggttcgcccccgac (SEQ ID NO: 171) |
| E26 | nsa227F | gaagacggggcacccaccnnscggttcgcccccgacgtg (SEQ ID NO: 172) |
| R27 | nsa228F | gacggggcacccaccgagnnsttcgcccccgacgtgcgc (SEQ ID NO: 173) |
| F28 | nsa229F | ggggcacccaccgagcggnnsgcccccgacgtgcgctgg (SEQ ID NO: 174) |
| A29 | nsa230F | gcacccaccgagcggttcnnscccgacgtgcgctggacc (SEQ ID NO: 175) |
| P30 | nsa231F | cccaccgagcggttcgccnnsgacgtgcgctggaccggt (SEQ ID NO: 176) |
| D31 | nsa232F | accgagcggttcgcccccnnsgtgcgctggaccggtgtg (SEQ ID NO: 177) |
| V32 | nsa233F | gagcggttcgcccccgacnnscgctggaccggtgtgctg (SEQ ID NO: 178) |
| R33 | nsa234F | cggttcgcccccgacgtgnnstggaccggtgtgctggcc (SEQ ID NO: 179) |
| W34 | nsa235F | ttcgcccccgacgtgcgcnnsaccggtgtgctggcccag (SEQ ID NO: 180) |
| T35 | nsa236F | gcccccgacgtgcgctggnnsggtgtgctggcccagcag (SEQ ID NO: 181) |
| G36 | nsa237F | cccgacgtgcgctggaccnnsgtgctggcccagcagctc (SEQ ID NO: 182) |
| V37 | nsa238F | gacgtgcgctggaccggtnnsctggcccagcagctcgga (SEQ ID NO: 183) |
| L38 | nsa239F | gtgcgctggaccggtgtgnnsgcccagcagctcggagcg (SEQ ID NO: 184) |
| A39 | nsa240F | cgctggaccggtgtgctgnnscagcagctcggagcggac (SEQ ID NO: 185) |
| Q40 | nsa241F | tggaccggtgtgctggccnnscagctcggagcggacttc (SEQ ID NO: 186) |
| Q41 | nsa242F | accggtgtgctggcccagnnsctcggagcggacttcgag (SEQ ID NO: 187) |
| L42 | nsa243F | ggtgtgctggcccagcagnnsggagcggacttcgaggtg (SEQ ID NO: 188) |
| G43 | nsa244F | gtgctggcccagcagctcnnsgcggacttcgaggtgatc (SEQ ID NO: 189) |
| A44 | nsa245F | ctggcccagcagctcggannsgacttcgaggtgatcgag (SEQ ID NO: 190) |
| D45 | nsa246F | gcccagcagctcggagcgnnsttcgaggtgatcgaggag (SEQ ID NO: 191) |
| F46 | nsa247F | cagcagctcggagcggacnnsgaggtgatcgaggaggga (SEQ ID NO: 192) |
| E47 | nsa248F | cagctcggagcggacttcnnsgtgatcgaggagggactg (SEQ ID NO: 193) |
| V48 | nsa249F | ctcggagcggacttcgagnnsatcgaggagggactgagc (SEQ ID NO: 194) |

TABLE 8-1-continued

| Site-Saturation Forward Primers | | |
|---|---|---|
| Residue | Primer | Primer Sequence |
| I49 | nsa250F | ggagcggacttcgaggtgnnsgaggagggactgagcgcg (SEQ ID NO: 195) |
| E50 | nsa251F | gcggacttcgaggtgatcnnsgagggactgagcgcgcgc (SEQ ID NO: 196) |
| E51 | nsa252F | gacttcgaggtgatcgagnnsggactgagcgcgcgcacc (SEQ ID NO: 197) |
| G52 | nsa253F | ttcgaggtgatcgaggagnnsctgagcgcgcgcaccacc (SEQ ID NO: 198) |
| L53 | nsa193F | gaggtgatcgaggagggannsagcgcgcgcaccaccaac (SEQ ID NO: 199) |
| S54 | nsa173F | gtgatcgaggagggactgnnsgcgcgcaccaccaacatc (SEQ ID NO: 200) |
| A55 | nsa174F | atcgaggagggactgagcnnscgcaccaccaacatcgac (SEQ ID NO: 201) |
| R56 | nsa257F | gaggagggactgagcgcgnnsaccaccaacatcgacgac (SEQ ID NO: 202) |
| T57 | nsa258F | gagggactgagcgcgcgcnnsaccaacatcgacgacccc (SEQ ID NO: 203) |
| T58 | nsa259F | ggactgagcgcgcgcaccnnsaacatcgacgaccccacc (SEQ ID NO: 204) |
| N59 | nsa260F | ctgagcgcgcgcaccaccnnsatcgacgaccccaccgat (SEQ ID NO: 205) |
| I60 | nsa261F | agcgcgcgcaccaccaacnnsgacgaccccaccgatccg (SEQ ID NO: 206) |
| D61 | nsa262F | gcgcgcaccaccaacatcnnsgaccccaccgatccgcgg (SEQ ID NO: 207) |
| D62 | nsa263F | cgcaccaccaacatcgacnnscccaccgatccgcggctc (SEQ ID NO: 208) |
| P63 | nsa264F | accaccaacatcgacgacnnsaccgatccgcggctcaac (SEQ ID NO: 209) |
| T64 | nsa194F | accaacatcgacgaccccnnsgatccgcggctcaacggc (SEQ ID NO: 210) |
| D65 | nsa195F | aacatcgacgaccccaccnnsccgcggctcaacggcgcg (SEQ ID NO: 211) |
| P66 | nsa267F | atcgacgaccccaccgatnnscggctcaacggcgcgagc (SEQ ID NO: 212) |
| R67 | nsa196F | gacgaccccaccgatccgnnsctcaacggcgcgagctac (SEQ ID NO: 213) |
| L68 | nsa269F | gaccccaccgatccgcggnnsaacggcgcgagctacctg (SEQ ID NO: 214) |
| N69 | nsa270F | cccaccgatccgcggctcnnsggcgcgagctacctgccg (SEQ ID NO: 215) |
| G70 | nsa271F | accgatccgcggctcaacnnsgcgagctacctgccgtcg (SEQ ID NO: 216) |
| A71 | nsa272F | gatccgcggctcaacggcnnsagctacctgccgtcgtgc (SEQ ID NO: 217) |
| S72 | nsa273F | ccgcggctcaacggcgcgnnstacctgccgtcgtgcctc (SEQ ID NO: 218) |
| Y73 | nsa274F | cggctcaacggcgcgagcnnsctgccgtcgtgcctcgcg (SEQ ID NO: 219) |
| L74 | nsa275F | ctcaacggcgcgagctacnnsccgtcgtgcctcgcgacg (SEQ ID NO: 220) |
| P75 | nsa276F | aacggcgcgagctacctgnnstcgtgcctcgcgacgcac (SEQ ID NO: 221) |
| S76 | nsa277F | ggcgcgagctacctgccgnnstgcctcgcgacgcacctg (SEQ ID NO: 222) |
| C77 | nsa278F | gcgagctacctgccgtcgnnsctcgcgacgcacctgccg (SEQ ID NO: 223) |
| L78 | nsa279F | agctacctgccgtcgtgcnnsgcgacgcacctgccgctc (SEQ ID NO: 224) |
| A79 | nsa280F | tacctgccgtcgtgcctcnnsacgcacctgccgctcgac (SEQ ID NO: 225) |
| T80 | nsa281F | ctgccgtcgtgcctcgcgnnscacctgccgctcgacctg (SEQ ID NO: 226) |
| H81 | nsa282F | ccgtcgtgcctcgcgacgnnsctgccgctcgacctggtg (SEQ ID NO: 227) |
| L82 | nsa283F | tcgtgcctcgcgacgcacnnsccgctcgacctggtgatc (SEQ ID NO: 228) |
| P83 | nsa284F | tgcctcgcgacgcacctgnnsctcgacctggtgatcatc (SEQ ID NO: 229) |
| L84 | nsa285F | ctcgcgacgcacctgccgnnsgacctggtgatcatcatg (SEQ ID NO: 230) |
| D85 | nsa286F | gcgacgcacctgccgctcnnsctggtgatcatcatgctg (SEQ ID NO: 231) |
| L86 | nsa287F | acgcacctgccgctcgacnnsgtgatcatcatgctgggc (SEQ ID NO: 232) |

TABLE 8-1-continued

| Site-Saturation Forward Primers | | |
|---|---|---|
| Residue | Primer | Primer Sequence |
| V87 | nsa288F | cacctgccgctcgacctgnnsatcatcatgctgggcacc (SEQ ID NO: 233) |
| I88 | nsa289F | ctgccgctcgacctggtgnnsatcatgctgggcaccaac (SEQ ID NO: 234) |
| I89 | nsa290F | ccgctcgacctggtgatcnnsatgctgggcaccaacgac (SEQ ID NO: 235) |
| M90 | nsa291F | ctcgacctggtgatcatcnnsctgggcaccaacgacacc (SEQ ID NO: 236) |
| L91 | nsa292F | gacctggtgatcatcatgnnsggcaccaacgacaccaag (SEQ ID NO: 237) |
| G92 | nsa293F | ctggtgatcatcatgctgnnsaccaacgacaccaaggcc (SEQ ID NO: 238) |
| T93 | nsa294F | gtgatcatcatgctgggcnnsaacgacaccaaggcctac (SEQ ID NO: 239) |
| N94 | nsa175F | atcatcatgctgggcaccnnsgacaccaaggcctacttc (SEQ ID NO: 240) |
| D95 | nsa197F | atcatgctgggcaccaacnnsaccaaggcctacttccgg (SEQ ID NO: 241) |
| T96 | nsa297F | atgctgggcaccaacgacnnsaaggcctacttccggcgc (SEQ ID NO: 242) |
| K97 | nsa176F | ctgggcaccaacgacaccnnsgcctacttccggcgcacc (SEQ ID NO: 243) |
| A98 | nsa299F | ggcaccaacgacaccaagnnstacttccggcgcaccccg (SEQ ID NO: 244) |
| Y99 | nsa177F | accaacgacaccaaggccnnsttccggcgcaccccgctc (SEQ ID NO: 245) |
| F100 | nsa301F | aacgacaccaaggcctacXXXcggcgcaccccgctcgac (SEQ ID NO: 246) |
| R101 | nsa302F | gacaccaaggcctacttcXXXcgcaccccgctcgacatc (SEQ ID NO: 247) |
| R102 | nsa303F | accaaggcctacttccggnnsaccccgctcgacatcgcg (SEQ ID NO: 248) |
| T103 | nsa304F | aaggcctacttccggcgcnnsccgctcgacatcgcgctg (SEQ ID NO: 249) |
| P104 | nsa305F | gcctacttccggcgcaccnnsctcgacatcgcgctgggc (SEQ ID NO: 250) |
| L105 | nsa306F | tacttccggcgcaccccgnnsgacatcgcgctgggcatg (SEQ ID NO: 251) |
| D106 | nsa307F | ttccggcgcaccccgctcnnsatcgcgctgggcatgtcg (SEQ ID NO: 252) |
| I107 | nsa308F | cggcgcaccccgctcgacnnsgcgctgggcatgtcggtg (SEQ ID NO: 253) |
| A108 | nsa309F | cgcaccccgctcgacatcnnsctgggcatgtcggtgctc (SEQ ID NO: 254) |
| L109 | nsa310F | accccgctcgacatcgcgnnsggcatgtcggtgctcgtc (SEQ ID NO: 255) |
| G110 | nsa311F | ccgctcgacatcgcgctgnnsatgtcggtgctcgtcacg (SEQ ID NO: 256) |
| M111 | nsa312F | ctcgacatcgcgctgggcnnstcggtgctcgtcacgcag (SEQ ID NO: 257) |
| S112 | nsa313F | gacatcgcgctgggcatgnnsgtgctcgtcacgcaggtg (SEQ ID NO: 258) |
| V113 | nsa314F | atcgcgctgggcatgtcgnnsctcgtcacgcaggtgctc (SEQ ID NO: 259) |
| L114 | nsa315F | gcgctgggcatgtcggtgnnsgtcacgcaggtgctcacc (SEQ ID NO: 260) |
| V115 | nsa316F | ctgggcatgtcggtgctcnnsacgcaggtgctcaccagc (SEQ ID NO: 261) |
| T116 | nsa317F | ggcatgtcggtgctcgtcnnscaggtgctcaccagcgcg (SEQ ID NO: 262) |
| Q117 | nsa318F | atgtcggtgctcgtcacgnnsgtgctcaccagcgcgggc (SEQ ID NO: 263) |
| V118 | nsa319F | tcggtgctcgtcacgcagnnsctcaccagcgcgggcggc (SEQ ID NO: 264) |
| L119 | nsa320F | gtgctcgtcacgcaggtgnnsaccagcgcgggcggcgtc (SEQ ID NO: 265) |
| T120 | nsa321F | ctcgtcacgcaggtgctcnnsagcgcgggcggcgtcggc (SEQ ID NO: 266) |
| S121 | nsa322F | gtcacgcaggtgctcaccnnsgcgggcggcgtcggcacc (SEQ ID NO: 267) |
| A122 | nsa323F | acgcaggtgctcaccagcnnsggcggcgtcggcaccacg (SEQ ID NO: 268) |
| G123 | nsa324F | caggtgctcaccagcgcgnnsggcgtcggcaccacgtac (SEQ ID NO: 269) |
| G124 | nsa325F | gtgctcaccagcgcgggcnnsgtcggcaccacgtacccg (SEQ ID NO: 270) |

TABLE 8-1-continued

Site-Saturation Forward Primers

| Residue | Primer | Primer Sequence |
|---|---|---|
| V125 | nsa198F | ctcaccagcgcgggcggcnnsggcaccacgtacccggca (SEQ ID NO: 271) |
| G126 | nsa327F | accagcgcgggcggcgtcnnsaccacgtacccggcaccc (SEQ ID NO: 272) |
| T127 | nsa328F | agcgcgggcggcgtcggcnnsacgtacccggcacccaag (SEQ ID NO: 273) |
| T128 | nsa329F | gcgggcggcgtcggcaccnnstacccggcacccaaggtg (SEQ ID NO: 274) |
| Y129 | nsa330F | ggcggcgtcggcaccacgnnsccggcacccaaggtgctg (SEQ ID NO: 275) |
| P130 | nsa331F | ggcgtcggcaccacgtacnnsgcacccaaggtgctggtg (SEQ ID NO: 276) |
| A131 | nsa332F | gtcggcaccacgtacccgnnscccaaggtgctggtggtc (SEQ ID NO: 277) |
| P132 | nsa333F | ggcaccacgtacccggcannsaaggtgctggtggtctcg (SEQ ID NO: 278) |
| K133 | nsa334F | accacgtacccggcacccnnsgtgctggtggtctcgccg (SEQ ID NO: 279) |
| V134 | nsa335F | acgtacccggcacccaagnnsctggtggtctcgccgcca (SEQ ID NO: 280) |
| L135 | nsa336F | tacccggcacccaaggtgnnsgtggtctcgccgccaccg (SEQ ID NO: 281) |
| V136 | nsa337F | ccggcacccaaggtgctgnnsgtctcgccgccaccgctg (SEQ ID NO: 282) |
| V137 | nsa338F | gcacccaaggtgctggtgnnstcgccgccaccgctggcg (SEQ ID NO: 283) |
| S138 | nsa339F | cccaaggtgctggtggtcnnsccgccaccgctggcgccc (SEQ ID NO: 284) |
| P139 | nsa340F | aaggtgctggtggtctcgnnsccaccgctggcgcccatg (SEQ ID NO: 285) |
| P140 | nsa341F | gtgctggtggtctcgccgnnsccgctggcgcccatgccg (SEQ ID NO: 286) |
| P141 | nsa342F | ctggtggtctcgccgccannsctggcgcccatgccgcac (SEQ ID NO: 287) |
| L142 | nsa343F | gtggtctcgccgccaccgnnsgcgcccatgccgcacccc (SEQ ID NO: 288) |
| A143 | nsa344F | gtctcgccgccaccgctgnnscccatgccgcacccctgg (SEQ ID NO: 289) |
| P144 | nsa345F | tcgccgccaccgctggcgnnsatgccgcacccctggttc (SEQ ID NO: 290) |
| M145 | nsa346F | ccgccaccgctggcgcccnnsccgcacccctggttccag (SEQ ID NO: 291) |
| P146 | nsa178F | ccaccgctggcgcccatgnnscacccctggttccagttg (SEQ ID NO: 292) |
| H147 | nsa348F | ccgctggcgcccatgccgnnsccctggttccagttgatc (SEQ ID NO: 293) |
| P148 | nsa199F | ctggcgcccatgccgcacnnstggttccagttgatcttc (SEQ ID NO: 294) |
| W149 | nsa179F | gcgcccatgccgcaccccnnsttccagttgatcttcgag (SEQ ID NO: 295) |
| F150 | nsa180F | cccatgccgcacccctggnnscagttgatcttcgagggc (SEQ ID NO: 296) |
| Q151 | nsa352F | atgccgcacccctggttcnnsttgatcttcgagggcggc (SEQ ID NO: 297) |
| L152 | nsa353F | ccgcacccctggttccagnnsatcttcgagggcggcgag (SEQ ID NO: 298) |
| I153 | nsa200F | cacccctggttccagttgnnsttcgagggcggcgagcag (SEQ ID NO: 299) |
| F154 | nsa201F | ccctggttccagttgatcnnsgagggcggcgagcagaag (SEQ ID NO: 300) |
| E155 | nsa356F | tggttccagttgatcttcnnsggcggcgagcagaagacc (SEQ ID NO: 301) |
| G156 | nsa357F | ttccagttgatcttcgagnnsggcgagcagaagaccact (SEQ ID NO: 302) |
| G157 | nsa358F | cagttgatcttcgagggcnnsgagcagaagaccactgag (SEQ ID NO: 303) |
| E158 | nsa359F | ttgatcttcgagggcggcnnscagaagaccactgagctc (SEQ ID NO: 304) |
| Q159 | nsa360F | atcttcgagggcggcgagnnsaagaccactgagctcgcc (SEQ ID NO: 305) |
| K160 | nsa361F | ttcgagggcggcgagcagnnsaccactgagctcgcccgc (SEQ ID NO: 306) |
| T161 | nsa362F | gagggcggcgagcagaagnnsactgagctcgcccgcgtg (SEQ ID NO: 307) |
| T162 | nsa363F | ggcggcgagcagaagaccnnsgagctcgcccgcgtgtac (SEQ ID NO: 308) |

TABLE 8-1-continued

| Site-Saturation Forward Primers | | |
|---|---|---|
| Residue | Primer | Primer Sequence |
| E163 | nsa364F | ggcgagcagaagaccactnnsctcgcccgcgtgtacagc (SEQ ID NO: 309) |
| L164 | nsa365F | gagcagaagaccactgagnnsgcccgcgtgtacagcgcg (SEQ ID NO: 310) |
| A165 | nsa366F | cagaagaccactgagctcnnscgcgtgtacagcgcgctc (SEQ ID NO: 311) |
| R166 | nsa367F | aagaccactgagctcgccnnsgtgtacagcgcgctcgcg (SEQ ID NO: 312) |
| V167 | nsa368F | accactgagctcgcccgcnnstacagcgcgctcgcgtcg (SEQ ID NO: 313) |
| Y168 | nsa369F | actgagctcgcccgcgtgnnsagcgcgctcgcgtcgttc (SEQ ID NO: 314) |
| S169 | nsa370F | gagctcgcccgcgtgtacnnsgcgctcgcgtcgttcatg (SEQ ID NO: 315) |
| A170 | nsa371F | ctcgcccgcgtgtacagcnnsctcgcgtcgttcatgaag (SEQ ID NO: 316) |
| L171 | nsa372F | gcccgcgtgtacagcgcgnnsgcgtcgttcatgaaggtg (SEQ ID NO: 317) |
| A172 | nsa373F | cgcgtgtacagcgcgctcnnstcgttcatgaaggtgccg (SEQ ID NO: 318) |
| S173 | nsa374F | gtgtacagcgcgctcgcgnnsttcatgaaggtgccgttc (SEQ ID NO: 319) |
| F174 | nsa375F | tacagcgcgctcgcgtcgnnsatgaaggtgccgttcttc (SEQ ID NO: 320) |
| M175 | nsa376F | agcgcgctcgcgtcgttcnnsaaggtgccgttcttcgac (SEQ ID NO: 321) |
| K176 | nsa377F | gcgctcgcgtcgttcatgnnsgtgccgttcttcgacgcg (SEQ ID NO: 322) |
| V177 | nsa378F | ctcgcgtcgttcatgaagnnsccgttcttcgacgcgggt (SEQ ID NO: 323) |
| P178 | nsa379F | gcgtcgttcatgaaggtgnnsttcttcgacgcgggttcg (SEQ ID NO: 324) |
| F179 | nsa380F | tcgttcatgaaggtgccgnnsttcgacgcgggttcggtg (SEQ ID NO: 325) |
| F180 | nsa381F | ttcatgaaggtgccgttcnnsgacgcgggttcggtgatc (SEQ ID NO: 326) |
| D181 | nsa382F | atgaaggtgccgttcttcnnsgcgggttcggtgatcagc (SEQ ID NO: 327) |
| A182 | nsa383F | aaggtgccgttcttcgacnnsggttcggtgatcagcacc (SEQ ID NO: 328) |
| G183 | nsa384F | gtgccgttcttcgacgcgnnstcggtgatcagcaccgac (SEQ ID NO: 329) |
| S184 | nsa385F | ccgttcttcgacgcgggtnnsgtgatcagcaccgacggc (SEQ ID NO: 330) |
| V185 | nsa386F | ttcttcgacgcgggttcgnnsatcagcaccgacggcgtc (SEQ ID NO: 331) |
| I186 | nsa387F | ttcgacgcgggttcggtgnnsagcaccgacggcgtcgac (SEQ ID NO: 332) |
| S187 | nsa388F | gacgcgggttcggtgatcnnsaccgacggcgtcgacgga (SEQ ID NO: 333) |
| T188 | nsa389F | gcgggttcggtgatcagcnnsgacggcgtcgacggaatc (SEQ ID NO: 334) |
| D189 | nsa390F | ggttcggtgatcagcaccnnsggcgtcgacggaatccac (SEQ ID NO: 335) |
| G190 | nsa391F | tcggtgatcagcaccgacnnsgtcgacggaatccacttc (SEQ ID NO: 336) |
| V191 | nsa392F | gtgatcagcaccgacggcnnsgacggaatccacttcacc (SEQ ID NO: 337) |
| D192 | nsa393F | atcagcaccgacggcgtcnnsggaatccacttcaccgag (SEQ ID NO: 338) |
| G193 | nsa394F | agcaccgacggcgtcgacnnsatccacttcaccgaggcc (SEQ ID NO: 339) |
| I194 | nsa181F | accgacggcgtcgacggannscacttcaccgaggccaac (SEQ ID NO: 340) |
| H195 | nsa396F | gacggcgtcgacggaatcnnsttcaccgaggccaacaat (SEQ ID NO: 341) |
| F196 | nsa182F | ggcgtcgacggaatccacnnsaccgaggccaacaatcgc (SEQ ID NO: 342) |
| T197 | nsa398F | gtcgacggaatccacttcnnsgaggccaacaatcgcgat (SEQ ID NO: 343) |
| E198 | nsa399F | gacggaatccacttcaccnnsgccaacaatcgcgatctc (SEQ ID NO: 344) |
| A199 | nsa400F | ggaatccacttcaccgagnnsaacaatcgcgatctcggg (SEQ ID NO: 345) |
| N200 | nsa401F | atccacttcaccgaggccnnsaatcgcgatctcggggtg (SEQ ID NO: 346) |

TABLE 8-1-continued

| Site-Saturation Forward Primers | | |
|---|---|---|
| Residue | Primer | Primer Sequence |
| N201 | nsa402F | cacttcaccgaggccaacnnscgcgatctcggggtggcc (SEQ ID NO: 347) |
| R202 | nsa403F | ttcaccgaggccaacaatnnsgatctcggggtggccctc (SEQ ID NO: 348) |
| D203 | nsa404F | accgaggccaacaatcgcnnsctcggggtggccctcgcg (SEQ ID NO: 349) |
| L204 | nsa405F | gaggccaacaatcgcgatnnsggggtggccctcgcggaa (SEQ ID NO: 350) |
| G205 | nsa406F | gccaacaatcgcgatctcnnsgtggccctcgcggaacag (SEQ ID NO: 351) |
| V206 | nsa407F | aacaatcgcgatctcgggnnsgccctcgcggaacaggtg (SEQ ID NO: 352) |
| A207 | nsa408F | aatcgcgatctcggggtgnnsctcgcggaacaggtgcag (SEQ ID NO: 353) |
| L208 | nsa409F | cgcgatctcggggtggccnnsgcggaacaggtgcagagc (SEQ ID NO: 354) |
| A209 | nsa410F | gatctcggggtggccctcnnsgaacaggtgcagagcctg (SEQ ID NO: 355) |
| E210 | nsa411F | ctcggggtggccctcgcgnnscaggtgcagagcctgctg (SEQ ID NO: 356) |
| Q211 | nsa412F | ggggtggccctcgcggaannsgtgcagagcctgctgtaa (SEQ ID NO: 357) |
| V212 | nsa413F | gtggccctcgcggaacagnnscagagcctgctgtaaaag (SEQ ID NO: 358) |
| Q213 | nsa414F | gccctcgcggaacaggtgnnsagcctgctgtaaaagggc (SEQ ID NO: 359) |
| S214 | nsa415F | ctcgcggaacaggtgcagnnsctgctgtaaaagggcgaa (SEQ ID NO: 360) |
| L215 | nsa416F | gcggaacaggtgcagagcnnsctgtaaaagggcgaattc (SEQ ID NO: 361) |
| L216 | nsa417F | gaacaggtgcagagcctgnnstaaaagggcgaattctgc (SEQ ID NO: 362) |

TABLE 8-2

| Site-Saturation Reverse Primer Sequences | | |
|---|---|---|
| Residue | Primer | Primer Sequence |
| M1 | nsa202R | ACACAGAATTCGCTTGGCSNNGGTTAATTCCTCCTGTTA (SEQ ID NO: 363) |
| A2 | nsa203R | GAAACACAGAATTCGCTTSNNCATGGTTAATTCCTCCTG (SEQ ID NO: 364) |
| K3 | nsa204R | ACCGAAACACAGAATTCGSNNGGCCATGGTTAATTCCTC (SEQ ID NO: 365) |
| R4 | nsa205R | ATCACCGAAACACAGAATSNNCTTGGCCATGGTTAATTC (SEQ ID NO: 366) |
| I5 | nsa206R | GGAATCACCGAAACACAGSNNTCGCTTGGCCATGGTTAA (SEQ ID NO: 367) |
| L6 | nsa207R | CAGGGAATCACCGAAACASNNAATTCGCTTGGCCATGGT (SEQ ID NO: 368) |
| C7 | nsa208R | GGTCAGGGAATCACCGAASNNCAGAATTCGCTTGGCCAT (SEQ ID NO: 369) |
| F8 | nsa209R | CCAGGTCAGGGAATCACCSNNACACAGAATTCGCTTGGC (SEQ ID NO: 370) |
| G9 | nsa210R | GCCCCAGGTCAGGGAATCSNNGAAACACAGAATTCGCTT (SEQ ID NO: 371) |
| D10 | nsa168R | CCAGCCCCAGGTCAGGGASNNACCGAAACACAGAATTCG (SEQ ID NO: 372) |
| S11 | nsa212R | GACCCAGCCCCAGGTCAGSNNATCACCGAAACACAGAAT (SEQ ID NO: 373) |

TABLE 8-2-continued

| Site-Saturation Reverse Primer Sequences | | |
|---|---|---|
| Residue | Primer | Primer Sequence |
| L12 | nsa169R | GGGGACCCAGCCCCAGGTSNNGGAATCACCGAAACACAG (SEQ ID NO: 374) |
| T13 | nsa170R | GACGGGGACCCAGCCCCASNNCAGGGAATCACCGAAACA (SEQ ID NO: 375) |
| W14 | nsa171R | TTCGACGGGGACCCAGCCSNNGGTCAGGGAATCACCGAA (SEQ ID NO: 376) |
| G15 | nsa216R | GTCTTCGACGGGGACCCASNNCCAGGTCAGGGAATCACC (SEQ ID NO: 377) |
| W16 | nsa172R | CCCGTCTTCGACGGGGACSNNGCCCCAGGTCAGGGAATC (SEQ ID NO: 378) |
| V17 | nsa218R | TGCCCCGTCTTCGACGGGSNNCCAGCCCCAGGTCAGGGA (SEQ ID NO: 379) |
| P18 | nsa219R | GGGTGCCCCGTCTTCGACSNNGACCCAGCCCCAGGTCAG (SEQ ID NO: 380) |
| V19 | nsa220R | GGTGGGTGCCCCGTCTTCSNNGGGGACCCAGCCCCAGGT (SEQ ID NO: 381) |
| E20 | nsa221R | CTCGGTGGGTGCCCCGTCSNNGACGGGGACCCAGCCCCA (SEQ ID NO: 382) |
| D21 | nsa222R | CCGCTCGGTGGGTGCCCCSNNTTCGACGGGGACCCAGCC (SEQ ID NO: 383) |
| G22 | nsa223R | GAACCGCTCGGTGGGTGCSNNGTCTTCGACGGGGACCCA (SEQ ID NO: 384) |
| A23 | nsa224R | GGCGAACCGCTCGGTGGGSNNCCCGTCTTCGACGGGGAC (SEQ ID NO: 385) |
| P24 | nsa191R | GGGGGCGAACCGCTCGGTSNNTGCCCCGTCTTCGACGGG (SEQ ID NO: 386) |
| T25 | nsa192R | GTCGGGGGCGAACCGCTCSNNGGGTGCCCCGTCTTCGAC (SEQ ID NO: 387) |
| E26 | nsa227R | CACGTCGGGGGCGAACCGSNNGGTGGGTGCCCCGTCTTC (SEQ ID NO: 388) |
| R27 | nsa228R | GCGCACGTCGGGGGCGAASNNCTCGGTGGGTGCCCCGTC (SEQ ID NO: 389) |
| F28 | nsa229R | CCAGCGCACGTCGGGGGCSNNCCGCTCGGTGGGTGCCCC (SEQ ID NO: 390) |
| A29 | nsa230R | GGTCCAGCGCACGTCGGGSNNGAACCGCTCGGTGGGTGC (SEQ ID NO: 391) |
| P30 | nsa231R | ACCGGTCCAGCGCACGTCSNNGGCGAACCGCTCGGTGGG (SEQ ID NO: 392) |
| D31 | nsa232R | CACACCGGTCCAGCGCACSNNGGGGGCGAACCGCTCGGT (SEQ ID NO: 393) |
| V32 | nsa233R | CAGCACACCGGTCCAGCGSNNGTCGGGGGCGAACCGCTC (SEQ ID NO: 394) |
| R33 | nsa234R | GGCCAGCACACCGGTCCASNNCACGTCGGGGGCGAACCG (SEQ ID NO: 395) |
| W34 | nsa235R | CTGGGCCAGCACACCGGTSNNGCGCACGTCGGGGGCGAA (SEQ ID NO: 396) |
| T35 | nsa236R | CTGCTGGGCCAGCACACCSNNCCAGCGCACGTCGGGGGC (SEQ ID NO: 397) |
| G36 | nsa237R | GAGCTGCTGGGCCAGCACSNNGGTCCAGCGCACGTCGGG (SEQ ID NO: 398) |

TABLE 8-2-continued

| Site-Saturation Reverse Primer Sequences | | |
|---|---|---|
| Residue | Primer | Primer Sequence |
| V37 | nsa238R | TCCGAGCTGCTGGGCCAGSNNACCGGTCCAGCGCACGTC (SEQ ID NO: 399) |
| L38 | nsa239R | CGCTCCGAGCTGCTGGGCSNNCACACCGGTCCAGCGCAC (SEQ ID NO: 400) |
| A39 | nsa240R | GTCCGCTCCGAGCTGCTGSNNCAGCACACCGGTCCAGCG (SEQ ID NO: 401) |
| Q40 | nsa241R | GAAGTCCGCTCCGAGCTGSNNGGCCAGCACACCGGTCCA (SEQ ID NO: 402) |
| Q41 | nsa242R | CTCGAAGTCCGCTCCGAGSNNCTGGGCCAGCACACCGGT (SEQ ID NO: 403) |
| L42 | nsa243R | CACCTCGAAGTCCGCTCCSNNCTGCTGGGCCAGCACACC (SEQ ID NO: 404) |
| G43 | nsa244R | GATCACCTCGAAGTCCGCSNNGAGCTGCTGGGCCAGCAC (SEQ ID NO: 405) |
| A44 | nsa245R | CTCGATCACCTCGAAGTCSNNTCCGAGCTGCTGGGCCAG (SEQ ID NO: 406) |
| D45 | nsa246R | CTCCTCGATCACCTCGAASNNCGCTCCGAGCTGCTGGGC (SEQ ID NO: 407) |
| F46 | nsa247R | TCCCTCCTCGATCACCTCSNNGTCCGCTCCGAGCTGCTG (SEQ ID NO: 408) |
| E47 | nsa248R | CAGTCCCTCCTCGATCACSNNGAAGTCCGCTCCGAGCTG (SEQ ID NO: 409) |
| V48 | nsa249R | GCTCAGTCCCTCCTCGATSNNCTCGAAGTCCGCTCCGAG (SEQ ID NO: 410) |
| I49 | nsa250R | CGCGCTCAGTCCCTCCTCSNNCACCTCGAAGTCCGCTCC (SEQ ID NO: 411) |
| E50 | nsa251R | GCGCGCGCTCAGTCCCTCSNNGATCACCTCGAAGTCCGC (SEQ ID NO: 412) |
| E51 | nsa252R | GGTGCGCGCGCTCAGTCCSNNCTCGATCACCTCGAAGTC (SEQ ID NO: 413) |
| G52 | nsa253R | GGTGGTGCGCGCGCTCAGSNNCTCCTCGATCACCTCGAA (SEQ ID NO: 414) |
| L53 | nsa193R | GTTGGTGGTGCGCGCGCTSNNTCCCTCCTCGATCACCTC (SEQ ID NO: 415) |
| S54 | nsa173R | GATGTTGGTGGTGCGCGCSNNCAGTCCCTCCTCGATCAC (SEQ ID NO: 416) |
| A55 | nsa174R | GTCGATGTTGGTGGTGCGSNNGCTCAGTCCCTCCTCGAT (SEQ ID NO: 417) |
| R56 | nsa257R | GTCGTCGATGTTGGTGGTSNNCGCGCTCAGTCCCTCCTC (SEQ ID NO: 418) |
| T57 | nsa258R | GGGGTCGTCGATGTTGGTSNNGCGCGCGCTCAGTCCCTC (SEQ ID NO: 419) |
| T58 | nsa259R | GGTGGGGTCGTCGATGTTSNNGGTGCGCGCGCTCAGTCC (SEQ ID NO: 420) |
| N59 | nsa260R | ATCGGTGGGGTCGTCGATSNNGGTGGTGCGCGCGCTCAG (SEQ ID NO: 421) |
| I60 | nsa261R | CGGATCGGTGGGGTCGTCSNNGTTGGTGGTGCGCGCGCT (SEQ ID NO: 422) |
| D61 | nsa262R | CCGCGGATCGGTGGGGTCSNNGATGTTGGTGGTGCGCGC (SEQ ID NO: 423) |

TABLE 8-2-continued

Site-Saturation Reverse Primer Sequences

| Residue | Primer | Primer Sequence |
|---|---|---|
| D62 | nsa263R | GAGCCGCGGATCGGTGGGSNNGTCGATGTTGGTGGTGCG (SEQ ID NO: 424) |
| P63 | nsa264R | GTTGAGCCGCGGATCGGTSNNGTCGTCGATGTTGGTGGT (SEQ ID NO: 425) |
| T64 | nsa194R | GCCGTTGAGCCGCGGATCSNNGGGGTCGTCGATGTTGGT (SEQ ID NO: 426) |
| D65 | nsa195R | CGCGCCGTTGAGCCGCGGSNNGGTGGGGTCGTCGATGTT (SEQ ID NO: 427) |
| P66 | nsa267R | GCTCGCGCCGTTGAGCCGSNNATCGGTGGGGTCGTCGAT (SEQ ID NO: 428) |
| R67 | nsa196R | GTAGCTCGCGCCGTTGAGSNNCGGATCGGTGGGGTCGTC (SEQ ID NO: 429) |
| L68 | nsa269R | CAGGTAGCTCGCGCCGTTSNNCCGCGGATCGGTGGGGTC (SEQ ID NO: 430) |
| N69 | nsa270R | CGGCAGGTAGCTCGCGCCSNNGAGCCGCGGATCGGTGGG (SEQ ID NO: 431) |
| G70 | nsa271R | CGACGGCAGGTAGCTCGCSNNGTTGAGCCGCGGATCGGT (SEQ ID NO: 432) |
| A71 | nsa272R | GCACGACGGCAGGTAGCTSNNGCCGTTGAGCCGCGGATC (SEQ ID NO: 433) |
| S72 | nsa273R | GAGGCACGACGGCAGGTASNNCGCGCCGTTGAGCCGCGG (SEQ ID NO: 434) |
| Y73 | nsa274R | CGCGAGGCACGACGGCAGSNNGCTCGCGCCGTTGAGCCG (SEQ ID NO: 435) |
| L74 | nsa275R | CGTCGCGAGGCACGACGGSNNGTAGCTCGCGCCGTTGAG (SEQ ID NO: 436) |
| P75 | nsa276R | GTGCGTCGCGAGGCACGASNNCAGGTAGCTCGCGCCGTT (SEQ ID NO: 437) |
| S76 | nsa277R | CAGGTGCGTCGCGAGGCASNNCGGCAGGTAGCTCGCGCC (SEQ ID NO: 438) |
| C77 | nsa278R | CGGCAGGTGCGTCGCGAGSNNCGACGGCAGGTAGCTCGC (SEQ ID NO: 439) |
| L78 | nsa279R | GAGCGGCAGGTGCGTCGCSNNGCACGACGGCAGGTAGCT (SEQ ID NO: 440) |
| A79 | nsa280R | GTCGAGCGGCAGGTGCGTSNNGAGGCACGACGGCAGGTA (SEQ ID NO: 441) |
| T80 | nsa281R | CAGGTCGAGCGGCAGGTGSNNCGCGAGGCACGACGGCAG (SEQ ID NO: 442) |
| H81 | nsa282R | CACCAGGTCGAGCGGCAGSNNCGTCGCGAGGCACGACGG (SEQ ID NO: 443) |
| L82 | nsa283R | GATCACCAGGTCGAGCGGSNNGTGCGTCGCGAGGCACGA (SEQ ID NO: 444) |
| P83 | nsa284R | GATGATCACCAGGTCGAGSNNCAGGTGCGTCGCGAGGCA (SEQ ID NO: 445) |
| L84 | nsa285R | CATGATGATCACCAGGTCSNNCGGCAGGTGCGTCGCGAG (SEQ ID NO: 446) |
| D85 | nsa286R | CAGCATGATGATCACCAGSNNGAGCGGCAGGTGCGTCGC (SEQ ID NO: 447) |
| L86 | nsa287R | GCCCAGCATGATGATCACSNNGTCGAGCGGCAGGTGCGT (SEQ ID NO: 448) |

TABLE 8-2-continued

| Site-Saturation Reverse Primer Sequences | | |
|---|---|---|
| Residue | Primer | Primer Sequence |
| V87 | nsa288R | GGTGCCCAGCATGATGATSNNCAGGTCGAGCGGCAGGTG (SEQ ID NO: 449) |
| I88 | nsa289R | GTTGGTGCCCAGCATGATSNNCACCAGGTCGAGCGGCAG (SEQ ID NO: 450) |
| I89 | nsa290R | GTCGTTGGTGCCCAGCATSNNGATCACCAGGTCGAGCGG (SEQ ID NO: 451) |
| M90 | nsa291R | GGTGTCGTTGGTGCCCAGSNNGATGATCACCAGGTCGAG (SEQ ID NO: 452) |
| L91 | nsa292R | CTTGGTGTCGTTGGTGCCSNNCATGATGATCACCAGGTC (SEQ ID NO: 453) |
| G92 | nsa293R | GGCCTTGGTGTCGTTGGTSNNCAGCATGATGATCACCAG (SEQ ID NO: 454) |
| T93 | nsa294R | GTAGGCCTTGGTGTCGTTSNNGCCCAGCATGATGATCAC (SEQ ID NO: 455) |
| N94 | nsa175R | GAAGTAGGCCTTGGTGTCSNNGGTGCCCAGCATGATGAT (SEQ ID NO: 456) |
| D95 | nsa197R | CCGGAAGTAGGCCTTGGTSNNGTTGGTGCCCAGCATGAT (SEQ ID NO: 457) |
| T96 | nsa297R | GCGCCGGAAGTAGGCCTTSNNGTCGTTGGTGCCCAGCAT (SEQ ID NO: 458) |
| K97 | nsa176R | GGTGCGCCGGAAGTAGGCSNNGGTGTCGTTGGTGCCCAG (SEQ ID NO: 459) |
| A98 | nsa299R | CGGGGTGCGCCGGAAGTASNNCTTGGTGTCGTTGGTGCC (SEQ ID NO: 460) |
| Y99 | nsa177R | GAGCGGGGTGCGCCGGAASNNGGCCTTGGTGTCGTTGGT (SEQ ID NO: 461) |
| F100 | nsa301R | GTCGAGCGGGGTGCGCCGSNNGTAGGCCTTGGTGTCGTT (SEQ ID NO: 462) |
| R101 | nsa302R | GATGTCGAGCGGGGTGCGSNNGAAGTAGGCCTTGGTGTC (SEQ ID NO: 463) |
| R102 | nsa303R | CGCGATGTCGAGCGGGGTSNNCCGGAAGTAGGCCTTGGT (SEQ ID NO: 464) |
| T103 | nsa304R | CAGCGCGATGTCGAGCGGSNNGCGCCGGAAGTAGGCCTT (SEQ ID NO: 465) |
| P104 | nsa305R | GCCCAGCGCGATGTCGAGSNNGGTGCGCCGGAAGTAGGC (SEQ ID NO: 466) |
| L105 | nsa306R | CATGCCCAGCGCGATGTCSNNCGGGGTGCGCCGGAAGTA (SEQ ID NO: 467) |
| D106 | nsa307R | CGACATGCCCAGCGCGATSNNGAGCGGGGTGCGCCGGAA (SEQ ID NO: 468) |
| I107 | nsa308R | CACCGACATGCCCAGCGCSNNGTCGAGCGGGGTGCGCCG (SEQ ID NO: 469) |
| A108 | nsa309R | GAGCACCGACATGCCCAGSNNGATGTCGAGCGGGGTGCG (SEQ ID NO: 470) |
| L109 | nsa310R | GACGAGCACCGACATGCCSNNCGCGATGTCGAGCGGGGT (SEQ ID NO: 471) |
| G110 | nsa311R | CGTGACGAGCACCGACATSNNCAGCGCGATGTCGAGCGG (SEQ ID NO: 472) |
| M111 | nsa312R | CTGCGTGACGAGCACCGASNNGCCCAGCGCGATGTCGAG (SEQ ID NO: 473) |

TABLE 8-2-continued

| Site-Saturation Reverse Primer Sequences | | |
|---|---|---|
| Residue | Primer | Primer Sequence |
| S112 | nsa313R | CACCTGCGTGACGAGCACSNNCATGCCCAGCGCGATGTC (SEQ ID NO: 474) |
| V113 | nsa314R | GAGCACCTGCGTGACGAGSNNCGACATGCCCAGCGCGAT (SEQ ID NO: 475) |
| L114 | nsa315R | GGTGAGCACCTGCGTGACSNNCACCGACATGCCCAGCGC (SEQ ID NO: 476) |
| V115 | nsa316R | GCTGGTGAGCACCTGCGTSNNGAGCACCGACATGCCCAG (SEQ ID NO: 477) |
| T116 | nsa317R | CGCGCTGGTGAGCACCTGSNNGACGAGCACCGACATGCC (SEQ ID NO: 478) |
| Q117 | nsa318R | GCCCGCGCTGGTGAGCACSNNCGTGACGAGCACCGACAT (SEQ ID NO: 479) |
| V118 | nsa319R | GCCGCCCGCGCTGGTGAGSNNCTGCGTGACGAGCACCGA (SEQ ID NO: 480) |
| L119 | nsa320R | GACGCCGCCCGCGCTGGTSNNCACCTGCGTGACGAGCAC (SEQ ID NO: 481) |
| T120 | nsa321R | GCCGACGCCGCCCGCGCTSNNGAGCACCTGCGTGACGAG (SEQ ID NO: 482) |
| S121 | nsa322R | GGTGCCGACGCCGCCCGCSNNGGTGAGCACCTGCGTGAC (SEQ ID NO: 483) |
| A122 | nsa323R | CGTGGTGCCGACGCCGCCSNNGCTGGTGAGCACCTGCGT (SEQ ID NO: 484) |
| G123 | nsa324R | GTACGTGGTGCCGACGCCSNNCGCGCTGGTGAGCACCTG (SEQ ID NO: 485) |
| G124 | nsa325R | CGGGTACGTGGTGCCGACSNNGCCCGCGCTGGTGAGCAC (SEQ ID NO: 486) |
| V125 | nsa198R | TGCCGGGTACGTGGTGCCSNNGCCGCCCGCGCTGGTGAG (SEQ ID NO: 487) |
| G126 | nsa327R | GGGTGCCGGGTACGTGGTSNNGACGCCGCCCGCGCTGGT (SEQ ID NO: 488) |
| T127 | nsa328R | CTTGGGTGCCGGGTACGTSNNGCCGACGCCGCCCGCGCT (SEQ ID NO: 489) |
| T128 | nsa329R | CACCTTGGGTGCCGGGTASNNGGTGCCGACGCCGCCCGC (SEQ ID NO: 490) |
| Y129 | nsa330R | CAGCACCTTGGGTGCCGGSNNCGTGGTGCCGACGCCGCC (SEQ ID NO: 491) |
| P130 | nsa331R | CACCAGCACCTTGGGTGCSNNGTACGTGGTGCCGACGCC (SEQ ID NO: 492) |
| A131 | nsa332R | GACCACCAGCACCTTGGGSNNCGGGTACGTGGTGCCGAC (SEQ ID NO: 493) |
| P132 | nsa333R | CGAGACCACCAGCACCTTSNNTGCCGGGTACGTGGTGCC (SEQ ID NO: 494) |
| K133 | nsa334R | CGGCGAGACCACCAGCACSNNGGGTGCCGGGTACGTGGT (SEQ ID NO: 495) |
| V134 | nsa335R | TGGCGGCGAGACCACCAGSNNCTTGGGTGCCGGGTACGT (SEQ ID NO: 496) |
| L135 | nsa336R | CGGTGGCGGCGAGACCACSNNCACCTTGGGTGCCGGGTA (SEQ ID NO: 497) |
| V136 | nsa337R | CAGCGGTGGCGGCGAGACSNNCAGCACCTTGGGTGCCGG (SEQ ID NO: 498) |

TABLE 8-2-continued

Site-Saturation Reverse Primer Sequences

| Residue | Primer | Primer Sequence |
|---|---|---|
| V137 | nsa338R | CGCCAGCGGTGGCGGCGASNNCACCAGCACCTTGGGTGC (SEQ ID NO: 499) |
| S138 | nsa339R | GGGCGCCAGCGGTGGCGGSNNGACCACCAGCACCTTGGG (SEQ ID NO: 500) |
| P139 | nsa340R | CATGGGCGCCAGCGGTGGSNNCGAGACCACCAGCACCTT (SEQ ID NO: 501) |
| P140 | nsa341R | CGGCATGGGCGCCAGCGGSNNCGGCGAGACCACCAGCAC (SEQ ID NO: 502) |
| P141 | nsa342R | GTGCGGCATGGGCGCCAGSNNTGGCGGCGAGACCACCAG (SEQ ID NO: 503) |
| L142 | nsa343R | GGGGTGCGGCATGGGCGCSNNCGGTGGCGGCGAGACCAC (SEQ ID NO: 504) |
| A143 | nsa344R | CCAGGGGTGCGGCATGGGSNNCAGCGGTGGCGGCGAGAC (SEQ ID NO: 505) |
| P144 | nsa345R | GAACCAGGGGTGCGGCATSNNCGCCAGCGGTGGCGGCGA (SEQ ID NO: 506) |
| M145 | nsa346R | CTGGAACCAGGGGTGCGGSNNGGGCGCCAGCGGTGGCGG (SEQ ID NO: 507) |
| P146 | nsa178R | CAACTGGAACCAGGGGTGSNNCATGGGCGCCAGCGGTGG (SEQ ID NO: 508) |
| H147 | nsa348R | GATCAACTGGAACCAGGGSNNCGGCATGGGCGCCAGCGG (SEQ ID NO: 509) |
| P148 | nsa199R | GAAGATCAACTGGAACCASNNGTGCGGCATGGGCGCCAG (SEQ ID NO: 510) |
| W149 | nsa179R | CTCGAAGATCAACTGGAASNNGGGGTGCGGCATGGGCGC (SEQ ID NO: 511) |
| F150 | nsa180R | GCCCTCGAAGATCAACTGSNNCCAGGGGTGCGGCATGGG (SEQ ID NO: 512) |
| Q151 | nsa352R | GCCGCCCTCGAAGATCAASNNGAACCAGGGGTGCGGCAT (SEQ ID NO: 513) |
| L152 | nsa353R | CTCGCCGCCCTCGAAGATSNNCTGGAACCAGGGGTGCGG (SEQ ID NO: 514) |
| I153 | nsa200R | CTGCTCGCCGCCCTCGAASNNCAACTGGAACCAGGGGTG (SEQ ID NO: 515) |
| F154 | nsa201R | CTTCTGCTCGCCGCCCTCSNNGATCAACTGGAACCAGGG (SEQ ID NO: 516) |
| E155 | nsa356R | GGTCTTCTGCTCGCCGCCSNNGAAGATCAACTGGAACCA (SEQ ID NO: 517) |
| G156 | nsa357R | AGTGGTCTTCTGCTCGCCSNNCTCGAAGATCAACTGGAA (SEQ ID NO: 518) |
| G157 | nsa358R | CTCAGTGGTCTTCTGCTCSNNGCCCTCGAAGATCAACTG (SEQ ID NO: 519) |
| E158 | nsa359R | GAGCTCAGTGGTCTTCTGSNNGCCGCCCTCGAAGATCAA (SEQ ID NO: 520) |
| Q159 | nsa360R | GGCGAGCTCAGTGGTCTTSNNCTCGCCGCCCTCGAAGAT (SEQ ID NO: 521) |
| K160 | nsa361R | GCGGGCGAGCTCAGTGGTSNNCTGCTCGCCGCCCTCGAA (SEQ ID NO: 522) |
| T161 | nsa362R | CACGCGGGCGAGCTCAGTSNNCTTCTGCTCGCCGCCCTC (SEQ ID NO: 523) |

TABLE 8-2-continued

| Site-Saturation Reverse Primer Sequences | | |
|---|---|---|
| Residue | Primer | Primer Sequence |
| T162 | nsa363R | GTACACGCGGGCGAGCTCSNNGGTCTTCTGCTCGCCGCC (SEQ ID NO: 524) |
| E163 | nsa364R | GCTGTACACGCGGGCGAGSNNAGTGGTCTTCTGCTCGCC (SEQ ID NO: 525) |
| L164 | nsa365R | CGCGCTGTACACGCGGGCSNNCTCAGTGGTCTTCTGCTC (SEQ ID NO: 526) |
| A165 | nsa366R | GAGCGCGCTGTACACGCGSNNGAGCTCAGTGGTCTTCTG (SEQ ID NO: 527) |
| R166 | nsa367R | CGCGAGCGCGCTGTACACSNNGGCGAGCTCAGTGGTCTT (SEQ ID NO: 528) |
| V167 | nsa368R | CGACGCGAGCGCGCTGTASNNGCGGGCGAGCTCAGTGGT (SEQ ID NO: 529) |
| Y168 | nsa369R | GAACGACGCGAGCGCGCTSNNCACGCGGGCGAGCTCAGT (SEQ ID NO: 530) |
| S169 | nsa370R | CATGAACGACGCGAGCGCSNNGTACACGCGGGCGAGCTC (SEQ ID NO: 531) |
| A170 | nsa371R | CTTCATGAACGACGCGAGSNNGCTGTACACGCGGGCGAG (SEQ ID NO: 532) |
| L171 | nsa372R | CACCTTCATGAACGACGCSNNCGCGCTGTACACGCGGGC (SEQ ID NO: 533) |
| A172 | nsa373R | CGGCACCTTCATGAACGASNNGAGCGCGCTGTACACGCG (SEQ ID NO: 534) |
| S173 | nsa374R | GAACGGCACCTTCATGAASNNCGCGAGCGCGCTGTACAC (SEQ ID NO: 535) |
| F174 | nsa375R | GAAGAACGGCACCTTCATSNNCGACGCGAGCGCGCTGTA (SEQ ID NO: 536) |
| M175 | nsa376R | GTCGAAGAACGGCACCTTSNNGAACGACGCGAGCGCGCT (SEQ ID NO: 537) |
| K176 | nsa377R | CGCGTCGAAGAACGGCACSNNCATGAACGACGCGAGCGC (SEQ ID NO: 538) |
| V177 | nsa378R | ACCCGCGTCGAAGAACGGSNNCTTCATGAACGACGCGAG (SEQ ID NO: 539) |
| P178 | nsa379R | CGAACCCGCGTCGAAGAASNNCACCTTCATGAACGACGC (SEQ ID NO: 540) |
| F179 | nsa380R | CACCGAACCCGCGTCGAASNNCGGCACCTTCATGAACGA (SEQ ID NO: 541) |
| F180 | nsa381R | GATCACCGAACCCGCGTCSNNGAACGGCACCTTCATGAA (SEQ ID NO: 542) |
| D181 | nsa382R | GCTGATCACCGAACCCGCSNNGAAGAACGGCACCTTCAT (SEQ ID NO: 543) |
| A182 | nsa383R | GGTGCTGATCACCGAACCSNNGTCGAAGAACGGCACCTT (SEQ ID NO: 544) |
| G183 | nsa384R | GTCGGTGCTGATCACCGASNNCGCGTCGAAGAACGGCAC (SEQ ID NO: 545) |
| S184 | nsa385R | GCCGTCGGTGCTGATCACSNNACCCGCGTCGAAGAACGG (SEQ ID NO: 546) |
| V185 | nsa386R | GACGCCGTCGGTGCTGATSNNCGAACCCGCGTCGAAGAA (SEQ ID NO: 547) |
| I186 | nsa387R | GTCGACGCCGTCGGTGCTSNNCACCGAACCCGCGTCGAA (SEQ ID NO: 548) |

TABLE 8-2-continued

Site-Saturation Reverse Primer Sequences

| Residue | Primer | Primer Sequence |
|---|---|---|
| S187 | nsa388R | TCCGTCGACGCCGTCGGTSNNGATCACCGAACCCGCGTC (SEQ ID NO: 549) |
| T188 | nsa389R | GATTCCGTCGACGCCGTCSNNGCTGATCACCGAACCCGC (SEQ ID NO: 550) |
| D189 | nsa390R | GTGGATTCCGTCGACGCCSNNGGTGCTGATCACCGAACC (SEQ ID NO: 551) |
| G190 | nsa391R | GAAGTGGATTCCGTCGACSNNGTCGGTGCTGATCACCGA (SEQ ID NO: 552) |
| V191 | nsa392R | GGTGAAGTGGATTCCGTCSNNGCCGTCGGTGCTGATCAC (SEQ ID NO: 553) |
| D192 | nsa393R | CTCGGTGAAGTGGATTCCSNNGACGCCGTCGGTGCTGAT (SEQ ID NO: 554) |
| G193 | nsa394R | GGCCTCGGTGAAGTGGATSNNGTCGACGCCGTCGGTGCT (SEQ ID NO: 555) |
| I194 | nsa181R | GTTGGCCTCGGTGAAGTGSNNTCCGTCGACGCCGTCGGT (SEQ ID NO: 556) |
| H195 | nsa396R | ATTGTTGGCCTCGGTGAASNNGATTCCGTCGACGCCGTC (SEQ ID NO: 557) |
| F196 | nsa182R | GCGATTGTTGGCCTCGGTSNNGTGGATTCCGTCGACGCC (SEQ ID NO: 558) |
| T197 | nsa398R | ATCGCGATTGTTGGCCTCSNNGAAGTGGATTCCGTCGAC (SEQ ID NO: 559) |
| E198 | nsa399R | GAGATCGCGATTGTTGGCSNNGGTGAAGTGGATTCCGTC (SEQ ID NO: 560) |
| A199 | nsa400R | CCCGAGATCGCGATTGTTSNNCTCGGTGAAGTGGATTCC (SEQ ID NO: 561) |
| N200 | nsa401R | CACCCCGAGATCGCGATTSNNGGCCTCGGTGAAGTGGAT (SEQ ID NO: 562) |
| N201 | nsa402R | GGCCACCCCGAGATCGCGSNNGTTGGCCTCGGTGAAGTG (SEQ ID NO: 563) |
| R202 | nsa403R | GAGGGCCACCCCGAGATCSNNATTGTTGGCCTCGGTGAA (SEQ ID NO: 564) |
| D203 | nsa404R | CGCGAGGGCCACCCCGAGSNNGCGATTGTTGGCCTCGGT (SEQ ID NO: 565) |
| L204 | nsa405R | TTCCGCGAGGGCCACCCCSNNATCGCGATTGTTGGCCTC (SEQ ID NO: 566) |
| G205 | nsa406R | CTGTTCCGCGAGGGCCACSNNGAGATCGCGATTGTTGGC (SEQ ID NO: 567) |
| V206 | nsa407R | CACCTGTTCCGCGAGGGCSNNCCCGAGATCGCGATTGTT (SEQ ID NO: 568) |
| A207 | nsa408R | CTGCACCTGTTCCGCGAGSNNCACCCCGAGATCGCGATT (SEQ ID NO: 569) |
| L208 | nsa409R | GCTCTGCACCTGTTCCGCSNNGGCCACCCCGAGATCGCG (SEQ ID NO: 570) |
| A209 | nsa410R | CAGGCTCTGCACCTGTTCSNNGAGGGCCACCCCGAGATC (SEQ ID NO: 571) |
| E210 | nsa411R | CAGCAGGCTCTGCACCTGSNNCGCGAGGGCCACCCCGAG (SEQ ID NO: 572) |
| Q211 | nsa412R | TTACAGCAGGCTCTGCACSNNTTCCGCGAGGGCCACCCC (SEQ ID NO: 573) |

TABLE 8-2-continued

| Site-Saturation Reverse Primer Sequences | | |
|---|---|---|
| Residue | Primer | Primer Sequence |
| V212 | nsa413R | CTTTTACAGCAGGCTCTGSNNCTGTTCCGCGAGGGCCAC (SEQ ID NO: 574) |
| Q213 | nsa414R | GCCCTTTTACAGCAGGCTSNNCACCTGTTCCGCGAGGGC (SEQ ID NO: 575) |
| S214 | nsa415R | TTCGCCCTTTTACAGCAGSNNCTGCACCTGTTCCGCGAG (SEQ ID NO: 576) |
| L215 | nsa416R | GAATTCGCCCTTTTACAGSNNGCTCTGCACCTGTTCCGC (SEQ ID NO: 577) |
| L216 | nsa417R | GCAGAATTCGCCCTTTTASNNCAGGCTCTGCACCTGTTC (SEQ ID NO: 578) |

QC Method to Create Site-Saturation Libraries

The QC reaction consisted of 40.25 μL of sterile distilled $H_2O$, 5 μL of PfuTurbo 10× buffer from the kit, 1 μL dNTPs from the kit, 1.25 μL of forward primer (100 ng/μL), 1.25 μL reverse primer (100 ng/μL), 0.25 μL of pMSAT-NcoI miniprep DNA as template (~50 ng), and 1 μL of PfuTurbo from the kit, for a total of 50 μL. The cycling conditions were 95° C. for 1 min, once, followed by 19-20 cycles of 95° C. for 30 to 45 sec, 55° C. for 1 min, and 68° C. for 5 to 8 min. To analyze the reaction, 5 μL of the reaction was run on a 0.8% E-gel (Invitrogen) upon completion. Next, DpnI digestion was carried out twice sequentially, with 1 μL and 0.5 μL of enzyme at 37° C. for 2 to 8 hours. A negative control was carried out under similar conditions, but without any primers. Then, 1 μL of the DpnI-digested reaction product was transformed into 50 μL of one-shot TOP10 electrocompetent cells (Invitrogen) using a BioRad electroporator. Then, 300 μL of SOC provided with the TOP10 cells (Invitrogen) were added to the electroporated cells and incubated with shaking for 1 hour before plating on LA plates containing 10 ppm kanamycin. The plates were incubated at 37° C. overnight. After this incubation, 96 colonies from each of the libraries (i.e., each site) were inoculated in 200 μL of LB containing 10-50 ppm of kanamycin in 96-well microtiter plates. The plates were frozen at −80° C. after addition of glycerol to 20% final concentration, and they were used for high throughput sequencing at Genaissance with the M13F and M13R primers.

QCMS Method to Create Site-Saturation Libraries

The QCMS reaction consisted of 19.25 μL of sterile distilled $H_2O$, 2.5 μL of 10× buffer from the kit, 1 μL dNTPs from the kit, 1 μL of 5' phosphorylated forward primer (100 ng/μL), 0.25 μL of pMSAT-NcoI miniprep DNA as template (~50 ng), and 1 μL of the enzyme blend from the kit for a total of 25 μL. The cycling conditions were 95° C. for 1 min once, followed by 30 cycles of 95° C. for 1 min, 55° C. for 1 min, and 68° C. for 8 min. To analyze the reaction product, 5 μL of the reaction were run on a 0.8% E-gel (Invitrogen) upon completion. Next, DpnI digestion was carried out twice sequentially, with 0.5 μL of enzyme at 37° C. for 2 to 8 hours. The controls, transformation, and sequencing was performed as for the QC method described above.

Details of Screening Plate Preparation

Using a sterilized stamping tool with 96 pins, the frozen clones from each sequenced library plate were stamped on to a large LA plate containing 10 ppm kanamycin. The plate was then incubated overnight at 37° C. Individual mutant clones each representing each one of the 19 substitutions (or as many that were obtained) were inoculated into a Costar 96-well plate containing 195 μL of LB made with 2 fold greater yeast extract and 10 ppm kanamycin. Each mutant clone for a given site was inoculated in quadruplicate. The plate was grown at 37° C. and 225 rpm shaking for 18 hrs in a humidified chamber. In a separate 96-well plate, 26 μL of BugBuster (Novagen) with DNase were added to each well. Next, 125 μL of the library clone cultures were added to the BugBuster-containing plate in corresponding wells and the plate was frozen at 80° C. The plate was thawed, frozen and thawed again before use of the lysates in the peracid formation and peracid hydrolysis assays described herein.

Combinatorial Libraries and Mutants

From the screening of the single site-saturation libraries, the important sites and substitutions were identified and combined in different combinatorial libraries. For example, libraries described in Table 8-3 were created using the following sites and substitutions:

L12C, Q, G
T25S, G, P
L53H, Q, G, S
S54V, L, A, P, T, R
A55G, T
R67T, Q, N, G, E, L, F
K97R
V125S, G, R, A, P
F154Y
F196G

TABLE 8-3

| Libraries | | | |
|---|---|---|---|
| Library | Description | Parent Template | Method |
| NSAA1 | L12G S54(NNS) | L12G | QC |
| NSAA2 | S54V L12(NNS) | S54V | QC |
| NSAA3 | L12(NNS) S54(NNS) | WT | QCMS |
| NSAB1 | S54V T25(NNS) | S54V | QC |
| NSAB2 | S54V R67(NNS) | S54V | QC |
| NSAB3 | S54V V125(NNS) | S54V | QC |
| NSAB4 | L12I S54V T25(NNS) | L12I S54V | QC |
| NSAB5 | L12I S54V R67(NNS) | L12I S54V | QC |
| NSAB6 | L12I S54V V125(NNS) | L12I S54V | QC |
| NSAC1 | S54(NNS) R67(NNS) V125(NNS) | WT | QCMS |
| NSAC2 | 43 primer library; 10 sites (100 ng total primers) | S54V | QCMS |

TABLE 8-3-continued

| Libraries | | | |
|---|---|---|---|
| Library | Description | Parent Template | Method |
| NSAC3 | same as nsaC2 but 300 ng total primers | S54V | QCMS |
| NSAC4 | 32 primer library, 8 sites (100 ng total primers) | S54V | QCMS |
| NSAC5 | same as nsaC4 but 300 ng total primers | S54V | QCMS |
| NSAC6 | 8 primers, 7 substitutions, 5 sites (100 ng total primers) | S54V | QCMS |
| NSAC7 | same as nsaC6 but 300 ng total primers | S54V | QCMS |

*NNS indicates site-saturation library

**All parent templates were derived from the pMSAT-NcoI plasmid and contained mutations at the indicated codons with in the *M. smegmatis* perhydrolase gene The QC or QCMS methods were used to create the combinations. The QC reaction was carried out as described above, with the exception being the template plasmid, which consisted of 0.25 μL of miniprep DNA of the L12G mutant, S54V mutant, or the L12I S54V double mutant plasmid derived from pMSAT-NcoI. The QCMS reaction was also carried out as described above, with the exception of template and primers. In this case, 0.25 μL of the pMSAT-NcoI template were used for NSAC1 and NSAA3 or S54V template for NSAC2-C7 libraries. The NSAA3 and the NSAC1 libraries were made using 100 ng of each of the primers shown in the Table 8-4. The NSAC2, NSAC4, and NSAC6 libraries were made with a total of 100 ng of all primers (all primers being equimolar), and NSAC3, NSAC5, NSAC7 libraries were made with a total of 300 ng of all primers (all primers being approximately equimolar)

TABLE 8-4

| Libraries | | |
|---|---|---|
| Libraries | Primer Name | Primer Sequence |
| NSAC1 | S54NNS-FP | gtgatcgaggagggactgnnsgcgcgcaccaccaacatc (SEQ ID NO: 579) |
| NSAC1 | R67NNS-FP | acgaccccaccgatccgnnsctcaacggcgcgagctac (SEQ ID NO: 580) |
| NSAC1 | V125NNS-FP | ctcaccagcgcgggcggcnnsggcaccacgtacccggca (SEQ ID NO: 581) |
| NSAC2-C5 | L12C | ctgtgtttcggtgattccTGCacctggggctgggtcccc (SEQ ID NO: 582) |
| NSAC2-C7 | L12Q | ctgtgtttcggtgattccCAGacctggggctgggtcccc (SEQ ID NO: 583) |
| NSAC2-C5 | L12I | ctgtgtttcggtgattccATCacctggggctgggtcccc (SEQ ID NO: 584) |
| NSAC2-C3 | L12M | ctgtgtttcggtgattccATGacctggggctgggtcccc (SEQ ID NO: 585) |
| NSAC2-C3 | L12T | ctgtgtttcggtgattccACGacctggggctgggtcccc (SEQ ID NO: 586) |
| NSA2-C5 | T25S | gtcgaagacggggcacccAGCgagcggttcgcccccgac (SEQ ID NO: 587) |
| NSAC2-C5 | T25G | gtcgaagacggggcacccGGCgagcggttcgcccccgac (SEQ ID NO: 588) |
| NSAC2-C3 | T25P | gtcgaagacggggcacccCCGgagcggttcgcccccgac (SEQ ID NO: 589) |
| NSAC2-C7 | L53H | gaggtgatcgaggagggaCACagcgcgcgcaccaccaac (SEQ ID NO: 590) |
| NSAC2-C3 | L53Q | gaggtgatcgaggagggaCAGagcgcgcgcaccaccaac (SEQ ID NO: 591) |
| NSAC2-C3 | L53G | gaggtgatcgaggagggaGGCagcgcgcgcaccaccaac (SEQ ID NO: 592) |
| NSAC2-C3 | L53S | gaggtgatcgaggagggaAGCagcgcgcgcaccaccaac (SEQ ID NO: 593) |
| NSAC2-C7 | L53HS54V | gaggtgatcgaggagggaCACGTGgcgcgcaccaccaac (SEQ ID NO: 594) |
| NSAC2-C3 | L53QS54V | gaggtgatcgaggagggaCAGGTGgcgcgcaccaccaac (SEQ ID NO: 595) |
| NSAC2-C3 | L53GS54V | gaggtgatcgaggagggaGGCGTGgcgcgcaccaccaac (SEQ ID NO: 596) |

TABLE 8-4-continued

| Libraries | | |
|---|---|---|
| Libraries | Primer Name | Primer Sequence |
| NSAC2-C3 | L53SS54V | gaggtgatcgaggagggaAGCGTGgcgcgcaccaccaac (SEQ ID NO: 597) |
| NSAC2-C7 | S54V | gtgatcgaggagggactgGTGgcgcgcaccaccaacatc (SEQ ID NO: 598) |
| NSAC2-C5 | S54L | gtgatcgaggagggactgCTGgcgcgcaccaccaacatc (SEQ ID NO: 599) |
| NSAC2-C5 | A55G | atcgaggagggactgagcGGCcgcaccaccaacatcgac (SEQ ID NO: 600) |
| NSAC2-C5 | A55T | atcgaggagggactgagcACGcgcaccaccaacatcgac (SEQ ID NO: 601) |
| NSAC2-C5 | A55GS54V | atcgaggagggactgGTGGGCcgcaccaccaacatcgac (SEQ ID NO: 602) |
| NSAC2-C5 | A55TS54V | atcgaggagggactgGTGACGcgcaccaccaacatcgac (SEQ ID NO: 603) |
| NSAC2-C5 | R67T | gacgaccccaccgatccgACGctcaacggcgcgagctac (SEQ ID NO: 604) |
| NSAC2-C5 | R67Q | gacgaccccaccgatccgCAGctcaacggcgcgagctac (SEQ ID NO: 605) |
| NSAC2-C7 | R67N | gacgaccccaccgatccgAACctcaacggcgcgagctac (SEQ ID NO: 606) |
| NSAC2-C5 | K97R | ctgggcaccaacgacaccCGCgcctacttccggcgcacc (SEQ ID NO: 607) |
| NSAC2-C5 | V125S | ctcaccagcgcgggcggcAGCggcaccacgtacccggca (SEQ ID NO: 608) |
| NSAC2-C7 | V125G | ctcaccagcgcgggcggcGGCggcaccacgtacccggca (SEQ ID NO: 609) |
| NSAC2-C5 | V125R | ctcaccagcgcgggcggcCGCggcaccacgtacccggca (SEQ ID NO: 610) |
| NSAC2-C5 | V125A | ctcaccagcgcgggcggcGCGggcaccacgtacccggca (SEQ ID NO: 611) |
| NSAC2-C5 | V125P | ctcaccagcgcgggcggcCCGggcaccacgtacccggca (SEQ ID NO: 612) |
| NSAC2-C3 | F154Y | ccctggttccagttgatcTACgagggcggcgagcagaag (SEQ ID NO: 613) |
| NSAC2-C3 | F196G | ggcgtcgacggaatccacGGCaccgaggccaacaatcgc (SEQ ID NO: 614) |
| NSAC2-C7 | R67G-re | gacgaccccaccgatccgGGCctcaacggcgcgagctac (SEQ ID NO: 615) |
| NSAC2-C5 | R67E-re | gacgaccccaccgatccgGAGctcaacggcgcgagctac (SEQ ID NO: 616) |
| NSAC2-C5 | R67F-re | gacgaccccaccgatccgTTCctcaacggcgcgagctac (SEQ ID NO: 617) |
| NSAC2-C5 | R67L-re | gacgaccccaccgatccgCTGctcaacggcgcgagctac (SEQ ID NO: 618) |
| NSAC2-C5 | S54P | gtgatcgaggagggactgCCGgcgcgcaccaccaacatc (SEQ ID NO: 619) |
| NSAC2-C5 | S54R | gtgatcgaggagggactgCGCgcgcgcaccaccaacatc (SEQ ID NO: 620) |
| NSAC2-C5 | S54G | gtgatcgaggagggactgGGCgcgcgcaccaccaacatc (SEQ ID NO: 621) |

TABLE 8-4-continued

| Libraries | | |
|---|---|---|
| Libraries | Primer Name | Primer Sequence |
| NSAC2-C5 | S54T | gtgatcgaggagggactgACGgcgcgcaccaccaacatc (SEQ ID NO: 622) |
| NSAC2-C7 | S54I | gtgatcgaggagggactgATCgcgcgcaccaccaacatc (SEQ ID NO: 623) |
| NSAC2-C5 | S54K | gtgatcgaggagggactgAAGgcgcgcaccaccaacatc (SEQ ID NO: 624) |

Screening of Combinatorial Libraries and Mutants

For each of the NSAB1-B6 libraries, a 96-well plate full of clones was first sequenced. Once the sequencing results were analyzed, the mutants obtained for each library were inoculated in quadruplicate, similar to the site-saturation libraries described above. For the NSAC1-C7 libraries, 96 colonies per/plate/library were initially inoculated, and each plate was screened without sequencing. Upon screening, some libraries looked better than others. Several plates for each of the NSAC1, C2, C4, C6 libraries were screened. The "winners" from these single isolate screening plates were then streaked out for singles or directly screened in quadruplicate just like the site-saturation libraries (i.e., as described above). Only the "winners" identified were sequenced.

Example 9

Improved Properties of Multiply Mutated Perhydrolase Variants

In this Example, experiments conducted to assess the properties of multiply-mutated perhydrolase variants are described. In these experiments, combinatorial mutants obtained from combinatorial libraries were tested in their performance in perhydrolysis, peracid hydrolysis and perhydrolysis to hydrolysis ratio. These parameters were measured in the HPLC or ABTS assays described in Example 2, above. Combinatorial variants tested were:

L12I S54V,
L12M S54T,
L12T S54V,
L12Q T25S S54V,
L53H S54V,
S54P V125R,
S54V V125G,
S54V F196G,
S54V K97R V125G, and
A55G R67T K97R V125G, As is indicated in Table 9-1 below, all of these variants were better than wild type enzyme in at least one of the properties of interest.

TABLE 9-1

| Results for Multiple Variants | | | |
|---|---|---|---|
| | Fold-Improvement in Property | | |
| Multiple Variant | Perhydrolysis | Peracid Hydrolysis | Ratio |
| L12I S54V | 2 | 2.5 | |
| L12M S54T | 1.6 | 3 | |
| L12T S54V | 1.5 | 2.5 | |
| L12Q T25S S54V | | 4 to 5 | |
| L53H S54V | 2 | | 4 to 5 |
| S54P V125R | | | 4 |
| S54V V125G | 2 | | 4 |
| S54V F196G | | | 2 |
| S54V K97R V125G | 2 | | |
| A55G R67T K97R V125G | 1.6 | | 4 to 5 |

Example 10

PAF and PAD Assays of Perhydrolase Variants

In this Example, assay results for PAF and PAD testing of perhydrolase variants are provided. The tests were conducted as described in Example 1, above. In addition, Tables are provided in which the protein expression of the variant was greater than wild-type under the same culture conditions (described herein). These results are indicated as the "protein performance index." Thus, a number greater than "1" in the protein performance index indicates that more protein was made for the particular variant than the wild-type. In the following Tables, "WT" indicates the wild-type amino acid residue; "Pos" indicates the position in the amino acid sequence; "Mut." and "Var" indicate the amino acid residue substituted at that particular position; "prot." indicates "protein; and "Perf. Ind" indicates the performance index.

TABLE 10-1

| PAF Assay Results | | | |
|---|---|---|---|
| Position | WT/Pos/Mutation | Variant | PAF Perf. Ind. |
| 3 | K003Y | Y | 1.058244 |
| 3 | K003I | I | 1.053242 |
| 3 | K003L | L | 1.038686 |
| 3 | K003T | T | 1.009071 |
| 3 | K003H | H | 1.00528 |
| 4 | R004Q | Q | 1.025332 |
| 5 | I005T | T | 1.12089 |
| 5 | I005S | S | 1.023576 |
| 6 | L006V | V | 1.072388 |
| 6 | L006I | I | 1.066182 |
| 6 | L006T | T | 1.062078 |

TABLE 10-1-continued

PAF Assay Results

| Position | WT/Pos/ Mutation | Variant | PAF Perf. Ind. |
|---|---|---|---|
| 7 | C007K | K | 2.687956 |
| 7 | C007Y | Y | 2.08507 |
| 7 | C007I | I | 1.758096 |
| 7 | C007H | H | 1.731475 |
| 7 | C007A | A | 1.423943 |
| 7 | C007G | G | 1.393781 |
| 7 | C007M | M | 1.126028 |
| 10 | D010L | L | 3.97014 |
| 10 | D010W | W | 3.179778 |
| 10 | D010K | K | 2.133852 |
| 10 | D010Y | Y | 1.508981 |
| 10 | D010T | T | 1.473387 |
| 10 | D010I | I | 1.281927 |
| 12 | L012Q | Q | 2.651732 |
| 12 | L012C | C | 2.289224 |
| 12 | L012A | A | 1.100171 |
| 15 | G015A | A | 1.543799 |
| 15 | G015S | S | 1.05273 |
| 17 | V017G | G | 1.173641 |
| 17 | V017R | R | 1.09735 |
| 17 | V017A | A | 1.012116 |
| 18 | P018Y | Y | 1.332844 |
| 18 | P018N | N | 1.331062 |
| 18 | P018C | C | 1.261104 |
| 18 | P018E | E | 1.217708 |
| 18 | P018V | V | 1.185736 |
| 18 | P018R | R | 1.16328 |
| 18 | P018Q | Q | 1.124133 |
| 18 | P018H | H | 1.120443 |
| 18 | P018G | G | 1.068272 |
| 19 | V019G | G | 1.317001 |
| 19 | V019S | S | 1.235759 |
| 19 | V019R | R | 1.025471 |
| 19 | V019L | L | 1.002833 |
| 21 | D021K | K | 1.062138 |
| 21 | D021W | W | 1.040173 |
| 22 | G022A | A | 1.554264 |
| 22 | G022T | T | 1.032118 |
| 22 | G022S | S | 1.022133 |
| 25 | T025G | G | 1.857878 |
| 25 | T025S | S | 1.59954 |
| 25 | T025A | A | 1.327579 |
| 25 | T025I | I | 1.019417 |
| 26 | E026M | M | 2.002044 |
| 26 | E026A | A | 1.927099 |
| 26 | E026R | R | 1.484814 |
| 26 | E026K | K | 1.464368 |
| 26 | E026T | T | 1.441939 |
| 26 | E026C | C | 1.403045 |
| 26 | E026V | V | 1.392881 |
| 26 | E026N | N | 1.366419 |
| 26 | E026H | H | 1.329562 |
| 26 | E026L | L | 1.295378 |
| 26 | E026G | G | 1.283477 |
| 26 | E026S | S | 1.271403 |
| 26 | E026W | W | 1.251752 |
| 27 | R027K | K | 1.215697 |
| 28 | F028M | M | 1.331874 |
| 28 | F028A | A | 1.269493 |
| 28 | F028W | W | 1.156698 |
| 28 | F028L | L | 1.08849 |
| 28 | F028S | S | 1.046063 |
| 29 | A029W | W | 1.912244 |
| 29 | A029V | V | 1.799733 |
| 29 | A029R | R | 1.757225 |
| 29 | A029Y | Y | 1.697554 |
| 29 | A029G | G | 1.595061 |
| 29 | A029S | S | 1.486877 |
| 29 | A029T | T | 1.424584 |
| 29 | A029E | E | 1.115768 |
| 29 | A029C | C | 1.07522 |
| 30 | P030K | K | 1.207673 |
| 30 | P030R | R | 1.164892 |
| 30 | P030V | V | 1.063047 |
| 30 | P030T | T | 1.05383 |
| 30 | P030A | A | 1.045476 |
| 30 | P030S | S | 1.031747 |
| 30 | P030Q | Q | 1.013468 |
| 30 | P030H | H | 1.012332 |
| 30 | P030E | E | 1.006761 |
| 31 | D031W | W | 1.834044 |
| 31 | D031L | L | 1.810564 |
| 31 | D031T | T | 1.450556 |
| 31 | D031G | G | 1.441703 |
| 31 | D031F | F | 1.438268 |
| 31 | D031N | N | 1.339422 |
| 31 | D031V | V | 1.280091 |
| 31 | D031A | A | 1.240923 |
| 31 | D031R | R | 1.222181 |
| 31 | D031S | S | 1.152736 |
| 31 | D031E | E | 1.132795 |
| 31 | D031Q | Q | 1.069797 |
| 32 | V032K | K | 1.08606 |
| 32 | V032R | R | 1.045435 |
| 33 | R033S | S | 1.000491 |
| 36 | G036I | I | 1.320156 |
| 36 | G036K | K | 1.265563 |
| 36 | G036L | L | 1.237473 |
| 38 | L038L | L | 6.528092 |
| 38 | L038V | V | 5.735873 |
| 38 | L038C | C | 4.182031 |
| 38 | L038K | K | 4.135067 |
| 38 | L038A | A | 3.844719 |
| 38 | L038S | S | 2.467764 |
| 40 | Q040K | K | 2.613726 |
| 40 | Q040I | I | 2.576806 |
| 40 | Q040W | W | 2.394926 |
| 40 | Q040L | L | 2.144687 |
| 40 | Q040T | T | 2.006487 |
| 40 | Q040R | R | 1.885154 |
| 40 | Q040Y | Y | 1.825366 |
| 40 | Q040G | G | 1.785768 |
| 40 | Q040S | S | 1.565973 |
| 40 | Q040N | N | 1.528677 |
| 40 | Q040D | D | 1.16151 |
| 40 | Q040E | E | 1.075259 |
| 41 | Q041K | K | 1.381385 |
| 41 | Q041R | R | 1.190317 |
| 41 | Q041W | W | 1.141041 |
| 41 | Q041H | H | 1.123719 |
| 41 | Q041S | S | 1.107641 |
| 41 | Q041Y | Y | 1.091652 |
| 41 | Q041V | V | 1.070265 |
| 41 | Q041A | A | 1.032945 |
| 41 | Q041L | L | 1.000416 |
| 42 | L042K | K | 2.463086 |
| 42 | L042W | W | 2.056507 |
| 42 | L042H | H | 1.917245 |
| 42 | L042R | R | 1.378137 |
| 42 | L042G | G | 1.172748 |
| 42 | L042T | T | 1.079826 |
| 42 | L042F | F | 1.072948 |
| 43 | G043A | A | 1.49082 |
| 43 | G043C | C | 1.47701 |
| 43 | G043K | K | 1.424919 |
| 43 | G043M | M | 1.371202 |
| 43 | G043Y | Y | 1.262703 |
| 43 | G043E | E | 1.250311 |
| 43 | G043L | L | 1.216516 |
| 43 | G043R | R | 1.215829 |
| 43 | G043S | S | 1.178103 |
| 43 | G043H | H | 1.169457 |
| 43 | G043P | P | 1.080176 |
| 44 | A044F | F | 2.84399 |
| 44 | A044V | V | 2.133682 |
| 44 | A044C | C | 1.796096 |
| 44 | A044L | L | 1.607918 |
| 44 | A044W | W | 1.395243 |

TABLE 10-1-continued

PAF Assay Results

| Position | WT/Pos/ Mutation | Variant | PAF Perf. Ind. |
|---|---|---|---|
| 44 | A044M | M | 1.199028 |
| 45 | D045K | K | 1.342858 |
| 45 | D045T | T | 1.268367 |
| 45 | D045R | R | 1.158768 |
| 45 | D045W | W | 1.145157 |
| 45 | D045S | S | 1.133098 |
| 45 | D045G | G | 1.12761 |
| 45 | D045H | H | 1.127539 |
| 45 | D045F | F | 1.11152 |
| 45 | D045L | L | 1.054441 |
| 45 | D045V | V | 1.050576 |
| 45 | D045Q | Q | 1.04498 |
| 45 | D045A | A | 1.037993 |
| 46 | F046E | E | 1.247552 |
| 46 | F046D | D | 1.174794 |
| 46 | F046G | G | 1.016913 |
| 46 | F046K | K | 1.003326 |
| 47 | E047R | R | 2.448525 |
| 47 | E047T | T | 1.960505 |
| 47 | E047P | P | 1.361173 |
| 47 | E047S | S | 1.278809 |
| 47 | E047H | H | 1.266229 |
| 47 | E047G | G | 1.197541 |
| 47 | E047K | K | 1.19183 |
| 47 | E047F | F | 1.092281 |
| 47 | E047I | I | 1.030029 |
| 49 | I049G | G | 1.342918 |
| 49 | I049H | H | 1.265204 |
| 49 | I049S | S | 1.238211 |
| 49 | I049K | K | 1.230871 |
| 49 | I049V | V | 1.203314 |
| 49 | I049L | L | 1.136805 |
| 49 | I049Y | Y | 1.068104 |
| 49 | I049R | R | 1.052285 |
| 49 | I049E | E | 1.015762 |
| 49 | I049M | M | 1.00526 |
| 50 | E050L | L | 1.191901 |
| 50 | E050M | M | 1.178039 |
| 50 | E050A | A | 1.124087 |
| 51 | E051V | V | 1.471315 |
| 51 | E051A | A | 1.279983 |
| 51 | E051G | G | 1.217963 |
| 51 | E051T | T | 1.182792 |
| 51 | E051L | L | 1.112889 |
| 51 | E051I | I | 1.072835 |
| 53 | L053H | H | 5.05321 |
| 53 | L053Q | Q | 1.480206 |
| 53 | L053G | G | 1.317357 |
| 53 | L053S | S | 1.161011 |
| 53 | L053T | T | 1.019146 |
| 54 | S054P | P | 5.198689 |
| 54 | S054I | I | 4.775938 |
| 54 | S054V | V | 4.722033 |
| 54 | S054A | A | 3.455902 |
| 54 | S054R | R | 3.375793 |
| 54 | S054L | L | 2.015828 |
| 54 | S054T | T | 1.459971 |
| 54 | S054K | K | 1.438715 |
| 54 | S054G | G | 1.429605 |
| 54 | S054C | C | 1.259773 |
| 54 | S054Q | Q | 1.03365 |
| 55 | A055G | G | 1.694814 |
| 55 | A055T | T | 1.692885 |
| 57 | T057S | S | 1.633613 |
| 57 | T057R | R | 1.605072 |
| 57 | T057V | V | 1.281788 |
| 57 | T057I | I | 1.189062 |
| 59 | N059W | W | 1.035044 |
| 59 | N059R | R | 1.002315 |
| 60 | I060H | H | 1.02415 |
| 60 | I060R | R | 1.003947 |
| 61 | D061H | H | 1.439407 |
| 61 | D061S | S | 1.259714 |
| 61 | D061R | R | 1.105425 |

TABLE 10-1-continued

PAF Assay Results

| Position | WT/Pos/ Mutation | Variant | PAF Perf. Ind. |
|---|---|---|---|
| 61 | D061I | I | 1.076937 |
| 61 | D061F | F | 1.00566 |
| 62 | D062E | E | 1.019293 |
| 63 | P063G | G | 1.709657 |
| 63 | P063T | T | 1.499483 |
| 63 | P063M | M | 1.460336 |
| 63 | P063S | S | 1.416192 |
| 63 | P063K | K | 1.404615 |
| 63 | P063A | A | 1.347541 |
| 63 | P063Y | Y | 1.346046 |
| 63 | P063W | W | 1.34587 |
| 63 | P063V | V | 1.313631 |
| 63 | P063R | R | 1.310696 |
| 63 | P063F | F | 1.246299 |
| 63 | P063L | L | 1.146416 |
| 63 | P063Q | Q | 1.093179 |
| 64 | T064G | G | 1.234467 |
| 64 | T064S | S | 1.114348 |
| 65 | D065A | A | 1.312312 |
| 65 | D065S | S | 1.166849 |
| 65 | D065H | H | 1.096335 |
| 66 | P066R | R | 1.846257 |
| 66 | P066V | V | 1.828926 |
| 66 | P066H | H | 1.589631 |
| 66 | P066I | I | 1.588219 |
| 66 | P066G | G | 1.499901 |
| 66 | P066Q | Q | 1.463705 |
| 66 | P066T | T | 1.410091 |
| 66 | P066S | S | 1.390845 |
| 66 | P066Y | Y | 1.330685 |
| 66 | P066L | L | 1.137635 |
| 66 | P066N | N | 1.122261 |
| 67 | R067N | N | 1.580401 |
| 67 | R067G | G | 1.390129 |
| 67 | R067T | T | 1.284643 |
| 67 | R067F | F | 1.25763 |
| 67 | R067L | L | 1.203316 |
| 67 | R067Q | Q | 1.164899 |
| 67 | R067W | W | 1.066028 |
| 67 | R067E | E | 1.044676 |
| 67 | R067P | P | 1.012761 |
| 68 | L068E | E | 1.435218 |
| 68 | L068W | W | 1.209193 |
| 68 | L068I | I | 1.125898 |
| 68 | L068G | G | 1.092454 |
| 68 | L068V | V | 1.088042 |
| 68 | L068H | H | 1.051612 |
| 68 | L068T | T | 1.032331 |
| 69 | N069V | V | 1.989028 |
| 69 | N069K | K | 1.71908 |
| 69 | N069R | R | 1.493163 |
| 69 | N069I | I | 1.469946 |
| 69 | N069H | H | 1.357968 |
| 69 | N069T | T | 1.351305 |
| 69 | N069L | L | 1.299547 |
| 69 | N069S | S | 1.205171 |
| 69 | N069G | G | 1.19653 |
| 69 | N069Q | Q | 1.074622 |
| 69 | N069W | W | 1.049602 |
| 69 | N069C | C | 1.048373 |
| 71 | A071S | S | 1.751794 |
| 71 | A071T | T | 1.700442 |
| 71 | A071H | H | 1.697558 |
| 71 | A071G | G | 1.58881 |
| 71 | A071I | I | 1.507841 |
| 71 | A071E | E | 1.445699 |
| 71 | A071K | K | 1.441146 |
| 71 | A071R | R | 1.401499 |
| 71 | A071N | N | 1.232241 |
| 71 | A071L | L | 1.231991 |
| 71 | A071F | F | 1.127538 |
| 71 | A071C | C | 1.00977 |
| 72 | S072L | L | 1.257945 |
| 72 | S072H | H | 1.208899 |

TABLE 10-1-continued

PAF Assay Results

| Position | WT/Pos/ Mutation | Variant | PAF Perf. Ind. |
|---|---|---|---|
| 72 | S072G | G | 1.198197 |
| 72 | S072T | T | 1.10065 |
| 72 | S072V | V | 1.080089 |
| 72 | S072Y | Y | 1.066178 |
| 73 | Y073R | R | 1.2555 |
| 73 | Y073Q | Q | 1.23429 |
| 73 | Y073S | S | 1.165683 |
| 73 | Y073K | K | 1.070678 |
| 76 | S076P | P | 1.229172 |
| 77 | C077T | T | 1.120603 |
| 77 | C077V | V | 1.052586 |
| 77 | C077G | G | 1.013806 |
| 78 | L078G | G | 4.975852 |
| 78 | L078H | H | 4.824004 |
| 78 | L078E | E | 3.007159 |
| 78 | L078N | N | 2.683604 |
| 78 | L078T | T | 1.867711 |
| 78 | L078Q | Q | 1.726942 |
| 78 | L078V | V | 1.534239 |
| 78 | L078I | I | 1.434206 |
| 78 | L078Y | Y | 1.387889 |
| 79 | A079H | H | 1.927914 |
| 79 | A079L | L | 1.796126 |
| 79 | A0791 | I | 1.592463 |
| 79 | A079M | M | 1.499635 |
| 79 | A079N | N | 1.475806 |
| 79 | A079Q | Q | 1.472484 |
| 79 | A079R | R | 1.465943 |
| 79 | A079W | W | 1.270538 |
| 79 | A079T | T | 1.169146 |
| 79 | A079E | E | 1.123457 |
| 80 | T080C | C | 1.310752 |
| 80 | T080V | V | 1.230659 |
| 80 | T080G | G | 1.160318 |
| 80 | T080A | A | 1.000722 |
| 82 | L082P | P | 1.456374 |
| 82 | L082G | G | 1.379439 |
| 82 | L082R | R | 1.339485 |
| 82 | L082H | H | 1.332844 |
| 82 | L082K | K | 1.1909 |
| 82 | L082T | T | 1.17992 |
| 82 | L082I | I | 1.171013 |
| 82 | L082S | S | 1.153417 |
| 82 | L082V | V | 1.019854 |
| 83 | P083K | K | 1.369406 |
| 83 | P083G | G | 1.313431 |
| 83 | P083H | H | 1.265876 |
| 83 | P083R | R | 1.194464 |
| 83 | P083S | S | 1.171208 |
| 84 | L084K | K | 1.099089 |
| 84 | L084H | H | 1.008187 |
| 85 | D085Q | Q | 3.093245 |
| 85 | D085R | R | 2.379647 |
| 85 | D085S | S | 2.284009 |
| 85 | D085H | H | 1.548556 |
| 85 | D085N | N | 1.539497 |
| 85 | D085G | G | 1.413812 |
| 85 | D085T | T | 1.329395 |
| 85 | D085E | E | 1.117228 |
| 85 | D085F | F | 1.008028 |
| 86 | L086A | A | 1.376284 |
| 86 | L086C | C | 1.156625 |
| 86 | L086G | G | 1.145834 |
| 95 | D095E | E | 2.044825 |
| 96 | T096S | S | 1.044425 |
| 97 | K097R | R | 2.798748 |
| 97 | K097Q | Q | 1.136975 |
| 100 | F100W | W | 1.082799 |
| 100 | F100E | E | 1.0116 |
| 101 | R101K | K | 1.244945 |
| 103 | T103W | W | 1.261503 |
| 103 | T103Y | Y | 1.193299 |
| 103 | T103G | G | 1.113343 |
| 103 | T103K | K | 1.093573 |

TABLE 10-1-continued

PAF Assay Results

| Position | WT/Pos/ Mutation | Variant | PAF Perf. Ind. |
|---|---|---|---|
| 103 | T103I | I | 1.076338 |
| 103 | T103L | L | 1.050734 |
| 104 | P104H | H | 2.837034 |
| 104 | P104T | T | 2.696977 |
| 104 | P104G | G | 2.672719 |
| 104 | P104V | V | 2.585315 |
| 104 | P104S | S | 2.481687 |
| 104 | P104I | I | 2.431309 |
| 104 | P104W | W | 2.051785 |
| 104 | P104C | C | 1.951282 |
| 104 | P104E | E | 1.837373 |
| 104 | P104F | F | 1.785718 |
| 104 | P104N | N | 1.624722 |
| 104 | P104R | R | 1.618032 |
| 104 | P104Q | Q | 1.343174 |
| 104 | P104M | M | 1.093185 |
| 105 | L105P | P | 1.713219 |
| 105 | L105C | C | 1.557999 |
| 105 | L105F | F | 1.295759 |
| 105 | L105W | W | 1.283998 |
| 105 | L105G | G | 1.078743 |
| 106 | D106K | K | 1.278457 |
| 106 | D106L | L | 1.198148 |
| 106 | D106G | G | 1.178297 |
| 106 | D106H | H | 1.090134 |
| 106 | D106E | E | 1.084931 |
| 106 | D106T | T | 1.061622 |
| 106 | D106I | I | 1.036191 |
| 106 | D106F | F | 1.021513 |
| 106 | D106C | C | 1.005553 |
| 107 | I107E | E | 2.551108 |
| 107 | I107S | S | 2.044692 |
| 107 | I107N | N | 1.810584 |
| 107 | I107G | G | 1.764761 |
| 107 | I107V | V | 1.001703 |
| 108 | A108L | L | 1.407382 |
| 108 | A108T | T | 1.050964 |
| 109 | L109N | N | 1.523277 |
| 109 | L109W | W | 1.296964 |
| 109 | L109Q | Q | 1.182653 |
| 109 | L109Y | Y | 1.155328 |
| 109 | L109I | I | 1.053129 |
| 109 | L109D | D | 1.003394 |
| 111 | M111K | K | 1.977248 |
| 111 | M111I | I | 1.949343 |
| 111 | M111L | L | 1.546317 |
| 111 | M111T | T | 1.489808 |
| 111 | M111F | F | 1.467344 |
| 111 | M111V | V | 1.466478 |
| 111 | M111Y | Y | 1.42589 |
| 111 | M111S | S | 1.031939 |
| 112 | S112L | L | 1.027928 |
| 112 | S112H | H | 1.001485 |
| 113 | V113L | L | 1.503622 |
| 113 | V113H | H | 1.339003 |
| 113 | V113K | K | 1.192607 |
| 113 | V113R | R | 1.133751 |
| 113 | V113Y | Y | 1.113256 |
| 113 | V113F | F | 1.045057 |
| 113 | V113Q | Q | 1.032496 |
| 115 | V115W | W | 1.234 |
| 115 | V115T | T | 1.145757 |
| 115 | V115L | L | 1.117398 |
| 115 | V115G | G | 1.089596 |
| 115 | V115I | I | 1.050387 |
| 115 | V115Y | Y | 1.032052 |
| 116 | T116G | G | 1.095496 |
| 116 | T116A | A | 1.006702 |
| 117 | Q117H | H | 2.327857 |
| 117 | Q117T | T | 2.233854 |
| 117 | Q117Y | Y | 2.227983 |
| 117 | Q117W | W | 2.155359 |
| 117 | Q117V | V | 2.154646 |
| 117 | Q117G | G | 2.080223 |

TABLE 10-1-continued

| PAF Assay Results | | | |
|---|---|---|---|
| Position | WT/Pos/ Mutation | Variant | PAF Perf. Ind. |
| 117 | Q117A | A | 2.048752 |
| 117 | Q117S | S | 1.949232 |
| 117 | Q117F | F | 1.573776 |
| 117 | Q117R | R | 1.564466 |
| 117 | Q117M | M | 1.541944 |
| 117 | Q117E | E | 1.145341 |
| 118 | V118Y | Y | 1.25067 |
| 118 | V118K | K | 1.125917 |
| 118 | V118G | G | 1.083422 |
| 120 | T120S | S | 1.089798 |
| 121 | S121L | L | 1.348931 |
| 121 | S121W | W | 1.333741 |
| 121 | S121R | R | 1.25879 |
| 121 | S121K | K | 1.241105 |
| 121 | S121G | G | 1.204547 |
| 121 | S121C | C | 1.177769 |
| 121 | S121N | N | 1.143954 |
| 121 | S121T | T | 1.132507 |
| 121 | S121A | A | 1.120633 |
| 121 | S121V | V | 1.120454 |
| 122 | A122H | H | 1.137861 |
| 122 | A122I | I | 1.133601 |
| 122 | A122T | T | 1.083131 |
| 122 | A122K | K | 1.082552 |
| 122 | A122V | V | 1.041449 |
| 122 | A122S | S | 1.031411 |
| 124 | G124L | L | 1.91642 |
| 124 | G124I | I | 1.853337 |
| 124 | G124T | T | 1.63716 |
| 124 | G124H | H | 1.588068 |
| 124 | G124V | V | 1.441979 |
| 124 | G124F | F | 1.320782 |
| 124 | G124S | S | 1.269245 |
| 124 | G124Y | Y | 1.234423 |
| 124 | G124R | R | 1.144212 |
| 124 | G124Q | Q | 1.123498 |
| 125 | V125G | G | 2.948291 |
| 125 | V125S | S | 1.942881 |
| 125 | V125A | A | 1.689696 |
| 125 | V125P | P | 1.50166 |
| 125 | V125R | R | 1.301534 |
| 125 | V125D | D | 1.238852 |
| 125 | V125Y | Y | 1.080394 |
| 125 | V125I | I | 1.010779 |
| 126 | G126T | T | 1.577938 |
| 126 | G126P | P | 1.171092 |
| 126 | G126L | L | 1.169527 |
| 127 | T127H | H | 1.57251 |
| 127 | T127V | V | 1.073821 |
| 127 | T127I | I | 1.063668 |
| 127 | T127S | S | 1.046984 |
| 128 | T128L | L | 1.064623 |
| 128 | T128K | K | 1.062947 |
| 148 | P148V | V | 2.426937 |
| 148 | P148K | K | 1.786508 |
| 148 | P148L | L | 1.638438 |
| 148 | P148A | A | 1.637334 |
| 148 | P148R | R | 1.509086 |
| 148 | P148T | T | 1.501359 |
| 148 | P148Y | Y | 1.459512 |
| 148 | P148S | S | 1.45564 |
| 148 | P148E | E | 1.417449 |
| 148 | P148F | F | 1.367568 |
| 148 | P148Q | Q | 1.334517 |
| 148 | P148D | D | 1.030185 |
| 150 | F150L | L | 1.290835 |
| 150 | F150E | E | 1.228159 |
| 153 | I153K | K | 1.618543 |
| 153 | I153H | H | 1.464262 |
| 153 | I153T | T | 1.271928 |
| 153 | I153L | L | 1.270149 |
| 153 | I153F | F | 1.227821 |
| 153 | I153A | A | 1.194659 |
| 154 | F154Y | Y | 1.323693 |

TABLE 10-1-continued

| PAF Assay Results | | | |
|---|---|---|---|
| Position | WT/Pos/ Mutation | Variant | PAF Perf. Ind. |
| 196 | F196H | H | 1.774774 |
| 196 | F196L | L | 1.768072 |
| 196 | F196C | C | 1.738263 |
| 196 | F196M | M | 1.647608 |
| 196 | F196G | G | 1.590716 |
| 196 | F196S | S | 1.577837 |
| 196 | F196Y | Y | 1.414589 |
| 196 | F196V | V | 1.395387 |
| 196 | F196I | I | 1.320955 |
| 196 | F196W | W | 1.014435 |

The following Table provides variants with PAF results that were better than those observed for wild-type *M. smegmatis* perhydrolase. In this Table, the middle column indicates the amino acid residue in the wild-type perhydrolase (WT), followed by the position number and the variant amino acid in that position (Var).

TABLE 10-2

| Variants with PAF Values Better Than Wild-Type | | |
|---|---|---|
| Pos | WT/Pos./ Var | Peracid formation relative to WT |
| 2 | A002W | 1.75 |
| 2 | A002D | 1.30 |
| 2 | A002F | 1.24 |
| 2 | A002I | 1.18 |
| 2 | A002G | 1.15 |
| 2 | A002S | 1.01 |
| 3 | K003Y | 1.06 |
| 3 | K003I | 1.05 |
| 3 | K003L | 1.04 |
| 3 | K003T | 1.01 |
| 3 | K003H | 1.01 |
| 4 | R004Q | 1.03 |
| 5 | I005T | 1.12 |
| 5 | I005S | 1.02 |
| 6 | L006V | 1.07 |
| 6 | L006I | 1.07 |
| 6 | L006T | 1.06 |
| 7 | C007K | 2.69 |
| 7 | C007Y | 2.09 |
| 7 | C007I | 1.76 |
| 7 | C007H | 1.73 |
| 7 | C007A | 1.42 |
| 7 | C007G | 1.39 |
| 7 | C007M | 1.13 |
| 8 | F008R | 1.43 |
| 8 | F008V | 1.18 |
| 8 | F008G | 1.09 |
| 8 | F008H | 1.02 |
| 10 | D010L | 3.97 |
| 10 | D010W | 3.18 |
| 10 | D010K | 2.13 |
| 10 | D010Y | 1.51 |
| 10 | D010T | 1.47 |
| 10 | D010I | 1.28 |
| 12 | L012Q | 2.65 |
| 12 | L012C | 2.29 |
| 12 | L012A | 1.10 |
| 15 | G015A | 1.54 |
| 15 | G015S | 1.05 |
| 17 | V017G | 1.17 |
| 17 | V017R | 1.10 |
| 17 | V017A | 1.01 |
| 18 | P018Y | 1.33 |
| 18 | P018N | 1.33 |
| 18 | P018C | 1.26 |
| 18 | P018E | 1.22 |

TABLE 10-2-continued

Variants with PAF Values Better Than Wild-Type

| Pos | WT/Pos./Var | Peracid formation relative to WT |
|---|---|---|
| 18 | P018V | 1.19 |
| 18 | P018R | 1.16 |
| 18 | P018Q | 1.12 |
| 18 | P018H | 1.12 |
| 18 | P018G | 1.07 |
| 19 | V019G | 1.32 |
| 19 | V019S | 1.24 |
| 19 | V019R | 1.03 |
| 19 | V019L | 1.00 |
| 20 | E020W | 2.94 |
| 20 | E020G | 2.36 |
| 20 | E020T | 2.22 |
| 20 | E020L | 2.20 |
| 20 | E020H | 2.17 |
| 20 | E020V | 2.11 |
| 20 | E020S | 2.01 |
| 20 | E020C | 1.57 |
| 20 | E020N | 1.40 |
| 20 | E020A | 1.29 |
| 20 | E020Q | 1.27 |
| 21 | D021K | 1.58 |
| 21 | D021W | 1.55 |
| 21 | D021L | 1.46 |
| 21 | D021A | 1.46 |
| 21 | D021G | 1.37 |
| 21 | D021Y | 1.30 |
| 21 | D021F | 1.30 |
| 21 | D021S | 1.24 |
| 22 | G022A | 1.55 |
| 22 | G022T | 1.03 |
| 22 | G022S | 1.02 |
| 25 | T025G | 1.86 |
| 25 | T025S | 1.60 |
| 25 | T025A | 1.33 |
| 25 | T025I | 1.02 |
| 26 | E026M | 2.00 |
| 26 | E026A | 1.93 |
| 26 | E026R | 1.48 |
| 26 | E026K | 1.46 |
| 26 | E026T | 1.44 |
| 26 | E026C | 1.40 |
| 26 | E026V | 1.39 |
| 26 | E026N | 1.37 |
| 26 | E026H | 1.33 |
| 26 | E026L | 1.30 |
| 26 | E026G | 1.28 |
| 26 | E026S | 1.27 |
| 26 | E026W | 1.25 |
| 27 | R027K | 1.22 |
| 28 | F028M | 1.33 |
| 28 | F028A | 1.27 |
| 28 | F028W | 1.16 |
| 28 | F028L | 1.09 |
| 28 | F028S | 1.05 |
| 29 | A029W | 1.91 |
| 29 | A029V | 1.80 |
| 29 | A029R | 1.76 |
| 29 | A029Y | 1.70 |
| 29 | A029G | 1.60 |
| 29 | A029S | 1.49 |
| 29 | A029T | 1.42 |
| 29 | A029E | 1.12 |
| 29 | A029C | 1.08 |
| 30 | P030K | 1.21 |
| 30 | P030R | 1.16 |
| 30 | P030V | 1.06 |
| 30 | P030T | 1.05 |
| 30 | P030A | 1.05 |
| 30 | P030S | 1.03 |
| 30 | P030Q | 1.01 |
| 30 | P030H | 1.01 |
| 30 | P030E | 1.01 |
| 31 | D031W | 1.83 |
| 31 | D031L | 1.81 |
| 31 | D031T | 1.45 |

TABLE 10-2-continued

Variants with PAF Values Better Than Wild-Type

| Pos | WT/Pos./Var | Peracid formation relative to WT |
|---|---|---|
| 31 | D031G | 1.44 |
| 31 | D031F | 1.44 |
| 31 | D031N | 1.34 |
| 31 | D031V | 1.28 |
| 31 | D031A | 1.24 |
| 31 | D031R | 1.22 |
| 31 | D031S | 1.15 |
| 31 | D031E | 1.13 |
| 31 | D031Q | 1.07 |
| 32 | V032K | 1.09 |
| 32 | V032R | 1.05 |
| 33 | R033S | 1.00 |
| 36 | G036I | 1.32 |
| 36 | G036K | 1.27 |
| 36 | G036L | 1.24 |
| 37 | V037S | 1.40 |
| 37 | V037I | 1.26 |
| 37 | V037A | 1.25 |
| 37 | V037H | 1.21 |
| 37 | V037L | 1.16 |
| 37 | V037C | 1.09 |
| 37 | V037T | 1.05 |
| 39 | A039L | 1.43 |
| 39 | A039K | 1.36 |
| 39 | A039Y | 1.36 |
| 39 | A039I | 1.26 |
| 39 | A039T | 1.26 |
| 39 | A039W | 1.23 |
| 39 | A039V | 1.21 |
| 39 | A039G | 1.17 |
| 39 | A039R | 1.17 |
| 39 | A039E | 1.09 |
| 40 | Q040K | 2.61 |
| 40 | Q040I | 2.58 |
| 40 | Q040W | 2.39 |
| 40 | Q040L | 2.14 |
| 40 | Q040T | 2.01 |
| 40 | Q040R | 1.89 |
| 40 | Q040Y | 1.83 |
| 40 | Q040G | 1.79 |
| 40 | Q040S | 1.57 |
| 40 | Q040N | 1.53 |
| 40 | Q040D | 1.16 |
| 40 | Q040E | 1.08 |
| 41 | Q041K | 1.38 |
| 41 | Q041R | 1.19 |
| 41 | Q041W | 1.14 |
| 41 | Q041H | 1.12 |
| 41 | Q041S | 1.11 |
| 41 | Q041Y | 1.09 |
| 41 | Q041V | 1.07 |
| 41 | Q041A | 1.03 |
| 41 | Q041L | 1.00 |
| 42 | L042K | 2.46 |
| 42 | L042W | 2.06 |
| 42 | L042H | 1.92 |
| 42 | L042R | 1.38 |
| 42 | L042G | 1.17 |
| 42 | L042T | 1.08 |
| 42 | L042F | 1.07 |
| 43 | G043A | 1.49 |
| 43 | G043C | 1.48 |
| 43 | G043K | 1.42 |
| 43 | G043M | 1.37 |
| 43 | G043Y | 1.26 |
| 43 | G043E | 1.25 |
| 43 | G043L | 1.22 |
| 43 | G043R | 1.22 |
| 43 | G043S | 1.18 |
| 43 | G043H | 1.17 |
| 43 | G043P | 1.08 |
| 44 | A044F | 2.84 |
| 44 | A044V | 2.13 |
| 44 | A044C | 1.80 |
| 44 | A044L | 1.61 |

TABLE 10-2-continued

Variants with PAF Values Better Than Wild-Type

| Pos | WT/Pos./ Var | Peracid formation relative to WT |
|---|---|---|
| 44 | A044W | 1.40 |
| 44 | A044M | 1.20 |
| 45 | D045K | 1.34 |
| 45 | D045T | 1.27 |
| 45 | D045R | 1.16 |
| 45 | D045W | 1.15 |
| 45 | D045S | 1.13 |
| 45 | D045G | 1.13 |
| 45 | D045H | 1.13 |
| 45 | D045F | 1.11 |
| 45 | D045L | 1.05 |
| 45 | D045V | 1.05 |
| 45 | D045Q | 1.04 |
| 45 | D045A | 1.04 |
| 46 | F046E | 1.25 |
| 46 | F046D | 1.17 |
| 46 | F046G | 1.02 |
| 46 | F046K | 1.00 |
| 47 | E047R | 2.45 |
| 47 | E047T | 1.96 |
| 47 | E047P | 1.36 |
| 47 | E047S | 1.28 |
| 47 | E047H | 1.27 |
| 47 | E047G | 1.20 |
| 47 | E047K | 1.19 |
| 47 | E047F | 1.09 |
| 47 | E047I | 1.03 |
| 49 | I049G | 1.34 |
| 49 | I049H | 1.27 |
| 49 | I049S | 1.24 |
| 49 | I049K | 1.23 |
| 49 | I049V | 1.20 |
| 49 | I049L | 1.14 |
| 49 | I049Y | 1.07 |
| 49 | I049R | 1.05 |
| 49 | I049E | 1.02 |
| 49 | I049M | 1.01 |
| 50 | E050L | 1.19 |
| 50 | E050M | 1.18 |
| 50 | E050A | 1.12 |
| 51 | E051V | 1.47 |
| 51 | E051A | 1.28 |
| 51 | E051G | 1.22 |
| 51 | E051T | 1.18 |
| 51 | E051L | 1.11 |
| 51 | E051I | 1.07 |
| 53 | L053H | 5.05 |
| 53 | L053Q | 1.48 |
| 53 | L053G | 1.32 |
| 53 | L053S | 1.16 |
| 53 | L053T | 1.02 |
| 54 | S054P | 5.20 |
| 54 | S054I | 4.78 |
| 54 | S054V | 4.72 |
| 54 | S054A | 3.46 |
| 54 | S054R | 3.38 |
| 54 | S054L | 2.02 |
| 54 | S054T | 1.46 |
| 54 | S054K | 1.44 |
| 54 | S054G | 1.43 |
| 54 | S054C | 1.26 |
| 54 | S054Q | 1.03 |
| 55 | A055G | 1.69 |
| 55 | A055T | 1.69 |
| 57 | T057S | 1.63 |
| 57 | T057R | 1.61 |
| 57 | T057V | 1.28 |
| 57 | T057I | 1.19 |
| 59 | N059W | 1.13 |
| 59 | N059R | 1.09 |
| 59 | N059T | 1.07 |
| 59 | N059S | 1.06 |
| 59 | N059Q | 1.02 |
| 60 | I060H | 1.02 |
| 60 | I060R | 1.00 |

TABLE 10-2-continued

Variants with PAF Values Better Than Wild-Type

| Pos | WT/Pos./ Var | Peracid formation relative to WT |
|---|---|---|
| 61 | D061H | 1.44 |
| 61 | D061S | 1.26 |
| 61 | D061R | 1.11 |
| 61 | D061I | 1.08 |
| 61 | D061F | 1.01 |
| 62 | D062E | 1.02 |
| 63 | P063G | 1.71 |
| 63 | P063T | 1.50 |
| 63 | P063M | 1.46 |
| 63 | P063S | 1.42 |
| 63 | P063K | 1.40 |
| 63 | P063A | 1.35 |
| 63 | P063Y | 1.35 |
| 63 | P063W | 1.35 |
| 63 | P063V | 1.31 |
| 63 | P063R | 1.31 |
| 63 | P063F | 1.25 |
| 63 | P063L | 1.15 |
| 63 | P063Q | 1.09 |
| 64 | T064G | 1.23 |
| 64 | T064S | 1.11 |
| 65 | D065A | 1.31 |
| 65 | D065S | 1.17 |
| 65 | D065H | 1.10 |
| 66 | P066R | 1.85 |
| 66 | P066V | 1.83 |
| 66 | P066H | 1.59 |
| 66 | P066I | 1.59 |
| 66 | P066G | 1.50 |
| 66 | P066Q | 1.46 |
| 66 | P066T | 1.41 |
| 66 | P066S | 1.39 |
| 66 | P066Y | 1.33 |
| 66 | P066L | 1.14 |
| 66 | P066N | 1.12 |
| 67 | R067N | 1.58 |
| 67 | R067G | 1.39 |
| 67 | R067T | 1.28 |
| 67 | R067F | 1.26 |
| 67 | R067L | 1.20 |
| 67 | R067Q | 1.16 |
| 67 | R067W | 1.07 |
| 67 | R067E | 1.04 |
| 67 | R067P | 1.01 |
| 68 | L068E | 1.44 |
| 68 | L068W | 1.21 |
| 68 | L068I | 1.13 |
| 68 | L068G | 1.09 |
| 68 | L068V | 1.09 |
| 68 | L068H | 1.05 |
| 68 | L068T | 1.03 |
| 69 | N069V | 1.99 |
| 69 | N069K | 1.72 |
| 69 | N069R | 1.49 |
| 69 | N069I | 1.47 |
| 69 | N069H | 1.36 |
| 69 | N069T | 1.35 |
| 69 | N069L | 1.30 |
| 69 | N069S | 1.21 |
| 69 | N069G | 1.20 |
| 69 | N069Q | 1.07 |
| 69 | N069W | 1.05 |
| 69 | N069C | 1.05 |
| 71 | A071S | 1.75 |
| 71 | A071T | 1.70 |
| 71 | A071H | 1.70 |
| 71 | A071G | 1.59 |
| 71 | A071I | 1.51 |
| 71 | A071E | 1.45 |
| 71 | A071K | 1.44 |
| 71 | A071R | 1.40 |
| 71 | A071N | 1.23 |
| 71 | A071L | 1.23 |
| 71 | A071F | 1.13 |
| 71 | A071C | 1.01 |

TABLE 10-2-continued

Variants with PAF Values Better Than Wild-Type

| Pos | WT/Pos./Var | Peracid formation relative to WT |
|---|---|---|
| 72 | S072L | 1.26 |
| 72 | S072H | 1.21 |
| 72 | S072G | 1.20 |
| 72 | S072T | 1.10 |
| 72 | S072V | 1.08 |
| 72 | S072Y | 1.07 |
| 73 | Y073R | 1.26 |
| 73 | Y073Q | 1.23 |
| 73 | Y073S | 1.17 |
| 73 | Y073K | 1.07 |
| 74 | L074S | 2.72 |
| 74 | L074G | 1.95 |
| 74 | L074W | 1.38 |
| 75 | P075R | 1.60 |
| 75 | P075S | 1.39 |
| 75 | P075T | 1.28 |
| 75 | P075Q | 1.21 |
| 75 | P075G | 1.16 |
| 75 | P075H | 1.05 |
| 75 | P075W | 1.04 |
| 76 | S076P | 1.23 |
| 77 | C077T | 1.12 |
| 77 | C077V | 1.05 |
| 77 | C077G | 1.01 |
| 78 | L078G | 4.98 |
| 78 | L078H | 4.82 |
| 78 | L078E | 3.01 |
| 78 | L078N | 2.68 |
| 78 | L078T | 1.87 |
| 78 | L078Q | 1.73 |
| 78 | L078V | 1.53 |
| 78 | L078I | 1.43 |
| 78 | L078Y | 1.39 |
| 79 | A079H | 1.93 |
| 79 | A079L | 1.80 |
| 79 | A079I | 1.59 |
| 79 | A079M | 1.50 |
| 79 | A079N | 1.48 |
| 79 | A079Q | 1.47 |
| 79 | A079R | 1.47 |
| 79 | A079W | 1.27 |
| 79 | A079T | 1.17 |
| 79 | A079E | 1.12 |
| 80 | T080C | 1.31 |
| 80 | T080V | 1.23 |
| 80 | T080G | 1.16 |
| 80 | T080A | 1.00 |
| 81 | H081K | 1.52 |
| 81 | H081L | 1.23 |
| 81 | H081N | 1.17 |
| 81 | H081G | 1.17 |
| 81 | H081A | 1.15 |
| 81 | H081C | 1.13 |
| 81 | H081W | 1.13 |
| 81 | H081V | 1.10 |
| 81 | H081F | 1.10 |
| 81 | H081S | 1.04 |
| 82 | L082P | 1.46 |
| 82 | L082G | 1.38 |
| 82 | L082R | 1.34 |
| 82 | L082H | 1.33 |
| 82 | L082K | 1.19 |
| 82 | L082T | 1.18 |
| 82 | L082I | 1.17 |
| 82 | L082S | 1.15 |
| 82 | L082V | 1.02 |
| 83 | P083K | 1.37 |
| 83 | P083G | 1.31 |
| 83 | P083H | 1.27 |
| 83 | P083R | 1.19 |
| 83 | P083S | 1.17 |
| 84 | L084K | 1.10 |
| 84 | L084H | 1.01 |
| 85 | D085Q | 3.09 |
| 85 | D085R | 2.38 |

TABLE 10-2-continued

Variants with PAF Values Better Than Wild-Type

| Pos | WT/Pos./Var | Peracid formation relative to WT |
|---|---|---|
| 85 | D085S | 2.28 |
| 85 | D085H | 1.55 |
| 85 | D085N | 1.54 |
| 85 | D085G | 1.41 |
| 85 | D085T | 1.33 |
| 85 | D085E | 1.12 |
| 85 | D085F | 1.01 |
| 86 | L086A | 1.38 |
| 86 | L086C | 1.16 |
| 86 | L086G | 1.15 |
| 88 | I088H | 1.20 |
| 88 | I088T | 1.03 |
| 88 | I088G | 1.01 |
| 90 | M090T | 1.27 |
| 90 | M090I | 1.13 |
| 90 | M090V | 1.08 |
| 90 | M090S | 1.06 |
| 90 | M090L | 1.02 |
| 91 | L091G | 1.21 |
| 91 | L091T | 1.06 |
| 92 | G092V | 1.49 |
| 92 | G092S | 1.26 |
| 93 | T093Y | 5.26 |
| 93 | T093F | 3.52 |
| 93 | T093A | 1.38 |
| 93 | T093C | 1.08 |
| 95 | D095E | 2.04 |
| 96 | T096S | 1.04 |
| 97 | K097R | 2.80 |
| 97 | K097Q | 1.14 |
| 98 | A098L | 2.22 |
| 98 | A098H | 2.09 |
| 98 | A098I | 2.05 |
| 98 | A098Y | 2.02 |
| 98 | A098S | 1.73 |
| 98 | A098T | 1.72 |
| 98 | A098G | 1.57 |
| 98 | A098C | 1.30 |
| 98 | A098N | 1.24 |
| 98 | A098D | 1.11 |
| 98 | A098P | 1.10 |
| 100 | F100W | 1.08 |
| 100 | F100E | 1.01 |
| 101 | R101K | 1.24 |
| 103 | T103W | 1.26 |
| 103 | T103Y | 1.19 |
| 103 | T103G | 1.11 |
| 103 | T103K | 1.09 |
| 103 | T103I | 1.08 |
| 103 | T103L | 1.05 |
| 104 | P104H | 2.84 |
| 104 | P104T | 2.70 |
| 104 | P104G | 2.67 |
| 104 | P104V | 2.59 |
| 104 | P104S | 2.48 |
| 104 | P104I | 2.43 |
| 104 | P104W | 2.05 |
| 104 | P104C | 1.95 |
| 104 | P104E | 1.84 |
| 104 | P104F | 1.79 |
| 104 | P104N | 1.62 |
| 104 | P104R | 1.62 |
| 104 | P104Q | 1.34 |
| 104 | P104M | 1.09 |
| 105 | L105P | 1.71 |
| 105 | L105C | 1.56 |
| 105 | L105F | 1.30 |
| 105 | L105W | 1.28 |
| 105 | L105G | 1.08 |
| 106 | D106K | 1.28 |
| 106 | D106L | 1.20 |
| 106 | D106G | 1.18 |
| 106 | D106H | 1.09 |
| 106 | D106E | 1.08 |
| 106 | D106T | 1.06 |

TABLE 10-2-continued

Variants with PAF Values Better Than Wild-Type

| Pos | WT/Pos./Var | Peracid formation relative to WT |
|---|---|---|
| 106 | D106I | 1.04 |
| 106 | D106F | 1.02 |
| 106 | D106C | 1.01 |
| 107 | I107E | 2.55 |
| 107 | I107S | 2.04 |
| 107 | I107N | 1.81 |
| 107 | I107G | 1.76 |
| 107 | I107V | 1.00 |
| 108 | A108L | 1.41 |
| 108 | A108T | 1.05 |
| 109 | L109N | 1.52 |
| 109 | L109W | 1.30 |
| 109 | L109Q | 1.18 |
| 109 | L109Y | 1.16 |
| 109 | L109I | 1.05 |
| 109 | L109D | 1.00 |
| 111 | M111K | 1.98 |
| 111 | M111I | 1.95 |
| 111 | M111L | 1.55 |
| 111 | M111T | 1.49 |
| 111 | M111F | 1.47 |
| 111 | M111V | 1.47 |
| 111 | M111Y | 1.43 |
| 111 | M111S | 1.03 |
| 112 | S112L | 1.03 |
| 112 | S112H | 1.00 |
| 113 | V113L | 1.50 |
| 113 | V113H | 1.34 |
| 113 | V113K | 1.19 |
| 113 | V113R | 1.13 |
| 113 | V113Y | 1.11 |
| 113 | V113F | 1.05 |
| 113 | V113Q | 1.03 |
| 115 | V115W | 1.23 |
| 115 | V115T | 1.15 |
| 115 | V115L | 1.12 |
| 115 | V115G | 1.09 |
| 115 | V115I | 1.05 |
| 115 | V115Y | 1.03 |
| 116 | T116G | 1.10 |
| 116 | T116A | 1.01 |
| 117 | Q117H | 2.33 |
| 117 | Q117T | 2.23 |
| 117 | Q117Y | 2.23 |
| 117 | Q117W | 2.16 |
| 117 | Q117V | 2.15 |
| 117 | Q117G | 2.08 |
| 117 | Q117A | 2.05 |
| 117 | Q117S | 1.95 |
| 117 | Q117F | 1.57 |
| 117 | Q117R | 1.56 |
| 117 | Q117M | 1.54 |
| 117 | Q117E | 1.15 |
| 118 | V118Y | 1.25 |
| 118 | V118K | 1.13 |
| 118 | V118G | 1.08 |
| 120 | T120S | 1.09 |
| 121 | S121L | 1.35 |
| 121 | S121W | 1.33 |
| 121 | S121R | 1.26 |
| 121 | S121K | 1.24 |
| 121 | S121G | 1.20 |
| 121 | S121C | 1.18 |
| 121 | S121N | 1.14 |
| 121 | S121T | 1.13 |
| 121 | S121A | 1.12 |
| 121 | S121V | 1.12 |
| 122 | A122H | 1.14 |
| 122 | A122I | 1.13 |
| 122 | A122T | 1.08 |
| 122 | A122K | 1.08 |
| 122 | A122V | 1.04 |
| 122 | A122S | 1.03 |
| 123 | G123D | 1.73 |
| 123 | G123V | 1.40 |

TABLE 10-2-continued

Variants with PAF Values Better Than Wild-Type

| Pos | WT/Pos./Var | Peracid formation relative to WT |
|---|---|---|
| 123 | G123P | 1.32 |
| 123 | G123E | 1.13 |
| 123 | G123T | 1.06 |
| 123 | G123H | 1.00 |
| 124 | G124L | 1.92 |
| 124 | G124I | 1.85 |
| 124 | G124T | 1.64 |
| 124 | G124H | 1.59 |
| 124 | G124V | 1.44 |
| 124 | G124F | 1.32 |
| 124 | G124S | 1.27 |
| 124 | G124Y | 1.23 |
| 124 | G124R | 1.14 |
| 124 | G124Q | 1.12 |
| 125 | V125G | 2.95 |
| 125 | V125S | 1.94 |
| 125 | V125A | 1.69 |
| 125 | V125P | 1.50 |
| 125 | V125R | 1.30 |
| 125 | V125D | 1.24 |
| 125 | V125Y | 1.08 |
| 125 | V125I | 1.01 |
| 126 | G126T | 1.58 |
| 126 | G126P | 1.17 |
| 126 | G126L | 1.17 |
| 127 | T127H | 1.57 |
| 127 | T127V | 1.07 |
| 127 | T127I | 1.06 |
| 127 | T127S | 1.05 |
| 128 | T128L | 1.06 |
| 128 | T128K | 1.06 |
| 130 | P130T | 1.19 |
| 130 | P130H | 1.17 |
| 130 | P130K | 1.16 |
| 130 | P130G | 1.16 |
| 130 | P130S | 1.16 |
| 130 | P130V | 1.15 |
| 130 | P130W | 1.15 |
| 130 | P130I | 1.12 |
| 130 | P130L | 1.12 |
| 130 | P130R | 1.11 |
| 130 | P130F | 1.08 |
| 130 | P130E | 1.00 |
| 131 | A131L | 1.83 |
| 131 | A131R | 1.76 |
| 131 | A131H | 1.72 |
| 131 | A131G | 1.66 |
| 131 | A131W | 1.61 |
| 131 | A131V | 1.59 |
| 131 | A131P | 1.52 |
| 131 | A131Y | 1.50 |
| 131 | A131S | 1.48 |
| 131 | A131E | 1.36 |
| 131 | A131D | 1.31 |
| 131 | A131Q | 1.29 |
| 132 | P132Y | 1.57 |
| 132 | P132S | 1.13 |
| 133 | K133Y | 1.12 |
| 133 | K133L | 1.05 |
| 133 | K133H | 1.02 |
| 134 | V134G | 1.71 |
| 134 | V134T | 1.25 |
| 134 | V134N | 1.18 |
| 134 | V134S | 1.16 |
| 134 | V134L | 1.13 |
| 134 | V134I | 1.12 |
| 136 | V136T | 1.13 |
| 137 | V137M | 1.22 |
| 137 | V137L | 1.09 |
| 137 | V137T | 1.08 |
| 137 | V137A | 1.07 |
| 137 | V137G | 1.02 |
| 138 | S138I | 1.15 |
| 138 | S138G | 1.05 |
| 140 | P140A | 1.90 |

TABLE 10-2-continued

Variants with PAF Values Better Than Wild-Type

| Pos | WT/Pos./Var | Peracid formation relative to WT |
|---|---|---|
| 140 | P140T | 1.74 |
| 140 | P140S | 1.31 |
| 141 | P141L | 2.32 |
| 141 | P141I | 2.29 |
| 141 | P141H | 2.07 |
| 141 | P141V | 1.96 |
| 141 | P141T | 1.84 |
| 141 | P141S | 1.70 |
| 141 | P141R | 1.65 |
| 141 | P141G | 1.64 |
| 141 | P141Q | 1.39 |
| 141 | P141N | 1.32 |
| 141 | P141A | 1.10 |
| 142 | L142W | 2.41 |
| 142 | L142K | 1.60 |
| 142 | L142F | 1.05 |
| 143 | A143K | 3.16 |
| 143 | A143H | 2.90 |
| 143 | A143L | 2.51 |
| 143 | A143V | 2.45 |
| 143 | A143W | 2.27 |
| 143 | A143T | 2.18 |
| 143 | A143R | 2.15 |
| 143 | A143S | 1.77 |
| 143 | A143Q | 1.74 |
| 143 | A143F | 1.56 |
| 143 | A143P | 1.53 |
| 143 | A143G | 1.48 |
| 143 | A143D | 1.45 |
| 143 | A143E | 1.43 |
| 143 | A143C | 1.39 |
| 143 | A143N | 1.30 |
| 144 | P144Y | 2.34 |
| 144 | P144K | 2.09 |
| 144 | P144H | 1.94 |
| 144 | P144F | 1.82 |
| 144 | P144R | 1.76 |
| 144 | P144S | 1.69 |
| 144 | P144T | 1.46 |
| 144 | P144G | 1.45 |
| 144 | P144D | 1.45 |
| 144 | P144N | 1.44 |
| 144 | P144L | 1.43 |
| 144 | P144Q | 1.37 |
| 144 | P144M | 1.24 |
| 144 | P144A | 1.09 |
| 145 | M145L | 1.72 |
| 145 | M145F | 1.49 |
| 145 | M145R | 1.15 |
| 145 | M145W | 1.15 |
| 145 | M145C | 1.02 |
| 145 | M145T | 1.01 |
| 147 | H147A | 1.28 |
| 147 | H147S | 1.26 |
| 147 | H147T | 1.20 |
| 147 | H147P | 1.12 |
| 147 | H147E | 1.11 |
| 148 | P148V | 2.43 |
| 148 | P148K | 1.79 |
| 148 | P148L | 1.64 |
| 148 | P148A | 1.64 |
| 148 | P148R | 1.51 |
| 148 | P148T | 1.50 |
| 148 | P148Y | 1.46 |
| 148 | P148S | 1.46 |
| 148 | P148E | 1.42 |
| 148 | P148F | 1.37 |
| 148 | P148Q | 1.33 |
| 148 | P148D | 1.03 |
| 150 | F150L | 1.29 |
| 150 | F150E | 1.23 |
| 151 | Q151D | 1.47 |
| 151 | Q151R | 1.36 |
| 151 | Q151P | 1.35 |
| 151 | Q151A | 1.29 |
| 151 | Q151T | 1.24 |
| 151 | Q151M | 1.24 |
| 151 | Q151E | 1.14 |
| 151 | Q151K | 1.07 |
| 151 | Q151H | 1.06 |
| 151 | Q151S | 1.05 |
| 151 | Q151C | 1.05 |
| 151 | Q151Y | 1.01 |
| 152 | L152V | 1.22 |
| 152 | L152K | 1.21 |
| 152 | L152R | 1.20 |
| 152 | L152W | 1.18 |
| 152 | L152T | 1.12 |
| 152 | L152S | 1.12 |
| 152 | L152Y | 1.09 |
| 152 | L152H | 1.09 |
| 152 | L152G | 1.08 |
| 152 | L152E | 1.08 |
| 152 | L152Q | 1.07 |
| 152 | L152D | 1.07 |
| 152 | L152I | 1.04 |
| 152 | L152C | 1.00 |
| 153 | I153K | 1.62 |
| 153 | I153H | 1.46 |
| 153 | I153T | 1.27 |
| 153 | I153L | 1.27 |
| 153 | I153F | 1.23 |
| 153 | I153A | 1.19 |
| 154 | F154Y | 1.32 |
| 155 | E155T | 1.49 |
| 155 | E155R | 1.47 |
| 155 | E155L | 1.31 |
| 155 | E155Y | 1.27 |
| 155 | E155K | 1.23 |
| 155 | E155G | 1.17 |
| 155 | E155S | 1.08 |
| 155 | E155D | 1.08 |
| 155 | E155F | 1.07 |
| 156 | G156P | 1.44 |
| 156 | G156T | 1.15 |
| 156 | G156K | 1.10 |
| 156 | G156M | 1.09 |
| 156 | G156C | 1.07 |
| 156 | G156N | 1.07 |
| 156 | G156R | 1.05 |
| 156 | G156H | 1.04 |
| 156 | G156S | 1.02 |
| 157 | G157T | 1.74 |
| 157 | G157R | 1.51 |
| 157 | G157S | 1.30 |
| 157 | G157K | 1.28 |
| 157 | G157F | 1.27 |
| 157 | G157V | 1.23 |
| 157 | G157H | 1.14 |
| 157 | G157I | 1.11 |
| 158 | E158H | 2.40 |
| 158 | E158K | 2.08 |
| 158 | E158F | 2.06 |
| 158 | E158R | 1.99 |
| 158 | E158Y | 1.77 |
| 158 | E158W | 1.77 |
| 158 | E158L | 1.59 |
| 158 | E158S | 1.57 |
| 158 | E158V | 1.52 |
| 158 | E158Q | 1.49 |
| 158 | E158C | 1.46 |
| 158 | E158A | 1.45 |
| 158 | E158T | 1.45 |
| 158 | E158P | 1.41 |
| 158 | E158N | 1.41 |
| 158 | E158M | 1.39 |
| 158 | E158I | 1.38 |
| 158 | E158D | 1.35 |
| 159 | Q159R | 1.15 |
| 159 | Q159C | 1.13 |

TABLE 10-2-continued

Variants with PAF Values Better Than Wild-Type

| Pos | WT/Pos./ Var | Peracid formation relative to WT |
|---|---|---|
| 159 | Q159S | 1.10 |
| 159 | Q159D | 1.09 |
| 159 | Q159A | 1.08 |
| 159 | Q159M | 1.07 |
| 159 | Q159P | 1.06 |
| 159 | Q159L | 1.02 |
| 161 | T161R | 3.61 |
| 161 | T161Y | 2.40 |
| 161 | T161H | 1.82 |
| 161 | T161W | 1.41 |
| 161 | T161I | 1.40 |
| 161 | T161V | 1.27 |
| 161 | T161L | 1.25 |
| 161 | T161Q | 1.04 |
| 162 | T162K | 1.22 |
| 162 | T162R | 1.17 |
| 162 | T162W | 1.15 |
| 162 | T162Y | 1.03 |
| 162 | T162H | 1.02 |
| 163 | E163L | 1.50 |
| 163 | E163Y | 1.41 |
| 163 | E163H | 1.32 |
| 163 | E163G | 1.25 |
| 163 | E163W | 1.21 |
| 163 | E163V | 1.13 |
| 163 | E163R | 1.12 |
| 163 | E163S | 1.12 |
| 163 | E163A | 1.11 |
| 163 | E163C | 1.11 |
| 163 | E163F | 1.07 |
| 165 | A165R | 1.70 |
| 165 | A165K | 1.35 |
| 165 | A165F | 1.23 |
| 165 | A165Q | 1.21 |
| 165 | A165V | 1.21 |
| 165 | A165Y | 1.20 |
| 165 | A165T | 1.18 |
| 165 | A165I | 1.17 |
| 165 | A165P | 1.14 |
| 165 | A165L | 1.08 |
| 165 | A165G | 1.05 |
| 165 | A165N | 1.01 |
| 165 | A165S | 1.00 |
| 166 | R166Y | 1.29 |
| 166 | R166L | 1.27 |
| 166 | R166I | 1.26 |
| 166 | R166W | 1.25 |
| 166 | R166H | 1.20 |
| 166 | R166T | 1.19 |
| 166 | R166V | 1.17 |
| 166 | R166K | 1.17 |
| 166 | R166S | 1.16 |
| 166 | R166G | 1.15 |
| 167 | V167T | 1.13 |
| 167 | V167I | 1.08 |
| 167 | V167Y | 1.07 |
| 167 | V167H | 1.03 |
| 168 | Y168G | 1.89 |
| 168 | Y168T | 1.51 |
| 168 | Y168V | 1.19 |
| 169 | S169Y | 1.26 |
| 169 | S169R | 1.24 |
| 169 | S169K | 1.21 |
| 169 | S169I | 1.16 |
| 169 | S169T | 1.15 |
| 169 | S169L | 1.08 |
| 169 | S169C | 1.03 |
| 169 | S169Q | 1.02 |
| 170 | A170K | 1.71 |
| 170 | A170G | 1.59 |
| 170 | A170I | 1.59 |
| 170 | A170S | 1.47 |
| 170 | A170F | 1.44 |
| 170 | A170T | 1.40 |
| 170 | A170E | 1.28 |

TABLE 10-2-continued

Variants with PAF Values Better Than Wild-Type

| Pos | WT/Pos./ Var | Peracid formation relative to WT |
|---|---|---|
| 170 | A170D | 1.27 |
| 170 | A170N | 1.21 |
| 170 | A170V | 1.20 |
| 170 | A170C | 1.15 |
| 170 | A170Q | 1.15 |
| 170 | A170L | 1.05 |
| 170 | A170W | 1.04 |
| 170 | A170M | 1.03 |
| 171 | L171K | 2.05 |
| 171 | L171H | 1.67 |
| 171 | L171T | 1.54 |
| 171 | L171I | 1.53 |
| 171 | L171S | 1.43 |
| 171 | L171F | 1.30 |
| 171 | L171G | 1.26 |
| 171 | L171Y | 1.20 |
| 171 | L171V | 1.02 |
| 172 | A172I | 1.70 |
| 172 | A172S | 1.59 |
| 172 | A172W | 1.43 |
| 172 | A172G | 1.41 |
| 172 | A172V | 1.40 |
| 172 | A172T | 1.25 |
| 172 | A172L | 1.20 |
| 172 | A172C | 1.20 |
| 173 | S173Y | 1.19 |
| 173 | S173K | 1.17 |
| 173 | S173W | 1.16 |
| 173 | S173L | 1.15 |
| 173 | S173R | 1.09 |
| 173 | S173H | 1.07 |
| 173 | S173T | 1.06 |
| 174 | F174G | 1.60 |
| 174 | F174P | 1.54 |
| 174 | F174Q | 1.42 |
| 174 | F174C | 1.32 |
| 174 | F174S | 1.16 |
| 174 | F174L | 1.05 |
| 175 | M175T | 2.21 |
| 175 | M175G | 2.04 |
| 175 | M175V | 1.93 |
| 175 | M175L | 1.61 |
| 175 | M175Q | 1.56 |
| 175 | M175R | 1.55 |
| 175 | M175N | 1.39 |
| 175 | M175W | 1.25 |
| 176 | K176W | 1.19 |
| 176 | K176T | 1.04 |
| 176 | K176Y | 1.04 |
| 176 | K176V | 1.04 |
| 176 | K176G | 1.01 |
| 178 | P178L | 1.82 |
| 178 | P178Y | 1.38 |
| 178 | P178K | 1.34 |
| 178 | P178W | 1.14 |
| 178 | P178G | 1.09 |
| 179 | F179L | 1.15 |
| 179 | F179Y | 1.05 |
| 180 | F180L | 1.30 |
| 180 | F180I | 1.20 |
| 180 | F180V | 1.14 |
| 180 | F180Y | 1.12 |
| 180 | F180W | 1.11 |
| 180 | F180K | 1.08 |
| 180 | F180T | 1.01 |
| 181 | D181A | 1.35 |
| 181 | D181K | 1.33 |
| 181 | D181Y | 1.29 |
| 181 | D181W | 1.26 |
| 181 | D181L | 1.25 |
| 181 | D181R | 1.23 |
| 181 | D181S | 1.21 |
| 181 | D181Q | 1.14 |
| 181 | D181E | 1.10 |
| 181 | D181G | 1.09 |

TABLE 10-2-continued

| Variants with PAF Values Better Than Wild-Type | | |
|---|---|---|
| Pos | WT/Pos./ Var | Peracid formation relative to WT |
| 181 | D181C | 1.09 |
| 181 | D181P | 1.03 |
| 181 | D181T | 1.02 |
| 182 | A182T | 1.14 |
| 184 | S184Y | 1.06 |
| 184 | S184F | 1.05 |
| 184 | S184T | 1.04 |
| 184 | S184H | 1.02 |
| 185 | V185K | 1.37 |
| 185 | V185Y | 1.37 |
| 185 | V185W | 1.36 |
| 185 | V185H | 1.30 |
| 185 | V185L | 1.23 |
| 185 | V185R | 1.15 |
| 185 | V185G | 1.12 |
| 185 | V185T | 1.11 |
| 185 | V185S | 1.09 |
| 185 | V185I | 1.07 |
| 185 | V185F | 1.02 |
| 186 | I186G | 1.86 |
| 186 | I186T | 1.51 |
| 186 | I186A | 1.46 |
| 186 | I186S | 1.39 |
| 186 | I186V | 1.28 |
| 186 | I186L | 1.17 |
| 186 | I186F | 1.01 |
| 187 | S187K | 1.45 |
| 187 | S187Y | 1.43 |
| 187 | S187I | 1.38 |
| 187 | S187L | 1.37 |
| 187 | S187W | 1.30 |
| 187 | S187H | 1.29 |
| 187 | S187V | 1.23 |
| 187 | S187T | 1.12 |
| 187 | S187R | 1.04 |
| 187 | S187G | 1.03 |
| 187 | S187F | 1.02 |
| 188 | T188Y | 1.48 |
| 188 | T188V | 1.22 |
| 188 | T188S | 1.16 |
| 188 | T188I | 1.13 |
| 188 | T188H | 1.11 |
| 188 | T188R | 1.01 |
| 189 | D189L | 1.30 |
| 189 | D189H | 1.25 |
| 189 | D189W | 1.09 |
| 190 | G190W | 1.88 |
| 190 | G190K | 1.01 |
| 191 | V191Y | 1.32 |
| 191 | V191H | 1.30 |
| 191 | V191W | 1.20 |
| 191 | V191S | 1.20 |
| 191 | V191K | 1.17 |
| 191 | V191I | 1.14 |
| 191 | V191F | 1.13 |
| 191 | V191R | 1.05 |
| 191 | V191L | 1.04 |
| 196 | F196H | 1.77 |
| 196 | F196L | 1.77 |
| 196 | F196C | 1.74 |
| 196 | F196M | 1.65 |
| 196 | F196G | 1.59 |
| 196 | F196S | 1.58 |
| 196 | F196Y | 1.41 |
| 196 | F196V | 1.40 |
| 196 | F196I | 1.32 |
| 196 | F196W | 1.01 |
| 197 | T197L | 1.21 |
| 198 | E198R | 1.82 |
| 198 | E198I | 1.80 |
| 198 | E198V | 1.60 |
| 198 | E198W | 1.59 |
| 198 | E198L | 1.57 |
| 198 | E198P | 1.52 |
| 198 | E198Y | 1.48 |
| 198 | E198C | 1.38 |
| 198 | E198F | 1.37 |
| 198 | E198Q | 1.28 |
| 198 | E198T | 1.25 |
| 198 | E198N | 1.24 |
| 198 | E198M | 1.18 |
| 198 | E198S | 1.06 |
| 199 | A199C | 1.77 |
| 199 | A199K | 1.72 |
| 199 | A199E | 1.56 |
| 199 | A199L | 1.38 |
| 199 | A199T | 1.33 |
| 199 | A199R | 1.33 |
| 199 | A199V | 1.32 |
| 199 | A199D | 1.31 |
| 199 | A199H | 1.27 |
| 199 | A199Y | 1.24 |
| 199 | A199F | 1.23 |
| 199 | A199S | 1.20 |
| 199 | A199G | 1.14 |
| 199 | A199M | 1.07 |
| 201 | N201Y | 1.29 |
| 201 | N201F | 1.16 |
| 201 | N201G | 1.08 |
| 202 | R202W | 1.97 |
| 202 | R202F | 1.89 |
| 202 | R202E | 1.69 |
| 202 | R202H | 1.64 |
| 202 | R202T | 1.55 |
| 202 | R202S | 1.49 |
| 202 | R202A | 1.48 |
| 202 | R202C | 1.44 |
| 202 | R202M | 1.43 |
| 202 | R202L | 1.43 |
| 202 | R202G | 1.39 |
| 202 | R202I | 1.33 |
| 203 | D203L | 2.42 |
| 203 | D203R | 2.23 |
| 203 | D203I | 1.99 |
| 203 | D203W | 1.99 |
| 203 | D203F | 1.92 |
| 203 | D203H | 1.84 |
| 203 | D203C | 1.78 |
| 203 | D203S | 1.66 |
| 203 | D203V | 1.66 |
| 203 | D203G | 1.63 |
| 203 | D203Q | 1.60 |
| 203 | D203A | 1.53 |
| 203 | D203E | 1.34 |
| 203 | D203N | 1.05 |

The following Table, provides variants with a PAF PI greater than 1.5.

TABLE 10-3

| PAF PI > 1.5 | |
|---|---|
| Wild-Type Residue/Pos. | Variant Amino Acid(s) |
| A2 | W |
| C7 | H, I, K, Y |
| D10 | K, L, W, Y |
| L12 | C, Q |
| G15 | A |
| E20 | C, G, H, L, S, T, V, W |
| D21 | K, W |
| G22 | A |
| T25 | G, S |
| E26 | A, M |
| A29 | G, R, V, W, Y |
| D31 | L, W |

TABLE 10-3-continued

| PAF PI > 1.5 | |
|---|---|
| Wild-Type Residue/Pos. | Variant Amino Acid(s) |
| Q40 | G, I, K, L, N, R, S, T, W, Y |
| L42 | H, K, W |
| A44 | C, F, L, V |
| E47 | R, T |
| L53 | H |
| S54 | A, I, L, P, R, V |
| A55 | G, T |
| T57 | R, S |
| P63 | G |
| P66 | H, I, R, V |
| R67 | N |
| N69 | K, V |
| A71 | G, H, I, S, T |
| L74 | G, S |
| P75 | R |
| L78 | E, G, H, N, Q, T, V |
| A79 | H, I, L |
| H81 | K |
| D85 | H, N, Q, R, S |
| T93 | F, Y |
| D95 | E |
| K97 | R |
| A98 | G, H, I, L, S, T, Y |
| P104 | C, E, F, G, H, I, N, R, S, T, V, W |
| L105 | C, P |
| I107 | E, G, N, S |
| L109 | N |
| M111 | I, K, L |
| V113 | L |
| Q117 | A, F, G, H, M, R, S, T, V, W, Y |
| G123 | D, H, I, L, T |
| G124 | I, L |
| V125 | A, G, P, S |
| G126 | T |
| T127 | H |
| A131 | G, H, L, P, R, V, W, Y |
| P132 | Y |
| V134 | G |
| P140 | A, T, |
| P141 | G, H, I, L, R, S, T, V |
| L142 | K, W |
| A143 | F, H, K, L, P, Q, R, S, T, V, W |
| P144 | F, H, K, R, S, Y |
| M145 | L |
| P148 | A, K, L, R, T, V |
| I153 | K |
| G157 | R, T |
| E158 | F, H, K, L, R, S, V, W, Y |
| T161 | H, R, Y |
| A165 | T |
| Y168 | G, T |
| A170 | G, I, K |
| L171 | H, I, K, T |
| A172 | I, S |
| F174 | G, P |
| M175 | G, L, Q, R, T, V |
| P178 | L |
| F196 | C, G, H, L, M, S |
| G190 | W |
| E198 | I, L, P, R, V, W |
| A199 | C, E, K |
| R202 | E, F, H, T, W |
| D203 | A, C, F, G, H, I, L, Q, R,S, V, W |
| V206 | E, F, G, H, K, R, S, |
| A209 | K |
| E210 | H, K, S, T, V, W |
| Q211 | K |
| V212 | W |

Table 10-4 provides variants with PAF PI values greater than 2.0.

TABLE 10-4

| Variants with PAF PI > 2.0 | |
|---|---|
| Wild-Type Residue/Pos. | Amino Acid Variant(s) |
| C7 | K, Y |
| D10 | K. L, W |
| L12 | C, Q |
| E20 | G, H, L, S, T, V, W |
| E26 | M |
| Q40 | I, K, L, T, W |
| L42 | K, W |
| A44 | F, V |
| E47 | R |
| L53 | H |
| S54 | A, I, L, P, R, V |
| L74 | S |
| L78 | E, G, H, N |
| D85 | Q, R, S |
| T93 | F, Y |
| D95 | E |
| K97 | R |
| A98 | H, I, L, Y |
| P104 | G, H, I, S, T. V, W |
| I107 | E, S |
| Q117 | A, G, H, T, V, W, Y |
| V125 | G |
| P141 | H, I, L |
| L142 | W |
| A143 | H, K, L, R, T, V, W |
| P144 | K, Y |
| P148 | V |
| E158 | F, H, K |
| T161 | R, Y |
| L171 | K |
| M175 | G, T |
| D203 | L, R |
| V206 | E, F, K |
| E210 | T |

The following Table provides PAD assay results for various variants.

TABLE 10-5

| PAD Assay Results | | | |
|---|---|---|---|
| Position | WT/Pos/ Mutation | Variant | PAD Perf. Ind. |
| 1 | M001A | A | <0.01 |
| 1 | M001E | E | <0.01 |
| 1 | M001F | F | <0.01 |
| 1 | M001G | G | <0.01 |
| 1 | M001K | K | <0.01 |
| 1 | M001N | N | <0.01 |
| 1 | M001P | P | <0.01 |
| 1 | M001R | R | <0.01 |
| 1 | M001S | S | <0.01 |
| 1 | M001T | T | <0.01 |
| 1 | M001W | W | <0.01 |
| 1 | M001V | V | 0.944944 |
| 3 | K003V | V | 0.835476 |
| 4 | R004L | L | <0.01 |
| 4 | R004V | V | 0.079216 |
| 4 | R004I | I | 0.153122 |
| 4 | R004W | W | 0.484006 |
| 4 | R004G | G | 0.78952 |
| 4 | R004S | S | 0.907174 |
| 4 | R004E | E | 0.970668 |
| 4 | R004Y | Y | 0.983327 |
| 4 | R004H | H | 0.986096 |
| 4 | R004Q | Q | 0.98766 |
| 4 | R004T | T | 0.999841 |

TABLE 10-5-continued

PAD Assay Results

| Position | WT/Pos/ Mutation | Variant | PAD Perf. Ind. |
|---|---|---|---|
| 5 | I005G | G | <0.01 |
| 5 | I005N | N | <0.01 |
| 5 | I005P | P | <0.01 |
| 5 | I005R | R | <0.01 |
| 5 | I005W | W | <0.01 |
| 5 | I005F | F | 0.15045 |
| 5 | I005S | S | 0.367738 |
| 5 | I005H | H | 0.626022 |
| 5 | I005T | T | 0.7212 |
| 5 | I005V | V | 0.917243 |
| 6 | L006S | S | <0.01 |
| 6 | L006K | K | <0.01 |
| 6 | L006G | G | <0.01 |
| 6 | L006H | H | <0.01 |
| 6 | L006R | R | <0.01 |
| 6 | L006W | W | <0.01 |
| 6 | L006E | E | <0.01 |
| 6 | L006Q | Q | <0.01 |
| 6 | L006V | V | 0.352616 |
| 6 | L006T | T | 0.354148 |
| 6 | L006I | I | 0.819654 |
| 7 | C007S | S | <0.01 |
| 7 | C007R | R | <0.01 |
| 7 | C007L | L | <0.01 |
| 7 | C007P | P | <0.01 |
| 7 | C007T | T | <0.01 |
| 7 | C007W | W | <0.01 |
| 7 | C007Y | Y | 0.544454 |
| 7 | C007M | M | 0.678238 |
| 7 | C007G | G | 0.686018 |
| 10 | D010W | W | <0.01 |
| 10 | D010K | K | <0.01 |
| 10 | D010Y | Y | <0.01 |
| 10 | D010T | T | <0.01 |
| 10 | D010I | I | <0.01 |
| 10 | D010V | V | <0.01 |
| 10 | D010S | S | <0.01 |
| 10 | D010G | G | <0.01 |
| 10 | D010R | R | <0.01 |
| 10 | D010A | A | <0.01 |
| 10 | D010M | M | <0.01 |
| 10 | D010N | N | <0.01 |
| 10 | D010P | P | <0.01 |
| 10 | D010E | E | 0.147899 |
| 11 | S011T | T | <0.01 |
| 11 | S011V | V | <0.01 |
| 11 | S011D | D | <0.01 |
| 11 | S011E | E | <0.01 |
| 11 | S011F | F | <0.01 |
| 11 | S011G | G | <0.01 |
| 11 | S011L | L | <0.01 |
| 11 | S011Q | Q | <0.01 |
| 11 | S011R | R | <0.01 |
| 11 | S011H | H | 0.332012 |
| 11 | S011K | K | 0.399168 |
| 11 | S011A | A | 0.528328 |
| 11 | S011I | I | 0.562735 |
| 12 | L012V | V | <0.01 |
| 12 | L012S | S | <0.01 |
| 12 | L012G | G | <0.01 |
| 12 | L012R | R | <0.01 |
| 12 | L012D | D | <0.01 |
| 12 | L012P | P | <0.01 |
| 12 | L012W | W | <0.0162738575856614 |
| 12 | L012T | T | 0.064264 |
| 12 | L012A | A | 0.074567 |
| 12 | L012K | K | 0.134919 |
| 12 | L012H | H | 0.164894 |
| 12 | L012F | F | 0.171369 |
| 12 | L012Q | Q | 0.219754 |
| 12 | L012C | C | 0.221492 |
| 12 | L012N | N | 0.655242 |
| 13 | T013F | F | <0.01 |
| 13 | T013R | R | <0.01 |
| 13 | T013W | W | <0.01 |
| 13 | T013Q | Q | 0.508867 |
| 13 | T013V | V | 0.625148 |
| 13 | T013S | S | 0.682494 |
| 13 | T013G | G | 0.768701 |
| 14 | W014I | I | <0.01 |
| 14 | W014S | S | <0.01 |
| 14 | W014G | G | <0.01 |
| 14 | W014K | K | <0.01 |
| 14 | W014V | V | <0.01 |
| 14 | W014L | L | <0.01 |
| 14 | W014T | T | <0.01 |
| 14 | W014R | R | <0.01 |
| 14 | W014N | N | <0.01 |
| 14 | W014P | P | <0.01 |
| 14 | W014E | E | 0.150043 |
| 14 | W014F | F | 0.218073 |
| 14 | W014A | A | 0.271277 |
| 14 | W014Y | Y | 0.64896 |
| 14 | W014W | W | 0.989643 |
| 15 | G015C | C | <0.01 |
| 15 | G015N | N | <0.01 |
| 15 | G015D | D | <0.01 |
| 15 | G015E | E | <0.01 |
| 15 | G015H | H | <0.01 |
| 15 | G015K | K | <0.01 |
| 15 | G015L | L | <0.01 |
| 15 | G015P | P | <0.01 |
| 15 | G015R | R | <0.01 |
| 15 | G015Y | Y | <0.01 |
| 15 | G015A | A | 0.614319 |
| 15 | G015S | S | 0.631317 |
| 16 | W016S | S | <0.01 |
| 16 | W016G | G | <0.01 |
| 16 | W016H | H | <0.01 |
| 16 | W016N | N | <0.01 |
| 16 | W016R | R | <0.01 |
| 16 | W016T | T | <0.01 |
| 16 | W016P | P | 0.150383 |
| 16 | W016Q | Q | 0.312038 |
| 16 | W016M | M | 0.370155 |
| 16 | W016A | A | 0.553088 |
| 16 | W016D | D | 0.569713 |
| 16 | W016E | E | 0.647375 |
| 16 | W016V | V | 0.875327 |
| 17 | V017A | A | 0.675391 |
| 17 | V017E | E | 0.749717 |
| 17 | V017G | G | 0.838345 |
| 17 | V017K | K | 0.844479 |
| 17 | V017F | F | 0.847091 |
| 17 | V017T | T | 0.861827 |
| 17 | V017Y | Y | 0.876678 |
| 17 | V017R | R | 0.936013 |
| 17 | V017P | P | 0.956795 |
| 17 | V017I | I | 0.993337 |
| 17 | V017L | L | 0.996217 |
| 18 | P018A | A | <0.01 |
| 18 | P018M | M | <0.01 |
| 18 | P018S | S | 0.066689 |
| 19 | V019P | P | <0.01 |
| 19 | V019M | M | 0.117174 |
| 19 | V019R | R | 0.343385 |
| 19 | V019Q | Q | 0.395965 |
| 19 | V019A | A | 0.554598 |
| 19 | V019G | G | 0.55596 |
| 19 | V019S | S | 0.573928 |
| 19 | V019E | E | 0.620236 |
| 19 | V019Y | Y | 0.696626 |
| 19 | V019D | D | 0.785756 |
| 19 | V019L | L | 0.910961 |
| 19 | V019K | K | 0.965611 |
| 21 | D021V | V | <0.01 |
| 21 | D021P | P | 0.534939 |
| 21 | D021S | S | 0.689672 |
| 21 | D021E | E | 0.864655 |
| 21 | D021F | F | 0.876655 |

TABLE 10-5-continued

PAD Assay Results

| Position | WT/Pos/ Mutation | Variant | PAD Perf. Ind. |
|---|---|---|---|
| 21 | D021W | W | 0.894205 |
| 21 | D021L | L | 0.971454 |
| 22 | G022K | K | <0.01 |
| 22 | G022W | W | 0.231005 |
| 22 | G022R | R | 0.563069 |
| 22 | G022V | V | 0.850851 |
| 22 | G022S | S | 0.981692 |
| 23 | A023R | R | 0.283095 |
| 23 | A023S | S | 0.335177 |
| 23 | A023G | G | 0.350575 |
| 23 | A023F | F | 0.438047 |
| 23 | A023V | V | 0.598414 |
| 23 | A023Q | Q | 0.732052 |
| 23 | A023P | P | 0.733451 |
| 23 | A023W | W | 0.801206 |
| 23 | A023M | M | 0.946802 |
| 23 | A023Y | Y | 0.962455 |
| 24 | P024S | S | 0.614708 |
| 24 | P024Q | Q | 0.652848 |
| 24 | P024T | T | 0.663925 |
| 24 | P024A | A | 0.681992 |
| 24 | P024G | G | 0.755229 |
| 24 | P024I | I | 0.853247 |
| 24 | P024R | R | 0.907892 |
| 24 | P024H | H | 0.969695 |
| 25 | T025P | P | <0.01 |
| 25 | T025H | H | <0.01 |
| 25 | T025L | L | <0.01 |
| 25 | T025R | R | <0.01 |
| 25 | T025M | M | <0.01 |
| 25 | T025E | E | <0.01 |
| 25 | T025D | D | <0.01 |
| 25 | T025K | K | 0.133406 |
| 25 | T025W | W | 0.144315 |
| 25 | T025I | I | 0.350917 |
| 25 | T025G | G | 0.426214 |
| 25 | T025C | C | 0.509792 |
| 25 | T025V | V | 0.514769 |
| 25 | T025S | S | 0.576256 |
| 25 | T025A | A | 0.863346 |
| 26 | E026S | S | 0.280953 |
| 26 | E026T | T | 0.39705 |
| 26 | E026W | W | 0.471182 |
| 26 | E026N | N | 0.47572 |
| 26 | E026R | R | 0.813632 |
| 26 | E026G | G | 0.869755 |
| 26 | E026C | C | 0.939981 |
| 26 | E026V | V | 0.966156 |
| 26 | E026P | P | 0.993535 |
| 27 | R027W | W | <0.01 |
| 27 | R027T | T | <0.0149789677895526 |
| 27 | R027P | P | 0.483512 |
| 27 | R027C | C | 0.58498 |
| 27 | R027S | S | 0.686775 |
| 27 | R027G | G | 0.836174 |
| 27 | R027E | E | 0.925988 |
| 27 | R027V | V | 0.943209 |
| 28 | F028G | G | <0.01 |
| 28 | F028H | H | <0.01 |
| 28 | F028I | I | <0.01 |
| 28 | F028R | R | <0.01 |
| 28 | F028P | P | 0.385272 |
| 28 | F028V | V | 0.531941 |
| 28 | F028S | S | 0.696363 |
| 29 | A029V | V | 0.43718 |
| 29 | A029T | T | 0.467508 |
| 29 | A029S | S | 0.546873 |
| 29 | A029Y | Y | 0.593264 |
| 29 | A029P | P | 0.622623 |
| 29 | A029R | R | 0.728312 |
| 29 | A029W | W | 0.738583 |
| 29 | A029M | M | 0.768108 |
| 29 | A029G | G | 0.802278 |
| 29 | A029E | E | 0.844095 |
| 29 | A029D | D | 0.996225 |

TABLE 10-5-continued

PAD Assay Results

| Position | WT/Pos/ Mutation | Variant | PAD Perf. Ind. |
|---|---|---|---|
| 30 | P030M | M | 0.78893 |
| 30 | P030Q | Q | 0.905135 |
| 30 | P030A | A | 0.918048 |
| 31 | D031E | E | 0.882779 |
| 32 | V032P | P | <0.01 |
| 32 | V032R | R | 0.715259 |
| 33 | R033D | D | <0.01 |
| 33 | R033E | E | <0.01 |
| 33 | R033H | H | <0.01 |
| 33 | R033P | P | <0.01 |
| 33 | R033W | W | <0.01 |
| 33 | R033V | V | 0.935183 |
| 34 | W034R | R | <0.01 |
| 34 | W034E | E | <0.01 |
| 34 | W034K | K | <0.01 |
| 34 | W034Q | Q | 0.041311 |
| 34 | W034S | S | 0.079486 |
| 34 | W034T | T | 0.153641 |
| 34 | W034V | V | 0.72591 |
| 34 | W034G | G | 0.880049 |
| 34 | W034I | I | 0.93831 |
| 35 | T035Q | Q | <0.01 |
| 35 | T035N | N | <0.01 |
| 35 | T035R | R | <0.01 |
| 35 | T035K | K | <0.01 |
| 35 | T035L | L | <0.01 |
| 35 | T035P | P | <0.01 |
| 35 | T035W | W | <0.01 |
| 35 | T035Y | Y | <0.01 |
| 35 | T035V | V | 0.344374 |
| 36 | G036P | P | <0.01 |
| 36 | G036S | S | 0.25722 |
| 36 | G036T | T | 0.326076 |
| 36 | G036V | V | 0.375828 |
| 36 | G036M | M | 0.536338 |
| 36 | G036N | N | 0.557724 |
| 36 | G036W | W | 0.682701 |
| 36 | G036Q | Q | 0.712029 |
| 36 | G036R | R | 0.897684 |
| 38 | L038K | K | <0.01 |
| 38 | L038G | G | <0.01 |
| 38 | L038E | E | <0.01 |
| 38 | L038P | P | <0.01 |
| 38 | L038Q | Q | <0.01 |
| 38 | L038R | R | <0.01 |
| 38 | L038W | W | <0.01 |
| 40 | Q040P | P | <0.01 |
| 41 | Q041V | V | <0.01 |
| 41 | Q041S | S | 0.222419 |
| 41 | Q041P | P | 0.662368 |
| 41 | Q041Y | Y | 0.701492 |
| 41 | Q041W | W | 0.878483 |
| 42 | L042W | W | <0.01 |
| 42 | L042H | H | <0.01 |
| 42 | L042T | T | <0.01 |
| 42 | L042D | D | <0.01 |
| 42 | L042Q | Q | 0.280991 |
| 42 | L042S | S | 0.450557 |
| 42 | L042R | R | 0.64188 |
| 42 | L042I | I | 0.658658 |
| 42 | L042V | V | 0.725221 |
| 42 | L042M | M | 0.73687 |
| 42 | L042G | G | 0.759964 |
| 43 | G043S | S | 0.233902 |
| 43 | G043P | P | 0.310899 |
| 43 | G043V | V | 0.332639 |
| 43 | G043Q | Q | 0.475759 |
| 43 | G043R | R | 0.585481 |
| 43 | G043C | C | 0.725373 |
| 43 | G043I | I | 0.766408 |
| 43 | G043K | K | 0.856798 |
| 43 | G043M | M | 0.877674 |
| 43 | G043Y | Y | 0.944457 |
| 43 | G043H | H | 0.957156 |
| 44 | A044S | S | <0.01 |

TABLE 10-5-continued

PAD Assay Results

| Position | WT/Pos/ Mutation | Variant | PAD Perf. Ind. |
|---|---|---|---|
| 44 | A044Y | Y | <0.01 |
| 44 | A044T | T | <0.01 |
| 44 | A044R | R | <0.01 |
| 44 | A044D | D | <0.01 |
| 44 | A044H | H | <0.01 |
| 44 | A044P | P | <0.01 |
| 44 | A044E | E | 0.028463 |
| 44 | A044V | V | 0.504951 |
| 44 | A044F | F | 0.803847 |
| 44 | A044W | W | 0.847767 |
| 44 | A044M | M | 0.975188 |
| 44 | A044L | L | 0.99381 |
| 45 | D045S | S | 0.382964 |
| 45 | D045T | T | 0.438291 |
| 45 | D045R | R | 0.492492 |
| 45 | D045V | V | 0.500129 |
| 45 | D045P | P | 0.531241 |
| 45 | D045Q | Q | 0.568687 |
| 45 | D045W | W | 0.582004 |
| 45 | D045H | H | 0.779564 |
| 45 | D045L | L | 0.781626 |
| 45 | D045M | M | 0.78286 |
| 45 | D045G | G | 0.839279 |
| 45 | D045A | A | 0.841569 |
| 45 | D045C | C | 0.844725 |
| 45 | D045K | K | 0.867296 |
| 46 | F046H | H | <0.01 |
| 46 | F046T | T | 0.429962 |
| 46 | F046W | W | 0.633171 |
| 46 | F046S | S | 0.656356 |
| 46 | F046V | V | 0.786355 |
| 46 | F046I | I | 0.882982 |
| 46 | F046G | G | 0.944614 |
| 47 | E047P | P | 0.357072 |
| 47 | E047R | R | 0.620501 |
| 47 | E047N | N | 0.627512 |
| 47 | E047S | S | 0.628088 |
| 47 | E047M | M | 0.703134 |
| 47 | E047A | A | 0.757492 |
| 47 | E047F | F | 0.763159 |
| 47 | E047C | C | 0.772744 |
| 47 | E047T | T | 0.837562 |
| 47 | E047D | D | 0.975388 |
| 47 | E047H | H | 0.99217 |
| 48 | V048R | R | <0.01 |
| 48 | V048W | W | <0.01 |
| 48 | V048S | S | 0.423613 |
| 48 | V048G | G | 0.873544 |
| 48 | V048N | N | 0.980906 |
| 48 | V048E | E | 0.987222 |
| 49 | I049P | P | 0.161279 |
| 49 | I049R | R | 0.29139 |
| 49 | I049W | W | 0.676641 |
| 49 | I049H | H | 0.740799 |
| 49 | I049S | S | 0.789362 |
| 49 | I049E | E | 0.876247 |
| 49 | I049V | V | 0.972022 |
| 50 | E050R | R | <0.01 |
| 50 | E050W | W | 0.14091 |
| 50 | E050V | V | 0.425221 |
| 50 | E050I | I | 0.575369 |
| 50 | E050S | S | 0.645021 |
| 50 | E050Q | Q | 0.906441 |
| 50 | E050L | L | 0.967983 |
| 51 | E051R | R | <0.01 |
| 51 | E051P | P | <0.01 |
| 51 | E051I | I | 0.044391 |
| 51 | E051W | W | 0.165053 |
| 51 | E051V | V | 0.367755 |
| 51 | E051Q | Q | 0.761883 |
| 51 | E051L | L | 0.927544 |
| 52 | G052H | H | <0.01 |
| 52 | G052S | S | <0.01 |
| 52 | G052V | V | <0.01 |
| 52 | G052T | T | <0.01 |
| 52 | G052M | M | <0.01 |
| 52 | G052F | F | <0.01 |
| 52 | G052I | I | 0.069022 |
| 52 | G052P | P | 0.242545 |
| 52 | G052L | L | 0.244397 |
| 52 | G052Q | Q | 0.283827 |
| 52 | G052R | R | 0.349923 |
| 52 | G052E | E | 0.549067 |
| 52 | G052A | A | 0.793929 |
| 53 | L053R | R | <0.01 |
| 53 | L053W | W | <0.01 |
| 53 | L053P | P | <0.01 |
| 53 | L053D | D | <0.01328259968325 |
| 53 | L053E | E | 0.191623 |
| 53 | L053K | K | 0.237686 |
| 53 | L053S | S | 0.260431 |
| 53 | L053G | G | 0.32712 |
| 53 | L053V | V | 0.652864 |
| 53 | L053I | I | 0.659806 |
| 53 | L053Q | Q | 0.717093 |
| 53 | L053T | T | 0.842042 |
| 54 | S054F | F | <0.01 |
| 54 | S054W | W | <0.01 |
| 54 | S054H | H | <0.01 |
| 54 | S054K | K | 0.083519 |
| 54 | S054I | I | 0.116295 |
| 54 | S054Y | Y | 0.124722 |
| 54 | S054G | G | 0.170484 |
| 54 | S054L | L | 0.258821 |
| 54 | S054V | V | 0.285755 |
| 54 | S054E | E | 0.296919 |
| 54 | S054T | T | 0.329279 |
| 54 | S054R | R | 0.354857 |
| 54 | S054M | M | 0.482666 |
| 54 | S054Q | Q | 0.531633 |
| 54 | S054D | D | 0.647787 |
| 54 | S054C | C | 0.87772 |
| 55 | A055V | V | <0.01 |
| 55 | A055I | I | <0.01 |
| 55 | A055P | P | <0.01 |
| 55 | A055W | W | <0.01 |
| 55 | A055Y | Y | 0.176777 |
| 55 | A055R | R | 0.245648 |
| 55 | A055T | T | 0.415054 |
| 55 | A055G | G | 0.731513 |
| 55 | A055L | L | 0.866592 |
| 55 | A055S | S | 0.866756 |
| 55 | A055H | H | 0.921909 |
| 56 | R056C | C | <0.01 |
| 56 | R056G | G | <0.01 |
| 56 | R056T | T | <0.01 |
| 56 | R056E | E | <0.01 |
| 56 | R056H | H | <0.01 |
| 56 | R056K | K | <0.01 |
| 56 | R056P | P | <0.01 |
| 56 | R056Q | Q | <0.01 |
| 56 | R056W | W | <0.01 |
| 56 | R056Y | Y | <0.01 |
| 56 | R056S | S | 0.123501 |
| 56 | R056L | L | 0.237933 |
| 56 | R056N | N | 0.267811 |
| 56 | R056A | A | 0.68802 |
| 57 | T057R | R | <0.01 |
| 57 | T057P | P | <0.01 |
| 57 | T057W | W | <0.01 |
| 57 | T057N | N | 0.245605 |
| 57 | T057C | C | 0.398001 |
| 57 | T057Y | Y | 0.551709 |
| 57 | T057H | H | 0.605386 |
| 57 | T057A | A | 0.651879 |
| 57 | T057L | L | 0.762087 |
| 57 | T057V | V | 0.86913 |
| 57 | T057I | I | 0.870692 |
| 58 | T058E | E | <0.01 |
| 58 | T058G | G | <0.01 |

TABLE 10-5-continued

PAD Assay Results

| Position | WT/Pos/ Mutation | Variant | PAD Perf. Ind. |
|---|---|---|---|
| 58 | T058K | K | <0.01 |
| 58 | T058P | P | <0.01 |
| 58 | T058R | R | <0.01 |
| 58 | T058W | W | <0.01 |
| 58 | T058Y | Y | <0.01 |
| 58 | T058M | M | 0.026886 |
| 58 | T058A | A | 0.361258 |
| 58 | T058V | V | 0.955494 |
| 58 | T058S | S | 0.964758 |
| 59 | N059R | R | <0.01 |
| 59 | N059M | M | <0.01 |
| 59 | N059P | P | <0.01 |
| 59 | N059Q | Q | 0.165409 |
| 59 | N059T | T | 0.501362 |
| 59 | N059S | S | 0.651989 |
| 59 | N059K | K | 0.731191 |
| 59 | N059E | E | 0.879272 |
| 59 | N059V | V | 0.887341 |
| 59 | N059G | G | 0.890006 |
| 59 | N059F | F | 0.911279 |
| 59 | N059A | A | 0.929578 |
| 59 | N059Y | Y | 0.99189 |
| 59 | N059C | C | 0.99959 |
| 60 | I060P | P | 0.318965 |
| 60 | I060D | D | 0.660273 |
| 60 | I060C | C | 0.668516 |
| 60 | I060M | M | 0.682237 |
| 60 | I060A | A | 0.788799 |
| 60 | I060R | R | 0.809655 |
| 60 | I060L | L | 0.913226 |
| 60 | I060E | E | 0.923286 |
| 60 | I060K | K | 0.959958 |
| 60 | I060S | S | 0.999829 |
| 61 | D061F | F | 0.698154 |
| 61 | D061A | A | 0.708121 |
| 61 | D061C | C | 0.848446 |
| 61 | D061Y | Y | 0.948278 |
| 61 | D061V | V | 0.968066 |
| 61 | D061N | N | 0.999276 |
| 62 | D062T | T | <0.01 |
| 62 | D062I | I | <0.01 |
| 62 | D062V | V | <0.01 |
| 62 | D062H | H | <0.01 |
| 62 | D062W | W | <0.01 |
| 62 | D062S | S | <0.01 |
| 62 | D062L | L | <0.01 |
| 62 | D062G | G | <0.01 |
| 62 | D062R | R | <0.01 |
| 62 | D062M | M | <0.01 |
| 62 | D062P | P | <0.01 |
| 62 | D062Q | Q | <0.01 |
| 62 | D062A | A | 0.113753 |
| 62 | D062C | C | 0.490736 |
| 62 | D062E | E | 0.602369 |
| 63 | P063A | A | 0.598416 |
| 63 | P063R | R | 0.801911 |
| 63 | P063S | S | 0.898408 |
| 63 | P063M | M | 0.908904 |
| 63 | P063F | F | 0.925844 |
| 63 | P063Y | Y | 0.948378 |
| 64 | T064R | R | 0.106209 |
| 64 | T064D | D | 0.640095 |
| 64 | T064W | W | 0.691185 |
| 64 | T064Q | Q | 0.865168 |
| 64 | T064C | C | 0.876862 |
| 64 | T064P | P | 0.936023 |
| 64 | T064H | H | 0.960718 |
| 64 | T064N | N | 0.983933 |
| 64 | T064S | S | 0.987972 |
| 65 | D065V | V | 0.199467 |
| 65 | D065R | R | 0.215599 |
| 65 | D065H | H | 0.398178 |
| 65 | D065Y | Y | 0.42301 |
| 65 | D065P | P | 0.423122 |
| 65 | D065S | S | 0.468174 |

TABLE 10-5-continued

PAD Assay Results

| Position | WT/Pos/ Mutation | Variant | PAD Perf. Ind. |
|---|---|---|---|
| 65 | D065W | W | 0.50219 |
| 65 | D065T | T | 0.5039 |
| 65 | D065G | G | 0.51655 |
| 65 | D065I | I | 0.617391 |
| 65 | D065A | A | 0.723321 |
| 66 | P066N | N | 0.381273 |
| 66 | P066Q | Q | 0.422614 |
| 66 | P066G | G | 0.444859 |
| 66 | P066R | R | 0.508806 |
| 66 | P066C | C | 0.523524 |
| 66 | P066A | A | 0.563865 |
| 66 | P066F | F | 0.672865 |
| 66 | P066Y | Y | 0.699931 |
| 66 | P066D | D | 0.718749 |
| 66 | P066I | I | 0.844376 |
| 66 | P066V | V | 0.89302 |
| 66 | P066H | H | 0.947771 |
| 66 | P066L | L | 0.987271 |
| 67 | R067F | F | <0.0149736260903786 |
| 67 | R067W | W | <0.0171329732205367 |
| 67 | R067P | P | 0.036575 |
| 67 | R067E | E | 0.113415 |
| 67 | R067V | V | 0.1203 |
| 67 | R067Q | Q | 0.126838 |
| 67 | R067L | L | 0.156654 |
| 67 | R067A | A | 0.215271 |
| 67 | R067T | T | 0.315404 |
| 67 | R067N | N | 0.333066 |
| 67 | R067G | G | 0.40823 |
| 67 | R067K | K | 0.986487 |
| 68 | L068G | G | <0.01 |
| 68 | L068A | A | <0.01 |
| 68 | L068M | M | 0.02834 |
| 68 | L068C | C | 0.05996 |
| 68 | L068S | S | 0.071622 |
| 68 | L068N | N | 0.100981 |
| 68 | L068E | E | 0.131505 |
| 68 | L068H | H | 0.222734 |
| 68 | L068Q | Q | 0.254448 |
| 68 | L068F | F | 0.254797 |
| 68 | L068T | T | 0.324904 |
| 68 | L068P | P | 0.35297 |
| 68 | L068D | D | 0.443469 |
| 68 | L068Y | Y | 0.447862 |
| 68 | L068R | R | 0.465293 |
| 68 | L068V | V | 0.507389 |
| 68 | L068W | W | 0.561612 |
| 68 | L068I | I | 0.727312 |
| 69 | N069Y | Y | 0.173925 |
| 69 | N069W | W | 0.55063 |
| 69 | N069P | P | 0.591783 |
| 69 | N069R | R | 0.828172 |
| 69 | N069G | G | 0.976332 |
| 70 | G070M | M | <0.01 |
| 70 | G070T | T | <0.01 |
| 70 | G070P | P | <0.01 |
| 70 | G070V | V | <0.01 |
| 70 | G070C | C | <0.01 |
| 70 | G070R | R | <0.01 |
| 70 | G070Y | Y | <0.01 |
| 70 | G070K | K | <0.01 |
| 70 | G070N | N | <0.01 |
| 70 | G070Q | Q | <0.01 |
| 70 | G070F | F | <0.01 |
| 70 | G070I | I | 0.270463 |
| 70 | G070E | E | 0.33356 |
| 70 | G070S | S | 0.638917 |
| 71 | A071P | P | <0.01 |
| 71 | A071N | N | 0.613838 |
| 71 | A071D | D | 0.646588 |
| 71 | A071G | G | 0.675895 |
| 71 | A071S | S | 0.693249 |
| 71 | A071R | R | 0.771492 |
| 71 | A071H | H | 0.781953 |
| 71 | A071I | I | 0.786894 |

TABLE 10-5-continued

| PAD Assay Results | | | |
|---|---|---|---|
| Position | WT/Pos/ Mutation | Variant | PAD Perf. Ind. |
| 71 | A071T | T | 0.79386 |
| 71 | A071E | E | 0.809505 |
| 71 | A071L | L | 0.838126 |
| 71 | A071F | F | 0.985677 |
| 71 | A071C | C | 0.993683 |
| 72 | S072Y | Y | 0.069096 |
| 72 | S072W | W | 0.339835 |
| 72 | S072P | P | 0.555612 |
| 72 | S072Q | Q | 0.655328 |
| 72 | S072L | L | 0.703483 |
| 72 | S072R | R | 0.742354 |
| 72 | S072D | D | 0.800127 |
| 72 | S072V | V | 0.82827 |
| 72 | S072E | E | 0.930527 |
| 72 | S072T | T | 0.973836 |
| 73 | Y073P | P | <0.01 |
| 73 | Y073R | R | 0.262561 |
| 73 | Y073L | L | 0.497588 |
| 73 | Y073G | G | 0.509699 |
| 73 | Y073H | H | 0.515737 |
| 73 | Y073I | I | 0.641914 |
| 73 | Y073S | S | 0.676285 |
| 73 | Y073V | V | 0.73535 |
| 73 | Y073N | N | 0.758401 |
| 73 | Y073D | D | 0.803442 |
| 73 | Y073Q | Q | 0.866092 |
| 73 | Y073K | K | 0.944166 |
| 76 | S076W | W | <0.01 |
| 76 | S076Y | Y | 0.177113 |
| 76 | S076F | F | 0.461095 |
| 76 | S076Q | Q | 0.900789 |
| 77 | C077Y | Y | <0.01 |
| 77 | C077R | R | <0.01 |
| 77 | C077W | W | <0.01 |
| 77 | C077F | F | <0.01 |
| 77 | C077N | N | <0.01 |
| 77 | C077P | P | <0.01 |
| 77 | C077G | G | 0.181068 |
| 77 | C077L | L | 0.734708 |
| 77 | C077S | S | 0.764136 |
| 77 | C077V | V | 0.802259 |
| 77 | C077A | A | 0.912937 |
| 78 | L078E | E | <0.01 |
| 78 | L078N | N | <0.01 |
| 78 | L078A | A | <0.01 |
| 78 | L078P | P | <0.01 |
| 78 | L078R | R | <0.01 |
| 78 | L078S | S | <0.01 |
| 78 | L078M | M | 0.477538 |
| 78 | L078Q | Q | 0.519566 |
| 78 | L078C | C | 0.779536 |
| 78 | L078Y | Y | 0.809511 |
| 78 | L078V | V | 0.827484 |
| 79 | A079H | H | <0.01 |
| 79 | A079F | F | <0.01 |
| 79 | A079V | V | <0.01 |
| 79 | A079C | C | 0.026887 |
| 79 | A079Q | Q | 0.268704 |
| 79 | A079E | E | 0.272158 |
| 79 | A079N | N | 0.281684 |
| 79 | A079M | M | 0.284387 |
| 79 | A079R | R | 0.321618 |
| 79 | A079W | W | 0.530746 |
| 79 | A079T | T | 0.598368 |
| 79 | A079I | I | 0.673986 |
| 79 | A079S | S | 0.779628 |
| 79 | A079G | G | 0.915372 |
| 79 | A079P | P | 0.94147 |
| 79 | A079L | L | 0.958677 |
| 80 | T080W | W | <0.01 |
| 80 | T080L | L | <0.01 |
| 80 | T080K | K | <0.01 |
| 80 | T080R | R | <0.01 |
| 80 | T080E | E | <0.01 |
| 80 | T080P | P | <0.01 |

TABLE 10-5-continued

| PAD Assay Results | | | |
|---|---|---|---|
| Position | WT/Pos/ Mutation | Variant | PAD Perf. Ind. |
| 80 | T080H | H | 0.049717 |
| 80 | T080Y | Y | 0.107973 |
| 80 | T080I | I | 0.146188 |
| 80 | T080N | N | 0.529867 |
| 82 | L082R | R | <0.01 |
| 82 | L082S | S | <0.01 |
| 82 | L082W | W | <0.01 |
| 82 | L082V | V | 0.187819 |
| 82 | L082G | G | 0.310823 |
| 82 | L082T | T | 0.377413 |
| 82 | L082H | H | 0.468806 |
| 82 | L082I | I | 0.508005 |
| 82 | L082K | K | 0.508537 |
| 82 | L082P | P | 0.516154 |
| 82 | L082A | A | 0.976228 |
| 83 | P083T | T | <0.01 |
| 83 | P083V | V | 0.186837 |
| 83 | P083L | L | 0.211018 |
| 83 | P083H | H | 0.611439 |
| 83 | P083W | W | 0.621496 |
| 83 | P083G | G | 0.677444 |
| 83 | P083S | S | 0.789585 |
| 83 | P083Q | Q | 0.818267 |
| 83 | P083D | D | 0.831344 |
| 83 | P083F | F | 0.99445 |
| 84 | L084W | W | <0.01 |
| 84 | L084V | V | 0.416576 |
| 84 | L084P | P | 0.43025 |
| 84 | L084T | T | 0.438956 |
| 84 | L084A | A | 0.453182 |
| 84 | L084Q | Q | 0.516002 |
| 84 | L084S | S | 0.550862 |
| 84 | L084R | R | 0.565943 |
| 84 | L084N | N | 0.665228 |
| 84 | L084K | K | 0.79008 |
| 84 | L084D | D | 0.85276 |
| 84 | L084I | I | 0.870124 |
| 84 | L084H | H | 0.993217 |
| 85 | D085I | I | 0.100248 |
| 85 | D085L | L | 0.241561 |
| 85 | D085V | V | 0.25268 |
| 85 | D085W | W | 0.341677 |
| 85 | D085P | P | 0.543807 |
| 85 | D085Y | Y | 0.554364 |
| 85 | D085S | S | 0.675803 |
| 85 | D085T | T | 0.708548 |
| 85 | D085N | N | 0.781957 |
| 85 | D085Q | Q | 0.988545 |
| 86 | L086H | H | <0.01 |
| 86 | L086S | S | <0.01 |
| 86 | L086R | R | <0.01 |
| 86 | L086E | E | <0.01 |
| 86 | L086F | F | <0.01 |
| 86 | L086Q | Q | <0.01 |
| 86 | L086W | W | 0.077717 |
| 86 | L086V | V | 0.120133 |
| 86 | L086T | T | 0.284184 |
| 86 | L086G | G | 0.696393 |
| 86 | L086Y | Y | 0.815121 |
| 86 | L086P | P | 0.987233 |
| 87 | V087S | S | <0.01 |
| 87 | V087G | G | <0.01 |
| 87 | V087Y | Y | <0.01 |
| 87 | V087R | R | <0.01 |
| 87 | V087K | K | <0.01 |
| 87 | V087D | D | <0.01 |
| 87 | V087F | F | 0.103908 |
| 87 | V087T | T | 0.147618 |
| 87 | V087A | A | 0.16806 |
| 87 | V087M | M | 0.751854 |
| 89 | I089H | H | <0.01 |
| 89 | I089S | S | <0.01 |
| 89 | I089G | G | <0.01 |
| 89 | I089W | W | <0.01 |
| 89 | I089Q | Q | <0.01 |

TABLE 10-5-continued

PAD Assay Results

| Position | WT/Pos/ Mutation | Variant | PAD Perf. Ind. |
|---|---|---|---|
| 89 | I089D | D | <0.01 |
| 89 | I089E | E | <0.01 |
| 89 | I089R | R | <0.01 |
| 89 | I089F | F | 0.745747 |
| 89 | I089V | V | 0.820031 |
| 89 | I089T | T | 0.900425 |
| 94 | N094L | L | <0.01 |
| 94 | N094T | T | <0.01 |
| 94 | N094V | V | <0.01 |
| 94 | N094H | H | <0.01 |
| 94 | N094R | R | <0.01 |
| 94 | N094W | W | <0.01 |
| 94 | N094M | M | 0.031458 |
| 94 | N094C | C | 0.072751 |
| 94 | N094Y | Y | 0.123924 |
| 94 | N094G | G | 0.532837 |
| 94 | N094A | A | 0.74316 |
| 94 | N094P | P | 0.789771 |
| 94 | N094S | S | 0.877698 |
| 95 | D095A | A | <0.01 |
| 95 | D095C | C | <0.01 |
| 95 | D095G | G | <0.01 |
| 95 | D095H | H | <0.01 |
| 95 | D095K | K | <0.01 |
| 95 | D095L | L | <0.01 |
| 95 | D095N | N | <0.01 |
| 95 | D095Q | Q | <0.01 |
| 95 | D095R | R | <0.01 |
| 95 | D095S | S | <0.01 |
| 95 | D095T | T | <0.01 |
| 95 | D095V | V | <0.01 |
| 95 | D095W | W | <0.01 |
| 95 | D095Y | Y | <0.01 |
| 95 | D095E | E | 0.754335 |
| 96 | T096I | I | <0.01 |
| 96 | T096W | W | <0.01 |
| 96 | T096Y | Y | <0.01 |
| 96 | T096R | R | 0.136108 |
| 96 | T096V | V | 0.58611 |
| 96 | T096S | S | 0.786547 |
| 96 | T096P | P | 0.885134 |
| 97 | K097Q | Q | <0.01 |
| 97 | K097G | G | <0.01 |
| 97 | K097I | I | <0.01 |
| 97 | K097W | W | <0.01 |
| 97 | K097L | L | <0.01 |
| 97 | K097V | V | <0.01 |
| 97 | K097Y | Y | <0.01 |
| 97 | K097S | S | <0.01 |
| 97 | K097T | T | <0.01 |
| 97 | K097D | D | <0.01 |
| 97 | K097M | M | 0.216645 |
| 97 | K097A | A | 0.227977 |
| 97 | K097P | P | 0.26585 |
| 97 | K097R | R | 0.587184 |
| 99 | Y099R | R | 0.291941 |
| 99 | Y099V | V | 0.311502 |
| 99 | Y099S | S | 0.367181 |
| 99 | Y099W | W | 0.566038 |
| 99 | Y099H | H | 0.591623 |
| 99 | Y099I | I | 0.60574 |
| 99 | Y099G | G | 0.700083 |
| 99 | Y099P | P | 0.813989 |
| 99 | Y099A | A | 0.822549 |
| 99 | Y099L | L | 0.856204 |
| 100 | F100W | W | <0.01 |
| 100 | F100K | K | <0.01 |
| 100 | F100D | D | <0.01 |
| 100 | F100E | E | 0.152427 |
| 100 | F100S | S | 0.852784 |
| 101 | R101W | W | <0.01 |
| 101 | R101K | K | 0.068708 |
| 101 | R101Q | Q | 0.107171 |
| 101 | R101V | V | 0.442582 |
| 101 | R101D | D | 0.800722 |

TABLE 10-5-continued

PAD Assay Results

| Position | WT/Pos/ Mutation | Variant | PAD Perf. Ind. |
|---|---|---|---|
| 101 | R101Y | Y | 0.803109 |
| 101 | R101P | P | 0.855496 |
| 101 | R101N | N | 0.918012 |
| 101 | R101C | C | 0.946306 |
| 101 | R101I | I | 0.955711 |
| 101 | R101F | F | 0.965422 |
| 102 | R102W | W | <0.01 |
| 102 | R102F | F | 0.226881 |
| 102 | R102G | G | 0.270733 |
| 102 | R102C | C | 0.363718 |
| 102 | R102V | V | 0.60605 |
| 102 | R102D | D | 0.684234 |
| 102 | R102P | P | 0.894709 |
| 102 | R102S | S | 0.960127 |
| 103 | T103W | W | <0.01 |
| 103 | T103Y | Y | <0.01 |
| 103 | T103G | G | <0.01 |
| 103 | T103K | K | <0.01 |
| 103 | T103I | I | <0.01 |
| 103 | T103L | L | <0.01 |
| 103 | T103H | H | <0.01 |
| 103 | T103A | A | <0.01 |
| 103 | T103V | V | <0.01 |
| 103 | T103S | S | <0.01 |
| 103 | T103C | C | <0.01 |
| 103 | T103R | R | <0.01 |
| 103 | T103N | N | <0.01 |
| 103 | T103F | F | <0.01 |
| 103 | T103P | P | <0.01 |
| 104 | P104R | R | <0.01 |
| 104 | P104A | A | <0.01 |
| 104 | P104L | L | <0.01 |
| 104 | P104W | W | 0.232802 |
| 104 | P104T | T | 0.333526 |
| 104 | P104S | S | 0.529113 |
| 104 | P104Q | Q | 0.847699 |
| 104 | P104F | F | 0.863543 |
| 104 | P104G | G | 0.984538 |
| 105 | L105V | V | <0.01 |
| 105 | L105A | A | <0.01 |
| 105 | L105M | M | <0.01 |
| 105 | L105E | E | 0.528458 |
| 105 | L105S | S | 0.609931 |
| 105 | L105Y | Y | 0.620029 |
| 105 | L105T | T | 0.638962 |
| 105 | L105P | P | 0.902642 |
| 106 | D106R | R | 0.559786 |
| 106 | D106Q | Q | 0.617485 |
| 106 | D106P | P | 0.632087 |
| 106 | D106N | N | 0.642667 |
| 106 | D106M | M | 0.855673 |
| 106 | D106I | I | 0.915931 |
| 106 | D106L | L | 0.99561 |
| 107 | I107E | E | <0.01 |
| 107 | I107G | G | <0.01 |
| 107 | I107F | F | <0.01 |
| 107 | I107Q | Q | <0.01 |
| 107 | I107R | R | <0.01 |
| 107 | I107H | H | <0.01 |
| 107 | I107W | W | <0.01 |
| 107 | I107P | P | 0.318743 |
| 107 | I107Y | Y | 0.524182 |
| 107 | I107A | A | 0.795478 |
| 107 | I107N | N | 0.929935 |
| 107 | I107V | V | 0.96863 |
| 108 | A108D | D | <0.01 |
| 108 | A108F | F | <0.01 |
| 108 | A108H | H | <0.01 |
| 108 | A108I | I | <0.01 |
| 108 | A108N | N | <0.01 |
| 108 | A108P | P | <0.01 |
| 108 | A108R | R | <0.01 |
| 108 | A108E | E | 0.60726 |
| 108 | A108Q | Q | 0.734472 |
| 108 | A108T | T | 0.865471 |

TABLE 10-5-continued

| PAD Assay Results | | | |
|---|---|---|---|
| Position | WT/Pos/ Mutation | Variant | PAD Perf. Ind. |
| 108 | A108V | V | 0.950481 |
| 109 | L109W | W | <0.01 |
| 109 | L109D | D | 0.106206 |
| 109 | L109I | I | 0.144257 |
| 109 | L109E | E | 0.194168 |
| 109 | L109R | R | 0.210346 |
| 109 | L109H | H | 0.220153 |
| 109 | L109Q | Q | 0.222755 |
| 109 | L109F | F | 0.317718 |
| 109 | L109A | A | 0.323528 |
| 109 | L109S | S | 0.378623 |
| 109 | L109P | P | 0.434661 |
| 109 | L109G | G | 0.51022 |
| 109 | L109V | V | 0.539733 |
| 109 | L109M | M | 0.628881 |
| 109 | L109N | N | 0.658369 |
| 109 | L109T | T | 0.79132 |
| 109 | L109Y | Y | 0.825105 |
| 110 | G110T | T | <0.01 |
| 110 | G110L | L | <0.01 |
| 110 | G110W | W | <0.01 |
| 110 | G110Y | Y | <0.01 |
| 110 | G110P | P | 0.224284 |
| 110 | G110I | I | 0.232219 |
| 110 | G110S | S | 0.30218 |
| 110 | G110Q | Q | 0.343918 |
| 110 | G110R | R | 0.476072 |
| 110 | G110H | H | 0.73456 |
| 110 | G110N | N | 0.770851 |
| 110 | G110M | M | 0.816422 |
| 111 | M111R | R | <0.01 |
| 111 | M111S | S | 0.139078 |
| 111 | M111H | H | 0.192733 |
| 111 | M111G | G | 0.315165 |
| 111 | M111P | P | 0.566892 |
| 111 | M111E | E | 0.668985 |
| 111 | M111L | L | 0.67115 |
| 111 | M111K | K | 0.706165 |
| 111 | M111T | T | 0.763332 |
| 111 | M111F | F | 0.776934 |
| 111 | M111D | D | 0.78777 |
| 111 | M111V | V | 0.92522 |
| 112 | S112Y | Y | <0.01 |
| 112 | S112R | R | <0.01 |
| 112 | S112P | P | <0.01 |
| 112 | S112H | H | 0.380254 |
| 112 | S112V | V | 0.479716 |
| 112 | S112M | M | 0.564157 |
| 112 | S112W | W | 0.582165 |
| 112 | S112K | K | 0.678369 |
| 112 | S112T | T | 0.721644 |
| 112 | S112N | N | 0.850159 |
| 112 | S112F | F | 0.878895 |
| 112 | S112A | A | 0.943049 |
| 113 | V113S | S | 0.572415 |
| 113 | V113G | G | 0.579385 |
| 113 | V113K | K | 0.716865 |
| 113 | V113H | H | 0.763416 |
| 113 | V113W | W | 0.803685 |
| 113 | V113L | L | 0.854963 |
| 113 | V113T | T | 0.861744 |
| 113 | V113D | D | 0.871104 |
| 113 | V113E | E | 0.936465 |
| 113 | V113C | C | 0.937598 |
| 113 | V113F | F | 0.959822 |
| 113 | V113Y | Y | 0.981976 |
| 114 | L114H | H | <0.01 |
| 114 | L114E | E | <0.01 |
| 114 | L114F | F | <0.01 |
| 114 | L114K | K | <0.01 |
| 114 | L114R | R | <0.01 |
| 114 | L114W | W | <0.01 |
| 114 | L114Y | Y | <0.01 |
| 114 | L114Q | Q | 0.115737 |
| 114 | L114P | P | 0.275464 |
| 114 | L114S | S | 0.545726 |
| 114 | L114V | V | 0.595416 |
| 114 | L114N | N | 0.77333 |
| 115 | V115H | H | <0.01 |
| 115 | V115K | K | <0.01 |
| 115 | V115I | I | 0.994833 |
| 116 | T116Y | Y | 0.466112 |
| 116 | T116V | V | 0.571817 |
| 116 | T116R | R | 0.619823 |
| 116 | T116L | L | 0.681201 |
| 116 | T116W | W | 0.748358 |
| 116 | T116I | I | 0.760474 |
| 116 | T116Q | Q | 0.768867 |
| 116 | T116P | P | 0.836786 |
| 116 | T116G | G | 0.901886 |
| 116 | T116E | E | 0.906124 |
| 116 | T116A | A | 0.952003 |
| 116 | T116S | S | 0.963005 |
| 117 | Q117W | W | 0.707035 |
| 117 | Q117V | V | 0.761971 |
| 117 | Q117G | G | 0.794858 |
| 117 | Q117S | S | 0.86512 |
| 118 | V118K | K | <0.01 |
| 118 | V118W | W | <0.01 |
| 118 | V118E | E | <0.01 |
| 118 | V118R | R | 0.069623 |
| 118 | V118P | P | 0.222399 |
| 118 | V118D | D | 0.40168 |
| 118 | V118I | I | 0.545694 |
| 118 | V118G | G | 0.559239 |
| 118 | V118S | S | 0.815888 |
| 118 | V118A | A | 0.852723 |
| 118 | V118T | T | 0.91759 |
| 118 | V118M | M | 0.933469 |
| 118 | V118F | F | 0.998467 |
| 119 | L119G | G | <0.01 |
| 119 | L119S | S | <0.01 |
| 119 | L119F | F | <0.01 |
| 119 | L119R | R | <0.01 |
| 119 | L119P | P | <0.01 |
| 119 | L119T | T | 0.102922 |
| 119 | L119N | N | 0.113151 |
| 119 | L119V | V | 0.150373 |
| 119 | L119W | W | 0.203313 |
| 119 | L119C | C | 0.244106 |
| 119 | L119D | D | 0.280381 |
| 119 | L119E | E | 0.322167 |
| 119 | L119I | I | 0.427476 |
| 119 | L119H | H | 0.462912 |
| 119 | L119Y | Y | 0.556343 |
| 120 | T120P | P | <0.01 |
| 120 | T120H | H | 0.498304 |
| 120 | T120R | R | 0.599376 |
| 120 | T120A | A | 0.663543 |
| 120 | T120Q | Q | 0.781096 |
| 120 | T120C | C | 0.924433 |
| 121 | S121P | P | 0.384623 |
| 121 | S121R | R | 0.701237 |
| 121 | S121W | W | 0.772781 |
| 121 | S121K | K | 0.77795 |
| 121 | S121G | G | 0.992545 |
| 122 | A122G | G | <0.01 |
| 122 | A122D | D | 0.059137 |
| 122 | A122F | F | 0.148369 |
| 122 | A122H | H | 0.169443 |
| 122 | A122R | R | 0.396041 |
| 122 | A122S | S | 0.431258 |
| 122 | A122K | K | 0.450105 |
| 122 | A122E | E | 0.467766 |
| 122 | A122T | T | 0.520454 |
| 122 | A122P | P | 0.548155 |
| 122 | A122I | I | 0.647406 |
| 122 | A122N | N | 0.704284 |
| 122 | A122Q | Q | 0.741587 |
| 122 | A122W | W | 0.862265 |

TABLE 10-5-continued

PAD Assay Results

| Position | WT/Pos/ Mutation | Variant | PAD Perf. Ind. |
|---|---|---|---|
| 122 | A122V | V | 0.886387 |
| 122 | A122M | M | 0.938855 |
| 124 | G124I | I | <0.01 |
| 124 | G124H | H | <0.01 |
| 124 | G124M | M | <0.01 |
| 124 | G124W | W | <0.01 |
| 124 | G124P | P | <0.01 |
| 124 | G124A | A | 0.031196 |
| 124 | G124Q | Q | 0.208313 |
| 124 | G124T | T | 0.315233 |
| 124 | G124V | V | 0.329769 |
| 124 | G124R | R | 0.409769 |
| 124 | G124L | L | 0.536625 |
| 124 | G124S | S | 0.555215 |
| 124 | G124Y | Y | 0.559199 |
| 124 | G124N | N | 0.599171 |
| 124 | G124D | D | 0.63784 |
| 124 | G124C | C | 0.672179 |
| 124 | G124F | F | 0.950801 |
| 125 | V125W | W | 0.24527 |
| 125 | V125E | E | 0.385171 |
| 125 | V125R | R | 0.466062 |
| 125 | V125C | C | 0.541228 |
| 125 | V125D | D | 0.541318 |
| 125 | V125P | P | 0.622352 |
| 125 | V125F | F | 0.627367 |
| 125 | V125S | S | 0.790998 |
| 125 | V125Y | Y | 0.813593 |
| 125 | V125A | A | 0.925641 |
| 125 | V125I | I | 0.941326 |
| 126 | G126I | I | <0.010426347441542 |
| 126 | G126V | V | 0.175001 |
| 126 | G126Y | Y | 0.234673 |
| 126 | G126L | L | 0.540613 |
| 126 | G126A | A | 0.552538 |
| 126 | G126E | E | 0.599533 |
| 126 | G126P | P | 0.673809 |
| 126 | G126T | T | 0.737666 |
| 126 | G126R | R | 0.761417 |
| 126 | G126N | N | 0.846727 |
| 126 | G126S | S | 0.902662 |
| 126 | G126C | C | 0.980807 |
| 127 | T127L | L | <0.01 |
| 127 | T127E | E | <0.01 |
| 127 | T127Q | Q | 0.151533 |
| 127 | T127I | I | 0.203586 |
| 127 | T127H | H | 0.60105 |
| 127 | T127D | D | 0.61747 |
| 127 | T127M | M | 0.639504 |
| 127 | T127C | C | 0.653314 |
| 127 | T127V | V | 0.683337 |
| 127 | T127G | G | 0.710564 |
| 127 | T127P | P | 0.773291 |
| 127 | T127S | S | 0.828003 |
| 128 | T128D | D | 0.662836 |
| 129 | Y129W | W | <0.01 |
| 129 | Y129G | G | <0.01 |
| 129 | Y129K | K | <0.01 |
| 129 | Y129V | V | <0.01 |
| 129 | Y129T | T | 0.138769 |
| 129 | Y129A | A | 0.173554 |
| 129 | Y129R | R | 0.178362 |
| 129 | Y129M | M | 0.211662 |
| 129 | Y129D | D | 0.228506 |
| 129 | Y129L | L | 0.270643 |
| 129 | Y129N | N | 0.530034 |
| 129 | Y129P | P | 0.588917 |
| 129 | Y129C | C | 0.610384 |
| 129 | Y129S | S | 0.692051 |
| 129 | Y129F | F | 0.713199 |
| 146 | P146W | W | 0.680806 |
| 146 | P146T | T | 0.756105 |
| 146 | P146V | V | 0.768041 |
| 146 | P146S | S | 0.956673 |
| 148 | P148Q | Q | 0.975963 |

TABLE 10-5-continued

PAD Assay Results

| Position | WT/Pos/ Mutation | Variant | PAD Perf. Ind. |
|---|---|---|---|
| 149 | W149R | R | <0.01 |
| 149 | W149E | E | <0.01 |
| 149 | W149P | P | <0.01 |
| 149 | W149C | C | 0.1164 |
| 149 | W149I | I | 0.235936 |
| 149 | W149A | A | 0.311848 |
| 149 | W149S | S | 0.329233 |
| 149 | W149Q | Q | 0.402387 |
| 149 | W149T | T | 0.440303 |
| 149 | W149G | G | 0.44856 |
| 149 | W149M | M | 0.494615 |
| 149 | W149F | F | 0.495779 |
| 149 | W149L | L | 0.637667 |
| 149 | W149Y | Y | 0.747652 |
| 150 | F150P | P | 0.31768 |
| 150 | F150N | N | 0.362798 |
| 150 | F150G | G | 0.458431 |
| 150 | F150V | V | 0.511676 |
| 150 | F150A | A | 0.539571 |
| 150 | F150T | T | 0.580879 |
| 150 | F150W | W | 0.622886 |
| 150 | F150M | M | 0.625886 |
| 150 | F150E | E | 0.727755 |
| 150 | F150C | C | 0.778063 |
| 150 | F150I | I | 0.78431 |
| 150 | F150K | K | 0.848249 |
| 153 | I153N | N | 0.890296 |
| 154 | F154T | T | <0.01 |
| 154 | F154D | D | <0.01 |
| 154 | F154E | E | <0.01 |
| 154 | F154G | G | <0.01 |
| 154 | F154L | L | <0.01 |
| 154 | F154P | P | <0.01 |
| 154 | F154V | V | <0.01 |
| 154 | F154S | S | 0.287767 |
| 154 | F154Q | Q | 0.973299 |
| 194 | I194S | S | <0.01 |
| 194 | I194A | A | <0.01 |
| 194 | I194C | C | <0.01 |
| 194 | I194P | P | <0.01 |
| 194 | I194F | F | <0.01 |
| 194 | I194W | W | <0.01 |
| 194 | I194R | R | <0.01 |
| 194 | I194Y | Y | <0.01 |
| 194 | I194G | G | 0.044503 |
| 194 | I194L | L | 0.577811 |
| 194 | I194V | V | 0.780569 |
| 196 | F196H | H | <0.01 |
| 196 | F196G | G | <0.01 |
| 196 | F196S | S | <0.01 |
| 196 | F196Q | Q | <0.01 |
| 196 | F196A | A | <0.01 |
| 196 | F196K | K | <0.01 |
| 196 | F196N | N | <0.01 |
| 196 | F196R | R | <0.01 |
| 196 | F196W | W | 0.38122 |
| 196 | F196P | P | 0.385754 |
| 196 | F196V | V | 0.675769 |
| 196 | F196M | M | 0.709899 |
| 196 | F196Y | Y | 0.970105 |

The following Table provides variants that are better than wild-type at degrading peracids (i.e., the performance index for the variant is better than the wild-type).

TABLE 10-6

Variants with Peracid Degradation Greater Than Wild-Type

| Pos. | WT/Pos./Var. | PAD PI |
|---|---|---|
| 1 | M001I | 1.19 |
| 1 | M001L | 2.11 |

TABLE 10-6-continued

| Variants with Peracid Degradation Greater Than Wild-Type | | |
|---|---|---|
| Pos. | WT/Pos./Var. | PAD PI |
| 2 | A002D | 1.05 |
| 2 | A002R | 1.17 |
| 2 | A002W | 1.17 |
| 2 | A002P | 1.17 |
| 2 | A002Q | 1.29 |
| 2 | A002E | 1.38 |
| 3 | K003T | 1.03 |
| 3 | K003S | 1.17 |
| 3 | K003Q | 1.19 |
| 3 | K003R | 1.29 |
| 3 | K003Y | 1.39 |
| 3 | K003M | 1.44 |
| 3 | K003P | 1.45 |
| 3 | K003C | 1.52 |
| 3 | K003L | 1.84 |
| 3 | K003H | 1.89 |
| 3 | K003A | 2.14 |
| 3 | K003I | 2.44 |
| 3 | K003E | 3.51 |
| 3 | K003G | 3.74 |
| 4 | R004D | 1.18 |
| 4 | R004C | 1.34 |
| 4 | R004P | 1.44 |
| 4 | R004A | 1.64 |
| 5 | I005M | 1.09 |
| 5 | I005E | 1.59 |
| 5 | I005L | 1.63 |
| 5 | I005A | 1.88 |
| 5 | I005C | 2.47 |
| 5 | I005D | 3.11 |
| 6 | L006C | 1.22 |
| 6 | L006M | 1.44 |
| 6 | L006A | 1.99 |
| 7 | C007A | 1.03 |
| 7 | C007H | 1.37 |
| 7 | C007I | 1.48 |
| 7 | C007E | 1.63 |
| 7 | C007K | 2.95 |
| 8 | F008M | 1.11 |
| 8 | F008L | 1.31 |
| 8 | F008A | 1.33 |
| 8 | F008C | 4.01 |
| 10 | D010L | 2.04 |
| 13 | T013I | 1.05 |
| 13 | T013E | 1.09 |
| 13 | T013L | 1.47 |
| 13 | T013M | 1.47 |
| 13 | T013C | 1.55 |
| 13 | T013A | 1.88 |
| 13 | T013N | 2.61 |
| 13 | T013P | 2.73 |
| 16 | W016K | 1.03 |
| 16 | W016I | 1.06 |
| 16 | W016Y | 1.09 |
| 16 | W016L | 1.16 |
| 17 | V017S | 1.04 |
| 18 | P018N | 1.42 |
| 18 | P018Q | 3.26 |
| 18 | P018R | 3.97 |
| 18 | P018C | 4.16 |
| 18 | P018Y | 4.17 |
| 18 | P018V | 4.85 |
| 18 | P018E | 4.87 |
| 18 | P018G | 4.96 |
| 18 | P018H | 6.05 |
| 18 | P018L | 7.40 |
| 20 | E020D | 1.14 |
| 20 | E020S | 1.18 |
| 20 | E020H | 1.20 |
| 20 | E020T | 1.25 |
| 20 | E020V | 1.27 |
| 20 | E020A | 1.28 |
| 20 | E020W | 1.30 |
| 20 | E020N | 1.34 |
| 20 | E020P | 1.43 |
| 20 | E020Q | 1.56 |
| 20 | E020C | 1.76 |
| 21 | D021S | 1.11 |
| 21 | D021E | 1.39 |
| 21 | D021F | 1.41 |
| 21 | D021W | 1.44 |
| 21 | D021L | 1.57 |
| 21 | D021A | 1.75 |
| 21 | D021G | 1.76 |
| 21 | D021K | 1.80 |
| 21 | D021Y | 2.01 |
| 22 | G022I | 1.03 |
| 22 | G022T | 1.16 |
| 22 | G022E | 1.19 |
| 22 | G022L | 1.35 |
| 22 | G022P | 1.36 |
| 22 | G022Q | 1.44 |
| 22 | G022A | 1.66 |
| 23 | A023H | 1.04 |
| 23 | A023L | 1.30 |
| 24 | P024C | 1.04 |
| 24 | P024K | 1.36 |
| 24 | P024L | 1.51 |
| 26 | E026M | 1.10 |
| 26 | E026H | 1.19 |
| 26 | E026D | 1.39 |
| 26 | E026A | 1.45 |
| 26 | E026K | 1.47 |
| 26 | E026L | 1.71 |
| 27 | R027I | 1.41 |
| 27 | R027K | 1.55 |
| 27 | R027L | 2.60 |
| 27 | R027A | 2.78 |
| 28 | F028E | 1.04 |
| 28 | F028W | 1.17 |
| 28 | F028C | 1.21 |
| 28 | F028Y | 1.36 |
| 28 | F028M | 1.37 |
| 28 | F028A | 1.48 |
| 28 | F028L | 2.02 |
| 28 | F028D | 2.07 |
| 29 | A029C | 1.15 |
| 30 | P030H | 1.08 |
| 30 | P030G | 1.09 |
| 30 | P030R | 1.14 |
| 30 | P030L | 1.17 |
| 30 | P030E | 1.24 |
| 30 | P030Y | 1.31 |
| 30 | P030I | 1.38 |
| 30 | P030K | 1.39 |
| 30 | P030S | 1.49 |
| 30 | P030T | 1.64 |
| 30 | P030V | 1.74 |
| 31 | D031V | 1.08 |
| 31 | D031T | 1.11 |
| 31 | D031Q | 1.13 |
| 31 | D031W | 1.14 |
| 31 | D031G | 1.16 |
| 31 | D031A | 1.18 |
| 31 | D031S | 1.23 |
| 31 | D031F | 1.39 |
| 31 | D031R | 1.49 |
| 31 | D031N | 1.55 |
| 31 | D031L | 1.61 |
| 32 | V032S | 1.09 |
| 32 | V032N | 1.61 |
| 32 | V032W | 1.71 |
| 32 | V032Q | 1.74 |
| 32 | V032G | 2.65 |
| 32 | V032M | 3.41 |
| 32 | V032I | 3.51 |
| 32 | V032A | 3.64 |
| 32 | V032E | 3.92 |
| 32 | V032D | 4.19 |
| 32 | V032L | 4.72 |
| 32 | V032K | 4.73 |
| 33 | R033S | 1.01 |

TABLE 10-6-continued

Variants with Peracid Degradation Greater Than Wild-Type

| Pos. | WT/Pos./Var. | PAD PI |
|---|---|---|
| 33 | R033N | 1.30 |
| 33 | R033A | 1.32 |
| 33 | R033C | 1.73 |
| 33 | R033G | 2.63 |
| 33 | R033K | 2.72 |
| 33 | R033L | 2.90 |
| 34 | W034P | 1.21 |
| 34 | W034M | 1.22 |
| 34 | W034C | 1.49 |
| 34 | W034A | 2.29 |
| 35 | T035M | 2.72 |
| 35 | T035A | 3.85 |
| 35 | T035C | 4.72 |
| 35 | T035I | 5.38 |
| 35 | T035E | 5.73 |
| 36 | G036C | 1.06 |
| 36 | G036A | 1.07 |
| 36 | G036H | 1.10 |
| 36 | G036K | 1.71 |
| 36 | G036I | 1.81 |
| 36 | G036L | 2.49 |
| 36 | G036D | 2.50 |
| 37 | V037I | 1.04 |
| 37 | V037L | 1.16 |
| 37 | V037S | 1.49 |
| 37 | V037N | 1.52 |
| 37 | V037C | 1.63 |
| 37 | V037A | 2.00 |
| 37 | V037P | 2.10 |
| 38 | L038V | 1.12 |
| 39 | A039W | 1.02 |
| 39 | A039Y | 1.13 |
| 40 | Q040N | 1.00 |
| 40 | Q040I | 1.10 |
| 40 | Q040E | 1.28 |
| 40 | Q040R | 1.48 |
| 40 | Q040L | 1.49 |
| 40 | Q040D | 1.59 |
| 40 | Q040S | 1.65 |
| 40 | Q040T | 1.81 |
| 40 | Q040Y | 2.02 |
| 40 | Q040G | 2.17 |
| 40 | Q040W | 2.59 |
| 40 | Q040K | 3.64 |
| 41 | Q041G | 1.09 |
| 41 | Q041H | 1.14 |
| 41 | Q041R | 1.27 |
| 41 | Q041K | 1.61 |
| 41 | Q041L | 1.92 |
| 41 | Q041A | 2.58 |
| 42 | L042F | 1.02 |
| 42 | L042P | 1.34 |
| 42 | L042K | 1.41 |
| 42 | L042C | 1.43 |
| 43 | G043A | 1.07 |
| 43 | G043L | 1.82 |
| 43 | G043E | 1.88 |
| 44 | A044C | 1.92 |
| 45 | D045F | 1.04 |
| 46 | F046C | 1.16 |
| 46 | F046A | 1.25 |
| 46 | F046E | 1.31 |
| 46 | F046D | 1.39 |
| 46 | F046M | 1.42 |
| 46 | F046K | 1.46 |
| 46 | F046P | 1.50 |
| 46 | F046L | 1.54 |
| 47 | E047L | 1.02 |
| 47 | E047K | 1.06 |
| 47 | E047G | 1.10 |
| 47 | E047I | 1.15 |
| 48 | V048Q | 1.39 |
| 48 | V048F | 1.42 |
| 48 | V048A | 1.63 |
| 48 | V048M | 1.79 |
| 48 | V048C | 2.25 |

TABLE 10-6-continued

Variants with Peracid Degradation Greater Than Wild-Type

| Pos. | WT/Pos./Var. | PAD PI |
|---|---|---|
| 48 | V048L | 2.29 |
| 48 | V048P | 3.08 |
| 49 | I049Y | 1.02 |
| 49 | I049M | 1.02 |
| 49 | I049L | 1.03 |
| 49 | I049G | 1.12 |
| 49 | I049K | 1.26 |
| 49 | I049A | 1.87 |
| 50 | E050P | 1.02 |
| 50 | E050M | 1.04 |
| 50 | E050G | 1.11 |
| 50 | E050D | 1.22 |
| 50 | E050A | 1.23 |
| 51 | E051T | 1.17 |
| 51 | E051M | 1.20 |
| 51 | E051D | 1.28 |
| 51 | E051G | 1.34 |
| 51 | E051K | 2.00 |
| 51 | E051A | 2.72 |
| 52 | G052W | 2.47 |
| 53 | L053H | 1.70 |
| 54 | S054N | 1.29 |
| 54 | S054P | 1.30 |
| 54 | S054A | 1.41 |
| 55 | A055N | 1.05 |
| 55 | A055K | 1.08 |
| 55 | A055C | 1.26 |
| 57 | T057S | 1.01 |
| 57 | T057G | 1.05 |
| 58 | T058L | 1.12 |
| 58 | T058H | 1.49 |
| 59 | N059Q | 1.86 |
| 59 | N059T | 5.63 |
| 59 | N059S | 7.32 |
| 59 | N059K | 8.21 |
| 59 | N059E | 9.88 |
| 59 | N059V | 9.97 |
| 59 | N059G | 10.00 |
| 59 | N059F | 10.23 |
| 59 | N059A | 10.44 |
| 59 | N059Y | 11.14 |
| 59 | N059C | 11.23 |
| 59 | N059D | 11.72 |
| 59 | N059W | 12.80 |
| 59 | N059L | 14.74 |
| 60 | I060G | 1.04 |
| 60 | I060V | 1.06 |
| 60 | I060H | 1.07 |
| 60 | I060Y | 1.19 |
| 61 | D061P | 1.13 |
| 61 | D061Q | 1.16 |
| 61 | D061L | 1.20 |
| 61 | D061G | 1.25 |
| 61 | D061S | 1.35 |
| 61 | D061R | 1.59 |
| 61 | D061I | 1.66 |
| 61 | D061H | 1.67 |
| 61 | D061K | 1.72 |
| 63 | P063K | 1.02 |
| 63 | P063V | 1.04 |
| 63 | P063Q | 1.05 |
| 63 | P063W | 1.11 |
| 63 | P063G | 1.22 |
| 63 | P063L | 1.23 |
| 63 | P063T | 1.32 |
| 64 | T064G | 1.08 |
| 64 | T064M | 1.09 |
| 64 | T064A | 1.20 |
| 64 | T064L | 1.22 |
| 66 | P066S | 1.02 |
| 66 | P066T | 1.10 |
| 69 | N069D | 1.11 |
| 69 | N069A | 1.13 |
| 69 | N069Q | 1.14 |
| 69 | N069C | 1.20 |
| 69 | N069L | 1.20 |

TABLE 10-6-continued

| Variants with Peracid Degradation Greater Than Wild-Type | | |
|---|---|---|
| Pos. | WT/Pos./Var. | PAD PI |
| 69 | N069S | 1.42 |
| 69 | N069T | 1.43 |
| 69 | N069H | 1.52 |
| 69 | N069K | 1.59 |
| 69 | N069V | 1.73 |
| 69 | N069I | 1.75 |
| 70 | G070L | 1.01 |
| 70 | G070A | 1.41 |
| 70 | G070H | 1.90 |
| 71 | A071K | 1.01 |
| 71 | A071M | 1.11 |
| 72 | S072F | 1.15 |
| 72 | S072G | 1.76 |
| 72 | S072M | 2.13 |
| 72 | S072C | 2.18 |
| 72 | S072H | 2.48 |
| 72 | S072N | 2.85 |
| 72 | S072A | 3.52 |
| 73 | Y073M | 1.13 |
| 73 | Y073C | 1.20 |
| 73 | Y073A | 1.40 |
| 74 | L074F | 1.13 |
| 74 | L074M | 1.21 |
| 74 | L074A | 2.90 |
| 75 | P075E | 1.19 |
| 75 | P075L | 1.19 |
| 75 | P075W | 1.31 |
| 75 | P075Y | 1.32 |
| 75 | P075V | 1.39 |
| 75 | P075C | 1.42 |
| 75 | P075D | 2.09 |
| 76 | S076C | 1.06 |
| 76 | S076T | 1.11 |
| 76 | S076A | 1.11 |
| 76 | S076H | 1.11 |
| 76 | S076P | 1.20 |
| 76 | S076V | 1.35 |
| 76 | S076K | 1.53 |
| 76 | S076M | 1.61 |
| 76 | S076D | 1.94 |
| 76 | S076E | 2.09 |
| 76 | S076G | 2.15 |
| 76 | S076L | 4.70 |
| 77 | C077T | 1.03 |
| 77 | C077D | 1.05 |
| 78 | L078T | 1.10 |
| 78 | L078I | 1.11 |
| 78 | L078G | 1.38 |
| 78 | L078H | 1.57 |
| 80 | T080V | 1.01 |
| 80 | T080Q | 1.07 |
| 80 | T080A | 1.11 |
| 80 | T080C | 1.15 |
| 80 | T080S | 1.40 |
| 80 | T080G | 1.50 |
| 81 | H081N | 1.00 |
| 81 | H081L | 1.03 |
| 81 | H081W | 1.09 |
| 81 | H081C | 1.09 |
| 81 | H081A | 1.45 |
| 81 | H081M | 1.54 |
| 82 | L082M | 1.06 |
| 83 | P083C | 1.01 |
| 83 | P083R | 1.09 |
| 83 | P083N | 1.10 |
| 83 | P083K | 1.16 |
| 83 | P083E | 1.26 |
| 83 | P083M | 1.88 |
| 83 | P083A | 2.36 |
| 84 | L084F | 1.01 |
| 84 | L084G | 1.01 |
| 85 | D085R | 1.03 |
| 85 | D085A | 1.09 |
| 85 | D085H | 1.24 |
| 85 | D085E | 1.25 |
| 85 | D085C | 1.50 |

TABLE 10-6-continued

| Variants with Peracid Degradation Greater Than Wild-Type | | |
|---|---|---|
| Pos. | WT/Pos./Var. | PAD PI |
| 85 | D085G | 1.60 |
| 85 | D085F | 1.98 |
| 86 | L086C | 2.44 |
| 86 | L086A | 3.32 |
| 87 | V087P | 1.64 |
| 87 | V087C | 2.22 |
| 87 | V087L | 4.30 |
| 88 | I088M | 1.09 |
| 88 | I088P | 3.51 |
| 89 | I089L | 1.22 |
| 89 | I089A | 1.83 |
| 89 | I089P | 1.91 |
| 90 | M090C | 1.09 |
| 90 | M090E | 1.15 |
| 90 | M090A | 1.41 |
| 90 | M090D | 2.88 |
| 91 | L091I | 1.05 |
| 91 | L091C | 1.27 |
| 91 | L091A | 1.45 |
| 91 | L091D | 1.47 |
| 92 | G092C | 2.05 |
| 93 | T093A | 1.05 |
| 96 | T096F | 1.24 |
| 96 | T096G | 1.28 |
| 96 | T096L | 1.93 |
| 96 | T096M | 2.53 |
| 96 | T096C | 3.76 |
| 96 | T096A | 4.20 |
| 98 | A098Y | 1.15 |
| 98 | A098P | 1.26 |
| 98 | A098N | 1.40 |
| 98 | A098C | 1.42 |
| 98 | A098L | 1.47 |
| 98 | A098D | 2.19 |
| 100 | F100C | 1.28 |
| 100 | F100T | 1.42 |
| 100 | F100N | 1.45 |
| 100 | F100A | 2.02 |
| 100 | F100M | 2.19 |
| 101 | R101L | 1.12 |
| 102 | R102Q | 1.19 |
| 102 | R102Y | 1.29 |
| 102 | R102L | 1.64 |
| 102 | R102A | 1.79 |
| 104 | P104V | 1.02 |
| 104 | P104H | 1.03 |
| 104 | P104N | 1.44 |
| 104 | P104C | 1.83 |
| 104 | P104E | 1.97 |
| 104 | P104I | 2.05 |
| 104 | P104M | 2.24 |
| 105 | L105Q | 1.04 |
| 105 | L105H | 1.23 |
| 105 | L105R | 1.25 |
| 105 | L105G | 1.40 |
| 105 | L105W | 1.71 |
| 105 | L105F | 1.73 |
| 105 | L105C | 1.92 |
| 106 | D106S | 1.02 |
| 106 | D106W | 1.07 |
| 106 | D106E | 1.09 |
| 106 | D106C | 1.10 |
| 106 | D106A | 1.13 |
| 106 | D106H | 1.18 |
| 106 | D106K | 1.24 |
| 106 | D106T | 1.38 |
| 106 | D106F | 1.45 |
| 106 | D106G | 1.45 |
| 106 | D106V | 1.68 |
| 107 | I107L | 1.04 |
| 107 | I107S | 1.33 |
| 107 | I107C | 1.41 |
| 107 | I107T | 1.53 |
| 108 | A108S | 1.00 |
| 108 | A108G | 1.13 |
| 108 | A108L | 2.56 |

TABLE 10-6-continued

| Variants with Peracid Degradation Greater Than Wild-Type | | |
|---|---|---|
| Pos. | WT/Pos./Var. | PAD PI |
| 108 | A108K | 2.97 |
| 110 | G110A | 1.01 |
| 110 | G110D | 1.40 |
| 110 | G110C | 1.43 |
| 110 | G110E | 1.76 |
| 110 | G110F | 2.29 |
| 111 | M111C | 1.01 |
| 111 | M111A | 1.02 |
| 111 | M111I | 1.03 |
| 111 | M111Y | 1.06 |
| 111 | M111W | 1.23 |
| 111 | M111N | 1.31 |
| 112 | S112L | 1.00 |
| 112 | S112E | 1.16 |
| 113 | V113M | 1.06 |
| 113 | V113Q | 1.11 |
| 113 | V113R | 1.11 |
| 113 | V113P | 1.14 |
| 113 | V113N | 1.22 |
| 113 | V113A | 1.31 |
| 114 | L114T | 1.05 |
| 114 | L114A | 1.07 |
| 114 | L114G | 1.14 |
| 114 | L114C | 1.14 |
| 114 | L114I | 1.17 |
| 114 | L114M | 1.28 |
| 115 | V115C | 1.08 |
| 115 | V115S | 1.14 |
| 115 | V115Q | 1.15 |
| 115 | V115A | 1.19 |
| 115 | V115T | 1.28 |
| 115 | V115L | 1.30 |
| 115 | V115M | 1.32 |
| 115 | V115R | 1.63 |
| 115 | V115F | 1.69 |
| 115 | V115G | 1.76 |
| 115 | V115Y | 2.07 |
| 115 | V115D | 2.21 |
| 115 | V115P | 2.21 |
| 115 | V115W | 2.48 |
| 116 | T116N | 1.05 |
| 116 | T116C | 1.05 |
| 116 | T116H | 1.08 |
| 116 | T116M | 1.39 |
| 117 | Q117F | 1.02 |
| 117 | Q117R | 1.05 |
| 117 | Q117T | 1.10 |
| 117 | Q117H | 1.12 |
| 117 | Q117Y | 1.13 |
| 117 | Q117P | 1.13 |
| 117 | Q117E | 1.21 |
| 117 | Q117A | 1.73 |
| 117 | Q117M | 1.89 |
| 118 | V118L | 1.05 |
| 118 | V118C | 1.14 |
| 118 | V118Y | 1.34 |
| 118 | V118Q | 1.50 |
| 119 | L119A | 1.02 |
| 120 | T120V | 1.07 |
| 120 | T120S | 1.07 |
| 120 | T120K | 1.09 |
| 120 | T120M | 1.22 |
| 120 | T120L | 1.26 |
| 120 | T120N | 1.42 |
| 120 | T120E | 1.53 |
| 120 | T120I | 1.56 |
| 120 | T120Y | 1.61 |
| 121 | S121E | 1.04 |
| 121 | S121N | 1.06 |
| 121 | S121Q | 1.09 |
| 121 | S121T | 1.26 |
| 121 | S121L | 1.49 |
| 121 | S121A | 1.55 |
| 121 | S121V | 1.59 |
| 121 | S121C | 1.64 |
| 122 | A122L | 1.02 |

TABLE 10-6-continued

| Variants with Peracid Degradation Greater Than Wild-Type | | |
|---|---|---|
| Pos. | WT/Pos./Var. | PAD PI |
| 123 | G123K | 1.12 |
| 123 | G123A | 1.19 |
| 123 | G123Y | 1.24 |
| 123 | G123M | 1.38 |
| 123 | G123L | 1.38 |
| 123 | G123W | 1.39 |
| 125 | V125G | 1.09 |
| 126 | G126M | 1.17 |
| 126 | G126D | 1.22 |
| 127 | T127A | 1.10 |
| 128 | T128M | 1.06 |
| 128 | T128H | 1.08 |
| 128 | T128V | 1.15 |
| 128 | T128P | 1.16 |
| 128 | T128W | 1.23 |
| 128 | T128S | 1.27 |
| 128 | T128A | 1.31 |
| 128 | T128Q | 1.34 |
| 128 | T128N | 1.36 |
| 128 | T128K | 1.57 |
| 128 | T128R | 1.70 |
| 128 | T128F | 1.71 |
| 128 | T128L | 1.72 |
| 128 | T128Y | 1.81 |
| 131 | A131R | 1.04 |
| 132 | P132N | 1.05 |
| 132 | P132L | 2.24 |
| 132 | P132E | 3.02 |
| 132 | P132Y | 4.78 |
| 132 | P132G | 4.98 |
| 132 | P132S | 5.05 |
| 132 | P132C | 5.68 |
| 132 | P132A | 6.08 |
| 132 | P132Q | 6.15 |
| 133 | K133Y | 1.44 |
| 133 | K133L | 1.92 |
| 134 | V134C | 1.37 |
| 134 | V134G | 1.42 |
| 134 | V134S | 1.44 |
| 134 | V134L | 1.45 |
| 134 | V134A | 1.64 |
| 134 | V134P | 1.71 |
| 134 | V134M | 1.89 |
| 134 | V134N | 2.80 |
| 135 | L135D | 2.90 |
| 136 | V136T | 1.13 |
| 136 | V136L | 1.13 |
| 136 | V136C | 1.23 |
| 136 | V136A | 1.60 |
| 137 | V137M | 1.13 |
| 137 | V137L | 1.27 |
| 137 | V137C | 1.42 |
| 137 | V137A | 1.46 |
| 138 | S138G | 1.11 |
| 138 | S138C | 1.18 |
| 138 | S138A | 1.28 |
| 138 | S138N | 1.31 |
| 138 | S138P | 1.39 |
| 140 | P140C | 1.07 |
| 140 | P140A | 1.83 |
| 140 | P140H | 2.25 |
| 140 | P140F | 2.89 |
| 140 | P140G | 3.11 |
| 141 | P141A | 1.08 |
| 143 | A143C | 1.07 |
| 143 | A143E | 1.13 |
| 143 | A143D | 1.22 |
| 143 | A143L | 1.28 |
| 143 | A143H | 1.36 |
| 143 | A143K | 1.37 |
| 144 | P144M | 1.01 |
| 144 | P144F | 1.08 |
| 144 | P144Q | 1.08 |
| 144 | P144K | 1.09 |
| 144 | P144R | 1.14 |
| 144 | P144L | 1.15 |

TABLE 10-6-continued

| Variants with Peracid Degradation Greater Than Wild-Type | | |
|---|---|---|
| Pos. | WT/Pos./Var. | PAD PI |
| 144 | P144D | 1.38 |
| 144 | P144N | 1.49 |
| 144 | P144H | 1.60 |
| 144 | P144Y | 1.65 |
| 146 | P146N | 1.00 |
| 146 | P146G | 1.04 |
| 146 | P146R | 1.06 |
| 146 | P146M | 1.23 |
| 146 | P146A | 1.36 |
| 146 | P146Y | 1.44 |
| 146 | P146F | 1.53 |
| 146 | P146H | 1.57 |
| 146 | P146C | 1.69 |
| 146 | P146L | 2.00 |
| 147 | H147Q | 1.03 |
| 147 | H147W | 1.05 |
| 147 | H147K | 1.06 |
| 147 | H147E | 1.10 |
| 147 | H147Y | 1.12 |
| 147 | H147C | 1.17 |
| 147 | H147D | 1.18 |
| 147 | H147P | 1.21 |
| 147 | H147N | 1.25 |
| 147 | H147L | 1.29 |
| 147 | H147M | 1.44 |
| 148 | P148V | 1.04 |
| 148 | P148A | 1.06 |
| 148 | P148T | 1.09 |
| 148 | P148E | 1.19 |
| 148 | P148G | 1.20 |
| 148 | P148S | 1.21 |
| 148 | P148R | 1.25 |
| 148 | P148K | 1.30 |
| 148 | P148D | 1.34 |
| 148 | P148Y | 1.37 |
| 148 | P148L | 1.39 |
| 148 | P148F | 1.50 |
| 149 | W149H | 1.01 |
| 150 | F150Y | 1.07 |
| 150 | F150H | 1.18 |
| 150 | F150L | 1.30 |
| 151 | Q151P | 1.91 |
| 151 | Q151E | 2.07 |
| 151 | Q151K | 2.19 |
| 151 | Q151H | 2.19 |
| 151 | Q151S | 2.25 |
| 151 | Q151R | 2.32 |
| 151 | Q151T | 2.37 |
| 151 | Q151C | 2.55 |
| 151 | Q151Y | 2.75 |
| 151 | Q151D | 2.81 |
| 151 | Q151A | 2.93 |
| 151 | Q151M | 6.36 |
| 152 | L152M | 1.10 |
| 152 | L152C | 1.14 |
| 152 | L152E | 1.23 |
| 152 | L152A | 1.29 |
| 152 | L152Y | 1.37 |
| 152 | L152W | 1.55 |
| 153 | I153V | 1.15 |
| 153 | I153A | 1.49 |
| 153 | I153L | 1.50 |
| 153 | I153T | 1.62 |
| 153 | I153S | 1.66 |
| 153 | I153F | 1.75 |
| 153 | I153P | 1.87 |
| 153 | I153H | 2.00 |
| 153 | I153K | 2.44 |
| 154 | F154Y | 4.96 |
| 155 | E155S | 1.12 |
| 155 | E155G | 1.12 |
| 155 | E155T | 1.19 |
| 155 | E155D | 1.24 |
| 155 | E155K | 1.33 |
| 155 | E155N | 1.79 |
| 155 | E155L | 2.07 |

TABLE 10-6-continued

| Variants with Peracid Degradation Greater Than Wild-Type | | |
|---|---|---|
| Pos. | WT/Pos./Var. | PAD PI |
| 155 | E155A | 2.59 |
| 155 | E155P | 2.60 |
| 155 | E155Y | 2.65 |
| 155 | E155M | 2.91 |
| 156 | G156S | 1.04 |
| 156 | G156K | 1.11 |
| 156 | G156E | 1.14 |
| 156 | G156R | 1.21 |
| 156 | G156A | 1.21 |
| 156 | G156P | 1.29 |
| 156 | G156C | 1.37 |
| 156 | G156N | 1.38 |
| 156 | G156H | 1.40 |
| 156 | G156Y | 1.40 |
| 156 | G156T | 1.53 |
| 156 | G156M | 1.62 |
| 156 | G156D | 1.62 |
| 157 | G157I | 1.33 |
| 157 | G157F | 1.42 |
| 157 | G157K | 1.47 |
| 157 | G157H | 1.57 |
| 158 | E158H | 1.01 |
| 158 | E158P | 1.19 |
| 158 | E158Q | 1.24 |
| 158 | E158S | 1.27 |
| 158 | E158A | 1.28 |
| 158 | E158R | 1.29 |
| 158 | E158W | 1.31 |
| 158 | E158C | 1.37 |
| 158 | E158N | 1.58 |
| 158 | E158M | 1.73 |
| 158 | E158F | 1.77 |
| 158 | E158K | 1.88 |
| 158 | E158L | 1.96 |
| 158 | E158Y | 2.48 |
| 159 | Q159H | 1.48 |
| 160 | K160N | 1.12 |
| 160 | K160A | 1.14 |
| 160 | K160R | 1.15 |
| 160 | K160D | 1.19 |
| 160 | K160C | 1.29 |
| 160 | K160Q | 1.41 |
| 160 | K160M | 1.47 |
| 160 | K160P | 1.66 |
| 161 | T161L | 1.16 |
| 161 | T161V | 1.24 |
| 161 | T161Q | 1.50 |
| 161 | T161M | 1.72 |
| 161 | T161Y | 2.62 |
| 162 | T162R | 1.23 |
| 162 | T162G | 1.82 |
| 162 | T162S | 2.01 |
| 162 | T162W | 2.04 |
| 162 | T162I | 2.21 |
| 162 | T162Q | 2.45 |
| 162 | T162Y | 2.89 |
| 162 | T162K | 3.13 |
| 162 | T162F | 3.23 |
| 162 | T162M | 3.49 |
| 162 | T162C | 3.57 |
| 162 | T162L | 3.59 |
| 162 | T162N | 3.84 |
| 162 | T162H | 3.91 |
| 162 | T162P | 4.37 |
| 163 | E163N | 1.00 |
| 163 | E163C | 1.08 |
| 163 | E163D | 1.08 |
| 163 | E163A | 1.79 |
| 163 | E163Y | 1.89 |
| 163 | E163L | 1.94 |
| 164 | L164Q | 1.01 |
| 164 | L164V | 1.02 |
| 164 | L164S | 1.11 |
| 164 | L164M | 1.26 |
| 164 | L164N | 1.31 |
| 164 | L164R | 1.61 |

TABLE 10-6-continued

Variants with Peracid Degradation Greater Than Wild-Type

| Pos. | WT/Pos./Var. | PAD PI |
|---|---|---|
| 164 | L164P | 2.41 |
| 165 | A165G | 1.07 |
| 165 | A165V | 1.13 |
| 165 | A165N | 1.20 |
| 165 | A165R | 1.29 |
| 165 | A165Q | 1.32 |
| 165 | A165T | 1.32 |
| 165 | A165P | 1.34 |
| 165 | A165C | 1.42 |
| 165 | A165L | 1.55 |
| 165 | A165M | 1.56 |
| 165 | A165D | 1.69 |
| 166 | R166W | 1.08 |
| 166 | R166F | 1.10 |
| 166 | R166K | 1.20 |
| 166 | R166N | 1.21 |
| 166 | R166Y | 1.22 |
| 166 | R166M | 1.29 |
| 166 | R166I | 1.39 |
| 166 | R166P | 1.50 |
| 166 | R166L | 1.50 |
| 166 | R166A | 1.51 |
| 166 | R166D | 1.55 |
| 166 | R166H | 1.56 |
| 167 | V167I | 1.00 |
| 167 | V167S | 1.86 |
| 167 | V167H | 2.11 |
| 167 | V167Y | 2.15 |
| 167 | V167R | 2.25 |
| 167 | V167Q | 2.41 |
| 167 | V167T | 2.47 |
| 167 | V167L | 2.56 |
| 167 | V167G | 2.83 |
| 167 | V167M | 3.84 |
| 167 | V167A | 4.99 |
| 167 | V167C | 5.37 |
| 167 | V167D | 5.54 |
| 167 | V167P | 6.08 |
| 168 | Y168F | 5.17 |
| 168 | Y168L | 5.39 |
| 169 | S169Y | 1.10 |
| 169 | S169A | 1.13 |
| 169 | S169R | 1.19 |
| 169 | S169K | 1.27 |
| 169 | S169Q | 1.37 |
| 169 | S169C | 1.38 |
| 169 | S169M | 1.40 |
| 169 | S169L | 1.47 |
| 169 | S169I | 1.53 |
| 170 | A170C | 1.06 |
| 170 | A170E | 1.17 |
| 170 | A170F | 1.17 |
| 170 | A170N | 1.17 |
| 170 | A170M | 1.28 |
| 170 | A170D | 1.32 |
| 170 | A170P | 1.33 |
| 171 | L171H | 1.07 |
| 171 | L171G | 1.33 |
| 171 | L171Y | 1.35 |
| 171 | L171T | 1.36 |
| 171 | L171V | 1.39 |
| 171 | L171I | 1.42 |
| 171 | L171K | 1.53 |
| 171 | L171A | 1.66 |
| 171 | L171C | 1.73 |
| 171 | L171S | 1.76 |
| 171 | L171Q | 1.93 |
| 171 | L171F | 1.97 |
| 171 | L171M | 2.22 |
| 171 | L171N | 2.79 |
| 172 | A172M | 1.06 |
| 172 | A172L | 1.22 |
| 172 | A172D | 1.42 |
| 172 | A172Y | 1.76 |
| 173 | S173T | 1.29 |
| 173 | S173H | 1.49 |

TABLE 10-6-continued

Variants with Peracid Degradation Greater Than Wild-Type

| Pos. | WT/Pos./Var. | PAD PI |
|---|---|---|
| 173 | S173I | 2.22 |
| 173 | S173F | 2.30 |
| 173 | S173R | 2.47 |
| 173 | S173V | 2.54 |
| 173 | S173E | 2.65 |
| 173 | S173P | 2.66 |
| 173 | S173A | 2.72 |
| 173 | S173M | 3.01 |
| 173 | S173K | 3.01 |
| 173 | S173C | 3.07 |
| 173 | S173Y | 3.54 |
| 173 | S173W | 3.67 |
| 173 | S173L | 3.86 |
| 174 | F174H | 1.05 |
| 174 | F174K | 1.17 |
| 174 | F174P | 1.46 |
| 174 | F174Y | 1.66 |
| 174 | F174L | 1.83 |
| 174 | F174A | 2.09 |
| 174 | F174M | 2.20 |
| 175 | M175N | 1.02 |
| 175 | M175E | 1.43 |
| 176 | K176C | 1.01 |
| 176 | K176R | 1.03 |
| 176 | K176E | 1.08 |
| 176 | K176W | 1.16 |
| 176 | K176D | 1.18 |
| 176 | K176A | 1.19 |
| 176 | K176F | 1.28 |
| 176 | K176V | 1.33 |
| 176 | K176M | 1.33 |
| 178 | P178K | 1.70 |
| 178 | P178T | 2.28 |
| 178 | P178V | 2.70 |
| 178 | P178G | 2.95 |
| 178 | P178S | 3.06 |
| 178 | P178Q | 3.64 |
| 178 | P178M | 3.87 |
| 178 | P178E | 4.15 |
| 178 | P178A | 4.39 |
| 178 | P178D | 6.44 |
| 178 | P178Y | 6.91 |
| 178 | P178L | 7.15 |
| 179 | F179G | 1.16 |
| 179 | F179V | 1.17 |
| 179 | F179Y | 1.47 |
| 179 | F179E | 1.80 |
| 179 | F179L | 1.89 |
| 180 | F180W | 1.81 |
| 180 | F180C | 1.94 |
| 180 | F180I | 2.11 |
| 180 | F180L | 2.13 |
| 180 | F180A | 2.70 |
| 180 | F180Y | 2.99 |
| 180 | F180N | 3.05 |
| 180 | F180V | 3.24 |
| 180 | F180M | 4.36 |
| 181 | D181A | 1.23 |
| 183 | G183P | 1.02 |
| 183 | G183R | 1.09 |
| 183 | G183Y | 1.45 |
| 183 | G183L | 1.50 |
| 183 | G183C | 1.99 |
| 184 | S184Y | 1.09 |
| 184 | S184Q | 1.16 |
| 184 | S184I | 1.21 |
| 184 | S184V | 1.25 |
| 184 | S184F | 1.27 |
| 184 | S184K | 1.61 |
| 184 | S184A | 1.69 |
| 184 | S184M | 1.77 |
| 184 | S184E | 1.86 |
| 184 | S184N | 1.93 |
| 184 | S184L | 2.00 |
| 184 | S184D | 2.24 |
| 184 | S184C | 2.39 |

TABLE 10-6-continued

Variants with Peracid Degradation Greater Than Wild-Type

| Pos. | WT/Pos./Var. | PAD PI |
|---|---|---|
| 185 | V185F | 1.20 |
| 185 | V185Q | 1.41 |
| 185 | V185M | 1.46 |
| 186 | I186L | 1.14 |
| 186 | I186M | 1.38 |
| 186 | I186A | 1.79 |
| 186 | I186D | 4.29 |
| 187 | S187K | 1.16 |
| 187 | S187D | 1.40 |
| 187 | S187G | 1.46 |
| 187 | S187L | 1.46 |
| 187 | S187H | 1.51 |
| 187 | S187I | 1.58 |
| 187 | S187N | 1.59 |
| 187 | S187C | 1.67 |
| 187 | S187A | 1.72 |
| 187 | S187M | 1.87 |
| 188 | T188N | 1.69 |
| 188 | T188E | 1.97 |
| 189 | D189A | 1.18 |
| 189 | D189T | 1.21 |
| 189 | D189I | 1.27 |
| 189 | D189L | 1.30 |
| 190 | G190C | 1.17 |
| 190 | G190Y | 1.39 |
| 190 | G190P | 1.86 |
| 190 | G190D | 2.02 |
| 190 | G190H | 2.92 |
| 190 | G190A | 3.42 |
| 190 | G190M | 5.54 |
| 191 | V191T | 1.03 |
| 191 | V191R | 1.91 |
| 191 | V191K | 2.17 |
| 191 | V191F | 2.75 |
| 191 | V191C | 2.81 |
| 191 | V191Y | 4.34 |
| 191 | V191L | 4.69 |
| 191 | V191A | 5.06 |
| 191 | V191E | 5.46 |
| 191 | V191Q | 5.83 |
| 191 | V191D | 6.03 |
| 191 | V191M | 7.34 |
| 193 | G193S | 1.60 |
| 193 | G193E | 3.15 |
| 193 | G193Q | 4.29 |
| 193 | G193V | 5.21 |
| 195 | H195P | 1.16 |
| 195 | H195M | 1.28 |
| 195 | H195K | 1.33 |
| 195 | H195Y | 1.49 |
| 195 | H195E | 1.70 |
| 195 | H195D | 1.93 |
| 196 | F196I | 1.12 |
| 196 | F196L | 1.17 |
| 196 | F196C | 1.18 |
| 197 | T197H | 1.24 |
| 197 | T197A | 1.42 |
| 197 | T197M | 2.38 |
| 198 | E198T | 1.16 |
| 198 | E198S | 1.18 |
| 198 | E198F | 1.21 |
| 198 | E198V | 1.44 |
| 198 | E198Q | 1.46 |
| 198 | E198A | 1.46 |
| 198 | E198I | 1.48 |
| 198 | E198L | 1.54 |
| 198 | E198N | 1.67 |
| 198 | E198P | 1.72 |
| 198 | E198Y | 1.77 |
| 198 | E198W | 1.78 |
| 198 | E198C | 1.83 |
| 198 | E198M | 1.86 |
| 198 | E198R | 1.88 |
| 199 | A199F | 1.15 |
| 199 | A199H | 1.15 |
| 199 | A199R | 1.17 |
| 199 | A199T | 1.22 |
| 199 | A199E | 1.31 |
| 199 | A199D | 1.33 |
| 199 | A199V | 1.45 |
| 199 | A199K | 1.53 |
| 199 | A199Y | 1.59 |
| 199 | A199L | 1.65 |
| 199 | A199C | 2.45 |
| 201 | N201D | 1.64 |
| 202 | R202M | 1.76 |
| 202 | R202G | 1.82 |
| 202 | R202S | 1.84 |
| 202 | R202C | 1.93 |
| 202 | R202A | 1.97 |
| 202 | R202I | 1.99 |
| 202 | R202E | 2.05 |
| 202 | R202L | 2.05 |
| 202 | R202T | 2.06 |
| 202 | R202H | 2.09 |
| 202 | R202F | 2.16 |
| 202 | R202W | 2.52 |
| 203 | D203Q | 1.03 |
| 203 | D203S | 1.13 |
| 203 | D203I | 1.19 |
| 203 | D203N | 1.28 |
| 203 | D203G | 1.33 |
| 203 | D203F | 1.34 |
| 203 | D203H | 1.54 |
| 203 | D203P | 1.71 |
| 203 | D203R | 1.77 |
| 203 | D203A | 1.96 |
| 203 | D203L | 2.08 |
| 203 | D203C | 2.09 |

The following Table provides variants that exhibited peracid degradation that was less than wild-type.

TABLE 10-7

Variants with Peracid Degradation Results Less than Wild-Type

| Pos | WT/Pos./Var. | PAD PI |
|---|---|---|
| 1 | M001V | 0.94 |
| 2 | A002Y | 0.46 |
| 2 | A002N | 0.59 |
| 2 | A002V | 0.60 |
| 2 | A002I | 0.61 |
| 2 | A002T | 0.61 |
| 2 | A002S | 0.66 |
| 2 | A002G | 0.84 |
| 2 | A002F | 0.93 |
| 3 | K003V | 0.84 |
| 4 | R004L | 0.01 |
| 4 | R004V | 0.08 |
| 4 | R004I | 0.15 |
| 4 | R004W | 0.48 |
| 4 | R004G | 0.79 |
| 4 | R004S | 0.91 |
| 4 | R004E | 0.97 |
| 4 | R004Y | 0.98 |
| 4 | R004H | 0.99 |
| 4 | R004Q | 0.99 |
| 4 | R004T | 1.00 |
| 5 | I005G | 0.01 |
| 5 | I005N | 0.01 |
| 5 | I005P | 0.01 |
| 5 | I005R | 0.01 |
| 5 | I005F | 0.15 |
| 5 | I005S | 0.37 |
| 5 | I005H | 0.63 |
| 5 | I005T | 0.72 |
| 5 | I005V | 0.92 |
| 6 | L006S | 0.01 |

TABLE 10-7-continued

Variants with Peracid Degradation Results Less than Wild-Type

| Pos | WT/Pos./Var. | PAD PI |
|---|---|---|
| 6 | L006K | 0.01 |
| 6 | L006G | 0.01 |
| 6 | L006H | 0.01 |
| 6 | L006R | 0.01 |
| 6 | L006W | 0.01 |
| 6 | L006E | 0.01 |
| 6 | L006Q | 0.01 |
| 6 | L006V | 0.35 |
| 6 | L006T | 0.35 |
| 6 | L006I | 0.82 |
| 7 | C007S | 0.01 |
| 7 | C007R | 0.01 |
| 7 | C007Y | 0.54 |
| 7 | C007M | 0.68 |
| 7 | C007G | 0.69 |
| 8 | F008S | 0.01 |
| 8 | F008R | 0.46 |
| 8 | F008H | 0.64 |
| 8 | F008G | 0.65 |
| 8 | F008T | 0.77 |
| 8 | F008K | 0.83 |
| 8 | F008P | 0.83 |
| 8 | F008V | 0.85 |
| 8 | F008Y | 0.90 |
| 8 | F008N | 0.96 |
| 9 | G009H | 0.01 |
| 9 | G009T | 0.01 |
| 10 | D010W | 0.01 |
| 10 | D010K | 0.01 |
| 10 | D010Y | 0.01 |
| 10 | D010T | 0.01 |
| 10 | D010I | 0.01 |
| 10 | D010V | 0.01 |
| 10 | D010S | 0.01 |
| 10 | D010G | 0.01 |
| 10 | D010R | 0.01 |
| 10 | D010A | 0.01 |
| 10 | D010M | 0.01 |
| 10 | D010N | 0.01 |
| 10 | D010P | 0.01 |
| 10 | D010E | 0.15 |
| 11 | S011T | 0.01 |
| 11 | S011V | 0.01 |
| 11 | S011D | 0.01 |
| 11 | S011E | 0.01 |
| 11 | S011F | 0.01 |
| 11 | S011G | 0.01 |
| 11 | S011L | 0.01 |
| 11 | S011Q | 0.01 |
| 11 | S011R | 0.01 |
| 11 | S011H | 0.33 |
| 11 | S011K | 0.40 |
| 11 | S011A | 0.53 |
| 11 | S011I | 0.56 |
| 12 | L012V | 0.01 |
| 12 | L012S | 0.01 |
| 12 | L012G | 0.01 |
| 12 | L012R | 0.01 |
| 12 | L012D | 0.01 |
| 12 | L012P | 0.01 |
| 12 | L012W | 0.02 |
| 12 | L012T | 0.06 |
| 12 | L012A | 0.07 |
| 12 | L012K | 0.13 |
| 12 | L012H | 0.16 |
| 12 | L012F | 0.17 |
| 12 | L012Q | 0.22 |
| 12 | L012C | 0.22 |
| 12 | L012N | 0.66 |
| 13 | T013Q | 0.51 |
| 13 | T013V | 0.63 |
| 13 | T013S | 0.68 |
| 13 | T013G | 0.77 |
| 14 | W014I | 0.01 |
| 14 | W014S | 0.01 |
| 14 | W014G | 0.01 |
| 14 | W014K | 0.01 |
| 14 | W014V | 0.01 |
| 14 | W014L | 0.01 |
| 14 | W014T | 0.01 |
| 14 | W014R | 0.01 |
| 14 | W014N | 0.01 |
| 14 | W014P | 0.01 |
| 14 | W014E | 0.15 |
| 14 | W014F | 0.22 |
| 14 | W014A | 0.27 |
| 14 | W014Y | 0.66 |
| 15 | G015C | 0.01 |
| 15 | G015N | 0.01 |
| 15 | G015D | 0.01 |
| 15 | G015E | 0.01 |
| 15 | G015P | 0.01 |
| 15 | G015A | 0.61 |
| 15 | G015S | 0.63 |
| 16 | W016S | 0.01 |
| 16 | W016G | 0.01 |
| 16 | W016H | 0.01 |
| 16 | W016T | 0.01 |
| 16 | W016R | 0.01 |
| 16 | W016N | 0.01 |
| 16 | W016P | 0.15 |
| 16 | W016Q | 0.31 |
| 16 | W016M | 0.37 |
| 16 | W016A | 0.55 |
| 16 | W016D | 0.57 |
| 16 | W016E | 0.65 |
| 16 | W016V | 0.88 |
| 17 | V017A | 0.68 |
| 17 | V017E | 0.75 |
| 17 | V017G | 0.84 |
| 17 | V017K | 0.84 |
| 17 | V017F | 0.85 |
| 17 | V017T | 0.86 |
| 17 | V017Y | 0.88 |
| 17 | V017R | 0.94 |
| 17 | V017P | 0.96 |
| 17 | V017I | 0.99 |
| 17 | V017L | 1.00 |
| 18 | P018S | 0.07 |
| 19 | V019P | 0.01 |
| 19 | V019M | 0.12 |
| 19 | V019R | 0.34 |
| 19 | V019Q | 0.40 |
| 19 | V019A | 0.55 |
| 19 | V019G | 0.56 |
| 19 | V019S | 0.57 |
| 19 | V019E | 0.62 |
| 19 | V019Y | 0.70 |
| 19 | V019D | 0.79 |
| 19 | V019L | 0.91 |
| 19 | V019K | 0.97 |
| 20 | E020L | 0.73 |
| 20 | E020G | 0.78 |
| 21 | D021P | 0.86 |
| 22 | G022K | 0.01 |
| 22 | G022W | 0.23 |
| 22 | G022R | 0.56 |
| 22 | G022V | 0.85 |
| 22 | G022S | 0.98 |
| 23 | A023R | 0.28 |
| 23 | A023S | 0.34 |
| 23 | A023G | 0.35 |
| 23 | A023F | 0.44 |
| 23 | A023V | 0.60 |
| 23 | A023Q | 0.73 |
| 23 | A023P | 0.73 |
| 23 | A023W | 0.80 |
| 23 | A023M | 0.95 |
| 23 | A023Y | 0.96 |
| 24 | P024S | 0.61 |
| 24 | P024Q | 0.65 |
| 24 | P024T | 0.66 |

TABLE 10-7-continued

Variants with Peracid Degradation Results Less than Wild-Type

| Pos | WT/Pos./Var. | PAD PI |
|---|---|---|
| 24 | P024A | 0.68 |
| 24 | P024G | 0.76 |
| 24 | P024I | 0.85 |
| 24 | P024R | 0.91 |
| 24 | P024H | 0.97 |
| 25 | T025P | 0.01 |
| 25 | T025H | 0.01 |
| 25 | T025L | 0.01 |
| 25 | T025R | 0.01 |
| 25 | T025M | 0.01 |
| 25 | T025E | 0.01 |
| 25 | T025D | 0.01 |
| 25 | T025K | 0.13 |
| 25 | T025W | 0.14 |
| 25 | T025I | 0.35 |
| 25 | T025G | 0.43 |
| 25 | T025C | 0.51 |
| 25 | T025V | 0.51 |
| 25 | T025S | 0.58 |
| 25 | T025A | 0.86 |
| 26 | E026S | 0.28 |
| 26 | E026T | 0.40 |
| 26 | E026W | 0.47 |
| 26 | E026N | 0.48 |
| 26 | E026R | 0.81 |
| 26 | E026G | 0.87 |
| 26 | E026C | 0.94 |
| 26 | E026V | 0.97 |
| 26 | E026P | 0.99 |
| 27 | R027W | 0.01 |
| 27 | R027T | 0.01 |
| 27 | R027P | 0.48 |
| 27 | R027C | 0.58 |
| 27 | R027S | 0.69 |
| 27 | R027G | 0.84 |
| 27 | R027E | 0.93 |
| 27 | R027V | 0.94 |
| 28 | F028G | 0.01 |
| 28 | F028P | 0.39 |
| 28 | F028V | 0.53 |
| 28 | F028S | 0.70 |
| 29 | A029V | 0.44 |
| 29 | A029T | 0.47 |
| 29 | A029S | 0.55 |
| 29 | A029Y | 0.59 |
| 29 | A029P | 0.62 |
| 29 | A029R | 0.73 |
| 29 | A029W | 0.74 |
| 29 | A029M | 0.77 |
| 29 | A029G | 0.80 |
| 29 | A029E | 0.84 |
| 29 | A029D | 1.00 |
| 30 | P030M | 0.79 |
| 30 | P030Q | 0.91 |
| 30 | P030A | 0.92 |
| 31 | D031E | 0.88 |
| 32 | V032P | 0.01 |
| 32 | V032R | 0.72 |
| 33 | R033V | 0.94 |
| 34 | W034R | 0.01 |
| 34 | W034E | 0.01 |
| 34 | W034Q | 0.04 |
| 34 | W034S | 0.08 |
| 34 | W034T | 0.15 |
| 34 | W034V | 0.73 |
| 34 | W034G | 0.88 |
| 34 | W034I | 0.94 |
| 35 | T035Q | 0.01 |
| 35 | T035N | 0.01 |
| 35 | T035R | 0.01 |
| 35 | T035V | 0.34 |
| 36 | G036S | 0.26 |
| 36 | G036T | 0.33 |
| 36 | G036V | 0.38 |
| 36 | G036M | 0.54 |
| 36 | G036N | 0.56 |

TABLE 10-7-continued

Variants with Peracid Degradation Results Less than Wild-Type

| Pos | WT/Pos./Var. | PAD PI |
|---|---|---|
| 36 | G036W | 0.68 |
| 36 | G036Q | 0.71 |
| 36 | G036R | 0.90 |
| 37 | V037T | 0.81 |
| 37 | V037H | 0.96 |
| 37 | V037W | 0.98 |
| 38 | L038K | 0.01 |
| 38 | L038G | 0.01 |
| 38 | L038E | 0.01 |
| 38 | L038P | 0.01 |
| 38 | L038Q | 0.01 |
| 38 | L038R | 0.01 |
| 38 | L038D | 0.12 |
| 38 | L038S | 0.29 |
| 38 | L038A | 0.63 |
| 38 | L038C | 0.72 |
| 39 | A039S | 0.01 |
| 39 | A039G | 0.30 |
| 39 | A039N | 0.43 |
| 39 | A039R | 0.64 |
| 39 | A039I | 0.71 |
| 39 | A039P | 0.74 |
| 39 | A039T | 0.79 |
| 39 | A039M | 0.81 |
| 39 | A039E | 0.83 |
| 39 | A039C | 0.92 |
| 39 | A039K | 0.96 |
| 39 | A039L | 0.97 |
| 39 | A039V | 0.98 |
| 40 | Q040P | 0.01 |
| 41 | Q041V | 0.01 |
| 41 | Q041S | 0.22 |
| 41 | Q041P | 0.66 |
| 41 | Q041Y | 0.70 |
| 41 | Q041W | 0.88 |
| 42 | L042W | 0.01 |
| 42 | L042H | 0.01 |
| 42 | L042T | 0.01 |
| 42 | L042Q | 0.28 |
| 42 | L042S | 0.45 |
| 42 | L042R | 0.64 |
| 42 | L042I | 0.66 |
| 42 | L042V | 0.73 |
| 42 | L042M | 0.74 |
| 42 | L042G | 0.76 |
| 43 | G043S | 0.23 |
| 43 | G043P | 0.31 |
| 43 | G043V | 0.33 |
| 43 | G043Q | 0.48 |
| 43 | G043R | 0.59 |
| 43 | G043C | 0.73 |
| 43 | G043I | 0.77 |
| 43 | G043K | 0.86 |
| 43 | G043M | 0.88 |
| 43 | G043Y | 0.94 |
| 43 | G043H | 0.96 |
| 44 | A044S | 0.01 |
| 44 | A044Y | 0.01 |
| 44 | A044T | 0.01 |
| 44 | A044R | 0.01 |
| 44 | A044E | 0.03 |
| 44 | A044V | 0.50 |
| 44 | A044F | 0.80 |
| 44 | A044W | 0.85 |
| 44 | A044M | 0.98 |
| 44 | A044L | 0.99 |
| 45 | D045S | 0.38 |
| 45 | D045T | 0.44 |
| 45 | D045R | 0.49 |
| 45 | D045V | 0.50 |
| 45 | D045P | 0.53 |
| 45 | D045Q | 0.57 |
| 45 | D045W | 0.58 |
| 45 | D045H | 0.78 |
| 45 | D045L | 0.78 |
| 45 | D045M | 0.78 |

TABLE 10-7-continued

Variants with Peracid Degradation Results Less than Wild-Type

| Pos | WT/Pos./Var. | PAD PI |
|---|---|---|
| 45 | D045G | 0.84 |
| 45 | D045A | 0.84 |
| 45 | D045C | 0.84 |
| 45 | D045K | 0.87 |
| 46 | F046T | 0.43 |
| 46 | F046W | 0.63 |
| 46 | F046S | 0.66 |
| 46 | F046V | 0.79 |
| 46 | F046I | 0.88 |
| 46 | F046G | 0.94 |
| 47 | E047P | 0.36 |
| 47 | E047R | 0.62 |
| 47 | E047N | 0.63 |
| 47 | E047S | 0.63 |
| 47 | E047M | 0.70 |
| 47 | E047A | 0.76 |
| 47 | E047F | 0.76 |
| 47 | E047C | 0.77 |
| 47 | E047T | 0.84 |
| 47 | E047D | 0.98 |
| 47 | E047H | 0.99 |
| 48 | V048R | 0.01 |
| 48 | V048S | 0.42 |
| 48 | V048G | 0.87 |
| 48 | V048N | 0.98 |
| 48 | V048E | 0.99 |
| 49 | I049P | 0.16 |
| 49 | I049R | 0.29 |
| 49 | I049W | 0.68 |
| 49 | I049H | 0.74 |
| 49 | I049S | 0.79 |
| 49 | I049E | 0.88 |
| 49 | I049V | 0.97 |
| 50 | E050R | 0.01 |
| 50 | E050W | 0.14 |
| 50 | E050V | 0.43 |
| 50 | E050I | 0.58 |
| 50 | E050S | 0.65 |
| 50 | E050Q | 0.91 |
| 50 | E050L | 0.97 |
| 51 | E051R | 0.01 |
| 51 | E051I | 0.04 |
| 51 | E051W | 0.17 |
| 51 | E051V | 0.37 |
| 51 | E051Q | 0.76 |
| 51 | E051L | 0.93 |
| 52 | G052H | 0.01 |
| 52 | G052S | 0.01 |
| 52 | G052V | 0.01 |
| 52 | G052T | 0.01 |
| 52 | G052M | 0.01 |
| 52 | G052F | 0.01 |
| 52 | G052I | 0.07 |
| 52 | G052P | 0.24 |
| 52 | G052L | 0.24 |
| 52 | G052Q | 0.28 |
| 52 | G052R | 0.35 |
| 52 | G052E | 0.55 |
| 52 | G052A | 0.79 |
| 53 | L053R | 0.01 |
| 53 | L053W | 0.01 |
| 53 | L053P | 0.01 |
| 53 | L053D | 0.01 |
| 53 | L053E | 0.19 |
| 53 | L053K | 0.24 |
| 53 | L053S | 0.26 |
| 53 | L053G | 0.33 |
| 53 | L053V | 0.65 |
| 53 | L053I | 0.66 |
| 53 | L053Q | 0.72 |
| 53 | L053T | 0.84 |
| 54 | S054F | 0.01 |
| 54 | S054W | 0.01 |
| 54 | S054H | 0.01 |
| 54 | S054K | 0.08 |
| 54 | S054I | 0.12 |

TABLE 10-7-continued

Variants with Peracid Degradation Results Less than Wild-Type

| Pos | WT/Pos./Var. | PAD PI |
|---|---|---|
| 54 | S054Y | 0.12 |
| 54 | S054G | 0.17 |
| 54 | S054L | 0.26 |
| 54 | S054V | 0.29 |
| 54 | S054E | 0.30 |
| 54 | S054T | 0.33 |
| 54 | S054R | 0.35 |
| 54 | S054M | 0.48 |
| 54 | S054Q | 0.53 |
| 54 | S054D | 0.65 |
| 54 | S054C | 0.88 |
| 55 | A055V | 0.01 |
| 55 | A055I | 0.01 |
| 55 | A055P | 0.01 |
| 55 | A055W | 0.01 |
| 55 | A055Y | 0.18 |
| 55 | A055R | 0.25 |
| 55 | A055T | 0.42 |
| 55 | A055G | 0.73 |
| 55 | A055L | 0.87 |
| 55 | A055S | 0.87 |
| 55 | A055H | 0.92 |
| 56 | R056C | 0.01 |
| 56 | R056G | 0.01 |
| 56 | R056T | 0.01 |
| 56 | R056E | 0.01 |
| 56 | R056Q | 0.01 |
| 56 | R056S | 0.12 |
| 56 | R056L | 0.24 |
| 56 | R056N | 0.27 |
| 56 | R056A | 0.69 |
| 57 | T057R | 0.01 |
| 57 | T057P | 0.01 |
| 57 | T057N | 0.25 |
| 57 | T057C | 0.40 |
| 57 | T057Y | 0.55 |
| 57 | T057H | 0.61 |
| 57 | T057A | 0.65 |
| 57 | T057L | 0.76 |
| 57 | T057V | 0.87 |
| 57 | T057I | 0.87 |
| 58 | T058M | 0.03 |
| 58 | T058A | 0.36 |
| 58 | T058V | 0.96 |
| 58 | T058S | 0.96 |
| 59 | N059R | 0.01 |
| 59 | N059M | 0.01 |
| 59 | N059P | 0.01 |
| 60 | I060P | 0.32 |
| 60 | I060D | 0.66 |
| 60 | I060C | 0.67 |
| 60 | I060M | 0.68 |
| 60 | I060A | 0.79 |
| 60 | I060R | 0.81 |
| 60 | I060L | 0.91 |
| 60 | I060E | 0.92 |
| 60 | I060K | 0.96 |
| 60 | I060S | 1.00 |
| 61 | D061F | 0.70 |
| 61 | D061A | 0.71 |
| 61 | D061C | 0.85 |
| 61 | D061Y | 0.95 |
| 61 | D061V | 0.97 |
| 61 | D061N | 1.00 |
| 62 | D062T | 0.01 |
| 62 | D062I | 0.01 |
| 62 | D062V | 0.01 |
| 62 | D062H | 0.01 |
| 62 | D062W | 0.01 |
| 62 | D062S | 0.01 |
| 62 | D062L | 0.01 |
| 62 | D062G | 0.01 |
| 62 | D062R | 0.01 |
| 62 | D062M | 0.01 |
| 62 | D062P | 0.01 |
| 62 | D062Q | 0.01 |

TABLE 10-7-continued

Variants with Peracid Degradation Results Less than Wild-Type

| Pos | WT/Pos./Var. | PAD PI |
|---|---|---|
| 62 | D062A | 0.11 |
| 62 | D062C | 0.49 |
| 62 | D062E | 0.60 |
| 63 | P063A | 0.60 |
| 63 | P063R | 0.80 |
| 63 | P063S | 0.90 |
| 63 | P063M | 0.91 |
| 63 | P063F | 0.93 |
| 63 | P063Y | 0.95 |
| 64 | T064R | 0.11 |
| 64 | T064D | 0.64 |
| 64 | T064W | 0.69 |
| 64 | T064Q | 0.87 |
| 64 | T064C | 0.88 |
| 64 | T064P | 0.94 |
| 64 | T064H | 0.96 |
| 64 | T064N | 0.98 |
| 64 | T064S | 0.99 |
| 65 | D065V | 0.20 |
| 65 | D065R | 0.22 |
| 65 | D065H | 0.40 |
| 65 | D065Y | 0.42 |
| 65 | D065P | 0.42 |
| 65 | D065S | 0.47 |
| 65 | D065W | 0.50 |
| 65 | D065T | 0.50 |
| 65 | D065G | 0.52 |
| 65 | D065I | 0.62 |
| 65 | D065A | 0.72 |
| 66 | P066N | 0.38 |
| 66 | P066Q | 0.42 |
| 66 | P066G | 0.44 |
| 66 | P066R | 0.51 |
| 66 | P066C | 0.52 |
| 66 | P066A | 0.56 |
| 66 | P066F | 0.67 |
| 66 | P066Y | 0.70 |
| 66 | P066D | 0.72 |
| 66 | P066I | 0.84 |
| 66 | P066V | 0.89 |
| 66 | P066H | 0.95 |
| 66 | P066L | 0.99 |
| 67 | R067F | 0.01 |
| 67 | R067W | 0.02 |
| 67 | R067P | 0.04 |
| 67 | R067E | 0.11 |
| 67 | R067V | 0.12 |
| 67 | R067Q | 0.13 |
| 67 | R067L | 0.16 |
| 67 | R067A | 0.22 |
| 67 | R067T | 0.32 |
| 67 | R067N | 0.33 |
| 67 | R067G | 0.41 |
| 67 | R067K | 0.99 |
| 68 | L068G | 0.01 |
| 68 | L068A | 0.01 |
| 68 | L068M | 0.03 |
| 68 | L068C | 0.06 |
| 68 | L068S | 0.07 |
| 68 | L068N | 0.10 |
| 68 | L068E | 0.13 |
| 68 | L068H | 0.22 |
| 68 | L068Q | 0.25 |
| 68 | L068F | 0.25 |
| 68 | L068T | 0.32 |
| 68 | L068P | 0.35 |
| 68 | L068D | 0.44 |
| 68 | L068Y | 0.45 |
| 68 | L068R | 0.47 |
| 68 | L068V | 0.51 |
| 68 | L068W | 0.56 |
| 68 | L068I | 0.73 |
| 69 | N069Y | 0.17 |
| 69 | N069W | 0.55 |
| 69 | N069P | 0.59 |
| 69 | N069R | 0.83 |

TABLE 10-7-continued

Variants with Peracid Degradation Results Less than Wild-Type

| Pos | WT/Pos./Var. | PAD PI |
|---|---|---|
| 69 | N069G | 0.98 |
| 70 | G070M | 0.01 |
| 70 | G070T | 0.01 |
| 70 | G070P | 0.01 |
| 70 | G070V | 0.01 |
| 70 | G070C | 0.01 |
| 70 | G070R | 0.01 |
| 70 | G070Y | 0.01 |
| 70 | G070K | 0.01 |
| 70 | G070N | 0.01 |
| 70 | G070Q | 0.01 |
| 70 | G070F | 0.01 |
| 70 | G070I | 0.27 |
| 70 | G070E | 0.33 |
| 70 | G070S | 0.64 |
| 71 | A071P | 0.01 |
| 71 | A071N | 0.61 |
| 71 | A071D | 0.65 |
| 71 | A071G | 0.68 |
| 71 | A071S | 0.69 |
| 71 | A071R | 0.77 |
| 71 | A071H | 0.78 |
| 71 | A071I | 0.79 |
| 71 | A071T | 0.79 |
| 71 | A071E | 0.81 |
| 71 | A071L | 0.84 |
| 71 | A071F | 0.99 |
| 71 | A071C | 0.99 |
| 72 | S072Y | 0.07 |
| 72 | S072W | 0.34 |
| 72 | S072P | 0.56 |
| 72 | S072Q | 0.66 |
| 72 | S072L | 0.70 |
| 72 | S072R | 0.74 |
| 72 | S072D | 0.80 |
| 72 | S072V | 0.83 |
| 72 | S072E | 0.93 |
| 72 | S072T | 0.97 |
| 73 | Y073P | 0.01 |
| 73 | Y073R | 0.26 |
| 73 | Y073L | 0.50 |
| 73 | Y073G | 0.51 |
| 73 | Y073H | 0.52 |
| 73 | Y073I | 0.64 |
| 73 | Y073S | 0.68 |
| 73 | Y073V | 0.74 |
| 73 | Y073N | 0.76 |
| 73 | Y073D | 0.80 |
| 73 | Y073Q | 0.87 |
| 73 | Y073K | 0.94 |
| 74 | L074S | 0.01 |
| 74 | L074G | 0.57 |
| 74 | L074V | 0.61 |
| 74 | L074I | 0.64 |
| 74 | L074W | 0.67 |
| 74 | L074Y | 0.86 |
| 75 | P075M | 0.30 |
| 75 | P075R | 0.46 |
| 75 | P075Q | 0.61 |
| 75 | P075S | 0.63 |
| 75 | P075T | 0.69 |
| 75 | P075I | 0.74 |
| 75 | P075H | 0.86 |
| 75 | P075K | 0.88 |
| 75 | P075G | 0.93 |
| 76 | S076W | 0.01 |
| 76 | S076Y | 0.18 |
| 76 | S076F | 0.46 |
| 76 | S076Q | 0.90 |
| 77 | C077Y | 0.01 |
| 77 | C077R | 0.01 |
| 77 | C077W | 0.01 |
| 77 | C077F | 0.01 |
| 77 | C077G | 0.18 |
| 77 | C077L | 0.73 |
| 77 | C077S | 0.76 |

TABLE 10-7-continued

| Variants with Peracid Degradation Results Less than Wild-Type | | |
|---|---|---|
| Pos | WT/Pos./Var. | PAD PI |
| 77 | C077V | 0.80 |
| 77 | C077A | 0.91 |
| 78 | L078E | 0.01 |
| 78 | L078N | 0.01 |
| 78 | L078M | 0.48 |
| 78 | L078Q | 0.52 |
| 78 | L078C | 0.78 |
| 78 | L078Y | 0.81 |
| 78 | L078V | 0.83 |
| 79 | A079H | 0.01 |
| 79 | A079F | 0.01 |
| 79 | A079C | 0.03 |
| 79 | A079Q | 0.27 |
| 79 | A079E | 0.27 |
| 79 | A079N | 0.28 |
| 79 | A079M | 0.28 |
| 79 | A079R | 0.32 |
| 79 | A079W | 0.53 |
| 79 | A079T | 0.60 |
| 79 | A079I | 0.67 |
| 79 | A079S | 0.78 |
| 79 | A079G | 0.92 |
| 79 | A079P | 0.94 |
| 79 | A079L | 0.96 |
| 80 | T080W | 0.01 |
| 80 | T080L | 0.01 |
| 80 | T080K | 0.01 |
| 80 | T080R | 0.01 |
| 80 | T080E | 0.01 |
| 80 | T080P | 0.01 |
| 80 | T080H | 0.05 |
| 80 | T080Y | 0.11 |
| 80 | T080I | 0.15 |
| 80 | T080N | 0.53 |
| 81 | H081R | 0.01 |
| 81 | H081Y | 0.14 |
| 81 | H081K | 0.56 |
| 81 | H081S | 0.69 |
| 81 | H081V | 0.71 |
| 81 | H081P | 0.72 |
| 81 | H081Q | 0.75 |
| 81 | H081G | 0.80 |
| 81 | H081F | 0.90 |
| 82 | L082R | 0.01 |
| 82 | L082S | 0.01 |
| 82 | L082W | 0.01 |
| 82 | L082V | 0.19 |
| 82 | L082G | 0.31 |
| 82 | L082T | 0.38 |
| 82 | L082H | 0.47 |
| 82 | L082I | 0.51 |
| 82 | L082K | 0.51 |
| 82 | L082P | 0.52 |
| 82 | L082A | 0.98 |
| 83 | P083T | 0.01 |
| 83 | P083V | 0.19 |
| 83 | P083L | 0.21 |
| 83 | P083H | 0.61 |
| 83 | P083W | 0.62 |
| 83 | P083G | 0.68 |
| 83 | P083S | 0.79 |
| 83 | P083Q | 0.82 |
| 83 | P083D | 0.83 |
| 83 | P083F | 0.99 |
| 84 | L084W | 0.01 |
| 84 | L084V | 0.42 |
| 84 | L084P | 0.43 |
| 84 | L084T | 0.44 |
| 84 | L084A | 0.45 |
| 84 | L084Q | 0.52 |
| 84 | L084S | 0.55 |
| 84 | L084R | 0.57 |
| 84 | L084N | 0.67 |
| 84 | L084K | 0.79 |
| 84 | L084D | 0.85 |
| 84 | L084I | 0.87 |

TABLE 10-7-continued

| Variants with Peracid Degradation Results Less than Wild-Type | | |
|---|---|---|
| Pos | WT/Pos./Var. | PAD PI |
| 84 | L084H | 0.99 |
| 85 | D085I | 0.10 |
| 85 | D085L | 0.24 |
| 85 | D085V | 0.25 |
| 85 | D085W | 0.34 |
| 85 | D085P | 0.54 |
| 85 | D085Y | 0.55 |
| 85 | D085S | 0.68 |
| 85 | D085T | 0.71 |
| 85 | D085N | 0.78 |
| 85 | D085Q | 0.99 |
| 86 | L086H | 0.01 |
| 86 | L086S | 0.01 |
| 86 | L086R | 0.01 |
| 86 | L086E | 0.01 |
| 86 | L086Q | 0.01 |
| 86 | L086W | 0.08 |
| 86 | L086V | 0.12 |
| 86 | L086T | 0.28 |
| 86 | L086G | 0.70 |
| 86 | L086Y | 0.82 |
| 86 | L086P | 0.99 |
| 87 | V087S | 0.01 |
| 87 | V087G | 0.01 |
| 87 | V087Y | 0.01 |
| 87 | V087R | 0.01 |
| 87 | V087K | 0.01 |
| 87 | V087D | 0.01 |
| 87 | V087F | 0.10 |
| 87 | V087T | 0.15 |
| 87 | V087A | 0.17 |
| 87 | V087M | 0.75 |
| 88 | I088H | 0.01 |
| 88 | I088T | 0.01 |
| 88 | I088G | 0.01 |
| 88 | I088N | 0.01 |
| 88 | I088Q | 0.01 |
| 89 | I089H | 0.01 |
| 89 | I089S | 0.01 |
| 89 | I089G | 0.01 |
| 89 | I089W | 0.01 |
| 89 | I089Q | 0.01 |
| 89 | I089E | 0.01 |
| 89 | I089F | 0.75 |
| 89 | I089V | 0.82 |
| 89 | I089T | 0.90 |
| 90 | M090S | 0.01 |
| 90 | M090W | 0.01 |
| 90 | M090G | 0.01 |
| 90 | M090P | 0.01 |
| 90 | M090V | 0.08 |
| 90 | M090T | 0.15 |
| 90 | M090R | 0.36 |
| 90 | M090I | 0.66 |
| 90 | M090Q | 0.77 |
| 90 | M090L | 0.98 |
| 91 | L091G | 0.01 |
| 91 | L091T | 0.01 |
| 91 | L091Q | 0.01 |
| 91 | L091E | 0.01 |
| 91 | L091S | 0.43 |
| 91 | L091V | 0.79 |
| 91 | L091M | 0.88 |
| 92 | G092V | 0.01 |
| 92 | G092S | 0.01 |
| 92 | G092E | 0.01 |
| 92 | G092F | 0.01 |
| 93 | T093Q | 0.01 |
| 93 | T093Y | 0.03 |
| 93 | T093D | 0.23 |
| 93 | T093S | 0.49 |
| 93 | T093F | 0.54 |
| 93 | T093C | 0.95 |
| 94 | N094L | 0.01 |
| 94 | N094T | 0.01 |
| 94 | N094V | 0.01 |

TABLE 10-7-continued

Variants with Peracid Degradation Results Less than Wild-Type

| Pos | WT/Pos./Var. | PAD PI |
|---|---|---|
| 94 | N094H | 0.01 |
| 94 | N094R | 0.01 |
| 94 | N094W | 0.01 |
| 94 | N094M | 0.03 |
| 94 | N094C | 0.07 |
| 94 | N094Y | 0.12 |
| 94 | N094G | 0.53 |
| 94 | N094A | 0.74 |
| 94 | N094P | 0.79 |
| 94 | N094S | 0.88 |
| 95 | D095E | 0.75 |
| 96 | T096I | 0.01 |
| 96 | T096W | 0.01 |
| 96 | T096Y | 0.01 |
| 96 | T096R | 0.14 |
| 96 | T096V | 0.59 |
| 96 | T096S | 0.79 |
| 96 | T096P | 0.89 |
| 97 | K097Q | 0.01 |
| 97 | K097G | 0.01 |
| 97 | K097I | 0.01 |
| 97 | K097W | 0.01 |
| 97 | K097L | 0.01 |
| 97 | K097V | 0.01 |
| 97 | K097Y | 0.01 |
| 97 | K097S | 0.01 |
| 97 | K097T | 0.01 |
| 97 | K097M | 0.22 |
| 97 | K097A | 0.23 |
| 97 | K097P | 0.27 |
| 97 | K097R | 0.59 |
| 98 | A098T | 0.27 |
| 98 | A098G | 0.56 |
| 98 | A098S | 0.65 |
| 98 | A098I | 0.65 |
| 98 | A098H | 0.92 |
| 99 | Y099R | 0.29 |
| 99 | Y099V | 0.31 |
| 99 | Y099S | 0.37 |
| 99 | Y099W | 0.57 |
| 99 | Y099H | 0.59 |
| 99 | Y099I | 0.61 |
| 99 | Y099G | 0.70 |
| 99 | Y099P | 0.81 |
| 99 | Y099A | 0.82 |
| 99 | Y099L | 0.86 |
| 100 | F100W | 0.01 |
| 100 | F100K | 0.01 |
| 100 | F100D | 0.01 |
| 100 | F100E | 0.15 |
| 100 | F100S | 0.85 |
| 101 | R101W | 0.01 |
| 101 | R101K | 0.07 |
| 101 | R101Q | 0.11 |
| 101 | R101V | 0.44 |
| 101 | R101D | 0.80 |
| 101 | R101Y | 0.80 |
| 101 | R101P | 0.86 |
| 101 | R101N | 0.92 |
| 101 | R101C | 0.95 |
| 101 | R101I | 0.96 |
| 101 | R101F | 0.97 |
| 102 | R102W | 0.01 |
| 102 | R102F | 0.23 |
| 102 | R102G | 0.27 |
| 102 | R102C | 0.36 |
| 102 | R102V | 0.61 |
| 102 | R102D | 0.68 |
| 102 | R102P | 0.89 |
| 102 | R102S | 0.96 |
| 103 | T103W | 0.01 |
| 103 | T103Y | 0.01 |
| 103 | T103G | 0.01 |
| 103 | T103K | 0.01 |
| 103 | T103I | 0.01 |
| 103 | T103L | 0.01 |
| 103 | T103H | 0.01 |
| 103 | T103A | 0.01 |
| 103 | T103V | 0.01 |
| 103 | T103S | 0.01 |
| 103 | T103C | 0.01 |
| 103 | T103R | 0.01 |
| 103 | T103N | 0.01 |
| 103 | T103F | 0.01 |
| 103 | T103P | 0.01 |
| 104 | P104R | 0.01 |
| 104 | P104W | 0.23 |
| 104 | P104T | 0.33 |
| 104 | P104S | 0.53 |
| 104 | P104Q | 0.85 |
| 104 | P104F | 0.86 |
| 104 | P104G | 0.98 |
| 105 | L105V | 0.01 |
| 105 | L105E | 0.53 |
| 105 | L105S | 0.61 |
| 105 | L105Y | 0.62 |
| 105 | L105T | 0.64 |
| 105 | L105P | 0.90 |
| 106 | D106R | 0.56 |
| 106 | D106Q | 0.62 |
| 106 | D106P | 0.63 |
| 106 | D106N | 0.64 |
| 106 | D106M | 0.86 |
| 106 | D106I | 0.92 |
| 106 | D106L | 1.00 |
| 107 | I107E | 0.01 |
| 107 | I107G | 0.01 |
| 107 | I107F | 0.01 |
| 107 | I107Q | 0.01 |
| 107 | I107R | 0.01 |
| 107 | I107P | 0.32 |
| 107 | I107Y | 0.52 |
| 107 | I107A | 0.80 |
| 107 | I107N | 0.93 |
| 107 | I107V | 0.97 |
| 108 | A108E | 0.61 |
| 108 | A108Q | 0.73 |
| 108 | A108T | 0.87 |
| 108 | A108V | 0.95 |
| 109 | L109W | 0.01 |
| 109 | L109D | 0.11 |
| 109 | L109I | 0.14 |
| 109 | L109E | 0.19 |
| 109 | L109R | 0.21 |
| 109 | L109H | 0.22 |
| 109 | L109Q | 0.22 |
| 109 | L109F | 0.32 |
| 109 | L109A | 0.32 |
| 109 | L109S | 0.38 |
| 109 | L109P | 0.43 |
| 109 | L109G | 0.51 |
| 109 | L109V | 0.54 |
| 109 | L109M | 0.63 |
| 109 | L109N | 0.66 |
| 109 | L109T | 0.79 |
| 109 | L109Y | 0.83 |
| 110 | G110T | 0.01 |
| 110 | G110W | 0.01 |
| 110 | G110Y | 0.01 |
| 110 | G110P | 0.22 |
| 110 | G110I | 0.23 |
| 110 | G110S | 0.30 |
| 110 | G110Q | 0.34 |
| 110 | G110R | 0.48 |
| 110 | G110H | 0.73 |
| 110 | G110N | 0.77 |
| 110 | G110M | 0.82 |
| 111 | M111R | 0.01 |
| 111 | M111S | 0.14 |
| 111 | M111H | 0.19 |
| 111 | M111G | 0.32 |
| 111 | M111P | 0.57 |

TABLE 10-7-continued

Variants with Peracid Degradation Results Less than Wild-Type

| Pos | WT/Pos./Var. | PAD PI |
|---|---|---|
| 111 | M111E | 0.67 |
| 111 | M111L | 0.67 |
| 111 | M111K | 0.71 |
| 111 | M111T | 0.76 |
| 111 | M111F | 0.78 |
| 111 | M111D | 0.79 |
| 111 | M111V | 0.93 |
| 112 | S112Y | 0.01 |
| 112 | S112R | 0.01 |
| 112 | S112P | 0.01 |
| 112 | S112H | 0.38 |
| 112 | S112V | 0.48 |
| 112 | S112M | 0.56 |
| 112 | S112W | 0.58 |
| 112 | S112K | 0.68 |
| 112 | S112T | 0.72 |
| 112 | S112N | 0.85 |
| 112 | S112F | 0.88 |
| 112 | S112A | 0.94 |
| 113 | V113S | 0.57 |
| 113 | V113G | 0.58 |
| 113 | V113K | 0.72 |
| 113 | V113H | 0.76 |
| 113 | V113W | 0.80 |
| 113 | V113L | 0.85 |
| 113 | V113T | 0.86 |
| 113 | V113D | 0.87 |
| 113 | V113E | 0.94 |
| 113 | V113C | 0.94 |
| 113 | V113F | 0.96 |
| 113 | V113Y | 0.98 |
| 114 | L114H | 0.01 |
| 114 | L114E | 0.01 |
| 114 | L114Q | 0.12 |
| 114 | L114P | 0.28 |
| 114 | L114S | 0.55 |
| 114 | L114V | 0.60 |
| 114 | L114N | 0.77 |
| 115 | V115I | 0.99 |
| 116 | T116Y | 0.47 |
| 116 | T116V | 0.57 |
| 116 | T116R | 0.62 |
| 116 | T116L | 0.68 |
| 116 | T116W | 0.75 |
| 116 | T116I | 0.76 |
| 116 | T116Q | 0.77 |
| 116 | T116P | 0.84 |
| 116 | T116G | 0.90 |
| 116 | T116E | 0.91 |
| 116 | T116A | 0.95 |
| 116 | T116S | 0.96 |
| 117 | Q117W | 0.71 |
| 117 | Q117V | 0.76 |
| 117 | Q117G | 0.79 |
| 117 | Q117S | 0.87 |
| 118 | V118K | 0.01 |
| 118 | V118W | 0.01 |
| 118 | V118E | 0.01 |
| 118 | V118R | 0.07 |
| 118 | V118P | 0.22 |
| 118 | V118D | 0.40 |
| 118 | V118I | 0.55 |
| 118 | V118G | 0.56 |
| 118 | V118S | 0.82 |
| 118 | V118A | 0.85 |
| 118 | V118T | 0.92 |
| 118 | V118M | 0.93 |
| 118 | V118F | 1.00 |
| 119 | L119G | 0.01 |
| 119 | L119S | 0.01 |
| 119 | L119F | 0.01 |
| 119 | L119R | 0.01 |
| 119 | L119P | 0.01 |
| 119 | L119T | 0.10 |
| 119 | L119N | 0.11 |
| 119 | L119V | 0.15 |

TABLE 10-7-continued

Variants with Peracid Degradation Results Less than Wild-Type

| Pos | WT/Pos./Var. | PAD PI |
|---|---|---|
| 119 | L119W | 0.20 |
| 119 | L119C | 0.24 |
| 119 | L119D | 0.28 |
| 119 | L119E | 0.32 |
| 119 | L119I | 0.43 |
| 119 | L119H | 0.46 |
| 119 | L119Y | 0.56 |
| 120 | T120P | 0.01 |
| 120 | T120H | 0.50 |
| 120 | T120R | 0.60 |
| 120 | T120A | 0.66 |
| 120 | T120Q | 0.78 |
| 120 | T120C | 0.92 |
| 121 | S121P | 0.38 |
| 121 | S121R | 0.70 |
| 121 | S121W | 0.77 |
| 121 | S121K | 0.78 |
| 121 | S121G | 0.99 |
| 122 | A122G | 0.01 |
| 122 | A122D | 0.06 |
| 122 | A122F | 0.15 |
| 122 | A122H | 0.17 |
| 122 | A122R | 0.40 |
| 122 | A122S | 0.43 |
| 122 | A122K | 0.45 |
| 122 | A122E | 0.47 |
| 122 | A122T | 0.52 |
| 122 | A122P | 0.55 |
| 122 | A122I | 0.65 |
| 122 | A122N | 0.70 |
| 122 | A122Q | 0.74 |
| 122 | A122W | 0.86 |
| 122 | A122V | 0.89 |
| 122 | A122M | 0.94 |
| 123 | G123C | 0.30 |
| 123 | G123Q | 0.31 |
| 123 | G123T | 0.54 |
| 123 | G123E | 0.56 |
| 123 | G123V | 0.59 |
| 123 | G123R | 0.60 |
| 123 | G123N | 0.71 |
| 123 | G123H | 0.74 |
| 123 | G123F | 0.80 |
| 123 | G123P | 0.81 |
| 123 | G123D | 0.84 |
| 124 | G124I | 0.01 |
| 124 | G124H | 0.01 |
| 124 | G124M | 0.01 |
| 124 | G124W | 0.01 |
| 124 | G124P | 0.01 |
| 124 | G124A | 0.03 |
| 124 | G124Q | 0.21 |
| 124 | G124T | 0.32 |
| 124 | G124V | 0.33 |
| 124 | G124R | 0.41 |
| 124 | G124L | 0.54 |
| 124 | G124S | 0.56 |
| 124 | G124Y | 0.56 |
| 124 | G124N | 0.60 |
| 124 | G124D | 0.64 |
| 124 | G124C | 0.67 |
| 124 | G124F | 0.95 |
| 125 | V125W | 0.25 |
| 125 | V125E | 0.39 |
| 125 | V125R | 0.47 |
| 125 | V125C | 0.54 |
| 125 | V125D | 0.54 |
| 125 | V125P | 0.62 |
| 125 | V125F | 0.63 |
| 125 | V125S | 0.79 |
| 125 | V125Y | 0.81 |
| 125 | V125A | 0.93 |
| 125 | V125I | 0.94 |
| 126 | G126I | 0.01 |
| 126 | G126V | 0.18 |
| 126 | G126Y | 0.23 |

TABLE 10-7-continued

Variants with Peracid Degradation Results Less than Wild-Type

| Pos | WT/Pos./Var. | PAD PI |
|---|---|---|
| 126 | G126L | 0.54 |
| 126 | G126A | 0.55 |
| 126 | G126E | 0.60 |
| 126 | G126P | 0.67 |
| 126 | G126T | 0.74 |
| 126 | G126R | 0.76 |
| 126 | G126N | 0.85 |
| 126 | G126S | 0.90 |
| 126 | G126C | 0.98 |
| 127 | T127L | 0.01 |
| 127 | T127E | 0.01 |
| 127 | T127Q | 0.15 |
| 127 | T127I | 0.20 |
| 127 | T127H | 0.60 |
| 127 | T127D | 0.62 |
| 127 | T127M | 0.64 |
| 127 | T127C | 0.65 |
| 127 | T127V | 0.68 |
| 127 | T127G | 0.71 |
| 127 | T127P | 0.77 |
| 127 | T127S | 0.83 |
| 128 | T128D | 0.66 |
| 129 | Y129W | 0.01 |
| 129 | Y129G | 0.01 |
| 129 | Y129K | 0.01 |
| 129 | Y129V | 0.01 |
| 129 | Y129T | 0.14 |
| 129 | Y129A | 0.17 |
| 129 | Y129R | 0.18 |
| 129 | Y129M | 0.21 |
| 129 | Y129D | 0.23 |
| 129 | Y129L | 0.27 |
| 129 | Y129N | 0.53 |
| 129 | Y129P | 0.59 |
| 129 | Y129C | 0.61 |
| 129 | Y129S | 0.69 |
| 129 | Y129F | 0.71 |
| 130 | P130T | 0.01 |
| 130 | P130H | 0.01 |
| 130 | P130G | 0.01 |
| 130 | P130S | 0.01 |
| 130 | P130L | 0.09 |
| 130 | P130E | 0.22 |
| 130 | P130W | 0.28 |
| 130 | P130V | 0.37 |
| 130 | P130I | 0.41 |
| 130 | P130A | 0.44 |
| 130 | P130F | 0.48 |
| 130 | P130R | 0.53 |
| 130 | P130K | 0.55 |
| 130 | P130C | 0.64 |
| 130 | P130M | 0.76 |
| 131 | A131W | 0.01 |
| 131 | A131D | 0.40 |
| 131 | A131Y | 0.48 |
| 131 | A131L | 0.59 |
| 131 | A131S | 0.68 |
| 131 | A131P | 0.71 |
| 131 | A131Q | 0.74 |
| 131 | A131V | 0.78 |
| 131 | A131H | 0.82 |
| 131 | A131G | 0.87 |
| 131 | A131E | 0.97 |
| 132 | P132V | 0.01 |
| 132 | P132T | 0.01 |
| 132 | P132W | 0.01 |
| 132 | P132F | 0.01 |
| 132 | P132I | 0.01 |
| 132 | P132H | 0.01 |
| 132 | P132R | 0.01 |
| 132 | P132D | 0.01 |
| 133 | K133C | 0.01 |
| 133 | K133A | 0.10 |
| 133 | K133V | 0.23 |
| 133 | K133G | 0.31 |
| 133 | K133H | 0.31 |

TABLE 10-7-continued

Variants with Peracid Degradation Results Less than Wild-Type

| Pos | WT/Pos./Var. | PAD PI |
|---|---|---|
| 133 | K133M | 0.33 |
| 133 | K133T | 0.39 |
| 133 | K133I | 0.45 |
| 133 | K133Q | 0.52 |
| 133 | K133S | 0.58 |
| 133 | K133F | 0.59 |
| 133 | K133P | 0.71 |
| 133 | K133E | 0.76 |
| 133 | K133R | 0.83 |
| 133 | K133W | 0.99 |
| 134 | V134Q | 0.79 |
| 134 | V134T | 0.86 |
| 134 | V134I | 0.89 |
| 135 | L135T | 0.01 |
| 135 | L135W | 0.01 |
| 135 | L135K | 0.01 |
| 135 | L135S | 0.01 |
| 135 | L135F | 0.01 |
| 135 | L135G | 0.01 |
| 135 | L135R | 0.01 |
| 135 | L135P | 0.01 |
| 135 | L135Q | 0.17 |
| 135 | L135V | 0.43 |
| 135 | L135E | 0.63 |
| 135 | L135M | 0.78 |
| 136 | V136P | 0.01 |
| 136 | V136E | 0.20 |
| 136 | V136N | 0.40 |
| 137 | V137N | 0.01 |
| 137 | V137G | 0.26 |
| 137 | V137S | 0.29 |
| 137 | V137I | 0.70 |
| 137 | V137T | 0.93 |
| 138 | S138I | 0.35 |
| 138 | S138V | 0.69 |
| 139 | P139S | 0.01 |
| 139 | P139G | 0.01 |
| 139 | P139R | 0.01 |
| 139 | P139C | 0.01 |
| 139 | P139D | 0.01 |
| 139 | P139E | 0.01 |
| 139 | P139F | 0.01 |
| 139 | P139H | 0.01 |
| 139 | P139I | 0.01 |
| 139 | P139K | 0.01 |
| 139 | P139N | 0.01 |
| 139 | P139Q | 0.01 |
| 139 | P139T | 0.01 |
| 139 | P139V | 0.01 |
| 140 | P140T | 0.01 |
| 140 | P140S | 0.01 |
| 140 | P140V | 0.01 |
| 140 | P140W | 0.01 |
| 140 | P140I | 0.01 |
| 140 | P140Y | 0.01 |
| 140 | P140Q | 0.01 |
| 140 | P140R | 0.01 |
| 141 | P141R | 0.01 |
| 141 | P141G | 0.01 |
| 141 | P141S | 0.02 |
| 141 | P141T | 0.12 |
| 141 | P141V | 0.16 |
| 141 | P141Q | 0.37 |
| 141 | P141I | 0.38 |
| 141 | P141L | 0.65 |
| 141 | P141H | 0.79 |
| 141 | P141N | 0.97 |
| 142 | L142W | 0.01 |
| 142 | L142I | 0.28 |
| 142 | L142S | 0.31 |
| 142 | L142Q | 0.33 |
| 142 | L142V | 0.33 |
| 142 | L142P | 0.44 |
| 142 | L142F | 0.54 |
| 142 | L142A | 0.56 |
| 142 | L142K | 0.66 |

TABLE 10-7-continued

Variants with Peracid Degradation Results Less than Wild-Type

| Pos | WT/Pos./Var. | PAD PI |
|---|---|---|
| 142 | L142C | 0.70 |
| 143 | A143W | 0.01 |
| 143 | A143P | 0.39 |
| 143 | A143G | 0.42 |
| 143 | A143S | 0.63 |
| 143 | A143F | 0.68 |
| 143 | A143Q | 0.81 |
| 143 | A143N | 0.82 |
| 143 | A143T | 0.97 |
| 143 | A143R | 0.99 |
| 143 | A143V | 0.99 |
| 144 | P144G | 0.62 |
| 144 | P144A | 0.79 |
| 144 | P144T | 0.81 |
| 144 | P144S | 0.92 |
| 145 | M145W | 0.01 |
| 145 | M145G | 0.26 |
| 145 | M145E | 0.48 |
| 145 | M145I | 0.53 |
| 145 | M145Q | 0.57 |
| 145 | M145L | 0.61 |
| 145 | M145V | 0.63 |
| 145 | M145R | 0.69 |
| 145 | M145F | 0.77 |
| 145 | M145P | 0.78 |
| 145 | M145S | 0.78 |
| 145 | M145T | 0.79 |
| 145 | M145A | 0.79 |
| 145 | M145Y | 0.82 |
| 145 | M145C | 0.93 |
| 146 | P146W | 0.68 |
| 146 | P146T | 0.76 |
| 146 | P146V | 0.77 |
| 146 | P146S | 0.96 |
| 147 | H147S | 0.75 |
| 147 | H147T | 0.84 |
| 147 | H147I | 0.92 |
| 147 | H147V | 0.92 |
| 147 | H147R | 0.94 |
| 147 | H147A | 0.98 |
| 148 | P148Q | 0.98 |
| 149 | W149R | 0.01 |
| 149 | W149E | 0.01 |
| 149 | W149P | 0.01 |
| 149 | W149C | 0.12 |
| 149 | W149I | 0.24 |
| 149 | W149A | 0.31 |
| 149 | W149S | 0.33 |
| 149 | W149Q | 0.40 |
| 149 | W149T | 0.44 |
| 149 | W149G | 0.45 |
| 149 | W149M | 0.49 |
| 149 | W149F | 0.50 |
| 149 | W149L | 0.64 |
| 149 | W149Y | 0.75 |
| 150 | F150P | 0.32 |
| 150 | F150N | 0.36 |
| 150 | F150G | 0.46 |
| 150 | F150V | 0.51 |
| 150 | F150A | 0.54 |
| 150 | F150T | 0.58 |
| 150 | F150W | 0.62 |
| 150 | F150M | 0.63 |
| 150 | F150E | 0.73 |
| 150 | F150C | 0.78 |
| 150 | F150I | 0.78 |
| 150 | F150K | 0.85 |
| 151 | Q151L | 0.01 |
| 151 | Q151V | 0.01 |
| 151 | Q151F | 0.01 |
| 151 | Q151I | 0.01 |
| 151 | Q151W | 0.32 |
| 152 | L152I | 0.61 |
| 152 | L152P | 0.61 |
| 152 | L152T | 0.69 |
| 152 | L152Q | 0.76 |

TABLE 10-7-continued

Variants with Peracid Degradation Results Less than Wild-Type

| Pos | WT/Pos./Var. | PAD PI |
|---|---|---|
| 152 | L152G | 0.77 |
| 152 | L152S | 0.84 |
| 152 | L152D | 0.86 |
| 152 | L152V | 0.88 |
| 152 | L152R | 0.91 |
| 152 | L152K | 0.91 |
| 152 | L152H | 0.92 |
| 153 | I153N | 0.89 |
| 154 | F154T | 0.01 |
| 154 | F154G | 0.01 |
| 154 | F154V | 0.01 |
| 154 | F154S | 0.29 |
| 154 | F154Q | 0.97 |
| 155 | E155R | 0.01 |
| 155 | E155F | 0.23 |
| 155 | E155V | 0.47 |
| 155 | E155I | 0.65 |
| 155 | E155Q | 0.69 |
| 156 | G156I | 0.01 |
| 156 | G156F | 0.73 |
| 156 | G156W | 0.90 |
| 156 | G156L | 0.94 |
| 156 | G156V | 0.97 |
| 157 | G157R | 0.01 |
| 157 | G157P | 0.01 |
| 157 | G157S | 0.19 |
| 157 | G157V | 0.40 |
| 157 | G157C | 0.61 |
| 157 | G157E | 0.84 |
| 157 | G157M | 0.85 |
| 157 | G157A | 0.87 |
| 157 | G157D | 0.94 |
| 157 | G157T | 0.99 |
| 158 | E158V | 0.89 |
| 158 | E158D | 0.89 |
| 158 | E158T | 0.91 |
| 158 | E158I | 0.94 |
| 159 | Q159A | 0.28 |
| 159 | Q159C | 0.31 |
| 159 | Q159P | 0.49 |
| 159 | Q159D | 0.63 |
| 159 | Q159L | 0.70 |
| 159 | Q159G | 0.72 |
| 159 | Q159S | 0.73 |
| 159 | Q159R | 0.74 |
| 159 | Q159M | 0.84 |
| 159 | Q159E | 0.97 |
| 160 | K160W | 0.01 |
| 160 | K160G | 0.30 |
| 160 | K160H | 0.57 |
| 160 | K160S | 0.70 |
| 160 | K160L | 0.95 |
| 160 | K160I | 1.00 |
| 161 | T161R | 0.01 |
| 161 | T161H | 0.01 |
| 161 | T161W | 0.01 |
| 161 | T161N | 0.01 |
| 161 | T161G | 0.43 |
| 161 | T161C | 0.56 |
| 161 | T161S | 0.57 |
| 161 | T161I | 0.98 |
| 163 | E163F | 0.27 |
| 163 | E163R | 0.49 |
| 163 | E163V | 0.55 |
| 163 | E163P | 0.77 |
| 163 | E163G | 0.80 |
| 163 | E163H | 0.82 |
| 163 | E163S | 0.85 |
| 163 | E163W | 0.98 |
| 164 | L164Y | 0.01 |
| 164 | L164A | 0.01 |
| 164 | L164D | 0.01 |
| 164 | L164E | 0.01 |
| 164 | L164G | 0.01 |
| 164 | L164H | 0.12 |
| 164 | L164F | 0.86 |

TABLE 10-7-continued

Variants with Peracid Degradation Results Less than Wild-Type

| Pos | WT/Pos./Var. | PAD PI |
|---|---|---|
| 164 | L164C | 0.91 |
| 164 | L164T | 0.99 |
| 165 | A165I | 0.59 |
| 165 | A165K | 0.82 |
| 165 | A165Y | 0.84 |
| 165 | A165S | 0.94 |
| 165 | A165F | 1.00 |
| 166 | R166T | 0.74 |
| 166 | R166V | 0.76 |
| 166 | R166G | 0.91 |
| 166 | R166S | 0.95 |
| 168 | Y168G | 0.01 |
| 168 | Y168T | 0.01 |
| 168 | Y168V | 0.01 |
| 168 | Y168I | 0.01 |
| 168 | Y168C | 0.01 |
| 168 | Y168Q | 0.01 |
| 169 | S169P | 0.89 |
| 169 | S169T | 0.97 |
| 170 | A170I | 0.44 |
| 170 | A170S | 0.47 |
| 170 | A170G | 0.62 |
| 170 | A170T | 0.72 |
| 170 | A170V | 0.74 |
| 170 | A170K | 0.83 |
| 170 | A170W | 0.83 |
| 170 | A170L | 0.85 |
| 170 | A170Q | 0.89 |
| 170 | A170Y | 0.89 |
| 171 | L171R | 0.01 |
| 172 | A172K | 0.01 |
| 172 | A172R | 0.01 |
| 172 | A172E | 0.01 |
| 172 | A172Q | 0.18 |
| 172 | A172V | 0.39 |
| 172 | A172W | 0.45 |
| 172 | A172P | 0.58 |
| 172 | A172I | 0.58 |
| 172 | A172T | 0.71 |
| 172 | A172N | 0.76 |
| 172 | A172G | 0.84 |
| 172 | A172S | 0.85 |
| 172 | A172C | 0.86 |
| 174 | F174W | 0.01 |
| 174 | F174Q | 0.46 |
| 174 | F174C | 0.48 |
| 174 | F174R | 0.52 |
| 174 | F174S | 0.61 |
| 174 | F174T | 0.64 |
| 174 | F174V | 0.67 |
| 174 | F174G | 0.91 |
| 175 | M175P | 0.08 |
| 175 | M175A | 0.66 |
| 175 | M175Y | 0.72 |
| 175 | M175G | 0.75 |
| 175 | M175W | 0.76 |
| 175 | M175V | 0.81 |
| 175 | M175Q | 0.83 |
| 175 | M175L | 0.86 |
| 175 | M175R | 0.86 |
| 175 | M175T | 0.90 |
| 176 | K176S | 0.72 |
| 176 | K176G | 0.73 |
| 176 | K176P | 0.78 |
| 176 | K176L | 0.92 |
| 176 | K176Y | 0.93 |
| 176 | K176N | 0.94 |
| 176 | K176T | 0.97 |
| 176 | K176Q | 0.97 |
| 178 | P178W | 0.02 |
| 179 | F179Q | 0.01 |
| 179 | F179S | 0.34 |
| 179 | F179W | 0.86 |
| 179 | F179H | 0.93 |
| 179 | F179N | 0.95 |
| 180 | F180K | 0.01 |

TABLE 10-7-continued

Variants with Peracid Degradation Results Less than Wild-Type

| Pos | WT/Pos./Var. | PAD PI |
|---|---|---|
| 180 | F180T | 0.01 |
| 180 | F180R | 0.01 |
| 180 | F180S | 0.01 |
| 180 | F180G | 0.01 |
| 180 | F180Q | 0.01 |
| 181 | D181Y | 0.01 |
| 181 | D181W | 0.01 |
| 181 | D181L | 0.01 |
| 181 | D181T | 0.01 |
| 181 | D181V | 0.01 |
| 181 | D181R | 0.22 |
| 181 | D181K | 0.47 |
| 181 | D181G | 0.52 |
| 181 | D181S | 0.55 |
| 181 | D181Q | 0.60 |
| 181 | D181P | 0.66 |
| 181 | D181E | 0.72 |
| 181 | D181C | 0.85 |
| 182 | A182I | 0.01 |
| 182 | A182R | 0.01 |
| 182 | A182Q | 0.01 |
| 182 | A182P | 0.01 |
| 182 | A182T | 0.11 |
| 182 | A182N | 0.53 |
| 182 | A182S | 0.85 |
| 182 | A182G | 0.94 |
| 182 | A182C | 0.99 |
| 183 | G183S | 0.01 |
| 183 | G183Q | 0.01 |
| 183 | G183V | 0.01 |
| 183 | G183F | 0.19 |
| 183 | G183H | 0.95 |
| 183 | G183D | 0.99 |
| 184 | S184T | 0.60 |
| 184 | S184H | 0.74 |
| 184 | S184G | 0.82 |
| 184 | S184P | 0.85 |
| 185 | V185W | 0.01 |
| 185 | V185H | 0.01 |
| 185 | V185G | 0.01 |
| 185 | V185D | 0.01 |
| 185 | V185S | 0.53 |
| 185 | V185Y | 0.58 |
| 185 | V185I | 0.63 |
| 185 | V185R | 0.79 |
| 185 | V185K | 0.79 |
| 185 | V185C | 0.83 |
| 185 | V185E | 0.88 |
| 185 | V185T | 0.91 |
| 185 | V185L | 0.93 |
| 186 | I186G | 0.01 |
| 186 | I186S | 0.01 |
| 186 | I186R | 0.01 |
| 186 | I186P | 0.01 |
| 186 | I186T | 0.23 |
| 186 | I186V | 0.48 |
| 186 | I186F | 0.76 |
| 187 | S187P | 0.01 |
| 187 | S187T | 0.23 |
| 187 | S187Q | 0.35 |
| 187 | S187W | 0.52 |
| 187 | S187R | 0.55 |
| 187 | S187V | 0.58 |
| 187 | S187F | 0.65 |
| 187 | S187Y | 0.80 |
| 188 | T188H | 0.01 |
| 188 | T188R | 0.01 |
| 188 | T188F | 0.01 |
| 188 | T188Y | 0.09 |
| 188 | T188I | 0.10 |
| 188 | T188V | 0.15 |
| 188 | T188L | 0.42 |
| 188 | T188M | 0.75 |
| 188 | T188G | 0.79 |
| 188 | T188C | 0.87 |
| 188 | T188S | 0.91 |

TABLE 10-7-continued

Variants with Peracid Degradation Results Less than Wild-Type

| Pos | WT/Pos./Var. | PAD PI |
|---|---|---|
| 188 | T188A | 0.95 |
| 189 | D189F | 0.37 |
| 189 | D189R | 0.39 |
| 189 | D189N | 0.57 |
| 189 | D189V | 0.71 |
| 189 | D189W | 0.76 |
| 189 | D189E | 0.77 |
| 189 | D189G | 0.80 |
| 189 | D189S | 0.81 |
| 189 | D189M | 0.88 |
| 189 | D189C | 0.94 |
| 189 | D189H | 0.95 |
| 189 | D189P | 0.97 |
| 190 | G190V | 0.01 |
| 190 | G190S | 0.01 |
| 190 | G190Q | 0.29 |
| 190 | G190W | 0.41 |
| 190 | G190R | 0.51 |
| 190 | G190K | 0.57 |
| 190 | G190L | 0.82 |
| 191 | V191H | 0.01 |
| 191 | V191W | 0.01 |
| 191 | V191S | 0.01 |
| 191 | V191G | 0.01 |
| 191 | V191N | 0.01 |
| 191 | V191I | 0.02 |
| 192 | D192S | 0.01 |
| 192 | D192P | 0.01 |
| 192 | D192F | 0.01 |
| 192 | D192H | 0.01 |
| 192 | D192I | 0.01 |
| 192 | D192Q | 0.01 |
| 192 | D192R | 0.01 |
| 192 | D192T | 0.01 |
| 192 | D192V | 0.01 |
| 192 | D192W | 0.01 |
| 192 | D192N | 0.15 |
| 192 | D192C | 0.56 |
| 193 | G193H | 0.01 |
| 193 | G193C | 0.01 |
| 193 | G193T | 0.01 |
| 193 | G193N | 0.01 |
| 194 | I194S | 0.01 |
| 194 | I194A | 0.01 |
| 194 | I194C | 0.01 |
| 194 | I194P | 0.01 |
| 194 | I194F | 0.01 |
| 194 | I194W | 0.01 |
| 194 | I194R | 0.01 |
| 194 | I194Y | 0.01 |
| 194 | I194G | 0.04 |
| 194 | I194L | 0.58 |
| 194 | I194V | 0.78 |
| 195 | H195S | 0.08 |
| 195 | H195C | 0.10 |
| 195 | H195L | 0.18 |
| 195 | H195N | 0.22 |
| 195 | H195R | 0.24 |
| 195 | H195F | 0.40 |
| 195 | H195V | 0.60 |
| 195 | H195Q | 0.96 |
| 195 | H195A | 0.98 |
| 196 | F196H | 0.01 |
| 196 | F196G | 0.01 |
| 196 | F196S | 0.01 |
| 196 | F196Q | 0.01 |
| 196 | F196W | 0.38 |
| 196 | F196P | 0.39 |
| 196 | F196V | 0.68 |
| 196 | F196M | 0.71 |
| 196 | F196Y | 0.97 |
| 197 | T197R | 0.01 |
| 197 | T197L | 0.65 |
| 197 | T197S | 0.75 |
| 197 | T197G | 0.81 |
| 197 | T197I | 0.84 |
| 197 | T197C | 0.86 |
| 197 | T197V | 0.89 |
| 197 | T197N | 0.91 |
| 199 | A199M | 0.93 |
| 199 | A199S | 0.99 |
| 199 | A199G | 0.99 |
| 201 | N201Y | 0.01 |
| 201 | N201T | 0.01 |
| 201 | N201V | 0.01 |
| 201 | N201R | 0.01 |
| 201 | N201S | 0.06 |
| 201 | N201H | 0.10 |
| 201 | N201G | 0.30 |
| 201 | N201L | 0.35 |
| 201 | N201F | 0.67 |
| 201 | N201E | 0.72 |
| 203 | D203V | 0.50 |
| 203 | D203W | 0.52 |
| 203 | D203E | 0.90 |

The following Table provides variants that have protein performance indices ("Prot. PI") better than wild-type.

TABLE 10-8

Sites with Protein PI Values Better Than Wild-Type

| Pos | WT/Pos./Var. | Prot. PI |
|---|---|---|
| 2 | A002Y | 1.61 |
| 2 | A002N | 1.30 |
| 2 | A002I | 1.25 |
| 2 | A002V | 1.18 |
| 2 | A002T | 1.17 |
| 2 | A002S | 1.15 |
| 5 | I005M | 1.29 |
| 7 | C007A | 1.22 |
| 7 | C007G | 1.07 |
| 7 | C007M | 1.03 |
| 8 | F008N | 1.23 |
| 8 | F008M | 1.05 |
| 8 | F008G | 1.03 |
| 8 | F008P | 1.01 |
| 11 | S011H | 1.06 |
| 11 | S011A | 1.04 |
| 11 | S011D | 1.03 |
| 11 | S011E | 1.01 |
| 11 | S011Q | 1.01 |
| 12 | L012N | 1.06 |
| 12 | L012Q | 1.05 |
| 13 | T013V | 1.17 |
| 14 | W014Y | 1.02 |
| 16 | W016Y | 1.02 |
| 17 | V017A | 1.21 |
| 17 | V017E | 1.11 |
| 17 | V017F | 1.09 |
| 17 | V017I | 1.08 |
| 17 | V017K | 1.06 |
| 17 | V017T | 1.03 |
| 18 | P018C | 2.56 |
| 18 | P018H | 2.50 |
| 18 | P018L | 2.50 |
| 18 | P018E | 2.47 |
| 18 | P018G | 2.47 |
| 18 | P018N | 2.35 |
| 18 | P018V | 2.30 |
| 18 | P018Q | 2.13 |
| 18 | P018R | 2.01 |
| 18 | P018Y | 1.68 |
| 18 | P018S | 1.05 |
| 19 | V019G | 1.39 |
| 19 | V019A | 1.23 |
| 19 | V019E | 1.10 |
| 19 | V019Q | 1.07 |

TABLE 10-8-continued

| Sites with Protein PI Values Better Than Wild-Type | | |
|---|---|---|
| Pos | WT/Pos./Var. | Prot. PI |
| 19 | V019K | 1.03 |
| 19 | V019M | 1.00 |
| 20 | E020G | 1.11 |
| 20 | E020P | 1.08 |
| 20 | E020A | 1.08 |
| 20 | E020N | 1.01 |
| 20 | E020V | 1.01 |
| 22 | G022A | 1.07 |
| 22 | G022I | 1.03 |
| 23 | A023F | 1.03 |
| 24 | P024T | 1.43 |
| 24 | P024G | 1.34 |
| 24 | P024S | 1.31 |
| 24 | P024H | 1.15 |
| 24 | P024I | 1.11 |
| 24 | P024L | 1.06 |
| 25 | T025C | 1.37 |
| 25 | T025V | 1.30 |
| 25 | T025G | 1.27 |
| 25 | T025A | 1.23 |
| 25 | T025I | 1.19 |
| 25 | T025P | 1.10 |
| 25 | T025M | 1.04 |
| 29 | A029G | 1.22 |
| 29 | A029P | 1.07 |
| 29 | A029M | 1.06 |
| 29 | A029D | 1.06 |
| 29 | A029V | 1.05 |
| 29 | A029S | 1.05 |
| 29 | A029T | 1.02 |
| 29 | A029E | 1.02 |
| 30 | P030E | 1.20 |
| 30 | P030A | 1.15 |
| 30 | P030S | 1.12 |
| 30 | P030L | 1.07 |
| 30 | P030Q | 1.06 |
| 30 | P030K | 1.06 |
| 30 | P030H | 1.05 |
| 30 | P030Y | 1.04 |
| 32 | V032M | 1.11 |
| 32 | V032A | 1.10 |
| 32 | V032I | 1.08 |
| 32 | V032Q | 1.03 |
| 32 | V032L | 1.01 |
| 35 | T035C | 1.16 |
| 36 | G036C | 1.09 |
| 36 | G036N | 1.08 |
| 36 | G036Q | 1.07 |
| 36 | G036S | 1.06 |
| 36 | G036A | 1.00 |
| 37 | V037N | 1.09 |
| 39 | A039V | 1.18 |
| 39 | A039E | 1.03 |
| 46 | F046A | 1.05 |
| 46 | F046C | 1.01 |
| 47 | E047I | 1.02 |
| 54 | S054A | 1.33 |
| 54 | S054C | 1.21 |
| 54 | S054E | 1.16 |
| 54 | S054D | 1.08 |
| 54 | S054H | 1.06 |
| 54 | S054N | 1.01 |
| 54 | S054M | 1.01 |
| 55 | A055N | 1.12 |
| 55 | A055S | 1.08 |
| 56 | R056Q | 1.02 |
| 58 | T058V | 1.13 |
| 60 | I060A | 1.20 |
| 60 | I060M | 1.14 |
| 60 | I060V | 1.06 |
| 60 | I060L | 1.02 |
| 61 | D061A | 1.41 |
| 61 | D061N | 1.12 |
| 61 | D061V | 1.10 |
| 61 | D061Y | 1.03 |
| 61 | D061Q | 1.02 |

TABLE 10-8-continued

| Sites with Protein PI Values Better Than Wild-Type | | |
|---|---|---|
| Pos | WT/Pos./Var. | Prot. PI |
| 61 | D061L | 1.00 |
| 62 | D062A | 1.06 |
| 62 | D062M | 1.06 |
| 63 | P063S | 1.17 |
| 63 | P063Y | 1.12 |
| 63 | P063M | 1.09 |
| 63 | P063Q | 1.08 |
| 63 | P063A | 1.06 |
| 63 | P063V | 1.06 |
| 63 | P063R | 1.02 |
| 63 | P063T | 1.02 |
| 64 | T064Q | 1.13 |
| 64 | T064M | 1.07 |
| 64 | T064R | 1.05 |
| 64 | T064C | 1.05 |
| 64 | T064S | 1.03 |
| 66 | P066Q | 1.91 |
| 66 | P066G | 1.78 |
| 66 | P066N | 1.62 |
| 66 | P066C | 1.51 |
| 66 | P066I | 1.51 |
| 66 | P066R | 1.26 |
| 66 | P066H | 1.23 |
| 66 | P066V | 1.12 |
| 66 | P066Y | 1.08 |
| 66 | P066A | 1.03 |
| 66 | P066F | 1.02 |
| 67 | R067Q | 1.60 |
| 67 | R067L | 1.46 |
| 67 | R067A | 1.39 |
| 67 | R067V | 1.24 |
| 67 | R067P | 1.04 |
| 67 | R067F | 1.01 |
| 68 | L068A | 1.07 |
| 68 | L068V | 1.01 |
| 68 | L068G | 1.00 |
| 69 | N069C | 1.18 |
| 69 | N069G | 1.06 |
| 69 | N069D | 1.05 |
| 69 | N069S | 1.03 |
| 70 | G070A | 1.08 |
| 72 | S072L | 1.07 |
| 72 | S072A | 1.06 |
| 72 | S072Y | 1.03 |
| 73 | Y073N | 1.25 |
| 73 | Y073Q | 1.20 |
| 73 | Y073C | 1.18 |
| 73 | Y073D | 1.09 |
| 73 | Y073V | 1.08 |
| 73 | Y073M | 1.05 |
| 73 | Y073L | 1.03 |
| 74 | L074I | 1.45 |
| 74 | L074Y | 1.19 |
| 74 | L074V | 1.18 |
| 74 | L074A | 1.01 |
| 75 | P075M | 1.22 |
| 75 | P075S | 1.18 |
| 75 | P075T | 1.10 |
| 75 | P075Y | 1.08 |
| 75 | P075C | 1.06 |
| 75 | P075Q | 1.04 |
| 75 | P075L | 1.02 |
| 75 | P075E | 1.00 |
| 76 | S076W | 1.06 |
| 77 | C077L | 1.44 |
| 77 | C077V | 1.33 |
| 77 | C077A | 1.20 |
| 77 | C077S | 1.19 |
| 77 | C077T | 1.18 |
| 78 | L078I | 1.06 |
| 78 | L078V | 1.04 |
| 79 | A079C | 1.16 |
| 79 | A079E | 1.12 |
| 79 | A079S | 1.09 |
| 79 | A079Q | 1.05 |
| 79 | A079M | 1.04 |

TABLE 10-8-continued

| Sites with Protein PI Values Better Than Wild-Type | | |
|---|---|---|
| Pos | WT/Pos./Var. | Prot. PI |
| 79 | A079R | 1.02 |
| 80 | T080S | 1.12 |
| 80 | T080E | 1.02 |
| 80 | T080Q | 1.02 |
| 82 | L082G | 1.24 |
| 82 | L082R | 1.15 |
| 82 | L082V | 1.14 |
| 82 | L082S | 1.13 |
| 82 | L082P | 1.11 |
| 82 | L082M | 1.07 |
| 82 | L082K | 1.03 |
| 82 | L082A | 1.00 |
| 83 | P083G | 1.01 |
| 84 | L084V | 1.23 |
| 86 | L086Q | 3.66 |
| 89 | I089V | 1.09 |
| 89 | I089L | 1.07 |
| 93 | T093Q | 2.03 |
| 96 | T096A | 1.32 |
| 96 | T096V | 1.12 |
| 96 | T096S | 1.05 |
| 96 | T096G | 1.03 |
| 97 | K097A | 1.11 |
| 97 | K097R | 1.02 |
| 98 | A098S | 1.17 |
| 98 | A098T | 1.03 |
| 98 | A098N | 1.01 |
| 99 | Y099S | 1.45 |
| 99 | Y099L | 1.39 |
| 99 | Y099H | 1.30 |
| 99 | Y099A | 1.29 |
| 99 | Y099V | 1.28 |
| 99 | Y099G | 1.23 |
| 99 | Y099W | 1.20 |
| 99 | Y099I | 1.11 |
| 100 | F100M | 1.20 |
| 100 | F100N | 1.12 |
| 100 | F100W | 1.06 |
| 100 | F100S | 1.02 |
| 101 | R101L | 1.33 |
| 101 | R101N | 1.11 |
| 101 | R101Q | 1.03 |
| 101 | R101D | 1.02 |
| 102 | R102Q | 1.09 |
| 103 | T103G | 1.20 |
| 103 | T103S | 1.14 |
| 103 | T103H | 1.14 |
| 103 | T103N | 1.07 |
| 103 | T103K | 1.05 |
| 103 | T103P | 1.01 |
| 104 | P104S | 1.44 |
| 104 | P104V | 1.40 |
| 104 | P104E | 1.37 |
| 104 | P104C | 1.34 |
| 104 | P104N | 1.32 |
| 104 | P104T | 1.29 |
| 104 | P104G | 1.25 |
| 104 | P104Q | 1.24 |
| 104 | P104H | 1.11 |
| 104 | P104I | 1.07 |
| 104 | P104M | 1.01 |
| 105 | L105Y | 1.18 |
| 105 | L105H | 1.07 |
| 105 | L105G | 1.07 |
| 105 | L105C | 1.05 |
| 105 | L105Q | 1.03 |
| 105 | L105T | 1.00 |
| 105 | L105P | 1.00 |
| 106 | D106E | 1.02 |
| 107 | I107S | 1.05 |
| 107 | I107V | 1.04 |
| 107 | I107C | 1.00 |
| 108 | A108G | 1.15 |
| 108 | A108S | 1.14 |
| 108 | A108T | 1.08 |
| 109 | L109E | 1.24 |

TABLE 10-8-continued

| Sites with Protein PI Values Better Than Wild-Type | | |
|---|---|---|
| Pos | WT/Pos./Var. | Prot. PI |
| 109 | L1091 | 1.21 |
| 109 | L109D | 1.15 |
| 109 | L109N | 1.13 |
| 109 | L109F | 1.11 |
| 109 | L109Q | 1.08 |
| 109 | L109A | 1.07 |
| 109 | L109H | 1.06 |
| 109 | L109V | 1.06 |
| 109 | L109M | 1.00 |
| 110 | G110S | 1.01 |
| 112 | S112N | 1.09 |
| 112 | S112E | 1.05 |
| 113 | V113C | 1.06 |
| 113 | V113N | 1.01 |
| 114 | L114C | 1.10 |
| 114 | L114A | 1.03 |
| 114 | L114M | 1.00 |
| 115 | V115I | 1.14 |
| 115 | V115C | 1.14 |
| 115 | V115A | 1.11 |
| 115 | V115M | 1.05 |
| 115 | V115L | 1.02 |
| 116 | T116N | 1.68 |
| 116 | T116H | 1.48 |
| 116 | T116G | 1.44 |
| 116 | T116C | 1.30 |
| 116 | T116E | 1.29 |
| 116 | T116Q | 1.29 |
| 116 | T116M | 1.28 |
| 116 | T116S | 1.24 |
| 116 | T116Y | 1.09 |
| 116 | T116A | 1.08 |
| 116 | T116R | 1.03 |
| 116 | T116L | 1.03 |
| 117 | Q117S | 1.13 |
| 117 | Q117H | 1.12 |
| 117 | Q117E | 1.10 |
| 117 | Q117T | 1.06 |
| 117 | Q117A | 1.03 |
| 118 | V118C | 1.28 |
| 118 | V118A | 1.20 |
| 118 | V118I | 1.01 |
| 119 | L119C | 1.18 |
| 119 | L119A | 1.18 |
| 119 | L119N | 1.14 |
| 119 | L119I | 1.06 |
| 119 | L119S | 1.05 |
| 119 | L119V | 1.04 |
| 119 | L119E | 1.04 |
| 119 | L119R | 1.00 |
| 120 | T120S | 1.35 |
| 120 | T120E | 1.19 |
| 120 | T120C | 1.14 |
| 120 | T120K | 1.12 |
| 120 | T120N | 1.10 |
| 120 | T120A | 1.09 |
| 120 | T120H | 1.07 |
| 120 | T120Q | 1.05 |
| 120 | T120Y | 1.01 |
| 120 | T120L | 1.00 |
| 121 | S121N | 1.17 |
| 121 | S121L | 1.12 |
| 121 | S121A | 1.10 |
| 121 | S121C | 1.09 |
| 121 | S121G | 1.07 |
| 121 | S121R | 1.06 |
| 121 | S121K | 1.04 |
| 121 | S121E | 1.01 |
| 121 | S121Q | 1.01 |
| 122 | A122N | 1.11 |
| 122 | A122L | 1.07 |
| 122 | A122P | 1.07 |
| 122 | A122M | 1.06 |
| 122 | A122V | 1.05 |
| 122 | A122S | 1.05 |
| 122 | A122E | 1.04 |

TABLE 10-8-continued

Sites with Protein PI Values Better Than Wild-Type

| Pos | WT/Pos./Var. | Prot. PI |
|---|---|---|
| 122 | A122I | 1.04 |
| 122 | A122Q | 1.02 |
| 124 | G124M | 1.36 |
| 124 | G124A | 1.20 |
| 124 | G124N | 1.18 |
| 124 | G124C | 1.07 |
| 124 | G124Q | 1.02 |
| 125 | V125I | 1.05 |
| 126 | G126N | 1.04 |
| 126 | G126E | 1.02 |
| 126 | G126A | 1.02 |
| 127 | T127A | 1.10 |
| 127 | T127S | 1.08 |
| 127 | T127V | 1.06 |
| 127 | T127C | 1.04 |
| 127 | T127G | 1.04 |
| 127 | T127D | 1.03 |
| 127 | T127E | 1.03 |
| 127 | T127M | 1.02 |
| 128 | T128N | 1.29 |
| 128 | T128M | 1.28 |
| 128 | T128Q | 1.24 |
| 128 | T128A | 1.23 |
| 128 | T128H | 1.19 |
| 128 | T128P | 1.18 |
| 128 | T128D | 1.14 |
| 128 | T128K | 1.10 |
| 128 | T128S | 1.07 |
| 128 | T128V | 1.05 |
| 128 | T128R | 1.03 |
| 128 | T128F | 1.01 |
| 129 | Y129F | 1.44 |
| 129 | Y129C | 1.42 |
| 129 | Y129A | 1.39 |
| 129 | Y129D | 1.35 |
| 129 | Y129M | 1.28 |
| 129 | Y129N | 1.24 |
| 129 | Y129L | 1.22 |
| 129 | Y129P | 1.11 |
| 129 | Y129G | 1.10 |
| 129 | Y129S | 1.08 |
| 129 | Y129W | 1.01 |
| 129 | Y129V | 1.00 |
| 130 | P130G | 1.11 |
| 130 | P130E | 1.08 |
| 130 | P130K | 1.05 |
| 130 | P130A | 1.03 |
| 130 | P130M | 1.03 |
| 133 | K133Q | 1.13 |
| 133 | K133S | 1.02 |
| 133 | K133A | 1.01 |
| 133 | K133R | 1.01 |
| 133 | K133E | 1.01 |
| 135 | L135M | 1.01 |
| 136 | V136L | 1.03 |
| 138 | S138A | 1.44 |
| 138 | S138C | 1.17 |
| 138 | S138G | 1.09 |
| 141 | P141A | 1.13 |
| 141 | P141G | 1.02 |
| 142 | L142I | 1.05 |
| 143 | A143G | 1.17 |
| 145 | M145I | 1.16 |
| 145 | M145L | 1.07 |
| 147 | H147L | 1.09 |
| 147 | H147C | 1.04 |
| 149 | W149G | 1.39 |
| 149 | W149A | 1.35 |
| 149 | W149M | 1.32 |
| 149 | W149S | 1.28 |
| 149 | W149F | 1.27 |
| 149 | W149Y | 1.15 |
| 149 | W149Q | 1.10 |
| 149 | W149L | 1.06 |
| 150 | F150A | 1.70 |
| 150 | F150M | 1.69 |

TABLE 10-8-continued

Sites with Protein PI Values Better Than Wild-Type

| Pos | WT/Pos./Var. | Prot. PI |
|---|---|---|
| 150 | F150N | 1.52 |
| 150 | F150C | 1.41 |
| 150 | F150P | 1.38 |
| 150 | F150K | 1.33 |
| 150 | F150E | 1.32 |
| 150 | F150T | 1.27 |
| 150 | F150V | 1.26 |
| 150 | F150W | 1.26 |
| 150 | F150Y | 1.24 |
| 150 | F150I | 1.19 |
| 150 | F150L | 1.14 |
| 150 | F150G | 1.13 |
| 150 | F150H | 1.09 |
| 151 | Q151K | 1.04 |
| 153 | I153N | 1.04 |
| 157 | G157A | 1.00 |
| 159 | Q159E | 1.14 |
| 159 | Q159A | 1.13 |
| 159 | Q159G | 1.03 |
| 161 | T161C | 1.01 |
| 162 | T162C | 1.17 |
| 162 | T162I | 1.16 |
| 162 | T162H | 1.08 |
| 162 | T162L | 1.05 |
| 162 | T162F | 1.05 |
| 162 | T162Y | 1.03 |
| 164 | L164M | 1.09 |
| 164 | L164V | 1.08 |
| 165 | A165G | 1.14 |
| 165 | A165Q | 1.05 |
| 165 | A165S | 1.05 |
| 166 | R166M | 1.26 |
| 166 | R166K | 1.19 |
| 166 | R166G | 1.19 |
| 166 | R166N | 1.16 |
| 166 | R166D | 1.16 |
| 166 | R166A | 1.12 |
| 166 | R166L | 1.08 |
| 166 | R166T | 1.04 |
| 167 | V167L | 1.13 |
| 167 | V167H | 1.12 |
| 167 | V167G | 1.08 |
| 167 | V167M | 1.04 |
| 167 | V167I | 1.04 |
| 167 | V167S | 1.04 |
| 167 | V167C | 1.01 |
| 168 | Y168F | 1.28 |
| 168 | Y168L | 1.27 |
| 170 | A170C | 1.02 |
| 171 | L171I | 1.16 |
| 172 | A172C | 1.09 |
| 172 | A172G | 1.07 |
| 175 | M175Y | 1.35 |
| 175 | M175L | 1.19 |
| 175 | M175W | 1.14 |
| 175 | M175N | 1.11 |
| 175 | M175R | 1.02 |
| 176 | K176R | 1.06 |
| 176 | K176Q | 1.02 |
| 178 | P178E | 1.05 |
| 182 | A182C | 1.03 |
| 183 | G183S | 1.08 |
| 184 | S184E | 1.39 |
| 184 | S184A | 1.31 |
| 184 | S184M | 1.25 |
| 184 | S184G | 1.15 |
| 184 | S184D | 1.15 |
| 184 | S184C | 1.14 |
| 184 | S184Q | 1.09 |
| 184 | S184H | 1.07 |
| 184 | S184N | 1.03 |
| 184 | S184V | 1.03 |
| 184 | S184K | 1.02 |
| 185 | V185I | 1.03 |
| 186 | I186M | 1.11 |
| 188 | T188C | 2.04 |

TABLE 10-8-continued

| Sites with Protein PI Values Better Than Wild-Type | | |
|---|---|---|
| Pos | WT/Pos./Var. | Prot. PI |
| 188 | T188I | 1.85 |
| 188 | T188L | 1.76 |
| 188 | T188M | 1.60 |
| 188 | T188V | 1.53 |
| 188 | T188S | 1.52 |
| 188 | T188R | 1.41 |
| 188 | T188A | 1.40 |
| 188 | T188G | 1.32 |
| 188 | T188N | 1.24 |
| 191 | V191C | 1.04 |
| 194 | I194L | 1.32 |
| 194 | I194C | 1.17 |
| 194 | I194A | 1.15 |
| 194 | I194W | 1.12 |
| 194 | I194V | 1.03 |
| 194 | I194Y | 1.01 |
| 196 | F196L | 1.09 |
| 201 | N201H | 1.49 |

The following Table provides variants that have a PAD PI that is greater than 1.5, a PAF that is greater than or equal to 0.1, and a protein PI that is greater than or equal to 0.1

TABLE 10-9

| PAD PI > 1.5 with PAF ≥ 0.1 and protein PI ≥ 0.1 | |
|---|---|
| Wild-Type Amino Acid/Pos. | Variant Amino Acid |
| M1 | L |
| K3 | A, C, H, I, L |
| R4 | A |
| I5 | A, C, E, L |
| L6 | A |
| C7 | K |
| T13 | A, C |
| P18 | C, E, G, H, L, Q, R, V, Y |
| E20 | C, Q |
| D21 | A, G, K, L, Y |
| G22 | A |
| P24 | L |
| E26 | L |
| R27 | A, K, L |
| F28 | D, L |
| P30 | T, V |
| D31 | L, N |
| V32 | A, D, E, G, I, K, L, M, N, Q, W |
| R33 | C, G, K, L |
| T35 | A, C, I, M |
| G36 | K |
| Q40 | D, G, K, S, T, W, Y |
| Q41 | A, K, L |
| G43 | E, L |
| A44 | C |
| F46 | L |
| V48 | A, C, L, M, P |
| I49 | A |
| E51 | A |
| L53 | H |
| N59 | A, C, D, E, F, G, K, L, Q, S, T, V, W, Y |
| D61 | I, K, R |
| N69 | H, I, K, V |
| S72 | A, C, G, H, M, N |
| P75 | D, G, K, S, T, W, Y |
| S76 | D, E, G, M |
| T80 | G |
| H81 | M |

TABLE 10-9-continued

| PAD PI > 1.5 with PAF ≥ 0.1 and protein PI ≥ 0.1 | |
|---|---|
| Wild-Type Amino Acid/Pos. | Variant Amino Acid |
| P83 | A, M |
| D85 | F, G |
| L86 | C |
| V87 | C, L |
| I89 | A |
| T96 | A, C, L, M |
| A98 | D |
| F100 | A, M |
| R102 | A, L |
| P104 | C, E, I, M |
| L105 | C, F, W |
| D106 | V |
| I107 | T |
| G110 | E, L |
| V115 | G |
| Q117 | A, M |
| V118 | Q |
| T120 | E, I, Y |
| S121 | A, C, V |
| T128 | F, K, L, R, Y |
| P132 | A, C, E, G, L, Q, S, Y |
| K133 | L |
| V134 | A, M |
| V136 | A |
| P140 | A |
| P144 | H, Y |
| P146 | C, F, H, L |
| P148 | F |
| Q151 | A, C, D, E, H, K, P, R, S, T, Y |
| L152 | W |
| I153 | F, H, K, P, S, T |
| F154 | Y |
| E155 | A, L, M, N, P, Y |
| G156 | D, M, T |
| G157 | H |
| E158 | F, K, L, M, N, Y |
| T161 | M, Q |
| T162 | C, F, G, H, I, K, L, M, N, P, Q, S, W, Y |
| E163 | A, L, Y |
| A165 | D, L, M |
| R166 | A, D, H, L |
| V167 | A, C, D, G, H, L, M, P, Q, R, S, T, Y |
| Y168 | F, L |
| S169 | I |
| L171 | A, C, F, K, M, N, Q, S |
| S173 | A, C, E, F, I, K, L, M, P, R, V, W, Y |
| F174 | A, L, M, Y |
| P178 | A, D, E, G, K, L, M, Q, S, T, V, Y |
| F179 | L |
| G190 | A, H, M |
| V191 | A, C, D, E, F, K, L, M, Q, R, Y |
| G193 | S, V |
| T197 | M |
| E198 | C, L, M, N, P, R, W, Y |
| A199 | C, K, L, Y |
| R202 | A, C, E, F, G, H, I, L, M, S, T, W |
| D203 | A, C, H, L, R |
| G205 | A |
| V206 | C, E, F, G, H, K, L, M, N, P, R |
| A209 | E, L |
| E210 | D, K |
| Q211 | M, N, P |
| S214 | A, C, D, F, G, I, K, L, R, T, V, W, |
| L215 | E, M, T, V, Y |

The following Table provides variants with a PAD PI that is less than 0.5, a PAF that is greater than or equal to 0.1, and a protein PI that is greater than or equal to 0.1.

TABLE 10-10

| PAD PI < 0.5 with PAF ≥ 0.1, and Protein PI ≥ 0.1 | |
|---|---|
| Wild-Type Residue/Pos. | Amino Acid Variant(s) |
| A2 | Y |
| R4 | I, L, V |
| I5 | S |
| L6 | S, T, V |
| F8 | R |
| D10 | G |
| L12 | A, C, F, G, K, Q, R, S, T, V |
| W14 | F, G, I, K, L, R, S, T, V |
| G15 | C, N |
| P18 | S |
| V19 | M, Q, R |
| G22 | K, W |
| A23 | G, R, S, |
| T25 | G, H, I, K, L, M, P, R, W |
| E26 | N, S, T, W |
| R27 | P, T, W |
| F28 | G |
| A29 | T, V |
| T35 | N, Q, V |
| G36 | S, T |
| L38 | G, S |
| Q41 | S, V |
| L42 | Q, S, T |
| G43 | P, Q, S, V |
| D45 | R, S, T |
| F46 | T |
| E47 | P |
| V48 | S |
| I49 | P, R |
| E50 | V |
| E51 | I, V |
| G52 | H, L, S, V |
| L53 | E, G, K, R, S |
| S54 | F, G, I, K, L, R, T, V, W, Y |
| A55 | I, R, T, V |
| R56 | C, G, S, T |
| T57 | C, N |
| T58 | A, M |
| N59 | M, R |
| I60 | P |
| D62 | C, G, H, I, L, R, S, T, V, W |
| T64 | R |
| D65 | H, R, S, V, Y |
| P66 | G, N, Q |
| R67 | E, F, G, L, N, P, Q, T, V, W |
| L68 | A, C, E, F, G, H, M, N, P, Q, R, S, T, Y |
| N69 | Y |
| G70 | C, T |
| S72 | W, Y |
| Y73 | L, R |
| P75 | M, R |
| S76 | F, W, Y |
| C77 | F, W, Y |
| L78 | M |
| A79 | C, E, H, M, N, Q, R |
| T80 | H, I, K, L, W, Y |
| H81 | R, Y |
| L82 | G, H, R, S, T, V, W |
| P83 | T, V |
| L84 | A, T, V, W |
| D85 | I, L, V, W |
| L86 | H, S, T, V, W |
| V87 | A, F, G, S, T, Y |

TABLE 10-10-continued

| PAD PI < 0.5 with PAF ≥ 0.1, and Protein PI ≥ 0.1 | |
|---|---|
| Wild-Type Residue/Pos. | Amino Acid Variant(s) |
| I88 | T, V |
| I89 | S |
| M90 | S, T, V |
| L91 | T, V |
| T93 | S, Y |
| N94 | H, L, T, V |
| T96 | I, R, W, Y |
| K97 | G, I, L, P, Q, S, T, V, Y |
| A98 | T |
| Y99 | S, V |
| F100 | E, K, W |
| R101 | K, Q, V, W |
| R102 | C, G |
| T103 | A, C, F, G, H, I, K, L, N, P, R, S, V, W, Y |
| P104 | R, T |
| L105 | V |
| I107 | P, Q |
| L109 | A, D, E, F, H, I, Q, R, S, W |
| G110 | Q, S, T |
| M111 | G, H, R, S |
| S112 | H, R, V, Y |
| L114 | Q |
| T116 | Y |
| V118 | P, R, W |
| L119 | C, D, E, F, G, H, I, N, R, S, T, V, W |
| T120 | H |
| S121 | P |
| A122 | D, E, F, G, H, K, R, S |
| G123 | C |
| G124 | A, H, I, M, Q, R, T, V, W |
| V125 | E, R, W |
| G126 | I, V, Y |
| T127 | E, I, L, Q |
| Y129 | A, D, G, K, L, M, R, T, V, W |
| P130 | A, E, F, G, H, I, L, S, T, V, W |
| A131 | D, W, Y |
| P132 | F, H, I, T, V |
| K133 | A, C, G, H, I, M, T, V |
| L135 | F, Q, S, T, V |
| V137 | S |
| S138 | I |
| P139 | S |
| P140 | S |
| P141 | G, I, Q, R, S, T, V |
| L142 | Q, S, V |
| A143 | G, P, W |
| M145 | E, G, W |
| W149 | A, C, F, G, I, M, Q, S, T |
| F150 | G, N, P, W |
| E155 | F, R, V |
| G156 | I |
| G157 | R, S, V |
| Q159 | A, C, P |
| K160 | G |
| T161 | G, H, R, W |
| E163 | F, R |
| Y168 | C, I, V |
| A170 | I, S |
| A172 | Q, V |
| F174 | C, Q, W |
| F179 | Q, S |
| G190 | S, V, W |
| V191 | G, H, I, N, S, W |
| G193 | C, H, T |
| I194 | A, C, G, S |
| F196 | G, Q, W |
| T197 | R |

TABLE 10-10-continued

| PAD PI < 0.5 with PAF ≥ 0.1, and Protein PI ≥ 0.1 | |
|---|---|
| Wild-Type Residue/Pos. | Amino Acid Variant(s) |
| N201 | G, H, L, R, S, T, V, Y |
| D203 | V |
| L208 | Q, S, V, Y |
| V212 | G |
| L215 | A, C, G, K, P, R |
| L216 | G, I, T |

In addition to the assay results described above, various mutations were found to result in unstable protein such that perhydrolase protein was not expressed. Thus, in contrast to the substitutions that resulted in enhanced expression as compared to wild-type, there were some substitutions that are not as favorable, at least under the conditions used herein. However, it is not intended that the present invention exclude these substitutions, as it is contemplated that these substitutions, taken alone or in combination will find use in alternative embodiments of the present invention.

TABLE 10-11

| Mutations that Produced Unstable Protein | |
|---|---|
| Wild-Type/ Pos. | Variant Amino Acid |
| M1 | A, E, F, G, K, N, P, R, S, T, W |
| I5 | W |
| C7 | L, P, T, W |
| G9 | A, C, E, K, L, P, Q, R, V |
| T13 | F, R, W |
| G15 | H, K, L, R, Y |
| P18 | A |
| D21 | V |
| F28 | H, I, R |
| R33 | D, E, H, P, W |
| W34 | K |
| T35 | K, L, P, W, Y |
| G36 | P |
| V37 | Q, R |
| L38 | W |
| A39 | F |
| L42 | D |
| A44 | D, H, P |
| F46 | H |
| V48 | W |
| E51 | P |
| R56 | H, K, P, W, Y |
| T57 | W |
| T58 | E, G, K, P, R, W, Y |
| L74 | D, H, P, Q, R, T |
| C77 | N, P |
| L78 | A, P, R, S |
| A79 | V |
| L86 | F |
| I88 | R, Y |
| I89 | D, R |
| L91 | H, K, P, R, W, Y |
| G92 | A, D, L, M, P, R, T, W, Y |
| T93 | P, R, V, W |
| D95 | A, D, G, H, K, L, N, Q, R, S, T, V, W, Y |
| K97 | D |
| P104 | A, L |
| L105 | A, M |
| I107 | H, W |
| A108 | D, F, H, I, N, P, R |
| G110 | L |
| L114 | F, K, R, W, Y |
| V115 | H, K, |
| V134 | D, K, R, W, Y |

TABLE 10-11-continued

| Mutations that Produced Unstable Protein | |
|---|---|
| Wild-Type/ Pos. | Variant Amino Acid |
| V136 | R, W |
| V137 | D, E, F, P, R, W |
| S138 | E, F, H, L, M, Q, R, W, Y |
| P139 | L, W, Y |
| P140 | D, K, L, M |
| L142 | D, G, M, N, R, T |
| H147 | G |
| F154 | E, L, P, |
| T161 | D, E, P |
| Y168 | D, E, H, K, N, P, R, S, W |
| L171 | D |
| F179 | A, P, R |
| F180 | E |
| D181 | F, H, I, M, N |
| A182 | H, K, L, M, W, Y |
| I186 | K, W, Y |
| T188 | D, K, P, Q, W |
| F196 | A, K, N, R |

The following Table provides performance indices obtained in PAF and PAD assays for various variants, as well as the protein performance index.

TABLE 10-12

| Performance Indices | | | | |
|---|---|---|---|---|
| Wild-Type Res./Pos. | Mut. | PAF PI | PAD PI | Prot. PI |
| M1 | A | −0.12 | −0.12 | −0.01 |
| M1 | E | −0.12 | −0.12 | −0.01 |
| M1 | F | −0.12 | −0.12 | −0.01 |
| M1 | G | −0.12 | −0.12 | −0.01 |
| M1 | I | 0.96 | 1.19 | 0.31 |
| M1 | K | −0.12 | −0.12 | −0.01 |
| M1 | L | 0.75 | 2.11 | 0.30 |
| M1 | M | 1.00 | 1.00 | 1.00 |
| M1 | N | −0.12 | −0.12 | −0.01 |
| M1 | P | −0.12 | −0.12 | −0.01 |
| M1 | R | −0.12 | −0.12 | −0.01 |
| M1 | S | −0.12 | −0.12 | −0.01 |
| M1 | T | −0.12 | −0.12 | −0.01 |
| M1 | V | 0.87 | 0.94 | 0.52 |
| M1 | W | −0.12 | −0.12 | −0.01 |
| A2 | A | 1.00 | 1.00 | 1.00 |
| A2 | D | 1.30 | 1.05 | 0.77 |
| A2 | E | 0.61 | 1.38 | 0.52 |
| A2 | F | 1.24 | 0.93 | 0.89 |
| A2 | G | 1.15 | 0.84 | 0.95 |
| A2 | I | 1.18 | 0.61 | 1.25 |
| A2 | N | 0.93 | 0.59 | 1.30 |
| A2 | P | 0.52 | 1.17 | 0.68 |
| A2 | Q | 0.81 | 1.29 | 0.65 |
| A2 | R | 0.90 | 1.17 | 0.70 |
| A2 | S | 1.01 | 0.66 | 1.15 |
| A2 | T | 0.98 | 0.61 | 1.17 |
| A2 | V | 0.89 | 0.60 | 1.18 |
| A2 | W | 1.75 | 1.17 | 0.53 |
| A2 | Y | 0.84 | 0.46 | 1.61 |
| K3 | A | 0.86 | 2.14 | 0.48 |
| K3 | C | 0.81 | 1.52 | 0.67 |
| K3 | E | 0.12 | 3.51 | 0.11 |
| K3 | G | 0.72 | 3.74 | 0.08 |
| K3 | H | 1.01 | 1.89 | 0.30 |
| K3 | I | 1.05 | 2.44 | 0.16 |
| K3 | K | 1.00 | 1.00 | 1.00 |
| K3 | L | 1.04 | 1.84 | 0.50 |
| K3 | M | 0.85 | 1.44 | 0.71 |
| K3 | P | 0.80 | 1.45 | 0.59 |
| K3 | Q | 0.87 | 1.19 | 0.69 |
| K3 | R | 0.87 | 1.29 | 0.46 |
| K3 | S | 0.94 | 1.17 | 0.44 |

TABLE 10-12-continued

Performance Indices

| Wild-Type Res./Pos. | Mut. | PAF PI | PAD PI | Prot. PI |
|---|---|---|---|---|
| K3 | T | 1.01 | 1.03 | 0.71 |
| K3 | V | 0.81 | 0.84 | 0.33 |
| K3 | Y | 1.06 | 1.39 | 0.86 |
| R4 | A | 0.41 | 1.64 | 0.29 |
| R4 | C | 0.71 | 1.34 | 0.35 |
| R4 | D | 0.27 | 1.18 | 0.32 |
| R4 | E | 0.32 | 0.97 | 0.25 |
| R4 | G | 0.79 | 0.79 | 0.41 |
| R4 | H | 0.92 | 0.99 | 0.59 |
| R4 | I | 0.24 | 0.15 | 0.18 |
| R4 | L | 0.21 | −0.03 | 0.18 |
| R4 | P | 0.14 | 1.44 | 0.13 |
| R4 | Q | 1.03 | 0.99 | 0.70 |
| R4 | R | 1.00 | 1.00 | 1.00 |
| R4 | S | 0.65 | 0.91 | 0.64 |
| R4 | T | 0.80 | 1.00 | 0.69 |
| R4 | V | 0.29 | 0.08 | 0.22 |
| R4 | W | 0.04 | 0.48 | 0.12 |
| R4 | Y | 0.63 | 0.98 | 0.39 |
| I5 | A | 0.60 | 1.88 | 0.62 |
| I5 | C | 0.44 | 2.47 | 0.54 |
| I5 | D | −0.13 | 3.11 | 0.06 |
| I5 | E | 0.67 | 1.59 | 0.33 |
| I5 | F | −0.13 | 0.15 | 0.06 |
| I5 | G | 0.05 | −3.88 | 0.10 |
| I5 | H | 0.55 | 0.63 | 0.18 |
| I5 | I | 1.00 | 1.00 | 1.00 |
| I5 | L | 0.80 | 1.63 | 0.96 |
| I5 | M | 0.63 | 1.09 | 1.29 |
| I5 | N | −0.13 | −2.15 | 0.12 |
| I5 | P | −0.13 | −0.86 | 0.08 |
| I5 | R | −0.13 | −6.48 | 0.08 |
| I5 | S | 1.02 | 0.37 | 0.39 |
| I5 | T | 1.12 | 0.72 | 0.25 |
| I5 | V | 0.94 | 0.92 | 0.54 |
| I5 | W | −0.13 | −0.44 | −0.01 |
| L6 | A | 0.87 | 1.99 | 0.26 |
| L6 | C | 0.85 | 1.22 | 0.55 |
| L6 | E | −0.20 | −0.59 | 0.09 |
| L6 | G | 0.23 | −3.45 | 0.12 |
| L6 | H | 0.23 | −1.08 | 0.09 |
| L6 | I | 1.07 | 0.82 | 0.86 |
| L6 | K | 0.41 | −1.16 | 0.05 |
| L6 | L | 1.00 | 1.00 | 1.00 |
| L6 | M | 0.92 | 1.44 | 0.63 |
| L6 | Q | −0.20 | −1.63 | 0.12 |
| L6 | R | 0.06 | −1.59 | 0.12 |
| L6 | S | 0.58 | −1.26 | 0.23 |
| L6 | T | 1.06 | 0.35 | 0.40 |
| L6 | V | 1.07 | 0.35 | 0.44 |
| L6 | W | 0.06 | −2.97 | 0.09 |
| C7 | A | 1.42 | 1.03 | 1.22 |
| C7 | C | 1.00 | 1.00 | 1.00 |
| C7 | E | −0.26 | 1.63 | 0.20 |
| C7 | G | 1.39 | 0.69 | 1.07 |
| C7 | H | 1.73 | 1.37 | 0.41 |
| C7 | I | 1.76 | 1.48 | 0.31 |
| C7 | K | 2.69 | 2.95 | 0.21 |
| C7 | L | −0.26 | −0.16 | −0.01 |
| C7 | M | 1.13 | 0.68 | 1.03 |
| C7 | P | −0.26 | −0.16 | −0.01 |
| C7 | R | 0.22 | −1.04 | 0.15 |
| C7 | S | 0.62 | −2.83 | 0.10 |
| C7 | T | −0.26 | −0.16 | −0.01 |
| C7 | W | −0.26 | −0.16 | −0.01 |
| C7 | Y | 2.09 | 0.54 | 0.67 |
| F8 | A | 0.55 | 1.33 | 0.96 |
| F8 | C | −0.11 | 4.01 | 0.10 |
| F8 | F | 1.00 | 1.00 | 1.00 |
| F8 | G | 1.09 | 0.65 | 1.03 |
| F8 | H | 1.02 | 0.64 | 0.97 |
| F8 | K | 0.81 | 0.83 | 0.95 |
| F8 | L | 0.77 | 1.31 | 0.90 |
| F8 | M | 0.56 | 1.11 | 1.05 |
| F8 | N | −0.11 | 0.96 | 1.23 |
| F8 | P | 1.00 | 0.83 | 1.01 |
| F8 | R | 1.43 | 0.46 | 0.73 |
| F8 | S | 0.71 | −2.75 | 0.13 |
| F8 | T | 0.88 | 0.77 | 0.94 |
| F8 | V | 1.18 | 0.85 | 0.88 |
| F8 | Y | 0.96 | 0.90 | 0.85 |
| G9 | A | −0.15 | −0.18 | −0.01 |
| G9 | C | −0.15 | −0.18 | −0.01 |
| G9 | E | −0.15 | −0.18 | −0.01 |
| G9 | G | 1.00 | 1.00 | 1.00 |
| G9 | H | 0.29 | −0.06 | 0.16 |
| G9 | K | −0.15 | −0.18 | −0.01 |
| G9 | L | −0.15 | −0.18 | −0.01 |
| G9 | P | −0.15 | −0.18 | −0.01 |
| G9 | Q | −0.15 | −0.18 | −0.01 |
| G9 | R | −0.15 | −0.18 | −0.01 |
| G9 | T | 0.21 | −2.56 | 0.12 |
| G9 | V | −0.15 | −0.18 | −0.01 |
| D10 | A | −0.29 | −14.24 | 0.02 |
| D10 | D | 1.00 | 1.00 | 1.00 |
| D10 | E | 0.01 | 0.15 | 0.72 |
| D10 | G | 0.41 | −0.92 | 0.17 |
| D10 | I | 1.28 | −6.86 | 0.04 |
| D10 | K | 2.13 | −5.30 | 0.02 |
| D10 | L | 3.97 | 2.04 | 0.02 |
| D10 | M | −0.29 | −5.94 | 0.04 |
| D10 | N | −0.29 | −2.23 | 0.07 |
| D10 | P | −0.29 | −4.16 | 0.05 |
| D10 | R | 0.22 | −4.36 | 0.06 |
| D10 | S | 0.79 | −0.58 | 0.06 |
| D10 | T | 1.47 | −0.45 | 0.06 |
| D10 | V | 0.98 | −4.22 | 0.06 |
| D10 | W | 3.18 | −3.70 | 0.02 |
| D10 | Y | 1.51 | −4.97 | 0.03 |
| S11 | A | 0.25 | 0.53 | 1.04 |
| S11 | D | −0.25 | −0.22 | 1.03 |
| S11 | E | −0.25 | −0.23 | 1.01 |
| S11 | F | −0.25 | −0.13 | 0.68 |
| S11 | G | −0.25 | −0.09 | 0.86 |
| S11 | H | −0.25 | 0.33 | 1.06 |
| S11 | I | −0.25 | 0.56 | 0.63 |
| S11 | K | −0.25 | 0.40 | 0.62 |
| S11 | L | −0.25 | −0.22 | 0.68 |
| S11 | Q | −0.25 | −0.26 | 1.01 |
| S11 | R | −0.25 | −0.08 | 0.69 |
| S11 | S | 1.00 | 1.00 | 1.00 |
| S11 | T | 0.04 | −0.36 | 0.87 |
| S11 | V | 0.03 | −0.15 | 0.59 |
| L12 | A | 1.10 | 0.07 | 0.71 |
| L12 | C | 2.29 | 0.22 | 0.81 |
| L12 | D | 0.04 | 0.00 | 0.39 |
| L12 | F | 0.13 | 0.17 | 0.60 |
| L12 | G | 0.44 | −0.06 | 0.60 |
| L12 | H | 0.02 | 0.16 | 0.77 |
| L12 | K | 0.18 | 0.13 | 0.40 |
| L12 | L | 1.00 | 1.00 | 1.00 |
| L12 | N | 0.53 | 0.66 | 1.06 |
| L12 | P | 0.03 | −0.16 | 0.31 |
| L12 | Q | 2.65 | 0.22 | 1.05 |
| L12 | R | 0.23 | −0.02 | 0.34 |
| L12 | S | 0.54 | −0.07 | 0.80 |
| L12 | T | 0.68 | 0.06 | 0.89 |
| L12 | V | 0.98 | −0.05 | 0.51 |
| L12 | W | 0.03 | 0.02 | 0.33 |
| T13 | A | 0.25 | 1.88 | 0.72 |
| T13 | C | 0.56 | 1.55 | 0.78 |
| T13 | E | −0.10 | 1.09 | 0.44 |
| T13 | F | −0.10 | −0.11 | −0.02 |
| T13 | G | 0.32 | 0.77 | 0.57 |
| T13 | I | 0.12 | 1.05 | 0.69 |
| T13 | L | 0.55 | 1.47 | 0.76 |
| T13 | M | 0.17 | 1.47 | 0.94 |
| T13 | N | −0.10 | 2.61 | 0.27 |
| T13 | P | −0.10 | 2.73 | 0.17 |
| T13 | Q | 0.01 | 0.51 | 0.98 |

TABLE 10-12-continued

| Wild-Type Res./Pos. | Mut. | PAF PI | PAD PI | Prot. PI |
|---|---|---|---|---|
| | | Performance Indices | | |
| T13 | R | −0.10 | −0.11 | −0.02 |
| T13 | S | 0.73 | 0.68 | 0.88 |
| T13 | T | 1.00 | 1.00 | 1.00 |
| T13 | V | 0.19 | 0.63 | 1.17 |
| T13 | W | −0.10 | −0.11 | −0.02 |
| W14 | A | −0.23 | 0.27 | 0.94 |
| W14 | E | 0.06 | 0.15 | 0.80 |
| W14 | F | 0.29 | 0.22 | 0.71 |
| W14 | G | 0.30 | −0.97 | 0.70 |
| W14 | I | 0.33 | −0.42 | 0.66 |
| W14 | K | 0.29 | −0.17 | 0.71 |
| W14 | L | 0.25 | −0.36 | 0.82 |
| W14 | N | −0.23 | −0.12 | 0.81 |
| W14 | P | −0.23 | −0.29 | 0.34 |
| W14 | R | 0.23 | −0.40 | 0.66 |
| W14 | S | 0.31 | −0.99 | 0.69 |
| W14 | T | 0.24 | −0.77 | 0.64 |
| W14 | V | 0.26 | −0.49 | 0.58 |
| W14 | W | 1.00 | 1.00 | 1.00 |
| W14 | Y | 0.31 | 0.66 | 1.02 |
| G15 | A | 1.54 | 0.61 | 0.87 |
| G15 | C | 0.71 | −0.27 | 0.66 |
| G15 | D | −0.18 | 0.01 | 0.26 |
| G15 | E | −0.18 | −1.42 | 0.11 |
| G15 | G | 1.00 | 1.00 | 1.00 |
| G15 | H | −0.18 | −0.14 | −0.01 |
| G15 | K | −0.18 | −0.14 | −0.01 |
| G15 | L | −0.18 | −0.14 | −0.01 |
| G15 | N | 0.46 | −0.63 | 0.71 |
| G15 | P | −0.18 | −5.42 | 0.09 |
| G15 | R | −0.18 | −0.14 | −0.01 |
| G15 | S | 1.05 | 0.63 | 0.76 |
| G15 | Y | −0.18 | −0.14 | −0.01 |
| W16 | A | 0.12 | 0.55 | 0.50 |
| W16 | D | 0.02 | 0.57 | 0.32 |
| W16 | E | 0.06 | 0.65 | 0.46 |
| W16 | G | 0.05 | −0.07 | 0.38 |
| W16 | H | 0.03 | −0.02 | 0.55 |
| W16 | I | 0.02 | 1.06 | 0.74 |
| W16 | K | 0.01 | 1.03 | 0.73 |
| W16 | L | −0.48 | 1.16 | 0.76 |
| W16 | M | 0.04 | 0.37 | 0.56 |
| W16 | N | 0.02 | −0.03 | 0.43 |
| W16 | P | 0.03 | 0.15 | 0.37 |
| W16 | Q | 0.05 | 0.31 | 0.47 |
| W16 | R | 0.03 | −0.41 | 0.30 |
| W16 | S | 0.09 | −0.17 | 0.39 |
| W16 | T | 0.03 | −0.31 | 0.41 |
| W16 | V | 0.01 | 0.88 | 0.76 |
| W16 | W | 1.00 | 1.00 | 1.00 |
| W16 | Y | 0.22 | 1.09 | 1.02 |
| V17 | A | 1.01 | 0.68 | 1.21 |
| V17 | E | 0.82 | 0.75 | 1.11 |
| V17 | F | 0.92 | 0.85 | 1.09 |
| V17 | G | 1.17 | 0.84 | 0.93 |
| V17 | I | 0.95 | 0.99 | 1.08 |
| V17 | K | 0.94 | 0.84 | 1.06 |
| V17 | L | 0.90 | 1.00 | 0.76 |
| V17 | P | 0.77 | 0.96 | 0.97 |
| V17 | R | 1.10 | 0.94 | 0.76 |
| V17 | S | 0.96 | 1.04 | 0.89 |
| V17 | T | 0.93 | 0.86 | 1.03 |
| V17 | V | 1.00 | 1.00 | 1.00 |
| V17 | Y | 0.91 | 0.88 | 0.99 |
| P18 | A | −0.28 | −0.94 | −0.03 |
| P18 | C | 1.26 | 4.16 | 2.56 |
| P18 | E | 1.22 | 4.87 | 2.47 |
| P18 | G | 1.07 | 4.96 | 2.47 |
| P18 | H | 1.12 | 6.05 | 2.50 |
| P18 | L | 0.93 | 7.40 | 2.50 |
| P18 | N | 1.33 | 1.42 | 2.35 |
| P18 | P | 1.00 | 1.00 | 1.00 |
| P18 | Q | 1.12 | 3.26 | 2.13 |
| P18 | R | 1.16 | 3.97 | 2.01 |
| P18 | S | 0.11 | 0.07 | 1.05 |

TABLE 10-12-continued

| Wild-Type Res./Pos. | Mut. | PAF PI | PAD PI | Prot. PI |
|---|---|---|---|---|
| | | Performance Indices | | |
| P18 | V | 1.19 | 4.85 | 2.30 |
| P18 | Y | 1.33 | 4.17 | 1.68 |
| V19 | A | 0.61 | 0.55 | 1.23 |
| V19 | D | 0.77 | 0.79 | 0.80 |
| V19 | E | 0.74 | 0.62 | 1.10 |
| V19 | G | 1.32 | 0.56 | 1.39 |
| V19 | K | 0.96 | 0.97 | 1.03 |
| V19 | L | 1.00 | 0.91 | 0.90 |
| V19 | M | 0.33 | 0.12 | 1.00 |
| V19 | P | 0.00 | −0.41 | 0.76 |
| V19 | Q | 0.93 | 0.40 | 1.07 |
| V19 | R | 1.03 | 0.34 | 0.82 |
| V19 | S | 1.24 | 0.57 | 0.80 |
| V19 | V | 1.00 | 1.00 | 1.00 |
| V19 | Y | 0.94 | 0.70 | 0.92 |
| E20 | A | 1.29 | 1.28 | 1.08 |
| E20 | C | 1.57 | 1.76 | 0.71 |
| E20 | D | 0.87 | 1.14 | 0.97 |
| E20 | E | 1.00 | 1.00 | 1.00 |
| E20 | G | 2.36 | 0.78 | 1.11 |
| E20 | H | 2.17 | 1.20 | 0.92 |
| E20 | L | 2.20 | 0.73 | 0.92 |
| E20 | N | 1.40 | 1.34 | 1.01 |
| E20 | P | 1.00 | 1.43 | 1.08 |
| E20 | Q | 1.27 | 1.56 | 0.99 |
| E20 | S | 2.01 | 1.18 | 0.91 |
| E20 | T | 2.22 | 1.25 | 0.94 |
| E20 | V | 2.11 | 1.27 | 1.01 |
| E20 | W | 2.94 | 1.30 | 0.79 |
| D21 | A | 1.46 | 1.75 | 0.84 |
| D21 | D | 1.00 | 1.00 | 1.00 |
| D21 | E | 0.84 | 1.39 | 0.85 |
| D21 | F | 1.30 | 1.41 | 0.81 |
| D21 | G | 1.37 | 1.76 | 0.93 |
| D21 | K | 1.58 | 1.80 | 0.74 |
| D21 | L | 1.46 | 1.57 | 0.82 |
| D21 | P | 0.81 | 0.86 | 0.74 |
| D21 | S | 1.24 | 1.11 | 0.73 |
| D21 | V | −0.17 | −0.12 | −0.02 |
| D21 | W | 1.55 | 1.44 | 0.61 |
| D21 | Y | 1.30 | 2.01 | 0.42 |
| G22 | A | 1.55 | 1.66 | 1.07 |
| G22 | E | 0.15 | 1.19 | 0.56 |
| G22 | G | 1.00 | 1.00 | 1.00 |
| G22 | I | 0.37 | 1.03 | 1.03 |
| G22 | K | 0.23 | −0.22 | 0.78 |
| G22 | L | 0.38 | 1.35 | 0.84 |
| G22 | P | 0.28 | 1.36 | 0.80 |
| G22 | Q | 0.35 | 1.44 | 0.96 |
| G22 | R | 0.11 | 0.56 | 0.73 |
| G22 | S | 1.02 | 0.98 | 0.94 |
| G22 | T | 1.03 | 1.16 | 0.80 |
| G22 | V | 0.40 | 0.85 | 0.89 |
| G22 | W | 0.25 | 0.23 | 0.58 |
| A23 | A | 1.00 | 1.00 | 1.00 |
| A23 | F | 0.05 | 0.44 | 1.03 |
| A23 | G | 0.45 | 0.35 | 0.93 |
| A23 | H | 0.16 | 1.04 | 0.93 |
| A23 | L | 0.30 | 1.30 | 0.75 |
| A23 | M | 0.85 | 0.95 | 0.90 |
| A23 | P | −0.11 | 0.73 | 0.82 |
| A23 | Q | 0.23 | 0.73 | 0.91 |
| A23 | R | 0.11 | 0.28 | 0.80 |
| A23 | S | 0.69 | 0.34 | 0.87 |
| A23 | V | 0.20 | 0.60 | 0.73 |
| A23 | W | 0.29 | 0.80 | 0.71 |
| A23 | Y | 0.20 | 0.96 | 0.73 |
| P24 | A | 0.54 | 0.68 | 0.88 |
| P24 | C | 0.54 | 1.04 | 0.87 |
| P24 | G | 0.49 | 0.76 | 1.34 |
| P24 | H | 0.42 | 0.97 | 1.15 |
| P24 | I | 0.42 | 0.85 | 1.11 |
| P24 | K | 0.52 | 1.36 | 0.71 |
| P24 | L | 0.58 | 1.51 | 1.06 |
| P24 | P | 1.00 | 1.00 | 1.00 |

TABLE 10-12-continued

| | | Performance Indices | | |
|---|---|---|---|---|
| Wild-Type Res./Pos. | Mut. | PAF PI | PAD PI | Prot. PI |
| P24 | Q | 0.50 | 0.65 | 0.93 |
| P24 | R | 0.58 | 0.91 | 0.85 |
| P24 | S | 0.53 | 0.61 | 1.31 |
| P24 | T | 0.44 | 0.66 | 1.43 |
| T25 | A | 1.33 | 0.86 | 1.23 |
| T25 | C | 0.67 | 0.51 | 1.37 |
| T25 | D | 0.03 | −0.07 | 0.87 |
| T25 | E | 0.08 | −0.29 | 0.98 |
| T25 | G | 1.86 | 0.43 | 1.27 |
| T25 | H | 0.42 | −0.02 | 0.94 |
| T25 | I | 1.02 | 0.35 | 1.19 |
| T25 | K | 0.36 | 0.13 | 0.87 |
| T25 | L | 0.40 | −0.04 | 0.95 |
| T25 | M | 0.29 | −0.10 | 1.04 |
| T25 | P | 0.97 | −0.05 | 1.10 |
| T25 | R | 0.32 | −0.06 | 0.94 |
| T25 | S | 1.60 | 0.58 | 0.95 |
| T25 | T | 1.00 | 1.00 | 1.00 |
| T25 | V | 0.91 | 0.51 | 1.30 |
| T25 | W | 0.33 | 0.14 | 0.86 |
| E26 | A | 1.93 | 1.45 | 0.79 |
| E26 | C | 1.40 | 0.94 | 0.82 |
| E26 | D | 0.65 | 1.39 | 0.90 |
| E26 | E | 1.00 | 1.00 | 1.00 |
| E26 | G | 1.28 | 0.87 | 0.82 |
| E26 | H | 1.33 | 1.19 | 0.71 |
| E26 | K | 1.46 | 1.47 | 0.77 |
| E26 | L | 1.30 | 1.71 | 0.77 |
| E26 | M | 2.00 | 1.10 | 0.89 |
| E26 | N | 1.37 | 0.48 | 0.88 |
| E26 | P | 0.43 | 0.99 | 0.63 |
| E26 | R | 1.48 | 0.81 | 0.77 |
| E26 | S | 1.27 | 0.28 | 0.92 |
| E26 | T | 1.44 | 0.40 | 0.82 |
| E26 | V | 1.39 | 0.97 | 0.85 |
| E26 | W | 1.25 | 0.47 | 0.68 |
| R27 | A | 0.45 | 2.78 | 0.67 |
| R27 | C | 0.35 | 0.58 | 0.50 |
| R27 | E | 0.58 | 0.93 | 0.46 |
| R27 | G | 0.42 | 0.84 | 0.24 |
| R27 | I | 0.72 | 1.41 | 0.70 |
| R27 | K | 1.22 | 1.55 | 0.69 |
| R27 | L | 0.48 | 2.60 | 0.51 |
| R27 | P | 0.93 | 0.48 | 0.46 |
| R27 | R | 1.00 | 1.00 | 1.00 |
| R27 | S | 0.53 | 0.69 | 0.56 |
| R27 | T | 0.41 | 0.01 | 0.74 |
| R27 | V | 0.71 | 0.94 | 0.85 |
| R27 | W | 0.21 | −0.59 | 0.33 |
| F28 | A | 1.27 | 1.48 | 0.92 |
| F28 | C | 0.93 | 1.21 | 0.87 |
| F28 | D | 0.67 | 2.07 | 0.40 |
| F28 | E | 0.51 | 1.04 | 0.85 |
| F28 | F | 1.00 | 1.00 | 1.00 |
| F28 | G | 0.74 | −1.53 | 0.50 |
| F28 | H | −0.20 | −0.19 | −0.01 |
| F28 | I | −0.20 | −0.19 | −0.01 |
| F28 | L | 1.09 | 2.02 | 0.51 |
| F28 | M | 1.33 | 1.37 | 0.70 |
| F28 | P | 0.02 | 0.39 | 0.42 |
| F28 | R | −0.20 | −0.19 | −0.01 |
| F28 | S | 1.05 | 0.70 | 0.82 |
| F28 | V | 0.86 | 0.53 | 0.85 |
| F28 | W | 1.16 | 1.17 | 0.89 |
| F28 | Y | 0.99 | 1.36 | 0.77 |
| A29 | A | 1.00 | 1.00 | 1.00 |
| A29 | C | 1.08 | 1.15 | 0.76 |
| A29 | D | 0.87 | 1.00 | 1.06 |
| A29 | E | 1.12 | 0.84 | 1.02 |
| A29 | G | 1.60 | 0.80 | 1.22 |
| A29 | M | 0.67 | 0.77 | 1.06 |
| A29 | P | 0.78 | 0.62 | 1.07 |
| A29 | R | 1.76 | 0.73 | 0.81 |
| A29 | S | 1.49 | 0.55 | 1.05 |
| A29 | T | 1.42 | 0.47 | 1.02 |

TABLE 10-12-continued

| | | Performance Indices | | |
|---|---|---|---|---|
| Wild-Type Res./Pos. | Mut. | PAF PI | PAD PI | Prot. PI |
| A29 | V | 1.80 | 0.44 | 1.05 |
| A29 | W | 1.91 | 0.74 | 0.82 |
| A29 | Y | 1.70 | 0.59 | 0.96 |
| P30 | A | 1.05 | 0.92 | 1.15 |
| P30 | E | 1.01 | 1.24 | 1.20 |
| P30 | G | 0.90 | 1.09 | 0.99 |
| P30 | H | 1.01 | 1.08 | 1.05 |
| P30 | I | 0.97 | 1.38 | 0.95 |
| P30 | K | 1.21 | 1.39 | 1.06 |
| P30 | L | 0.96 | 1.17 | 1.07 |
| P30 | M | 0.96 | 0.79 | 0.94 |
| P30 | P | 1.00 | 1.00 | 1.00 |
| P30 | Q | 1.01 | 0.91 | 1.06 |
| P30 | R | 1.16 | 1.14 | 0.94 |
| P30 | S | 1.03 | 1.49 | 1.12 |
| P30 | T | 1.05 | 1.64 | 1.00 |
| P30 | V | 1.06 | 1.74 | 0.99 |
| P30 | Y | 0.79 | 1.31 | 1.04 |
| D31 | A | 1.24 | 1.18 | 0.80 |
| D31 | D | 1.00 | 1.00 | 1.00 |
| D31 | E | 1.13 | 0.88 | 0.93 |
| D31 | F | 1.44 | 1.39 | 0.65 |
| D31 | G | 1.44 | 1.16 | 0.79 |
| D31 | L | 1.81 | 1.61 | 0.65 |
| D31 | N | 1.34 | 1.55 | 0.62 |
| D31 | Q | 1.07 | 1.13 | 0.74 |
| D31 | R | 1.22 | 1.49 | 0.50 |
| D31 | S | 1.15 | 1.23 | 0.55 |
| D31 | T | 1.45 | 1.11 | 0.76 |
| D31 | V | 1.28 | 1.08 | 0.50 |
| D31 | W | 1.83 | 1.14 | 0.60 |
| V32 | A | 0.43 | 3.64 | 1.10 |
| V32 | D | 0.45 | 4.19 | 0.95 |
| V32 | E | 0.57 | 3.92 | 1.00 |
| V32 | G | 0.58 | 2.65 | 0.98 |
| V32 | I | 0.91 | 3.51 | 1.08 |
| V32 | K | 1.09 | 4.73 | 0.75 |
| V32 | L | 0.96 | 4.72 | 1.01 |
| V32 | M | 0.64 | 3.41 | 1.11 |
| V32 | N | 0.54 | 1.61 | 0.99 |
| V32 | P | 0.01 | −1.17 | 0.31 |
| V32 | Q | 0.64 | 1.74 | 1.03 |
| V32 | R | 1.05 | 0.72 | 0.51 |
| V32 | S | 0.77 | 1.09 | 0.85 |
| V32 | V | 1.00 | 1.00 | 1.00 |
| V32 | W | 0.94 | 1.71 | 0.70 |
| R33 | A | 0.20 | 1.32 | 0.52 |
| R33 | C | 0.44 | 1.73 | 0.95 |
| R33 | D | −0.16 | −0.30 | −0.02 |
| R33 | E | −0.16 | −0.30 | −0.02 |
| R33 | G | 0.64 | 2.63 | 0.47 |
| R33 | H | −0.16 | −0.30 | −0.02 |
| R33 | K | 0.85 | 2.72 | 0.81 |
| R33 | L | 0.34 | 2.90 | 0.74 |
| R33 | N | 0.90 | 1.30 | 0.92 |
| R33 | P | −0.16 | −0.30 | −0.02 |
| R33 | R | 1.00 | 1.00 | 1.00 |
| R33 | S | 1.00 | 1.01 | 0.79 |
| R33 | V | 0.50 | 0.94 | 0.89 |
| R33 | W | −0.16 | −0.30 | −0.02 |
| W34 | A | −0.15 | 2.29 | 0.41 |
| W34 | C | −0.15 | 1.49 | 0.52 |
| W34 | E | −0.15 | −1.86 | 0.17 |
| W34 | G | 0.12 | 0.88 | 0.23 |
| W34 | I | 0.18 | 0.94 | 0.75 |
| W34 | K | −0.15 | −0.15 | −0.02 |
| W34 | M | 0.16 | 1.22 | 0.91 |
| W34 | P | −0.15 | 1.21 | 0.26 |
| W34 | Q | 0.02 | 0.04 | 0.25 |
| W34 | R | 0.22 | −0.33 | 0.16 |
| W34 | S | 0.47 | 0.08 | 0.29 |
| W34 | T | 0.36 | 0.15 | 0.29 |
| W34 | V | 0.24 | 0.73 | 0.71 |
| W34 | W | 1.00 | 1.00 | 1.00 |
| T35 | A | 0.45 | 3.85 | 0.98 |

TABLE 10-12-continued

| Performance Indices | | | | |
|---|---|---|---|---|
| Wild-Type Res./Pos. | Mut. | PAF PI | PAD PI | Prot. PI |
| T35 | C | 0.55 | 4.72 | 1.16 |
| T35 | E | 0.30 | 5.73 | 0.26 |
| T35 | I | 0.63 | 5.38 | 0.45 |
| T35 | K | −0.13 | −0.54 | −0.01 |
| T35 | L | −0.13 | −0.54 | −0.01 |
| T35 | M | 0.17 | 2.72 | 0.40 |
| T35 | N | 0.20 | −2.29 | 0.43 |
| T35 | P | −0.13 | −0.54 | −0.01 |
| T35 | Q | 0.57 | −2.07 | 0.52 |
| T35 | R | 0.18 | −11.34 | 0.23 |
| T35 | T | 1.00 | 1.00 | 1.00 |
| T35 | V | 0.71 | 0.34 | 0.81 |
| T35 | W | −0.13 | −0.54 | −0.01 |
| T35 | Y | −0.13 | −0.54 | −0.01 |
| G36 | A | 0.63 | 1.07 | 1.00 |
| G36 | C | 0.53 | 1.06 | 1.09 |
| G36 | D | −0.12 | 2.50 | 0.28 |
| G36 | G | −0.12 | −0.10 | −0.02 |
| G36 | H | 0.73 | 1.10 | 0.98 |
| G36 | I | 1.32 | 1.81 | 0.31 |
| G36 | K | 1.27 | 1.71 | 0.84 |
| G36 | L | 1.24 | 2.49 | 0.39 |
| G36 | M | 0.85 | 0.54 | 0.85 |
| G36 | N | 0.49 | 0.56 | 1.08 |
| G36 | P | −0.12 | −0.10 | −0.02 |
| G36 | Q | 0.56 | 0.71 | 1.07 |
| G36 | R | 0.99 | 0.90 | 0.85 |
| G36 | S | 0.78 | 0.26 | 1.06 |
| G36 | T | 0.76 | 0.33 | 0.83 |
| G36 | V | 0.95 | 0.38 | 0.42 |
| G36 | W | 0.91 | 0.68 | 0.57 |
| V37 | A | 1.25 | 2.00 | 0.63 |
| V37 | C | 1.09 | 1.63 | 0.68 |
| V37 | H | 1.21 | 0.96 | 0.78 |
| V37 | I | 1.26 | 1.04 | 0.77 |
| V37 | L | 1.16 | 1.16 | 0.71 |
| V37 | N | 0.90 | 1.52 | 1.09 |
| V37 | P | 0.53 | 2.10 | 0.73 |
| V37 | Q | −0.11 | −0.14 | −0.02 |
| V37 | R | −0.11 | −0.14 | −0.02 |
| V37 | S | 1.40 | 1.49 | 0.81 |
| V37 | T | 1.05 | 0.81 | 0.63 |
| V37 | V | −0.11239 | −0.14412 | −0.02 |
| V37 | W | 0.92 | 0.98 | 0.62 |
| L38 | A | 0.59 | 0.63 | 0.78 |
| L38 | C | 0.64 | 0.72 | 0.89 |
| L38 | D | −0.15 | 0.12 | 0.24 |
| L38 | E | −0.15 | −0.61 | 0.26 |
| L38 | G | 0.15 | −0.72 | 0.32 |
| L38 | K | 0.63 | −0.22 | 0.16 |
| L38 | L | 1.00 | 1.00 | 1.00 |
| L38 | P | −0.15 | −0.78 | 0.28 |
| L38 | Q | −0.15 | −0.02 | 0.47 |
| L38 | R | −0.15 | −0.96 | 0.34 |
| L38 | S | 0.38 | 0.29 | 0.48 |
| L38 | V | 0.88 | 1.12 | 0.73 |
| L38 | W | −0.15 | −0.11 | −0.02 |
| A39 | A | 1.00 | 1.00 | 1.00 |
| A39 | C | 0.63 | 0.92 | 0.50 |
| A39 | E | 1.09 | 0.83 | 1.03 |
| A39 | F | −0.17 | −0.11 | −0.02 |
| A39 | G | 1.17 | 0.30 | 0.92 |
| A39 | I | 1.26 | 0.71 | 0.91 |
| A39 | K | 1.36 | 0.96 | 0.90 |
| A39 | L | 1.43 | 0.97 | 0.93 |
| A39 | M | 0.52 | 0.81 | 0.46 |
| A39 | N | 0.51 | 0.43 | 0.45 |
| A39 | P | 0.69 | 0.74 | 0.45 |
| A39 | R | 1.17 | 0.64 | 0.94 |
| A39 | S | 0.49 | −4.31 | 0.16 |
| A39 | T | 1.26 | 0.79 | 0.92 |
| A39 | V | 1.21 | 0.98 | 1.18 |
| A39 | W | 1.23 | 1.02 | 0.94 |
| A39 | Y | 1.36 | 1.13 | 0.90 |
| Q40 | D | 1.16 | 1.59 | 0.69 |

TABLE 10-12-continued

| Performance Indices | | | | |
|---|---|---|---|---|
| Wild-Type Res./Pos. | Mut. | PAF PI | PAD PI | Prot. PI |
| Q40 | E | 1.08 | 1.28 | 0.81 |
| Q40 | G | 1.79 | 2.17 | 0.93 |
| Q40 | I | 2.58 | 1.10 | 0.49 |
| Q40 | K | 2.61 | 3.64 | 0.52 |
| Q40 | L | 2.14 | 1.49 | 0.53 |
| Q40 | N | 1.53 | 1.00 | 0.78 |
| Q40 | P | 0.45 | −0.19 | 0.24 |
| Q40 | Q | 1.00 | 1.00 | 1.00 |
| Q40 | R | 1.89 | 1.48 | 0.61 |
| Q40 | S | 1.57 | 1.65 | 0.87 |
| Q40 | T | 2.01 | 1.81 | 0.75 |
| Q40 | W | 2.39 | 2.59 | 0.54 |
| Q40 | Y | 1.83 | 2.02 | 0.65 |
| Q41 | A | 1.03 | 2.58 | 0.73 |
| Q41 | G | 0.97 | 1.09 | 0.77 |
| Q41 | H | 1.12 | 1.14 | 0.89 |
| Q41 | K | 1.38 | 1.61 | 0.70 |
| Q41 | L | 1.00 | 1.92 | 0.79 |
| Q41 | P | 0.21 | 0.66 | 0.45 |
| Q41 | Q | 1.00 | 1.00 | 1.00 |
| Q41 | R | 1.19 | 1.27 | 0.74 |
| Q41 | S | 1.11 | 0.22 | 0.92 |
| Q41 | V | 1.07 | −0.05 | 0.90 |
| Q41 | W | 1.14 | 0.88 | 0.71 |
| Q41 | Y | 1.09 | 0.70 | 0.82 |
| L42 | C | 0.76 | 1.43 | 0.68 |
| L42 | D | −0.14 | −0.17 | −0.02 |
| L42 | F | 1.07 | 1.02 | 0.48 |
| L42 | G | 1.17 | 0.76 | 0.50 |
| L42 | H | 1.92 | −0.33 | 0.15 |
| L42 | I | 0.97 | 0.66 | 0.83 |
| L42 | K | 2.46 | 1.41 | 0.13 |
| L42 | L | 1.00 | 1.00 | 1.00 |
| L42 | M | 0.78 | 0.74 | 0.95 |
| L42 | P | 0.71 | 1.34 | 0.23 |
| L42 | Q | 0.57 | 0.28 | 0.40 |
| L42 | R | 1.38 | 0.64 | 0.15 |
| L42 | S | 0.97 | 0.45 | 0.46 |
| L42 | T | 1.08 | −0.04 | 0.41 |
| L42 | V | 0.91 | 0.73 | 0.74 |
| L42 | W | 2.06 | −0.70 | 0.14 |
| G43 | A | 1.49 | 1.07 | 0.45 |
| G43 | C | 1.48 | 0.73 | 0.36 |
| G43 | E | 1.25 | 1.88 | 0.66 |
| G43 | G | 1.00 | 1.00 | 1.00 |
| G43 | H | 1.17 | 0.96 | 0.63 |
| G43 | I | 0.94 | 0.77 | 0.42 |
| G43 | K | 1.42 | 0.86 | 0.65 |
| G43 | L | 1.22 | 1.82 | 0.42 |
| G43 | M | 1.37 | 0.88 | 0.28 |
| G43 | P | 1.08 | 0.31 | 0.65 |
| G43 | Q | 0.91 | 0.48 | 0.63 |
| G43 | R | 1.22 | 0.59 | 0.57 |
| G43 | S | 1.18 | 0.23 | 0.79 |
| G43 | V | 0.93 | 0.33 | 0.44 |
| G43 | Y | 1.26 | 0.94 | 0.36 |
| A44 | A | 1.00 | 1.00 | 1.00 |
| A44 | C | 1.80 | 1.92 | 0.46 |
| A44 | D | −0.17 | −0.11 | −0.01 |
| A44 | E | −0.17 | 0.03 | 0.10 |
| A44 | F | 2.84 | 0.80 | 0.99 |
| A44 | H | −0.17 | −0.11 | −0.01 |
| A44 | L | 1.61 | 0.99 | 0.87 |
| A44 | M | 1.20 | 0.98 | 0.71 |
| A44 | P | −0.17 | −0.11 | −0.01 |
| A44 | R | 0.29 | −2.17 | 0.08 |
| A44 | S | 0.52 | −0.92 | 0.16 |
| A44 | T | 0.30 | −1.11 | 0.14 |
| A44 | V | 2.13 | 0.50 | 0.94 |
| A44 | W | 1.40 | 0.85 | 0.61 |
| A44 | Y | 0.30 | −0.23 | 0.10 |
| D45 | A | 1.04 | 0.84 | 0.99 |
| D45 | C | 0.83 | 0.84 | 0.48 |
| D45 | D | 1.00 | 1.00 | 1.00 |
| D45 | F | 1.11 | 1.04 | 0.66 |

TABLE 10-12-continued

| Wild-Type Res./Pos. | Mut. | PAF PI | PAD PI | Prot. PI |
|---|---|---|---|---|
| | | Performance Indices | | |
| D45 | G | 1.13 | 0.84 | 0.94 |
| D45 | H | 1.13 | 0.78 | 0.70 |
| D45 | K | 1.34 | 0.87 | 0.86 |
| D45 | L | 1.05 | 0.78 | 0.55 |
| D45 | M | 0.86 | 0.78 | 0.88 |
| D45 | P | 0.75 | 0.53 | 0.72 |
| D45 | Q | 1.04 | 0.57 | 0.81 |
| D45 | R | 1.16 | 0.49 | 0.72 |
| D45 | S | 1.13 | 0.38 | 0.95 |
| D45 | T | 1.27 | 0.44 | 0.86 |
| D45 | V | 1.05 | 0.50 | 0.70 |
| D45 | W | 1.15 | 0.58 | 0.54 |
| F46 | A | 0.92 | 1.25 | 1.05 |
| F46 | C | 0.84 | 1.16 | 1.01 |
| F46 | D | 1.17 | 1.39 | 0.54 |
| F46 | E | 1.25 | 1.31 | 0.38 |
| F46 | F | 1.00 | 1.00 | 1.00 |
| F46 | G | 1.02 | 0.94 | 0.61 |
| F46 | H | −0.13 | −0.13 | −0.01 |
| F46 | I | 0.90 | 0.88 | 0.91 |
| F46 | K | 1.00 | 1.46 | 0.48 |
| F46 | L | 0.78 | 1.54 | 0.74 |
| F46 | M | 0.78 | 1.42 | 0.81 |
| F46 | P | 0.64 | 1.50 | 0.26 |
| F46 | S | 0.73 | 0.66 | 0.72 |
| F46 | T | 0.86 | 0.43 | 0.79 |
| F46 | V | 0.82 | 0.79 | 0.89 |
| F46 | W | 0.94 | 0.63 | 0.91 |
| E47 | A | 0.95 | 0.76 | 0.84 |
| E47 | C | 0.83 | 0.77 | 0.99 |
| E47 | D | 0.99 | 0.98 | 0.97 |
| E47 | E | 1.00 | 1.00 | 1.00 |
| E47 | F | 1.09 | 0.76 | 0.96 |
| E47 | G | 1.20 | 1.10 | 0.76 |
| E47 | H | 1.27 | 0.99 | 0.93 |
| E47 | I | 1.03 | 1.15 | 1.02 |
| E47 | K | 1.19 | 1.06 | 0.89 |
| E47 | L | 1.00 | 1.02 | 0.96 |
| E47 | M | 0.90 | 0.70 | 0.84 |
| E47 | N | 0.91 | 0.63 | 0.99 |
| E47 | P | 1.36 | 0.36 | 0.49 |
| E47 | R | 2.45 | 0.62 | 0.75 |
| E47 | S | 1.28 | 0.63 | 0.83 |
| E47 | T | 1.96 | 0.84 | 0.98 |
| V48 | A | 0.60 | 1.63 | 0.47 |
| V48 | C | 0.83 | 2.25 | 0.91 |
| V48 | E | 0.02 | 0.99 | 0.18 |
| V48 | F | 0.67 | 1.42 | 0.57 |
| V48 | G | 0.61 | 0.87 | 0.25 |
| V48 | L | 0.92 | 2.29 | 0.91 |
| V48 | M | 0.85 | 1.79 | 0.71 |
| V48 | N | −0.15 | 0.98 | 0.23 |
| V48 | P | 0.21 | 3.08 | 0.34 |
| V48 | Q | 0.19 | 1.39 | 0.32 |
| V48 | R | 0.76 | −1.17 | 0.15 |
| V48 | S | 0.65 | 0.42 | 0.40 |
| V48 | V | 1.00 | 1.00 | 1.00 |
| V48 | W | −0.15 | −0.19 | −0.02 |
| I49 | A | 0.92 | 1.87 | 0.58 |
| I49 | E | 1.02 | 0.88 | 0.75 |
| I49 | G | 1.34 | 1.12 | 0.28 |
| I49 | H | 1.27 | 0.74 | 0.77 |
| I49 | I | 1.00 | 1.00 | 1.00 |
| I49 | K | 1.23 | 1.26 | 0.72 |
| I49 | L | 1.14 | 1.03 | 0.93 |
| I49 | M | 1.01 | 1.02 | 0.69 |
| I49 | P | 0.47 | 0.16 | 0.29 |
| I49 | R | 1.05 | 0.29 | 0.56 |
| I49 | S | 1.24 | 0.79 | 0.70 |
| I49 | V | 1.20 | 0.97 | 0.94 |
| I49 | W | 0.70 | 0.68 | 0.64 |
| I49 | Y | 1.07 | 1.02 | 0.82 |
| E50 | A | 1.12 | 1.23 | 0.58 |
| E50 | D | 0.78 | 1.22 | 0.80 |
| E50 | E | 1.00 | 1.00 | 1.00 |

TABLE 10-12-continued

| Wild-Type Res./Pos. | Mut. | PAF PI | PAD PI | Prot. PI |
|---|---|---|---|---|
| | | Performance Indices | | |
| E50 | G | 0.93 | 1.11 | 0.60 |
| E50 | I | 0.84 | 0.58 | 0.67 |
| E50 | L | 1.19 | 0.97 | 0.41 |
| E50 | M | 1.18 | 1.04 | 0.38 |
| E50 | P | 0.85 | 1.02 | 0.71 |
| E50 | Q | 0.98 | 0.91 | 0.70 |
| E50 | R | 0.46 | −0.77 | 0.20 |
| E50 | S | 0.87 | 0.65 | 0.76 |
| E50 | V | 1.00 | 0.43 | 0.81 |
| E50 | W | 0.75 | 0.14 | 0.19 |
| E51 | A | 1.28 | 2.72 | 0.74 |
| E51 | D | 0.66 | 1.28 | 0.91 |
| E51 | E | 1.00 | 1.00 | 1.00 |
| E51 | G | 1.22 | 1.34 | 0.84 |
| E51 | I | 1.07 | 0.04 | 0.52 |
| E51 | K | 0.38 | 2.00 | 0.36 |
| E51 | L | 1.11 | 0.93 | 0.57 |
| E51 | M | 0.40 | 1.20 | 0.84 |
| E51 | P | −0.12 | −0.39 | −0.02 |
| E51 | Q | 0.98 | 0.76 | 0.84 |
| E51 | R | 0.35 | −0.97 | 0.29 |
| E51 | T | 1.18 | 1.17 | 0.48 |
| E51 | V | 1.47 | 0.37 | 0.70 |
| E51 | W | 0.44 | 0.17 | 0.22 |
| G52 | A | 0.54 | 0.79 | 0.90 |
| G52 | E | −0.12 | 0.55 | 0.41 |
| G52 | F | −0.12 | −0.08 | 0.52 |
| G52 | G | 1.00 | 1.00 | 1.00 |
| G52 | H | 0.18 | −0.60 | 0.49 |
| G52 | I | 0.10 | 0.07 | 0.80 |
| G52 | L | 0.17 | 0.24 | 0.58 |
| G52 | M | 0.05 | −0.64 | 0.56 |
| G52 | P | −0.12 | 0.24 | 0.76 |
| G52 | Q | −0.12 | 0.28 | 0.52 |
| G52 | R | −0.12 | 0.35 | 0.18 |
| G52 | S | 0.13 | −0.18 | 0.83 |
| G52 | T | 0.10 | −0.17 | 0.76 |
| G52 | V | 0.10 | −0.16 | 0.86 |
| G52 | W | 0.92 | 2.47 | 0.13 |
| L53 | D | 0.01 | 0.01 | 0.72 |
| L53 | E | 0.88 | 0.19 | 0.77 |
| L53 | G | 1.32 | 0.33 | 0.80 |
| L53 | H | 5.05 | 1.70 | 0.27 |
| L53 | I | 0.55 | 0.66 | 0.88 |
| L53 | K | 0.89 | 0.24 | 0.70 |
| L53 | L | 1.00 | 1.00 | 1.00 |
| L53 | P | −0.11 | −0.64 | 0.07 |
| L53 | Q | 1.48 | 0.72 | 0.89 |
| L53 | R | 0.20 | −0.02 | 0.66 |
| L53 | S | 1.16 | 0.26 | 0.95 |
| L53 | T | 1.02 | 0.84 | 0.75 |
| L53 | V | 0.52 | 0.65 | 0.88 |
| L53 | W | 0.02 | −0.07 | 0.77 |
| S54 | A | 3.46 | 1.41 | 1.33 |
| S54 | C | 1.26 | 0.88 | 1.21 |
| S54 | D | −0.17 | 0.65 | 1.08 |
| S54 | E | −0.17 | 0.30 | 1.16 |
| S54 | F | 0.74 | −0.14 | 0.91 |
| S54 | G | 1.43 | 0.17 | 0.93 |
| S54 | H | −0.17 | 0.00 | 1.06 |
| S54 | I | 4.78 | 0.12 | 0.94 |
| S54 | K | 1.44 | 0.08 | 0.78 |
| S54 | L | 2.02 | 0.26 | 0.59 |
| S54 | M | 0.01 | 0.48 | 1.01 |
| S54 | N | 0.29 | 1.29 | 1.01 |
| S54 | P | 5.20 | 1.30 | 0.98 |
| S54 | Q | 1.03 | 0.53 | 0.99 |
| S54 | R | 3.38 | 0.35 | 0.84 |
| S54 | S | 1.00 | 1.00 | 1.00 |
| S54 | T | 1.46 | 0.33 | 0.88 |
| S54 | V | 4.72 | 0.29 | 0.95 |
| S54 | W | 0.11 | −0.07 | 0.83 |
| S54 | Y | 0.37 | 0.12 | 0.89 |
| A55 | A | −0.11 | −0.15 | −0.01 |
| A55 | C | 0.14 | 1.26 | 0.98 |

TABLE 10-12-continued

Performance Indices

| Wild-Type Res./Pos. | Mut. | PAF PI | PAD PI | Prot. PI |
|---|---|---|---|---|
| A55 | G | 1.69 | 0.73 | 0.98 |
| A55 | H | 0.04 | 0.92 | 0.93 |
| A55 | I | 0.34 | -0.43 | 0.80 |
| A55 | K | 0.52 | 1.08 | 0.68 |
| A55 | L | 0.11 | 0.87 | 0.81 |
| A55 | N | 0.34 | 1.05 | 1.12 |
| A55 | P | -0.11 | -0.01 | 0.84 |
| A55 | R | 0.56 | 0.25 | 0.99 |
| A55 | S | 0.76 | 0.87 | 1.08 |
| A55 | T | 1.69 | 0.42 | 0.91 |
| A55 | V | 0.49 | -0.51 | 0.96 |
| A55 | W | 0.00 | -0.05 | 0.88 |
| A55 | Y | 0.00 | 0.18 | 0.94 |
| R56 | A | 0.22 | 0.69 | 0.85 |
| R56 | C | 0.45 | -0.02 | 0.93 |
| R56 | E | -0.12 | -0.04 | 0.16 |
| R56 | G | 0.30 | -0.59 | 0.56 |
| R56 | H | -0.12 | -0.37 | -0.02 |
| R56 | K | -0.12 | -0.37 | -0.02 |
| R56 | L | 0.05 | 0.24 | 0.87 |
| R56 | N | 0.18 | 0.27 | 0.31 |
| R56 | P | -0.12 | -0.37 | -0.02 |
| R56 | Q | 0.01 | -0.01 | 1.02 |
| R56 | R | 1.00 | 1.00 | 1.00 |
| R56 | S | 0.39 | 0.12 | 0.55 |
| R56 | T | 0.10 | -0.37 | 0.85 |
| R56 | W | -0.12 | -0.37 | -0.02 |
| R56 | Y | -0.12 | -0.37 | -0.02 |
| T57 | A | 0.60 | 0.65 | 0.59 |
| T57 | C | 0.60 | 0.40 | 0.85 |
| T57 | G | 0.92 | 1.05 | 0.53 |
| T57 | H | 0.83 | 0.61 | 0.23 |
| T57 | I | 1.19 | 0.87 | 0.65 |
| T57 | L | 0.63 | 0.76 | 0.95 |
| T57 | N | 0.89 | 0.25 | 0.69 |
| T57 | P | 0.33 | -0.87 | 0.13 |
| T57 | R | 1.61 | -0.66 | 0.14 |
| T57 | S | 1.63 | 1.01 | 0.88 |
| T57 | T | 1.00 | 1.00 | 1.00 |
| T57 | V | 1.28 | 0.87 | 0.84 |
| T57 | W | -0.08 | -0.10 | -0.01 |
| T57 | Y | 0.52 | 0.55 | 0.43 |
| T58 | A | 0.65 | 0.36 | 0.76 |
| T58 | E | -0.19 | -0.10 | -0.02 |
| T58 | G | -0.19 | -0.10 | -0.02 |
| T58 | H | 0.89 | 1.49 | 0.74 |
| T58 | K | -0.19 | -0.10 | -0.02 |
| T58 | L | 0.88 | 1.12 | 0.78 |
| T58 | M | 0.56 | 0.03 | 0.50 |
| T58 | P | -0.19 | -0.10 | -0.02 |
| T58 | R | -0.19 | -0.10 | -0.02 |
| T58 | S | 0.82 | 0.96 | 0.90 |
| T58 | T | 1.00 | 1.00 | 1.00 |
| T58 | V | 0.56 | 0.96 | 1.13 |
| T58 | W | -0.19 | -0.10 | -0.02 |
| T58 | Y | -0.19 | -0.10 | -0.02 |
| N59 | A | 0.35 | 10.44 | 0.73 |
| N59 | C | 0.40 | 11.23 | 0.78 |
| N59 | D | 0.52 | 11.72 | 0.67 |
| N59 | E | 0.66 | 9.88 | 0.38 |
| N59 | F | 0.82 | 10.23 | 0.57 |
| N59 | G | 0.88 | 10.00 | 0.66 |
| N59 | K | 0.89 | 8.21 | 0.31 |
| N59 | L | 0.88 | 14.74 | 0.32 |
| N59 | M | 0.42 | -1.42 | 0.72 |
| N59 | N | 1.00 | 1.00 | 1.00 |
| N59 | P | 0.12 | -55.11 | 0.14 |
| N59 | Q | 1.02 | 1.86 | 0.73 |
| N59 | R | 1.09 | -11.28 | 0.39 |
| N59 | S | 1.06 | 7.32 | 0.74 |
| N59 | T | 1.07 | 5.63 | 0.56 |
| N59 | V | 0.81 | 9.97 | 0.96 |
| N59 | W | 1.13 | 12.80 | 0.59 |
| N59 | Y | 0.80 | 11.14 | 0.61 |
| I60 | A | 0.81 | 0.79 | 1.20 |
| I60 | C | 0.69 | 0.67 | 0.97 |
| I60 | D | 0.83 | 0.66 | 0.56 |
| I60 | E | 0.87 | 0.92 | 0.83 |
| I60 | G | 1.00 | 1.04 | 0.86 |
| I60 | H | 1.02 | 1.07 | 0.96 |
| I60 | I | 1.00 | 1.00 | 1.00 |
| I60 | K | 0.99 | 0.96 | 0.73 |
| I60 | L | 0.95 | 0.91 | 1.02 |
| I60 | M | 0.96 | 0.68 | 1.14 |
| I60 | P | 0.23 | 0.32 | 0.31 |
| I60 | R | 1.00 | 0.81 | 0.79 |
| I60 | S | 0.78 | 1.00 | 0.92 |
| I60 | V | 0.87 | 1.06 | 1.06 |
| I60 | Y | 0.78 | 1.19 | 0.89 |
| D61 | A | 0.70 | 0.71 | 1.41 |
| D61 | C | 0.79 | 0.85 | 0.92 |
| D61 | D | 1.00 | 1.00 | 1.00 |
| D61 | F | 1.01 | 0.70 | 0.61 |
| D61 | G | 0.81 | 1.25 | 0.84 |
| D61 | H | 1.44 | 1.67 | 0.97 |
| D61 | I | 1.08 | 1.66 | 0.98 |
| D61 | K | 0.92 | 1.72 | 0.97 |
| D61 | L | 0.80 | 1.20 | 1.00 |
| D61 | N | 0.79 | 1.00 | 1.12 |
| D61 | P | 0.83 | 1.13 | 0.97 |
| D61 | Q | 0.89 | 1.16 | 1.02 |
| D61 | R | 1.11 | 1.59 | 0.69 |
| D61 | S | 1.26 | 1.35 | 0.97 |
| D61 | V | 0.95 | 0.97 | 1.10 |
| D61 | Y | 0.84 | 0.95 | 1.03 |
| D62 | A | -0.24 | 0.11 | 1.06 |
| D62 | C | 0.52 | 0.49 | 0.96 |
| D62 | E | 1.02 | 0.60 | 0.93 |
| D62 | G | 0.28 | -0.21 | 0.86 |
| D62 | H | 0.61 | -0.01 | 0.89 |
| D62 | I | 0.72 | -0.25 | 0.92 |
| D62 | L | 0.51 | -0.37 | 0.95 |
| D62 | M | 0.03 | -0.24 | 1.06 |
| D62 | P | -0.24 | -0.55 | 0.69 |
| D62 | Q | -0.24 | -0.35 | 0.86 |
| D62 | R | 0.12 | -0.81 | 0.62 |
| D62 | S | 0.57 | -0.10 | 0.88 |
| D62 | T | 0.76 | -0.41 | 0.76 |
| D62 | V | 0.62 | -0.26 | 0.87 |
| D62 | W | 0.58 | -0.45 | 0.79 |
| P63 | A | 1.35 | 0.60 | 1.06 |
| P63 | F | 1.25 | 0.93 | 0.97 |
| P63 | G | 1.71 | 1.22 | 1.00 |
| P63 | K | 1.40 | 1.02 | 0.99 |
| P63 | L | 1.15 | 1.23 | 0.84 |
| P63 | M | 1.46 | 0.91 | 1.09 |
| P63 | Q | 1.09 | 1.05 | 1.08 |
| P63 | R | 1.31 | 0.80 | 1.02 |
| P63 | S | 1.42 | 0.90 | 1.17 |
| P63 | T | 1.50 | 1.32 | 1.02 |
| P63 | V | 1.31 | 1.04 | 1.06 |
| P63 | W | 1.35 | 1.11 | 0.86 |
| P63 | Y | 1.35 | 0.95 | 1.12 |
| T64 | A | 0.96 | 1.20 | 0.97 |
| T64 | C | 0.78 | 0.88 | 1.05 |
| T64 | D | 0.87 | 0.64 | 0.81 |
| T64 | G | 1.23 | 1.08 | 1.00 |
| T64 | H | 0.89 | 0.96 | 0.90 |
| T64 | L | 0.63 | 1.22 | 0.93 |
| T64 | M | 0.68 | 1.09 | 1.07 |
| T64 | N | 0.69 | 0.98 | 0.91 |
| T64 | P | 0.76 | 0.94 | 0.61 |
| T64 | Q | 0.76 | 0.87 | 1.13 |
| T64 | R | 0.15 | 0.11 | 1.05 |
| T64 | S | 1.11 | 0.99 | 1.03 |
| T64 | T | 1.00 | 1.00 | 1.00 |
| T64 | W | 0.71 | 0.69 | 0.72 |
| D65 | A | 1.31 | 0.72 | 0.72 |
| D65 | D | 1.00 | 1.00 | 1.00 |
| D65 | G | 0.80 | 0.52 | 0.88 |

TABLE 10-12-continued

Performance Indices

| Wild-Type Res./Pos. | Mut. | PAF PI | PAD PI | Prot. PI |
|---|---|---|---|---|
| D65 | H | 1.10 | 0.40 | 0.71 |
| D65 | I | 0.53 | 0.62 | 0.46 |
| D65 | P | −0.33 | 0.42 | 0.08 |
| D65 | R | 0.41 | 0.22 | 0.84 |
| D65 | S | 1.17 | 0.47 | 0.76 |
| D65 | T | 0.90 | 0.50 | 0.68 |
| D65 | V | 0.88 | 0.20 | 0.64 |
| D65 | W | 0.77 | 0.50 | 0.65 |
| D65 | Y | 0.83 | 0.42 | 0.64 |
| P66 | A | 0.50 | 0.56 | 1.03 |
| P66 | C | 0.51 | 0.52 | 1.51 |
| P66 | D | 1.00 | 0.72 | 0.90 |
| P66 | F | 0.95 | 0.67 | 1.02 |
| P66 | G | 1.50 | 0.44 | 1.78 |
| P66 | H | 1.59 | 0.95 | 1.23 |
| P66 | I | 1.59 | 0.84 | 1.51 |
| P66 | L | 1.14 | 0.99 | 0.92 |
| P66 | N | 1.12 | 0.38 | 1.62 |
| P66 | P | −0.09 | −0.11 | −0.01 |
| P66 | Q | 1.46 | 0.42 | 1.91 |
| P66 | R | 1.85 | 0.51 | 1.26 |
| P66 | S | 1.39 | 1.02 | 0.98 |
| P66 | T | 1.41 | 1.10 | 0.72 |
| P66 | V | 1.83 | 0.89 | 1.12 |
| P66 | Y | 1.33 | 0.70 | 1.08 |
| R67 | A | −0.20 | 0.22 | 1.39 |
| R67 | E | 1.04 | 0.11 | 0.85 |
| R67 | F | 1.26 | 0.01 | 1.01 |
| R67 | G | 1.39 | 0.41 | 0.81 |
| R67 | K | 0.91 | 0.99 | 0.76 |
| R67 | L | 1.20 | 0.16 | 1.46 |
| R67 | N | 1.58 | 0.33 | 1.00 |
| R67 | P | 1.01 | 0.04 | 1.04 |
| R67 | Q | 1.16 | 0.13 | 1.60 |
| R67 | R | 1.00 | 1.00 | 1.00 |
| R67 | T | 1.28 | 0.32 | 0.76 |
| R67 | V | 0.89 | 0.12 | 1.24 |
| R67 | W | 1.07 | 0.02 | 0.95 |
| L68 | A | 0.59 | −0.11 | 1.07 |
| L68 | C | 0.76 | 0.06 | 0.85 |
| L68 | D | −0.16 | 0.44 | 0.55 |
| L68 | E | 1.44 | 0.13 | 0.87 |
| L68 | F | 0.70 | 0.25 | 1.00 |
| L68 | G | 1.09 | −0.08 | 1.00 |
| L68 | H | 1.05 | 0.22 | 0.89 |
| L68 | I | 1.13 | 0.73 | 0.86 |
| L68 | L | 1.00 | 1.00 | 1.00 |
| L68 | M | 0.59 | 0.03 | 0.99 |
| L68 | N | 0.51 | 0.10 | 0.95 |
| L68 | P | 0.29 | 0.35 | 0.82 |
| L68 | Q | 0.50 | 0.25 | 0.90 |
| L68 | R | 0.19 | 0.47 | 0.75 |
| L68 | S | 0.99 | 0.07 | 0.93 |
| L68 | T | 1.03 | 0.32 | 0.92 |
| L68 | V | 1.09 | 0.51 | 1.01 |
| L68 | W | 1.21 | 0.56 | 0.88 |
| L68 | Y | 0.71 | 0.45 | 0.97 |
| N69 | A | 0.92 | 1.13 | 0.93 |
| N69 | C | 1.05 | 1.20 | 1.18 |
| N69 | D | 0.90 | 1.11 | 1.05 |
| N69 | G | 1.20 | 0.98 | 1.06 |
| N69 | H | 1.36 | 1.52 | 0.73 |
| N69 | I | 1.47 | 1.75 | 0.69 |
| N69 | K | 1.72 | 1.59 | 0.84 |
| N69 | L | 1.30 | 1.20 | 0.36 |
| N69 | N | 1.00 | 1.00 | 1.00 |
| N69 | P | 1.00 | 0.59 | 0.66 |
| N69 | Q | 1.07 | 1.14 | 0.74 |
| N69 | R | 1.49 | 0.83 | 0.84 |
| N69 | S | 1.21 | 1.42 | 1.03 |
| N69 | T | 1.35 | 1.43 | 0.87 |
| N69 | V | 1.99 | 1.73 | 0.87 |
| N69 | W | 1.05 | 0.55 | 0.36 |
| N69 | Y | 0.88 | 0.17 | 0.44 |
| G70 | A | 0.85 | 1.41 | 1.08 |
| G70 | C | 0.12 | −0.90 | 0.40 |
| G70 | E | −0.16 | 0.33 | 0.28 |
| G70 | F | 0.00 | −0.36 | 0.21 |
| G70 | G | 1.00 | 1.00 | 1.00 |
| G70 | H | 0.04 | 1.90 | 0.26 |
| G70 | I | 0.04 | 0.27 | 0.33 |
| G70 | K | 0.03 | −0.80 | 0.26 |
| G70 | L | 0.03 | 1.01 | 0.30 |
| G70 | M | 0.62 | −0.72 | 0.29 |
| G70 | N | 0.02 | −0.76 | 0.37 |
| G70 | P | 0.16 | −0.58 | 0.29 |
| G70 | Q | 0.02 | −0.83 | 0.36 |
| G70 | R | 0.08 | −1.84 | 0.25 |
| G70 | S | 0.69 | 0.64 | 0.88 |
| G70 | T | 0.27 | −0.10 | 0.45 |
| G70 | V | 0.16 | −0.52 | 0.34 |
| G70 | Y | 0.08 | −0.33 | 0.38 |
| A71 | A | 1.00 | 1.00 | 1.00 |
| A71 | C | 1.01 | 0.99 | 0.85 |
| A71 | D | 0.70 | 0.65 | 0.68 |
| A71 | E | 1.45 | 0.81 | 0.83 |
| A71 | F | 1.13 | 0.99 | 0.75 |
| A71 | G | 1.59 | 0.68 | 0.85 |
| A71 | H | 1.70 | 0.78 | 0.75 |
| A71 | I | 1.51 | 0.79 | 0.81 |
| A71 | K | 1.44 | 1.01 | 0.76 |
| A71 | L | 1.23 | 0.84 | 0.85 |
| A71 | M | 0.98 | 1.11 | 0.81 |
| A71 | N | 1.23 | 0.61 | 0.77 |
| A71 | P | −0.14 | −0.05 | 0.46 |
| A71 | R | 1.40 | 0.77 | 0.71 |
| A71 | S | 1.75 | 0.69 | 0.84 |
| A71 | T | 1.70 | 0.79 | 0.83 |
| S72 | A | 0.55 | 3.52 | 1.06 |
| S72 | C | 0.56 | 2.18 | 0.96 |
| S72 | D | 0.40 | 0.80 | 0.90 |
| S72 | E | 0.61 | 0.93 | 0.99 |
| S72 | F | 0.94 | 1.15 | 0.80 |
| S72 | G | 1.20 | 1.76 | 0.87 |
| S72 | H | 1.21 | 2.48 | 0.82 |
| S72 | L | 1.26 | 0.70 | 1.07 |
| S72 | M | 0.36 | 2.13 | 0.94 |
| S72 | N | 0.42 | 2.85 | 0.99 |
| S72 | P | −0.25 | 0.56 | 0.63 |
| S72 | Q | 0.62 | 0.66 | 0.98 |
| S72 | R | 0.86 | 0.74 | 0.87 |
| S72 | S | 1.00 | 1.00 | 1.00 |
| S72 | T | 1.10 | 0.97 | 0.88 |
| S72 | V | 1.08 | 0.83 | 0.90 |
| S72 | W | 0.98 | 0.34 | 0.92 |
| S72 | Y | 1.07 | 0.07 | 1.03 |
| Y73 | A | −0.10 | 1.40 | 0.82 |
| Y73 | C | −0.10 | 1.20 | 1.18 |
| Y73 | D | 0.13 | 0.80 | 1.09 |
| Y73 | G | 0.71 | 0.51 | 0.95 |
| Y73 | H | 0.67 | 0.52 | 0.96 |
| Y73 | I | 0.82 | 0.64 | 0.97 |
| Y73 | K | 1.07 | 0.94 | 0.95 |
| Y73 | L | 0.98 | 0.50 | 1.03 |
| Y73 | M | −0.10 | 1.13 | 1.05 |
| Y73 | N | 0.56 | 0.76 | 1.25 |
| Y73 | P | 0.64 | −0.54 | 0.42 |
| Y73 | Q | 1.23 | 0.87 | 1.20 |
| Y73 | R | 1.26 | 0.26 | 0.96 |
| Y73 | S | 1.17 | 0.68 | 0.77 |
| Y73 | V | 0.88 | 0.74 | 1.08 |
| Y73 | Y | −0.10 | −0.10 | −0.02 |
| L74 | A | 0.07 | 2.90 | 1.01 |
| L74 | D | −0.18 | −0.18 | −0.03 |
| L74 | F | 0.99 | 1.13 | 0.58 |
| L74 | G | 1.95 | 0.57 | 0.18 |
| L74 | H | −0.18 | −0.18 | −0.03 |
| L74 | I | 0.86 | 0.64 | 1.45 |
| L74 | L | 1.00 | 1.00 | 1.00 |
| L74 | M | 0.15 | 1.21 | 0.79 |

TABLE 10-12-continued

Performance Indices

| Wild-Type Res./Pos. | Mut. | PAF PI | PAD PI | Prot. PI |
|---|---|---|---|---|
| L74 | P | −0.18 | −0.18 | −0.03 |
| L74 | Q | −0.18 | −0.18 | −0.03 |
| L74 | R | −0.18 | −0.18 | −0.03 |
| L74 | S | 2.72 | −1.52 | 0.25 |
| L74 | T | −0.18 | −0.18 | −0.03 |
| L74 | V | 0.90 | 0.61 | 1.18 |
| L74 | W | 1.38 | 0.67 | 0.50 |
| L74 | Y | 0.90 | 0.86 | 1.19 |
| P75 | C | 0.54 | 1.42 | 1.06 |
| P75 | D | 0.67 | 2.09 | 0.86 |
| P75 | E | 0.83 | 1.19 | 1.00 |
| P75 | G | 1.16 | 0.93 | 0.81 |
| P75 | H | 1.05 | 0.86 | 0.89 |
| P75 | I | 0.69 | 0.74 | 0.78 |
| P75 | K | 0.60 | 0.88 | 0.91 |
| P75 | L | 0.44 | 1.19 | 1.02 |
| P75 | M | 0.36 | 0.30 | 1.22 |
| P75 | P | 1.00 | 1.00 | 1.00 |
| P75 | Q | 1.21 | 0.61 | 1.04 |
| P75 | R | 1.60 | 0.46 | 0.89 |
| P75 | S | 1.39 | 0.63 | 1.18 |
| P75 | T | 1.28 | 0.69 | 1.10 |
| P75 | V | 0.93 | 1.39 | 0.90 |
| P75 | W | 1.04 | 1.31 | 0.84 |
| P75 | Y | 0.69 | 1.32 | 1.08 |
| S76 | A | 0.38 | 1.11 | 0.60 |
| S76 | C | 0.39 | 1.06 | 0.67 |
| S76 | D | 0.41 | 1.94 | 0.49 |
| S76 | E | 0.47 | 2.09 | 0.58 |
| S76 | F | 0.44 | 0.46 | 0.68 |
| S76 | G | 0.64 | 2.15 | 0.69 |
| S76 | H | 0.85 | 1.11 | 0.79 |
| S76 | K | 0.59 | 1.53 | 0.32 |
| S76 | L | 0.74 | 4.70 | 0.27 |
| S76 | M | 0.49 | 1.61 | 0.45 |
| S76 | P | 1.23 | 1.20 | 0.67 |
| S76 | Q | 0.84 | 0.90 | 0.88 |
| S76 | S | 1.00 | 1.00 | 1.00 |
| S76 | T | 0.75 | 1.11 | 0.80 |
| S76 | V | 0.67 | 1.35 | 0.78 |
| S76 | W | 0.57 | −0.25 | 1.06 |
| S76 | Y | 0.31 | 0.18 | 0.75 |
| C77 | A | 0.83 | 0.91 | 1.20 |
| C77 | C | 1.00 | 1.00 | 1.00 |
| C77 | D | 0.92 | 1.05 | 0.45 |
| C77 | F | 0.25 | −0.61 | 0.75 |
| C77 | G | 1.01 | 0.18 | 0.53 |
| C77 | L | 0.98 | 0.73 | 1.44 |
| C77 | N | −0.13 | −0.06 | −0.04 |
| C77 | P | −0.13 | −0.06 | −0.04 |
| C77 | R | 0.70 | −1.02 | 0.34 |
| C77 | S | 0.95 | 0.76 | 1.19 |
| C77 | T | 1.12 | 1.03 | 1.18 |
| C77 | V | 1.05 | 0.80 | 1.33 |
| C77 | W | 0.39 | −0.24 | 0.73 |
| C77 | Y | 0.95 | −0.01 | 0.66 |
| L78 | A | −0.11 | −0.14 | −0.01 |
| L78 | C | 0.92 | 0.78 | 0.91 |
| L78 | E | 3.01 | −1.14 | 0.16 |
| L78 | G | 4.98 | 1.38 | 0.12 |
| L78 | H | 4.82 | 1.57 | 0.25 |
| L78 | I | 1.43 | 1.11 | 1.06 |
| L78 | L | 1.00 | 1.00 | 1.00 |
| L78 | M | 0.52 | 0.48 | 0.75 |
| L78 | N | 2.68 | −0.41 | 0.22 |
| L78 | P | −0.11 | −0.14 | −0.01 |
| L78 | Q | 1.73 | 0.52 | 0.46 |
| L78 | R | −0.11 | −0.14 | −0.01 |
| L78 | S | −0.11 | −0.14 | −0.01 |
| L78 | T | 1.87 | 1.10 | 0.47 |
| L78 | V | 1.53 | 0.83 | 1.04 |
| L78 | Y | 1.39 | 0.81 | 0.46 |
| A79 | A | −0.15 | −0.13 | −0.02 |
| A79 | C | 0.97 | 0.03 | 1.16 |
| A79 | E | 1.12 | 0.27 | 1.12 |
| A79 | F | −0.15 | −2.02 | 0.17 |
| A79 | G | 0.92 | 0.92 | 0.99 |
| A79 | H | 1.93 | −0.09 | 0.85 |
| A79 | I | 1.59 | 0.67 | 0.87 |
| A79 | L | 1.80 | 0.96 | 0.88 |
| A79 | M | 1.50 | 0.28 | 1.04 |
| A79 | N | 1.48 | 0.28 | 0.97 |
| A79 | P | 0.70 | 0.94 | 0.81 |
| A79 | Q | 1.47 | 0.27 | 1.05 |
| A79 | R | 1.47 | 0.32 | 1.02 |
| A79 | S | 0.82 | 0.78 | 1.09 |
| A79 | T | 1.17 | 0.60 | 0.90 |
| A79 | V | −0.15 | −0.13 | −0.02 |
| A79 | W | 1.27 | 0.53 | 0.46 |
| T80 | A | 1.00 | 1.11 | 0.90 |
| T80 | C | 1.31 | 1.15 | 0.91 |
| T80 | E | 0.07 | −0.16 | 1.02 |
| T80 | G | 1.16 | 1.50 | 0.81 |
| T80 | H | 0.21 | 0.05 | 0.66 |
| T80 | I | 0.50 | 0.15 | 0.78 |
| T80 | K | 0.15 | −0.32 | 0.74 |
| T80 | L | 0.15 | −0.11 | 0.68 |
| T80 | N | 0.53 | 0.53 | 0.97 |
| T80 | P | −0.11 | −0.05 | 0.55 |
| T80 | Q | 0.91 | 1.07 | 1.02 |
| T80 | R | 0.08 | −0.22 | 0.78 |
| T80 | S | 0.96 | 1.40 | 1.12 |
| T80 | T | 1.00 | 1.00 | 1.00 |
| T80 | V | 1.23 | 1.01 | 0.93 |
| T80 | W | 0.23 | −0.86 | 0.46 |
| T80 | Y | 0.15 | 0.11 | 0.69 |
| H81 | A | 1.15 | 1.45 | 0.98 |
| H81 | C | 1.13 | 1.09 | 0.92 |
| H81 | F | 1.10 | 0.90 | 0.87 |
| H81 | G | 1.17 | 0.80 | 0.94 |
| H81 | H | 1.00 | 1.00 | 1.00 |
| H81 | K | 1.52 | 0.56 | 0.31 |
| H81 | L | 1.23 | 1.03 | 0.93 |
| H81 | M | 0.94 | 1.54 | 0.82 |
| H81 | N | 1.17 | 1.00 | 0.82 |
| H81 | P | −0.10 | 0.72 | 0.42 |
| H81 | Q | 0.85 | 0.75 | 1.00 |
| H81 | R | 0.34 | −0.29 | 0.85 |
| H81 | S | 1.04 | 0.69 | 0.94 |
| H81 | V | 1.10 | 0.71 | 0.89 |
| H81 | W | 1.13 | 1.09 | 0.90 |
| H81 | Y | 0.77 | 0.14 | 0.76 |
| L82 | A | 0.62 | 0.98 | 1.00 |
| L82 | G | 1.38 | 0.31 | 1.24 |
| L82 | H | 1.33 | 0.47 | 0.95 |
| L82 | I | 1.17 | 0.51 | 0.58 |
| L82 | K | 1.19 | 0.51 | 1.03 |
| L82 | L | 1.00 | 1.00 | 1.00 |
| L82 | M | 0.65 | 1.06 | 1.07 |
| L82 | P | 1.46 | 0.52 | 1.11 |
| L82 | R | 1.34 | −0.18 | 1.15 |
| L82 | S | 1.15 | 0.00 | 1.13 |
| L82 | T | 1.18 | 0.38 | 0.97 |
| L82 | V | 1.02 | 0.19 | 1.14 |
| L82 | W | 0.27 | −0.46 | 0.93 |
| P83 | A | 0.36 | 2.36 | 0.66 |
| P83 | C | 0.53 | 1.01 | 0.81 |
| P83 | D | 0.75 | 0.83 | 0.92 |
| P83 | E | 0.84 | 1.26 | 0.92 |
| P83 | F | 0.76 | 0.99 | 0.69 |
| P83 | G | 1.31 | 0.68 | 1.01 |
| P83 | H | 1.27 | 0.61 | 0.93 |
| P83 | K | 1.37 | 1.16 | 0.88 |
| P83 | L | 0.04 | 0.21 | 0.19 |
| P83 | M | 0.58 | 1.88 | 0.71 |
| P83 | N | 0.70 | 1.10 | 0.90 |
| P83 | P | 1.00 | 1.00 | 1.00 |
| P83 | Q | 0.73 | 0.82 | 0.95 |
| P83 | R | 1.19 | 1.09 | 0.78 |
| P83 | S | 1.17 | 0.79 | 0.89 |

TABLE 10-12-continued

Performance Indices

| Wild-Type Res./Pos. | Mut. | PAF PI | PAD PI | Prot. PI |
|---|---|---|---|---|
| P83 | T | 0.86 | −0.02 | 0.62 |
| P83 | V | 0.78 | 0.19 | 0.72 |
| P83 | W | 0.98 | 0.62 | 0.69 |
| L84 | A | 0.45 | 0.45 | 0.76 |
| L84 | D | 0.19 | 0.85 | 0.48 |
| L84 | F | 0.72 | 1.01 | 0.74 |
| L84 | G | 0.77 | 1.01 | 0.53 |
| L84 | H | 1.01 | 0.99 | 0.66 |
| L84 | I | 0.90 | 0.87 | 0.99 |
| L84 | K | 1.10 | 0.79 | 0.59 |
| L84 | L | 1.00 | 1.00 | 1.00 |
| L84 | N | 0.54 | 0.67 | 0.86 |
| L84 | P | −0.12 | 0.43 | 0.58 |
| L84 | Q | 0.41 | 0.52 | 0.93 |
| L84 | R | 0.56 | 0.57 | 0.71 |
| L84 | S | 0.75 | 0.55 | 0.93 |
| L84 | T | 0.86 | 0.44 | 0.95 |
| L84 | V | 0.79 | 0.42 | 1.23 |
| L84 | W | 0.36 | −0.28 | 0.91 |
| D85 | A | 0.79 | 1.09 | 0.63 |
| D85 | C | 0.88 | 1.50 | 0.56 |
| D85 | D | 1.00 | 1.00 | 1.00 |
| D85 | E | 1.12 | 1.25 | 0.97 |
| D85 | F | 1.01 | 1.98 | 0.52 |
| D85 | G | 1.41 | 1.60 | 0.69 |
| D85 | H | 1.55 | 1.24 | 0.76 |
| D85 | I | 0.55 | 0.10 | 0.46 |
| D85 | L | 0.53 | 0.24 | 0.52 |
| D85 | N | 1.54 | 0.78 | 0.86 |
| D85 | P | 0.97 | 0.54 | 0.63 |
| D85 | Q | 3.09 | 0.99 | 0.82 |
| D85 | R | 2.38 | 1.03 | 0.66 |
| D85 | S | 2.28 | 0.68 | 0.93 |
| D85 | T | 1.33 | 0.71 | 0.77 |
| D85 | V | 0.61 | 0.25 | 0.65 |
| D85 | W | 0.87 | 0.34 | 0.72 |
| D85 | Y | 0.98 | 0.55 | 0.78 |
| L86 | A | 1.38 | 3.32 | 0.40 |
| L86 | C | 1.16 | 2.44 | 0.85 |
| L86 | E | 0.06 | −0.92 | 0.46 |
| L86 | F | −0.15 | −0.26 | −0.02 |
| L86 | G | 1.15 | 0.70 | 0.83 |
| L86 | H | 0.88 | −0.72 | 0.57 |
| L86 | L | 1.00 | 1.00 | 1.00 |
| L86 | P | −0.15 | 0.99 | 0.22 |
| L86 | Q | −0.15 | −2.60 | 3.66 |
| L86 | R | 0.43 | −4.46 | 0.26 |
| L86 | S | 0.78 | −0.36 | 0.78 |
| L86 | T | 0.96 | 0.28 | 0.75 |
| L86 | V | 0.92 | 0.12 | 0.93 |
| L86 | W | 0.67 | 0.08 | 0.78 |
| L86 | Y | 0.85 | 0.82 | 0.92 |
| V87 | A | 0.65 | 0.17 | 0.88 |
| V87 | C | 0.67 | 2.22 | 0.93 |
| V87 | D | −0.09 | −2.53 | 0.32 |
| V87 | F | 0.60 | 0.10 | 0.56 |
| V87 | G | 0.46 | −2.95 | 0.54 |
| V87 | K | 0.04 | −8.34 | 0.26 |
| V87 | L | 0.71 | 4.30 | 0.84 |
| V87 | M | 0.73 | 0.75 | 0.86 |
| V87 | P | 0.07 | 1.64 | 0.39 |
| V87 | R | 0.07 | −1.33 | 0.44 |
| V87 | S | 0.59 | −0.09 | 0.67 |
| V87 | T | 0.63 | 0.15 | 0.71 |
| V87 | V | 1.00 | 1.00 | 1.00 |
| V87 | Y | 0.33 | −1.24 | 0.42 |
| I88 | G | 1.01 | −2.63 | 0.27 |
| I88 | H | 1.20 | −6.25 | 0.21 |
| I88 | I | 1.00 | 1.00 | 1.00 |
| I88 | M | 0.24 | 1.09 | 0.86 |
| I88 | N | −0.14 | −0.55 | 0.29 |
| I88 | P | −0.14 | 3.51 | 0.18 |
| I88 | Q | 0.01 | −1.10 | 0.36 |
| I88 | R | −0.14 | −0.32 | −0.02 |
| I88 | T | 1.03 | −0.16 | 0.52 |
| I88 | Y | −0.14 | −0.32 | −0.02 |
| I89 | A | 0.55 | 1.83 | 0.63 |
| I89 | D | −0.10 | −0.14 | −0.02 |
| I89 | E | −0.10 | −2.05 | 0.24 |
| I89 | F | 0.68 | 0.75 | 0.90 |
| I89 | G | 0.64 | −3.84 | 0.29 |
| I89 | H | 1.00 | −1.01 | 0.33 |
| I89 | I | 1.00 | 1.00 | 1.00 |
| I89 | L | 0.87 | 1.22 | 1.07 |
| I89 | P | 0.38 | 1.91 | 0.30 |
| I89 | Q | 0.25 | −0.30 | 0.32 |
| I89 | R | −0.10 | −0.14 | −0.02 |
| I89 | S | 0.71 | −1.66 | 0.49 |
| I89 | T | 0.94 | 0.90 | 0.60 |
| I89 | V | 0.91 | 0.82 | 1.09 |
| I89 | W | 0.53 | −2.63 | 0.27 |
| M90 | A | 0.78 | 1.41 | 0.67 |
| M90 | C | 0.79 | 1.09 | 0.83 |
| M90 | D | −0.24 | 2.88 | 0.15 |
| M90 | E | −0.24 | 1.15 | 0.29 |
| M90 | G | 0.57 | −1.22 | 0.33 |
| M90 | I | 1.13 | 0.66 | 0.74 |
| M90 | L | 1.02 | 0.98 | 0.84 |
| M90 | M | 1.00 | 1.00 | 1.00 |
| M90 | P | −0.24 | −0.36 | 0.28 |
| M90 | Q | 0.68 | 0.77 | 0.71 |
| M90 | R | −0.24 | 0.36 | 0.23 |
| M90 | S | 1.06 | −0.17 | 0.56 |
| M90 | T | 1.27 | 0.15 | 0.59 |
| M90 | V | 1.08 | 0.08 | 0.62 |
| M90 | W | 0.79 | −4.04 | 0.21 |
| L91 | A | 0.57 | 1.45 | 0.81 |
| L91 | C | 0.67 | 1.27 | 0.87 |
| L91 | D | −0.12 | 1.47 | 0.12 |
| L91 | E | −0.12 | −0.51 | 0.13 |
| L91 | G | 1.21 | −0.58 | 0.17 |
| L91 | H | −0.12 | −0.13 | −0.01 |
| L91 | I | 0.98 | 1.05 | 0.89 |
| L91 | K | −0.12 | −0.13 | −0.01 |
| L91 | L | 1.00 | 1.00 | 1.00 |
| L91 | M | 0.28 | 0.88 | 0.80 |
| L91 | P | −0.12 | −0.13 | −0.01 |
| L91 | Q | 0.05 | −0.14 | 0.18 |
| L91 | R | −0.12 | −0.13 | −0.01 |
| L91 | S | 0.92 | 0.43 | 0.24 |
| L91 | T | 1.06 | −0.11 | 0.36 |
| L91 | V | 0.94 | 0.79 | 0.72 |
| L91 | W | −0.12 | −0.13 | −0.01 |
| L91 | Y | −0.12 | −0.13 | −0.01 |
| G92 | A | −0.10 | −0.18 | −0.02 |
| G92 | C | −0.10 | 2.05 | 0.18 |
| G92 | D | −0.10 | −0.18 | −0.02 |
| G92 | E | −0.10 | −2.31 | 0.21 |
| G92 | F | −0.10 | −3.24 | 0.17 |
| G92 | G | 1.00 | 1.00 | 1.00 |
| G92 | L | −0.10 | −0.18 | −0.02 |
| G92 | M | −0.10 | −0.18 | −0.02 |
| G92 | P | −0.10 | −0.18 | −0.02 |
| G92 | R | −0.10 | −0.18 | −0.02 |
| G92 | S | 1.26 | −2.96 | 0.21 |
| G92 | T | −0.10 | −0.18 | −0.02 |
| G92 | V | 1.49 | −3.03 | 0.20 |
| G92 | W | −0.10 | −0.18 | −0.02 |
| G92 | Y | −0.10 | −0.18 | −0.02 |
| T93 | A | 1.38 | 1.05 | 0.50 |
| T93 | C | 1.08 | 0.95 | 0.64 |
| T93 | D | −0.18 | 0.23 | 0.22 |
| T93 | F | 3.52 | 0.54 | 0.63 |
| T93 | P | −0.18 | −0.19 | −0.02 |
| T93 | Q | −0.18 | −6.75 | 2.03 |
| T93 | R | −0.18 | −0.19 | −0.02 |
| T93 | S | 0.89 | 0.49 | 0.89 |
| T93 | T | 1.00 | 1.00 | 1.00 |
| T93 | V | −0.18 | −0.19 | −0.02 |
| T93 | W | −0.18 | −0.19 | −0.02 |

TABLE 10-12-continued

Performance Indices

| Wild-Type Res./Pos. | Mut. | PAF PI | PAD PI | Prot. PI |
|---|---|---|---|---|
| T93 | Y | 5.26 | 0.03 | 0.77 |
| N94 | A | −0.45 | 0.74 | 0.96 |
| N94 | C | 0.01 | 0.07 | 0.94 |
| N94 | G | 0.15 | 0.53 | 0.76 |
| N94 | H | 0.11 | −0.94 | 0.77 |
| N94 | L | 0.61 | −0.18 | 0.49 |
| N94 | M | −0.45 | 0.03 | 0.94 |
| N94 | N | 1.00 | 1.00 | 1.00 |
| N94 | P | −0.45 | 0.79 | 0.40 |
| N94 | R | 0.10 | −8.20 | 0.19 |
| N94 | S | 0.10 | 0.88 | 0.84 |
| N94 | T | 0.25 | −1.43 | 0.66 |
| N94 | V | 0.15 | −0.39 | 0.65 |
| N94 | W | 0.10 | −1.20 | 0.69 |
| N94 | Y | 0.08 | 0.12 | 0.76 |
| D95 | A | −0.14 | −0.14 | −0.01 |
| D95 | C | −0.14 | −0.14 | −0.01 |
| D95 | D | 1.00 | 1.00 | 1.00 |
| D95 | E | 2.04 | 0.75 | 0.66 |
| D95 | G | −0.14 | −0.14 | −0.01 |
| D95 | H | −0.14 | −0.14 | −0.01 |
| D95 | K | −0.14 | −0.14 | −0.01 |
| D95 | L | −0.14 | −0.14 | −0.01 |
| D95 | N | −0.14 | −0.14 | −0.01 |
| D95 | Q | −0.14 | −0.14 | −0.01 |
| D95 | R | −0.14 | −0.14 | −0.01 |
| D95 | S | −0.14 | −0.14 | −0.01 |
| D95 | T | −0.14 | −0.14 | −0.01 |
| D95 | V | −0.14 | −0.14 | −0.01 |
| D95 | W | −0.14 | −0.14 | −0.01 |
| D95 | Y | −0.14 | −0.14 | −0.01 |
| T96 | A | 0.36 | 4.20 | 1.32 |
| T96 | C | 0.44 | 3.76 | 0.79 |
| T96 | F | 0.53 | 1.24 | 0.69 |
| T96 | G | 0.78 | 1.28 | 1.03 |
| T96 | I | 0.95 | −0.22 | 0.88 |
| T96 | L | 0.92 | 1.93 | 0.93 |
| T96 | M | 0.39 | 2.53 | 0.80 |
| T96 | P | −0.11 | 0.89 | 0.35 |
| T96 | R | 0.17 | 0.14 | 0.50 |
| T96 | S | 1.04 | 0.79 | 1.05 |
| T96 | T | 1.00 | 1.00 | 1.00 |
| T96 | V | 0.81 | 0.59 | 1.12 |
| T96 | W | 0.38 | −4.29 | 0.51 |
| T96 | Y | 0.38 | −3.73 | 0.59 |
| K97 | A | 0.01 | 0.23 | 1.11 |
| K97 | D | −0.23 | −0.17 | −0.01 |
| K97 | G | 0.84 | −0.64 | 0.39 |
| K97 | I | 0.74 | −0.55 | 0.47 |
| K97 | K | 1.00 | 1.00 | 1.00 |
| K97 | L | 0.38 | −0.28 | 0.30 |
| K97 | M | 0.02 | 0.22 | 0.95 |
| K97 | P | 0.16 | 0.27 | 0.36 |
| K97 | Q | 1.14 | 0.00 | 0.73 |
| K97 | R | 2.80 | 0.59 | 1.02 |
| K97 | S | 0.28 | −0.46 | 0.58 |
| K97 | T | 0.22 | −0.42 | 0.51 |
| K97 | V | 0.31 | −0.45 | 0.51 |
| K97 | W | 0.42 | −2.32 | 0.13 |
| K97 | Y | 0.29 | −0.65 | 0.38 |
| A98 | A | 1.00 | 1.00 | 1.00 |
| A98 | C | 1.30 | 1.42 | 1.00 |
| A98 | D | 1.11 | 2.19 | 0.81 |
| A98 | G | 1.57 | 0.56 | 0.97 |
| A98 | H | 2.09 | 0.92 | 0.82 |
| A98 | I | 2.05 | 0.65 | 0.72 |
| A98 | L | 2.22 | 1.47 | 0.71 |
| A98 | N | 1.24 | 1.40 | 1.01 |
| A98 | P | 1.10 | 1.26 | 0.90 |
| A98 | S | 1.73 | 0.65 | 1.17 |
| A98 | T | 1.72 | 0.27 | 1.03 |
| A98 | Y | 2.02 | 1.15 | 0.87 |
| Y99 | A | 0.66 | 0.82 | 1.29 |
| Y99 | G | 0.83 | 0.70 | 1.23 |
| Y99 | H | 0.77 | 0.59 | 1.30 |
| Y99 | I | 0.81 | 0.61 | 1.11 |
| Y99 | L | 0.66 | 0.86 | 1.39 |
| Y99 | P | 0.89 | 0.81 | 1.00 |
| Y99 | R | 0.61 | 0.29 | 0.97 |
| Y99 | S | 0.72 | 0.37 | 1.45 |
| Y99 | V | 0.61 | 0.31 | 1.28 |
| Y99 | W | 0.68 | 0.57 | 1.20 |
| Y99 | Y | 1.00 | 1.00 | 1.00 |
| F100 | A | 0.78 | 2.02 | 0.93 |
| F100 | C | 0.73 | 1.28 | 0.78 |
| F100 | D | 0.38 | −0.03 | 0.33 |
| F100 | E | 1.01 | 0.15 | 0.83 |
| F100 | F | 1.00 | 1.00 | 1.00 |
| F100 | K | 0.65 | −0.60 | 0.53 |
| F100 | M | 0.79 | 2.19 | 1.20 |
| F100 | N | 0.91 | 1.45 | 1.12 |
| F100 | S | 0.87 | 0.85 | 1.02 |
| F100 | T | 0.95 | 1.42 | 0.71 |
| F100 | W | 1.08 | −0.03 | 1.06 |
| R101 | C | 0.71 | 0.95 | 0.96 |
| R101 | D | 0.85 | 0.80 | 1.02 |
| R101 | F | 0.84 | 0.97 | 0.66 |
| R101 | I | 0.79 | 0.96 | 0.68 |
| R101 | K | 1.24 | 0.07 | 0.90 |
| R101 | L | 0.83 | 1.12 | 1.33 |
| R101 | N | 0.72 | 0.92 | 1.11 |
| R101 | P | 0.50 | 0.86 | 0.75 |
| R101 | Q | 0.86 | 0.11 | 1.03 |
| R101 | R | 1.00 | 1.00 | 1.00 |
| R101 | V | 0.74 | 0.44 | 0.90 |
| R101 | W | 0.95 | 0.00 | 0.89 |
| R101 | Y | 0.74 | 0.80 | 0.67 |
| R102 | A | 0.19 | 1.79 | 0.98 |
| R102 | C | 0.22 | 0.36 | 0.78 |
| R102 | D | 0.01 | 0.68 | 0.26 |
| R102 | F | 0.46 | 0.23 | 0.31 |
| R102 | G | 0.44 | 0.27 | 0.43 |
| R102 | L | 0.33 | 1.64 | 0.95 |
| R102 | P | −0.07 | 0.89 | 0.26 |
| R102 | Q | 0.67 | 1.19 | 1.09 |
| R102 | R | 1.00 | 1.00 | 1.00 |
| R102 | S | 0.46 | 0.96 | 0.98 |
| R102 | V | 0.28 | 0.61 | 0.80 |
| R102 | W | 0.29 | −1.03 | 0.34 |
| R102 | Y | 0.40 | 1.29 | 0.70 |
| T103 | A | 0.97 | −9.64 | 0.89 |
| T103 | C | 0.90 | −6.91 | 0.89 |
| T103 | F | 0.74 | −3.39 | 0.85 |
| T103 | G | 1.11 | −5.27 | 1.20 |
| T103 | H | 0.99 | −4.15 | 1.14 |
| T103 | I | 1.08 | −5.15 | 0.89 |
| T103 | K | 1.09 | −4.36 | 1.05 |
| T103 | L | 1.05 | −1.86 | 0.88 |
| T103 | N | 0.77 | −6.03 | 1.07 |
| T103 | P | 0.69 | −5.11 | 1.01 |
| T103 | R | 0.87 | −6.30 | 0.96 |
| T103 | S | 0.92 | −1.36 | 1.14 |
| T103 | T | 1.00 | 1.00 | 1.00 |
| T103 | V | 0.95 | −1.95 | 0.90 |
| T103 | W | 1.26 | −2.60 | 0.77 |
| T103 | Y | 1.19 | −4.68 | 0.88 |
| P104 | A | −0.41 | −0.19 | −0.04 |
| P104 | C | 1.95 | 1.83 | 1.34 |
| P104 | E | 1.84 | 1.97 | 1.37 |
| P104 | F | 1.79 | 0.86 | 0.67 |
| P104 | G | 2.67 | 0.98 | 1.25 |
| P104 | H | 2.84 | 1.03 | 1.11 |
| P104 | I | 2.43 | 2.05 | 1.07 |
| P104 | L | −0.41 | −0.19 | −0.04 |
| P104 | M | 1.09 | 2.24 | 1.01 |
| P104 | N | 1.62 | 1.44 | 1.32 |
| P104 | P | 1.00 | 1.00 | 1.00 |
| P104 | Q | 1.34 | 0.85 | 1.24 |
| P104 | R | 1.62 | −0.39 | 0.83 |
| P104 | S | 2.48 | 0.53 | 1.44 |

TABLE 10-12-continued

| Wild-Type Res./Pos. | Mut. | PAF PI | PAD PI | Prot. PI |
|---|---|---|---|---|
| | | Performance Indices | | |
| P104 | T | 2.70 | 0.33 | 1.29 |
| P104 | V | 2.59 | 1.02 | 1.40 |
| P104 | W | 2.05 | 0.23 | 0.59 |
| L105 | A | −0.11 | −0.18 | −0.02 |
| L105 | C | 1.56 | 1.92 | 1.05 |
| L105 | E | −0.11 | 0.53 | 0.26 |
| L105 | F | 1.30 | 1.73 | 0.95 |
| L105 | G | 1.08 | 1.40 | 1.07 |
| L105 | H | 0.85 | 1.23 | 1.07 |
| L105 | L | 1.00 | 1.00 | 1.00 |
| L105 | M | −0.11 | −0.18 | −0.02 |
| L105 | P | 1.71 | 0.90 | 1.00 |
| L105 | Q | 0.94 | 1.04 | 1.03 |
| L105 | R | 0.99 | 1.25 | 0.94 |
| L105 | S | 0.93 | 0.61 | 0.95 |
| L105 | T | 0.92 | 0.64 | 1.00 |
| L105 | V | 0.15 | −0.97 | 0.37 |
| L105 | W | 1.28 | 1.71 | 0.78 |
| L105 | Y | 0.72 | 0.62 | 1.18 |
| D106 | A | 0.72 | 1.13 | 0.69 |
| D106 | C | 1.01 | 1.10 | 0.80 |
| D106 | D | 1.00 | 1.00 | 1.00 |
| D106 | E | 1.08 | 1.09 | 1.02 |
| D106 | F | 1.02 | 1.45 | 0.34 |
| D106 | G | 1.18 | 1.45 | 0.67 |
| D106 | H | 1.09 | 1.18 | 0.66 |
| D106 | I | 1.04 | 0.92 | 0.45 |
| D106 | K | 1.28 | 1.24 | 0.68 |
| D106 | L | 1.20 | 1.00 | 0.56 |
| D106 | M | 0.73 | 0.86 | 0.77 |
| D106 | N | 0.92 | 0.64 | 0.91 |
| D106 | P | −0.17 | 0.63 | 0.18 |
| D106 | Q | 0.92 | 0.62 | 0.94 |
| D106 | R | 0.98 | 0.56 | 0.91 |
| D106 | S | 0.98 | 1.02 | 0.81 |
| D106 | T | 1.06 | 1.38 | 0.64 |
| D106 | V | 0.98 | 1.68 | 0.61 |
| D106 | W | 0.78 | 1.07 | 0.34 |
| I107 | A | 0.81 | 0.80 | 0.83 |
| I107 | C | 0.95 | 1.41 | 1.00 |
| I107 | E | 2.55 | −0.28 | 0.21 |
| I107 | F | 0.99 | −0.02 | 0.19 |
| I107 | G | 1.76 | −10.12 | 0.25 |
| I107 | H | −0.07 | −0.20 | −0.02 |
| I107 | I | 1.00 | 1.00 | 1.00 |
| I107 | L | 0.96 | 1.04 | 0.52 |
| I107 | N | 1.81 | 0.93 | 0.56 |
| I107 | P | 0.65 | 0.32 | 0.40 |
| I107 | Q | 0.53 | −0.02 | 0.43 |
| I107 | R | 0.08 | −2.75 | 0.28 |
| I107 | S | 2.04 | 1.33 | 1.05 |
| I107 | T | 0.64 | 1.53 | 0.95 |
| I107 | V | 1.00 | 0.97 | 1.04 |
| I107 | W | −0.07 | −0.20 | −0.02 |
| I107 | Y | 0.49 | 0.52 | 0.23 |
| A108 | A | −0.12 | −0.07 | −0.02 |
| A108 | D | −0.12 | −0.07 | −0.02 |
| A108 | E | 0.14 | 0.61 | 0.25 |
| A108 | F | −0.12 | −0.07 | −0.02 |
| A108 | G | 0.99 | 1.13 | 1.15 |
| A108 | H | −0.12 | −0.07 | −0.02 |
| A108 | I | −0.12 | −0.07 | −0.02 |
| A108 | K | 0.60 | 2.97 | 0.31 |
| A108 | L | 1.41 | 2.56 | 0.20 |
| A108 | N | −0.12 | −0.07 | −0.02 |
| A108 | P | −0.12 | −0.07 | −0.02 |
| A108 | Q | 0.58 | 0.73 | 0.98 |
| A108 | R | −0.12 | −0.07 | −0.02 |
| A108 | S | 0.94 | 1.00 | 1.14 |
| A108 | T | 1.05 | 0.87 | 1.08 |
| A108 | V | 0.76 | 0.95 | 0.99 |
| L109 | A | 0.34 | 0.32 | 1.07 |
| L109 | D | 1.00 | 0.11 | 1.15 |
| L109 | E | 0.74 | 0.19 | 1.24 |
| L109 | F | 0.83 | 0.32 | 1.11 |

TABLE 10-12-continued

| Wild-Type Res./Pos. | Mut. | PAF PI | PAD PI | Prot. PI |
|---|---|---|---|---|
| | | Performance Indices | | |
| L109 | G | 0.82 | 0.51 | 0.88 |
| L109 | H | 0.85 | 0.22 | 1.06 |
| L109 | I | 1.05 | 0.14 | 1.21 |
| L109 | L | 1.00 | 1.00 | 1.00 |
| L109 | M | 0.74 | 0.63 | 1.00 |
| L109 | N | 1.52 | 0.66 | 1.13 |
| L109 | P | 0.79 | 0.43 | 0.35 |
| L109 | Q | 1.18 | 0.22 | 1.08 |
| L109 | R | 0.48 | 0.21 | 0.95 |
| L109 | S | 0.79 | 0.38 | 0.94 |
| L109 | T | 0.63 | 0.79 | 0.87 |
| L109 | V | 0.52 | 0.54 | 1.06 |
| L109 | W | 1.30 | −0.02 | 0.88 |
| L109 | Y | 1.16 | 0.83 | 0.79 |
| G110 | A | 0.91 | 1.01 | 0.88 |
| G110 | C | 0.35 | 1.43 | 0.56 |
| G110 | D | 0.76 | 1.40 | 0.87 |
| G110 | E | 0.26 | 1.76 | 0.46 |
| G110 | F | 0.04 | 2.29 | 0.30 |
| G110 | G | 1.00 | 1.00 | 1.00 |
| G110 | H | 0.63 | 0.73 | 0.46 |
| G110 | I | 0.06 | 0.23 | 0.32 |
| G110 | L | −0.20 | −0.12 | −0.02 |
| G110 | M | 0.16 | 0.82 | 0.34 |
| G110 | N | 0.70 | 0.77 | 0.89 |
| G110 | P | 0.02 | 0.22 | 0.50 |
| G110 | Q | 0.44 | 0.34 | 0.77 |
| G110 | R | 0.05 | 0.48 | 0.45 |
| G110 | S | 0.79 | 0.30 | 1.01 |
| G110 | T | 0.45 | −0.05 | 0.42 |
| G110 | W | −0.20 | −1.18 | 0.20 |
| G110 | Y | 0.01 | −0.88 | 0.40 |
| M111 | A | 0.65 | 1.02 | 0.89 |
| M111 | C | 0.92 | 1.01 | 0.95 |
| M111 | D | −0.27 | 0.79 | 0.37 |
| M111 | E | 0.25 | 0.67 | 0.56 |
| M111 | F | 1.47 | 0.78 | 0.75 |
| M111 | G | 0.85 | 0.32 | 0.44 |
| M111 | H | 0.98 | 0.19 | 0.40 |
| M111 | I | 1.95 | 1.03 | 0.91 |
| M111 | K | 1.98 | 0.71 | 0.58 |
| M111 | L | 1.55 | 0.67 | 0.93 |
| M111 | M | 1.00 | 1.00 | 1.00 |
| M111 | N | 0.49 | 1.31 | 0.79 |
| M111 | P | −0.27 | 0.57 | 0.39 |
| M111 | R | 0.27 | −0.99 | 0.34 |
| M111 | S | 1.03 | 0.14 | 0.52 |
| M111 | T | 1.49 | 0.76 | 0.77 |
| M111 | V | 1.47 | 0.93 | 0.88 |
| M111 | W | 0.96 | 1.23 | 0.30 |
| M111 | Y | 1.43 | 1.06 | 0.65 |
| S112 | A | 0.58 | 0.94 | 0.98 |
| S112 | E | 0.71 | 1.16 | 1.05 |
| S112 | F | 0.37 | 0.88 | 0.61 |
| S112 | H | 1.00 | 0.38 | 0.93 |
| S112 | K | 0.84 | 0.68 | 0.92 |
| S112 | L | 1.03 | 1.00 | 0.80 |
| S112 | M | 0.43 | 0.56 | 0.98 |
| S112 | N | 0.52 | 0.85 | 1.09 |
| S112 | P | −0.19 | −0.82 | 0.33 |
| S112 | R | 0.20 | −0.44 | 0.99 |
| S112 | S | 1.00 | 1.00 | 1.00 |
| S112 | T | 0.95 | 0.72 | 0.87 |
| S112 | V | 0.86 | 0.48 | 0.73 |
| S112 | W | 0.74 | 0.58 | 0.85 |
| S112 | Y | 0.68 | −0.10 | 0.90 |
| V113 | A | 0.71 | 1.31 | 0.70 |
| V113 | C | 0.87 | 0.94 | 1.06 |
| V113 | D | 0.78 | 0.87 | 0.97 |
| V113 | E | 0.91 | 0.94 | 0.99 |
| V113 | F | 1.05 | 0.96 | 0.80 |
| V113 | G | 0.96 | 0.58 | 0.89 |
| V113 | H | 1.34 | 0.76 | 0.84 |
| V113 | K | 1.19 | 0.72 | 0.92 |
| V113 | L | 1.50 | 0.85 | 0.85 |

TABLE 10-12-continued

| Performance Indices | | | | |
|---|---|---|---|---|
| Wild-Type Res./Pos. | Mut. | PAF PI | PAD PI | Prot. PI |
| V113 | M | 0.78 | 1.06 | 0.93 |
| V113 | N | 0.88 | 1.22 | 1.01 |
| V113 | P | 0.72 | 1.14 | 0.65 |
| V113 | Q | 1.03 | 1.11 | 0.94 |
| V113 | R | 1.13 | 1.11 | 0.82 |
| V113 | S | 0.80 | 0.57 | 0.91 |
| V113 | T | 0.94 | 0.86 | 0.89 |
| V113 | V | 1.00 | 1.00 | 1.00 |
| V113 | W | 0.91 | 0.80 | 0.76 |
| V113 | Y | 1.11 | 0.98 | 0.85 |
| L114 | A | 0.78 | 1.07 | 1.03 |
| L114 | C | 0.78 | 1.14 | 1.10 |
| L114 | E | 0.32 | −0.14 | 0.42 |
| L114 | F | −0.11 | −0.21 | −0.02 |
| L114 | G | 0.96 | 1.14 | 0.78 |
| L114 | H | 0.92 | −0.55 | 0.21 |
| L114 | I | 0.97 | 1.17 | 0.86 |
| L114 | K | −0.11 | −0.21 | −0.02 |
| L114 | L | 1.00 | 1.00 | 1.00 |
| L114 | M | 0.73 | 1.28 | 1.00 |
| L114 | N | 0.65 | 0.77 | 0.95 |
| L114 | P | 0.30 | 0.28 | 0.42 |
| L114 | Q | 0.59 | 0.12 | 0.68 |
| L114 | R | −0.11 | −0.21 | −0.02 |
| L114 | S | 0.87 | 0.55 | 0.72 |
| L114 | T | 0.88 | 1.05 | 0.82 |
| L114 | V | 0.91 | 0.60 | 0.84 |
| L114 | W | −0.11 | −0.21 | −0.02 |
| L114 | Y | −0.11 | −0.21 | −0.02 |
| V115 | A | 0.60 | 1.19 | 1.11 |
| V115 | C | 0.73 | 1.08 | 1.14 |
| V115 | D | −0.15 | 2.21 | 0.19 |
| V115 | F | 0.54 | 1.69 | 0.32 |
| V115 | G | 1.09 | 1.76 | 0.43 |
| V115 | H | −0.15 | −0.13 | −0.02 |
| V115 | I | 1.05 | 0.99 | 1.14 |
| V115 | K | −0.15 | −0.13 | −0.02 |
| V115 | L | 1.12 | 1.30 | 1.02 |
| V115 | M | 0.48 | 1.32 | 1.05 |
| V115 | P | −0.15 | 2.21 | 0.26 |
| V115 | Q | −0.15 | 1.15 | 0.32 |
| V115 | R | 0.10 | 1.63 | 0.21 |
| V115 | S | 0.95 | 1.14 | 0.72 |
| V115 | T | 1.15 | 1.28 | 0.72 |
| V115 | V | 1.00 | 1.00 | 1.00 |
| V115 | W | 1.23 | 2.48 | 0.17 |
| V115 | Y | 1.03 | 2.07 | 0.28 |
| T116 | A | 1.01 | 0.95 | 1.08 |
| T116 | C | 0.89 | 1.05 | 1.30 |
| T116 | E | 0.86 | 0.91 | 1.29 |
| T116 | G | 1.10 | 0.90 | 1.44 |
| T116 | H | 1.00 | 1.08 | 1.48 |
| T116 | I | 0.80 | 0.76 | 0.82 |
| T116 | L | 0.77 | 0.68 | 1.03 |
| T116 | M | 0.83 | 1.39 | 1.28 |
| T116 | N | 0.93 | 1.05 | 1.68 |
| T116 | P | 0.74 | 0.84 | 0.99 |
| T116 | Q | 0.95 | 0.77 | 1.29 |
| T116 | R | 0.64 | 0.62 | 1.03 |
| T116 | S | 0.88 | 0.96 | 1.24 |
| T116 | T | 1.00 | 1.00 | 1.00 |
| T116 | V | 0.86 | 0.57 | 0.85 |
| T116 | W | 0.89 | 0.75 | 0.96 |
| T116 | Y | 0.90 | 0.47 | 1.09 |
| Q117 | A | 2.05 | 1.73 | 1.03 |
| Q117 | E | 1.15 | 1.21 | 1.10 |
| Q117 | F | 1.57 | 1.02 | 0.61 |
| Q117 | G | 2.08 | 0.79 | 0.97 |
| Q117 | H | 2.33 | 1.12 | 1.12 |
| Q117 | M | 1.54 | 1.89 | 0.87 |
| Q117 | P | −0.25 | 1.13 | 0.61 |
| Q117 | Q | 1.00 | 1.00 | 1.00 |
| Q117 | R | 1.56 | 1.05 | 1.00 |
| Q117 | S | 1.95 | 0.87 | 1.13 |
| Q117 | T | 2.23 | 1.10 | 1.06 |
| Q117 | V | 2.15 | 0.76 | 0.67 |
| Q117 | W | 2.16 | 0.71 | 0.57 |
| Q117 | Y | 2.23 | 1.13 | 0.76 |
| V118 | A | 0.84 | 0.85 | 1.20 |
| V118 | C | 0.78 | 1.14 | 1.28 |
| V118 | D | −0.14 | 0.40 | 0.38 |
| V118 | E | −0.14 | −0.43 | 0.37 |
| V118 | F | 0.86 | 1.00 | 0.89 |
| V118 | G | 1.08 | 0.56 | 0.67 |
| V118 | I | 0.96 | 0.55 | 1.01 |
| V118 | K | 1.13 | −2.50 | 0.28 |
| V118 | L | 0.93 | 1.05 | 0.93 |
| V118 | M | 0.60 | 0.93 | 0.90 |
| V118 | P | 0.12 | 0.22 | 0.52 |
| V118 | Q | 0.38 | 1.50 | 0.57 |
| V118 | R | 0.36 | 0.07 | 0.46 |
| V118 | S | 0.95 | 0.82 | 0.96 |
| V118 | T | 0.99 | 0.92 | 0.90 |
| V118 | V | 1.00 | 1.00 | 1.00 |
| V118 | W | 0.83 | −1.28 | 0.42 |
| V118 | Y | 1.25 | 1.34 | 0.60 |
| L119 | A | 0.81 | 1.02 | 1.18 |
| L119 | C | 0.76 | 0.24 | 1.18 |
| L119 | D | 0.24 | 0.28 | 0.97 |
| L119 | E | 0.45 | 0.32 | 1.04 |
| L119 | F | 0.56 | −0.61 | 0.93 |
| L119 | G | 0.93 | −0.06 | 0.97 |
| L119 | H | 0.91 | 0.46 | 0.89 |
| L119 | I | 0.90 | 0.43 | 1.06 |
| L119 | L | 1.00 | 1.00 | 1.00 |
| L119 | N | 0.58 | 0.11 | 1.14 |
| L119 | P | −0.14 | −0.01 | 0.71 |
| L119 | R | 0.43 | −0.66 | 1.00 |
| L119 | S | 0.83 | −0.17 | 1.05 |
| L119 | T | 0.97 | 0.10 | 0.94 |
| L119 | V | 0.89 | 0.15 | 1.04 |
| L119 | W | 0.77 | 0.20 | 0.88 |
| L119 | Y | 0.77 | 0.56 | 0.89 |
| T120 | A | 0.25 | 0.66 | 1.09 |
| T120 | C | 0.75 | 0.92 | 1.14 |
| T120 | E | 0.58 | 1.53 | 1.19 |
| T120 | H | 0.88 | 0.50 | 1.07 |
| T120 | I | 0.91 | 1.56 | 1.00 |
| T120 | K | 0.87 | 1.09 | 1.12 |
| T120 | L | 0.80 | 1.26 | 1.00 |
| T120 | M | 0.05 | 1.22 | 0.98 |
| T120 | N | 0.37 | 1.42 | 1.10 |
| T120 | P | 0.07 | −0.45 | 0.82 |
| T120 | Q | 0.26 | 0.78 | 1.05 |
| T120 | R | 0.24 | 0.60 | 0.99 |
| T120 | S | 1.09 | 1.07 | 1.35 |
| T120 | T | 1.00 | 1.00 | 1.00 |
| T120 | V | 0.26 | 1.07 | 0.93 |
| T120 | Y | 0.57 | 1.61 | 1.01 |
| S121 | A | 1.12 | 1.55 | 1.10 |
| S121 | C | 1.18 | 1.64 | 1.09 |
| S121 | E | 0.89 | 1.04 | 1.01 |
| S121 | G | 1.20 | 0.99 | 1.07 |
| S121 | K | 1.24 | 0.78 | 1.04 |
| S121 | L | 1.35 | 1.49 | 1.12 |
| S121 | N | 1.14 | 1.06 | 1.17 |
| S121 | P | 0.83 | 0.38 | 0.92 |
| S121 | Q | 0.92 | 1.09 | 1.01 |
| S121 | R | 1.26 | 0.70 | 1.06 |
| S121 | S | 1.00 | 1.00 | 1.00 |
| S121 | T | 1.13 | 1.26 | 0.93 |
| S121 | V | 1.12 | 1.59 | 0.97 |
| S121 | W | 1.33 | 0.77 | 0.91 |
| A122 | A | 1.00 | 1.00 | 1.00 |
| A122 | D | 0.26 | 0.06 | 0.77 |
| A122 | E | 0.71 | 0.47 | 1.04 |
| A122 | F | 0.97 | 0.15 | 0.87 |
| A122 | G | 0.93 | −0.42 | 0.85 |
| A122 | H | 1.14 | 0.17 | 1.00 |
| A122 | I | 1.13 | 0.65 | 1.04 |

TABLE 10-12-continued

| Wild-Type Res./Pos. | Mut. | PAF PI | PAD PI | Prot. PI |
|---|---|---|---|---|
| | | Performance Indices | | |
| A122 | K | 1.08 | 0.45 | 0.96 |
| A122 | L | 0.93 | 1.02 | 1.07 |
| A122 | M | 0.81 | 0.94 | 1.06 |
| A122 | N | 0.83 | 0.70 | 1.11 |
| A122 | P | 0.61 | 0.55 | 1.07 |
| A122 | Q | 0.69 | 0.74 | 1.02 |
| A122 | R | 0.71 | 0.40 | 0.94 |
| A122 | S | 1.03 | 0.43 | 1.05 |
| A122 | T | 1.08 | 0.52 | 0.97 |
| A122 | V | 1.04 | 0.89 | 1.05 |
| A122 | W | 0.99 | 0.86 | 0.88 |
| G123 | A | 0.89 | 1.19 | 0.96 |
| G123 | C | 0.95 | 0.30 | 0.92 |
| G123 | D | 1.73 | 0.84 | 0.90 |
| G123 | E | 1.13 | 0.56 | 0.96 |
| G123 | F | 0.84 | 0.80 | 0.85 |
| G123 | G | 1.00 | 1.00 | 1.00 |
| G123 | H | 1.00 | 0.74 | 0.84 |
| G123 | K | 0.97 | 1.12 | 0.93 |
| G123 | L | 0.99 | 1.38 | 0.79 |
| G123 | M | 0.84 | 1.38 | 0.85 |
| G123 | N | 0.89 | 0.71 | 0.92 |
| G123 | P | 1.32 | 0.81 | 0.89 |
| G123 | Q | 0.01 | 0.31 | 0.37 |
| G123 | R | 0.66 | 0.60 | 0.83 |
| G123 | T | 1.06 | 0.54 | 0.85 |
| G123 | V | 1.40 | 0.59 | 0.89 |
| G123 | W | 0.95 | 1.39 | 0.77 |
| G123 | Y | 0.96 | 1.24 | 0.87 |
| G124 | A | 0.84 | 0.03 | 1.20 |
| G124 | C | 0.72 | 0.67 | 1.07 |
| G124 | D | 0.76 | 0.64 | 0.99 |
| G124 | F | 1.32 | 0.95 | 0.70 |
| G124 | G | 1.00 | 1.00 | 1.00 |
| G124 | H | 1.59 | −0.10 | 0.98 |
| G124 | I | 1.85 | −0.08 | 0.92 |
| G124 | L | 1.92 | 0.54 | 0.98 |
| G124 | M | 0.97 | −0.05 | 1.36 |
| G124 | N | 0.98 | 0.60 | 1.18 |
| G124 | P | −0.11 | −0.08 | 0.37 |
| G124 | Q | 1.12 | 0.21 | 1.02 |
| G124 | R | 1.14 | 0.41 | 0.88 |
| G124 | S | 1.27 | 0.56 | 1.00 |
| G124 | T | 1.64 | 0.32 | 0.97 |
| G124 | V | 1.44 | 0.33 | 0.93 |
| G124 | W | 0.73 | −0.31 | 0.84 |
| G124 | Y | 1.23 | 0.56 | 0.66 |
| V125 | A | 1.69 | 0.93 | 0.91 |
| V125 | C | 0.96 | 0.54 | 0.67 |
| V125 | D | 1.24 | 0.54 | 0.76 |
| V125 | E | 0.81 | 0.39 | 0.73 |
| V125 | F | 0.96 | 0.63 | 0.77 |
| V125 | G | 2.95 | 1.09 | 0.60 |
| V125 | I | 1.01 | 0.94 | 1.05 |
| V125 | P | 1.50 | 0.62 | 0.83 |
| V125 | R | 1.30 | 0.47 | 0.82 |
| V125 | S | 1.94 | 0.79 | 0.75 |
| V125 | V | 1.00 | 1.00 | 1.00 |
| V125 | W | 0.37 | 0.25 | 0.48 |
| V125 | Y | 1.08 | 0.81 | 0.82 |
| G126 | A | 0.96 | 0.55 | 1.02 |
| G126 | C | 0.35 | 0.98 | 0.96 |
| G126 | D | 0.33 | 1.22 | 0.93 |
| G126 | E | 0.67 | 0.60 | 1.02 |
| G126 | G | 1.00 | 1.00 | 1.00 |
| G126 | I | 0.84 | 0.01 | 0.81 |
| G126 | L | 1.17 | 0.54 | 0.90 |
| G126 | M | 0.43 | 1.17 | 0.92 |
| G126 | N | 0.38 | 0.85 | 1.04 |
| G126 | P | 1.17 | 0.67 | 0.82 |
| G126 | R | 0.43 | 0.76 | 0.89 |
| G126 | S | 0.76 | 0.90 | 0.90 |
| G126 | T | 1.58 | 0.74 | 0.90 |
| G126 | V | 0.89 | 0.18 | 0.84 |
| G126 | Y | 0.54 | 0.23 | 0.82 |

TABLE 10-12-continued

| Wild-Type Res./Pos. | Mut. | PAF PI | PAD PI | Prot. PI |
|---|---|---|---|---|
| | | Performance Indices | | |
| T127 | A | 0.73 | 1.10 | 1.10 |
| T127 | C | 0.76 | 0.65 | 1.04 |
| T127 | D | 0.46 | 0.62 | 1.03 |
| T127 | E | 0.40 | −0.01 | 1.03 |
| T127 | G | 0.95 | 0.71 | 1.04 |
| T127 | H | 1.57 | 0.60 | 0.99 |
| T127 | I | 1.06 | 0.20 | 0.91 |
| T127 | L | 0.90 | −0.03 | 0.94 |
| T127 | M | 0.79 | 0.64 | 1.02 |
| T127 | P | 0.14 | 0.77 | 0.95 |
| T127 | Q | 0.55 | 0.15 | 0.86 |
| T127 | S | 1.05 | 0.83 | 1.08 |
| T127 | T | 1.00 | 1.00 | 1.00 |
| T127 | V | 1.07 | 0.68 | 1.06 |
| T128 | A | 0.76 | 1.31 | 1.23 |
| T128 | D | 0.78 | 0.66 | 1.14 |
| T128 | F | 0.79 | 1.71 | 1.01 |
| T128 | H | 0.99 | 1.08 | 1.19 |
| T128 | K | 1.06 | 1.57 | 1.10 |
| T128 | L | 1.06 | 1.72 | 0.97 |
| T128 | M | 0.72 | 1.06 | 1.28 |
| T128 | N | 0.70 | 1.36 | 1.29 |
| T128 | P | 0.87 | 1.16 | 1.18 |
| T128 | Q | 0.78 | 1.34 | 1.24 |
| T128 | R | 0.87 | 1.70 | 1.03 |
| T128 | S | 0.92 | 1.27 | 1.07 |
| T128 | T | 1.00 | 1.00 | 1.00 |
| T128 | V | 0.98 | 1.15 | 1.05 |
| T128 | W | 0.92 | 1.23 | 0.95 |
| T128 | Y | 0.95 | 1.81 | 0.96 |
| Y129 | A | 0.64 | 0.17 | 1.39 |
| Y129 | C | 0.66 | 0.61 | 1.42 |
| Y129 | D | 0.35 | 0.23 | 1.35 |
| Y129 | F | 0.71 | 0.71 | 1.44 |
| Y129 | G | 0.39 | −0.56 | 1.10 |
| Y129 | K | 0.31 | −0.29 | 1.00 |
| Y129 | L | 0.78 | 0.27 | 1.22 |
| Y129 | M | 0.68 | 0.21 | 1.28 |
| Y129 | N | 0.46 | 0.53 | 1.24 |
| Y129 | P | 0.15 | 0.59 | 1.11 |
| Y129 | R | 0.38 | 0.18 | 1.00 |
| Y129 | S | 0.67 | 0.69 | 1.08 |
| Y129 | T | 0.46 | 0.14 | 1.00 |
| Y129 | V | 0.24 | −0.29 | 1.00 |
| Y129 | W | 0.47 | −0.15 | 1.01 |
| Y129 | Y | 1.00 | 1.00 | 1.00 |
| P130 | A | 0.82 | 0.44 | 1.03 |
| P130 | C | 0.95 | 0.64 | 0.93 |
| P130 | E | 1.00 | 0.22 | 1.08 |
| P130 | F | 1.08 | 0.48 | 0.89 |
| P130 | G | 1.16 | −0.19 | 1.11 |
| P130 | H | 1.17 | 0.01 | 1.00 |
| P130 | I | 1.12 | 0.41 | 0.94 |
| P130 | K | 1.16 | 0.55 | 1.05 |
| P130 | L | 1.12 | 0.09 | 0.98 |
| P130 | M | 0.66 | 0.76 | 1.03 |
| P130 | P | 1.00 | 1.00 | 1.00 |
| P130 | R | 1.11 | 0.53 | 0.95 |
| P130 | S | 1.16 | −0.14 | 0.96 |
| P130 | T | 1.19 | −0.06 | 0.96 |
| P130 | V | 1.15 | 0.37 | 0.94 |
| P130 | W | 1.15 | 0.28 | 0.80 |
| A131 | A | 1.00 | 1.00 | 1.00 |
| A131 | D | 1.31 | 0.40 | 0.80 |
| A131 | E | 1.36 | 0.97 | 0.88 |
| A131 | G | 1.66 | 0.87 | 0.83 |
| A131 | H | 1.72 | 0.82 | 0.75 |
| A131 | L | 1.83 | 0.59 | 0.73 |
| A131 | P | 1.52 | 0.71 | 0.94 |
| A131 | Q | 1.29 | 0.74 | 0.69 |
| A131 | R | 1.76 | 1.04 | 0.61 |
| A131 | S | 1.48 | 0.68 | 0.87 |
| A131 | V | 1.59 | 0.78 | 0.89 |
| A131 | W | 1.61 | −0.42 | 0.65 |
| A131 | Y | 1.50 | 0.48 | 0.73 |

TABLE 10-12-continued

Performance Indices

| Wild-Type Res./Pos. | Mut. | PAF PI | PAD PI | Prot. PI |
|---|---|---|---|---|
| P132 | A | 0.49 | 6.08 | 0.94 |
| P132 | C | 0.49 | 5.68 | 0.94 |
| P132 | D | −0.11 | −7.16 | 0.62 |
| P132 | E | 0.19 | 3.02 | 0.80 |
| P132 | F | 0.76 | −1.33 | 0.49 |
| P132 | G | 0.83 | 4.98 | 0.79 |
| P132 | H | 0.50 | −1.95 | 0.68 |
| P132 | I | 0.58 | −3.19 | 0.64 |
| P132 | L | 0.87 | 2.24 | 0.67 |
| P132 | N | 0.30 | 1.05 | 0.83 |
| P132 | P | 0.09 | 6.91 | 1.03 |
| P132 | Q | 0.41 | 6.15 | 0.91 |
| P132 | R | 0.02 | −2.19 | 0.65 |
| P132 | S | 1.13 | 5.05 | 0.96 |
| P132 | T | 0.85 | −2.01 | 0.75 |
| P132 | V | 0.85 | −2.29 | 0.78 |
| P132 | W | 0.77 | −2.64 | 0.37 |
| P132 | Y | 1.57 | 4.78 | 0.60 |
| K133 | A | 0.67 | 0.10 | 1.01 |
| K133 | C | 0.56 | −0.11 | 0.72 |
| K133 | E | 0.63 | 0.76 | 1.01 |
| K133 | F | 0.86 | 0.59 | 0.73 |
| K133 | G | 0.97 | 0.31 | 0.87 |
| K133 | H | 1.02 | 0.31 | 0.87 |
| K133 | I | 0.89 | 0.45 | 0.78 |
| K133 | K | 1.00 | 1.00 | 1.00 |
| K133 | L | 1.05 | 1.92 | 0.76 |
| K133 | M | 0.68 | 0.33 | 0.98 |
| K133 | P | 0.39 | 0.71 | 0.89 |
| K133 | Q | 0.69 | 0.52 | 1.13 |
| K133 | R | 0.78 | 0.83 | 1.01 |
| K133 | S | 0.84 | 0.58 | 1.02 |
| K133 | T | 0.93 | 0.39 | 0.97 |
| K133 | V | 0.90 | 0.23 | 0.87 |
| K133 | W | 0.97 | 0.99 | 0.46 |
| K133 | Y | 1.12 | 1.44 | 0.75 |
| V134 | A | 0.75 | 1.64 | 0.87 |
| V134 | C | 0.77 | 1.37 | 0.91 |
| V134 | D | −0.08 | −0.08 | −0.02 |
| V134 | G | 1.71 | 1.42 | 0.45 |
| V134 | I | 1.12 | 0.89 | 0.99 |
| V134 | K | −0.08 | −0.08 | −0.02 |
| V134 | L | 1.13 | 1.45 | 0.78 |
| V134 | M | 0.82 | 1.89 | 0.83 |
| V134 | N | 1.18 | 2.80 | 0.25 |
| V134 | P | −0.08 | 1.71 | 0.43 |
| V134 | Q | 0.04 | 0.79 | 0.44 |
| V134 | R | −0.08 | −0.08 | −0.02 |
| V134 | S | 1.16 | 1.44 | 0.62 |
| V134 | T | 1.25 | 0.86 | 0.82 |
| V134 | V | 1.00 | 1.00 | 1.00 |
| V134 | W | −0.08 | −0.08 | −0.02 |
| V134 | Y | −0.08 | −0.08 | −0.02 |
| L135 | D | −0.13 | 2.90 | 0.27 |
| L135 | E | −0.13 | 0.63 | 0.39 |
| L135 | F | 0.34 | −0.03 | 0.45 |
| L135 | G | 0.33 | −1.71 | 0.28 |
| L135 | K | 0.66 | −1.23 | 0.28 |
| L135 | L | 1.00 | 1.00 | 1.00 |
| L135 | M | 0.77 | 0.78 | 1.01 |
| L135 | P | −0.13 | −1.31 | 0.22 |
| L135 | Q | 0.34 | 0.17 | 0.66 |
| L135 | R | 0.06 | −1.41 | 0.25 |
| L135 | S | 0.50 | −0.65 | 0.44 |
| L135 | T | 0.73 | −0.42 | 0.50 |
| L135 | V | 0.83 | 0.43 | 0.82 |
| L135 | W | 0.71 | −0.42 | 0.36 |
| V136 | A | 0.60 | 1.60 | 0.66 |
| V136 | C | 0.57 | 1.23 | 0.87 |
| V136 | E | −0.09 | 0.20 | 0.25 |
| V136 | L | 0.98 | 1.13 | 1.03 |
| V136 | N | −0.09 | 0.40 | 0.26 |
| V136 | P | −0.09 | −0.12 | 0.52 |
| V136 | R | −0.09 | −0.12 | −0.02 |
| V136 | T | 1.13 | 1.13 | 0.68 |
| V136 | V | 1.00 | 1.00 | 1.00 |
| V136 | W | −0.09 | −0.12 | −0.02 |
| V137 | A | 1.07 | 1.46 | 0.64 |
| V137 | C | 0.98 | 1.42 | 0.85 |
| V137 | D | −0.17 | −0.23 | −0.01 |
| V137 | E | −0.17 | −0.23 | −0.01 |
| V137 | F | −0.17 | −0.23 | −0.01 |
| V137 | G | 1.02 | 0.26 | 0.13 |
| V137 | I | 0.98 | 0.70 | 0.83 |
| V137 | L | 1.09 | 1.27 | 0.82 |
| V137 | M | 1.22 | 1.13 | 0.89 |
| V137 | N | 0.46 | −1.29 | 0.15 |
| V137 | P | −0.17 | −0.23 | −0.01 |
| V137 | R | −0.17 | −0.23 | −0.01 |
| V137 | S | 0.96 | 0.29 | 0.50 |
| V137 | T | 1.08 | 0.93 | 0.73 |
| V137 | V | 1.00 | 1.00 | 1.00 |
| V137 | W | −0.17 | −0.23 | −0.01 |
| V137 | Y | −0.17 | −0.23 | −0.01 |
| S138 | A | 0.69 | 1.28 | 1.44 |
| S138 | C | 0.64 | 1.18 | 1.17 |
| S138 | E | −0.13 | −0.19 | −0.02 |
| S138 | F | −0.13 | −0.19 | −0.02 |
| S138 | G | 1.05 | 1.11 | 1.09 |
| S138 | H | −0.13 | −0.19 | −0.02 |
| S138 | I | 1.15 | 0.35 | 0.56 |
| S138 | L | −0.13 | −0.19 | −0.02 |
| S138 | M | −0.13 | −0.19 | −0.02 |
| S138 | N | 0.62 | 1.31 | 0.77 |
| S138 | P | 0.54 | 1.39 | 0.45 |
| S138 | Q | −0.13 | −0.19 | −0.02 |
| S138 | R | −0.13 | −0.19 | −0.02 |
| S138 | S | 1.00 | 1.00 | 1.00 |
| S138 | V | 1.00 | 0.69 | 0.67 |
| S138 | W | −0.13 | −0.19 | −0.02 |
| S138 | Y | −0.13 | −0.19 | −0.02 |
| P139 | C | 0.08 | −0.12 | 0.18 |
| P139 | D | −0.13 | −1.44 | 0.15 |
| P139 | E | −0.13 | −5.11 | 0.19 |
| P139 | F | −0.13 | −4.13 | 0.16 |
| P139 | G | 0.50 | −3.08 | 0.23 |
| P139 | H | −0.13 | −6.03 | 0.19 |
| P139 | I | −0.13 | −3.71 | 0.21 |
| P139 | K | −0.13 | −4.09 | 0.12 |
| P139 | L | −0.13 | −0.17 | −0.02 |
| P139 | N | −0.13 | −2.11 | 0.16 |
| P139 | P | 1.00 | 1.00 | 1.00 |
| P139 | Q | −0.13 | −0.32 | 0.18 |
| P139 | R | 0.37 | −1.04 | 0.23 |
| P139 | S | 0.88 | −0.52 | 0.43 |
| P139 | T | 0.01 | −3.48 | 0.15 |
| P139 | V | −0.13 | −1.70 | 0.17 |
| P139 | W | −0.13 | −0.17 | −0.02 |
| P139 | Y | −0.13 | −0.17 | −0.02 |
| P140 | A | 1.90 | 1.83 | 0.61 |
| P140 | C | 0.39 | 1.07 | 0.40 |
| P140 | D | −0.45 | −0.23 | −0.02 |
| P140 | F | −0.45 | 2.89 | 0.19 |
| P140 | G | 0.96 | 3.11 | 0.20 |
| P140 | H | 0.59 | 2.25 | 0.23 |
| P140 | I | 0.45 | −1.03 | 0.24 |
| P140 | K | −0.45 | −0.23 | −0.02 |
| P140 | L | −0.45 | −0.23 | −0.02 |
| P140 | M | −0.45 | −0.23 | −0.02 |
| P140 | P | 1.00 | 1.00 | 1.00 |
| P140 | Q | −0.45 | −1.32 | 0.32 |
| P140 | R | −0.45 | −2.74 | 0.25 |
| P140 | S | 1.31 | −1.22 | 0.43 |
| P140 | T | 1.74 | −0.78 | 0.29 |
| P140 | V | 0.50 | −1.12 | 0.34 |
| P140 | W | 0.50 | −0.97 | 0.17 |
| P140 | Y | 0.32 | −1.90 | 0.24 |
| P141 | A | 1.10 | 1.08 | 1.13 |
| P141 | G | 1.64 | −0.05 | 1.02 |
| P141 | H | 2.07 | 0.79 | 0.93 |

TABLE 10-12-continued

Performance Indices

| Wild-Type Res./Pos. | Mut. | PAF PI | PAD PI | Prot. PI |
|---|---|---|---|---|
| P141 | I | 2.29 | 0.38 | 0.90 |
| P141 | L | 2.32 | 0.65 | 0.74 |
| P141 | N | 1.32 | 0.97 | 0.96 |
| P141 | P | 1.00 | 1.00 | 1.00 |
| P141 | Q | 1.39 | 0.37 | 0.88 |
| P141 | R | 1.65 | −0.26 | 0.61 |
| P141 | S | 1.70 | 0.02 | 0.90 |
| P141 | T | 1.84 | 0.12 | 0.82 |
| P141 | V | 1.96 | 0.16 | 0.72 |
| L142 | A | 0.80 | 0.56 | 0.67 |
| L142 | C | 0.74 | 0.70 | 0.78 |
| L142 | D | −0.12 | −0.13 | −0.01 |
| L142 | F | 1.05 | 0.54 | 0.46 |
| L142 | G | −0.12 | −0.13 | −0.01 |
| L142 | I | 0.64 | 0.28 | 1.05 |
| L142 | K | 1.60 | 0.66 | 0.23 |
| L142 | L | 1.00 | 1.00 | 1.00 |
| L142 | M | −0.12 | −0.13 | −0.01 |
| L142 | N | −0.12 | −0.13 | −0.01 |
| L142 | P | 0.54 | 0.44 | 0.48 |
| L142 | Q | 0.67 | 0.33 | 0.49 |
| L142 | R | −0.12 | −0.13 | −0.01 |
| L142 | S | 0.84 | 0.31 | 0.65 |
| L142 | T | −0.12 | −0.13 | −0.01 |
| L142 | V | 0.84 | 0.33 | 0.82 |
| L142 | W | 2.41 | −1.89 | 0.16 |
| A143 | A | 1.00 | 1.00 | 1.00 |
| A143 | C | 1.39 | 1.07 | 0.81 |
| A143 | D | 1.45 | 1.22 | 0.71 |
| A143 | E | 1.43 | 1.13 | 0.71 |
| A143 | F | 1.56 | 0.68 | 0.99 |
| A143 | G | 1.48 | 0.42 | 1.17 |
| A143 | H | 2.90 | 1.36 | 0.70 |
| A143 | K | 3.16 | 1.37 | 0.62 |
| A143 | L | 2.51 | 1.28 | 0.71 |
| A143 | N | 1.30 | 0.82 | 0.79 |
| A143 | P | 1.53 | 0.39 | 0.63 |
| A143 | Q | 1.74 | 0.81 | 0.72 |
| A143 | R | 2.15 | 0.99 | 0.62 |
| A143 | S | 1.77 | 0.63 | 0.98 |
| A143 | T | 2.18 | 0.97 | 0.74 |
| A143 | V | 2.45 | 0.99 | 0.81 |
| A143 | W | 2.27 | −0.21 | 0.37 |
| P144 | A | 1.09 | 0.79 | 0.91 |
| P144 | D | 1.45 | 1.38 | 0.60 |
| P144 | F | 1.82 | 1.08 | 0.66 |
| P144 | G | 1.45 | 0.62 | 0.78 |
| P144 | H | 1.94 | 1.60 | 0.66 |
| P144 | K | 2.09 | 1.09 | 0.67 |
| P144 | L | 1.43 | 1.15 | 0.86 |
| P144 | M | 1.24 | 1.01 | 0.76 |
| P144 | N | 1.44 | 1.49 | 0.74 |
| P144 | P | 1.00 | 1.00 | 1.00 |
| P144 | Q | 1.37 | 1.08 | 0.77 |
| P144 | R | 1.76 | 1.14 | 0.68 |
| P144 | S | 1.69 | 0.92 | 0.77 |
| P144 | T | 1.46 | 0.81 | 0.80 |
| P144 | Y | 2.34 | 1.65 | 0.70 |
| M145 | A | 0.44 | 0.79 | 0.94 |
| M145 | C | 1.02 | 0.93 | 0.94 |
| M145 | E | 0.28 | 0.48 | 0.74 |
| M145 | F | 1.49 | 0.77 | 0.95 |
| M145 | G | 0.48 | 0.26 | 0.92 |
| M145 | I | 0.79 | 0.53 | 1.16 |
| M145 | L | 1.72 | 0.61 | 1.07 |
| M145 | M | 1.00 | 1.00 | 1.00 |
| M145 | P | 0.64 | 0.78 | 0.78 |
| M145 | Q | 0.68 | 0.57 | 0.86 |
| M145 | R | 1.15 | 0.69 | 0.78 |
| M145 | S | 0.64 | 0.78 | 0.91 |
| M145 | T | 1.01 | 0.79 | 0.91 |
| M145 | V | 0.72 | 0.63 | 1.00 |
| M145 | W | 1.15 | −0.13 | 0.49 |
| M145 | Y | 0.94 | 0.82 | 0.68 |
| P146 | A | 0.20 | 1.36 | 0.73 |
| P146 | C | 0.31 | 1.69 | 0.62 |
| P146 | F | 0.55 | 1.53 | 0.51 |
| P146 | G | 0.24 | 1.04 | 0.51 |
| P146 | H | 0.50 | 1.57 | 0.56 |
| P146 | L | 0.56 | 2.00 | 0.53 |
| P146 | M | 0.39 | 1.23 | 0.79 |
| P146 | N | 0.37 | 1.00 | 0.78 |
| P146 | P | 1.00 | 1.00 | 1.00 |
| P146 | R | 0.36 | 1.06 | 0.66 |
| P146 | S | 0.46 | 0.96 | 0.82 |
| P146 | T | 0.38 | 0.76 | 0.80 |
| P146 | V | 0.55 | 0.77 | 0.89 |
| P146 | W | 0.56 | 0.68 | 0.64 |
| P146 | Y | 0.35 | 1.44 | 0.54 |
| H147 | A | 1.28 | 0.98 | 0.96 |
| H147 | C | 0.94 | 1.17 | 1.04 |
| H147 | D | 0.95 | 1.18 | 1.00 |
| H147 | E | 1.11 | 1.10 | 0.96 |
| H147 | G | −0.12 | −0.15 | −0.02 |
| H147 | H | 1.00 | 1.00 | 1.00 |
| H147 | I | 0.89 | 0.92 | 0.89 |
| H147 | K | 0.94 | 1.06 | 0.89 |
| H147 | L | 0.69 | 1.29 | 1.09 |
| H147 | M | 0.73 | 1.44 | 0.86 |
| H147 | N | 0.84 | 1.25 | 0.98 |
| H147 | P | 1.12 | 1.21 | 0.71 |
| H147 | Q | 0.71 | 1.03 | 0.86 |
| H147 | R | 0.89 | 0.94 | 0.69 |
| H147 | S | 1.26 | 0.75 | 0.92 |
| H147 | T | 1.20 | 0.84 | 0.85 |
| H147 | V | 0.96 | 0.92 | 0.90 |
| H147 | W | 0.88 | 1.05 | 0.79 |
| H147 | Y | 0.75 | 1.12 | 0.94 |
| P148 | A | 1.64 | 1.06 | 0.96 |
| P148 | D | 1.03 | 1.34 | 0.74 |
| P148 | E | 1.42 | 1.19 | 0.76 |
| P148 | F | 1.37 | 1.50 | 0.64 |
| P148 | G | 0.87 | 1.20 | 0.70 |
| P148 | K | 1.79 | 1.30 | 0.72 |
| P148 | L | 1.64 | 1.39 | 0.74 |
| P148 | P | 1.00 | 1.00 | 1.00 |
| P148 | Q | 1.33 | 0.98 | 0.81 |
| P148 | R | 1.51 | 1.25 | 0.79 |
| P148 | S | 1.46 | 1.21 | 0.74 |
| P148 | T | 1.50 | 1.09 | 0.79 |
| P148 | V | 2.43 | 1.04 | 0.76 |
| P148 | Y | 1.46 | 1.37 | 0.72 |
| W149 | A | 0.21 | 0.31 | 1.35 |
| W149 | C | 0.18 | 0.12 | 0.93 |
| W149 | E | 0.00 | −0.04 | 0.85 |
| W149 | F | 0.53 | 0.50 | 1.27 |
| W149 | G | 0.26 | 0.45 | 1.39 |
| W149 | H | 0.60 | 1.01 | 0.81 |
| W149 | I | 0.21 | 0.24 | 0.83 |
| W149 | L | 0.30 | 0.64 | 1.06 |
| W149 | M | 0.33 | 0.49 | 1.32 |
| W149 | P | −0.32 | −0.16 | 0.92 |
| W149 | Q | 0.11 | 0.40 | 1.10 |
| W149 | R | 0.04 | −0.32 | 0.67 |
| W149 | S | 0.16 | 0.33 | 1.28 |
| W149 | T | 0.26 | 0.44 | 0.84 |
| W149 | W | 1.00 | 1.00 | 1.00 |
| W149 | Y | 0.58 | 0.75 | 1.15 |
| F150 | A | 0.01 | 0.54 | 1.70 |
| F150 | C | 0.43 | 0.78 | 1.41 |
| F150 | E | 1.23 | 0.73 | 1.32 |
| F150 | F | 1.00 | 1.00 | 1.00 |
| F150 | G | 0.14 | 0.46 | 1.13 |
| F150 | H | 0.53 | 1.18 | 1.09 |
| F150 | I | 0.40 | 0.78 | 1.19 |
| F150 | K | 0.41 | 0.85 | 1.33 |
| F150 | L | 1.29 | 1.30 | 1.14 |
| F150 | M | 0.80 | 0.63 | 1.69 |
| F150 | N | 0.55 | 0.36 | 1.52 |
| F150 | P | 0.18 | 0.32 | 1.38 |

TABLE 10-12-continued

Performance Indices

| Wild-Type Res./Pos. | Mut. | PAF PI | PAD PI | Prot. PI |
|---|---|---|---|---|
| F150 | T | 0.37 | 0.58 | 1.27 |
| F150 | V | 0.22 | 0.51 | 1.26 |
| F150 | W | 0.19 | 0.62 | 1.26 |
| F150 | Y | 0.72 | 1.07 | 1.24 |
| Q151 | A | 1.29 | 2.93 | 0.46 |
| Q151 | C | 1.05 | 2.55 | 0.38 |
| Q151 | D | 1.47 | 2.81 | 0.83 |
| Q151 | E | 1.14 | 2.07 | 0.99 |
| Q151 | F | 0.31 | −8.08 | 0.21 |
| Q151 | H | 1.06 | 2.19 | 0.94 |
| Q151 | I | 0.08 | −2.76 | 0.16 |
| Q151 | K | 1.07 | 2.19 | 1.04 |
| Q151 | L | 0.40 | −1.53 | 0.17 |
| Q151 | M | 1.24 | 6.36 | 0.24 |
| Q151 | P | 1.35 | 1.91 | 0.50 |
| Q151 | Q | 1.00 | 1.00 | 1.00 |
| Q151 | R | 1.36 | 2.32 | 0.68 |
| Q151 | S | 1.05 | 2.25 | 0.86 |
| Q151 | T | 1.24 | 2.37 | 0.64 |
| Q151 | V | 0.36 | −1.65 | 0.25 |
| Q151 | W | 0.77 | 0.32 | 0.33 |
| Q151 | Y | 1.01 | 2.75 | 0.41 |
| L152 | A | 0.88 | 1.29 | 0.85 |
| L152 | C | 1.00 | 1.14 | 0.87 |
| L152 | D | 1.07 | 0.86 | 0.81 |
| L152 | E | 1.08 | 1.23 | 0.93 |
| L152 | G | 1.08 | 0.77 | 0.85 |
| L152 | H | 1.09 | 0.92 | 0.93 |
| L152 | I | 1.04 | 0.61 | 0.77 |
| L152 | K | 1.21 | 0.91 | 0.93 |
| L152 | L | 1.00 | 1.00 | 1.00 |
| L152 | M | 0.99 | 1.10 | 0.82 |
| L152 | P | 0.81 | 0.61 | 0.54 |
| L152 | Q | 1.07 | 0.76 | 0.84 |
| L152 | R | 1.20 | 0.91 | 0.89 |
| L152 | S | 1.12 | 0.84 | 0.84 |
| L152 | T | 1.12 | 0.69 | 0.82 |
| L152 | V | 1.22 | 0.88 | 0.83 |
| L152 | W | 1.18 | 1.55 | 0.74 |
| L152 | Y | 1.09 | 1.37 | 0.89 |
| I153 | A | 1.19 | 1.49 | 0.76 |
| I153 | F | 1.23 | 1.75 | 0.47 |
| I153 | H | 1.46 | 2.00 | 0.56 |
| I153 | I | 1.00 | 1.00 | 1.00 |
| I153 | K | 1.62 | 2.44 | 0.43 |
| I153 | L | 1.27 | 1.50 | 0.82 |
| I153 | N | 0.72 | 0.89 | 1.04 |
| I153 | P | 0.25 | 1.87 | 0.31 |
| I153 | S | 0.87 | 1.66 | 0.61 |
| I153 | T | 1.27 | 1.62 | 0.64 |
| I153 | V | 0.96 | 1.15 | 0.78 |
| F154 | D | −0.19 | −1.06 | −0.02 |
| F154 | E | −0.19 | −1.06 | −0.02 |
| F154 | F | 1.00 | 1.00 | 1.00 |
| F154 | G | −0.19 | −0.64 | 0.17 |
| F154 | L | −0.19 | −1.06 | −0.02 |
| F154 | P | −0.19 | −1.06 | −0.02 |
| F154 | Q | 0.39 | 0.97 | 0.45 |
| F154 | S | 0.13 | 0.29 | 0.35 |
| F154 | T | 0.12 | −1.76 | 0.19 |
| F154 | V | −0.19 | −14.19 | 0.18 |
| F154 | Y | 1.32 | 4.96 | 0.92 |
| E155 | A | 0.99 | 2.59 | 0.83 |
| E155 | D | 1.08 | 1.24 | 0.89 |
| E155 | E | 1.00 | 1.00 | 1.00 |
| E155 | F | 1.07 | 0.23 | 0.60 |
| E155 | G | 1.17 | 1.12 | 0.82 |
| E155 | I | 0.95 | 0.65 | 0.61 |
| E155 | K | 1.23 | 1.33 | 0.83 |
| E155 | L | 1.31 | 2.07 | 0.60 |
| E155 | M | 0.73 | 2.91 | 0.74 |
| E155 | N | 0.79 | 1.79 | 0.86 |
| E155 | P | 0.79 | 2.60 | 0.65 |
| E155 | Q | 0.90 | 0.69 | 0.87 |
| E155 | R | 1.47 | −0.07 | 0.71 |
| E155 | S | 1.08 | 1.12 | 0.82 |
| E155 | T | 1.49 | 1.19 | 0.76 |
| E155 | V | 0.79 | 0.47 | 0.63 |
| E155 | Y | 1.27 | 2.65 | 0.55 |
| G156 | A | 0.99 | 1.21 | 0.88 |
| G156 | C | 1.07 | 1.37 | 0.84 |
| G156 | D | 0.96 | 1.62 | 0.93 |
| G156 | E | 0.94 | 1.14 | 0.91 |
| G156 | F | 0.90 | 0.73 | 0.78 |
| G156 | G | 1.00 | 1.00 | 1.00 |
| G156 | H | 1.04 | 1.40 | 0.84 |
| G156 | I | 0.70 | −0.08 | 0.44 |
| G156 | K | 1.10 | 1.11 | 0.88 |
| G156 | L | 0.90 | 0.94 | 0.74 |
| G156 | M | 1.09 | 1.62 | 0.80 |
| G156 | N | 1.07 | 1.38 | 0.97 |
| G156 | P | 1.44 | 1.29 | 0.59 |
| G156 | R | 1.05 | 1.21 | 0.80 |
| G156 | S | 1.02 | 1.04 | 0.88 |
| G156 | T | 1.15 | 1.53 | 0.79 |
| G156 | V | 0.88 | 0.97 | 0.58 |
| G156 | W | 0.89 | 0.90 | 0.56 |
| G156 | Y | 0.96 | 1.40 | 0.80 |
| G157 | A | 0.77 | 0.87 | 1.00 |
| G157 | C | 0.96 | 0.61 | 0.92 |
| G157 | D | 0.93 | 0.94 | 0.41 |
| G157 | E | 0.98 | 0.84 | 0.61 |
| G157 | F | 1.27 | 1.42 | 0.61 |
| G157 | G | 1.00 | 1.00 | 1.00 |
| G157 | H | 1.14 | 1.57 | 0.70 |
| G157 | I | 1.11 | 1.33 | 0.36 |
| G157 | K | 1.28 | 1.47 | 0.46 |
| G157 | M | 0.96 | 0.85 | 0.70 |
| G157 | P | 0.86 | 0.01 | 0.31 |
| G157 | R | 1.51 | −0.10 | 0.42 |
| G157 | S | 1.30 | 0.19 | 0.93 |
| G157 | T | 1.74 | 0.99 | 0.68 |
| G157 | V | 1.23 | 0.40 | 0.59 |
| E158 | A | 1.45 | 1.28 | 0.91 |
| E158 | C | 1.46 | 1.37 | 0.67 |
| E158 | D | 1.35 | 0.89 | 0.82 |
| E158 | E | 1.00 | 1.00 | 1.00 |
| E158 | F | 2.06 | 1.77 | 0.46 |
| E158 | H | 2.40 | 1.01 | 0.59 |
| E158 | I | 1.38 | 0.94 | 0.76 |
| E158 | K | 2.08 | 1.88 | 0.62 |
| E158 | L | 1.59 | 1.96 | 0.70 |
| E158 | M | 1.39 | 1.73 | 0.71 |
| E158 | N | 1.41 | 1.58 | 0.82 |
| E158 | P | 1.41 | 1.19 | 0.85 |
| E158 | Q | 1.49 | 1.24 | 0.85 |
| E158 | R | 1.99 | 1.29 | 0.62 |
| E158 | S | 1.57 | 1.27 | 0.82 |
| E158 | T | 1.45 | 0.91 | 0.77 |
| E158 | V | 1.52 | 0.89 | 0.81 |
| E158 | W | 1.77 | 1.31 | 0.67 |
| E158 | Y | 1.77 | 2.48 | 0.57 |
| Q159 | A | 1.08 | 0.28 | 1.13 |
| Q159 | C | 1.13 | 0.31 | 0.79 |
| Q159 | D | 1.09 | 0.63 | 0.90 |
| Q159 | E | 0.99 | 0.97 | 1.14 |
| Q159 | G | 0.96 | 0.72 | 1.03 |
| Q159 | H | 0.96 | 1.48 | 0.90 |
| Q159 | L | 1.02 | 0.70 | 0.83 |
| Q159 | M | 1.07 | 0.84 | 0.83 |
| Q159 | P | 1.06 | 0.49 | 0.81 |
| Q159 | Q | 1.00 | 1.00 | 1.00 |
| Q159 | R | 1.15 | 0.74 | 0.76 |
| Q159 | S | 1.10 | 0.73 | 0.81 |
| K160 | A | 0.39 | 1.14 | 0.86 |
| K160 | C | 0.48 | 1.29 | 0.77 |
| K160 | D | −0.15 | 1.19 | 0.40 |
| K160 | G | 0.91 | 0.30 | 0.56 |
| K160 | H | 0.98 | 0.57 | 0.65 |
| K160 | I | 0.97 | 1.00 | 0.78 |

TABLE 10-12-continued

| Performance Indices | | | | |
|---|---|---|---|---|
| Wild-Type Res./Pos. | Mut. | PAF PI | PAD PI | Prot. PI |
| K160 | K | 1.00 | 1.00 | 1.00 |
| K160 | L | 0.97 | 0.95 | 0.77 |
| K160 | M | 0.31 | 1.47 | 0.78 |
| K160 | N | 0.37 | 1.12 | 0.65 |
| K160 | P | −0.15 | 1.66 | 0.31 |
| K160 | Q | 0.45 | 1.41 | 0.75 |
| K160 | R | 0.83 | 1.15 | 0.76 |
| K160 | S | 0.85 | 0.70 | 0.74 |
| K160 | W | 0.89 | −0.34 | 0.21 |
| T161 | C | 0.84 | 0.56 | 1.01 |
| T161 | D | −0.14 | −0.21 | −0.02 |
| T161 | E | −0.14 | −0.21 | −0.02 |
| T161 | G | 0.92 | 0.43 | 0.94 |
| T161 | H | 1.82 | −0.15 | 0.42 |
| T161 | I | 1.40 | 0.98 | 0.91 |
| T161 | L | 1.25 | 1.16 | 0.81 |
| T161 | M | 0.57 | 1.72 | 0.83 |
| T161 | N | 0.80 | −0.86 | 0.32 |
| T161 | P | −0.14 | −0.21 | −0.02 |
| T161 | Q | 1.04 | 1.50 | 0.90 |
| T161 | R | 3.61 | −1.68 | 0.42 |
| T161 | S | 0.92 | 0.57 | 0.98 |
| T161 | T | 1.00 | 1.00 | 1.00 |
| T161 | V | 1.27 | 1.24 | 1.00 |
| T161 | W | 1.41 | 0.00 | 0.52 |
| T161 | Y | 2.40 | 2.62 | 0.23 |
| T162 | C | 0.95 | 3.57 | 1.17 |
| T162 | F | 0.99 | 3.23 | 1.05 |
| T162 | G | 1.00 | 1.82 | 0.88 |
| T162 | H | 1.02 | 3.91 | 1.08 |
| T162 | I | 0.99 | 2.21 | 1.16 |
| T162 | K | 1.22 | 3.13 | 0.98 |
| T162 | L | 1.00 | 3.59 | 1.05 |
| T162 | M | 0.77 | 3.49 | 0.89 |
| T162 | N | 0.83 | 3.84 | 0.98 |
| T162 | P | 0.96 | 4.37 | 0.81 |
| T162 | Q | 0.93 | 2.45 | 0.89 |
| T162 | R | 1.17 | 1.23 | 0.80 |
| T162 | S | 0.98 | 2.01 | 0.97 |
| T162 | T | 1.00 | 1.00 | 1.00 |
| T162 | W | 1.15 | 2.04 | 0.85 |
| T162 | Y | 1.03 | 2.89 | 1.03 |
| E163 | A | 1.11 | 1.79 | 0.73 |
| E163 | C | 1.11 | 1.08 | 0.67 |
| E163 | D | 0.90 | 1.08 | 0.82 |
| E163 | E | 1.00 | 1.00 | 1.00 |
| E163 | F | 1.07 | 0.27 | 0.49 |
| E163 | G | 1.25 | 0.80 | 0.79 |
| E163 | H | 1.32 | 0.82 | 0.69 |
| E163 | L | 1.50 | 1.94 | 0.58 |
| E163 | N | 0.91 | 1.00 | 0.77 |
| E163 | P | 0.08 | 0.77 | 0.30 |
| E163 | R | 1.12 | 0.49 | 0.72 |
| E163 | S | 1.12 | 0.85 | 0.81 |
| E163 | V | 1.13 | 0.55 | 0.69 |
| E163 | W | 1.21 | 0.98 | 0.49 |
| E163 | Y | 1.41 | 1.89 | 0.60 |
| L164 | A | −0.14 | −0.85 | 0.21 |
| L164 | C | 0.09 | 0.91 | 0.63 |
| L164 | D | −0.14 | −0.85 | 0.12 |
| L164 | E | −0.14 | −0.48 | 0.18 |
| L164 | F | 0.50 | 0.86 | 0.94 |
| L164 | G | −0.14 | −0.14 | 0.19 |
| L164 | H | 0.02 | 0.12 | 0.16 |
| L164 | L | 1.00 | 1.00 | 1.00 |
| L164 | M | 0.69 | 1.26 | 1.09 |
| L164 | N | −0.14 | 1.31 | 0.26 |
| L164 | P | −0.14 | 2.41 | 0.17 |
| L164 | Q | −0.14 | 1.01 | 0.24 |
| L164 | R | −0.14 | 1.61 | 0.17 |
| L164 | S | 0.32 | 1.11 | 0.25 |
| L164 | T | 0.82 | 0.99 | 0.52 |
| L164 | V | 0.87 | 1.02 | 1.08 |
| L164 | Y | 0.43 | −1.28 | 0.20 |
| A165 | A | 1.00 | 1.00 | 1.00 |

TABLE 10-12-continued

| Performance Indices | | | | |
|---|---|---|---|---|
| Wild-Type Res./Pos. | Mut. | PAF PI | PAD PI | Prot. PI |
| A165 | C | 0.99 | 1.42 | 0.97 |
| A165 | D | 0.89 | 1.69 | 0.62 |
| A165 | F | 1.23 | 1.00 | 0.74 |
| A165 | G | 1.05 | 1.07 | 1.14 |
| A165 | I | 1.17 | 0.59 | 0.64 |
| A165 | K | 1.35 | 0.82 | 0.78 |
| A165 | L | 1.08 | 1.55 | 0.70 |
| A165 | M | 0.97 | 1.56 | 0.77 |
| A165 | N | 1.01 | 1.20 | 0.91 |
| A165 | P | 1.14 | 1.34 | 0.91 |
| A165 | Q | 1.21 | 1.32 | 1.05 |
| A165 | R | 1.70 | 1.29 | 0.87 |
| A165 | S | 1.00 | 0.94 | 1.05 |
| A165 | T | 1.18 | 1.32 | 0.83 |
| A165 | V | 1.21 | 1.13 | 0.88 |
| A165 | Y | 1.20 | 0.84 | 0.67 |
| R166 | A | 0.73 | 1.51 | 1.12 |
| R166 | D | 0.56 | 1.55 | 1.16 |
| R166 | F | 1.00 | 1.10 | 0.85 |
| R166 | G | 1.15 | 0.91 | 1.19 |
| R166 | H | 1.20 | 1.56 | 0.97 |
| R166 | I | 1.26 | 1.39 | 0.86 |
| R166 | K | 1.17 | 1.20 | 1.19 |
| R166 | L | 1.27 | 1.50 | 1.08 |
| R166 | M | 0.65 | 1.29 | 1.26 |
| R166 | N | 0.75 | 1.21 | 1.16 |
| R166 | P | 0.43 | 1.50 | 0.97 |
| R166 | R | 1.00 | 1.00 | 1.00 |
| R166 | S | 1.16 | 0.95 | 0.98 |
| R166 | T | 1.19 | 0.74 | 1.04 |
| R166 | V | 1.17 | 0.76 | 0.94 |
| R166 | W | 1.25 | 1.08 | 0.80 |
| R166 | Y | 1.29 | 1.22 | 0.85 |
| V167 | A | 0.56 | 4.99 | 0.98 |
| V167 | C | 0.79 | 5.37 | 1.01 |
| V167 | D | 0.56 | 5.54 | 0.98 |
| V167 | G | 0.99 | 2.83 | 1.08 |
| V167 | H | 1.03 | 2.11 | 1.12 |
| V167 | I | 1.08 | 1.00 | 1.04 |
| V167 | L | 0.84 | 2.56 | 1.13 |
| V167 | M | 0.53 | 3.84 | 1.04 |
| V167 | P | 0.31 | 6.08 | 0.85 |
| V167 | Q | 0.55 | 2.41 | 0.97 |
| V167 | R | 0.78 | 2.25 | 0.88 |
| V167 | S | 0.96 | 1.86 | 1.04 |
| V167 | T | 1.13 | 2.47 | 0.96 |
| V167 | V | 1.00 | 1.00 | 1.00 |
| V167 | Y | 1.07 | 2.15 | 0.94 |
| Y168 | C | 0.69 | −4.73 | 0.57 |
| Y168 | D | −0.11 | −1.98 | −0.03 |
| Y168 | E | −0.11 | −1.98 | −0.03 |
| Y168 | F | 0.68 | 5.17 | 1.28 |
| Y168 | G | 1.89 | −40.74 | 0.23 |
| Y168 | H | −0.11 | −1.98 | −0.03 |
| Y168 | I | 0.83 | −0.59 | 0.90 |
| Y168 | K | −0.11 | −1.98 | −0.03 |
| Y168 | L | 0.59 | 5.39 | 1.27 |
| Y168 | N | −0.11 | −1.98 | −0.03 |
| Y168 | P | −0.11 | −1.98 | −0.03 |
| Y168 | Q | 0.28 | −8.27 | 0.25 |
| Y168 | R | −0.11 | −1.98 | −0.03 |
| Y168 | S | −0.11 | −1.98 | −0.03 |
| Y168 | T | 1.51 | −22.96 | 0.39 |
| Y168 | V | 1.19 | −12.96 | 0.57 |
| Y168 | W | −0.11 | −1.98 | −0.03 |
| Y168 | Y | 1.00 | 1.00 | 1.00 |
| S169 | A | 0.94 | 1.13 | 0.95 |
| S169 | C | 1.03 | 1.38 | 0.78 |
| S169 | I | 1.16 | 1.53 | 0.66 |
| S169 | K | 1.21 | 1.27 | 0.94 |
| S169 | L | 1.08 | 1.47 | 0.82 |
| S169 | M | 0.86 | 1.40 | 0.86 |
| S169 | P | 0.87 | 0.89 | 0.69 |
| S169 | Q | 1.02 | 1.37 | 0.88 |
| S169 | R | 1.24 | 1.19 | 0.77 |

TABLE 10-12-continued

| Wild-Type Res./Pos. | Mut. | PAF PI | PAD PI | Prot. PI |
|---|---|---|---|---|
| | | Performance Indices | | |
| S169 | S | 1.00 | 1.00 | 1.00 |
| S169 | T | 1.15 | 0.97 | 0.82 |
| S169 | Y | 1.26 | 1.10 | 0.77 |
| A170 | A | 1.00 | 1.00 | 1.00 |
| A170 | C | 1.15 | 1.06 | 1.02 |
| A170 | D | 1.27 | 1.32 | 0.88 |
| A170 | E | 1.28 | 1.17 | 0.99 |
| A170 | F | 1.44 | 1.17 | 0.83 |
| A170 | G | 1.59 | 0.62 | 0.96 |
| A170 | I | 1.59 | 0.44 | 0.95 |
| A170 | K | 1.71 | 0.83 | 0.96 |
| A170 | L | 1.05 | 0.85 | 0.87 |
| A170 | M | 1.03 | 1.28 | 0.93 |
| A170 | N | 1.21 | 1.17 | 0.96 |
| A170 | P | 0.75 | 1.33 | 0.80 |
| A170 | Q | 1.15 | 0.89 | 0.98 |
| A170 | S | 1.47 | 0.47 | 0.99 |
| A170 | T | 1.40 | 0.72 | 0.86 |
| A170 | V | 1.20 | 0.74 | 0.83 |
| A170 | W | 1.04 | 0.83 | 0.82 |
| A170 | Y | 0.80 | 0.89 | 0.89 |
| L171 | A | 0.35 | 1.66 | 0.79 |
| L171 | C | 0.56 | 1.73 | 0.97 |
| L171 | D | −0.06 | −0.13 | −0.01 |
| L171 | F | 1.30 | 1.97 | 0.87 |
| L171 | G | 1.26 | 1.33 | 0.50 |
| L171 | H | 1.67 | 1.07 | 0.61 |
| L171 | I | 1.53 | 1.42 | 1.16 |
| L171 | K | 2.05 | 1.53 | 0.31 |
| L171 | L | 1.00 | 1.00 | 1.00 |
| L171 | M | 0.53 | 2.22 | 0.90 |
| L171 | N | 0.96 | 2.79 | 0.40 |
| L171 | Q | 0.97 | 1.93 | 0.67 |
| L171 | R | 0.71 | −0.20 | 0.24 |
| L171 | S | 1.43 | 1.76 | 0.72 |
| L171 | T | 1.54 | 1.36 | 0.80 |
| L171 | V | 1.02 | 1.39 | 0.92 |
| L171 | Y | 1.20 | 1.35 | 0.88 |
| A172 | A | 1.00 | 1.00 | 1.00 |
| A172 | C | 1.20 | 0.86 | 1.09 |
| A172 | D | −0.15 | 1.42 | 0.16 |
| A172 | E | −0.15 | −0.44 | 0.19 |
| A172 | G | 1.41 | 0.84 | 1.07 |
| A172 | I | 1.70 | 0.58 | 0.30 |
| A172 | K | 0.95 | −0.43 | 0.17 |
| A172 | L | 1.20 | 1.22 | 0.70 |
| A172 | M | 0.84 | 1.06 | 0.84 |
| A172 | N | 0.37 | 0.76 | 0.30 |
| A172 | P | −0.15 | 0.58 | 0.16 |
| A172 | Q | 0.27 | 0.18 | 0.34 |
| A172 | R | 0.44 | −0.18 | 0.20 |
| A172 | S | 1.59 | 0.85 | 0.96 |
| A172 | T | 1.25 | 0.71 | 0.85 |
| A172 | V | 1.40 | 0.39 | 0.53 |
| A172 | W | 1.43 | 0.45 | 0.12 |
| A172 | Y | 0.87 | 1.76 | 0.13 |
| S173 | A | 0.81 | 2.72 | 0.95 |
| S173 | C | 0.82 | 3.07 | 0.59 |
| S173 | E | 0.78 | 2.65 | 0.90 |
| S173 | F | 0.96 | 2.30 | 0.71 |
| S173 | H | 1.07 | 1.49 | 0.95 |
| S173 | I | 0.99 | 2.22 | 0.78 |
| S173 | K | 1.17 | 3.01 | 0.91 |
| S173 | L | 1.15 | 3.86 | 0.77 |
| S173 | M | 0.80 | 3.01 | 0.84 |
| S173 | P | 0.19 | 2.66 | 0.35 |
| S173 | R | 1.09 | 2.47 | 0.82 |
| S173 | S | 1.00 | 1.00 | 1.00 |
| S173 | T | 1.06 | 1.29 | 0.89 |
| S173 | V | 0.95 | 2.54 | 0.75 |
| S173 | W | 1.16 | 3.67 | 0.67 |
| S173 | Y | 1.19 | 3.54 | 0.81 |
| F174 | A | 0.59 | 2.09 | 0.61 |
| F174 | C | 1.32 | 0.48 | 0.65 |
| F174 | F | 1.00 | 1.00 | 1.00 |

TABLE 10-12-continued

| Wild-Type Res./Pos. | Mut. | PAF PI | PAD PI | Prot. PI |
|---|---|---|---|---|
| | | Performance Indices | | |
| F174 | G | 1.60 | 0.91 | 0.85 |
| F174 | H | 0.93 | 1.05 | 0.86 |
| F174 | K | 0.86 | 1.17 | 0.76 |
| F174 | L | 1.05 | 1.83 | 0.82 |
| F174 | M | 0.91 | 2.20 | 0.55 |
| F174 | P | 1.54 | 1.46 | 0.13 |
| F174 | Q | 1.42 | 0.46 | 0.82 |
| F174 | R | 0.70 | 0.52 | 0.95 |
| F174 | S | 1.16 | 0.61 | 0.75 |
| F174 | T | 0.80 | 0.64 | 0.62 |
| F174 | V | 0.60 | 0.67 | 0.82 |
| F174 | W | 0.96 | −0.02 | 0.85 |
| F174 | Y | 0.84 | 1.66 | 0.77 |
| M175 | A | 0.70 | 0.66 | 0.95 |
| M175 | E | 0.95 | 1.43 | 0.89 |
| M175 | G | 2.04 | 0.75 | 0.67 |
| M175 | L | 1.61 | 0.86 | 1.19 |
| M175 | M | 1.00 | 1.00 | 1.00 |
| M175 | N | 1.39 | 1.02 | 1.11 |
| M175 | P | −0.20 | 0.08 | 0.16 |
| M175 | Q | 1.56 | 0.83 | 0.98 |
| M175 | R | 1.55 | 0.86 | 1.02 |
| M175 | T | 2.21 | 0.90 | 0.98 |
| M175 | V | 1.93 | 0.81 | 1.00 |
| M175 | W | 1.25 | 0.76 | 1.14 |
| M175 | Y | 0.77 | 0.72 | 1.35 |
| K176 | A | 0.42 | 1.19 | 0.84 |
| K176 | C | 0.58 | 1.01 | 0.87 |
| K176 | D | 0.62 | 1.18 | 0.74 |
| K176 | E | 0.67 | 1.08 | 0.88 |
| K176 | F | 0.36 | 1.28 | 0.31 |
| K176 | G | 1.01 | 0.73 | 0.80 |
| K176 | K | 1.00 | 1.00 | 1.00 |
| K176 | L | 1.00 | 0.92 | 0.58 |
| K176 | M | 0.56 | 1.33 | 0.74 |
| K176 | N | 0.60 | 0.94 | 0.85 |
| K176 | P | 0.01 | 0.78 | 0.27 |
| K176 | Q | 0.59 | 0.97 | 1.02 |
| K176 | R | 0.71 | 1.03 | 1.06 |
| K176 | S | 0.76 | 0.72 | 0.93 |
| K176 | T | 1.04 | 0.97 | 0.70 |
| K176 | V | 1.04 | 1.33 | 0.71 |
| K176 | W | 1.19 | 1.16 | 0.41 |
| K176 | Y | 1.04 | 0.93 | 0.60 |
| P178 | A | 0.31 | 4.39 | 0.96 |
| P178 | D | 0.18 | 6.44 | 0.93 |
| P178 | E | 0.40 | 4.15 | 1.05 |
| P178 | G | 1.09 | 2.95 | 0.67 |
| P178 | K | 1.34 | 1.70 | 0.73 |
| P178 | L | 1.82 | 7.15 | 0.53 |
| P178 | M | 0.53 | 3.87 | 0.78 |
| P178 | P | 0.06 | 5.02 | 0.93 |
| P178 | Q | 0.15 | 3.64 | 0.93 |
| P178 | S | 0.62 | 3.06 | 0.95 |
| P178 | T | 0.70 | 2.28 | 0.81 |
| P178 | V | 0.67 | 2.70 | 0.78 |
| P178 | W | 1.14 | 0.02 | 0.64 |
| P178 | Y | 1.38 | 6.91 | 0.74 |
| F179 | A | −0.18 | −0.22 | −0.02 |
| F179 | E | 0.02 | 1.80 | 0.20 |
| F179 | F | 1.00 | 1.00 | 1.00 |
| F179 | G | 0.03 | 1.16 | 0.36 |
| F179 | H | 0.79 | 0.93 | 0.91 |
| F179 | L | 1.15 | 1.89 | 0.43 |
| F179 | N | 0.77 | 0.95 | 0.46 |
| F179 | P | −0.18 | −0.22 | −0.02 |
| F179 | Q | 0.46 | −0.87 | 0.46 |
| F179 | R | −0.18 | −0.22 | −0.02 |
| F179 | S | 0.78 | 0.34 | 0.62 |
| F179 | V | 0.70 | 1.17 | 0.69 |
| F179 | W | 0.89 | 0.86 | 0.62 |
| F179 | Y | 1.05 | 1.47 | 0.65 |
| F180 | A | 0.03 | 2.70 | 0.27 |
| F180 | C | 0.65 | 1.94 | 0.66 |
| F180 | E | −0.14 | −0.55 | −0.02 |

TABLE 10-12-continued

Performance Indices

| Wild-Type Res./Pos. | Mut. | PAF PI | PAD PI | Prot. PI |
|---|---|---|---|---|
| F180 | F | 1.00 | 1.00 | 1.00 |
| F180 | G | 0.37 | −5.96 | 0.20 |
| F180 | I | 1.20 | 2.11 | 0.79 |
| F180 | K | 1.08 | −6.98 | 0.24 |
| F180 | L | 1.30 | 2.13 | 0.86 |
| F180 | M | 0.71 | 4.36 | 0.96 |
| F180 | N | −0.14 | 3.05 | 0.29 |
| F180 | Q | 0.21 | −1.87 | 0.36 |
| F180 | R | 0.64 | −3.57 | 0.26 |
| F180 | S | 0.56 | −2.05 | 0.29 |
| F180 | T | 1.01 | −0.68 | 0.33 |
| F180 | V | 1.14 | 3.24 | 0.76 |
| F180 | W | 1.11 | 1.81 | 0.90 |
| F180 | Y | 1.12 | 2.99 | 0.84 |
| D181 | A | 1.35 | 1.23 | 0.65 |
| D181 | C | 1.09 | 0.85 | 0.56 |
| D181 | D | 1.00 | 1.00 | 1.00 |
| D181 | E | 1.10 | 0.72 | 0.78 |
| D181 | F | −0.15 | −0.17 | −0.01 |
| D181 | G | 1.09 | 0.52 | 0.37 |
| D181 | H | −0.15 | −0.17 | −0.01 |
| D181 | I | −0.15 | −0.17 | −0.01 |
| D181 | K | 1.33 | 0.47 | 0.41 |
| D181 | L | 1.25 | −0.16 | 0.16 |
| D181 | M | −0.15 | −0.17 | −0.01 |
| D181 | N | −0.15 | −0.17 | −0.01 |
| D181 | P | 1.03 | 0.66 | 0.60 |
| D181 | Q | 1.14 | 0.60 | 0.54 |
| D181 | R | 1.23 | 0.22 | 0.45 |
| D181 | S | 1.21 | 0.55 | 0.56 |
| D181 | T | 1.02 | −0.32 | 0.24 |
| D181 | V | 0.88 | −0.34 | 0.21 |
| D181 | W | 1.26 | −0.52 | 0.28 |
| D181 | Y | 1.29 | −0.25 | 0.25 |
| A182 | A | 1.00 | 1.00 | 1.00 |
| A182 | C | 0.97 | 0.99 | 1.03 |
| A182 | G | 0.92 | 0.94 | 0.90 |
| A182 | H | −0.14 | −0.18 | −0.02 |
| A182 | I | 0.89 | −2.48 | 0.20 |
| A182 | K | −0.14 | −0.18 | −0.02 |
| A182 | L | −0.14 | −0.18 | −0.02 |
| A182 | M | −0.14 | −0.18 | −0.02 |
| A182 | N | −0.14 | 0.53 | 0.14 |
| A182 | P | −0.14 | −1.13 | 0.12 |
| A182 | Q | 0.03 | −0.84 | 0.14 |
| A182 | R | 0.25 | −2.69 | 0.12 |
| A182 | S | 0.87 | 0.85 | 0.90 |
| A182 | T | 1.14 | 0.11 | 0.48 |
| A182 | W | −0.14 | −0.18 | −0.02 |
| A182 | Y | −0.14 | −0.18 | −0.02 |
| G183 | C | 0.56 | 1.99 | 0.92 |
| G183 | D | 0.30 | 0.99 | 0.62 |
| G183 | F | 0.68 | 0.19 | 0.75 |
| G183 | G | 1.00 | 1.00 | 1.00 |
| G183 | H | 0.98 | 0.95 | 0.87 |
| G183 | L | 0.82 | 1.50 | 0.47 |
| G183 | P | −0.18 | 1.02 | 0.33 |
| G183 | Q | 0.66 | −0.20 | 0.97 |
| G183 | R | 0.92 | 1.09 | 0.90 |
| G183 | S | 0.94 | −0.08 | 1.08 |
| G183 | V | 0.56 | −2.47 | 0.57 |
| G183 | Y | 0.97 | 1.45 | 0.79 |
| S184 | A | 0.60 | 1.69 | 1.31 |
| S184 | C | 0.81 | 2.39 | 1.14 |
| S184 | D | 0.84 | 2.24 | 1.15 |
| S184 | E | 0.94 | 1.86 | 1.39 |
| S184 | F | 1.05 | 1.27 | 0.89 |
| S184 | G | 0.99 | 0.82 | 1.15 |
| S184 | H | 1.02 | 0.74 | 1.07 |
| S184 | I | 0.92 | 1.21 | 0.96 |
| S184 | K | 0.97 | 1.61 | 1.02 |
| S184 | L | 0.80 | 2.00 | 0.98 |
| S184 | M | 0.51 | 1.77 | 1.25 |
| S184 | N | 0.64 | 1.93 | 1.03 |
| S184 | P | −0.15 | 0.85 | 0.40 |
| S184 | Q | 0.89 | 1.16 | 1.09 |
| S184 | S | 1.00 | 1.00 | 1.00 |
| S184 | T | 1.04 | 0.60 | 0.94 |
| S184 | V | 0.80 | 1.25 | 1.03 |
| S184 | Y | 1.06 | 1.09 | 0.84 |
| V185 | C | 0.65 | 0.83 | 0.96 |
| V185 | D | 0.40 | −2.49 | 0.21 |
| V185 | E | 0.73 | 0.88 | 0.76 |
| V185 | F | 1.02 | 1.20 | 0.83 |
| V185 | G | 1.12 | −3.67 | 0.47 |
| V185 | H | 1.30 | −0.58 | 0.71 |
| V185 | I | 1.07 | 0.63 | 1.03 |
| V185 | K | 1.37 | 0.79 | 0.66 |
| V185 | L | 1.23 | 0.93 | 0.75 |
| V185 | M | 0.39 | 1.46 | 0.77 |
| V185 | Q | 0.77 | 1.41 | 0.73 |
| V185 | R | 1.15 | 0.79 | 0.57 |
| V185 | S | 1.09 | 0.53 | 0.75 |
| V185 | T | 1.11 | 0.91 | 0.79 |
| V185 | V | 1.00 | 1.00 | 1.00 |
| V185 | W | 1.36 | −0.44 | 0.53 |
| V185 | Y | 1.37 | 0.58 | 0.65 |
| I186 | A | 1.46 | 1.79 | 0.90 |
| I186 | D | −0.13 | 4.29 | 0.19 |
| I186 | F | 1.01 | 0.76 | 0.77 |
| I186 | G | 1.86 | −5.42 | 0.35 |
| I186 | I | 1.00 | 1.00 | 1.00 |
| I186 | K | −0.13 | −0.36 | −0.01 |
| I186 | L | 1.17 | 1.14 | 0.84 |
| I186 | M | 0.86 | 1.38 | 1.11 |
| I186 | P | −0.13 | −2.95 | 0.25 |
| I186 | R | 0.62 | −6.69 | 0.25 |
| I186 | S | 1.39 | −0.21 | 0.65 |
| I186 | T | 1.51 | 0.23 | 0.79 |
| I186 | V | 1.28 | 0.48 | 0.93 |
| I186 | W | −0.13 | −0.36 | −0.01 |
| I186 | Y | −0.13 | −0.36 | −0.01 |
| S187 | A | 0.51 | 1.72 | 0.86 |
| S187 | C | 0.70 | 1.67 | 0.79 |
| S187 | D | 0.59 | 1.40 | 0.82 |
| S187 | F | 1.02 | 0.65 | 0.73 |
| S187 | G | 1.03 | 1.46 | 0.88 |
| S187 | H | 1.29 | 1.51 | 0.68 |
| S187 | I | 1.38 | 1.58 | 0.78 |
| S187 | K | 1.45 | 1.16 | 0.76 |
| S187 | L | 1.37 | 1.46 | 0.75 |
| S187 | M | 0.49 | 1.87 | 0.85 |
| S187 | N | 0.59 | 1.59 | 0.90 |
| S187 | P | 0.44 | −0.31 | 0.78 |
| S187 | Q | 0.63 | 0.35 | 0.94 |
| S187 | R | 1.04 | 0.55 | 0.82 |
| S187 | S | 1.00 | 1.00 | 1.00 |
| S187 | T | 1.12 | 0.23 | 0.74 |
| S187 | V | 1.23 | 0.58 | 0.89 |
| S187 | W | 1.30 | 0.52 | 0.73 |
| S187 | Y | 1.43 | 0.80 | 0.76 |
| T188 | A | 0.97 | 0.95 | 1.40 |
| T188 | C | 0.60 | 0.87 | 2.04 |
| T188 | D | −0.05 | −0.14 | −0.02 |
| T188 | E | 0.24 | 1.97 | 0.44 |
| T188 | F | 0.96 | −0.20 | 0.63 |
| T188 | G | 0.93 | 0.79 | 1.32 |
| T188 | H | 1.11 | −0.79 | 0.74 |
| T188 | I | 1.13 | 0.10 | 1.85 |
| T188 | K | −0.05 | −0.14 | −0.02 |
| T188 | L | 0.76 | 0.42 | 1.76 |
| T188 | M | 0.49 | 0.75 | 1.60 |
| T188 | N | 0.69 | 1.69 | 1.24 |
| T188 | P | −0.05 | −0.14 | −0.02 |
| T188 | Q | −0.05 | −0.14 | −0.02 |
| T188 | R | 1.01 | −0.47 | 1.41 |
| T188 | S | 1.16 | 0.91 | 1.52 |
| T188 | T | 1.00 | 1.00 | 1.00 |
| T188 | V | 1.22 | 0.15 | 1.53 |
| T188 | W | −0.05 | −0.14 | −0.02 |

TABLE 10-12-continued

| Performance Indices | | | | |
|---|---|---|---|---|
| Wild-Type Res./Pos. | Mut. | PAF PI | PAD PI | Prot. PI |
| T188 | Y | 1.48 | 0.09 | 0.47 |
| D189 | A | 0.05 | 1.18 | 0.53 |
| D189 | C | 0.19 | 0.94 | 0.56 |
| D189 | D | 0.03 | 0.89 | 0.90 |
| D189 | E | 0.35 | 0.77 | 0.85 |
| D189 | F | 0.83 | 0.37 | 0.63 |
| D189 | G | 0.80 | 0.80 | 0.83 |
| D189 | H | 1.25 | 0.95 | 0.78 |
| D189 | I | 0.73 | 1.27 | 0.69 |
| D189 | L | 1.30 | 1.30 | 0.61 |
| D189 | M | 0.06 | 0.88 | 0.48 |
| D189 | N | 0.22 | 0.57 | 0.80 |
| D189 | P | −0.12 | 0.97 | 0.67 |
| D189 | R | 0.86 | 0.39 | 0.65 |
| D189 | S | 0.88 | 0.81 | 0.85 |
| D189 | T | 1.00 | 1.21 | 0.73 |
| D189 | V | 0.73 | 0.71 | 0.72 |
| D189 | W | 1.09 | 0.76 | 0.60 |
| I194 | A | 0.29 | 0.00 | 1.15 |
| I194 | C | 0.27 | −0.02 | 1.17 |
| I194 | F | 0.07 | −0.03 | 0.95 |
| I194 | G | 0.10 | 0.04 | 0.34 |
| I194 | I | 1.00 | 1.00 | 1.00 |
| I194 | L | 0.80 | 0.58 | 1.32 |
| I194 | P | 0.15 | −1.42 | 0.16 |
| I194 | R | 0.02 | −0.40 | 0.77 |
| I194 | S | 0.30 | −0.15 | 0.48 |
| I194 | V | 0.37 | 0.78 | 1.03 |
| I194 | W | 0.04 | −0.09 | 1.12 |
| I194 | Y | −0.32 | −0.01 | 1.01 |
| F196 | A | −0.13 | −0.13 | −0.02 |
| F196 | C | 1.74 | 1.18 | 0.70 |
| F196 | F | 1.00 | 1.00 | 1.00 |
| F196 | G | 1.59 | −0.30 | 0.60 |
| F196 | H | 1.77 | −0.24 | 0.23 |
| F196 | I | 1.32 | 1.12 | 0.81 |
| F196 | K | −0.13 | −0.13 | −0.02 |
| F196 | L | 1.77 | 1.17 | 1.09 |
| F196 | M | 1.65 | 0.71 | 0.93 |
| F196 | N | −0.13 | −0.13 | −0.02 |

TABLE 10-12-continued

| Performance Indices | | | | |
|---|---|---|---|---|
| Wild-Type Res./Pos. | Mut. | PAF PI | PAD PI | Prot. PI |
| F196 | P | 0.05 | 0.39 | 0.42 |
| F196 | Q | 1.00 | −0.25 | 0.40 |
| F196 | R | −0.13 | −0.13 | −0.02 |
| F196 | S | 1.58 | −1.57 | 0.29 |
| F196 | V | 1.40 | 0.68 | 0.51 |
| F196 | W | 1.01 | 0.38 | 0.88 |
| F196 | Y | 1.41 | 0.97 | 0.73 |

Example 11

Figure 20:
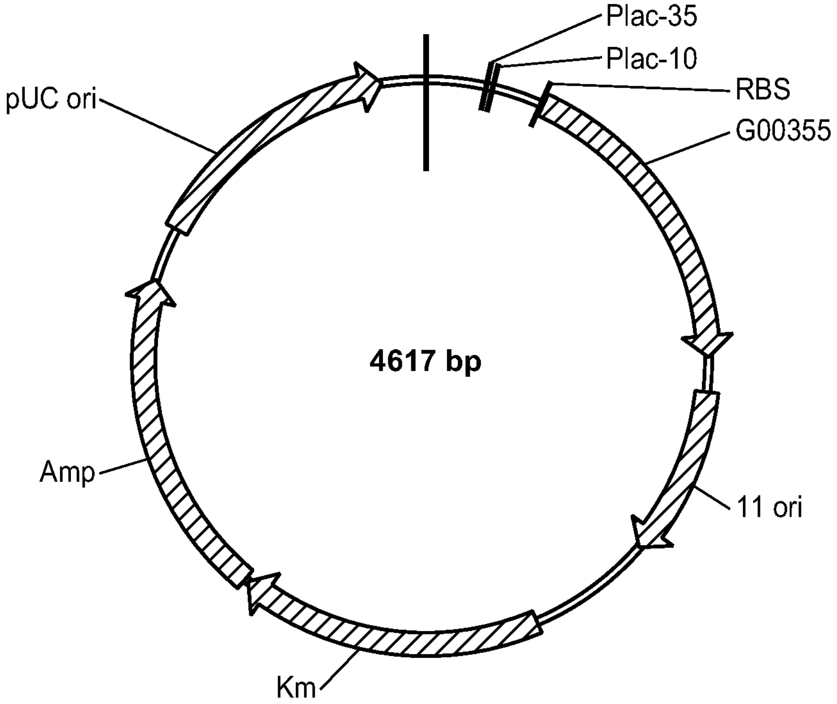
FIG. 20 provides a map of plasmid pMC355rbs.

Cloning and Expression of a *Sinorhizobium meliloti* RSM02162 *M. smegmatis* Perhydrolase Homologue In this Example, cloning and expression of a *S. meliloti* perhydrolase homologue are described. The sequences used in cloning and expression are provided below. The gene RSM02162 (SEQ ID NO:625) was synthesized by DNA2.0. The gene was given the designation "G00355" and was provided cloned into the commercially available vector, pDRIVE (InvivoGen). The gene was amplified by PCR from this clone using the primer set G00355rbsF/G00355R, Taq DNA polymerase (Roche) as per the manufacturer's directions, with G00355 as the template (10 ng/50 μl reaction) and 10 picomoles (per 50 μl reaction) of each primer. The amplification was carried out in an MJ Research PCR machine using 30 cycles of (1 minute at 95° C.; 1 minute at 55° C.; and 1 minute at 72° C.). The amplification of the correct size fragment was confirmed by agarose gel electrophoresis. The fragment was cloned directly into pCR2.1TOPO (Invitrogen) and transformed into *E. coli* Top10 cells (Invitrogen). Transformants were selected on L agar containing carbenicillin (100 μg/ml) at 37° C. The correct construct was confirmed by sequence analysis and designated "pMC355rbs." FIG. 20 provides a map of this plasmid.

```
Primer sequences:
G00355rbsF
                                                          (SEQ ID NO: 626)
5'-ggccctaacaggaggaattaaccatggtggaaaaacgttccgttctgtgc-3'

G00355R
                                                          (SEQ ID NO: 627)
5'-Gcgcgcttagaacagagccgctactttgtcagc-3'

Gene sequence (including stop codon) of RSM02162:
                                                          (SEQ ID NO: 625)
5'-
atggtggaaaaacgttccgttctgtgctttggtgattctctgacttggggctggattccggtgaaagagagctccccaactctgcgtt
acccatacgaacagcgttggaccggtgctatggctgcacgtctgggtgatggttaccacatcattgaagaaggcctgtccgctcgt
actactagcctggacgacccaaacgacgctcgtctgaacggctctacctacctgccgatggctctggcttcacctgccactgga
tctggtaatcattatgctgggtaccaacgacaccaaaagctactttcatcgtaccccatacgagattgccaacggcatgggtaaact
ggtaggtcaggtcctgacctgtgcaggtggtgttggtacgccttatccagcaccgaaagtcctggtggttgcacctccaccactgg
caccaatgccagatccgtggttcgaaggtatgttcggcggtggttacgagaaatctaaggaactgtccggtctgtacaaagcactg
gctgatttcatgaaagtggagttcttcgcagcgggtgattgtatctccaccgacggtatcgacggtatccacctgagcgctgaaacc
aacatccgcctgggtcatgctattgctgacaaagtagcggctctgttctaa-3'

G00355 Protein sequence:
                                                          (SEQ ID NO: 628)
MVEKRSVLCFGDSLTWGWIPVKESSPTLRYPYEQRWTGAMAARLGDGYHIIEEG
LSARTTSLDDPNDARLNGSTYLPMALASHLPLDLVIIMLGTNDTKSYFHRTPYEIA
NGMGKLVGQVLTCAGGVGTPYPAPKVLVVAPPPLAPMPDPWFEGMFGGGYEKS
KELSGLYKALADFMKVEFFAAGDCISTDGIDGIHLSAETNIRLGHAIADKVAALF
```

-continued

Complete sequence of pDRIVEG00355:

(SEQ ID NO: 629)

gcgcccaatacgcaaaccgcctctccccgcgcgttggccgattcattaatgcagctggcacgacaggtttcccgactggaaagc
gggcagtgagcgcaacgcaattaatgtgagttagctcactcattaggcaccccaggctttacactttatgcttccggctcgtatgttg
tgtggaattgtgagcggataacaatttcacacaggaaacagctatgaccatgattacgccaagctctaatacgactcactataggg
aaagctcggtaccacgcatgctgcagacgcgttacgtatcggatccagaattcgtgattttagaacagagccgctactttgtcagca
atagcatgacccaggcggatgttggtttcagcgctcaggtggataccgtcgataccgtcggtggagatacaatcacccgctgcga
agaactccactttcatgaaatcagccagtgctttgtacagaccggacagttccttagatttctcgtaaccaccgccgaacatacctte
gaaccacggatctggcattggtgccagtggtggaggtgcaaccaccaggactttcggtgctggataaggcgtaccaacaccacc
tgcacaggtcaggacctgacctaccagtttacccatgccgttggcaatctcgtatggggtacgatgaaagtagcttttggtgtcgttg
gtacccagcataatgattaccagatccagtggcaggtgagaagccagagccatcggcaggtaggtagagccgttcagacgagc
gtcgtttgggtcgtccaggctagtagtacgagcggacaggccttcttcaatgatgtggtaaccatcacccagacgtgcagccatag
caccggtccaacgctgttcgtatgggtaacgcagagttggggagctctctttcaccggaatccagccccaagtcagagaatcacc
aaagcacagaacggaacgttttccaccataatctgaattcgtcgacaagcttctcgagcctaggctagctctagaccacacgtgtg
ggggcccgagctcgcggccgctgtattctatagtgtcacctaaatggccgcacaattcactggccgtcgttttacaacgtcgtgact
gggaaaaccctggcgttacccaacttaatcgccttgcagcacatccccctttcgccagctggcgtaatagcgaagaggcccgcac
cgatcgcccttcccaacagttgcgcagcctgaatggcgaatggaaattgtaagcgttaatattttgttaaaattcgcgttaaatttttgt
taaatcagctcattttttaaccaataggccgaaatcggcaaaatcccttataaatcaaaagaatagaccgagatagggttgagtgttg
ttccagtttggaacaagagtccactattaaagaacgtggactccaacgtcaaagggcgaaaaaccgtctatcagggcgatggccc
actacgtgaaccatcaccctaatcaagttttttggggtcgaggtgccgtaaagcactaaatcggaaccctaaagggagcccccgat
ttagagcttgacggggaaagccggcgaacgtggcgagaaaggaagggaagaaagcgaaaggagcgggcgctagggcgctg
gcaagtgtagcggtcacgctgcgcgtaaccaccacacccgccgcgcttaatgcgccgctacagggcgcgtcaggtggcactttt
cggggaaatgtgcgcggaacccctatttgtttatttttctaaatacattcaaatatgtatccgctcatgagacaataaccctgataaatg
cttcaataatattgaaaaaggaagagtatgagtattcaacatttccgtgtcgcccttattcccttttttgcggcattttgccttcctgtttttt
gctcacccagaaacgctggtgaaagtaaaagatgctgaagatcagttgggtgcacgagtgggttacatcgaactggatctcaaca
gcggtaagatccttgagagttttcgccccgaagaacgttttccaatgatgagcacttttaaagttctgctatgtggcgcggtattatcc
cgtattgacgccgggcaagagcaactcggtcgccgcatacactaactcagaatgacttggttgagtactcaccagtcacagaaaa
gcatcaacggatggcatgacagtaagagaattatgcagtgctgccataaccatgagtgataacactgcggccaacttacactgac
aacgatcggaggaccgaaggagctaaccgcttttttgcacaacatgggggatcatgtaactcgccttgatcgttgggaaccggag
ctgaatgaagccataccaaacgacgagcgtgacaccacgatgcctgtagcaatggcaacaacgttgcgcaaactattaactggc
gaactacttactctagcttcccggcaacaattaatagactggatggaggcggataaagttgcaggaccacttctgcgctcggccctt
ccggctggctggtttattgctgataaatctggagccggtgagcgtgggtctcgcggtatcattgcagcactggggccagatggtaa
gccctcccgtatcgtagttatctacacgacggggagtcaggcaactatggatgaacgaaatagacagatcgctgagataggtgcc
tcactgattaagcattggtaactgtcagaccaagtttactcatatatactttagattgatttaaaacttcatttttaatttaaaaggatctag
gtgaagatcctttttgataatctcatgaacaataaaactgtctgcttacataaacagtaatacaaggggtgttatgagccatattcaac
gggaaacgtcttgctctaggccgcgattaaattccaacatggatgctgatttatatgggtataaatgggctcgcgataatgtcgggc
aatcaggtgcgacaatctatcgattgtatgggaagcccgatgcgccagagttgtttctgaaacatggcaaaggtagcgttgccaat
gatgttacagatgagatggtcagactaaactggctgacggaatttatgcctcttccgaccatcaagcattttatccgtactcctgatga
tgcatggttactcaccactgcgatccccgggaaaacagcattccaggtattagaagaatatcctgattcaggtgaaaatattgagat
gcgctggcagtgttcctgcgccggagcattcgattcctgtttgtaattgtccttttaacagcgatcgcgtatttcgtctcgctcaggcg
caatcacgaatgaataacggtttggttgatgcgagtgattttgatgacgagcgtaatggctggcctgttgaacaagtctggaaagaa
atgcataaacttttgccattctcaccggattcagtcgtcactcatggtgatttctcacagataaccttatttttgacgaggggaaattaat
aggttgtattgatgttggacgagtcggaatcgcagaccgataccaggatcttgccatcctatggaactgcctcggtgagttttctcct
tcattacagaaacggctttttcaaaaatatggtattgataatcctgatatgaataaattgcagtttcatttgatgctcgatgagtttttctaa
gaattaattcatgaccaaaatcccttaacgtgagttttcgttccactgagcgtcagaccccgtagaaaagatcaaaggatcttcttga
gatcctttttttctgcgcgtaatctgctgcttgcaaacaaaaaaaccaccgctaccagcggtggtttgtttgccggatcaagagctac
caactctttttccgaaggtaactggcttcagcagagcgcagataccaaatactgtccttctagtgtagccgtagttaggccaccactt
caagaactctgtagcaccgcctacatacctcgctctgctaatcctgttaccagtggctgctgccagtggcgataagtcgtgtcttacc
gggttggactcaagacgatagttaccggataaggcgcagcggtcgggctgaacggggggttcgtgcacacagcccagcttgga
gcgaacgacctacaccgaactgagatacctacagcgtgagctatgagaaagcgccacgcttcccgaagggagaaaggcggac
aggtatccggtaagcggcagggtcggaacaggagagcgcacgagggagcttccagggggaaacgcctggtatctttatagtcc
tgtcgggtttcgccacctctgacttgagcgtcgatttttgtgatgctcgtcaggggggcggagcctatggaaaaacgccagcaacg
cggcctttttacggttcctggccttttgctggccttttgctcacatgttctttcctgcgttatcccctgattctgtggataaccgtattaccg
cctttgagtgagctgataccgctcgccgcagccgaacgaccgagcgcagcgagtcagtgagcgaggaagcggaaga Complete sequence pMC355rbs:

(SEQ ID NO: 630)

agcgcccaatacgcaaaccgcctctccccgcgcgttggccgattcattaatgcagctggcacgacaggtttcccgactggaaag
cgggcagtgagcgcaacgcaattaatgtgagttagctcactcattaggcaccccaggctttacactttatgcttccggctcgtatgtt
gtgtggaattgtgagcggataacaatttcacacaggaaacagctatgaccatgattacgccaagcttggtaccgagctcggatcca
ctagtaacggccgccagtgtgctggaattcgcccttggccctaacaggaggaattaaccatggtggaaaaacgttccgttctgtgc
tttggtgattctctgacttggggctggattccggtgaaagagagctccccaactctgcgttacccatacgaacagcgttggaccggt
gctatggctgcacgtctgggtgatggttaccacatcattgaagaaggcctgtccgctcgtactactagcctggacgacccaaacga
cgctcgtctgaacggctctacctacctgccgatggctctggcactcacctgccactggatctggtaatcattatgctgggtaccaac
gacaccaaaagctactttcatcgtaccccatacgagattgccaacggcatgggtaaactggtaggtcaggtcctgacctgtgcag
gtggtgttggtacgccttatccagcaccgaaagtcctggtggttgcacctccaccactggcaccaatgccagatccgtggttcgaa
ggtatgttcggcggtggttacgagaaatctaaggaactgtccggtctgtacaaagcactggctgatttcatgaaagtggagttcttc
gcagcgggtgattgtatctccaccgacggtatcgacggtatccacctgagcgctgaaaccaacatccgcctgggtcatgctattgc
tgacaaagtagcggctctgttctaagcgcgcaagggcgaattctgcagatatccatcacactggcggccgctcgagcatgcatct
agagggcccaattcgccctatagtgagtcgtattacaattcactggccgtcgttttacaacgtcgtgactgggaaaaccctggcgtt
acccaacttaatcgccttgcagcacatccccctttcgccagctggcgtaatagcgaagaggcccgcaccgatcgcccttcccaac
agttgcgcagcctgaatggcgaatggacgcgccctgtagcggcgcattaagcgcggcgggtgtggtggttacgcgcagcgtga
ccgctacacttgccagcgccctagcgcccgctcctttcgctttcttcccttcctttctcgccacgttcgccggctttccccgtcaagct
ctaaatcgggggctccctttagggttccgatttagtgctttacggcacctcgaccccaaaaaacttgattagggtgatggttcacgta
gtgggccatcgccctgatagacggtttttcgccctttgacgttggagtccacgttctttaatagtggactcttgttccaaactggaaca
acactcaaccctatctcggtctattcttttgatttataagggatttgccgatttcggcctattggttaaaaaatgagctgatttaacaaaa
atttaacgcgaattttaacaaaattcagggcgcaagggctgctaaaggaagcggaacacgtagaaagccagtccgcagaaacg -continued

```
gtgctgaccccggatgaatgtcagctactgggctatctggacaagggaaaacgcaagcgcaaagagaaagcaggtagcttgca
gtgggcttacatggcgatagctagactgggcggttttatggacagcaagcgaaccggaattgccagctggggcgccctctggta
aggttgggaagccctgcaaagtaaactggatggctttcttgccgccaaggatctgatggcgcaggggatcaagatctgatcaaga
gacaggatgaggatcgtttcgcatgattgaacaagatggattgcacgcaggttctccggccgcttgggtggagaggctattcggct
atgactgggcacaacagacaatcggctgctctgatgccgccgtgttccggctgtcagcgcaggggcgcccggttctttttgtcaag
accgacctgtccggtgccctgaatgaactgcaggacgaggcagcgcggctatcgtggctggccacgacgggcgttccttgcgc
agctgtgctcgacgttgtcactgaagcgggaagggactggctgctattgggcgaagtgccggggcaggatctcctgtcatccca
ccttgctcctgccgagaaagtatccatcatggctgatgcaatgcggcggctgcatacgcttgatccggctacctgcccattcgacc
accaagcgaaacatcgcatcgagcgagcacgtactcggatggaagccggtcttgtcgatcaggatgatctggacgaagagcatc
aggggctcgcgccagccgaactgttcgccaggctcaaggcgcgcatgcccgacggcgaggatctcgtcgtgacccatggcga
tgcctgcttgccgaatatcatggtggaaaatggccgcttttctggattcatcgactgtggccggctgggtgtggcggaccgctatca
ggacatagcgttggctacccgtgatattgctgaagagcttggcggcgaatgggctgaccgcttcctcgtgctttacggtatcgccg
ctcccgattcgcagcgcatcgccttctatcgccttcttgacgagttcttctgaattgaaaaaggaagagtatgagtattcaacatttcc
gtgtcgcccttattcccttttttgcggcattttgccttcctgtttttgctcacccagaaacgctggtgaaagtaaaagatgctgaagatc
agttgggtgcacgagtgggttacatcgaactggatctcaacagcggtaagatccttgagagttttcgccccgaagaacgttttccaa
tgatgagcacttttaaagttctgctatgtggcgcggtattatcccgtattgacgccgggcaagagcaactcggtcgccgcatacact
attctcagaatgacttggttgagtactcaccagtcacagaaaagcatcttacggatggcatgacagtaagagaattatgcagtgctg
ccataaccatgagtgataacactgcggccaacttacttctgacaacgatcggaggaccgaaggagctaaccgcttttttgcacaac
atgggggatcatgtaactcgccttgatcgttgggaaccggagctgaatgaagccataccaaacgacgagcgtgacaccacgatg
cctgtagcaatggcaacaacgttgcgcaaactattaactggcgaactacttactctagcttcccggcaacaattaatagactggatg
gaggcggataaagttgcaggaccacttctgcgctcggcccttccggctggctggtttattgctgataaatctggagccggtgagcg
tgggtctcgcggtatcattgcagcactggggccagatggtaagccctcccgtatcgtagttatctacacgacggggagtcaggca
actatggatgaacgaaatagacagatcgctgagataggtgcctcactgattaagcattggtaactgtcagaccaagtttactcatata
tactttagattgatttaaaacttcatttttaatttaaaaggatctaggtgaagatcctttttgataatctcatgaccaaaatcccttaacgtg
agttttcgttccactgagcgtcagaccccgtagaaaagatcaaaggatcttcttgagatcctttttttctgcgcgtaatctgctgcttgc
aaacaaaaaaaccaccgctaccagcggtggtttgtttgccggatcaagagctaccaactctttttccgaaggtaactggcttcagca
gagcgcagataccaaatactgttcttctagtgtagccgtagttaggccaccacttcaagaactctgtagcaccgcctacatacctcg
ctctgctaatcctgttaccagtggctgctgccagtggcgataagtcgtgtcttaccgggttggactcaagacgatagttaccggata
aggcgcagcggtcgggctgaacggggggttcgtgcacacagcccagcttggagcgaacgacctacaccgaactgagatacct
acagcgtgagctatgagaaagcgccacgcttcccgaagggagaaaggcggacaggtatccggtaagcggcagggtcggaac
aggagagcgcacgagggagcttccagggggaaacgcctggtatctttatagtcctgtcgggtttcgccacctctgacttgagcgt
cgatttttgtgatgctcgtcaggggggcggagcctatggaaaaacgccagcaacgcggcctttttacggttcctggccttttgctgg
ccttttgctcacatgttctttcctgcgttatcccctgattctgtggataaccgtattaccgcctttgagtgagctgataccgctcgccgca
gccgaacgaccgagcgcagcgagtcagtgagcgaggaagcggaag
```

Expression of the Homologue from pMC355rbs

To express the *S. meliloti* RSM02162 protein from the plasmid pMC355rbs (See, FIG. 20, for a map of this plasmid), a single colony was inoculated into a 5 mls of L broth containing 100 μg/ml carbenicillin and grown overnight at 37° C. with shaking at 200 rpm. Lysates were prepared by pelleting the cells from 1 ml of the overnight culture by centrifugation and lysed with BugBuster (Novagen). The supernatants were assayed using the pNA activity assay, perhydrolysis assay, and a pNC6 assay (to test its ability to hydrolyze carbon chains longer than C4), as described herein.

Assay Results

The following Table (Table 11-1) provides a comparison of the hydrolysis activity of pNA by G00355 as compared to the *M. smegmatis* perhydrolase

TABLE 11-1

| pNA Hydrolysis Activity | | |
|---|---|---|
| Strain | pNA Hydrolysis Rate* | Rate Compared to Perhydrolase |
| *E. coli*/pMSATNcoI | 85 | 1 |
| *E. coli*/pMC355rbs | 80 | 0.94 |
| *E. coli*/pCR2.1 | 34.6 | 0.41 |

*Rate is absorbance units/min read at 405 nm in a spectrophotometer.

The following Table (Table 11-2) provides a comparison of the perhydrolysis of triacetin by G00355 compared to the *M. smegmatis* perhydrolase.

TABLE 11-2

| Triacetin Perhydrolysis Activity | | |
|---|---|---|
| | Perhydrolysis Activity | |
| Strain | Max | Vmax |
| *E. coli*/pMSATNcoI | 1.04 | 11.88 |
| *E. coli*/pMC355rbs | 1.17 | 25.05 |
| *E. coli*/pCR2.1 | 0.1 | 2.9 |

The following Table (Table 11-3) provides a comparison of pNC6 hydrolysis by G00355 compared to the *M. smegmatis* perhydrolase.

TABLE 11-3

| pNC6 Hydrolysis Activity | | |
|---|---|---|
| Strain | pNC6 Hydrolysis Rate* | Rate Compared to Ms. Perhydrolase |
| *E. coli*/pMSATNcoI | 0.58 | 1 |
| *E. coli*/pMC355rbs | 6.57 | 11.3 |
| *E. coli*/pCR2.1 | 0.47 | 0.8 |

*Rate is absorbance units/min read at 405 nm in a spectrophotometer.

As these results indicate, the homologue RSM02162 from *S. meliloti* identified by amino acid sequence homology to the *M. smegmatis* perhydrolase demonstrated similar, albeit less perhydrolysis activity than the *M. smegmatis* perhydrolase. However, this enzyme exhibited different substrate specificity, as it was able to hydrolyze pNC6, while the wild-type *M. smegmatis* perhydrolase cannot.

The results of the pNC6 hydrolysis assay indicated that certain positions/substitutions provided an improvement in the ability of the enzyme to utilize longer chain substrates The positions and substitutions identified in preliminary screens are provided in the following Table. It is not intended that the present invention be limited to these specific positions and substitutions, as it is contemplated that additional positions and/or substitutions will also provide improved activity on longer chain substrates.

TABLE 11-4

| Positions/Substitutions with Improved Activity in PNC6 Assay | |
|---|---|
| Wild-Type Residue/Position | Amino Acid Variant(s) |
| L12 | G, P, Q |
| S54 | L, T |
| I153 | F, P |
| F154 | Q, S, T, V |
| I194 | G |
| F196 | A, C, G, I, N, P, Q, S, V |

Example 12

Amplification of Genes Encoding *M. smegmatis* Perhydrolase Homologues from Environmental Isolates In this Example, methods used to amplify genes encoding *M. smegmatis* perhydrolase homologues from environmental isolates are described.

Organisms from soil samples that were positive for the transesterification reaction were purified to single colonies. To amplify the genes by PCR, the degenerate primer sets 1AF/5AR and 1eF5iR were used in a PCR reaction containing isolated chromosomal DNA from 8 environmental strains exhibiting the transesterification reaction. The PCR reaction was carried out using Taq DNA polymerase (Roche) as per the manufacturer's protocol, with 1 μg of chromosomal DNA added as template and 10 picomoles of each primer in a 50 μl reaction. The reaction was carried out for 30 cycles of (1 minute at 95° C.; 1 minute at 50° C., and 1 minute at 72° C.). Since the partial coding sequence of the perhydrolase gene from *Mycobacterium parafortuitum* was already isolated, the same strain was used as a positive control. The strains were designated as: 2G, 2D, 9B, 14B, 18D, 19C, 20A. As indicated below, 20A was typed as *Mycobacterium parafortuitum*, and 9B is *Mycobacterium gilvum*. Based on protein homology, it was inferred that 2D is also *M. parafortuitum* and 14B is *M. gilvum*.

Primer Sequences

1AF:

(SEQ ID NO: 631)
5'-gccaagcgaattctgtgtttcggngaytcnyt-3'

5AR:

(SEQ ID NO: 632)
5'-cgattgttcgcctcgtgtgaartgnrtnccrtc-3'

1eF:

(SEQ ID NO: 633)
5'-acggtcctgtgctttggngaytcnyt-3'

5iR:

(SEQ ID NO: 634)
5'-ccgctggtcctcatctggrtgntcnccrtc-3'

Amplification with the above primer sets was expected to yield bands of approximately 500 bp. In all cases except 2G, the 1AF/5AR primer set produced a band of the expected size. In the case of 19C, both primer sets produced bands of the expected size. The ~500 bp bands were purified from agarose gels using a gel purification kit (Qiagen) and analyzed by sequencing. While the strains 2G and 19C yielded bands of the expected size with both primer sets they were not the fragments encoding the *M. smegmatis* perhydrolase homologue.

Partial Sequences of 2D Perhydrolase Homologue and Protein:

Gene:

(SEQ ID NO: 635)
```
5'-attctgtgtttcggggattccttgacgtggggatggatccctgtcga
agaaggtgtgcccaccgagcggttcccgcgtgacgtccggtggaccggcg
tgctggccgacctgctgggcgaccgctacgaggtgatcgaggaaggcctg
tcggcgcgcaccaccaccgccgacgacccggccgacccccggctcaacgg
ttcgcagtatctgccgtcgtgtctggccagccatctgccgctggacctgg
tgatcctgatgctcggcatcaacgacaccaaggcgaattttggccgcacc
ccgttcgacatcgccaccggtatgggagtgcttgccacgcaggtgctcac
cagcgccggtggcgtggggaccagctatcccgcgccgcaggtgctgatcg
tggcgccgccgccgctgggcgagctgccccacccctggttcgacctggtg
ttctccggcggccgtgagaagaccgccgagttggcccgcgtgtacagcgc
gctggcgtcgttcatgaaggtgccgttcttcgacgccggctcggtgatca
gcaccgacggcgtggacggcacccacttcacacgaggcgaaacaatcga
```

Protein:

(SEQ ID NO: 636)
```
ILCFGDSLTWGWIPVEEGVPTERFPRDVRWTGVLADLLGDRYEVIEEGLS
ARTTTADDPADPRLNGSQYLPSCLASHLPLDLVILMLGINDTKANFGRTP
FDIATGMGVLATQVLTSAGGVGTSYPAPQVLIVAPPPLGELPHPWFDLVF
SGGREKTAELARVYSALASFMKVPFFDAGSVISTDGVDGTHFTRGETI
```

Partial Sequences of 9B Perhydrolase Homologue and Protein:

Gene:

(SEQ ID NO: 637)
```
5'-taccgtcgatgtgtggcctcgtgtgaagtgggtgccgttgccaagcg
aattctgtgtttcggggattcgttgacgtggggctggatcccggtcgagg
aaggtgtacccacccaacgttttccgaagcgggtgcgctggaccggggtg
ctggccgacgaactgggtgctggctatgaggttgtcgaggaggggttgag
cgcgcgcaccaccaccgctgacgaccctaccgatccccggctgaacggct
cggactacctccccgcatgcctggccagccacctgccgctggacctggtg
atcctgatgctcgggaccaacgacaccaaggcgaatctgaatcgcacacc
cgtcgacatcgccagcggaatgggcgtcctggccacccaggtgctcacca
gcgcgggcggggtcggcaccagctacccggccccgcaggtgttgatcgtg
gcaccgccgccgctggccgagatgccgcacccgtggttcgagctggtctt
cgacggcggccgggagaagaccgcccaactggcccgggtgtacagcgcgc
tggcgtcgttcatgaaggtgccgttcttcgacgccggatcggtgatcagc
accgacggtgtcgacggcacccacttcacacgaggcgaaacaatcgac
cgg
```

Protein:

(SEQ ID NO: 638)
```
GGRCVASCEVGAVAKRILCFGDSLTWGWIPVEEGVPTQRFPKRVRWTGVL
ADELGAGYEVVEEGLSARTTTADDPTDPRLNGSDYLPACLASHLPLDLVI
LMLGTNDTKANLNRTPVDIASGMGVLATQVLTSAGGVGTSYPAPQVLIVA
PPPLAEMPHPWFELVFDGGREKTAQLARVYSALASFMKVPFFDAGSVIST
DGVDGTHFTRGETIDR
```

Partial Sequences of 14B Perhydrolase Homologue and Protein:

Gene:

(SEQ ID NO: 639)
```
5'-attctgtgtttcggagattcgttgacgtggggctggatcccggtcga
ggaaggtgtacccacccaacgttttccgaagcgggtgcgctggaccgggg
tgctggccgacgaactgggtgctggctatgaggttgtcgaggaggggttg
agcgcgcgcaccaccaccgctgacgaccctaccgatccccggctgaacgg
ctcggactacctccccgcatgcctggccagccacctgccgctggacctgg
tgatcctgatgctcgggaccaacgacaccaaggcgaatctgaatcgcaca
cccgtcgacatcgccagcggaatgggcgtcctggccacccaggtgctcac
cagcgcgggcggggtcggcaccagctacccggccccgcaggtgttgatcg
tggcaccgccgccgctggccgagatgccgcacccgtggttcgagctggtc
ttcgacggcggccgggagaagaccgcccaactggcccgggtgtacagcgc
```

-continued

```
gctggcgtcgttcatgaaggtgccgttcttcgacgccggatcggtgatca
gcaccgacggtgtcgacggcacccacttcacacgagg
```

Protein:

(SEQ ID NO: 640)

```
ILCFGDSLTWGWIPVEEGVPTQRFPKRVRWTGVLADELGAGYEVVEEGLS
ARTTTADDPTDPRLNGSDYLPACLASHLPLDLVILMLGTNDTKANLNRTP
VDIASGMGVLATQVLTSAGGVGTSYPAPQVLIVAPPPLAEMPHPWFELVF
DGGREKTAQLARVYSALASFMKVPFFDAGSVISTDGVDGTHFTR
```

Partial Sequences of 20A Perhydrolase Homologue and Protein:

Gene:

(SEQ ID NO: 641)

```
5'-ttgccaagcggaattctgtgtttcggggattctttgacgtggggatg
gatccctgtcgaagaaggtgtgcccaccgagcggttcccgcgtgacgtcc
ggtggaccggcgtgctggccgacctgctgggcgaccgctacgaggtgatc
gaggaaggcctgtcggcgcgcaccaccaccgccgacgaccccggccgaccc
ccggctcaacggttcgcagtatctgccgtcgtgtctggccagccatctgc
cgctggacctggtgatcctgatgctcggcatcaacgacaccaaggcgaat
tttggccgcaccccgttcgacatcgccaccggtatgggagtgcttgccac
gcaggtgctcaccagcgccggtggcgtggggaccagctatcccgcgccgc
aggtgctgatcgtggcgccgccgccgctgggcgagctgccccacccctgg
ttcgacctggtgttctccggcggccgtgagaagaccgccgagttggcccg
cgtgtacagcgcgctggcgtcgttcatgaaggtgccgttcttcgacgccg
gctcggtgatcagcaccgacggcgtggacggcacccacttcacacgaggc
gaaacaatcga-3'
```

Protein:

(SEQ ID NO: 642)

```
LPSGILCFGDSLTWGWIPVEEGVPTERFPRDVRWTGVLADLLGDRYEVIE
EGLSARTTTADDPADPRLNGSQYLPSCLASHLPLDLVILMLGINDTKANF
GRTPFDIATGMGVLATQVLTSAGGVGTSYPAPQVLIVAPPPLGELPHPWF
DLVFSGGREKTAELARVYSALASFMKVPFFDAGSVISTDGVDGTHFTRG
ETI
```

Identification of the Natural Isolates

To type the environmental isolates used in this Example, plates of the purified strains were sent to MIDI for 16S rRNA typing. 20A is *Mycobacterium parafortuitum,* 9B is *Mycobacterium gilvum*. By protein homology we infer that 2D is also *M. parafortuitum* and 14B is *M. gilvum.*

Example 13

Sequence and Taxonomic Analyses of Perhydrolase Homologues

In this Example, sequence and taxonomic analyses of *M. smegmatis* perhydrolase homologues are provided Taxonomic Assignment The basic "List of 60" protein sequences accessed from public databases and used for construction of primer sets for screening of metagenomic libraries (BRAIN) was converted into a document illustrating the microbial taxonomic origins of the proteins, as described below. This information was used to produce the following alignment.

```
                                        1                                                 50
MSAT                              (1)   -------------MAKRILCFGDSLUWGWVPVEDGAPU-ERFAPDVRWUG
14B natural isolate               (1)   -----------------ILCFGDSLTWGWIPVEEGVPT-QRFPKRVRWTG
20A                               (1)   -------------LPSGILCFGDSLTWGWIPVEEGVPT-ERFPRDVRWTG
2D natural isolate                (1)   -----------------ILCFGDSLTWGWIPVEEGVPT-ERFPRDVRWTG
9B Natural Isolate                (1)   -GGRCVASCEVGAVAKRILCFGDSLTWGWIPVEEGVPT-QRFPKRVRWTG
M. parafortuitum CO1              (1)   -------------MAKRILCFGDSLTWGWIPVEEGVPT-ERFPRDVRWTG
Sm-RSM05666                       (1)   --------------MKTVLCYGDSLTWGYDATGSG-----RHALEDRWPS
At-Q8UAC0                         (1)   --------------MKTVLAFGDSLTWGADPATG---L--RHPVEHRWPD
At-Q8UFG4                         (1)   -------------MVKSVLCFGDSLTWGSNAETGG-----RHSHDDLWPS
M091_M4aE11                       (1)   --------------MKTILAYGDSLTYGANPIPGGP----RHAYEDRWPT
M1-RML000301                      (1)   MAGGTRLDECTGERMKTVLCYGDSLTWGYNAEGG------RHALEDRWPS
P.dejongeii RVM04532              (1)   --------------MKTILCFGDSNTWGYDPASMTAPFPRRHGPEVRWTG
Q92XZ1 Sinorhizobium meliloti     (1)   ---------MEETVARTVLCFGDSNTHGQVPGRGPLDR---YRREQRWGG
Q98MY5 Mesorhizobium loti         (1)   --------------MKTVLCYGDSLTWGYNAEGG------RHALEDRWPS
RSM02162_Sm                       (1)   -----------MVEKRSVLCFGDSLTWGWIPVKESSPT-LRYPYEQRWTG
S261_M2aA12                       (1)   --------------MKNILAFGDSLTWGFVAGQDAR-----HPFETRWPN
Sma1993 Sinorhizobium             (1)   MTINSHSWRTLMVEKRSVLCFGDSLTWGWIPVKESSPT-LRYPPEQRWTG
meliloti
Consensus                         (1)                   KTILCFGDSLTWGWIPV EG P   RHP E RW G

                                        51                                               100
MSAT                              (37)  VLAQQLGADFEVIE--EGLSARUUNIDDPUDPRL-NGASYLPSCLAUHLP
14B natural isolate               (33)  VLADELGAGYEVVE--EGLSARTTTADDPTDPRL-NGSDYLPACLASHLP
20A                               (37)  VLADLLGDRYEVIE--EGLSARTTTADDPADPRL-NGSQYLPSCLASHLP
2D natural isolate                (33)  VLADLLGDRYEVIE--EGLSARTTTADDPADPRL-NGSQYLPSCLASHLP
9B Natural Isolate                (49)  VLADELGAGYEVVE--EGLSARTTTADDPTDPRL-NGSDYLPACLASHLP
M. parafortuitum CO1              (37)  VLADLLGDRYEVIE--EGLSARTTTAEDPADPRL-NGSQYLPSCLASHLP
Sm-RSM05666                       (32)  VLQKALGSDAHVIA--EGLNGRTTAYDDHLADCDRNGARVLPTVLHTHAP
At-Q8UAC0                         (32)  VLEAELAGKAKVHP--EGLGGRTTCYDDHAGPACANGARALEVALSCHMP
At-Q8UFG4                         (33)  VLQKALGSDVHVIFTHEGLGGRTTAYDDHTGDCDRNGARLLPTLLHSHAP
M091_M4aE11                       (33)  ALEQGLGGKARVIA--EGLGGRTTVHDDWFANADANGARVLPTLLESHSP
M1-RML000301                      (45)  VLQASLGGGVQVIA--DGLNGRTTAFDDHLAGADANGARLLPTALTTHAP
P.dejongeii RVM04532              (37)  VLAKALGAGFRVIE--EGQNGRTTVHEDPLNICR-KGKDYLPACLESHKP
Q92XZ1 Sinorhizobium meliloti     (39)  VLQGLLGPNWQVIE--EGLSGRTTVHDDPIEGSLKNGRIYLRPCLQSHAP
Q98MY5 Mesorhizobium loti         (31)  VLQASLGGGVQVIA--DGLNGRTTAFDDHLAGADANGARLLPTALTTHAP
RSM02162_Sm                       (39)  AMAARLGDGYHIIE--EGLSARTTSLDDPNDARL-NGSTYLPMALASHLP
S261_M2aA12                       (32)  ALAAGLGGKARVIE--EGQNGRTTVFDDAATFESRNGSVALPLLLISHQP
Sma1993 Sinorhizobium             (50)  AMAARLGDGYHIIE--EGLSARTTSLDDPNDARL-NGSTYLPMALASHLP
meliloti
Consensus                         (51)  VLA  LGG Y VIE  EGLSGRTT  DDP D  L NGS YLPT  LASHLP

                                        101                                              150
MSAT                              (84)  LDLVIIMLGUNDUKAYFRRUPLDIA--LGMSVLVUQVLUSAGGVGUUYPA
14B natural isolate               (80)  LDLVILMLGTNDTKANLNRTPVDIA--SGMGVLATQVLTSAGGVGTSYPA
20A                               (84)  LDLVILMLGINDTKANFGRTPFDIA--TGMGVLATQVLTSAGGVGTSYPA
```

-continued

```
2D natural isolate              (80) LDLVILMLGINDTKANFGRTPFDIA--TGMGVLATQVLTSAGGVGTSYPA
9B Natural Isolate              (96) LDLVILMLGTNDTKANLNATPVDIA--SGMGVLATQVLTSAGGVGTSYPA
M. parafortuitum CO1            (84) LDLVILMLGTNDTKANFGRTPFDIA--TGMGVLATQVLTSAGGVGTSYPA
Sm-RSM05666                     (80) LDLIVFMLGSNDMKPIIHGTAFGAV--KGIERLVNLVRAHDWPTETE-EG
At-Q8UAC0                       (80) LDLVIIMLGINDIKPVHGGRAEAAV--SGMARLAQIVETFIYKPREA--V
At-Q8UFG4                       (83) LDMVIIMLGTNDMKPAIHGSAIVAFTMKGVERLVKLTRNHVWQVSDW-EA
M091_M4aE11                     (81) LDLIVIMLGTNDIKPHHGRTAGEAG--RGMARLVQIIRGHYAGRMQD--E
M1-RML000301                    (93) IDLIVIMLGANDMKPWIHGNPVAAK--QGIQRLIDIVRGHDYPFDWP--A
P.dejongeii RVM04532            (84) LDLVILMLGTNDLKSTFNVPPGEIA--AGAGVLGRMILAGDAGPENR--P
Q92XZ1 Sinorhizobium meliloti   (87) LDLIIIMLGTNDLKARFNMPPSEVA--MGIGCLVHDIRELSPGRTGN--D
Q98MY5 Mesorhizobium loti       (79) IDLIVIMLGANDMKPWIHGNPVAAK--QGIQRLIDIVRGHDYPFDWP--A
RSM02162_Sm                     (86) LDLVIIMLGTNDTKSYFHRTPYEIA--NGMGKLVGQVLTCAGGVGLPYPA
S261_M2aA12                     (80) LDLVIIMLGTNDIKFAARCRAFDAS--MGMERLIQIVRSANYMKGYK--I
Sma1993 Sinorhizobium           (97) LDLVIIMLGTNDTKSYFHRTPYEIA--NGMGKLVGQVLTCAGGVGTPYPA
meliloti
Consensus                      (101) LDLVIIMLGTNDMKA   RTP DIA   GMGRLV  VLT AGGVG    A

                                     151                                            200
MSAT                           (132) PKVLVVSPPPLAPM-PHPWFQLIF-EGGEQKUUELARVYSALASFMKVPF
14B natural isolate            (128) PQVLIVAPPPLAEM-PHPWFELVF-DGGREKTAQLARVYSALASFMKVPF
20A                            (132) PQVLIVAPPPLGEL-PHPWFDLVF-SGGREKTAELARVYSALASFMKVPF
2D natural isolate             (128) PQVLIVAPPPLGEL-PHPWFDLVF-SGGREKTAELARVYSALASFMKVPF
9B Natural Isolate             (144) PQVLIVAPPPLAEM-PHPWFELVF-DGGREKTAQLARVYSALASFMKVPF
M. parafortuitum CO1           (132) PQVLIVAPPPLGEL-PHPWFDLVF-SGGREKTAELARVYSALASFMKVPF
Sm-RSM05666                    (127) PEILIVSPPPLCET--ANSAFAAMFAGGVEQSAMLAPLYRDLADELDCGF
At-Q8UAC0                      (126) PKLLIVAPPPCVAG---PGGEPAG-GRDIEQSMRLAPLYRKLAAELGHHF
At-Q8UFG4                      (132) PDVLIVAPPQLCETANPFMGAIFRDAIDESAMLASVFTYRDLADELDCGF
M091_M4aE11                    (127) PQIILVSPPPIILGDWADMMDHFGPHEAIATSVDFAREYKKRADEQKVHF
Ml-RML000301                   (139) PQILIVSPPVVSRT--ENADFREMFAGGDEASKQLAPQYAALADEVGCGF
P. dejongeii RVM04532          (130) PQLLLMCPPKVRDLSAMPDLDAKI-PHGAARSAEFPRHYKAQAVALKCEY
Q92XZ1 Sinorhizobium meliloti  (133) PEIMIVAPPPMLED--LKEWESIF-SGAQEKSRKLALEFEIMADSLEAHF
Q98MY5 Mesorhizobium loti      (125) PQILIVSPPVVSRT--ENADFREMFAGGDEASKQLAPQYAALADEVGCGF
RSM02162_Sm                    (134) PKVLVVAPPPLAPM-PDPWFEGMF-GGGYEKSKELSGLYKALADFMKVEF
S261_M2aA12                    (126) PEILIISPPSLVPT--QDEWFNDLWGHAIAESKLFAKHYKRVAEELKVHF
Sma1993 Sinorhizobium          (145) PKVLVVAPPPLAPM-PDPWFEGMF-GGGYEKSKELSGLYKALADFMKVEF
meliloti
Consensus                      (151) PQVLIVAPPPL EM   P FE VF  GG EKS  LARVY ALAD MKV F

                                     201                                     241
MSAT                           (180) FDAGSVISUDGVDGIHFUEANNRDLGVALAEQVRSLL---- (SEQ ID NO: 643)
14B natural isolate            (176) FDAGSVISTDGVDGTHFIR--------------------- (SEQ ID NO: 644)
20A                            (180) FDAGSVISTDGVDGTHFTRGETI------------------ (SEQ ID NO: 645)
2D natural isolate             (176) FDAGSVISTDGVDGTHFTRGETI------------------ (SEQ ID NO: 646)
9B Natural Isolate             (192) FDAGSVISTDGVDGTHFTRGETIDR---------------- (SEQ ID NO: 647)
M. parafortuitum CO1           (180) FDAGSVISTDGVDGIHFTRGEQST----------------- (SEQ ID NO: 648)
Sm-RSM05666                    (175) FDGGSVARTTPIDGVHLDAENTRAVGRGLEPVVRMMLGL-- (SEQ ID NO: 649)
At-Q8UAC0                      (172) FDAGSVASASPVDGVHLDASATAAIGRALAAPVRDILG--- (SEQ ID NO: 650)
At-Q8UFG4                      (182) FDAGSVARTTPVDGVHLDAENTRAIGRGLEPVVRMMLGL-- (SEQ ID NO: 651)
M091_M4aE11                    (177) FDAGTVATTSKADGIHLDPANTRAIGAGLVPLVKQVLGL-- (SEQ ID NO: 652)
Ml-RML000301                   (187) FDAGTVAQTTPLDGVHLDAENTRNIGKALTSVVRVML---- (SEQ ID NO: 653)
P. dejongeii RVM04532          (179) FNSQEIVETSPVDGIHLEASEHLKLGEALAEKVKVLLG--- (SEQ ID NO: 654)
Q92XZ1 Sinorhizobium meliloti  (180) FDAGTVCQCSPADGFHIDEDAHRLLGEALAQEVLAIGWPDA (SEQ ID NO: 655)
Q98MY5 Mesorhizobium loti      (173) FDAGTVAQTTPLDGVHLDAENTRNIGKALTSVVRVMLEL-- (SEQ ID NO: 656)
RSM02162_Sm                    (182) FAAGDCISTDGIDGIHLSAETNIRLGHAIADKVAALF---- (SEQ ID NO: 657)
S261_M2aA12                    (174) FDAGTVAVADKTDGGHLDAVNTKAIGVALVPVVKSILAL-- (SEQ ID NO: 658)
Sma1993 Sinorhizobium          (193) FAAGDCISTDGIDGIHLSAETNIRLGHAIADKVAALF---- (SEQ ID NO: 659)
meliloti
Consensus                      (201) FDAGSVISTD VDGIHLDA  T  IG AL   VR LL (SEQ ID NO: 660)
```

The alignment tree from the CLUSTALW alignment (which approximates to a phylogenetic tree) suggests 3 or 4 groupings.

From this alignment, a hypothetical protein sequence was constructed from the consensus sequence. Where no consensus existed the site was filled with the Per amino acid; gaps were ignored. This provided a Per-consensus sequence:

```
                                              (SEQ ID NO: 661)
  1 TILCFGDSLT WGWIPVEEGA PTERHPPEVR WTGVLAQQLG
    GDYEVIEEGL

 51 SGRTTNIDDP TDPRLNGSSY LPTCLASHLP LDLVIIMLGT
    NDMKAYFRRT

101 PLDIALGMGR LVTQVLTSAG GVGTTYPAPQ VLIVAPPPLA
    EMPHPWFELV
```

-continued

```
151 FEGGEEKSTE LARVYSALAD FMKVPFFDAG SVISTDGVDG
    IHLDAANTRD

201 IGVALAEQVR SLL
```

This consensus sequence was used for a BLASTP search against a non-redundant database. This search identified 55 hits. The majority of the 'hits' were GDSL or GDSI type molecules covering a wide range of microbial diversity. However, only the first 14 'hits' had e-values and bit-values in the reliable range. At first sight, this appeared to provide further molecules with a GDSL/N-G/ARTT motif, but this was found to be due to differences in coding (Swiss Prot vs GenBank)

The screening of 3 environmental libraries (at BRAIN) resulted in 10 clones with a GDSL motif. A further 2 clones were derived from the BRAIN library. The following Table (Table 13-1) lists the clones and indicates their activity.

TABLE 13-1

| Clones with GDSL Motifs | | |
|---|---|---|
| Library | Clone | Perhydrolase Activity |
| S248Fa | S248_M40cD4 | No |
| S248Fa | S248_M44aA5 | No |
| S248Fa | S248_M18bH12 | Not Perhydrolase |
| S248Fa | S248_M36bC5 | Not Perhydrolase |
| S248Fa | S248_M50cD9 | Not Perhydrolase |
| S248Fa | S248_M2bB11 | ? Low |
| S261 | S261_M2aA12 | Yes |
| S279 | S279_M75bA2 | Not done |
| S279 | S279_M11aC12 | Not GDSL |
| S279 | S279_M70aE8 | ? Low |
| M091 | M091_M4aE11 | Not tested |
| BRAIN | Est114 | No |
| BRAIN | Est105 | Not done |

M40cD4

Strongest hit: arylesterase of *Brucella melitensis* (46% identical). Motifs: GDSL-GAND; GQTT instead of GRTT. Sequence alignment against the core list of organisms places it close to *Caulobacter vibrioides* and *Brucella melitensis* in the alpha-Proteobacteria.

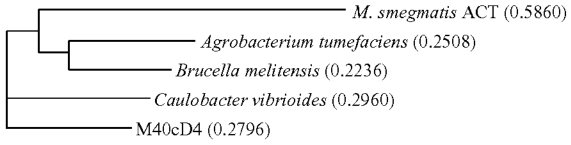

M44aA5

Strongest hit: Acyl-CoA thioesterase of *Pseudomonas aeruginosa* (43% identical). Motifs: GDSL-GGND; no GRTT or equivalent. Sequence alignment against the core list of organisms places it close to *Pseudomonas* sp in the gamma-Proteobacteria.

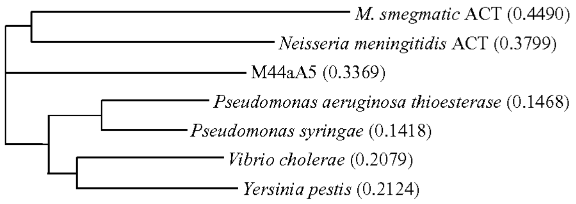

M2bB11

Strongest hit: arylesterase of *Brucella melitensis*. Motifs: GDSL-GAND; no GRTT or equivalent. Sequence alignment against the core list of organisms shows no strong association placing it between the alpha- and gamma-Proteobacteria.

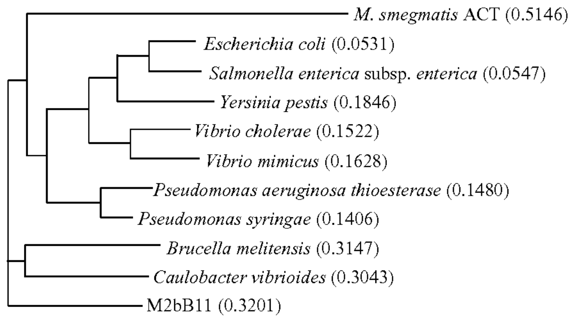

M2aA12

Strongest hit: arylesterase of *Agrobacterium tumefaciens* (42% identical) Motifs: GDSL-GRTT-GTND. Sequence alignment against the core list of organisms places it close to *Agrobacterium tumefaciens* in the alpha-Proteobacteria.

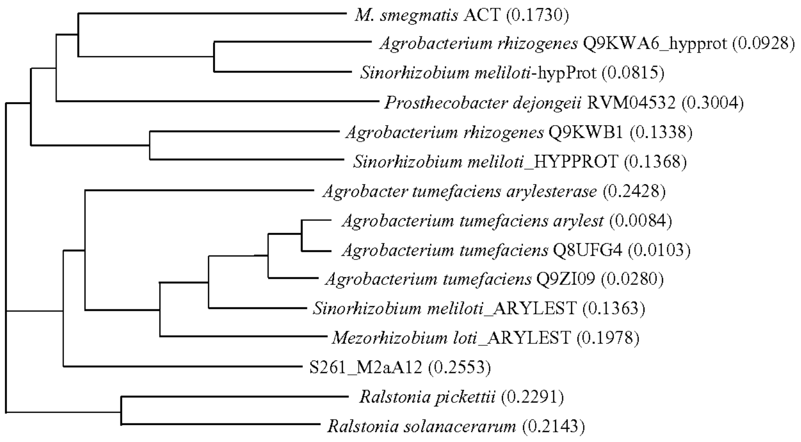

M75bA2

Strongest hit: incomplete. BLAST search revealed nothing significant. Motifs: GDSL-GTND; no GRTT or equivalent. Sequence alignment against the core list of organisms shows no convincing associations. The closest neighbors appear to be the *Vibrio-Aeromonas* groups of the gamma-Proteobacteria.

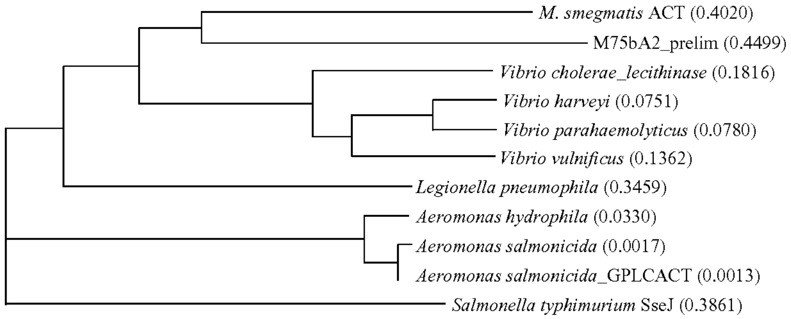

M70aE8

Strongest hit: acyl-CoA thioesterase from *E. coli* (30% identical), and aryl esterase hydrolase from *Vibrio mimicus* (27% identical). Based on incomplete sequence GDSL-type esterase (BRAIN) from *Neisseria meningitidis* (50% identical). Motifs: GDSL-GGND; no GRTT—replaced with GRTV. Sequence alignment against the core list of organisms shows the closest association to *Neisseria meningitidis*, a member of the beta-Proteobacteria.

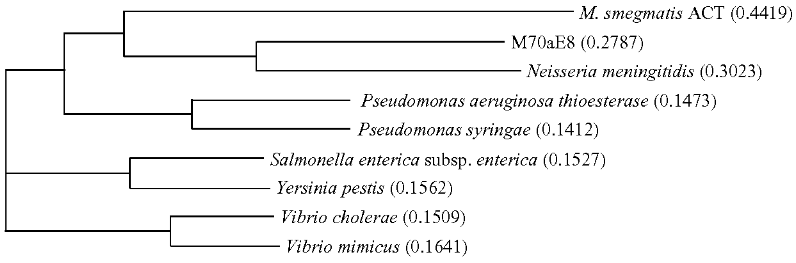

M4aE11

Strongest hit: arylesterase from *Agrobacterium tumefaciens* (59% identity) Motifs: GDSL-GRTT-GTND. Sequence alignment against the core list of organisms shows the closest association to members of the alpha-Proteobacteria such as *Agrobacterium*.

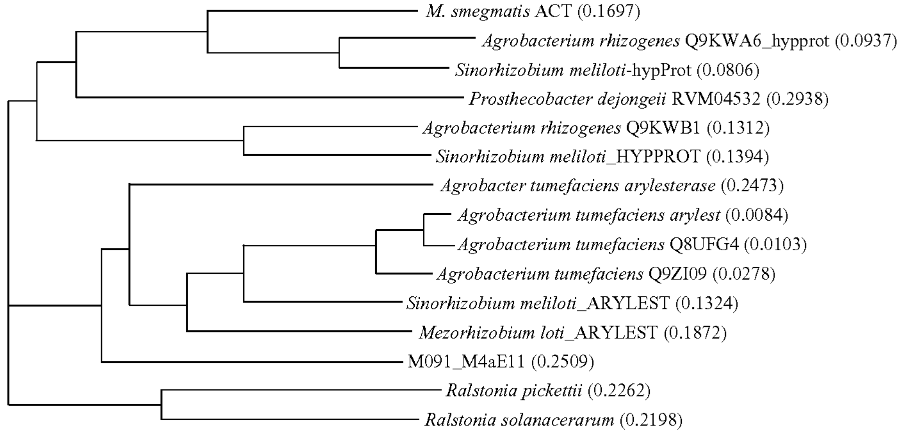

Est114

Strongest hit: phosphatidylcholine sterol acyltransferase from *Aeromonas hydrophila* (gamma-Proteobacteria) (30% identical). Motifs: GDSL-GPND; no GRTT but GATT may be an equivalent. Sequence alignment against the core list of organisms shows the closest association to *Acidophilium* sp. and *Aeromonas/Vibrio* within the gamma-Proteobacteria.

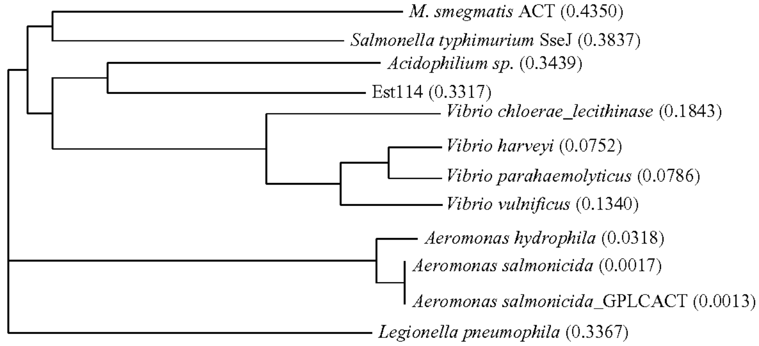

Est105

Strongest hit: *Pseudomonas aeruginosa* outer membrane esterase, and hypothetical protein *Pseudomonas putida* (27% identical). Motifs: GDSL-GAND, no GRTT or equivalent. Sequence alignment against the core list of organisms shows the closest association to members of the gamma-Proteobacteria.

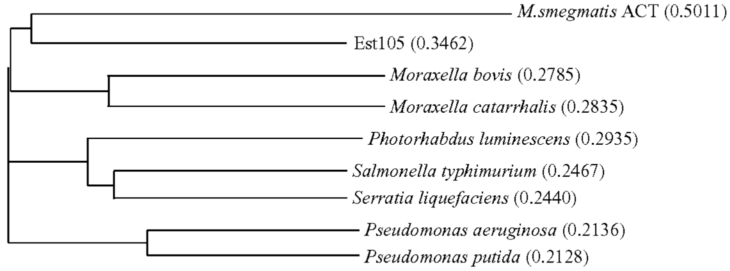

An overall alignment of these clones/sequences (here shown underlined) indicates that they are scattered throughout the alignment tree of strains indicating that the metagenomic screening has provided a variety of sequences and not a limited diversity.
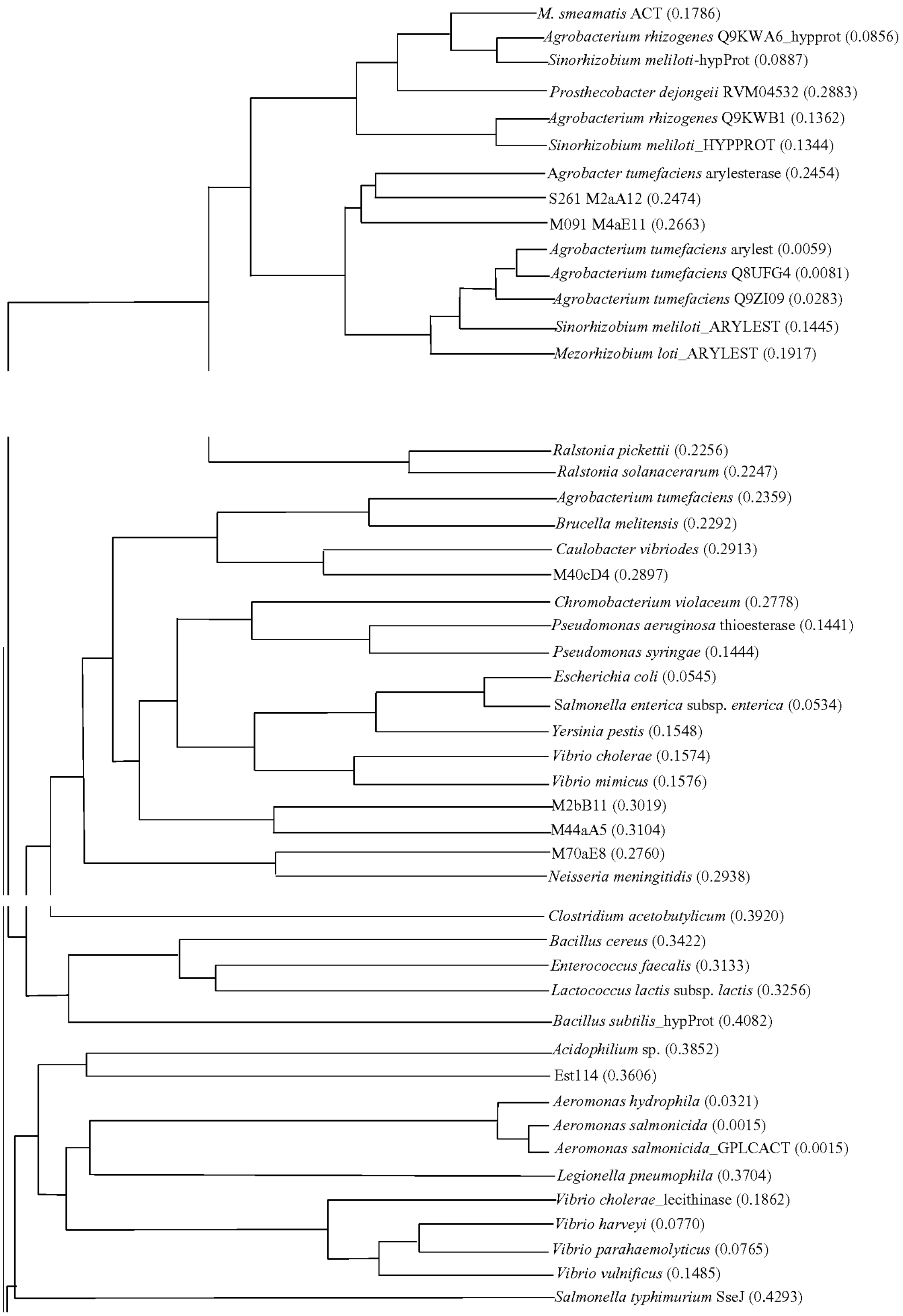

-continued

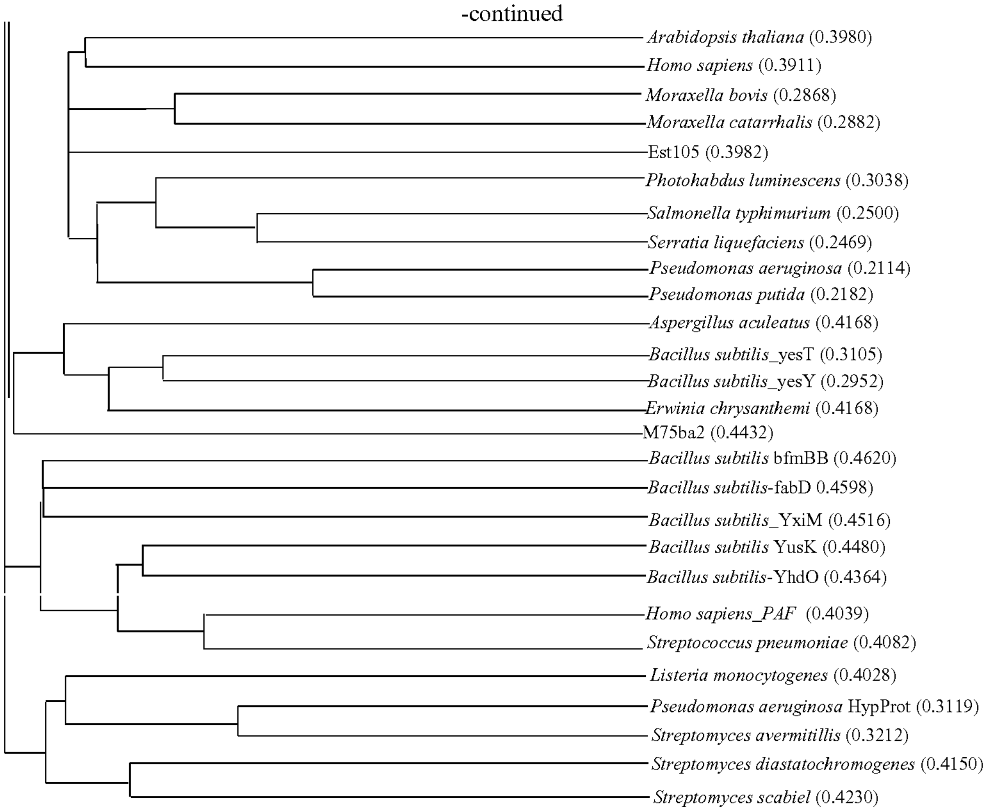

Gene Mining for GRTT-Type Esterases (clones with perhydrolase activity)

*Sinorhizobium meliloti* Sma1993-hypothetical protein_Sme

Motifs: GDSL-ARTT-GTND

*Sinorhizobium meliloti* Q92XZ1-hypothetical protein_Sme

Motifs: GDSN-GRTT-GTND

*Mesorhizobium loti* Q98MY5-arylesterase_Mlo

Motifs: GDSL-GRTT-GAND

*Moraxella bovis* AAK53448 (lipase)

Motifs: GDSL-GSND, no GRTT or equivalent in this sequence order.

(perhydrolase activity low, questionable sequence)

*Agrobacterium tumefaciens* Q8UACO

Motifs: GDSL-GRTT-GTND

*Agrobacterium tumefaciens* Q8UFG4

Motifs: GDSL-GRTT-GTND

*Mesorhizobium loti* RMLO00301

Motifs: GDSL-GRTT-GAND

*Sinorhizobium meliloti* RSM05666

Motifs: GDSL-GRTT-GSND (this clone was inactive for perhydrolase activity; and probably represents a false negative)

*Sinorhizobium meliloti* RSM02162

Motifs: GDSL-ARTT-GTND

*Prosthecobacter dejongeii* RVM05432

Motifs: GDSN-GRTT-GTND

A GDS$x_1$-$x_2$RTT-G$x_3$ND motif characterizes the active clones/sequences, where:

$X_1$=L or N $X_2$=A or G $X_3$=T or A or S

The *Moraxella bovis* AAK53448 sequence does not fit this pattern and is excluded from the alignment analysis provided below:

Multiple Sequence Alignment of Active Clones/Sequences

| | | 1 50 |
|---|---|---|
| ACT MSMEG | (1) | -------------MAKRILCFGDSLUWGWVPVEDGAPU-ERFAPDVRWUG |
| Q98MY5 *Mesorhizobium loti* | (1) | --------------MKTVLCYGDSLTWGYNAEGGR------HALEDRWPS |
| Sma1993 *Sinorhizobium meliloti* | (1) | MTINSHSWRTLMVEKRSVLCFGDSLTWGWIPVKESSPT-LRYPYEQRWTG |
| Q92XZ1 *Sinorhizobium meliloti* | (1) | ---------MEETVARTVLCFGDSNTHGQVPGRGPLDR---YRREQRWGG |
| *P. dejongeii* RVM04532 | (1) | --------------MKTILCFGDSNTWGYDPASMTAPFPRRHGPEVRWTG |
| RSM05666_Sm | (1) | --------------MKTVLCYGDSLTWGYDATGSG-----RHALEDRWPS |
| RSM02162_Sm | (1) | -----------MVEKRSVLCFGDSLTWGWIPVKESSPT-LRYPYEQRWTG |
| At-Q8UAC0 | (1) | --------------MKTVLAFGDSLTWGADPATGLR-----HPVEHRWPD |
| At-Q8UFG4 | (1) | -------------MVKSVLCFGDSLTWGSNAETGG-----RHSHDDLWPS |

-continued

Multiple Sequence Alignment of Active Clones/Sequences

| | | |
|---|---|---|
| M1-RML000301 | (1) | MAGGTRLDECTGERMKTVLCYGDSLTWGYNAEGGR------HALEDRWPS |
| S261_M2aA12 | (1) | --------------MKNILAFGDSLTWGFVAGQDA-----RHPFETRWPN |
| M091_M4aE11 | (1) | --------------MKTILAYGDSLTYGANPIPGG-PR---HAYEDRWPT |
| Consensus | (1) | MKTVLCFGDSLTWGY P G RHA E RWP |
| | | 51 100 |
| ACT MSMEG | (37) | VLAQQLGADFEVIE--EGLSARUUNIDDPUDPRL-NGASYLPSCLAUHLP |
| Q98MY5 *Mesorhizobium loti* | (31) | VLQASLGGGVQVIA--DGLNGRTTAFDDHLAGADRNGARLLPTALTTHAP |
| Sma1993 *Sinorhizobium meliloti* | (50) | AMAARLGDGYHIIE--EGLSARTTSLDDPNDARL-NGSTYLPMALASHLP |
| Q92XZ1 *Sinorhizobium meliloti* | (39) | VLQGLLGPNWQVIE--EGLSGRTTVHDDPIEGSLKNGRIYLRPCLQSHAP |
| *P. dejongeii* RVM04532 | (37) | VLAKALGAGFRVIE--EGQNGRTTVHEDPLNICR-KGKDYLPACLESHKP |
| RSM05666_Sm | (32) | VLQKALGSDAHVIA--EGLNGRTTAYDDHLADCDRNGARVLPTVLHTHAP |
| RSM02162_Sm | (39) | AMAARLGDGYHIIE--EGLSARTTSLDDPNDARL-NGSTYLPMALASHLP |
| At-Q8UAC0 | (32) | VLEAELAGKAKVHP--EGLGGRTTCYDDHAGPACRNGARALEVALSCHMP |
| At-Q8UFG4 | (33) | VLQKALGSDVHVIFTHEGLGGRTTAYDDHTGDCDRNGARLLPTLLHSHAP |
| M1-RML000301 | (45) | VLQASLGGGVQVIA--DGLNGRTTAFDDHLAGADRNGARLLPTALTTHAP |
| S261_M2aA12 | (32) | ALAAGLGGKARVIE--EGQNGRTTVFDDAATFESRNGSVALPLLLISHQP |
| M091_M4aE11 | (33) | ALEQGLGGKARVIA--EGLGGRTTVHDDWFANADRNGARVLPTLLESHSP |
| Consensus | (51) | VL A LGG VIE EGL GRTTAHDD A RNGAR LPT L SHAP |
| | | 101 150 |
| ACT MSMEG | (84) | LDLVIIMLGUNDUKAYFRRUPLDIA--LGMSVLVUQVLUSAGGVGUUYTA |
| Q98MY5 *Mesorhizobium loti* | (79) | IDLIVIMLGANDMKPWIHGNPVAAK--QGIQRLIDIVRGHDYPFDWPAP- |
| Sma1993 *Sinorhizobium meliloti* | (97) | LDLVIIMLGTNDTKSYFHRTPYEIA--NGMGKLVGQVLTCAGGVGTPYPA |
| Q92XZ1 *Sinorhizobium meliloti* | (87) | LDLIIIMLGTNDLKRRFNMPPSEVA--MGIGCLVHDIRELSPGRTGN--- |
| *P. dejongeii* RVM04532 | (84) | LDLVILMLGTNDLKSTFNVPPGEIA--AGAGVLGRMILAGDAGPENR-PP |
| RSM05666_Sm | (80) | LDLIVFMLGSNDMKPIIHGTAFGAV--KGIERLVNLVRRHDWPTETEEG- |
| RSM02162_Sm | (86) | LDLVIIMLGTNDTKSYFHRTPYEIA--NGMGKLVGQVLTCAGGVGTPYPA |
| At-Q8UAC0 | (80) | LDLVIIMLGTNDIKPVHGGRAEAAVS--GMRRLAQIVETFIYKPREAVP- |
| At-Q8UFG4 | (83) | LDMVIIMLGTNDMKPAIHGSAIVAFTMKGVERLVKLTRNHVWQVSDWEAP |
| M1-RML000301 | (93) | IDLIVIMLGANDMKPWIHGNPVAAK--QGIQRLIDIVRGHDYPFDWPAP- |
| S261_M2aA12 | (80) | LDLVIIMLGTNDIKFAARCRAFDAS--MGMERLIQIVRSANYMKGYKIP- |
| M091_M4aE11 | (81) | LDLIVIMLGTNDIKPHHGRTAGEAG--RGMARLVQIIRGHYAGRMQDEP- |
| Consensus | (101) | LDLVIIMLGTNDMKP H P EAA GM RLV IVR YG P |
| | | 151 200 |
| ACT MSMEG | (132) | PKVLVVSPPPLAPMPHPWFQLIFE--GGEQKUUELARVYSALASFMKVPF |
| Q98MY5 *Mesorhizobium loti* | (126) | -QILIVSPPVVSRTENADFREMFAG--GDEASKQLAPQYAALADEVGCGF |
| Sma1993 *Sinorhizobium meliloti* | (145) | PKVLWAPPPLAPMPDPWFEGMFG--GGYEKSKELSGLYKALADFMKVEF |
| Q92XZ1 *Sinorhizobium meliloti* | (132) | DPEIMIVAPPPMLEDLKEWESIFS--GAQEKSRKLALEFEIMADSLEAHF |
| *P. dejongeii* RVM04532 | (131) | QLLLMCPPKVRDLSAMPDLDAKIP--HGAARSAEFPRHYKAQAVALKCEY |
| RSM05666_Sm | (127) | PEILIVSPPPLCETANSAFAAMFAG--GVEQSAMLAPLYRDLADELDCGF |
| RSM02162_Sm | (134) | PKVLVVAPPPLAPMPDPWFEGMFG--GGYEKSKELSGLYKALADFMKVEF |
| At-Q8UAC0 | (127) | -KLLIVAPPPCVAGPGGEPAGGRD----IEQSMRLAPLYRKLAAELGHHF |
| At-Q8UFG4 | (133) | -DVLIVAPPQLCETANPFMGAIFRDAIDESAMLASVFTYRDLADELDCGF |
| M1-RML000301 | (140) | -QILIVSPPVVSRTENADFREMFAG--GDEASKQLAPQYAALADEVGCGF |
| S261_M2aA12 | (127) | -EILIISPPSLVPTQDEWFNDLWG--HAIAESKLFAKHYKRVAEELKVHF |
| M091_M4aE11 | (128) | -QIILVSPPPIILGDWADMMDHFGPHEAIATSVDFAREYKKRADEQKVHF |
| Consensus | (151) | ILIVSPPPL T DF AMFG G E SK LA YKALADELK F |
| | | 201 241 |
| ACT MSMEG | (180) | FDAGSVISUDGVDGIHFUEANNRDLGVALAEQVRSLL---- (SEQ ID NO: 662) |
| Q98MY5 *Mesorhizobium loti* | (173) | FDAGTVAQTTPLDGVHLDAENTRNIGKALTSVVRVMLEL-- (SEQ ID NO: 663) |
| Sma1993 *Sinorhizobium meliloti* | (193) | FAAGDCISTDGIDGIHLSAETNIRLGHAIADKVAALF---- (SEQ ID NO: 664) |
| Q92XZ1 *Sinorhizobium meliloti* | (180) | FDAGTVCQCSPADGFHIDEDAHRLLGEALAQEVLAIGWPDA (SEQ ID NO: 665) |
| *P. dejongeii* RVM04532 | (179) | FNSQEIVETSPVDGIHLEASEHLKLGEALAEKVKVLLG--- (SEQ ID NO: 666) |
| RSM05666_Sm | (175) | FDGGSVARTTPIDGVHLDAENTRAVGRGLEPVVRMMLGL-- (SEQ ID NO: 667) |
| RSM02162_Sm | (182) | FAAGDCISTDGIDGIHLSAETNIRLGHAIADKVAALF---- (SEQ ID NO: 668) |
| At-Q8UAC0 | (172) | FDAGSVASASPVDGVHLDASATAAIGRALAAPVRDILG--- (SEQ ID NO: 669) |
| At-Q8UFG4 | (182) | FDAGSVARTTPVDGVHLDAENTRAIGRGLEPVVRMMLGL-- (SEQ ID NO: 670) |
| M1-RML000301 | (187) | FDAGTVAQTTPLDGVHLDAENTRNIGKALTSVVRVML---- (SEQ ID NO: 671) |
| S261_M2aA12 | (174) | FDAGTVAVADKTDGGHLDAVNTKAIGVALVPVVKSILAL-- (SEQ ID NO: 672) |
| M091_M4aE11 | (177) | FDAGTVATTSKADGIHLDPANTRAIGAGLVPLVKQVLGL-- (SEQ ID NO: 673) |
| Consensus | (201) | FDAGTVA TSPVDGIHLDAENTR IG ALA VVR LLG (SEQ ID NO: 674) |

A guide tree (i.e., an approximation of a phylogenetic tree) of the CLUSTALW alignment of active clones/sequences is provided below.

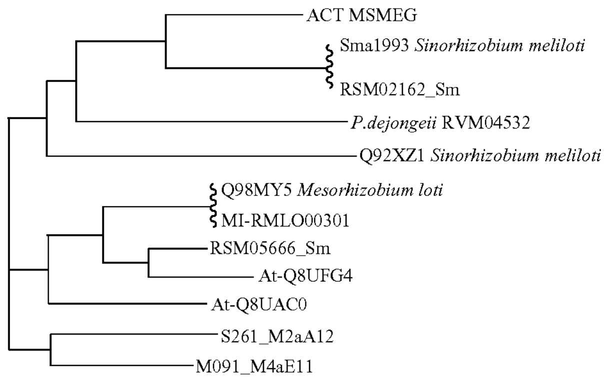

TABLE 13-2

Similarity and Identity of Clones/Sequences Compared to *M. smegmatis* Perhydrolase

| Clone/Sequence | % Identity | % Similarity |
|---|---|---|
| *Sinorhizobium meliloti* Sma1993 | 55.5 | 71.6 |
| *Sinorhizobium meliloti* Q92XZ1 | 38.7 | 54.7 |
| *Mesorhizobium loti* Q98MY5 | 38.8 | 53.4 |
| *Moraxella bovis* AAK53448 | 5.0 | 9.7 |
| *Agrobacterium tumefaciens* Q8UACO | 36.7 | 47.7 |
| *Agrobacterium tumefaciens* Q8UFG4 | 37.1 | 50.4 |
| *Mesorhizobium loti* RMLO00301 | 34.8 | 50.9 |
| *Sinorhizobium meliloti* RSM05666 | 37.4 | 52.5 |
| *Sinorhizobium meliloti* RSM02162 | 58.3 | 75.2 |
| *Prosthecobacter dejongeii* RVM05432 | 41.6 | 55.7 |
| S261_M2aA12 | 39.3 | 54.3 |
| M091_M4aE11 | 34.7 | 50.2 |

Based on the results, the active clones were found to have an overall identity to *M. smegmatis* perhydrolase of 38.7-58.3%. *Moraxella bovis* AAK53448 was found to be an exception and the (translated) amino acid sequence is questionable.

Redundancy

From the analyses above, it was evident that some redundancy exists in the alignment provided at the beginning of this Example that will have added undue weighting to the consensus sequence. Also, further GDSL-GRTT sequences were added. Thus, in the revised alignment below, the following changes were made:

Removed:
- Natural isolate 14B
- Natural isolate 2D
- RSM02162_Sm
- Q98MY5 *Mesorhizobium loti*

Added:
- BAB16197 (Arh II)
- BAB16192 (Arh I)
- NP 00197751 (Mlo II)
- NP 00216984 (Bce)
- NP 522806 (Rso)

Non-redundant alignment:

```
                                        1                                                50
20A                              (1)    -------------LPSGILCFGDSLTWGWIPVEEGVPTERFP-RDVRWTG
9B Natural Isolate               (1)    -GGRCVASCEVGAVAKRILCFGDSLTWGWIPVEEGVPTQRFP-KRVRWTG
M. parafortuitum CO1             (1)    -------------MAKRILCFGDSLTWGWIPVEEGVPTERFP-RDVRWTG
MSAT                             (1)    -------------MAKRILCFGDSLTWGWVPVEDGAPTERFA-PDVRWTG
Sm-RSM05666                      (1)    --------------MKTVLCYGDSLTWGYDATG-----SGRHALEDRWPS
At-Q8UAC0                        (1)    --------------MKTVLAFGDSLTWGADPAT-----GLRHPVEHRWPD
At-Q8UFG4                        (1)    -------------MVKSVLCFGDSLTWGSNAET-----GGRHSHDDLWPS
M091_M4aE11                      (1)    --------------MKTILAYGDSLTYGANPIP----GGPRHAYEDRWPT
M1-RML000301                     (1)    MAGGTRLDECTGERMKTVLCYGDSLTWGYNAE------GGRHALEDRWPS
P. dejongeii RVM04532            (1)    --------------MKTILCFGDSNTWGYDPASMTAPFPRRHGPEVRWTG
Q92XZ1 Sinorhizobium meliloti    (1)    ---------MEETVARTVLCFGDSNTHGQVPG--RGPLDRYR-REQRWGG
S261_M2aA12                      (1)    --------------MKNILAFGDSLTWGFVAG-----QDARHPFETRWPN
Sma1993 Sinorhizobium meliloti   (1)    MTINSHSWRTLMVEKRSVLCFGDSLTWGWIPVKESSPTLRYP-YEQRWTG
ZP_00197751                      (1)    --------------MKTILCYGDSLTWGYDAVG-----PSRHAYEDRWPS
ZP_00216984                      (1)    ----------MTMTQKTVLCYGDSNTHGTRPMTHAGGLGRFA-REERWTG
BAB16192                         (1)    -----MICHKGGEEMRSVLCYGDSNTHGQIPG--GSPLDRYG-PNERWPG
BAB16197                         (1)    -----------MAESRSILCFGDSLTWGWIPVPESSPTLRYP-FEQRWTG
NP_522806                        (1)    --------------MQQILLYSDSLSWGIIPG-----TRARLPFAARWAG
Consensus                        (1)                  MKTILCFGDSLTWGWIPV    P  RR   E RW G

                                        51                                              100
20A                             (37)    VLADLLGDRYEVIE---EGLSARTTTADDPADPRLN-GSQYLPSCLASHL
9B Natural Isolate              (49)    VLADELGAGYEVVE---EGLSARTTTADDPTDPRLN-GSDYLPACLASHL
M. parafortuitum CO1            (37)    VLADLLGDRYEVIE---EGLSARTTTAEDPADPRLN-GSQYLPSCLASHL
MSAT                            (37)    VLAQQLGADFEVIE---EGLSARTTNIDDPTDPRLN-GASYLPSCLATHL
Sm-RSM05666                     (32)    VLQKALGSDAHVIA---EGLNGRTTAYDDHLADCDRNGARVLPTVLHTHA
At-Q8UAC0                       (32)    VLEAELAGKAKVHP---EGLGGRTTCYDDHAGPACANGARALEVALSCHM
```

-continued

```
At-Q8UFG4                          (33) VLQKALGSDVHVIFT-HEGLGGRTTAYDDHTGDCDRNGARLLPTLLHSHA
M091_M4aE11                        (33) ALEQGLGGKARVIA---EGLGGRTTVHDDWFANADRNGARVLPTLLESHS
Ml-RML000301                       (45) VLQASLGGGVQVIA---DGLNGRTTAFDDHLAGADANGARLLPTALTTHA
P. dejongeii RVM04532              (37) VLAKALGAGFRVIE---EGQNGRTTVHEDPLNICRK-GKDYLPACLESHK
Q92XZ1 Sinorhizobium meliloti      (39) VLQGLLGPNWQVIE---EGLSGRTTVHDDPIEGSLKNGRIYLRPCLQSHA
S261_M2aA12                        (32) ALAAGLGGKARVIE---EGQNGRTTVFDDAATFESRNGSVALPLLLISHQ
Sma1993 Sinorhizobium meliloti     (50) AMAARLGDGYHIIE---EGLSARTTSLDDPNDARLN-GSTYLPMALASHL
ZP_00197751                        (32) VLQGRLGSSARVIA---EGLCGRTTAFDDWVAGADANGARILPTLLATHS
ZP_00216984                        (40) VLAQTLGASWRVIE---EGLPARTTVHDDPIEGRHKNGLSYLRACVESHL
BAB16192                           (43) VLRRELGSQWYVIE---EGLSGRTTVRDDPIEGTMKNGRTYLRPCLMSHA
BAB16197                           (39) AMAAALGDGYSIIE---EGLSARTTSVEDPNDPRLN-GSAYLPMALASHL
NP_522806                          (32) VMEHALQAQGHAVRIVEDCLNGRTTVLDDPARPGRN-GLQGLAQRIEAHA
Consensus                          (51) VLA  LGA Y VIE   EGL GRIT  DDP D   RNGA YLP  L SH

                                        101                                           150
20A                                (83) PLDLVILMLGINDTKANFGRTPFD--IATGMGVLATQVLTSAGG-VGTSY
9B Natural Isolate                 (95) PLDLVILMLGTNDTKANLNRTPVD--IASGMGVLATQVLTSAGG-VGTSY
M. parafortuitum CO1               (83) PLDLVILMLGTNDTKANFGRTPFD--IATGMGVLATQVLTSAGG-VGTSY
MSAT                               (83) PLDLVIIMLGTNDTKAYFRRTPLD--IALGMSVLVTQVLTSAGG-VGTTY
Sm-RSM05666                        (79) PLDLIVFMLGSNDMKPIIHGTAFG--AVKGIERLVNLVRRHDWPT--ETE
At-Q8UAC0                          (79) PLDLVIIMLGTNDIKPVHGGRAEA--AVSGMARLAQIVETFIYK---PRE
At-Q8UFG4                          (82) PLDMVIIMLGTNDMKPAIHGSAIVAFTMKGVERLVKLTRNHVWQV--SDW
M091_M4aE11                        (80) PLDLIVIMLGTNDIKPHHGRTAGE--AGRGMARLVQIIRGHYAG---RMQ
Ml-RML000301                       (92) PIDLIVIMLGANDMKPWIHGNPVA--AKQGIQRLIDIVRGHDYP---FDW
P. dejongeii RVM04532              (83) PLDLVILMLGTNDLKSTFNVPPGE--IAAGAGVLGRMILAGDA---GPEN
Q92XZ1 Sinorhizobium meliloti      (86) PLDLIIIMLGTNDLKRRFNMPPSE--VAMGIGCLVHDIRELSP---GRTG
S261_M2aA12                        (79) PLDLVIIMLGTNDIKFAARCRAFD--ASMGMERLIQIVRSANYM---KGY
Sma1993 Sinorhizobium meliloti     (96) PLDLVIIMLGTNDTKSYFHRTPYE--IANGMGKLVGQVLTCAGG-VGTPY
ZP_00197751                        (79) PLDLVIVMLGTNDMKSFVCGRAIG--AKQGMERIVQIIRGQPYS---FNY
ZP_00216984                        (87) PVDVVVLMLGTNDLKTRFSVTPAD--IATSVGVLLAKIAACGA---GPSG
BAB16192                           (90) ILDLVIIMLGTNDLKARFGQPPSE--VAMGIGCLVYDIRELAP---GPGG
BAB16197                           (85) PLDLVIILLGTNDTKSYFRRTPYE--IANGMGKLAGQVLTSAGG-IGTPY
NP_522806                          (81) PLALVILMLGTNDFQAIFRHTAQD--AAQGVAQLVRAIRQAPIEP---GM
Consensus                         (101) PLDLVIIMLGTNDLKA F  TP D  IA GMGRLV  VR   G   G  Y

                                        151                                           200
20A                               (130) PAPQVLIVAPPPLGELPHPWFDL--VFSGGREKTAELARVYSALASFMKV
9B Natural Isolate                (142) PAPQVLIVAPPPLAEMPHPWFEL--VFDGGREKTAQLARVYSALASFMKV
M. parafortuitum CO1              (130) PAPQVLIVAPPPLGELPHPWFDL--VFSGGREKTAELARVYSALASFMKV
MSAT                              (130) PAPKVLVVSPPPLAPMPHPWFQL--IFEGGEQKTTELARVYSALASFMKV
Sm-RSM05666                       (125) EGPEILIVSPPPLCETANSAFAAMFAGGVEQSAMLAP--LYRDLADELDC
At-Q8UAC0                         (124) AVPKLLIVAPPPCVAGP--GGEPAGGRDIEQSMRLAP--LYRKLAAELGH
At-Q8UFG4                         (130) EAPDVLIVAPPQLCETANPFMGAIFRDAIDESAMLASVFTYRDLADELDC
M091_M4aE11                       (125) DEPQIILVSPPPIILGDWADMMDHFGPHEAIATSVDFAREYKKRADEQKV
Ml-RML000301                      (137) PAPQILIVSPPVVSRTENADFREMFAGGDEASKQLAP--QYAALADEVGC
P. dejongeii RVM04532             (128) RPPQLLLMCPPKVRDLSAMPDLDAKIPHGAAR-SAEFPRHYKAQAVALKC
Q92XZ1 Sinorhizobium meliloti     (131) NDPEIMIVAPPPMLEDLKEWES---IFSGAQEKSRKLALEFEIMADSLEA
S261_M2aA12                       (124) KIPEILIISPPSLVPTQDEWFNDLWGHAIAESKLFAK--HYKRVAEELKV
Sma1993 Sinorhizobium meliloti    (143) PAPKVLVVAPPPLAPMPDPWFEG--MFGGGYEKSKELSGLYKALADFMKV
ZP_00197751                       (124) KVPSILLVAPPPLCATENSDFAEIFEGGMAESQKLAP--LYAALAQQTGC
ZP_00216984                       (132) ASPKLVLMAPAPIVEVGFLGEI---FAGGAAK-SRQLAKRYEQVASDAGA
BAB16192                          (135) KPPEIMVVAPPPMLDDIKEWEP---IFSGAQEKSRRLALEFEIIADSLEV
BAB16197                          (132) PAPKLLIVSPPPLAPMPDPWFEG--MFGGGYEKSLELAKQYKALANFLKV
NP_522806                         (126) PVPPVLIVVPPAITAPAGAMADK---FADAQPKCAGLAQAYRATAQTLGC
Consensus                         (151)  AP ILIVAPPPL E    WF    IFGGA  KS  LA  YKALA  LKV

                                        201                                      248
20A                               (178) PFFDAGSVISTDGVDGTHFTRGETI----------------------- (SEQ ID NO: 675)
9B Natural Isolate                (190) PFFDAGSVISTDGVDGTHFTRGETIDR--------------------- (SEQ ID NO: 676)
M. parafortuitum CO1              (178) PFFDAGSVISTDGVDGIHFTRGEQST---------------------- (SEQ ID NO: 677)
MSAT                              (178) PFFDAGSVISTDGVDGIHFTEANNRDLGVALAEQVRSLL--------- (SEQ ID NO: 678)
Sm-RSM05666                       (173) GFFDGGSVARTTPIDGVHLDAENTRAVGRGLEPVVRMMLGL------- (SEQ ID NO: 679)
At-Q8UAC0                         (170) HFFDAGSVASASPVDGVHLDASATAAIGRALAAPVRDILG-------- (SEQ ID NO: 680)
At-Q8UFG4                         (180) GFFDAGSVARTTPVDGVHLDAENTRAIGRGLEPVVRMMLGL------- (SEQ ID NO: 681)
M091_M4aE11                       (175) HFFDAGTVATTSKADGIHLDPANTRAIGAGLVPLVKQVLGL------- (SEQ ID NO: 682)
Ml-RML000301                      (185) GFFDAGTVAQTTPLDGVHLDAENTRNIGKALTSVVRVML--------- (SEQ ID NO: 683)
P. dejongeii RVM04532             (177) EYFFSQEIVETSPVDGIHLEASEHLKLGEALAEKVKVLLG-------- (SEQ ID NO: 684)
Q92XZ1 Sinorhizobium meliloti     (178) HFFDAGTVCQCSPADGFHIDEDAHRLLGEALAQEVLAIGWPDA----- (SEQ ID NO: 685)
S261_M2aA12                       (172) HFFDAGTVAVADKTDGGHLDAVNTKAIGVALVPVVKSILAL------- (SEQ ID NO: 686)
Sma1993 Sinorhizobium meliloti    (191) EFFAAGDCISTDGIDGIHLSAETNIRLGHAIADKVAALF--------- (SEQ ID NO: 687
ZP_00197751                       (172) AFFDAGTVARTTPLDGIHLDAENTRAIGAGLEPVVRQALGL------- (SEQ ID NO: 688)
ZP_00216984                       (178) HFLDAGAIVEVSPVDGVHFAADQHRVLGQRVAALLQQIA--------- (SEQ ID NO: 689)
BAB16192                          (182) HFFDAATVASCDPCDGFHINREAHEALGTALAREVEAIGWR------- (SEQ ID NO: 690)
BAB16197                          (180) DFLDAGEFVKIDGCDGIHFSAETNITLGHAIAAKVEAIFSQEAKNAAA (SEQ ID NO: 691)
NP_522806                         (173) HVFDANSVTPASAVDGIHLDADQHAQLGRAMAQVVGTLLAQ------- (SEQ ID NO: 692)
Consensus                         (201)  FFDAGSV  TSPVDGIHLDAENTR LG ALA  VR IL (SEQ ID NO: 693)
```

The guide tree to the CLUSTALW alignment (which approximates to a phylogenetic tree) clearly indicates 3 groupings:

1) GDSL-ARTT group including Act

2) GDSL-GRTT group composed of members of the *Rhizobiales* and the metagenome; and 3) Intermediate group of mixed motifs.

It is also contemplated that the results suggest some form of gene duplication and mutation events in the *Rhizobiales* and lateral gene transfer to *Mycobacterium*.

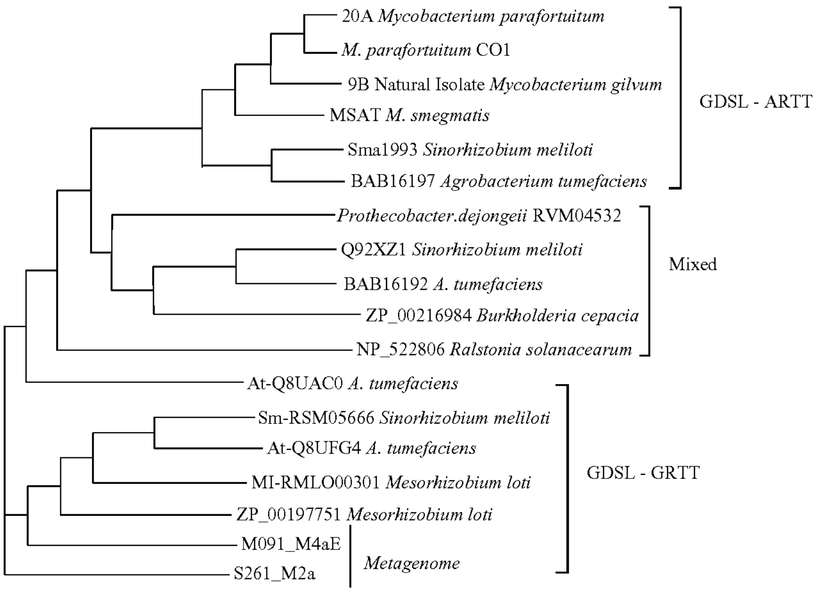

Using the non-redundant alignment a new Act consensus was constructed called "Act chimera".

```
                                          (SEQ ID NO: 694)
  1 KTILCFGDSL TWGWIPVEDG APTERRAPEV RWTGVLAQQL
    GADYEVIEEG

 51 LSGRTTNIDD PTDPRLRNGA SYLPSCLASH LPLDLVIIML
    GTNDLKAYFR
```

-continued

```
101 RTPLDIALGM GRLVTQVRTS AGGVGTTYPA PKILIVAPPP
    LAEMPHPWFQ

151 LIFGGAEQKS TELARVYKAL ASFLKVPFFD AGSVISTSPV
    DGIHLDAENT

201 RDLGVALAEQ VRSIL
```

An alignment of Act-chimera with Ms Act (Chimera align) indicates 91.6% similarity and 86.0% identity, as indicated below.

```
                        1                                                 50
MSAT             (1)  MAKRILCFGDSLTWGWVPVEDGAPTERFAPDVRWTGVLAQQLGADFEVIE
Act-Chimera      (1)  --KTILCFGDSLTWGWIPVEDGAPTERRAPEVRWTGVLAQQLGADYEVIE
Consensus        (1)    K ILCFGDSLTWGWIPVEDGAPTER APDVRWTGVLAQQLGADFEVIE

                        51                                               100
MSAT            (51)  EGLSARTTNIDDPTDPRLN-GASYLPSCLATHLPLDLVIIMLGTNDTKAY
Act-Chimera     (49)  EGLSGRTTNIDDPTDPRLRNGASYLPSCLASHLPLDLVIIMLGTNDLKAY
Consensus       (51)  EGLSARTTNIDDPTDPRL  GASYLPSCLASHLPLDLVIIMLGTND KAY

                        101                                              150
MSAT           (100)  FRRTPLDIALGMSVLVTQVLTSAGGVGTTYPAPKVLVVSPPPLAPMPHPW
Act-Chimera     (99)  FRRTPLDIALGMGRLVTQVRTSAGGVGTTYPAPKILIVAPPPLAEMPHPW
Consensus      (101)  FRRTPLDIALGM  LVTQV TSAGGVGTTYPAPKILIVAPPPLA MPHPW

                        151                                              200
MSAT           (150)  FQLIFEGGEQKTTELARVYSALASFMKVPFFDAGSVISTDGVDGIHFTEA
Act-Chimera    (149)  FQLIFGGAEQKSTELARVYKALASFLKVPFFDAGSVISTSPVDGIHLDAE
Consensus      (151)  FQLIF GAEQKSTELARVY ALASFLKVPFFDAGSVIST  VDGIH

                        201            217
MSAT           (200)  NNRDLGVALAEQVRSLL  (SEQ ID NO: 695)
Act-Chimera    (199)  NTRDLGVALAEQVRSIL  (SEQ ID NO: 694)
Consensus      (201)  N RDLGVALAEQVRSIL  (SEQ ID NO: 696)
```

A BLASTP search with Act-chimera did not reveal any further sequences.

The Act-chimera is "forced" on the Per sequence at the positions where no consensus exists. However, a basic 'unforced' consensus sequence did not provide any more information from a blastp search or from alignment analysis. Thus, comparison with the most distant homologues in the blastp 'hit' list was considered more useful in defining the important residues/positions in Act sequence space. This was a useful exercise, as these sequences were not used in the non-redundant alignment.

For example, *Rhodopirellula baltica* (NP__865748; Psp; a *Planctomycetes* and quite different from either *Mycobacterium* or *Rhizobiales*), was compared as shown below.

alpha-Proteobacteria). A few members of the beta-Proteobacteria were found, but no *Mycobacterium* sp. This provides an indication that the perhydrolase (Per) gene/protein is not widely distributed in nature.

The *Mycobacterium* protein is characterized by the GDSL-ARTT motif, whereas most of the *Rhizobiales* are characterized by a GDSL-GRTT motif. There are also some mixed or intermediate motifs (e.g., GDSN-GRTT, GDSN-ARTT and SDSL-GRTT). This may indicate gene duplication and mutation event and lateral gene transfer. The consensus residues identified in these experiments were L6, W14, R27, W34, L38, R56, D62, L74, L78, H81, P83, M90, K97, G110, L114, L135, F180, and G205.

```
                  1                                                50
MSAT          (1) MAKRILCFGDSLTWGWVPVEDGAPTERFAPDVRWTGVLA---QQLGADFE
NP_865746     (1) -MHSILIYGDSLSWGIIPGTR----RRFAFHQRWPGVMEIELRQTGIDAR
Consensus     (1)     IL FGDSLSWG IP        RFA   RW GVL     Q G D

                  51                                               100
MSAT         (48) VIEEGLSARTTNIDDPTDPRLNGASYLPSCLATHLPLDLVIIMLGTNDTK
NP_865746    (46) VIEDCLNGRRTVLEDPIKPGRNGLDGLQQRIEINSPLSLVVLFLGTNDFQ
Consensus    (51) VIED L AR T IDDP  P  NG   L   I    PL LVII LGTND

                  101                                              150
MSAT         (98) AYFRRTPLDIALGMSVLVTQVLTSAGGVGTTYPAPKVLVVSPPPLAPMPH
NP_865746    (96) SVHEFHAEQSAQGLALLV--DAIRRSPFEPGMPTPKILLVAPPTVHH-PK
Consensus   (101) A         A GLALLV              P PKILLVAPP L   P

                  151                                              200
MSAT        (148) PWFQLIFEGGEQKTTELARVYSALASFMKVPFFDAGSVISTDGVDGIHFT
NP_865746   (143) LDMAAKFQNAETKSTGLADAIRKVSTEHSCEFFDAATVTTTSVVDGVHLD
Consensus   (151)       F  AE KST LA      LAS     FFDAASV ST  VDGIH

                  201                 222
MSAT        (198) EANNRDLGVALAEQVRSLL---  (SEQ ID NO: 695)
NP_865746   (193) QEQHQALGTALASTIAEILADC  (SEQ ID NO: 697)
Consensus   (201)   N   LG ALA  I  IL  (SEQ ID NO: 698)
```

The following is an alignment with *Ralstonia eutropha* (Reu):

```
                  1                                                50
MSAT          (1) ---------MAKRILCFGDSLTWGWVPVEDGAPTERFAPDVRWTGVLA--
ZP_00166901   (1) MPLTAPSEVDPLQILVYADSLSWGIVPGTR----RRLPFPVRWPGRLELG
Consensus     (1)              IL FADSLSWG VP        R    VRW G L

                  51                                               100
MSAT         (40) --QQLGADFEVIEEGLSARTTNIDDPTDPRLNGASYLPSCLATHLPLDLV
ZP_00166901  (47) LNADGGAPVRIIEDCLNGRRTVWDDPFKPGRNGLQGLAQRIEIHSPVALV
Consensus    (51)      GA   IIED L AR T  DDP  P  NG   L   I  H PL LV

                  101                                              150
MSAT         (88) IIMLGTNDTKAYFRRTPLDIALGMSVLVTQVLTSAGGVGTTYPAPKVLVV
ZP_00166901  (97) VLMLGNNDFQSMHPHNAWHAAQGVGALV--HAIRTAPIEPGMPVPPILVV
Consensus   (101) IIMLG ND  A         A GM  LV       A I    P P ILVV

                  151                                              200
MSAT        (138) SPPPLAPMPHPWFQLIFEGGEQKTTELARVYSALASFMKVPFFDAGSVIS
ZP_00166901 (145) VPPPIRT-PCGPLAPKFAGGEHKWAGLPEALRELCATVDCSLFDAGTVIQ
Consensus   (151) PPPI   P       F GGE K   L      L A M    FDAGSVI

                  201                               237
MSAT        (188) TDGVDGIHFTEANNRDLGVALAEQVRSLL-------- (SEQ ID NO: 695)
ZP_00166901 (194) SSAVDGVHLDADAHVALGDALQPVVRALLAESSGHPS (SEQ ID NO: 699)
Consensus   (201) S AVDGIH        LG AL   VRALL (SEQ ID NO: 700)
```

Based on these results, the following conclusions were made. A BLASTp nr-database search with a perhydrolase consensus sequence revealed GDSL or GDSI lipases/esterases from a wide diversity of organisms. However, only 12 or 14 of these were reliable homologues of Per. Nearly all of these were derived from 1 small group of bacteria, namely the *Rhizobiales* (i.e., Gram-negative soil bacteria belonging the Using the non-redundant alignment and comparison with distant homologues the follow sequence space can be defined starting at position 5 of the *M. smegmatis* perhydrolase and ending at position 195, with perhydrolase shown in residues in bold. [I, V][L][X][F, Y][G,S][D][S][L,N][T, S][W, Y, H][G][X]$_{2}$[P, A][X]$_{14}$[R, L][W][X]$_{7}$[L][X]$_{5}$[V, I][I, V, H][X][E. D][G, C][L, Q][X][G,A][R][T][T][X]$_{2}$[D, E][D][X]$_{7}$[G]

[X]$_3$[L][X]$_6$[H][X][P, I][L, I, V][D, A][V, I][X]$_2$[M, L][L][G][X][N][D][X]$_{36}$[P][X]$_6$[P][P, A][X]$_{31}$[A][X]$_{19}$[D][G][X][H] (SEQ ID NO:701)

In sum, it is clear from the analyses above that the active clones/sequences with a GDS$x_1$-$x_2$RTT-G$x_3$ND motif have all been found among the alpha-Proteobacteria-Gram-negative bacteria associated with the soil rhizosphere. This is in sharp contrast to the prototype perhydrolase from *M. smegmatis* a high GC content Gram-positive bacterium assigned to the class Actinobacteria. This division is illustrated in FIG. 2, which provides a phylogenetic tree, showing the major branches of the bacteria and the origin of the active clones/sequences compared to *M. smegmatis.*

Example 14

Native Molecular Weight Estimation of Homologues of the Perhydrolase

In this Example, experiments conducted to estimate the native molecular weights of *M. smegmatis* perhydrolase homologues are described.

Preparation of Samples for Purification (Size Determination)

A single colony of the desired strains was inoculated in 50 ml Terrific Broth and incubated overnight at 37° C. with shaking at 200 rpm. The cells were pelleted by centrifugation for 10 minutes at 7000 rpm in a Sorvall SuperSpeed Centrifuge. The pellets were then resuspended in 10 ml 25 mM Bis-Tris (pH 6.5) and lysed by passage through a French pressure cell twice. The lysates were then centrifuged at 15000 rpm in a Sorvall SuperSpeed Centrifuge. The soluble fraction was heat treated at 55° C. for 1 hour to precipitate cellular proteins. The samples were then centrifuged at 10000 rpm in a Sorvall SuperSpeed Centrifuge and the soluble fractions used for further purification or assay.

Sizing Columns

The supernatants (prepared as described above) were run on a Sephadex 200 sizing column in 20 mM phosphate (pH 8.0), with a flow rate of 0.5 ml/min. The column was calibrated prior to running the samples with MW standards (listed below) and purified *M. smegmatis* perhydrolase protein. The crude sample elution volumes were determined by collecting 0.5 ml fractions, and assaying the fractions for pNB activity. Molecular weights and elution volumes of the standards:

Thyroglobulin MW 669 kDa: elution volume 16 ml

Aldolase MW 158 kDa: elution volume 24 ml

Ovalbumin MW 43 kDa: elution volume 26 ml

Ribonuclease MW 14 kDa: elution volume 32 ml

Perhydrolase elution volume 24 ml

Results

The following Table (Table 14-1) provides the elution volume of some of the *M. smegmatis* perhydrolase homologues identified herein.

TABLE 14-1

Elution Volume (Estimated Molecular Weight) of *M. smegmatis* Perhydrolase Homologues

| Homologue Sample | Elution Volume (ml) |
|---|---|
| pLO_SmeI | 24 |
| pET26_SmeII | 24 |
| pET26_MIO | 24 |
| pET26b_Stm | 24 |
| pET26b_Mbo | 24 |
| M7OaEB_pET26 | 32 |
| pET26_m2aA12 | 24 |
| pET26b_S2487am | 32 |
| *S. meliloti* RSM02162 (G00355) | 24 |
| PET_M2aAl2 (5261) | 24 |
| *M. smegmatis* Perhydrolase | 24 |

The data in the above Table and the assay results obtained for these homologues indicated that these enzymes have an amino acid sequence similar to the *M. smegmatis* perhydrolase. As with the *M. smegmatis* perhydrolase, these homologues exhibit perhydrolysis activity as multimers. As described herein, the perhydrolase is an octamer, while the homologues, although they elute in a similar volume, are contemplated to be dimers, trimers, tetramers, hexamers, and/or octamers.

Example 15

Crystal Structure of Perhydrolase

In this Example, the crystallographic analysis of the perhydrolase is described. Perhydrolase crystals were obtained under two conditions: 2.0 M $[NH_4]_2SO_4$, 2% PEG400, 0.1 M Tris pH 7.1 (giving triclinic, P1 crystals) and 1.0 M ammonium dihydrogen phosphate, and 0.1M sodium citrate pH 5.6 (giving tetragonal, P4 crystals) Both crystal forms gave suitable diffraction beyond 2.0 Å resolution. Derivative protein for a MAD phase determination using selenium replacing sulfur containing methionine resulting in a protein molecule having four selenomethionines the N-terminal methionine is cleaved proteolytically. Of the two forms, triclininc P1 a=83.77 Å b=90.07 Å c=112.115 Å $\alpha$=73.32° $\beta$, 77.30° $\gamma$=88.07° and P4 a=b=98.18 Å c=230.12 Å, the P4 crystal gave data that was possible to use for structure determination. Three wavelength MAD datasets were collected at wavelengths corresponding to the Se absorption edge, near the inflection point and a third, away from the absorption edge.

Three hundred and thirty-three frames (0.3 degree oscillations per frame) for each wavelength with 1 sec exposure time were collected from a single tetragonal space group P4 crystal. The structure could be solved with either SOLVE or SHELX computer programs giving similar solutions for the 32 possible Se positions. The map was fitted using the program "O". It was possible to trace electron density for residues 3-216 in each of the eight independent molecules. The final structure of these eight molecules was refined using CNS. The current crystallographic R-factor is 21%. The coordinates are provided below.

| | | | | | | | | | | |
|---|---|---|---|---|---|---|---|---|---|---|
| CRYST1 | 98.184 | 98.184 | 230.119 | 90.00 | 90.00 | 90.00 | | | | |
| SCALE1 | | 0.010185 | 0.000000 | 0.000000 | | 0.000000 | | | | |
| SCALE2 | | 0.000000 | 0.010185 | 0.000000 | | 0.000000 | | | | |
| SCALE3 | | 0.000000 | 0.000000 | 0.004346 | | 0.000000 | | | | |
| ATOM | 1 | CB | LYS | 3 | −8.167 | −61.964 | 18.588 | 1.000 | 40.95 | |
| ATOM | 2 | CG | LYS | 3 | −8.685 | −63.192 | 19.323 | 1.000 | 22.95 | |
| ATOM | 3 | CD | LYS | 3 | −8.635 | −64.400 | 18.399 | 1.000 | 14.97 | |
| ATOM | 4 | CE | LYS | 3 | −7.963 | −65.575 | 19.090 | 1.000 | 19.83 | |

-continued

| | | | | | | | | | |
|---|---|---|---|---|---|---|---|---|---|
| ATOM | 5 | NZ | LYS | 3 | −7.359 | −66.511 | 18.099 | 1.000 | 44.28 |
| ATOM | 6 | C | LYS | 3 | −9.684 | −60.377 | 17.426 | 1.000 | 13.89 |
| ATOM | 7 | O | LYS | 3 | −9.087 | −59.356 | 17.767 | 1.000 | 12.50 |
| ATOM | 8 | N | LYS | 3 | −8.000 | −61.626 | 16.153 | 1.000 | 15.57 |
| ATOM | 9 | CA | LYS | 3 | −8.919 | −61.686 | 17.284 | 1.000 | 20.71 |
| ATOM | 10 | N | ARG | 4 | −10.987 | −60.381 | 17.166 | 1.000 | 24.56 |
| ATOM | 11 | CA | ARG | 4 | −11.695 | −59.097 | 17.204 | 1.000 | 22.65 |
| ATOM | 12 | CB | ARG | 4 | −12.299 | −58.822 | 15.822 | 1.000 | 21.44 |
| ATOM | 13 | CG | ARG | 4 | −11.232 | −58.465 | 14.792 | 1.000 | 21.56 |
| ATOM | 14 | CD | ARG | 4 | −11.845 | −58.181 | 13.431 | 1.000 | 29.29 |
| ATOM | 15 | NE | ARG | 4 | −11.660 | −56.790 | 13.020 | 1.000 | 32.87 |
| ATOM | 16 | CZ | ARG | 4 | −12.643 | −56.013 | 12.585 | 1.000 | 30.24 |
| ATOM | 17 | NH1 | ARG | 4 | −13.879 | −56.487 | 12.494 | 1.000 | 17.82 |
| ATOM | 18 | NH2 | ARG | 4 | −12.399 | −54.760 | 12.229 | 1.000 | 44.53 |
| ATOM | 19 | C | ARG | 4 | −12.735 | −59.054 | 18.308 | 1.000 | 14.59 |
| ATOM | 20 | O | ARG | 4 | −13.604 | −59.909 | 18.456 | 1.000 | 18.72 |
| ATOM | 21 | N | ILE | 5 | −12.639 | −58.012 | 19.131 | 1.000 | 13.45 |
| ATOM | 22 | CA | ILE | 5 | −13.549 | −57.882 | 20.263 | 1.000 | 12.08 |
| ATOM | 23 | CB | ILE | 5 | −12.747 | −57.835 | 21.578 | 1.000 | 15.40 |
| ATOM | 24 | CG2 | ILE | 5 | −13.678 | −57.677 | 22.765 | 1.000 | 5.80 |
| ATOM | 25 | CG1 | ILE | 5 | −11.811 | −59.034 | 21.741 | 1.000 | 11.66 |
| ATOM | 26 | CD1 | ILE | 5 | −10.437 | −58.632 | 22.232 | 1.000 | 19.35 |
| ATOM | 27 | C | ILE | 5 | −14.420 | −56.640 | 20.142 | 1.000 | 8.96 |
| ATOM | 28 | O | ILE | 5 | −13.905 | −55.529 | 20.021 | 1.000 | 13.31 |
| ATOM | 29 | N | LEU | 6 | −15.736 | −56.833 | 20.169 | 1.000 | 13.04 |
| ATOM | 30 | CA | LEU | 6 | −16.675 | −55.728 | 20.059 | 1.000 | 8.54 |
| ATOM | 31 | CB | LEU | 6 | −17.879 | −56.087 | 19.178 | 1.000 | 7.42 |
| ATOM | 32 | CG | LEU | 6 | −18.959 | −54.996 | 19.120 | 1.000 | 14.12 |
| ATOM | 33 | CD1 | LEU | 6 | −18.446 | −53.783 | 18.359 | 1.000 | 12.19 |
| ATOM | 34 | CD2 | LEU | 6 | −20.245 | −55.512 | 18.494 | 1.000 | 27.94 |
| ATOM | 35 | C | LEU | 6 | −17.170 | −55.293 | 21.436 | 1.000 | 2.72 |
| ATOM | 36 | O | LEU | 6 | −17.719 | −56.101 | 22.179 | 1.000 | 13.36 |
| ATOM | 37 | N | CYS | 7 | −16.978 | −54.020 | 21.756 | 1.000 | 1.38 |
| ATOM | 38 | CA | CYS | 7 | −17.472 | −53.469 | 23.011 | 1.000 | 3.17 |
| ATOM | 39 | CB | CYS | 7 | −16.411 | −52.582 | 23.667 | 1.000 | 7.01 |
| ATOM | 40 | SG | CYS | 7 | −14.867 | −53.471 | 23.992 | 1.000 | 11.21 |
| ATOM | 41 | C | CYS | 7 | −18.755 | −52.685 | 22.776 | 1.000 | 0.65 |
| ATOM | 42 | O | CYS | 7 | −18.756 | −51.627 | 22.145 | 1.000 | 4.76 |
| ATOM | 43 | N | PHE | 8 | −19.859 | −53.228 | 23.281 | 1.000 | 0.00 |
| ATOM | 44 | CA | PHE | 8 | −21.147 | −52.568 | 23.053 | 1.000 | 1.14 |
| ATOM | 45 | CB | PHE | 8 | −22.115 | −53.578 | 22.443 | 1.000 | 5.54 |
| ATOM | 46 | CG | PHE | 8 | −23.421 | −53.000 | 21.937 | 1.000 | 3.36 |
| ATOM | 47 | CD1 | PHE | 8 | −23.456 | −52.212 | 20.800 | 1.000 | 0.89 |
| ATOM | 48 | CD2 | PHE | 8 | −24.602 | −53.262 | 22.614 | 1.000 | 1.39 |
| ATOM | 49 | CE1 | PHE | 8 | −24.644 | −51.683 | 20.333 | 1.000 | 0.00 |
| ATOM | 50 | CE2 | PHE | 8 | −25.793 | −52.733 | 22.148 | 1.000 | 4.42 |
| ATOM | 51 | CZ | PHE | 8 | −25.818 | −51.944 | 21.012 | 1.000 | 2.71 |
| ATOM | 52 | C | PHE | 8 | −21.677 | −51.978 | 24.346 | 1.000 | 4.46 |
| ATOM | 53 | O | PHE | 8 | −21.873 | −52.672 | 25.348 | 1.000 | 6.98 |
| ATOM | 54 | N | GLY | 9 | −21.923 | −50.666 | 24.384 | 1.000 | 5.61 |
| ATOM | 55 | CA | GLY | 9 | −22.396 | −50.109 | 25.646 | 1.000 | 5.44 |
| ATOM | 56 | C | GLY | 9 | −22.860 | −48.673 | 25.522 | 1.000 | 5.66 |
| ATOM | 57 | O | GLY | 9 | −23.229 | −48.222 | 24.440 | 1.000 | 14.54 |
| ATOM | 58 | N | ASP | 10 | −22.837 | −47.964 | 26.641 | 1.000 | 3.89 |
| ATOM | 59 | CA | ASP | 10 | −23.322 | −46.596 | 26.734 | 1.000 | 5.17 |
| ATOM | 60 | CB | ASP | 10 | −24.331 | −46.467 | 27.880 | 1.000 | 2.99 |
| ATOM | 61 | CG | ASP | 10 | −23.807 | −47.052 | 29.175 | 1.000 | 7.05 |
| ATOM | 62 | OD1 | ASP | 10 | −22.617 | −46.829 | 29.494 | 1.000 | 17.93 |
| ATOM | 63 | OD2 | ASP | 10 | −24.564 | −47.738 | 29.895 | 1.000 | 10.98 |
| ATOM | 64 | C | ASP | 10 | −22.154 | −45.642 | 26.939 | 1.000 | 5.15 |
| ATOM | 65 | O | ASP | 10 | −21.022 | −45.940 | 26.556 | 1.000 | 5.62 |
| ATOM | 66 | N | SER | 11 | −22.423 | −44.497 | 27.554 | 1.000 | 9.02 |
| ATOM | 67 | CA | SER | 11 | −21.394 | −43.493 | 27.802 | 1.000 | 3.43 |
| ATOM | 68 | CB | SER | 11 | −22.014 | −42.331 | 28.585 | 1.000 | 7.25 |
| ATOM | 69 | OG | SER | 11 | −22.640 | −42.813 | 29.763 | 1.000 | 18.93 |
| ATOM | 70 | C | SER | 11 | −20.199 | −44.046 | 28.561 | 1.000 | 7.58 |
| ATOM | 71 | O | SER | 11 | −19.089 | −43.508 | 28.501 | 1.000 | 16.71 |
| ATOM | 72 | N | LEU | 12 | −20.393 | −45.133 | 29.308 | 1.000 | 6.56 |
| ATOM | 73 | CA | LEU | 12 | −19.264 | −45.696 | 30.046 | 1.000 | 16.41 |
| ATOM | 74 | CB | LEU | 12 | −19.711 | −46.759 | 31.042 | 1.000 | 17.05 |
| ATOM | 75 | CG | LEU | 12 | −20.598 | −46.336 | 32.210 | 1.000 | 18.22 |
| ATOM | 76 | CD1 | LEU | 12 | −20.866 | −47.527 | 33.123 | 1.000 | 7.48 |
| ATOM | 77 | CD2 | LEU | 12 | −19.973 | −45.184 | 32.988 | 1.000 | 10.83 |
| ATOM | 78 | C | LEU | 12 | −18.269 | −46.285 | 29.048 | 1.000 | 14.99 |
| ATOM | 79 | O | LEU | 12 | −17.065 | −46.307 | 29.267 | 1.000 | 6.10 |
| ATOM | 80 | N | THR | 13 | −18.828 | −46.764 | 27.940 | 1.000 | 14.77 |
| ATOM | 81 | CA | THR | 13 | −18.014 | −47.347 | 26.876 | 1.000 | 8.83 |
| ATOM | 82 | CB | THR | 13 | −18.828 | −48.381 | 26.080 | 1.000 | 6.87 |
| ATOM | 83 | OG1 | THR | 13 | −19.109 | −49.487 | 26.949 | 1.000 | 10.08 |

-continued

| | | | | | | | | | |
|---|---|---|---|---|---|---|---|---|---|
| ATOM | 84 | CG2 | THR | 13 | −18.033 | −48.940 | 24.914 | 1.000 | 16.85 |
| ATOM | 85 | C | THR | 13 | −17.490 | −46.245 | 25.970 | 1.000 | 4.56 |
| ATOM | 86 | O | THR | 13 | −16.315 | −46.220 | 25.616 | 1.000 | 11.71 |
| ATOM | 87 | N | TRP | 14 | −18.376 | −45.317 | 25.612 | 1.000 | 5.57 |
| ATOM | 88 | CA | TRP | 14 | −17.992 | −44.210 | 24.742 | 1.000 | 7.21 |
| ATOM | 89 | CB | TRP | 14 | −19.208 | −43.329 | 24.453 | 1.000 | 6.90 |
| ATOM | 90 | CG | TRP | 14 | −18.917 | −42.183 | 23.537 | 1.000 | 11.88 |
| ATOM | 91 | CD2 | TRP | 14 | −18.731 | −40.813 | 23.924 | 1.000 | 13.72 |
| ATOM | 92 | CE2 | TRP | 14 | −18.483 | −40.081 | 22.745 | 1.000 | 11.95 |
| ATOM | 93 | CE3 | TRP | 14 | −18.752 | −40.147 | 25.152 | 1.000 | 10.63 |
| ATOM | 94 | CD1 | TRP | 14 | −18.779 | −42.222 | 22.181 | 1.000 | 8.28 |
| ATOM | 95 | NE1 | TRP | 14 | −18.517 | −40.963 | 21.694 | 1.000 | 7.16 |
| ATOM | 96 | CZ2 | TRP | 14 | −18.255 | −38.705 | 22.763 | 1.000 | 5.39 |
| ATOM | 97 | CZ3 | TRP | 14 | −18.526 | −38.783 | 25.168 | 1.000 | 12.55 |
| ATOM | 98 | CH2 | TRP | 14 | −18.282 | −38.084 | 23.981 | 1.000 | 12.81 |
| ATOM | 99 | C | TRP | 14 | −16.880 | −43.353 | 25.327 | 1.000 | 5.41 |
| ATOM | 100 | O | TRP | 14 | −16.107 | −42.745 | 24.582 | 1.000 | 4.90 |
| ATOM | 101 | N | GLY | 15 | −16.794 | −43.283 | 26.652 | 1.000 | 8.94 |
| ATOM | 102 | CA | GLY | 15 | −15.794 | −42.475 | 27.318 | 1.000 | 4.51 |
| ATOM | 103 | C | GLY | 15 | −16.249 | −41.098 | 27.755 | 1.000 | 10.98 |
| ATOM | 104 | O | GLY | 15 | −15.480 | −40.136 | 27.646 | 1.000 | 15.11 |
| ATOM | 105 | N | TRP | 16 | −17.471 | −40.952 | 28.255 | 1.000 | 23.34 |
| ATOM | 106 | CA | TRP | 16 | −17.988 | −39.691 | 28.792 | 1.000 | 15.10 |
| ATOM | 107 | CB | TRP | 16 | −19.408 | −39.890 | 29.327 | 1.000 | 6.11 |
| ATOM | 108 | CG | TRP | 16 | −20.139 | −38.694 | 29.846 | 1.000 | 1.78 |
| ATOM | 109 | CD2 | TRP | 16 | −21.229 | −38.008 | 29.213 | 1.000 | 8.98 |
| ATOM | 110 | CE2 | TRP | 16 | −21.613 | −36.942 | 30.051 | 1.000 | 7.76 |
| ATOM | 111 | CE3 | TRP | 16 | −21.923 | −38.186 | 28.009 | 1.000 | 15.66 |
| ATOM | 112 | CD1 | TRP | 16 | −19.927 | −38.021 | 31.016 | 1.000 | 0.35 |
| ATOM | 113 | NE1 | TRP | 16 | −20.798 | −36.973 | 31.154 | 1.000 | 8.35 |
| ATOM | 114 | CZ2 | TRP | 16 | −22.649 | −36.063 | 29.734 | 1.000 | 5.16 |
| ATOM | 115 | CZ3 | TRP | 16 | −22.952 | −37.317 | 27.692 | 1.000 | 5.34 |
| ATOM | 116 | CH2 | TRP | 16 | −23.306 | −36.269 | 28.551 | 1.000 | 4.72 |
| ATOM | 117 | C | TRP | 16 | −17.059 | −39.154 | 29.881 | 1.000 | 7.85 |
| ATOM | 118 | O | TRP | 16 | −16.846 | −39.815 | 30.899 | 1.000 | 3.97 |
| ATOM | 119 | N | VAL | 17 | −16.533 | −37.952 | 29.685 | 1.000 | 5.45 |
| ATOM | 120 | CA | VAL | 17 | −15.750 | −37.256 | 30.695 | 1.000 | 12.08 |
| ATOM | 121 | CB | VAL | 17 | −14.822 | −36.191 | 30.082 | 1.000 | 17.55 |
| ATOM | 122 | CG1 | VAL | 17 | −14.084 | −35.443 | 31.185 | 1.000 | 11.59 |
| ATOM | 123 | CG2 | VAL | 17 | −13.841 | −36.807 | 29.099 | 1.000 | 7.77 |
| ATOM | 124 | C | VAL | 17 | −16.673 | −36.565 | 31.696 | 1.000 | 13.86 |
| ATOM | 125 | O | VAL | 17 | −17.390 | −35.618 | 31.351 | 1.000 | 1.02 |
| ATOM | 126 | N | PRO | 18 | −16.660 | −37.034 | 32.936 | 1.000 | 8.38 |
| ATOM | 127 | CD | PRO | 18 | −15.770 | −38.071 | 33.476 | 1.000 | 8.64 |
| ATOM | 128 | CA | PRO | 18 | −17.572 | −36.501 | 33.948 | 1.000 | 9.99 |
| ATOM | 129 | CB | PRO | 18 | −17.201 | −37.294 | 35.208 | 1.000 | 12.31 |
| ATOM | 130 | CG | PRO | 18 | −15.817 | −37.789 | 34.954 | 1.000 | 7.46 |
| ATOM | 131 | C | PRO | 18 | −17.327 | −35.017 | 34.191 | 1.000 | 13.05 |
| ATOM | 132 | O | PRO | 18 | −16.163 | −34.619 | 34.306 | 1.000 | 18.63 |
| ATOM | 133 | N | VAL | 19 | −18.381 | −34.211 | 34.266 | 1.000 | 6.92 |
| ATOM | 134 | CA | VAL | 19 | −18.214 | −32.793 | 34.585 | 1.000 | 9.29 |
| ATOM | 135 | CB | VAL | 19 | −18.482 | −31.856 | 33.388 | 1.000 | 5.33 |
| ATOM | 136 | CG1 | VAL | 19 | −17.377 | −31.995 | 32.354 | 1.000 | 6.78 |
| ATOM | 137 | CG2 | VAL | 19 | −19.850 | −32.150 | 32.796 | 1.000 | 3.72 |
| ATOM | 138 | C | VAL | 19 | −19.151 | −32.380 | 35.710 | 1.000 | 12.02 |
| ATOM | 139 | O | VAL | 19 | −20.217 | −32.962 | 35.913 | 1.000 | 14.52 |
| ATOM | 140 | N | GLU | 20 | −18.771 | −31.351 | 36.467 | 1.000 | 17.17 |
| ATOM | 141 | CA | GLU | 20 | −19.662 | −30.994 | 37.575 | 1.000 | 13.30 |
| ATOM | 142 | CB | GLU | 20 | −18.918 | −30.130 | 38.595 | 1.000 | 25.34 |
| ATOM | 143 | CG | GLU | 20 | −18.276 | −30.968 | 39.702 | 1.000 | 31.46 |
| ATOM | 144 | CD | GLU | 20 | −16.871 | −30.487 | 40.017 | 1.000 | 35.91 |
| ATOM | 145 | OE1 | GLU | 20 | −16.143 | −30.157 | 39.055 | 1.000 | 40.11 |
| ATOM | 146 | OE2 | GLU | 20 | −16.507 | −30.431 | 41.210 | 1.000 | 45.47 |
| ATOM | 147 | C | GLU | 20 | −20.913 | −30.294 | 37.080 | 1.000 | 7.56 |
| ATOM | 148 | O | GLU | 20 | −21.964 | −30.361 | 37.723 | 1.000 | 11.30 |
| ATOM | 149 | N | ASP | 21 | −20.852 | −29.610 | 35.936 | 1.000 | 19.38 |
| ATOM | 150 | CA | ASP | 21 | −22.099 | −28.983 | 35.471 | 1.000 | 23.47 |
| ATOM | 151 | CB | ASP | 21 | −21.815 | −27.740 | 34.640 | 1.000 | 17.53 |
| ATOM | 152 | CG | ASP | 21 | −21.114 | −27.991 | 33.326 | 1.000 | 14.93 |
| ATOM | 153 | OD1 | ASP | 21 | −20.984 | −29.159 | 32.908 | 1.000 | 26.78 |
| ATOM | 154 | OD2 | ASP | 21 | −20.685 | −26.996 | 32.694 | 1.000 | 8.74 |
| ATOM | 155 | C | ASP | 21 | −22.959 | −29.988 | 34.707 | 1.000 | 19.54 |
| ATOM | 156 | O | ASP | 21 | −23.988 | −29.627 | 34.131 | 1.000 | 22.49 |
| ATOM | 157 | N | GLY | 22 | −22.550 | −31.250 | 34.697 | 1.000 | 13.19 |
| ATOM | 158 | CA | GLY | 22 | −23.279 | −32.377 | 34.166 | 1.000 | 15.71 |
| ATOM | 159 | C | GLY | 22 | −23.507 | −32.377 | 32.659 | 1.000 | 20.02 |
| ATOM | 160 | O | GLY | 22 | −23.370 | −33.431 | 32.036 | 1.000 | 23.32 |
| ATOM | 161 | N | ALA | 23 | −23.846 | −31.235 | 32.138 | 1.000 | 26.40 |
| ATOM | 162 | CA | ALA | 23 | −24.265 | −30.672 | 30.873 | 1.000 | 28.79 |

-continued

| | | | | | | | | | |
|---|---|---|---|---|---|---|---|---|---|
| ATOM | 163 | CB | ALA | 23 | −24.483 | −29.192 | 31.152 | 1.000 | 32.86 |
| ATOM | 164 | C | ALA | 23 | −23.309 | −30.988 | 29.745 | 1.000 | 22.68 |
| ATOM | 165 | O | ALA | 23 | −22.922 | −32.189 | 29.753 | 1.000 | 40.02 |
| ATOM | 166 | N | PRO | 24 | −22.847 | −30.255 | 28.748 | 1.000 | 12.97 |
| ATOM | 167 | CD | PRO | 24 | −22.892 | −28.855 | 28.309 | 1.000 | 15.92 |
| ATOM | 168 | CA | PRO | 24 | −22.051 | −31.028 | 27.767 | 1.000 | 5.31 |
| ATOM | 169 | CB | PRO | 24 | −22.024 | −30.134 | 26.520 | 1.000 | 4.03 |
| ATOM | 170 | CG | PRO | 24 | −22.002 | −28.762 | 27.105 | 1.000 | 6.80 |
| ATOM | 171 | C | PRO | 24 | −20.622 | −31.273 | 28.222 | 1.000 | 14.45 |
| ATOM | 172 | O | PRO | 24 | −20.034 | −30.591 | 29.056 | 1.000 | 19.65 |
| ATOM | 173 | N | THR | 25 | −20.062 | −32.310 | 27.600 | 1.000 | 13.21 |
| ATOM | 174 | CA | THR | 25 | −18.685 | −32.690 | 27.894 | 1.000 | 11.82 |
| ATOM | 175 | CB | THR | 25 | −18.691 | −33.772 | 28.987 | 1.000 | 12.19 |
| ATOM | 176 | OG1 | THR | 25 | −17.348 | −34.104 | 29.355 | 1.000 | 19.38 |
| ATOM | 177 | CG2 | THR | 25 | −19.372 | −35.027 | 28.454 | 1.000 | 0.00 |
| ATOM | 178 | C | THR | 25 | −18.009 | −33.160 | 26.620 | 1.000 | 14.10 |
| ATOM | 179 | O | THR | 25 | −18.555 | −33.019 | 25.518 | 1.000 | 16.46 |
| ATOM | 180 | N | GLU | 26 | −16.818 | −33.724 | 26.762 | 1.000 | 12.30 |
| ATOM | 181 | CA | GLU | 26 | −16.157 | −34.314 | 25.598 | 1.000 | 13.24 |
| ATOM | 182 | CB | GLU | 26 | −14.909 | −33.518 | 25.225 | 1.000 | 15.75 |
| ATOM | 183 | CG | GLU | 26 | −15.211 | −32.066 | 24.873 | 1.000 | 25.45 |
| ATOM | 184 | CD | GLU | 26 | −15.451 | −31.152 | 26.056 | 1.000 | 27.41 |
| ATOM | 185 | OE1 | GLU | 26 | −14.687 | −31.210 | 27.048 | 1.000 | 22.86 |
| ATOM | 186 | OE2 | GLU | 26 | −16.416 | −30.347 | 26.012 | 1.000 | 17.32 |
| ATOM | 187 | C | GLU | 26 | −15.850 | −35.775 | 25.891 | 1.000 | 8.80 |
| ATOM | 188 | O | GLU | 26 | −16.279 | −36.316 | 26.909 | 1.000 | 2.55 |
| ATOM | 189 | N | ARG | 27 | −15.121 | −36.421 | 25.001 | 1.000 | 13.28 |
| ATOM | 190 | CA | ARG | 27 | −14.783 | −37.838 | 25.124 | 1.000 | 12.71 |
| ATOM | 191 | CB | ARG | 27 | −14.857 | −38.447 | 23.726 | 1.000 | 6.07 |
| ATOM | 192 | CG | ARG | 27 | −14.491 | −39.908 | 23.585 | 1.000 | 4.38 |
| ATOM | 193 | CD | ARG | 27 | −14.879 | −40.387 | 22.186 | 1.000 | 11.29 |
| ATOM | 194 | NE | ARG | 27 | −14.974 | −41.840 | 22.110 | 1.000 | 13.10 |
| ATOM | 195 | CZ | ARG | 27 | −15.191 | −42.517 | 20.992 | 1.000 | 9.74 |
| ATOM | 196 | NH1 | ARG | 27 | −15.337 | −41.868 | 19.842 | 1.000 | 11.38 |
| ATOM | 197 | NH2 | ARG | 27 | −15.262 | −43.839 | 21.029 | 1.000 | 0.00 |
| ATOM | 198 | C | ARG | 27 | −13.413 | −38.031 | 25.746 | 1.000 | 8.79 |
| ATOM | 199 | O | ARG | 27 | −12.534 | −37.181 | 25.579 | 1.000 | 17.59 |
| ATOM | 200 | N | PHE | 28 | −13.183 | −39.133 | 26.461 | 1.000 | 12.29 |
| ATOM | 201 | CA | PHE | 28 | −11.826 | −39.379 | 26.955 | 1.000 | 9.91 |
| ATOM | 202 | CB | PHE | 28 | −11.783 | −40.575 | 27.900 | 1.000 | 10.13 |
| ATOM | 203 | CG | PHE | 28 | −12.084 | −40.263 | 29.355 | 1.000 | 11.54 |
| ATOM | 204 | CD1 | PHE | 28 | −11.250 | −39.431 | 30.084 | 1.000 | 8.88 |
| ATOM | 205 | CD2 | PHE | 28 | −13.194 | −40.802 | 29.979 | 1.000 | 11.27 |
| ATOM | 206 | CE1 | PHE | 28 | −11.535 | −39.156 | 31.408 | 1.000 | 8.90 |
| ATOM | 207 | CE2 | PHE | 28 | −13.486 | −40.533 | 31.305 | 1.000 | 5.41 |
| ATOM | 208 | CZ | PHE | 28 | −12.647 | −39.703 | 32.020 | 1.000 | 0.61 |
| ATOM | 209 | C | PHE | 28 | −10.901 | −39.635 | 25.770 | 1.000 | 11.56 |
| ATOM | 210 | O | PHE | 28 | −11.370 | −40.112 | 24.736 | 1.000 | 13.14 |
| ATOM | 211 | N | ALA | 29 | −9.612 | −39.349 | 25.896 | 1.000 | 13.02 |
| ATOM | 212 | CA | ALA | 29 | −8.674 | −39.656 | 24.818 | 1.000 | 13.91 |
| ATOM | 213 | CB | ALA | 29 | −7.275 | −39.163 | 25.151 | 1.000 | 6.49 |
| ATOM | 214 | C | ALA | 29 | −8.662 | −41.157 | 24.545 | 1.000 | 15.68 |
| ATOM | 215 | O | ALA | 29 | −8.937 | −41.954 | 25.446 | 1.000 | 31.74 |
| ATOM | 216 | N | PRO | 30 | −8.345 | −41.537 | 23.314 | 1.000 | 11.44 |
| ATOM | 217 | CD | PRO | 30 | −7.982 | −40.660 | 22.192 | 1.000 | 12.10 |
| ATOM | 218 | CA | PRO | 30 | −8.326 | −42.955 | 22.936 | 1.000 | 18.85 |
| ATOM | 219 | CB | PRO | 30 | −7.822 | −42.956 | 21.494 | 1.000 | 16.38 |
| ATOM | 220 | CG | PRO | 30 | −7.283 | −41.593 | 21.244 | 1.000 | 14.74 |
| ATOM | 221 | C | PRO | 30 | −7.386 | −43.767 | 23.826 | 1.000 | 13.40 |
| ATOM | 222 | O | PRO | 30 | −7.570 | −44.969 | 23.979 | 1.000 | 8.18 |
| ATOM | 223 | N | ASP | 31 | −6.396 | −43.115 | 24.412 | 1.000 | 22.50 |
| ATOM | 224 | CA | ASP | 31 | −5.426 | −43.715 | 25.312 | 1.000 | 26.63 |
| ATOM | 225 | CB | ASP | 31 | −4.170 | −42.841 | 25.398 | 1.000 | 30.41 |
| ATOM | 226 | CG | ASP | 31 | −3.792 | −42.143 | 24.108 | 1.000 | 39.21 |
| ATOM | 227 | OD1 | ASP | 31 | −2.577 | −42.086 | 23.802 | 1.000 | 39.00 |
| ATOM | 228 | OD2 | ASP | 31 | −4.673 | −41.634 | 23.375 | 1.000 | 37.50 |
| ATOM | 229 | C | ASP | 31 | −5.985 | −43.926 | 26.721 | 1.000 | 17.49 |
| ATOM | 230 | O | ASP | 31 | −5.482 | −44.784 | 27.450 | 1.000 | 25.27 |
| ATOM | 231 | N | VAL | 32 | −6.989 | −43.150 | 27.092 | 1.000 | 14.45 |
| ATOM | 232 | CA | VAL | 32 | −7.592 | −43.125 | 28.421 | 1.000 | 12.64 |
| ATOM | 233 | CB | VAL | 32 | −7.966 | −41.683 | 28.814 | 1.000 | 10.68 |
| ATOM | 234 | CG1 | VAL | 32 | −8.580 | −41.609 | 30.199 | 1.000 | 13.66 |
| ATOM | 235 | CG2 | VAL | 32 | −6.742 | −40.774 | 28.752 | 1.000 | 20.51 |
| ATOM | 236 | C | VAL | 32 | −8.808 | −44.042 | 28.507 | 1.000 | 9.73 |
| ATOM | 237 | O | VAL | 32 | −8.890 | −44.834 | 29.452 | 1.000 | 2.23 |
| ATOM | 238 | N | ARG | 33 | −9.722 | −43.964 | 27.553 | 1.000 | 10.63 |
| ATOM | 239 | CA | ARG | 33 | −10.888 | −44.824 | 27.410 | 1.000 | 6.85 |
| ATOM | 240 | CB | ARG | 33 | −11.369 | −44.833 | 25.961 | 1.000 | 16.41 |
| ATOM | 241 | CG | ARG | 33 | −12.281 | −43.727 | 25.488 | 1.000 | 21.19 |

-continued

| | | | | | | | | | | |
|---|---|---|---|---|---|---|---|---|---|---|
| ATOM | 242 | CD | ARG | 33 | −12.464 | −43.806 | 23.974 | 1.000 | 26.66 |
| ATOM | 243 | NE | ARG | 33 | −11.862 | −42.659 | 23.309 | 1.000 | 30.35 |
| ATOM | 244 | CZ | ARG | 33 | −11.493 | −42.567 | 22.044 | 1.000 | 31.60 |
| ATOM | 245 | NH1 | ARG | 33 | −11.658 | −43.585 | 21.214 | 1.000 | 34.85 |
| ATOM | 246 | NH2 | ARG | 33 | −10.952 | −41.433 | 21.610 | 1.000 | 52.70 |
| ATOM | 247 | C | ARG | 33 | −10.600 | −46.279 | 27.775 | 1.000 | 9.71 |
| ATOM | 248 | O | ARG | 33 | −9.603 | −46.830 | 27.300 | 1.000 | 16.85 |
| ATOM | 249 | N | TRP | 34 | −11.450 | −46.924 | 28.577 | 1.000 | 10.64 |
| ATOM | 250 | CA | TRP | 34 | −11.166 | −48.311 | 28.952 | 1.000 | 6.46 |
| ATOM | 251 | CB | TRP | 34 | −12.149 | −48.855 | 29.979 | 1.000 | 12.45 |
| ATOM | 252 | CG | TRP | 34 | −13.561 | −49.106 | 29.583 | 1.000 | 6.95 |
| ATOM | 253 | CD2 | TRP | 34 | −14.104 | −50.199 | 28.835 | 1.000 | 9.27 |
| ATOM | 254 | CE2 | TRP | 34 | −15.493 | −49.986 | 28.723 | 1.000 | 5.43 |
| ATOM | 255 | CE3 | TRP | 34 | −13.571 | −51.345 | 28.240 | 1.000 | 14.72 |
| ATOM | 256 | CD1 | TRP | 34 | −14.622 | −48.298 | 29.888 | 1.000 | 4.49 |
| ATOM | 257 | NE1 | TRP | 34 | −15.786 | −48.820 | 29.374 | 1.000 | 4.03 |
| ATOM | 258 | CZ2 | TRP | 34 | −16.337 | −50.864 | 28.050 | 1.000 | 8.19 |
| ATOM | 259 | CZ3 | TRP | 34 | −14.405 | −52.216 | 27.572 | 1.000 | 12.73 |
| ATOM | 260 | CH2 | TRP | 34 | −15.778 | −51.976 | 27.479 | 1.000 | 8.32 |
| ATOM | 261 | C | TRP | 34 | −11.111 | −49.214 | 27.723 | 1.000 | 7.27 |
| ATOM | 262 | O | TRP | 34 | −10.393 | −50.222 | 27.767 | 1.000 | 11.53 |
| ATOM | 263 | N | THR | 35 | −11.839 | −48.887 | 26.659 | 1.000 | 1.15 |
| ATOM | 264 | CA | THR | 35 | −11.730 | −49.673 | 25.431 | 1.000 | 5.29 |
| ATOM | 265 | CB | THR | 35 | −12.708 | −49.239 | 24.331 | 1.000 | 3.10 |
| ATOM | 266 | OG1 | THR | 35 | −12.629 | −47.820 | 24.163 | 1.000 | 15.85 |
| ATOM | 267 | CG2 | THR | 35 | −14.146 | −49.549 | 24.726 | 1.000 | 5.16 |
| ATOM | 268 | C | THR | 35 | −10.307 | −49.555 | 24.882 | 1.000 | 14.32 |
| ATOM | 269 | O | THR | 35 | −9.738 | −50.494 | 24.333 | 1.000 | 12.77 |
| ATOM | 270 | N | GLY | 36 | −9.756 | −48.361 | 25.060 | 1.000 | 15.72 |
| ATOM | 271 | CA | GLY | 36 | −8.392 | −48.056 | 24.689 | 1.000 | 15.87 |
| ATOM | 272 | C | GLY | 36 | −7.407 | −48.785 | 25.583 | 1.000 | 14.86 |
| ATOM | 273 | O | GLY | 36 | −6.374 | −49.252 | 25.101 | 1.000 | 22.97 |
| ATOM | 274 | N | VAL | 37 | −7.686 | −48.905 | 26.884 | 1.000 | 12.48 |
| ATOM | 275 | CA | VAL | 37 | −6.696 | −49.577 | 27.728 | 1.000 | 11.76 |
| ATOM | 276 | CB | VAL | 37 | −6.921 | −49.365 | 29.229 | 1.000 | 10.95 |
| ATOM | 277 | CG1 | VAL | 37 | −6.092 | −50.382 | 30.009 | 1.000 | 0.00 |
| ATOM | 278 | CG2 | VAL | 37 | −6.577 | −47.940 | 29.630 | 1.000 | 10.31 |
| ATOM | 279 | C | VAL | 37 | −6.707 | −51.081 | 27.471 | 1.000 | 16.75 |
| ATOM | 280 | O | VAL | 37 | −5.669 | −51.735 | 27.494 | 1.000 | 14.29 |
| ATOM | 281 | N | LEU | 38 | −7.911 | −51.586 | 27.238 | 1.000 | 14.60 |
| ATOM | 282 | CA | LEU | 38 | −8.094 | −52.999 | 26.917 | 1.000 | 11.25 |
| ATOM | 283 | CB | LEU | 38 | −9.573 | −53.266 | 26.660 | 1.000 | 12.92 |
| ATOM | 284 | CG | LEU | 38 | −9.975 | −54.663 | 26.198 | 1.000 | 15.77 |
| ATOM | 285 | CD1 | LEU | 38 | −9.747 | −55.691 | 27.293 | 1.000 | 0.00 |
| ATOM | 286 | CD2 | LEU | 38 | −11.425 | −54.677 | 25.733 | 1.000 | 24.28 |
| ATOM | 287 | C | LEU | 38 | −7.224 | −53.347 | 25.720 | 1.000 | 7.67 |
| ATOM | 288 | O | LEU | 38 | −6.408 | −54.262 | 25.740 | 1.000 | 13.04 |
| ATOM | 289 | N | ALA | 39 | −7.404 | −52.568 | 24.659 | 1.000 | 9.64 |
| ATOM | 290 | CA | ALA | 39 | −6.603 | −52.667 | 23.451 | 1.000 | 3.53 |
| ATOM | 291 | CB | ALA | 39 | −6.894 | −51.487 | 22.530 | 1.000 | 6.32 |
| ATOM | 292 | C | ALA | 39 | −5.112 | −52.704 | 23.761 | 1.000 | 9.32 |
| ATOM | 293 | O | ALA | 39 | −4.411 | −53.632 | 23.367 | 1.000 | 28.59 |
| ATOM | 294 | N | GLN | 40 | −4.653 | −51.665 | 24.456 | 1.000 | 21.51 |
| ATOM | 295 | CA | GLN | 40 | −3.251 | −51.553 | 24.833 | 1.000 | 18.93 |
| ATOM | 296 | CB | GLN | 40 | −2.974 | −50.365 | 25.744 | 1.000 | 28.00 |
| ATOM | 297 | CG | GLN | 40 | −3.597 | −49.034 | 25.378 | 1.000 | 37.51 |
| ATOM | 298 | CD | GLN | 40 | −3.070 | −47.877 | 26.214 | 1.000 | 40.85 |
| ATOM | 299 | OE1 | GLN | 40 | −1.998 | −47.335 | 25.933 | 1.000 | 61.34 |
| ATOM | 300 | NE2 | GLN | 40 | −3.809 | −47.475 | 27.248 | 1.000 | 9.83 |
| ATOM | 301 | C | GLN | 40 | −2.822 | −52.851 | 25.525 | 1.000 | 10.96 |
| ATOM | 302 | O | GLN | 40 | −1.856 | −53.475 | 25.106 | 1.000 | 18.66 |
| ATOM | 303 | N | GLN | 41 | −3.563 | −53.239 | 26.552 | 1.000 | 15.02 |
| ATOM | 304 | CA | GLN | 41 | −3.253 | −54.423 | 27.337 | 1.000 | 22.27 |
| ATOM | 305 | CB | GLN | 41 | −4.258 | −54.582 | 28.484 | 1.000 | 16.69 |
| ATOM | 306 | CG | GLN | 41 | −4.064 | −53.605 | 29.624 | 1.000 | 14.55 |
| ATOM | 307 | CD | GLN | 41 | −2.788 | −53.852 | 30.406 | 1.000 | 16.86 |
| ATOM | 308 | OE1 | GLN | 41 | −2.759 | −54.650 | 31.344 | 1.000 | 13.75 |
| ATOM | 309 | NE2 | GLN | 41 | −1.731 | −53.158 | 30.008 | 1.000 | 21.79 |
| ATOM | 310 | C | GLN | 41 | −3.261 | −55.694 | 26.493 | 1.000 | 28.40 |
| ATOM | 311 | O | GLN | 41 | −2.442 | −56.589 | 26.703 | 1.000 | 26.71 |
| ATOM | 312 | N | LEU | 42 | −4.190 | −55.776 | 25.546 | 1.000 | 28.62 |
| ATOM | 313 | CA | LEU | 42 | −4.373 | −57.007 | 24.780 | 1.000 | 26.50 |
| ATOM | 314 | CB | LEU | 42 | −5.707 | −56.920 | 24.012 | 1.000 | 19.31 |
| ATOM | 315 | CG | LEU | 42 | −6.934 | −57.122 | 24.914 | 1.000 | 16.32 |
| ATOM | 316 | CD1 | LEU | 42 | −8.226 | −57.077 | 24.119 | 1.000 | 10.94 |
| ATOM | 317 | CD2 | LEU | 42 | −6.810 | −58.438 | 25.673 | 1.000 | 15.03 |
| ATOM | 318 | C | LEU | 42 | −3.217 | −57.312 | 23.846 | 1.000 | 23.29 |
| ATOM | 319 | O | LEU | 42 | −2.770 | −58.457 | 23.728 | 1.000 | 20.82 |
| ATOM | 320 | N | GLY | 43 | −2.693 | −56.312 | 23.141 | 1.000 | 22.18 |

-continued

| | | | | | | | | | |
|---|---|---|---|---|---|---|---|---|---|
| ATOM | 321 | CA | GLY | 43 | −1.605 | −56.590 | 22.215 | 1.000 | 18.95 |
| ATOM | 322 | C | GLY | 43 | −2.086 | −56.793 | 20.791 | 1.000 | 23.97 |
| ATOM | 323 | O | GLY | 43 | −3.284 | −56.838 | 20.514 | 1.000 | 27.50 |
| ATOM | 324 | N | ALA | 44 | −1.136 | −56.927 | 19.879 | 1.000 | 22.72 |
| ATOM | 325 | CA | ALA | 44 | −1.317 | −57.012 | 18.448 | 1.000 | 24.25 |
| ATOM | 326 | CB | ALA | 44 | 0.048 | −56.939 | 17.755 | 1.000 | 13.44 |
| ATOM | 327 | C | ALA | 44 | −2.034 | −58.272 | 17.990 | 1.000 | 23.83 |
| ATOM | 328 | O | ALA | 44 | −2.146 | −58.520 | 16.787 | 1.000 | 17.77 |
| ATOM | 329 | N | ASP | 45 | −2.524 | −59.086 | 18.917 | 1.000 | 21.59 |
| ATOM | 330 | CA | ASP | 45 | −3.230 | −60.298 | 18.495 | 1.000 | 17.80 |
| ATOM | 331 | CB | ASP | 45 | −2.705 | −61.491 | 19.296 | 1.000 | 18.22 |
| ATOM | 332 | CG | ASP | 45 | −1.201 | −61.625 | 19.113 | 1.000 | 24.69 |
| ATOM | 333 | OD1 | ASP | 45 | −0.710 | −61.174 | 18.053 | 1.000 | 34.10 |
| ATOM | 334 | OD2 | ASP | 45 | −0.517 | −62.159 | 20.007 | 1.000 | 33.14 |
| ATOM | 335 | C | ASP | 45 | −4.732 | −60.107 | 18.647 | 1.000 | 11.82 |
| ATOM | 336 | O | ASP | 45 | −5.535 | −60.992 | 18.364 | 1.000 | 23.89 |
| ATOM | 337 | N | PHE | 46 | −5.097 | −58.914 | 19.097 | 1.000 | 9.27 |
| ATOM | 338 | CA | PHE | 46 | −6.485 | −58.519 | 19.253 | 1.000 | 12.25 |
| ATOM | 339 | CB | PHE | 46 | −6.909 | −58.479 | 20.722 | 1.000 | 14.52 |
| ATOM | 340 | CG | PHE | 46 | −6.474 | −59.693 | 21.529 | 1.000 | 11.99 |
| ATOM | 341 | CD1 | PHE | 46 | −5.160 | −59.814 | 21.956 | 1.000 | 12.17 |
| ATOM | 342 | CD2 | PHE | 46 | −7.383 | −60.690 | 21.846 | 1.000 | 8.34 |
| ATOM | 343 | CE1 | PHE | 46 | −4.760 | −60.917 | 22.683 | 1.000 | 13.46 |
| ATOM | 344 | CE2 | PHE | 46 | −6.990 | −61.794 | 22.575 | 1.000 | 6.30 |
| ATOM | 345 | CZ | PHE | 46 | −5.680 | −61.904 | 22.998 | 1.000 | 8.44 |
| ATOM | 346 | C | PHE | 46 | −6.725 | −57.149 | 18.615 | 1.000 | 13.30 |
| ATOM | 347 | O | PHE | 46 | −5.816 | −56.366 | 18.366 | 1.000 | 27.22 |
| ATOM | 348 | N | GLU | 47 | −7.992 | −56.883 | 18.349 | 1.000 | 12.78 |
| ATOM | 349 | CA | GLU | 47 | −8.469 | −55.616 | 17.833 | 1.000 | 9.15 |
| ATOM | 350 | CB | GLU | 47 | −8.667 | −55.644 | 16.325 | 1.000 | 11.20 |
| ATOM | 351 | CG | GLU | 47 | −8.791 | −54.276 | 15.670 | 1.000 | 21.84 |
| ATOM | 352 | CD | GLU | 47 | −9.726 | −54.293 | 14.474 | 1.000 | 25.88 |
| ATOM | 353 | OE1 | GLU | 47 | −9.575 | −55.205 | 13.632 | 1.000 | 30.74 |
| ATOM | 354 | OE2 | GLU | 47 | −10.602 | −53.408 | 14.388 | 1.000 | 7.59 |
| ATOM | 355 | C | GLU | 47 | −9.781 | −55.280 | 18.550 | 1.000 | 11.37 |
| ATOM | 356 | O | GLU | 47 | −10.722 | −56.071 | 18.545 | 1.000 | 11.73 |
| ATOM | 357 | N | VAL | 48 | −9.775 | −54.103 | 19.160 | 1.000 | 10.53 |
| ATOM | 358 | CA | VAL | 48 | −10.954 | −53.604 | 19.843 | 1.000 | 8.11 |
| ATOM | 359 | CB | VAL | 48 | −10.595 | −52.826 | 21.115 | 1.000 | 9.71 |
| ATOM | 360 | CG1 | VAL | 48 | −11.842 | −52.251 | 21.773 | 1.000 | 15.31 |
| ATOM | 361 | CG2 | VAL | 48 | −9.849 | −53.732 | 22.085 | 1.000 | 7.41 |
| ATOM | 362 | C | VAL | 48 | −11.745 | −52.714 | 18.882 | 1.000 | 12.72 |
| ATOM | 363 | O | VAL | 48 | −11.147 | −51.879 | 18.203 | 1.000 | 10.16 |
| ATOM | 364 | N | ILE | 49 | −13.046 | −52.943 | 18.862 | 1.000 | 13.04 |
| ATOM | 365 | CA | ILE | 49 | −14.031 | −52.170 | 18.122 | 1.000 | 14.10 |
| ATOM | 366 | CB | ILE | 49 | −14.879 | −53.068 | 17.203 | 1.000 | 16.77 |
| ATOM | 367 | CG2 | ILE | 49 | −15.735 | −52.214 | 16.285 | 1.000 | 1.57 |
| ATOM | 368 | CG1 | ILE | 49 | −14.049 | −54.081 | 16.415 | 1.000 | 18.10 |
| ATOM | 369 | CD1 | ILE | 49 | −14.687 | −54.559 | 15.133 | 1.000 | 14.33 |
| ATOM | 370 | C | ILE | 49 | −14.930 | −51.406 | 19.091 | 1.000 | 9.02 |
| ATOM | 371 | O | ILE | 49 | −15.531 | −52.013 | 19.983 | 1.000 | 15.82 |
| ATOM | 372 | N | GLU | 50 | −15.000 | −50.085 | 18.932 | 1.000 | 5.34 |
| ATOM | 373 | CA | GLU | 50 | −15.730 | −49.277 | 19.911 | 1.000 | 12.03 |
| ATOM | 374 | CB | GLU | 50 | −14.967 | −47.984 | 20.222 | 1.000 | 10.36 |
| ATOM | 375 | CG | GLU | 50 | −13.623 | −48.203 | 20.889 | 1.000 | 7.32 |
| ATOM | 376 | CD | GLU | 50 | −12.768 | −46.966 | 21.056 | 1.000 | 7.06 |
| ATOM | 377 | OE1 | GLU | 50 | −12.744 | −46.077 | 20.177 | 1.000 | 5.78 |
| ATOM | 378 | OE2 | GLU | 50 | −12.079 | −46.870 | 22.101 | 1.000 | 25.19 |
| ATOM | 379 | C | GLU | 50 | −17.145 | −48.962 | 19.446 | 1.000 | 6.79 |
| ATOM | 380 | O | GLU | 50 | −17.358 | −48.318 | 18.423 | 1.000 | 8.80 |
| ATOM | 381 | N | GLU | 51 | −18.118 | −49.429 | 20.225 | 1.000 | 9.34 |
| ATOM | 382 | CA | GLU | 51 | −19.524 | −49.179 | 19.924 | 1.000 | 16.23 |
| ATOM | 383 | CB | GLU | 51 | −20.173 | −50.400 | 19.270 | 1.000 | 15.22 |
| ATOM | 384 | CG | GLU | 51 | −19.757 | −50.596 | 17.820 | 1.000 | 18.39 |
| ATOM | 385 | CD | GLU | 51 | −20.348 | −49.531 | 16.917 | 1.000 | 17.99 |
| ATOM | 386 | OE1 | GLU | 51 | −21.352 | −48.912 | 17.332 | 1.000 | 26.29 |
| ATOM | 387 | OE2 | GLU | 51 | −19.820 | −49.309 | 15.809 | 1.000 | 15.93 |
| ATOM | 388 | C | GLU | 51 | −20.295 | −48.788 | 21.184 | 1.000 | 10.51 |
| ATOM | 389 | O | GLU | 51 | −21.202 | −49.495 | 21.623 | 1.000 | 7.29 |
| ATOM | 390 | N | GLY | 52 | −19.906 | −47.655 | 21.751 | 1.000 | 5.90 |
| ATOM | 391 | CA | GLY | 52 | −20.533 | −47.140 | 22.961 | 1.000 | 3.93 |
| ATOM | 392 | C | GLY | 52 | −21.329 | −45.887 | 22.635 | 1.000 | 6.21 |
| ATOM | 393 | O | GLY | 52 | −20.785 | −44.950 | 22.057 | 1.000 | 16.40 |
| ATOM | 394 | N | LEU | 53 | −22.607 | −45.890 | 22.989 | 1.000 | 11.68 |
| ATOM | 395 | CA | LEU | 53 | −23.498 | −44.764 | 22.710 | 1.000 | 7.60 |
| ATOM | 396 | CB | LEU | 53 | −24.627 | −45.195 | 21.792 | 1.000 | 4.45 |
| ATOM | 397 | CG | LEU | 53 | −25.576 | −44.164 | 21.185 | 1.000 | 3.84 |
| ATOM | 398 | CD1 | LEU | 53 | −26.721 | −43.872 | 22.141 | 1.000 | 15.09 |
| ATOM | 399 | CD2 | LEU | 53 | −24.856 | −42.874 | 20.817 | 1.000 | 3.41 |

-continued

| | | | | | | | | | |
|---|---|---|---|---|---|---|---|---|---|
| ATOM | 400 | C | LEU | 53 | −24.035 | −44.204 | 24.023 | 1.000 | 5.05 |
| ATOM | 401 | O | LEU | 53 | −24.664 | −44.920 | 24.801 | 1.000 | 5.74 |
| ATOM | 402 | N | SER | 54 | −23.771 | −42.918 | 24.251 | 1.000 | 9.85 |
| ATOM | 403 | CA | SER | 54 | −24.192 | −42.296 | 25.502 | 1.000 | 10.24 |
| ATOM | 404 | CB | SER | 54 | −23.797 | −40.819 | 25.524 | 1.000 | 7.63 |
| ATOM | 405 | OG | SER | 54 | −22.395 | −40.683 | 25.640 | 1.000 | 4.65 |
| ATOM | 406 | C | SER | 54 | −25.695 | −42.448 | 25.691 | 1.000 | 7.74 |
| ATOM | 407 | O | SER | 54 | −26.438 | −42.326 | 24.717 | 1.000 | 10.39 |
| ATOM | 408 | N | ALA | 55 | −26.127 | −42.713 | 26.920 | 1.000 | 0.00 |
| ATOM | 409 | CA | ALA | 55 | −27.554 | −42.749 | 27.218 | 1.000 | 0.00 |
| ATOM | 410 | CB | ALA | 55 | −28.209 | −41.474 | 26.713 | 1.000 | 0.00 |
| ATOM | 411 | C | ALA | 55 | −28.235 | −43.982 | 26.640 | 1.000 | 6.11 |
| ATOM | 412 | O | ALA | 55 | −29.442 | −44.179 | 26.816 | 1.000 | 2.57 |
| ATOM | 413 | N | ARG | 56 | −27.474 | −44.843 | 25.971 | 1.000 | 8.50 |
| ATOM | 414 | CA | ARG | 56 | −27.997 | −46.084 | 25.433 | 1.000 | 5.94 |
| ATOM | 415 | CB | ARG | 56 | −26.919 | −46.868 | 24.672 | 1.000 | 0.00 |
| ATOM | 416 | CG | ARG | 56 | −27.420 | −48.244 | 24.247 | 1.000 | 2.73 |
| ATOM | 417 | CD | ARG | 56 | −26.467 | −48.951 | 23.307 | 1.000 | 0.00 |
| ATOM | 418 | NE | ARG | 56 | −26.552 | −48.440 | 21.935 | 1.000 | 6.44 |
| ATOM | 419 | CZ | ARG | 56 | −25.465 | −48.325 | 21.170 | 1.000 | 11.18 |
| ATOM | 420 | NH1 | ARG | 56 | −24.283 | −48.678 | 21.666 | 1.000 | 0.00 |
| ATOM | 421 | NH2 | ARG | 56 | −25.549 | −47.861 | 19.928 | 1.000 | 1.13 |
| ATOM | 422 | C | ARG | 56 | −28.539 | −47.009 | 26.526 | 1.000 | 12.43 |
| ATOM | 423 | O | ARG | 56 | −27.886 | −47.179 | 27.556 | 1.000 | 10.16 |
| ATOM | 424 | N | THR | 57 | −29.697 | −47.592 | 26.262 | 1.000 | 9.24 |
| ATOM | 425 | CA | THR | 57 | −30.376 | −48.548 | 27.120 | 1.000 | 9.36 |
| ATOM | 426 | CB | THR | 57 | −31.855 | −48.161 | 27.315 | 1.000 | 4.78 |
| ATOM | 427 | OG1 | THR | 57 | −32.608 | −48.509 | 26.146 | 1.000 | 3.70 |
| ATOM | 428 | CG2 | THR | 57 | −31.992 | −46.656 | 27.484 | 1.000 | 0.00 |
| ATOM | 429 | C | THR | 57 | −30.284 | −49.953 | 26.532 | 1.000 | 10.18 |
| ATOM | 430 | O | THR | 57 | −29.873 | −50.099 | 25.378 | 1.000 | 12.60 |
| ATOM | 431 | N | THR | 58 | −30.648 | −50.987 | 27.286 | 1.000 | 5.87 |
| ATOM | 432 | CA | THR | 58 | −30.574 | −52.349 | 26.769 | 1.000 | 1.65 |
| ATOM | 433 | CB | THR | 58 | −30.850 | −53.410 | 27.853 | 1.000 | 5.35 |
| ATOM | 434 | OG1 | THR | 58 | −32.151 | −53.196 | 28.413 | 1.000 | 12.48 |
| ATOM | 435 | CG2 | THR | 58 | −29.859 | −53.311 | 29.002 | 1.000 | 11.47 |
| ATOM | 436 | C | THR | 58 | −31.556 | −52.569 | 25.624 | 1.000 | 1.31 |
| ATOM | 437 | O | THR | 58 | −31.162 | −52.902 | 24.506 | 1.000 | 7.78 |
| ATOM | 438 | N | ASN | 59 | −32.856 | −52.404 | 25.867 | 1.000 | 4.91 |
| ATOM | 439 | CA | ASN | 59 | −33.810 | −52.604 | 24.772 | 1.000 | 11.25 |
| ATOM | 440 | CB | ASN | 59 | −34.150 | −54.090 | 24.624 | 1.000 | 9.19 |
| ATOM | 441 | CG | ASN | 59 | −35.186 | −54.548 | 25.629 | 1.000 | 9.50 |
| ATOM | 442 | OD1 | ASN | 59 | −35.293 | −54.000 | 26.725 | 1.000 | 13.36 |
| ATOM | 443 | ND2 | ASN | 59 | −35.965 | −55.556 | 25.263 | 1.000 | 4.31 |
| ATOM | 444 | C | ASN | 59 | −35.070 | −51.775 | 24.960 | 1.000 | 8.67 |
| ATOM | 445 | O | ASN | 59 | −36.172 | −52.160 | 24.574 | 1.000 | 12.75 |
| ATOM | 446 | N | ILE | 60 | −34.938 | −50.587 | 25.548 | 1.000 | 10.46 |
| ATOM | 447 | CA | ILE | 60 | −36.128 | −49.752 | 25.722 | 1.000 | 10.70 |
| ATOM | 448 | CB | ILE | 60 | −36.572 | −49.721 | 27.198 | 1.000 | 11.36 |
| ATOM | 449 | CG2 | ILE | 60 | −35.465 | −49.223 | 28.112 | 1.000 | 0.00 |
| ATOM | 450 | CG1 | ILE | 60 | −37.872 | −48.940 | 27.417 | 1.000 | 8.05 |
| ATOM | 451 | CD1 | ILE | 60 | −38.291 | −48.800 | 28.860 | 1.000 | 27.90 |
| ATOM | 452 | C | ILE | 60 | −35.879 | −48.350 | 25.177 | 1.000 | 16.37 |
| ATOM | 453 | O | ILE | 60 | −34.813 | −47.773 | 25.374 | 1.000 | 28.53 |
| ATOM | 454 | N | ASP | 61 | −36.861 | −47.811 | 24.470 | 1.000 | 18.37 |
| ATOM | 455 | CA | ASP | 61 | −36.838 | −46.520 | 23.821 | 1.000 | 12.62 |
| ATOM | 456 | CB | ASP | 61 | −38.110 | −46.353 | 22.977 | 1.000 | 12.58 |
| ATOM | 457 | CG | ASP | 61 | −38.111 | −47.199 | 21.725 | 1.000 | 12.09 |
| ATOM | 458 | OD1 | ASP | 61 | −37.044 | −47.723 | 21.349 | 1.000 | 16.37 |
| ATOM | 459 | OD2 | ASP | 61 | −39.197 | −47.332 | 21.122 | 1.000 | 23.20 |
| ATOM | 460 | C | ASP | 61 | −36.796 | −45.350 | 24.794 | 1.000 | 11.54 |
| ATOM | 461 | O | ASP | 61 | −37.626 | −45.279 | 25.702 | 1.000 | 8.66 |
| ATOM | 462 | N | ASP | 62 | −35.860 | −44.428 | 24.603 | 1.000 | 8.03 |
| ATOM | 463 | CA | ASP | 62 | −35.844 | −43.228 | 25.431 | 1.000 | 14.39 |
| ATOM | 464 | CB | ASP | 62 | −34.430 | −42.656 | 25.565 | 1.000 | 13.94 |
| ATOM | 465 | CG | ASP | 62 | −34.384 | −41.598 | 26.656 | 1.000 | 18.06 |
| ATOM | 466 | OD1 | ASP | 62 | −33.609 | −41.768 | 27.622 | 1.000 | 13.05 |
| ATOM | 467 | OD2 | ASP | 62 | −35.129 | −40.604 | 26.536 | 1.000 | 20.19 |
| ATOM | 468 | C | ASP | 62 | −36.759 | −42.162 | 24.844 | 1.000 | 13.14 |
| ATOM | 469 | O | ASP | 62 | −36.506 | −41.698 | 23.731 | 1.000 | 14.36 |
| ATOM | 470 | N | PRO | 63 | −37.800 | −41.751 | 25.553 | 1.000 | 8.49 |
| ATOM | 471 | CD | PRO | 63 | −38.102 | −42.088 | 26.951 | 1.000 | 4.73 |
| ATOM | 472 | CA | PRO | 63 | −38.805 | −40.853 | 24.972 | 1.000 | 16.60 |
| ATOM | 473 | CB | PRO | 63 | −39.802 | −40.646 | 26.123 | 1.000 | 11.61 |
| ATOM | 474 | CG | PRO | 63 | −39.020 | −40.960 | 27.352 | 1.000 | 8.04 |
| ATOM | 475 | C | PRO | 63 | −38.251 | −39.504 | 24.531 | 1.000 | 19.70 |
| ATOM | 476 | O | PRO | 63 | −38.924 | −38.738 | 23.835 | 1.000 | 10.26 |
| ATOM | 477 | N | THR | 64 | −37.024 | −39.180 | 24.922 | 1.000 | 22.29 |
| ATOM | 478 | CA | THR | 64 | −36.429 | −37.908 | 24.534 | 1.000 | 19.30 |

| | | | | | | | | | |
|---|---|---|---|---|---|---|---|---|---|
| ATOM | 479 | CB | THR | 64 | −35.852 | −37.191 | 25.769 | 1.000 | 20.62 |
| ATOM | 480 | OG1 | THR | 64 | −34.550 | −37.713 | 26.045 | 1.000 | 30.42 |
| ATOM | 481 | CG2 | THR | 64 | −36.718 | −37.467 | 26.992 | 1.000 | 7.89 |
| ATOM | 482 | C | THR | 64 | −35.329 | −38.087 | 23.497 | 1.000 | 19.22 |
| ATOM | 483 | O | THR | 64 | −34.609 | −37.132 | 23.183 | 1.000 | 11.15 |
| ATOM | 484 | N | ASP | 65 | −35.189 | −39.301 | 22.965 | 1.000 | 15.61 |
| ATOM | 485 | CA | ASP | 65 | −34.139 | −39.542 | 21.967 | 1.000 | 18.78 |
| ATOM | 486 | CB | ASP | 65 | −32.777 | −39.286 | 22.605 | 1.000 | 20.50 |
| ATOM | 487 | CG | ASP | 65 | −31.613 | −39.348 | 21.638 | 1.000 | 17.33 |
| ATOM | 488 | OD1 | ASP | 65 | −31.767 | −39.935 | 20.550 | 1.000 | 19.33 |
| ATOM | 489 | OD2 | ASP | 65 | −30.538 | −38.810 | 21.983 | 1.000 | 15.26 |
| ATOM | 490 | C | ASP | 65 | −34.241 | −40.945 | 21.382 | 1.000 | 14.84 |
| ATOM | 491 | O | ASP | 65 | −33.982 | −41.936 | 22.060 | 1.000 | 8.38 |
| ATOM | 492 | N | PRO | 66 | −34.638 | −41.026 | 20.115 | 1.000 | 15.75 |
| ATOM | 493 | CD | PRO | 66 | −34.896 | −39.870 | 19.235 | 1.000 | 23.61 |
| ATOM | 494 | CA | PRO | 66 | −34.882 | −42.301 | 19.441 | 1.000 | 9.14 |
| ATOM | 495 | CB | PRO | 66 | −35.693 | −41.871 | 18.206 | 1.000 | 14.38 |
| ATOM | 496 | CG | PRO | 66 | −35.210 | −40.494 | 17.902 | 1.000 | 16.45 |
| ATOM | 497 | C | PRO | 66 | −33.621 | −43.029 | 18.995 | 1.000 | 8.15 |
| ATOM | 498 | O | PRO | 66 | −33.695 | −44.041 | 18.283 | 1.000 | 12.38 |
| ATOM | 499 | N | ARG | 67 | −32.446 | −42.557 | 19.404 | 1.000 | 11.98 |
| ATOM | 500 | CA | ARG | 67 | −31.209 | −43.225 | 19.020 | 1.000 | 7.77 |
| ATOM | 501 | CB | ARG | 67 | −30.081 | −42.211 | 18.831 | 1.000 | 8.16 |
| ATOM | 502 | CG | ARG | 67 | −30.162 | −41.308 | 17.614 | 1.000 | 7.27 |
| ATOM | 503 | CD | ARG | 67 | −29.078 | −40.228 | 17.713 | 1.000 | 11.05 |
| ATOM | 504 | NE | ARG | 67 | −29.378 | −39.266 | 18.769 | 1.000 | 11.17 |
| ATOM | 505 | CZ | ARG | 67 | −28.768 | −38.115 | 19.001 | 1.000 | 13.35 |
| ATOM | 506 | NH1 | ARG | 67 | −27.756 | −37.708 | 18.245 | 1.000 | 3.80 |
| ATOM | 507 | NH2 | ARG | 67 | −29.168 | −37.347 | 20.010 | 1.000 | 9.93 |
| ATOM | 508 | C | ARG | 67 | −30.728 | −44.239 | 20.048 | 1.000 | 8.92 |
| ATOM | 509 | O | ARG | 67 | −29.714 | −44.887 | 19.774 | 1.000 | 13.65 |
| ATOM | 510 | N | LEU | 68 | −31.389 | −44.365 | 21.191 | 1.000 | 9.14 |
| ATOM | 511 | CA | LEU | 68 | −30.805 | −45.057 | 22.335 | 1.000 | 13.92 |
| ATOM | 512 | CB | LEU | 68 | −31.052 | −44.223 | 23.608 | 1.000 | 7.80 |
| ATOM | 513 | CG | LEU | 68 | −30.899 | −42.707 | 23.481 | 1.000 | 8.78 |
| ATOM | 514 | CD1 | LEU | 68 | −31.285 | −41.987 | 24.770 | 1.000 | 13.12 |
| ATOM | 515 | CD2 | LEU | 68 | −29.477 | −42.333 | 23.090 | 1.000 | 3.77 |
| ATOM | 516 | C | LEU | 68 | −31.299 | −46.478 | 22.571 | 1.000 | 16.19 |
| ATOM | 517 | O | LEU | 68 | −30.895 | −47.092 | 23.574 | 1.000 | 5.21 |
| ATOM | 518 | N | ASN | 69 | −32.139 | −47.056 | 21.716 | 1.000 | 7.75 |
| ATOM | 519 | CA | ASN | 69 | −32.520 | −48.457 | 21.927 | 1.000 | 6.53 |
| ATOM | 520 | CB | ASN | 69 | −33.807 | −48.842 | 21.198 | 1.000 | 6.25 |
| ATOM | 521 | CG | ASN | 69 | −34.377 | −50.172 | 21.658 | 1.000 | 11.70 |
| ATOM | 522 | OD1 | ASN | 69 | −33.732 | −51.219 | 21.664 | 1.000 | 2.64 |
| ATOM | 523 | ND2 | ASN | 69 | −35.646 | −50.164 | 22.057 | 1.000 | 10.84 |
| ATOM | 524 | C | ASN | 69 | −31.406 | −49.404 | 21.480 | 1.000 | 8.62 |
| ATOM | 525 | O | ASN | 69 | −31.204 | −49.617 | 20.287 | 1.000 | 14.61 |
| ATOM | 526 | N | GLY | 70 | −30.697 | −49.972 | 22.452 | 1.000 | 8.79 |
| ATOM | 527 | CA | GLY | 70 | −29.582 | −50.854 | 22.212 | 1.000 | 1.64 |
| ATOM | 528 | C | GLY | 70 | −29.911 | −52.031 | 21.316 | 1.000 | 6.17 |
| ATOM | 529 | O | GLY | 70 | −29.189 | −52.293 | 20.355 | 1.000 | 12.06 |
| ATOM | 530 | N | ALA | 71 | −30.982 | −52.744 | 21.622 | 1.000 | 1.39 |
| ATOM | 531 | CA | ALA | 71 | −31.442 | −53.885 | 20.843 | 1.000 | 5.92 |
| ATOM | 532 | CB | ALA | 71 | −32.688 | −54.457 | 21.529 | 1.000 | 3.81 |
| ATOM | 533 | C | ALA | 71 | −31.766 | −53.565 | 19.392 | 1.000 | 4.67 |
| ATOM | 534 | O | ALA | 71 | −31.565 | −54.391 | 18.490 | 1.000 | 0.00 |
| ATOM | 535 | N | SER | 72 | −32.295 | −52.371 | 19.121 | 1.000 | 3.88 |
| ATOM | 536 | CA | SER | 72 | −32.687 | −52.033 | 17.752 | 1.000 | 6.33 |
| ATOM | 537 | CB | SER | 72 | −33.678 | −50.870 | 17.759 | 1.000 | 4.05 |
| ATOM | 538 | OG | SER | 72 | −33.023 | −49.637 | 18.004 | 1.000 | 25.62 |
| ATOM | 539 | C | SER | 72 | −31.468 | −51.730 | 16.884 | 1.000 | 7.90 |
| ATOM | 540 | O | SER | 72 | −31.568 | −51.720 | 15.658 | 1.000 | 12.06 |
| ATOM | 541 | N | TYR | 73 | −30.315 | −51.505 | 17.498 | 1.000 | 8.51 |
| ATOM | 542 | CA | TYR | 73 | −29.070 | −51.210 | 16.789 | 1.000 | 8.77 |
| ATOM | 543 | CB | TYR | 73 | −28.394 | −50.029 | 17.478 | 1.000 | 10.31 |
| ATOM | 544 | CG | TYR | 73 | −27.124 | −49.453 | 16.913 | 1.000 | 11.92 |
| ATOM | 545 | CD1 | TYR | 73 | −27.113 | −48.329 | 16.090 | 1.000 | 8.49 |
| ATOM | 546 | CE1 | TYR | 73 | −25.931 | −47.812 | 15.586 | 1.000 | 1.47 |
| ATOM | 547 | CD2 | TYR | 73 | −25.888 | −50.018 | 17.201 | 1.000 | 10.36 |
| ATOM | 548 | CE2 | TYR | 73 | −24.704 | −49.512 | 16.703 | 1.000 | 9.07 |
| ATOM | 549 | CZ | TYR | 73 | −24.727 | −48.398 | 15.890 | 1.000 | 5.36 |
| ATOM | 550 | OH | TYR | 73 | −23.544 | −47.902 | 15.391 | 1.000 | 10.80 |
| ATOM | 551 | C | TYR | 73 | −28.148 | −52.419 | 16.730 | 1.000 | 13.31 |
| ATOM | 552 | O | TYR | 73 | −27.404 | −52.630 | 15.764 | 1.000 | 10.40 |
| ATOM | 553 | N | LEU | 74 | −28.172 | −53.261 | 17.759 | 1.000 | 8.99 |
| ATOM | 554 | CA | LEU | 74 | −27.204 | −54.342 | 17.901 | 1.000 | 7.76 |
| ATOM | 555 | CB | LEU | 74 | −27.554 | −55.155 | 19.155 | 1.000 | 9.47 |
| ATOM | 556 | CG | LEU | 74 | −26.402 | −55.532 | 20.080 | 1.000 | 10.36 |
| ATOM | 557 | CD1 | LEU | 74 | −26.786 | −56.729 | 20.939 | 1.000 | 25.33 |

-continued

| | | | | | | | | | | |
|---|---|---|---|---|---|---|---|---|---|---|
| ATOM | 558 | CD2 | LEU | 74 | −25.137 | −55.819 | 19.288 | 1.000 | 13.92 |
| ATOM | 559 | C | LEU | 74 | −27.088 | −55.253 | 16.687 | 1.000 | 5.72 |
| ATOM | 560 | O | LEU | 74 | −25.980 | −55.383 | 16.141 | 1.000 | 7.01 |
| ATOM | 561 | N | PRO | 75 | −28.141 | −55.907 | 16.219 | 1.000 | 6.99 |
| ATOM | 562 | CD | PRO | 75 | −29.553 | −55.794 | 16.615 | 1.000 | 1.55 |
| ATOM | 563 | CA | PRO | 75 | −27.965 | −56.896 | 15.140 | 1.000 | 7.57 |
| ATOM | 564 | CB | PRO | 75 | −29.384 | −57.401 | 14.855 | 1.000 | 5.01 |
| ATOM | 565 | CG | PRO | 75 | −30.158 | −57.063 | 16.086 | 1.000 | 6.27 |
| ATOM | 566 | C | PRO | 75 | −27.364 | −56.285 | 13.882 | 1.000 | 4.16 |
| ATOM | 567 | O | PRO | 75 | −26.651 | −56.971 | 13.158 | 1.000 | 4.35 |
| ATOM | 568 | N | SER | 76 | −27.640 | −55.014 | 13.615 | 1.000 | 6.22 |
| ATOM | 569 | CA | SER | 76 | −27.050 | −54.322 | 12.473 | 1.000 | 0.00 |
| ATOM | 570 | CB | SER | 76 | −27.758 | −52.978 | 12.261 | 1.000 | 0.00 |
| ATOM | 571 | OG | SER | 76 | −29.120 | −53.249 | 11.920 | 1.000 | 0.00 |
| ATOM | 572 | C | SER | 76 | −25.554 | −54.127 | 12.674 | 1.000 | 0.69 |
| ATOM | 573 | O | SER | 76 | −24.767 | −54.280 | 11.740 | 1.000 | 4.06 |
| ATOM | 574 | N | CYS | 77 | −25.202 | −53.802 | 13.911 | 1.000 | 2.82 |
| ATOM | 575 | CA | CYS | 77 | −23.851 | −53.599 | 14.384 | 1.000 | 2.99 |
| ATOM | 576 | CB | CYS | 77 | −23.878 | −53.202 | 15.868 | 1.000 | 0.00 |
| ATOM | 577 | SG | CYS | 77 | −22.325 | −52.508 | 16.451 | 1.000 | 8.78 |
| ATOM | 578 | C | CYS | 77 | −22.962 | −54.831 | 14.225 | 1.000 | 13.77 |
| ATOM | 579 | O | CYS | 77 | −21.828 | −54.700 | 13.755 | 1.000 | 12.12 |
| ATOM | 580 | N | LEU | 78 | −23.455 | −55.996 | 14.621 | 1.000 | 15.71 |
| ATOM | 581 | CA | LEU | 78 | −22.751 | −57.268 | 14.538 | 1.000 | 10.13 |
| ATOM | 582 | CB | LEU | 78 | −23.617 | −58.387 | 15.129 | 1.000 | 2.73 |
| ATOM | 583 | CG | LEU | 78 | −23.777 | −58.354 | 16.651 | 1.000 | 7.98 |
| ATOM | 584 | CD1 | LEU | 78 | −24.866 | −59.319 | 17.085 | 1.000 | 3.36 |
| ATOM | 585 | CD2 | LEU | 78 | −22.451 | −58.676 | 17.330 | 1.000 | 8.53 |
| ATOM | 586 | C | LEU | 78 | −22.385 | −57.650 | 13.106 | 1.000 | 9.88 |
| ATOM | 587 | O | LEU | 78 | −21.222 | −57.855 | 12.761 | 1.000 | 12.55 |
| ATOM | 588 | N | ALA | 79 | −23.407 | −57.748 | 12.271 | 1.000 | 11.93 |
| ATOM | 589 | CA | ALA | 79 | −23.297 | −58.022 | 10.848 | 1.000 | 2.98 |
| ATOM | 590 | CB | ALA | 79 | −24.699 | −58.042 | 10.255 | 1.000 | 0.32 |
| ATOM | 591 | C | ALA | 79 | −22.393 | −57.026 | 10.127 | 1.000 | 7.73 |
| ATOM | 592 | O | ALA | 79 | −21.724 | −57.408 | 9.163 | 1.000 | 13.15 |
| ATOM | 593 | N | THR | 80 | −22.337 | −55.774 | 10.560 | 1.000 | 10.93 |
| ATOM | 594 | CA | THR | 80 | −21.427 | −54.757 | 10.044 | 1.000 | 6.56 |
| ATOM | 595 | CB | THR | 80 | −21.703 | −53.373 | 10.669 | 1.000 | 9.10 |
| ATOM | 596 | OG1 | THR | 80 | −23.013 | −52.897 | 10.320 | 1.000 | 4.47 |
| ATOM | 597 | CG2 | THR | 80 | −20.722 | −52.328 | 10.148 | 1.000 | 8.02 |
| ATOM | 598 | C | THR | 80 | −19.970 | −55.117 | 10.317 | 1.000 | 10.87 |
| ATOM | 599 | O | THR | 80 | −19.103 | −55.052 | 9.450 | 1.000 | 12.66 |
| ATOM | 600 | N | HIS | 81 | −19.659 | −55.512 | 11.548 | 1.000 | 13.90 |
| ATOM | 601 | CA | HIS | 81 | −18.282 | −55.720 | 11.978 | 1.000 | 13.04 |
| ATOM | 602 | CB | HIS | 81 | −18.119 | −55.195 | 13.418 | 1.000 | 15.15 |
| ATOM | 603 | CG | HIS | 81 | −18.279 | −53.704 | 13.502 | 1.000 | 10.10 |
| ATOM | 604 | CD2 | HIS | 81 | −19.202 | −52.927 | 14.111 | 1.000 | 6.25 |
| ATOM | 605 | ND1 | HIS | 81 | −17.404 | −52.833 | 12.889 | 1.000 | 7.20 |
| ATOM | 606 | CE1 | HIS | 81 | −17.775 | −51.589 | 13.117 | 1.000 | 7.73 |
| ATOM | 607 | NE2 | HIS | 81 | −18.867 | −51.616 | 13.863 | 1.000 | 6.24 |
| ATOM | 608 | C | HIS | 81 | −17.827 | −57.166 | 11.896 | 1.000 | 9.61 |
| ATOM | 609 | O | HIS | 81 | −16.674 | −57.460 | 12.216 | 1.000 | 10.35 |
| ATOM | 610 | N | LEU | 82 | −18.689 | −58.081 | 11.470 | 1.000 | 4.74 |
| ATOM | 611 | CA | LEU | 82 | −18.257 | −59.461 | 11.247 | 1.000 | 6.06 |
| ATOM | 612 | CB | LEU | 82 | −19.399 | −60.263 | 10.631 | 1.000 | 6.90 |
| ATOM | 613 | CG | LEU | 82 | −20.535 | −60.716 | 11.541 | 1.000 | 6.83 |
| ATOM | 614 | CD1 | LEU | 82 | −21.388 | −61.774 | 10.851 | 1.000 | 11.79 |
| ATOM | 615 | CD2 | LEU | 82 | −19.987 | −61.246 | 12.856 | 1.000 | 23.45 |
| ATOM | 616 | C | LEU | 82 | −17.042 | −59.500 | 10.337 | 1.000 | 6.51 |
| ATOM | 617 | O | LEU | 82 | −16.972 | −58.722 | 9.375 | 1.000 | 1.45 |
| ATOM | 618 | N | PRO | 83 | −16.056 | −60.360 | 10.556 | 1.000 | 7.15 |
| ATOM | 619 | CD | PRO | 83 | −14.823 | −60.374 | 9.731 | 1.000 | 0.00 |
| ATOM | 620 | CA | PRO | 83 | −16.043 | −61.394 | 11.583 | 1.000 | 5.44 |
| ATOM | 621 | CB | PRO | 83 | −14.941 | −62.341 | 11.067 | 1.000 | 9.33 |
| ATOM | 622 | CG | PRO | 83 | −13.968 | −61.405 | 10.415 | 1.000 | 7.09 |
| ATOM | 623 | C | PRO | 83 | −15.638 | −60.922 | 12.973 | 1.000 | 10.31 |
| ATOM | 624 | O | PRO | 83 | −14.716 | −60.125 | 13.110 | 1.000 | 16.21 |
| ATOM | 625 | N | LEU | 84 | −16.319 | −61.434 | 13.994 | 1.000 | 14.34 |
| ATOM | 626 | CA | LEU | 84 | −16.009 | −61.132 | 15.382 | 1.000 | 10.66 |
| ATOM | 627 | CB | LEU | 84 | −17.165 | −60.373 | 16.049 | 1.000 | 7.23 |
| ATOM | 628 | CG | LEU | 84 | −17.485 | −59.010 | 15.434 | 1.000 | 2.01 |
| ATOM | 629 | CD1 | LEU | 84 | −18.843 | −58.518 | 15.902 | 1.000 | 8.19 |
| ATOM | 630 | CD2 | LEU | 84 | −16.382 | −58.019 | 15.766 | 1.000 | 5.93 |
| ATOM | 631 | C | LEU | 84 | −15.734 | −62.386 | 16.203 | 1.000 | 7.34 |
| ATOM | 632 | O | LEU | 84 | −16.299 | −63.447 | 15.945 | 1.000 | 8.40 |
| ATOM | 633 | N | ASP | 85 | −14.879 | −62.247 | 17.208 | 1.000 | 8.68 |
| ATOM | 634 | CA | ASP | 85 | −14.607 | −63.332 | 18.146 | 1.000 | 10.21 |
| ATOM | 635 | CB | ASP | 85 | −13.093 | −63.433 | 18.382 | 1.000 | 15.96 |
| ATOM | 636 | CG | ASP | 85 | −12.338 | −63.789 | 17.117 | 1.000 | 11.01 |

-continued

| | | | | | | | | | |
|---|---|---|---|---|---|---|---|---|---|
| ATOM | 637 | OD1 | ASP | 85 | −12.343 | −64.975 | 16.727 | 1.000 | 9.49 |
| ATOM | 638 | OD2 | ASP | 85 | −11.739 | −62.878 | 16.518 | 1.000 | 28.18 |
| ATOM | 639 | C | ASP | 85 | −15.313 | −63.142 | 19.477 | 1.000 | 0.00 |
| ATOM | 640 | O | ASP | 85 | −15.778 | −64.067 | 20.137 | 1.000 | 5.48 |
| ATOM | 641 | N | LEU | 86 | −15.414 | −61.907 | 19.958 | 1.000 | 7.62 |
| ATOM | 642 | CA | LEU | 86 | −16.080 | −61.695 | 21.243 | 1.000 | 8.84 |
| ATOM | 643 | CB | LEU | 86 | −15.085 | −61.690 | 22.403 | 1.000 | 12.15 |
| ATOM | 644 | CG | LEU | 86 | −15.655 | −61.580 | 23.822 | 1.000 | 13.98 |
| ATOM | 645 | CD1 | LEU | 86 | −16.562 | −62.757 | 24.151 | 1.000 | 7.12 |
| ATOM | 646 | CD2 | LEU | 86 | −14.535 | −61.477 | 24.850 | 1.000 | 10.28 |
| ATOM | 647 | C | LEU | 86 | −16.841 | −60.374 | 21.221 | 1.000 | 6.69 |
| ATOM | 648 | O | LEU | 86 | −16.327 | −59.409 | 20.649 | 1.000 | 8.05 |
| ATOM | 649 | N | VAL | 87 | −18.013 | −60.361 | 21.842 | 1.000 | 4.26 |
| ATOM | 650 | CA | VAL | 87 | −18.752 | −59.127 | 22.049 | 1.000 | 2.21 |
| ATOM | 651 | CB | VAL | 87 | −20.150 | −59.126 | 21.413 | 1.000 | 8.44 |
| ATOM | 652 | CG1 | VAL | 87 | −20.848 | −57.808 | 21.722 | 1.000 | 2.51 |
| ATOM | 653 | CG2 | VAL | 87 | −20.104 | −59.352 | 19.911 | 1.000 | 0.00 |
| ATOM | 654 | C | VAL | 87 | −18.893 | −58.869 | 23.551 | 1.000 | 7.05 |
| ATOM | 655 | O | VAL | 87 | −19.472 | −59.660 | 24.289 | 1.000 | 5.76 |
| ATOM | 656 | N | ILE | 88 | −18.351 | −57.746 | 24.010 | 1.000 | 7.24 |
| ATOM | 657 | CA | ILE | 88 | −18.499 | −57.336 | 25.400 | 1.000 | 6.18 |
| ATOM | 658 | CB | ILE | 88 | −17.233 | −56.652 | 25.938 | 1.000 | 6.54 |
| ATOM | 659 | CG2 | ILE | 88 | −17.458 | −56.098 | 27.333 | 1.000 | 11.40 |
| ATOM | 660 | CG1 | ILE | 88 | −16.001 | −57.559 | 25.902 | 1.000 | 6.21 |
| ATOM | 661 | CD1 | ILE | 88 | −14.734 | −56.856 | 26.339 | 1.000 | 7.20 |
| ATOM | 662 | C | ILE | 88 | −19.693 | −56.394 | 25.506 | 1.000 | 4.68 |
| ATOM | 663 | O | ILE | 88 | −19.817 | −55.458 | 24.716 | 1.000 | 10.14 |
| ATOM | 664 | N | ILE | 89 | −20.574 | −56.672 | 26.457 | 1.000 | 7.74 |
| ATOM | 665 | CA | ILE | 89 | −21.765 | −55.857 | 26.645 | 1.000 | 12.20 |
| ATOM | 666 | CB | ILE | 89 | −23.052 | −56.635 | 26.306 | 1.000 | 12.51 |
| ATOM | 667 | CG2 | ILE | 89 | −24.253 | −55.703 | 26.339 | 1.000 | 11.52 |
| ATOM | 668 | CG1 | ILE | 89 | −22.981 | −57.390 | 24.979 | 1.000 | 6.47 |
| ATOM | 669 | CD1 | ILE | 89 | −24.250 | −58.111 | 24.597 | 1.000 | 8.71 |
| ATOM | 670 | C | ILE | 89 | −21.861 | −55.340 | 28.078 | 1.000 | 11.05 |
| ATOM | 671 | O | ILE | 89 | −22.169 | −56.106 | 28.989 | 1.000 | 3.02 |
| ATOM | 672 | N | MET | 90 | −21.590 | −54.049 | 28.236 | 1.000 | 7.01 |
| ATOM | 673 | CA | MET | 90 | −21.808 | −53.359 | 29.492 | 1.000 | 11.48 |
| ATOM | 674 | CB | MET | 90 | −20.535 | −52.721 | 30.043 | 1.000 | 9.27 |
| ATOM | 675 | CG | MET | 90 | −20.756 | −52.097 | 31.415 | 1.000 | 10.33 |
| ATOM | 676 | XD | MET | 90 | −19.202 | −51.706 | 32.246 | 1.000 | 17.92 |
| ATOM | 677 | CE | MET | 90 | −18.544 | −50.475 | 31.124 | 1.000 | 12.70 |
| ATOM | 678 | C | MET | 90 | −22.872 | −52.262 | 29.325 | 1.000 | 12.90 |
| ATOM | 679 | O | MET | 90 | −22.524 | −51.143 | 28.954 | 1.000 | 0.00 |
| ATOM | 680 | N | LEU | 91 | −24.108 | −52.639 | 29.604 | 1.000 | 8.70 |
| ATOM | 681 | CA | LEU | 91 | −25.292 | −51.802 | 29.511 | 1.000 | 10.58 |
| ATOM | 682 | CB | LEU | 91 | −26.114 | −52.105 | 28.254 | 1.000 | 9.42 |
| ATOM | 683 | CG | LEU | 91 | −25.573 | −51.564 | 26.932 | 1.000 | 4.10 |
| ATOM | 684 | CD1 | LEU | 91 | −26.427 | −52.046 | 25.772 | 1.000 | 0.00 |
| ATOM | 685 | CD2 | LEU | 91 | −25.506 | −50.044 | 26.961 | 1.000 | 2.02 |
| ATOM | 686 | C | LEU | 91 | −26.169 | −52.031 | 30.734 | 1.000 | 2.21 |
| ATOM | 687 | O | LEU | 91 | −25.989 | −53.066 | 31.388 | 1.000 | 10.59 |
| ATOM | 688 | N | GLY | 92 | −27.087 | −51.117 | 31.025 | 1.000 | 4.69 |
| ATOM | 689 | CA | GLY | 92 | −27.963 | −51.321 | 32.172 | 1.000 | 7.16 |
| ATOM | 690 | C | GLY | 92 | −28.189 | −50.092 | 33.027 | 1.000 | 0.00 |
| ATOM | 691 | O | GLY | 92 | −29.266 | −49.924 | 33.603 | 1.000 | 8.09 |
| ATOM | 692 | N | THR | 93 | −27.204 | −49.219 | 33.133 | 1.000 | 0.16 |
| ATOM | 693 | CA | THR | 93 | −27.241 | −48.005 | 33.929 | 1.000 | 9.42 |
| ATOM | 694 | CB | THR | 93 | −25.927 | −47.205 | 33.768 | 1.000 | 17.05 |
| ATOM | 695 | OG1 | THR | 93 | −24.811 | −48.063 | 34.024 | 1.000 | 26.81 |
| ATOM | 696 | CG2 | THR | 93 | −25.847 | −46.068 | 34.778 | 1.000 | 0.34 |
| ATOM | 697 | C | THR | 93 | −28.386 | −47.075 | 33.551 | 1.000 | 9.26 |
| ATOM | 698 | O | THR | 93 | −29.037 | −46.491 | 34.419 | 1.000 | 14.18 |
| ATOM | 699 | N | ASN | 94 | −28.614 | −46.927 | 32.250 | 1.000 | 0.69 |
| ATOM | 700 | CA | ASN | 94 | −29.609 | −45.981 | 31.755 | 1.000 | 5.12 |
| ATOM | 701 | CB | ASN | 94 | −29.333 | −45.677 | 30.274 | 1.000 | 9.42 |
| ATOM | 702 | CG | ASN | 94 | −27.990 | −44.983 | 30.120 | 1.000 | 10.74 |
| ATOM | 703 | OD1 | ASN | 94 | −27.679 | −44.062 | 30.873 | 1.000 | 21.66 |
| ATOM | 704 | ND2 | ASN | 94 | −27.175 | −45.417 | 29.174 | 1.000 | 18.23 |
| ATOM | 705 | C | ASN | 94 | −31.029 | −46.481 | 31.986 | 1.000 | 5.80 |
| ATOM | 706 | O | ASN | 94 | −31.889 | −45.654 | 32.317 | 1.000 | 4.04 |
| ATOM | 707 | N | ASP | 95 | −31.282 | −47.777 | 31.863 | 1.000 | 4.02 |
| ATOM | 708 | CA | ASP | 95 | −32.568 | −48.411 | 32.137 | 1.000 | 7.86 |
| ATOM | 709 | CB | ASP | 95 | −32.522 | −49.913 | 31.880 | 1.000 | 5.49 |
| ATOM | 710 | CG | ASP | 95 | −32.090 | −50.392 | 30.521 | 1.000 | 10.09 |
| ATOM | 711 | OD1 | ASP | 95 | −30.998 | −50.021 | 30.040 | 1.000 | 16.22 |
| ATOM | 712 | OD2 | ASP | 95 | −32.843 | −51.184 | 29.907 | 1.000 | 15.98 |
| ATOM | 713 | C | ASP | 95 | −33.020 | −48.208 | 33.591 | 1.000 | 9.17 |
| ATOM | 714 | O | ASP | 95 | −34.188 | −48.361 | 33.958 | 1.000 | 0.43 |
| ATOM | 715 | N | THR | 96 | −32.051 | −47.882 | 34.421 | 1.000 | 11.45 |

-continued

| | | | | | | | | | |
|---|---|---|---|---|---|---|---|---|---|
| ATOM | 716 | CA | THR | 96 | −32.122 | −47.529 | 35.823 | 1.000 | 16.75 |
| ATOM | 717 | CB | THR | 96 | −30.697 | −47.638 | 36.412 | 1.000 | 24.78 |
| ATOM | 718 | OG1 | THR | 96 | −30.607 | −48.784 | 37.274 | 1.000 | 17.62 |
| ATOM | 719 | CG2 | THR | 96 | −30.350 | −46.409 | 37.229 | 1.000 | 12.12 |
| ATOM | 720 | C | THR | 96 | −32.697 | −46.132 | 35.997 | 1.000 | 12.12 |
| ATOM | 721 | O | THR | 96 | −33.047 | −45.678 | 37.088 | 1.000 | 10.94 |
| ATOM | 722 | N | LYS | 97 | −32.820 | −45.406 | 34.883 | 1.000 | 12.18 |
| ATOM | 723 | CA | LYS | 97 | −33.387 | −44.060 | 34.954 | 1.000 | 14.27 |
| ATOM | 724 | CB | LYS | 97 | −33.247 | −43.336 | 33.620 | 1.000 | 13.25 |
| ATOM | 725 | CG | LYS | 97 | −31.996 | −42.477 | 33.500 | 1.000 | 11.50 |
| ATOM | 726 | CD | LYS | 97 | −31.819 | −41.935 | 32.086 | 1.000 | 3.08 |
| ATOM | 727 | CE | LYS | 97 | −30.344 | −41.856 | 31.717 | 1.000 | 0.00 |
| ATOM | 728 | NZ | LYS | 97 | −30.131 | −41.152 | 30.416 | 1.000 | 0.00 |
| ATOM | 729 | C | LYS | 97 | −34.848 | −44.112 | 35.403 | 1.000 | 12.44 |
| ATOM | 730 | O | LYS | 97 | −35.636 | −44.914 | 34.911 | 1.000 | 8.04 |
| ATOM | 731 | N | ALA | 98 | −35.179 | −43.246 | 36.355 | 1.000 | 11.97 |
| ATOM | 732 | CA | ALA | 98 | −36.454 | −43.218 | 37.047 | 1.000 | 4.97 |
| ATOM | 733 | CB | ALA | 98 | −36.522 | −41.982 | 37.943 | 1.000 | 3.36 |
| ATOM | 734 | C | ALA | 98 | −37.641 | −43.246 | 36.100 | 1.000 | 12.00 |
| ATOM | 735 | O | ALA | 98 | −38.651 | −43.905 | 36.355 | 1.000 | 22.61 |
| ATOM | 736 | N | TYR | 99 | −37.535 | −42.518 | 34.988 | 1.000 | 12.39 |
| ATOM | 737 | CA | TYR | 99 | −38.695 | −42.403 | 34.107 | 1.000 | 7.25 |
| ATOM | 738 | CB | TYR | 99 | −38.521 | −41.297 | 33.087 | 1.000 | 9.11 |
| ATOM | 739 | CG | TYR | 99 | −37.300 | −41.251 | 32.217 | 1.000 | 15.58 |
| ATOM | 740 | CD1 | TYR | 99 | −37.261 | −41.912 | 30.995 | 1.000 | 13.09 |
| ATOM | 741 | CE1 | TYR | 99 | −36.144 | −41.874 | 30.186 | 1.000 | 9.06 |
| ATOM | 742 | CD2 | TYR | 99 | −36.173 | −40.533 | 32.598 | 1.000 | 14.48 |
| ATOM | 743 | CE2 | TYR | 99 | −35.051 | −40.482 | 31.796 | 1.000 | 15.13 |
| ATOM | 744 | CZ | TYR | 99 | −35.044 | −41.154 | 30.591 | 1.000 | 11.74 |
| ATOM | 745 | OH | TYR | 99 | −33.925 | −41.102 | 29.794 | 1.000 | 6.20 |
| ATOM | 746 | C | TYR | 99 | −38.990 | −43.726 | 33.413 | 1.000 | 11.25 |
| ATOM | 747 | O | TYR | 99 | −40.121 | −43.927 | 32.963 | 1.000 | 12.89 |
| ATOM | 748 | N | PHE | 100 | −37.993 | −44.606 | 33.351 | 1.000 | 4.63 |
| ATOM | 749 | CA | PHE | 100 | −38.237 | −45.908 | 32.731 | 1.000 | 1.01 |
| ATOM | 750 | CB | PHE | 100 | −36.903 | −46.556 | 32.348 | 1.000 | 3.41 |
| ATOM | 751 | CG | PHE | 100 | −36.316 | −45.980 | 31.070 | 1.000 | 11.77 |
| ATOM | 752 | CD1 | PHE | 100 | −35.018 | −45.506 | 31.032 | 1.000 | 7.50 |
| ATOM | 753 | CD2 | PHE | 100 | −37.080 | −45.919 | 29.917 | 1.000 | 16.94 |
| ATOM | 754 | CE1 | PHE | 100 | −34.489 | −44.981 | 29.868 | 1.000 | 7.31 |
| ATOM | 755 | CE2 | PHE | 100 | −36.557 | −45.398 | 28.748 | 1.000 | 12.92 |
| ATOM | 756 | CZ | PHE | 100 | −35.260 | −44.925 | 28.722 | 1.000 | 7.58 |
| ATOM | 757 | C | PHE | 100 | −39.051 | −46.829 | 33.628 | 1.000 | 6.94 |
| ATOM | 758 | O | PHE | 100 | −39.711 | −47.750 | 33.131 | 1.000 | 9.31 |
| ATOM | 759 | N | ARG | 101 | −39.032 | −46.629 | 34.943 | 1.000 | 12.10 |
| ATOM | 760 | CA | ARG | 101 | −39.783 | −47.468 | 35.869 | 1.000 | 12.96 |
| ATOM | 761 | CB | ARG | 101 | −41.294 | −47.296 | 35.695 | 1.000 | 16.21 |
| ATOM | 762 | CG | ARG | 101 | −41.890 | −45.959 | 36.087 | 1.000 | 19.51 |
| ATOM | 763 | CD | ARG | 101 | −43.376 | −45.918 | 35.740 | 1.000 | 25.82 |
| ATOM | 764 | NE | ARG | 101 | −43.818 | −44.553 | 35.466 | 1.000 | 31.88 |
| ATOM | 765 | CZ | ARG | 101 | −43.797 | −43.583 | 36.373 | 1.000 | 33.97 |
| ATOM | 766 | NH1 | ARG | 101 | −43.355 | −43.839 | 37.599 | 1.000 | 43.49 |
| ATOM | 767 | NH2 | ARG | 101 | −44.206 | −42.361 | 36.067 | 1.000 | 44.85 |
| ATOM | 768 | C | ARG | 101 | −39.472 | −48.955 | 35.704 | 1.000 | 12.20 |
| ATOM | 769 | O | ARG | 101 | −40.376 | −49.782 | 35.878 | 1.000 | 12.48 |
| ATOM | 770 | N | ARG | 102 | −38.238 | −49.319 | 35.378 | 1.000 | 8.86 |
| ATOM | 771 | CA | ARG | 102 | −37.887 | −50.733 | 35.264 | 1.000 | 11.00 |
| ATOM | 772 | CB | ARG | 102 | −36.899 | −50.962 | 34.115 | 1.000 | 6.96 |
| ATOM | 773 | CG | ARG | 102 | −37.497 | −50.805 | 32.720 | 1.000 | 9.64 |
| ATOM | 774 | CD | ARG | 102 | −36.518 | −51.198 | 31.624 | 1.000 | 8.07 |
| ATOM | 775 | NE | ARG | 102 | −37.140 | −51.842 | 30.474 | 1.000 | 4.64 |
| ATOM | 776 | CZ | ARG | 102 | −36.540 | −52.606 | 29.571 | 1.000 | 7.34 |
| ATOM | 777 | NH1 | ARG | 102 | −35.240 | −52.877 | 29.628 | 1.000 | 1.45 |
| ATOM | 778 | NH2 | ARG | 102 | −37.232 | −53.131 | 28.567 | 1.000 | 6.11 |
| ATOM | 779 | C | ARG | 102 | −37.320 | −51.275 | 36.577 | 1.000 | 11.09 |
| ATOM | 780 | O | ARG | 102 | −36.734 | −50.567 | 37.394 | 1.000 | 10.02 |
| ATOM | 781 | N | THR | 103 | −37.497 | −52.573 | 36.785 | 1.000 | 11.01 |
| ATOM | 782 | CA | THR | 103 | −36.898 | −53.307 | 37.893 | 1.000 | 12.65 |
| ATOM | 783 | CB | THR | 103 | −37.844 | −54.376 | 38.462 | 1.000 | 7.64 |
| ATOM | 784 | OG1 | THR | 103 | −38.083 | −55.384 | 37.468 | 1.000 | 11.29 |
| ATOM | 785 | CG2 | THR | 103 | −39.199 | −53.771 | 38.790 | 1.000 | 15.33 |
| ATOM | 786 | C | THR | 103 | −35.618 | −53.966 | 37.390 | 1.000 | 10.55 |
| ATOM | 787 | O | THR | 103 | −35.409 | −53.986 | 36.173 | 1.000 | 9.17 |
| ATOM | 788 | N | PRO | 104 | −34.765 | −54.474 | 38.264 | 1.000 | 10.17 |
| ATOM | 789 | CD | PRO | 104 | −34.799 | −54.363 | 39.731 | 1.000 | 14.03 |
| ATOM | 790 | CA | PRO | 104 | −33.598 | −55.230 | 37.803 | 1.000 | 6.81 |
| ATOM | 791 | CB | PRO | 104 | −32.968 | −55.748 | 39.094 | 1.000 | 5.25 |
| ATOM | 792 | CG | PRO | 104 | −33.402 | −54.759 | 40.129 | 1.000 | 8.07 |
| ATOM | 793 | C | PRO | 104 | −34.010 | −56.400 | 36.911 | 1.000 | 5.89 |
| ATOM | 794 | O | PRO | 104 | −33.251 | −56.728 | 35.998 | 1.000 | 5.49 |

-continued

| | | | | | | | | | |
|---|---|---|---|---|---|---|---|---|---|
| ATOM | 795 | N | LEU | 105 | −35.164 | −56.994 | 37.173 | 1.000 | 2.55 |
| ATOM | 796 | CA | LEU | 105 | −35.690 | −58.071 | 36.341 | 1.000 | 10.27 |
| ATOM | 797 | CB | LEU | 105 | −36.989 | −58.642 | 36.890 | 1.000 | 11.51 |
| ATOM | 798 | CG | LEU | 105 | −37.304 | −60.122 | 36.695 | 1.000 | 16.39 |
| ATOM | 799 | CD1 | LEU | 105 | −38.804 | −60.319 | 36.480 | 1.000 | 4.05 |
| ATOM | 800 | CD2 | LEU | 105 | −36.533 | −60.744 | 35.542 | 1.000 | 15.49 |
| ATOM | 801 | C | LEU | 105 | −35.923 | −57.566 | 34.915 | 1.000 | 14.30 |
| ATOM | 802 | O | LEU | 105 | −35.415 | −58.168 | 33.969 | 1.000 | 14.22 |
| ATOM | 803 | N | ASP | 106 | −36.686 | −56.484 | 34.791 | 1.000 | 11.11 |
| ATOM | 804 | CA | ASP | 106 | −36.922 | −55.878 | 33.482 | 1.000 | 8.08 |
| ATOM | 805 | CB | ASP | 106 | −37.636 | −54.538 | 33.621 | 1.000 | 14.02 |
| ATOM | 806 | CG | ASP | 106 | −39.046 | −54.638 | 34.152 | 1.000 | 13.88 |
| ATOM | 807 | OD1 | ASP | 106 | −39.726 | −55.653 | 33.875 | 1.000 | 19.94 |
| ATOM | 808 | OD2 | ASP | 106 | −39.479 | −53.686 | 34.843 | 1.000 | 4.29 |
| ATOM | 809 | C | ASP | 106 | −35.607 | −55.668 | 32.734 | 1.000 | 7.79 |
| ATOM | 810 | O | ASP | 106 | −35.504 | −55.987 | 31.554 | 1.000 | 10.52 |
| ATOM | 811 | N | ILE | 107 | −34.614 | −55.131 | 33.438 | 1.000 | 5.00 |
| ATOM | 812 | CA | ILE | 107 | −33.321 | −54.814 | 32.845 | 1.000 | 6.63 |
| ATOM | 813 | CB | ILE | 107 | −32.444 | −54.016 | 33.828 | 1.000 | 14.49 |
| ATOM | 814 | CG2 | ILE | 107 | −31.125 | −53.622 | 33.184 | 1.000 | 7.24 |
| ATOM | 815 | CG1 | ILE | 107 | −33.146 | −52.790 | 34.415 | 1.000 | 16.93 |
| ATOM | 816 | CD1 | ILE | 107 | −32.174 | −51.779 | 34.992 | 1.000 | 19.38 |
| ATOM | 817 | C | ILE | 107 | −32.564 | −56.059 | 32.405 | 1.000 | 5.12 |
| ATOM | 818 | O | ILE | 107 | −31.877 | −56.024 | 31.381 | 1.000 | 4.80 |
| ATOM | 819 | N | ALA | 108 | −32.691 | −57.148 | 33.157 | 1.000 | 5.34 |
| ATOM | 820 | CA | ALA | 108 | −32.021 | −58.398 | 32.812 | 1.000 | 4.25 |
| ATOM | 821 | CB | ALA | 108 | −32.089 | −59.399 | 33.956 | 1.000 | 2.49 |
| ATOM | 822 | C | ALA | 108 | −32.637 | −59.018 | 31.568 | 1.000 | 2.89 |
| ATOM | 823 | O | ALA | 108 | −31.952 | −59.619 | 30.738 | 1.000 | 11.68 |
| ATOM | 824 | N | LEU | 109 | −33.956 | −58.864 | 31.449 | 1.000 | 0.00 |
| ATOM | 825 | CA | LEU | 109 | −34.609 | −59.401 | 30.251 | 1.000 | 6.18 |
| ATOM | 826 | CB | LEU | 109 | −36.125 | −59.391 | 30.435 | 1.000 | 12.37 |
| ATOM | 827 | CG | LEU | 109 | −36.674 | −60.463 | 31.386 | 1.000 | 15.66 |
| ATOM | 828 | CD1 | LEU | 109 | −37.985 | −60.004 | 32.001 | 1.000 | 27.44 |
| ATOM | 829 | CD2 | LEU | 109 | −36.854 | −61.794 | 30.672 | 1.000 | 3.14 |
| ATOM | 830 | C | LEU | 109 | −34.171 | −58.620 | 29.022 | 1.000 | 10.30 |
| ATOM | 831 | O | LEU | 109 | −34.035 | −59.139 | 27.915 | 1.000 | 18.00 |
| ATOM | 832 | N | GLY | 110 | −33.918 | −57.323 | 29.193 | 1.000 | 11.78 |
| ATOM | 833 | CA | GLY | 110 | −33.426 | −56.535 | 28.069 | 1.000 | 8.26 |
| ATOM | 834 | C | GLY | 110 | −32.028 | −56.976 | 27.666 | 1.000 | 7.06 |
| ATOM | 835 | O | GLY | 110 | −31.757 | −57.155 | 26.482 | 1.000 | 18.68 |
| ATOM | 836 | N | MET | 111 | −31.149 | −57.149 | 28.651 | 1.000 | 5.04 |
| ATOM | 837 | CA | MET | 111 | −29.812 | −57.661 | 28.414 | 1.000 | 4.52 |
| ATOM | 838 | CB | MET | 111 | −28.962 | −57.717 | 29.683 | 1.000 | 1.61 |
| ATOM | 839 | CG | MET | 111 | −27.663 | −58.503 | 29.542 | 1.000 | 0.00 |
| ATOM | 840 | XD | MET | 111 | −26.456 | −57.694 | 28.453 | 1.000 | 16.83 |
| ATOM | 841 | CE | MET | 111 | −25.895 | −56.355 | 29.497 | 1.000 | 5.08 |
| ATOM | 842 | C | MET | 111 | −29.915 | −59.066 | 27.821 | 1.000 | 6.40 |
| ATOM | 843 | O | MET | 111 | −29.098 | −59.476 | 27.005 | 1.000 | 8.66 |
| ATOM | 844 | N | SER | 112 | −30.937 | −59.795 | 28.270 | 1.000 | 9.55 |
| ATOM | 845 | CA | SER | 112 | −31.140 | −61.133 | 27.731 | 1.000 | 8.05 |
| ATOM | 846 | CB | SER | 112 | −32.322 | −61.821 | 28.405 | 1.000 | 10.37 |
| ATOM | 847 | OG | SER | 112 | −33.488 | −61.744 | 27.609 | 1.000 | 8.11 |
| ATOM | 848 | C | SER | 112 | −31.341 | −61.034 | 26.217 | 1.000 | 6.07 |
| ATOM | 849 | O | SER | 112 | −30.761 | −61.823 | 25.471 | 1.000 | 9.26 |
| ATOM | 850 | N | VAL | 113 | −32.142 | −60.065 | 25.803 | 1.000 | 4.80 |
| ATOM | 851 | CA | VAL | 113 | −32.424 | −59.788 | 24.401 | 1.000 | 9.22 |
| ATOM | 852 | CB | VAL | 113 | −33.414 | −58.615 | 24.266 | 1.000 | 9.35 |
| ATOM | 853 | CG1 | VAL | 113 | −33.350 | −57.979 | 22.886 | 1.000 | 0.53 |
| ATOM | 854 | CG2 | VAL | 113 | −34.830 | −59.090 | 24.567 | 1.000 | 15.43 |
| ATOM | 855 | C | VAL | 113 | −31.149 | −59.490 | 23.616 | 1.000 | 18.19 |
| ATOM | 856 | O | VAL | 113 | −31.027 | −59.900 | 22.456 | 1.000 | 17.08 |
| ATOM | 857 | N | LEU | 114 | −30.199 | −58.791 | 24.235 | 1.000 | 16.22 |
| ATOM | 858 | CA | LEU | 114 | −28.948 | −58.431 | 23.570 | 1.000 | 9.05 |
| ATOM | 859 | CB | LEU | 114 | −28.220 | −57.329 | 24.341 | 1.000 | 4.93 |
| ATOM | 860 | CG | LEU | 114 | −28.938 | −55.983 | 24.427 | 1.000 | 6.23 |
| ATOM | 861 | CD1 | LEU | 114 | −28.122 | −54.973 | 25.221 | 1.000 | 8.47 |
| ATOM | 862 | CD2 | LEU | 114 | −29.228 | −55.450 | 23.032 | 1.000 | 0.00 |
| ATOM | 863 | C | LEU | 114 | −28.018 | −59.628 | 23.407 | 1.000 | 5.15 |
| ATOM | 864 | O | LEU | 114 | −27.310 | −59.762 | 22.410 | 1.000 | 8.05 |
| ATOM | 865 | N | VAL | 115 | −28.028 | −60.503 | 24.403 | 1.000 | 5.78 |
| ATOM | 866 | CA | VAL | 115 | −27.223 | −61.717 | 24.373 | 1.000 | 8.93 |
| ATOM | 867 | CB | VAL | 115 | −27.202 | −62.383 | 25.762 | 1.000 | 8.05 |
| ATOM | 868 | CG1 | VAL | 115 | −26.501 | −63.729 | 25.720 | 1.000 | 0.00 |
| ATOM | 869 | CG2 | VAL | 115 | −26.543 | −61.439 | 26.759 | 1.000 | 0.00 |
| ATOM | 870 | C | VAL | 115 | −27.763 | −62.685 | 23.330 | 1.000 | 9.50 |
| ATOM | 871 | O | VAL | 115 | −27.007 | −63.390 | 22.662 | 1.000 | 9.58 |
| ATOM | 872 | N | THR | 116 | −29.087 | −62.715 | 23.179 | 1.000 | 8.15 |
| ATOM | 873 | CA | THR | 116 | −29.688 | −63.617 | 22.199 | 1.000 | 8.38 |

-continued

| | | | | | | | | | |
|---|---|---|---|---|---|---|---|---|---|
| ATOM | 874 | CB | THR | 116 | −31.222 | −63.622 | 22.327 | 1.000 | 12.50 |
| ATOM | 875 | OG1 | THR | 116 | −31.575 | −64.207 | 23.585 | 1.000 | 13.40 |
| ATOM | 876 | CG2 | THR | 116 | −31.848 | −64.479 | 21.233 | 1.000 | 10.82 |
| ATOM | 877 | C | THR | 116 | −29.316 | −63.241 | 20.771 | 1.000 | 5.56 |
| ATOM | 878 | O | THR | 116 | −29.011 | −64.127 | 19.966 | 1.000 | 5.27 |
| ATOM | 879 | N | GLN | 117 | −29.345 | −61.945 | 20.473 | 1.000 | 8.17 |
| ATOM | 880 | CA | GLN | 117 | −28.956 | −61.430 | 19.160 | 1.000 | 9.93 |
| ATOM | 881 | CB | GLN | 117 | −29.166 | −59.920 | 19.080 | 1.000 | 3.66 |
| ATOM | 882 | CG | GLN | 117 | −30.592 | −59.440 | 19.279 | 1.000 | 6.21 |
| ATOM | 883 | CD | GLN | 117 | −30.699 | −57.933 | 19.390 | 1.000 | 7.09 |
| ATOM | 884 | OE1 | GLN | 117 | −29.801 | −57.260 | 19.896 | 1.000 | 12.85 |
| ATOM | 885 | NE2 | GLN | 117 | −31.811 | −57.376 | 18.914 | 1.000 | 7.39 |
| ATOM | 886 | C | GLN | 117 | −27.499 | −61.761 | 18.847 | 1.000 | 11.60 |
| ATOM | 887 | O | GLN | 117 | −27.105 | −62.023 | 17.706 | 1.000 | 9.03 |
| ATOM | 888 | N | VAL | 118 | −26.652 | −61.751 | 19.879 | 1.000 | 11.77 |
| ATOM | 889 | CA | VAL | 118 | −25.258 | −62.146 | 19.659 | 1.000 | 8.34 |
| ATOM | 890 | CB | VAL | 118 | −24.340 | −61.768 | 20.831 | 1.000 | 0.49 |
| ATOM | 891 | CG1 | VAL | 118 | −22.892 | −62.118 | 20.499 | 1.000 | 21.94 |
| ATOM | 892 | CG2 | VAL | 118 | −24.452 | −60.291 | 21.169 | 1.000 | 3.31 |
| ATOM | 893 | C | VAL | 118 | −25.166 | −63.652 | 19.417 | 1.000 | 10.48 |
| ATOM | 894 | O | VAL | 118 | −24.354 | −64.107 | 18.607 | 1.000 | 10.54 |
| ATOM | 895 | N | LEU | 119 | −25.993 | −64.431 | 20.112 | 1.000 | 7.97 |
| ATOM | 896 | CA | LEU | 119 | −25.916 | −65.885 | 19.993 | 1.000 | 8.73 |
| ATOM | 897 | CB | LEU | 119 | −26.679 | −66.572 | 21.135 | 1.000 | 8.06 |
| ATOM | 898 | CG | LEU | 119 | −25.981 | −66.556 | 22.498 | 1.000 | 21.06 |
| ATOM | 899 | CD1 | LEU | 119 | −26.800 | −67.296 | 23.548 | 1.000 | 5.53 |
| ATOM | 900 | CD2 | LEU | 119 | −24.580 | −67.150 | 22.403 | 1.000 | 21.96 |
| ATOM | 901 | C | LEU | 119 | −26.446 | −66.362 | 18.649 | 1.000 | 5.78 |
| ATOM | 902 | O | LEU | 119 | −26.022 | −67.409 | 18.153 | 1.000 | 14.06 |
| ATOM | 903 | N | THR | 120 | −27.364 | −65.608 | 18.053 | 1.000 | 8.82 |
| ATOM | 904 | CA | THR | 120 | −27.964 | −65.985 | 16.780 | 1.000 | 0.00 |
| ATOM | 905 | CB | THR | 120 | −29.497 | −65.798 | 16.815 | 1.000 | 6.15 |
| ATOM | 906 | OG1 | THR | 120 | −29.805 | −64.405 | 16.969 | 1.000 | 10.14 |
| ATOM | 907 | CG2 | THR | 120 | −30.121 | −66.535 | 17.994 | 1.000 | 0.76 |
| ATOM | 908 | C | THR | 120 | −27.419 | −65.198 | 15.594 | 1.000 | 10.30 |
| ATOM | 909 | O | THR | 120 | −28.061 | −65.190 | 14.537 | 1.000 | 13.46 |
| ATOM | 910 | N | SER | 121 | −26.272 | −64.533 | 15.700 | 1.000 | 11.26 |
| ATOM | 911 | CA | SER | 121 | −25.774 | −63.675 | 14.636 | 1.000 | 7.70 |
| ATOM | 912 | CB | SER | 121 | −25.000 | −62.487 | 15.240 | 1.000 | 5.36 |
| ATOM | 913 | OG | SER | 121 | −23.826 | −62.954 | 15.886 | 1.000 | 3.70 |
| ATOM | 914 | C | SER | 121 | −24.852 | −64.353 | 13.629 | 1.000 | 7.89 |
| ATOM | 915 | O | SER | 121 | −24.360 | −63.660 | 12.730 | 1.000 | 13.24 |
| ATOM | 916 | N | ALA | 122 | −24.603 | −65.645 | 13.755 | 1.000 | 11.50 |
| ATOM | 917 | CA | ALA | 122 | −23.748 | −66.370 | 12.820 | 1.000 | 12.48 |
| ATOM | 918 | CB | ALA | 122 | −23.820 | −67.868 | 13.098 | 1.000 | 3.73 |
| ATOM | 919 | C | ALA | 122 | −24.124 | −66.083 | 11.370 | 1.000 | 7.92 |
| ATOM | 920 | O | ALA | 122 | −25.311 | −66.050 | 11.042 | 1.000 | 8.42 |
| ATOM | 921 | N | GLY | 123 | −23.125 | −65.859 | 10.529 | 1.000 | 7.14 |
| ATOM | 922 | CA | GLY | 123 | −23.316 | −65.625 | 9.115 | 1.000 | 3.98 |
| ATOM | 923 | C | GLY | 123 | −23.643 | −64.196 | 8.735 | 1.000 | 12.34 |
| ATOM | 924 | O | GLY | 123 | −23.445 | −63.822 | 7.571 | 1.000 | 1.55 |
| ATOM | 925 | N | GLY | 124 | −24.132 | −63.404 | 9.683 | 1.000 | 19.09 |
| ATOM | 926 | CA | GLY | 124 | −24.506 | −62.016 | 9.471 | 1.000 | 13.26 |
| ATOM | 927 | C | GLY | 124 | −25.277 | −61.809 | 8.186 | 1.000 | 10.25 |
| ATOM | 928 | O | GLY | 124 | −26.403 | −62.278 | 8.018 | 1.000 | 10.97 |
| ATOM | 929 | N | VAL | 125 | −24.684 | −61.110 | 7.217 | 1.000 | 12.50 |
| ATOM | 930 | CA | VAL | 125 | −25.365 | −60.956 | 5.930 | 1.000 | 9.40 |
| ATOM | 931 | CB | VAL | 125 | −25.557 | −59.477 | 5.559 | 1.000 | 14.11 |
| ATOM | 932 | CG1 | VAL | 125 | −26.156 | −59.326 | 4.168 | 1.000 | 13.51 |
| ATOM | 933 | CG2 | VAL | 125 | −26.455 | −58.786 | 6.578 | 1.000 | 22.31 |
| ATOM | 934 | C | VAL | 125 | −24.588 | −61.675 | 4.833 | 1.000 | 6.71 |
| ATOM | 935 | O | VAL | 125 | −23.580 | −61.151 | 4.368 | 1.000 | 4.54 |
| ATOM | 936 | N | GLY | 126 | −25.047 | −62.850 | 4.427 | 1.000 | 14.20 |
| ATOM | 937 | CA | GLY | 126 | −24.466 | −63.654 | 3.377 | 1.000 | 9.15 |
| ATOM | 938 | C | GLY | 126 | −23.012 | −64.018 | 3.580 | 1.000 | 10.06 |
| ATOM | 939 | O | GLY | 126 | −22.225 | −64.068 | 2.629 | 1.000 | 4.29 |
| ATOM | 940 | N | THR | 127 | −22.595 | −64.295 | 4.811 | 1.000 | 6.29 |
| ATOM | 941 | CA | THR | 127 | −21.214 | −64.701 | 5.050 | 1.000 | 3.83 |
| ATOM | 942 | CB | THR | 127 | −20.470 | −63.707 | 5.957 | 1.000 | 8.35 |
| ATOM | 943 | OG1 | THR | 127 | −20.719 | −64.001 | 7.339 | 1.000 | 16.55 |
| ATOM | 944 | CG2 | THR | 127 | −20.987 | −62.295 | 5.716 | 1.000 | 11.34 |
| ATOM | 945 | C | THR | 127 | −21.143 | −66.099 | 5.663 | 1.000 | 1.10 |
| ATOM | 946 | O | THR | 127 | −22.159 | −66.699 | 6.001 | 1.000 | 4.52 |
| ATOM | 947 | N | THR | 128 | −19.921 | −66.590 | 5.790 | 1.000 | 9.21 |
| ATOM | 948 | CA | THR | 128 | −19.546 | −67.893 | 6.299 | 1.000 | 8.72 |
| ATOM | 949 | CB | THR | 128 | −18.451 | −68.505 | 5.397 | 1.000 | 10.99 |
| ATOM | 950 | OG1 | THR | 128 | −17.447 | −67.497 | 5.236 | 1.000 | 7.85 |
| ATOM | 951 | CG2 | THR | 128 | −18.976 | −68.853 | 4.015 | 1.000 | 3.45 |
| ATOM | 952 | C | THR | 128 | −18.995 | −67.821 | 7.718 | 1.000 | 13.03 |

-continued

| | | | | | | | | | |
|---|---|---|---|---|---|---|---|---|---|
| ATOM | 953 | O | THR | 128 | −18.450 | −68.788 | 8.255 | 1.000 | 8.50 |
| ATOM | 954 | N | TYR | 129 | −19.127 | −66.646 | 8.315 | 1.000 | 10.20 |
| ATOM | 955 | CA | TYR | 129 | −18.542 | −66.357 | 9.615 | 1.000 | 7.58 |
| ATOM | 956 | CB | TYR | 129 | −18.323 | −64.853 | 9.722 | 1.000 | 8.22 |
| ATOM | 957 | CG | TYR | 129 | −17.246 | −64.280 | 8.835 | 1.000 | 11.97 |
| ATOM | 958 | CD1 | TYR | 129 | −17.514 | −63.176 | 8.031 | 1.000 | 8.62 |
| ATOM | 959 | CE1 | TYR | 129 | −16.547 | −62.636 | 7.211 | 1.000 | 7.23 |
| ATOM | 960 | CD2 | TYR | 129 | −15.970 | −64.827 | 8.799 | 1.000 | 12.10 |
| ATOM | 961 | CE2 | TYR | 129 | −14.991 | −64.290 | 7.982 | 1.000 | 16.92 |
| ATOM | 962 | CZ | TYR | 129 | −15.288 | −63.196 | 7.193 | 1.000 | 16.10 |
| ATOM | 963 | OH | TYR | 129 | −14.315 | −62.655 | 6.383 | 1.000 | 11.56 |
| ATOM | 964 | C | TYR | 129 | −19.416 | −66.840 | 10.765 | 1.000 | 9.63 |
| ATOM | 965 | O | TYR | 129 | −20.644 | −66.723 | 10.714 | 1.000 | 13.75 |
| ATOM | 966 | N | PRO | 130 | −18.789 | −67.380 | 11.804 | 1.000 | 8.51 |
| ATOM | 967 | CD | PRO | 130 | −17.336 | −67.523 | 12.004 | 1.000 | 10.11 |
| ATOM | 968 | CA | PRO | 130 | −19.549 | −67.914 | 12.938 | 1.000 | 5.53 |
| ATOM | 969 | CB | PRO | 130 | −18.522 | −68.804 | 13.647 | 1.000 | 8.51 |
| ATOM | 970 | CG | PRO | 130 | −17.227 | −68.097 | 13.397 | 1.000 | 11.17 |
| ATOM | 971 | C | PRO | 130 | −19.983 | −66.791 | 13.872 | 1.000 | 7.77 |
| ATOM | 972 | O | PRO | 130 | −19.500 | −65.667 | 13.730 | 1.000 | 2.72 |
| ATOM | 973 | N | ALA | 131 | −20.873 | −67.117 | 14.799 | 1.000 | 7.61 |
| ATOM | 974 | CA | ALA | 131 | −21.305 | −66.205 | 15.844 | 1.000 | 2.73 |
| ATOM | 975 | CB | ALA | 131 | −22.537 | −66.747 | 16.554 | 1.000 | 0.00 |
| ATOM | 976 | C | ALA | 131 | −20.174 | −65.984 | 16.842 | 1.000 | 8.30 |
| ATOM | 977 | O | ALA | 131 | −19.502 | −66.942 | 17.223 | 1.000 | 12.18 |
| ATOM | 978 | N | PRO | 132 | −19.937 | −64.752 | 17.273 | 1.000 | 14.28 |
| ATOM | 979 | CD | PRO | 132 | −20.610 | −63.516 | 16.842 | 1.000 | 11.04 |
| ATOM | 980 | CA | PRO | 132 | −18.901 | −64.505 | 18.284 | 1.000 | 12.37 |
| ATOM | 981 | CB | PRO | 132 | −18.696 | −62.992 | 18.181 | 1.000 | 14.35 |
| ATOM | 982 | CG | PRO | 132 | −20.032 | −62.472 | 17.753 | 1.000 | 12.70 |
| ATOM | 983 | C | PRO | 132 | −19.395 | −64.884 | 19.675 | 1.000 | 12.80 |
| ATOM | 984 | O | PRO | 132 | −20.608 | −65.027 | 19.856 | 1.000 | 21.24 |
| ATOM | 985 | N | LYS | 133 | −18.497 | −65.051 | 20.641 | 1.000 | 14.17 |
| ATOM | 986 | CA | LYS | 133 | −18.903 | −65.337 | 22.017 | 1.000 | 14.31 |
| ATOM | 987 | CB | LYS | 133 | −17.760 | −65.881 | 22.869 | 1.000 | 14.22 |
| ATOM | 988 | CG | LYS | 133 | −17.050 | −67.101 | 22.317 | 1.000 | 13.51 |
| ATOM | 989 | CD | LYS | 133 | −15.746 | −67.358 | 23.057 | 1.000 | 18.76 |
| ATOM | 990 | CE | LYS | 133 | −15.463 | −68.849 | 23.174 | 1.000 | 21.23 |
| ATOM | 991 | NZ | LYS | 133 | −15.154 | −69.237 | 24.580 | 1.000 | 37.08 |
| ATOM | 992 | C | LYS | 133 | −19.441 | −64.066 | 22.667 | 1.000 | 10.23 |
| ATOM | 993 | O | LYS | 133 | −19.319 | −62.982 | 22.091 | 1.000 | 4.45 |
| ATOM | 994 | N | VAL | 134 | −20.032 | −64.194 | 23.853 | 1.000 | 4.74 |
| ATOM | 995 | CA | VAL | 134 | −20.562 | −63.000 | 24.507 | 1.000 | 10.55 |
| ATOM | 996 | CB | VAL | 134 | −22.106 | −62.964 | 24.490 | 1.000 | 11.86 |
| ATOM | 997 | CG1 | VAL | 134 | −22.586 | −61.523 | 24.423 | 1.000 | 0.00 |
| ATOM | 998 | CG2 | VAL | 134 | −22.659 | −63.778 | 23.334 | 1.000 | 29.88 |
| ATOM | 999 | C | VAL | 134 | −20.129 | −62.885 | 25.963 | 1.000 | 12.01 |
| ATOM | 1000 | O | VAL | 134 | −20.215 | −63.837 | 26.736 | 1.000 | 27.94 |
| ATOM | 1001 | N | LEU | 135 | −19.676 | −61.703 | 26.357 | 1.000 | 12.21 |
| ATOM | 1002 | CA | LEU | 135 | −19.364 | −61.443 | 27.757 | 1.000 | 14.41 |
| ATOM | 1003 | CB | LEU | 135 | −17.975 | −60.835 | 27.898 | 1.000 | 17.37 |
| ATOM | 1004 | CG | LEU | 135 | −17.123 | −61.223 | 29.105 | 1.000 | 18.57 |
| ATOM | 1005 | CD1 | LEU | 135 | −15.993 | −60.213 | 29.264 | 1.000 | 4.42 |
| ATOM | 1006 | CD2 | LEU | 135 | −17.932 | −61.341 | 30.387 | 1.000 | 6.01 |
| ATOM | 1007 | C | LEU | 135 | −20.397 | −60.497 | 28.360 | 1.000 | 17.03 |
| ATOM | 1008 | O | LEU | 135 | −20.485 | −59.326 | 27.984 | 1.000 | 14.19 |
| ATOM | 1009 | N | VAL | 136 | −21.196 | −60.988 | 29.303 | 1.000 | 19.10 |
| ATOM | 1010 | CA | VAL | 136 | −22.167 | −60.110 | 29.954 | 1.000 | 14.45 |
| ATOM | 1011 | CB | VAL | 136 | −23.344 | −60.925 | 30.511 | 1.000 | 13.65 |
| ATOM | 1012 | CG1 | VAL | 136 | −24.272 | −60.045 | 31.335 | 1.000 | 8.06 |
| ATOM | 1013 | CG2 | VAL | 136 | −24.080 | −61.596 | 29.362 | 1.000 | 0.00 |
| ATOM | 1014 | C | VAL | 136 | −21.498 | −59.327 | 31.073 | 1.000 | 10.63 |
| ATOM | 1015 | O | VAL | 136 | −20.929 | −59.948 | 31.971 | 1.000 | 7.12 |
| ATOM | 1016 | N | VAL | 137 | −21.556 | −57.997 | 31.027 | 1.000 | 7.93 |
| ATOM | 1017 | CA | VAL | 137 | −20.882 | −57.215 | 32.056 | 1.000 | 6.63 |
| ATOM | 1018 | CB | VAL | 137 | −19.699 | −56.397 | 31.497 | 1.000 | 6.08 |
| ATOM | 1019 | CG1 | VAL | 137 | −19.115 | −55.512 | 32.595 | 1.000 | 6.59 |
| ATOM | 1020 | CG2 | VAL | 137 | −18.609 | −57.291 | 30.936 | 1.000 | 10.34 |
| ATOM | 1021 | C | VAL | 137 | −21.828 | −56.255 | 32.775 | 1.000 | 6.02 |
| ATOM | 1022 | O | VAL | 137 | −22.319 | −55.273 | 32.219 | 1.000 | 11.10 |
| ATOM | 1023 | N | SER | 138 | −22.061 | −56.558 | 34.040 | 1.000 | 6.05 |
| ATOM | 1024 | CA | SER | 138 | −22.800 | −55.715 | 34.972 | 1.000 | 9.77 |
| ATOM | 1025 | CB | SER | 138 | −23.139 | −56.523 | 36.223 | 1.000 | 16.98 |
| ATOM | 1026 | OG | SER | 138 | −23.850 | −55.804 | 37.202 | 1.000 | 19.18 |
| ATOM | 1027 | C | SER | 138 | −21.944 | −54.496 | 35.276 | 1.000 | 8.41 |
| ATOM | 1028 | O | SER | 138 | −20.779 | −54.646 | 35.652 | 1.000 | 13.52 |
| ATOM | 1029 | N | PRO | 139 | −22.459 | −53.287 | 35.096 | 1.000 | 12.22 |
| ATOM | 1030 | CD | PRO | 139 | −23.803 | −52.952 | 34.599 | 1.000 | 11.54 |
| ATOM | 1031 | CA | PRO | 139 | −21.657 | −52.087 | 35.389 | 1.000 | 6.14 |

-continued

| | | | | | | | | | |
|---|---|---|---|---|---|---|---|---|---|
| ATOM | 1032 | CB | PRO | 139 | −22.422 | −51.015 | 34.608 | 1.000 | 7.78 |
| ATOM | 1033 | CG | PRO | 139 | −23.848 | −51.455 | 34.731 | 1.000 | 3.74 |
| ATOM | 1034 | C | PRO | 139 | −21.620 | −51.775 | 36.875 | 1.000 | 3.92 |
| ATOM | 1035 | O | PRO | 139 | −22.460 | −52.217 | 37.664 | 1.000 | 10.47 |
| ATOM | 1036 | N | PRO | 140 | −20.636 | −51.014 | 37.347 | 1.000 | 8.52 |
| ATOM | 1037 | CD | PRO | 140 | −19.524 | −50.412 | 36.611 | 1.000 | 3.33 |
| ATOM | 1038 | CA | PRO | 140 | −20.591 | −50.724 | 38.788 | 1.000 | 13.50 |
| ATOM | 1039 | CB | PRO | 140 | −19.251 | −50.012 | 38.971 | 1.000 | 12.27 |
| ATOM | 1040 | CG | PRO | 140 | −18.843 | −49.543 | 37.623 | 1.000 | 6.73 |
| ATOM | 1041 | C | PRO | 140 | −21.748 | −49.832 | 39.228 | 1.000 | 15.77 |
| ATOM | 1042 | O | PRO | 140 | −22.321 | −49.073 | 38.445 | 1.000 | 21.96 |
| ATOM | 1043 | N | PRO | 141 | −22.103 | −49.939 | 40.505 | 1.000 | 4.93 |
| ATOM | 1044 | CD | PRO | 141 | −21.487 | −50.799 | 41.528 | 1.000 | 0.26 |
| ATOM | 1045 | CA | PRO | 141 | −23.230 | −49.172 | 41.036 | 1.000 | 3.17 |
| ATOM | 1046 | CB | PRO | 141 | −23.254 | −49.560 | 42.521 | 1.000 | 4.18 |
| ATOM | 1047 | CG | PRO | 141 | −22.591 | −50.897 | 42.556 | 1.000 | 0.00 |
| ATOM | 1048 | C | PRO | 141 | −23.014 | −47.671 | 40.890 | 1.000 | 10.32 |
| ATOM | 1049 | O | PRO | 141 | −21.876 | −47.203 | 40.900 | 1.000 | 17.58 |
| ATOM | 1050 | N | LEU | 142 | −24.120 | −46.942 | 40.760 | 1.000 | 9.20 |
| ATOM | 1051 | CA | LEU | 142 | −24.079 | −45.490 | 40.729 | 1.000 | 7.44 |
| ATOM | 1052 | CB | LEU | 142 | −25.421 | −44.900 | 40.288 | 1.000 | 7.55 |
| ATOM | 1053 | CG | LEU | 142 | −25.775 | −45.119 | 38.812 | 1.000 | 13.23 |
| ATOM | 1054 | CD1 | LEU | 142 | −27.262 | −44.901 | 38.566 | 1.000 | 0.00 |
| ATOM | 1055 | CD2 | LEU | 142 | −24.932 | −44.218 | 37.921 | 1.000 | 1.85 |
| ATOM | 1056 | C | LEU | 142 | −23.711 | −44.945 | 42.109 | 1.000 | 13.38 |
| ATOM | 1057 | O | LEU | 142 | −23.764 | −45.680 | 43.099 | 1.000 | 20.55 |
| ATOM | 1058 | N | ALA | 143 | −23.363 | −43.670 | 42.126 | 1.000 | 15.81 |
| ATOM | 1059 | CA | ALA | 143 | −22.960 | −42.941 | 43.322 | 1.000 | 13.69 |
| ATOM | 1060 | CB | ALA | 143 | −21.461 | −42.676 | 43.239 | 1.000 | 3.16 |
| ATOM | 1061 | C | ALA | 143 | −23.762 | −41.656 | 43.475 | 1.000 | 16.69 |
| ATOM | 1062 | O | ALA | 143 | −24.500 | −41.280 | 42.552 | 1.000 | 10.61 |
| ATOM | 1063 | N | PRO | 144 | −23.668 | −40.968 | 44.609 | 1.000 | 19.19 |
| ATOM | 1064 | CD | PRO | 144 | −22.997 | −41.377 | 45.852 | 1.000 | 16.93 |
| ATOM | 1065 | CA | PRO | 144 | −24.315 | −39.659 | 44.745 | 1.000 | 19.29 |
| ATOM | 1066 | CB | PRO | 144 | −23.730 | −39.076 | 46.031 | 1.000 | 17.13 |
| ATOM | 1067 | CG | PRO | 144 | −22.904 | −40.130 | 46.664 | 1.000 | 12.97 |
| ATOM | 1068 | C | PRO | 144 | −24.009 | −38.723 | 43.578 | 1.000 | 17.14 |
| ATOM | 1069 | O | PRO | 144 | −22.902 | −38.626 | 43.048 | 1.000 | 12.89 |
| ATOM | 1070 | N | MET | 145 | −25.049 | −38.002 | 43.161 | 1.000 | 18.09 |
| ATOM | 1071 | CA | MET | 145 | −24.925 | −37.064 | 42.052 | 1.000 | 14.70 |
| ATOM | 1072 | CB | MET | 145 | −25.912 | −37.398 | 40.942 | 1.000 | 21.06 |
| ATOM | 1073 | CG | MET | 145 | −25.711 | −38.740 | 40.263 | 1.000 | 24.88 |
| ATOM | 1074 | XD | MET | 145 | −27.259 | −39.577 | 39.860 | 1.000 | 18.47 |
| ATOM | 1075 | CE | MET | 145 | −27.956 | −39.804 | 41.495 | 1.000 | 34.91 |
| ATOM | 1076 | C | MET | 145 | −25.155 | −35.645 | 42.559 | 1.000 | 11.49 |
| ATOM | 1077 | O | MET | 145 | −26.205 | −35.342 | 43.116 | 1.000 | 18.46 |
| ATOM | 1078 | N | PRO | 146 | −24.182 | −34.763 | 42.367 | 1.000 | 6.41 |
| ATOM | 1079 | CD | PRO | 146 | −22.909 | −34.993 | 41.683 | 1.000 | 8.62 |
| ATOM | 1080 | CA | PRO | 146 | −24.325 | −33.388 | 42.851 | 1.000 | 10.88 |
| ATOM | 1081 | CB | PRO | 146 | −22.916 | −32.814 | 42.759 | 1.000 | 10.59 |
| ATOM | 1082 | CG | PRO | 146 | −22.064 | −33.819 | 42.072 | 1.000 | 12.17 |
| ATOM | 1083 | C | PRO | 146 | −25.292 | −32.588 | 41.972 | 1.000 | 13.13 |
| ATOM | 1084 | O | PRO | 146 | −25.999 | −31.712 | 42.484 | 1.000 | 17.39 |
| ATOM | 1085 | N | HIS | 147 | −25.311 | −32.901 | 40.677 | 1.000 | 10.50 |
| ATOM | 1086 | CA | HIS | 147 | −26.203 | −32.215 | 39.758 | 1.000 | 9.69 |
| ATOM | 1087 | CB | HIS | 147 | −25.865 | −32.480 | 38.279 | 1.000 | 14.24 |
| ATOM | 1088 | CG | HIS | 147 | −26.441 | −31.373 | 37.431 | 1.000 | 6.69 |
| ATOM | 1089 | CD2 | HIS | 147 | −25.875 | −30.297 | 36.850 | 1.000 | 5.99 |
| ATOM | 1090 | ND1 | HIS | 147 | −27.780 | −31.296 | 37.134 | 1.000 | 11.40 |
| ATOM | 1091 | CE1 | HIS | 147 | −28.018 | −30.226 | 36.391 | 1.000 | 11.68 |
| ATOM | 1092 | NE2 | HIS | 147 | −26.871 | −29.600 | 36.201 | 1.000 | 12.68 |
| ATOM | 1093 | C | HIS | 147 | −27.658 | −32.596 | 40.013 | 1.000 | 5.47 |
| ATOM | 1094 | O | HIS | 147 | −28.052 | −33.761 | 39.960 | 1.000 | 11.15 |
| ATOM | 1095 | N | PRO | 148 | −28.463 | −31.575 | 40.291 | 1.000 | 12.88 |
| ATOM | 1096 | CD | PRO | 148 | −28.098 | −30.148 | 40.322 | 1.000 | 12.98 |
| ATOM | 1097 | CA | PRO | 148 | −29.877 | −31.806 | 40.602 | 1.000 | 13.30 |
| ATOM | 1098 | CB | PRO | 148 | −30.440 | −30.401 | 40.811 | 1.000 | 14.82 |
| ATOM | 1099 | CG | PRO | 148 | −29.426 | −29.455 | 40.267 | 1.000 | 16.64 |
| ATOM | 1100 | C | PRO | 148 | −30.600 | −32.508 | 39.456 | 1.000 | 15.39 |
| ATOM | 1101 | O | PRO | 148 | −31.525 | −33.290 | 39.689 | 1.000 | 15.71 |
| ATOM | 1102 | N | TRP | 149 | −30.218 | −32.263 | 38.201 | 1.000 | 21.29 |
| ATOM | 1103 | CA | TRP | 149 | −30.909 | −32.947 | 37.109 | 1.000 | 15.64 |
| ATOM | 1104 | CB | TRP | 149 | −30.571 | −32.328 | 35.750 | 1.000 | 17.31 |
| ATOM | 1105 | CG | TRP | 149 | −31.296 | −33.043 | 34.639 | 1.000 | 10.06 |
| ATOM | 1106 | CD2 | TRP | 149 | −32.715 | −33.086 | 34.444 | 1.000 | 4.30 |
| ATOM | 1107 | CE2 | TRP | 149 | −32.952 | −33.862 | 33.295 | 1.000 | 8.55 |
| ATOM | 1108 | CE3 | TRP | 149 | −33.805 | −32.541 | 35.129 | 1.000 | 4.24 |
| ATOM | 1109 | CD1 | TRP | 149 | −30.748 | −33.774 | 33.629 | 1.000 | 11.09 |
| ATOM | 1110 | NE1 | TRP | 149 | −31.736 | −34.272 | 32.813 | 1.000 | 5.61 |

-continued

| | | | | | | | | | |
|---|---|---|---|---|---|---|---|---|---|
| ATOM | 1111 | CZ2 | TRP | 149 | −34.240 | −34.107 | 32.815 | 1.000 | 12.36 |
| ATOM | 1112 | CZ3 | TRP | 149 | −35.076 | −32.785 | 34.654 | 1.000 | 13.41 |
| ATOM | 1113 | CH2 | TRP | 149 | −35.286 | −33.563 | 33.505 | 1.000 | 14.13 |
| ATOM | 1114 | C | TRP | 149 | −30.566 | −34.432 | 37.101 | 1.000 | 12.85 |
| ATOM | 1115 | O | TRP | 149 | −31.447 | −35.290 | 37.033 | 1.000 | 7.92 |
| ATOM | 1116 | N | PHE | 150 | −29.270 | −34.728 | 37.186 | 1.000 | 11.11 |
| ATOM | 1117 | CA | PHE | 150 | −28.841 | −36.125 | 37.305 | 1.000 | 11.76 |
| ATOM | 1118 | CB | PHE | 150 | −27.321 | −36.192 | 37.483 | 1.000 | 8.65 |
| ATOM | 1119 | CG | PHE | 150 | −26.581 | −36.170 | 36.150 | 1.000 | 13.44 |
| ATOM | 1120 | CD1 | PHE | 150 | −25.315 | −35.623 | 36.047 | 1.000 | 14.41 |
| ATOM | 1121 | CD2 | PHE | 150 | −27.167 | −36.697 | 35.014 | 1.000 | 12.01 |
| ATOM | 1122 | CE1 | PHE | 150 | −24.650 | −35.604 | 34.838 | 1.000 | 14.96 |
| ATOM | 1123 | CE2 | PHE | 150 | −26.511 | −36.684 | 33.797 | 1.000 | 13.41 |
| ATOM | 1124 | CZ | PHE | 150 | −25.246 | −36.136 | 33.711 | 1.000 | 18.95 |
| ATOM | 1125 | C | PHE | 150 | −29.555 | −36.813 | 38.459 | 1.000 | 10.90 |
| ATOM | 1126 | O | PHE | 150 | −30.059 | −37.930 | 38.354 | 1.000 | 7.95 |
| ATOM | 1127 | N | GLN | 151 | −29.606 | −36.120 | 39.598 | 1.000 | 12.36 |
| ATOM | 1128 | CA | GLN | 151 | −30.294 | −36.665 | 40.759 | 1.000 | 19.45 |
| ATOM | 1129 | CB | GLN | 151 | −30.306 | −35.680 | 41.932 | 1.000 | 12.11 |
| ATOM | 1130 | CG | GLN | 151 | −28.947 | −35.446 | 42.561 | 1.000 | 16.34 |
| ATOM | 1131 | CD | GLN | 151 | −29.048 | −34.481 | 43.734 | 1.000 | 22.05 |
| ATOM | 1132 | OE1 | GLN | 151 | −29.693 | −34.803 | 44.729 | 1.000 | 39.76 |
| ATOM | 1133 | NE2 | GLN | 151 | −28.423 | −33.317 | 43.598 | 1.000 | 16.49 |
| ATOM | 1134 | C | GLN | 151 | −31.745 | −37.027 | 40.441 | 1.000 | 20.77 |
| ATOM | 1135 | O | GLN | 151 | −32.232 | −38.044 | 40.936 | 1.000 | 19.36 |
| ATOM | 1136 | N | LEU | 152 | −32.397 | −36.183 | 39.644 | 1.000 | 11.67 |
| ATOM | 1137 | CA | LEU | 152 | −33.818 | −36.360 | 39.365 | 1.000 | 13.95 |
| ATOM | 1138 | CB | LEU | 152 | −34.438 | −35.101 | 38.764 | 1.000 | 14.14 |
| ATOM | 1139 | CG | LEU | 152 | −34.837 | −33.957 | 39.688 | 1.000 | 12.09 |
| ATOM | 1140 | CD1 | LEU | 152 | −34.781 | −32.631 | 38.935 | 1.000 | 11.66 |
| ATOM | 1141 | CD2 | LEU | 152 | −36.225 | −34.162 | 40.274 | 1.000 | 12.14 |
| ATOM | 1142 | C | LEU | 152 | −34.053 | −37.544 | 38.428 | 1.000 | 13.07 |
| ATOM | 1143 | O | LEU | 152 | −34.913 | −38.372 | 38.729 | 1.000 | 13.96 |
| ATOM | 1144 | N | ILE | 153 | −33.310 | −37.613 | 37.326 | 1.000 | 13.21 |
| ATOM | 1145 | CA | ILE | 153 | −33.519 | −38.661 | 36.334 | 1.000 | 12.12 |
| ATOM | 1146 | CB | ILE | 153 | −32.814 | −38.377 | 34.991 | 1.000 | 9.74 |
| ATOM | 1147 | CG2 | ILE | 153 | −33.360 | −37.106 | 34.355 | 1.000 | 0.00 |
| ATOM | 1148 | CG1 | ILE | 153 | −31.284 | −38.333 | 35.061 | 1.000 | 8.16 |
| ATOM | 1149 | CD1 | ILE | 153 | −30.635 | −38.332 | 33.684 | 1.000 | 0.00 |
| ATOM | 1150 | C | ILE | 153 | −33.054 | −40.024 | 36.836 | 1.000 | 9.56 |
| ATOM | 1151 | O | ILE | 153 | −33.540 | −41.043 | 36.342 | 1.000 | 4.79 |
| ATOM | 1152 | N | PHE | 154 | −32.138 | −40.069 | 37.797 | 1.000 | 12.41 |
| ATOM | 1153 | CA | PHE | 154 | −31.645 | −41.349 | 38.301 | 1.000 | 8.75 |
| ATOM | 1154 | CB | PHE | 154 | −30.113 | −41.372 | 38.348 | 1.000 | 8.88 |
| ATOM | 1155 | CG | PHE | 154 | −29.456 | −41.758 | 37.031 | 1.000 | 8.38 |
| ATOM | 1156 | CD1 | PHE | 154 | −28.597 | −40.887 | 36.384 | 1.000 | 9.10 |
| ATOM | 1157 | CD2 | PHE | 154 | −29.703 | −42.990 | 36.458 | 1.000 | 0.00 |
| ATOM | 1158 | CE1 | PHE | 154 | −28.000 | −41.232 | 35.188 | 1.000 | 9.85 |
| ATOM | 1159 | CE2 | PHE | 154 | −29.119 | −43.344 | 35.260 | 1.000 | 5.02 |
| ATOM | 1160 | CZ | PHE | 154 | −28.258 | −42.468 | 34.624 | 1.000 | 8.39 |
| ATOM | 1161 | C | PHE | 154 | −32.199 | −41.648 | 39.690 | 1.000 | 11.55 |
| ATOM | 1162 | O | PHE | 154 | −31.683 | −42.515 | 40.400 | 1.000 | 10.77 |
| ATOM | 1163 | N | GLU | 155 | −33.246 | −40.936 | 40.093 | 1.000 | 15.11 |
| ATOM | 1164 | CA | GLU | 155 | −33.898 | −41.221 | 41.367 | 1.000 | 19.95 |
| ATOM | 1165 | CB | GLU | 155 | −35.134 | −40.343 | 41.542 | 1.000 | 26.08 |
| ATOM | 1166 | CG | GLU | 155 | −35.558 | −40.107 | 42.980 | 1.000 | 33.00 |
| ATOM | 1167 | CD | GLU | 155 | −36.339 | −41.267 | 43.568 | 1.000 | 44.51 |
| ATOM | 1168 | OE1 | GLU | 155 | −37.432 | −41.585 | 43.051 | 1.000 | 49.47 |
| ATOM | 1169 | OE2 | GLU | 155 | −35.862 | −41.867 | 44.558 | 1.000 | 61.39 |
| ATOM | 1170 | C | GLU | 155 | −34.270 | −42.702 | 41.449 | 1.000 | 18.82 |
| ATOM | 1171 | O | GLU | 155 | −34.978 | −43.212 | 40.582 | 1.000 | 14.49 |
| ATOM | 1172 | N | GLY | 156 | −33.779 | −43.376 | 42.481 | 1.000 | 12.58 |
| ATOM | 1173 | CA | GLY | 156 | −33.993 | −44.787 | 42.696 | 1.000 | 6.50 |
| ATOM | 1174 | C | GLY | 156 | −33.061 | −45.684 | 41.914 | 1.000 | 12.22 |
| ATOM | 1175 | O | GLY | 156 | −33.205 | −46.914 | 41.914 | 1.000 | 27.90 |
| ATOM | 1176 | N | GLY | 157 | −32.082 | −45.107 | 41.224 | 1.000 | 9.19 |
| ATOM | 1177 | CA | GLY | 157 | −31.216 | −45.877 | 40.358 | 1.000 | 8.21 |
| ATOM | 1178 | C | GLY | 157 | −30.007 | −46.514 | 40.991 | 1.000 | 8.61 |
| ATOM | 1179 | O | GLY | 157 | −29.563 | −47.579 | 40.549 | 1.000 | 17.22 |
| ATOM | 1180 | N | GLU | 158 | −29.442 | −45.887 | 42.018 | 1.000 | 7.58 |
| ATOM | 1181 | CA | GLU | 158 | −28.299 | −46.453 | 42.721 | 1.000 | 7.50 |
| ATOM | 1182 | CB | GLU | 158 | −27.807 | −45.505 | 43.814 | 1.000 | 9.84 |
| ATOM | 1183 | CG | GLU | 158 | −26.756 | −46.097 | 44.739 | 1.000 | 11.00 |
| ATOM | 1184 | CD | GLU | 158 | −26.031 | −45.053 | 45.564 | 1.000 | 24.40 |
| ATOM | 1185 | OE1 | GLU | 158 | −26.158 | −43.845 | 45.267 | 1.000 | 33.57 |
| ATOM | 1186 | OE2 | GLU | 158 | −25.325 | −45.439 | 46.523 | 1.000 | 39.11 |
| ATOM | 1187 | C | GLU | 158 | −28.696 | −47.807 | 43.302 | 1.000 | 13.34 |
| ATOM | 1188 | O | GLU | 158 | −27.956 | −48.787 | 43.225 | 1.000 | 29.78 |
| ATOM | 1189 | N | GLN | 159 | −29.895 | −47.840 | 43.875 | 1.000 | 10.17 |

-continued

| | | | | | | | | | | |
|---|---|---|---|---|---|---|---|---|---|---|
| ATOM | 1190 | CA | GLN | 159 | −30.481 | −49.058 | 44.406 | 1.000 | 15.50 |
| ATOM | 1191 | CB | GLN | 159 | −31.856 | −48.764 | 45.017 | 1.000 | 19.57 |
| ATOM | 1192 | CG | GLN | 159 | −32.548 | −49.952 | 45.647 | 1.000 | 24.93 |
| ATOM | 1193 | CD | GLN | 159 | −31.737 | −50.676 | 46.704 | 1.000 | 30.24 |
| ATOM | 1194 | OE1 | GLN | 159 | −31.940 | −50.499 | 47.909 | 1.000 | 40.80 |
| ATOM | 1195 | NE2 | GLN | 159 | −30.800 | −51.510 | 46.265 | 1.000 | 20.75 |
| ATOM | 1196 | C | GLN | 159 | −30.605 | −50.132 | 43.336 | 1.000 | 17.89 |
| ATOM | 1197 | O | GLN | 159 | −30.218 | −51.285 | 43.544 | 1.000 | 21.71 |
| ATOM | 1198 | N | LYS | 160 | −31.154 | −49.791 | 42.168 | 1.000 | 15.99 |
| ATOM | 1199 | CA | LYS | 160 | −31.361 | −50.855 | 41.176 | 1.000 | 6.75 |
| ATOM | 1200 | CB | LYS | 160 | −32.314 | −50.369 | 40.090 | 1.000 | 10.24 |
| ATOM | 1201 | CG | LYS | 160 | −33.666 | −49.907 | 40.607 | 1.000 | 6.13 |
| ATOM | 1202 | CD | LYS | 160 | −34.386 | −49.041 | 39.581 | 1.000 | 11.21 |
| ATOM | 1203 | CE | LYS | 160 | −35.897 | −49.190 | 39.702 | 1.000 | 9.55 |
| ATOM | 1204 | NZ | LYS | 160 | −36.616 | −48.235 | 38.811 | 1.000 | 20.37 |
| ATOM | 1205 | C | LYS | 160 | −30.029 | −51.305 | 40.591 | 1.000 | 14.32 |
| ATOM | 1206 | O | LYS | 160 | −29.842 | −52.475 | 40.257 | 1.000 | 14.42 |
| ATOM | 1207 | N | THR | 161 | −29.082 | −50.375 | 40.465 | 1.000 | 10.29 |
| ATOM | 1208 | CA | THR | 161 | −27.771 | −50.734 | 39.933 | 1.000 | 13.43 |
| ATOM | 1209 | CB | THR | 161 | −26.878 | −49.508 | 39.672 | 1.000 | 10.03 |
| ATOM | 1210 | OG1 | THR | 161 | −27.070 | −48.557 | 40.730 | 1.000 | 30.01 |
| ATOM | 1211 | CG2 | THR | 161 | −27.263 | −48.788 | 38.389 | 1.000 | 13.57 |
| ATOM | 1212 | C | THR | 161 | −27.057 | −51.683 | 40.896 | 1.000 | 12.06 |
| ATOM | 1213 | O | THR | 161 | −26.160 | −52.415 | 40.481 | 1.000 | 6.51 |
| ATOM | 1214 | N | THR | 162 | −27.457 | −51.664 | 42.165 | 1.000 | 8.39 |
| ATOM | 1215 | CA | THR | 162 | −26.894 | −52.551 | 43.177 | 1.000 | 9.75 |
| ATOM | 1216 | CB | THR | 162 | −27.286 | −52.130 | 44.604 | 1.000 | 12.96 |
| ATOM | 1217 | OG1 | THR | 162 | −26.705 | −50.863 | 44.941 | 1.000 | 11.98 |
| ATOM | 1218 | CG2 | THR | 162 | −26.735 | −53.132 | 45.605 | 1.000 | 20.35 |
| ATOM | 1219 | C | THR | 162 | −27.349 | −53.991 | 42.956 | 1.000 | 10.87 |
| ATOM | 1220 | O | THR | 162 | −26.764 | −54.942 | 43.471 | 1.000 | 12.87 |
| ATOM | 1221 | N | GLU | 163 | −28.410 | −54.170 | 42.174 | 1.000 | 16.58 |
| ATOM | 1222 | CA | GLU | 163 | −28.949 | −55.496 | 41.905 | 1.000 | 20.69 |
| ATOM | 1223 | CB | GLU | 163 | −30.486 | −55.450 | 41.861 | 1.000 | 21.36 |
| ATOM | 1224 | CG | GLU | 163 | −31.136 | −54.918 | 43.122 | 1.000 | 19.81 |
| ATOM | 1225 | CD | GLU | 163 | −30.918 | −55.799 | 44.332 | 1.000 | 20.57 |
| ATOM | 1226 | OE1 | GLU | 163 | −30.336 | −56.894 | 44.181 | 1.000 | 13.38 |
| ATOM | 1227 | OE2 | GLU | 163 | −31.340 | −55.394 | 45.441 | 1.000 | 37.36 |
| ATOM | 1228 | C | GLU | 163 | −28.455 | −56.101 | 40.596 | 1.000 | 12.31 |
| ATOM | 1229 | O | GLU | 163 | −28.614 | −57.306 | 40.384 | 1.000 | 8.17 |
| ATOM | 1230 | N | LEU | 164 | −27.880 | −55.296 | 39.710 | 1.000 | 14.12 |
| ATOM | 1231 | CA | LEU | 164 | −27.561 | −55.746 | 38.356 | 1.000 | 8.92 |
| ATOM | 1232 | CB | LEU | 164 | −26.960 | −54.602 | 37.541 | 1.000 | 5.54 |
| ATOM | 1233 | CG | LEU | 164 | −27.903 | −53.857 | 36.593 | 1.000 | 10.39 |
| ATOM | 1234 | CD1 | LEU | 164 | −29.295 | −53.740 | 37.197 | 1.000 | 23.43 |
| ATOM | 1235 | CD2 | LEU | 164 | −27.352 | −52.485 | 36.240 | 1.000 | 2.48 |
| ATOM | 1236 | C | LEU | 164 | −26.621 | −56.943 | 38.361 | 1.000 | 6.54 |
| ATOM | 1237 | O | LEU | 164 | −26.847 | −57.925 | 37.653 | 1.000 | 4.26 |
| ATOM | 1238 | N | ALA | 165 | −25.562 | −56.865 | 39.159 | 1.000 | 7.24 |
| ATOM | 1239 | CA | ALA | 165 | −24.609 | −57.965 | 39.239 | 1.000 | 11.41 |
| ATOM | 1240 | CB | ALA | 165 | −23.542 | −57.659 | 40.276 | 1.000 | 11.40 |
| ATOM | 1241 | C | ALA | 165 | −25.312 | −59.284 | 39.551 | 1.000 | 16.26 |
| ATOM | 1242 | O | ALA | 165 | −24.980 | −60.302 | 38.947 | 1.000 | 18.13 |
| ATOM | 1243 | N | ARG | 166 | −26.266 | −59.245 | 40.469 | 1.000 | 20.04 |
| ATOM | 1244 | CA | ARG | 166 | −27.014 | −60.397 | 40.947 | 1.000 | 10.10 |
| ATOM | 1245 | CB | ARG | 166 | −27.875 | −59.992 | 42.145 | 1.000 | 15.40 |
| ATOM | 1246 | CG | ARG | 166 | −28.600 | −61.127 | 42.843 | 1.000 | 15.67 |
| ATOM | 1247 | CD | ARG | 166 | −29.286 | −60.640 | 44.115 | 1.000 | 20.34 |
| ATOM | 1248 | NE | ARG | 166 | −30.097 | −59.453 | 43.851 | 1.000 | 31.99 |
| ATOM | 1249 | CZ | ARG | 166 | −31.261 | −59.505 | 43.202 | 1.000 | 37.46 |
| ATOM | 1250 | NH1 | ARG | 166 | −31.718 | −60.673 | 42.770 | 1.000 | 41.26 |
| ATOM | 1251 | NH2 | ARG | 166 | −31.974 | −58.410 | 42.979 | 1.000 | 44.85 |
| ATOM | 1252 | C | ARG | 166 | −27.899 | −60.991 | 39.862 | 1.000 | 10.33 |
| ATOM | 1253 | O | ARG | 166 | −27.862 | −62.186 | 39.569 | 1.000 | 11.28 |
| ATOM | 1254 | N | VAL | 167 | −28.724 | −60.143 | 39.253 | 1.000 | 10.14 |
| ATOM | 1255 | CA | VAL | 167 | −29.647 | −60.637 | 38.231 | 1.000 | 8.08 |
| ATOM | 1256 | CB | VAL | 167 | −30.800 | −59.642 | 38.007 | 1.000 | 12.63 |
| ATOM | 1257 | CG1 | VAL | 167 | −31.873 | −60.262 | 37.129 | 1.000 | 23.15 |
| ATOM | 1258 | CG2 | VAL | 167 | −31.423 | −59.212 | 39.331 | 1.000 | 16.49 |
| ATOM | 1259 | C | VAL | 167 | −28.941 | −60.943 | 36.916 | 1.000 | 8.93 |
| ATOM | 1260 | O | VAL | 167 | −29.342 | −61.889 | 36.230 | 1.000 | 11.00 |
| ATOM | 1261 | N | TYR | 168 | −27.906 | −60.209 | 36.507 | 1.000 | 6.53 |
| ATOM | 1262 | CA | TYR | 168 | −27.225 | −60.549 | 35.262 | 1.000 | 5.82 |
| ATOM | 1263 | CB | TYR | 168 | −26.220 | −59.494 | 34.815 | 1.000 | 12.35 |
| ATOM | 1264 | CG | TYR | 168 | −26.746 | −58.249 | 34.148 | 1.000 | 10.53 |
| ATOM | 1265 | CD1 | TYR | 168 | −25.898 | −57.415 | 33.429 | 1.000 | 4.25 |
| ATOM | 1266 | CE1 | TYR | 168 | −26.377 | −56.273 | 32.816 | 1.000 | 3.59 |
| ATOM | 1267 | CD2 | TYR | 168 | −28.085 | −57.889 | 34.230 | 1.000 | 9.22 |
| ATOM | 1268 | CE2 | TYR | 168 | −28.565 | −56.750 | 33.624 | 1.000 | 11.67 |

-continued

| | | | | | | | | | |
|---|---|---|---|---|---|---|---|---|---|
| ATOM | 1269 | CZ | TYR | 168 | −27.708 | −55.940 | 32.912 | 1.000 | 8.76 |
| ATOM | 1270 | OH | TYR | 168 | −28.194 | −54.801 | 32.308 | 1.000 | 13.56 |
| ATOM | 1271 | C | TYR | 168 | −26.466 | −61.863 | 35.444 | 1.000 | 9.45 |
| ATOM | 1272 | O | TYR | 168 | −26.398 | −62.696 | 34.544 | 1.000 | 5.20 |
| ATOM | 1273 | N | SER | 169 | −25.896 | −61.972 | 36.648 | 1.000 | 5.94 |
| ATOM | 1274 | CA | SER | 169 | −25.145 | −63.174 | 36.999 | 1.000 | 11.65 |
| ATOM | 1275 | CB | SER | 169 | −24.663 | −63.109 | 38.445 | 1.000 | 12.52 |
| ATOM | 1276 | OG | SER | 169 | −23.611 | −64.024 | 38.688 | 1.000 | 13.86 |
| ATOM | 1277 | C | SER | 169 | −26.034 | −64.389 | 36.740 | 1.000 | 14.93 |
| ATOM | 1278 | O | SER | 169 | −25.709 | −65.240 | 35.912 | 1.000 | 25.35 |
| ATOM | 1279 | N | ALA | 170 | −27.161 | −64.434 | 37.448 | 1.000 | 9.54 |
| ATOM | 1280 | CA | ALA | 170 | −28.154 | −65.483 | 37.259 | 1.000 | 7.33 |
| ATOM | 1281 | CB | ALA | 170 | −29.397 | −65.155 | 38.069 | 1.000 | 3.12 |
| ATOM | 1282 | C | ALA | 170 | −28.495 | −65.659 | 35.785 | 1.000 | 12.27 |
| ATOM | 1283 | O | ALA | 170 | −28.526 | −66.772 | 35.262 | 1.000 | 20.56 |
| ATOM | 1284 | N | LEU | 171 | −28.753 | −64.558 | 35.081 | 1.000 | 15.11 |
| ATOM | 1285 | CA | LEU | 171 | −29.115 | −64.661 | 33.665 | 1.000 | 17.04 |
| ATOM | 1286 | CB | LEU | 171 | −29.329 | −63.272 | 33.076 | 1.000 | 13.64 |
| ATOM | 1287 | CG | LEU | 171 | −29.846 | −63.164 | 31.645 | 1.000 | 21.08 |
| ATOM | 1288 | CD1 | LEU | 171 | −28.692 | −63.043 | 30.658 | 1.000 | 45.18 |
| ATOM | 1289 | CD2 | LEU | 171 | −30.734 | −64.340 | 31.270 | 1.000 | 17.34 |
| ATOM | 1290 | C | LEU | 171 | −28.052 | −65.404 | 32.868 | 1.000 | 18.57 |
| ATOM | 1291 | O | LEU | 171 | −28.328 | −66.409 | 32.219 | 1.000 | 17.64 |
| ATOM | 1292 | N | ALA | 172 | −26.825 | −64.890 | 32.920 | 1.000 | 22.46 |
| ATOM | 1293 | CA | ALA | 172 | −25.735 | −65.489 | 32.157 | 1.000 | 17.47 |
| ATOM | 1294 | CB | ALA | 172 | −24.454 | −64.699 | 32.377 | 1.000 | 10.29 |
| ATOM | 1295 | C | ALA | 172 | −25.549 | −66.953 | 32.536 | 1.000 | 13.15 |
| ATOM | 1296 | O | ALA | 172 | −25.192 | −67.797 | 31.713 | 1.000 | 17.25 |
| ATOM | 1297 | N | SER | 173 | −25.802 | −67.242 | 33.809 | 1.000 | 11.55 |
| ATOM | 1298 | CA | SER | 173 | −25.653 | −68.595 | 34.337 | 1.000 | 15.80 |
| ATOM | 1299 | CB | SER | 173 | −25.837 | −68.578 | 35.856 | 1.000 | 15.14 |
| ATOM | 1300 | OG | SER | 173 | −26.298 | −69.837 | 36.293 | 1.000 | 15.66 |
| ATOM | 1301 | C | SER | 173 | −26.640 | −69.565 | 33.691 | 1.000 | 10.39 |
| ATOM | 1302 | O | SER | 173 | −26.263 | −70.667 | 33.284 | 1.000 | 5.06 |
| ATOM | 1303 | N | PHE | 174 | −27.882 | −69.119 | 33.601 | 1.000 | 6.57 |
| ATOM | 1304 | CA | PHE | 174 | −28.970 | −69.778 | 32.908 | 1.000 | 4.04 |
| ATOM | 1305 | CB | PHE | 174 | −30.288 | −69.024 | 33.114 | 1.000 | 4.43 |
| ATOM | 1306 | CG | PHE | 174 | −31.524 | −69.765 | 32.626 | 1.000 | 3.57 |
| ATOM | 1307 | CD1 | PHE | 174 | −32.219 | −70.606 | 33.475 | 1.000 | 0.40 |
| ATOM | 1308 | CD2 | PHE | 174 | −31.988 | −69.615 | 31.331 | 1.000 | 11.71 |
| ATOM | 1309 | CE1 | PHE | 174 | −33.343 | −71.281 | 33.051 | 1.000 | 1.63 |
| ATOM | 1310 | CE2 | PHE | 174 | −33.114 | −70.285 | 30.886 | 1.000 | 10.57 |
| ATOM | 1311 | CZ | PHE | 174 | −33.795 | −71.119 | 31.756 | 1.000 | 10.59 |
| ATOM | 1312 | C | PHE | 174 | −28.701 | −69.872 | 31.408 | 1.000 | 8.80 |
| ATOM | 1313 | O | PHE | 174 | −28.846 | −70.949 | 30.834 | 1.000 | 0.14 |
| ATOM | 1314 | N | MET | 175 | −28.328 | −68.751 | 30.793 | 1.000 | 7.91 |
| ATOM | 1315 | CA | MET | 175 | −28.058 | −68.739 | 29.356 | 1.000 | 5.97 |
| ATOM | 1316 | CB | MET | 175 | −28.103 | −67.321 | 28.780 | 1.000 | 0.00 |
| ATOM | 1317 | CG | MET | 175 | −29.492 | −66.712 | 28.751 | 1.000 | 7.42 |
| ATOM | 1318 | XD | MET | 175 | −29.573 | −65.056 | 28.023 | 1.000 | 16.37 |
| ATOM | 1319 | CE | MET | 175 | −30.064 | −65.488 | 26.348 | 1.000 | 21.02 |
| ATOM | 1320 | C | MET | 175 | −26.715 | −69.399 | 29.045 | 1.000 | 6.31 |
| ATOM | 1321 | O | MET | 175 | −26.332 | −69.479 | 27.880 | 1.000 | 8.17 |
| ATOM | 1322 | N | LYS | 176 | −26.020 | −69.872 | 30.070 | 1.000 | 8.77 |
| ATOM | 1323 | CA | LYS | 176 | −24.762 | −70.598 | 29.939 | 1.000 | 10.68 |
| ATOM | 1324 | CB | LYS | 176 | −24.970 | −71.945 | 29.239 | 1.000 | 10.45 |
| ATOM | 1325 | CG | LYS | 176 | −25.907 | −72.900 | 29.971 | 1.000 | 3.74 |
| ATOM | 1326 | CD | LYS | 176 | −25.133 | −73.755 | 30.964 | 1.000 | 5.05 |
| ATOM | 1327 | CE | LYS | 176 | −26.084 | −74.568 | 31.833 | 1.000 | 6.09 |
| ATOM | 1328 | NZ | LYS | 176 | −26.739 | −73.721 | 32.861 | 1.000 | 24.38 |
| ATOM | 1329 | C | LYS | 176 | −23.733 | −69.760 | 29.190 | 1.000 | 12.34 |
| ATOM | 1330 | O | LYS | 176 | −23.084 | −70.178 | 28.231 | 1.000 | 24.85 |
| ATOM | 1331 | N | VAL | 177 | −23.601 | −68.520 | 29.648 | 1.000 | 12.09 |
| ATOM | 1332 | CA | VAL | 177 | −22.709 | −67.581 | 28.953 | 1.000 | 12.10 |
| ATOM | 1333 | CB | VAL | 177 | −23.569 | −66.629 | 28.106 | 1.000 | 9.74 |
| ATOM | 1334 | CG1 | VAL | 177 | −23.831 | −65.319 | 28.835 | 1.000 | 18.59 |
| ATOM | 1335 | CG2 | VAL | 177 | −22.921 | −66.372 | 26.753 | 1.000 | 20.30 |
| ATOM | 1336 | C | VAL | 177 | −21.848 | −66.876 | 29.982 | 1.000 | 13.62 |
| ATOM | 1337 | O | VAL | 177 | −22.292 | −66.730 | 31.126 | 1.000 | 20.25 |
| ATOM | 1338 | N | PRO | 178 | −20.635 | −66.454 | 29.637 | 1.000 | 10.56 |
| ATOM | 1339 | CD | PRO | 178 | −20.019 | −66.530 | 28.312 | 1.000 | 2.11 |
| ATOM | 1340 | CA | PRO | 178 | −19.760 | −65.842 | 30.642 | 1.000 | 10.32 |
| ATOM | 1341 | CB | PRO | 178 | −18.433 | −65.656 | 29.913 | 1.000 | 6.70 |
| ATOM | 1342 | CG | PRO | 178 | −18.623 | −66.026 | 28.499 | 1.000 | 0.81 |
| ATOM | 1343 | C | PRO | 178 | −20.281 | −64.483 | 31.119 | 1.000 | 20.65 |
| ATOM | 1344 | O | PRO | 178 | −20.796 | −63.674 | 30.351 | 1.000 | 22.70 |
| ATOM | 1345 | N | PHE | 179 | −20.124 | −64.253 | 32.412 | 1.000 | 22.55 |
| ATOM | 1346 | CA | PHE | 179 | −20.474 | −63.025 | 33.107 | 1.000 | 19.13 |
| ATOM | 1347 | CB | PHE | 179 | −21.518 | −63.283 | 34.194 | 1.000 | 8.91 |

-continued

| | | | | | | | | | |
|---|---|---|---|---|---|---|---|---|---|
| ATOM | 1348 | CG | PHE | 179 | −21.661 | −62.215 | 35.268 | 1.000 | 8.12 |
| ATOM | 1349 | CD1 | PHE | 179 | −22.433 | −61.087 | 35.044 | 1.000 | 10.36 |
| ATOM | 1350 | CD2 | PHE | 179 | −21.031 | −62.337 | 36.499 | 1.000 | 2.04 |
| ATOM | 1351 | CE1 | PHE | 179 | −22.590 | −60.103 | 36.004 | 1.000 | 2.43 |
| ATOM | 1352 | CE2 | PHE | 179 | −21.183 | −61.367 | 37.470 | 1.000 | 0.76 |
| ATOM | 1353 | CZ | PHE | 179 | −21.963 | −60.248 | 37.228 | 1.000 | 2.96 |
| ATOM | 1354 | C | PHE | 179 | −19.231 | −62.400 | 33.736 | 1.000 | 13.74 |
| ATOM | 1355 | O | PHE | 179 | −18.309 | −63.110 | 34.128 | 1.000 | 15.60 |
| ATOM | 1356 | N | PHE | 180 | −19.214 | −61.080 | 33.838 | 1.000 | 14.28 |
| ATOM | 1357 | CA | PHE | 180 | −18.178 | −60.371 | 34.573 | 1.000 | 13.03 |
| ATOM | 1358 | CB | PHE | 180 | −17.004 | −59.952 | 33.686 | 1.000 | 17.94 |
| ATOM | 1359 | CG | PHE | 180 | −15.933 | −59.164 | 34.433 | 1.000 | 21.76 |
| ATOM | 1360 | CD1 | PHE | 180 | −14.960 | −59.807 | 35.176 | 1.000 | 21.38 |
| ATOM | 1361 | CD2 | PHE | 180 | −15.904 | −57.780 | 34.391 | 1.000 | 19.62 |
| ATOM | 1362 | CE1 | PHE | 180 | −13.979 | −59.108 | 35.859 | 1.000 | 15.07 |
| ATOM | 1363 | CE2 | PHE | 180 | −14.941 | −57.064 | 35.075 | 1.000 | 21.73 |
| ATOM | 1364 | CZ | PHE | 180 | −13.979 | −57.727 | 35.816 | 1.000 | 21.65 |
| ATOM | 1365 | C | PHE | 180 | −18.822 | −59.164 | 35.256 | 1.000 | 12.16 |
| ATOM | 1366 | O | PHE | 180 | −19.594 | −58.423 | 34.648 | 1.000 | 11.01 |
| ATOM | 1367 | N | ASP | 181 | −18.504 | −58.988 | 36.536 | 1.000 | 7.72 |
| ATOM | 1368 | CA | ASP | 181 | −19.062 | −57.864 | 37.286 | 1.000 | 10.61 |
| ATOM | 1369 | CB | ASP | 181 | −19.521 | −58.346 | 38.659 | 1.000 | 5.77 |
| ATOM | 1370 | CG | ASP | 181 | −19.986 | −57.225 | 39.559 | 1.000 | 4.11 |
| ATOM | 1371 | OD1 | ASP | 181 | −20.116 | −56.076 | 39.092 | 1.000 | 8.61 |
| ATOM | 1372 | OD2 | ASP | 181 | −20.217 | −57.508 | 40.750 | 1.000 | 11.49 |
| ATOM | 1373 | C | ASP | 181 | −18.037 | −56.743 | 37.378 | 1.000 | 15.44 |
| ATOM | 1374 | O | ASP | 181 | −17.023 | −56.872 | 38.060 | 1.000 | 16.84 |
| ATOM | 1375 | N | ALA | 182 | −18.293 | −55.639 | 36.672 | 1.000 | 18.65 |
| ATOM | 1376 | CA | ALA | 182 | −17.359 | −54.517 | 36.678 | 1.000 | 18.00 |
| ATOM | 1377 | CB | ALA | 182 | −17.778 | −53.459 | 35.668 | 1.000 | 7.66 |
| ATOM | 1378 | C | ALA | 182 | −17.240 | −53.911 | 38.075 | 1.000 | 18.92 |
| ATOM | 1379 | O | ALA | 182 | −16.198 | −53.340 | 38.400 | 1.000 | 8.61 |
| ATOM | 1380 | N | GLY | 183 | −18.296 | −54.044 | 38.872 | 1.000 | 15.67 |
| ATOM | 1381 | CA | GLY | 183 | −18.374 | −53.516 | 40.219 | 1.000 | 13.53 |
| ATOM | 1382 | C | GLY | 183 | −17.444 | −54.230 | 41.176 | 1.000 | 14.96 |
| ATOM | 1383 | O | GLY | 183 | −17.268 | −53.846 | 42.330 | 1.000 | 25.31 |
| ATOM | 1384 | N | SER | 184 | −16.830 | −55.306 | 40.696 | 1.000 | 16.38 |
| ATOM | 1385 | CA | SER | 184 | −15.940 | −56.105 | 41.525 | 1.000 | 12.32 |
| ATOM | 1386 | CB | SER | 184 | −16.009 | −57.574 | 41.116 | 1.000 | 14.55 |
| ATOM | 1387 | OG | SER | 184 | −15.237 | −57.867 | 39.967 | 1.000 | 12.36 |
| ATOM | 1388 | C | SER | 184 | −14.516 | −55.572 | 41.439 | 1.000 | 13.33 |
| ATOM | 1389 | O | SER | 184 | −13.644 | −55.986 | 42.204 | 1.000 | 12.05 |
| ATOM | 1390 | N | VAL | 185 | −14.276 | −54.640 | 40.515 | 1.000 | 9.89 |
| ATOM | 1391 | CA | VAL | 185 | −12.902 | −54.156 | 40.358 | 1.000 | 14.54 |
| ATOM | 1392 | CB | VAL | 185 | −12.320 | −54.649 | 39.021 | 1.000 | 16.34 |
| ATOM | 1393 | CG1 | VAL | 185 | −12.034 | −56.141 | 39.100 | 1.000 | 13.09 |
| ATOM | 1394 | CG2 | VAL | 185 | −13.274 | −54.346 | 37.877 | 1.000 | 20.34 |
| ATOM | 1395 | C | VAL | 185 | −12.802 | −52.642 | 40.445 | 1.000 | 20.13 |
| ATOM | 1396 | O | VAL | 185 | −11.718 | −52.101 | 40.682 | 1.000 | 11.67 |
| ATOM | 1397 | N | ILE | 186 | −13.912 | −51.929 | 40.260 | 1.000 | 19.83 |
| ATOM | 1398 | CA | ILE | 186 | −13.905 | −50.479 | 40.381 | 1.000 | 13.97 |
| ATOM | 1399 | CB | ILE | 186 | −13.716 | −49.752 | 39.031 | 1.000 | 8.30 |
| ATOM | 1400 | CG2 | ILE | 186 | −12.362 | −50.070 | 38.428 | 1.000 | 12.39 |
| ATOM | 1401 | CG1 | ILE | 186 | −14.830 | −50.005 | 38.014 | 1.000 | 10.45 |
| ATOM | 1402 | CD1 | ILE | 186 | −14.956 | −48.929 | 36.957 | 1.000 | 3.60 |
| ATOM | 1403 | C | ILE | 186 | −15.209 | −49.957 | 40.979 | 1.000 | 13.38 |
| ATOM | 1404 | O | ILE | 186 | −16.256 | −50.583 | 40.857 | 1.000 | 12.90 |
| ATOM | 1405 | N | SER | 187 | −15.120 | −48.788 | 41.596 | 1.000 | 11.99 |
| ATOM | 1406 | CA | SER | 187 | −16.287 | −48.046 | 42.052 | 1.000 | 9.16 |
| ATOM | 1407 | CB | SER | 187 | −16.110 | −47.594 | 43.498 | 1.000 | 10.88 |
| ATOM | 1408 | OG | SER | 187 | −14.889 | −46.879 | 43.658 | 1.000 | 16.58 |
| ATOM | 1409 | C | SER | 187 | −16.517 | −46.839 | 41.145 | 1.000 | 11.87 |
| ATOM | 1410 | O | SER | 187 | −15.567 | −46.304 | 40.563 | 1.000 | 16.73 |
| ATOM | 1411 | N | THR | 188 | −17.767 | −46.410 | 41.015 | 1.000 | 15.17 |
| ATOM | 1412 | CA | THR | 188 | −18.077 | −45.244 | 40.189 | 1.000 | 13.51 |
| ATOM | 1413 | CB | THR | 188 | −19.571 | −45.151 | 39.848 | 1.000 | 12.88 |
| ATOM | 1414 | OG1 | THR | 188 | −19.969 | −46.308 | 39.101 | 1.000 | 16.33 |
| ATOM | 1415 | CG2 | THR | 188 | −19.843 | −43.943 | 38.961 | 1.000 | 8.08 |
| ATOM | 1416 | C | THR | 188 | −17.639 | −43.978 | 40.916 | 1.000 | 14.09 |
| ATOM | 1417 | O | THR | 188 | −18.293 | −43.535 | 41.860 | 1.000 | 10.72 |
| ATOM | 1418 | N | ASP | 189 | −16.518 | −43.414 | 40.474 | 1.000 | 15.51 |
| ATOM | 1419 | CA | ASP | 189 | −15.911 | −42.313 | 41.210 | 1.000 | 11.58 |
| ATOM | 1420 | CB | ASP | 189 | −14.407 | −42.594 | 41.362 | 1.000 | 12.86 |
| ATOM | 1421 | CG | ASP | 189 | −14.158 | −43.791 | 42.261 | 1.000 | 4.55 |
| ATOM | 1422 | OD1 | ASP | 189 | −14.915 | −43.960 | 43.239 | 1.000 | 13.27 |
| ATOM | 1423 | OD2 | ASP | 189 | −13.208 | −44.549 | 41.989 | 1.000 | 6.91 |
| ATOM | 1424 | C | ASP | 189 | −16.120 | −40.949 | 40.567 | 1.000 | 15.34 |
| ATOM | 1425 | O | ASP | 189 | −15.910 | −39.948 | 41.263 | 1.000 | 18.48 |
| ATOM | 1426 | N | GLY | 190 | −16.510 | −40.918 | 39.303 | 1.000 | 19.39 |

-continued

| | | | | | | | | | |
|---|---|---|---|---|---|---|---|---|---|
| ATOM | 1427 | CA | GLY | 190 | −16.710 | −39.718 | 38.515 | 1.000 | 15.08 |
| ATOM | 1428 | C | GLY | 190 | −17.385 | −38.613 | 39.303 | 1.000 | 18.57 |
| ATOM | 1429 | O | GLY | 190 | −18.263 | −38.908 | 40.119 | 1.000 | 20.64 |
| ATOM | 1430 | N | VAL | 191 | −16.952 | −37.381 | 39.057 | 1.000 | 13.86 |
| ATOM | 1431 | CA | VAL | 191 | −17.428 | −36.226 | 39.806 | 1.000 | 10.59 |
| ATOM | 1432 | CB | VAL | 191 | −16.825 | −34.905 | 39.286 | 1.000 | 17.05 |
| ATOM | 1433 | CG1 | VAL | 191 | −15.324 | −34.875 | 39.559 | 1.000 | 30.84 |
| ATOM | 1434 | CG2 | VAL | 191 | −17.092 | −34.701 | 37.803 | 1.000 | 8.10 |
| ATOM | 1435 | C | VAL | 191 | −18.950 | −36.129 | 39.774 | 1.000 | 10.47 |
| ATOM | 1436 | O | VAL | 191 | −19.542 | −35.686 | 40.761 | 1.000 | 13.60 |
| ATOM | 1437 | N | ASP | 192 | −19.571 | −36.534 | 38.668 | 1.000 | 1.46 |
| ATOM | 1438 | CA | ASP | 192 | −21.018 | −36.447 | 38.540 | 1.000 | 0.70 |
| ATOM | 1439 | CB | ASP | 192 | −21.387 | −36.356 | 37.056 | 1.000 | 2.10 |
| ATOM | 1440 | CG | ASP | 192 | −20.918 | −37.566 | 36.268 | 1.000 | 9.82 |
| ATOM | 1441 | OD1 | ASP | 192 | −20.296 | −38.478 | 36.857 | 1.000 | 8.20 |
| ATOM | 1442 | OD2 | ASP | 192 | −21.182 | −37.597 | 35.047 | 1.000 | 6.78 |
| ATOM | 1443 | C | ASP | 192 | −21.754 | −37.622 | 39.173 | 1.000 | 7.73 |
| ATOM | 1444 | O | ASP | 192 | −22.988 | −37.674 | 39.136 | 1.000 | 7.10 |
| ATOM | 1445 | N | GLY | 193 | −21.027 | −38.572 | 39.753 | 1.000 | 15.10 |
| ATOM | 1446 | CA | GLY | 193 | −21.631 | −39.747 | 40.351 | 1.000 | 17.83 |
| ATOM | 1447 | C | GLY | 193 | −22.153 | −40.758 | 39.352 | 1.000 | 18.93 |
| ATOM | 1448 | O | GLY | 193 | −22.820 | −41.732 | 39.718 | 1.000 | 10.12 |
| ATOM | 1449 | N | ILE | 194 | −21.867 | −40.565 | 38.062 | 1.000 | 11.77 |
| ATOM | 1450 | CA | ILE | 194 | −22.330 | −41.546 | 37.081 | 1.000 | 7.87 |
| ATOM | 1451 | CB | ILE | 194 | −23.401 | −40.945 | 36.154 | 1.000 | 9.95 |
| ATOM | 1452 | CG2 | ILE | 194 | −23.790 | −41.927 | 35.063 | 1.000 | 0.00 |
| ATOM | 1453 | CG1 | ILE | 194 | −24.643 | −40.441 | 36.896 | 1.000 | 9.90 |
| ATOM | 1454 | CD1 | ILE | 194 | −25.248 | −39.237 | 36.206 | 1.000 | 8.85 |
| ATOM | 1455 | C | ILE | 194 | −21.191 | −42.068 | 36.225 | 1.000 | 2.97 |
| ATOM | 1456 | O | ILE | 194 | −21.086 | −43.251 | 35.924 | 1.000 | 6.72 |
| ATOM | 1457 | N | HIS | 195 | −20.277 | −41.195 | 35.792 | 1.000 | 6.33 |
| ATOM | 1458 | CA | HIS | 195 | −19.256 | −41.719 | 34.884 | 1.000 | 10.76 |
| ATOM | 1459 | CB | HIS | 195 | −19.089 | −40.790 | 33.673 | 1.000 | 11.36 |
| ATOM | 1460 | CG | HIS | 195 | −20.402 | −40.647 | 32.958 | 1.000 | 11.50 |
| ATOM | 1461 | CD2 | HIS | 195 | −20.981 | −41.395 | 31.989 | 1.000 | 5.43 |
| ATOM | 1462 | ND1 | HIS | 195 | −21.283 | −39.633 | 33.253 | 1.000 | 7.30 |
| ATOM | 1463 | CE1 | HIS | 195 | −22.351 | −39.753 | 32.485 | 1.000 | 9.11 |
| ATOM | 1464 | NE2 | HIS | 195 | −22.192 | −40.814 | 31.711 | 1.000 | 8.18 |
| ATOM | 1465 | C | HIS | 195 | −17.918 | −41.941 | 35.577 | 1.000 | 8.63 |
| ATOM | 1466 | O | HIS | 195 | −17.762 | −41.602 | 36.743 | 1.000 | 13.71 |
| ATOM | 1467 | N | PHE | 196 | −17.010 | −42.529 | 34.812 | 1.000 | 6.37 |
| ATOM | 1468 | CA | PHE | 196 | −15.725 | −43.017 | 35.249 | 1.000 | 9.06 |
| ATOM | 1469 | CB | PHE | 196 | −15.233 | −44.136 | 34.320 | 1.000 | 5.38 |
| ATOM | 1470 | CG | PHE | 196 | −16.048 | −45.412 | 34.451 | 1.000 | 10.20 |
| ATOM | 1471 | CD1 | PHE | 196 | −15.822 | −46.481 | 33.602 | 1.000 | 8.01 |
| ATOM | 1472 | CD2 | PHE | 196 | −17.027 | −45.509 | 35.427 | 1.000 | 6.21 |
| ATOM | 1473 | CE1 | PHE | 196 | −16.571 | −47.637 | 33.722 | 1.000 | 11.17 |
| ATOM | 1474 | CE2 | PHE | 196 | −17.779 | −46.662 | 35.546 | 1.000 | 14.06 |
| ATOM | 1475 | CZ | PHE | 196 | −17.549 | −47.727 | 34.694 | 1.000 | 13.03 |
| ATOM | 1476 | C | PHE | 196 | −14.663 | −41.925 | 35.273 | 1.000 | 12.92 |
| ATOM | 1477 | O | PHE | 196 | −14.757 | −40.983 | 34.494 | 1.000 | 15.16 |
| ATOM | 1478 | N | THR | 197 | −13.694 | −42.112 | 36.158 | 1.000 | 13.17 |
| ATOM | 1479 | CA | THR | 197 | −12.477 | −41.318 | 36.183 | 1.000 | 17.95 |
| ATOM | 1480 | CB | THR | 197 | −11.886 | −41.168 | 37.593 | 1.000 | 20.94 |
| ATOM | 1481 | OG1 | THR | 197 | −11.650 | −42.458 | 38.173 | 1.000 | 20.14 |
| ATOM | 1482 | CG2 | THR | 197 | −12.882 | −40.454 | 38.499 | 1.000 | 31.55 |
| ATOM | 1483 | C | THR | 197 | −11.443 | −41.978 | 35.269 | 1.000 | 10.26 |
| ATOM | 1484 | O | THR | 197 | −11.713 | −43.037 | 34.705 | 1.000 | 14.53 |
| ATOM | 1485 | N | GLU | 198 | −10.283 | −41.362 | 35.133 | 1.000 | 9.05 |
| ATOM | 1486 | CA | GLU | 198 | −9.192 | −41.943 | 34.362 | 1.000 | 12.89 |
| ATOM | 1487 | CB | GLU | 198 | −8.023 | −40.960 | 34.314 | 1.000 | 20.40 |
| ATOM | 1488 | CG | GLU | 198 | −6.903 | −41.349 | 33.362 | 1.000 | 32.30 |
| ATOM | 1489 | CD | GLU | 198 | −5.764 | −40.346 | 33.328 | 1.000 | 35.77 |
| ATOM | 1490 | OE1 | GLU | 198 | −5.127 | −40.141 | 34.385 | 1.000 | 42.59 |
| ATOM | 1491 | OE2 | GLU | 198 | −5.498 | −39.761 | 32.256 | 1.000 | 25.40 |
| ATOM | 1492 | C | GLU | 198 | −8.779 | −43.279 | 34.970 | 1.000 | 16.23 |
| ATOM | 1493 | O | GLU | 198 | −8.636 | −44.296 | 34.292 | 1.000 | 14.85 |
| ATOM | 1494 | N | ALA | 199 | −8.596 | −43.284 | 36.291 | 1.000 | 11.36 |
| ATOM | 1495 | CA | ALA | 199 | −8.233 | −44.489 | 37.022 | 1.000 | 5.99 |
| ATOM | 1496 | CB | ALA | 199 | −8.047 | −44.154 | 38.499 | 1.000 | 2.34 |
| ATOM | 1497 | C | ALA | 199 | −9.273 | −45.594 | 36.873 | 1.000 | 7.89 |
| ATOM | 1498 | O | ALA | 199 | −8.922 | −46.767 | 36.748 | 1.000 | 16.70 |
| ATOM | 1499 | N | ASN | 200 | −10.548 | −45.210 | 36.897 | 1.000 | 13.48 |
| ATOM | 1500 | CA | ASN | 200 | −11.644 | −46.155 | 36.715 | 1.000 | 11.59 |
| ATOM | 1501 | CB | ASN | 200 | −13.007 | −45.474 | 36.805 | 1.000 | 4.12 |
| ATOM | 1502 | CG | ASN | 200 | −13.492 | −45.192 | 38.209 | 1.000 | 11.67 |
| ATOM | 1503 | OD1 | ASN | 200 | −13.045 | −45.767 | 39.200 | 1.000 | 6.19 |
| ATOM | 1504 | ND2 | ASN | 200 | −14.455 | −44.276 | 38.330 | 1.000 | 13.74 |
| ATOM | 1505 | C | ASN | 200 | −11.505 | −46.869 | 35.366 | 1.000 | 8.88 |

-continued

| | | | | | | | | | |
|---|---|---|---|---|---|---|---|---|---|
| ATOM | 1506 | O | ASN | 200 | −11.667 | −48.084 | 35.305 | 1.000 | 9.08 |
| ATOM | 1507 | N | ASN | 201 | −11.208 | −46.111 | 34.315 | 1.000 | 14.48 |
| ATOM | 1508 | CA | ASN | 201 | −11.074 | −46.639 | 32.963 | 1.000 | 14.27 |
| ATOM | 1509 | CB | ASN | 201 | −10.903 | −45.495 | 31.960 | 1.000 | 16.17 |
| ATOM | 1510 | CG | ASN | 201 | −12.221 | −44.853 | 31.570 | 1.000 | 14.25 |
| ATOM | 1511 | OD1 | ASN | 201 | −13.050 | −45.436 | 30.871 | 1.000 | 13.77 |
| ATOM | 1512 | ND2 | ASN | 201 | −12.441 | −43.624 | 32.021 | 1.000 | 16.01 |
| ATOM | 1513 | C | ASN | 201 | −9.908 | −47.620 | 32.870 | 1.000 | 12.95 |
| ATOM | 1514 | O | ASN | 201 | −10.050 | −48.720 | 32.334 | 1.000 | 11.02 |
| ATOM | 1515 | N | ARG | 202 | −8.775 | −47.207 | 33.412 | 1.000 | 15.80 |
| ATOM | 1516 | CA | ARG | 202 | −7.571 | −48.020 | 33.532 | 1.000 | 14.85 |
| ATOM | 1517 | CB | ARG | 202 | −6.491 | −47.250 | 34.294 | 1.000 | 17.85 |
| ATOM | 1518 | CG | ARG | 202 | −5.109 | −47.874 | 34.325 | 1.000 | 17.66 |
| ATOM | 1519 | CD | ARG | 202 | −4.141 | −47.026 | 35.143 | 1.000 | 19.69 |
| ATOM | 1520 | NE | ARG | 202 | −3.646 | −45.881 | 34.388 | 1.000 | 30.64 |
| ATOM | 1521 | CZ | ARG | 202 | −2.410 | −45.407 | 34.412 | 1.000 | 36.54 |
| ATOM | 1522 | NH1 | ARG | 202 | −1.470 | −45.972 | 35.164 | 1.000 | 35.38 |
| ATOM | 1523 | NH2 | ARG | 202 | −2.093 | −44.353 | 33.669 | 1.000 | 23.31 |
| ATOM | 1524 | C | ARG | 202 | −7.862 | −49.344 | 34.229 | 1.000 | 6.52 |
| ATOM | 1525 | O | ARG | 202 | −7.636 | −50.401 | 33.644 | 1.000 | 9.98 |
| ATOM | 1526 | N | ASP | 203 | −8.365 | −49.285 | 35.464 | 1.000 | 3.83 |
| ATOM | 1527 | CA | ASP | 203 | −8.597 | −50.500 | 36.237 | 1.000 | 12.72 |
| ATOM | 1528 | CB | ASP | 203 | −9.148 | −50.181 | 37.631 | 1.000 | 9.96 |
| ATOM | 1529 | CG | ASP | 203 | −8.170 | −49.370 | 38.458 | 1.000 | 16.04 |
| ATOM | 1530 | OD1 | ASP | 203 | −6.980 | −49.324 | 38.086 | 1.000 | 18.66 |
| ATOM | 1531 | OD2 | ASP | 203 | −8.584 | −48.772 | 39.474 | 1.000 | 22.09 |
| ATOM | 1532 | C | ASP | 203 | −9.548 | −51.455 | 35.524 | 1.000 | 18.07 |
| ATOM | 1533 | O | ASP | 203 | −9.383 | −52.674 | 35.579 | 1.000 | 12.38 |
| ATOM | 1534 | N | LEU | 204 | −10.550 | −50.890 | 34.859 | 1.000 | 23.73 |
| ATOM | 1535 | CA | LEU | 204 | −11.541 | −51.706 | 34.169 | 1.000 | 21.34 |
| ATOM | 1536 | CB | LEU | 204 | −12.745 | −50.872 | 33.727 | 1.000 | 26.39 |
| ATOM | 1537 | CG | LEU | 204 | −14.123 | −51.510 | 33.908 | 1.000 | 26.92 |
| ATOM | 1538 | CD1 | LEU | 204 | −15.079 | −51.066 | 32.809 | 1.000 | 10.26 |
| ATOM | 1539 | CD2 | LEU | 204 | −14.019 | −53.027 | 33.942 | 1.000 | 35.07 |
| ATOM | 1540 | C | LEU | 204 | −10.938 | −52.392 | 32.948 | 1.000 | 10.84 |
| ATOM | 1541 | O | LEU | 204 | −11.212 | −53.567 | 32.707 | 1.000 | 16.23 |
| ATOM | 1542 | N | GLY | 205 | −10.143 | −51.649 | 32.189 | 1.000 | 8.26 |
| ATOM | 1543 | CA | GLY | 205 | −9.534 | −52.173 | 30.984 | 1.000 | 6.27 |
| ATOM | 1544 | C | GLY | 205 | −8.472 | −53.215 | 31.265 | 1.000 | 8.34 |
| ATOM | 1545 | O | GLY | 205 | −8.228 | −54.094 | 30.436 | 1.000 | 9.21 |
| ATOM | 1546 | N | VAL | 206 | −7.829 | −53.130 | 32.425 | 1.000 | 8.74 |
| ATOM | 1547 | CA | VAL | 206 | −6.833 | −54.135 | 32.796 | 1.000 | 9.33 |
| ATOM | 1548 | CB | VAL | 206 | −5.942 | −53.653 | 33.957 | 1.000 | 16.14 |
| ATOM | 1549 | CG1 | VAL | 206 | −5.020 | −54.754 | 34.457 | 1.000 | 6.58 |
| ATOM | 1550 | CG2 | VAL | 206 | −5.124 | −52.445 | 33.514 | 1.000 | 6.33 |
| ATOM | 1551 | C | VAL | 206 | −7.526 | −55.447 | 33.154 | 1.000 | 5.34 |
| ATOM | 1552 | O | VAL | 206 | −7.118 | −56.498 | 32.664 | 1.000 | 5.68 |
| ATOM | 1553 | N | ALA | 207 | −8.564 | −55.384 | 33.982 | 1.000 | 4.56 |
| ATOM | 1554 | CA | ALA | 207 | −9.349 | −56.547 | 34.369 | 1.000 | 8.39 |
| ATOM | 1555 | CB | ALA | 207 | −10.323 | −56.180 | 35.490 | 1.000 | 0.79 |
| ATOM | 1556 | C | ALA | 207 | −10.144 | −57.160 | 33.219 | 1.000 | 10.03 |
| ATOM | 1557 | O | ALA | 207 | −10.485 | −58.346 | 33.261 | 1.000 | 13.69 |
| ATOM | 1558 | N | LEU | 208 | −10.471 | −56.382 | 32.193 | 1.000 | 14.72 |
| ATOM | 1559 | CA | LEU | 208 | −11.278 | −56.888 | 31.082 | 1.000 | 11.49 |
| ATOM | 1560 | CB | LEU | 208 | −12.065 | −55.755 | 30.422 | 1.000 | 12.04 |
| ATOM | 1561 | CG | LEU | 208 | −13.325 | −55.317 | 31.175 | 1.000 | 10.97 |
| ATOM | 1562 | CD1 | LEU | 208 | −13.985 | −54.127 | 30.497 | 1.000 | 18.17 |
| ATOM | 1563 | CD2 | LEU | 208 | −14.302 | −56.477 | 31.290 | 1.000 | 17.03 |
| ATOM | 1564 | C | LEU | 208 | −10.391 | −57.604 | 30.067 | 1.000 | 6.10 |
| ATOM | 1565 | O | LEU | 208 | −10.857 | −58.502 | 29.369 | 1.000 | 15.12 |
| ATOM | 1566 | N | ALA | 209 | −9.132 | −57.191 | 30.019 | 1.000 | 10.78 |
| ATOM | 1567 | CA | ALA | 209 | −8.103 | −57.815 | 29.203 | 1.000 | 16.00 |
| ATOM | 1568 | CB | ALA | 209 | −6.827 | −56.992 | 29.220 | 1.000 | 18.55 |
| ATOM | 1569 | C | ALA | 209 | −7.829 | −59.238 | 29.694 | 1.000 | 19.15 |
| ATOM | 1570 | O | ALA | 209 | −7.639 | −60.143 | 28.882 | 1.000 | 13.89 |
| ATOM | 1571 | N | GLU | 210 | −7.822 | −59.396 | 31.015 | 1.000 | 9.97 |
| ATOM | 1572 | CA | GLU | 210 | −7.645 | −60.692 | 31.653 | 1.000 | 11.15 |
| ATOM | 1573 | CB | GLU | 210 | −7.535 | −60.520 | 33.168 | 1.000 | 21.07 |
| ATOM | 1574 | CG | GLU | 210 | −6.097 | −60.365 | 33.647 | 1.000 | 39.63 |
| ATOM | 1575 | CD | GLU | 210 | −5.696 | −58.921 | 33.860 | 1.000 | 47.94 |
| ATOM | 1576 | OE1 | GLU | 210 | −5.958 | −58.391 | 34.960 | 1.000 | 64.71 |
| ATOM | 1577 | OE2 | GLU | 210 | −5.097 | −58.319 | 32.949 | 1.000 | 43.70 |
| ATOM | 1578 | C | GLU | 210 | −8.791 | −61.634 | 31.308 | 1.000 | 10.80 |
| ATOM | 1579 | O | GLU | 210 | −8.589 | −62.787 | 30.927 | 1.000 | 10.93 |
| ATOM | 1580 | N | GLN | 211 | −10.007 | −61.120 | 31.441 | 1.000 | 10.29 |
| ATOM | 1581 | CA | GLN | 211 | −11.190 | −61.871 | 31.035 | 1.000 | 17.12 |
| ATOM | 1582 | CB | GLN | 211 | −12.443 | −61.052 | 31.363 | 1.000 | 15.73 |
| ATOM | 1583 | CG | GLN | 211 | −12.542 | −60.709 | 32.844 | 1.000 | 19.97 |
| ATOM | 1584 | CD | GLN | 211 | −12.936 | −61.923 | 33.671 | 1.000 | 20.12 |

-continued

| | | | | | | | | | | |
|---|---|---|---|---|---|---|---|---|---|---|
| ATOM | 1585 | OE1 | GLN | 211 | −13.886 | −62.628 | 33.331 | 1.000 | 17.44 |
| ATOM | 1586 | NE2 | GLN | 211 | −12.218 | −62.166 | 34.759 | 1.000 | 12.84 |
| ATOM | 1587 | C | GLN | 211 | −11.146 | −62.237 | 29.556 | 1.000 | 19.66 |
| ATOM | 1588 | O | GLN | 211 | −11.399 | −63.384 | 29.170 | 1.000 | 12.73 |
| ATOM | 1589 | N | VAL | 212 | −10.822 | −61.287 | 28.679 | 1.000 | 17.48 |
| ATOM | 1590 | CA | VAL | 212 | −10.785 | −61.612 | 27.249 | 1.000 | 19.02 |
| ATOM | 1591 | CB | VAL | 212 | −10.426 | −60.369 | 26.415 | 1.000 | 14.47 |
| ATOM | 1592 | CG1 | VAL | 212 | −10.189 | −60.744 | 24.958 | 1.000 | 15.00 |
| ATOM | 1593 | CG2 | VAL | 212 | −11.527 | −59.320 | 26.523 | 1.000 | 8.88 |
| ATOM | 1594 | C | VAL | 212 | −9.816 | −62.745 | 26.936 | 1.000 | 23.29 |
| ATOM | 1595 | O | VAL | 212 | −10.192 | −63.735 | 26.294 | 1.000 | 25.62 |
| ATOM | 1596 | N | ARG | 213 | −8.557 | −62.645 | 27.361 | 1.000 | 21.16 |
| ATOM | 1597 | CA | ARG | 213 | −7.617 | −63.740 | 27.126 | 1.000 | 22.08 |
| ATOM | 1598 | CB | ARG | 213 | −6.251 | −63.462 | 27.752 | 1.000 | 19.45 |
| ATOM | 1599 | CG | ARG | 213 | −5.577 | −62.178 | 27.300 | 1.000 | 20.41 |
| ATOM | 1600 | CD | ARG | 213 | −4.621 | −61.690 | 28.380 | 1.000 | 26.40 |
| ATOM | 1601 | NE | ARG | 213 | −3.847 | −60.527 | 27.952 | 1.000 | 29.86 |
| ATOM | 1602 | CZ | ARG | 213 | −3.556 | −59.504 | 28.745 | 1.000 | 26.00 |
| ATOM | 1603 | NH1 | ARG | 213 | −3.968 | −59.485 | 30.007 | 1.000 | 15.34 |
| ATOM | 1604 | NH2 | ARG | 213 | −2.847 | −58.491 | 28.268 | 1.000 | 17.74 |
| ATOM | 1605 | C | ARG | 213 | −8.157 | −65.052 | 27.695 | 1.000 | 21.76 |
| ATOM | 1606 | O | ARG | 213 | −7.893 | −66.138 | 27.182 | 1.000 | 28.34 |
| ATOM | 1607 | N | SER | 214 | −8.924 | −64.952 | 28.780 | 1.000 | 15.76 |
| ATOM | 1608 | CA | SER | 214 | −9.486 | −66.151 | 29.389 | 1.000 | 15.09 |
| ATOM | 1609 | CB | SER | 214 | −10.043 | −65.824 | 30.781 | 1.000 | 19.35 |
| ATOM | 1610 | OG | SER | 214 | −11.053 | −66.745 | 31.144 | 1.000 | 46.77 |
| ATOM | 1611 | C | SER | 214 | −10.561 | −66.790 | 28.529 | 1.000 | 15.48 |
| ATOM | 1612 | O | SER | 214 | −10.692 | −68.016 | 28.535 | 1.000 | 24.87 |
| ATOM | 1613 | N | LEU | 215 | −11.355 | −66.030 | 27.772 | 1.000 | 21.40 |
| ATOM | 1614 | CA | LEU | 215 | −12.367 | −66.673 | 26.938 | 1.000 | 21.52 |
| ATOM | 1615 | CB | LEU | 215 | −13.655 | −65.855 | 26.860 | 1.000 | 22.40 |
| ATOM | 1616 | CG | LEU | 215 | −14.176 | −65.153 | 28.103 | 1.000 | 20.48 |
| ATOM | 1617 | CD1 | LEU | 215 | −15.071 | −63.990 | 27.697 | 1.000 | 27.15 |
| ATOM | 1618 | CD2 | LEU | 215 | −14.931 | −66.118 | 29.006 | 1.000 | 13.10 |
| ATOM | 1619 | C | LEU | 215 | −11.884 | −66.920 | 25.510 | 1.000 | 20.60 |
| ATOM | 1620 | O | LEU | 215 | −12.536 | −67.682 | 24.789 | 1.000 | 31.41 |
| ATOM | 1621 | N | LEU | 216 | −10.790 | −66.303 | 25.077 | 1.000 | 21.43 |
| ATOM | 1622 | CA | LEU | 216 | −10.291 | −66.503 | 23.718 | 1.000 | 19.55 |
| ATOM | 1623 | CB | LEU | 216 | −10.114 | −65.148 | 23.021 | 1.000 | 19.47 |
| ATOM | 1624 | CG | LEU | 216 | −11.385 | −64.305 | 22.870 | 1.000 | 16.11 |
| ATOM | 1625 | CD1 | LEU | 216 | −11.095 | −63.042 | 22.076 | 1.000 | 17.60 |
| ATOM | 1626 | CD2 | LEU | 216 | −12.495 | −65.108 | 22.211 | 1.000 | 4.00 |
| ATOM | 1627 | C | LEU | 216 | −8.983 | −67.283 | 23.688 | 1.000 | 24.37 |
| ATOM | 1628 | OT1 | LEU | 216 | −8.472 | −67.525 | 22.571 | 1.000 | 29.22 |
| ATOM | 1629 | OT2 | LEU | 216 | −8.463 | −67.655 | 24.758 | 1.000 | 19.02 |

In addition to the above-described determinations, a carbamate-inhibited perhydrolase crystal was also produced and analyzed. In these experiments, a N-hexylcarbamate derivative of wild type perhydrolase was used. Wild-type perhydrolase (14.5 mg in 1 mL, 67 mM NaPO4 pH 7 buffer) was titrated at room temperature with 1.25 μL aliquots of 400 mM p-nitrophenyl-N-hexylcarbamate dissolved in DMSO. Perhydrolase activity was measured with p-nitrophenylbutyrate assay (See, Example 2), as a function of time after each addition of the inhibitor. Several additions over several hours were required for complete inhibition of the enzyme. After inhibition was complete, the buffer of the inhibited enzyme solution was exchanged for 10 mM HEPES pH 8.3. This solution was stored at −80° C. until used for crystallization screening experiments were conducted as described above. The inhibitor p-nitrophenyl-N-hexylcarbamate was prepared by methods known in the art (See e.g., Hosie et al., J. Biol. Chem., 262:260-264 [1987]). Briefly, the carbamate-inhibited perhydrolase was crystallized by vapor diffusion using the hanging drop method known in the art. A ml solution of inhibited perhydrolase (15 mg/ml in 10 mM HEPES, pH 8.2), was mixed with 4 μL of a reservoir solution (30% PEG-4,000 with 0.2 M lithium sulfate and 0.1 M Tris, pH 8.5) on a plastic coverslip, then inverted and sealed for a well of 6×4 Linbro plate containing 0.5 ml of the reservoir solution and allowed to equilibrate. Crystals formed within a few days. The crystals were flash frozen in liquid nitrogen and analyzed as described above.

While the native octamer was determined in space group P4 with unit cell dimensions:

a=98.184 b=98.184 and c=230.119 α=90.00 β=90.00 γ=90.00, this crystal diffracted to about 2.0 Å. The carbamate-inhibited crystal grew in the space group P1 with unit cell dimensions a=67.754, b=80.096, and c=85.974 α=104.10°, β=112.10°, and γ=97.40° and these crystals diffract to a resolution exceeding 1.0 Å.

The carbamate was bound in a manner to exploit the interactions between the keto oxygen of the carbamate and residues forming the oxyanion hole, the amide N atoms of Ser 11 and Ala 55 and Asn 94 ND2. The hydrophobic side chain extends along the hydrophobic surface of the binding site out into the surface opening between pairs of dimers in the octamer structure. The carbamate moiety direction highlights the pivotal role of the S54V mutation. The hydrophobic moiety passes adjacent to the side chain of ser 54. Mutating the serine side to valine increased the hydrophobicity, and also served as a gatekeeper to prevent hydrophilic nucleophiles (e.g., water) for competing with desired deacylating nucleophiles. The t residues surrounding the carbamate moiety on the same and neighboring molecules forming the extended entry are expected to influence the selection of the optimal de-acylating nucleophile.

In addition, residues with surface-accessible side chain atoms were identified using the program "AreaMol," within the CCP4 program package. Table 15-1 lists these residues. In this Table, the residue number, residue name, number of surface-accessible side chain atoms having at least 10.0 square atoms of accessible surface area, and maximum surface area (square angstroms) for any side chain atom within that residue (or CA for GLY residues) in the octameric structure of perhydrolase are provided.

TABLE 15-1

| Surface-Accessible Side Chain Atoms | | | |
|---|---|---|---|
| Residue Number | Residue Name | Number of Accessible Side Chain Atoms | Maximum Surface Area (Square Angstroms) |
| 1 | ALA | 1 | 15.7 |
| 3 | LYS' | 2 | 54.10 |
| 17 | VAL | 1 | 29.5 |
| 19 | VAL | 1 | 28.0 |
| 20 | GLU | 4 | 30.2 |
| 21 | ASP | 2 | 41.3 |
| 24 | PRO | 2 | 23.2 |
| 26 | GLU | 3 | 36.3 |
| 29 | ALA | 1 | 34.4 |
| 30 | PRP | 3 | 32.7 |
| 31 | ASP | 3 | 50.6 |
| 32 | VAL | 1 | 27.0 |
| 39 | ALA | 1 | 27.5 |
| 40 | GLN | 3 | 38.7 |
| 41 | GLN | 2 | 22.1 |
| 43 | GLY | 1 | 20.4 |
| 44 | ALA | 1 | 63.8 |
| 45 | ASP | 3 | 52.7 |
| 46 | PHE | 2 | 17.1 |
| 47 | GLU | 3 | 29.6 |
| 61 | ASP | 3 | 53.1 |
| 63 | PRO | 3 | 28.0 |
| 64 | THR | 1 | 15.7 |
| 65 | ASP | 1 | 10.8 |
| 66 | PRO | 3 | 33.5 |
| 67 | ARG | 2 | 20.3 |
| 69 | ASN | 1 | 11.0 |
| 72 | SER | 2 | 26.6 |
| 75 | PRO | 2 | 17.4 |
| 83 | PRO | 2 | 15.1 |
| 85 | ASP | 1 | 36.80 |
| 98 | ALA | 1 | 14.60 |
| 101 | ARG | 4 | 25.0 |
| 102 | ARG | 1 | 19.9 |
| 103 | THR | 1 | 43.7 |
| 104 | PRO | 1 | 17.90 |
| 105 | LEU | 1 | 10.1 |
| 113 | VAL | 1 | 17.3 |
| 116 | THR | 2 | 39.5 |
| 117 | GLN | 2 | 15.3 |
| 119 | LEU | 3 | 21.4 |
| 120 | THR | 2 | 34.1 |
| 122 | ALA | 1 | 38.0 |
| 123 | GLY | 1 | 11.0 |
| 126 | GLY | 1 | 11.9 |
| 128 | THR | 2 | 18.2 |
| 129 | TYR | 1 | 17.6 |
| 130 | PRO | 3 | 30.2 |
| 131 | ALA | 1 | 13.7 |
| 133 | LYS | 3 | 46.9 |
| 141 | PRO | 3 | 25.3 |
| 143 | ALA | 1 | 19.8 |
| 144 | PRO | 3 | 34.90 |
| 146 | PRO | 2 | 24.30 |
| 148 | PRO | 3 | 24.1 |
| 151 | GLN | 3 | 35.6 |
| 152 | LEU | 1 | 12.90 |
| 155 | GLU | 3 | 53.0 |
| 156 | GLY | 1 | 28.9 |
| 158 | GLU | 3 | 30.3 |
| 159 | GLN | 4 | 44.9 |

TABLE 15-1-continued

| Surface-Accessible Side Chain Atoms | | | |
|---|---|---|---|
| Residue Number | Residue Name | Number of Accessible Side Chain Atoms | Maximum Surface Area (Square Angstroms) |
| 160 | LYS | 2 | 21.5 |
| 162 | THR | 2 | 25.0 |
| 163 | GLU | 2 | 23.3 |
| 165 | ALA | 1 | 23.1 |
| 169 | SER | 1 | 39.1 |
| 173 | SER | 2 | 33.3 |
| 174 | PHE | 1 | 11.1 |
| 175 | MET | 1 | 18.5 |
| 176 | LYS | 2 | 21.4 |
| 178 | PRO | 1 | 12.0 |
| 179 | PHE | 2 | 14.0 |
| 180 | PHE | 1 | 13.9 |
| 181 | ASP | 1 | 24.9 |
| 184 | SER | 1 | 27.0 |
| 185 | VAL | 1 | 27.5 |
| 187 | SER | 2 | 34.0 |
| 189 | ASP | 2 | 25.4 |
| 191 | VAL | 2 | 24.5 |
| 197 | THR | 2 | 21.6 |
| 198 | GLU | 3 | 43.5 |
| 199 | ALA | 1 | 50.5 |
| 202 | ARG | 3 | 37.2 |
| 203 | ASP | 2 | 30.9 |
| 206 | VAL | 2 | 45.2 |
| 210 | GLU | 3 | 34.6 |
| 211 | GLN | 2 | 19.6 |
| 213 | ARG | 5 | 30.8 |
| 214 | SER | 2 | 20.8 |
| 215 | LEU | 1 | 25.80 |

Example 16

Stain Removal

In this Example, experiments conducted to assess the stain removal abilities of perhydrolase are described.

Figure 21:
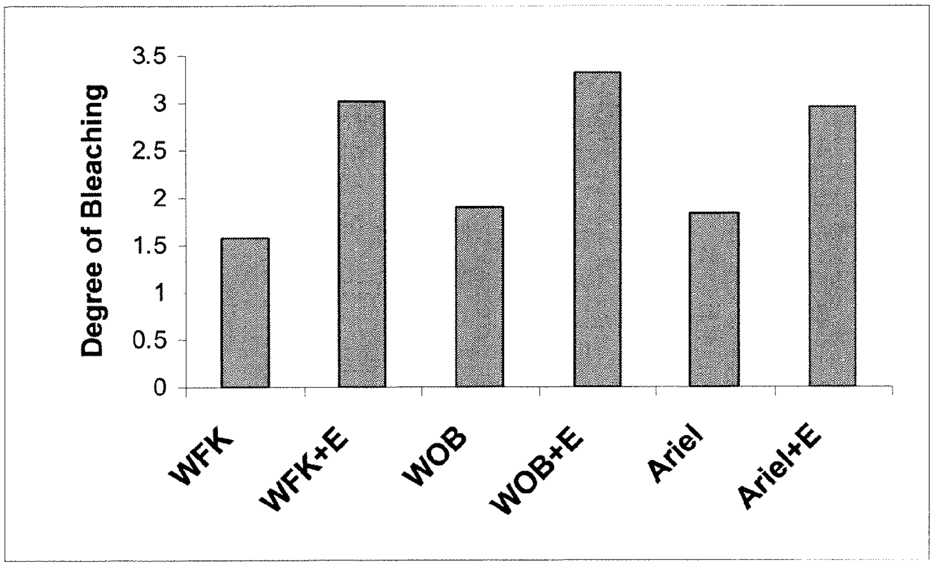
FIG. 21 provides a graph showing the degree of bleaching by three detergents tested alone and in comparison with the *M. smegmatis* perhydrolase of the present invention.

Individual wells of 24 well culture plates were used to mimic conditions found in ordinary washing machines. Each well was filled with commercially available detergent (e.g., Ariel [Procter & Gamble], WOB [AATCC], and WFK [WFK]), and pre-stained cloth discs cut to fit inside of each well were added. Temperature and agitation were accomplished by attaching the plate to the inside of a common laboratory incubator/shaker. To measure bleaching effectiveness of the perhydrolase, fabric stained with tea (EMPA #167, available commercially from Test Fabrics) was used. A single cloth disc was placed in each well, and 1 ml of detergent liquid, containing enzyme, ester substrate, and peroxide was added. After agitation at 100-300 rpm @ 20-60° C., the fabric discs were removed, rinsed with tap water, and allowed to dry overnight. The reflectance of each individual cloth disc was measured, and plotted as an "L" value. These results are provided in FIG. 21, which shows that the addition of the perhydrolase of the present invention to the detergent consistently provides a greater degree of bleaching than the detergents alone. In this Figure, "E" indicates the results for each of the detergents tested in combination with the perhydrolase of the present invention.

Example 17

Cotton Bleaching

In this Example, experiments to assess the use of the perhydrolase of the present invention for bleaching of cotton fabrics are described.

In these experiments, six cotton swatches per canister were treated at 55° C. for 60 minutes in a Launder-O-meter. The substrates used in these experiments were: 3 (3"×3") 428U and 3 (3"×3") 400U per experiments. Two different types of 100% unbleached cotton fabrics from Testfabrics were tested (style 428U (desized but not bleached army carded cotton sateen); and style 400U (desized but not bleached cotton print cloth). The liquor ratio was about 26 to 1 (~7.7 g fabric/~200 ml volume liquor). The perhydrolase enzyme was tested at 12.7 mgP/ml, with ethyl acetate (3% (v/v)), hydrogen peroxide (1500 ppm), and Triton X-100 (0.001%), in a sodium phosphate buffer (100 mM) for pH 7 and pH 8; as well as in a sodium carbonate (100 mM) buffer, for pH 9 and pH 10.

Bleaching effects were quantified with total color difference by taking 4 CIE L*a*b* values per each swatch before and after the treatments using a Chroma Meter CR-200 (Minolta), and total color difference of the swatches after the treatments were calculated according to the following:

Total color difference $$(\Delta E)=\sqrt{(\Delta L^2+\Delta a^2+\Delta b^2)}$$

(where ΔL, Δa, Δb, are differences in CIE L*, CIE a*, and CIE b* values respectively before and after the treatments).

Figure 22:
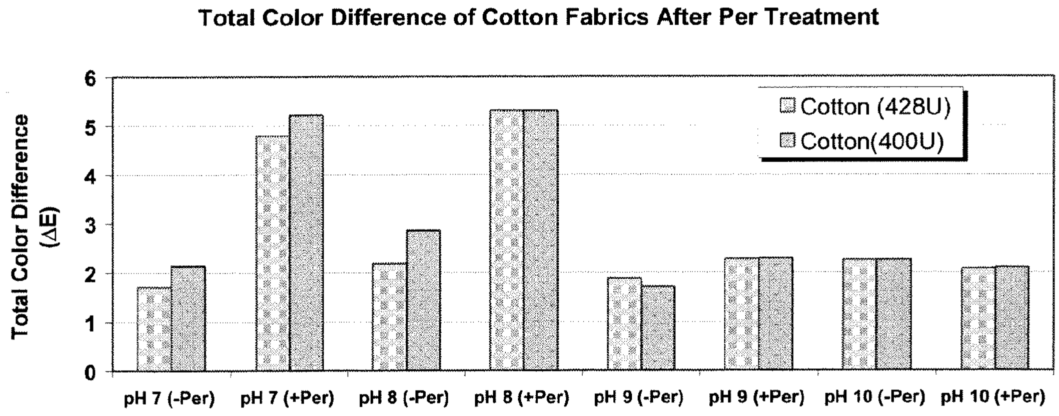
FIG. 22 provides a graph showing the bleaching ability of the *M. smegmatis* perhydrolase tested on cotton.

Higher ΔE values indicate greater bleaching effects. The results (See, FIG. 22) indicated that the perhydrolase showed significantly improved bleaching effects on both types of 100% cotton fabrics at pH 7 and pH 8 under the conditions tested.

It was also observed that high amounts of motes (e.g., pigmented spots) disappeared on the enzyme treated substrates.

Example 18

Linen Bleaching

In this Example, experiments conducted to assess the linen bleaching capability of the perhydrolase of the present invention are described. The same methods and conditions as describe above for cotton testing (in Example 17) were used to test linen swatches. As indicated above, experiments were conduction in a Launder-O-meter using a linen fabric (linen suiting, Style L-53; Testfabrics).

Figure 23:
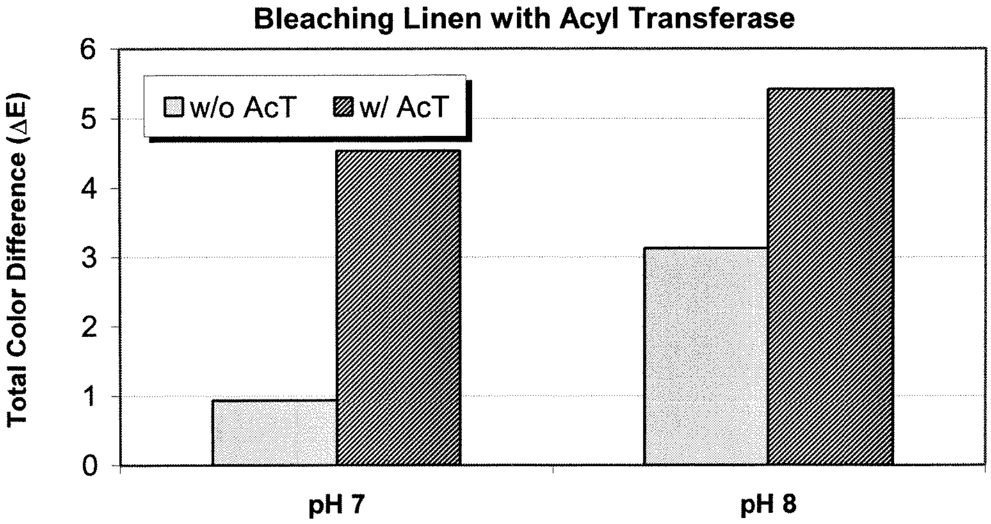
FIG. 23 provides a graph showing the bleaching ability of the *M. smegmatis* perhydrolase tested on linen.

In these experiments, 3 (4"×4") linen swatches were treated with 12.7 mgP/ml of the perhydrolase enzyme with ethyl acetate (3% v/v), hydrogen peroxide (1200 ppm), and Triton X-100 (0.001%), in a sodium phosphate buffer (100 mM) for pH 7 and pH 8. The bleaching effects were calculated as described above in Example 17. FIG. 23 provides a graph showing the bleaching effects of the perhydrolase of the present invention tested at pH 7 and pH 8 on linen.

Example 19

Detergent Compositions

In the following Example, various detergent compositions are exemplified. In these formulations, the enzymes levels are expressed by pure enzyme by weight of the total composition and unless otherwise specified, the detergent ingredients are expressed by weight of the total compositions. The abbreviated component identifications therein have the following meanings:

LAS: Sodium linear $C_{11-13}$ alkyl benzene sulfonate.

TAS: Sodium tallow alkyl sulfate.

CxyAS: Sodium $C_{1x}$-$C_{1y}$ alkyl sulfate.

CxyEz: $C_{1x}$-$C_{1y}$ predominantly linear primary alcohol condensed with an average of z moles of ethylene oxide.

CxyAEzS: $C_{1x}$-$C_{1y}$ sodium alkyl sulfate condensed with an average of z moles of ethylene oxide. Added molecule name in the examples.

Nonionic: Mixed ethoxylated/propoxylated fatty alcohol e.g. Plurafac LF404 being an alcohol with an average degree of ethoxylation of 3.8 and an average degree of propoxylation of 4.5.

QAS: $R_2.N+(CH_3)_2(C_2H_4OH)$ with $R_2=C_{12}$-$C_{14}$.

Silicate: Amorphous Sodium Silicate ($SiO_2$:$Na_2O$ ratio=1.6-3.2:1).

Metasilicate: Sodium metasilicate ($SiO_2$:$Na_2O$ ratio=1.0).

Zeolite A: Hydrated Aluminosilicate of formula $Na_{12}(AlO_2SiO_2)_{12}.27H_2O$ SKS-6: Crystalline layered silicate of formula δ-$Na_2Si_2O_5$.

Sulphate: Anhydrous sodium sulphate.

STPP: Sodium Tripolyphosphate.

MA/AA: Random copolymer of 4:1 acrylate/maleate, average molecular weight about 70,000-80,000.

AA: Sodium polyacrylate polymer of average molecular weight 4,500.

Polycarboxylate: Copolymer comprising mixture of carboxylated monomers such as acrylate, maleate and methyacrylate with a MW ranging between 2,000-80,000 such as Sokolan commercially available from BASF, being a copolymer of acrylic acid, MW4,500.

BB1: 3-(3,4-Dihydroisoquinolinium)propane sulfonate

BB2 1-(3,4-dihydroisoquinolinium)-decane-2-sulfate

PB1: Sodium perborate monohydrate.

PB4: Sodium perborate tetrahydrate of nominal formula $NaBO_3.4H_2O$.

Percarbonate: Sodium percarbonate of nominal formula $2Na_2CO_3.3H_2O_2$.

TAED: Tetraacetyl ethylene diamine.

NOBS: Nonanoyloxybenzene sulfonate in the form of the sodium salt.

DTPA: Diethylene triamine pentaacetic acid.

HEDP: 1,1-hydroxyethane diphosphonic acid.

DETPMP: Diethyltriamine penta(methylene)phosphonate, marketed by Monsanto under the Trade name Dequest 2060.

EDDS: Ethylenediamine-N,N'-disuccinic acid, (S,S) isomer in the form of its sodium salt Diamine: Dimethyl aminopropyl amine; 1,6-hezane diamine; 1,3-propane diamine; 2-methyl-1,5-pentane diamine; 1,3-pentanediamine; 1-methyl-diaminopropane.

DETBCHD 5,12-diethyl-1,5,8,12-tetraazabicyclo[6,6,2]hexadecane, dichloride, Mn(II) salt PAAC: Pentaamine acetate cobalt(III) salt.

Paraffin: Paraffin oil sold under the tradename Winog 70 by Wintershall.

Paraffin Sulfonate: A Paraffin oil or wax in which some of the hydrogen atoms have been replaced by sulfonate groups.

Aldose oxidase: Oxidase enzyme sold under the tradename Aldose Oxidase by Novozymes A/S Galactose oxidase: Galactose oxidase from Sigma Protease: Proteolytic enzyme sold under the tradename Savinase, Alcalase, Everlase by Novo Nordisk A/S, and the following from Genencor International, Inc: "Protease A" described in U.S. Pat. No. RE 34,606 in FIGS. 1A, 1B, and 7, and at column 11, lines 11-37; "Protease B" described in U.S. Pat. No. 5,955,340 and U.S. Pat. No. 5,700,676 in FIGS. 1A, 1B and 5, as well as Table 1; and "Protease C" described in U.S. Pat. No. 6,312,936 and U.S. Pat. No. 6,482,628 in FIGS. 1-3 [SEQ ID 3], and at column 25, line 12, "Protease D" being the variant 101/G103A/104I/159/D232V/236H/245R/248D/252K (BPN' numbering) described in WO 99/20723.

Amylase: Amylolytic enzyme sold under the tradename Purafact Ox $Am^R$ described in WO 94/18314, WO96/05295 sold by Genencor; Natalase®, Termamyl®, Fungamyl® and Duramyl®, all available from Novozymes A/S.

Lipase: Lipolytic enzyme sold under the tradename Lipolase Lipolase Ultra by Novozymes A/S and Lipomax by Gist-Brocades.

Cellulase: Cellulytic enzyme sold under the tradename Carezyme, Celluzyme and/or Endolase by Novozymes A/S.

Pectin Lyase: Pectaway® and Pectawash® available from Novozymes A/S.

PVP: Polyvinylpyrrolidone with an average molecular weight of 60,000

PVNO: Polyvinylpyridine-N-Oxide, with an average molecular weight of 50,000.

PVPVI: Copolymer of vinylimidazole and vinylpyrrolidone, with an average molecular weight of 20,000.

Brightener 1: Disodium 4,4'-bis(2-sulphostyryl)biphenyl.

Silicone antifoam: Polydimethylsiloxane foam controller with siloxane-oxyalkylene copolymer as dispersing agent with a ratio of said foam controller to said dispersing agent of 10:1 to 100:1.

Suds Suppressor: 12% Silicone/silica, 18% stearyl alcohol, 70% starch in granular form.

SRP 1: Anionically end capped poly esters.

PEG X: Polyethylene glycol, of a molecular weight of x.

PVP K60®: Vinylpyrrolidone homopolymer (average MW 160,000)

Jeffamine® ED-2001: Capped polyethylene glycol from Huntsman

Isachem® AS: A branched alcohol alkyl sulphate from Enichem

MME PEG (2000): Monomethyl ether polyethylene glycol (MW 2000) from Fluka Chemie AG.

DC3225C: Silicone suds suppresser, mixture of Silicone oil and Silica from Dow Corning.

TEPAE: Tetreaethylenepentaamine ethoxylate.

BTA: Benzotriazole.

Betaine: $(CH_3)_3N^+CH_2COO^-$

Sugar: Industry grade D-glucose or food grade sugar

CFAA: $C_{12}$-$C_{14}$ alkyl N-methyl glucamide

TPKFA: $C_{12}$-$C_{14}$ topped whole cut fatty acids.

Clay: A hydrated aluminumu silicate in a general formula $Al_2O_3SiO_2.xH_2O$. Types: Kaolinite, montmorillonite, atapulgite, illite, bentonite, halloysite.

MCAEM: Esters in the formula of $R^1O_x[(R^2)_m(R^3)_n]_p$ pH: Measured as a 1% solution in distilled water at 20° C.

Example 20

Liquid Laundry Detergents

The following liquid laundry detergent compositions of the present invention are prepared.

| | I | II | III | IV | V |
|---|---|---|---|---|---|
| LAS | 18.0 | — | 6.0 | — | — |
| $C_{12}$-$C_{15}$ $AE_{1.8}S$ | — | 2.0 | 8.0 | 11.0 | 5.0 |
| $C_8$-$C_{10}$ propyl dimethyl amine | 2.0 | 2.0 | 2.0 | 2.0 | 1.0 |
| $C_{12}$-$C_{14}$ alkyl dimethyl amine oxide | — | — | — | — | 2.0 |
| $C_{12}$-$C_{15}$ AS | — | 17.0 | — | 7.0 | 8.0 |
| CFAA | — | 5.0 | 4.0 | 4.0 | 3.0 |
| $C_{12}$-$C_{14}$ Fatty alcohol ethoxylate | 12.0 | 6.0 | 1.0 | 1.0 | 1.0 |
| $C_{12}$-$C_{18}$ Fatty acid | 11.0 | 11.0 | 4.0 | 4.0 | 3.0 |
| Citric acid (anhydrous) | 5.0 | 1.0 | 3.0 | 3.0 | 2.0 |
| DETPMP | 1.0 | 1.0 | 1.0 | 1.0 | 0.5 |
| Monoethanolamine | 11.0 | 8.0 | 5.0 | 5.0 | 2.0 |
| Sodium hydroxide | 1.0 | 1.0 | 2.5 | 1.0 | 1.5 |
| Percarbonate | — | 3.5 | — | 2.5 | — |
| Propanediol | 12.7 | 14.5 | 13.1 | 10. | 8.0 |
| Ethanol | 1.8 | 1.8 | 4.7 | 5.4 | 1.0 |
| Pectin Lyase | — | — | — | 0.005 | — |
| Amylase | — | 0.002 | — | | — |
| Cellulase | — | — | 0.0002 | | 0.0001 |
| Lipase | 0.1 | — | 0.1 | — | 0.1 |
| Protease A | 0.05 | 0.3 | 0.055 | 0.5 | 0.2 |
| Aldose Oxidase | 0.03 | — | 0.3 | — | 0.003 |
| PAAC | 0.01 | 0.01 | — | — | — |
| DETBCHD | — | — | 0.02 | 0.01 | — |
| SRP1 | 0.5 | 0.5 | — | 0.3 | 0.3 |
| Boric acid | 2.4 | 2.4 | 2.8 | 2.8 | 2.4 |
| Sodium xylene sulfonate | — | — | 3.0 | — | — |
| DC 3225C | 1.0 | 1.0 | 1.0 | 1.0 | 1.0 |
| 2-butyl-octanol | 0.03 | 0.04 | 0.04 | 0.03 | 0.03 |
| DTPA | 0.5 | 0.4 | 0.35 | 0.28 | 0.4 |
| Brightener 1 | 0.18 | 0.10 | 0.11 | — | — |
| Perhydrolase | 0.05 | 0.3 | 0.08 | 0.5 | 0.2 |
| MCAEM ($C_{12}$-$C_{13}$ $E_{6.5}$ Acetate) | 3.0 | 8.0 | 12.0 | 1.5 | 4.8 |

Balance to 100% perfume/dye and/or water

Example 21

Hand-Dish Liquid Detergent Compositions

The following hand dish liquid detergent compositions of the present invention are prepared.

| | I | II | III | IV | V | VI |
|---|---|---|---|---|---|---|
| $C_{12}$-$C_{15}AE_{1.8}S$ | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| $C_{10}$-$C_{18}$ Alkyl Dimethyl Amine Oxide | 5.0 | 3.0 | 7.0 | — | — | — |
| Betaine | 3.0 | — | 1.0 | 3.0 | 1.0 | — |
| $C_{12}$ poly-OH fatty acid amide | — | — | — | 3.0 | — | 1.0 |
| $C_{14}$ poly-OH fatty acid amide | — | 1.5 | — | — | — | — |
| $C_{11}E_9$ | 2.0 | — | 4.0 | — | — | 20.0 |
| DTPA | — | — | — | — | 0.2 | — |
| Tri-sodium Citrate dihydrate | 0.25 | — | — | 0.7 | — | — |
| Diamine | 1.0 | 5.0 | 7.0 | 1.0 | 5.0 | 7.0 |
| $MgCl_2$ | 0.25 | — | — | 1.0 | — | — |
| Protease A | 0.02 | 0.01 | 0.02 | 0.01 | 0.02 | 0.05 |
| Amylase | 0.001 | — | — | 0.002 | — | 0.001 |
| Aldose Oxidase | 0.03 | — | 0.02 | — | 0.05 | — |
| Sodium Cumene Sulphonate | — | — | — | 2.0 | 1.5 | 3.0 |
| PAAC | 0.01 | 0.01 | 0.02 | — | — | — |
| DETBCHD | — | — | — | 0.01 | 0.02 | 0.01 |
| PB1 | 1.5 | 2.8 | 1.2 | — | — | — |
| Perhydrolase | 0.02 | 0.01 | 0.03 | 0.01 | 0.02 | 0.05 |

-continued

| | I | II | III | IV | V | VI |
|---|---|---|---|---|---|---|
| MCAEM ($C_{14}$-$C_{15}E_7$ Acetate) | 3.4 | 2.8 | 4.0 | 2.6 | 4.6 | 6.8 |

Balance to 100% perfume/dye and/or water

The pH of Compositions (I)-(VI) is about 8 to about 11

Example 22

Liquid Automatic Dishwashing Detergent

The following liquid automatic dishwashing detergent compositions of the present are prepared.

| | I | II | III | IV | V |
|---|---|---|---|---|---|
| STPP | 16 | 16 | 18 | 16 | 16 |
| Potassium Sulfate | — | 10 | 8 | — | 10 |
| 1,2 propanediol | 6.0 | 0.5 | 2.0 | 6.0 | 0.5 |
| Boric Acid | 4.0 | 3.0 | 3.0 | 4.0 | 3.0 |
| $CaCl_2$ dihydrate | 0.04 | 0.04 | 0.04 | 0.04 | 0.04 |
| Nonionic | 0.5 | 0.5 | 0.5 | 0.5 | 0.5 |
| Protease B | 0.03 | 0.03 | 0.03 | 0.03 | 0.03 |
| Amylase | 0.02 | | 0.02 | 0.02 | — |
| Aldose Oxidase | — | 0.15 | 0.02 | — | 0.01 |
| Galactose Oxidase | — | — | 0.01 | — | 0.01 |
| PAAC | 0.01 | — | — | 0.01 | — |
| DETBCHD | — | 0.01 | — | — | 0.01 |
| Perhydrolase | 0.1 | 0.03 | 0.05 | 0.03 | 0.06 |
| MCAEM ($C_{14}$-$C_{15}E_{12}$ Acetate) | 5.0 | 3.0 | 12.0 | 8.0 | 1.0 |

Balance to 100% perfume/dye and/or water

Example 23

Laundry Compositions

The following laundry compositions of present invention, which may be in the form of granules or tablet, are prepared.

| Base Product | I | II | III | IV | V |
|---|---|---|---|---|---|
| $C_{14}$-$C_{15}$AS or TAS | 8.0 | 5.0 | 3.0 | 3.0 | 3.0 |
| LAS | 8.0 | — | 8.0 | — | 7.0 |
| $C_{12}$-$C_{15}AE_3S$ | 0.5 | 2.0 | 1.0 | — | — |
| $C_{12}$-$C_{15}E_5$ or $E_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |
| MA/AA | 2.0 | 2.0 | 2.0 | — | — |
| AA | — | — | — | — | 4.0 |
| 3Na Citrate $2H_2O$ | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |
| Percarbonate | — | — | 3.8 | 5.2 | — |
| NOBS | 1.9 | — | — | — | — |
| NACA OBS | — | — | 2.0 | — | — |
| TAED | 0.5 | 2.0 | 2.0 | 5.0 | 1.00 |
| BB1 | 0.06 | — | 0.34 | — | 0.14 |

-continued

| Base Product | I | II | III | IV | V |
|---|---|---|---|---|---|
| BB2 | — | 0.14 | — | 0.20 | — |
| Anhydrous Na Carbonate | 15.0 | 18.0 | 8.0 | 15.0 | 15.0 |
| Sulfate | 5.0 | 12.0 | 2.0 | 17.0 | 3.0 |
| Silicate | — | 1.0 | — | — | 8.0 |
| Protease B | 0.033 | 0.033 | — | — | — |
| Protease C | — | — | 0.033 | 0.046 | 0.033 |
| Lipase | — | 0.008 | — | — | — |
| Amylase | 0.001 | — | — | — | 0.001 |
| Cellulase | — | 0.0014 | — | — | — |
| Pectin Lyase | 0.001 | 0.001 | 0.001 | 0.001 | 0.001 |
| Aldose Oxidase | 0.03 | — | 0.05 | — | — |
| PAAC | — | 0.01 | — | — | 0.05 |
| Perhydrolase | 0.03 | 0.05 | 1.0 | 0.06 | 0.1 |
| MCAEM** | 2.0 | 5.0 | 12.0 | 3.5 | 6.8 |

Balance to 100% Moisture and/or Minors*

Perfume/Dye, Brightener/SRP1/Na Carboxymethylcellulose/Photobleach/$MgSO_4$/PVPVI/Suds suppressor/High Molecular PEG/Clay.

**MCAEM is selected from the group consisting of $C_9$-$C_{11}E_{2.5}$ Acetate, $[C_{12}H_{25}N(CH_3)(CH_2CH_2OAc)_2]^+ Cl^-$, $(CH_3)_2NCH_2CH_2OCH_2CH_2OAc$, or mixtures thereof..

Example 24

Liquid Laundry Detergents

The following liquid laundry detergent formulations of the present invention are prepared.

| | I | I | II | III | IV | V |
|---|---|---|---|---|---|---|
| LAS | 11.5 | 11.5 | 9.0 | — | 4.0 | — |
| $C_{12}$-$C_{15}AE_{2.85}S$ | — | — | 3.0 | 18.0 | — | 16.0 |
| $C_{14}$-$C_{15}E_{2.5}S$ | 11.5 | 11.5 | 3.0 | — | 16.0 | — |
| $C_{12}$-$C_{13}E_9$ | — | — | 3.0 | 2.0 | 2.0 | 1.0 |
| $C_{12}$-$C_{13}E_7$ | 3.2 | 3.2 | — | — | — | — |
| CFAA | — | — | — | 5.0 | — | 3.0 |
| TPKFA | 2.0 | 2.0 | — | 2.0 | 0.5 | 2.0 |
| Citric Acid (Anhydrous) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| Na Culmene Sulfonate | 4.0 | 4.0 | 1.0 | 3.0 | 1.2 | — |
| Borate | 0.6 | 0.6 | — | 3.0 | 2.0 | 3.0 |
| Na hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Mono-ethanolamine | 3.0 | 3.0 | 1.5 | 1.0 | 2.5 | 1.0 |
| TEPAE | 2.0 | 2.0 | — | 1.0 | 1.0 | 1.0 |
| PB1 | | — | 4.5 | — | 2.8 | — |
| Protease A | 0.03 | 0.03 | 0.01 | 0.03 | 0.02 | 0.02 |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | | — | — |
| Aldose Oxidase | 0.05 | — | — | 0.05 | — | 0.02 |
| Galactose oxidase | — | 0.04 | | | | |
| Perhydrolase | 0.03 | 0.05 | 0.01 | 0.03 | 0.08 | 0.02 |
| MCAEM ($C_{12}$-$C_{12}E_6$ Acetate) | 3.2 | 4.6 | 1.8 | 3.5 | 6.2 | 2.8 |
| PAAC | 0.03 | 0.03 | 0.02 | — | — | — |
| DETBCHD | — | — | — | 0.02 | 0.01 | — |
| SRP 1 | 0.2 | 0.2 | — | 0.1 | — | — |
| DTPA | — | — | — | 0.3 | — | — |
| PVNO | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |

Balance to 100% perfume/dye, and/or water

Example 25

Compact High-Density Dishwashing Detergents

The following compact high density dishwashing detergent of the present invention are prepared:

| | I | II | III | IV | V | VI |
|---|---|---|---|---|---|---|
| STPP | — | 45.0 | 45.0 | — | — | 40.0 |
| 3Na Citrate $2H_2O$ | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |
| PB1 | — | — | 4.5 | — | — | — |
| PB4 | — | — | — | 5.0 | — | — |
| Percarbonate | — | — | — | — | — | 4.8 |
| BB1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| PAAC | 0.03 | 0.05 | 0.02 | — | — | — |
| Paraffin | 0.5 | 0.4 | 0.4 | 0.6 | — | — |
| Protease B | 0.072 | 0.053 | 0.053 | 0.026 | 0.059 | 0.01 |
| Amylase | 0.012 | — | 0.012 | — | 0.021 | 0.006 |

-continued

| | I | II | III | IV | V | VI |
|---|---|---|---|---|---|---|
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| Perhydrolase | 0.072 | 0.053 | 0.053 | 0.026 | 0.059 | 0.01 |
| MCAEM ($C_{12}$-$C_{13}E_{6.5}$ Acetate) | 3.5 | 2.8 | 1.6 | 7.5 | 4.2 | 0.8 |
| BTA | 0.3 | 0.2 | 0.2 | 0.3 | 0.3 | 0.3 |
| Polycarboxylate | 6.0 | — | — | — | 4.0 | 0.9 |
| Perfume | 0.2 | 0.1 | 0.1 | 0.2 | 0.2 | 0.2 |

Balance to 100% Moisture and/or Minors*

*Brightener/Dye/SRP1/Na Carboxymethylcellulose/Photobleach/$MgSO_4$/PVPVI/Suds suppressor/High Molecular PEG/Clay.

The pH of compositions (I) through (VI) is from about 9.6 to about 11.3.

Example 26

Tablet Detergent Compositions

The following tablet detergent compositions of the present invention are prepared by compression of a granular dishwashing detergent composition at a pressure of 13KN/cm$^2$ using a standard 12 head rotary press.

| | I | II | III | IV | V | VI | VII | VIII |
|---|---|---|---|---|---|---|---|---|
| STPP | — | 48.8 | 44.7 | 38.2 | — | 42.4 | 46.1 | 36.0 |
| 3Na Citrate $2H_2O$ | 20.0 | — | — | — | 35.9 | — | — | — |
| Na Carbonate | 20.0 | 5.0 | 14.0 | 15.4 | 8.0 | 23.0 | 20.0 | 28.0 |
| Silicate | 15.0 | 14.8 | 15.0 | 12.6 | 23.4 | 2.9 | 4.3 | 4.2 |
| Lipase | 0.001 | — | 0.01 | — | 0.02 | — | — | — |
| Protease B | 0.042 | 0.072 | 0.042 | 0.031 | — | — | — | — |
| Protease C | — | — | — | — | 0.052 | 0.023 | 0.023 | 0.029 |
| Perhydrolase | 0.01 | 0.08 | 0.05 | 0.04 | 0.052 | 0.023 | 0.023 | 0.029 |
| MCAEM ($C_{12}$-$C_{13}E_{6.5}$ Acetate) | 2.8 | 6.5 | 4.5 | 3.8 | 4.6 | 2.8 | 2.8 | 2.8 |
| Amylase | 0.012 | 0.012 | 0.012 | — | 0.015 | — | 0.017 | 0.002 |
| Pectin Lyase | 0.005 | — | — | 0.002 | — | — | — | — |
| Aldose Oxidase | — | 0.03 | — | 0.02 | 0.02 | — | 0.03 | — |
| PB1 | — | — | 3.8 | — | 7.8 | — | — | 8.5 |
| Percarbonate | 6.0 | — | — | 6.0 | — | 5.0 | — | — |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| PAAC | 0.01 | 0.01 | 0.02 | — | — | — | — | — |
| DETBCHD | — | — | — | 0.02 | 0.02 | — | — | — |
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |
| Glycerol | — | — | — | — | — | 0.4 | — | 0.5 |
| Perfume | — | — | — | 0.05 | 0.2 | 0.2 | 0.2 | 0.2 |

Balance to 100% Moisture and/or Minors*

*Brightener/Dye/SRP1/Na Carboxymethylcellulose/Photobleach/$MgSO_4$/PVPVI/Suds suppressor/High Molecular PEG/Clay.

The pH of Compositions (I) through 7(VIII) is from about 10 to about 11.5.

The tablet weight of Compositions 7(I) through 7(VIII) is from about 20 grams to about 30 grams.

Example 27

Liquid Hard Surface Cleaning Detergents

The following liquid hard surface cleaning detergent compositions of the present invention are prepared.

| | I | II | III | IV | V | VI | VII |
|---|---|---|---|---|---|---|---|
| $C_9$-$C_{11}E_5$ | 2.4 | 1.9 | 2.5 | 2.5 | 2.5 | 2.4 | 2.5 |
| $C_{12}$-$C_{14}E_5$ | 3.6 | 2.9 | 2.5 | 2.5 | 2.5 | 3.6 | 2.5 |
| $C_7$-$C_9E_6$ | — | — | — | — | 8.0 | — | — |
| $C_{12}$-$C_{14}E_{21}$ | 1.0 | 0.8 | 4.0 | 2.0 | 2.0 | 1.0 | 2.0 |
| LAS | — | — | — | 0.8 | 0.8 | — | 0.8 |
| Sodium culmene sulfonate | 1.5 | 2.6 | — | 1.5 | 1.5 | 1.5 | 1.5 |
| Isachem ® AS | 0.6 | 0.6 | — | — | — | 0.6 | — |
| $Na_2CO_3$ | 0.6 | 0.13 | 0.6 | 0.1 | 0.2 | 0.6 | 0.2 |
| 3Na Citrate $2H_2O$ | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | — | 0.5 | — | — |
| PAAC | — | — | — | 0.03 | 0.03 | 0.03 | — |
| DETBCHD | 0.03 | 0.05 | 0.05 | — | — | — | — |
| Protease B | 0.07 | 0.05 | 0.05 | 0.03 | 0.06 | 0.01 | 0.04 |
| Amylase | 0.12 | 0.01 | 0.01 | — | 0.02 | — | 0.01 |
| Lipase | — | 0.001 | — | 0.005 | — | 0.005 | — |
| Perhydrolase | 0.07 | 0.05 | 0.08 | 0.03 | 0.06 | 0.01 | 0.04 |
| MCAEM ($C_{12}$-$C_{15}E_8$ Acetate) | 3.5 | 5.6 | 4.8 | 5.3 | 3.6 | 8.0 | 4.7 |
| Pectin Lyase | 0.001 | — | 0.001 | — | — | — | 0.002 |
| PB1 | — | 4.6 | — | 3.8 | — | — | — |
| Aldose Oxidase | 0.05 | — | 0.03 | — | 0.02 | 0.02 | 0.05 |

Balance to 100% perfume/dye, and/or water
The pH of Compositions (I) through (VII) is from about 7.4 to about 9.5.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Having described the preferred embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. A cleaning, bleaching or disinfecting composition, comprising an isolated perhydrolase, which is a homolog of *M. smegmatis* perhydrolase and is a SGNH-hydrolase family polypeptide, which comprises:

a) the motifs GDSL, GRTT, and GAND; and b) the amino acid residues corresponding to L6, W14, W34, L38, R56, D62, L74, L78, H81, P83, M90, K97, G110, L114, L135, F180, G205, S11, D192, and H195 of SEQ ID NO: 2;

wherein said perhydrolase exhibits:

i) perhydrolysis activity that is at least about 0.2 compared to the perhydrolysis activity exhibited by *M. smegmatis* perhydrolase; and ii) a perhydrolysis to hydrolysis ratio that is greater than 1;

wherein said perhydrolysis activity and said perhydrolysis to hydrolysis ratio is determined using the perhydrolysis and hydrolysis assays as described in Example 2.

2. The composition of claim 1, wherein said perhydrolase has at least 90% amino acid sequence identity to the amino acid sequence set forth in SEQ ID NO: 97.

3. The composition of claim 2, wherein said perhydrolase is *Mesorhizobium loti* Mlo I (Q98MY5) and comprises the amino acid sequence as set out in SEQ ID NO: 97.

4. A cleaning composition according to any one of claims 1, comprising:

a) at least 0.0001 weight percent of said perhydrolase;

b) a molecule comprising an ester moiety; and c) optionally, an adjunct ingredient.

5. The cleaning composition of claim 4, wherein said composition comprises:

a) at least 0.0001 weight percent of said perhydrolase;

b) a material selected from the group consisting of: a peroxygen source, hydrogen peroxide and mixtures thereof, said peroxygen source being selected from the group consisting of:

i) a per-salt;

ii) an organic peroxyacid;

iii) urea hydrogen peroxide;

iv) a carbohydrate and carbohydrate oxidase mixture, and v) mixtures thereof;

c) from about 0.01 to about 50 weight percent of a molecule comprising an ester moiety; and d) optionally, an adjunct ingredient.

6. The cleaning composition of claim 4, wherein said adjunct ingredient is selected from the group consisting of: surfactants, builders, chelating agents, dye transfer inhibiting agents, deposition aids, dispersants, enzymes, and enzyme stabilizers, catalytic materials, bleach activators, bleach boosters, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, pigments and mixtures thereof.

7. The cleaning composition of claim 5, wherein:

a) said per-salt is selected from the group consisting of alkalimetal perborate, alkalimetal percarbonate, alkalimetal perphosphates, alkalimetal persulphates and mixtures thereof;

b) said carbohydrate is selected from the group consisting of mono-carbohydrates, di-carbohydrates, tri-carbohydrates, oligo-carbohydrates and mixtures thereof;

c) said carbohydrate oxidase is selected from the group consisting of aldose oxidase (IUPAC classification EC1.1.3.9), galactose oxidase (IUPAC classification EC1.1.3.9), cellobiose oxidase (IUPAC classification EC1.1.3.25), pyranose oxidase (IUPAC classification EC1.1.3.10), sorbose oxidase (IUPAC classification EC1.1.3.11) hexose oxidase (IUPAC classification EC1.1.3.5), glucose oxidase (IUPAC classification EC1.1.3.4) and mixtures thereof; and d) said molecule comprising an ester moiety has the formula:

$$R^1O_x[(R^2)_m(R^3)_n]_p$$

i) wherein $R^1$ is a moiety selected from the group consisting of H, substituted or unsubstituted alkyl, heteroalkyl, alkenyl, alkynyl, aryl, alkylaryl, alkylheteroaryl, and heteroaryl;

ii) each $R^2$ is an alkoxylate moiety;

iii) $R^3$ is an ester-forming moiety having the formula: $R^4CO$— wherein $R^4$ is H, alkyl, alkenyl, alkynyl, aryl, alkylaryl, alkylheteroaryl, and heteroaryl;

iv) x is 1 when $R^1$ is H; when $R^1$ is not H, x is an integer that is equal to or less than the number of carbons in $R^1$;

v) p is an integer that is equal to or less than x;

vi) m is an integer from 0 to 50; and vii) n is at least 1.

8. The cleaning composition of claim 7, wherein:

a) $R^1$ is an $C_2$-$C_{32}$ substituted or unsubstituted alkyl or heteroalkyl moiety;

b) each $R^2$ is independently an ethoxylate or propoxylate moiety;

c) m is an integer from 1 to 12; and d) $R^3$ is an ester-forming moiety having the formula: $R^4CO$— wherein $R^4$ is:

i) a substituted or unsubstituted alkyl, alkenyl or alkynyl moiety comprising from 1 to 22 carbon atoms; or ii) a substituted or unsubstituted aryl, alkylaryl, alkylheteroaryl or heteroaryl moiety comprising from 4 to 22 carbon atoms.

9. The cleaning composition of claim 4, wherein the molecule comprising the ester moiety has the formula:

$$R^1O_x[(R^2)_m(R^3)_n]_p$$

wherein:

a) $R^1$ is H or a moiety that comprises a primary, secondary, tertiary or quaternary amine moiety, said $R^1$ moiety that comprises an amine moiety being selected from the group consisting of substituted or unsubstituted alkyl, heteroalkyl, alkenyl, alkynyl, aryl, alkylaryl, alkylheteroaryl, and heteroaryl;

b) each $R^2$ is an alkoxylate moiety;

c) $R^3$ is an ester-forming moiety having the formula: $R^4CO$— wherein $R^4$ may be H, substituted or unsubstituted alkyl, alkenyl, alkynyl, aryl, alkylaryl, alkylheteroaryl, and heteroaryl;

d) x is 1 when $R^1$ is H; when $R^1$ is not H, x is an integer that is equal to or less than the number of carbons in $R^1$;

e) p is an integer that is equal to or less than x f) m is an integer from 0 to 12; and g) n is at least 1; and optionally wherein said molecule comprising an ester moiety has a weight average molecular weight of less than 600,000 Daltons.

10. The cleaning composition of claim 4, wherein said molecule comprising an ester moiety is selected from triacetin, ethylene glycol diacetate and propylene glycol diacetate.

11. The composition of claim 1, wherein said composition is a bleaching or disinfecting composition, further comprising at least one additional enzyme or enzyme derivative selected from the group consisting of: proteases, amylases, lipases, mannanases, pectinases, cutinases, oxidoreductases, endoglycosidases, lysozyme, bacterial cell wall degrading enzymes, fungal cell wall degrading enzymes, hemicellulases, and cellulases.

12. A method of disinfecting and/or bleaching a surface or an article, the method comprising contacting said surface or article with the composition of claim 1, optionally wherein the surface or article is selected from textiles, hard surfaces, paper, pulp, hair, teeth, skin, medical devices, medical equipment, industrial equipment and fermenters.

13. A method of cleaning comprising the steps of: a) contacting a surface and/or an article comprising a fabric with a cleaning composition of claim 1; and b) optionally washing and/or rinsing the surface or material.

* * * * *

SEQUENCE LISTING

```
<160> NUMBER OF SEQ ID NOS: 711

<210> SEQ ID NO 1
<211> LENGTH: 651
<212> TYPE: DNA
<213> ORGANISM: Mycobacterium smegmatis
```

<400> SEQUENCE: 1
atggccaagc gaattctgtg tttcggtgat tccctgacct ggggctgggt ccccgtcgaa 60
gacggggcac ccaccgagcg gttcgccccc gacgtgcgct ggaccggtgt gctggcccag 120
cagctcggag cggacttcga ggtgatcgag gagggactga gcgcgcgcac caccaacatc 180
gacgacccca ccgatccgcg gctcaacggc gcgagctacc tgccgtcgtg cctcgcgacg 240
cacctgccgc tcgacctggt gatcatcatg ctgggcacca acgacaccaa ggcctacttc 300
cggcgcaccc cgctcgacat cgcgctgggc atgtcggtgc tcgtcacgca ggtgctcacc 360
agcgcgggcg gcgtcggcac cacgtacccg gcacccaagg tgctggtggt ctcgccgcca 420
ccgctggcgc ccatgccgca cccctggttc cagttgatct tcgagggcgg cgagcagaag 480
accactgagc tcgcccgcgt gtacagcgcg ctcgcgtcgt tcatgaaggt gccgttcttc 540
gacgcgggtt cggtgatcag caccgacggc gtcgacggaa tccacttcac cgaggccaac 600
aatcgcgatc tcggggtggc cctcgcggaa caggtgcgga gcctgctgta a 651

<210> SEQ ID NO 2
<211> LENGTH: 216
<212> TYPE: PRT
<213> ORGANISM: Mycobacterium smegmatis

<400> SEQUENCE: 2

Met Ala Lys Arg Ile Leu Cys Phe Gly Asp Ser Leu Thr Trp Gly Trp
1 5 10 15

Val Pro Val Glu Asp Gly Ala Pro Thr Glu Arg Phe Ala Pro Asp Val
20 25 30

Arg Trp Thr Gly Val Leu Ala Gln Gln Leu Gly Ala Asp Phe Glu Val
35 40 45

Ile Glu Glu Gly Leu Ser Ala Arg Thr Thr Asn Ile Asp Asp Pro Thr
50 55 60

Asp Pro Arg Leu Asn Gly Ala Ser Tyr Leu Pro Ser Cys Leu Ala Thr
65 70 75 80

His Leu Pro Leu Asp Leu Val Ile Ile Met Leu Gly Thr Asn Asp Thr
85 90 95

Lys Ala Tyr Phe Arg Arg Thr Pro Leu Asp Ile Ala Leu Gly Met Ser
100 105 110

Val Leu Val Thr Gln Val Leu Thr Ser Ala Gly Gly Val Gly Thr Thr
115 120 125

Tyr Pro Ala Pro Lys Val Leu Val Val Ser Pro Pro Pro Leu Ala Pro
130 135 140

Met Pro His Pro Trp Phe Gln Leu Ile Phe Glu Gly Gly Glu Gln Lys
145 150 155 160

Thr Thr Glu Leu Ala Arg Val Tyr Ser Ala Leu Ala Ser Phe Met Lys
165 170 175

Val Pro Phe Phe Asp Ala Gly Ser Val Ile Ser Thr Asp Gly Val Asp
180 185 190

Gly Ile His Phe Thr Glu Ala Asn Asn Arg Asp Leu Gly Val Ala Leu
195 200 205

Ala Glu Gln Val Arg Ser Leu Leu
210 215

<210> SEQ ID NO 3
<211> LENGTH: 19
<212> TYPE: PRT

<213> ORGANISM: Mycobacterium parafortuitum

<400> SEQUENCE: 3

Lys Val Pro Phe Phe Asp Ala Gly Ser Val Ile Ser Thr Asp Gly Val
1               5                   10                  15

Asp Gly Ile

<210> SEQ ID NO 4
<211> LENGTH: 19
<212> TYPE: PRT
<213> ORGANISM: Mycobacterium parafortuitum

<400> SEQUENCE: 4

Gly Thr Arg Arg Ile Leu Ser Phe Gly Asp Ser Leu Thr Trp Gly Trp
1               5                   10                  15

Ile Pro Val

<210> SEQ ID NO 5
<211> LENGTH: 59
<212> TYPE: DNA
<213> ORGANISM: Artificial Sequence
<220> FEATURE:
<223> OTHER INFORMATION: primer

<400> SEQUENCE: 5
ctaacaggag gaattaacca tggccaagcg aattctgtgt ttcggtgatt ccctgacct      59

<210> SEQ ID NO 6
<211> LENGTH: 59
<212> TYPE: DNA
<213> ORGANISM: Artificial Sequence
<220> FEATURE:
<223> OTHER INFORMATION: primer

<400> SEQUENCE: 6
gcgcgcggat ccgcgcgctt acagcaggct ccgcacctgt tccgcgaggg ccaccccga      59

<210> SEQ ID NO 7
<211> LENGTH: 10
<212> TYPE: DNA
<213> ORGANISM: Mycobacterium smegmatis

<400> SEQUENCE: 7
ggctgggggc                                                            10

<210> SEQ ID NO 8
<211> LENGTH: 1779
<212> TYPE: DNA
<213> ORGANISM: Mycobacterium smegmatis

<400> SEQUENCE: 8
atgcacttac gtcccgctct gacgtggctc ctggttgtcg gtctgttcat atcggtcgtc     60
ggatgttcgt cgtccccgga tccggccgac cggttctcgg cgttcgccga ggcgctgggc    120
cgcaaggatg cggccgcggc ggccgcccag accagcgatc cggcggccgc ggaggcggcc    180
atcaccgcga tgctggccgg gatgggcgac gccgcgaacg tctcggtggc cgccgaaccc    240
gaggaaggcg acgacgcggg cgcgacgctg aagtacacgt ggacctgggg tgagggccgc    300
gacttcggct acgacaccac cgcgacggcg gccaaatccg gtgacgactg gctgatcacc    360
tggtccccca ccgtgttgca ccgcgacctc accccggatc tgcgcttcca gtacagcgag    420
gacagcgaat tgcagacccc ggtgctcgac cgcaccggcc agccgttgat gacatggcag    480

-continued accgtcggtg tcatcactgt cgaacgcgca catccggagt cggccgcacc gctcgccgcc 540
ctgctggcgc ccttcgatcc gaccaccacc accgaatcgg tcaccgcaca actcaattcg 600
acgaccgatg accgcgtgac ggtgatgaag ctgcgcgagg acgatctggg tcaggtgcgc 660
gatcagctcg cgcagatccc cggcgtgacc gtgcgtgagc agggtgagct gctcaccgcc 720
gaccggcagc tgtcctcgcc cgccatcagc ggcctggacg agctgtggca cgaccggatc 780
accgccaacg cgggctggtc ggtgtacctg gtcgacgccg acggtgcacc cgcacaacag 840
ctcacgtcca cgccgcccaa ggacaccggg cccgtgcgca ccacgctgga cctgcgcatg 900
caactgctcg cgcagcaggc cgtggccaag gagacccgcc cggccgtggt ggtcgcgatc 960
tccggatcga ccgggggcat cctggccgcc gcacagaacc cggccgccga tccgcaaggt 1020
gcgatcgcgt tttcgggcct gtacccgccg gggtcgacgt tcaagaccat caccacggcg 1080
gcagccctcg acgcgggcct ggccaccccg gacacaccgg tggcctgccc gggtgagctc 1140
accatcgaga accgcacgat ccccaacgac gacaacttcg acctgggcac cgtgccgttg 1200
tcgtcggcgt tctcgcactc ctgcaacacc agcatggccg ccctgtccga cgagctgccg 1260
cccaacgcac tgaccgacat ggcaaaggac ttcgggatcg gcgtcgactt catggtgccc 1320
ggcctgacca ccgtgaccgg ccgtgtcccc aacgccgaca acgccgccca gcgtgtcgag 1380
aacggcatcg gccagggcac cgtgaccgtc agcccgttcg gcctcgccgt cgccgaggcc 1440
agcctggcgc acggttcgac gatcctgccg acgctggtcg acggcgagaa gaccacggcc 1500
gacaccccgt cggtgccgtt gccgcccaac atcaccgacg cgctgcgcgc gatgatgcgc 1560
ggaacggtca ccgagggcac ggccaccgcg ttgagcgaca tccccgacct gggcggcaag 1620
accggcacgg cggaattcgg cgacaacacg cactcgcacg gctggttcgc gggcatcgcg 1680
ggcgacatcg cgttcgcgac gctggtggtc ggcggcgact cgtcggcacc ggccgtcgcg 1740
atctcaggag acttcctgcg ccccgcgctc gccggctag 1779

<210> SEQ ID NO 9
<211> LENGTH: 592
<212> TYPE: PRT
<213> ORGANISM: Mycobacterium smegmatis

<400> SEQUENCE: 9

Met His Leu Arg Pro Ala Leu Thr Trp Leu Leu Val Val Gly Leu Phe
1 5 10 15

Ile Ser Val Val Gly Cys Ser Ser Ser Pro Asp Pro Ala Asp Arg Phe
20 25 30

Ser Ala Phe Ala Glu Ala Leu Gly Arg Lys Asp Ala Ala Ala Ala Ala
35 40 45

Ala Gln Thr Ser Asp Pro Ala Ala Ala Glu Ala Ala Ile Thr Ala Met
50 55 60

Leu Ala Gly Met Gly Asp Ala Ala Asn Val Ser Val Ala Ala Glu Pro
65 70 75 80

Glu Glu Gly Asp Asp Ala Gly Ala Thr Leu Lys Tyr Thr Trp Thr Trp
85 90 95

Gly Glu Gly Arg Asp Phe Gly Tyr Asp Thr Thr Ala Thr Ala Ala Lys
100 105 110

Ser Gly Asp Asp Trp Leu Ile Thr Trp Ser Pro Thr Val Leu His Arg
115 120 125

Asp Leu Thr Pro Asp Leu Arg Phe Gln Tyr Ser Glu Asp Ser Glu Leu
130 135 140

```
Gln Thr Pro Val Leu Asp Arg Thr Gly Gln Pro Leu Met Thr Trp Gln
145                 150                 155                 160

Thr Val Gly Val Ile Thr Val Glu Arg Ala His Pro Glu Ser Ala Ala
                165                 170                 175

Pro Leu Ala Ala Leu Leu Ala Pro Phe Asp Pro Thr Thr Thr Thr Glu
            180                 185                 190

Ser Val Thr Ala Gln Leu Asn Ser Thr Thr Asp Asp Arg Val Thr Val
        195                 200                 205

Met Lys Leu Arg Glu Asp Asp Leu Gly Gln Val Arg Asp Gln Leu Ala
    210                 215                 220

Gln Ile Pro Gly Val Thr Val Arg Glu Gln Gly Glu Leu Leu Thr Ala
225                 230                 235                 240

Asp Arg Gln Leu Ser Ser Pro Ala Ile Ser Gly Leu Asp Glu Leu Trp
                245                 250                 255

His Asp Arg Ile Thr Ala Asn Ala Gly Trp Ser Val Tyr Leu Val Asp
            260                 265                 270

Ala Asp Gly Ala Pro Ala Gln Gln Leu Thr Ser Thr Pro Pro Lys Asp
        275                 280                 285

Thr Gly Pro Val Arg Thr Thr Leu Asp Leu Arg Met Gln Leu Leu Ala
    290                 295                 300

Gln Gln Ala Val Ala Lys Glu Thr Arg Pro Ala Val Val Val Ala Ile
305                 310                 315                 320

Ser Gly Ser Thr Gly Gly Ile Leu Ala Ala Ala Gln Asn Pro Ala Ala
                325                 330                 335

Asp Pro Gln Gly Ala Ile Ala Phe Ser Gly Leu Tyr Pro Pro Gly Ser
            340                 345                 350

Thr Phe Lys Thr Ile Thr Thr Ala Ala Ala Leu Asp Ala Gly Leu Ala
        355                 360                 365

Thr Pro Asp Thr Pro Val Ala Cys Pro Gly Glu Leu Thr Ile Glu Asn
    370                 375                 380

Arg Thr Ile Pro Asn Asp Asp Asn Phe Asp Leu Gly Thr Val Pro Leu
385                 390                 395                 400

Ser Ser Ala Phe Ser His Ser Cys Asn Thr Ser Met Ala Ala Leu Ser
                405                 410                 415

Asp Glu Leu Pro Pro Asn Ala Leu Thr Asp Met Ala Lys Asp Phe Gly
            420                 425                 430

Ile Gly Val Asp Phe Met Val Pro Gly Leu Thr Thr Val Thr Gly Arg
        435                 440                 445

Val Pro Asn Ala Asp Asn Ala Ala Gln Arg Val Glu Asn Gly Ile Gly
    450                 455                 460

Gln Gly Thr Val Thr Val Ser Pro Phe Gly Leu Ala Val Ala Glu Ala
465                 470                 475                 480

Ser Leu Ala His Gly Ser Thr Ile Leu Pro Thr Leu Val Asp Gly Glu
                485                 490                 495

Lys Thr Thr Ala Asp Thr Pro Ser Val Pro Leu Pro Pro Asn Ile Thr
            500                 505                 510

Asp Ala Leu Arg Ala Met Met Arg Gly Thr Val Thr Glu Gly Thr Ala
        515                 520                 525

Thr Ala Leu Ser Asp Ile Pro Asp Leu Gly Gly Lys Thr Gly Thr Ala
    530                 535                 540

Glu Phe Gly Asp Asn Thr His Ser His Gly Trp Phe Ala Gly Ile Ala
545                 550                 555                 560
```

```
Gly Asp Ile Ala Phe Ala Thr Leu Val Val Gly Gly Asp Ser Ser Ala
                565                 570                 575

Pro Ala Val Ala Ile Ser Gly Asp Phe Leu Arg Pro Ala Leu Ala Gly
            580                 585                 590


<210> SEQ ID NO 10
<211> LENGTH: 592
<212> TYPE: PRT
<213> ORGANISM: Artificial Sequence
<220> FEATURE:
<223> OTHER INFORMATION: penicillin binding protein

<400> SEQUENCE: 10

Met His Leu Arg Pro Ala Leu Thr Trp Leu Leu Val Val Gly Leu Phe
1               5                   10                  15

Ile Ser Val Val Gly Cys Ser Ser Ser Pro Asp Pro Ala Asp Arg Phe
            20                  25                  30

Ser Ala Phe Ala Glu Ala Leu Gly Arg Lys Asp Ala Ala Ala Ala Ala
        35                  40                  45

Ala Gln Thr Ser Asp Pro Ala Ala Ala Glu Ala Ala Ile Thr Ala Met
    50                  55                  60

Leu Ala Gly Met Gly Asp Ala Ala Asn Val Ser Val Ala Ala Glu Pro
65                  70                  75                  80

Glu Glu Gly Asp Asp Ala Gly Ala Thr Leu Lys Tyr Thr Trp Thr Trp
                85                  90                  95

Gly Glu Gly Arg Asp Phe Gly Tyr Asp Thr Thr Ala Thr Ala Ala Lys
            100                 105                 110

Ser Gly Asp Asp Trp Leu Ile Thr Trp Ser Pro Thr Val Leu His Arg
        115                 120                 125

Asp Leu Thr Pro Asp Leu Arg Phe Gln Tyr Ser Glu Asp Ser Glu Leu
    130                 135                 140

Gln Thr Pro Val Leu Asp Arg Thr Gly Gln Pro Leu Met Thr Trp Gln
145                 150                 155                 160

Thr Val Gly Val Ile Thr Val Glu Arg Ala His Pro Glu Ser Ala Ala
                165                 170                 175

Pro Leu Ala Ala Leu Leu Ala Pro Phe Asp Pro Thr Thr Thr Thr Glu
            180                 185                 190

Ser Val Thr Ala Gln Leu Asn Ser Thr Thr Asp Asp Arg Val Thr Val
        195                 200                 205

Met Lys Leu Arg Glu Asp Asp Leu Gly Gln Val Arg Asp Gln Leu Ala
    210                 215                 220

Gln Ile Pro Gly Val Thr Val Arg Glu Gln Gly Glu Leu Leu Thr Ala
225                 230                 235                 240

Asp Arg Gln Leu Ser Ser Pro Ala Ile Ser Gly Leu Asp Glu Leu Trp
                245                 250                 255

His Asp Arg Ile Thr Ala Asn Ala Gly Trp Ser Val Tyr Leu Val Asp
            260                 265                 270

Ala Asp Gly Ala Pro Ala Gln Gln Leu Thr Ser Thr Pro Pro Lys Asp
        275                 280                 285

Thr Gly Pro Val Arg Thr Thr Leu Asp Leu Arg Met Gln Leu Leu Ala
    290                 295                 300

Gln Gln Ala Val Ala Lys Glu Thr Arg Pro Ala Val Val Val Ala Ile
305                 310                 315                 320

Ser Gly Ser Thr Gly Gly Ile Leu Ala Ala Ala Gln Asn Pro Ala Ala
                325                 330                 335
```

```
Asp Pro Gln Gly Ala Ile Ala Phe Ser Gly Leu Tyr Pro Pro Gly Ser
            340                 345                 350

Thr Phe Lys Thr Ile Thr Thr Ala Ala Ala Leu Asp Ala Gly Leu Ala
        355                 360                 365

Thr Pro Asp Thr Pro Val Ala Cys Pro Gly Glu Leu Thr Ile Glu Asn
    370                 375                 380

Arg Thr Ile Pro Asn Asp Asp Asn Phe Asp Leu Gly Thr Val Pro Leu
385                 390                 395                 400

Ser Ser Ala Phe Ser His Ser Cys Asn Thr Ser Met Ala Ala Leu Ser
                405                 410                 415

Asp Glu Leu Pro Pro Asn Ala Leu Thr Asp Met Ala Lys Asp Phe Gly
            420                 425                 430

Ile Gly Val Asp Phe Met Val Pro Gly Leu Thr Thr Val Thr Gly Arg
        435                 440                 445

Val Pro Asn Ala Asp Asn Ala Ala Gln Arg Val Glu Asn Gly Ile Gly
    450                 455                 460

Gln Gly Thr Val Thr Val Ser Pro Phe Gly Leu Ala Val Ala Glu Ala
465                 470                 475                 480

Ser Leu Ala His Gly Ser Thr Ile Leu Pro Thr Leu Val Asp Gly Glu
                485                 490                 495

Lys Thr Thr Ala Asp Thr Pro Ser Val Pro Leu Pro Pro Asn Ile Thr
            500                 505                 510

Asp Ala Leu Arg Ala Met Met Arg Gly Thr Val Thr Glu Gly Thr Ala
        515                 520                 525

Thr Ala Leu Ser Asp Ile Pro Asp Leu Gly Gly Lys Thr Gly Thr Ala
    530                 535                 540

Glu Phe Gly Asp Asn Thr His Ser His Gly Trp Phe Ala Gly Ile Ala
545                 550                 555                 560

Gly Asp Ile Ala Phe Ala Thr Leu Val Val Gly Gly Asp Ser Ser Ala
                565                 570                 575

Pro Ala Val Ala Ile Ser Gly Asp Phe Leu Arg Pro Ala Leu Ala Gly
            580                 585                 590
```

<210> SEQ ID NO 11
<211> LENGTH: 43
<212> TYPE: DNA
<213> ORGANISM: Artificial Sequence
<220> FEATURE:
<223> OTHER INFORMATION: primer

<400> SEQUENCE: 11
atgggtaccc gacgaattct gtccttcggt gattccctga cct 43

<210> SEQ ID NO 12
<211> LENGTH: 51
<212> TYPE: DNA
<213> ORGANISM: Artificial Sequence
<220> FEATURE:
<223> OTHER INFORMATION: primer

<400> SEQUENCE: 12
gattccgtcg acgccgtcgg tgctgatcac cgaacccgcg tcgaagaacg g 51

<210> SEQ ID NO 13
<211> LENGTH: 4189
<212> TYPE: DNA
<213> ORGANISM: Artificial Sequence
<220> FEATURE:
<223> OTHER INFORMATION: pMSATNcoI plasmid

<400> SEQUENCE: 13
agcgcccaat acgcaaaccg cctctccccg cgcgttggcc gattcattaa tgcagctggc 60
acgacaggtt tcccgactgg aaagcgggca gtgagcgcaa cgcaattaat gtgagttagc 120
tcactcatta ggcaccccag gctttacact ttatgcttcc ggctcgtatg ttgtgtggaa 180
ttgtgagcgg ataacaattt cacacaggaa acagctatga ccatgattac gccaagctat 240
ttaggtgaca ctatagaata ctcaagctat gcatcaagct tggtaccgag ctcggatcca 300
ctagtaacgg ccgccagtgt gctggaattc gcccttctaa caggaggaat taaccatggc 360
caagcgaatt ctgtgtttcg gtgattccct gacctggggc tgggtccccg tcgaagacgg 420
ggcacccacc gagcggttcg cccccgacgt gcgctggacc ggtgtgctgg cccagcagct 480
cggagcggac ttcgaggtga tcgaggaggg actgagcgcg cgcaccacca acatcgacga 540
ccccaccgat ccgcggctca acggcgcgag ctacctgccg tcgtgcctcg cgacgcacct 600
gccgctcgac ctggtgatca tcatgctggg caccaacgac accaaggcct acttccggcg 660
caccccgctc gacatcgcgc tgggcatgtc ggtgctcgtc acgcaggtgc tcaccagcgc 720
gggcggcgtc ggcaccacgt acccggcacc caaggtgctg gtggtctcgc cgccaccgct 780
ggcgcccatg ccgcacccct ggttccagtt gatcttcgag ggcggcgagc agaagaccac 840
tgagctcgcc cgcgtgtaca gcgcgctcgc gtcgttcatg aaggtgccgt tcttcgacgc 900
gggttcggtg atcagcaccg acggcgtcga cggaatccac ttcaccgagg ccaacaatcg 960
cgatctcggg gtggccctcg cggaacaggt gcagagcctg ctgtaaaagg gcgaattctg 1020
cagatatcca tcacactggc ggccgctcga gcatgcatct agagggccca attcgcccta 1080
tagtgagtcg tattacaatt cactggccgt cgttttacaa cgtcgtgact gggaaaaccc 1140
tggcgttacc caacttaatc gccttgcagc acatccccct ttcgccagct ggcgtaatag 1200
cgaagaggcc cgcaccgatc gcccttccca acagttgcgc agcctatacg tacggcagtt 1260
taaggtttac acctataaaa gagagagccg ttatcgtctg tttgtggatg tacagagtga 1320
tattattgac acgccggggc gacggatggt gatccccctg gccagtgcac gtctgctgtc 1380
agataaagtc tcccgtgaac tttacccggt ggtgcatatc ggggatgaaa gctggcgcat 1440
gatgaccacc gatatggcca gtgtgccggt ctccgttatc ggggaagaag tggctgatct 1500
cagccaccgc gaaaatgaca tcaaaaacgc cattaacctg atgttctggg gaatataaat 1560
gtcaggcatg agattatcaa aaaggatctt cacctagatc cttttcacgt agaaagccag 1620
tccgcagaaa cggtgctgac cccggatgaa tgtcagctac tgggctatct ggacaaggga 1680
aaacgcaagc gcaaagagaa agcaggtagc ttgcagtggg cttacatggc gatagctaga 1740
ctgggcggtt ttatggacag caagcgaacc ggaattgcca gctggggcgc cctctggtaa 1800
ggttgggaag ccctgcaaag taaactggat ggctttctcg ccgccaagga tctgatggcg 1860
caggggatca agctctgatc aagagacagg atgaggatcg tttcgcatga ttgaacaaga 1920
tggattgcac gcaggttctc cggccgcttg ggtggagagg ctattcggct atgactgggc 1980
acaacagaca atcggctgct ctgatgccgc cgtgttccgg ctgtcagcgc aggggcgccc 2040
ggttcttttt gtcaagaccg acctgtccgg tgccctgaat gaactgcaag acgaggcagc 2100
gcggctatcg tggctggcca cgacgggcgt tccttgcgca gctgtgctcg acgttgtcac 2160
tgaagcggga agggactggc tgctattggg cgaagtgccg ggcaggatc tcctgtcatc 2220
tcaccttgct cctgccgaga aagtatccat catggctgat gcaatgcggc ggctgcatac 2280

```
gcttgatccg gctacctgcc cattcgacca ccaagcgaaa catcgcatcg agcgagcacg   2340

tactcggatg gaagccggtc ttgtcgatca ggatgatctg gacgaagagc atcaggggct   2400

cgcgccagcc gaactgttcg ccaggctcaa ggcgagcatg cccgacggcg aggatctcgt   2460

cgtgacccat ggcgatgcct gcttgccgaa tatcatggtg gaaaatggcc gcttttctgg   2520

attcatcgac tgtggccggc tgggtgtggc ggaccgctat caggacatag cgttggctac   2580

ccgtgatatt gctgaagagc ttggcggcga atgggctgac cgcttcctcg tgctttacgg   2640

tatcgccgct cccgattcgc agcgcatcgc cttctatcgc cttcttgacg agttcttctg   2700

aattattaac gcttacaatt tcctgatgcg gtattttctc cttacgcatc tgtgcggtat   2760

ttcacaccgc atacaggtgg cacttttcgg ggaaatgtgc gcggaacccc tatttgttta   2820

tttttctaaa tacattcaaa tatgtatccg ctcatgagac aataaccctg ataaatgctt   2880

caataatagc acgtgaggag ggccaccatg gccaagttga ccagtgccgt tccggtgctc   2940

accgcgcgcg acgtcgccgg agcggtcgag ttctggaccg accggctcgg gttctcccgg   3000

gacttcgtgg aggacgactt cgccggtgtg gtccgggacg acgtgaccct gttcatcagc   3060

gcggtccagg accaggtggt gccggacaac accctggcct gggtgtgggt gcgcggcctg   3120

gacgagctgt acgccgagtg gtcggaggtc gtgtccacga acttccggga cgcctccggg   3180

ccggccatga ccgagatcgg cgagcagccg tgggggcggg agttcgccct gcgcgacccg   3240

gccggcaact gcgtgcactt cgtggccgag gagcaggact gacacgtgct aaaacttcat   3300

ttttaattta aaaggatcta ggtgaagatc ctttttgata atctcatgac caaaatccct   3360

taacgtgagt tttcgttcca ctgagcgtca gaccccgtag aaaagatcaa aggatcttct   3420

tgagatcctt tttttctgcg cgtaatctgc tgcttgcaaa caaaaaaacc accgctacca   3480

gcggtggttt gtttgccgga tcaagagcta ccaactcttt ttccgaaggt aactggcttc   3540

agcagagcgc agataccaaa tactgtcctt ctagtgtagc cgtagttagg ccaccacttc   3600

aagaactctg tagcaccgcc tacatacctc gctctgctaa tcctgttacc agtggctgct   3660

gccagtggcg ataagtcgtg tcttaccggg ttggactcaa gacgatagtt accggataag   3720

gcgcagcggt cgggctgaac ggggggttcg tgcacacagc ccagcttgga gcgaacgacc   3780

tacaccgaac tgagatacct acagcgtgag ctatgagaaa gcgccacgct tcccgaaggg   3840

agaaaggcgg acaggtatcc ggtaagcggc agggtcggaa caggagagcg cacgagggag   3900

cttccagggg gaaacgcctg gtatctttat agtcctgtcg ggtttcgcca cctctgactt   3960

gagcgtcgat ttttgtgatg ctcgtcaggg gggcggagcc tatggaaaaa cgccagcaac   4020

gcggcctttt tacggttcct gggcttttgc tggccttttg ctcacatgtt ctttcctgcg   4080

ttatcccctg attctgtgga taaccgtatt accgcctttg agtgagctga taccgctcgc   4140

cgcagccgaa cgaccgagcg cagcgagtca gtgagcgagg aagcggaag               4189
```

```
<210> SEQ ID NO 14
<211> LENGTH: 226
<212> TYPE: PRT
<213> ORGANISM: Agrobacterium rhizogenes

<400> SEQUENCE: 14

Met Ala Glu Ser Arg Ser Ile Leu Cys Phe Gly Asp Ser Leu Thr Trp
1               5                   10                  15

Gly Trp Ile Pro Val Pro Glu Ser Ser Pro Thr Leu Arg Tyr Pro Phe
            20                  25                  30

Glu Gln Arg Trp Thr Gly Ala Met Ala Ala Leu Gly Asp Gly Tyr
```

```
        35                  40                  45

Ser Ile Ile Glu Glu Gly Leu Ser Ala Arg Thr Thr Ser Val Glu Asp
    50                  55                  60

Pro Asn Asp Pro Arg Leu Asn Gly Ser Ala Tyr Leu Pro Met Ala Leu
65                  70                  75                  80

Ala Ser His Leu Pro Leu Asp Leu Val Ile Ile Leu Leu Gly Thr Asn
                85                  90                  95

Asp Thr Lys Ser Tyr Phe Arg Arg Thr Pro Tyr Glu Ile Ala Asn Gly
            100                 105                 110

Met Gly Lys Leu Ala Gly Gln Val Leu Thr Ser Ala Gly Gly Ile Gly
        115                 120                 125

Thr Pro Tyr Pro Ala Pro Lys Leu Leu Ile Val Ser Pro Pro Pro Leu
    130                 135                 140

Ala Pro Met Pro Asp Pro Trp Phe Glu Gly Met Phe Gly Gly Gly Tyr
145                 150                 155                 160

Glu Lys Ser Leu Glu Leu Ala Lys Gln Tyr Lys Ala Leu Ala Asn Phe
                165                 170                 175

Leu Lys Val Asp Phe Leu Asp Ala Gly Glu Phe Val Lys Thr Asp Gly
            180                 185                 190

Cys Asp Gly Ile His Phe Ser Ala Glu Thr Asn Ile Thr Leu Gly His
        195                 200                 205

Ala Ile Ala Ala Lys Val Glu Ala Ile Phe Ser Gln Glu Ala Lys Asn
    210                 215                 220

Ala Ala
225


<210> SEQ ID NO 15
<211> LENGTH: 226
<212> TYPE: PRT
<213> ORGANISM: Rhizobium rhizogenes

<400> SEQUENCE: 15

Met Ala Glu Ser Arg Ser Ile Leu Cys Phe Gly Asp Ser Leu Thr Trp
1               5                   10                  15

Gly Trp Ile Pro Val Pro Glu Ser Ser Pro Thr Leu Arg Tyr Pro Phe
            20                  25                  30

Glu Gln Arg Trp Thr Gly Ala Met Ala Ala Ala Leu Gly Asp Gly Tyr
        35                  40                  45

Ser Ile Ile Glu Glu Gly Leu Ser Ala Arg Thr Thr Ser Val Glu Asp
    50                  55                  60

Pro Asn Asp Pro Arg Leu Asn Gly Ser Ala Tyr Leu Pro Met Ala Leu
65                  70                  75                  80

Ala Ser His Leu Pro Leu Asp Leu Val Ile Ile Leu Leu Gly Thr Asn
                85                  90                  95

Asp Thr Lys Ser Tyr Phe Arg Arg Thr Pro Tyr Glu Ile Ala Asn Gly
            100                 105                 110

Met Gly Lys Leu Ala Gly Gln Val Leu Thr Ser Ala Gly Gly Ile Gly
        115                 120                 125

Thr Pro Tyr Pro Ala Pro Lys Leu Leu Ile Val Ser Pro Pro Pro Leu
    130                 135                 140

Ala Pro Met Pro Asp Pro Trp Phe Glu Gly Met Phe Gly Gly Gly Tyr
145                 150                 155                 160

Glu Lys Ser Leu Glu Leu Ala Lys Gln Tyr Lys Ala Leu Ala Asn Phe
                165                 170                 175
```

```
Leu Lys Val Asp Phe Leu Asp Ala Gly Glu Phe Val Lys Thr Asp Gly
            180                 185                 190

Cys Asp Gly Ile His Phe Ser Ala Glu Thr Asn Ile Thr Leu Gly His
        195                 200                 205

Ala Ile Ala Ala Lys Val Glu Ala Ile Phe Ser Gln Glu Ala Lys Asn
    210                 215                 220

Ala Ala
225


<210> SEQ ID NO 16
<211> LENGTH: 229
<212> TYPE: PRT
<213> ORGANISM: Sinorhizobium meliloti

<400> SEQUENCE: 16

Met Thr Ile Asn Ser His Ser Trp Arg Thr Leu Met Val Glu Lys Arg
1               5                   10                  15

Ser Val Leu Cys Phe Gly Asp Ser Leu Thr Trp Gly Trp Ile Pro Val
            20                  25                  30

Lys Glu Ser Ser Pro Thr Leu Arg Tyr Pro Tyr Glu Gln Arg Trp Thr
        35                  40                  45

Gly Ala Met Ala Ala Arg Leu Gly Asp Gly Tyr His Ile Ile Glu Glu
    50                  55                  60

Gly Leu Ser Ala Arg Thr Thr Ser Leu Asp Asp Pro Asn Asp Ala Arg
65                  70                  75                  80

Leu Asn Gly Ser Thr Tyr Leu Pro Met Ala Leu Ala Ser His Leu Pro
                85                  90                  95

Leu Asp Leu Val Ile Ile Met Leu Gly Thr Asn Asp Thr Lys Ser Tyr
            100                 105                 110

Phe His Arg Thr Pro Tyr Glu Ile Ala Asn Gly Met Gly Lys Leu Val
        115                 120                 125

Gly Gln Val Leu Thr Cys Ala Gly Gly Val Gly Thr Pro Tyr Pro Ala
    130                 135                 140

Pro Lys Val Leu Val Val Ala Pro Pro Pro Leu Ala Pro Met Pro Asp
145                 150                 155                 160

Pro Trp Phe Glu Gly Met Phe Gly Gly Gly Tyr Glu Lys Ser Lys Glu
                165                 170                 175

Leu Ser Gly Leu Tyr Lys Ala Leu Ala Asp Phe Met Lys Val Glu Phe
            180                 185                 190

Phe Ala Ala Gly Asp Cys Ile Ser Thr Asp Gly Ile Asp Gly Ile His
        195                 200                 205

Leu Ser Ala Glu Thr Asn Ile Arg Leu Gly His Ala Ile Ala Asp Lys
    210                 215                 220

Val Ala Ala Leu Phe
225


<210> SEQ ID NO 17
<211> LENGTH: 218
<212> TYPE: PRT
<213> ORGANISM: Sinorhizobium meliloti

<400> SEQUENCE: 17

Met Val Glu Lys Arg Ser Val Leu Cys Phe Gly Asp Ser Leu Thr Trp
1               5                   10                  15

Gly Trp Ile Pro Val Lys Glu Ser Ser Pro Thr Leu Arg Tyr Pro Tyr
            20                  25                  30
```

Glu Gln Arg Trp Thr Gly Ala Met Ala Ala Arg Leu Gly Asp Gly Tyr
35 40 45

His Ile Ile Glu Glu Gly Leu Ser Ala Arg Thr Thr Ser Leu Asp Asp
50 55 60

Pro Asn Asp Ala Arg Leu Asn Gly Ser Thr Tyr Leu Pro Met Ala Leu
65 70 75 80

Ala Ser His Leu Pro Leu Asp Leu Val Ile Ile Met Leu Gly Thr Asn
85 90 95

Asp Thr Lys Ser Tyr Phe His Arg Thr Pro Tyr Glu Ile Ala Asn Gly
100 105 110

Met Gly Lys Leu Val Gly Gln Val Leu Thr Cys Ala Gly Gly Val Gly
115 120 125

Thr Pro Tyr Pro Ala Pro Lys Val Leu Val Val Ala Pro Pro Pro Leu
130 135 140

Ala Pro Met Pro Asp Pro Trp Phe Glu Gly Met Phe Gly Gly Gly Tyr
145 150 155 160

Glu Lys Ser Lys Glu Leu Ser Gly Leu Tyr Lys Ala Leu Ala Asp Phe
165 170 175

Met Lys Val Glu Phe Phe Ala Ala Gly Asp Cys Ile Ser Thr Asp Gly
180 185 190

Ile Asp Gly Ile His Leu Ser Ala Glu Thr Asn Ile Arg Leu Gly His
195 200 205

Ala Ile Ala Asp Lys Val Ala Ala Leu Phe
210 215

<210> SEQ ID NO 18
<211> LENGTH: 216
<212> TYPE: PRT
<213> ORGANISM: Mycobacterium smegmatis

<400> SEQUENCE: 18

Met Ala Lys Arg Ile Leu Cys Phe Gly Asp Ser Leu Thr Trp Gly Trp
1 5 10 15

Val Pro Val Glu Asp Gly Ala Pro Thr Glu Arg Phe Ala Pro Asp Val
20 25 30

Arg Trp Thr Gly Val Leu Ala Gln Gln Leu Gly Ala Asp Phe Glu Val
35 40 45

Ile Glu Glu Gly Leu Ser Ala Arg Thr Thr Asn Ile Asp Asp Pro Thr
50 55 60

Asp Pro Arg Leu Asn Gly Ala Ser Tyr Leu Pro Ser Cys Leu Ala Thr
65 70 75 80

His Leu Pro Leu Asp Leu Val Ile Ile Met Leu Gly Thr Asn Asp Thr
85 90 95

Lys Ala Tyr Phe Arg Arg Thr Pro Leu Asp Ile Ala Leu Gly Met Ser
100 105 110

Val Leu Val Thr Gln Val Leu Thr Ser Ala Gly Gly Val Gly Thr Thr
115 120 125

Tyr Pro Ala Pro Lys Val Leu Val Val Ser Pro Pro Pro Leu Ala Pro
130 135 140

Met Pro His Pro Trp Phe Gln Leu Ile Phe Glu Gly Gly Glu Gln Lys
145 150 155 160

Thr Thr Glu Leu Ala Arg Val Tyr Ser Ala Leu Ala Ser Phe Met Lys
165 170 175

Val Pro Phe Phe Asp Ala Gly Ser Val Ile Ser Thr Asp Gly Val Asp
180 185 190

```
Gly Ile His Phe Thr Glu Ala Asn Asn Arg Asp Leu Gly Val Ala Leu
        195                 200                 205

Ala Glu Gln Val Arg Ser Leu Leu
    210                 215


<210> SEQ ID NO 19
<211> LENGTH: 194
<212> TYPE: PRT
<213> ORGANISM: Mycobacterium parafortuitum

<400> SEQUENCE: 19

Gly Thr Arg Arg Ile Leu Ser Phe Gly Asp Ser Leu Thr Trp Gly Trp
1               5                   10                  15

Ile Pro Val Glu Glu Gly Val Pro Thr Glu Arg Phe Pro Arg Asp Val
            20                  25                  30

Arg Trp Thr Gly Val Leu Ala Asp Leu Leu Gly Asp Arg Tyr Glu Val
        35                  40                  45

Ile Glu Glu Gly Leu Ser Ala Arg Thr Thr Thr Ala Glu Asp Pro Ala
    50                  55                  60

Asp Pro Arg Leu Asn Gly Ser Gln Tyr Leu Pro Ser Cys Leu Ala Ser
65                  70                  75                  80

His Leu Pro Leu Asp Leu Val Ile Leu Met Leu Gly Thr Asn Asp Thr
                85                  90                  95

Lys Ala Asn Phe Gly Arg Thr Pro Phe Asp Ile Ala Thr Gly Met Gly
            100                 105                 110

Val Leu Ala Thr Gln Val Leu Thr Ser Ala Gly Gly Val Gly Thr Ser
        115                 120                 125

Tyr Pro Ala Pro Gln Val Leu Ile Val Ala Pro Pro Pro Leu Gly Glu
    130                 135                 140

Leu Pro His Pro Trp Phe Asp Leu Val Phe Ser Gly Gly Arg Glu Lys
145                 150                 155                 160

Thr Ala Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile


<210> SEQ ID NO 20
<211> LENGTH: 216
<212> TYPE: PRT
<213> ORGANISM: Prosthecobacter dejongeii

<400> SEQUENCE: 20

Met Lys Thr Ile Leu Cys Phe Gly Asp Ser Asn Thr Trp Gly Tyr Asp
1               5                   10                  15

Pro Ala Ser Met Thr Ala Pro Phe Pro Arg Arg His Gly Pro Glu Val
            20                  25                  30

Arg Trp Thr Gly Val Leu Ala Lys Ala Leu Gly Ala Gly Phe Arg Val
        35                  40                  45

Ile Glu Glu Gly Gln Asn Gly Arg Thr Thr Val His Glu Asp Pro Leu
    50                  55                  60

Asn Ile Cys Arg Lys Gly Lys Asp Tyr Leu Pro Ala Cys Leu Glu Ser
65                  70                  75                  80

His Lys Pro Leu Asp Leu Val Ile Leu Met Leu Gly Thr Asn Asp Leu
                85                  90                  95
```

```
Lys Ser Thr Phe Asn Val Pro Pro Gly Glu Ile Ala Ala Gly Ala Gly
            100                 105                 110

Val Leu Gly Arg Met Ile Leu Ala Gly Asp Ala Gly Pro Glu Asn Arg
        115                 120                 125

Pro Pro Gln Leu Leu Leu Met Cys Pro Pro Lys Val Arg Asp Leu Ser
    130                 135                 140

Ala Met Pro Asp Leu Asp Ala Lys Ile Pro His Gly Ala Ala Arg Ser
145                 150                 155                 160

Ala Glu Phe Pro Arg His Tyr Lys Ala Gln Ala Val Ala Leu Lys Cys
                165                 170                 175

Glu Tyr Phe Asn Ser Gln Glu Ile Val Glu Thr Ser Pro Val Asp Gly
            180                 185                 190

Ile His Leu Glu Ala Ser Glu His Leu Lys Leu Gly Glu Ala Leu Ala
        195                 200                 205

Glu Lys Val Lys Val Leu Leu Gly
    210                 215
```

<210> SEQ ID NO 21
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 21
acggtcctgt gctttggnga ytcnyt 26

<210> SEQ ID NO 22
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n is a, c, g, or t

<400> SEQUENCE: 22
acggtcctgt gctttggnga yagyyt 26

<210> SEQ ID NO 23
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 23
gcggtcctgt tctwnggnga ytcnyt 26

<210> SEQ ID NO 24
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 24
gcggtcctgt tctwnggnga yagyyt 26

<210> SEQ ID NO 25
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 25
gctcgaaccg tcctctgttt tggngaytcn yt 32

<210> SEQ ID NO 26
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t

<400> SEQUENCE: 26
gctcgaaccg tcctctgttt tggngayagy yt 32

<210> SEQ ID NO 27
<211> LENGTH: 29
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 27
gctcgaaccg tcctctgttt nggngaytc 29

<210> SEQ ID NO 28
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 28
gctcgaaccg tcctctgttt tggngaytcn ytn 33

<210> SEQ ID NO 29
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 29
gctcgaaccg tcctctgttt tggngaytcn ytg 33

<210> SEQ ID NO 30
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 30
gccaagcgaa ttctgtgttt cggngaytcn yt 32

<210> SEQ ID NO 31
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t

<400> SEQUENCE: 31
gccaagcgaa ttctgtgttt cggngayagy yt 32

<210> SEQ ID NO 32
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 32
attccgcgct tcagrtcrtt nvtncc 26

<210> SEQ ID NO 33
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 33
attccgcgct tcagrtcrtt nwgncc 26

<210> SEQ ID NO 34
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 34
attccgcgct tcagrtcrtt nscncc 26

<210> SEQ ID NO 35
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 35
attccgcgct tcagrtcrtt nrancc 26

<210> SEQ ID NO 36
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 36
attccgcgct tcagrtcrtt nrtncc 26

<210> SEQ ID NO 37
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 37
attccgcgct tcagrtcrtt nytncc 26

<210> SEQ ID NO 38
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 38
attccgcgct tcagrtcrtt nsgncc 26

<210> SEQ ID NO 39
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 39
attccgcgct tcagrtcrtt nwcncc 26

<210> SEQ ID NO 40
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 40
attccgcgct tcagrtcrtt nyancc 26

<210> SEQ ID NO 41
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 41
attccgcgct tgrsrtcrtt nrtncc 26

<210> SEQ ID NO 42
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 42
attccgcgct tgrsrtcrtt nytncc 26

<210> SEQ ID NO 43
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)

<223> OTHER INFORMATION: n is a, c, g, or t

<400> SEQUENCE: 43
attccgcgct tgrsrtcrtt nsgncc 26

<210> SEQ ID NO 44
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(26)
<223> OTHER INFORMATION: n is a, c, g, or t

<400> SEQUENCE: 44
attccgcgct tgrsrtcrtt nwcnnn 26

<210> SEQ ID NO 45
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 45
attccgcgct tgrsrtcrtt nyancc 26

<210> SEQ ID NO 46
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 46
gcgccggaag taggccttgg trtcrttnvt ncc 33

<210> SEQ ID NO 47
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 47
gcgccggaag taggccttgg trtcrttnwg ncc 33

<210> SEQ ID NO 48
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 48
gcgccggaag taggccttgg trtcrttnsc ncc 33

<210> SEQ ID NO 49
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 49
gcgccggaag taggccttgg trtcrttnra ncc 33

<210> SEQ ID NO 50
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 50
cggaattatc atgctgggna bnaayga 27

<210> SEQ ID NO 51
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:

<221> NAME/KEY: misc_feature
<222> LOCATION: (22)..(22)
<223> OTHER INFORMATION: n is a, c, g, or t

<400> SEQUENCE: 51
cggaattatc atgctgggnc wnaayga 27

<210> SEQ ID NO 52
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 52
cggaattatc atgctgggng snaayga 27

<210> SEQ ID NO 53
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 53
cggaattatc atgctgggnt ynaayga 27

<210> SEQ ID NO 54
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 54
ccggaattat catgctnggn abnaayga 28

<210> SEQ ID NO 55
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 55
ccggaattat catgctnggn cwnaayga 28

<210> SEQ ID NO 56
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 56
ccggaattat catgctnggn gsnaayga 28

<210> SEQ ID NO 57
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 57
ccggaattat catgctnggn tynaayga 28

<210> SEQ ID NO 58
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)

<223> OTHER INFORMATION: n is a, c, g, or t

<400> SEQUENCE: 58
acccttagcg tttggrtgnr tnccrtc 27

<210> SEQ ID NO 59
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 59
atccttagcg tttggrtgna vnccrtc 27

<210> SEQ ID NO 60
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 60
aatcttagcc gtgrrrtgnr tnccrtc 27

<210> SEQ ID NO 61
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 61
aatcttagcc gtgrrrtgnr cnccrtc 27

<210> SEQ ID NO 62
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 62
aatcttagcc gtgrrrtgnt rnccrtc 27

<210> SEQ ID NO 63
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 63
ccgctggtcc tcatctggrt gnrtnccrtc 30

<210> SEQ ID NO 64
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 64
ccgctggtcc tcatctggrt gnrcnccrtc 30

<210> SEQ ID NO 65
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 65
ccgctggtcc tcatctggrt gntrnccrtc 30

<210> SEQ ID NO 66
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t
<220> FEATURE:

<221> NAME/KEY: misc_feature
<222> LOCATION: (25)..(25)
<223> OTHER INFORMATION: n is a, c, g, or t

<400> SEQUENCE: 66
ccgctggtcc tcatcraart gnrtncc 27

<210> SEQ ID NO 67
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 67
cgattgttcg cctcgtgtga artgnrtncc rtc 33

<210> SEQ ID NO 68
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 68
cgattgttcg cctcgtgtga artgnrcncc rtc 33

<210> SEQ ID NO 69
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 69
cgattgttcg cctcgtgtga artgntrncc rtc 33

<210> SEQ ID NO 70
<211> LENGTH: 603
<212> TYPE: DNA
<213> ORGANISM: Artificial Sequence
<220> FEATURE:
<223> OTHER INFORMATION: S248_M2bB11 clone

<400> SEQUENCE: 70
atgttcgcgc tttgcacggc cgcgtcagcg gcccccgatc gcaccgtcgt cttttttggg 60

```
gacagcctga ccgcggggta cggcctcgat gacccgcaga cccagtccta cccggccagg    120

atccaggaga aggtcgacgc cgcgggcctg cgctggaagg tcgtgaatgc cggcctctcg    180

ggcgagacga gcgccggcgg cctgcggcgg gtcgactggg tgctcggcca gcacatcgac    240

gcctttgtcc tggcgcttgg cgccaacgat ggcctgcggg ggatcgaccc ccaggtcacg    300

agggccaatc tccaggagat catcaaccgg gtccgctccc ggtggccccg cgcggcgatc    360

gtcatcgccg ggatgaaaat gccccagagc atgggacagg actacgccgc gaattttgac    420

cggatcttcc ccggtctcgc cgcgaggaat tcggccacgc tcatcccctt tctattagaa    480

ggggtcgccg cccatcctag cctcaaccaa ggcgacggca tccacccgac ggccgccggg    540

gacgcactcg ttgcagggac cgtgtggacg tacctgcttc cgatcctgcg gtcagcacac    600

taa                                                                  603
```

<210> SEQ ID NO 71
<211> LENGTH: 200
<212> TYPE: PRT
<213> ORGANISM: Artificial Sequence
<220> FEATURE:
<223> OTHER INFORMATION: S248_M2bB11 clone

<400> SEQUENCE: 71

```
Met Phe Ala Leu Cys Thr Ala Ala Ser Ala Ala Pro Asp Arg Thr Val
1               5                   10                  15

Val Phe Phe Gly Asp Ser Leu Thr Ala Gly Tyr Gly Leu Asp Asp Pro
            20                  25                  30

Gln Thr Gln Ser Tyr Pro Ala Arg Ile Gln Glu Lys Val Asp Ala Ala
        35                  40                  45

Gly Leu Arg Trp Lys Val Val Asn Ala Gly Leu Ser Gly Glu Thr Ser
    50                  55                  60

Ala Gly Gly Leu Arg Arg Val Asp Trp Val Leu Gly Gln His Ile Asp
65                  70                  75                  80

Ala Phe Val Leu Ala Leu Gly Ala Asn Asp Gly Leu Arg Gly Ile Asp
                85                  90                  95

Pro Gln Val Thr Arg Ala Asn Leu Gln Glu Ile Ile Asn Arg Val Arg
            100                 105                 110

Ser Arg Trp Pro Arg Ala Ala Ile Val Ile Ala Gly Met Lys Met Pro
        115                 120                 125

Gln Ser Met Gly Gln Asp Tyr Ala Ala Asn Phe Asp Arg Ile Phe Pro
    130                 135                 140

Gly Leu Ala Ala Arg Asn Ser Ala Thr Leu Ile Pro Phe Leu Leu Glu
145                 150                 155                 160

Gly Val Ala Ala His Pro Ser Leu Asn Gln Gly Asp Gly Ile His Pro
                165                 170                 175

Thr Ala Ala Gly Asp Ala Leu Val Ala Gly Thr Val Trp Thr Tyr Leu
            180                 185                 190

Leu Pro Ile Leu Arg Ser Ala His
        195                 200
```

<210> SEQ ID NO 72
<211> LENGTH: 626
<212> TYPE: PRT
<213> ORGANISM: Artificial Sequence
<220> FEATURE:
<223> OTHER INFORMATION: S248_M40cD4 clone

<400> SEQUENCE: 72

Ala Thr Gly Cys Gly Cys Thr Thr Thr Gly Cys Thr Ala Ala Gly Cys
1 5 10 15

Thr Cys Ala Cys Thr Gly Cys Cys Gly Thr Cys Ala Thr Cys Thr Thr
20 25 30

Thr Gly Cys Cys Cys Thr Gly Ala Thr Ala Gly Thr Cys Thr Thr Gly
35 40 45

Cys Ala Cys Ala Gly Cys Cys Cys Cys Cys Thr Thr Gly Cys Cys Gly
50 55 60

Cys Cys Gly Cys Cys Gly Cys Gly Cys Cys Gly Cys Cys Cys Ala Cys
65 70 75 80

Cys Gly Thr Gly Ala Thr Gly Gly Thr Gly Thr Thr Thr Gly Gly Cys
85 90 95

Gly Ala Cys Ala Gly Thr Cys Thr Gly Ala Cys Cys Gly Cys Cys Gly
100 105 110

Gly Gly Thr Thr Gly Gly Gly Ala Thr Thr Gly Cys Cys Gly Gly Cys
115 120 125

Cys Gly Ala Thr Gly Cys Thr Gly Cys Ala Thr Thr Thr Cys Cys Gly
130 135 140

Gly Cys Gly Cys Ala Gly Cys Thr Cys Cys Ala Gly Gly Cys Ala Ala
145 150 155 160

Ala Gly Cys Thr Gly Cys Ala Cys Gly Ala Thr Ala Thr Gly Gly Gly
165 170 175

Thr Ala Thr Cys Cys Thr Gly Cys Ala Gly Ala Ala Ala Thr Cys Gly
180 185 190

Cys Cys Gly Cys Gly Cys Gly Cys Gly Cys Cys Ala Cys Cys Thr Cys
195 200 205

Gly Gly Gly Gly Cys Ala Ala Ala Cys Gly Ala Cys Gly Gly Cys Cys
210 215 220

Gly Gly Cys Gly Gly Gly Thr Thr Gly Gly Cys Gly Ala Gly Cys Cys
225 230 235 240

Thr Thr Gly Cys Gly Gly Ala Thr Gly Cys Gly Cys Thr Gly Gly Cys
245 250 255

Cys Gly Cys Ala Ala Ala Gly Cys Cys Gly Gly Ala Thr Thr Thr Gly
260 265 270

Gly Thr Gly Ala Thr Cys Cys Thr Cys Gly Ala Ala Cys Thr Cys Gly
275 280 285

Gly Cys Gly Cys Cys Ala Ala Thr Gly Ala Cys Ala Thr Gly Cys Thr
290 295 300

Gly Cys Gly Cys Gly Cys Gly Gly Thr Cys Gly Ala Thr Cys Cys Gly
305 310 315 320

Gly Cys Cys Ala Gly Cys Gly Thr Gly Cys Gly Cys Gly Cys Cys Ala
325 330 335

Ala Thr Cys Thr Cys Gly Ala Thr Gly Cys Ala Ala Thr Gly Ala Thr
340 345 350

Gly Ala Cys Gly Ala Ala Ala Ala Thr Cys Cys Ala Gly Gly Cys Gly
355 360 365

Ala Gly Cys Gly Gly Cys Gly Cys Thr Ala Ala Ala Cys Thr Gly Cys
370 375 380

Thr Gly Cys Thr Gly Ala Cys Cys Gly Gly Ala Ala Thr Gly Cys Ala
385 390 395 400

Gly Gly Cys Gly Gly Cys Gly Cys Cys Cys Ala Ala Thr Thr Gly Gly
405 410 415

```
Gly Gly Cys Gly Ala Gly Gly Ala Cys Thr Ala Thr Ala Ala Gly Cys
            420                 425                 430

Ala Cys Gly Ala Thr Thr Thr Cys Gly Ala Cys Cys Gly Cys Cys Thr
        435                 440                 445

Thr Thr Ala Thr Cys Cys Cys Gly Ala Gly Cys Thr Thr Gly Cys Gly
    450                 455                 460

Ala Ala Gly Gly Cys Gly Cys Ala Cys Gly Gly Gly Gly Thr Gly Ala
465                 470                 475                 480

Cys Gly Cys Thr Thr Thr Ala Thr Cys Cys Ala Thr Thr Cys Thr Thr
                485                 490                 495

Thr Cys Thr Thr Gly Ala Thr Gly Gly Gly Gly Thr Gly Gly Cys Gly
            500                 505                 510

Cys Thr Gly Gly Ala Cys Cys Cys Gly Gly Cys Gly Cys Thr Gly Ala
        515                 520                 525

Ala Cys Cys Ala Gly Gly Cys Gly Gly Ala Thr Gly Gly Ala Ala Thr
    530                 535                 540

Gly Cys Ala Cys Cys Cys Gly Ala Ala Cys Gly Cys Cys Ala Ala Gly
545                 550                 555                 560

Gly Gly Gly Gly Thr Cys Gly Cys Cys Gly Thr Gly Ala Thr Cys Gly
                565                 570                 575

Thr Cys Gly Ala Cys Cys Gly Thr Ala Thr Cys Gly Cys Gly Cys Cys
            580                 585                 590

Cys Gly Thr Cys Gly Thr Cys Gly Cys Cys Ala Ala Gly Ala Thr Gly
        595                 600                 605

Cys Thr Gly Ala Gly Ala Gly Gly Cys Cys Ala Gly Thr Cys Ala Thr
    610                 615                 620

Ala Ala
625
```

<210> SEQ ID NO 73
<211> LENGTH: 208
<212> TYPE: PRT
<213> ORGANISM: Artificial Sequence
<220> FEATURE:
<223> OTHER INFORMATION: S248_M40cD4 clone

<400> SEQUENCE: 73

```
Met Arg Phe Ala Lys Leu Thr Ala Val Ile Phe Ala Leu Ile Val Leu
1               5                   10                  15

His Ser Pro Leu Ala Ala Ala Ala Pro Pro Thr Val Met Val Phe Gly
            20                  25                  30

Asp Ser Leu Thr Ala Gly Leu Gly Leu Pro Ala Asp Ala Ala Phe Pro
        35                  40                  45

Ala Gln Leu Gln Ala Lys Leu His Asp Met Gly Ile Pro Ala Glu Ile
    50                  55                  60

Ala Ala Arg Ala Thr Ser Gly Gln Thr Thr Ala Gly Gly Leu Ala Ser
65                  70                  75                  80

Leu Ala Asp Ala Leu Ala Ala Lys Pro Asp Leu Val Ile Leu Glu Leu
                85                  90                  95

Gly Ala Asn Asp Met Leu Arg Ala Val Asp Pro Ala Ser Val Arg Ala
            100                 105                 110

Asn Leu Asp Ala Met Met Thr Lys Ile Gln Ala Ser Gly Ala Lys Leu
        115                 120                 125

Leu Leu Thr Gly Met Gln Ala Ala Pro Asn Trp Gly Glu Asp Tyr Lys
    130                 135                 140
```

-continued

```
His Asp Phe Asp Arg Leu Tyr Pro Glu Leu Ala Lys Ala His Gly Val
145                 150                 155                 160

Thr Leu Tyr Pro Phe Phe Leu Asp Gly Val Ala Leu Asp Pro Ala Leu
                165                 170                 175

Asn Gln Ala Asp Gly Met His Pro Asn Ala Lys Gly Val Ala Val Ile
            180                 185                 190

Val Asp Arg Ile Ala Pro Val Val Ala Lys Met Leu Arg Gly Gln Ser
        195                 200                 205


<210> SEQ ID NO 74
<211> LENGTH: 705
<212> TYPE: DNA
<213> ORGANISM: Artificial Sequence
<220> FEATURE:
<223> OTHER INFORMATION: S248_M44aA5 clone

<400> SEQUENCE: 74

atgatcgcat ggcttaccgg atgcggcagc gcaaagacgc aaccgcagcc cgcaagttcc      60

atcccgccat ccagtattcc agcaaccgca aaacctgcga caacggatat cagaccgatc     120

atcgttgctt tcggcgacag cctgactgca ggatacggcg tcagtagtga acaaagctat     180

ccggccaatc ttcaacgcga tctggatgcg cgtggatatc atgcccacgt catcaacgaa     240

ggcatcagcg gcaacacatc gaaagacggc gttctcaggg cccaggcgat tgcggcactc     300

catccggctg tcgtcatcgt tgccttcggc ggcaacgacg gtctgcgtgg cctccccatc     360

ggagacacgg aaatgaatct ggcaacgatc atctcaacca tgcagcatgc ccatgccaag     420

gtaattttag gcggaattac tttgcctccc aactatggca gcgaatacat cgccaaattc     480

aatgcgatct ataaaaagca ggcagccgcg tatcatgtgc ccctgctgcc cttcatgctg     540

aagggggtgt atggcgtgcc cggttccatg cagagcgacg gcatccatcc gaccgccaag     600

ggctgccagc aagtggccag aaacttcctg cccttgttat tgccgctcct gcacaaatca     660

gggaagaaat ccatggagtc gaaagcattg tctcgacgtc attaa                     705


<210> SEQ ID NO 75
<211> LENGTH: 234
<212> TYPE: PRT
<213> ORGANISM: Artificial Sequence
<220> FEATURE:
<223> OTHER INFORMATION: S248_M44aA5 clone

<400> SEQUENCE: 75

Met Ile Ala Trp Leu Thr Gly Cys Gly Ser Ala Lys Thr Gln Pro Gln
1               5                   10                  15

Pro Ala Ser Ser Ile Pro Pro Ser Ser Ile Pro Ala Thr Ala Lys Pro
            20                  25                  30

Ala Thr Thr Asp Ile Arg Pro Ile Ile Val Ala Phe Gly Asp Ser Leu
        35                  40                  45

Thr Ala Gly Tyr Gly Val Ser Ser Glu Gln Ser Tyr Pro Ala Asn Leu
    50                  55                  60

Gln Arg Asp Leu Asp Ala Arg Gly Tyr His Ala His Val Ile Asn Glu
65                  70                  75                  80

Gly Ile Ser Gly Asn Thr Ser Lys Asp Gly Val Leu Arg Ala Gln Ala
                85                  90                  95

Ile Ala Ala Leu His Pro Ala Val Val Ile Val Ala Phe Gly Gly Asn
            100                 105                 110

Asp Gly Leu Arg Gly Leu Pro Ile Gly Asp Thr Glu Met Asn Leu Ala
        115                 120                 125
```

```
Thr Ile Ile Ser Thr Met Gln His Ala His Ala Lys Val Ile Leu Gly
    130                 135                 140

Gly Ile Thr Leu Pro Pro Asn Tyr Gly Ser Glu Tyr Ile Ala Lys Phe
145                 150                 155                 160

Asn Ala Ile Tyr Lys Lys Gln Ala Ala Ala Tyr His Val Pro Leu Leu
                165                 170                 175

Pro Phe Met Leu Lys Gly Val Tyr Gly Val Pro Gly Ser Met Gln Ser
            180                 185                 190

Asp Gly Ile His Pro Thr Ala Lys Gly Cys Gln Gln Val Ala Arg Asn
        195                 200                 205

Phe Leu Pro Leu Leu Leu Pro Leu Leu His Lys Ser Gly Lys Lys Ser
    210                 215                 220

Met Glu Ser Lys Ala Leu Ser Arg Arg His
225                 230


<210> SEQ ID NO 76
<211> LENGTH: 639
<212> TYPE: DNA
<213> ORGANISM: Artificial Sequence
<220> FEATURE:
<223> OTHER INFORMATION: S261_M2aA12 clone

<400> SEQUENCE: 76

atgaaaaaca tccttgcatt tggcgacagt ctgacctggg gttttgtggc cggacaggat      60

gcgcgccatc cgtttgaaac ccgctggcca aacgcattgg cggccggcct tgggggcaaa     120

gcccgcgtaa ttgaagaggg tcagaacggc cgcactacgg tgttcgacga tgccgccacc     180

ttcgaatctc gaaatggctc ggtggcattg ccgctgctac tgatcagcca ccagccgttg     240

gacctggtaa tcatcatgct cggcaccaat gacatcaagt ttgccgcccg ctgccgcgcc     300

tttgatgctt caatgggcat ggaacggctg atccagatcg tcagaagtgc caactacatg     360

aagggctaca agatacctga aatcctcatc atatcgccgc ccagcctcgt gccgacgcag     420

gatgaatggt tcaacgacct ctggggccat gccatcgccg agtcaaaact cttcgccaag     480

cactacaagc gcgtggccga agaactgaaa gtgcatttct ttgatgcagg cacggtggcc     540

gtcgccgaca agaccgacgg cggacatctc gatgctgtga atactaaagc cattggcgtc     600

gcattggtgc cggtggtgaa atcaatactc gctctctaa                            639


<210> SEQ ID NO 77
<211> LENGTH: 212
<212> TYPE: PRT
<213> ORGANISM: Artificial Sequence
<220> FEATURE:
<223> OTHER INFORMATION: S261_M2aA12 clone

<400> SEQUENCE: 77

Met Lys Asn Ile Leu Ala Phe Gly Asp Ser Leu Thr Trp Gly Phe Val
1               5                   10                  15

Ala Gly Gln Asp Ala Arg His Pro Phe Glu Thr Arg Trp Pro Asn Ala
            20                  25                  30

Leu Ala Ala Gly Leu Gly Gly Lys Ala Arg Val Ile Glu Glu Gly Gln
        35                  40                  45

Asn Gly Arg Thr Thr Val Phe Asp Asp Ala Ala Thr Phe Glu Ser Arg
    50                  55                  60

Asn Gly Ser Val Ala Leu Pro Leu Leu Leu Ile Ser His Gln Pro Leu
65                  70                  75                  80
```

```
Asp Leu Val Ile Ile Met Leu Gly Thr Asn Asp Ile Lys Phe Ala Ala
                85                  90                  95

Arg Cys Arg Ala Phe Asp Ala Ser Met Gly Met Glu Arg Leu Ile Gln
            100                 105                 110

Ile Val Arg Ser Ala Asn Tyr Met Lys Gly Tyr Lys Ile Pro Glu Ile
        115                 120                 125

Leu Ile Ile Ser Pro Pro Ser Leu Val Pro Thr Gln Asp Glu Trp Phe
    130                 135                 140

Asn Asp Leu Trp Gly His Ala Ile Ala Glu Ser Lys Leu Phe Ala Lys
145                 150                 155                 160

His Tyr Lys Arg Val Ala Glu Glu Leu Lys Val His Phe Phe Asp Ala
                165                 170                 175

Gly Thr Val Ala Val Ala Asp Lys Thr Asp Gly Gly His Leu Asp Ala
            180                 185                 190

Val Asn Thr Lys Ala Ile Gly Val Ala Leu Val Pro Val Val Lys Ser
        195                 200                 205

Ile Leu Ala Leu
    210
```

<210> SEQ ID NO 78
<211> LENGTH: 546
<212> TYPE: DNA
<213> ORGANISM: Artificial Sequence
<220> FEATURE:
<223> OTHER INFORMATION: S279_M70aE8 clone

<400> SEQUENCE: 78

```
atgccgaaaa tagccaaact cgcgccgtcg gatgtgatcg tagctttcgg cgacagtctg      60

acgttcggca ccggcgcaac ggaagcggag agttatccca tcgtgctcgc acaattgatc     120

ggtcgcaccg tggtgcgcgc gggtgtgccg ggtgaggtaa ccgaaggcgg gcttgcgcgc     180

ctgaccgacg ttatcgaaga acacaagccg aagctgatta ttgtttgcct gggcggcaac     240

gacatgctgc gcaaggtcca ggaagaccag acccgcgcca atttgcgcgc cattattaaa     300

accatcaagg cgcaaggcat cgccgtggta ctggtcggtg tgccgaagcc cgcgctggtg     360

accagtgcgc cgccgttcta cgaggagatc gccaaagagt tcggtatccc ttacgaaggc     420

aagattgtta ccgacgtgtt gtaccaacgc gatcagaaat ccgattccat acatcccaat     480

gccaaaggct atcggcgcat ggccgaagcg atagccacgc tgctgaaaaa atccggagcc     540

atttaa                                                                546
```

<210> SEQ ID NO 79
<211> LENGTH: 181
<212> TYPE: PRT
<213> ORGANISM: Artificial Sequence
<220> FEATURE:
<223> OTHER INFORMATION: S279_M70aE8 clone

<400> SEQUENCE: 79

```
Met Pro Lys Ile Ala Lys Leu Ala Pro Ser Asp Val Ile Val Ala Phe
1               5                   10                  15

Gly Asp Ser Leu Thr Phe Gly Thr Gly Ala Thr Glu Ala Glu Ser Tyr
            20                  25                  30

Pro Ile Val Leu Ala Gln Leu Ile Gly Arg Thr Val Val Arg Ala Gly
        35                  40                  45

Val Pro Gly Glu Val Thr Glu Gly Gly Leu Ala Arg Leu Thr Asp Val
    50                  55                  60
```

Ile Glu Glu His Lys Pro Lys Leu Ile Ile Val Cys Leu Gly Gly Asn
65 70 75 80

Asp Met Leu Arg Lys Val Gln Glu Asp Gln Thr Arg Ala Asn Leu Arg
85 90 95

Ala Ile Ile Lys Thr Ile Lys Ala Gln Gly Ile Ala Val Val Leu Val
100 105 110

Gly Val Pro Lys Pro Ala Leu Val Thr Ser Ala Pro Pro Phe Tyr Glu
115 120 125

Glu Ile Ala Lys Glu Phe Gly Ile Pro Tyr Glu Gly Lys Ile Val Thr
130 135 140

Asp Val Leu Tyr Gln Arg Asp Gln Lys Ser Asp Ser Ile His Pro Asn
145 150 155 160

Ala Lys Gly Tyr Arg Arg Met Ala Glu Ala Ile Ala Thr Leu Leu Lys
165 170 175

Lys Ser Gly Ala Ile
180

<210> SEQ ID NO 80
<211> LENGTH: 1209
<212> TYPE: DNA
<213> ORGANISM: Artificial Sequence
<220> FEATURE:
<223> OTHER INFORMATION: S279_M75bA2 clone

<400> SEQUENCE: 80
atggaacgga ccggccgcgc tggcgatcgg tgtcggcgtg gggctggcga gcctgagccc 60
ggtcgcgctg gcgacgccgc cgcggggcac cgtgccggtg ttcacccgat cggggacagc 120
ctgacggacg agtattttga gccgttcttc cagtgggggt tctgcgggaa gtcgtgggcc 180
gagattttgg tggagacggg gcgggcgagc atgggcccga cggcgcagca ggcggggatc 240
agcgagccgg agggatggtc ggatccgcgg aacacggggt atcagcacaa ctgggcgcgg 300
tactcgtgga gctcctcaga cgcgctgacc gaggagtcgc cgggggcgac gctgagcgtg 360
ctgcttgggg cggagtacgc ggtggtgttc attgggacca acgacttcaa tccgtcgtgg 420
ccggcgtatc agagcgtgta tctgagccag tggagcgacg agcagatcga cacgtacgtg 480
aacggggtgg tgcagaacat cgcgcagatg gtggactcgc tgaagtcggt cggggcgaag 540
gtggtgcttg cgccgccggt ggattttcag ttcgcggggt tcctgcggaa ctcatgcccg 600
gatccgatgc tgcgcgagca ggcgggtatt ctgacacgga agtgccacga ccgggtgcgg 660
tcgatggcgc ggcagaagca cgtggtgttc gtggacatgt ggcggctgaa ccgcgatttg 720
ttcggcaacg ggttcgcgat cagctacggc cttcggaaca cggtgcgcgt gggggactcg 780
gagatcgggc tgcaactggc cgggctgacg ggatcggcgg ggctggttcc ggacgggatc 840
catccgcagc gggtggtgca ggggatctgg gcgaatgcgt tcatcgtggg tctgaacgcg 900
catggggcga acatcgcgcc catcggcgag gcggagatgt gcgcgatggg gggggtcgtg 960
tacgggggaa cggacacgct ggcgaacttc ctgccgccgg tcgcgggcta cgtggaggac 1020
ttccgcaacg cgggggactt cgtgtgcacg gcggacttca accatgacct tggcgtgacg 1080
ccgacggaca tcttcgcgtt catcaacgcg tggttcatga atgatccctc ggcgcggatg 1140
agcaacccgg agcacacgca gatcgaggac atcttcgtgt ttctgaatct gtggctggtg 1200
gggtgctaa 1209

<210> SEQ ID NO 81
<211> LENGTH: 402

<212> TYPE: PRT
<213> ORGANISM: Artificial Sequence
<220> FEATURE:
<223> OTHER INFORMATION: S279_M75bA2 clone

<400> SEQUENCE: 81

```
Met Glu Arg Thr Gly Arg Ala Gly Asp Arg Cys Arg Arg Gly Ala Gly
1               5                   10                  15

Glu Pro Glu Pro Gly Arg Ala Gly Asp Ala Ala Ala Gly His Arg Ala
            20                  25                  30

Gly Val His Pro Ile Gly Asp Ser Leu Thr Asp Glu Tyr Phe Glu Pro
        35                  40                  45

Phe Phe Gln Trp Gly Phe Cys Gly Lys Ser Trp Ala Glu Ile Leu Val
    50                  55                  60

Glu Thr Gly Arg Ala Ser Met Gly Pro Thr Ala Gln Gln Ala Gly Ile
65                  70                  75                  80

Ser Glu Pro Glu Gly Trp Ser Asp Pro Arg Asn Thr Gly Tyr Gln His
                85                  90                  95

Asn Trp Ala Arg Tyr Ser Trp Ser Ser Ser Asp Ala Leu Thr Glu Glu
            100                 105                 110

Ser Pro Gly Ala Thr Leu Ser Val Leu Leu Gly Ala Glu Tyr Ala Val
        115                 120                 125

Val Phe Ile Gly Thr Asn Asp Phe Asn Pro Ser Trp Pro Ala Tyr Gln
    130                 135                 140

Ser Val Tyr Leu Ser Gln Trp Ser Asp Glu Gln Ile Asp Thr Tyr Val
145                 150                 155                 160

Asn Gly Val Val Gln Asn Ile Ala Gln Met Val Asp Ser Leu Lys Ser
                165                 170                 175

Val Gly Ala Lys Val Val Leu Ala Pro Pro Val Asp Phe Gln Phe Ala
            180                 185                 190

Gly Phe Leu Arg Asn Ser Cys Pro Asp Pro Met Leu Arg Glu Gln Ala
        195                 200                 205

Gly Ile Leu Thr Arg Lys Cys His Asp Arg Val Arg Ser Met Ala Arg
    210                 215                 220

Gln Lys His Val Val Phe Val Asp Met Trp Arg Leu Asn Arg Asp Leu
225                 230                 235                 240

Phe Gly Asn Gly Phe Ala Ile Ser Tyr Gly Leu Arg Asn Thr Val Arg
                245                 250                 255

Val Gly Asp Ser Glu Ile Gly Leu Gln Leu Ala Gly Leu Thr Gly Ser
            260                 265                 270

Ala Gly Leu Val Pro Asp Gly Ile His Pro Gln Arg Val Val Gln Gly
        275                 280                 285

Ile Trp Ala Asn Ala Phe Ile Val Gly Leu Asn Ala His Gly Ala Asn
    290                 295                 300

Ile Ala Pro Ile Gly Glu Ala Glu Met Cys Ala Met Gly Gly Val Val
305                 310                 315                 320

Tyr Gly Gly Thr Asp Thr Leu Ala Asn Phe Leu Pro Pro Val Ala Gly
                325                 330                 335

Tyr Val Glu Asp Phe Arg Asn Ala Gly Asp Phe Val Cys Thr Ala Asp
            340                 345                 350

Phe Asn His Asp Leu Gly Val Thr Pro Thr Asp Ile Phe Ala Phe Ile
        355                 360                 365

Asn Ala Trp Phe Met Asn Asp Pro Ser Ala Arg Met Ser Asn Pro Glu
    370                 375                 380
```

-continued

```
His Thr Gln Ile Glu Asp Ile Phe Val Phe Leu Asn Leu Trp Leu Val
385                 390                 395                 400

Gly Cys


<210> SEQ ID NO 82
<211> LENGTH: 648
<212> TYPE: DNA
<213> ORGANISM: Artificial Sequence
<220> FEATURE:
<223> OTHER INFORMATION: M091_M4aE11 clone

<400> SEQUENCE: 82

atgaagacca ttctcgccta tggcgacagc ctgacctatg gggccaaccc gatcccgggc      60

gggccgcggc atgcctatga ggatcgctgg cccacggcgc tggagcaggg gctgggcggc     120

aaggcgcggg tgattgccga ggggctgggt ggtcgcacca cggtgcatga cgactggttt     180

gcgaatgcgg acaggaacgg tgcgcgggtg ctgccgacgc tgctcgagag ccattcgccg     240

ctcgacctga tcgtcatcat gctcggcacc aacgacatca agccgcatca cgggcggacg     300

gccggcgagg ccgggcgggg catggcgcgg ctggtgcaga tcatccgcgg gcactatgcc     360

ggccgcatgc aggacgagcc gcagatcatc ctcgtgtcgc cgccgccgat catcctcggc     420

gactgggcgg acatgatgga ccatttcggc ccgcacgaag cgatcgccac ctcggtggat     480

ttcgctcgcg agtacaagaa gcgggccgac gagcagaagg tgcatttctt cgacgccggc     540

acggtggcga cgaccagcaa ggccgatggc atccacctcg acccggccaa tacgcgcgcc     600

atcggggcag ggctggtgcc gctggtgaag caggtgctcg gcctgtaa                  648


<210> SEQ ID NO 83
<211> LENGTH: 215
<212> TYPE: PRT
<213> ORGANISM: Artificial Sequence
<220> FEATURE:
<223> OTHER INFORMATION: M091_M4aE11 clone

<400> SEQUENCE: 83

Met Lys Thr Ile Leu Ala Tyr Gly Asp Ser Leu Thr Tyr Gly Ala Asn
1               5                   10                  15

Pro Ile Pro Gly Gly Pro Arg His Ala Tyr Glu Asp Arg Trp Pro Thr
            20                  25                  30

Ala Leu Glu Gln Gly Leu Gly Gly Lys Ala Arg Val Ile Ala Glu Gly
        35                  40                  45

Leu Gly Gly Arg Thr Thr Val His Asp Asp Trp Phe Ala Asn Ala Asp
    50                  55                  60

Arg Asn Gly Ala Arg Val Leu Pro Thr Leu Leu Glu Ser His Ser Pro
65                  70                  75                  80

Leu Asp Leu Ile Val Ile Met Leu Gly Thr Asn Asp Ile Lys Pro His
                85                  90                  95

His Gly Arg Thr Ala Gly Glu Ala Gly Arg Gly Met Ala Arg Leu Val
            100                 105                 110

Gln Ile Ile Arg Gly His Tyr Ala Gly Arg Met Gln Asp Glu Pro Gln
        115                 120                 125

Ile Ile Leu Val Ser Pro Pro Pro Ile Ile Leu Gly Asp Trp Ala Asp
    130                 135                 140

Met Met Asp His Phe Gly Pro His Glu Ala Ile Ala Thr Ser Val Asp
145                 150                 155                 160

Phe Ala Arg Glu Tyr Lys Lys Arg Ala Asp Glu Gln Lys Val His Phe
                165                 170                 175
```

-continued

```
Phe Asp Ala Gly Thr Val Ala Thr Thr Ser Lys Ala Asp Gly Ile His
            180                 185                 190

Leu Asp Pro Ala Asn Thr Arg Ala Ile Gly Ala Gly Leu Val Pro Leu
        195                 200                 205

Val Lys Gln Val Leu Gly Leu
    210                 215


<210> SEQ ID NO 84
<211> LENGTH: 1830
<212> TYPE: DNA
<213> ORGANISM: Artificial Sequence
<220> FEATURE:
<223> OTHER INFORMATION: Est105 clone

<400> SEQUENCE: 84

atgcgcacgc ttcaccgaag cctgctcgca agcgcggccg cgctttttct agcggcatcc     60

ggcaacgcaa cggcgcagtt ctcgaacgtc tatttcttcg gcgacagcct gaccgacgcg    120

ggttccttca agcctgtgct gcctcctggt acaggattat tcacgacgaa tcccggcccg    180

gtatggccgc aggtattcgg ggcgaactac ggcgtcgcgg tgacgcccgc aaaccagggt    240

gggaccgatt atgcgcaggg tggcgcgcgc gtgacgagcc tgcctggcgt tccgacgtcg    300

cagccgaccg gcagcgcggt accgatcgct acgcagattt cgcagttcct cggctcgggt    360

ccggcggatc cgaacgcatt ctattcggtg tggggcggcg cgaacgacat ctttttccag    420

ctggggttgg cgcaggcggg catggcgacg ccggcgcagg tccagtcggc cgtcggcttg    480

gccgcggtcc agctggcgca ggcaactgcg gcgctcaacg ccagcggcgc gcgattcatc    540

acggttatca acgtgccgga catcggtaaa acgccgttcg gcgtcggctc cggtcaagga    600

gcgcagatca ccgctctgtc gtctttcttc aacagcacgc tgttcggcgc gctcgacgcc    660

acgggcatcc agacgatgcg cgtgaacggg ttcgcggtgc tgaacgaggt ggtcgcggac    720

ccggcggctt atggcttcgc gaatgcatca acgccagcgt gcggggccac gccatcgctc    780

gtctgcacgt cggcgaactt cgtcacgccc ttggccgcgc agaccttcct cttcgcagac    840

ggcgttcacc ccaccacggc cgggcacgcc ctcatcgccc aagcggtcca ggcgatgatc    900

accggtcccc aacagatggc ggcgttgggc gacgccccgc tcgccgtcga gcaggccaac    960

ttccgcgcgc tcgacaaccg catgtggtcg agcctcaatg cgccgcgcag cccgggcaag   1020

ctccagggtt gggcggccta cgactacagc cacacggacc tgcaggcggg accgaccaat   1080

ggcagcggac acatgaacac cgttgcggtc ggggtcgaca tgaaagtctc cgatcatatg   1140

ctcgccggcg cgatgttcgg ctataccaac accaagggcg acttcggcgg ccccggcggc   1200

ggatacacac tgaagcagcc tgtgggcact gcctatgcgg gttacggcgt gggcccttgg   1260

tatgtcggcg cgacgctcgg cacaggtggc ctcgactact cggacgtcac gcgcgccatc   1320

ccgcttggct tggcggttcg caccgagagc gccgaggccc gaggctacga gttcacgggc   1380

cggatcctcg gcggctactg gttcacgatg cgcgacctga tgcacgggcc gtacgcgcgt   1440

ctcgcgtgga cgaaggccgt cgtcaagcgg ttttccgagg agagcaccga cagcacggcg   1500

ttgaactacg acaggcagga gcgcaagcaa ctgctgtgga gcctcggatg gcaactcgcc   1560

ggcaacgtcg gcagcatccg tccctacgcg cgggcgacct gggagatcga ctccaaggat   1620

caggaccgca gcgttggcgc atcgtcggtc acgctgggcg gcttttacag tgttccggtc   1680

gcgaagccgg acaatagcta tgcgctcttc agcctcggcg cgagtaccga gctcgggagc   1740

gtcaccgggt ttgtcgcggg ctcggccacc gcaggccggg cggatgccaa ctattgggcg   1800
```

gtcacggtcg gcctgcggat gccgttgtag 1830

<210> SEQ ID NO 85
<211> LENGTH: 609
<212> TYPE: PRT
<213> ORGANISM: Artificial Sequence
<220> FEATURE:
<223> OTHER INFORMATION: Est105 clone

<400> SEQUENCE: 85

Met Arg Thr Leu His Arg Ser Leu Leu Ala Ser Ala Ala Ala Leu Phe
1 5 10 15

Leu Ala Ala Ser Gly Asn Ala Thr Ala Gln Phe Ser Asn Val Tyr Phe
20 25 30

Phe Gly Asp Ser Leu Thr Asp Ala Gly Ser Phe Lys Pro Val Leu Pro
35 40 45

Pro Gly Thr Gly Leu Phe Thr Thr Asn Pro Gly Pro Val Trp Pro Gln
50 55 60

Val Phe Gly Ala Asn Tyr Gly Val Ala Val Thr Pro Ala Asn Gln Gly
65 70 75 80

Gly Thr Asp Tyr Ala Gln Gly Gly Ala Arg Val Thr Ser Leu Pro Gly
85 90 95

Val Pro Thr Ser Gln Pro Thr Gly Ser Ala Val Pro Ile Ala Thr Gln
100 105 110

Ile Ser Gln Phe Leu Gly Ser Gly Pro Ala Asp Pro Asn Ala Phe Tyr
115 120 125

Ser Val Trp Gly Gly Ala Asn Asp Ile Phe Phe Gln Leu Gly Leu Ala
130 135 140

Gln Ala Gly Met Ala Thr Pro Ala Gln Val Gln Ser Ala Val Gly Leu
145 150 155 160

Ala Ala Val Gln Leu Ala Gln Ala Thr Ala Ala Leu Asn Ala Ser Gly
165 170 175

Ala Arg Phe Ile Thr Val Ile Asn Val Pro Asp Ile Gly Lys Thr Pro
180 185 190

Phe Gly Val Gly Ser Gly Gln Gly Ala Gln Ile Thr Ala Leu Ser Ser
195 200 205

Phe Phe Asn Ser Thr Leu Phe Gly Ala Leu Asp Ala Thr Gly Ile Gln
210 215 220

Thr Met Arg Val Asn Gly Phe Ala Val Leu Asn Glu Val Val Ala Asp
225 230 235 240

Pro Ala Ala Tyr Gly Phe Ala Asn Ala Ser Thr Pro Ala Cys Gly Ala
245 250 255

Thr Pro Ser Leu Val Cys Thr Ser Ala Asn Phe Val Thr Pro Leu Ala
260 265 270

Ala Gln Thr Phe Leu Phe Ala Asp Gly Val His Pro Thr Thr Ala Gly
275 280 285

His Ala Leu Ile Ala Gln Ala Val Gln Ala Met Ile Thr Gly Pro Gln
290 295 300

Gln Met Ala Ala Leu Gly Asp Ala Pro Leu Ala Val Glu Gln Ala Asn
305 310 315 320

Phe Arg Ala Leu Asp Asn Arg Met Trp Ser Ser Leu Asn Ala Pro Arg
325 330 335

Ser Pro Gly Lys Leu Gln Gly Trp Ala Ala Tyr Asp Tyr Ser His Thr
340 345 350

```
Asp Leu Gln Ala Gly Pro Thr Asn Gly Ser Gly His Met Asn Thr Val
        355                 360                 365

Ala Val Gly Val Asp Met Lys Val Ser Asp His Met Leu Ala Gly Ala
    370                 375                 380

Met Phe Gly Tyr Thr Asn Thr Lys Gly Asp Phe Gly Gly Pro Gly Gly
385                 390                 395                 400

Gly Tyr Thr Leu Lys Gln Pro Val Gly Thr Ala Tyr Ala Gly Tyr Gly
                405                 410                 415

Val Gly Pro Trp Tyr Val Gly Ala Thr Leu Gly Thr Gly Gly Leu Asp
            420                 425                 430

Tyr Ser Asp Val Thr Arg Ala Ile Pro Leu Gly Leu Ala Val Arg Thr
        435                 440                 445

Glu Ser Ala Glu Ala Arg Gly Tyr Glu Phe Thr Gly Arg Ile Leu Gly
    450                 455                 460

Gly Tyr Trp Phe Thr Met Arg Asp Leu Met His Gly Pro Tyr Ala Arg
465                 470                 475                 480

Leu Ala Trp Thr Lys Ala Val Val Lys Arg Phe Ser Glu Glu Ser Thr
                485                 490                 495

Asp Ser Thr Ala Leu Asn Tyr Asp Arg Gln Glu Arg Lys Gln Leu Leu
            500                 505                 510

Trp Ser Leu Gly Trp Gln Leu Ala Gly Asn Val Gly Ser Ile Arg Pro
        515                 520                 525

Tyr Ala Arg Ala Thr Trp Glu Ile Asp Ser Lys Asp Gln Asp Arg Ser
    530                 535                 540

Val Gly Ala Ser Ser Val Thr Leu Gly Gly Phe Tyr Ser Val Pro Val
545                 550                 555                 560

Ala Lys Pro Asp Asn Ser Tyr Ala Leu Phe Ser Leu Gly Ala Ser Thr
                565                 570                 575

Glu Leu Gly Ser Val Thr Gly Phe Val Ala Gly Ser Ala Thr Ala Gly
            580                 585                 590

Arg Ala Asp Ala Asn Tyr Trp Ala Val Thr Val Gly Leu Arg Met Pro
        595                 600                 605

Leu
```

<210> SEQ ID NO 86
<211> LENGTH: 921
<212> TYPE: DNA
<213> ORGANISM: Artificial Sequence
<220> FEATURE:
<223> OTHER INFORMATION: Est114 clone

<400> SEQUENCE: 86

```
atggggcgat cgagagttct gaaggctgtt ttcctggtgg cgtgccttgt gggtcggctc      60

gcggcgcatg ccgaggcgtc gcccatcgtg gtctacggcg atagcctctc tgacaacggc     120

aatctgtttg cgctcaccgg cggtgtcgcg ccgccctcgc cgccgtactt caacggacgg     180

ttttctaatg gcccggtggc cgtggagtat ctcgcggccg cgctgggatc tccgctgatc     240

gatttcgcgg tcggcggggc gacgaccggc ctcggcgtca acggcgatcc cggtggttcg     300

ccgacgagtc tcggcgcggc gggattgccg gggcttcaga cgacattcgc cgccacgcaa     360

ggcacgctgg gtccgtacgt tggtggtctc ttcgtggtgt gggcgggtcc gaacgacttc     420

ttgtcgccct cgccgcttga cacgaacgct tttcagattg cgaaccgggc cgtgtccaac     480

atcctcggcg tggtggcatc acttcaggca ctcggcgtcg agcgcatcct cgtccccggc     540

atgcccgatc tcggtctgac gcccgctctt cagcccatcg caggcgcagc caccgcgttc     600
```

```
accgatttgt tcaactcgat gctgcgcgcg ggcttgccga acgacgtgct gtacctggac    660

acggcgacaa tcttccgatc gatcgtggca gaccctgggg cctacggctt gaccaacgtg    720

accacgccgt gcctgattgg tgcgaccgtc tgcgcgaatc cggatcagta cctgttctgg    780

gatggtattc atcctacgac ggcggggcac gcgatcttgg gcaatgccct cgtcgcccag    840

gcagtccccg agcccgcgac catggtgctc gtgctgacgg gtctgtccat gcacgtgatt    900

gcgcgccggc ggcgggcgta a                                              921
```

<210> SEQ ID NO 87
<211> LENGTH: 306
<212> TYPE: PRT
<213> ORGANISM: Artificial Sequence
<220> FEATURE:
<223> OTHER INFORMATION: Est114 clone

<400> SEQUENCE: 87

```
Met Gly Arg Ser Arg Val Leu Lys Ala Val Phe Leu Val Ala Cys Leu
1               5                   10                  15

Val Gly Arg Leu Ala Ala His Ala Glu Ala Ser Pro Ile Val Val Tyr
            20                  25                  30

Gly Asp Ser Leu Ser Asp Asn Gly Asn Leu Phe Ala Leu Thr Gly Gly
        35                  40                  45

Val Ala Pro Pro Ser Pro Pro Tyr Phe Asn Gly Arg Phe Ser Asn Gly
    50                  55                  60

Pro Val Ala Val Glu Tyr Leu Ala Ala Ala Leu Gly Ser Pro Leu Ile
65                  70                  75                  80

Asp Phe Ala Val Gly Gly Ala Thr Thr Gly Leu Gly Val Asn Gly Asp
                85                  90                  95

Pro Gly Gly Ser Pro Thr Ser Leu Gly Ala Ala Gly Leu Pro Gly Leu
            100                 105                 110

Gln Thr Thr Phe Ala Ala Thr Gln Gly Thr Leu Gly Pro Tyr Val Gly
        115                 120                 125

Gly Leu Phe Val Val Trp Ala Gly Pro Asn Asp Phe Leu Ser Pro Ser
    130                 135                 140

Pro Leu Asp Thr Asn Ala Phe Gln Ile Ala Asn Arg Ala Val Ser Asn
145                 150                 155                 160

Ile Leu Gly Val Val Ala Ser Leu Gln Ala Leu Gly Val Glu Arg Ile
                165                 170                 175

Leu Val Pro Gly Met Pro Asp Leu Gly Leu Thr Pro Ala Leu Gln Pro
            180                 185                 190

Ile Ala Gly Ala Ala Thr Ala Phe Thr Asp Leu Phe Asn Ser Met Leu
        195                 200                 205

Arg Ala Gly Leu Pro Asn Asp Val Leu Tyr Leu Asp Thr Ala Thr Ile
    210                 215                 220

Phe Arg Ser Ile Val Ala Asp Pro Gly Ala Tyr Gly Leu Thr Asn Val
225                 230                 235                 240

Thr Thr Pro Cys Leu Ile Gly Ala Thr Val Cys Ala Asn Pro Asp Gln
                245                 250                 255

Tyr Leu Phe Trp Asp Gly Ile His Pro Thr Thr Ala Gly His Ala Ile
            260                 265                 270

Leu Gly Asn Ala Leu Val Ala Gln Ala Val Pro Glu Pro Ala Thr Met
        275                 280                 285

Val Leu Val Leu Thr Gly Leu Ser Met His Val Ile Ala Arg Arg Arg
    290                 295                 300
```

Arg Ala
305

<210> SEQ ID NO 88
<211> LENGTH: 687
<212> TYPE: DNA
<213> ORGANISM: Sinorhizobium meliloti

<400> SEQUENCE: 88
atgacaatca acagccattc atggaggacg ttaatggtgg aaaagcgctc agtactgtgc 60
tttggggatt cgctgacatg ggctggattt ccggtgaagg gatcctcacc gaccttgcgc 120
tatccctatg aacaacggtg gaccggcgca atggccgcga ggcttggcga cggttaccac 180
atcatcgaag aggggctgag cgcccgcacc accagcctcg acgaccccaa cgacgcgcgg 240
ctcaacggca gcacctacct gcccatggca ctcgccagcc acctcccact cgacctcgtc 300
atcatcatgc tgggcacgaa cgacacgaaa tcctatttcc accgcacgcc ttacgagatc 360
gccaacggca tgggcaagct agtcggccag gtgctgacct gcgccggtgg cgtcggcacg 420
ccatatcccg cgccgaaggt gcttgtcgtc gctccgccgc cgctcgcgcc gatgcccgac 480
ccgtggttcg aaggcatgtt cggcggcggc tacgagaagt cgaaggaact ctccggcctc 540
tacaaggcgc ttgccgattt catgaaggtc gagtttttcg ccgccggtga ttgcatttcc 600
accgatggga tcgacggcat tcacctctcg gcggaaacca acatcagact cgggcacgcg 660
atcgcggaca aagttgcggc gttgttc 687

<210> SEQ ID NO 89
<211> LENGTH: 229
<212> TYPE: PRT
<213> ORGANISM: Sinorhizobium meliloti

<400> SEQUENCE: 89

Met Thr Ile Asn Ser His Ser Trp Arg Thr Leu Met Val Glu Lys Arg
1 5 10 15

Ser Val Leu Cys Phe Gly Asp Ser Leu Thr Trp Gly Trp Ile Pro Val
20 25 30

Lys Gly Ser Ser Pro Thr Leu Arg Tyr Pro Tyr Glu Gln Arg Trp Thr
35 40 45

Gly Ala Met Ala Ala Arg Leu Gly Asp Gly Tyr His Ile Ile Glu Glu
50 55 60

Gly Leu Ser Ala Arg Thr Thr Ser Leu Asp Asp Pro Asn Asp Ala Arg
65 70 75 80

Leu Asn Gly Ser Thr Tyr Leu Pro Met Ala Leu Ala Ser His Leu Pro
85 90 95

Leu Asp Leu Val Ile Ile Met Leu Gly Thr Asn Asp Thr Lys Ser Tyr
100 105 110

Phe His Arg Thr Pro Tyr Glu Ile Ala Asn Gly Met Gly Lys Leu Val
115 120 125

Gly Gln Val Leu Thr Cys Ala Gly Gly Val Gly Thr Pro Tyr Pro Ala
130 135 140

Pro Lys Val Leu Val Val Ala Pro Pro Pro Leu Ala Pro Met Pro Asp
145 150 155 160

Pro Trp Phe Glu Gly Met Phe Gly Gly Gly Tyr Glu Lys Ser Lys Glu
165 170 175

Leu Ser Gly Leu Tyr Lys Ala Leu Ala Asp Phe Met Lys Val Glu Phe
180 185 190

Phe Ala Ala Gly Asp Cys Ile Ser Thr Asp Gly Ile Asp Gly Ile His
195 200 205

Leu Ser Ala Glu Thr Asn Ile Arg Leu Gly His Ala Ile Ala Asp Lys
210 215 220

Val Ala Ala Leu Phe
225

<210> SEQ ID NO 90
<211> LENGTH: 663
<212> TYPE: DNA
<213> ORGANISM: Sinorhizobium meliloti

<400> SEQUENCE: 90
atggaggaga cagtggcacg gaccgttcta tgcttcggag attccaacac tcacggccag 60
gtacctggcc gcggaccgct tgatcgctac cgacgcgaac agcgctgggg cggtgttctg 120
caaggcctgc tcggcccgaa ctggcaggtt atcgaagaag gcctgagcgg acgcacgacc 180
gtgcatgacg atccgatcga aggttcgctc aagaacggcc ggacctatct gcgcccctgt 240
ctgcagagcc atgcaccact cgaccttatc atcattatgc tcggcaccaa tgacctgaag 300
cggcgcttca acatgccacc gtccgaggtc gcaatgggca tcggctgtct cgtgcacgat 360
atccgagaac tctcgcccgg ccggaccggc aacgatcccg aaatcatgat cgtcgccccg 420
ccgccgatgc tggaagatct caaggaatgg gagtcgattt tctcaggcgc acaggaaaaa 480
tctcgcaagc tggcgctgga gttcgagata atggcggatt ctctggaggc gcatttcttc 540
gacgccggta cggtctgcca gtgttcgccg gccgatggct tccacatcga cgaggatgcc 600
caccgcctgc tcggcgaggc tctcgcccag gaagtgctgg cgatcgggtg gcccgatgcg 660
taa 663

<210> SEQ ID NO 91
<211> LENGTH: 220
<212> TYPE: PRT
<213> ORGANISM: Sinorhizobium meliloti

<400> SEQUENCE: 91

Met Glu Glu Thr Val Ala Arg Thr Val Leu Cys Phe Gly Asp Ser Asn
1 5 10 15

Thr His Gly Gln Val Pro Gly Arg Gly Pro Leu Asp Arg Tyr Arg Arg
20 25 30

Glu Gln Arg Trp Gly Gly Val Leu Gln Gly Leu Leu Gly Pro Asn Trp
35 40 45

Gln Val Ile Glu Glu Gly Leu Ser Gly Arg Thr Thr Val His Asp Asp
50 55 60

Pro Ile Glu Gly Ser Leu Lys Asn Gly Arg Thr Tyr Leu Arg Pro Cys
65 70 75 80

Leu Gln Ser His Ala Pro Leu Asp Leu Ile Ile Ile Met Leu Gly Thr
85 90 95

Asn Asp Leu Lys Arg Arg Phe Asn Met Pro Pro Ser Glu Val Ala Met
100 105 110

Gly Ile Gly Cys Leu Val His Asp Ile Arg Glu Leu Ser Pro Gly Arg
115 120 125

Thr Gly Asn Asp Pro Glu Ile Met Ile Val Ala Pro Pro Pro Met Leu
130 135 140

Glu Asp Leu Lys Glu Trp Glu Ser Ile Phe Ser Gly Ala Gln Glu Lys
145 150 155 160

```
Ser Arg Lys Leu Ala Leu Glu Phe Glu Ile Met Ala Asp Ser Leu Glu
                165                 170                 175

Ala His Phe Phe Asp Ala Gly Thr Val Cys Gln Cys Ser Pro Ala Asp
            180                 185                 190

Gly Phe His Ile Asp Glu Asp Ala His Arg Leu Leu Gly Glu Ala Leu
        195                 200                 205

Ala Gln Glu Val Leu Ala Ile Gly Trp Pro Asp Ala
    210                 215                 220


<210> SEQ ID NO 92
<211> LENGTH: 642
<212> TYPE: DNA
<213> ORGANISM: Sinorhizobium meliloti

<400> SEQUENCE: 92

atgaagacag tcctttgcta cggtgacagt ctgacctggg gatacgatgc aaccggttcc      60

ggccggcatg cgctggagga ccgttggccg agcgtgctgc agaaggcgct cggttcggac     120

gcgcatgtca tcgccgaagg gctgaacggg cggacgaccg cctatgacga ccatctcgcc     180

gattgcgacc ggaacggcgc gcgtgtcctc ccgacggtcc tgcacaccca cgcgccactc     240

gatctcatcg tgttcatgct cggctcgaac gacatgaagc cgatcattca cggcaccgct     300

ttcggcgcgg tgaagggcat cgagcgcctc gtcaatctgg tgcgcaggca cgactggccg     360

acggaaacgg aggaggggcc cgagattctc atcgtctcgc cgccgccgct ctgcgagacg     420

gccaacagcg cctttgccgc catgttcgcg ggcggggtcg agcaatccgc aatgctggcg     480

ccgctttatc gcgatctcgc cgacgagctc gactgcggct tcttcgacgg cggatcggtg     540

gccaggacga cgccgatcga cggtgtccac ctcgacgcgg agaacacccg ggcggtcggc     600

agagggttgg agcctgtcgt gcggatgatg ctcgggcttt aa                        642


<210> SEQ ID NO 93
<211> LENGTH: 213
<212> TYPE: PRT
<213> ORGANISM: Sinorhizobium meliloti

<400> SEQUENCE: 93

Met Lys Thr Val Leu Cys Tyr Gly Asp Ser Leu Thr Trp Gly Tyr Asp
1               5                   10                  15

Ala Thr Gly Ser Gly Arg His Ala Leu Glu Asp Arg Trp Pro Ser Val
            20                  25                  30

Leu Gln Lys Ala Leu Gly Ser Asp Ala His Val Ile Ala Glu Gly Leu
        35                  40                  45

Asn Gly Arg Thr Thr Ala Tyr Asp Asp His Leu Ala Asp Cys Asp Arg
    50                  55                  60

Asn Gly Ala Arg Val Leu Pro Thr Val Leu His Thr His Ala Pro Leu
65                  70                  75                  80

Asp Leu Ile Val Phe Met Leu Gly Ser Asn Asp Met Lys Pro Ile Ile
                85                  90                  95

His Gly Thr Ala Phe Gly Ala Val Lys Gly Ile Glu Arg Leu Val Asn
            100                 105                 110

Leu Val Arg Arg His Asp Trp Pro Thr Glu Thr Glu Glu Gly Pro Glu
        115                 120                 125

Ile Leu Ile Val Ser Pro Pro Pro Leu Cys Glu Thr Ala Asn Ser Ala
    130                 135                 140

Phe Ala Ala Met Phe Ala Gly Gly Val Glu Gln Ser Ala Met Leu Ala
```

145 150 155 160

Pro Leu Tyr Arg Asp Leu Ala Asp Glu Leu Asp Cys Gly Phe Phe Asp
165 170 175

Gly Gly Ser Val Ala Arg Thr Thr Pro Ile Asp Gly Val His Leu Asp
180 185 190

Ala Glu Asn Thr Arg Ala Val Gly Arg Gly Leu Glu Pro Val Val Arg
195 200 205

Met Met Leu Gly Leu
210

<210> SEQ ID NO 94
<211> LENGTH: 645
<212> TYPE: DNA
<213> ORGANISM: Agrobacterium tumefaciens

<400> SEQUENCE: 94
atggtgaagt cggtcctctg ctttggcgat tccctcacct ggggatcaaa tgcggaaacg 60
ggtggccggc acagccatga cgatctttgg ccgagcgtct tgcagaaggc gctcggtcct 120
gacgtgcatg tgattcacga aggtctgggt ggtcgcacca ccgcctatga cgacaacacc 180
gccgattgcg accgcaacgg cgcgcgggtt cttccgacgt tgttgcacag ccatgcgccg 240
ctggatctgg tgattgtcat gctcgggacc aacgacctga agccgtcaat ccatggatcg 300
gcgatcgttg ccatgaaggg tgtcgaaagg ctggtgaagc tcacgcgcaa ccacatctgg 360
caggtgccgg actgggaggc gcctgacgtg ctgatcgtcg caccgccgca gctgtgtgaa 420
acggccaatc cgttcatggg cgcgatcttt cgtgatgcga tcgatgaatc ggcgatgctg 480
gcgtccgttt accgggacct tgccgacgag cttgattgcg gctttttcga tgcgggttcc 540
gtcgcccgaa cgacgccggt ggatggcgtt catctcgatg ctgaaaatac gcgggccatc 600
gggcgggggc tggagcccgt cgttcgcatg atgctcggac tttaa 645

<210> SEQ ID NO 95
<211> LENGTH: 214
<212> TYPE: PRT
<213> ORGANISM: Agrobacterium tumefaciens

<400> SEQUENCE: 95

Met Val Lys Ser Val Leu Cys Phe Gly Asp Ser Leu Thr Trp Gly Ser
1 5 10 15

Asn Ala Glu Thr Gly Gly Arg His Ser His Asp Asp Leu Trp Pro Ser
20 25 30

Val Leu Gln Lys Ala Leu Gly Pro Asp Val His Val Ile His Glu Gly
35 40 45

Leu Gly Gly Arg Thr Thr Ala Tyr Asp Asp Asn Thr Ala Asp Cys Asp
50 55 60

Arg Asn Gly Ala Arg Val Leu Pro Thr Leu Leu His Ser His Ala Pro
65 70 75 80

Leu Asp Leu Val Ile Val Met Leu Gly Thr Asn Asp Leu Lys Pro Ser
85 90 95

Ile His Gly Ser Ala Ile Val Ala Met Lys Gly Val Glu Arg Leu Val
100 105 110

Lys Leu Thr Arg Asn His Ile Trp Gln Val Pro Asp Trp Glu Ala Pro
115 120 125

Asp Val Leu Ile Val Ala Pro Pro Gln Leu Cys Glu Thr Ala Asn Pro
130 135 140

Phe Met Gly Ala Ile Phe Arg Asp Ala Ile Asp Glu Ser Ala Met Leu
145 150 155 160

Ala Ser Val Tyr Arg Asp Leu Ala Asp Glu Leu Asp Cys Gly Phe Phe
165 170 175

Asp Ala Gly Ser Val Ala Arg Thr Thr Pro Val Asp Gly Val His Leu
180 185 190

Asp Ala Glu Asn Thr Arg Ala Ile Gly Arg Gly Leu Glu Pro Val Val
195 200 205

Arg Met Met Leu Gly Leu
210

<210> SEQ ID NO 96
<211> LENGTH: 636
<212> TYPE: DNA
<213> ORGANISM: Mesorhizobium loti

<400> SEQUENCE: 96
atgaagacgg tgctttgcta cggcgactcg ctgacctggg gctacaatgc cgaaggcggc 60
cgccatgcgc tggaagaccg ctggccgagc gtgctgcaag cagcgttagg cgccggcgtg 120
caagtgattg ccgatggcct caacggccgc accacggcct tcgacgatca tctggccggt 180
gctgatcgca acggcgccag gctgctgccg acggtcctga cgacgcacgc gccgatcgac 240
ctgatcatct tcatgctcgg cgccaacgac atgaagcctt ggatccacgg caatccggtc 300
gcagccaagc aaggcatcca gcggttgatc gacatcgtgc gtggtcacga ctacccgttc 360
gactggccgg cgccgcagat cctgatcgtc gcgccgcctg tagtcagccg caccgaaaat 420
gccgacttca aggaaatgtt cgccggtggc gatgacgcct cgaagttttt ggcaccgcaa 480
tatgccgcgc tcgccgacga agccggctgt ggcttcttcg acgccggcag cgtggcccaa 540
accacaccgc tcgatggcgt tcacctcgat gccgaaaaca cgcgagaaat cggcaaggcg 600
ctgacgccga tcgtgcgcgt catgctggaa ttgtaa 636

<210> SEQ ID NO 97
<211> LENGTH: 211
<212> TYPE: PRT
<213> ORGANISM: Mesorhizobium loti

<400> SEQUENCE: 97

Met Lys Thr Val Leu Cys Tyr Gly Asp Ser Leu Thr Trp Gly Tyr Asn
1 5 10 15

Ala Glu Gly Gly Arg His Ala Leu Glu Asp Arg Trp Pro Ser Val Leu
20 25 30

Gln Ala Ala Leu Gly Ala Gly Val Gln Val Ile Ala Asp Gly Leu Asn
35 40 45

Gly Arg Thr Thr Ala Phe Asp Asp His Leu Ala Gly Ala Asp Arg Asn
50 55 60

Gly Ala Arg Leu Leu Pro Thr Val Leu Thr Thr His Ala Pro Ile Asp
65 70 75 80

Leu Ile Ile Phe Met Leu Gly Ala Asn Asp Met Lys Pro Trp Ile His
85 90 95

Gly Asn Pro Val Ala Ala Lys Gln Gly Ile Gln Arg Leu Ile Asp Ile
100 105 110

Val Arg Gly His Asp Tyr Pro Phe Asp Trp Pro Ala Pro Gln Ile Leu
115 120 125

Ile Val Ala Pro Pro Val Val Ser Arg Thr Glu Asn Ala Asp Phe Lys
130 135 140

-continued

```
Glu Met Phe Ala Gly Gly Asp Asp Ala Ser Lys Phe Leu Ala Pro Gln
145                 150                 155                 160

Tyr Ala Ala Leu Ala Asp Glu Ala Gly Cys Gly Phe Phe Asp Ala Gly
                165                 170                 175

Ser Val Ala Gln Thr Thr Pro Leu Asp Gly Val His Leu Asp Ala Glu
            180                 185                 190

Asn Thr Arg Glu Ile Gly Lys Ala Leu Thr Pro Ile Val Arg Val Met
        195                 200                 205

Leu Glu Leu
    210


<210> SEQ ID NO 98
<211> LENGTH: 1851
<212> TYPE: DNA
<213> ORGANISM: Moraxella bovis

<400> SEQUENCE: 98

atgaaaaaat ccgcctttgc caaatactca gcacttgccc taatggttgg gatgtgcctg     60

cacaccgctt acgccaagga gtttagccaa gtcatcattt ttggggacag cttgtccgat    120

acaggtcgcc taaaagatat ggtcgcccga aaagatggca cccttggcaa caccttacag    180

ccatctttta ccaccaaccc cgaccctgta tggtcaagct tatttgccca aagttatggc    240

aaaaccgcca gtcccaacac gcctgacaat cccactggca ctaactatgc cgtgggcgga    300

gctcgctctg gctcggaggt caattggaat ggttttgtga atgtaccctc caccaaaacg    360

caaatcaccg accatttgac cgccacaggt ggcaaagccg accctaatac cctgtatgcc    420

atttggattg gctctaatga cttaatttca gcttctcaag ccaccacaac agccgaagcc    480

caaaacgcca ttaaaggtgc ggtaactcgc accgtgatag acatcgaaac actcaatcaa    540

gcaggggcga caaccatttt ggtgccaaat gtgcctgatt tgagcctcac gccccgagcc    600

atctatggcg aaagcctcat ggcaggcgtg caagacaaag ccaaactcgc ctcaagtctg    660

tataatagcg gtctgtttga agcattaaat caatccaccg ccaacatcat ccctgccaac    720

acctttgccc tactccaaga agcgaccaca aataaagaag cctttggttt taaaaacacg    780

caaggcgtgg cgtgtcaaat gcccgctcgt accacagggg cggatgatgt ggcttctact    840

tccttggcat gtaccaaagc caatcttata gaaaacgggg caaatgacac ctacgccttt    900

gccgatgaca ttcacccatc gggacgcacg caccgcattt tggcacagta ttaccgttct    960

atcatggacg cccctactca catgggtaaa ctctcaggcg agcttgtcaa aacaggttca   1020

gcccacgacc gtcatgttta ccgtcagctt gacaggctta gtggctcaca gcacagcatt   1080

tgggcaaacg tctatgccag cgaccgtacc gaccccacca cccaaatcgg cttggacgtg   1140

gcaggttcat caagccatac aggggcgtat ctgagccacc aaaaccaaga ttatgtgctg   1200

gatgacaccc tatcatcaga tgtcaaaacc attggcatgg ggctgtatca tcgccatgac   1260

atcggcaatg tccgtctaaa aggcgtggca ggtatcgacc gacttagcgt ggatacgcac   1320

cgccatatcg actgggaggg gacaagccgt tcgcacaccg cagataccac cgccagacgt   1380

tttcatgcag ggctacaagc cagctatggc atagacatgg gcaaagccac cgtgcgtccg   1440

cttatcggcg tacatgccca aaaagtcaaa gtaaatgaca tgaccgagag cgaatcaact   1500

ttatccaccg ccatgcgttt tggcgagcaa gaacaaaagt ccctacaagg cgagattggc   1560

gtcgatgtgg cttatccgat tagccctgct ttgactctga cgggcggtat cgctcacgct   1620

catgagttta acgatgatga acgcaccatt aatgccactt taacctccat tcgtgaatac   1680
```

acgaagggct ttaatacaag cgttagcacc gacaaatctc acgccaccac cgctcatctg 1740
ggcgtacaag ggcaacttgg caaggcaaat attcatgcag gcgttcacgc cacccaccaa 1800
gacagcgata cagacgtggg tggttcgctt ggggttcgct tgatgtttta a 1851

<210> SEQ ID NO 99
<211> LENGTH: 616
<212> TYPE: PRT
<213> ORGANISM: Moraxella bovis

<400> SEQUENCE: 99

Met Lys Lys Ser Ala Phe Ala Lys Tyr Ser Ala Leu Ala Leu Met Val
1 5 10 15

Gly Met Cys Leu His Thr Ala Tyr Ala Lys Glu Phe Ser Gln Val Ile
20 25 30

Ile Phe Gly Asp Ser Leu Ser Asp Thr Gly Arg Leu Lys Asp Met Val
35 40 45

Ala Arg Lys Asp Gly Thr Leu Gly Asn Thr Leu Gln Pro Ser Phe Thr
50 55 60

Thr Asn Pro Asp Pro Val Trp Ser Ser Leu Phe Ala Gln Ser Tyr Gly
65 70 75 80

Lys Thr Ala Ser Pro Asn Thr Pro Asp Asn Pro Thr Gly Thr Asn Tyr
85 90 95

Ala Val Gly Gly Ala Arg Ser Gly Ser Glu Val Asn Trp Asn Gly Phe
100 105 110

Val Asn Val Pro Ser Thr Lys Thr Gln Ile Thr Asp His Leu Thr Ala
115 120 125

Thr Gly Gly Lys Ala Asp Pro Asn Thr Leu Tyr Ala Ile Trp Ile Gly
130 135 140

Ser Asn Asp Leu Ile Ser Ala Ser Gln Ala Thr Thr Thr Ala Glu Ala
145 150 155 160

Gln Asn Ala Ile Lys Gly Ala Val Thr Arg Thr Val Ile Asp Ile Glu
165 170 175

Thr Leu Asn Gln Ala Gly Ala Thr Thr Ile Leu Val Pro Asn Val Pro
180 185 190

Asp Leu Ser Leu Thr Pro Arg Ala Ile Tyr Gly Glu Ser Leu Met Ala
195 200 205

Gly Val Gln Asp Lys Ala Lys Leu Ala Ser Ser Leu Tyr Asn Ser Gly
210 215 220

Leu Phe Glu Ala Leu Asn Gln Ser Thr Ala Asn Ile Ile Pro Ala Asn
225 230 235 240

Thr Phe Ala Leu Leu Gln Glu Ala Thr Thr Asn Lys Glu Ala Phe Gly
245 250 255

Phe Lys Asn Thr Gln Gly Val Ala Cys Gln Met Pro Ala Arg Thr Thr
260 265 270

Gly Ala Asp Asp Val Ala Ser Thr Ser Leu Ala Cys Thr Lys Ala Asn
275 280 285

Leu Ile Glu Asn Gly Ala Asn Asp Thr Tyr Ala Phe Ala Asp Asp Ile
290 295 300

His Pro Ser Gly Arg Thr His Arg Ile Leu Ala Gln Tyr Tyr Arg Ser
305 310 315 320

Ile Met Asp Ala Pro Thr His Met Gly Lys Leu Ser Gly Glu Leu Val
325 330 335

Lys Thr Gly Ser Ala His Asp Arg His Val Tyr Arg Gln Leu Asp Arg

```
            340                 345                 350

Leu Ser Gly Ser Gln His Ser Ile Trp Ala Asn Val Tyr Ala Ser Asp
        355                 360                 365

Arg Thr Asp Pro Thr Thr Gln Ile Gly Leu Asp Val Ala Gly Ser Ser
    370                 375                 380

Ser His Thr Gly Ala Tyr Leu Ser His Gln Asn Gln Asp Tyr Val Leu
385                 390                 395                 400

Asp Asp Thr Leu Ser Ser Asp Val Lys Thr Ile Gly Met Gly Leu Tyr
                405                 410                 415

His Arg His Asp Ile Gly Asn Val Arg Leu Lys Gly Val Ala Gly Ile
            420                 425                 430

Asp Arg Leu Ser Val Asp Thr His Arg His Ile Asp Trp Glu Gly Thr
        435                 440                 445

Ser Arg Ser His Thr Ala Asp Thr Thr Ala Arg Arg Phe His Ala Gly
    450                 455                 460

Leu Gln Ala Ser Tyr Gly Ile Asp Met Gly Lys Ala Thr Val Arg Pro
465                 470                 475                 480

Leu Ile Gly Val His Ala Gln Lys Val Lys Val Asn Asp Met Thr Glu
                485                 490                 495

Ser Glu Ser Thr Leu Ser Thr Ala Met Arg Phe Gly Glu Gln Glu Gln
            500                 505                 510

Lys Ser Leu Gln Gly Glu Ile Gly Val Asp Val Ala Tyr Pro Ile Ser
        515                 520                 525

Pro Ala Leu Thr Leu Thr Gly Gly Ile Ala His Ala His Glu Phe Asn
    530                 535                 540

Asp Asp Glu Arg Thr Ile Asn Ala Thr Leu Thr Ser Ile Arg Glu Tyr
545                 550                 555                 560

Thr Lys Gly Phe Asn Thr Ser Val Ser Thr Asp Lys Ser His Ala Thr
                565                 570                 575

Thr Ala His Leu Gly Val Gln Gly Gln Leu Gly Lys Ala Asn Ile His
            580                 585                 590

Ala Gly Val His Ala Thr His Gln Asp Ser Asp Thr Asp Val Gly Gly
        595                 600                 605

Ser Leu Gly Val Arg Leu Met Phe
    610                 615


<210> SEQ ID NO 100
<211> LENGTH: 597
<212> TYPE: DNA
<213> ORGANISM: Chromobacterium violaceum

<400> SEQUENCE: 100

atgcgctcta tcgtctgcaa aatgctgttc cctttgttgc tgctgtggca gctgcccgcc      60

ctggccgcca ccgtgctggt gttcggcgac agcctgtccg ccggctacgg cctggccccg     120

ggccagggat gggcggcgct gctggcgcgc gacctctcgc cccggcacaa ggtggtcaac     180

gccagcgtgt ccggcgaaac cagcgccggc ggcctgtcca ggctgcccga cgcgctcgcc     240

cgccaccagc ccgacgtgct ggtgctggaa ctcggcgcca acgatggcct gcgcggcctg     300

ccgatggctg acatgaggcg caacctgcag cggatgatag acctggccca ggcgcgcaag     360

gccaaggtgc tgctggtggg catggcgctg ccacccaact atggcccccg ctacggcgcc     420

gagttccgcg ccgtttatga cgatttggcc cgccgcaacc gcctggccta cgtgccgctg     480

ctggtcgagg gcttcgccgg cgacctcggc gccttccagc ccgacggcct gcatccccgc     540
```

gcggagaagc aggccaccat gatgcgcacg gtcaaggcaa aactgccagt gaaataa 597

<210> SEQ ID NO 101
<211> LENGTH: 198
<212> TYPE: PRT
<213> ORGANISM: Chromobacterium violaceum

<400> SEQUENCE: 101

Met Arg Ser Ile Val Cys Lys Met Leu Phe Pro Leu Leu Leu Leu Trp
1 5 10 15

Gln Leu Pro Ala Leu Ala Ala Thr Val Leu Val Phe Gly Asp Ser Leu
20 25 30

Ser Ala Gly Tyr Gly Leu Ala Pro Gly Gln Gly Trp Ala Ala Leu Leu
35 40 45

Ala Arg Asp Leu Ser Pro Arg His Lys Val Val Asn Ala Ser Val Ser
50 55 60

Gly Glu Thr Ser Ala Gly Gly Leu Ser Arg Leu Pro Asp Ala Leu Ala
65 70 75 80

Arg His Gln Pro Asp Val Leu Val Leu Glu Leu Gly Ala Asn Asp Gly
85 90 95

Leu Arg Gly Leu Pro Met Ala Asp Met Arg Arg Asn Leu Gln Arg Met
100 105 110

Ile Asp Leu Ala Gln Ala Arg Lys Ala Lys Val Leu Leu Val Gly Met
115 120 125

Ala Leu Pro Pro Asn Tyr Gly Pro Arg Tyr Gly Ala Glu Phe Arg Ala
130 135 140

Val Tyr Asp Asp Leu Ala Arg Arg Asn Arg Leu Ala Tyr Val Pro Leu
145 150 155 160

Leu Val Glu Gly Phe Ala Gly Asp Leu Gly Ala Phe Gln Pro Asp Gly
165 170 175

Leu His Pro Arg Ala Glu Lys Gln Ala Thr Met Met Arg Thr Val Lys
180 185 190

Ala Lys Leu Pro Val Lys
195

<210> SEQ ID NO 102
<211> LENGTH: 576
<212> TYPE: DNA
<213> ORGANISM: Vibrio vulnificus

<400> SEQUENCE: 102
atgtttttcc tttctagcgt cgcacacgca accgagaaag tgttaattct tggcgacagc 60
ctaagtgcag gatacaacat gtctgcagag caggcttggc ctaatttgtt accagaagca 120
ttgaatacat acggaaaaaa cgtagaagtg atcaacgcca gtatctctgg agacacaacc 180
ggcaatggac tatctcgtct gcctgagttg ttaaaaacgc actcaccaga ctgggtgctt 240
attgagttgg gtgccaatga tggcttgcga ggtttcccgc ataaagtgat ctcttcaaac 300
ctttcgcgaa tgattcaact cagtaaagcc tcagacgcta aagtcgcatt gatgcaaatt 360
cgtgtaccgc ctaactatgg caagcgctac accgatgcat ttgtcgaact ctaccctacg 420
cttgctgaac atcaccaagt cccgttgctc ccctttttct tagaggaagt gatcgtgaaa 480
ccggaatgga tgatgcctga tggcttacac ccaatgcccg aagctcagcc ttggatcgct 540
caatttgttg caaaaacgtt ttacaaacat ctctaa 576

<210> SEQ ID NO 103

<211> LENGTH: 191
<212> TYPE: PRT
<213> ORGANISM: Vibrio vulnificus

<400> SEQUENCE: 103

Met Phe Phe Leu Ser Ser Val Ala His Ala Thr Glu Lys Val Leu Ile
1 5 10 15

Leu Gly Asp Ser Leu Ser Ala Gly Tyr Asn Met Ser Ala Glu Gln Ala
20 25 30

Trp Pro Asn Leu Leu Pro Glu Ala Leu Asn Thr Tyr Gly Lys Asn Val
35 40 45

Glu Val Ile Asn Ala Ser Ile Ser Gly Asp Thr Thr Gly Asn Gly Leu
50 55 60

Ser Arg Leu Pro Glu Leu Leu Lys Thr His Ser Pro Asp Trp Val Leu
65 70 75 80

Ile Glu Leu Gly Ala Asn Asp Gly Leu Arg Gly Phe Pro His Lys Val
85 90 95

Ile Ser Ser Asn Leu Ser Arg Met Ile Gln Leu Ser Lys Ala Ser Asp
100 105 110

Ala Lys Val Ala Leu Met Gln Ile Arg Val Pro Pro Asn Tyr Gly Lys
115 120 125

Arg Tyr Thr Asp Ala Phe Val Glu Leu Tyr Pro Thr Leu Ala Glu His
130 135 140

His Gln Val Pro Leu Leu Pro Phe Phe Leu Glu Glu Val Ile Val Lys
145 150 155 160

Pro Glu Trp Met Met Pro Asp Gly Leu His Pro Met Pro Glu Ala Gln
165 170 175

Pro Trp Ile Ala Gln Phe Val Ala Lys Thr Phe Tyr Lys His Leu
180 185 190

<210> SEQ ID NO 104
<211> LENGTH: 693
<212> TYPE: DNA
<213> ORGANISM: Ralstonia eutropha

<400> SEQUENCE: 104
atgccattga ccgcgccgtc tgaagtcgat ccgctgcaaa tcctggtcta tgccgattcg 60
ctttcgtggg gcatcgtgcc cggcacccgc cggcggcttc ccttcccggt tcgctggcca 120
ggccggctcg aactcggcct gaacgccgac ggcggcgccc cggtccgcat catcgaggac 180
tgcctgaacg gccggcgcac cgtctgggac gacccattca aaccgggccg caacggcttg 240
caagggctgg cgcagcgcat cgagatccat tccccggtgg cgctcgtggt tttgatgctg 300
ggcaacaacg atttccagtc catgcatccg cacaacgcct ggcatgcggc acagggcgtc 360
ggcgcgctgg tccacgccat ccggacggcg ccgatcgaac cgggaatgcc ggtgccgccg 420
atcctggtgg tggtgccgcc gccgatccgc acgccctgcg ggccgctcgc gcccaagttc 480
gccggcggcg aacacaagtg ggcaggcctg cccgaggcgc tgcgcgaact gtgcgccact 540
gtcgactgct cgctgttcga tgcgggtacc gtgatccaga gcagtgccgt cgacggcgta 600
caccttgacg ccgatgccca tgtcgccctg ggcgatgccc tgcaaccggt cgttcgtgcg 660
ctgctcgccg aatcctcggg acatccctcc taa 693

<210> SEQ ID NO 105
<211> LENGTH: 230
<212> TYPE: PRT
<213> ORGANISM: Ralstonia eutropha

<400> SEQUENCE: 105

Met Pro Leu Thr Ala Pro Ser Glu Val Asp Pro Leu Gln Ile Leu Val
1 5 10 15

Tyr Ala Asp Ser Leu Ser Trp Gly Ile Val Pro Gly Thr Arg Arg Arg
20 25 30

Leu Pro Phe Pro Val Arg Trp Pro Gly Arg Leu Glu Leu Gly Leu Asn
35 40 45

Ala Asp Gly Gly Ala Pro Val Arg Ile Ile Glu Asp Cys Leu Asn Gly
50 55 60

Arg Arg Thr Val Trp Asp Asp Pro Phe Lys Pro Gly Arg Asn Gly Leu
65 70 75 80

Gln Gly Leu Ala Gln Arg Ile Glu Ile His Ser Pro Val Ala Leu Val
85 90 95

Val Leu Met Leu Gly Asn Asn Asp Phe Gln Ser Met His Pro His Asn
100 105 110

Ala Trp His Ala Ala Gln Gly Val Gly Ala Leu Val His Ala Ile Arg
115 120 125

Thr Ala Pro Ile Glu Pro Gly Met Pro Val Pro Pro Ile Leu Val Val
130 135 140

Val Pro Pro Pro Ile Arg Thr Pro Cys Gly Pro Leu Ala Pro Lys Phe
145 150 155 160

Ala Gly Gly Glu His Lys Trp Ala Gly Leu Pro Glu Ala Leu Arg Glu
165 170 175

Leu Cys Ala Thr Val Asp Cys Ser Leu Phe Asp Ala Gly Thr Val Ile
180 185 190

Gln Ser Ser Ala Val Asp Gly Val His Leu Asp Ala Asp Ala His Val
195 200 205

Ala Leu Gly Asp Ala Leu Gln Pro Val Val Arg Ala Leu Leu Ala Glu
210 215 220

Ser Ser Gly His Pro Ser
225 230

<210> SEQ ID NO 106
<211> LENGTH: 1971
<212> TYPE: DNA
<213> ORGANISM: Salmonella typhimurium

<400> SEQUENCE: 106
atgacccaaa agcgtaccct gctaaaatac ggcatactct cgctggcgct ggccgcgcca 60
ttatctgcct gtgcgtttga ctctcttacg gtgattggcg atagccttag cgataccggt 120
aataacggtc gctggacctg ggatagtggt caaaataagc tctacgacga acagttggcc 180
gaacgatatg ggctggaatt aagcccttcc agcaatggcg gctctaatta tgccgccggc 240
ggcgcgacgg cgaccccgga attaaacccg caggataata ccgcggatca ggtacggcag 300
tggcttgcca aaacgggggg aaaagccgac cacaacggtt tgtatattca ctgggtcggc 360
ggaaacgatc tggcggcggc catcgcgcaa ccaaccatgg cacagcaaat agccggtaat 420
agcgccacta gcgcggcggc gcaggtaggg ctgttactgg atgccggcgc cgggctggtc 480
gtggtgccaa acgtaccgga tattagtgcg acgccaatgc ttctggaggc ggtaatcacc 540
gctgggctgg gcgcagcggc gcccccggcg ctaaaagcgg cgttagatgc gctggcggag 600
ggcgctacgc ccgatttcgc cagtcggcaa caggcgatcc gcaaggcgct gctggcggcg 660
gctgcaacgg taagcagcaa tccatttatt cagcaactgc tcgttgaaca actgctggcg 720
ggctatgaag cggcggcagg gcaggcgtca gctctgaccg attattataa tcagatggaa 780
gagaaggggc tggagcaaca cggcggcaat atagcccgtg ccgatatcaa cggcctcttt 840
aaggaaattc ttgccaaccc gcaggcgttt ggtctgacaa ataccgtagg tatggcctgc 900
ccgcctggcg tatccgcttc ggcgtgctcc tcggcaatgc ctggatttaa tgcgtcgcag 960
gactatgtgt ttgccgatca tttacatccc ggtccgcagg tccataccat tattgcgcaa 1020
tatattcagt cgatcattgc cgcgccggta caggcgacat acctgaacca aagcgttcag 1080
tcgatggcgc aaggcagtcg taccacgctt gacagccgtt atcagcagct tcgccagggg 1140
gaaaatcctg ttggttcgct gggcatgttc ggcggataca gcgggggata tcaacgttat 1200
gataataatg aggccgacgg gaacggtaat cataataatc tgacggttgg cgtcgattat 1260
cagcttaacg agcaggttct gctgggaggg ctgatagccg gttctctgga taagcaacat 1320
cctgacgata attatcgtta tgatgcccgc ggttttcagg ccgccgtatt cagccattta 1380
cgcgccggtc aggcgtggct ggatagcgat ttacactttc tgtccgctaa attcagtaac 1440
attcagcgca gtataacgct cggtgcgcta agacgggtgg aagagggcga aaccaacggt 1500
cggctgtcgg gcgcgagctt aaccagcggt tatgattttg tcatggtgcc gtggttaacg 1560
accggaccga tgctgcaata tgcatgggat tacagccacg ttaatggtta tagcgagaag 1620
ctcaatacca gtacatcaat gcgttttggt gaccaaaacg cccattcgca ggtgggtagc 1680
gcgggttggc gtctggatct tcgccacagc atcattcact cctgggcgca gattaattat 1740
cgccgtcagt ttggcgatga tacgtatgtg gcgaacggcg gccttaaatc gaccgcgctg 1800
acgtttagcc gcgacggaaa aacgcaggat aaaaactggg ttgatatcgc gattggcgca 1860
gattttccgc tgtcggcaac ggtgtccgct ttcgccgggc tgtcgcaaac ggcagggtta 1920
agcgatggca atcaaacccg ttataacgtt gggtttagcg cccgatttta a 1971

<210> SEQ ID NO 107
<211> LENGTH: 656
<212> TYPE: PRT
<213> ORGANISM: Salmonella typhimurium

<400> SEQUENCE: 107

Met Thr Gln Lys Arg Thr Leu Leu Lys Tyr Gly Ile Leu Ser Leu Ala
1 5 10 15

Leu Ala Ala Pro Leu Ser Ala Cys Ala Phe Asp Ser Leu Thr Val Ile
20 25 30

Gly Asp Ser Leu Ser Asp Thr Gly Asn Asn Gly Arg Trp Thr Trp Asp
35 40 45

Ser Gly Gln Asn Lys Leu Tyr Asp Glu Gln Leu Ala Glu Arg Tyr Gly
50 55 60

Leu Glu Leu Ser Pro Ser Ser Asn Gly Gly Ser Asn Tyr Ala Ala Gly
65 70 75 80

Gly Ala Thr Ala Thr Pro Glu Leu Asn Pro Gln Asp Asn Thr Ala Asp
85 90 95

Gln Val Arg Gln Trp Leu Ala Lys Thr Gly Gly Lys Ala Asp His Asn
100 105 110

Gly Leu Tyr Ile His Trp Val Gly Gly Asn Asp Leu Ala Ala Ala Ile
115 120 125

Ala Gln Pro Thr Met Ala Gln Gln Ile Ala Gly Asn Ser Ala Thr Ser
130 135 140

Ala Ala Ala Gln Val Gly Leu Leu Leu Asp Ala Gly Ala Gly Leu Val

-continued

```
145                 150                 155                 160

Val Val Pro Asn Val Pro Asp Ile Ser Ala Thr Pro Met Leu Leu Glu
                165                 170                 175

Ala Val Ile Thr Ala Gly Leu Gly Ala Ala Ala Pro Pro Ala Leu Lys
            180                 185                 190

Ala Ala Leu Asp Ala Leu Ala Glu Gly Ala Thr Pro Asp Phe Ala Ser
        195                 200                 205

Arg Gln Gln Ala Ile Arg Lys Ala Leu Leu Ala Ala Ala Ala Thr Val
    210                 215                 220

Ser Ser Asn Pro Phe Ile Gln Gln Leu Leu Val Glu Gln Leu Leu Ala
225                 230                 235                 240

Gly Tyr Glu Ala Ala Ala Gly Gln Ala Ser Ala Leu Thr Asp Tyr Tyr
                245                 250                 255

Asn Gln Met Glu Glu Lys Gly Leu Glu Gln His Gly Gly Asn Ile Ala
            260                 265                 270

Arg Ala Asp Ile Asn Gly Leu Phe Lys Glu Ile Leu Ala Asn Pro Gln
        275                 280                 285

Ala Phe Gly Leu Thr Asn Thr Val Gly Met Ala Cys Pro Pro Gly Val
    290                 295                 300

Ser Ala Ser Ala Cys Ser Ser Ala Met Pro Gly Phe Asn Ala Ser Gln
305                 310                 315                 320

Asp Tyr Val Phe Ala Asp His Leu His Pro Gly Pro Gln Val His Thr
                325                 330                 335

Ile Ile Ala Gln Tyr Ile Gln Ser Ile Ile Ala Ala Pro Val Gln Ala
            340                 345                 350

Thr Tyr Leu Asn Gln Ser Val Gln Ser Met Ala Gln Gly Ser Arg Thr
        355                 360                 365

Thr Leu Asp Ser Arg Tyr Gln Gln Leu Arg Gln Gly Glu Asn Pro Val
    370                 375                 380

Gly Ser Leu Gly Met Phe Gly Gly Tyr Ser Gly Gly Tyr Gln Arg Tyr
385                 390                 395                 400

Asp Asn Asn Glu Ala Asp Gly Asn Gly Asn His Asn Asn Leu Thr Val
                405                 410                 415

Gly Val Asp Tyr Gln Leu Asn Glu Gln Val Leu Leu Gly Gly Leu Ile
            420                 425                 430

Ala Gly Ser Leu Asp Lys Gln His Pro Asp Asp Asn Tyr Arg Tyr Asp
        435                 440                 445

Ala Arg Gly Phe Gln Ala Ala Val Phe Ser His Leu Arg Ala Gly Gln
    450                 455                 460

Ala Trp Leu Asp Ser Asp Leu His Phe Leu Ser Ala Lys Phe Ser Asn
465                 470                 475                 480

Ile Gln Arg Ser Ile Thr Leu Gly Ala Leu Arg Arg Val Glu Glu Gly
                485                 490                 495

Glu Thr Asn Gly Arg Leu Ser Gly Ala Ser Leu Thr Ser Gly Tyr Asp
            500                 505                 510

Phe Val Met Val Pro Trp Leu Thr Thr Gly Pro Met Leu Gln Tyr Ala
        515                 520                 525

Trp Asp Tyr Ser His Val Asn Gly Tyr Ser Glu Lys Leu Asn Thr Ser
    530                 535                 540

Thr Ser Met Arg Phe Gly Asp Gln Asn Ala His Ser Gln Val Gly Ser
545                 550                 555                 560

Ala Gly Trp Arg Leu Asp Leu Arg His Ser Ile Ile His Ser Trp Ala
                565                 570                 575
```

-continued

```
Gln Ile Asn Tyr Arg Arg Gln Phe Gly Asp Asp Thr Tyr Val Ala Asn
            580                 585                 590

Gly Gly Leu Lys Ser Thr Ala Leu Thr Phe Ser Arg Asp Gly Lys Thr
        595                 600                 605

Gln Asp Lys Asn Trp Val Asp Ile Ala Ile Gly Ala Asp Phe Pro Leu
    610                 615                 620

Ser Ala Thr Val Ser Ala Phe Ala Gly Leu Ser Gln Thr Ala Gly Leu
625                 630                 635                 640

Ser Asp Gly Asn Gln Thr Arg Tyr Asn Val Gly Phe Ser Ala Arg Phe
                645                 650                 655
```

<210> SEQ ID NO 108
<211> LENGTH: 222
<212> TYPE: PRT
<213> ORGANISM: Agrobacterium rhizogenes

<400> SEQUENCE: 108

```
Met Ile Cys His Lys Gly Gly Glu Glu Met Arg Ser Val Leu Cys Tyr
1               5                   10                  15

Gly Asp Ser Asn Thr His Gly Gln Ile Pro Gly Gly Ser Pro Leu Asp
            20                  25                  30

Arg Tyr Gly Pro Asn Glu Arg Trp Pro Gly Val Leu Arg Arg Glu Leu
        35                  40                  45

Gly Ser Gln Trp Tyr Val Ile Glu Glu Gly Leu Ser Gly Arg Thr Thr
    50                  55                  60

Val Arg Asp Asp Pro Ile Glu Gly Thr Met Lys Asn Gly Arg Thr Tyr
65                  70                  75                  80

Leu Arg Pro Cys Leu Met Ser His Ala Ile Leu Asp Leu Val Ile Ile
                85                  90                  95

Met Leu Gly Thr Asn Asp Leu Lys Ala Arg Phe Gly Gln Pro Pro Ser
            100                 105                 110

Glu Val Ala Met Gly Ile Gly Cys Leu Val Tyr Asp Ile Arg Glu Leu
        115                 120                 125

Ala Pro Gly Pro Gly Gly Lys Pro Pro Glu Ile Met Val Val Ala Pro
    130                 135                 140

Pro Pro Met Leu Asp Asp Ile Lys Glu Trp Glu Pro Ile Phe Ser Gly
145                 150                 155                 160

Ala Gln Glu Lys Ser Arg Arg Leu Ala Leu Glu Phe Glu Ile Ile Ala
                165                 170                 175

Asp Ser Leu Glu Val His Phe Phe Asp Ala Ala Thr Val Ala Ser Cys
            180                 185                 190

Asp Pro Cys Asp Gly Phe His Ile Asn Arg Glu Ala His Glu Ala Leu
        195                 200                 205

Gly Thr Ala Leu Ala Arg Glu Val Glu Ala Ile Gly Trp Arg
    210                 215                 220
```

<210> SEQ ID NO 109
<211> LENGTH: 672
<212> TYPE: DNA
<213> ORGANISM: Agrobacterium rhizogenes

<400> SEQUENCE: 109

```
atgatttgcc ataaaggtgg ggaggaaatg cggtcagtct tatgctacgg cgactcgaat      60

acgcacggcc agattccggg gggctcaccg ctcgaccgat acgggccgaa cgagcgctgg     120

cctggcgttt tgagacggga gcttggaagc cagtggtatg tgatcgagga gggcctgagt     180
```

```
ggccgcacga cggttcgcga cgatccgatc gagggcacga tgaaaaacgg ccggacctac    240

ctgcgtccgt gcctcatgag ccacgcgatc ctcgatctcg tgattatcat gctcgggacg    300

aacgacctga aagcgcgctt cggtcaaccg ccatcggaag tggcgatggg gatcggctgc    360

ctcgtctacg atatcaggga gctggcgccc ggaccgggcg gcaagccccc cgaaatcatg    420

gtggttgctc cgccgccgat gctggacgat atcaaggaat gggaacccat attttccggc    480

gcccaggaga aatcccggcg tctcgcgctt gagtttgaaa ttattgctga ttcgcttgaa    540

gtacacttct ttgacgccgc gaccgtcgca tcgtgtgatc cttgcgatgg ttttcacatc    600

aaccgggaag cgcatgaagc cttgggaaca gcgcttgcca gggaagtgga ggcgatcggt    660

tggagatgat ga                                                        672
```

```
<210> SEQ ID NO 110
<211> LENGTH: 227
<212> TYPE: PRT
<213> ORGANISM: Agrobacterium rhizogenes

<400> SEQUENCE: 110

Met Ala Glu Ser Arg Ser Ile Leu Cys Phe Gly Asp Ser Leu Thr Trp
1               5                   10                  15

Gly Trp Ile Pro Val Pro Glu Ser Ser Pro Thr Leu Arg Tyr Pro Phe
            20                  25                  30

Glu Gln Arg Trp Thr Gly Ala Met Ala Ala Ala Leu Gly Asp Gly Tyr
        35                  40                  45

Ser Ile Ile Glu Glu Gly Leu Ser Ala Arg Thr Thr Ser Val Glu Asp
    50                  55                  60

Pro Asn Asp Pro Arg Leu Asn Gly Ser Ala Tyr Leu Pro Met Ala Leu
65                  70                  75                  80

Ala Ser His Leu Pro Leu Asp Leu Val Ile Ile Leu Leu Gly Thr Asn
                85                  90                  95

Asp Thr Lys Ser Tyr Phe Arg Arg Thr Pro Tyr Glu Ile Ala Asn Gly
            100                 105                 110

Met Gly Lys Leu Ala Gly Gln Val Leu Thr Ser Ala Gly Gly Ile Gly
        115                 120                 125

Thr Pro Tyr Pro Ala Pro Lys Leu Leu Ile Val Ser Pro Pro Pro Leu
    130                 135                 140

Ala Pro Met Pro Asp Pro Trp Phe Glu Gly Met Phe Gly Gly Gly Tyr
145                 150                 155                 160

Glu Lys Ser Leu Glu Leu Ala Lys Gln Tyr Lys Ala Leu Ala Asn Phe
                165                 170                 175

Leu Lys Val Asp Phe Leu Asp Ala Gly Glu Phe Val Lys Thr Asp Gly
            180                 185                 190

Cys Asp Gly Ile His Phe Ser Ala Glu Thr Asn Ile Thr Leu Gly His
        195                 200                 205

Ala Ile Ala Ala Lys Val Glu Ala Ile Phe Ser Gln Glu Ala Lys Asn
    210                 215                 220

Ala Ala Ala
225


<210> SEQ ID NO 111
<211> LENGTH: 684
<212> TYPE: DNA
<213> ORGANISM: Agrobacterium rhizogenes

<400> SEQUENCE: 111
```

```
atggcagaga gccgctcaat attatgtttt ggggattcac tcacatgggg ttggattccg     60

gtaccggagt cgtcgccgac gctcagatat ccctttgagc agcgctggac cggtgcaatg    120

gctgcggcac tcggtgacgg ctattcaatc atcgaggaag gcctttccgc ccgcacgacc    180

agcgtcgagg atccgaacga tcccaggctg aacggcagcg cctacctgcc gatggcgctc    240

gccagccatc tgccgctcga tctcgtcatc atccttctcg gcaccaacga caccaagtcc    300

tatttccgcc gcacgcccta tgagatcgcc aacggcatgg gcaagcttgc cggacaggtt    360

ctgacctcgg ccggcgggat cggcacgccc taccctgccc cgaagcttct gatcgtttcg    420

ccgccgccgc tcgctcccat gcctgacccg tggttcgaag gcatgttcgg tggcggttac    480

gaaaagtcgc tcgaactcgc aaagcagtac aaggcgctcg ccaacttcct gaaggtcgac    540

ttcctcgacg ccggcgagtt tgtaaagacc gacggctgcg atggaatcca tttctccgcc    600

gagacgaaca tcacgctcgg ccatgcgatc gcggcgaagg tcgaagcgat tttctcacaa    660

gaggcgaaga acgctgcggc ttag                                           684
```

<210> SEQ ID NO 112
<211> LENGTH: 212
<212> TYPE: PRT
<213> ORGANISM: Mesorhizobium loti

<400> SEQUENCE: 112

```
Met Lys Thr Ile Leu Cys Tyr Gly Asp Ser Leu Thr Trp Gly Tyr Asp
1               5                   10                  15

Ala Val Gly Pro Ser Arg His Ala Tyr Glu Asp Arg Trp Pro Ser Val
            20                  25                  30

Leu Gln Gly Arg Leu Gly Ser Ser Ala Arg Val Ile Ala Glu Gly Leu
        35                  40                  45

Cys Gly Arg Thr Thr Ala Phe Asp Asp Trp Val Ala Gly Ala Asp Arg
    50                  55                  60

Asn Gly Ala Arg Ile Leu Pro Thr Leu Leu Ala Thr His Ser Pro Leu
65                  70                  75                  80

Asp Leu Val Ile Val Met Leu Gly Thr Asn Asp Met Lys Ser Phe Val
                85                  90                  95

Cys Gly Arg Ala Ile Gly Ala Lys Gln Gly Met Glu Arg Ile Val Gln
            100                 105                 110

Ile Ile Arg Gly Gln Pro Tyr Ser Phe Asn Tyr Lys Val Pro Ser Ile
        115                 120                 125

Leu Leu Val Ala Pro Pro Pro Leu Cys Ala Thr Glu Asn Ser Asp Phe
    130                 135                 140

Ala Glu Ile Phe Glu Gly Gly Met Ala Glu Ser Gln Lys Leu Ala Pro
145                 150                 155                 160

Leu Tyr Ala Ala Leu Ala Gln Gln Thr Gly Cys Ala Phe Phe Asp Ala
                165                 170                 175

Gly Thr Val Ala Arg Thr Thr Pro Leu Asp Gly Ile His Leu Asp Ala
            180                 185                 190

Glu Asn Thr Arg Ala Ile Gly Ala Gly Leu Glu Pro Val Val Arg Gln
        195                 200                 205

Ala Leu Gly Leu
    210
```

<210> SEQ ID NO 113
<211> LENGTH: 699
<212> TYPE: DNA

<213> ORGANISM: Mesorhizobium loti

<400> SEQUENCE: 113
atgaagacca tcctttgtta cggtgactcc ctcacttggg gctatgatgc cgtcggaccc 60
atgaagacca tcctttgtta cggtgactcc ctcacttggg gctatgatgc cgtcggaccc 120
tcacggcatg cttatgagga tcgatggccc tccgtactgc aaggccgcct cggtagcagt 180
gcgcgggtga tcgccgaggg gctttgcggc cgcacaactg cgtttgacga ctgggtcgct 240
ggtgcggacc ggaacggtgc gcgcatcctg ccgacgcttc ttgcgaccca ttcaccgctt 300
gacctcgtta tcgtcatgct cgggacgaac gacatgaaat cgttcgtttg cgggcgcgct 360
atcggcgcca agcaggggat ggagcggatc gtccagatca tccgcgggca gccttattcc 420
ttcaattata aggtaccgtc gattcttctc gtggcgccgc cgccgctgtg cgctaccgaa 480
aacagcgatt tcgcggaaat ttttgaaggt ggcatggctg aatcgcaaaa gctcgcgccg 540
ctttatgccg cgctggccca gcaaaccgga tgcgccttct tcgatgcagg cactgtggcc 600
cgcacgacac cgctcgacgg tattcacctc gatgctgaaa acacgcgcgc cattggtgcc 660
ggcctggagc cggtggtccg ccaagcgctt ggattgtga 699

<210> SEQ ID NO 114
<211> LENGTH: 213
<212> TYPE: PRT
<213> ORGANISM: Ralstonia solanacearum

<400> SEQUENCE: 114

Met Gln Gln Ile Leu Leu Tyr Ser Asp Ser Leu Ser Trp Gly Ile Ile
1 5 10 15

Pro Gly Thr Arg Arg Arg Leu Pro Phe Ala Ala Arg Trp Ala Gly Val
20 25 30

Met Glu His Ala Leu Gln Ala Gln Gly His Ala Val Arg Ile Val Glu
35 40 45

Asp Cys Leu Asn Gly Arg Thr Thr Val Leu Asp Asp Pro Ala Arg Pro
50 55 60

Gly Arg Asn Gly Leu Gln Gly Leu Ala Gln Arg Ile Glu Ala His Ala
65 70 75 80

Pro Leu Ala Leu Val Ile Leu Met Leu Gly Thr Asn Asp Phe Gln Ala
85 90 95

Ile Phe Arg His Thr Ala Gln Asp Ala Ala Gln Gly Val Ala Gln Leu
100 105 110

Val Arg Ala Ile Arg Gln Ala Pro Ile Glu Pro Gly Met Pro Val Pro
115 120 125

Pro Val Leu Ile Val Val Pro Pro Ala Ile Thr Ala Pro Ala Gly Ala
130 135 140

Met Ala Asp Lys Phe Ala Asp Ala Gln Pro Lys Cys Ala Gly Leu Ala
145 150 155 160

Gln Ala Tyr Arg Ala Thr Ala Gln Thr Leu Gly Cys His Val Phe Asp
165 170 175

Ala Asn Ser Val Thr Pro Ala Ser Arg Val Asp Gly Ile His Leu Asp
180 185 190

Ala Asp Gln His Ala Gln Leu Gly Arg Ala Met Ala Gln Val Val Gly
195 200 205

Thr Leu Leu Ala Gln
210

<210> SEQ ID NO 115
<211> LENGTH: 642
<212> TYPE: DNA
<213> ORGANISM: Ralstonia solanacearum

<400> SEQUENCE: 115
atgcaacaga tcctgctcta ttccgactcg ctctcctggg gcatcatccc cggcacccgc 60
cggcgcctgc cgttcgccgc ccgctgggcc ggggtcatgg aacacgcgct gcaggcgcaa 120
gggcacgccg tgcgcatcgt cgaagactgc ctcaatggac gcaccacggt gctcgacgat 180
cccgcgcggc cggggcgcaa cggactgcag gggctcgcgc agcggatcga agcgcacgcc 240
ccgcttgccc tggtcatcct gatgctcggc accaacgact tccaggcgat cttccggcac 300
accgcccagg acgcggcgca aggcgtggcg cagctggtgc gggccatccg ccaggcgccg 360
atcgaacccg gcatgccggt gccgcccgtg ctgatcgtgg tgccgccggc catcaccgcg 420
ccggccgggg cgatggccga caagtttgcc gacgcgcagc ccaagtgcgc cggccttgcg 480
caggcctatc gggcaacggc gcaaacgcta ggctgccacg tcttcgatgc gaacagcgtc 540
acgccggcca gccgcgtgga cggcatccac ctcgatgccg accagcatgc gcagctgggc 600
cgggcgatgg cgcaggtcgt cgggacgctg cttgcgcaat aa 642

<210> SEQ ID NO 116
<211> LENGTH: 651
<212> TYPE: DNA
<213> ORGANISM: Burkholderia cepacia

<400> SEQUENCE: 116
atgacgatga cgcagaaaac cgtgctctgc tacggcgatt cgaacacgca tggcacacgc 60
ccgatgacgc atgctggcgg actggggcgg tttgcacgcg aagaacgctg gaccggcgtg 120
ctggcgcaaa cgctcggtgc gagctggcgg gtcattgaag aagggttgcc cgcgcgtacg 180
accgtgcatg acgatccgat cgaaggccgg cacaagaatg gtttgtcgta tctgcgcgcg 240
tgcgtcgaaa gccacttgcc cgtcgatgtc gtcgtgctga tgctcgggac caacgatctg 300
aagacacgct tctcggtcac gcccgccgac atcgcgacat cggtcggcgt attgcttgcc 360
aagatcgctg cgtgcggcgc cggtccgtcc ggtgcgtcac cgaagctcgt gctgatggcg 420
cctgcgccga tcgtcgaggt cggattcctc ggcgagatct ttgcgggcgg cgcagcgaag 480
tcgcggcagc tcgcgaagcg gtacgaacag gtggcaagcg atgccggtgc gcactttctc 540
gatgccggcg cgatcgtcga ggtgagcccg gtggatggcg ttcacttcgc ggccgatcag 600
catcgtgtgc tcgggcagcg ggtcgctgcc cttctgcagc agattgcgta a 651

<210> SEQ ID NO 117
<211> LENGTH: 216
<212> TYPE: PRT
<213> ORGANISM: Burkholderia cepacia

<400> SEQUENCE: 117

Met Thr Met Thr Gln Lys Thr Val Leu Cys Tyr Gly Asp Ser Asn Thr
1 5 10 15

His Gly Thr Arg Pro Met Thr His Ala Gly Gly Leu Gly Arg Phe Ala
20 25 30

Arg Glu Glu Arg Trp Thr Gly Val Leu Ala Gln Thr Leu Gly Ala Ser
35 40 45

Trp Arg Val Ile Glu Glu Gly Leu Pro Ala Arg Thr Thr Val His Asp
50 55 60

-continued

```
Asp Pro Ile Glu Gly Arg His Lys Asn Gly Leu Ser Tyr Leu Arg Ala
65                  70                  75                  80

Cys Val Glu Ser His Leu Pro Val Asp Val Val Val Leu Met Leu Gly
                85                  90                  95

Thr Asn Asp Leu Lys Thr Arg Phe Ser Val Thr Pro Ala Asp Ile Ala
            100                 105                 110

Thr Ser Val Gly Val Leu Leu Ala Lys Ile Ala Ala Cys Gly Ala Gly
        115                 120                 125

Pro Ser Gly Ala Ser Pro Lys Leu Val Leu Met Ala Pro Ala Pro Ile
    130                 135                 140

Val Glu Val Gly Phe Leu Gly Glu Ile Phe Ala Gly Gly Ala Ala Lys
145                 150                 155                 160

Ser Arg Gln Leu Ala Lys Arg Tyr Glu Gln Val Ala Ser Asp Ala Gly
                165                 170                 175

Ala His Phe Leu Asp Ala Gly Ala Ile Val Glu Val Ser Pro Val Asp
            180                 185                 190

Gly Val His Phe Ala Ala Asp Gln His Arg Val Leu Gly Gln Arg Val
        195                 200                 205

Ala Ala Leu Leu Gln Gln Ile Ala
    210                 215
```

<210> SEQ ID NO 118
<211> LENGTH: 214
<212> TYPE: PRT
<213> ORGANISM: Pirellula spp.

<400> SEQUENCE: 118

```
Met His Ser Ile Leu Ile Tyr Gly Asp Ser Leu Ser Trp Gly Ile Ile
1               5                   10                  15

Pro Gly Thr Arg Arg Arg Phe Ala Phe His Gln Arg Trp Pro Gly Val
            20                  25                  30

Met Glu Ile Glu Leu Arg Gln Thr Gly Ile Asp Ala Arg Val Ile Glu
        35                  40                  45

Asp Cys Leu Asn Gly Arg Arg Thr Val Leu Glu Asp Pro Ile Lys Pro
    50                  55                  60

Gly Arg Asn Gly Leu Asp Gly Leu Gln Gln Arg Ile Glu Ile Asn Ser
65                  70                  75                  80

Pro Leu Ser Leu Val Val Leu Phe Leu Gly Thr Asn Asp Phe Gln Ser
                85                  90                  95

Val His Glu Phe His Ala Glu Gln Ser Ala Gln Gly Leu Ala Leu Leu
            100                 105                 110

Val Asp Ala Ile Arg Arg Ser Pro Phe Glu Pro Gly Met Pro Thr Pro
        115                 120                 125

Lys Ile Leu Leu Val Ala Pro Pro Thr Val His His Pro Lys Leu Asp
    130                 135                 140

Met Ala Ala Lys Phe Gln Asn Ala Glu Thr Lys Ser Thr Gly Leu Ala
145                 150                 155                 160

Asp Ala Ile Arg Lys Val Ser Thr Glu His Ser Cys Glu Phe Phe Asp
                165                 170                 175

Ala Ala Thr Val Thr Thr Thr Ser Val Val Asp Gly Val His Leu Asp
            180                 185                 190

Gln Glu Gln His Gln Ala Leu Gly Thr Ala Leu Ala Ser Thr Ile Ala
        195                 200                 205

Glu Ile Leu Ala Asp Cys
    210
```

<210> SEQ ID NO 119
<211> LENGTH: 645
<212> TYPE: DNA
<213> ORGANISM: Pirellula spp.

<400> SEQUENCE: 119
atgcattcaa tcctcatcta tggcgattct ctcagttggg gaatcattcc cggcacgcgt 60
cgtcgcttcg cgttccatca gcgttggccg ggcgtcatgg agattgaact gcgacaaact 120
ggaatcgatg cccgcgtcat cgaagactgc ctcaatggcc gacgaaccgt cttggaagat 180
ccaatcaaac ccggacgcaa tggcctggat ggtttgcagc aacggatcga aatcaattca 240
cctctgtcac tggtcgtgct ctttctgggg accaacgatt tccagtccgt ccacgaattc 300
catgccgagc aatcggcaca aggactcgca ctgcttgtcg acgccattcg tcgctcccct 360
ttcgaaccag gaatgccgac accgaaaatc ctgcttgtcg caccaccgac ggttcaccac 420
ccgaaacttg atatggcggc gaagttccaa aacgcggaaa cgaaatcgac gggactcgca 480
gatgcgattc gcaaggtctc aacagaacac tcctgcgaat tcttcgatgc ggccacggtc 540
accacaacaa gtgtcgtcga cggagtccat ctcgatcaag aacaacatca agcactcggt 600
accgcactgg catcgacaat cgctgaaata ctagcagact gttga 645

<210> SEQ ID NO 120
<211> LENGTH: 708
<212> TYPE: DNA
<213> ORGANISM: Artificial Sequence
<220> FEATURE:
<223> OTHER INFORMATION: S248_M31bA11 clone
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t

<400> SEQUENCE: 120
cggaattatc atgctgggtt ttaatgacca gcgcgagagg atcaacgaca acctcgatta 60
ctgggacgcc taccactccg tcctgggcga gagacagttt tattccggca attccaagat 120
gttcgtcccc atcaccaaga tcgcggtgaa ggcgcgcaag acccggttca ccaatcagat 180
ttttcctcag tccggccgca acgtcgatgt caccaccacg gacggcacac tcccccacgc 240
caccatgtcc ctggtcgagc actacatccg ggcctgccgc ctgcgcaccc agatcgttcc 300
ggccctgatc gttaacggcg attgcgaagg catgtacagc atctatgtcg gctggtcgaa 360
aaccaccaag catgttgttt cacgtgaaac aaagccggtc gaaagcgacg gcatggaatt 420
tcccgaactg ggcgaagccg acgacatcac cgaagaaacg cttgagtgtg gccttcccga 480
catcgaattg atctcggacg ccgatcttct cgtccttcca ccagcgccga caacattcca 540
aggcgcttga gatgggcggg ttcggtcacg atcttgcgcc gtggacaagg gcaaggtccg 600
cagatgatcg acgaggcgcg atcaccgaga tgccgcgacg atctgtcgac gctatgtcac 660
cagcgcatgt ccgacggtgg aatgcaagac aggtnggntn gatcgggg 708

<210> SEQ ID NO 121

<211> LENGTH: 229
<212> TYPE: PRT
<213> ORGANISM: Artificial Sequence
<220> FEATURE:
<223> OTHER INFORMATION: S248_M31bA11 clone

<400> SEQUENCE: 121

Arg Asn Tyr His Ala Gly Phe Pro Ala Arg Glu Asp Gln Arg Gln Pro
1 5 10 15

Arg Leu Leu Gly Arg Leu Pro Leu Arg Pro Gly Arg Glu Thr Val Leu
20 25 30

Phe Arg Gln Phe Gln Asp Val Arg Pro His His Gln Asp Arg Gly Glu
35 40 45

Gly Ala Gln Asp Pro Val His Gln Ser Asp Phe Ser Ser Val Arg Pro
50 55 60

Gln Arg Arg Cys His His His Gly Arg His Thr Pro Pro Arg His His
65 70 75 80

Val Pro Gly Arg Ala Leu His Pro Gly Leu Pro Pro Ala His Pro Asp
85 90 95

Arg Ser Gly Pro Asp Arg Arg Arg Leu Arg Arg His Val Gln His Leu
100 105 110

Cys Arg Leu Val Glu Asn His Gln Ala Cys Cys Phe Thr Asn Lys Ala
115 120 125

Gly Arg Lys Arg Arg His Gly Ile Ser Arg Thr Gly Arg Ser Arg Arg
130 135 140

His His Arg Arg Asn Ala Val Trp Pro Ser Arg His Arg Ile Asp Leu
145 150 155 160

Gly Arg Arg Ser Ser Arg Pro Ser Thr Ser Ala Asp Asn Ile Pro Arg
165 170 175

Arg Leu Arg Trp Ala Gly Ser Val Thr Ile Leu Arg Arg Gly Gln Gly
180 185 190

Gln Gly Pro Gln Met Ile Asp Glu Ala Arg Ser Pro Arg Cys Arg Asp
195 200 205

Asp Leu Ser Thr Leu Cys His Gln Arg Met Ser Asp Gly Gly Met Gln
210 215 220

Asp Arg Ser Gly Ala
225

<210> SEQ ID NO 122
<211> LENGTH: 231
<212> TYPE: PRT
<213> ORGANISM: Artificial Sequence
<220> FEATURE:
<223> OTHER INFORMATION: S248_M31bA11 clone

<400> SEQUENCE: 122

Gly Ile Ile Met Leu Gly Phe Asn Asp Gln Arg Glu Arg Ile Asn Asp
1 5 10 15

Asn Leu Asp Tyr Trp Asp Ala Tyr His Ser Val Leu Gly Glu Arg Gln
20 25 30

Phe Tyr Ser Gly Asn Ser Lys Met Phe Val Pro Ile Thr Lys Ile Ala
35 40 45

Val Lys Ala Arg Lys Thr Arg Phe Thr Asn Gln Ile Phe Pro Gln Ser
50 55 60

Gly Arg Asn Val Asp Val Thr Thr Thr Asp Gly Thr Leu Pro His Ala
65 70 75 80

Thr Met Ser Leu Val Glu His Tyr Ile Arg Ala Cys Arg Leu Arg Thr

```
                85                  90                  95

Gln Ile Val Pro Ala Leu Ile Val Asn Gly Asp Cys Glu Gly Met Tyr
            100                 105                 110

Ser Ile Tyr Val Gly Trp Ser Lys Thr Thr Lys His Val Val Ser Arg
        115                 120                 125

Glu Thr Lys Pro Val Glu Ser Asp Gly Met Glu Phe Pro Glu Leu Gly
    130                 135                 140

Glu Ala Asp Asp Ile Thr Glu Glu Thr Leu Glu Cys Gly Leu Pro Asp
145                 150                 155                 160

Ile Glu Leu Ile Ser Asp Ala Asp Leu Leu Val Leu Pro Pro Ala Pro
                165                 170                 175

Thr Thr Phe Gln Gly Ala Asp Gly Arg Val Arg Ser Arg Ser Cys Ala
            180                 185                 190

Val Asp Lys Gly Lys Val Arg Arg Ser Thr Arg Arg Asp His Arg Asp
        195                 200                 205

Ala Ala Thr Ile Cys Arg Arg Tyr Val Thr Ser Ala Cys Pro Thr Val
    210                 215                 220

Glu Cys Lys Thr Gly Asp Arg
225                 230


<210> SEQ ID NO 123
<211> LENGTH: 229
<212> TYPE: PRT
<213> ORGANISM: Artificial Sequence
<220> FEATURE:
<223> OTHER INFORMATION: S248_M31bA11 clone

<400> SEQUENCE: 123

Glu Leu Ser Cys Trp Val Leu Met Thr Ser Ala Arg Gly Ser Thr Thr
1               5                   10                  15

Thr Ser Ile Thr Gly Thr Pro Thr Thr Pro Ser Trp Ala Arg Asp Ser
            20                  25                  30

Phe Ile Pro Ala Ile Pro Arg Cys Ser Ser Pro Ser Pro Arg Ser Arg
        35                  40                  45

Arg Arg Ala Arg Pro Gly Ser Pro Ile Arg Phe Phe Leu Ser Pro Ala
    50                  55                  60

Ala Thr Ser Met Ser Pro Pro Arg Thr Ala His Ser Pro Thr Pro Pro
65                  70                  75                  80

Cys Pro Trp Ser Ser Thr Thr Ser Gly Pro Ala Ala Cys Ala Pro Arg
                85                  90                  95

Ser Phe Arg Pro Ser Leu Thr Ala Ile Ala Lys Ala Cys Thr Ala Ser
            100                 105                 110

Met Ser Ala Gly Arg Lys Pro Pro Ser Met Leu Phe His Val Lys Gln
        115                 120                 125

Ser Arg Ser Lys Ala Thr Ala Trp Asn Phe Pro Asn Trp Ala Lys Pro
    130                 135                 140

Thr Thr Ser Pro Lys Lys Arg Leu Ser Val Ala Phe Pro Thr Ser Asn
145                 150                 155                 160

Ser Arg Thr Pro Ile Phe Ser Ser Phe His Gln Arg Arg Gln His Ser
                165                 170                 175

Lys Ala Leu Glu Met Gly Gly Phe Gly His Asp Leu Ala Pro Trp Thr
            180                 185                 190

Arg Ala Arg Ser Ala Asp Asp Arg Arg Gly Ala Ile Thr Glu Met Pro
        195                 200                 205

Arg Arg Ser Val Asp Ala Met Ser Pro Ala His Val Arg Arg Trp Asn
```

210 215 220

Ala Arg Gln Ile Gly
225

<210> SEQ ID NO 124
<211> LENGTH: 5
<212> TYPE: PRT
<213> ORGANISM: Artificial Sequence
<220> FEATURE:
<223> OTHER INFORMATION: synthetic putative block V

<400> SEQUENCE: 124

Asp Gly Thr His Pro
1 5

<210> SEQ ID NO 125
<211> LENGTH: 1216
<212> TYPE: DNA
<213> ORGANISM: Artificial Sequence
<220> FEATURE:
<223> OTHER INFORMATION: M091_M24dG12 clone

<400> SEQUENCE: 125
gcctgatggc ttcgagttcg tcgaattcac ctcgccccag cccggcgtgc tggaggcggt 60
gtttgaaaag ctgggtttca ccctggtcgc caagcaccgg tccaaggatg tggtgctgta 120
ccgccagaac ggcatcaact tcatcctgaa ccgcgagccc cacagccagg ccgcctactt 180
tggtgccgag catggcccct ccgcctgtgg cctggccttc cgtgtgaagg atgcgcataa 240
ggcttataac cgcgcgctgg aactgggcgc ccagcccatc gagatcccca ccggccccat 300
ggaactgcgc ctgcccgcca tcaagggcat tggcggcgcc gcctctgtat ttgatcgacc 360
gctttgaaga cggcaagtcc atctacgaca tcgacttcga gttcatcgaa ggcgtggacc 420
gccgccccgc ggggcatggc ctgaacgaga tcgatcacct cacgcacaac gtgtaccggg 480
gccgcatggg cttctgggcc aacttctacg aaaagctgtt caacttccgc gaaatccgct 540
acttcgacat ccagggcgaa tacacgggcc tgacctccaa ggccatgacc gcgcccgacg 600
gcaagattcg catcccgctg aacgaagagt ccaagcaggg cggcggccag atcgaagaat 660
ttttgatgca attcaacggc gagggcattc agcacatcgc gctgatctgc gacaacctgc 720
tggacgtggt ggacaagctg ggcatggccg gcgtgcagct ggccaccgcg cccaacgagg 780
tctattacga aatgctggac acccgcctgc ccggccacgg ccagccggtg cccgagctgc 840
agtcgcgcgg catcttgctg gacggcacca cggccgacgg cacgcacccg cctgctagct 900
tcagatcttc tccacgccca tgctgggccc ggtgttcttc gaattcatcc agcgcgaggg 960
cgactaccgc gacggctttg gcgaaggcaa cttcaaggcg ctgttcgagt cgctggaacg 1020
cgaccagatc cgccgtggtg tgctgaacac ataagacatc agacatccag ggttaaccct 1080
gcacaggtgc ctatactgcg cgctccccgg aactcaaaag gatcccgatg tcgctccgta 1140
gcaccctgtt cagcaccctt ttggccggcg cagccactgt cgcgctggcg cagaacccgt 1200
ctgcccgctc acatcg 1216

<210> SEQ ID NO 126
<211> LENGTH: 394
<212> TYPE: PRT
<213> ORGANISM: Artificial Sequence
<220> FEATURE:
<223> OTHER INFORMATION: M091_M24dG12 clone

<400> SEQUENCE: 126

```
Ala Trp Leu Arg Val Arg Arg Ile His Leu Ala Pro Ala Arg Arg Ala
1               5                   10                  15

Gly Gly Gly Val Lys Ala Gly Phe His Pro Gly Arg Gln Ala Pro Val
            20                  25                  30

Gln Gly Cys Gly Ala Val Pro Pro Glu Arg His Gln Leu His Pro Glu
        35                  40                  45

Pro Arg Ala Pro Gln Pro Gly Arg Leu Leu Trp Cys Arg Ala Trp Pro
    50                  55                  60

Leu Arg Leu Trp Pro Gly Leu Pro Cys Glu Gly Cys Ala Gly Leu Pro
65                  70                  75                  80

Arg Ala Gly Thr Gly Arg Pro Ala His Arg Asp Pro His Arg Pro His
                85                  90                  95

Gly Thr Ala Pro Ala Arg His Gln Gly His Trp Arg Arg Arg Leu Cys
            100                 105                 110

Ile Ser Thr Ala Leu Lys Thr Ala Ser Pro Ser Thr Thr Ser Thr Ser
        115                 120                 125

Ser Ser Ser Lys Ala Trp Thr Ala Ala Pro Arg Gly Met Ala Thr Arg
    130                 135                 140

Ser Ile Thr Ser Arg Thr Thr Cys Thr Gly Ala Ala Trp Ala Ser Gly
145                 150                 155                 160

Pro Thr Ser Thr Lys Ser Cys Ser Thr Ser Ala Lys Ser Ala Thr Ser
                165                 170                 175

Thr Ser Arg Ala Asn Thr Arg Ala Pro Pro Arg Pro Pro Arg Pro Thr
            180                 185                 190

Ala Arg Phe Ala Ser Arg Thr Lys Ser Pro Ser Arg Ala Ala Ala Arg
        195                 200                 205

Ser Lys Asn Phe Cys Asn Ser Thr Ala Arg Ala Phe Ser Thr Ser Arg
    210                 215                 220

Ser Ala Thr Thr Cys Trp Thr Trp Trp Thr Ser Trp Ala Trp Pro Ala
225                 230                 235                 240

Cys Ser Trp Pro Pro Arg Pro Thr Arg Ser Ile Thr Lys Cys Trp Thr
                245                 250                 255

Pro Ala Cys Pro Ala Thr Ala Ser Arg Cys Pro Ser Cys Ser Arg Ala
            260                 265                 270

Ala Ser Cys Trp Thr Ala Pro Arg Pro Thr Ala Arg Thr Arg Leu Leu
        275                 280                 285

Ala Ser Asp Leu Leu His Ala His Ala Gly Pro Gly Val Leu Arg Ile
    290                 295                 300

His Pro Ala Arg Gly Arg Leu Pro Arg Arg Leu Trp Arg Arg Gln Leu
305                 310                 315                 320

Gln Gly Ala Val Arg Val Ala Gly Thr Arg Pro Asp Pro Pro Trp Cys
                325                 330                 335

Ala Glu His Ile Arg His Gln Thr Ser Arg Val Asn Pro Ala Gln Val
            340                 345                 350

Pro Ile Leu Arg Ala Pro Arg Asn Ser Lys Gly Ser Arg Cys Arg Ser
        355                 360                 365

Val Ala Pro Cys Ser Ala Pro Phe Trp Pro Ala Gln Pro Leu Ser Arg
    370                 375                 380

Trp Arg Arg Thr Arg Leu Pro Ala His Ile
385                 390
```

<210> SEQ ID NO 127
<211> LENGTH: 401

```
<212> TYPE: PRT
<213> ORGANISM: Artificial Sequence
<220> FEATURE:
<223> OTHER INFORMATION: M091_M24dG12 clone

<400> SEQUENCE: 127

Pro Asp Gly Phe Glu Phe Val Glu Phe Thr Ser Pro Gln Pro Gly Val
1               5                   10                  15

Leu Glu Ala Val Phe Glu Lys Leu Gly Phe Thr Leu Val Ala Lys His
            20                  25                  30

Arg Ser Lys Asp Val Val Leu Tyr Arg Gln Asn Gly Ile Asn Phe Ile
        35                  40                  45

Leu Asn Arg Glu Pro His Ser Gln Ala Ala Tyr Phe Gly Ala Glu His
    50                  55                  60

Gly Pro Ser Ala Cys Gly Leu Ala Phe Arg Val Lys Asp Ala His Lys
65                  70                  75                  80

Ala Tyr Asn Arg Ala Leu Glu Leu Gly Ala Gln Pro Ile Glu Ile Pro
                85                  90                  95

Thr Gly Pro Met Glu Leu Arg Leu Pro Ala Ile Lys Gly Ile Gly Gly
            100                 105                 110

Ala Ala Ser Val Phe Asp Arg Pro Leu Arg Arg Gln Val His Leu Arg
        115                 120                 125

His Arg Leu Arg Val His Arg Arg Arg Gly Pro Pro Pro Arg Gly Ala
    130                 135                 140

Trp Pro Glu Arg Asp Arg Ser Pro His Ala Gln Arg Val Pro Gly Pro
145                 150                 155                 160

His Gly Leu Leu Gly Gln Leu Leu Arg Lys Ala Val Gln Leu Pro Arg
                165                 170                 175

Asn Pro Leu Leu Arg His Pro Gly Arg Ile His Gly Pro Asp Leu Gln
            180                 185                 190

Gly His Asp Arg Ala Arg Arg Gln Asp Ser His Pro Ala Glu Arg Arg
        195                 200                 205

Val Gln Ala Gly Arg Arg Pro Asp Arg Arg Ile Phe Asp Ala Ile Gln
    210                 215                 220

Arg Arg Gly His Ser Ala His Arg Ala Asp Leu Arg Gln Pro Ala Gly
225                 230                 235                 240

Arg Gly Gly Gln Ala Gly His Gly Arg Arg Ala Ala Gly His Arg Ala
                245                 250                 255

Gln Arg Gly Leu Leu Arg Asn Ala Gly His Pro Pro Ala Arg Pro Arg
            260                 265                 270

Pro Ala Gly Ala Arg Ala Ala Val Ala Arg His Leu Ala Gly Arg His
        275                 280                 285

His Gly Arg Arg His Ala Pro Ala Cys Leu Gln Ile Phe Ser Thr Pro
    290                 295                 300

Met Leu Gly Pro Val Phe Phe Glu Phe Ile Gln Arg Glu Gly Asp Tyr
305                 310                 315                 320

Arg Asp Gly Phe Gly Glu Gly Asn Phe Lys Ala Leu Phe Glu Ser Leu
                325                 330                 335

Glu Arg Asp Gln Ile Arg Arg Gly Val Leu Asn Thr Asp Ile Arg His
            340                 345                 350

Pro Gly Leu Thr Leu His Arg Cys Leu Tyr Cys Ala Leu Pro Gly Thr
        355                 360                 365

Gln Lys Asp Pro Asp Val Ala Pro His Pro Val Gln His Pro Phe Gly
    370                 375                 380
```

Arg Arg Ser His Cys Arg Ala Gly Ala Glu Pro Val Cys Pro Leu Thr
385 390 395 400

Ser

<210> SEQ ID NO 128
<211> LENGTH: 400
<212> TYPE: PRT
<213> ORGANISM: Artificial Sequence
<220> FEATURE:
<223> OTHER INFORMATION: M091_M24dG12 clone

<400> SEQUENCE: 128

Leu Met Ala Ser Ser Ser Ser Asn Ser Pro Arg Pro Ser Pro Ala Cys
1 5 10 15

Trp Arg Arg Cys Leu Lys Ser Trp Val Ser Pro Trp Ser Pro Ser Thr
20 25 30

Gly Pro Arg Met Trp Cys Cys Thr Ala Arg Thr Ala Ser Thr Ser Ser
35 40 45

Thr Ala Ser Pro Thr Ala Arg Pro Pro Thr Leu Val Pro Ser Met Ala
50 55 60

Pro Pro Pro Val Ala Trp Pro Ser Val Arg Met Arg Ile Arg Leu Ile
65 70 75 80

Thr Ala Arg Trp Asn Trp Ala Pro Ser Pro Ser Arg Ser Pro Pro Ala
85 90 95

Pro Trp Asn Cys Ala Cys Pro Pro Ser Arg Ala Leu Ala Ala Pro Pro
100 105 110

Leu Tyr Leu Ile Asp Arg Phe Glu Asp Gly Lys Ser Ile Tyr Asp Ile
115 120 125

Asp Phe Glu Phe Ile Glu Gly Val Asp Arg Arg Pro Ala Gly His Gly
130 135 140

Leu Asn Glu Ile Asp His Leu Thr His Asn Val Tyr Arg Gly Arg Met
145 150 155 160

Gly Phe Trp Ala Asn Phe Tyr Glu Lys Leu Phe Asn Phe Arg Glu Ile
165 170 175

Arg Tyr Phe Asp Ile Gln Gly Glu Tyr Thr Gly Leu Thr Ser Lys Ala
180 185 190

Met Thr Ala Pro Asp Gly Lys Ile Arg Ile Pro Leu Asn Glu Glu Ser
195 200 205

Lys Gln Gly Gly Gly Gln Ile Glu Glu Phe Leu Met Gln Phe Asn Gly
210 215 220

Glu Gly Ile Gln His Ile Ala Leu Ile Cys Asp Asn Leu Leu Asp Val
225 230 235 240

Val Asp Lys Leu Gly Met Ala Gly Val Gln Leu Ala Thr Ala Pro Asn
245 250 255

Glu Val Tyr Tyr Glu Met Leu Asp Thr Arg Leu Pro Gly His Gly Gln
260 265 270

Pro Val Pro Glu Leu Gln Ser Arg Gly Ile Leu Leu Asp Gly Thr Thr
275 280 285

Ala Asp Gly Thr His Pro Pro Ala Ser Phe Arg Ser Ser Pro Arg Pro
290 295 300

Cys Trp Ala Arg Cys Ser Ser Asn Ser Ser Ser Ala Arg Ala Thr Thr
305 310 315 320

Ala Thr Ala Leu Ala Lys Ala Thr Ser Arg Arg Cys Ser Ser Arg Trp
325 330 335

Asn Ala Thr Arg Ser Ala Val Val Cys Thr His Lys Thr Ser Asp Ile

```
            340                 345                 350

Gln Gly Pro Cys Thr Gly Ala Tyr Thr Ala Arg Ser Pro Glu Leu Lys
        355                 360                 365

Arg Ile Pro Met Ser Leu Arg Ser Thr Leu Phe Ser Thr Leu Leu Ala
    370                 375                 380

Gly Ala Ala Thr Val Ala Leu Ala Gln Asn Pro Ser Ala Arg Ser His
385                 390                 395                 400


<210> SEQ ID NO 129
<211> LENGTH: 648
<212> TYPE: DNA
<213> ORGANISM: Artificial Sequence
<220> FEATURE:
<223> OTHER INFORMATION: M4aE11 clone

<400> SEQUENCE: 129

atgaagacca ttctcgccta tggcgacagc ctgacctatg ggccaaccc gatcccgggc      60

gggccgcggc atgcctatga ggatcgctgg cccacggcgc tggagcaggg gctgggcggc    120

aaggcgcggg tgattgccga ggggctgggt ggtcgcacca cggtgcatga cgactggttt    180

gcgaatgcgg acaggaacgg tgcgcgggtg ctgccgacgc tgctcgagag ccattcgccg    240

ctcgacctga tcgtcatcat gctcggcacc aacgacatca agccgcatca cgggcggacg    300

gccggcgagg ccgggcgggg catggcgcgg ctggtgcaga tcatccgcgg gcactatgcc    360

ggccgcatgc aggacgagcc gcagatcatc ctcgtgtcgc cgccgccgat catcctcggc    420

gactgggcgg acatgatgga ccatttcggc ccgcacgaag cgatcgccac ctcggtggat    480

ttcgctcgcg agtacaagaa gcgggccgac gagcagaagg tgcatttctt cgacgccggc    540

acggtggcga cgaccagcaa ggccgatggc atccacctcg acccggccaa tacgcgcgcc    600

atcggggcag ggctggtgcc gctggtgaag caggtgctcg gcctgtaa                 648


<210> SEQ ID NO 130
<211> LENGTH: 215
<212> TYPE: PRT
<213> ORGANISM: Artificial Sequence
<220> FEATURE:
<223> OTHER INFORMATION: M4aE11 clone

<400> SEQUENCE: 130

Met Lys Thr Ile Leu Ala Tyr Gly Asp Ser Leu Thr Tyr Gly Ala Asn
1               5                   10                  15

Pro Ile Pro Gly Gly Pro Arg His Ala Tyr Glu Asp Arg Trp Pro Thr
            20                  25                  30

Ala Leu Glu Gln Gly Leu Gly Gly Lys Ala Arg Val Ile Ala Glu Gly
        35                  40                  45

Leu Gly Gly Arg Thr Thr Val His Asp Asp Trp Phe Ala Asn Ala Asp
    50                  55                  60

Arg Asn Gly Ala Arg Val Leu Pro Thr Leu Leu Glu Ser His Ser Pro
65                  70                  75                  80

Leu Asp Leu Ile Val Ile Met Leu Gly Thr Asn Asp Ile Lys Pro His
                85                  90                  95

His Gly Arg Thr Ala Gly Glu Ala Gly Arg Gly Met Ala Arg Leu Val
            100                 105                 110

Gln Ile Ile Arg Gly His Tyr Ala Gly Arg Met Gln Asp Glu Pro Gln
        115                 120                 125

Ile Ile Leu Val Ser Pro Pro Pro Ile Ile Leu Gly Asp Trp Ala Asp
    130                 135                 140
```

-continued

```
Met Met Asp His Phe Gly Pro His Glu Ala Ile Ala Thr Ser Val Asp
145                 150                 155                 160

Phe Ala Arg Glu Tyr Lys Lys Arg Ala Asp Glu Gln Lys Val His Phe
                165                 170                 175

Phe Asp Ala Gly Thr Val Ala Thr Thr Ser Lys Ala Asp Gly Ile His
            180                 185                 190

Leu Asp Pro Ala Asn Thr Arg Ala Ile Gly Ala Gly Leu Val Pro Leu
        195                 200                 205

Val Lys Gln Val Leu Gly Leu
    210                 215
```

<210> SEQ ID NO 131
<211> LENGTH: 6297
<212> TYPE: DNA
<213> ORGANISM: Artificial Sequence
<220> FEATURE:
<223> OTHER INFORMATION: pMSATNcoI-1 plasmid

<400> SEQUENCE: 131

```
ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatatc cggatatagt tcctcctttc agcaaaaaac ccctcaagac ccgtttagag    240

gccccaaggg gttatgctag ttattgctca gcggtggcag cagccaactc agcttccttt    300

cgggctttgt tagcagccgg atccgcgcgc ttacagcagg ctccgcacct gttccgcgag    360

ggccaccccg agatcgcgat tgttggcctc ggtgaagtgg attccgtcga cgccgtcggt    420

gctgatcacc gaacccgcgt cgaagaacgg caccttcatg aacgacgcga gcgcgctgta    480

cacgcgggcg agctcagtgg tcttctgctc gccgccctcg aagatcaact ggaaccaggg    540

gtgcggcatg ggcgccagcg gtggcggcga gaccaccagc accttgggtg ccgggtacgt    600

ggtgccgacg ccgcccgcgc tggtgagcac ctgcgtgacg agcaccgaca tgcccagcgc    660

gatgtcgagc ggggtgcgcc ggaagtaggc cttggtgtcg ttggtgccca gcatgatgat    720

caccaggtcg agcggcaggt gcgtcgcgag gcacgacggc aggtagctcg cgccgttgag    780

ccgcggatcg gtggggtcgt cgatgttggt ggtgcgcgcg ctcagtccct cctcgatcac    840

ctcgaagtcc gctccgagct gctgggccag cacaccggtc cagcgcacgt cgggggcgaa    900

ccgctcggtg ggtgccccgt cttcgacggg gacccagccc caggtcaggg aatcaccgaa    960

acacagaatt cgcttggcca tggtatatct ccttcttaaa gttaaacaaa attatttcta   1020

gaggggaatt gttatccgct cacaattccc ctatagtgag tcgtattaat ttcgcgggat   1080

cgagatctcg atcctctacg ccggacgcat cgtggccggc atcaccggcg ccacaggtgc   1140

ggttgctggc gcctatatcg ccgacatcac cgatggggaa gatcgggctc gccacttcgg   1200

gctcatgagc gcttgtttcg gcgtgggtat ggtggcaggc cccgtggccg ggggactgtt   1260

gggcgccatc tccttgcatg caccattcct tgcggcggcg gtgctcaacg gcctcaacct   1320

actactgggc tgcttcctaa tgcaggagtc gcataaggga gagcgtcgag atcccggaca   1380

ccatcgaatg gcgcaaaacc tttcgcggta tggcatgata gcgcccggaa gagagtcaat   1440

tcagggtggt gaatgtgaaa ccagtaacgt tatacgatgt cgcagagtat gccggtgtct   1500

cttatcagac cgtttcccgc gtggtgaacc aggccagcca cgtttctgcg aaaacgcggg   1560

aaaaagtgga agcggcgatg gcggagctga attacattcc caaccgcgtg gcacaacaac   1620
```

```
tggcgggcaa acagtcgttg ctgattggcg ttgccacctc cagtctggcc ctgcacgcgc   1680
cgtcgcaaat tgtcgcggcg attaaatctc gcgccgatca actgggtgcc agcgtggtgg   1740
tgtcgatggt agaacgaagc ggcgtcgaag cctgtaaagc ggcggtgcac aatcttctcg   1800
cgcaacgcgt cagtgggctg atcattaact atccgctgga tgaccaggat gccattgctg   1860
tggaagctgc ctgcactaat gttccggcgt tatttcttga tgtctctgac cagacaccca   1920
tcaacagtat tattttctcc catgaagacg gtacgcgact gggcgtggag catctggtcg   1980
cattgggtca ccagcaaatc gcgctgttag cgggcccatt aagttctgtc tcggcgcgtc   2040
tgcgtctggc tggctggcat aaatatctca ctcgcaatca aattcagccg atagcggaac   2100
gggaaggcga ctggagtgcc atgtccggtt ttcaacaaac catgcaaatg ctgaatgagg   2160
gcatcgttcc cactgcgatg ctggttgcca acgatcagat ggcgctgggc gcaatgcgcg   2220
ccattaccga gtccgggctg cgcgttggtg cggatatctc ggtagtggga tacgacgata   2280
ccgaagacag ctcatgttat atcccgccgt taaccaccat caaacaggat tttcgcctgc   2340
tggggcaaac cagcgtggac cgcttgctgc aactctctca gggccaggcg gtgaagggca   2400
atcagctgtt gcccgtctca ctggtgaaaa gaaaaaccac cctggcgccc aatacgcaaa   2460
ccgcctctcc ccgcgcgttg gccgattcat taatgcagct ggcacgacag gtttcccgac   2520
tggaaagcgg gcagtgagcg caacgcaatt aatgtaagtt agctcactca ttaggcaccg   2580
ggatctcgac cgatgccctt gagagccttc aacccagtca gctccttccg gtgggcgcgg   2640
ggcatgacta tcgtcgccgc acttatgact gtcttcttta tcatgcaact cgtaggacag   2700
gtgccggcag cgctctgggt cattttcggc gaggaccgct ttcgctggag cgcgacgatg   2760
atcggcctgt cgcttgcggt attcggaatc ttgcacgccc tcgctcaagc cttcgtcact   2820
ggtcccgcca ccaaacgttt cggcgagaag caggccatta tcgccggcat ggcggccgac   2880
gcgctgggct acgtcttgct ggcgttcgcg acgcgaggct ggatggcctt ccccattatg   2940
attcttctcg cttccggcgg catcgggatg cccgcgttgc aggccatgct gtccaggcag   3000
gtagatgacg accatcaggg acagcttcaa ggatcgctcg cggctcttac cagcctaact   3060
tcgatcactg gaccgctgat cgtcacggcg atttatgccg cctcggcgag cacatggaac   3120
gggttggcat ggattgtagg cgccgcccta taccttgtct gcctccccgc gttgcgtcgc   3180
ggtgcatgga gccgggccac ctcgacctga atggaagccg gcggcacctc gctaacggat   3240
tcaccactcc aagaattgga gccaatcaat tcttgcggag aactgtgaat gcgcaaacca   3300
acccttggca gaacatatcc atcgcgtccg ccatctccag cagccgcacg cggcgcatct   3360
cgggcagcgt tgggtcctgg ccacgggtgc gcatgatcgt gctcctgtcg ttgaggaccc   3420
ggctaggctg gcggggttgc cttactggtt agcagaatga atcaccgata cgcgagcgaa   3480
cgtgaagcga ctgctgctgc aaaacgtctg cgacctgagc aacaacatga atggtcttcg   3540
gtttccgtgt ttcgtaaagt ctggaaacgc ggaagtcagc gccctgcacc attatgttcc   3600
ggatctgcat cgcaggatgc tgctggctac cctgtggaac acctacatct gtattaacga   3660
agcgctggca ttgaccctga gtgatttttc tctggtcccg ccgcatccat accgccagtt   3720
gtttaccctc acaacgttcc agtaaccggg catgttcatc atcagtaacc cgtatcgtga   3780
gcatcctctc tcgtttcatc ggtatcatta cccccatgaa cagaaatccc ccttacacgg   3840
aggcatcagt gaccaaacag gaaaaaaccg cccttaacat ggcccgcttt atcagaagcc   3900
agacattaac gcttctggag aaactcaacg agctggacgc ggatgaacag gcagacatct   3960
```

-continued

```
gtgaatcgct tcacgaccac gctgatgagc tttaccgcag ctgcctcgcg cgtttcggtg   4020
atgacggtga aaacctctga cacatgcagc tcccggagac ggtcacagct tgtctgtaag   4080
cggatgccgg gagcagacaa gcccgtcagg gcgcgtcagc gggtgttggc gggtgtcggg   4140
gcgcagccat gacccagtca cgtagcgata gcggagtgta tactggctta actatgcggc   4200
atcagagcag attgtactga gagtgcacca tatatgcggt gtgaaatacc gcacagatgc   4260
gtaaggagaa aataccgcat caggcgctct tccgcttcct cgctcactga ctcgctgcgc   4320
tcggtcgttc ggctgcggcg agcggtatca gctcactcaa aggcggtaat acggttatcc   4380
acagaatcag gggataacgc aggaaagaac atgtgagcaa aaggccagca aaaggccagg   4440
aaccgtaaaa aggccgcgtt gctggcgttt ttccataggc tccgcccccc tgacgagcat   4500
cacaaaaatc gacgctcaag tcagaggtgg cgaaacccga caggactata aagataccag   4560
gcgtttcccc ctggaagctc cctcgtgcgc tctcctgttc cgaccctgcc gcttaccgga   4620
tacctgtccg cctttctccc ttcgggaagc gtggcgcttt ctcatagctc acgctgtagg   4680
tatctcagtt cggtgtaggt cgttcgctcc aagctgggct gtgtgcacga accccccgtt   4740
cagcccgacc gctgcgcctt atccggtaac tatcgtcttg agtccaaccc ggtaagacac   4800
gacttatcgc cactggcagc agccactggt aacaggatta gcagagcgag gtatgtaggc   4860
ggtgctacag agttcttgaa gtggtggcct aactacggct acactagaag gacagtattt   4920
ggtatctgcg ctctgctgaa gccagttacc ttcggaaaaa gagttggtag ctcttgatcc   4980
ggcaaacaaa ccaccgctgg tagcggtggt ttttttgttt gcaagcagca gattacgcgc   5040
agaaaaaaag gatctcaaga agatcctttg atcttttcta cggggtctga cgctcagtgg   5100
aacgaaaact cacgttaagg gattttggtc atgagattat caaaaaggat cttcacctag   5160
atccttttaa attaaaaatg aagttttaaa tcaatctaaa gtatatatga gtaaacttgg   5220
tctgacagtt accaatgctt aatcagtgag gcacctatct cagcgatctg tctatttcgt   5280
tcatccatag ttgcctgact ccccgtcgtg tagataacta cgatacggga gggcttacca   5340
tctggcccca gtgctgcaat gataccgcga gacccacgct caccggctcc agatttatca   5400
gcaataaacc agccagccgg aagggccgag cgcagaagtg gtcctgcaac tttatccgcc   5460
tccatccagt ctattaattg ttgccgggaa gctagagtaa gtagttcgcc agttaatagt   5520
ttgcgcaacg ttgttgccat tgctgcaggc atcgtggtgt cacgctcgtc gtttggtatg   5580
gcttcattca gctccggttc ccaacgatca aggcgagtta catgatcccc catgttgtgc   5640
aaaaaagcgg ttagctcctt cggtcctccg atcgttgtca gaagtaagtt ggccgcagtg   5700
ttatcactca tggttatggc agcactgcat aattctctta ctgtcatgcc atccgtaaga   5760
tgcttttctg tgactggtga gtactcaacc aagtcattct gagaatagtg tatgcggcga   5820
ccgagttgct cttgcccggc gtcaacacgg gataataccg cgccacatag cagaacttta   5880
aaagtgctca tcattggaaa acgttcttcg gggcgaaaac tctcaaggat cttaccgctg   5940
ttgagatcca gttcgatgta acccactcgt gcacccaact gatcttcagc atcttttact   6000
ttcaccagcg tttctgggtg agcaaaaaca ggaaggcaaa atgccgcaaa aaagggaata   6060
agggcgacac ggaaatgttg aatactcata ctcttccttt ttcaatatta ttgaagcatt   6120
tatcagggtt attgtctcat gagcggatac atatttgaat gtatttagaa aaataaacaa   6180
ataggggttc cgcgcacatt tccccgaaaa gtgccacctg acgtctaaga aaccattatt   6240
atcatgacat taacctataa aaataggcgt atcacgaggc cctttcgtct tcaagaa      6297
```

<210> SEQ ID NO 132
<211> LENGTH: 14
<212> TYPE: PRT
<213> ORGANISM: Bacillus subtilis pnbA

<400> SEQUENCE: 132

Ala Thr Ala Ala Gly Gly Ala Gly Gly Thr Gly Ala Thr Cys
1 5 10

<210> SEQ ID NO 133
<211> LENGTH: 4100
<212> TYPE: DNA
<213> ORGANISM: Artificial Sequence
<220> FEATURE:
<223> OTHER INFORMATION: pAH502R plasmid

<400> SEQUENCE: 133
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgcgtaata cgactcacta tagggcgaat tgggtaccgg 660
gccccccctc gaggtcgacg gtatcgataa gcttgatatc gaattcctgc agcccggggg 720
atccgcccaa gcttaaggag gtgatctaga attccatggc caagcgaatt ctgtgtttcg 780
gtgattccct gacctggggc tgggtccccg tcgaagacgg ggcacccacc gagcggttcg 840
cccccgacgt gcgctggacc ggtgtgctgg cccagcagct cggagcggac ttcgaggtga 900
tcgaggaggg actgagcgcg cgcaccacca acatcgacga ccccaccgat ccgcggctca 960
acggcgcgag ctacctgccg tcgtgcctcg cgacgcacct gccgctcgac ctggtgatca 1020
tcatgctggg caccaacgac accaaggcct acttccggcg caccccgctc gacatcgcgc 1080
tgggcatgtc ggtgctcgtc acgcaggtgc tcaccagcgc gggcggcgtc ggcaccacgt 1140
acccggcacc caaggtgctg gtggtctcgc cgccaccgct ggcgcccatg ccgcacccct 1200
ggttccagtt gatcttcgag ggcggcgagc agaagaccac tgagctcgcc cgcgtgtaca 1260
gcgcgctcgc gtcgttcatg aaggtgccgt tcttcgacgc gggttcggtg atcagcaccg 1320
acggcgtcga cggaatccac ttcaccgagg ccaacaatcg cgatctcggg gtggccctcg 1380
cggaacaggt gcggagcctg ctgtaaaagg atccccggga agcttgcatg ggctagagcg 1440
gccgccaccg cggtggagct ccagcttttg ttccctttag tgagggttaa ttgcgcgctt 1500
ggcgtaatca tggtcatagc tgtttcctgt gtgaaattgt tatccgctca caattccaca 1560
caacatacga gccggaagca taaagtgtaa agcctggggt gcctaatgag tgagctaact 1620
cacattaatt gcgttgcgct cactgcccgc tttccagtcg ggaaacctgt cgtgccagct 1680
gcattaatga atcggccaac gcgcggggag aggcggtttg cgtattgggc gctcttccgc 1740
ttcctcgctc actgactcgc tgcgctcggt cgttcggctg cggcgagcgg tatcagctca 1800

```
ctcaaaggcg gtaatacggt tatccacaga atcaggggat aacgcaggaa agaacatgtg   1860
agcaaaaggc cagcaaaagg ccaggaaccg taaaaaggcc gcgttgctgg cgtttttcca   1920
taggctccgc ccccctgacg agcatcacaa aaatcgacgc tcaagtcaga ggtggcgaaa   1980
cccgacagga ctataaagat accaggcgtt tccccctgga agctccctcg tgcgctctcc   2040
tgttccgacc ctgccgctta ccggatacct gtccgccttt ctcccttcgg gaagcgtggc   2100
gctttctcat agctcacgct gtaggtatct cagttcggtg taggtcgttc gctccaagct   2160
gggctgtgtg cacgaacccc ccgttcagcc cgaccgctgc gccttatccg gtaactatcg   2220
tcttgagtcc aacccggtaa gacacgactt atcgccactg gcagcagcca ctggtaacag   2280
gattagcaga gcgaggtatg taggcggtgc tacagagttc ttgaagtggt ggcctaacta   2340
cggctacact agaaggacag tatttggtat ctgcgctctg ctgaagccag ttaccttcgg   2400
aaaaagagtt ggtagctctt gatccggcaa acaaaccacc gctggtagcg gtggtttttt   2460
tgtttgcaag cagcagatta cgcgcagaaa aaaaggatct caagaagatc ctttgatctt   2520
ttctacgggg tctgacgctc agtggaacga aaactcacgt taagggattt tggtcatgag   2580
attatcaaaa aggatcttca cctagatcct tttcgaccga ataaatacct gtgacggaag   2640
atcacttcgc agaataaata aatcctggtg tccctgttga taccgggaag ccctgggcca   2700
acttttggcg aaaatgagac gttgatcggc acgtaagagg ttccaacttt caccataatg   2760
aaataagatc actaccgggc gtattttttg agttgtcgag attttcagga gctaaggaag   2820
ctaaaatgga gaaaaaaatc actggatata ccaccgttga tatatcccaa tggcatcgta   2880
aagaacattt tgaggcattt cagtcagttg ctcaatgtac ctataaccag accgttcagc   2940
tggatattac ggccttttta aagaccgtaa agaaaaataa gcacaagttt tatccggcct   3000
ttattcacat tcttgcccgc ctgatgaatg ctcatccgga attacgtatg gcaatgaaag   3060
acggtgagct ggtgatatgg gatagtgttc acccttgtta caccgttttc catgagcaaa   3120
ctgaaacgtt ttcatcgctc tggagtgaat accacgacga tttccggcag tttctacaca   3180
tatattcgca agatgtggcg tgttacggtg aaaacctggc ctatttccct aaagggttta   3240
ttgagaatat gtttttcgtc tcagccaatc cctgggtgag tttcaccagt tttgatttaa   3300
acgtggccaa tatggacaac ttcttcgccc ccgttttcac catgggcaaat attatacgca  3360
aggcgacaag gtgctgatgc cgctggcgat tcaggttcat catgccgttt gtgatggctt   3420
ccatgtcggc agaatgctta atgaattaca acagtactgc gatgagtggc agggcggggc   3480
gtaatttttt taaggcagtt attggtgccc ttaaacgcct ggttgctacg cctgaataag   3540
tgataataag cggatgaatg gcagaaattc gaaagcaaat tcgacccggt cgtcggttca   3600
gggcagggtc gttaaatagc cgcttatgtc tattgctggt ttaccggttt attgactacc   3660
ggaagcagtg tgaccgtgtg cttctcaaat gcctgaggcc agtttgctca ggctctcccc   3720
gtggaggtaa taattgacga tatgatcctt tttttctgat caaaagtgct catcattgga   3780
aaacgttctt cggggcgaaa actctcaagg atcttaccgc tgttgagatc cagttcgatg   3840
taacccactc gtgcacccaa ctgatcttca gcatctttta ctttcaccag cgtttctggg   3900
tgagcaaaaa caggaaggca aaatgccgca aaaaagggaa taagggcgac acggaaatgt   3960
tgaatactca tactcttcct ttttcaatat tattgaagca tttatcaagg gttattgtct   4020
catgagcgga tacatatttg aatgtattta gaaaaataaa caaatagggg ttccgcgcac   4080
atttccccga aaagtgccac                                               4100
```

<210> SEQ ID NO 134
<211> LENGTH: 54
<212> TYPE: DNA
<213> ORGANISM: Artificial Sequence
<220> FEATURE:
<223> OTHER INFORMATION: primer

<400> SEQUENCE: 134
ccaagcttaa ggaggtgatc tagaattcca tggccaagcg aattctgtgt ttcg 54

<210> SEQ ID NO 135
<211> LENGTH: 30
<212> TYPE: DNA
<213> ORGANISM: Artificial Sequence
<220> FEATURE:
<223> OTHER INFORMATION: primer

<400> SEQUENCE: 135
ggggatcctt ttacagcagg ctccgcacct 30

<210> SEQ ID NO 136
<211> LENGTH: 9262
<212> TYPE: DNA
<213> ORGANISM: Artificial Sequence
<220> FEATURE:
<223> OTHER INFORMATION: pAH503 construct

<400> SEQUENCE: 136
ataattctac acagcccagt ccagactatt cggcactgaa attatgggtg aagtggtcaa 60
gacctcacta ggcaccttaa aaatagcgca ccctgaagaa gatttatttg aggtagccct 120
tgcctaccta gcttccaaga aagatatcct aacagcacaa gagcggaaag atgttttgtt 180
ctacatccag aacaacctct gctaaaattc ctgaaaaatt ttgcaaaaag ttgttgactt 240
tatctacaag gtgtggcata atgtgtggaa ttgtgagcgc tcacaattaa gcttaaggag 300
gtgatctaga attccatggc caagcgaatt ctgtgtttcg gtgattccct gacctggggc 360
tgggtccccg tcgaagacgg ggcacccacc gagcggttcg cccccgacgt gcgctggacc 420
ggtgtgctgg cccagcagct cggagcggac ttcgaggtga tcgaggaggg actgagcgcg 480
cgcaccacca acatcgacga ccccaccgat ccgcggctca acggcgcgag ctacctgccg 540
tcgtgcctcg cgacgcacct gccgctcgac ctggtgatca tcatgctggg caccaacgac 600
accaaggcct acttccggcg caccccgctc gacatcgcgc tgggcatgtc ggtgctcgtc 660
acgcaggtgc tcaccagcgc gggcggcgtc ggcaccacgt acccggctcc caaggtgctg 720
gtggtctcgc cgccaccgct ggcgcccatg ccgcacccct ggttccagtt gatcttcgag 780
ggcggcgagc agaagaccac tgagctcgcc cgcgtgtaca gcgcgctcgc gtcgttcatg 840
aaggtgccgt tcttcgacgc gggttcggtg atcagcaccg acggcgtcga cggaatccac 900
ttcaccgagg ccaacaatcg cgatctcggg gtggccctcg cggaacaggt gcggagcctg 960
ctgtaaaagg atccccagct tgttgataca ctaatgcttt tatataggga aaaggtggtg 1020
aactactgtg gaagttactg acgtaagatt acgggtcgac cgggaaaacc ctggcgttac 1080
ccaacttaat cgccttgcag cacatccccc tttcgccagc tggcgtaata gcgaagaggc 1140
ccgcaccgat cgcccttccc aacagttgcg cagcctgaat ggcgaatggc gctttgcctg 1200
gtttccggca ccagaagcgg tgccggaaag ctggctggag tgcgatcttc ctgaggccga 1260
tactgtcgtc gtcccctcaa actggcagat gcacggttac gatgcgccca tctacaccaa 1320
cgtaacctat cccattacgg tcaatccgcc gtttgttccc acggagaatc cgacgggttg 1380

-continued

```
ttactcgctc acatttaatg ttgatgaaag ctggctacag gaaggccaga cgcgaattat   1440
ttttgatggc gttaactcgg cgtttcatct gtggtgcaac gggcgctggg tcggttacgg   1500
ccaggacagt cgtttgccgt ctgaatttga cctgagcgca tttttacgcg ccggagaaaa   1560
ccgcctcgcg gtgatggtgc tgcgttggag tgacggcagt tatctggaag atcaggatat   1620
gtggcggatg agcggcattt tccgtgacgt ctcgttgctg cataaaccga ctacacaaat   1680
cagcgatttc catgttgcca ctcgctttaa tgatgatttc agccgcgctg tactggaggc   1740
tgaagttcag atgtgcggcg agttgcgtga ctacctacgg gtaacagttt ctttatggca   1800
gggtgaaacg caggtcgcca gcggcaccgc gcctttcggc ggtgaaatta tcgatgagcg   1860
tggtggttat gccgatcgcg tcacactacg tctgaacgtc gaaaacccga aactgtggag   1920
cgccgaaatc ccgaatctct atcgtgcggt ggttgaactg cacaccgccg acggcacgct   1980
gattgaagca gaagcctgcg atgtcggttt ccgcgaggtg cggattgaaa atggtctgct   2040
gctgctgaac ggcaagccgt tgctgattcg aggcgttaac cgtcacgagc atcatcctct   2100
gcatggtcag gtcatggatg agcagacgat ggtgcaggat atcctgctga tgaagcagaa   2160
caactttaac gccgtgcgct gttcgcatta tccgaaccat ccgctgtggt acacgctgtg   2220
cgaccgctac ggcctgtatg tggtggatga agccaatatt gaaacccacg gcatggtgcc   2280
aatgaatcgt ctgaccgatg atccgcgctg gctaccggcg atgagcgaac gcgtaacgcg   2340
aatggtgcag cgcgatcgta atcacccgag tgtgatcatc tggtcgctgg ggaatgaatc   2400
aggccacggc gctaatcacg acgcgctgta tcgctggatc aaatctgtcg atccttcccg   2460
cccggtgcag tatgaaggcg gcggagccga caccacggcc accgatatta tttgcccgat   2520
gtacgcgcgc gtggatgaag accagccctt cccggctgtg ccgaaatggt ccatcaaaaa   2580
atggctttcg ctacctggag agacgcgccc gctgatcctt tgcgaatacg cccacgcgat   2640
gggtaacagt cttggcggtt tcgctaaata ctggcaggcg tttcgtcagt atccccgttt   2700
acagggcggc ttcgtctggg actgggtgga tcagtcgctg attaaatatg atgaaaacgg   2760
caacccgtgg tcggcttacg gcggtgattt tggcgatacg ccgaacgatc gccagttctg   2820
tatgaacggt ctggtctttg ccgaccgcac gccgcatcca gcgctgacgg aagcaaaaca   2880
ccagcagcag tttttccagt tccgtttatc cgggcaaacc atcgaagtga ccagcgaata   2940
cctgttccgt catagcgata acgagctcct gcactggatg gtggcgctgg atggtaagcc   3000
gctggcaagc ggtgaagtgc ctctggatgt cgctccacaa ggtaaacagt tgattgaact   3060
gcctgaacta ccgcagccgg agagcgccgg gcaactctgg ctcacagtac gcgtagtgca   3120
accgaacgcg accgcatggt cagaagccgg gcacatcagc gcctggcagc agtggcgtct   3180
ggcggaaaac ctcagtgtga cgctccccgc cgcgtcccac gccatcccgc atctgaccac   3240
cagcgaaatg gatttttgca tcgagctggg taataagcgt tggcaattta accgccagtc   3300
aggctttctt tcacagatgt ggattggcga taaaaaacaa ctgctgacgc cgctgcgcga   3360
tcagttcacc cgtgcaccgc tggataacga cattggcgta agtgaagcga cccgcattga   3420
ccctaacgcc tgggtcgaac gctggaaggc ggcgggccat taccaggccg aagcagcgtt   3480
gttgcagtgc acggcagata cacttgctga tgcggtgctg attacgaccg ctcacgcgtg   3540
gcagcatcag gggaaaacct tatttatcag ccggaaaacc taccggattg atggtagtgg   3600
tcaaatggcg attaccgttg atgttgaagt ggcgagcgat acaccgcatc cggcgcggat   3660
tggcctgaac tgccagctgg cgcaggtagc agagcgggta aactggctcg gattagggcc   3720
```

-continued

```
gcaagaaaac tatcccgacc gccttactgc cgcctgtttt gaccgctggg atctgccatt   3780
gtcagacatg tataccccgt acgtcttccc gagcgaaaac ggtctgcgct gcgggacgcg   3840
cgaattgaat tatggcccac accagtggcg cggcgacttc cagttcaaca tcagccgcta   3900
cagtcaacag caactgatgg aaaccagcca tcgccatctg ctgcacgcgg aagaaggcac   3960
atggctgaat atcgacggtt tccatatggg gattggtggc gacgactcct ggagcccgtc   4020
agtatcggcg gaattacagc tgagcgccgg tcgctaccat taccagttgg tctggtgtca   4080
aaaataataa taaccgggca ggccatgtct gcccgtattt cgcgtaagga aatccattat   4140
gtactatttc aagctaattc cggtggaaac gaggtcatca tttccttccg aaaaaacggt   4200
tgcatttaaa tcttacatat gtaatacttt caaagactac atttgtaaga tttgatgttt   4260
gagtcggctg aaagatcgta cgtaccaatt attgtttcgt gattgttcaa gccataacac   4320
tgtagggata gtggaaagag tgcttcatct ggttacgatc aatcaaatat tcaaacggag   4380
ggagacgatt ttgatgaaac cagtaacgtt atacgatgtc gcagagtatg ccggtgtctc   4440
ttatcagacc gtttcccgcg tggtgaacca ggccagccac gtttctgcga aaacgcggga   4500
aaaagtggaa gcggcgatgg cggagctgaa ttacattccc aaccgcgtgg cacaacaact   4560
ggcgggcaaa cagtcgttgc tgattggcgt tgccacctcc agtctggccc tgcacgcgcc   4620
gtcgcaaatt gtcgcggcga ttaaatctcg cgccgatcaa ctgggtgcca gcgtggtggt   4680
gtcgatggta gaacgaagcg gcgtcgaagc ctgtaaagcg gcggtgcaca atcttctcgc   4740
gcaacgcgtc agtgggctga tcattaacta tccgctggat gaccaggatg ccattgctgt   4800
ggaagctgcc tgcactaatg ttccggcgtt atttcttgat gtctctgacc agacacccat   4860
caacagtatt attttctccc atgaagacgg tacgcgactg ggcgtggagc atctggtcgc   4920
attgggtcac cagcaaatcg cgctgttagc gggcccatta agttctgtct cggcgcgtct   4980
gcgtctggct ggctggcata aatatctcac tcgcaatcaa attcagccga tagcggaacg   5040
ggaaggcgac tggagtgcca tgtccggttt tcaacaaacc atgcaaatgc tgaatgaggg   5100
catcgttccc actgcgatgc tggttgccaa cgatcagatg gcgctgggcg caatgcgcgc   5160
cattaccgag tccgggctgc gcgttggtgc ggatatctcg gtagtgggat acgacgatac   5220
cgaagacagc tcatgttata tcccgccgtc aaccaccatc aaacaggatt ttcgcctgct   5280
ggggcaaacc agcgtggacc gcttgctgca actctctcag ggccaggcgg tgaagggcaa   5340
tcagctgttg cccgtctcac tggtgaaaag aaaaaccacc ctggcgccca atacgcaaac   5400
cgcctctccc cgcgcgttgg ccgattcatt aatgcagctg gcacgacagg tttcccgact   5460
ggaaagcggg cagtgagcgc aacgcaatta atgtgagtta ggcatcgcat cctgtctcgc   5520
gtcgtcggtg atgacggtga aaacctctga cacatgcagc tcccggagac ggtcacagct   5580
tgtctgtaag cggatgccgg gagcagacaa gcccgtcagg gcgcgtcagc gggtgttggc   5640
gggtgtcggg gcgcagccat gacccagtca cgtagcgata gcggagtgta tactggctta   5700
actatgcggc atcagagcag attgtactga gagtgcacca tatgcggtgt gaaataccgc   5760
acagatgcgt aaggagaaaa taccgcatca ggcgctcttc cgcttcctcg ctcactgact   5820
cgctgcgctc ggtcgttcgg ctgcggcgag cggtatcagc tcactcaaag gcggtaatac   5880
ggttatccac agaatcaggg gataacgcag gaaagaacat gtgagcaaaa ggccagcaaa   5940
aggccaggaa ccgtaaaaag gccgcgttgc tggcgttttt ccataggctc cgcccccctg   6000
acgagcatca caaaaatcga cgctcaagtc agaggtggcg aaacccgaca ggactataaa   6060
gataccaggc gtttccccct ggaagctccc tcgtgcgctc tcctgttccg accctgccgc   6120
```

-continued

```
ttaccggata cctgtccgcc tttctccctt cgggaagcgt ggcgctttct caatgctcac   6180
gctgtaggta tctcagttcg gtgtaggtcg ttcgctccaa gctgggctgt gtgcacgaac   6240
cccccgttca gcccgaccgc tgcgccttat ccggtaacta tcgtcttgag tccaacccgg   6300
taagacacga cttatcgcca ctggcagcag ccactggtaa caggattagc agagcgaggt   6360
atgtaggcgg tgctacagag ttcttgaagt ggtggcctaa ctacggctac actagaagga   6420
cagtatttgg tatctgcgct ctgctgaagc cagttacctt cggaaaaaga gttggtagct   6480
cttgatccgg caaacaaacc accgctggta gcggtggttt ttttgtttgc aagcagcaga   6540
ttacgcgcag aaaaaaagga tctcaagaag atcctttgat cttttctacg gggtctgacg   6600
ctcagtggaa cgaaaactca cgttaaggga ttttggtcat gagattatca aaaaggatct   6660
tcacctagat ccttttaaat taaaaatgaa gttttaaatc aatctaaagt atatatgagt   6720
aaacttggtc tgacagttac caatgcttaa tcagtgaggc acctatctca gcgatctgtc   6780
tatttcgttc atccatagtt gcctgactcc ccgtcgtgta gataactacg atacgggagg   6840
gcttaccatc tggccccagt gctgcaatga taccgcgaga cccacgctca ccggctccag   6900
atttatcagc aataaaccag ccagccggaa gggccgagcg cagaagtggt cctgcaactt   6960
tatccgcctc catccagtct attaattgtt gccgggaagc tagagtaagt agttcgccag   7020
ttaatagttt gcgcaacgtt gttgccattg ctgcaggcat cgtggtgtca cgctcgtcgt   7080
ttggtatggc ttcattcagc tccggttccc aacgatcaag gcgagttaca tgatccccca   7140
tgttgtgcaa aaaagcggtt agctccttcg gtcctccgat cgttgtcaga agtaagttgg   7200
ccgcagtgtt atcactcatg gttatggcag cactgcataa ttctcttact gtcatgccat   7260
ccgtaagatg cttttctgtg actggtgagt actcaaccaa gtcattctga gaatagtgta   7320
tgcggcgacc gagttgctct tgcccggcgt caacacggga taataccgcg ccacatagca   7380
gaactttaaa agtgctcatc attggaaaac gttcttcggg gcgaaaactc tcaaggatct   7440
taccgctgtt gagatccagt tcgatgtaac ccactcgtgc acccaactga tcttcagcat   7500
cttttacttt caccagcgtt tctgggtgag caaaaacagg aaggcaaaat gccgcaaaaa   7560
agggaataag ggcgacacgg aaatgttgaa tactcatact cttccttttt caatattatt   7620
gaagcattta tcagggttat tgtctcatga gcggatacat atttgaatgt atttagaaaa   7680
ataaacaaat aggggttccg cgcacatttc cccgaaaagt gccacctgac gtctaagaaa   7740
ccattattat catgacatta acctataaaa ataggcgtat cacgaggccc tttcgtcttc   7800
aagaattgat cctctagcac aaaagaaaaa cgaaatgata caccaatcag tgcaaaaaaa   7860
gatataatgg gagataagac ggttcgtgtt cgtgctgact tgcaccatat cataaaaatc   7920
gaaacagcaa agaatggcgg aaacgtaaaa gaagttatgg aaataagact tagaagcaaa   7980
cttaagagtg tgttgatagt gcagtatctt aaaattttgt ataataggaa ttgaagttaa   8040
attagatgct aaaaatttgt aattaagaag gagtgattac atgaacaaaa atataaaata   8100
ttctcaaaac tttttaacga gtgaaaaagt actcaaccaa ataataaaac aattgaattt   8160
aaaagaaacc gataccgttt acgaaattgg aacaggtaaa gggcatttaa cgacgaaact   8220
ggctaaaata agtaaacagg taacgtctat tgaattagac agtcatctat tcaacttatc   8280
gtcagaaaaa ttaaaactga atactcgtgt cactttaatt caccaagata ttctacagtt   8340
tcaattccct aacaaacaga ggtataaaat tgttgggagt attccttacc atttaagcac   8400
acaaattatt aaaaaagtgg tttttgaaag ccatgcgtct gacatctatc tgattgttga   8460
```

```
agaaggattc tacaagcgta ccttggatat tcaccgaaca ctagggttgc tcttgcacac   8520

tcaagtctcg attcagcaat tgcttaagct gccagcggaa tgctttcatc ctaaaccaaa   8580

agtaaacagt gtcttaataa aacttacccg ccataccaca gatgttccag ataaatattg   8640

gaagctatat acgtactttg tttcaaaatg ggtcaatcga gaatatcgtc aactgtttac   8700

taaaaatcag tttcatcaag caatgaaaca cgccaaagta aacaatttaa gtaccgttac   8760

ttatgagcaa gtattgtcta tttttaatag ttatctatta tttaacggga ggaaataatt   8820

ctatgagtcg cttttgtaaa tttggaaagt tacacgttac taaagggaat gtagataaat   8880

tattaggtat actactgaca gcttccaagg agctaaagag gtccctagac tctagacccg   8940

gggatctctg cagtcggatc tggtaatgac tctctagctt gaggcatcaa ataaaacgaa   9000

aggctcagtc gaaagactgg gcctttcgtt ttatctgttg tttgtcggtg aacgctctcc   9060

tgagtaggac aaatccgccg ctctagctaa gcagaaggcc atcctgacgg atggcctttt   9120

tgcgtttcta caaactcttg ttaactctag agctgcctgc cgcgtttcgg tgatgaagat   9180

cttcccgatg attaattaat tcagaacgct cggttgccgc cgggcgtttt ttatgcagca   9240

atggcaagaa cgttgctcta ga                                            9262
```

<210> SEQ ID NO 137
<211> LENGTH: 4335
<212> TYPE: DNA
<213> ORGANISM: Artificial Sequence
<220> FEATURE:
<223> OTHER INFORMATION: pAH505 plasmi

<400> SEQUENCE: 137

```
gatcttccaa gatatcctaa cagcacaaga gcggaaagat gttttgttct acatccagaa     60

caacctctgc taaaattcct gaaaaatttt gcaaaaagtt gttgacttta tctacaaggt    120

gtggcataat gtgtggaatt gtgagcgctc acaattaagc ttaaggaggt gatctagaat    180

tccatggcca agcgaattct gtgtttcggt gattccctga cctggggctg ggtccccgtc    240

gaagacgggg cacccaccga gcggttcgcc cccgacgtgc gctggaccgg tgtgctggcc    300

cagcagctcg gagcggactt cgaggtgatc gaggagggac tgagcgcgcg caccaccaac    360

atcgacgacc ccaccgatcc gcggctcaac ggcgcgagct acctgccgtc gtgcctcgcg    420

acgcacctgc cgctcgacct ggtgatcatc atgctgggca ccaacgacac caaggcctac    480

ttccggcgca ccccgctcga catcgcgctg ggcatgtcgg tgctcgtcac gcaggtgctc    540

accagcgcgg gcggcgtcgg caccacgtac ccggctccca aggtgctggt ggtctcgccg    600

ccaccgctgg cgcccatgcc gcacccctgg ttccagttga tcttcgaggg cggcgagcag    660

aagaccactg agctcgcccg cgtgtacagc gcgctcgcgt cgttcatgaa ggtgccgttc    720

ttcgacgcgg gttcggtgat cagcaccgac ggcgtcgacg gaatccactt caccgaggcc    780

aacaatcgcg atctcggggt ggccctcgcg gaacaggtgc ggagcctgct gtaaaaggat    840

cccatcgcat gcggtacctc tagaagaagc ttggagacaa ggtaaaggat aaaacagcac    900

aattccaaga aaaacacgat ttagaaccta aaaagaacga atttgaacta actcataacc    960

gagaggtaaa aaaagaacga agtcgagatc agggaatgag tttataaaat aaaaaaagca   1020

cctgaaaagg tgtctttttt tgatggtttt gaacttgttc tttcttatct tgatacatat   1080

agaaataacg tcatttttat tttagttgct gaaaggtgcg ttgaagtgtt ggtatgtatg   1140

tgttttaaag tattgaaaac ccttaaaatt ggttgcacag aaaaacccca tctgttaaag   1200

ttataagtga ctaaacaaat aactaaatag atgggggttt cttttaatat tatgtgtcct   1260
```

-continued

```
aatagtagca tttattcaga tgaaaaatca agggttttag tggacaagac aaaaagtgga   1320
aaagtgagac catggagaga aaagaaaatc gctaatgttg attactttga acttctgcat   1380
attcttgaat ttaaaaaggc tgaaagagta aaagattgtg ctgaaatatt agagtataaa   1440
caaaatcgtg aaacaggcga aagaaagttg tatcgagtgt ggttttgtaa atccaggctt   1500
tgtccaatgt gcaactggag gagagcaatg aaacatggca ttcagtcaca aaaggttgtt   1560
gctgaagtta ttaaacaaaa gccaacagtt cgttggttgt ttctcacatt aacagttaaa   1620
aatgtttatg atggcgaaga attaaataag agtttgtcag atatggctca aggatttcgc   1680
cgaatgatgc aatataaaaa aattaataaa aatcttgttg gttttatgcg tgcaacggaa   1740
gtgacaataa ataataaaga taattcttat aatcagcaca tgcatgtatt ggtatgtgtg   1800
gaaccaactt attttaagaa tacagaaaac tacgtgaatc aaaaacaatg gattcaattt   1860
tggaaaaagg caatgaaatt agactatgat ccaaatgtaa aagttcaaat gattcgaccg   1920
aaaaataaat ataaatcgga tatacaatcg gcaattgacg aaactgcaaa atatcctgta   1980
aaggatacgg attttatgac cgatgatgaa gaaaagaatt tgaaacgttt gtctgatttg   2040
gaggaaggtt tacaccgtaa aaggttaatc tcctatggtg gtttgttaaa agaaatacat   2100
aaaaaattaa accttgatga cacagaagaa ggcgatttga ttcatacaga tgatgacgaa   2160
aaagccgatg aagatggatt ttctattatt gcaatgtgga attgggaacg gaaaaattat   2220
tttattaaag agtagttcaa caaacgggcc agtttgttga agattagatg ctataattgt   2280
tattaaaagg attgaaggat gcttaggaag acgagttatt aatagctgaa taagaacggt   2340
gctctccaaa tattcttatt tagaaaagca aatctaaaat tatctgaaaa gggaatgaga   2400
atagtgaatg gaccaataat aatgactaga gaagaaagaa tgaagattgt tcatgaaatt   2460
aaggaacgaa tattggataa atatggggat gatgttaagg ctattggtgt ttatggctct   2520
cttggtcgtc agactgatgg gccctattcg gatattgaga tgatgtgtgt catgtcaaca   2580
gaggaagcag agttcagcca tgaatggaca accggtgagt ggaaggtgga agtgaatttt   2640
gatagcgaag agattctact agattatgca tctcaggtgg aatcagattg gccgcttaca   2700
catggtcaat tttctctat tttgccgatt tatgattcag gtggatactt agagaaagtg   2760
tatcaaactg ctaaatcggt agaagcccaa acgttccacg atgcgatttg tgcccttatc   2820
gtagaagagc tgtttgaata tgcaggcaaa tggcgtaata ttcgtgtgca aggaccgaca   2880
acatttctac catccttgac tgtacaggta gcaatggcag gtgccatgtt gattggtctg   2940
catcatcgca tctgttatac gacgagcgct tcggtcttaa ctgaagcagt taagcaatca   3000
gatcttcctt caggttatga ccatctgtgc cagttcgtaa tgtctggtca actttccgac   3060
tctgagaaac ttctggaatc gctagagaat ttctggaatg ggattcagga gtggacagaa   3120
cgacacggat atatagtgga tgtgtcaaaa cgcataccat tttgaacgat gacctctaat   3180
aattgttaat catgttggtt acgtatttat taacttctcc tagtattagt aattatcatg   3240
gctgtcatgg cgcattaacg gaataaaggg tgtgcttaaa tcgggccatt ttgcgtaata   3300
agaaaaagga ttaattatga gcgaattgaa ttaataataa ggtaatagat ttacattaga   3360
aaatgaaagg ggattttatg cgtgagaatg ttacagtcta tcccggcatt gccagtcggg   3420
gatattaaaa agagtatagg tttttattgc gataaactag gtttcacttt ggttcaccat   3480
gaagatggat tcgcagttct aatgtgtaat gaggttcgga ttcatctatg ggaggcaagt   3540
gatgaaggct ggcgctctcg tagtaatgat tcaccggttt gtacaggtgc ggagtcgttt   3600
```

-continued

```
attgctggta ctgctagttg ccgcattgaa gtagagggaa ttgatgaatt atatcaacat   3660

attaagcctt tgggcatttt gcaccccaat acatcattaa aagatcagtg gtgggatgaa   3720

cgagactttg cagtaattga tcccgacaac aatttgatta gctttttca acaaataaaa    3780

agctaaaatc tattattaat ctgttcagca atcgggcgcg attgctgaat aaaagatacg   3840

agagacctct cttgtatctt ttttattttg agtggttttg tccgttacac tagaaaaccg   3900

aaagacaata aaaatttat tcttgctgag tctggctttc ggtaagctag acaaaacgga    3960

caaaataaaa attggcaagg gtttaaaggt ggagattttt tgagtgatct tctcaaaaaa   4020

tactacctgt cccttgctga tttttaaacg agcacgagag caaaaccccc ctttgctgag   4080

gtggcagagg gcaggttttt ttgtttcttt tttctcgtaa aaaaaagaaa ggtcttaaag   4140

gttttatggt tttggtcggc actgccgaca gcctcgcagg acacacactt tatgaatata   4200

aagtatagtg tgttatactt tacttggaag tggttgccgg aaagagcgaa aatgcctcac   4260

atttgtgcca cctaaaaagg agcgatttac atatgagtta tgcagtttgt agaatgcaaa   4320

aagtgaaatc agggg                                                    4335
```

<210> SEQ ID NO 138
<211> LENGTH: 23
<212> TYPE: DNA
<213> ORGANISM: Artificial Sequence
<220> FEATURE:
<223> OTHER INFORMATION: primer

<400> SEQUENCE: 138

```
caggctgcgc aactgttggg aag                                            23
```

<210> SEQ ID NO 139
<211> LENGTH: 81
<212> TYPE: DNA
<213> ORGANISM: Artificial Sequence
<220> FEATURE:
<223> OTHER INFORMATION: primer

<400> SEQUENCE: 139

```
agtagttcac cacctttcc ctatataaaa gcattagtgt atcaatttca gatccacaat     60

tttttgcttc tcactcttta c                                              81
```

<210> SEQ ID NO 140
<211> LENGTH: 75
<212> TYPE: DNA
<213> ORGANISM: Artificial Sequence
<220> FEATURE:
<223> OTHER INFORMATION: primer

<400> SEQUENCE: 140

```
aattgataca ctaatgcttt tatataggga aaaggtggtg aactactatg gccaagcgaa    60

ttctgtgttt cggtg                                                     75
```

<210> SEQ ID NO 141
<211> LENGTH: 36
<212> TYPE: DNA
<213> ORGANISM: Artificial Sequence
<220> FEATURE:
<223> OTHER INFORMATION: primer

<400> SEQUENCE: 141

```
gtgagaggca ttcggatcct tttacagcag gctccg                              36
```

<210> SEQ ID NO 142
<211> LENGTH: 7239
<212> TYPE: DNA
<213> ORGANISM: Artificial Sequence
<220> FEATURE:
<223> OTHER INFORMATION: pBSFNASally plasmid

<400> SEQUENCE: 142
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgcgtaata cgactcacta tagggcgaat tggagctcca 660
ccgcggtggc ggccgctcta gaactagtgg atcccccggg ctgcaggaat tctccatttt 720
cttctgctat caaaataaca gactcgtgat tttccaaacg agctttcaaa aaagcctctg 780
ccccttgcaa atcggatgcc tgtctataaa attcccgata ttggttaaac agcggcgcaa 840
tggcggccgc atctgatgtc tttgcttggc gaatgttcat cttatttctt cctccctctc 900
aataattttt tcattctatc ccttttctgt aaagtttatt tttcagaata cttttatcat 960
catgctttga aaaaatatca cgataatatc cattgttctc acggaagcac acgcaggtca 1020
tttgaacgaa ttttttcgac aggaatttgc cgggactcag gagcatttaa cctaaaaaag 1080
catgacattt cagcataatg aacatttact catgtctatt ttcgttcttt tctgtatgaa 1140
aatagttatt tcgagtctct acggaaatag cgagagatga tatacctaaa tagagataaa 1200
atcatctcaa aaaaatgggt ctactaaaat attattccat ctattacaat aaattcacag 1260
aatagtcttt taagtaagtc tactctgaat ttttttaaaa ggagagggta aagagtgaga 1320
agcaaaaaat tgtggatcag tttgctgttt gctttagcgt taatctttac gatggcgttc 1380
ggcagcacat cctctgccca ggcggcaggg aaatcaaacg gggaaaagaa atatattgtc 1440
gggtttaaac agacaatgag cacgatgagc gccgctaaga agaaagatgt catttctgaa 1500
aaaggcggga aagtgcaaaa gcaattcaaa tatgtagacg cagcttcagc tacattaaac 1560
gaaaaagctg taaaagaatt gaaaaaagac ccgagcgtcg cttacgttga agaagatcac 1620
gtagcacatg cgtacgcgca gtccgtgcct tacggcgtat cacaaattaa agcccctgct 1680
ctgcactctc aaggctacac tggatcaaat gttaaagtag cggttatcga cagcggtatc 1740
gattcttctc atcctgattt aaaggtagca ggcggagcca gcatggttcc ttctgaaaca 1800
aatcctttcc aagacaacaa ctctcacgga actcacgttg ccggcacagt tgcggctctt 1860
aataactcaa tcggtgtatt aggcgttgcg ccaagcgcat cactttacgc tgtaaaagtt 1920
ctcggtgctg acggttccgg ccaatacagc tggatcatta acggaatcga gtgggcgatc 1980
gcaaacaata tggacgttat taacatgagc ctcggcggac cttctggttc tgctgcttta 2040
aaagcggcag ttgataaagc cgttgcatcc ggcgtcgtag tcgttgcggc agccggtaac 2100

-continued

```
gaaggcactt ccggcagctc aagcacagtg ggctaccctg gtaaataccc ttctgtcatt   2160
gcagtaggcg ctgttgacag cagcaaccaa agagcatctt tctcaagcgt aggacctgag   2220
cttgatgtca tggcacctgg cgtatctatc caaagcacgc ttcctggaaa caaatacggc   2280
gcgttgaacg gtacatcaat ggcatctccg cacgttgccg gagcggctgc tttgattctt   2340
tctaagcacc cgaactggac aaacactcaa gtccgcagca gtttagaaaa caccactaca   2400
aaacttggtg attctttcta ctatggaaaa gggctgatca acgtacaggc ggcagctcag   2460
taaaacataa aaaaccggcc ttggccccgc cggtttttta ttatttttct tcctccgcat   2520
gttcaatccg ctccataatc gacggatggc tccctctgaa aattttaacg agaaacggcg   2580
ggttgacccg gctcagtccc gtaacggcca agtcctgaaa cgtctcaatc gccgcttccc   2640
ggtttccggt cagctcaatg ccgtaacggt cggcggcgtt ttcctgatac cgggagacgg   2700
cattcgtaat cggatcctct agagtcgatt tttacaagaa ttagctttat ataatttctg   2760
tttttctaaa gttttatcag ctacaaaaga cagaaatgta ttgcaatctt caactaaatc   2820
catttgattc tctccaatat gacgtttaat aaatttctga aatacttgat ttctttgttt   2880
tttctcagta tacttttcca tgttataaca cataaaaaca acttagtttt cacaaactat   2940
gacaataaaa aaagttgctt tttccccttt ctatgtatgt tttttactag tcatttaaaa   3000
cgatacatta ataggtacga aaaagcaact ttttttgcgc ttaaaaccag tcataccaat   3060
aacttaaggg taactagcct cgccggcaat agttaccctt attatcaaga taagaaagaa   3120
aaggattttt cgctacgctc aaatccttta aaaaaacaca aaagaccaca ttttttaatg   3180
tggtctttat tcttcaacta aagcacccat tagttcaaca aacgaaaatt ggataaagtg   3240
ggatattttt aaaatatata tttatgttac agtaatattg acttttaaaa aaggattgat   3300
tctaatgaag aaagcagaca agtaagcctc ctaaattcac tttagataaa aatttaggag   3360
gcatatcaaa tgaactttaa taaaattgat ttagacaatt ggaagagaaa agagatattt   3420
aatcattatt tgaaccaaca aacgactttt agtataacca cagaaattga tattagtgtt   3480
ttataccgaa acataaaaca agaaggatat aaattttacc ctgcatttat tttcttagtg   3540
acaagggtga taaactcaaa tacagctttt agaactggtt acaatagcga cggagagtta   3600
ggttattggg ataagttaga gccactttat acaatttttg atggtgtatc taaaacattc   3660
tctggtattt ggactcctgt aaagaatgac ttcaaagagt tttatgattt ataccttttct   3720
gatgtagaga aatataatgg ttcggggaaa ttgtttccca aaacacctat acctgaaaat   3780
gctttttctc tttctattat tccatggact tcatttactg ggtttaactt aaatatcaat   3840
aataatagta attaccttct acccattatt acagcaggaa aattcattaa taaaggtaat   3900
tcaatatatt taccgctatc tttacaggta catcattctg tttgtgatgg ttatcatgca   3960
ggattgttta tgaactctat tcaggaattg tcagataggc ctaatgactg gcttttataa   4020
tatgagataa tgccgactgt actttttaca gtcggttttc taatgtcact aacctgcccc   4080
gttagttgaa gaaggttttt atattacagc tccagatcca tatccttctt tttctgaacc   4140
gacttctcct tttcgcttc tttattccaa ttgctttatt gacgttgagc ctcggaaccc   4200
ttaacaatcc caaaacttgt cgaatggtcg gcttaatagc tcacgctatg ccgacattcg   4260
tctgcaagtt tagttaaggg ttcttctcaa cgcacaataa attttctcgg cataaatgcg   4320
tggtctaatt tttattttta ataaccttga tagcaaaaaa tgccattcca atacaaaacc   4380
acatacctat aatcgaccgg aattaattct ccattttctt ctgctatcaa aataacagac   4440
tcgtgatttt ccaaacgagc tttcaaaaaa gcctctgccc cttgcaaatc ggatgcctgt   4500
```

-continued ctataaaatt cccgatattg gttaaacagc ggcgcaatgg cggccgcatc tgatgtcttt 4560
gcttggcgaa tgttcatctt atttcttcct ccctctcaat aattttttca ttctatccct 4620
tttctgtaaa gtttattttt cagaatactt ttatcatcat gctttgaaaa aatatcacga 4680
taatatccat tgttctcacg gaagcacacg caggtcattt gaacgaattt tttcgacagg 4740
aatttgccgg gactcaggag catttaacct aaaaaagcat gacatttcag cataatgaac 4800
atttactcat gtctattttc gttcttttct gtatgaaaat agttatttcg agtctctacg 4860
gaaatagcga gagatgatat acctaaatag agataaaatc atctcaaaaa aatgggtcta 4920
ctaaaatatt attccatcta ttacaataaa ttcacagaat agtcttttaa gtaagtctac 4980
tctgaatttt tttatcaagc ttatcgatac cgtcgacctc gagggggggc ccggtaccca 5040
gcttttgttc cctttagtga gggttaattg cgcgcttggc gtaatcatgg tcatagctgt 5100
ttcctgtgtg aaattgttat ccgctcacaa ttccacacaa catacgagcc ggaagcataa 5160
agtgtaaagc ctggggtgcc taatgagtga gctaactcac attaattgcg ttgcgctcac 5220
tgcccgcttt ccagtcggga aacctgtcgt gccagctgca ttaatgaatc ggccaacgcg 5280
cggggagagg cggtttgcgt attgggcgct cttccgcttc ctcgctcact gactcgctgc 5340
gctcggtcgt tcggctgcgg cgagcggtat cagctcactc aaaggcggta atacggttat 5400
ccacagaatc aggggataac gcaggaaaga acatgtgagc aaaaggccag caaaaggcca 5460
ggaaccgtaa aaaggccgcg ttgctggcgt ttttccatag gctccgcccc cctgacgagc 5520
atcacaaaaa tcgacgctca agtcagaggt ggcgaaaccc gacaggacta taaagatacc 5580
aggcgtttcc ccctggaagc tccctcgtgc gctctcctgt tccgaccctg ccgcttaccg 5640
gatacctgtc cgcctttctc ccttcgggaa gcgtggcgct ttctcatagc tcacgctgta 5700
ggtatctcag ttcggtgtag gtcgttcgct ccaagctggg ctgtgtgcac gaaccccccg 5760
ttcagcccga ccgctgcgcc ttatccggta actatcgtct tgagtccaac ccggtaagac 5820
acgacttatc gccactggca gcagccactg gtaacaggat tagcagagcg aggtatgtag 5880
gcggtgctac agagttcttg aagtggtggc ctaactacgg ctacactaga aggacagtat 5940
ttggtatctg cgctctgctg aagccagtta ccttcggaaa aagagttggt agctcttgat 6000
ccggcaaaca aaccaccgct ggtagcggtg gtttttttgt ttgcaagcag cagattacgc 6060
gcagaaaaaa aggatctcaa gaagatcctt tgatcttttc tacggggtct gacgctcagt 6120
ggaacgaaaa ctcacgttaa gggattttgg tcatgagatt atcaaaaagg atcttcacct 6180
agatcctttt aaattaaaaa tgaagtttta aatcaatcta aagtatatat gagtaaactt 6240
ggtctgacag ttaccaatgc ttaatcagtg aggcacctat ctcagcgatc tgtctatttc 6300
gttcatccat agttgcctga ctccccgtcg tgtagataac tacgatacgg gagggcttac 6360
catctggccc cagtgctgca atgataccgc gagacccacg ctcaccggct ccagatttat 6420
cagcaataaa ccagccagcc ggaagggccg agcgcagaag tggtcctgca actttatccg 6480
cctccatcca gtctattaat tgttgccggg aagctagagt aagtagttcg ccagttaata 6540
gtttgcgcaa cgttgttgcc attgctacag gcatcgtggt gtcacgctcg tcgtttggta 6600
tggcttcatt cagctccggt tcccaacgat caaggcgagt tacatgatcc cccatgttgt 6660
gcaaaaaagc ggttagctcc ttcggtcctc cgatcgttgt cagaagtaag ttggccgcag 6720
tgttatcact catggttatg gcagcactgc ataattctct tactgtcatg ccatccgtaa 6780
gatgcttttc tgtgactggt gagtactcaa ccaagtcatt ctgagaatag tgtatgcggc 6840
gaccgagttg ctcttgcccg gcgtcaatac gggataatac cgcgccacat agcagaactt 6900
taaaagtgct catcattgga aaacgttctt cggggcgaaa actctcaagg atcttaccgc 6960
tgttgagatc cagttcgatg taacccactc gtgcacccaa ctgatcttca gcatctttta 7020
ctttcaccag cgtttctggg tgagcaaaaa caggaaggca aaatgccgca aaaaagggaa 7080
taagggcgac acggaaatgt tgaatactca tactcttcct ttttcaatat tattgaagca 7140
tttatcaggg ttattgtctc atgagcggat acatatttga atgtatttag aaaaataaac 7200
aaataggggt tccgcgcaca tttccccgaa aagtgccac 7239

<210> SEQ ID NO 143
<211> LENGTH: 5520
<212> TYPE: DNA
<213> ORGANISM: Artificial Sequence
<220> FEATURE:
<223> OTHER INFORMATION: pCP609 clone

<400> SEQUENCE: 143
caggctgcgc aactgttggg aagggcgatc ggtgcgggcc tcttcgctat tacgccagct 60
ggcgaaaggg ggatgtgctg caaggcgatt aagttgggta acgccagggt tttcccagtc 120
acgacgttgt aaaacgacgg ccagtgagcg cgcgtaatac gactcactat agggcgaatt 180
ggagctccac cgcggtggcg gccgctctag aactagtgga tcccccgggc tgcaggaatt 240
ctccattttc ttctgctatc aaaataacag actcgtgatt ttccaaacga gctttcaaaa 300
aagcctctgc cccttgcaaa tcggatgcct gtctataaaa ttcccgatat tggttaaaca 360
gcggcgcaat ggcggccgca tctgatgtct ttgcttggcg aatgttcatc ttatttcttc 420
ctccctctca ataatttttt cattctatcc cttttctgta aagtttattt ttcagaatac 480
ttttatcatc atgctttgaa aaaatatcac gataatatcc attgttctca cggaagcaca 540
cgcaggtcat ttgaacgaat tttttcgaca ggaatttgcc gggactcagg agcatttaac 600
ctaaaaaagc atgacatttc agcataatga acatttactc atgtctattt tcgttctttt 660
ctgtatgaaa atagttattt cgagtctcta cggaaatagc gagagatgat atacctaaat 720
agagataaaa tcatctcaaa aaaatgggtc tactaaaata ttattccatc tattacaata 780
aattcacaga atagtctttt aagtaagtct actctgaatt tttttaaaag gagagggtaa 840
agagtgagaa gcaaaaaatt gtggatctga aattgataca ctaatgcttt tatataggga 900
aaaggtggtg aactactatg gccaagcgaa ttctgtgttt cggtgattcc ctgacctggg 960
gctgggtccc cgtcgaagac ggggcaccca ccgagcggtt cgcccccgac gtgcgctgga 1020
ccggtgtgct ggcccagcag ctcggagcgg acttcgaggt gatcgaggag ggactgagcg 1080
cgcgcaccac caacatcgac gaccccaccg atccgcggct caacggcgcg agctacctgc 1140
cgtcgtgcct cgcgacgcac ctgccgctcg acctggtgat catcatgctg ggcaccaacg 1200
acaccaaggc ctacttccgg cgcaccccgc tcgacatcgc gctgggcatg tcggtgctcg 1260
tcacgcaggt gctcaccagc gcgggcggcg tcggcaccac gtacccggct cccaaggtgc 1320
tggtggtctc gccgccaccg ctggcgccca tgccgcaccc ctggttccag ttgatcttcg 1380
agggcggcga gcagaagacc actgagctcg cccgcgtgta cagcgcgctc gcgtcgttca 1440
tgaaggtgcc gttcttcgac gcgggttcgg tgatcagcac cgacggcgtc gacggaatcc 1500
acttcaccga ggccaacaat cgcgatctcg gggtggccct cgcggaacag gtgcggagcc 1560
tgctgtaaaa ggatccgaat gcctctcaca agggcgaatt ctgcagatat ccatcacact 1620
ggcggccgct cgagcatgca tctagagggc ccaattcgcc ctatagtgag tcgtattaca 1680

-continued

```
attcactggc cgtcgtttta caacgtcgtg actgggaaaa ccctggcgtt acccaactta   1740
atcgccttgc agcacatccc cctttcgcca gctggcgtaa tagcgaagag gcccgcaccg   1800
atcgcccttc ccaacagttg cgcagcctga atggcgaatg gacgcgccct gtagcggcgc   1860
attaagcgcg gcgggtgtgg tggttacgcg cagcgtgacc gctacacttg ccagcgccct   1920
agcgcccgct cctttcgctt tcttcccttc ctttctcgcc acgttcgccg gctttccccg   1980
tcaagctcta aatcgggggc tccctttagg gttccgattt agtgctttac ggcacctcga   2040
ccccaaaaaa cttgattagg gtgatggttc acgtagtggg ccatcgccct gatagacggt   2100
ttttcgccct ttgacgttgg agtccacgtt ctttaatagt ggactcttgt tccaaactgg   2160
aacaacactc aaccctatct cggtctattc ttttgattta taagggattt tgccgatttc   2220
ggcctattgg ttaaaaaatg agctgattta acaaaaattt aacgcgaatt ttaacaaaat   2280
tcagggcgca agggctgcta aaggaagcgg aacacgtaga aagccagtcc gcagaaacgg   2340
tgctgacccc ggatgaatgt cagctactgg gctatctgga caagggaaaa cgcaagcgca   2400
aagagaaagc aggtagcttg cagtgggctt acatggcgat agctagactg ggcggtttta   2460
tggacagcaa gcgaaccgga attgccagct ggggcgccct ctggtaaggt tgggaagccc   2520
tgcaaagtaa actggatggc tttcttgccg ccaaggatct gatggcgcag gggatcaaga   2580
tctgatcaag agacaggatg aggatcgttt cgcatgattg aacaagatgg attgcacgca   2640
ggttctccgg ccgcttgggt ggagaggcta ttcggctatg actgggcaca acagacaatc   2700
ggctgctctg atgccgccgt gttccggctg tcagcgcagg ggcgcccggt tctttttgtc   2760
aagaccgacc tgtccggtgc cctgaatgaa ctgcaggacg aggcagcgcg gctatcgtgg   2820
ctggccacga cgggcgttcc ttgcgcagct gtgctcgacg ttgtcactga agcgggaagg   2880
gactggctgc tattgggcga agtgccgggg caggatctcc tgtcatccca ccttgctcct   2940
gccgagaaag tatccatcat ggctgatgca atgcggcggc tgcatacgct tgatccggct   3000
acctgcccat tcgaccacca agcgaaacat cgcatcgagc gagcacgtac tcggatggaa   3060
gccggtcttg tcgatcagga tgatctggac gaagagcatc aggggctcgc gccagccgaa   3120
ctgttcgcca ggctcaaggc gcgcatgccc gacggcgagg atctcgtcgt gacccatggc   3180
gatgcctgct tgccgaatat catggtggaa aatggccgct tttctggatt catcgactgt   3240
ggccggctgg gtgtggcgga ccgctatcag gacatagcgt tggctacccg tgatattgct   3300
gaagagcttg gcggcgaatg ggctgaccgc ttcctcgtgc tttacggtat cgccgctccc   3360
gattcgcagc gcatcgcctt ctatcgcctt cttgacgagt tcttctgaat tgaaaaagga   3420
agagtatgag tattcaacat ttccgtgtcg cccttattcc cttttttgcg gcattttgcc   3480
ttcctgtttt tgctcaccca gaaacgctgg tgaaagtaaa agatgctgaa gatcagttgg   3540
gtgcacgagt gggttacatc gaactggatc tcaacagcgg taagatcctt gagagttttc   3600
gccccgaaga acgttttcca atgatgagca cttttaaagt tctgctatgt ggcgcggtat   3660
tatcccgtat tgacgccggg caagagcaac tcggtcgccg catacactat tctcagaatg   3720
acttggttga gtactcacca gtcacagaaa agcatcttac ggatggcatg acagtaagag   3780
aattatgcag tgctgccata accatgagtg ataacactgc ggccaactta cttctgacaa   3840
cgatcggagg accgaaggag ctaaccgctt ttttgcacaa catgggggat catgtaactc   3900
gccttgatcg ttgggaaccg gagctgaatg aagccatacc aaacgacgag cgtgacacca   3960
cgatgcctgt agcaatggca acaacgttgc gcaaactatt aactggcgaa ctacttactc   4020
```

tagcttcccg gcaacaatta atagactgga tggaggcgga taaagttgca ggaccacttc 4080
tgcgctcggc ccttccggct ggctggttta ttgctgataa atctggagcc ggtgagcgtg 4140
ggtctcgcgg tatcattgca gcactggggc cagatggtaa gccctcccgt atcgtagtta 4200
tctacacgac ggggagtcag gcaactatgg atgaacgaaa tagacagatc gctgagatag 4260
gtgcctcact gattaagcat tggtaactgt cagaccaagt ttactcatat atactttaga 4320
ttgatttaaa acttcatttt taatttaaaa ggatctaggt gaagatcctt tttgataatc 4380
tcatgaccaa aatcccttaa cgtgagtttt cgttccactg agcgtcagac cccgtagaaa 4440
agatcaaagg atcttcttga gatccttttt ttctgcgcgt aatctgctgc ttgcaaacaa 4500
aaaaaccacc gctaccagcg gtggtttgtt tgccggatca agagctacca actctttttc 4560
cgaaggtaac tggcttcagc agagcgcaga taccaaatac tgttcttcta gtgtagccgt 4620
agttaggcca ccacttcaag aactctgtag caccgcctac atacctcgct ctgctaatcc 4680
tgttaccagt ggctgctgcc agtggcgata agtcgtgtct taccgggttg gactcaagac 4740
gatagttacc ggataaggcg cagcggtcgg gctgaacggg gggttcgtgc acacagccca 4800
gcttggagcg aacgacctac accgaactga gatacctaca gcgtgagcta tgagaaagcg 4860
ccacgcttcc cgaagggaga aaggcggaca ggtatccggt aagcggcagg gtcggaacag 4920
gagagcgcac gagggagctt ccagggggaa acgcctggta tctttatagt cctgtcgggt 4980
ttcgccacct ctgacttgag cgtcgatttt tgtgatgctc gtcagggggg cggagcctat 5040
ggaaaaacgc cagcaacgcg gcctttttac ggttcctggc cttttgctgg ccttttgctc 5100
acatgttctt tcctgcgtta tcccctgatt ctgtggataa ccgtattacc gcctttgagt 5160
gagctgatac cgctcgccgc agccgaacga ccgagcgcag cgagtcagtg agcgaggaag 5220
cggaagagcg cccaatacgc aaaccgcctc tccccgcgcg ttggccgatt cattaatgca 5280
gctggcacga caggtttccc gactggaaag cgggcagtga gcgcaacgca attaatgtga 5340
gttagctcac tcattaggca ccccaggctt tacactttat gcttccggct cgtatgttgt 5400
gtggaattgt gagcggataa caatttcaca caggaaacag ctatgaccat gattacgcca 5460
agcttggtac cgagctcgga tccactagta acggccgcca gtgtgctgga attcgccctt 5520

<210> SEQ ID NO 144
<211> LENGTH: 6640
<212> TYPE: DNA
<213> ORGANISM: Artificial Sequence
<220> FEATURE:
<223> OTHER INFORMATION: pCP649 clone

<400> SEQUENCE: 144
tagaactagt ggatcccccg ggctgcagga attctccatt ttcttctgct atcaaaataa 60
cagactcgtg attttccaaa cgagctttca aaaaagcctc tgccccttgc aaatcggatg 120
cctgtctata aaattcccga tattggttaa acagcggcgc aatggcggcc gcatctgatg 180
tctttgcttg gcgaatgttc atcttatttc ttcctccctc tcaataattt tttcattcta 240 tccctttttct gtaaagttta tttttcagaa tacttttatc atcatgcttt gaaaaaatat 300
cacgataata tccattgttc tcacggaagc acacgcaggt catttgaacg aatttttttcg 360 acaggaattt gccgggactc aggagcattt aacctaaaaa agcatgacat ttcagcataa 420
tgaacattta ctcatgtcta ttttcgttct tttctgtatg aaaatagtta tttcgagtct 480
ctacggaaat agcgagagat gatataccta aatagagata aaatcatctc aaaaaaatgg 540
gtctactaaa atattattcc atctattaca ataaattcac agaatagtct tttaagtaag 600

```
tctactctga atttttttaa aaggagaggg taaagagtga gaagcaaaaa attgtggatc    660
tgaaattgat acactaatgc ttttatatag ggaaaaggtg gtgaactact atggccaagc    720
gaattctgtg tttcggtgat tccctgacct ggggctgggt ccccgtcgaa gacggggcac    780
ccaccgagcg gttcgccccc gacgtgcgct ggaccggtgt gctggcccag cagctcggag    840
cggacttcga ggtgatcgag gagggactga gcgcgcgcac caccaacatc gacgacccca    900
ccgatccgcg gctcaacggc gcgagctacc tgccgtcgtg cctcgcgacg cacctgccgc    960
tcgacctggt gatcatcatg ctgggcacca acgacaccaa ggcctacttc cggcgcaccc   1020
cgctcgacat cgcgctgggc atgtcggtgc tcgtcacgca ggtgctcacc agcgcgggcg   1080
gcgtcggcac cacgtacccg gctcccaagg tgctggtggt ctcgccgcca ccgctggcgc   1140
ccatgccgca cccctggttc cagttgatct tcgagggcgg cgagcagaag accactgagc   1200
tcgcccgcgt gtacagcgcg ctcgcgtcgt tcatgaaggt gccgttcttc gacgcgggtt   1260
cggtgatcag caccgacggc gtcgacggaa tccacttcac cgaggccaac aatcgcgatc   1320
tcggggtggc cctcgcggaa caggtgcgga gcctgctgta acggaatgcc tctcacaagg   1380
atccaagccg aattctgcag atatccatca cactggcggc cgctcgagca tgcatctaga   1440
gtcgattttt acaagaatta gctttatata atttctgttt ttctaaagtt ttatcagcta   1500
caaaagacag aaatgtattg caatcttcaa ctaaatccat ttgattctct ccaatatgac   1560
gtttaataaa tttctgaaat acttgatttc tttgtttttt ctcagtatac ttttccatgt   1620
tataacacat aaaaacaact tagttttcac aaactatgac aataaaaaaa gttgcttttt   1680
ccccttttcta tgtatgtttt ttactagtca tttaaaacga tacattaata ggtacgaaaa   1740
agcaactttt tttgcgctta aaaccagtca taccaataac ttaagggtaa ctagcctcgc   1800
cggcaatagt taccctatt atcaagataa gaaagaaaag gatttttcgc tacgctcaaa   1860
tcctttaaaa aaacacaaaa gaccacattt tttaatgtgg tctttattct tcaactaaag   1920
cacccattag ttcaacaaac gaaaattgga taaagtggga tatttttaaa atatatattt   1980
atgttacagt aatattgact tttaaaaaag gattgattct aatgaagaaa gcagacaagt   2040
aagcctccta aattcacttt agataaaaat ttaggaggca tatcaaatga actttaataa   2100
aattgattta gacaattgga agagaaaaga gatatttaat cattatttga accaacaaac   2160
gacttttagt ataaccacag aaattgatat tagtgtttta taccgaaaca taaaacaaga   2220
aggatataaa ttttaccctg catttatttt cttagtgaca agggtgataa actcaaatac   2280
agcttttaga actggttaca atagcgacgg agagttaggt tattgggata agttagagcc   2340
actttataca atttttgatg gtgtatctaa aacattctct ggtatttgga ctcctgtaaa   2400
gaatgacttc aaagagtttt atgatttata cctttctgat gtagagaaat ataatggttc   2460
ggggaaattg tttcccaaaa cacctatacc tgaaaatgct tttctcttt ctattattcc   2520
atggacttca tttactgggt ttaacttaaa tatcaataat aatagtaatt accttctacc   2580
cattattaca gcaggaaaat tcattaataa aggtaattca atatatttac cgctatcttt   2640
acaggtacat cattctgttt gtgatggtta tcatgcagga ttgtttatga actctattca   2700
ggaattgtca gataggccta atgactggct tttataatat gagataatgc cgactgtact   2760
ttttacagtc ggttttctaa tgtcactaac ctgccccgtt agttgaagaa ggtttttata   2820
ttacagctcc agatccatat ccttcttttt ctgaaccgac ttctcctttt tcgcttcttt   2880
attccaattg ctttattgac gttgagcctc ggaaccctta acaatcccaa aacttgtcga   2940
```

-continued

```
atggtcggct taatagctca cgctatgccg acattcgtct gcaagtttag ttaagggttc   3000
ttctcaacgc acaataaatt ttctcggcat aaatgcgtgg tctaattttt atttttaata   3060
accttgatag caaaaaatgc cattccaata caaaaccaca tacctataat cgacctgcag   3120
gaattaattc ctccattttc ttctgctatc aaaataacag actcgtgatt ttccaaacga   3180
gctttcaaaa aagcctctgc cccttgcaaa tcggatgcct gtctataaaa ttcccgatat   3240
tggcttaaac agcggcgcaa tggcggccgc atctgatgtc tttgcttggc gaatgttcat   3300
cttatttctt cctccctctc aataattttt tcattctatc ccttttctgt aaagtttatt   3360
tttcagaata cttttatcat catgctttga aaaaaatatca cgataatatc cattgttctc   3420
acggaagcac acgcaggtca tttgaacgaa ttttttcgac aggaatttgc cgggactcag   3480
gagcatttaa cctaaaaaag catgacattt cagcataatg aacatttact catgtctatt   3540
ttcgttcttt tctgtatgaa aatagttatt tcgagtctct acggaaatag cgagagatga   3600
tatacctaaa tagagataaa atcatctcaa aaaaatgggt ctactaaaat attattccat   3660
ctattacaat aaattcacag aatagtcttt taagtaagtc tactctgaat ttttttatca   3720
agcttatcga taccgtcgac ctcgaggggg ggcccggtac ccagcttttg ttccctttag   3780
tgagggttaa ttgcgcgctt ggcgtaatca tggtcatagc tgtttcctgt gtgaaattgt   3840
tatccgctca caattccaca caacatacga gccggaagca taaagtgtaa agcctggggt   3900
gcctaatgag tgagctaact cacattaatt gcgttgcgct cactgcccgc tttccagtcg   3960
ggaaacctgt cgtgccagct gcattaatga atcggccaac gcgcggggag aggcggtttg   4020
cgtattgggc gctcttccgc ttcctcgctc actgactcgc tgcgctcggt cgttcggctg   4080
cggcgagcgg tatcagctca ctcaaaggcg gtaatacggt tatccacaga atcaggggat   4140
aacgcaggaa agaacatgtg agcaaaaggc cagcaaaagg ccaggaaccg taaaaaggcc   4200
gcgttgctgg cgtttttcca taggctccgc ccccctgacg agcatcacaa aaatcgacgc   4260
tcaagtcaga ggtggcgaaa cccgacagga ctataaagat accaggcgtt tccccctgga   4320
agctccctcg tgcgctctcc tgttccgacc ctgccgctta ccggatacct gtccgccttt   4380
ctcccttcgg gaagcgtggc gctttctcat agctcacgct gtaggtatct cagttcggtg   4440
taggtcgttc gctccaagct gggctgtgtg cacgaacccc ccgttcagcc cgaccgctgc   4500
gccttatccg gtaactatcg tcttgagtcc aacccggtaa gacacgactt atcgccactg   4560
gcagcagcca ctggtaacag gattagcaga gcgaggtatg taggcggtgc tacagagttc   4620
ttgaagtggt ggcctaacta cggctacact agaaggacag tatttggtat ctgcgctctg   4680
ctgaagccag ttaccttcgg aaaaagagtt ggtagctctt gatccggcaa acaaaccacc   4740
gctggtagcg gtggtttttt tgtttgcaag cagcagatta cgcgcagaaa aaaaggatct   4800
caagaagatc ctttgatctt ttctacgggg tctgacgctc agtggaacga aaactcacgt   4860
taagggattt tggtcatgag attatcaaaa aggatcttca cctagatcct tttaaattaa   4920
aaatgaagtt ttaaatcaat ctaaagtata tatgagtaaa cttggtctga cagttaccaa   4980
tgcttaatca gtgaggcacc tatctcagcg atctgtctat ttcgttcatc catagttgcc   5040
tgactccccg tcgtgtagat aactacgata cgggagggct taccatctgg ccccagtgct   5100
gcaatgatac cgcgagaccc acgctcaccg gctccagatt tatcagcaat aaaccagcca   5160
gccggaaggg ccgagcgcag aagtggtcct gcaactttat ccgcctccat ccagtctatt   5220
aattgttgcc gggaagctag agtaagtagt tcgccagtta atagtttgcg caacgttgtt   5280
gccattgcta caggcatcgt ggtgtcacgc tcgtcgtttg gtatggcttc attcagctcc   5340
```

ggttcccaac gatcaaggcg agttacatga tcccccatgt tgtgcaaaaa agcggttagc 5400
tccttcggtc ctccgatcgt tgtcagaagt aagttggccg cagtgttatc actcatggtt 5460
atggcagcac tgcataattc tcttactgtc atgccatccg taagatgctt ttctgtgact 5520
ggtgagtact caaccaagtc attctgagaa tagtgtatgc ggcgaccgag ttgctcttgc 5580
ccggcgtcaa tacgggataa taccgcgcca catagcagaa ctttaaaagt gctcatcatt 5640
ggaaaacgtt cttcggggcg aaaactctca aggatcttac cgctgttgag atccagttcg 5700
atgtaaccca ctcgtgcacc caactgatct tcagcatctt ttactttcac cagcgtttct 5760
gggtgagcaa aaacaggaag gcaaaatgcc gcaaaaaagg gaataagggc gacacggaaa 5820
tgttgaatac tcatactctt cctttttcaa tattattgaa gcatttatca gggttattgt 5880
ctcatgagcg gatacatatt tgaatgtatt tagaaaaata aacaaatagg ggttccgcgc 5940
acatttcccc gaaaagtgcc acctaaattg taagcgttaa tattttgtta aaattcgcgt 6000
taaatttttg ttaaatcagc tcatttttta accaataggc cgaaatcggc aaaatccctt 6060
ataaatcaaa agaatagacc gagatagggt tgagtgttgt tccagtttgg aacaagagtc 6120
cactattaaa gaacgtggac tccaacgtca aagggcgaaa aaccgtctat cagggcgatg 6180
gcccactacg tgaaccatca ccctaatcaa gttttttggg gtcgaggtgc cgtaaagcac 6240
taaatcggaa ccctaaaggg agcccccgat ttagagcttg acggggaaag ccggcgaacg 6300
tggcgagaaa ggaagggaag aaagcgaaag gagcgggcgc tagggcgctg gcaagtgtag 6360
cggtcacgct gcgcgtaacc accacacccg ccgcgcttaa tgcgccgcta cagggcgcgt 6420
cccattcgcc attcaggctg cgcaactgtt gggaagggcg atcggtgcgg gcctcttcgc 6480
tattacgcca gctggcgaaa gggggatgtg ctgcaaggcg attaagttgg gtaacgccag 6540
ggttttccca gtcacgacgt tgtaaaacga cggccagtga gcgcgcgtaa tacgactcac 6600
tatagggcga attggagctc caccgcggtg gcggccgctc 6640

<210> SEQ ID NO 145
<211> LENGTH: 8819
<212> TYPE: DNA
<213> ORGANISM: Artificial Sequence
<220> FEATURE:
<223> OTHER INFORMATION: pSECGT-MSAT plasmid

<400> SEQUENCE: 145
ctagagtcga ccacgcaggc cgccaggtag tcgacgttga tctcgcagcc gagcccggcc 60
ggaccggcgg cgctgagcgc gaggccgacg gcgggacggc cggcaccggt acgcggtggc 120
gggtcgagtt cggtgagcag cccaccggcg atcaggtcgt cgacgagcgc ggagacggtg 180
gcccgggtga gcccggtgac ggcggcaact cccgcgcggg agagccgatc tgtgctgttt 240
gccacggtat gcagcaccag cgcgagatta tgggctcgca cgctcgactg tcggacgggg 300
gcactggaac gagaagtcag gcgagccgtc acgcccttga caatgccaca tcctgagcaa 360
ataattcaac cactaaacaa atcaaccgcg tttcccggag gtaaccatgg ccaagcgaat 420
tctgtgtttc ggtgattccc tgacctgggg ctgggtcccc gtcgaagacg gggcacccac 480
cgagcggttc gcccccgacg tgcgctggac cggtgtgctg gcccagcagc tcggagcgga 540
cttcgaggtg atcgaggagg gactgagcgc gcgcaccacc aacatcgacg accccaccga 600
tccgcggctc aacggcgcga gctacctgcc gtcgtgcctc gcgacgcacc tgccgctcga 660
cctggtgatc atcatgctgg gcaccaacga caccaaggcc tacttccggc gcaccccgct 720

-continued

```
cgacatcgcg ctgggcatgt cggtgctcgt cacgcaggtg ctcaccagcg cgggcggcgt    780
cggcaccacg tacccggcac ccaaggtgct ggtggtctcg ccgccaccgc tggcgcccat    840
gccgcacccc tggttccagt tgatcttcga gggcggcgag cagaagacca ctgagctcgc    900
ccgcgtgtac agcgcgctcg cgtcgttcat gaaggtgccg ttcttcgacg cgggttcggt    960
gatcagcacc gacggcgtcg acggaatcca cttcaccgag gccaacaatc gcgatctcgg   1020
ggtggccctc gcggaacagg tgcggagcct gctgtaacgg gatccgcgag cggatcggct   1080
gaccggagcg gggaggagga cgggcggccg gcggaaaagt ccgccggtcc gctgaatcgc   1140
tccccgggca cggacgtggc agtatcagcg ccatgtccgg catatcccag ccctccgcat   1200
gccccgaatt cggcgtaatc atggtcatag ctgtttcctg tgtgaaattg ttatccgctc   1260
acaattccac acaacatacg agccggaagc ataaagtgta aagcctgggg tgcctaatga   1320
gtgagctaac tcacattaat tgcgttgcgc tcactgcccg ctttccagtc gggaaacctg   1380
tcgtgccagc tgcattaatg aatcggccaa cgcgcgggga gaggcggttt gcgtattggg   1440
cgctcttccg cttcctcgct cactgactcg ctgcgctcgg tcgttcggct gcggcgagcg   1500
gtatcagctc actcaaaggc ggtaatacgg ttatccacag aatcagggga taacgcagga   1560
aagaacatgt gagcaaaagg ccagcaaaag gccaggaacc gtaaaaaggc cgcgttgctg   1620
gcgtttttcc ataggctccg cccccctgac gagcatcaca aaaatcgacg ctcaagtcag   1680
aggtggcgaa acccgacagg actataaaga taccaggcgt ttccccctgg aagctccctc   1740
gtgcgctctc ctgttccgac cctgccgctt accggatacc tgtccgcctt tctcccttcg   1800
ggaagcgtgg cgctttctca tagctcacgc tgtaggtatc tcagttcggt gtaggtcgtt   1860
cgctccaagc tgggctgtgt gcacgaaccc cccgttcagc ccgaccgctg cgccttatcc   1920
ggtaactatc gtcttgagtc caacccggta agacacgact tatcgccact ggcagcagcc   1980
actggtaaca ggattagcag agcgaggtat gtaggcggtg ctacagagtt cttgaagtgg   2040
tggcctaact acggctacac tagaaggaca gtatttggta tctgcgctct gctgaagcca   2100
gttaccttcg gaaaaagagt tggtagctct tgatccggca aacaaaccac cgctggtagc   2160
ggtggttttt ttgtttgcaa gcagcagatt acgcgcagaa aaaaaggatc tcaagaagat   2220
cctttgatct tttctacggg gtctgacgct cagtggaacg aaaactcacg ttaagggatt   2280
ttggtcatga gattatcaaa aaggatcttc acctagatcc ttttaaatta aaaatgaagt   2340
tttaaatcaa tctaaagtat atatgagtaa acttggtctg acagttacca atgcttaatc   2400
agtgaggcac ctatctcagc gatctgtcta tttcgttcat ccatagttgc ctgactcccc   2460
gtcgtgtaga taactacgat acgggagggc ttaccatctg gccccagtgc tgcaatgata   2520
ccgcgagacc cacgctcacc ggctccagat ttatcagcaa taaaccagcc agccggaagg   2580
gccgagcgca gaagtggtcc tgcaacttta tccgcctcca tccagtctat taattgttgc   2640
cgggaagcta gagtaagtag ttcgccagtt aatagtttgc gcaacgttgt tgccattgct   2700
acaggcatcg tggtgtcacg ctcgtcgttt ggtatggctt cattcagctc cggttcccaa   2760
cgatcaaggc gagttacatg atcccccatg ttgtgcaaaa aagcggttag ctccttcggt   2820
cctccgatcg ttgtcagaag taagttggcc gcagtgttat cactcatggt tatggcagca   2880
ctgcataatt ctcttactgt catgccatcc gtaagatgct tttctgtgac tggtgagtac   2940
tcaaccaagt cattctgaga atagtgtatg cggcgaccga gttgctcttg cccggcgtca   3000
atacgggata ataccgcgcc acatagcaga actttaaaag tgctcatcat tggaaaacgt   3060
tcttcggggc gaaaactctc aaggatctta ccgctgttga gatccagttc gatgtaaccc   3120
```

-continued actcgtgcac ccaactgatc ttcagcatct tttactttca ccagcgtttc tgggtgagca 3180
aaaacaggaa ggcaaaatgc cgcaaaaaag ggaataaggg cgacacggaa atgttgaata 3240
ctcatactct tcctttttca atattattga agcatttatc agggttattg tctcatgagc 3300
ggatacatat ttgaatgtat ttagaaaaat aaacaaatag gggttccgcg cacatttccc 3360
cgaaaagtgc cacctgacgt ctaagaaacc attattatca tgacattaac ctataaaaat 3420
aggcgtatca cgaggccctt tcgtctcgcg cgtttcggtg atgacggtga aaacctcttg 3480
acacatgcag ctcccggaga cggtcacagc ttgtctgtaa gcggatgccg ggagcagaca 3540
agcccgtcag ggcgcgtcag cgggtgttgg cgggtgtcgg ggctggctta actatgcggc 3600
atcagagcag attgtactga gagtgcacca tatgcggtgt gaaataccgc acagatgcgt 3660
aaggagaaaa taccgcatca ggcgccattc gccattcagg ctgcgcaact gttgggaagg 3720
gcgatcggtg cgggcctctt cgctattacg ccagctggcg aaagggggat gtgctgcaag 3780
gcgattaagt tgggtaacgc cagggttttc ccagtcacga cgttgtaaaa cgacggccag 3840
taagcttgca tgcctgcagg agtggggagg cacgatggcc gctttggtcg acctcaacga 3900
gacgatgaag ccgtggaacg acaccacccc ggcggccctg ctggaccaca cccggcacta 3960
caccttcgac gtctgatcat cactgacgaa tcgaggtcga ggaaccgagc gtccgaggaa 4020
cacaggcgct tatcggttgg ccgcgagatt cctgtcgatc ctctcgtgca gcgcgattcc 4080
gagggaaacg gaaacgttga gagactcggt ctggctcatc atggggatgg aaaccgaggc 4140
ggaagacgcc tcctcgaaca ggtcggaagg cccacccttt tcgctgccga acagcaaggc 4200
cagccgatcc ggattgtccc cgagttcctt cacggaaatg tcgccatccg ccttgagcgt 4260
catcagctgc ataccgctgt cccgaatgaa ggcgatggcc tcctcgcgac cggagagaac 4320
gacgggaagg gagaagacgt aacctcggct ggccctttgg agacgccggt ccgcgatgct 4380
ggtgatgtca ctgtcgacca ggatgatccc cgacgctccg agcgcgagcg acgtgcgtac 4440
tatcgcgccg atgttcccga cgatcttcac cccgtcgaga acgacgacgt ccccacgccg 4500
gctcgcgata tcgccgaacc tggccgggcg agggacgcgg gcgatgccga atgtcttggc 4560
cttccgctcc cccttgaaca actggttgac gatcgaggag tcgatgaggc ggaccggtat 4620
gttctgccgc ccgcacagat ccagcaactc agatggaaaa ggactgctgt cgctgccgta 4680
gacctcgatg aactccaccc cggccgcgat gctgtgcatg aggggctcga cgtcctcgat 4740
caacgttgtc tttatgttgg atcgcgacgg cttggtgaca tcgatgatcc gctgcaccgc 4800
gggatcggac ggatttgcga tggtgtccaa ctcagtcatg gtcgtcctac cggctgctgt 4860
gttcagtgac gcgattcctg ggtgtgaca ccctacgcga cgatggcgga tggctgccct 4920
gaccggcaat caccaacgca aggggaagtc gtcgctctct ggcaaagctc cccgctcttc 4980
cccgtccggg acccgcgcgg tcgatccccg catatgaagt attcgccttg atcagtcccg 5040
gtggacgcgc cagcggcccg ccggagcgac ggactccccg acctcgatcg tgtcgccctg 5100
agcgtccacg tagacgttgc gtgagagcag gactgggccg ccgccgaccg caccgccctc 5160
accaccgacc gcgaccgcgc catggccgcc gccgacggcc tggtcgccgc cgccgcccgc 5220
cggttcggcg cctgacccga ccaacccccg cggggcgccg gcacttcgtg ctggcgcccc 5280
gcccccaccc accaggagac cgaccatgac cgacttcgac ggacgcctga ccgaggggac 5340
cgtgaacctg gtccaggacc ccaacggcgg tggctggtcc gcccactgcg ctgagcccgg 5400
ttgcgactgg gccgacttcg ccggaccgct cggcttccag ggcctcgtgg ccatcgctcg 5460

-continued

```
ccgacacacg cactgaccgc acgtcaaagc cccgccggat acccggcggg gctctcttcg   5520
gccctccaag tcacaccagc cccaaggggc gtcgggagtg gcggagggaa cctctggccc   5580
gattggtgcc aggattccca ccagaccaaa gagcaacggg ccggacttcg cacctccgac   5640
ccgtccgctc ccagactcgc gccccttagc cgggcgagac aggaacgttg ctcgtgccca   5700
gagtacggag cgatgccgag gcattgccag atcggcccgc cgggccccgc tgccactgcg   5760
ggaccgcaat tgcccacaca ccgggcaaac ggccgcgtat ctactgctca gaccgctgcc   5820
ggatggcagc gaagcgggcg atcgcgcgtg tgacgcgaga tgccgcccga ggcaaaagcg   5880
aacaccttgg gaaagaaaca acagagtttc ccgcacccct ccgacctgcg gtttctccgg   5940
acggggtgga tggggagagc ccgagaggcg acagcctctg ggaagtagga agcacgtcgc   6000
ggaccgaggc tgcccgactg cggaaagccg cccggtacag ccgccgccgg acgctgtggc   6060
ggatcagcgg ggacgccgcg tgcaagggct gcggccgcgc cctgatggac cctgcctccg   6120
gcgtgatcgt cgcccagacg gcggccggaa cgtccgtggt cctgggcctg atgcggtgcg   6180
ggcggatctg gctctgcccg gtctgcgccg ccacgatccg gcacaagcgg gccgaggaga   6240
tcaccgccgc cgtggtcgag tggatcaagc gcggggggac cgcctacctg gtcaccttca   6300
cggcccgcca tgggcacacg gaccggctcg cggacctcat ggacgccctc cagggcaccc   6360
ggaagacgcc ggacagcccc cggcggccgg gcgcctacca gcgactgatc acgggcggca   6420
cgtgggccgg acgccgggcc aaggacgggc accgggccgc cgaccgcgag ggcatccgag   6480
accggatcgg gtacgtcggc atgatccgcg cgaccgaagt caccgtgggg cagatcaacg   6540
gctggcaccc gcacatccac gcgatcgtcc tggtcggcgg ccggaccgag ggggagcggt   6600
ccgcgaagca gatcgtcgcc accttcgagc cgaccggcgc cgcgctcgac gagtggcagg   6660
ggcactggcg gtccgtgtgg accgccgccc tgcgcaaggt caaccccgcc ttcacgcccg   6720
acgaccggca cggcgtcgac ttcaagcggc tggagaccga gcgcgacgcc aacgacctcg   6780
ccgagtacat cgccaagacc caggacggga aggcgcccgc cctcgaactc gcccgcgccg   6840
acctcaagac ggcgaccggc gggaacgtcg ccccgttcga actcctcgga cggatcgggg   6900
acctgaccgg cggcatgacc gaggacgacg ccgccggggt cggctcgctg gagtggaacc   6960
tctcgcgctg gcacgagtac gagcgggcaa cccggggacg ccgggccatc gaatggaccc   7020
gctacctgcg gcagatgctc gggctcgacg gcggcgacac cgaggccgac gacctcgatc   7080
tgctcctggc ggccgacgcc gacggcgggg agctgcgggc cggggtcgcc gtgaccgagg   7140
acggatggca cgcggtcacc cgccgcgccc tcgacctcga ggcgacccgg gccgccgaag   7200
gcaaggacgg caacgaggat tcggcggccg tgggcgaacg ggtgcgggag gtcctggcgc   7260
tggccgacgc ggccgacaca gtggtggtgc tcacggcggg ggaggtggcc gaggcgtacg   7320
ccgacatgct cgccgccctc gcccagcgcc gcgaggaagc aactgcacgc cgacggcgag   7380
agcaggacga cgaccaggac gacgacgccg acgaccgcca ggagcgggcc gcccggcaca   7440
tcgcccggct cgcaagtggg cccacttcgc actaactcgc tccccccgc cgtacgtcat   7500
cccggtgacg tacggcgggg gtcggtgacg tacgcggcga cggcggccgg ggtcgaagcc   7560
gcgggagtaa tcctgggatt actcgcccgg ggtcggcccc gccggcactt cgtgcaggcg   7620
gtacctcgcg cccgactcgc ctcgctacga gacgtgccgc gtacggtcgt cggccatgag   7680
caccaccacc cccagggacg ccgacggcgc gaagctctgc gcctggtgcg gctcggagat   7740
caagcaatcc ggcgtcggcc ggagccggga ctactgccgc cgctcctgcc gccagcgggc   7800
gtacgaggcc cggcgccagc gcgaggcgat cgtgtccgcc gtggcgtcgg cagtcgctcg   7860
```

ccgagatacg tcacgtgacg aaatgcagca gccttccatt ccgtcacgtg acgaaactcg 7920
ggccgcaggt cagagcacgg ttccgcccgc tccggccctg ccggaccccc ggctgcagct 7980
cgcccggccg ccggtccccc tgccgtccgg cccgtcccag aggcagcgtc ggcggctcct 8040 gcctccccg cccggcgccg accgggaccc gcaaacccct tgatccgctg tcgggggtga 8100
tcactacggt gggtgccgaa gtgatcacgg ggaggactga tgcaccacca ggaccgggac 8160
caggaccagg cgttagcggc agtgctggcc gcactgctcc tggtcggcgg gacgctgatc 8220
gtgcgggagc tcctgggcct gtggcccgcc gtggcggtcg gcatggcgcc cgccctcgcc 8280
ctctacggag gcccgcccgc ggcccgccgg atagccgtcg cggtcgaggt ccgccggttc 8340
cgccggcatc ttgcccacca cgatcgggca gccggatgac cggccacgac ggagccgcac 8400
ggctgaccag ctcgacggcc gccacctcat cgcggcagca ggtgctcccc agcaacccac 8460
gacggggctc agggtcgcct cacgcggctc agcaccgcga cggcgggggt acggcgctcc 8520
gggaggctga caggcgctca gacggccgcg tagggccgcg agtcccccac ccctccccgc 8580
tgccctgtcg gcgagcacaa cggcgatgcc cgcagtcggc ggagcaggcg ccacgtaaac 8640
cgcccaccga tgccgccccc gtcgtgtgcg cgggccggtc ggcggccggg ccggagcggg 8700
gcgaagacag gagcgtcggc cgggccgtgg gccgggccgc gcggcccgct cgcgggccgc 8760
cttgatgacg tagggaaagt tgtaccgcaa aaaacgcagc ctgaactagt tgcgatcct 8819

<210> SEQ ID NO 146
<211> LENGTH: 8742
<212> TYPE: DNA
<213> ORGANISM: Artificial Sequence
<220> FEATURE:
<223> OTHER INFORMATION: pSEGT-phdA4 plasmid
<220> FEATURE:
<221> NAME/KEY: misc_feature
<222> LOCATION: (193)..(193)
<223> OTHER INFORMATION: n is a, c, g, or t

<400> SEQUENCE: 146
ctagagatcg aacttcatgt tcgagttctt gttcacgtag aagccggaga tgtgagaggt 60
gatctggaac tgctcaccct cgttggtggt gacctggagg taaagcaagt gacccttctg 120
gcggaggtgg taaggaacgg ggttccacgg ggagagagag atggccttga cggtcttggg 180
aaggggagct tcngcgcggg ggaggatggt cttgagagag ggggagctag taatgtcgta 240
cttggacagg gagtgctcct tctccgacgc atcagccacc tcagcggaga tggcatcgtg 300
cagagacaga cccccggagg taaccatggc caagcgaatt ctgtgtttcg gtgattccct 360
gacctggggc tgggtccccg tcgaagacgg ggcacccacc gagcggttcg cccccgacgt 420
gcgctggacc ggtgtgctgg cccagcagct cggagcggac ttcgaggtga tcgaggaggg 480
actgagcgcg cgcaccacca acatcgacga ccccaccgat ccgcggctca acggcgcgag 540
ctacctgccg tcgtgcctcg cgacgcacct gccgctcgac ctggtgatca tcatgctggg 600
caccaacgac accaaggcct acttccggcg caccccgctc gacatcgcgc tgggcatgtc 660
ggtgctcgtc acgcaggtgc tcaccagcgc gggcggcgtc ggcaccacgt acccggcacc 720
caaggtgctg gtggtctcgc cgccaccgct ggcgcccatg ccgcacccct ggttccagtt 780
gatcttcgag ggcggcgagc agaagaccac tgagctcgcc cgcgtgtaca gcgcgctcgc 840
gtcgttcatg aaggtgccgt tcttcgacgc gggttcggtg atcagcaccg acggcgtcga 900
cggaatccac ttcaccgagg ccaacaatcg cgatctcggg gtggccctcg cggaacaggt 960

-continued

```
gcggagcctg ctgtaacaat ggggatccgc gagcggatcg gctgaccgga gcggggagga   1020
ggacgggcgg ccggcggaaa agtccgccgg tccgctgaat cgctccccgg gcacggacgt   1080
ggcagtatca gcgccatgtc cggcatatcc cagccctccg catgccccga attcggcgta   1140
atcatggtca tagctgtttc ctgtgtgaaa ttgttatccg ctcacaattc cacacaacat   1200
acgagccgga agcataaagt gtaaagcctg gggtgcctaa tgagtgagct aactcacatt   1260
aattgcgttg cgctcactgc ccgctttcca gtcgggaaac ctgtcgtgcc agctgcatta   1320
atgaatcggc caacgcgcgg ggagaggcgg tttgcgtatt gggcgctctt ccgcttcctc   1380
gctcactgac tcgctgcgct cggtcgttcg gctgcggcga gcggtatcag ctcactcaaa   1440
ggcggtaata cggttatcca cagaatcagg ggataacgca ggaaagaaca tgtgagcaaa   1500
aggccagcaa aaggccagga accgtaaaaa ggccgcgttg ctggcgtttt tccataggct   1560
ccgcccccct gacgagcatc acaaaaatcg acgctcaagt cagaggtggc gaaacccgac   1620
aggactataa agataccagg cgtttccccc tggaagctcc ctcgtgcgct ctcctgttcc   1680
gaccctgccg cttaccggat acctgtccgc ctttctccct tcgggaagcg tggcgctttc   1740
tcatagctca cgctgtaggt atctcagttc ggtgtaggtc gttcgctcca agctgggctg   1800
tgtgcacgaa ccccccgttc agcccgaccg ctgcgcctta tccggtaact atcgtcttga   1860
gtccaacccg gtaagacacg acttatcgcc actggcagca gccactggta acaggattag   1920
cagagcgagg tatgtaggcg gtgctacaga gttcttgaag tggtggccta actacggcta   1980
cactagaagg acagtatttg gtatctgcgc tctgctgaag ccagttacct tcggaaaaag   2040
agttggtagc tcttgatccg gcaaacaaac caccgctggt agcggtggtt tttttgtttg   2100
caagcagcag attacgcgca gaaaaaaagg atctcaagaa gatcctttga tcttttctac   2160
ggggtctgac gctcagtgga acgaaaactc acgttaaggg attttggtca tgagattatc   2220
aaaaaggatc ttcacctaga tccttttaaa ttaaaaatga agttttaaat caatctaaag   2280
tatatatgag taaacttggt ctgacagtta ccaatgctta atcagtgagg cacctatctc   2340
agcgatctgt ctatttcgtt catccatagt tgcctgactc cccgtcgtgt agataactac   2400
gatacgggag ggcttaccat ctggccccag tgctgcaatg ataccgcgag acccacgctc   2460
accggctcca gatttatcag caataaacca gccagccgga agggccgagc gcagaagtgg   2520
tcctgcaact ttatccgcct ccatccagtc tattaattgt tgccgggaag ctagagtaag   2580
tagttcgcca gttaatagtt tgcgcaacgt tgttgccatt gctacaggca tcgtggtgtc   2640
acgctcgtcg tttggtatgg cttcattcag ctccggttcc caacgatcaa ggcgagttac   2700
atgatccccc atgttgtgca aaaaagcggt tagctccttc ggtcctccga tcgttgtcag   2760
aagtaagttg gccgcagtgt tatcactcat ggttatggca gcactgcata attctcttac   2820
tgtcatgcca tccgtaagat gcttttctgt gactggtgag tactcaacca agtcattctg   2880
agaatagtgt atgcggcgac cgagttgctc ttgcccggcg tcaatacggg ataataccgc   2940
gccacatagc agaactttaa aagtgctcat cattggaaaa cgttcttcgg ggcgaaaact   3000
ctcaaggatc ttaccgctgt tgagatccag ttcgatgtaa cccactcgtg cacccaactg   3060
atcttcagca tcttttactt tcaccagcgt ttctgggtga gcaaaaacag gaaggcaaaa   3120
tgccgcaaaa aagggaataa gggcgacacg gaaatgttga atactcatac tcttcctttt   3180
tcaatattat tgaagcattt atcagggtta ttgtctcatg agcggataca tatttgaatg   3240
tatttagaaa aataaacaaa taggggttcc gcgcacattt ccccgaaaag tgccacctga   3300
cgtctaagaa accattatta tcatgacatt aacctataaa aataggcgta tcacgaggcc   3360
```

-continued

```
ctttcgtctc gcgcgtttcg gtgatgacgg tgaaaacctc ttgacacatg cagctcccgg   3420
agacggtcac agcttgtctg taagcggatg ccgggagcag acaagcccgt cagggcgcgt   3480
cagcgggtgt tggcgggtgt cggggctggc ttaactatgc ggcatcagag cagattgtac   3540
tgagagtgca ccatatgcgg tgtgaaatac cgcacagatg cgtaaggaga aaataccgca   3600
tcaggcgcca ttcgccattc aggctgcgca actgttggga agggcgatcg gtgcgggcct   3660
cttcgctatt acgccagctg gcgaaagggg gatgtgctgc aaggcgatta agttgggtaa   3720
cgccagggtt ttcccagtca cgacgttgta aaacgacggc cagtaagctt gcatgcctgc   3780
aggagtgggg aggcacgatg gccgctttgg tcgacctcaa cgagacgatg aagccgtgga   3840
acgacaccac cccggcggcc ctgctggacc acacccggca ctacaccttc gacgtctgat   3900
catcactgac gaatcgaggt cgaggaaccg agcgtccgag gaacacaggc gcttatcggt   3960
tggccgcgag attcctgtcg atcctctcgt gcagcgcgat tccgagggaa acggaaacgt   4020
tgagagactc ggtctggctc atcatgggga tggaaaccga ggcggaagac gcctcctcga   4080
acaggtcgga aggcccaccc ttttcgctgc cgaacagcaa ggccagccga tccggattgt   4140
ccccgagttc cttcacggaa atgtcgccat ccgccttgag cgtcatcagc tgcataccgc   4200
tgtcccgaat gaaggcgatg gcctcctcgc gaccggagag aacgacggga agggagaaga   4260
cgtaacctcg gctggccctt tggagacgcc ggtccgcgat gctggtgatg tcactgtcga   4320
ccaggatgat ccccgacgct ccgagcgcga gcgacgtgcg tactatcgcg ccgatgttcc   4380
cgacgatctt caccccgtcg agaacgacga cgtccccacg ccggctcgcg atatcgccga   4440
acctggccgg gcgagggacg cgggcgatgc cgaatgtctt ggccttccgc tccccccttga   4500
acaactggtt gacgatcgag gagtcgatga ggcggaccgg tatgttctgc cgcccgcaca   4560
gatccagcaa ctcagatgga aaaggactgc tgtcgctgcc gtagacctcg atgaactcca   4620
ccccggccgc gatgctgtgc atgaggggct cgacgtcctc gatcaacgtt gtctttatgt   4680
tggatcgcga cggcttggtg acatcgatga tccgctgcac cgcgggatcg gacggatttg   4740
cgatggtgtc caactcagtc atggtcgtcc taccggctgc tgtgttcagt gacgcgattc   4800
ctggggtgtg acaccctacg cgacgatggc ggatggctgc cctgaccggc aatcaccaac   4860
gcaaggggaa gtcgtcgctc tctggcaaag ctccccgctc ttccccgtcc gggacccgcg   4920
cggtcgatcc ccgcatatga agtattcgcc ttgatcagtc ccggtggacg cgccagcggc   4980
ccgccggagc gacggactcc ccgacctcga tcgtgtcgcc ctgagcgtcc acgtagacgt   5040
tgcgtgagag caggactggg ccgccgccga ccgcaccgcc ctcaccaccg accgcgaccg   5100
cgccatggcc gccgccgacg gcctggtcgc cgccgccgcc cgccggttcg gcgcctgacc   5160
cgaccaaccc ccgcggggcg ccggcacttc gtgctggcgc cccgccccca cccaccagga   5220
gaccgaccat gaccgacttc gacggacgcc tgaccgaggg gaccgtgaac ctggtccagg   5280
accccaacgg cggtggctgg tccgcccact gcgctgagcc cggttgcgac tgggccgact   5340
tcgccggacc gctcggcttc cagggcctcg tggccatcgc tcgccgacac acgcactgac   5400
cgcacgtcaa agccccgccg gatacccggc ggggctctct tcggccctcc aagtcacacc   5460
agccccaagg ggcgtcggga gtggcggagg gaacctctgg cccgattggt gccaggattc   5520
ccaccagacc aaagagcaac gggccggact tcgcacctcc gacccgtccg ctcccagact   5580
cgcgcccctt agccgggcga gacaggaacg ttgctcgtgc ccagagtacg gagcgatgcc   5640
gaggcattgc cagatcggcc cgccgggccc cgctgccact gcgggaccgc aattgcccac   5700
```

-continued

```
acaccgggca aacggccgcg tatctactgc tcagaccgct gccggatggc agcgaagcgg   5760
gcgatcgcgc gtgtgacgcg agatgccgcc cgaggcaaaa gcgaacacct tgggaaagaa   5820
acaacagagt ttcccgcacc cctccgacct gcggtttctc cggacggggt ggatggggag   5880
agcccgagag gcgacagcct ctgggaagta ggaagcacgt cgcggaccga ggctgcccga   5940
ctgcggaaag ccgcccggta cagccgccgc cggacgctgt ggcggatcag cggggacgcc   6000
gcgtgcaagg gctgcggccg cgccctgatg gaccctgcct ccggcgtgat cgtcgcccag   6060
acggcggccg gaacgtccgt ggtcctgggc ctgatgcggt gcgggcggat ctggctctgc   6120
ccggtctgcg ccgccacgat ccggcacaag cgggccgagg agatcaccgc cgccgtggtc   6180
gagtggatca agcgcggggg gaccgcctac ctggtcacct tcacggcccg ccatgggcac   6240
acggaccggc tcgcggacct catggacgcc ctccagggca cccggaagac gccggacagc   6300
ccccggcggc cgggcgccta ccagcgactg atcacgggcg gcacgtgggc cggacgccgg   6360
gccaaggacg ggcaccgggc cgccgaccgc gagggcatcc gagaccggat cgggtacgtc   6420
ggcatgatcc gcgcgaccga agtcaccgtg ggcagatca acggctggca cccgcacatc    6480
cacgcgatcg tcctggtcgg cggccggacc gagggggagc ggtccgcgaa gcagatcgtc   6540
gccaccttcg agccgaccgg cgccgcgctc gacgagtggc aggggcactg gcggtccgtg   6600
tggaccgccg ccctgcgcaa ggtcaacccc gccttcacgc ccgacgaccg gcacggcgtc   6660
gacttcaagc ggctggagac cgagcgcgac gccaacgacc tcgccgagta catcgccaag   6720
acccaggacg ggaaggcgcc cgccctcgaa ctcgcccgcg ccgacctcaa gacggcgacc   6780
ggcgggaacg tcgccccgtt cgaactcctc ggacggatcg gggacctgac cggcggcatg   6840
accgaggacg acgccgccgg ggtcggctcg ctggagtgga acctctcgcg ctggcacgag   6900
tacgagcggg caacccgggg acgccgggcc atcgaatgga cccgctacct gcggcagatg   6960
ctcgggctcg acggcggcga caccgaggcc gacgacctcg atctgctcct ggcggccgac   7020
gccgacggcg gggagctgcg ggccggggtc gccgtgaccg aggacggatg gcacgcggtc   7080
acccgccgcg ccctcgacct cgaggcgacc cgggccgccg aaggcaagga cggcaacgag   7140
gattcggcgg ccgtgggcga acgggtgcgg gaggtcctgg cgctggccga cgcggccgac   7200
acagtggtgg tgctcacggc gggggaggtg gccgaggcgt acgccgacat gctcgccgcc   7260
ctcgcccagc gccgcgagga agcaactgca cgccgacggc gagagcagga cgacgaccag   7320
gacgacgacg ccgacgaccg ccaggagcgg gccgcccggc acatcgcccg gctcgcaagt   7380
gggcccactt cgcactaact cgctcccccc cgccgtacgt catcccggtg acgtacggcg   7440
ggggtcggtg acgtacgcgg cgacggcggc cggggtcgaa gccgcgggag taatcctggg   7500
attactcgcc cggggtcggc cccgccggca cttcgtgcag gcggtacctc gcgcccgact   7560
cgcctcgcta cgagacgtgc cgcgtacggt cgtcggccat gagcaccacc acccccaggg   7620
acgccgacgg cgcgaagctc tgcgcctggt gcggctcgga gatcaagcaa tccggcgtcg   7680
gccggagccg ggactactgc cgccgctcct gccgccagcg ggcgtacgag gcccggcgcc   7740
agcgcgaggc gatcgtgtcc gccgtggcgt cggcagtcgc tcgccgagat acgtcacgtg   7800
acgaaatgca gcagccttcc attccgtcac gtgacgaaac tcgggccgca ggtcagagca   7860
cggttccgcc cgctccggcc ctgccggacc cccggctgca gctcgcccgg ccgccggtcc   7920
ccctgccgtc cggcccgtcc cagaggcagc gtcggcggct cctgcctccc ccgcccggcg   7980
ccgaccggga cccgcaaacc ccttgatccg ctgtcggggg tgatcactac ggtgggtgcc   8040
gaagtgatca cggggaggac tgatgcacca ccaggaccgg gaccaggacc aggcgttagc   8100
```

```
ggcagtgctg gccgcactgc tcctggtcgg cgggacgctg atcgtgcggg agctcctggg   8160

cctgtggccc gccgtggcgg tcggcatggc gcccgccctc gccctctacg gaggcccgcc   8220

cgcggcccgc cggatagccg tcgcggtcga ggtccgccgg ttccgccggc atcttgccca   8280

ccacgatcgg gcagccggat gaccggccac gacggagccg cacggctgac cagctcgacg   8340

gccgccacct catcgcggca gcaggtgctc cccagcaacc cacgacgggg ctcagggtcg   8400

cctcacgcgg ctcagcaccg cgacggcggg ggtacggcgc tccgggaggc tgacaggcgc   8460

tcagacggcc gcgtagggcc gcgagtcccc cacccctccc cgctgccctg tcggcgagca   8520

caacggcgat gcccgcagtc ggcggagcag gcgccacgta aaccgcccac cgatgccgcc   8580

cccgtcgtgt gcgcgggccg gtcggcggcc gggccggagc ggggcgaaga caggagcgtc   8640

ggccgggccg tgggccgggc cgcgcggccc gctcgcgggc cgccttgatg acgtagggaa   8700

agttgtaccg caaaaaacgc agcctgaact agttgcgatc ct                      8742
```

<210> SEQ ID NO 147
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 147

```
taacaggagg aattaaccnn sgccaagcga attctgtgt                             39
```

<210> SEQ ID NO 148
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 148

```
caggaggaat taaccatgnn saagcgaatt ctgtgtttc                             39
```

<210> SEQ ID NO 149
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 149

```
gaggaattaa ccatggccnn scgaattctg tgtttcggt                             39
```

<210> SEQ ID NO 150
<211> LENGTH: 39
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (19)..(20)
<223> OTHER INFORMATION: n is a, c, g, or t

<400> SEQUENCE: 150
gaattaacca tggccaagnn sattctgtgt ttcggtgat 39

<210> SEQ ID NO 151
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 151
ttaaccatgg ccaagcgann sctgtgtttc ggtgattcc 39

<210> SEQ ID NO 152
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 152
accatggcca agcgaattnn stgtttcggt gattccctg 39

<210> SEQ ID NO 153
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 153
atggccaagc gaattctgnn sttcggtgat tccctgacc 39

<210> SEQ ID NO 154
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 154
gccaagcgaa ttctgtgtnn sggtgattcc ctgacctgg 39

<210> SEQ ID NO 155
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 155
aagcgaattc tgtgtttcnn sgattccctg acctggggc 39

<210> SEQ ID NO 156
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 156
cgaattctgt gtttcggtnn stccctgacc tggggctgg 39

<210> SEQ ID NO 157
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 157
attctgtgtt tcggtgatnn sctgacctgg ggctgggtc 39

<210> SEQ ID NO 158
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 158
ctgtgtttcg gtgattccnn sacctggggc tgggtcccc 39

<210> SEQ ID NO 159
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 159
tgtttcggtg attccctgnn stggggctgg gtccccgtc 39

<210> SEQ ID NO 160
<211> LENGTH: 39
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 160
ttcggtgatt ccctgaccnn sggctgggtc cccgtcgaa 39

<210> SEQ ID NO 161
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 161
ggtgattccc tgacctggnn stgggtcccc gtcgaagac 39

<210> SEQ ID NO 162
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 162
gattccctga cctggggcnn sgtccccgtc gaagacggg 39

<210> SEQ ID NO 163
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 163
tccctgacct ggggctggnn scccgtcgaa gacggggca 39

<210> SEQ ID NO 164
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 164
ctgacctggg gctgggtcnn sgtcgaagac ggggcaccc 39

<210> SEQ ID NO 165
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 165
acctggggct gggtccccnn sgaagacggg gcacccacc 39

<210> SEQ ID NO 166
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 166
tggggctggg tccccgtcnn sgacggggca cccaccgag 39

<210> SEQ ID NO 167
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 167
ggctgggtcc ccgtcgaann sggggcaccc accgagcgg 39

<210> SEQ ID NO 168
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 168
tgggtccccg tcgaagacnn sgcacccacc gagcggttc 39

<210> SEQ ID NO 169
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 169
gtccccgtcg aagacgggnn scccaccgag cggttcgcc 39

<210> SEQ ID NO 170
<211> LENGTH: 39
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 170
cccgtcgaag acggggcann saccgagcgg ttcgccccc 39

<210> SEQ ID NO 171
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 171
gtcgaagacg gggcacccnn sgagcggttc gcccccgac 39

<210> SEQ ID NO 172
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 172
gaagacgggg cacccaccnn scggttcgcc cccgacgtg 39

<210> SEQ ID NO 173
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 173
gacggggcac ccaccgagnn sttcgccccc gacgtgcgc 39

<210> SEQ ID NO 174
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 174
ggggcaccca ccgagcggnn sgcccccgac gtgcgctgg 39

<210> SEQ ID NO 175
<211> LENGTH: 39

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 175
gcacccaccg agcggttcnn scccgacgtg cgctggacc 39

<210> SEQ ID NO 176
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 176
cccaccgagc ggttcgccnn sgacgtgcgc tggaccggt 39

<210> SEQ ID NO 177
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 177
accgagcggt tcgcccccnn sgtgcgctgg accggtgtg 39

<210> SEQ ID NO 178
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 178
gagcggttcg cccccgacnn scgctggacc ggtgtgctg 39

<210> SEQ ID NO 179
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 179
cggttcgccc ccgacgtgnn stggaccggt gtgctggcc 39

<210> SEQ ID NO 180

<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 180
ttcgcccccg acgtgcgcnn saccggtgtg ctggcccag 39

<210> SEQ ID NO 181
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 181
gcccccgacg tgcgctggnn sggtgtgctg gcccagcag 39

<210> SEQ ID NO 182
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 182
cccgacgtgc gctggaccnn sgtgctggcc cagcagctc 39

<210> SEQ ID NO 183
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 183
gacgtgcgct ggaccggtnn sctggcccag cagctcgga 39

<210> SEQ ID NO 184
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 184
gtgcgctgga ccggtgtgnn sgcccagcag ctcggagcg 39

<210> SEQ ID NO 185
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 185
cgctggaccg gtgtgctgnn scagcagctc ggagcggac 39

<210> SEQ ID NO 186
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 186
tggaccggtg tgctggccnn scagctcgga gcggacttc 39

<210> SEQ ID NO 187
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 187
accggtgtgc tggcccagnn sctcggagcg gacttcgag 39

<210> SEQ ID NO 188
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 188
ggtgtgctgg cccagcagnn sggagcggac ttcgaggtg 39

<210> SEQ ID NO 189
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 189
gtgctggccc agcagctcnn sgcggacttc gaggtgatc 39

<210> SEQ ID NO 190
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 190
ctggcccagc agctcggann sgacttcgag gtgatcgag 39

<210> SEQ ID NO 191
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 191
gcccagcagc tcggagcgnn sttcgaggtg atcgaggag 39

<210> SEQ ID NO 192
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 192
cagcagctcg gagcggacnn sgaggtgatc gaggaggga 39

<210> SEQ ID NO 193
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 193
cagctcggag cggacttcnn sgtgatcgag gagggactg 39

<210> SEQ ID NO 194
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 194
ctcggagcgg acttcgagnn satcgaggag ggactgagc 39

<210> SEQ ID NO 195
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 195
ggagcggact tcgaggtgnn sgaggaggga ctgagcgcg 39

<210> SEQ ID NO 196
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 196
gcggacttcg aggtgatcnn sgagggactg agcgcgcgc 39

<210> SEQ ID NO 197
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 197
gacttcgagg tgatcgagnn sggactgagc gcgcgcacc 39

<210> SEQ ID NO 198
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 198
ttcgaggtga tcgaggagnn sctgagcgcg cgcaccacc 39

<210> SEQ ID NO 199
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 199
gaggtgatcg aggagggann sagcgcgcgc accaccaac 39

<210> SEQ ID NO 200
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 200
gtgatcgagg agggactgnn sgcgcgcacc accaacatc 39

<210> SEQ ID NO 201
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 201
atcgaggagg gactgagcnn scgcaccacc aacatcgac 39

<210> SEQ ID NO 202
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 202
gaggagggac tgagcgcgnn saccaccaac atcgacgac 39

<210> SEQ ID NO 203
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 203
gagggactga gcgcgcgcnn saccaacatc gacgacccc 39

<210> SEQ ID NO 204
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 204
ggactgagcg cgcgcaccnn saacatcgac gaccccacc 39

<210> SEQ ID NO 205
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 205
ctgagcgcgc gcaccaccnn satcgacgac cccaccgat 39

<210> SEQ ID NO 206
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 206
agcgcgcgca ccaccaacnn sgacgacccc accgatccg 39

<210> SEQ ID NO 207
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 207
gcgcgcacca ccaacatcnn sgaccccacc gatccgcgg 39

<210> SEQ ID NO 208
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 208
cgcaccacca acatcgacnn scccaccgat ccgcggctc 39

<210> SEQ ID NO 209
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 209
accaccaaca tcgacgacnn saccgatccg cggctcaac 39

<210> SEQ ID NO 210
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 210
accaacatcg acgaccccnn sgatccgcgg ctcaacggc 39

<210> SEQ ID NO 211
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 211
aacatcgacg accccaccnn sccgcggctc aacggcgcg 39

<210> SEQ ID NO 212
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 212
atcgacgacc ccaccgatnn scggctcaac ggcgcgagc 39

<210> SEQ ID NO 213
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 213
gacgacccca ccgatccgnn sctcaacggc gcgagctac 39

<210> SEQ ID NO 214
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 214
gaccccaccg atccgcggnn saacggcgcg agctacctg 39

<210> SEQ ID NO 215
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 215
cccaccgatc cgcggctcnn sggcgcgagc tacctgccg 39

<210> SEQ ID NO 216
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 216
accgatccgc ggctcaacnn sgcgagctac ctgccgtcg 39

<210> SEQ ID NO 217
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 217
gatccgcggc tcaacggcnn sagctacctg ccgtcgtgc 39

<210> SEQ ID NO 218
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 218
ccgcggctca acggcgcgnn stacctgccg tcgtgcctc 39

<210> SEQ ID NO 219
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 219
cggctcaacg gcgcgagcnn sctgccgtcg tgcctcgcg 39

<210> SEQ ID NO 220
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 220
ctcaacggcg cgagctacnn sccgtcgtgc ctcgcgacg 39

<210> SEQ ID NO 221
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 221
aacggcgcga gctacctgnn stcgtgcctc gcgacgcac 39

<210> SEQ ID NO 222
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 222
ggcgcgagct acctgccgnn stgcctcgcg acgcacctg 39

<210> SEQ ID NO 223
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 223
gcgagctacc tgccgtcgnn sctcgcgacg cacctgccg 39

<210> SEQ ID NO 224
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 224
agctacctgc cgtcgtgcnn sgcgacgcac ctgccgctc 39

<210> SEQ ID NO 225
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 225
tacctgccgt cgtgcctcnn sacgcacctg ccgctcgac 39

<210> SEQ ID NO 226
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 226
ctgccgtcgt gcctcgcgnn scacctgccg ctcgacctg 39

<210> SEQ ID NO 227
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 227
ccgtcgtgcc tcgcgacgnn sctgccgctc gacctggtg 39

<210> SEQ ID NO 228
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 228
tcgtgcctcg cgacgcacnn sccgctcgac ctggtgatc 39

<210> SEQ ID NO 229
<211> LENGTH: 39
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (19)..(20)
<223> OTHER INFORMATION: n is a, c, g, or t

<400> SEQUENCE: 229
tgcctcgcga cgcacctgnn sctcgacctg gtgatcatc 39

<210> SEQ ID NO 230
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 230
ctcgcgacgc acctgccgnn sgacctggtg atcatcatg 39

<210> SEQ ID NO 231
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 231
gcgacgcacc tgccgctcnn sctggtgatc atcatgctg 39

<210> SEQ ID NO 232
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 232
acgcacctgc cgctcgacnn sgtgatcatc atgctgggc 39

<210> SEQ ID NO 233
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 233
cacctgccgc tcgacctgnn satcatcatg ctgggcacc 39

<210> SEQ ID NO 234
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 234
ctgccgctcg acctggtgnn satcatgctg ggcaccaac 39

<210> SEQ ID NO 235
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 235
ccgctcgacc tggtgatcnn satgctgggc accaacgac 39

<210> SEQ ID NO 236
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 236
ctcgacctgg tgatcatcnn sctgggcacc aacgacacc 39

<210> SEQ ID NO 237
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 237
gacctggtga tcatcatgnn sggcaccaac gacaccaag 39

<210> SEQ ID NO 238
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 238
ctggtgatca tcatgctgnn saccaacgac accaaggcc 39

<210> SEQ ID NO 239
<211> LENGTH: 39
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 239
gtgatcatca tgctgggcnn saacgacacc aaggcctac 39

<210> SEQ ID NO 240
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 240
atcatcatgc tgggcaccnn sgacaccaag gcctacttc 39

<210> SEQ ID NO 241
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 241
atcatgctgg gcaccaacnn saccaaggcc tacttccgg 39

<210> SEQ ID NO 242
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 242
atgctgggca ccaacgacnn saaggcctac ttccggcgc 39

<210> SEQ ID NO 243
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 243
ctgggcacca acgacaccnn sgcctacttc cggcgcacc 39

<210> SEQ ID NO 244
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 244
ggcaccaacg acaccaagnn stacttccgg cgcaccccg 39

<210> SEQ ID NO 245
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 245
accaacgaca ccaaggccnn sttccggcgc accccgctc 39

<210> SEQ ID NO 246
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is a, c, g, or t

<400> SEQUENCE: 246
aacgacacca aggcctacnn ncggcgcacc ccgctcgac 39

<210> SEQ ID NO 247
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is a, c, g, or t

<400> SEQUENCE: 247
gacaccaagg cctacttcnn ncgcaccccg ctcgacatc 39

<210> SEQ ID NO 248
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 248
accaaggcct acttccggnn saccccgctc gacatcgcg 39

<210> SEQ ID NO 249
<211> LENGTH: 39
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 249
aaggcctact tccggcgcnn sccgctcgac atcgcgctg 39

<210> SEQ ID NO 250
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 250
gcctacttcc ggcgcaccnn sctcgacatc gcgctgggc 39

<210> SEQ ID NO 251
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 251
tacttccggc gcaccccgnn sgacatcgcg ctgggcatg 39

<210> SEQ ID NO 252
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 252
ttccggcgca ccccgctcnn satcgcgctg ggcatgtcg 39

<210> SEQ ID NO 253
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 253
cggcgcaccc cgctcgacnn sgcgctgggc atgtcggtg 39

<210> SEQ ID NO 254
<211> LENGTH: 39

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 254
cgcaccccgc tcgacatcnn sctgggcatg tcggtgctc 39

<210> SEQ ID NO 255
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 255
accccgctcg acatcgcgnn sggcatgtcg gtgctcgtc 39

<210> SEQ ID NO 256
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 256
ccgctcgaca tcgcgctgnn satgtcggtg ctcgtcacg 39

<210> SEQ ID NO 257
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 257
ctcgacatcg cgctgggcnn stcggtgctc gtcacgcag 39

<210> SEQ ID NO 258
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 258
gacatcgcgc tgggcatgnn sgtgctcgtc acgcaggtg 39

<210> SEQ ID NO 259

<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 259
atcgcgctgg gcatgtcgnn sctcgtcacg caggtgctc 39

<210> SEQ ID NO 260
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 260
gcgctgggca tgtcggtgnn sgtcacgcag gtgctcacc 39

<210> SEQ ID NO 261
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 261
ctgggcatgt cggtgctcnn sacgcaggtg ctcaccagc 39

<210> SEQ ID NO 262
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 262
ggcatgtcgg tgctcgtcnn scaggtgctc accagcgcg 39

<210> SEQ ID NO 263
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 263
atgtcggtgc tcgtcacgnn sgtgctcacc agcgcgggc 39

-continued

<210> SEQ ID NO 264
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 264
tcggtgctcg tcacgcagnn sctcaccagc gcgggcggc 39

<210> SEQ ID NO 265
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 265
gtgctcgtca cgcaggtgnn saccagcgcg ggcggcgtc 39

<210> SEQ ID NO 266
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 266
ctcgtcacgc aggtgctcnn sagcgcgggc ggcgtcggc 39

<210> SEQ ID NO 267
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 267
gtcacgcagg tgctcaccnn sgcgggcggc gtcggcacc 39

<210> SEQ ID NO 268
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 268
acgcaggtgc tcaccagcnn sggcggcgtc ggcaccacg 39

<210> SEQ ID NO 269
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 269
caggtgctca ccagcgcgnn sggcgtcggc accacgtac 39

<210> SEQ ID NO 270
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 270
gtgctcacca gcgcgggcnn sgtcggcacc acgtacccg 39

<210> SEQ ID NO 271
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 271
ctcaccagcg cgggcggcnn sggcaccacg tacccggca 39

<210> SEQ ID NO 272
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 272
accagcgcgg gcggcgtcnn saccacgtac ccggcaccc 39

<210> SEQ ID NO 273
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 273
agcgcgggcg gcgtcggcnn sacgtacccg gcacccaag 39

<210> SEQ ID NO 274
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 274
gcgggcggcg tcggcaccnn stacccggca cccaaggtg 39

<210> SEQ ID NO 275
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 275
ggcggcgtcg gcaccacgnn sccggcaccc aaggtgctg 39

<210> SEQ ID NO 276
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 276
ggcgtcggca ccacgtacnn sgcacccaag gtgctggtg 39

<210> SEQ ID NO 277
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 277
gtcggcacca cgtacccgnn scccaaggtg ctggtggtc 39

<210> SEQ ID NO 278
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 278
ggcaccacgt acccggcann saaggtgctg gtggtctcg 39

<210> SEQ ID NO 279
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 279
accacgtacc cggcacccnn sgtgctggtg gtctcgccg 39

<210> SEQ ID NO 280
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 280
acgtacccgg cacccaagnn sctggtggtc tcgccgcca 39

<210> SEQ ID NO 281
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 281
tacccggcac ccaaggtgnn sgtggtctcg ccgccaccg 39

<210> SEQ ID NO 282
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 282
ccggcaccca aggtgctgnn sgtctcgccg ccaccgctg 39

<210> SEQ ID NO 283
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 283
gcacccaagg tgctggtgnn stcgccgcca ccgctggcg 39

<210> SEQ ID NO 284
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 284
cccaaggtgc tggtggtcnn sccgccaccg ctggcgccc 39

<210> SEQ ID NO 285
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 285
aaggtgctgg tggtctcgnn sccaccgctg gcgcccatg 39

<210> SEQ ID NO 286
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 286
gtgctggtgg tctcgccgnn sccgctggcg cccatgccg 39

<210> SEQ ID NO 287
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 287
ctggtggtct cgccgccann sctggcgccc atgccgcac 39

<210> SEQ ID NO 288
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 288
gtggtctcgc cgccaccgnn sgcgcccatg ccgcacccc 39

<210> SEQ ID NO 289
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 289
gtctcgccgc caccgctgnn scccatgccg cacccctgg 39

<210> SEQ ID NO 290
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 290
tcgccgccac cgctggcgnn satgccgcac ccctggttc 39

<210> SEQ ID NO 291
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 291
ccgccaccgc tggcgcccnn sccgcacccc tggttccag 39

<210> SEQ ID NO 292
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 292
ccaccgctgg cgcccatgnn scacccctgg ttccagttg 39

<210> SEQ ID NO 293
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 293
ccgctggcgc ccatgccgnn sccctggttc cagttgatc                                    39

<210> SEQ ID NO 294
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 294
ctggcgccca tgccgcacnn stggttccag ttgatcttc                                    39

<210> SEQ ID NO 295
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 295
gcgcccatgc cgcaccccnn sttccagttg atcttcgag                                    39

<210> SEQ ID NO 296
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 296
cccatgccgc acccctggnn scagttgatc ttcgagggc                                    39

<210> SEQ ID NO 297
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 297
atgccgcacc cctggttcnn sttgatcttc gagggcggc                                    39

<210> SEQ ID NO 298
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 298
ccgcacccct ggttccagnn satcttcgag ggcggcgag 39

<210> SEQ ID NO 299
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 299
cacccctggt tccagttgnn sttcgagggc ggcgagcag 39

<210> SEQ ID NO 300
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 300
ccctggttcc agttgatcnn sgagggcggc gagcagaag 39

<210> SEQ ID NO 301
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 301
tggttccagt tgatcttcnn sggcggcgag cagaagacc 39

<210> SEQ ID NO 302
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 302
ttccagttga tcttcgagnn sggcgagcag aagaccact 39

<210> SEQ ID NO 303
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 303
cagttgatct tcgagggcnn sgagcagaag accactgag 39

<210> SEQ ID NO 304
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 304
ttgatcttcg agggcggcnn scagaagacc actgagctc 39

<210> SEQ ID NO 305
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 305
atcttcgagg gcggcgagnn saagaccact gagctcgcc 39

<210> SEQ ID NO 306
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 306
ttcgagggcg gcgagcagnn saccactgag ctcgcccgc 39

<210> SEQ ID NO 307
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 307
gagggcggcg agcagaagnn sactgagctc gcccgcgtg 39

<210> SEQ ID NO 308
<211> LENGTH: 39
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (19)..(20)
<223> OTHER INFORMATION: n is a, c, g, or t

<400> SEQUENCE: 308
ggcggcgagc agaagaccnn sgagctcgcc cgcgtgtac 39

<210> SEQ ID NO 309
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 309
ggcgagcaga agaccactnn sctcgcccgc gtgtacagc 39

<210> SEQ ID NO 310
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 310
gagcagaaga ccactgagnn sgcccgcgtg tacagcgcg 39

<210> SEQ ID NO 311
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 311
cagaagacca ctgagctcnn scgcgtgtac agcgcgctc 39

<210> SEQ ID NO 312
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 312
aagaccactg agctcgccnn sgtgtacagc gcgctcgcg 39

<210> SEQ ID NO 313
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 313
accactgagc tcgcccgcnn stacagcgcg ctcgcgtcg 39

<210> SEQ ID NO 314
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 314
actgagctcg cccgcgtgnn sagcgcgctc gcgtcgttc 39

<210> SEQ ID NO 315
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 315
gagctcgccc gcgtgtacnn sgcgctcgcg tcgttcatg 39

<210> SEQ ID NO 316
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 316
ctcgcccgcg tgtacagcnn sctcgcgtcg ttcatgaag 39

<210> SEQ ID NO 317
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 317
gcccgcgtgt acagcgcgnn sgcgtcgttc atgaaggtg 39

<210> SEQ ID NO 318
<211> LENGTH: 39
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 318
cgcgtgtaca gcgcgctcnn stcgttcatg aaggtgccg 39

<210> SEQ ID NO 319
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 319
gtgtacagcg cgctcgcgnn sttcatgaag gtgccgttc 39

<210> SEQ ID NO 320
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 320
tacagcgcgc tcgcgtcgnn satgaaggtg ccgttcttc 39

<210> SEQ ID NO 321
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 321
agcgcgctcg cgtcgttcnn saaggtgccg ttcttcgac 39

<210> SEQ ID NO 322
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 322
gcgctcgcgt cgttcatgnn sgtgccgttc ttcgacgcg 39

<210> SEQ ID NO 323
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 323
ctcgcgtcgt tcatgaagnn sccgttcttc gacgcgggt 39

<210> SEQ ID NO 324
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 324
gcgtcgttca tgaaggtgnn sttcttcgac gcgggttcg 39

<210> SEQ ID NO 325
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 325
tcgttcatga aggtgccgnn sttcgacgcg ggttcggtg 39

<210> SEQ ID NO 326
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 326
ttcatgaagg tgccgttcnn sgacgcgggt tcggtgatc 39

<210> SEQ ID NO 327
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 327
atgaaggtgc cgttcttcnn sgcgggttcg gtgatcagc 39

<210> SEQ ID NO 328
<211> LENGTH: 39
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 328
aaggtgccgt tcttcgacnn sggttcggtg atcagcacc 39

<210> SEQ ID NO 329
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 329
gtgccgttct tcgacgcgnn stcggtgatc agcaccgac 39

<210> SEQ ID NO 330
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 330
ccgttcttcg acgcgggtnn sgtgatcagc accgacggc 39

<210> SEQ ID NO 331
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 331
ttcttcgacg cgggttcgnn satcagcacc gacggcgtc 39

<210> SEQ ID NO 332
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 332
ttcgacgcgg gttcggtgnn sagcaccgac ggcgtcgac 39

<210> SEQ ID NO 333
<211> LENGTH: 39

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 333
gacgcgggtt cggtgatcnn saccgacggc gtcgacgga 39

<210> SEQ ID NO 334
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 334
gcgggttcgg tgatcagcnn sgacggcgtc gacggaatc 39

<210> SEQ ID NO 335
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 335
ggttcggtga tcagcaccnn sggcgtcgac ggaatccac 39

<210> SEQ ID NO 336
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 336
tcggtgatca gcaccgacnn sgtcgacgga atccacttc 39

<210> SEQ ID NO 337
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 337
gtgatcagca ccgacggcnn sgacggaatc cacttcacc 39

<210> SEQ ID NO 338

<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 338
atcagcaccg acggcgtcnn sggaatccac ttcaccgag 39

<210> SEQ ID NO 339
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 339
agcaccgacg gcgtcgacnn satccacttc accgaggcc 39

<210> SEQ ID NO 340
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 340
accgacggcg tcgacggann scacttcacc gaggccaac 39

<210> SEQ ID NO 341
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 341
gacggcgtcg acggaatcnn sttcaccgag gccaacaat 39

<210> SEQ ID NO 342
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 342
ggcgtcgacg gaatccacnn saccgaggcc aacaatcgc 39

<210> SEQ ID NO 343
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 343
gtcgacggaa tccacttcnn sgaggccaac aatcgcgat 39

<210> SEQ ID NO 344
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 344
gacggaatcc acttcaccnn sgccaacaat cgcgatctc 39

<210> SEQ ID NO 345
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 345
ggaatccact tcaccgagnn saacaatcgc gatctcggg 39

<210> SEQ ID NO 346
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 346
atccacttca ccgaggccnn saatcgcgat ctcggggtg 39

<210> SEQ ID NO 347
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 347
cacttcaccg aggccaacnn scgcgatctc ggggtggcc 39

<210> SEQ ID NO 348
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 348
ttcaccgagg ccaacaatnn sgatctcggg gtggccctc 39

<210> SEQ ID NO 349
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 349
accgaggcca acaatcgcnn sctcggggtg gccctcgcg 39

<210> SEQ ID NO 350
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 350
gaggccaaca atcgcgatnn sggggtggcc ctcgcggaa 39

<210> SEQ ID NO 351
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 351
gccaacaatc gcgatctcnn sgtggccctc gcggaacag 39

<210> SEQ ID NO 352
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 352
aacaatcgcg atctcgggnn sgccctcgcg gaacaggtg 39

<210> SEQ ID NO 353
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 353
aatcgcgatc tcggggtgnn sctcgcggaa caggtgcag 39

<210> SEQ ID NO 354
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 354
cgcgatctcg gggtggccnn sgcggaacag gtgcagagc 39

<210> SEQ ID NO 355
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 355
gatctcgggg tggccctcnn sgaacaggtg cagagcctg 39

<210> SEQ ID NO 356
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 356
ctcggggtgg ccctcgcgnn scaggtgcag agcctgctg 39

<210> SEQ ID NO 357
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 357

```
ggggtggccc tcgcggaann sgtgcagagc ctgctgtaa                          39


<210> SEQ ID NO 358
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 358

gtggccctcg cggaacagnn scagagcctg ctgtaaaag                          39


<210> SEQ ID NO 359
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 359

gccctcgcgg aacaggtgnn sagcctgctg taaaagggc                          39


<210> SEQ ID NO 360
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 360

ctcgcggaac aggtgcagnn sctgctgtaa aagggcgaa                          39


<210> SEQ ID NO 361
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 361

gcggaacagg tgcagagcnn sctgtaaaag ggcgaattc                          39


<210> SEQ ID NO 362
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 362
```

gaacaggtgc agagcctgnn staaaagggc gaattctgc 39

<210> SEQ ID NO 363
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 363
acacagaatt cgcttggcsn nggttaattc ctcctgtta 39

<210> SEQ ID NO 364
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 364
gaaacacaga attcgcttsn ncatggttaa ttcctcctg 39

<210> SEQ ID NO 365
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 365
accgaaacac agaattcgsn nggccatggt taattcctc 39

<210> SEQ ID NO 366
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 366
atcaccgaaa cacagaatsn ncttggccat ggttaattc 39

<210> SEQ ID NO 367
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 367
ggaatcaccg aaacacagsn ntcgcttggc catggttaa 39

<210> SEQ ID NO 368
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 368
cagggaatca ccgaaacasn naattcgctt ggccatggt 39

<210> SEQ ID NO 369
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 369
ggtcagggaa tcaccgaasn ncagaattcg cttggccat 39

<210> SEQ ID NO 370
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 370
ccaggtcagg gaatcaccsn nacacagaat tcgcttggc 39

<210> SEQ ID NO 371
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 371
gccccaggtc agggaatcsn ngaaacacag aattcgctt 39

<210> SEQ ID NO 372
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 372
ccagccccag gtcagggasn naccgaaaca cagaattcg 39

<210> SEQ ID NO 373
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 373
gacccagccc caggtcagsn natcaccgaa acacagaat 39

<210> SEQ ID NO 374
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 374
ggggacccag ccccaggtsn nggaatcacc gaaacacag 39

<210> SEQ ID NO 375
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 375
gacggggacc cagccccasn ncagggaatc accgaaaca 39

<210> SEQ ID NO 376
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 376
ttcgacgggg acccagccsn nggtcaggga atcaccgaa 39

<210> SEQ ID NO 377
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 377
gtcttcgacg gggacccasn nccaggtcag ggaatcacc 39

<210> SEQ ID NO 378
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 378
cccgtcttcg acggggacsn ngccccaggt cagggaatc 39

<210> SEQ ID NO 379
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 379
tgccccgtct tcgacgggsn nccagcccca ggtcaggga 39

<210> SEQ ID NO 380
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 380
gggtgccccg tcttcgacsn ngacccagcc ccaggtcag 39

<210> SEQ ID NO 381
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 381
ggtgggtgcc ccgtcttcsn nggggaccca gccccaggt 39

<210> SEQ ID NO 382
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 382
ctcggtgggt gccccgtcsn ngacggggac ccagcccca 39

<210> SEQ ID NO 383
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 383
ccgctcggtg ggtgccccsn nttcgacggg gacccagcc 39

<210> SEQ ID NO 384
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 384
gaaccgctcg gtgggtgcsn ngtcttcgac ggggaccca 39

<210> SEQ ID NO 385
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 385
ggcgaaccgc tcggtgggsn ncccgtcttc gacggggac 39

<210> SEQ ID NO 386
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 386
gggggcgaac cgctcggtsn ntgccccgtc ttcgacggg 39

<210> SEQ ID NO 387
<211> LENGTH: 39
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (20)..(21)
<223> OTHER INFORMATION: n is a, c, g, or t

<400> SEQUENCE: 387
gtcgggggcg aaccgctcsn ngggtgcccc gtcttcgac 39

<210> SEQ ID NO 388
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 388
cacgtcgggg gcgaaccgsn nggtgggtgc cccgtcttc 39

<210> SEQ ID NO 389
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 389
gcgcacgtcg gggcgaasn nctcggtggg tgccccgtc 39

<210> SEQ ID NO 390
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 390
ccagcgcacg tcgggggcsn nccgctcggt gggtgcccc 39

<210> SEQ ID NO 391
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 391
ggtccagcgc acgtcgggsn ngaaccgctc ggtgggtgc 39

<210> SEQ ID NO 392
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 392
accggtccag cgcacgtcsn nggcgaaccg ctcggtggg 39

<210> SEQ ID NO 393
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 393
cacaccggtc cagcgcacsn ngggggcgaa ccgctcggt 39

<210> SEQ ID NO 394
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 394
cagcacaccg gtccagcgsn ngtcgggggc gaaccgctc 39

<210> SEQ ID NO 395
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 395
ggccagcaca ccggtccasn ncacgtcggg ggcgaaccg 39

<210> SEQ ID NO 396
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 396
ctgggccagc acaccggtsn ngcgcacgtc gggggcgaa 39

<210> SEQ ID NO 397
<211> LENGTH: 39
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 397
ctgctgggcc agcacaccsn nccagcgcac gtcgggggc 39

<210> SEQ ID NO 398
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 398
gagctgctgg gccagcacsn nggtccagcg cacgtcggg 39

<210> SEQ ID NO 399
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 399
tccgagctgc tgggccagsn naccggtcca gcgcacgtc 39

<210> SEQ ID NO 400
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 400
cgctccgagc tgctgggcsn ncacaccggt ccagcgcac 39

<210> SEQ ID NO 401
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 401
gtccgctccg agctgctgsn ncagcacacc ggtccagcg 39

<210> SEQ ID NO 402
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 402
gaagtccgct ccgagctgsn nggccagcac accggtcca 39

<210> SEQ ID NO 403
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 403
ctcgaagtcc gctccgagsn nctgggccag cacaccggt 39

<210> SEQ ID NO 404
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 404
cacctcgaag tccgctccsn nctgctgggc cagcacacc 39

<210> SEQ ID NO 405
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 405
gatcacctcg aagtccgcsn ngagctgctg ggccagcac 39

<210> SEQ ID NO 406
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 406
ctcgatcacc tcgaagtcsn ntccgagctg ctgggccag 39

<210> SEQ ID NO 407
<211> LENGTH: 39
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 407
ctcctcgatc acctcgaasn ncgctccgag ctgctgggc 39

<210> SEQ ID NO 408
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 408
tccctcctcg atcacctcsn ngtccgctcc gagctgctg 39

<210> SEQ ID NO 409
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 409
cagtccctcc tcgatcacsn ngaagtccgc tccgagctg 39

<210> SEQ ID NO 410
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 410
gctcagtccc tcctcgatsn nctcgaagtc cgctccgag 39

<210> SEQ ID NO 411
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 411
cgcgctcagt ccctcctcsn ncacctcgaa gtccgctcc 39

<210> SEQ ID NO 412
<211> LENGTH: 39

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 412
gcgcgcgctc agtccctcsn ngatcacctc gaagtccgc 39

<210> SEQ ID NO 413
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 413
ggtgcgcgcg ctcagtccsn nctcgatcac ctcgaagtc 39

<210> SEQ ID NO 414
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 414
ggtggtgcgc gcgctcagsn nctcctcgat cacctcgaa 39

<210> SEQ ID NO 415
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 415
gttggtggtg cgcgcgctsn ntccctcctc gatcacctc 39

<210> SEQ ID NO 416
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 416
gatgttggtg gtgcgcgcsn ncagtccctc ctcgatcac 39

<210> SEQ ID NO 417

<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 417
gtcgatgttg gtggtgcgsn ngctcagtcc ctcctcgat 39

<210> SEQ ID NO 418
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 418
gtcgtcgatg ttggtggtsn ncgcgctcag tccctcctc 39

<210> SEQ ID NO 419
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 419
ggggtcgtcg atgttggtsn ngcgcgcgct cagtccctc 39

<210> SEQ ID NO 420
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 420
ggtggggtcg tcgatgttsn nggtgcgcgc gctcagtcc 39

<210> SEQ ID NO 421
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 421
atcggtgggg tcgtcgatsn nggtggtgcg cgcgctcag 39

<210> SEQ ID NO 422
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 422
cggatcggtg gggtcgtcsn ngttggtggt gcgcgcgct 39

<210> SEQ ID NO 423
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 423
ccgcggatcg gtggggtcsn ngatgttggt ggtgcgcgc 39

<210> SEQ ID NO 424
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 424
gagccgcgga tcggtgggsn ngtcgatgtt ggtggtgcg 39

<210> SEQ ID NO 425
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 425
gttgagccgc ggatcggtsn ngtcgtcgat gttggtggt 39

<210> SEQ ID NO 426
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 426
gccgttgagc cgcggatcsn nggggtcgtc gatgttggt 39

<210> SEQ ID NO 427
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 427
cgcgccgttg agccgcggsn nggtggggtc gtcgatgtt 39

<210> SEQ ID NO 428
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 428
gctcgcgccg ttgagccgsn natcggtggg gtcgtcgat 39

<210> SEQ ID NO 429
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 429
gtagctcgcg ccgttgagsn ncggatcggt ggggtcgtc 39

<210> SEQ ID NO 430
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 430
caggtagctc gcgccgttsn nccgcggatc ggtggggtc 39

<210> SEQ ID NO 431
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 431
cggcaggtag ctcgcgccsn ngagccgcgg atcggtggg 39

<210> SEQ ID NO 432
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 432
cgacggcagg tagctcgcsn ngttgagccg cggatcggt 39

<210> SEQ ID NO 433
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 433
gcacgacggc aggtagctsn ngccgttgag ccgcggatc 39

<210> SEQ ID NO 434
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 434
gaggcacgac ggcaggtasn ncgcgccgtt gagccgcgg 39

<210> SEQ ID NO 435
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 435
cgcgaggcac gacggcagsn ngctcgcgcc gttgagccg 39

<210> SEQ ID NO 436
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 436
cgtcgcgagg cacgacggsn ngtagctcgc gccgttgag 39

<210> SEQ ID NO 437
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 437
gtgcgtcgcg aggcacgasn ncaggtagct cgcgccgtt 39

<210> SEQ ID NO 438
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 438
caggtgcgtc gcgaggcasn ncggcaggta gctcgcgcc 39

<210> SEQ ID NO 439
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 439
cggcaggtgc gtcgcgagsn ncgacggcag gtagctcgc 39

<210> SEQ ID NO 440
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 440
gagcggcagg tgcgtcgcsn ngcacgacgg caggtagct 39

<210> SEQ ID NO 441
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 441
gtcgagcggc aggtgcgtsn ngaggcacga cggcaggta 39

<210> SEQ ID NO 442
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 442
caggtcgagc ggcaggtgsn ncgcgaggca cgacggcag 39

<210> SEQ ID NO 443
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 443
caccaggtcg agcggcagsn ncgtcgcgag gcacgacgg 39

<210> SEQ ID NO 444
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 444
gatcaccagg tcgagcggsn ngtgcgtcgc gaggcacga 39

<210> SEQ ID NO 445
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 445
gatgatcacc aggtcgagsn ncaggtgcgt cgcgaggca 39

<210> SEQ ID NO 446
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 446
catgatgatc accaggtcsn ncggcaggtg cgtcgcgag 39

<210> SEQ ID NO 447
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 447
cagcatgatg atcaccagsn ngagcggcag gtgcgtcgc 39

<210> SEQ ID NO 448
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 448
gcccagcatg atgatcacsn ngtcgagcgg caggtgcgt 39

<210> SEQ ID NO 449
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 449
ggtgcccagc atgatgatsn ncaggtcgag cggcaggtg 39

<210> SEQ ID NO 450
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 450
gttggtgccc agcatgatsn ncaccaggtc gagcggcag 39

<210> SEQ ID NO 451
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 451
gtcgttggtg cccagcatsn ngatcaccag gtcgagcgg 39

<210> SEQ ID NO 452
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 452
ggtgtcgttg gtgcccagsn ngatgatcac caggtcgag 39

<210> SEQ ID NO 453
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 453
cttggtgtcg ttggtgccsn ncatgatgat caccaggtc 39

<210> SEQ ID NO 454
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 454
ggccttggtg tcgttggtsn ncagcatgat gatcaccag 39

<210> SEQ ID NO 455
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 455
gtaggccttg gtgtcgttsn ngcccagcat gatgatcac 39

<210> SEQ ID NO 456
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 456
gaagtaggcc ttggtgtcsn nggtgcccag catgatgat 39

<210> SEQ ID NO 457
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 457
ccggaagtag gccttggtsn ngttggtgcc cagcatgat 39

<210> SEQ ID NO 458
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 458
gcgccggaag taggccttsn ngtcgttggt gcccagcat 39

<210> SEQ ID NO 459
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 459
ggtgcgccgg aagtaggcsn nggtgtcgtt ggtgcccag 39

<210> SEQ ID NO 460
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 460
cggggtgcgc cggaagtasn ncttggtgtc gttggtgcc 39

<210> SEQ ID NO 461
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 461
gagcggggtg cgccggaasn nggccttggt gtcgttggt 39

<210> SEQ ID NO 462
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 462
gtcgagcggg gtgcgccgsn ngtaggcctt ggtgtcgtt 39

<210> SEQ ID NO 463
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 463
gatgtcgagc ggggtgcgsn ngaagtaggc cttggtgtc 39

<210> SEQ ID NO 464
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 464
cgcgatgtcg agcggggtsn nccggaagta ggccttggt 39

<210> SEQ ID NO 465
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 465
cagcgcgatg tcgagcggsn ngcgccggaa gtaggcctt 39

<210> SEQ ID NO 466
<211> LENGTH: 39
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (20)..(21)
<223> OTHER INFORMATION: n is a, c, g, or t

<400> SEQUENCE: 466
gcccagcgcg atgtcgagsn nggtgcgccg gaagtaggc 39

<210> SEQ ID NO 467
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 467
catgcccagc gcgatgtcsn ncggggtgcg ccggaagta 39

<210> SEQ ID NO 468
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 468
cgacatgccc agcgcgatsn ngagcggggt gcgccggaa 39

<210> SEQ ID NO 469
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 469
caccgacatg cccagcgcsn ngtcgagcgg ggtgcgccg 39

<210> SEQ ID NO 470
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 470
gagcaccgac atgcccagsn ngatgtcgag cggggtgcg 39

<210> SEQ ID NO 471
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 471
gacgagcacc gacatgccsn ncgcgatgtc gagcggggt 39

<210> SEQ ID NO 472
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 472
cgtgacgagc accgacatsn ncagcgcgat gtcgagcgg 39

<210> SEQ ID NO 473
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 473
ctgcgtgacg agcaccgasn ngcccagcgc gatgtcgag 39

<210> SEQ ID NO 474
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 474
cacctgcgtg acgagcacsn ncatgcccag cgcgatgtc 39

<210> SEQ ID NO 475
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 475
gagcacctgc gtgacgagsn ncgacatgcc cagcgcgat 39

<210> SEQ ID NO 476
<211> LENGTH: 39
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 476
ggtgagcacc tgcgtgacsn ncaccgacat gcccagcgc 39

<210> SEQ ID NO 477
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 477
gctggtgagc acctgcgtsn ngagcaccga catgcccag 39

<210> SEQ ID NO 478
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 478
cgcgctggtg agcacctgsn ngacgagcac cgacatgcc 39

<210> SEQ ID NO 479
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 479
gcccgcgctg gtgagcacsn ncgtgacgag caccgacat 39

<210> SEQ ID NO 480
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 480
gccgcccgcg ctggtgagsn nctgcgtgac gagcaccga 39

<210> SEQ ID NO 481
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 481
gacgccgccc gcgctggtsn ncacctgcgt gacgagcac 39

<210> SEQ ID NO 482
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 482
gccgacgccg cccgcgctsn ngagcacctg cgtgacgag 39

<210> SEQ ID NO 483
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 483
ggtgccgacg ccgcccgcsn nggtgagcac ctgcgtgac 39

<210> SEQ ID NO 484
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 484
cgtggtgccg acgccgccsn ngctggtgag cacctgcgt 39

<210> SEQ ID NO 485
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 485
gtacgtggtg ccgacgccsn ncgcgctggt gagcacctg 39

<210> SEQ ID NO 486
<211> LENGTH: 39
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 486
cgggtacgtg gtgccgacsn ngcccgcgct ggtgagcac 39

<210> SEQ ID NO 487
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 487
tgccgggtac gtggtgccsn ngccgcccgc gctggtgag 39

<210> SEQ ID NO 488
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 488
gggtgccggg tacgtggtsn ngacgccgcc cgcgctggt 39

<210> SEQ ID NO 489
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 489
cttgggtgcc gggtacgtsn ngccgacgcc gcccgcgct 39

<210> SEQ ID NO 490
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 490
caccttgggt gccgggtasn nggtgccgac gccgcccgc 39

<210> SEQ ID NO 491
<211> LENGTH: 39

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 491
cagcaccttg ggtgccggsn ncgtggtgcc gacgccgcc 39

<210> SEQ ID NO 492
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 492
caccagcacc ttgggtgcsn ngtacgtggt gccgacgcc 39

<210> SEQ ID NO 493
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 493
gaccaccagc accttgggsn ncgggtacgt ggtgccgac 39

<210> SEQ ID NO 494
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 494
cgagaccacc agcaccttsn ntgccgggta cgtggtgcc 39

<210> SEQ ID NO 495
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 495
cggcgagacc accagcacsn ngggtgccgg gtacgtggt 39

<210> SEQ ID NO 496

<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 496
tggcggcgag accaccagsn ncttgggtgc cgggtacgt 39

<210> SEQ ID NO 497
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 497
cggtggcggc gagaccacsn ncaccttggg tgccgggta 39

<210> SEQ ID NO 498
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 498
cagcggtggc ggcgagacsn ncagcacctt gggtgccgg 39

<210> SEQ ID NO 499
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 499
cgccagcggt ggcggcgasn ncaccagcac cttgggtgc 39

<210> SEQ ID NO 500
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 500
gggcgccagc ggtggcggsn ngaccaccag caccttggg 39

<210> SEQ ID NO 501
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 501
catgggcgcc agcggtggsn ncgagaccac cagcacctt 39

<210> SEQ ID NO 502
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 502
cggcatgggc gccagcggsn ncggcgagac caccagcac 39

<210> SEQ ID NO 503
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 503
gtgcggcatg ggcgccagsn ntggcggcga gaccaccag 39

<210> SEQ ID NO 504
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 504
ggggtgcggc atgggcgcsn ncggtggcgg cgagaccac 39

<210> SEQ ID NO 505
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 505
ccaggggtgc ggcatgggsn ncagcggtgg cggcgagac 39

<210> SEQ ID NO 506
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 506
gaaccagggg tgcggcatsn ncgccagcgg tggcggcga 39

<210> SEQ ID NO 507
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 507
ctggaaccag gggtgcggsn ngggcgccag cggtggcgg 39

<210> SEQ ID NO 508
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 508
caactggaac caggggtgsn ncatgggcgc cagcggtgg 39

<210> SEQ ID NO 509
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 509
gatcaactgg aaccagggsn ncggcatggg cgccagcgg 39

<210> SEQ ID NO 510
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 510
gaagatcaac tggaaccasn ngtgcggcat gggcgccag 39

<210> SEQ ID NO 511
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 511
ctcgaagatc aactggaasn nggggtgcgg catgggcgc 39

<210> SEQ ID NO 512
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 512
gccctcgaag atcaactgsn nccaggggtg cggcatggg 39

<210> SEQ ID NO 513
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 513
gccgccctcg aagatcaasn ngaaccaggg gtgcggcat 39

<210> SEQ ID NO 514
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 514
ctcgccgccc tcgaagatsn nctggaacca ggggtgcgg 39

<210> SEQ ID NO 515
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 515
ctgctcgccg ccctcgaasn ncaactggaa ccaggggtg 39

<210> SEQ ID NO 516
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 516
cttctgctcg ccgccctcsn ngatcaactg gaaccaggg 39

<210> SEQ ID NO 517
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 517
ggtcttctgc tcgccgccsn ngaagatcaa ctggaacca 39

<210> SEQ ID NO 518
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 518
agtggtcttc tgctcgccsn nctcgaagat caactggaa 39

<210> SEQ ID NO 519
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 519
ctcagtggtc ttctgctcsn ngccctcgaa gatcaactg 39

<210> SEQ ID NO 520
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 520
gagctcagtg gtcttctgsn ngccgccctc gaagatcaa 39

<210> SEQ ID NO 521
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 521
ggcgagctca gtggtcttsn nctcgccgcc ctcgaagat 39

<210> SEQ ID NO 522
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 522
gcgggcgagc tcagtggtsn nctgctcgcc gccctcgaa 39

<210> SEQ ID NO 523
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 523
cacgcgggcg agctcagtsn ncttctgctc gccgccctc 39

<210> SEQ ID NO 524
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 524
gtacacgcgg gcgagctcsn nggtcttctg ctcgccgcc 39

<210> SEQ ID NO 525
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 525
gctgtacacg cgggcgagsn nagtggtctt ctgctcgcc 39

<210> SEQ ID NO 526
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 526
cgcgctgtac acgcgggcsn nctcagtggt cttctgctc 39

<210> SEQ ID NO 527
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 527
gagcgcgctg tacacgcgsn ngagctcagt ggtcttctg 39

<210> SEQ ID NO 528
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 528
cgcgagcgcg ctgtacacsn nggcgagctc agtggtctt 39

<210> SEQ ID NO 529
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 529
cgacgcgagc gcgctgtasn ngcgggcgag ctcagtggt 39

<210> SEQ ID NO 530
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 530
gaacgacgcg agcgcgctsn ncacgcgggc gagctcagt 39

<210> SEQ ID NO 531
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 531
catgaacgac gcgagcgcsn ngtacacgcg ggcgagctc 39

<210> SEQ ID NO 532
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 532
cttcatgaac gacgcgagsn ngctgtacac gcgggcgag 39

<210> SEQ ID NO 533
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 533
caccttcatg aacgacgcsn ncgcgctgta cacgcgggc 39

<210> SEQ ID NO 534
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 534
cggcaccttc atgaacgasn ngagcgcgct gtacacgcg 39

<210> SEQ ID NO 535
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 535
gaacggcacc ttcatgaasn ncgcgagcgc gctgtacac 39

<210> SEQ ID NO 536
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 536
gaagaacggc accttcatsn ncgacgcgag cgcgctgta 39

<210> SEQ ID NO 537
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 537
gtcgaagaac ggcaccttsn ngaacgacgc gagcgcgct 39

<210> SEQ ID NO 538
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 538
cgcgtcgaag aacggcacsn ncatgaacga cgcgagcgc 39

<210> SEQ ID NO 539
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 539
acccgcgtcg aagaacggsn ncttcatgaa cgacgcgag 39

<210> SEQ ID NO 540
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 540
cgaacccgcg tcgaagaasn ncaccttcat gaacgacgc 39

<210> SEQ ID NO 541
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 541
caccgaaccc gcgtcgaasn ncggcacctt catgaacga 39

<210> SEQ ID NO 542
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 542
gatcaccgaa cccgcgtcsn ngaacggcac cttcatgaa 39

<210> SEQ ID NO 543
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 543
gctgatcacc gaacccgcsn ngaagaacgg caccttcat 39

<210> SEQ ID NO 544
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 544
ggtgctgatc accgaaccsn ngtcgaagaa cggcacctt 39

<210> SEQ ID NO 545
<211> LENGTH: 39
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (20)..(21)
<223> OTHER INFORMATION: n is a, c, g, or t

<400> SEQUENCE: 545
gtcggtgctg atcaccgasn ncgcgtcgaa gaacggcac 39

<210> SEQ ID NO 546
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 546
gccgtcggtg ctgatcacsn nacccgcgtc gaagaacgg 39

<210> SEQ ID NO 547
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 547
gacgccgtcg gtgctgatsn ncgaacccgc gtcgaagaa 39

<210> SEQ ID NO 548
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 548
gtcgacgccg tcggtgctsn ncaccgaacc cgcgtcgaa 39

<210> SEQ ID NO 549
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 549
tccgtcgacg ccgtcggtsn ngatcaccga acccgcgtc 39

<210> SEQ ID NO 550
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 550
gattccgtcg acgccgtcsn ngctgatcac cgaacccgc 39

<210> SEQ ID NO 551
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 551
gtggattccg tcgacgccsn nggtgctgat caccgaacc 39

<210> SEQ ID NO 552
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 552
gaagtggatt ccgtcgacsn ngtcggtgct gatcaccga 39

<210> SEQ ID NO 553
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 553
ggtgaagtgg attccgtcsn ngccgtcggt gctgatcac 39

<210> SEQ ID NO 554
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 554
ctcggtgaag tggattccsn ngacgccgtc ggtgctgat 39

<210> SEQ ID NO 555
<211> LENGTH: 39
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 555
ggcctcggtg aagtggatsn ngtcgacgcc gtcggtgct 39

<210> SEQ ID NO 556
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 556
gttggcctcg gtgaagtgsn ntccgtcgac gccgtcggt 39

<210> SEQ ID NO 557
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 557
attgttggcc tcggtgaasn ngattccgtc gacgccgtc 39

<210> SEQ ID NO 558
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 558
gcgattgttg gcctcggtsn ngtggattcc gtcgacgcc 39

<210> SEQ ID NO 559
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 559
atcgcgattg ttggcctcsn ngaagtggat tccgtcgac 39

<210> SEQ ID NO 560
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 560
gagatcgcga ttgttggcsn nggtgaagtg gattccgtc 39

<210> SEQ ID NO 561
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 561
cccgagatcg cgattgttsn nctcggtgaa gtggattcc 39

<210> SEQ ID NO 562
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 562
caccccgaga tcgcgattsn nggcctcggt gaagtggat 39

<210> SEQ ID NO 563
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 563
ggccaccccg agatcgcgsn ngttggcctc ggtgaagtg 39

<210> SEQ ID NO 564
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 564
gagggccacc ccgagatcsn nattgttggc ctcggtgaa 39

<210> SEQ ID NO 565
<211> LENGTH: 39
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 565
cgcgagggcc accccgagsn ngcgattgtt ggcctcggt 39

<210> SEQ ID NO 566
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 566
ttccgcgagg gccaccccsn natcgcgatt gttggcctc 39

<210> SEQ ID NO 567
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 567
ctgttccgcg agggccacsn ngagatcgcg attgttggc 39

<210> SEQ ID NO 568
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 568
cacctgttcc gcgagggcsn ncccgagatc gcgattgtt 39

<210> SEQ ID NO 569
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 569
ctgcacctgt tccgcgagsn ncaccccgag atcgcgatt 39

<210> SEQ ID NO 570
<211> LENGTH: 39

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 570
gctctgcacc tgttccgcsn nggccacccc gagatcgcg 39

<210> SEQ ID NO 571
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 571
caggctctgc acctgttcsn ngagggccac cccgagatc 39

<210> SEQ ID NO 572
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 572
cagcaggctc tgcacctgsn ncgcgagggc caccccgag 39

<210> SEQ ID NO 573
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 573
ttacagcagg ctctgcacsn nttccgcgag ggccacccc 39

<210> SEQ ID NO 574
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 574
cttttacagc aggctctgsn nctgttccgc gagggccac 39

<210> SEQ ID NO 575

<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 575
gcccttttac agcaggctsn ncacctgttc cgcgagggc 39

<210> SEQ ID NO 576
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 576
ttcgcccttt tacagcagsn nctgcacctg ttccgcgag 39

<210> SEQ ID NO 577
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 577
gaattcgccc ttttacagsn ngctctgcac ctgttccgc 39

<210> SEQ ID NO 578
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 578
gcagaattcg cccttttasn ncaggctctg cacctgttc 39

<210> SEQ ID NO 579
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 579
gtgatcgagg agggactgnn sgcgcgcacc accaacatc 39

<210> SEQ ID NO 580
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 580
acgaccccac cgatccgnns ctcaacggcg cgagctac 38

<210> SEQ ID NO 581
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 581
ctcaccagcg cgggcggcnn sggcaccacg tacccggca 39

<210> SEQ ID NO 582
<211> LENGTH: 39
<212> TYPE: DNA
<213> ORGANISM: Artificial Sequence
<220> FEATURE:
<223> OTHER INFORMATION: primer

<400> SEQUENCE: 582
ctgtgtttcg gtgattcctg cacctggggc tgggtcccc 39

<210> SEQ ID NO 583
<211> LENGTH: 39
<212> TYPE: DNA
<213> ORGANISM: Artificial Sequence
<220> FEATURE:
<223> OTHER INFORMATION: primer

<400> SEQUENCE: 583
ctgtgtttcg gtgattccca gacctggggc tgggtcccc 39

<210> SEQ ID NO 584
<211> LENGTH: 39
<212> TYPE: DNA
<213> ORGANISM: Artificial Sequence
<220> FEATURE:
<223> OTHER INFORMATION: primer

<400> SEQUENCE: 584
ctgtgtttcg gtgattccat cacctggggc tgggtcccc 39

<210> SEQ ID NO 585
<211> LENGTH: 39
<212> TYPE: DNA
<213> ORGANISM: Artificial Sequence
<220> FEATURE:
<223> OTHER INFORMATION: primer

<400> SEQUENCE: 585
ctgtgtttcg gtgattccat gacctggggc tgggtcccc 39

<210> SEQ ID NO 586
<211> LENGTH: 39
<212> TYPE: DNA
<213> ORGANISM: Artificial Sequence
<220> FEATURE:
<223> OTHER INFORMATION: primer

<400> SEQUENCE: 586
ctgtgtttcg gtgattccac gacctggggc tgggtcccc 39

<210> SEQ ID NO 587
<211> LENGTH: 39
<212> TYPE: DNA
<213> ORGANISM: Artificial Sequence
<220> FEATURE:
<223> OTHER INFORMATION: primer

<400> SEQUENCE: 587
gtcgaagacg gggcacccag cgagcggttc gcccccgac 39

<210> SEQ ID NO 588
<211> LENGTH: 39
<212> TYPE: DNA
<213> ORGANISM: Artificial Sequence
<220> FEATURE:
<223> OTHER INFORMATION: primer

<400> SEQUENCE: 588
gtcgaagacg gggcacccgg cgagcggttc gcccccgac 39

<210> SEQ ID NO 589
<211> LENGTH: 39
<212> TYPE: DNA
<213> ORGANISM: Artificial Sequence
<220> FEATURE:
<223> OTHER INFORMATION: primer

<400> SEQUENCE: 589
gtcgaagacg gggcaccccc ggagcggttc gcccccgac 39

<210> SEQ ID NO 590
<211> LENGTH: 39
<212> TYPE: DNA
<213> ORGANISM: Artificial Sequence
<220> FEATURE:
<223> OTHER INFORMATION: primer

<400> SEQUENCE: 590
gaggtgatcg aggagggaca cagcgcgcgc accaccaac 39

<210> SEQ ID NO 591
<211> LENGTH: 39
<212> TYPE: DNA
<213> ORGANISM: Artificial Sequence
<220> FEATURE:
<223> OTHER INFORMATION: primer

<400> SEQUENCE: 591
gaggtgatcg aggagggaca gagcgcgcgc accaccaac 39

<210> SEQ ID NO 592
<211> LENGTH: 39
<212> TYPE: DNA
<213> ORGANISM: Artificial Sequence
<220> FEATURE:
<223> OTHER INFORMATION: primer

<400> SEQUENCE: 592
gaggtgatcg aggagggagg cagcgcgcgc accaccaac 39

<210> SEQ ID NO 593
<211> LENGTH: 39
<212> TYPE: DNA
<213> ORGANISM: Artificial Sequence
<220> FEATURE:
<223> OTHER INFORMATION: primer

<400> SEQUENCE: 593
gaggtgatcg aggagggaag cagcgcgcgc accaccaac 39

<210> SEQ ID NO 594
<211> LENGTH: 39
<212> TYPE: DNA
<213> ORGANISM: Artificial Sequence
<220> FEATURE:
<223> OTHER INFORMATION: primer

<400> SEQUENCE: 594
gaggtgatcg aggagggaca cgtggcgcgc accaccaac 39

<210> SEQ ID NO 595
<211> LENGTH: 39
<212> TYPE: DNA
<213> ORGANISM: Artificial Sequence
<220> FEATURE:
<223> OTHER INFORMATION: primer

<400> SEQUENCE: 595
gaggtgatcg aggagggaca ggtggcgcgc accaccaac 39

<210> SEQ ID NO 596
<211> LENGTH: 39
<212> TYPE: DNA
<213> ORGANISM: Artificial Sequence
<220> FEATURE:
<223> OTHER INFORMATION: primer

<400> SEQUENCE: 596
gaggtgatcg aggagggagg cgtggcgcgc accaccaac 39

<210> SEQ ID NO 597
<211> LENGTH: 39
<212> TYPE: DNA
<213> ORGANISM: Artificial Sequence
<220> FEATURE:
<223> OTHER INFORMATION: primer

<400> SEQUENCE: 597
gaggtgatcg aggagggaag cgtggcgcgc accaccaac 39

<210> SEQ ID NO 598
<211> LENGTH: 39
<212> TYPE: DNA
<213> ORGANISM: Artificial Sequence
<220> FEATURE:
<223> OTHER INFORMATION: primer

<400> SEQUENCE: 598
gtgatcgagg agggactggt ggcgcgcacc accaacatc 39

<210> SEQ ID NO 599

<211> LENGTH: 39
<212> TYPE: DNA
<213> ORGANISM: Artificial Sequence
<220> FEATURE:
<223> OTHER INFORMATION: primer

<400> SEQUENCE: 599
gtgatcgagg agggactgct ggcgcgcacc accaacatc 39

<210> SEQ ID NO 600
<211> LENGTH: 39
<212> TYPE: DNA
<213> ORGANISM: Artificial Sequence
<220> FEATURE:
<223> OTHER INFORMATION: primer

<400> SEQUENCE: 600
atcgaggagg gactgagcgg ccgcaccacc aacatcgac 39

<210> SEQ ID NO 601
<211> LENGTH: 39
<212> TYPE: DNA
<213> ORGANISM: Artificial Sequence
<220> FEATURE:
<223> OTHER INFORMATION: primer

<400> SEQUENCE: 601
atcgaggagg gactgagcac gcgcaccacc aacatcgac 39

<210> SEQ ID NO 602
<211> LENGTH: 39
<212> TYPE: DNA
<213> ORGANISM: Artificial Sequence
<220> FEATURE:
<223> OTHER INFORMATION: primer

<400> SEQUENCE: 602
atcgaggagg gactggtggg ccgcaccacc aacatcgac 39

<210> SEQ ID NO 603
<211> LENGTH: 39
<212> TYPE: DNA
<213> ORGANISM: Artificial Sequence
<220> FEATURE:
<223> OTHER INFORMATION: primer

<400> SEQUENCE: 603
atcgaggagg gactggtgac gcgcaccacc aacatcgac 39

<210> SEQ ID NO 604
<211> LENGTH: 39
<212> TYPE: DNA
<213> ORGANISM: Artificial Sequence
<220> FEATURE:
<223> OTHER INFORMATION: primer

<400> SEQUENCE: 604
gacgacccca ccgatccgac gctcaacggc gcgagctac 39

<210> SEQ ID NO 605
<211> LENGTH: 39
<212> TYPE: DNA
<213> ORGANISM: Artificial Sequence
<220> FEATURE:
<223> OTHER INFORMATION: primer

<400> SEQUENCE: 605
gacgacccca ccgatccgca gctcaacggc gcgagctac 39

<210> SEQ ID NO 606
<211> LENGTH: 39
<212> TYPE: DNA
<213> ORGANISM: Artificial Sequence
<220> FEATURE:
<223> OTHER INFORMATION: primer

<400> SEQUENCE: 606
gacgacccca ccgatccgaa cctcaacggc gcgagctac 39

<210> SEQ ID NO 607
<211> LENGTH: 39
<212> TYPE: DNA
<213> ORGANISM: Artificial Sequence
<220> FEATURE:
<223> OTHER INFORMATION: primer

<400> SEQUENCE: 607
ctgggcacca acgacacccg cgcctacttc cggcgcacc 39

<210> SEQ ID NO 608
<211> LENGTH: 39
<212> TYPE: DNA
<213> ORGANISM: Artificial Sequence
<220> FEATURE:
<223> OTHER INFORMATION: primer

<400> SEQUENCE: 608
ctcaccagcg cgggcggcag cggcaccacg tacccggca 39

<210> SEQ ID NO 609
<211> LENGTH: 39
<212> TYPE: DNA
<213> ORGANISM: Artificial Sequence
<220> FEATURE:
<223> OTHER INFORMATION: primer

<400> SEQUENCE: 609
ctcaccagcg cgggcggcgg cggcaccacg tacccggca 39

<210> SEQ ID NO 610
<211> LENGTH: 39
<212> TYPE: DNA
<213> ORGANISM: Artificial Sequence
<220> FEATURE:
<223> OTHER INFORMATION: primer

<400> SEQUENCE: 610
ctcaccagcg cgggcggccg cggcaccacg tacccggca 39

<210> SEQ ID NO 611
<211> LENGTH: 39
<212> TYPE: DNA
<213> ORGANISM: Artificial Sequence
<220> FEATURE:
<223> OTHER INFORMATION: primer

<400> SEQUENCE: 611
ctcaccagcg cgggcggcgc gggcaccacg tacccggca 39

<210> SEQ ID NO 612
<211> LENGTH: 39
<212> TYPE: DNA

<213> ORGANISM: Artificial Sequence
<220> FEATURE:
<223> OTHER INFORMATION: primer

<400> SEQUENCE: 612
ctcaccagcg cgggcggccc gggcaccacg tacccggca 39

<210> SEQ ID NO 613
<211> LENGTH: 39
<212> TYPE: DNA
<213> ORGANISM: Artificial Sequence
<220> FEATURE:
<223> OTHER INFORMATION: primer

<400> SEQUENCE: 613
ccctggttcc agttgatcta cgagggcggc gagcagaag 39

<210> SEQ ID NO 614
<211> LENGTH: 39
<212> TYPE: DNA
<213> ORGANISM: Artificial Sequence
<220> FEATURE:
<223> OTHER INFORMATION: primer

<400> SEQUENCE: 614
ggcgtcgacg gaatccacgg caccgaggcc aacaatcgc 39

<210> SEQ ID NO 615
<211> LENGTH: 39
<212> TYPE: DNA
<213> ORGANISM: Artificial Sequence
<220> FEATURE:
<223> OTHER INFORMATION: primer

<400> SEQUENCE: 615
gacgacccca ccgatccggg cctcaacggc gcgagctac 39

<210> SEQ ID NO 616
<211> LENGTH: 39
<212> TYPE: DNA
<213> ORGANISM: Artificial Sequence
<220> FEATURE:
<223> OTHER INFORMATION: primer

<400> SEQUENCE: 616
gacgacccca ccgatccgga gctcaacggc gcgagctac 39

<210> SEQ ID NO 617
<211> LENGTH: 39
<212> TYPE: DNA
<213> ORGANISM: Artificial Sequence
<220> FEATURE:
<223> OTHER INFORMATION: primer

<400> SEQUENCE: 617
gacgacccca ccgatccgtt cctcaacggc gcgagctac 39

<210> SEQ ID NO 618
<211> LENGTH: 39
<212> TYPE: DNA
<213> ORGANISM: Artificial Sequence
<220> FEATURE:
<223> OTHER INFORMATION: primer

<400> SEQUENCE: 618
gacgacccca ccgatccgct gctcaacggc gcgagctac 39

<210> SEQ ID NO 619
<211> LENGTH: 39
<212> TYPE: DNA
<213> ORGANISM: Artificial Sequence
<220> FEATURE:
<223> OTHER INFORMATION: primer

<400> SEQUENCE: 619
gtgatcgagg agggactgcc ggcgcgcacc accaacatc 39

<210> SEQ ID NO 620
<211> LENGTH: 39
<212> TYPE: DNA
<213> ORGANISM: Artificial Sequence
<220> FEATURE:
<223> OTHER INFORMATION: primer

<400> SEQUENCE: 620
gtgatcgagg agggactgcg cgcgcgcacc accaacatc 39

<210> SEQ ID NO 621
<211> LENGTH: 39
<212> TYPE: DNA
<213> ORGANISM: Artificial Sequence
<220> FEATURE:
<223> OTHER INFORMATION: primer

<400> SEQUENCE: 621
gtgatcgagg agggactggg cgcgcgcacc accaacatc 39

<210> SEQ ID NO 622
<211> LENGTH: 39
<212> TYPE: DNA
<213> ORGANISM: Artificial Sequence
<220> FEATURE:
<223> OTHER INFORMATION: primer

<400> SEQUENCE: 622
gtgatcgagg agggactgac ggcgcgcacc accaacatc 39

<210> SEQ ID NO 623
<211> LENGTH: 39
<212> TYPE: DNA
<213> ORGANISM: Artificial Sequence
<220> FEATURE:
<223> OTHER INFORMATION: primer

<400> SEQUENCE: 623
gtgatcgagg agggactgat cgcgcgcacc accaacatc 39

<210> SEQ ID NO 624
<211> LENGTH: 39
<212> TYPE: DNA
<213> ORGANISM: Artificial Sequence
<220> FEATURE:
<223> OTHER INFORMATION: primer

<400> SEQUENCE: 624
gtgatcgagg agggactgaa ggcgcgcacc accaacatc 39

<210> SEQ ID NO 625
<211> LENGTH: 657
<212> TYPE: DNA
<213> ORGANISM: Artificial Sequence
<220> FEATURE:

<223> OTHER INFORMATION: RSM02162 gene

<400> SEQUENCE: 625
atggtggaaa aacgttccgt tctgtgcttt ggtgattctc tgacttgggg ctggattccg 60
gtgaaagaga gctccccaac tctgcgttac ccatacgaac agcgttggac cggtgctatg 120
gctgcacgtc tgggtgatgg ttaccacatc attgaagaag gcctgtccgc tcgtactact 180
agcctggacg acccaaacga cgctcgtctg aacggctcta cctacctgcc gatggctctg 240
gcttctcacc tgccactgga tctggtaatc attatgctgg gtaccaacga caccaaaagc 300
tactttcatc gtaccccata cgagattgcc aacggcatgg gtaaactggt aggtcaggtc 360
ctgacctgtg caggtggtgt tggtacgcct tatccagcac cgaaagtcct ggtggttgca 420
cctccaccac tggcaccaat gccagatccg tggttcgaag gtatgttcgg cggtggttac 480
gagaaatcta aggaactgtc cggtctgtac aaagcactgg ctgatttcat gaaagtggag 540
ttcttcgcag cgggtgattg tatctccacc gacggtatcg acggtatcca cctgagcgct 600
gaaaccaaca tccgcctggg tcatgctatt gctgacaaag tagcggctct gttctaa 657

<210> SEQ ID NO 626
<211> LENGTH: 50
<212> TYPE: DNA
<213> ORGANISM: Artificial Sequence
<220> FEATURE:
<223> OTHER INFORMATION: primer

<400> SEQUENCE: 626
ggccctaaca ggaggaatta accatggtgg aaaaacgttc cgttctgtgc 50

<210> SEQ ID NO 627
<211> LENGTH: 33
<212> TYPE: DNA
<213> ORGANISM: Artificial Sequence
<220> FEATURE:
<223> OTHER INFORMATION: primer

<400> SEQUENCE: 627
gcgcgcttag aacagagccg ctactttgtc agc 33

<210> SEQ ID NO 628
<211> LENGTH: 218
<212> TYPE: PRT
<213> ORGANISM: Artificial Sequence
<220> FEATURE:
<223> OTHER INFORMATION: G00355 protein

<400> SEQUENCE: 628

Met Val Glu Lys Arg Ser Val Leu Cys Phe Gly Asp Ser Leu Thr Trp
1 5 10 15

Gly Trp Ile Pro Val Lys Glu Ser Ser Pro Thr Leu Arg Tyr Pro Tyr
20 25 30

Glu Gln Arg Trp Thr Gly Ala Met Ala Ala Arg Leu Gly Asp Gly Tyr
35 40 45

His Ile Ile Glu Glu Gly Leu Ser Ala Arg Thr Thr Ser Leu Asp Asp
50 55 60

Pro Asn Asp Ala Arg Leu Asn Gly Ser Thr Tyr Leu Pro Met Ala Leu
65 70 75 80

Ala Ser His Leu Pro Leu Asp Leu Val Ile Ile Met Leu Gly Thr Asn
85 90 95

Asp Thr Lys Ser Tyr Phe His Arg Thr Pro Tyr Glu Ile Ala Asn Gly

```
            100                 105                 110

Met Gly Lys Leu Val Gly Gln Val Leu Thr Cys Ala Gly Gly Val Gly
        115                 120                 125

Thr Pro Tyr Pro Ala Pro Lys Val Leu Val Val Ala Pro Pro Pro Leu
    130                 135                 140

Ala Pro Met Pro Asp Pro Trp Phe Glu Gly Met Phe Gly Gly Gly Tyr
145                 150                 155                 160

Glu Lys Ser Lys Glu Leu Ser Gly Leu Tyr Lys Ala Leu Ala Asp Phe
                165                 170                 175

Met Lys Val Glu Phe Phe Ala Ala Gly Asp Cys Ile Ser Thr Asp Gly
            180                 185                 190

Ile Asp Gly Ile His Leu Ser Ala Glu Thr Asn Ile Arg Leu Gly His
        195                 200                 205

Ala Ile Ala Asp Lys Val Ala Ala Leu Phe
    210                 215


<210> SEQ ID NO 629
<211> LENGTH: 4510
<212> TYPE: DNA
<213> ORGANISM: Artificial Sequence
<220> FEATURE:
<223> OTHER INFORMATION: pDRIVEG00355 plasmid

<400> SEQUENCE: 629

gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg ccaagctcta    240

atacgactca ctatagggaa agctcggtac cacgcatgct gcagacgcgt tacgtatcgg    300

atccagaatt cgtgatttta gaacagagcc gctactttgt cagcaatagc atgacccagg    360

cggatgttgg tttcagcgct caggtggata ccgtcgatac cgtcggtgga gatacaatca    420

cccgctgcga agaactccac tttcatgaaa tcagccagtg ctttgtacag accggacagt    480

tccttagatt tctcgtaacc accgccgaac ataccttcga accacggatc tggcattggt    540

gccagtggtg gaggtgcaac caccaggact ttcggtgctg gataaggcgt accaacacca    600

cctgcacagg tcaggacctg acctaccagt ttacccatgc cgttggcaat ctcgtatggg    660

gtacgatgaa agtagctttt ggtgtcgttg gtacccagca taatgattac cagatccagt    720

ggcaggtgag aagccagagc catcggcagg taggtagagc cgttcagacg agcgtcgttt    780

gggtcgtcca ggctagtagt acgagcggac aggccttctt caatgatgtg gtaaccatca    840

cccagacgtg cagccatagc accggtccaa cgctgttcgt atgggtaacg cagagttggg    900

gagctctctt tcaccggaat ccagccccaa gtcagagaat caccaaagca cagaacggaa    960

cgtttttcca ccataatctg aattcgtcga caagcttctc gagcctaggc tagctctaga   1020

ccacacgtgt gggggcccga gctcgcggcc gctgtattct atagtgtcac ctaaatggcc   1080

gcacaattca ctggccgtcg ttttacaacg tcgtgactgg gaaaaccctg gcgttaccca   1140

acttaatcgc cttgcagcac atcccccttt cgccagctgg cgtaatagcg aagaggcccg   1200

caccgatcgc ccttcccaac agttgcgcag cctgaatggc gaatggaaat tgtaagcgtt   1260

aatattttgt taaaattcgc gttaaatttt tgttaaatca gctcattttt taaccaatag   1320

gccgaaatcg gcaaaatccc ttataaatca aaagaataga ccgagatagg gttgagtgtt   1380
```

-continued

```
gttccagttt ggaacaagag tccactatta aagaacgtgg actccaacgt caaagggcga   1440
aaaaccgtct atcagggcga tggcccacta cgtgaaccat caccctaatc aagttttttg   1500
gggtcgaggt gccgtaaagc actaaatcgg aaccctaaag ggagcccccg atttagagct   1560
tgacggggaa agccggcgaa cgtggcgaga aaggaaggga agaaagcgaa aggagcgggc   1620
gctagggcgc tggcaagtgt agcggtcacg ctgcgcgtaa ccaccacacc cgccgcgctt   1680
aatgcgccgc tacagggcgc gtcaggtggc acttttcggg gaaatgtgcg cggaacccct   1740
atttgtttat ttttctaaat acattcaaat atgtatccgc tcatgagaca ataaccctga   1800
taaatgcttc aataatattg aaaaaggaag agtatgagta ttcaacattt ccgtgtcgcc   1860
cttattccct tttttgcggc attttgcctt cctgtttttg ctcacccaga aacgctggtg   1920
aaagtaaaag atgctgaaga tcagttgggt gcacgagtgg gttacatcga actggatctc   1980
aacagcggta agatccttga gagttttcgc cccgaagaac gttttccaat gatgagcact   2040
tttaaagttc tgctatgtgg cgcggtatta tcccgtattg acgccgggca agagcaactc   2100
ggtcgccgca tacactattc tcagaatgac ttggttgagt actcaccagt cacagaaaag   2160
catcttacgg atggcatgac agtaagagaa ttatgcagtg ctgccataac catgagtgat   2220
aacactgcgg ccaacttact tctgacaacg atcggaggac cgaaggagct aaccgctttt   2280
ttgcacaaca tgggggatca tgtaactcgc cttgatcgtt gggaaccgga gctgaatgaa   2340
gccataccaa acgacgagcg tgacaccacg atgcctgtag caatggcaac aacgttgcgc   2400
aaactattaa ctggcgaact acttactcta gcttcccggc aacaattaat agactggatg   2460
gaggcggata aagttgcagg accacttctg cgctcggccc ttccggctgg ctggtttatt   2520
gctgataaat ctggagccgg tgagcgtggg tctcgcggta tcattgcagc actggggcca   2580
gatggtaagc cctcccgtat cgtagttatc tacacgacgg ggagtcaggc aactatggat   2640
gaacgaaata gacagatcgc tgagataggt gcctcactga ttaagcattg gtaactgtca   2700
gaccaagttt actcatatat actttagatt gatttaaaac ttcattttta atttaaaagg   2760
atctaggtga agatcctttt tgataatctc atgaacaata aaactgtctg cttacataaa   2820
cagtaataca aggggtgtta tgagccatat tcaacgggaa acgtcttgct ctaggccgcg   2880
attaaattcc aacatggatg ctgatttata tgggtataaa tgggctcgcg ataatgtcgg   2940
gcaatcaggt gcgacaatct atcgattgta tgggaagccc gatgcgccag agttgtttct   3000
gaaacatggc aaaggtagcg ttgccaatga tgttacagat gagatggtca gactaaactg   3060
gctgacggaa tttatgcctc ttccgaccat caagcatttt atccgtactc ctgatgatgc   3120
atggttactc accactgcga tccccgggaa aacagcattc caggtattag aagaatatcc   3180
tgattcaggt gaaaatattg ttgatgcgct ggcagtgttc ctgcgccggt tgcattcgat   3240
tcctgtttgt aattgtcctt ttaacagcga tcgcgtattt cgtctcgctc aggcgcaatc   3300
acgaatgaat aacggtttgg ttgatgcgag tgattttgat gacgagcgta atggctggcc   3360
tgttgaacaa gtctggaaag aaatgcataa acttttgcca ttctcaccgg attcagtcgt   3420
cactcatggt gatttctcac ttgataacct tatttttgac gaggggaaat taataggttg   3480
tattgatgtt ggacgagtcg gaatcgcaga ccgataccag gatcttgcca tcctatggaa   3540
ctgcctcggt gagttttctc cttcattaca gaaacggctt tttcaaaaat atggtattga   3600
taatcctgat atgaataaat tgcagtttca tttgatgctc gatgagtttt tctaagaatt   3660
aattcatgac caaaatccct taacgtgagt tttcgttcca ctgagcgtca gaccccgtag   3720
aaaagatcaa aggatcttct tgagatcctt tttttctgcg cgtaatctgc tgcttgcaaa   3780
```

```
caaaaaaacc accgctacca gcggtggttt gtttgccgga tcaagagcta ccaactcttt   3840

ttccgaaggt aactggcttc agcagagcgc agataccaaa tactgtcctt ctagtgtagc   3900

cgtagttagg ccaccacttc aagaactctg tagcaccgcc tacatacctc gctctgctaa   3960

tcctgttacc agtggctgct gccagtggcg ataagtcgtg tcttaccggg ttggactcaa   4020

gacgatagtt accggataag gcgcagcggt cgggctgaac ggggggttcg tgcacacagc   4080

ccagcttgga gcgaacgacc tacaccgaac tgagatacct acagcgtgag ctatgagaaa   4140

gcgccacgct tcccgaaggg agaaaggcgg acaggtatcc ggtaagcggc agggtcggaa   4200

caggagagcg cacgagggag cttccagggg gaaacgcctg gtatctttat agtcctgtcg   4260

ggtttcgcca cctctgactt gagcgtcgat ttttgtgatg ctcgtcaggg gggcggagcc   4320

tatggaaaaa cgccagcaac gcggcctttt tacggttcct ggccttttgc tggccttttg   4380

ctcacatgtt ctttcctgcg ttatcccctg attctgtgga taaccgtatt accgcctttg   4440

agtgagctga taccgctcgc cgcagccgaa cgaccgagcg cagcgagtca gtgagcgagg   4500

aagcggaaga                                                          4510
```

<210> SEQ ID NO 630
<211> LENGTH: 4617
<212> TYPE: DNA
<213> ORGANISM: Artificial Sequence
<220> FEATURE:
<223> OTHER INFORMATION: pMC355rbs plasmid

<400> SEQUENCE: 630

```
agcgcccaat acgcaaaccg cctctccccg cgcgttggcc gattcattaa tgcagctggc     60

acgacaggtt tcccgactgg aaagcgggca gtgagcgcaa cgcaattaat gtgagttagc    120

tcactcatta ggcaccccag gctttacact ttatgcttcc ggctcgtatg ttgtgtggaa    180

ttgtgagcgg ataacaattt cacacaggaa acagctatga ccatgattac gccaagcttg    240

gtaccgagct cggatccact agtaacggcc gccagtgtgc tggaattcgc ccttggccct    300

aacaggagga attaaccatg gtggaaaaac gttccgttct gtgctttggt gattctctga    360

cttggggctg gattccggtg aaagagagct ccccaactct gcgttaccca tacgaacagc    420

gttggaccgg tgctatggct gcacgtctgg gtgatggtta ccacatcatt gaagaaggcc    480

tgtccgctcg tactactagc ctggacgacc caaacgacgc tcgtctgaac ggctctacct    540

acctgccgat ggctctggct tctcacctgc cactggatct ggtaatcatt atgctgggta    600

ccaacgacac caaaagctac tttcatcgta ccccatacga gattgccaac ggcatgggta    660

aactggtagg tcaggtcctg acctgtgcag gtggtgttgg tacgccttat ccagcaccga    720

aagtcctggt ggttgcacct ccaccactgg caccaatgcc agatccgtgg ttcgaaggta    780

tgttcggcgg tggttacgag aaatctaagg aactgtccgg tctgtacaaa gcactggctg    840

atttcatgaa agtggagttc ttcgcagcgg gtgattgtat ctccaccgac ggtatcgacg    900

gtatccacct gagcgctgaa accaacatcc gcctgggtca tgctattgct gacaaagtag    960

cggctctgtt ctaagcgcgc aagggcgaat tctgcagata tccatcacac tggcggccgc   1020

tcgagcatgc atctagaggg cccaattcgc cctatagtga gtcgtattac aattcactgg   1080

ccgtcgtttt acaacgtcgt gactgggaaa accctggcgt tacccaactt aatcgccttg   1140

cagcacatcc ccctttcgcc agctggcgta atagcgaaga ggcccgcacc gatcgccctt   1200

cccaacagtt gcgcagcctg aatggcgaat ggacgcgccc tgtagcggcg cattaagcgc   1260
```

-continued

```
ggcgggtgtg gtggttacgc gcagcgtgac cgctacactt gccagcgccc tagcgcccgc   1320
tcctttcgct ttcttccctt cctttctcgc cacgttcgcc ggctttcccc gtcaagctct   1380
aaatcggggg ctccctttag ggttccgatt tagtgcttta cggcacctcg accccaaaaa   1440
acttgattag ggtgatggtt cacgtagtgg gccatcgccc tgatagacgg tttttcgccc   1500
tttgacgttg gagtccacgt tctttaatag tggactcttg ttccaaactg gaacaacact   1560
caaccctatc tcggtctatt cttttgattt ataagggatt ttgccgattt cggcctattg   1620
gttaaaaaat gagctgattt aacaaaaatt taacgcgaat tttaacaaaa ttcagggcgc   1680
aagggctgct aaaggaagcg gaacacgtag aaagccagtc cgcagaaacg gtgctgaccc   1740
cggatgaatg tcagctactg ggctatctgg acaagggaaa acgcaagcgc aaagagaaag   1800
caggtagctt gcagtgggct tacatggcga tagctagact gggcggtttt atggacagca   1860
agcgaaccgg aattgccagc tggggcgccc tctggtaagg ttgggaagcc ctgcaaagta   1920
aactggatgg ctttcttgcc gccaaggatc tgatggcgca ggggatcaag atctgatcaa   1980
gagacaggat gaggatcgtt tcgcatgatt gaacaagatg gattgcacgc aggttctccg   2040
gccgcttggg tggagaggct attcggctat gactgggcac aacagacaat cggctgctct   2100
gatgccgccg tgttccggct gtcagcgcag gggcgcccgg ttctttttgt caagaccgac   2160
ctgtccggtg ccctgaatga actgcaggac gaggcagcgc ggctatcgtg gctggccacg   2220
acgggcgttc cttgcgcagc tgtgctcgac gttgtcactg aagcgggaag ggactggctg   2280
ctattgggcg aagtgccggg gcaggatctc ctgtcatccc accttgctcc tgccgagaaa   2340
gtatccatca tggctgatgc aatgcggcgg ctgcatacgc ttgatccggc tacctgccca   2400
ttcgaccacc aagcgaaaca tcgcatcgag cgagcacgta ctcggatgga agccggtctt   2460
gtcgatcagg atgatctgga cgaagagcat caggggctcg cgccagccga actgttcgcc   2520
aggctcaagg cgcgcatgcc cgacggcgag gatctcgtcg tgacccatgg cgatgcctgc   2580
ttgccgaata tcatggtgga aaatggccgc ttttctggat tcatcgactg tggccggctg   2640
ggtgtggcgg accgctatca ggacatagcg ttggctaccc gtgatattgc tgaagagctt   2700
ggcggcgaat gggctgaccg cttcctcgtg ctttacggta tcgccgctcc cgattcgcag   2760
cgcatcgcct tctatcgcct tcttgacgag ttcttctgaa ttgaaaaagg aagagtatga   2820
gtattcaaca tttccgtgtc gcccttattc cctttttgc ggcattttgc cttcctgttt    2880
ttgctcaccc agaaacgctg gtgaaagtaa aagatgctga agatcagttg ggtgcacgag   2940
tgggttacat cgaactggat ctcaacagcg gtaagatcct tgagagtttt cgccccgaag   3000
aacgttttcc aatgatgagc acttttaaag ttctgctatg tggcgcggta ttatcccgta   3060
ttgacgccgg gcaagagcaa ctcggtcgcc gcatacacta ttctcagaat gacttggttg   3120
agtactcacc agtcacagaa aagcatctta cggatggcat gacagtaaga gaattatgca   3180
gtgctgccat aaccatgagt gataacactg cggccaactt acttctgaca acgatcggag   3240
gaccgaagga gctaaccgct tttttgcaca acatgggga tcatgtaact cgccttgatc    3300
gttgggaacc ggagctgaat gaagccatac caaacgacga gcgtgacacc acgatgcctg   3360
tagcaatggc aacaacgttg cgcaaactat taactggcga actacttact ctagcttccc   3420
ggcaacaatt aatagactgg atggaggcgg ataaagttgc aggaccactt ctgcgctcgg   3480
cccttccggc tggctggttt attgctgata aatctggagc cggtgagcgt gggtctcgcg   3540
gtatcattgc agcactgggg ccagatggta agccctcccg tatcgtagtt atctacacga   3600
cggggagtca ggcaactatg gatgaacgaa atagacagat cgctgagata ggtgcctcac   3660
```

```
tgattaagca ttggtaactg tcagaccaag tttactcata tatactttag attgatttaa   3720

aacttcattt ttaatttaaa aggatctagg tgaagatcct ttttgataat ctcatgacca   3780

aaatccctta acgtgagttt tcgttccact gagcgtcaga ccccgtagaa aagatcaaag   3840

gatcttcttg agatcctttt tttctgcgcg taatctgctg cttgcaaaca aaaaaaccac   3900

cgctaccagc ggtggtttgt ttgccggatc aagagctacc aactcttttt ccgaaggtaa   3960

ctggcttcag cagagcgcag ataccaaata ctgttcttct agtgtagccg tagttaggcc   4020

accacttcaa gaactctgta gcaccgccta catacctcgc tctgctaatc ctgttaccag   4080

tggctgctgc cagtggcgat aagtcgtgtc ttaccgggtt ggactcaaga cgatagttac   4140

cggataaggc gcagcggtcg ggctgaacgg ggggttcgtg cacacagccc agcttggagc   4200

gaacgaccta caccgaactg agatacctac agcgtgagct atgagaaagc gccacgcttc   4260

ccgaagggag aaaggcggac aggtatccgg taagcggcag ggtcggaaca ggagagcgca   4320

cgagggagct tccaggggga aacgcctggt atctttatag tcctgtcggg tttcgccacc   4380

tctgacttga gcgtcgattt ttgtgatgct cgtcaggggg gcggagccta tggaaaaacg   4440

ccagcaacgc ggccttttta cggttcctgg ccttttgctg gccttttgct cacatgttct   4500

ttcctgcgtt atcccctgat tctgtggata accgtattac cgcctttgag tgagctgata   4560

ccgctcgccg cagccgaacg accgagcgca gcgagtcagt gagcgaggaa gcggaag      4617
```

<210> SEQ ID NO 631
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 631

```
gccaagcgaa ttctgtgttt cggngaytcn yt                                  32
```

<210> SEQ ID NO 632
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 632

```
cgattgttcg cctcgtgtga artgnrtncc rtc                                 33
```

<210> SEQ ID NO 633
<211> LENGTH: 26
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 633
acggtcctgt gctttggnga ytcnyt 26

<210> SEQ ID NO 634
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 634
ccgctggtcc tcatctggrt gntcnccrtc 30

<210> SEQ ID NO 635
<211> LENGTH: 596
<212> TYPE: DNA
<213> ORGANISM: Artificial Sequence
<220> FEATURE:
<223> OTHER INFORMATION: 2D Perhydrolase Homologue gene

<400> SEQUENCE: 635
attctgtgtt tcggggattc cttgacgtgg ggatggatcc ctgtcgaaga aggtgtgccc 60
accgagcggt tcccgcgtga cgtccggtgg accggcgtgc tggccgacct gctgggcgac 120
cgctacgagg tgatcgagga aggcctgtcg gcgcgcacca ccaccgccga cgacccggcc 180
gacccccggc tcaacggttc gcagtatctg ccgtcgtgtc tggccagcca tctgccgctg 240
gacctggtga tcctgatgct cggcatcaac gacaccaagg cgaattttgg ccgcaccccg 300
ttcgacatcg ccaccggtat gggagtgctt gccacgcagg tgctcaccag cgccggtggc 360
gtggggacca gctatcccgc gccgcaggtg ctgatcgtgg cgccgccgcc gctgggcgag 420
ctgccccacc cctggttcga cctggtgttc tccggcggcc gtgagaagac cgccgagttg 480
gcccgcgtgt acagcgcgct ggcgtcgttc atgaaggtgc cgttcttcga cgccggctcg 540
gtgatcagca ccgacggcgt ggacggcacc cacttcacac gaggcgaaac aatcga 596

<210> SEQ ID NO 636
<211> LENGTH: 198
<212> TYPE: PRT
<213> ORGANISM: Artificial Sequence
<220> FEATURE:
<223> OTHER INFORMATION: 2D Perhydrolase Homologue protein

<400> SEQUENCE: 636

Ile Leu Cys Phe Gly Asp Ser Leu Thr Trp Gly Trp Ile Pro Val Glu
1 5 10 15

Glu Gly Val Pro Thr Glu Arg Phe Pro Arg Asp Val Arg Trp Thr Gly
20 25 30

```
Val Leu Ala Asp Leu Leu Gly Asp Arg Tyr Glu Val Ile Glu Glu Gly
        35                  40                  45

Leu Ser Ala Arg Thr Thr Thr Ala Asp Asp Pro Ala Asp Pro Arg Leu
    50                  55                  60

Asn Gly Ser Gln Tyr Leu Pro Ser Cys Leu Ala Ser His Leu Pro Leu
65                  70                  75                  80

Asp Leu Val Ile Leu Met Leu Gly Ile Asn Asp Thr Lys Ala Asn Phe
                85                  90                  95

Gly Arg Thr Pro Phe Asp Ile Ala Thr Gly Met Gly Val Leu Ala Thr
            100                 105                 110

Gln Val Leu Thr Ser Ala Gly Gly Val Gly Thr Ser Tyr Pro Ala Pro
        115                 120                 125

Gln Val Leu Ile Val Ala Pro Pro Pro Leu Gly Glu Leu Pro His Pro
    130                 135                 140

Trp Phe Asp Leu Val Phe Ser Gly Gly Arg Glu Lys Thr Ala Glu Leu
145                 150                 155                 160

Ala Arg Val Tyr Ser Ala Leu Ala Ser Phe Met Lys Val Pro Phe Phe
                165                 170                 175

Asp Ala Gly Ser Val Ile Ser Thr Asp Gly Val Asp Gly Thr His Phe
            180                 185                 190

Thr Arg Gly Glu Thr Ile
        195
```

<210> SEQ ID NO 637
<211> LENGTH: 648
<212> TYPE: DNA
<213> ORGANISM: Mycobacterium gilvum

<400> SEQUENCE: 637

```
taccgtcgat gtgtggcctc gtgtgaagtg ggtgccgttg ccaagcgaat tctgtgtttc      60

ggggattcgt tgacgtgggg ctggatcccg gtcgaggaag gtgtacccac ccaacgtttt     120

ccgaagcggg tgcgctggac cggggtgctg gccgacgaac tgggtgctgg ctatgaggtt     180

gtcgaggagg ggttgagcgc gcgcaccacc accgctgacg accctaccga tccccggctg     240

aacggctcgg actacctccc cgcatgcctg gccagccacc tgccgctgga cctggtgatc     300

ctgatgctcg ggaccaacga caccaaggcg aatctgaatc gcacacccgt cgacatcgcc     360

agcggaatgg gcgtcctggc cacccaggtg ctcaccagcg cgggcggggt cggcaccagc     420

tacccggccc cgcaggtgtt gatcgtggca ccgccgccgc tggccgagat gccgcacccg     480

tggttcgagc tggtcttcga cggcggccgg gagaagaccg cccaactggc ccgggtgtac     540

agcgcgctgg cgtcgttcat gaaggtgccg ttcttcgacg ccggatcggt gatcagcacc     600

gacggtgtcg acggcaccca cttcacacga ggcgaaacaa tcgaccgg                  648
```

<210> SEQ ID NO 638
<211> LENGTH: 216
<212> TYPE: PRT
<213> ORGANISM: Mycobacterium gilvum

<400> SEQUENCE: 638

```
Gly Gly Arg Cys Val Ala Ser Cys Glu Val Gly Ala Val Ala Lys Arg
1               5                   10                  15

Ile Leu Cys Phe Gly Asp Ser Leu Thr Trp Gly Trp Ile Pro Val Glu
            20                  25                  30

Glu Gly Val Pro Thr Gln Arg Phe Pro Lys Arg Val Arg Trp Thr Gly
```

-continued

```
        35                  40                  45

Val Leu Ala Asp Glu Leu Gly Ala Gly Tyr Glu Val Val Glu Glu Gly
    50                  55                  60

Leu Ser Ala Arg Thr Thr Thr Ala Asp Asp Pro Thr Asp Pro Arg Leu
65                  70                  75                  80

Asn Gly Ser Asp Tyr Leu Pro Ala Cys Leu Ala Ser His Leu Pro Leu
                85                  90                  95

Asp Leu Val Ile Leu Met Leu Gly Thr Asn Asp Thr Lys Ala Asn Leu
            100                 105                 110

Asn Arg Thr Pro Val Asp Ile Ala Ser Gly Met Gly Val Leu Ala Thr
        115                 120                 125

Gln Val Leu Thr Ser Ala Gly Gly Val Gly Thr Ser Tyr Pro Ala Pro
    130                 135                 140

Gln Val Leu Ile Val Ala Pro Pro Pro Leu Ala Glu Met Pro His Pro
145                 150                 155                 160

Trp Phe Glu Leu Val Phe Asp Gly Gly Arg Glu Lys Thr Ala Gln Leu
                165                 170                 175

Ala Arg Val Tyr Ser Ala Leu Ala Ser Phe Met Lys Val Pro Phe Phe
            180                 185                 190

Asp Ala Gly Ser Val Ile Ser Thr Asp Gly Val Asp Gly Thr His Phe
        195                 200                 205

Thr Arg Gly Glu Thr Ile Asp Arg
    210                 215


<210> SEQ ID NO 639
<211> LENGTH: 584
<212> TYPE: DNA
<213> ORGANISM: Mycobacterium gilvum

<400> SEQUENCE: 639

attctgtgtt tcggagattc gttgacgtgg ggctggatcc cggtcgagga aggtgtaccc      60

acccaacgtt ttccgaagcg ggtgcgctgg accggggtgc tggccgacga actgggtgct     120

ggctatgagg ttgtcgagga ggggttgagc gcgcgcacca ccaccgctga cgaccctacc     180

gatccccggc tgaacggctc ggactacctc cccgcatgcc tggccagcca cctgccgctg     240

gacctggtga tcctgatgct cgggaccaac gacaccaagg cgaatctgaa tcgcacaccc     300

gtcgacatcg ccagcggaat gggcgtcctg gccacccagg tgctcaccag cgcgggcggg     360

gtcggcacca gctacccggc cccgcaggtg ttgatcgtgg caccgccgcc gctggccgag     420

atgccgcacc cgtggttcga gctggtcttc gacggcggcc gggagaagac cgcccaactg     480

gcccgggtgt acagcgcgct ggcgtcgttc atgaaggtgc cgttcttcga cgccggatcg     540

gtgatcagca ccgacggtgt cgacggcacc cacttcacac gagg                      584


<210> SEQ ID NO 640
<211> LENGTH: 194
<212> TYPE: PRT
<213> ORGANISM: Mycobacterium gilvum

<400> SEQUENCE: 640

Ile Leu Cys Phe Gly Asp Ser Leu Thr Trp Gly Trp Ile Pro Val Glu
1               5                   10                  15

Glu Gly Val Pro Thr Gln Arg Phe Pro Lys Arg Val Arg Trp Thr Gly
            20                  25                  30

Val Leu Ala Asp Glu Leu Gly Ala Gly Tyr Glu Val Val Glu Glu Gly
        35                  40                  45
```

```
Leu Ser Ala Arg Thr Thr Thr Ala Asp Asp Pro Thr Asp Pro Arg Leu
    50                  55                  60

Asn Gly Ser Asp Tyr Leu Pro Ala Cys Leu Ala Ser His Leu Pro Leu
65                  70                  75                  80

Asp Leu Val Ile Leu Met Leu Gly Thr Asn Asp Thr Lys Ala Asn Leu
                85                  90                  95

Asn Arg Thr Pro Val Asp Ile Ala Ser Gly Met Gly Val Leu Ala Thr
            100                 105                 110

Gln Val Leu Thr Ser Ala Gly Gly Val Gly Thr Ser Tyr Pro Ala Pro
        115                 120                 125

Gln Val Leu Ile Val Ala Pro Pro Pro Leu Ala Glu Met Pro His Pro
    130                 135                 140

Trp Phe Glu Leu Val Phe Asp Gly Gly Arg Glu Lys Thr Ala Gln Leu
145                 150                 155                 160

Ala Arg Val Tyr Ser Ala Leu Ala Ser Phe Met Lys Val Pro Phe Phe
                165                 170                 175

Asp Ala Gly Ser Val Ile Ser Thr Asp Gly Val Asp Gly Thr His Phe
            180                 185                 190

Thr Arg


<210> SEQ ID NO 641
<211> LENGTH: 608
<212> TYPE: DNA
<213> ORGANISM: Mycobacterium parafortuitum

<400> SEQUENCE: 641

ttgccaagcg gaattctgtg tttcggggat tctttgacgt ggggatggat ccctgtcgaa      60

gaaggtgtgc ccaccgagcg gttcccgcgt gacgtccggt ggaccggcgt gctggccgac     120

ctgctgggcg accgctacga ggtgatcgag gaaggcctgt cggcgcgcac caccaccgcc     180

gacgacccgg ccgacccccg gctcaacggt tcgcagtatc tgccgtcgtg tctggccagc     240

catctgccgc tggacctggt gatcctgatg ctcggcatca acgacaccaa ggcgaatttt     300

ggccgcaccc cgttcgacat cgccaccggt atgggagtgc ttgccacgca ggtgctcacc     360

agcgccggtg gcgtggggac cagctatccc gcgccgcagg tgctgatcgt ggcgccgccg     420

ccgctgggcg agctgcccca cccctggttc gacctggtgt tctccggcgg ccgtgagaag     480

accgccgagt tggcccgcgt gtacagcgcg ctggcgtcgt tcatgaaggt gccgttcttc     540

gacgccggct cggtgatcag caccgacggc gtggacggca cccacttcac acgaggcgaa     600

acaatcga                                                              608


<210> SEQ ID NO 642
<211> LENGTH: 202
<212> TYPE: PRT
<213> ORGANISM: Mycobacterium parafortuitum

<400> SEQUENCE: 642

Leu Pro Ser Gly Ile Leu Cys Phe Gly Asp Ser Leu Thr Trp Gly Trp
1               5                   10                  15

Ile Pro Val Glu Glu Gly Val Pro Thr Glu Arg Phe Pro Arg Asp Val
            20                  25                  30

Arg Trp Thr Gly Val Leu Ala Asp Leu Leu Gly Asp Arg Tyr Glu Val
        35                  40                  45

Ile Glu Glu Gly Leu Ser Ala Arg Thr Thr Thr Ala Asp Asp Pro Ala
    50                  55                  60
```

Asp Pro Arg Leu Asn Gly Ser Gln Tyr Leu Pro Ser Cys Leu Ala Ser
65 70 75 80

His Leu Pro Leu Asp Leu Val Ile Leu Met Leu Gly Ile Asn Asp Thr
85 90 95

Lys Ala Asn Phe Gly Arg Thr Pro Phe Asp Ile Ala Thr Gly Met Gly
100 105 110

Val Leu Ala Thr Gln Val Leu Thr Ser Ala Gly Gly Val Gly Thr Ser
115 120 125

Tyr Pro Ala Pro Gln Val Leu Ile Val Ala Pro Pro Pro Leu Gly Glu
130 135 140

Leu Pro His Pro Trp Phe Asp Leu Val Phe Ser Gly Gly Arg Glu Lys
145 150 155 160

Thr Ala Glu Leu Ala Arg Val Tyr Ser Ala Leu Ala Ser Phe Met Lys
165 170 175

Val Pro Phe Phe Asp Ala Gly Ser Val Ile Ser Thr Asp Gly Val Asp
180 185 190

Gly Thr His Phe Thr Arg Gly Glu Thr Ile
195 200

<210> SEQ ID NO 643
<211> LENGTH: 216
<212> TYPE: PRT
<213> ORGANISM: Mycobacterium smegmatis
<220> FEATURE:
<221> NAME/KEY: MISC_FEATURE
<222> LOCATION: (1)..(216)
<223> OTHER INFORMATION: Xaa is selenocysteine

<400> SEQUENCE: 643

Met Ala Lys Arg Ile Leu Cys Phe Gly Asp Ser Leu Xaa Trp Gly Trp
1 5 10 15

Val Pro Val Glu Asp Gly Ala Pro Xaa Glu Arg Phe Ala Pro Asp Val
20 25 30

Arg Trp Xaa Gly Val Leu Ala Gln Gln Leu Gly Ala Asp Phe Glu Val
35 40 45

Ile Glu Glu Gly Leu Ser Ala Arg Xaa Xaa Asn Ile Asp Asp Pro Xaa
50 55 60

Asp Pro Arg Leu Asn Gly Ala Ser Tyr Leu Pro Ser Cys Leu Ala Xaa
65 70 75 80

His Leu Pro Leu Asp Leu Val Ile Ile Met Leu Gly Xaa Asn Asp Xaa
85 90 95

Lys Ala Tyr Phe Arg Arg Xaa Pro Leu Asp Ile Ala Leu Gly Met Ser
100 105 110

Val Leu Val Xaa Gln Val Leu Xaa Ser Ala Gly Gly Val Gly Xaa Xaa
115 120 125

Tyr Pro Ala Pro Lys Val Leu Val Val Ser Pro Pro Pro Leu Ala Pro
130 135 140

Met Pro His Pro Trp Phe Gln Leu Ile Phe Glu Gly Gly Glu Gln Lys
145 150 155 160

Xaa Xaa Glu Leu Ala Arg Val Tyr Ser Ala Leu Ala Ser Phe Met Lys
165 170 175

Val Pro Phe Phe Asp Ala Gly Ser Val Ile Ser Xaa Asp Gly Val Asp
180 185 190

Gly Ile His Phe Xaa Glu Ala Asn Asn Arg Asp Leu Gly Val Ala Leu
195 200 205

```
Ala Glu Gln Val Arg Ser Leu Leu
    210                 215


<210> SEQ ID NO 644
<211> LENGTH: 194
<212> TYPE: PRT
<213> ORGANISM: Mycobacterium gilvum

<400> SEQUENCE: 644

Ile Leu Cys Phe Gly Asp Ser Leu Thr Trp Gly Trp Ile Pro Val Glu
1               5                   10                  15

Glu Gly Val Pro Thr Gln Arg Phe Pro Lys Arg Val Arg Trp Thr Gly
            20                  25                  30

Val Leu Ala Asp Glu Leu Gly Ala Gly Tyr Glu Val Val Glu Glu Gly
        35                  40                  45

Leu Ser Ala Arg Thr Thr Thr Ala Asp Asp Pro Thr Asp Pro Arg Leu
    50                  55                  60

Asn Gly Ser Asp Tyr Leu Pro Ala Cys Leu Ala Ser His Leu Pro Leu
65                  70                  75                  80

Asp Leu Val Ile Leu Met Leu Gly Thr Asn Asp Thr Lys Ala Asn Leu
                85                  90                  95

Asn Arg Thr Pro Val Asp Ile Ala Ser Gly Met Gly Val Leu Ala Thr
            100                 105                 110

Gln Val Leu Thr Ser Ala Gly Gly Val Gly Thr Ser Tyr Pro Ala Pro
        115                 120                 125

Gln Val Leu Ile Val Ala Pro Pro Pro Leu Ala Glu Met Pro His Pro
    130                 135                 140

Trp Phe Glu Leu Val Phe Asp Gly Gly Arg Glu Lys Thr Ala Gln Leu
145                 150                 155                 160

Ala Arg Val Tyr Ser Ala Leu Ala Ser Phe Met Lys Val Pro Phe Phe
                165                 170                 175

Asp Ala Gly Ser Val Ile Ser Thr Asp Gly Val Asp Gly Thr His Phe
            180                 185                 190

Thr Arg


<210> SEQ ID NO 645
<211> LENGTH: 202
<212> TYPE: PRT
<213> ORGANISM: Mycobacterium parafortuitum

<400> SEQUENCE: 645

Leu Pro Ser Gly Ile Leu Cys Phe Gly Asp Ser Leu Thr Trp Gly Trp
1               5                   10                  15

Ile Pro Val Glu Glu Gly Val Pro Thr Glu Arg Phe Pro Arg Asp Val
            20                  25                  30

Arg Trp Thr Gly Val Leu Ala Asp Leu Leu Gly Asp Arg Tyr Glu Val
        35                  40                  45

Ile Glu Glu Gly Leu Ser Ala Arg Thr Thr Thr Ala Asp Asp Pro Ala
    50                  55                  60

Asp Pro Arg Leu Asn Gly Ser Gln Tyr Leu Pro Ser Cys Leu Ala Ser
65                  70                  75                  80

His Leu Pro Leu Asp Leu Val Ile Leu Met Leu Gly Ile Asn Asp Thr
                85                  90                  95

Lys Ala Asn Phe Gly Arg Thr Pro Phe Asp Ile Ala Thr Gly Met Gly
            100                 105                 110

Val Leu Ala Thr Gln Val Leu Thr Ser Ala Gly Gly Val Gly Thr Ser
```

```
        115                 120                 125

Tyr Pro Ala Pro Gln Val Leu Ile Val Ala Pro Pro Pro Leu Gly Glu
    130                 135                 140

Leu Pro His Pro Trp Phe Asp Leu Val Phe Ser Gly Gly Arg Glu Lys
145                 150                 155                 160

Thr Ala Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Thr His Phe Thr Arg Gly Glu Thr Ile
        195                 200
```

<210> SEQ ID NO 646
<211> LENGTH: 198
<212> TYPE: PRT
<213> ORGANISM: Mycobacterium parafortuitum

<400> SEQUENCE: 646

```
Ile Leu Cys Phe Gly Asp Ser Leu Thr Trp Gly Trp Ile Pro Val Glu
1               5                   10                  15

Glu Gly Val Pro Thr Glu Arg Phe Pro Arg Asp Val Arg Trp Thr Gly
            20                  25                  30

Val Leu Ala Asp Leu Leu Gly Asp Arg Tyr Glu Val Ile Glu Glu Gly
        35                  40                  45

Leu Ser Ala Arg Thr Thr Thr Ala Asp Asp Pro Ala Asp Pro Arg Leu
    50                  55                  60

Asn Gly Ser Gln Tyr Leu Pro Ser Cys Leu Ala Ser His Leu Pro Leu
65                  70                  75                  80

Asp Leu Val Ile Leu Met Leu Gly Ile Asn Asp Thr Lys Ala Asn Phe
                85                  90                  95

Gly Arg Thr Pro Phe Asp Ile Ala Thr Gly Met Gly Val Leu Ala Thr
            100                 105                 110

Gln Val Leu Thr Ser Ala Gly Gly Val Gly Thr Ser Tyr Pro Ala Pro
        115                 120                 125

Gln Val Leu Ile Val Ala Pro Pro Pro Leu Gly Glu Leu Pro His Pro
    130                 135                 140

Trp Phe Asp Leu Val Phe Ser Gly Gly Arg Glu Lys Thr Ala Glu Leu
145                 150                 155                 160

Ala Arg Val Tyr Ser Ala Leu Ala Ser Phe Met Lys Val Pro Phe Phe
                165                 170                 175

Asp Ala Gly Ser Val Ile Ser Thr Asp Gly Val Asp Gly Thr His Phe
            180                 185                 190

Thr Arg Gly Glu Thr Ile
        195
```

<210> SEQ ID NO 647
<211> LENGTH: 216
<212> TYPE: PRT
<213> ORGANISM: Mycobacterium gilvum

<400> SEQUENCE: 647

```
Gly Gly Arg Cys Val Ala Ser Cys Glu Val Gly Ala Val Ala Lys Arg
1               5                   10                  15

Ile Leu Cys Phe Gly Asp Ser Leu Thr Trp Gly Trp Ile Pro Val Glu
            20                  25                  30

Glu Gly Val Pro Thr Gln Arg Phe Pro Lys Arg Val Arg Trp Thr Gly
```

```
        35                  40                  45

Val Leu Ala Asp Glu Leu Gly Ala Gly Tyr Glu Val Val Glu Glu Gly
    50                  55                  60

Leu Ser Ala Arg Thr Thr Thr Ala Asp Asp Pro Thr Asp Pro Arg Leu
65                  70                  75                  80

Asn Gly Ser Asp Tyr Leu Pro Ala Cys Leu Ala Ser His Leu Pro Leu
                85                  90                  95

Asp Leu Val Ile Leu Met Leu Gly Thr Asn Asp Thr Lys Ala Asn Leu
            100                 105                 110

Asn Arg Thr Pro Val Asp Ile Ala Ser Gly Met Gly Val Leu Ala Thr
        115                 120                 125

Gln Val Leu Thr Ser Ala Gly Gly Val Gly Thr Ser Tyr Pro Ala Pro
    130                 135                 140

Gln Val Leu Ile Val Ala Pro Pro Pro Leu Ala Glu Met Pro His Pro
145                 150                 155                 160

Trp Phe Glu Leu Val Phe Asp Gly Gly Arg Glu Lys Thr Ala Gln Leu
                165                 170                 175

Ala Arg Val Tyr Ser Ala Leu Ala Ser Phe Met Lys Val Pro Phe Phe
            180                 185                 190

Asp Ala Gly Ser Val Ile Ser Thr Asp Gly Val Asp Gly Thr His Phe
        195                 200                 205

Thr Arg Gly Glu Thr Ile Asp Arg
    210                 215


<210> SEQ ID NO 648
<211> LENGTH: 203
<212> TYPE: PRT
<213> ORGANISM: Mycobacterium parafortuitum CO1

<400> SEQUENCE: 648

Met Ala Lys Arg Ile Leu Cys Phe Gly Asp Ser Leu Thr Trp Gly Trp
1               5                   10                  15

Ile Pro Val Glu Glu Gly Val Pro Thr Glu Arg Phe Pro Arg Asp Val
            20                  25                  30

Arg Trp Thr Gly Val Leu Ala Asp Leu Leu Gly Asp Arg Tyr Glu Val
        35                  40                  45

Ile Glu Glu Gly Leu Ser Ala Arg Thr Thr Thr Ala Glu Asp Pro Ala
    50                  55                  60

Asp Pro Arg Leu Asn Gly Ser Gln Tyr Leu Pro Ser Cys Leu Ala Ser
65                  70                  75                  80

His Leu Pro Leu Asp Leu Val Ile Leu Met Leu Gly Thr Asn Asp Thr
                85                  90                  95

Lys Ala Asn Phe Gly Arg Thr Pro Phe Asp Ile Ala Thr Gly Met Gly
            100                 105                 110

Val Leu Ala Thr Gln Val Leu Thr Ser Ala Gly Gly Val Gly Thr Ser
        115                 120                 125

Tyr Pro Ala Pro Gln Val Leu Ile Val Ala Pro Pro Pro Leu Gly Glu
    130                 135                 140

Leu Pro His Pro Trp Phe Asp Leu Val Phe Ser Gly Gly Arg Glu Lys
145                 150                 155                 160

Thr Ala Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190
```

```
Gly Ile His Phe Thr Arg Gly Glu Gln Ser Thr
        195                 200


<210> SEQ ID NO 649
<211> LENGTH: 213
<212> TYPE: PRT
<213> ORGANISM: Sinorhizobium meliloti

<400> SEQUENCE: 649

Met Lys Thr Val Leu Cys Tyr Gly Asp Ser Leu Thr Trp Gly Tyr Asp
1               5                   10                  15

Ala Thr Gly Ser Gly Arg His Ala Leu Glu Asp Arg Trp Pro Ser Val
            20                  25                  30

Leu Gln Lys Ala Leu Gly Ser Asp Ala His Val Ile Ala Glu Gly Leu
        35                  40                  45

Asn Gly Arg Thr Thr Ala Tyr Asp Asp His Leu Ala Asp Cys Asp Arg
    50                  55                  60

Asn Gly Ala Arg Val Leu Pro Thr Val Leu His Thr His Ala Pro Leu
65                  70                  75                  80

Asp Leu Ile Val Phe Met Leu Gly Ser Asn Asp Met Lys Pro Ile Ile
                85                  90                  95

His Gly Thr Ala Phe Gly Ala Val Lys Gly Ile Glu Arg Leu Val Asn
            100                 105                 110

Leu Val Arg Arg His Asp Trp Pro Thr Glu Thr Glu Glu Gly Pro Glu
        115                 120                 125

Ile Leu Ile Val Ser Pro Pro Pro Leu Cys Glu Thr Ala Asn Ser Ala
    130                 135                 140

Phe Ala Ala Met Phe Ala Gly Gly Val Glu Gln Ser Ala Met Leu Ala
145                 150                 155                 160

Pro Leu Tyr Arg Asp Leu Ala Asp Glu Leu Asp Cys Gly Phe Phe Asp
                165                 170                 175

Gly Gly Ser Val Ala Arg Thr Thr Pro Ile Asp Gly Val His Leu Asp
            180                 185                 190

Ala Glu Asn Thr Arg Ala Val Gly Arg Gly Leu Glu Pro Val Val Arg
        195                 200                 205

Met Met Leu Gly Leu
    210


<210> SEQ ID NO 650
<211> LENGTH: 209
<212> TYPE: PRT
<213> ORGANISM: Agrobacterium tumefaciens

<400> SEQUENCE: 650

Met Lys Thr Val Leu Ala Phe Gly Asp Ser Leu Thr Trp Gly Ala Asp
1               5                   10                  15

Pro Ala Thr Gly Leu Arg His Pro Val Glu His Arg Trp Pro Asp Val
            20                  25                  30

Leu Glu Ala Glu Leu Ala Gly Lys Ala Lys Val His Pro Glu Gly Leu
        35                  40                  45

Gly Gly Arg Thr Thr Cys Tyr Asp Asp His Ala Gly Pro Ala Cys Arg
    50                  55                  60

Asn Gly Ala Arg Ala Leu Glu Val Ala Leu Ser Cys His Met Pro Leu
65                  70                  75                  80

Asp Leu Val Ile Ile Met Leu Gly Thr Asn Asp Ile Lys Pro Val His
                85                  90                  95
```

-continued

```
Gly Gly Arg Ala Glu Ala Ala Val Ser Gly Met Arg Arg Leu Ala Gln
            100                 105                 110

Ile Val Glu Thr Phe Ile Tyr Lys Pro Arg Glu Ala Val Pro Lys Leu
        115                 120                 125

Leu Ile Val Ala Pro Pro Pro Cys Val Ala Gly Pro Gly Gly Glu Pro
    130                 135                 140

Ala Gly Gly Arg Asp Ile Glu Gln Ser Met Arg Leu Ala Pro Leu Tyr
145                 150                 155                 160

Arg Lys Leu Ala Ala Glu Leu Gly His His Phe Phe Asp Ala Gly Ser
                165                 170                 175

Val Ala Ser Ala Ser Pro Val Asp Gly Val His Leu Asp Ala Ser Ala
            180                 185                 190

Thr Ala Ala Ile Gly Arg Ala Leu Ala Ala Pro Val Arg Asp Ile Leu
        195                 200                 205

Gly


<210> SEQ ID NO 651
<211> LENGTH: 220
<212> TYPE: PRT
<213> ORGANISM: Agrobacterium tumefaciens

<400> SEQUENCE: 651

Met Val Lys Ser Val Leu Cys Phe Gly Asp Ser Leu Thr Trp Gly Ser
1               5                   10                  15

Asn Ala Glu Thr Gly Gly Arg His Ser His Asp Asp Leu Trp Pro Ser
            20                  25                  30

Val Leu Gln Lys Ala Leu Gly Ser Asp Val His Val Ile Phe Thr His
        35                  40                  45

Glu Gly Leu Gly Gly Arg Thr Thr Ala Tyr Asp Asp His Thr Gly Asp
    50                  55                  60

Cys Asp Arg Asn Gly Ala Arg Leu Leu Pro Thr Leu Leu His Ser His
65                  70                  75                  80

Ala Pro Leu Asp Met Val Ile Ile Met Leu Gly Thr Asn Asp Met Lys
                85                  90                  95

Pro Ala Ile His Gly Ser Ala Ile Val Ala Phe Thr Met Lys Gly Val
            100                 105                 110

Glu Arg Leu Val Lys Leu Thr Arg Asn His Val Trp Gln Val Ser Asp
        115                 120                 125

Trp Glu Ala Pro Asp Val Leu Ile Val Ala Pro Pro Gln Leu Cys Glu
    130                 135                 140

Thr Ala Asn Pro Phe Met Gly Ala Ile Phe Arg Asp Ala Ile Asp Glu
145                 150                 155                 160

Ser Ala Met Leu Ala Ser Val Phe Thr Tyr Arg Asp Leu Ala Asp Glu
                165                 170                 175

Leu Asp Cys Gly Phe Phe Asp Ala Gly Ser Val Ala Arg Thr Thr Pro
            180                 185                 190

Val Asp Gly Val His Leu Asp Ala Glu Asn Thr Arg Ala Ile Gly Arg
        195                 200                 205

Gly Leu Glu Pro Val Val Arg Met Met Leu Gly Leu
    210                 215                 220


<210> SEQ ID NO 652
<211> LENGTH: 215
<212> TYPE: PRT
<213> ORGANISM: Artificial Sequence
<220> FEATURE:
```

<223> OTHER INFORMATION: M091_M4aE11 clone

<400> SEQUENCE: 652

Met Lys Thr Ile Leu Ala Tyr Gly Asp Ser Leu Thr Tyr Gly Ala Asn
1 5 10 15

Pro Ile Pro Gly Gly Pro Arg His Ala Tyr Glu Asp Arg Trp Pro Thr
20 25 30

Ala Leu Glu Gln Gly Leu Gly Gly Lys Ala Arg Val Ile Ala Glu Gly
35 40 45

Leu Gly Gly Arg Thr Thr Val His Asp Asp Trp Phe Ala Asn Ala Asp
50 55 60

Arg Asn Gly Ala Arg Val Leu Pro Thr Leu Leu Glu Ser His Ser Pro
65 70 75 80

Leu Asp Leu Ile Val Ile Met Leu Gly Thr Asn Asp Ile Lys Pro His
85 90 95

His Gly Arg Thr Ala Gly Glu Ala Gly Arg Gly Met Ala Arg Leu Val
100 105 110

Gln Ile Ile Arg Gly His Tyr Ala Gly Arg Met Gln Asp Glu Pro Gln
115 120 125

Ile Ile Leu Val Ser Pro Pro Pro Ile Ile Leu Gly Asp Trp Ala Asp
130 135 140

Met Met Asp His Phe Gly Pro His Glu Ala Ile Ala Thr Ser Val Asp
145 150 155 160

Phe Ala Arg Glu Tyr Lys Lys Arg Ala Asp Glu Gln Lys Val His Phe
165 170 175

Phe Asp Ala Gly Thr Val Ala Thr Thr Ser Lys Ala Asp Gly Ile His
180 185 190

Leu Asp Pro Ala Asn Thr Arg Ala Ile Gly Ala Gly Leu Val Pro Leu
195 200 205

Val Lys Gln Val Leu Gly Leu
210 215

<210> SEQ ID NO 653
<211> LENGTH: 223
<212> TYPE: PRT
<213> ORGANISM: Mesorhizobium loti

<400> SEQUENCE: 653

Met Ala Gly Gly Thr Arg Leu Asp Glu Cys Thr Gly Glu Arg Met Lys
1 5 10 15

Thr Val Leu Cys Tyr Gly Asp Ser Leu Thr Trp Gly Tyr Asn Ala Glu
20 25 30

Gly Gly Arg His Ala Leu Glu Asp Arg Trp Pro Ser Val Leu Gln Ala
35 40 45

Ser Leu Gly Gly Gly Val Gln Val Ile Ala Asp Gly Leu Asn Gly Arg
50 55 60

Thr Thr Ala Phe Asp Asp His Leu Ala Gly Ala Asp Arg Asn Gly Ala
65 70 75 80

Arg Leu Leu Pro Thr Ala Leu Thr Thr His Ala Pro Ile Asp Leu Ile
85 90 95

Val Ile Met Leu Gly Ala Asn Asp Met Lys Pro Trp Ile His Gly Asn
100 105 110

Pro Val Ala Ala Lys Gln Gly Ile Gln Arg Leu Ile Asp Ile Val Arg
115 120 125

Gly His Asp Tyr Pro Phe Asp Trp Pro Ala Pro Gln Ile Leu Ile Val

```
    130                 135                 140

Ser Pro Pro Val Val Ser Arg Thr Glu Asn Ala Asp Phe Arg Glu Met
145                 150                 155                 160

Phe Ala Gly Gly Asp Glu Ala Ser Lys Gln Leu Ala Pro Gln Tyr Ala
                165                 170                 175

Ala Leu Ala Asp Glu Val Gly Cys Gly Phe Phe Asp Ala Gly Thr Val
            180                 185                 190

Ala Gln Thr Thr Pro Leu Asp Gly Val His Leu Asp Ala Glu Asn Thr
        195                 200                 205

Arg Asn Ile Gly Lys Ala Leu Thr Ser Val Val Arg Val Met Leu
    210                 215                 220


<210> SEQ ID NO 654
<211> LENGTH: 216
<212> TYPE: PRT
<213> ORGANISM: Prosthecobacter dejongeii

<400> SEQUENCE: 654

Met Lys Thr Ile Leu Cys Phe Gly Asp Ser Asn Thr Trp Gly Tyr Asp
1               5                   10                  15

Pro Ala Ser Met Thr Ala Pro Phe Pro Arg Arg His Gly Pro Glu Val
            20                  25                  30

Arg Trp Thr Gly Val Leu Ala Lys Ala Leu Gly Ala Gly Phe Arg Val
        35                  40                  45

Ile Glu Glu Gly Gln Asn Gly Arg Thr Thr Val His Glu Asp Pro Leu
    50                  55                  60

Asn Ile Cys Arg Lys Gly Lys Asp Tyr Leu Pro Ala Cys Leu Glu Ser
65                  70                  75                  80

His Lys Pro Leu Asp Leu Val Ile Leu Met Leu Gly Thr Asn Asp Leu
                85                  90                  95

Lys Ser Thr Phe Asn Val Pro Pro Gly Glu Ile Ala Ala Gly Ala Gly
            100                 105                 110

Val Leu Gly Arg Met Ile Leu Ala Gly Asp Ala Gly Pro Glu Asn Arg
        115                 120                 125

Pro Pro Gln Leu Leu Leu Met Cys Pro Pro Lys Val Arg Asp Leu Ser
    130                 135                 140

Ala Met Pro Asp Leu Asp Ala Lys Ile Pro His Gly Ala Ala Arg Ser
145                 150                 155                 160

Ala Glu Phe Pro Arg His Tyr Lys Ala Gln Ala Val Ala Leu Lys Cys
                165                 170                 175

Glu Tyr Phe Asn Ser Gln Glu Ile Val Glu Thr Ser Pro Val Asp Gly
            180                 185                 190

Ile His Leu Glu Ala Ser Glu His Leu Lys Leu Gly Glu Ala Leu Ala
        195                 200                 205

Glu Lys Val Lys Val Leu Leu Gly
    210                 215


<210> SEQ ID NO 655
<211> LENGTH: 220
<212> TYPE: PRT
<213> ORGANISM: Sinorhizobium meliloti

<400> SEQUENCE: 655

Met Glu Glu Thr Val Ala Arg Thr Val Leu Cys Phe Gly Asp Ser Asn
1               5                   10                  15

Thr His Gly Gln Val Pro Gly Arg Gly Pro Leu Asp Arg Tyr Arg Arg
```

```
            20                  25                  30

Glu Gln Arg Trp Gly Gly Val Leu Gln Gly Leu Leu Gly Pro Asn Trp
        35                  40                  45

Gln Val Ile Glu Glu Gly Leu Ser Gly Arg Thr Thr Val His Asp Asp
    50                  55                  60

Pro Ile Glu Gly Ser Leu Lys Asn Gly Arg Ile Tyr Leu Arg Pro Cys
65                  70                  75                  80

Leu Gln Ser His Ala Pro Leu Asp Leu Ile Ile Ile Met Leu Gly Thr
                85                  90                  95

Asn Asp Leu Lys Arg Arg Phe Asn Met Pro Pro Ser Glu Val Ala Met
            100                 105                 110

Gly Ile Gly Cys Leu Val His Asp Ile Arg Glu Leu Ser Pro Gly Arg
        115                 120                 125

Thr Gly Asn Asp Pro Glu Ile Met Ile Val Ala Pro Pro Pro Met Leu
    130                 135                 140

Glu Asp Leu Lys Glu Trp Glu Ser Ile Phe Ser Gly Ala Gln Glu Lys
145                 150                 155                 160

Ser Arg Lys Leu Ala Leu Glu Phe Glu Ile Met Ala Asp Ser Leu Glu
                165                 170                 175

Ala His Phe Phe Asp Ala Gly Thr Val Cys Gln Cys Ser Pro Ala Asp
            180                 185                 190

Gly Phe His Ile Asp Glu Asp Ala His Arg Leu Leu Gly Glu Ala Leu
        195                 200                 205

Ala Gln Glu Val Leu Ala Ile Gly Trp Pro Asp Ala
    210                 215                 220


<210> SEQ ID NO 656
<211> LENGTH: 211
<212> TYPE: PRT
<213> ORGANISM: Mesorhizobium loti

<400> SEQUENCE: 656

Met Lys Thr Val Leu Cys Tyr Gly Asp Ser Leu Thr Trp Gly Tyr Asn
1               5                   10                  15

Ala Glu Gly Gly Arg His Ala Leu Glu Asp Arg Trp Pro Ser Val Leu
            20                  25                  30

Gln Ala Ser Leu Gly Gly Gly Val Gln Val Ile Ala Asp Gly Leu Asn
        35                  40                  45

Gly Arg Thr Thr Ala Phe Asp Asp His Leu Ala Gly Ala Asp Arg Asn
    50                  55                  60

Gly Ala Arg Leu Leu Pro Thr Ala Leu Thr Thr His Ala Pro Ile Asp
65                  70                  75                  80

Leu Ile Val Ile Met Leu Gly Ala Asn Asp Met Lys Pro Trp Ile His
                85                  90                  95

Gly Asn Pro Val Ala Ala Lys Gln Gly Ile Gln Arg Leu Ile Asp Ile
            100                 105                 110

Val Arg Gly His Asp Tyr Pro Phe Asp Trp Pro Ala Pro Gln Ile Leu
        115                 120                 125

Ile Val Ser Pro Pro Val Val Ser Arg Thr Glu Asn Ala Asp Phe Arg
    130                 135                 140

Glu Met Phe Ala Gly Gly Asp Glu Ala Ser Lys Gln Leu Ala Pro Gln
145                 150                 155                 160

Tyr Ala Ala Leu Ala Asp Glu Val Gly Cys Gly Phe Phe Asp Ala Gly
                165                 170                 175
```

```
Thr Val Ala Gln Thr Thr Pro Leu Asp Gly Val His Leu Asp Ala Glu
            180                 185                 190

Asn Thr Arg Asn Ile Gly Lys Ala Leu Thr Ser Val Val Arg Val Met
        195                 200                 205

Leu Glu Leu
    210


<210> SEQ ID NO 657
<211> LENGTH: 218
<212> TYPE: PRT
<213> ORGANISM: Sinorhizobium meliloti

<400> SEQUENCE: 657

Met Val Glu Lys Arg Ser Val Leu Cys Phe Gly Asp Ser Leu Thr Trp
1               5                   10                  15

Gly Trp Ile Pro Val Lys Glu Ser Ser Pro Thr Leu Arg Tyr Pro Tyr
            20                  25                  30

Glu Gln Arg Trp Thr Gly Ala Met Ala Ala Arg Leu Gly Asp Gly Tyr
        35                  40                  45

His Ile Ile Glu Glu Gly Leu Ser Ala Arg Thr Thr Ser Leu Asp Asp
    50                  55                  60

Pro Asn Asp Ala Arg Leu Asn Gly Ser Thr Tyr Leu Pro Met Ala Leu
65                  70                  75                  80

Ala Ser His Leu Pro Leu Asp Leu Val Ile Ile Met Leu Gly Thr Asn
                85                  90                  95

Asp Thr Lys Ser Tyr Phe His Arg Thr Pro Tyr Glu Ile Ala Asn Gly
            100                 105                 110

Met Gly Lys Leu Val Gly Gln Val Leu Thr Cys Ala Gly Gly Val Gly
        115                 120                 125

Thr Pro Tyr Pro Ala Pro Lys Val Leu Val Val Ala Pro Pro Pro Leu
    130                 135                 140

Ala Pro Met Pro Asp Pro Trp Phe Glu Gly Met Phe Gly Gly Gly Tyr
145                 150                 155                 160

Glu Lys Ser Lys Glu Leu Ser Gly Leu Tyr Lys Ala Leu Ala Asp Phe
                165                 170                 175

Met Lys Val Glu Phe Phe Ala Ala Gly Asp Cys Ile Ser Thr Asp Gly
            180                 185                 190

Ile Asp Gly Ile His Leu Ser Ala Glu Thr Asn Ile Arg Leu Gly His
        195                 200                 205

Ala Ile Ala Asp Lys Val Ala Ala Leu Phe
    210                 215


<210> SEQ ID NO 658
<211> LENGTH: 212
<212> TYPE: PRT
<213> ORGANISM: Artificial Sequence
<220> FEATURE:
<223> OTHER INFORMATION: primer

<400> SEQUENCE: 658

Met Lys Asn Ile Leu Ala Phe Gly Asp Ser Leu Thr Trp Gly Phe Val
1               5                   10                  15

Ala Gly Gln Asp Ala Arg His Pro Phe Glu Thr Arg Trp Pro Asn Ala
            20                  25                  30

Leu Ala Ala Gly Leu Gly Gly Lys Ala Arg Val Ile Glu Glu Gly Gln
        35                  40                  45

Asn Gly Arg Thr Thr Val Phe Asp Asp Ala Ala Thr Phe Glu Ser Arg
```

```
    50                  55                  60

Asn Gly Ser Val Ala Leu Pro Leu Leu Leu Ile Ser His Gln Pro Leu
65                  70                  75                  80

Asp Leu Val Ile Ile Met Leu Gly Thr Asn Asp Ile Lys Phe Ala Ala
                85                  90                  95

Arg Cys Arg Ala Phe Asp Ala Ser Met Gly Met Glu Arg Leu Ile Gln
            100                 105                 110

Ile Val Arg Ser Ala Asn Tyr Met Lys Gly Tyr Lys Ile Pro Glu Ile
        115                 120                 125

Leu Ile Ile Ser Pro Pro Ser Leu Val Pro Thr Gln Asp Glu Trp Phe
    130                 135                 140

Asn Asp Leu Trp Gly His Ala Ile Ala Glu Ser Lys Leu Phe Ala Lys
145                 150                 155                 160

His Tyr Lys Arg Val Ala Glu Glu Leu Lys Val His Phe Phe Asp Ala
                165                 170                 175

Gly Thr Val Ala Val Ala Asp Lys Thr Asp Gly Gly His Leu Asp Ala
            180                 185                 190

Val Asn Thr Lys Ala Ile Gly Val Ala Leu Val Pro Val Val Lys Ser
        195                 200                 205

Ile Leu Ala Leu
    210


<210> SEQ ID NO 659
<211> LENGTH: 229
<212> TYPE: PRT
<213> ORGANISM: Sinorhizobium meliloti

<400> SEQUENCE: 659

Met Thr Ile Asn Ser His Ser Trp Arg Thr Leu Met Val Glu Lys Arg
1               5                   10                  15

Ser Val Leu Cys Phe Gly Asp Ser Leu Thr Trp Gly Trp Ile Pro Val
            20                  25                  30

Lys Glu Ser Ser Pro Thr Leu Arg Tyr Pro Tyr Glu Gln Arg Trp Thr
        35                  40                  45

Gly Ala Met Ala Ala Arg Leu Gly Asp Gly Tyr His Ile Ile Glu Glu
    50                  55                  60

Gly Leu Ser Ala Arg Thr Thr Ser Leu Asp Asp Pro Asn Asp Ala Arg
65                  70                  75                  80

Leu Asn Gly Ser Thr Tyr Leu Pro Met Ala Leu Ala Ser His Leu Pro
                85                  90                  95

Leu Asp Leu Val Ile Ile Met Leu Gly Thr Asn Asp Thr Lys Ser Tyr
            100                 105                 110

Phe His Arg Thr Pro Tyr Glu Ile Ala Asn Gly Met Gly Lys Leu Val
        115                 120                 125

Gly Gln Val Leu Thr Cys Ala Gly Gly Val Gly Thr Pro Tyr Pro Ala
    130                 135                 140

Pro Lys Val Leu Val Val Ala Pro Pro Pro Leu Ala Pro Met Pro Asp
145                 150                 155                 160

Pro Trp Phe Glu Gly Met Phe Gly Gly Gly Tyr Glu Lys Ser Lys Glu
                165                 170                 175

Leu Ser Gly Leu Tyr Lys Ala Leu Ala Asp Phe Met Lys Val Glu Phe
            180                 185                 190

Phe Ala Ala Gly Asp Cys Ile Ser Thr Asp Gly Ile Asp Gly Ile His
        195                 200                 205
```

```
Leu Ser Ala Glu Thr Asn Ile Arg Leu Gly His Ala Ile Ala Asp Lys
    210                 215                 220

Val Ala Ala Leu Phe
225
```

<210> SEQ ID NO 660
<211> LENGTH: 222
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (101)..(103)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (111)..(113)
<223> OTHER INFORMATION: Xaa can be any naturally occurring amino acid
<220> FEATURE:
<221> NAME/KEY: misc_feature
<222> LOCATION: (120)..(121)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (131)..(134)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (150)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (160)..(161)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (168)..(169)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (196)..(196)
<223> OTHER INFORMATION: Xaa can be any naturally occurring amino acid
<220> FEATURE:
<221> NAME/KEY: misc_feature
<222> LOCATION: (205)..(206)
<223> OTHER INFORMATION: Xaa can be any naturally occurring amino acid
<220> FEATURE:
<221> NAME/KEY: misc_feature
<222> LOCATION: (208)..(209)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:

<221> NAME/KEY: misc_feature
<222> LOCATION: (215)..(217)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid

<400> SEQUENCE: 660

```
Lys Thr Ile Leu Cys Phe Gly Asp Ser Leu Thr Trp Gly Trp Ile Pro
1               5                   10                  15

Val Xaa Glu Gly Xaa Pro Xaa Xaa Xaa Arg His Pro Xaa Glu Xaa Arg
            20                  25                  30

Trp Xaa Gly Val Leu Ala Xaa Xaa Leu Gly Gly Xaa Tyr Xaa Val Ile
        35                  40                  45

Glu Xaa Xaa Glu Gly Leu Ser Gly Arg Thr Thr Xaa Xaa Asp Asp Pro
    50                  55                  60

Xaa Asp Xaa Xaa Leu Xaa Asn Gly Ser Xaa Tyr Leu Pro Thr Xaa Leu
65                  70                  75                  80

Ala Ser His Leu Pro Leu Asp Leu Val Ile Ile Met Leu Gly Thr Asn
                85                  90                  95

Asp Met Lys Ala Xaa Xaa Xaa Arg Thr Pro Xaa Asp Ile Ala Xaa Xaa
            100                 105                 110

Xaa Gly Met Gly Arg Leu Val Xaa Xaa Val Leu Thr Xaa Ala Gly Gly
        115                 120                 125

Val Gly Xaa Xaa Xaa Xaa Ala Pro Gln Val Leu Ile Val Ala Pro Pro
    130                 135                 140

Pro Leu Xaa Glu Met Xaa Xaa Xaa Pro Xaa Phe Glu Xaa Val Phe Xaa
145                 150                 155                 160

Xaa Gly Gly Xaa Glu Lys Ser Xaa Xaa Leu Ala Arg Val Tyr Xaa Ala
                165                 170                 175

Leu Ala Asp Xaa Met Lys Val Xaa Phe Phe Asp Ala Gly Ser Val Ile
            180                 185                 190

Ser Thr Asp Xaa Val Asp Gly Ile His Leu Asp Ala Xaa Xaa Thr Xaa
        195                 200                 205

Xaa Ile Gly Xaa Ala Leu Xaa Xaa Xaa Val Arg Xaa Leu Leu
    210                 215                 220
```

<210> SEQ ID NO 661
<211> LENGTH: 213
<212> TYPE: PRT
<213> ORGANISM: Artificial Sequence
<220> FEATURE:
<223> OTHER INFORMATION: consensus

<400> SEQUENCE: 661

```
Thr Ile Leu Cys Phe Gly Asp Ser Leu Thr Trp Gly Trp Ile Pro Val
1               5                   10                  15

Glu Glu Gly Ala Pro Thr Glu Arg His Pro Pro Glu Val Arg Trp Thr
            20                  25                  30

Gly Val Leu Ala Gln Gln Leu Gly Gly Asp Tyr Glu Val Ile Glu Glu
        35                  40                  45

Gly Leu Ser Gly Arg Thr Thr Asn Ile Asp Asp Pro Thr Asp Pro Arg
    50                  55                  60

Leu Asn Gly Ser Ser Tyr Leu Pro Thr Cys Leu Ala Ser His Leu Pro
65                  70                  75                  80

Leu Asp Leu Val Ile Ile Met Leu Gly Thr Asn Asp Met Lys Ala Tyr
                85                  90                  95
```

Phe Arg Arg Thr Pro Leu Asp Ile Ala Leu Gly Met Gly Arg Leu Val
100 105 110

Thr Gln Val Leu Thr Ser Ala Gly Gly Val Gly Thr Thr Tyr Pro Ala
115 120 125

Pro Gln Val Leu Ile Val Ala Pro Pro Pro Leu Ala Glu Met Pro His
130 135 140

Pro Trp Phe Glu Leu Val Phe Glu Gly Gly Glu Glu Lys Ser Thr Glu
145 150 155 160

Leu Ala Arg Val Tyr Ser Ala Leu Ala Asp Phe Met Lys Val Pro Phe
165 170 175

Phe Asp Ala Gly Ser Val Ile Ser Thr Asp Gly Val Asp Gly Ile His
180 185 190

Leu Asp Ala Ala Asn Thr Arg Asp Ile Gly Val Ala Leu Ala Glu Gln
195 200 205

Val Arg Ser Leu Leu
210

<210> SEQ ID NO 662
<211> LENGTH: 216
<212> TYPE: PRT
<213> ORGANISM: Artificial Sequence
<220> FEATURE:
<223> OTHER INFORMATION: ACT MSMEG clone
<220> FEATURE:
<221> NAME/KEY: MISC_FEATURE
<222> LOCATION: (1)..(216)
<223> OTHER INFORMATION: Xaa is selenocysteine

<400> SEQUENCE: 662

Met Ala Lys Arg Ile Leu Cys Phe Gly Asp Ser Leu Xaa Trp Gly Trp
1 5 10 15

Val Pro Val Glu Asp Gly Ala Pro Xaa Glu Arg Phe Ala Pro Asp Val
20 25 30

Arg Trp Xaa Gly Val Leu Ala Gln Gln Leu Gly Ala Asp Phe Glu Val
35 40 45

Ile Glu Glu Gly Leu Ser Ala Arg Xaa Xaa Asn Ile Asp Asp Pro Xaa
50 55 60

Asp Pro Arg Leu Asn Gly Ala Ser Tyr Leu Pro Ser Cys Leu Ala Xaa
65 70 75 80

His Leu Pro Leu Asp Leu Val Ile Ile Met Leu Gly Xaa Asn Asp Xaa
85 90 95

Lys Ala Tyr Phe Arg Arg Xaa Pro Leu Asp Ile Ala Leu Gly Met Ser
100 105 110

Val Leu Val Xaa Gln Val Leu Xaa Ser Ala Gly Gly Val Gly Xaa Xaa
115 120 125

Tyr Pro Ala Pro Lys Val Leu Val Val Ser Pro Pro Pro Leu Ala Pro
130 135 140

Met Pro His Pro Trp Phe Gln Leu Ile Phe Glu Gly Gly Glu Gln Lys
145 150 155 160

Xaa Xaa Glu Leu Ala Arg Val Tyr Ser Ala Leu Ala Ser Phe Met Lys
165 170 175

Val Pro Phe Phe Asp Ala Gly Ser Val Ile Ser Xaa Asp Gly Val Asp
180 185 190

Gly Ile His Phe Xaa Glu Ala Asn Asn Arg Asp Leu Gly Val Ala Leu
195 200 205

Ala Glu Gln Val Arg Ser Leu Leu 210 215

<210> SEQ ID NO 663
<211> LENGTH: 211
<212> TYPE: PRT
<213> ORGANISM: Mesorhizobium loti

<400> SEQUENCE: 663

Met Lys Thr Val Leu Cys Tyr Gly Asp Ser Leu Thr Trp Gly Tyr Asn
1 5 10 15

Ala Glu Gly Gly Arg His Ala Leu Glu Asp Arg Trp Pro Ser Val Leu
20 25 30

Gln Ala Ser Leu Gly Gly Gly Val Gln Val Ile Ala Asp Gly Leu Asn
35 40 45

Gly Arg Thr Thr Ala Phe Asp Asp His Leu Ala Gly Ala Asp Arg Asn
50 55 60

Gly Ala Arg Leu Leu Pro Thr Ala Leu Thr Thr His Ala Pro Ile Asp
65 70 75 80

Leu Ile Val Ile Met Leu Gly Ala Asn Asp Met Lys Pro Trp Ile His
85 90 95

Gly Asn Pro Val Ala Ala Lys Gln Gly Ile Gln Arg Leu Ile Asp Ile
100 105 110

Val Arg Gly His Asp Tyr Pro Phe Asp Trp Pro Ala Pro Gln Ile Leu
115 120 125

Ile Val Ser Pro Pro Val Val Ser Arg Thr Glu Asn Ala Asp Phe Arg
130 135 140

Glu Met Phe Ala Gly Gly Asp Glu Ala Ser Lys Gln Leu Ala Pro Gln
145 150 155 160

Tyr Ala Ala Leu Ala Asp Glu Val Gly Cys Gly Phe Phe Asp Ala Gly
165 170 175

Thr Val Ala Gln Thr Thr Pro Leu Asp Gly Val His Leu Asp Ala Glu
180 185 190

Asn Thr Arg Asn Ile Gly Lys Ala Leu Thr Ser Val Val Arg Val Met
195 200 205

Leu Glu Leu
210

<210> SEQ ID NO 664
<211> LENGTH: 229
<212> TYPE: PRT
<213> ORGANISM: Sinorhizobium meliloti

<400> SEQUENCE: 664

Met Thr Ile Asn Ser His Ser Trp Arg Thr Leu Met Val Glu Lys Arg
1 5 10 15

Ser Val Leu Cys Phe Gly Asp Ser Leu Thr Trp Gly Trp Ile Pro Val
20 25 30

Lys Glu Ser Ser Pro Thr Leu Arg Tyr Pro Tyr Glu Gln Arg Trp Thr
35 40 45

Gly Ala Met Ala Ala Arg Leu Gly Asp Gly Tyr His Ile Ile Glu Glu
50 55 60

Gly Leu Ser Ala Arg Thr Thr Ser Leu Asp Asp Pro Asn Asp Ala Arg
65 70 75 80

Leu Asn Gly Ser Thr Tyr Leu Pro Met Ala Leu Ala Ser His Leu Pro
85 90 95

Leu Asp Leu Val Ile Ile Met Leu Gly Thr Asn Asp Thr Lys Ser Tyr

```
            100                 105                 110

Phe His Arg Thr Pro Tyr Glu Ile Ala Asn Gly Met Gly Lys Leu Val
        115                 120                 125

Gly Gln Val Leu Thr Cys Ala Gly Gly Val Gly Thr Pro Tyr Pro Ala
    130                 135                 140

Pro Lys Val Leu Val Val Ala Pro Pro Pro Leu Ala Pro Met Pro Asp
145                 150                 155                 160

Pro Trp Phe Glu Gly Met Phe Gly Gly Gly Tyr Glu Lys Ser Lys Glu
                165                 170                 175

Leu Ser Gly Leu Tyr Lys Ala Leu Ala Asp Phe Met Lys Val Glu Phe
            180                 185                 190

Phe Ala Ala Gly Asp Cys Ile Ser Thr Asp Gly Ile Asp Gly Ile His
        195                 200                 205

Leu Ser Ala Glu Thr Asn Ile Arg Leu Gly His Ala Ile Ala Asp Lys
    210                 215                 220

Val Ala Ala Leu Phe
225


<210> SEQ ID NO 665
<211> LENGTH: 220
<212> TYPE: PRT
<213> ORGANISM: Sinorhizobium meliloti

<400> SEQUENCE: 665

Met Glu Glu Thr Val Ala Arg Thr Val Leu Cys Phe Gly Asp Ser Asn
1               5                   10                  15

Thr His Gly Gln Val Pro Gly Arg Gly Pro Leu Asp Arg Tyr Arg Arg
            20                  25                  30

Glu Gln Arg Trp Gly Gly Val Leu Gln Gly Leu Leu Gly Pro Asn Trp
        35                  40                  45

Gln Val Ile Glu Glu Gly Leu Ser Gly Arg Thr Thr Val His Asp Asp
    50                  55                  60

Pro Ile Glu Gly Ser Leu Lys Asn Gly Arg Ile Tyr Leu Arg Pro Cys
65                  70                  75                  80

Leu Gln Ser His Ala Pro Leu Asp Leu Ile Ile Ile Met Leu Gly Thr
                85                  90                  95

Asn Asp Leu Lys Arg Arg Phe Asn Met Pro Pro Ser Glu Val Ala Met
            100                 105                 110

Gly Ile Gly Cys Leu Val His Asp Ile Arg Glu Leu Ser Pro Gly Arg
        115                 120                 125

Thr Gly Asn Asp Pro Glu Ile Met Ile Val Ala Pro Pro Pro Met Leu
    130                 135                 140

Glu Asp Leu Lys Glu Trp Glu Ser Ile Phe Ser Gly Ala Gln Glu Lys
145                 150                 155                 160

Ser Arg Lys Leu Ala Leu Glu Phe Glu Ile Met Ala Asp Ser Leu Glu
                165                 170                 175

Ala His Phe Phe Asp Ala Gly Thr Val Cys Gln Cys Ser Pro Ala Asp
            180                 185                 190

Gly Phe His Ile Asp Glu Asp Ala His Arg Leu Leu Gly Glu Ala Leu
        195                 200                 205

Ala Gln Glu Val Leu Ala Ile Gly Trp Pro Asp Ala
    210                 215                 220


<210> SEQ ID NO 666
<211> LENGTH: 216
```

<212> TYPE: PRT
<213> ORGANISM: Prosthecobacter dejongeii

<400> SEQUENCE: 666

Met Lys Thr Ile Leu Cys Phe Gly Asp Ser Asn Thr Trp Gly Tyr Asp
1               5                   10                  15

Pro Ala Ser Met Thr Ala Pro Phe Pro Arg Arg His Gly Pro Glu Val
            20                  25                  30

Arg Trp Thr Gly Val Leu Ala Lys Ala Leu Gly Ala Gly Phe Arg Val
        35                  40                  45

Ile Glu Glu Gly Gln Asn Gly Arg Thr Thr Val His Glu Asp Pro Leu
    50                  55                  60

Asn Ile Cys Arg Lys Gly Lys Asp Tyr Leu Pro Ala Cys Leu Glu Ser
65                  70                  75                  80

His Lys Pro Leu Asp Leu Val Ile Leu Met Leu Gly Thr Asn Asp Leu
                85                  90                  95

Lys Ser Thr Phe Asn Val Pro Pro Gly Glu Ile Ala Ala Gly Ala Gly
            100                 105                 110

Val Leu Gly Arg Met Ile Leu Ala Gly Asp Ala Gly Pro Glu Asn Arg
        115                 120                 125

Pro Pro Gln Leu Leu Leu Met Cys Pro Pro Lys Val Arg Asp Leu Ser
    130                 135                 140

Ala Met Pro Asp Leu Asp Ala Lys Ile Pro His Gly Ala Ala Arg Ser
145                 150                 155                 160

Ala Glu Phe Pro Arg His Tyr Lys Ala Gln Ala Val Ala Leu Lys Cys
                165                 170                 175

Glu Tyr Phe Asn Ser Gln Glu Ile Val Glu Thr Ser Pro Val Asp Gly
            180                 185                 190

Ile His Leu Glu Ala Ser Glu His Leu Lys Leu Gly Glu Ala Leu Ala
        195                 200                 205

Glu Lys Val Lys Val Leu Leu Gly
    210                 215

<210> SEQ ID NO 667
<211> LENGTH: 213
<212> TYPE: PRT
<213> ORGANISM: Sinorhizobium meliloti

<400> SEQUENCE: 667

Met Lys Thr Val Leu Cys Tyr Gly Asp Ser Leu Thr Trp Gly Tyr Asp
1               5                   10                  15

Ala Thr Gly Ser Gly Arg His Ala Leu Glu Asp Arg Trp Pro Ser Val
            20                  25                  30

Leu Gln Lys Ala Leu Gly Ser Asp Ala His Val Ile Ala Glu Gly Leu
        35                  40                  45

Asn Gly Arg Thr Thr Ala Tyr Asp Asp His Leu Ala Asp Cys Asp Arg
    50                  55                  60

Asn Gly Ala Arg Val Leu Pro Thr Val Leu His Thr His Ala Pro Leu
65                  70                  75                  80

Asp Leu Ile Val Phe Met Leu Gly Ser Asn Asp Met Lys Pro Ile Ile
                85                  90                  95

His Gly Thr Ala Phe Gly Ala Val Lys Gly Ile Glu Arg Leu Val Asn
            100                 105                 110

Leu Val Arg Arg His Asp Trp Pro Thr Glu Thr Glu Glu Gly Pro Glu
        115                 120                 125

-continued

```
Ile Leu Ile Val Ser Pro Pro Pro Leu Cys Glu Thr Ala Asn Ser Ala
    130                 135                 140

Phe Ala Ala Met Phe Ala Gly Gly Val Glu Gln Ser Ala Met Leu Ala
145                 150                 155                 160

Pro Leu Tyr Arg Asp Leu Ala Asp Glu Leu Asp Cys Gly Phe Phe Asp
                165                 170                 175

Gly Gly Ser Val Ala Arg Thr Thr Pro Ile Asp Gly Val His Leu Asp
            180                 185                 190

Ala Glu Asn Thr Arg Ala Val Gly Arg Gly Leu Glu Pro Val Val Arg
        195                 200                 205

Met Met Leu Gly Leu
    210


<210> SEQ ID NO 668
<211> LENGTH: 218
<212> TYPE: PRT
<213> ORGANISM: Sinorhizobium meliloti

<400> SEQUENCE: 668

Met Val Glu Lys Arg Ser Val Leu Cys Phe Gly Asp Ser Leu Thr Trp
1               5                   10                  15

Gly Trp Ile Pro Val Lys Glu Ser Ser Pro Thr Leu Arg Tyr Pro Tyr
            20                  25                  30

Glu Gln Arg Trp Thr Gly Ala Met Ala Ala Arg Leu Gly Asp Gly Tyr
        35                  40                  45

His Ile Ile Glu Glu Gly Leu Ser Ala Arg Thr Thr Ser Leu Asp Asp
    50                  55                  60

Pro Asn Asp Ala Arg Leu Asn Gly Ser Thr Tyr Leu Pro Met Ala Leu
65                  70                  75                  80

Ala Ser His Leu Pro Leu Asp Leu Val Ile Ile Met Leu Gly Thr Asn
                85                  90                  95

Asp Thr Lys Ser Tyr Phe His Arg Thr Pro Tyr Glu Ile Ala Asn Gly
            100                 105                 110

Met Gly Lys Leu Val Gly Gln Val Leu Thr Cys Ala Gly Gly Val Gly
        115                 120                 125

Thr Pro Tyr Pro Ala Pro Lys Val Leu Val Val Ala Pro Pro Pro Leu
    130                 135                 140

Ala Pro Met Pro Asp Pro Trp Phe Glu Gly Met Phe Gly Gly Gly Tyr
145                 150                 155                 160

Glu Lys Ser Lys Glu Leu Ser Gly Leu Tyr Lys Ala Leu Ala Asp Phe
                165                 170                 175

Met Lys Val Glu Phe Phe Ala Ala Gly Asp Cys Ile Ser Thr Asp Gly
            180                 185                 190

Ile Asp Gly Ile His Leu Ser Ala Glu Thr Asn Ile Arg Leu Gly His
        195                 200                 205

Ala Ile Ala Asp Lys Val Ala Ala Leu Phe
    210                 215


<210> SEQ ID NO 669
<211> LENGTH: 209
<212> TYPE: PRT
<213> ORGANISM: Agrobacterium tumefaciens

<400> SEQUENCE: 669

Met Lys Thr Val Leu Ala Phe Gly Asp Ser Leu Thr Trp Gly Ala Asp
1               5                   10                  15
```

```
Pro Ala Thr Gly Leu Arg His Pro Val Glu His Arg Trp Pro Asp Val
            20                  25                  30

Leu Glu Ala Glu Leu Ala Gly Lys Ala Lys Val His Pro Glu Gly Leu
        35                  40                  45

Gly Gly Arg Thr Thr Cys Tyr Asp Asp His Ala Gly Pro Ala Cys Arg
    50                  55                  60

Asn Gly Ala Arg Ala Leu Glu Val Ala Leu Ser Cys His Met Pro Leu
65                  70                  75                  80

Asp Leu Val Ile Ile Met Leu Gly Thr Asn Asp Ile Lys Pro Val His
                85                  90                  95

Gly Gly Arg Ala Glu Ala Ala Val Ser Gly Met Arg Arg Leu Ala Gln
            100                 105                 110

Ile Val Glu Thr Phe Ile Tyr Lys Pro Arg Glu Ala Val Pro Lys Leu
        115                 120                 125

Leu Ile Val Ala Pro Pro Pro Cys Val Ala Gly Pro Gly Gly Glu Pro
    130                 135                 140

Ala Gly Gly Arg Asp Ile Glu Gln Ser Met Arg Leu Ala Pro Leu Tyr
145                 150                 155                 160

Arg Lys Leu Ala Ala Glu Leu Gly His His Phe Phe Asp Ala Gly Ser
                165                 170                 175

Val Ala Ser Ala Ser Pro Val Asp Gly Val His Leu Asp Ala Ser Ala
            180                 185                 190

Thr Ala Ala Ile Gly Arg Ala Leu Ala Ala Pro Val Arg Asp Ile Leu
        195                 200                 205

Gly


<210> SEQ ID NO 670
<211> LENGTH: 220
<212> TYPE: PRT
<213> ORGANISM: Agrobacterium tumefaciens

<400> SEQUENCE: 670

Met Val Lys Ser Val Leu Cys Phe Gly Asp Ser Leu Thr Trp Gly Ser
1               5                   10                  15

Asn Ala Glu Thr Gly Gly Arg His Ser His Asp Asp Leu Trp Pro Ser
            20                  25                  30

Val Leu Gln Lys Ala Leu Gly Ser Asp Val His Val Ile Phe Thr His
        35                  40                  45

Glu Gly Leu Gly Gly Arg Thr Thr Ala Tyr Asp Asp His Thr Gly Asp
    50                  55                  60

Cys Asp Arg Asn Gly Ala Arg Leu Leu Pro Thr Leu Leu His Ser His
65                  70                  75                  80

Ala Pro Leu Asp Met Val Ile Ile Met Leu Gly Thr Asn Asp Met Lys
                85                  90                  95

Pro Ala Ile His Gly Ser Ala Ile Val Ala Phe Thr Met Lys Gly Val
            100                 105                 110

Glu Arg Leu Val Lys Leu Thr Arg Asn His Val Trp Gln Val Ser Asp
        115                 120                 125

Trp Glu Ala Pro Asp Val Leu Ile Val Ala Pro Pro Gln Leu Cys Glu
    130                 135                 140

Thr Ala Asn Pro Phe Met Gly Ala Ile Phe Arg Asp Ala Ile Asp Glu
145                 150                 155                 160

Ser Ala Met Leu Ala Ser Val Phe Thr Tyr Arg Asp Leu Ala Asp Glu
                165                 170                 175
```

```
Leu Asp Cys Gly Phe Phe Asp Ala Gly Ser Val Ala Arg Thr Thr Pro
            180                 185                 190

Val Asp Gly Val His Leu Asp Ala Glu Asn Thr Arg Ala Ile Gly Arg
        195                 200                 205

Gly Leu Glu Pro Val Val Arg Met Met Leu Gly Leu
    210                 215                 220


<210> SEQ ID NO 671
<211> LENGTH: 223
<212> TYPE: PRT
<213> ORGANISM: Mesorhizobium loti

<400> SEQUENCE: 671

Met Ala Gly Gly Thr Arg Leu Asp Glu Cys Thr Gly Glu Arg Met Lys
1               5                   10                  15

Thr Val Leu Cys Tyr Gly Asp Ser Leu Thr Trp Gly Tyr Asn Ala Glu
            20                  25                  30

Gly Gly Arg His Ala Leu Glu Asp Arg Trp Pro Ser Val Leu Gln Ala
        35                  40                  45

Ser Leu Gly Gly Gly Val Gln Val Ile Ala Asp Gly Leu Asn Gly Arg
    50                  55                  60

Thr Thr Ala Phe Asp Asp His Leu Ala Gly Ala Asp Arg Asn Gly Ala
65                  70                  75                  80

Arg Leu Leu Pro Thr Ala Leu Thr Thr His Ala Pro Ile Asp Leu Ile
                85                  90                  95

Val Ile Met Leu Gly Ala Asn Asp Met Lys Pro Trp Ile His Gly Asn
            100                 105                 110

Pro Val Ala Ala Lys Gln Gly Ile Gln Arg Leu Ile Asp Ile Val Arg
        115                 120                 125

Gly His Asp Tyr Pro Phe Asp Trp Pro Ala Pro Gln Ile Leu Ile Val
    130                 135                 140

Ser Pro Pro Val Val Ser Arg Thr Glu Asn Ala Asp Phe Arg Glu Met
145                 150                 155                 160

Phe Ala Gly Gly Asp Glu Ala Ser Lys Gln Leu Ala Pro Gln Tyr Ala
                165                 170                 175

Ala Leu Ala Asp Glu Val Gly Cys Gly Phe Phe Asp Ala Gly Thr Val
            180                 185                 190

Ala Gln Thr Thr Pro Leu Asp Gly Val His Leu Asp Ala Glu Asn Thr
        195                 200                 205

Arg Asn Ile Gly Lys Ala Leu Thr Ser Val Val Arg Val Met Leu
    210                 215                 220


<210> SEQ ID NO 672
<211> LENGTH: 212
<212> TYPE: PRT
<213> ORGANISM: Artificial Sequence
<220> FEATURE:
<223> OTHER INFORMATION: S261_M2aA12 clone

<400> SEQUENCE: 672

Met Lys Asn Ile Leu Ala Phe Gly Asp Ser Leu Thr Trp Gly Phe Val
1               5                   10                  15

Ala Gly Gln Asp Ala Arg His Pro Phe Glu Thr Arg Trp Pro Asn Ala
            20                  25                  30

Leu Ala Ala Gly Leu Gly Gly Lys Ala Arg Val Ile Glu Glu Gly Gln
        35                  40                  45

Asn Gly Arg Thr Thr Val Phe Asp Asp Ala Ala Thr Phe Glu Ser Arg
```

```
    50                  55                  60

Asn Gly Ser Val Ala Leu Pro Leu Leu Leu Ile Ser His Gln Pro Leu
65                  70                  75                  80

Asp Leu Val Ile Ile Met Leu Gly Thr Asn Asp Ile Lys Phe Ala Ala
                85                  90                  95

Arg Cys Arg Ala Phe Asp Ala Ser Met Gly Met Glu Arg Leu Ile Gln
            100                 105                 110

Ile Val Arg Ser Ala Asn Tyr Met Lys Gly Tyr Lys Ile Pro Glu Ile
        115                 120                 125

Leu Ile Ile Ser Pro Pro Ser Leu Val Pro Thr Gln Asp Glu Trp Phe
    130                 135                 140

Asn Asp Leu Trp Gly His Ala Ile Ala Glu Ser Lys Leu Phe Ala Lys
145                 150                 155                 160

His Tyr Lys Arg Val Ala Glu Glu Leu Lys Val His Phe Phe Asp Ala
                165                 170                 175

Gly Thr Val Ala Val Ala Asp Lys Thr Asp Gly Gly His Leu Asp Ala
            180                 185                 190

Val Asn Thr Lys Ala Ile Gly Val Ala Leu Val Pro Val Val Lys Ser
        195                 200                 205

Ile Leu Ala Leu
    210


<210> SEQ ID NO 673
<211> LENGTH: 215
<212> TYPE: PRT
<213> ORGANISM: Artificial Sequence
<220> FEATURE:
<223> OTHER INFORMATION: M091_M4aE11 clone

<400> SEQUENCE: 673

Met Lys Thr Ile Leu Ala Tyr Gly Asp Ser Leu Thr Tyr Gly Ala Asn
1               5                   10                  15

Pro Ile Pro Gly Gly Pro Arg His Ala Tyr Glu Asp Arg Trp Pro Thr
            20                  25                  30

Ala Leu Glu Gln Gly Leu Gly Gly Lys Ala Arg Val Ile Ala Glu Gly
        35                  40                  45

Leu Gly Gly Arg Thr Thr Val His Asp Asp Trp Phe Ala Asn Ala Asp
    50                  55                  60

Arg Asn Gly Ala Arg Val Leu Pro Thr Leu Leu Glu Ser His Ser Pro
65                  70                  75                  80

Leu Asp Leu Ile Val Ile Met Leu Gly Thr Asn Asp Ile Lys Pro His
                85                  90                  95

His Gly Arg Thr Ala Gly Glu Ala Gly Arg Gly Met Ala Arg Leu Val
            100                 105                 110

Gln Ile Ile Arg Gly His Tyr Ala Gly Arg Met Gln Asp Glu Pro Gln
        115                 120                 125

Ile Ile Leu Val Ser Pro Pro Pro Ile Ile Leu Gly Asp Trp Ala Asp
    130                 135                 140

Met Met Asp His Phe Gly Pro His Glu Ala Ile Ala Thr Ser Val Asp
145                 150                 155                 160

Phe Ala Arg Glu Tyr Lys Lys Arg Ala Asp Glu Gln Lys Val His Phe
                165                 170                 175

Phe Asp Ala Gly Thr Val Ala Thr Thr Ser Lys Ala Asp Gly Ile His
            180                 185                 190

Leu Asp Pro Ala Asn Thr Arg Ala Ile Gly Ala Gly Leu Val Pro Leu
```

```
        195                 200                 205

Val Lys Gln Val Leu Gly Leu
    210                 215


<210> SEQ ID NO 674
<211> LENGTH: 224
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(26)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (45)..(47)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (65)..(66)
<223> OTHER INFORMATION: Xaa can be any naturally occurring amino acid
<220> FEATURE:
<221> NAME/KEY: misc_feature
<222> LOCATION: (68)..(70)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (102)..(103)
```

<223> OTHER INFORMATION: Xaa can be any naturally occurring amino acid
<220> FEATURE:
<221> NAME/KEY: misc_feature
<222> LOCATION: (105)..(106)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (112)..(114)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (125)..(127)
<223> OTHER INFORMATION: Xaa can be any naturally occurring amino acid
<220> FEATURE:
<221> NAME/KEY: misc_feature
<222> LOCATION: (130)..(134)
<223> OTHER INFORMATION: Xaa can be any naturally occurring amino acid
<220> FEATURE:
<221> NAME/KEY: misc_feature
<222> LOCATION: (136)..(138)
<223> OTHER INFORMATION: Xaa can be any naturally occurring amino acid
<220> FEATURE:
<221> NAME/KEY: misc_feature
<222> LOCATION: (148)..(149)
<223> OTHER INFORMATION: Xaa can be any naturally occurring amino acid
<220> FEATURE:
<221> NAME/KEY: misc_feature
<222> LOCATION: (151)..(153)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid
<220> FEATURE:
<221> NAME/KEY: misc_feature
<222> LOCATION: (161)..(163)
<223> OTHER INFORMATION: Xaa can be any naturally occurring amino acid
<220> FEATURE:
<221> NAME/KEY: misc_feature
<222> LOCATION: (165)..(165)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (173)..(174)
<223> OTHER INFORMATION: Xaa can be any naturally occurring amino acid
<220> FEATURE:
<221> NAME/KEY: misc_feature
<222> LOCATION: (184)..(185)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid

<400> SEQUENCE: 674

```
Met Lys Thr Val Leu Cys Phe Gly Asp Ser Leu Thr Trp Gly Tyr Xaa
1               5                   10                  15

Pro Xaa Xaa Gly Xaa Xaa Xaa Xaa Xaa Xaa Arg His Ala Xaa Glu Xaa
            20                  25                  30

Arg Trp Pro Xaa Val Leu Xaa Ala Xaa Leu Gly Gly Xaa Xaa Xaa Val
        35                  40                  45

Ile Glu Xaa Xaa Glu Gly Leu Xaa Gly Arg Thr Thr Ala His Asp Asp
    50                  55                  60

Xaa Xaa Ala Xaa Xaa Xaa Arg Asn Gly Ala Arg Xaa Leu Pro Thr Xaa
65                  70                  75                  80

Leu Xaa Ser His Ala Pro Leu Asp Leu Val Ile Ile Met Leu Gly Thr
                85                  90                  95

Asn Asp Met Lys Pro Xaa Xaa His Xaa Xaa Pro Xaa Glu Ala Ala Xaa
            100                 105                 110

Xaa Xaa Gly Met Xaa Arg Leu Val Xaa Ile Val Arg Xaa Xaa Xaa Tyr
        115                 120                 125

Gly Xaa Xaa Xaa Xaa Xaa Pro Xaa Xaa Xaa Ile Leu Ile Val Ser Pro
    130                 135                 140

Pro Pro Leu Xaa Xaa Thr Xaa Xaa Xaa Asp Phe Xaa Ala Met Phe Gly
145                 150                 155                 160

Xaa Xaa Xaa Gly Xaa Glu Xaa Ser Lys Xaa Leu Ala Xaa Xaa Tyr Lys
                165                 170                 175

Ala Leu Ala Asp Glu Leu Lys Xaa Xaa Phe Phe Asp Ala Gly Thr Val
            180                 185                 190

Ala Xaa Thr Ser Pro Val Asp Gly Ile His Leu Asp Ala Glu Asn Thr
        195                 200                 205

Arg Xaa Ile Gly Xaa Ala Leu Ala Xaa Val Val Arg Xaa Leu Leu Gly
    210                 215                 220
```

<210> SEQ ID NO 675
<211> LENGTH: 202
<212> TYPE: PRT
<213> ORGANISM: Mycobacterium parafortuitum

<400> SEQUENCE: 675

```
Leu Pro Ser Gly Ile Leu Cys Phe Gly Asp Ser Leu Thr Trp Gly Trp
1               5                   10                  15

Ile Pro Val Glu Glu Gly Val Pro Thr Glu Arg Phe Pro Arg Asp Val
            20                  25                  30

Arg Trp Thr Gly Val Leu Ala Asp Leu Leu Gly Asp Arg Tyr Glu Val
        35                  40                  45

Ile Glu Glu Gly Leu Ser Ala Arg Thr Thr Thr Ala Asp Asp Pro Ala
    50                  55                  60

Asp Pro Arg Leu Asn Gly Ser Gln Tyr Leu Pro Ser Cys Leu Ala Ser
65                  70                  75                  80

His Leu Pro Leu Asp Leu Val Ile Leu Met Leu Gly Ile Asn Asp Thr
```

```
                85                  90                  95

Lys Ala Asn Phe Gly Arg Thr Pro Phe Asp Ile Ala Thr Gly Met Gly
            100                 105                 110

Val Leu Ala Thr Gln Val Leu Thr Ser Ala Gly Gly Val Gly Thr Ser
        115                 120                 125

Tyr Pro Ala Pro Gln Val Leu Ile Val Ala Pro Pro Pro Leu Gly Glu
    130                 135                 140

Leu Pro His Pro Trp Phe Asp Leu Val Phe Ser Gly Gly Arg Glu Lys
145                 150                 155                 160

Thr Ala Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Thr His Phe Thr Arg Gly Glu Thr Ile
        195                 200


<210> SEQ ID NO 676
<211> LENGTH: 216
<212> TYPE: PRT
<213> ORGANISM: Mycobacterium gilvum

<400> SEQUENCE: 676

Gly Gly Arg Cys Val Ala Ser Cys Glu Val Gly Ala Val Ala Lys Arg
1               5                   10                  15

Ile Leu Cys Phe Gly Asp Ser Leu Thr Trp Gly Trp Ile Pro Val Glu
            20                  25                  30

Glu Gly Val Pro Thr Gln Arg Phe Pro Lys Arg Val Arg Trp Thr Gly
        35                  40                  45

Val Leu Ala Asp Glu Leu Gly Ala Gly Tyr Glu Val Val Glu Glu Gly
    50                  55                  60

Leu Ser Ala Arg Thr Thr Thr Ala Asp Asp Pro Thr Asp Pro Arg Leu
65                  70                  75                  80

Asn Gly Ser Asp Tyr Leu Pro Ala Cys Leu Ala Ser His Leu Pro Leu
                85                  90                  95

Asp Leu Val Ile Leu Met Leu Gly Thr Asn Asp Thr Lys Ala Asn Leu
            100                 105                 110

Asn Arg Thr Pro Val Asp Ile Ala Ser Gly Met Gly Val Leu Ala Thr
        115                 120                 125

Gln Val Leu Thr Ser Ala Gly Gly Val Gly Thr Ser Tyr Pro Ala Pro
    130                 135                 140

Gln Val Leu Ile Val Ala Pro Pro Pro Leu Ala Glu Met Pro His Pro
145                 150                 155                 160

Trp Phe Glu Leu Val Phe Asp Gly Gly Arg Glu Lys Thr Ala Gln Leu
                165                 170                 175

Ala Arg Val Tyr Ser Ala Leu Ala Ser Phe Met Lys Val Pro Phe Phe
            180                 185                 190

Asp Ala Gly Ser Val Ile Ser Thr Asp Gly Val Asp Gly Thr His Phe
        195                 200                 205

Thr Arg Gly Glu Thr Ile Asp Arg
    210                 215


<210> SEQ ID NO 677
<211> LENGTH: 203
<212> TYPE: PRT
<213> ORGANISM: Mesorhizobium parafortuitum
```

<400> SEQUENCE: 677

Met Ala Lys Arg Ile Leu Cys Phe Gly Asp Ser Leu Thr Trp Gly Trp
1 5 10 15

Ile Pro Val Glu Glu Gly Val Pro Thr Glu Arg Phe Pro Arg Asp Val
20 25 30

Arg Trp Thr Gly Val Leu Ala Asp Leu Leu Gly Asp Arg Tyr Glu Val
35 40 45

Ile Glu Glu Gly Leu Ser Ala Arg Thr Thr Thr Ala Glu Asp Pro Ala
50 55 60

Asp Pro Arg Leu Asn Gly Ser Gln Tyr Leu Pro Ser Cys Leu Ala Ser
65 70 75 80

His Leu Pro Leu Asp Leu Val Ile Leu Met Leu Gly Thr Asn Asp Thr
85 90 95

Lys Ala Asn Phe Gly Arg Thr Pro Phe Asp Ile Ala Thr Gly Met Gly
100 105 110

Val Leu Ala Thr Gln Val Leu Thr Ser Ala Gly Gly Val Gly Thr Ser
115 120 125

Tyr Pro Ala Pro Gln Val Leu Ile Val Ala Pro Pro Pro Leu Gly Glu
130 135 140

Leu Pro His Pro Trp Phe Asp Leu Val Phe Ser Gly Gly Arg Glu Lys
145 150 155 160

Thr Ala Glu Leu Ala Arg Val Tyr Ser Ala Leu Ala Ser Phe Met Lys
165 170 175

Val Pro Phe Phe Asp Ala Gly Ser Val Ile Ser Thr Asp Gly Val Asp
180 185 190

Gly Ile His Phe Thr Arg Gly Glu Gln Ser Thr
195 200

<210> SEQ ID NO 678
<211> LENGTH: 216
<212> TYPE: PRT
<213> ORGANISM: Mycobacterium smegmatis

<400> SEQUENCE: 678

Met Ala Lys Arg Ile Leu Cys Phe Gly Asp Ser Leu Thr Trp Gly Trp
1 5 10 15

Val Pro Val Glu Asp Gly Ala Pro Thr Glu Arg Phe Ala Pro Asp Val
20 25 30

Arg Trp Thr Gly Val Leu Ala Gln Gln Leu Gly Ala Asp Phe Glu Val
35 40 45

Ile Glu Glu Gly Leu Ser Ala Arg Thr Thr Asn Ile Asp Asp Pro Thr
50 55 60

Asp Pro Arg Leu Asn Gly Ala Ser Tyr Leu Pro Ser Cys Leu Ala Thr
65 70 75 80

His Leu Pro Leu Asp Leu Val Ile Ile Met Leu Gly Thr Asn Asp Thr
85 90 95

Lys Ala Tyr Phe Arg Arg Thr Pro Leu Asp Ile Ala Leu Gly Met Ser
100 105 110

Val Leu Val Thr Gln Val Leu Thr Ser Ala Gly Gly Val Gly Thr Thr
115 120 125

Tyr Pro Ala Pro Lys Val Leu Val Val Ser Pro Pro Pro Leu Ala Pro
130 135 140

Met Pro His Pro Trp Phe Gln Leu Ile Phe Glu Gly Gly Glu Gln Lys
145 150 155 160

```
Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu
    210                 215


<210> SEQ ID NO 679
<211> LENGTH: 213
<212> TYPE: PRT
<213> ORGANISM: Sinorhizobium meliloti

<400> SEQUENCE: 679

Met Lys Thr Val Leu Cys Tyr Gly Asp Ser Leu Thr Trp Gly Tyr Asp
1               5                   10                  15

Ala Thr Gly Ser Gly Arg His Ala Leu Glu Asp Arg Trp Pro Ser Val
            20                  25                  30

Leu Gln Lys Ala Leu Gly Ser Asp Ala His Val Ile Ala Glu Gly Leu
        35                  40                  45

Asn Gly Arg Thr Thr Ala Tyr Asp Asp His Leu Ala Asp Cys Asp Arg
    50                  55                  60

Asn Gly Ala Arg Val Leu Pro Thr Val Leu His Thr His Ala Pro Leu
65                  70                  75                  80

Asp Leu Ile Val Phe Met Leu Gly Ser Asn Asp Met Lys Pro Ile Ile
                85                  90                  95

His Gly Thr Ala Phe Gly Ala Val Lys Gly Ile Glu Arg Leu Val Asn
            100                 105                 110

Leu Val Arg Arg His Asp Trp Pro Thr Glu Thr Glu Glu Gly Pro Glu
        115                 120                 125

Ile Leu Ile Val Ser Pro Pro Pro Leu Cys Glu Thr Ala Asn Ser Ala
    130                 135                 140

Phe Ala Ala Met Phe Ala Gly Gly Val Glu Gln Ser Ala Met Leu Ala
145                 150                 155                 160

Pro Leu Tyr Arg Asp Leu Ala Asp Glu Leu Asp Cys Gly Phe Phe Asp
                165                 170                 175

Gly Gly Ser Val Ala Arg Thr Thr Pro Ile Asp Gly Val His Leu Asp
            180                 185                 190

Ala Glu Asn Thr Arg Ala Val Gly Arg Gly Leu Glu Pro Val Val Arg
        195                 200                 205

Met Met Leu Gly Leu
    210


<210> SEQ ID NO 680
<211> LENGTH: 209
<212> TYPE: PRT
<213> ORGANISM: Agrobacterium tumefaciens

<400> SEQUENCE: 680

Met Lys Thr Val Leu Ala Phe Gly Asp Ser Leu Thr Trp Gly Ala Asp
1               5                   10                  15

Pro Ala Thr Gly Leu Arg His Pro Val Glu His Arg Trp Pro Asp Val
            20                  25                  30

Leu Glu Ala Glu Leu Ala Gly Lys Ala Lys Val His Pro Glu Gly Leu
        35                  40                  45
```

Gly Gly Arg Thr Thr Cys Tyr Asp Asp His Ala Gly Pro Ala Cys Arg
50 55 60

Asn Gly Ala Arg Ala Leu Glu Val Ala Leu Ser Cys His Met Pro Leu
65 70 75 80

Asp Leu Val Ile Ile Met Leu Gly Thr Asn Asp Ile Lys Pro Val His
85 90 95

Gly Gly Arg Ala Glu Ala Ala Val Ser Gly Met Arg Arg Leu Ala Gln
100 105 110

Ile Val Glu Thr Phe Ile Tyr Lys Pro Arg Glu Ala Val Pro Lys Leu
115 120 125

Leu Ile Val Ala Pro Pro Pro Cys Val Ala Gly Pro Gly Gly Glu Pro
130 135 140

Ala Gly Gly Arg Asp Ile Glu Gln Ser Met Arg Leu Ala Pro Leu Tyr
145 150 155 160

Arg Lys Leu Ala Ala Glu Leu Gly His His Phe Phe Asp Ala Gly Ser
165 170 175

Val Ala Ser Ala Ser Pro Val Asp Gly Val His Leu Asp Ala Ser Ala
180 185 190

Thr Ala Ala Ile Gly Arg Ala Leu Ala Ala Pro Val Arg Asp Ile Leu
195 200 205

Gly

<210> SEQ ID NO 681
<211> LENGTH: 220
<212> TYPE: PRT
<213> ORGANISM: Agrobacterium tumefaciens

<400> SEQUENCE: 681

Met Val Lys Ser Val Leu Cys Phe Gly Asp Ser Leu Thr Trp Gly Ser
1 5 10 15

Asn Ala Glu Thr Gly Gly Arg His Ser His Asp Asp Leu Trp Pro Ser
20 25 30

Val Leu Gln Lys Ala Leu Gly Ser Asp Val His Val Ile Phe Thr His
35 40 45

Glu Gly Leu Gly Gly Arg Thr Thr Ala Tyr Asp Asp His Thr Gly Asp
50 55 60

Cys Asp Arg Asn Gly Ala Arg Leu Leu Pro Thr Leu Leu His Ser His
65 70 75 80

Ala Pro Leu Asp Met Val Ile Ile Met Leu Gly Thr Asn Asp Met Lys
85 90 95

Pro Ala Ile His Gly Ser Ala Ile Val Ala Phe Thr Met Lys Gly Val
100 105 110

Glu Arg Leu Val Lys Leu Thr Arg Asn His Val Trp Gln Val Ser Asp
115 120 125

Trp Glu Ala Pro Asp Val Leu Ile Val Ala Pro Pro Gln Leu Cys Glu
130 135 140

Thr Ala Asn Pro Phe Met Gly Ala Ile Phe Arg Asp Ala Ile Asp Glu
145 150 155 160

Ser Ala Met Leu Ala Ser Val Phe Thr Tyr Arg Asp Leu Ala Asp Glu
165 170 175

Leu Asp Cys Gly Phe Phe Asp Ala Gly Ser Val Ala Arg Thr Thr Pro
180 185 190

Val Asp Gly Val His Leu Asp Ala Glu Asn Thr Arg Ala Ile Gly Arg
195 200 205

Gly Leu Glu Pro Val Val Arg Met Met Leu Gly Leu
210 215 220

<210> SEQ ID NO 682
<211> LENGTH: 215
<212> TYPE: PRT
<213> ORGANISM: Artificial Sequence
<220> FEATURE:
<223> OTHER INFORMATION: M091_M4aE11 clone

<400> SEQUENCE: 682

Met Lys Thr Ile Leu Ala Tyr Gly Asp Ser Leu Thr Tyr Gly Ala Asn
1 5 10 15

Pro Ile Pro Gly Gly Pro Arg His Ala Tyr Glu Asp Arg Trp Pro Thr
20 25 30

Ala Leu Glu Gln Gly Leu Gly Gly Lys Ala Arg Val Ile Ala Glu Gly
35 40 45

Leu Gly Gly Arg Thr Thr Val His Asp Asp Trp Phe Ala Asn Ala Asp
50 55 60

Arg Asn Gly Ala Arg Val Leu Pro Thr Leu Leu Glu Ser His Ser Pro
65 70 75 80

Leu Asp Leu Ile Val Ile Met Leu Gly Thr Asn Asp Ile Lys Pro His
85 90 95

His Gly Arg Thr Ala Gly Glu Ala Gly Arg Gly Met Ala Arg Leu Val
100 105 110

Gln Ile Ile Arg Gly His Tyr Ala Gly Arg Met Gln Asp Glu Pro Gln
115 120 125

Ile Ile Leu Val Ser Pro Pro Pro Ile Ile Leu Gly Asp Trp Ala Asp
130 135 140

Met Met Asp His Phe Gly Pro His Glu Ala Ile Ala Thr Ser Val Asp
145 150 155 160

Phe Ala Arg Glu Tyr Lys Lys Arg Ala Asp Glu Gln Lys Val His Phe
165 170 175

Phe Asp Ala Gly Thr Val Ala Thr Thr Ser Lys Ala Asp Gly Ile His
180 185 190

Leu Asp Pro Ala Asn Thr Arg Ala Ile Gly Ala Gly Leu Val Pro Leu
195 200 205

Val Lys Gln Val Leu Gly Leu
210 215

<210> SEQ ID NO 683
<211> LENGTH: 223
<212> TYPE: PRT
<213> ORGANISM: Mesorhizobium loti

<400> SEQUENCE: 683

Met Ala Gly Gly Thr Arg Leu Asp Glu Cys Thr Gly Glu Arg Met Lys
1 5 10 15

Thr Val Leu Cys Tyr Gly Asp Ser Leu Thr Trp Gly Tyr Asn Ala Glu
20 25 30

Gly Gly Arg His Ala Leu Glu Asp Arg Trp Pro Ser Val Leu Gln Ala
35 40 45

Ser Leu Gly Gly Gly Val Gln Val Ile Ala Asp Gly Leu Asn Gly Arg
50 55 60

Thr Thr Ala Phe Asp Asp His Leu Ala Gly Ala Asp Arg Asn Gly Ala
65 70 75 80

Arg Leu Leu Pro Thr Ala Leu Thr Thr His Ala Pro Ile Asp Leu Ile

```
                85                  90                  95

Val Ile Met Leu Gly Ala Asn Asp Met Lys Pro Trp Ile His Gly Asn
            100                 105                 110

Pro Val Ala Ala Lys Gln Gly Ile Gln Arg Leu Ile Asp Ile Val Arg
        115                 120                 125

Gly His Asp Tyr Pro Phe Asp Trp Pro Ala Pro Gln Ile Leu Ile Val
    130                 135                 140

Ser Pro Pro Val Val Ser Arg Thr Glu Asn Ala Asp Phe Arg Glu Met
145                 150                 155                 160

Phe Ala Gly Gly Asp Glu Ala Ser Lys Gln Leu Ala Pro Gln Tyr Ala
                165                 170                 175

Ala Leu Ala Asp Glu Val Gly Cys Gly Phe Phe Asp Ala Gly Thr Val
            180                 185                 190

Ala Gln Thr Thr Pro Leu Asp Gly Val His Leu Asp Ala Glu Asn Thr
        195                 200                 205

Arg Asn Ile Gly Lys Ala Leu Thr Ser Val Val Arg Val Met Leu
    210                 215                 220


<210> SEQ ID NO 684
<211> LENGTH: 216
<212> TYPE: PRT
<213> ORGANISM: Prosthecobacter dejongeii

<400> SEQUENCE: 684

Met Lys Thr Ile Leu Cys Phe Gly Asp Ser Asn Thr Trp Gly Tyr Asp
1               5                   10                  15

Pro Ala Ser Met Thr Ala Pro Phe Pro Arg Arg His Gly Pro Glu Val
            20                  25                  30

Arg Trp Thr Gly Val Leu Ala Lys Ala Leu Gly Ala Gly Phe Arg Val
        35                  40                  45

Ile Glu Glu Gly Gln Asn Gly Arg Thr Thr Val His Glu Asp Pro Leu
    50                  55                  60

Asn Ile Cys Arg Lys Gly Lys Asp Tyr Leu Pro Ala Cys Leu Glu Ser
65                  70                  75                  80

His Lys Pro Leu Asp Leu Val Ile Leu Met Leu Gly Thr Asn Asp Leu
                85                  90                  95

Lys Ser Thr Phe Asn Val Pro Pro Gly Glu Ile Ala Ala Gly Ala Gly
            100                 105                 110

Val Leu Gly Arg Met Ile Leu Ala Gly Asp Ala Gly Pro Glu Asn Arg
        115                 120                 125

Pro Pro Gln Leu Leu Leu Met Cys Pro Pro Lys Val Arg Asp Leu Ser
    130                 135                 140

Ala Met Pro Asp Leu Asp Ala Lys Ile Pro His Gly Ala Ala Arg Ser
145                 150                 155                 160

Ala Glu Phe Pro Arg His Tyr Lys Ala Gln Ala Val Ala Leu Lys Cys
                165                 170                 175

Glu Tyr Phe Asn Ser Gln Glu Ile Val Glu Thr Ser Pro Val Asp Gly
            180                 185                 190

Ile His Leu Glu Ala Ser Glu His Leu Lys Leu Gly Glu Ala Leu Ala
        195                 200                 205

Glu Lys Val Lys Val Leu Leu Gly
    210                 215


<210> SEQ ID NO 685
<211> LENGTH: 220
```

<212> TYPE: PRT
<213> ORGANISM: Sinorhizobium meliloti

<400> SEQUENCE: 685

Met Glu Glu Thr Val Ala Arg Thr Val Leu Cys Phe Gly Asp Ser Asn
1 5 10 15

Thr His Gly Gln Val Pro Gly Arg Gly Pro Leu Asp Arg Tyr Arg Arg
20 25 30

Glu Gln Arg Trp Gly Gly Val Leu Gln Gly Leu Leu Gly Pro Asn Trp
35 40 45

Gln Val Ile Glu Glu Gly Leu Ser Gly Arg Thr Thr Val His Asp Asp
50 55 60

Pro Ile Glu Gly Ser Leu Lys Asn Gly Arg Ile Tyr Leu Arg Pro Cys
65 70 75 80

Leu Gln Ser His Ala Pro Leu Asp Leu Ile Ile Ile Met Leu Gly Thr
85 90 95

Asn Asp Leu Lys Arg Arg Phe Asn Met Pro Pro Ser Glu Val Ala Met
100 105 110

Gly Ile Gly Cys Leu Val His Asp Ile Arg Glu Leu Ser Pro Gly Arg
115 120 125

Thr Gly Asn Asp Pro Glu Ile Met Ile Val Ala Pro Pro Pro Met Leu
130 135 140

Glu Asp Leu Lys Glu Trp Glu Ser Ile Phe Ser Gly Ala Gln Glu Lys
145 150 155 160

Ser Arg Lys Leu Ala Leu Glu Phe Glu Ile Met Ala Asp Ser Leu Glu
165 170 175

Ala His Phe Phe Asp Ala Gly Thr Val Cys Gln Cys Ser Pro Ala Asp
180 185 190

Gly Phe His Ile Asp Glu Asp Ala His Arg Leu Leu Gly Glu Ala Leu
195 200 205

Ala Gln Glu Val Leu Ala Ile Gly Trp Pro Asp Ala
210 215 220

<210> SEQ ID NO 686
<211> LENGTH: 212
<212> TYPE: PRT
<213> ORGANISM: Artificial Sequence
<220> FEATURE:
<223> OTHER INFORMATION: S261_M2aA12 clone

<400> SEQUENCE: 686

Met Lys Asn Ile Leu Ala Phe Gly Asp Ser Leu Thr Trp Gly Phe Val
1 5 10 15

Ala Gly Gln Asp Ala Arg His Pro Phe Glu Thr Arg Trp Pro Asn Ala
20 25 30

Leu Ala Ala Gly Leu Gly Gly Lys Ala Arg Val Ile Glu Glu Gly Gln
35 40 45

Asn Gly Arg Thr Thr Val Phe Asp Asp Ala Ala Thr Phe Glu Ser Arg
50 55 60

Asn Gly Ser Val Ala Leu Pro Leu Leu Leu Ile Ser His Gln Pro Leu
65 70 75 80

Asp Leu Val Ile Ile Met Leu Gly Thr Asn Asp Ile Lys Phe Ala Ala
85 90 95

Arg Cys Arg Ala Phe Asp Ala Ser Met Gly Met Glu Arg Leu Ile Gln
100 105 110

Ile Val Arg Ser Ala Asn Tyr Met Lys Gly Tyr Lys Ile Pro Glu Ile

```
        115                 120                 125

Leu Ile Ile Ser Pro Pro Ser Leu Val Pro Thr Gln Asp Glu Trp Phe
    130                 135                 140

Asn Asp Leu Trp Gly His Ala Ile Ala Glu Ser Lys Leu Phe Ala Lys
145                 150                 155                 160

His Tyr Lys Arg Val Ala Glu Glu Leu Lys Val His Phe Phe Asp Ala
                165                 170                 175

Gly Thr Val Ala Val Ala Asp Lys Thr Asp Gly Gly His Leu Asp Ala
            180                 185                 190

Val Asn Thr Lys Ala Ile Gly Val Ala Leu Val Pro Val Val Lys Ser
        195                 200                 205

Ile Leu Ala Leu
    210


<210> SEQ ID NO 687
<211> LENGTH: 229
<212> TYPE: PRT
<213> ORGANISM: Sinorhizobium meliloti

<400> SEQUENCE: 687

Met Thr Ile Asn Ser His Ser Trp Arg Thr Leu Met Val Glu Lys Arg
1               5                   10                  15

Ser Val Leu Cys Phe Gly Asp Ser Leu Thr Trp Gly Trp Ile Pro Val
            20                  25                  30

Lys Glu Ser Ser Pro Thr Leu Arg Tyr Pro Tyr Glu Gln Arg Trp Thr
        35                  40                  45

Gly Ala Met Ala Ala Arg Leu Gly Asp Gly Tyr His Ile Ile Glu Glu
    50                  55                  60

Gly Leu Ser Ala Arg Thr Thr Ser Leu Asp Asp Pro Asn Asp Ala Arg
65                  70                  75                  80

Leu Asn Gly Ser Thr Tyr Leu Pro Met Ala Leu Ala Ser His Leu Pro
                85                  90                  95

Leu Asp Leu Val Ile Ile Met Leu Gly Thr Asn Asp Thr Lys Ser Tyr
            100                 105                 110

Phe His Arg Thr Pro Tyr Glu Ile Ala Asn Gly Met Gly Lys Leu Val
        115                 120                 125

Gly Gln Val Leu Thr Cys Ala Gly Gly Val Gly Thr Pro Tyr Pro Ala
    130                 135                 140

Pro Lys Val Leu Val Val Ala Pro Pro Pro Leu Ala Pro Met Pro Asp
145                 150                 155                 160

Pro Trp Phe Glu Gly Met Phe Gly Gly Gly Tyr Glu Lys Ser Lys Glu
                165                 170                 175

Leu Ser Gly Leu Tyr Lys Ala Leu Ala Asp Phe Met Lys Val Glu Phe
            180                 185                 190

Phe Ala Ala Gly Asp Cys Ile Ser Thr Asp Gly Ile Asp Gly Ile His
        195                 200                 205

Leu Ser Ala Glu Thr Asn Ile Arg Leu Gly His Ala Ile Ala Asp Lys
    210                 215                 220

Val Ala Ala Leu Phe
225


<210> SEQ ID NO 688
<211> LENGTH: 212
<212> TYPE: PRT
<213> ORGANISM: Mesorhizobium loti
```

<400> SEQUENCE: 688

Met Lys Thr Ile Leu Cys Tyr Gly Asp Ser Leu Thr Trp Gly Tyr Asp
1               5                   10                  15

Ala Val Gly Pro Ser Arg His Ala Tyr Glu Asp Arg Trp Pro Ser Val
            20                  25                  30

Leu Gln Gly Arg Leu Gly Ser Ser Ala Arg Val Ile Ala Glu Gly Leu
        35                  40                  45

Cys Gly Arg Thr Thr Ala Phe Asp Asp Trp Val Ala Gly Ala Asp Arg
    50                  55                  60

Asn Gly Ala Arg Ile Leu Pro Thr Leu Leu Ala Thr His Ser Pro Leu
65                  70                  75                  80

Asp Leu Val Ile Val Met Leu Gly Thr Asn Asp Met Lys Ser Phe Val
                85                  90                  95

Cys Gly Arg Ala Ile Gly Ala Lys Gln Gly Met Glu Arg Ile Val Gln
            100                 105                 110

Ile Ile Arg Gly Gln Pro Tyr Ser Phe Asn Tyr Lys Val Pro Ser Ile
        115                 120                 125

Leu Leu Val Ala Pro Pro Pro Leu Cys Ala Thr Glu Asn Ser Asp Phe
    130                 135                 140

Ala Glu Ile Phe Glu Gly Gly Met Ala Glu Ser Gln Lys Leu Ala Pro
145                 150                 155                 160

Leu Tyr Ala Ala Leu Ala Gln Gln Thr Gly Cys Ala Phe Phe Asp Ala
                165                 170                 175

Gly Thr Val Ala Arg Thr Thr Pro Leu Asp Gly Ile His Leu Asp Ala
            180                 185                 190

Glu Asn Thr Arg Ala Ile Gly Ala Gly Leu Glu Pro Val Val Arg Gln
        195                 200                 205

Ala Leu Gly Leu
    210

<210> SEQ ID NO 689
<211> LENGTH: 216
<212> TYPE: PRT
<213> ORGANISM: Burkholderia cepacia

<400> SEQUENCE: 689

Met Thr Met Thr Gln Lys Thr Val Leu Cys Tyr Gly Asp Ser Asn Thr
1               5                   10                  15

His Gly Thr Arg Pro Met Thr His Ala Gly Gly Leu Gly Arg Phe Ala
            20                  25                  30

Arg Glu Glu Arg Trp Thr Gly Val Leu Ala Gln Thr Leu Gly Ala Ser
        35                  40                  45

Trp Arg Val Ile Glu Glu Gly Leu Pro Ala Arg Thr Thr Val His Asp
    50                  55                  60

Asp Pro Ile Glu Gly Arg His Lys Asn Gly Leu Ser Tyr Leu Arg Ala
65                  70                  75                  80

Cys Val Glu Ser His Leu Pro Val Asp Val Val Val Leu Met Leu Gly
                85                  90                  95

Thr Asn Asp Leu Lys Thr Arg Phe Ser Val Thr Pro Ala Asp Ile Ala
            100                 105                 110

Thr Ser Val Gly Val Leu Leu Ala Lys Ile Ala Ala Cys Gly Ala Gly
        115                 120                 125

Pro Ser Gly Ala Ser Pro Lys Leu Val Leu Met Ala Pro Ala Pro Ile
    130                 135                 140

Val Glu Val Gly Phe Leu Gly Glu Ile Phe Ala Gly Gly Ala Ala Lys
145 150 155 160

Ser Arg Gln Leu Ala Lys Arg Tyr Glu Gln Val Ala Ser Asp Ala Gly
165 170 175

Ala His Phe Leu Asp Ala Gly Ala Ile Val Glu Val Ser Pro Val Asp
180 185 190

Gly Val His Phe Ala Ala Asp Gln His Arg Val Leu Gly Gln Arg Val
195 200 205

Ala Ala Leu Leu Gln Gln Ile Ala
210 215

<210> SEQ ID NO 690
<211> LENGTH: 222
<212> TYPE: PRT
<213> ORGANISM: Agrobacterium tumefaciens

<400> SEQUENCE: 690

Met Ile Cys His Lys Gly Gly Glu Glu Met Arg Ser Val Leu Cys Tyr
1 5 10 15

Gly Asp Ser Asn Thr His Gly Gln Ile Pro Gly Gly Ser Pro Leu Asp
20 25 30

Arg Tyr Gly Pro Asn Glu Arg Trp Pro Gly Val Leu Arg Arg Glu Leu
35 40 45

Gly Ser Gln Trp Tyr Val Ile Glu Glu Gly Leu Ser Gly Arg Thr Thr
50 55 60

Val Arg Asp Asp Pro Ile Glu Gly Thr Met Lys Asn Gly Arg Thr Tyr
65 70 75 80

Leu Arg Pro Cys Leu Met Ser His Ala Ile Leu Asp Leu Val Ile Ile
85 90 95

Met Leu Gly Thr Asn Asp Leu Lys Ala Arg Phe Gly Gln Pro Pro Ser
100 105 110

Glu Val Ala Met Gly Ile Gly Cys Leu Val Tyr Asp Ile Arg Glu Leu
115 120 125

Ala Pro Gly Pro Gly Gly Lys Pro Pro Glu Ile Met Val Val Ala Pro
130 135 140

Pro Pro Met Leu Asp Asp Ile Lys Glu Trp Glu Pro Ile Phe Ser Gly
145 150 155 160

Ala Gln Glu Lys Ser Arg Arg Leu Ala Leu Glu Phe Glu Ile Ile Ala
165 170 175

Asp Ser Leu Glu Val His Phe Phe Asp Ala Ala Thr Val Ala Ser Cys
180 185 190

Asp Pro Cys Asp Gly Phe His Ile Asn Arg Glu Ala His Glu Ala Leu
195 200 205

Gly Thr Ala Leu Ala Arg Glu Val Glu Ala Ile Gly Trp Arg
210 215 220

<210> SEQ ID NO 691
<211> LENGTH: 227
<212> TYPE: PRT
<213> ORGANISM: Agrobacterium tumefaciens

<400> SEQUENCE: 691

Met Ala Glu Ser Arg Ser Ile Leu Cys Phe Gly Asp Ser Leu Thr Trp
1 5 10 15

Gly Trp Ile Pro Val Pro Glu Ser Ser Pro Thr Leu Arg Tyr Pro Phe
20 25 30

-continued

```
Glu Gln Arg Trp Thr Gly Ala Met Ala Ala Ala Leu Gly Asp Gly Tyr
        35                  40                  45

Ser Ile Ile Glu Glu Gly Leu Ser Ala Arg Thr Thr Ser Val Glu Asp
    50                  55                  60

Pro Asn Asp Pro Arg Leu Asn Gly Ser Ala Tyr Leu Pro Met Ala Leu
65                  70                  75                  80

Ala Ser His Leu Pro Leu Asp Leu Val Ile Ile Leu Leu Gly Thr Asn
                85                  90                  95

Asp Thr Lys Ser Tyr Phe Arg Arg Thr Pro Tyr Glu Ile Ala Asn Gly
            100                 105                 110

Met Gly Lys Leu Ala Gly Gln Val Leu Thr Ser Ala Gly Gly Ile Gly
        115                 120                 125

Thr Pro Tyr Pro Ala Pro Lys Leu Leu Ile Val Ser Pro Pro Pro Leu
    130                 135                 140

Ala Pro Met Pro Asp Pro Trp Phe Glu Gly Met Phe Gly Gly Gly Tyr
145                 150                 155                 160

Glu Lys Ser Leu Glu Leu Ala Lys Gln Tyr Lys Ala Leu Ala Asn Phe
                165                 170                 175

Leu Lys Val Asp Phe Leu Asp Ala Gly Glu Phe Val Lys Thr Asp Gly
            180                 185                 190

Cys Asp Gly Ile His Phe Ser Ala Glu Thr Asn Ile Thr Leu Gly His
        195                 200                 205

Ala Ile Ala Ala Lys Val Glu Ala Ile Phe Ser Gln Glu Ala Lys Asn
    210                 215                 220

Ala Ala Ala
225
```

<210> SEQ ID NO 692
<211> LENGTH: 213
<212> TYPE: PRT
<213> ORGANISM: Ralstonia solanacearum

<400> SEQUENCE: 692

```
Met Gln Gln Ile Leu Leu Tyr Ser Asp Ser Leu Ser Trp Gly Ile Ile
1               5                   10                  15

Pro Gly Thr Arg Arg Arg Leu Pro Phe Ala Ala Arg Trp Ala Gly Val
            20                  25                  30

Met Glu His Ala Leu Gln Ala Gln Gly His Ala Val Arg Ile Val Glu
        35                  40                  45

Asp Cys Leu Asn Gly Arg Thr Thr Val Leu Asp Asp Pro Ala Arg Pro
    50                  55                  60

Gly Arg Asn Gly Leu Gln Gly Leu Ala Gln Arg Ile Glu Ala His Ala
65                  70                  75                  80

Pro Leu Ala Leu Val Ile Leu Met Leu Gly Thr Asn Asp Phe Gln Ala
                85                  90                  95

Ile Phe Arg His Thr Ala Gln Asp Ala Ala Gln Gly Val Ala Gln Leu
            100                 105                 110

Val Arg Ala Ile Arg Gln Ala Pro Ile Glu Pro Gly Met Pro Val Pro
        115                 120                 125

Pro Val Leu Ile Val Val Pro Pro Ala Ile Thr Ala Pro Ala Gly Ala
    130                 135                 140

Met Ala Asp Lys Phe Ala Asp Ala Gln Pro Lys Cys Ala Gly Leu Ala
145                 150                 155                 160

Gln Ala Tyr Arg Ala Thr Ala Gln Thr Leu Gly Cys His Val Phe Asp
                165                 170                 175
```

```
Ala Asn Ser Val Thr Pro Ala Ser Arg Val Asp Gly Ile His Leu Asp
            180                 185                 190

Ala Asp Gln His Ala Gln Leu Gly Arg Ala Met Ala Gln Val Val Gly
        195                 200                 205

Thr Leu Leu Ala Gln
    210
```

<210> SEQ ID NO 693
<211> LENGTH: 225
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (19)..(22)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (51)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(71)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (105)..(106)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (122)..(123)
<223> OTHER INFORMATION: Xaa can be any naturally occurring amino acid
<220> FEATURE:
<221> NAME/KEY: misc_feature
<222> LOCATION: (126)..(128)
<223> OTHER INFORMATION: Xaa can be any naturally occurring amino acid
<220> FEATURE:
<221> NAME/KEY: misc_feature
<222> LOCATION: (130)..(132)
<223> OTHER INFORMATION: Xaa can be any naturally occurring amino acid
<220> FEATURE:
<221> NAME/KEY: misc_feature
<222> LOCATION: (134)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (152)..(155)
<223> OTHER INFORMATION: Xaa can be any naturally occurring amino acid
<220> FEATURE:
<221> NAME/KEY: misc_feature
<222> LOCATION: (158)..(161)
<223> OTHER INFORMATION: Xaa can be any naturally occurring amino acid
<220> FEATURE:
<221> NAME/KEY: misc_feature
<222> LOCATION: (167)..(168)
<223> OTHER INFORMATION: Xaa can be any naturally occurring amino acid
<220> FEATURE:
<221> NAME/KEY: misc_feature
<222> LOCATION: (171)..(172)
<223> OTHER INFORMATION: Xaa can be any naturally occurring amino acid
<220> FEATURE:
<221> NAME/KEY: misc_feature
<222> LOCATION: (175)..(176)
<223> OTHER INFORMATION: Xaa can be any naturally occurring amino acid
<220> FEATURE:
<221> NAME/KEY: misc_feature
<222> LOCATION: (182)..(183)
<223> OTHER INFORMATION: Xaa can be any naturally occurring amino acid
<220> FEATURE:

<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (195)..(196)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (219)..(220)
<223> OTHER INFORMATION: Xaa can be any naturally occurring amino acid
<220> FEATURE:
<221> NAME/KEY: misc_feature
<222> LOCATION: (223)..(223)
<223> OTHER INFORMATION: Xaa can be any naturally occurring amino acid

<400> SEQUENCE: 693

```
Met Lys Thr Ile Leu Cys Phe Gly Asp Ser Leu Thr Trp Gly Trp Ile
1               5                   10                  15

Pro Val Xaa Xaa Xaa Xaa Pro Xaa Xaa Arg Arg Xaa Xaa Xaa Glu Xaa
            20                  25                  30

Arg Trp Xaa Gly Val Leu Ala Xaa Xaa Leu Gly Ala Xaa Tyr Xaa Val
        35                  40                  45

Ile Glu Xaa Xaa Xaa Glu Gly Leu Xaa Gly Arg Thr Thr Xaa Xaa Asp
    50                  55                  60

Asp Pro Xaa Asp Xaa Xaa Xaa Arg Asn Gly Ala Xaa Tyr Leu Pro Xaa
65                  70                  75                  80

Xaa Leu Xaa Ser His Xaa Pro Leu Asp Leu Val Ile Ile Met Leu Gly
                85                  90                  95

Thr Asn Asp Leu Lys Ala Xaa Phe Xaa Xaa Thr Pro Xaa Asp Xaa Xaa
            100                 105                 110

Ile Ala Xaa Gly Met Gly Arg Leu Val Xaa Xaa Val Arg Xaa Xaa Xaa
        115                 120                 125

Gly Xaa Xaa Xaa Gly Xaa Xaa Tyr Xaa Ala Pro Xaa Ile Leu Ile Val
    130                 135                 140

Ala Pro Pro Pro Leu Xaa Glu Xaa Xaa Xaa Xaa Trp Phe Xaa Xaa Xaa
145                 150                 155                 160

Xaa Ile Phe Gly Gly Ala Xaa Xaa Lys Ser Xaa Xaa Leu Ala Xaa Xaa
                165                 170                 175

Tyr Lys Ala Leu Ala Xaa Xaa Leu Lys Val Xaa Phe Phe Asp Ala Gly
            180                 185                 190

Ser Val Xaa Xaa Thr Ser Pro Val Asp Gly Ile His Leu Asp Ala Glu
        195                 200                 205

Asn Thr Arg Xaa Leu Gly Xaa Ala Leu Ala Xaa Xaa Val Arg Xaa Ile
    210                 215                 220

Leu
225
```

<210> SEQ ID NO 694
<211> LENGTH: 215
<212> TYPE: PRT
<213> ORGANISM: Artificial Sequence
<220> FEATURE:
<223> OTHER INFORMATION: consensus

<400> SEQUENCE: 694

```
Lys Thr Ile Leu Cys Phe Gly Asp Ser Leu Thr Trp Gly Trp Ile Pro
1               5                   10                  15

Val Glu Asp Gly Ala Pro Thr Glu Arg Arg Ala Pro Glu Val Arg Trp
            20                  25                  30

Thr Gly Val Leu Ala Gln Gln Leu Gly Ala Asp Tyr Glu Val Ile Glu
        35                  40                  45

Glu Gly Leu Ser Gly Arg Thr Thr Asn Ile Asp Asp Pro Thr Asp Pro
    50                  55                  60

Arg Leu Arg Asn Gly Ala Ser Tyr Leu Pro Ser Cys Leu Ala Ser His
65                  70                  75                  80

Leu Pro Leu Asp Leu Val Ile Ile Met Leu Gly Thr Asn Asp Leu Lys
                85                  90                  95

Ala Tyr Phe Arg Arg Thr Pro Leu Asp Ile Ala Leu Gly Met Gly Arg
            100                 105                 110

Leu Val Thr Gln Val Arg Thr Ser Ala Gly Gly Val Gly Thr Thr Tyr
        115                 120                 125

Pro Ala Pro Lys Ile Leu Ile Val Ala Pro Pro Pro Leu Ala Glu Met
    130                 135                 140

Pro His Pro Trp Phe Gln Leu Ile Phe Gly Gly Ala Glu Gln Lys Ser
145                 150                 155                 160

Thr Glu Leu Ala Arg Val Tyr Lys Ala Leu Ala Ser Phe Leu Lys Val
                165                 170                 175

Pro Phe Phe Asp Ala Gly Ser Val Ile Ser Thr Ser Pro Val Asp Gly
            180                 185                 190

Ile His Leu Asp Ala Glu Asn Thr Arg Asp Leu Gly Val Ala Leu Ala
        195                 200                 205

Glu Gln Val Arg Ser Ile Leu
    210                 215
```

<210> SEQ ID NO 695
<211> LENGTH: 216
<212> TYPE: PRT
<213> ORGANISM: Mycobacterium smegmatis

<400> SEQUENCE: 695

```
Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Ser Ala Arg Thr Thr Asn Ile Asp Asp Pro Thr
    50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Val Ser Pro Pro Pro Leu Ala Pro
    130                 135                 140
```

```
Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu
    210                 215


<210> SEQ ID NO 696
<211> LENGTH: 217
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (113)..(114)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (190)..(191)
<223> OTHER INFORMATION: Xaa can be any naturally occurring amino acid
<220> FEATURE:
<221> NAME/KEY: misc_feature
<222> LOCATION: (197)..(200)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid

<400> SEQUENCE: 696

Xaa Xaa Lys Xaa Ile Leu Cys Phe Gly Asp Ser Leu Thr Trp Gly Trp
1               5                   10                  15
```

```
Ile Pro Val Glu Asp Gly Ala Pro Thr Glu Arg Xaa Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Ser Ala Arg Thr Thr Asn Ile Asp Asp Pro Thr
    50                  55                  60

Asp Pro Arg Leu Xaa Xaa Gly Ala Ser Tyr Leu Pro Ser Cys Leu Ala
65                  70                  75                  80

Ser His Leu Pro Leu Asp Leu Val Ile Ile Met Leu Gly Thr Asn Asp
                85                  90                  95

Xaa Lys Ala Tyr Phe Arg Arg Thr Pro Leu Asp Ile Ala Leu Gly Met
            100                 105                 110

Xaa Xaa Leu Val Thr Gln Val Xaa Thr Ser Ala Gly Gly Val Gly Thr
        115                 120                 125

Thr Tyr Pro Ala Pro Lys Ile Leu Ile Val Ala Pro Pro Pro Leu Ala
    130                 135                 140

Xaa Met Pro His Pro Trp Phe Gln Leu Ile Phe Xaa Gly Ala Glu Gln
145                 150                 155                 160

Lys Ser Thr Glu Leu Ala Arg Val Tyr Xaa Ala Leu Ala Ser Phe Leu
                165                 170                 175

Lys Val Pro Phe Phe Asp Ala Gly Ser Val Ile Ser Thr Xaa Xaa Val
            180                 185                 190

Asp Gly Ile His Xaa Xaa Xaa Xaa Asn Xaa Arg Asp Leu Gly Val Ala
        195                 200                 205

Leu Ala Glu Gln Val Arg Ser Ile Leu
    210                 215


<210> SEQ ID NO 697
<211> LENGTH: 214
<212> TYPE: PRT
<213> ORGANISM: Rhodopirellula baltica

<400> SEQUENCE: 697

Met His Ser Ile Leu Ile Tyr Gly Asp Ser Leu Ser Trp Gly Ile Ile
1               5                   10                  15

Pro Gly Thr Arg Arg Arg Phe Ala Phe His Gln Arg Trp Pro Gly Val
            20                  25                  30

Met Glu Ile Glu Leu Arg Gln Thr Gly Ile Asp Ala Arg Val Ile Glu
        35                  40                  45

Asp Cys Leu Asn Gly Arg Arg Thr Val Leu Glu Asp Pro Ile Lys Pro
    50                  55                  60

Gly Arg Asn Gly Leu Asp Gly Leu Gln Gln Arg Ile Glu Ile Asn Ser
65                  70                  75                  80

Pro Leu Ser Leu Val Val Leu Phe Leu Gly Thr Asn Asp Phe Gln Ser
                85                  90                  95

Val His Glu Phe His Ala Glu Gln Ser Ala Gln Gly Leu Ala Leu Leu
            100                 105                 110

Val Asp Ala Ile Arg Arg Ser Pro Phe Glu Pro Gly Met Pro Thr Pro
        115                 120                 125

Lys Ile Leu Leu Val Ala Pro Pro Thr Val His His Pro Lys Leu Asp
    130                 135                 140

Met Ala Ala Lys Phe Gln Asn Ala Glu Thr Lys Ser Thr Gly Leu Ala
145                 150                 155                 160

Asp Ala Ile Arg Lys Val Ser Thr Glu His Ser Cys Glu Phe Phe Asp
```

```
                165                 170                 175

Ala Ala Thr Val Thr Thr Thr Ser Val Val Asp Gly Val His Leu Asp
            180                 185                 190

Gln Glu Gln His Gln Ala Leu Gly Thr Ala Leu Ala Ser Thr Ile Ala
        195                 200                 205

Glu Ile Leu Ala Asp Cys
    210


<210> SEQ ID NO 698
<211> LENGTH: 222
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(26)
<223> OTHER INFORMATION: Xaa can be any naturally occurring amino acid
<220> FEATURE:
<221> NAME/KEY: misc_feature
<222> LOCATION: (30)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (39)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
```

<221> NAME/KEY: misc_feature
<222> LOCATION: (70)..(71)
<223> OTHER INFORMATION: Xaa can be any naturally occurring amino acid
<220> FEATURE:
<221> NAME/KEY: misc_feature
<222> LOCATION: (74)..(76)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (82)..(85)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (99)..(100)
<223> OTHER INFORMATION: Xaa can be any naturally occurring amino acid
<220> FEATURE:
<221> NAME/KEY: misc_feature
<222> LOCATION: (102)..(110)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (119)..(132)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (146)..(148)
<223> OTHER INFORMATION: Xaa can be any naturally occurring amino acid
<220> FEATURE:
<221> NAME/KEY: misc_feature
<222> LOCATION: (150)..(156)
<223> OTHER INFORMATION: Xaa can be any naturally occurring amino acid
<220> FEATURE:
<221> NAME/KEY: misc_feature
<222> LOCATION: (158)..(159)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (169)..(173)
<223> OTHER INFORMATION: Xaa can be any naturally occurring amino acid
<220> FEATURE:
<221> NAME/KEY: misc_feature
<222> LOCATION: (177)..(181)
<223> OTHER INFORMATION: Xaa can be any naturally occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (192)..(193)
<223> OTHER INFORMATION: Xaa can be any naturally occurring amino acid
<220> FEATURE:
<221> NAME/KEY: misc_feature
<222> LOCATION: (199)..(202)
<223> OTHER INFORMATION: Xaa can be any naturally occurring amino acid
<220> FEATURE:
<221> NAME/KEY: misc_feature
<222> LOCATION: (204)..(206)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (213)..(214)
<223> OTHER INFORMATION: Xaa can be any naturally occurring amino acid
<220> FEATURE:
<221> NAME/KEY: misc_feature
<222> LOCATION: (216)..(217)
<223> OTHER INFORMATION: Xaa can be any naturally occurring amino acid
<220> FEATURE:
<221> NAME/KEY: misc_feature
<222> LOCATION: (220)..(222)
<223> OTHER INFORMATION: Xaa can be any naturally occurring amino acid

<400> SEQUENCE: 698

```
Xaa Xaa Xaa Xaa Ile Leu Xaa Phe Gly Asp Ser Leu Ser Trp Gly Xaa
1               5                   10                  15

Ile Pro Xaa Xaa Xaa Xaa Xaa Xaa Xaa Xaa Arg Phe Ala Xaa Xaa Xaa
            20                  25                  30

Arg Trp Xaa Gly Val Leu Xaa Xaa Xaa Xaa Xaa Gln Xaa Gly Xaa Asp
        35                  40                  45

Xaa Xaa Val Ile Glu Asp Xaa Leu Xaa Ala Arg Xaa Thr Xaa Ile Asp
    50                  55                  60

Asp Pro Xaa Xaa Pro Xaa Xaa Asn Gly Xaa Xaa Xaa Leu Xaa Xaa Xaa
65                  70                  75                  80

Ile Xaa Xaa Xaa Xaa Pro Leu Xaa Leu Val Ile Ile Xaa Leu Gly Thr
                85                  90                  95

Asn Asp Xaa Xaa Ala Xaa Xaa Xaa Xaa Xaa Xaa Xaa Xaa Xaa Ala Xaa
            100                 105                 110

Gly Leu Ala Leu Leu Val Xaa Xaa Xaa Xaa Xaa Xaa Xaa Xaa Xaa Xaa
        115                 120                 125

Xaa Xaa Xaa Xaa Pro Xaa Pro Lys Ile Leu Leu Val Ala Pro Pro Xaa
    130                 135                 140

Leu Xaa Xaa Xaa Pro Xaa Xaa Xaa Xaa Xaa Xaa Xaa Phe Xaa Xaa Ala
145                 150                 155                 160

Glu Xaa Lys Ser Thr Xaa Leu Ala Xaa Xaa Xaa Xaa Xaa Leu Ala Ser
                165                 170                 175

Xaa Xaa Xaa Xaa Xaa Phe Phe Asp Ala Ala Ser Val Xaa Ser Thr Xaa
            180                 185                 190

Xaa Val Asp Gly Ile His Xaa Xaa Xaa Xaa Asn Xaa Xaa Xaa Leu Gly
        195                 200                 205

Xaa Ala Leu Ala Xaa Xaa Ile Xaa Xaa Ile Leu Xaa Xaa Xaa
    210                 215                 220
```

<210> SEQ ID NO 699
<211> LENGTH: 230
<212> TYPE: PRT
<213> ORGANISM: Ralstonia eutropha

<400> SEQUENCE: 699

```
Met Pro Leu Thr Ala Pro Ser Glu Val Asp Pro Leu Gln Ile Leu Val
1               5                   10                  15

Tyr Ala Asp Ser Leu Ser Trp Gly Ile Val Pro Gly Thr Arg Arg Arg
            20                  25                  30

Leu Pro Phe Pro Val Arg Trp Pro Gly Arg Leu Glu Leu Gly Leu Asn
        35                  40                  45

Ala Asp Gly Gly Ala Pro Val Arg Ile Ile Glu Asp Cys Leu Asn Gly
    50                  55                  60

Arg Arg Thr Val Trp Asp Asp Pro Phe Lys Pro Gly Arg Asn Gly Leu
65                  70                  75                  80

Gln Gly Leu Ala Gln Arg Ile Glu Ile His Ser Pro Val Ala Leu Val
                85                  90                  95

Val Leu Met Leu Gly Asn Asn Asp Phe Gln Ser Met His Pro His Asn
            100                 105                 110

Ala Trp His Ala Ala Gln Gly Val Gly Ala Leu Val His Ala Ile Arg
        115                 120                 125

Thr Ala Pro Ile Glu Pro Gly Met Pro Val Pro Pro Ile Leu Val Val
    130                 135                 140

Val Pro Pro Pro Ile Arg Thr Pro Cys Gly Pro Leu Ala Pro Lys Phe
145                 150                 155                 160

Ala Gly Gly Glu His Lys Trp Ala Gly Leu Pro Glu Ala Leu Arg Glu
                165                 170                 175

Leu Cys Ala Thr Val Asp Cys Ser Leu Phe Asp Ala Gly Thr Val Ile
            180                 185                 190

Gln Ser Ser Ala Val Asp Gly Val His Leu Asp Ala Asp Ala His Val
        195                 200                 205

Ala Leu Gly Asp Ala Leu Gln Pro Val Val Arg Ala Leu Leu Ala Glu
    210                 215                 220

Ser Ser Gly His Pro Ser
225                 230
```

<210> SEQ ID NO 700
<211> LENGTH: 237
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (3)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(35)
<223> OTHER INFORMATION: Xaa can be any naturally occurring amino acid
<220> FEATURE:

<221> NAME/KEY: misc_feature
<222> LOCATION: (37)..(40)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (48)..(55)
<223> OTHER INFORMATION: Xaa can be any naturally occurring amino acid
<220> FEATURE:
<221> NAME/KEY: misc_feature
<222> LOCATION: (58)..(60)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(73)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid
<220> FEATURE:
<221> NAME/KEY: misc_feature
<222> LOCATION: (88)..(90)
<223> OTHER INFORMATION: Xaa can be any naturally occurring amino acid
<220> FEATURE:
<221> NAME/KEY: misc_feature
<222> LOCATION: (92)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (112)..(120)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid -continued
<220> FEATURE:
<221> NAME/KEY: misc_feature
<222> LOCATION: (125)..(126)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (139)..(142)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (151)..(151)
<223> OTHER INFORMATION: Xaa can be any naturally occurring amino acid
<220> FEATURE:
<221> NAME/KEY: misc_feature
<222> LOCATION: (156)..(158)
<223> OTHER INFORMATION: Xaa can be any naturally occurring amino acid
<220> FEATURE:
<221> NAME/KEY: misc_feature
<222> LOCATION: (160)..(166)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (174)..(176)
<223> OTHER INFORMATION: Xaa can be any naturally occurring amino acid
<220> FEATURE:
<221> NAME/KEY: misc_feature
<222> LOCATION: (178)..(183)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (189)..(192)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (209)..(216)
<223> OTHER INFORMATION: Xaa can be any naturally occurring amino acid
<220> FEATURE:
<221> NAME/KEY: misc_feature
<222> LOCATION: (219)..(219)

<223> OTHER INFORMATION: Xaa can be any naturally occurring amino acid
<220> FEATURE:
<221> NAME/KEY: misc_feature
<222> LOCATION: (222)..(224)
<223> OTHER INFORMATION: Xaa can be any naturally occurring amino acid
<220> FEATURE:
<221> NAME/KEY: misc_feature
<222> LOCATION: (230)..(237)
<223> OTHER INFORMATION: Xaa can be any naturally occurring amino acid

<400> SEQUENCE: 700

```
Xaa Xaa Xaa Xaa Xaa Xaa Xaa Xaa Xaa Xaa Xaa Xaa Xaa Ile Leu Xaa
1               5                   10                  15

Phe Ala Asp Ser Leu Ser Trp Gly Xaa Val Pro Xaa Xaa Xaa Xaa Xaa
            20                  25                  30

Xaa Xaa Xaa Arg Xaa Xaa Xaa Xaa Val Arg Trp Xaa Gly Xaa Leu Xaa
        35                  40                  45

Xaa Xaa Xaa Xaa Xaa Xaa Xaa Gly Ala Xaa Xaa Xaa Ile Ile Glu Asp
    50                  55                  60

Xaa Leu Xaa Ala Arg Xaa Thr Xaa Xaa Asp Asp Pro Xaa Xaa Pro Xaa
65                  70                  75                  80

Xaa Asn Gly Xaa Xaa Xaa Leu Xaa Xaa Xaa Ile Xaa Xaa His Xaa Pro
                85                  90                  95

Leu Xaa Leu Val Ile Ile Met Leu Gly Xaa Asn Asp Xaa Xaa Ala Xaa
            100                 105                 110

Xaa Xaa Xaa Xaa Xaa Xaa Xaa Xaa Ala Xaa Gly Met Xaa Xaa Leu Val
        115                 120                 125

Xaa Xaa Xaa Xaa Xaa Xaa Xaa Ala Xaa Ile Xaa Xaa Xaa Xaa Pro Xaa
    130                 135                 140

Pro Xaa Ile Leu Val Val Xaa Pro Pro Pro Ile Xaa Xaa Xaa Pro Xaa
145                 150                 155                 160

Xaa Xaa Xaa Xaa Xaa Xaa Phe Xaa Gly Gly Glu Xaa Lys Xaa Xaa Xaa
                165                 170                 175

Leu Xaa Xaa Xaa Xaa Xaa Xaa Leu Xaa Ala Xaa Met Xaa Xaa Xaa Xaa
            180                 185                 190

Phe Asp Ala Gly Ser Val Ile Xaa Ser Xaa Ala Val Asp Gly Ile His
        195                 200                 205

Xaa Xaa Xaa Xaa Xaa Xaa Xaa Xaa Leu Gly Xaa Ala Leu Xaa Xaa Xaa
    210                 215                 220

Val Arg Ala Leu Leu Xaa Xaa Xaa Xaa Xaa Xaa Xaa Xaa
225                 230                 235
```

<210> SEQ ID NO 701
<211> LENGTH: 189
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (1)..(44)
<223> OTHER INFORMATION: Xaa can be Ile or Val
<220> FEATURE:
<221> NAME/KEY: misc_feature
<222> LOCATION: (3)..(12)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Phe or Tyr
<220> FEATURE:
<221> NAME/KEY: misc_feature
<222> LOCATION: (5)..(5)

<223> OTHER INFORMATION: Xaa can be Gly or Ser
<220> FEATURE:
<221> NAME/KEY: misc_feature
<222> LOCATION: (8)..(8)
<223> OTHER INFORMATION: Xaa can be Asn or Leu
<220> FEATURE:
<221> NAME/KEY: misc_feature
<222> LOCATION: (9)..(9)
<223> OTHER INFORMATION: Xaa can be Thr or Ser
<220> FEATURE:
<221> NAME/KEY: misc_feature
<222> LOCATION: (10)..(10)
<223> OTHER INFORMATION: Xaa can be Trp, Tyr, or His
<220> FEATURE:
<221> NAME/KEY: misc_feature
<222> LOCATION: (14)..(134)
<223> OTHER INFORMATION: Xaa can be Ala or Pro
<220> FEATURE:
<221> NAME/KEY: misc_feature
<222> LOCATION: (29)..(29)
<223> OTHER INFORMATION: Xaa can be Arg or Leu
<220> FEATURE:
<221> NAME/KEY: misc_feature
<222> LOCATION: (45)..(45)
<223> OTHER INFORMATION: Xaa can be Ile, His, or Val
<220> FEATURE:
<221> NAME/KEY: misc_feature
<222> LOCATION: (47)..(47)
<223> OTHER INFORMATION: Xaa can be Asp or Glu
<220> FEATURE:
<221> NAME/KEY: misc_feature
<222> LOCATION: (48)..(48)
<223> OTHER INFORMATION: Xaa can be Cys or Gly
<220> FEATURE:
<221> NAME/KEY: misc_feature
<222> LOCATION: (49)..(49)
<223> OTHER INFORMATION: Xaa can be Leu or Gln
<220> FEATURE:
<221> NAME/KEY: misc_feature
<222> LOCATION: (51)..(51)
<223> OTHER INFORMATION: Xaa can be Gly or Ala
<220> FEATURE:
<221> NAME/KEY: misc_feature
<222> LOCATION: (57)..(57)
<223> OTHER INFORMATION: Xaa can be Asp or Glu
<220> FEATURE:
<221> NAME/KEY: misc_feature
<222> LOCATION: (79)..(79)
<223> OTHER INFORMATION: Xaa can be Ile or Pro
<220> FEATURE:
<221> NAME/KEY: misc_feature
<222> LOCATION: (80)..(80)
<223> OTHER INFORMATION: Xaa can be Ile, Leu, or Val
<220> FEATURE:
<221> NAME/KEY: misc_feature
<222> LOCATION: (81)..(81)
<223> OTHER INFORMATION: Xaa can be Ala or Asp
<220> FEATURE:
<221> NAME/KEY: misc_feature
<222> LOCATION: (85)..(85)
<223> OTHER INFORMATION: Xaa can be Leu or Met
<220> FEATURE:
<221> NAME/KEY: misc_feature
<222> LOCATION: (135)..(165)
<223> OTHER INFORMATION: Xaa can be any naturally occurring amino acid
<220> FEATURE:
<221> NAME/KEY: misc_feature
<222> LOCATION: (167)..(185)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid

<400> SEQUENCE: 701

```
Xaa Leu Xaa Xaa Xaa Asp Ser Xaa Xaa Xaa Gly Xaa Xaa Xaa Xaa Xaa
1               5                   10                  15
```

-continued

```
Xaa Xaa Xaa Xaa Xaa Xaa Xaa Xaa Xaa Xaa Xaa Xaa Xaa Trp Xaa Xaa
            20                  25                  30

Xaa Xaa Xaa Xaa Xaa Leu Xaa Xaa Xaa Xaa Xaa Xaa Xaa Xaa Xaa Xaa
        35                  40                  45

Xaa Xaa Xaa Arg Thr Thr Xaa Xaa Xaa Asp Xaa Xaa Xaa Xaa Xaa Xaa
    50                  55                  60

Xaa Gly Xaa Xaa Xaa Leu Xaa Xaa Xaa Xaa Xaa Xaa His Xaa Xaa Xaa
65                  70                  75                  80

Xaa Xaa Xaa Xaa Xaa Leu Gly Xaa Asn Asp Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Pro Xaa Xaa
        115                 120                 125

Xaa Xaa Xaa Xaa Pro Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Ala Xaa Xaa Xaa Xaa Xaa Xaa Xaa Xaa Xaa Xaa
                165                 170                 175

Xaa Xaa Xaa Xaa Xaa Xaa Xaa Xaa Xaa Asp Gly Xaa His
            180                 185


<210> SEQ ID NO 702
<211> LENGTH: 1380
<212> TYPE: DNA
<213> ORGANISM: Artificial Sequence
<220> FEATURE:
<223> OTHER INFORMATION: S279_M75bA2 clone

<400> SEQUENCE: 702

tgggcggttt cgcggagtcg agcagggaga gatgctcctg ggtcgtacga gttggtacgg     60

aggcatcgtt gaagatctca cgcctgcttg aatgcgcgcg gatatggaac ggaccggccg    120

cgctggcgat cggtgtcggc gtggggctgg cgagcctgag cccggtcgcg ctggcgacgc    180

cgccgcgggg caccgtgccg gtgttcaccc gatcggggac agcctgacgg acgagtattt    240

tgagccgttc ttccagtggg ggttctgcgg gaagtcgtgg gccgagattt tggtggagac    300

ggggcgggcg agcatgggcc cgacggcgca gcaggcgggg atcagcgagc cggagggatg    360

gtcggatccg cggaacacgg ggtatcagca caactgggcg cggtactcgt ggagctcctc    420

agacgcgctg accgaggagt cgccgggggc gacgctgagc gtgctgcttg gggcggagta    480

cgcggtggtg ttcattggga ccaacgactt caatccgtcg tggccggcgt atcagagcgt    540

gtatctgagc cagtggagcg acgagcagat cgacacgtac gtgaacgggg tggtgcagaa    600

catcgcgcag atggtggact cgctgaagtc ggtcggggcg aaggtggtgc ttgcgccgcc    660

ggtggatttt cagttcgcgg ggttcctgcg gaactcatgc ccggatccga tgctgcgcga    720

gcaggcgggt attctgacac ggaagtgcca cgaccgggtg cggtcgatgg cgcggcagaa    780

gcacgtggtg ttcgtggaca tgtggcggct gaaccgcgat ttgttcggca acgggttcgc    840

gatcagctac ggccttcgga acacggtgcg cgtgggggac tcggagatcg ggctgcaact    900

ggccgggctg acgggatcgg cggggctggt tccggacggg atccatccgc agcgggtggt    960

gcaggggatc tgggcgaatg cgttcatcgt gggtctgaac gcgcatgggg cgaacatcgc   1020

gcccatcggc gaggcggaga tgtgcgcgat ggggggggtc gtgtacgggg gaacggacac   1080
```

```
gctggcgaac ttcctgccgc cggtcgcggg ctacgtggag gacttccgca acgcggggga   1140

cttcgtgtgc acggcggact tcaaccatga ccttggcgtg acgccgacgg acatcttcgc   1200

gttcatcaac gcgtggttca tgaatgatcc ctcggcgcgg atgagcaacc cggagcacac   1260

gcagatcgag gacatcttcg tgtttctgaa tctgtggctg gtggggtgct gaggcagagt   1320

gggaaggggg tcagcccact tcgcgcgtct ggaagaggat gacggcgacg gagaggaaga   1380


<210> SEQ ID NO 703
<211> LENGTH: 457
<212> TYPE: PRT
<213> ORGANISM: Artificial Sequence
<220> FEATURE:
<223> OTHER INFORMATION: S248_M31bA11 clone

<400> SEQUENCE: 703

Gly Arg Phe Arg Gly Val Glu Gln Gly Glu Met Leu Leu Gly Arg Thr
1               5                   10                  15

Ser Trp Tyr Gly Gly Ile Val Glu Asp Leu Thr Pro Ala Met Arg Ala
            20                  25                  30

Asp Met Glu Arg Thr Gly Arg Ala Gly Asp Arg Cys Arg Arg Gly Ala
        35                  40                  45

Gly Glu Pro Glu Pro Gly Arg Ala Gly Asp Ala Ala Ala Gly His Arg
    50                  55                  60

Ala Gly Val His Pro Ile Gly Asp Ser Leu Thr Asp Glu Tyr Phe Glu
65                  70                  75                  80

Pro Phe Phe Gln Trp Gly Phe Cys Gly Lys Ser Trp Ala Glu Ile Leu
                85                  90                  95

Val Glu Thr Gly Arg Ala Ser Met Gly Pro Thr Ala Gln Gln Ala Gly
            100                 105                 110

Ile Ser Glu Pro Glu Gly Trp Ser Asp Pro Arg Asn Thr Gly Tyr Gln
        115                 120                 125

His Asn Trp Ala Arg Tyr Ser Trp Ser Ser Ser Asp Ala Leu Thr Glu
    130                 135                 140

Glu Ser Pro Gly Ala Thr Leu Ser Val Leu Leu Gly Ala Glu Tyr Ala
145                 150                 155                 160

Val Val Phe Ile Gly Thr Asn Asp Phe Asn Pro Ser Trp Pro Ala Tyr
                165                 170                 175

Gln Ser Val Tyr Leu Ser Gln Trp Ser Asp Glu Gln Ile Asp Thr Tyr
            180                 185                 190

Val Asn Gly Val Val Gln Asn Ile Ala Gln Met Val Asp Ser Leu Lys
        195                 200                 205

Ser Val Gly Ala Lys Val Val Leu Ala Pro Pro Val Asp Phe Gln Phe
    210                 215                 220

Ala Gly Phe Leu Arg Asn Ser Cys Pro Asp Pro Met Leu Arg Glu Gln
225                 230                 235                 240

Ala Gly Ile Leu Thr Arg Lys Cys His Asp Arg Val Arg Ser Met Ala
                245                 250                 255

Arg Gln Lys His Val Val Phe Val Asp Met Trp Arg Leu Asn Arg Asp
            260                 265                 270

Leu Phe Gly Asn Gly Phe Ala Ile Ser Tyr Gly Leu Arg Asn Thr Val
        275                 280                 285

Arg Val Gly Asp Ser Glu Ile Gly Leu Gln Leu Ala Gly Leu Thr Gly
    290                 295                 300

Ser Ala Gly Leu Val Pro Asp Gly Ile His Pro Gln Arg Val Val Gln
305                 310                 315                 320
```

```
Gly Ile Trp Ala Asn Ala Phe Ile Val Gly Leu Asn Ala His Gly Ala
                325                 330                 335

Asn Ile Ala Pro Ile Gly Glu Ala Glu Met Cys Ala Met Gly Gly Val
            340                 345                 350

Val Tyr Gly Gly Thr Asp Thr Leu Ala Asn Phe Leu Pro Pro Val Ala
        355                 360                 365

Gly Tyr Val Glu Asp Phe Arg Asn Ala Gly Asp Phe Val Cys Thr Ala
    370                 375                 380

Asp Phe Asn His Asp Leu Gly Val Thr Pro Thr Asp Ile Phe Ala Phe
385                 390                 395                 400

Ile Asn Ala Trp Phe Met Asn Asp Pro Ser Ala Arg Met Ser Asn Pro
                405                 410                 415

Glu His Thr Gln Ile Glu Asp Ile Phe Val Phe Leu Asn Leu Trp Leu
            420                 425                 430

Val Gly Cys Gly Arg Val Gly Arg Gly Ser Ala His Phe Ala Arg Leu
        435                 440                 445

Glu Glu Asp Asp Gly Asp Gly Glu Glu
    450                 455


<210> SEQ ID NO 704
<211> LENGTH: 4
<212> TYPE: PRT
<213> ORGANISM: Sinorhizobium meliloti

<400> SEQUENCE: 704

Gly Asp Ser Leu
1


<210> SEQ ID NO 705
<211> LENGTH: 4
<212> TYPE: PRT
<213> ORGANISM: Sinorhizobium meliloti

<400> SEQUENCE: 705

Ala Arg Thr Thr
1


<210> SEQ ID NO 706
<211> LENGTH: 4
<212> TYPE: PRT
<213> ORGANISM: Sinorhizobium meliloti

<400> SEQUENCE: 706

Gly Thr Asn Asp
1


<210> SEQ ID NO 707
<211> LENGTH: 4
<212> TYPE: PRT
<213> ORGANISM: Sinorhizobium meliloti

<400> SEQUENCE: 707

Gly Asp Ser Asn
1


<210> SEQ ID NO 708
<211> LENGTH: 4
<212> TYPE: PRT
<213> ORGANISM: Sinorhizobium meliloti

<400> SEQUENCE: 708
```

-continued

```
Gly Arg Thr Thr
1


<210> SEQ ID NO 709
<211> LENGTH: 4
<212> TYPE: PRT
<213> ORGANISM: Mesorhizobium loti

<400> SEQUENCE: 709

Gly Ala Asn Asp
1


<210> SEQ ID NO 710
<211> LENGTH: 4
<212> TYPE: PRT
<213> ORGANISM: Moraxella bovis

<400> SEQUENCE: 710

Gly Ser Asn Asp
1


<210> SEQ ID NO 711
<211> LENGTH: 4
<212> TYPE: PRT
<213> ORGANISM: Sinorhizobium meliloti

<400> SEQUENCE: 711

Ala Arg Thr Thr
1
```